US012729203B2

(12) United States Patent
Huo et al.

(10) Patent No.: US 12,729,203 B2
(45) Date of Patent: Sep. 8, 2026

(54) DEGRADATION OF BRUTON'S TYROSINE KINASE (BTK) BY CONJUGATION OF BTK INHIBITORS WITH E3 LIGASE LIGAND AND METHODS OF USE

(71) Applicant: BeOne Medicines I GmbH, Basel (CH)

(72) Inventors: Changxin Huo, Beijing (CN); Hexiang Wang, Beijing (CN); Gang Lv, Beijing (CN); Zhiwei Wang, Beijing (CN); Huaqing Liu, Beijing (CN)

(73) Assignee: BeOne Medicines I GmbH, Basel (CH)

(*) Notice: Subject to any disclaimer, the term of this patent is extended or adjusted under 35 U.S.C. 154(b) by 497 days.

(21) Appl. No.: 18/259,858

(22) PCT Filed: Dec. 30, 2021

(86) PCT No.: PCT/CN2021/142801

§ 371 (c)(1),
(2) Date: Jun. 29, 2023

(87) PCT Pub. No.: WO2022/143856

PCT Pub. Date: Jul. 7, 2022

(65) Prior Publication Data

US 2024/0246977 A1 Jul. 25, 2024

(30) Foreign Application Priority Data

Dec. 31, 2020 (WO) ................ PCT/CN2020/142567

(51) Int. Cl.
*C07D 487/04* (2006.01)
*A61K 31/5517* (2006.01)
*C07D 519/00* (2006.01)

(52) U.S. Cl.
CPC ........ *C07D 487/04* (2013.01); *A61K 31/5517* (2013.01); *C07D 519/00* (2013.01)

(58) Field of Classification Search
CPC . C07D 487/04; C07D 519/00; A61K 31/5517
See application file for complete search history.

(56) References Cited

U.S. PATENT DOCUMENTS

| | | | |
|---|---|---|---|
| 9,630,968 | B1 | 4/2017 | Lapierre et al. |
| 10,280,169 | B2 | 5/2019 | Hopkins |
| 10,584,101 | B2 | 3/2020 | Crew |
| 10,647,698 | B2 | 5/2020 | Crew |
| 2016/0045607 | A1 | 2/2016 | Crew |
| 2016/0096834 | A1 | 4/2016 | Gaillard |
| 2017/0008904 | A1 | 1/2017 | Crew |
| 2018/0050021 | A1 | 2/2018 | Ciulli |
| 2018/0072711 | A1 | 3/2018 | Crew |
| 2018/0194762 | A1 | 7/2018 | Atallah |
| 2019/0276459 | A1 | 9/2019 | Crews |
| 2020/0239430 | A1 | 7/2020 | Desantis |
| 2020/0297725 | A1 | 9/2020 | Crews |

FOREIGN PATENT DOCUMENTS

| | | | |
|---|---|---|---|
| CN | 104884458 | A | 9/2015 |
| CN | 110845500 | | 2/2020 |
| CN | 110845500 | A | 2/2020 |
| CN | 113387931 | | 9/2021 |
| CN | 113387931 | A | 9/2021 |
| WO | 0220740 | A2 | 3/2002 |
| WO | 2007026720 | A1 | 3/2007 |
| WO | 2014064131 | A2 | 5/2014 |
| WO | 2014108452 | A1 | 7/2014 |
| WO | 2015089337 | A1 | 6/2015 |
| WO | 2016054807 | A1 | 4/2016 |
| WO | 2016146985 | A1 | 9/2016 |
| WO | 2016149668 | A1 | 9/2016 |
| WO | 2016149989 | A1 | 9/2016 |
| WO | 2016197032 | A1 | 12/2016 |
| WO | 2016197114 | A1 | 12/2016 |
| WO | 2017011590 | A1 | 1/2017 |
| WO | 2017030814 | A1 | 2/2017 |
| WO | 2017079267 | A1 | 5/2017 |
| WO | 2017182418 | A1 | 10/2017 |
| WO | 2017197036 | A1 | 11/2017 |
| WO | 2017197046 | A1 | 11/2017 |
| WO | 2017197051 | A1 | 11/2017 |
| WO | 2017197056 | A1 | 11/2017 |
| WO | 2017201449 | A1 | 11/2017 |
| WO | 2017211924 | A1 | 12/2017 |
| WO | 2018033556 | A1 | 2/2018 |
| WO | 2018035080 | A1 | 2/2018 |
| WO | 2018098288 | | 5/2018 |
| WO | 2018098288 | A1 | 5/2018 |
| WO | 2018191577 | A1 | 10/2018 |
| WO | 2018237026 | A1 | 12/2018 |

(Continued)

OTHER PUBLICATIONS

Raina, K. et al., "Targeted protein knockdown using small molecule degraders," Current Opinion in Chemical Biology, 39:46-53, 2017.
Rankin, A. L. et al., "Selective inhibition of BTK prevents murine lupus and antibody-mediated glomerulonephritis," The Journal of Immunology, 191(9):4540-4550, 2013.
Sainan, A. et al., "Small-molecule PROTACs: An emerging and promising approach for the development of targeted therapy drugs", EBioMedicine, 36:552-562, 2018.
Sakamoto, Kathleen M., "Chimeric molecules to target proteins for ubiquitination and degradation," Methods Enzymol., 399:833-847, 2005.
Sakamoto, Kathleen M., "Protacs: chimeric molecules that target proteins to the Skp1-Cullin-F box complex for ubiquitination and degradation," Proc Natl Acad Sci USA, 98(15):8554-8559, 2001.
Shi, Q. et al., "Purine derivatives as potent Bruton's tyrosine kinase (BTK) inhibitors for autoimmune diseases," Bioorganic and Medicinal Chemistry Letters, 24:2206-2211, 2014.

(Continued)

*Primary Examiner* — Renee Claytor
*Assistant Examiner* — Christopher Lindsay Johnson
(74) *Attorney, Agent, or Firm* — Foley & Lardner LLP

(57) ABSTRACT

Disclosed herein are novel bifunctional compounds formed by conjugating BTK inhibitor moieties with E3 ligase Ligand moieties, which function to recruit targeted proteins to E3 ubiquitin ligase for degradation, and methods of preparation and uses thereof.

27 Claims, No Drawings

(56) References Cited

FOREIGN PATENT DOCUMENTS

| | | | |
|---|---|---|---|
| WO | 2019127008 | A1 | 7/2019 |
| WO | 2019140387 | A1 | 7/2019 |
| WO | 2019148150 | | 8/2019 |
| WO | 2019148150 | A1 | 8/2019 |
| WO | 2019186343 | A1 | 10/2019 |
| WO | 2019186358 | A1 | 10/2019 |
| WO | 2019222101 | A1 | 11/2019 |
| WO | 2020142228 | A1 | 7/2020 |
| WO | 2020163823 | A2 | 8/2020 |
| WO | 2020198711 | A1 | 10/2020 |
| WO | 2020201080 | A1 | 10/2020 |
| WO | 2021219070 | A1 | 11/2020 |
| WO | 2020239103 | A1 | 12/2020 |
| WO | 2020252397 | | 12/2020 |
| WO | 2020252397 | A1 | 12/2020 |
| WO | 2020263935 | | 12/2020 |
| WO | 2020263935 | A1 | 12/2020 |
| WO | 2021018018 | A1 | 2/2021 |
| WO | 2021053495 | | 3/2021 |
| WO | 2021053495 | A1 | 3/2021 |
| WO | 2021178920 | A1 | 9/2021 |
| WO | 2021180103 | | 9/2021 |
| WO | 2021180103 | A1 | 9/2021 |
| WO | 2021219070 | | 11/2021 |
| WO | 2023080732 | A1 | 5/2023 |
| WO | 2023183811 | A1 | 9/2023 |

OTHER PUBLICATIONS

Smith, C. I. E. et al., "Expression of Bruton's Agammaglobulinemia Tyrosine Kinase Gene, BTK, Is Selectively Down-Regulated in T Lymphocytes and Plasma Cells," J. Immunol., 152:557-565, 1994.

Sun, Y. et al., "PROTAC-induced BTK degradation as a novel therapy for mutated BTK C481S induced ibrutinib-resistant B-cell malignancies", Cell Research, 28(7):779-781, 2018.

Sun, Y. et al., "Degradation of Bruton's tyrosine kinase mutants by PROTACs for potential treatment of ibrutinib-resistant non-Hodgkin lymphomas", Leukemia, 33:2105-2110, 2019.

Swatek, K. N. et al., "Ubiquitin modifications," Cell Research, 26(4):399-422, 2016.

Tasso, B. et al., "The development of BTK inhibitors: a five-year update," Molecules, 26:1-31, 2021.

Tinworth, C. P. et al., "PROTAC-mediated degradation of Bruton's tyrosine kinase is inhibited by covalent binding", ACS Chemical Biology, 14(3):342-347, 2019.

Toure, M. et al., "Small-Molecule PROTACS: New Approaches to Protein Degradation," Angew. Chem. Int. Ed., 55(6):1966-1973, 2016.

Troup, R. I. et al., "Current strategies for the design of PROTAC linkers: a critical review," Exploration of Targerted Anti-tumor Therapy, 1:273-312, 2020.

Vetrie, D. et al., "The gene involved in X-linked agammaglobulinaemia is a member of the src family of protein-tyrosine kinases," Nature, 361:226-233, 1993.

Weng, G. et al., "PROTAC-DB: an online database of PROTACs," Nucleic Acids Research, 49:D1381-D1387, 2021.

Winter, G. E. et al., "Phthalimide conjugation as a strategy for in vivo target protein degradation," Science, 348(6241):1376-1381, 2015.

Woodhead, Steve, Presentation: "Structure Guided Design and Optimization of Selective Kinase Inhibitors from Fragment Starting Points," Takeda California, 33 pages, Apr. 14, 2016.

Xiao, M. et al., "Recent advances of degradation technologies based on PROTAC mechanism," Biomolecules, 12(1257):1-15, 2022.

Xie, H. et al., "Development of substituted phenyl dihydrouracil as the novel achiral cereblon ligands for targeted protein degradation," Journal of Medicinal Chemistry, 66:2904-2917, 2023.

Zeng, S. et al., "Proteolysis targeting chimera (PROTAC) in drug discovery paradigm: recent progress and future challenges," European Journal of Medicinal Chemistry, 210(112891):1-23, 2021.

Zhou, B. et al., "Discovery of a small-molecule degrader of bromodomain and extra-terminal (BET) proteins with picomolar cellular potencies and capable of achieving tumor regression," Journal of Medicinal Chemistry, 61:462-481, 2018.

Zhou, P. et al., "Harnessing the ubiquitination machinery to target the degradation of specific cellular proteins," Mol. Cell., 6(3):751-756, 2000.

Zorba, A. et al., "Delineating the role of cooperativity in the design of potent PROTACs for BTK," PNAS, 115(31 ):E7285-E7292, 2018.

International Search Report issued Apr. 2, 2022 in PCT/CN2021/142801.

Takayama, T., et al., "Ring-fused pyrazole derivatives as potent inhibitors of lymphocyte-specific kinase (Lck): Structure, Synthesis, and SAR," Bioorganic & Medicinal Chemistry Letters, vol. 12, pp. 112-116, Nov. 12, 2009.

*Abbvie Inc.*, v *BeiGene, Ltd et al.*, Civil Action No. 1:24-cv-08167, Complaint filed on Sep. 6, 2024, 59 pages.

Aqu, Alu et al., "BTK inhibitors in the treatment of hematological malignancies and inflammatory diseases: mechanisms and clinical studies," Journal of Hematology & Oncology, 15:138, 2022.

Ardley, H.C. et al., "E3 ubiquitin ligases," Essays Biochemistry, 41:15-30, 2005.

Bekes, M. et al., "PROTAC targeted protein degraders: the past is prologue," Nature Reviews, 21:181-200, 2022.

Boichenko, I. et al., "Chemical ligand space of cereblon," ACS Omega, 3:1163-1171, 2018.

Bondenson, D. P. et al., "Lessons in PROTAC design from selective degradation with a promiscuos warhead," Cell Chemical Biology, 25:15 pages, 2018.

Bradshaw, J. M., "The Src, Syk, and Tec family kinases: distinct types of molecular switches," Cell Signalling, 22(8):1175-1184, 2010.

Buhimschi, A. D. et al., "Targeting the C481S Ibrutinib-Resistance Mutation in Bruton's Tyrosine Kinase Using PROTAC-Mediated Degradation," Biochemistry, 57(26):3564-3575, 2018.

Burke, M. R. et al., "Overcoming cancer drug resistance utilizing PROTAC technology," Frontiers in Cell and Developmental Biology, 10(872729):1-22, 2022.

Burslem, G. M. et al., "Efficient synthesis of immunomodulatory drug analogues enables exploration of structure-degradation relationships," ChemMedChem, 13:1508-1512, 2018.

Caldwell, R. D. et al., "Discovery of Evobrutinib: an oral, potent, and highly selective, covalent Bruton's tyrosine kinase (BTK) inhibitor for the treatment of immunological diseases," Journal of Medicinal Chemistry, 62:7643-7655, 2019.

Casement, R. et al., "Mechanistic and structural features of PROTAC temary complexes," Chapter 5, Methods in Molecular Biology, 2365:35 pages, 2021.

Cermakova, K. et al., "Next-Generation Drugs and Probes for Chromatin Biology: From Targeted Protein Degradation to Phase Separation," Molecules, 23(1958):26 pages, 2018.

Conley, M. E. et al., "Primary B Cell Immunodeficiencies: Comparisons and Contrasts," Annu. Rev. Immunol., 27:199-227, 2009.

Crawford, J. J. et al., "Discovery of GDC-0853: a potent, selective, and noncovalent Bruton's tyrosine kinase inhibitor in early clinical development," Journal of Medicinal Chemistry, 61:2227-2245, 2018.

Crews, Craig M. et al., "Inducing Protein Degradation as a Therapeutic Strategy," J. Med. Chem., 61(2):403-404, 2018.

Cromm, P. M. et al., "Targeted protein degradation: from chemical biology to drug discovery," Cell Chemical Biology Review, 24:1181-1190, 2017.

Defendants' Memorandum in Support of Motion to Dismiss, citation: Civil Action 1:24-cv-08167 filed on Dec. 19, 2024, 37 pages.

Defendants' reply in support of motion to dismiss, citation: Civil Action No. 1:24-cv-8167, filed Feb. 14, 2025, 27 pages.

Desantis, J. et al., "PROTACs bearing piperazine-containing linkers: what effect on their protonation state?," RSC Adv., 12:21968-21977, 2022.

Di Paolo, J. A. et al., "Specific Btk inhibition suppresses B cell- and myeloid cell-mediated arthritis," Nat. Chem. Biol., 7(1):41-50, 2011.

(56) References Cited

OTHER PUBLICATIONS

Dobrovolsky, D. et al., "Bruton tyrosine kinase degradation as a therapeutic strategy for cancer," Blood, 133(9):952-961, 2019.
Dong, Y. et al., "Characteristic roadmap of linker governs the rational design of PROTACs," Acta Pharmaceutica Sinica B, 1-30, 2024.
Feng, Y. et al., "Bruton's tyrosine kinase (BTK) inhibitors in treating cancer: a patent review (2010-2018)," Expert Opinion on Therapeutic Patents, 29(4):217-241, 2019.
Gomez, E. B. et al., "Preclinical characterization of pirtobrutinib, a highly selective, noncovalent (reversible) BTK inhibitor," Blood, 142(1):62-72, 2023.
Grice, G. L. et al., "The Proteasome Distinguishes between Heterotypic and Homotypic Lysine-11-Linked Polyubiquitin Chains," Cell Rep., 12(4):545-553, 2015.
Gurcan, H. M. et al., "A review of the current use of rituximab in autoimmune diseases," Int. Immunopharmacol., 9:10-25, 2009.
Han, X. et al., "Discovery of ARD-69 as a highly potent proteolysis targeting chimera (PROTAC) degrader of androgen receptor (AR) for the treatment of prostate cancer," J. Med. Chem., 62:941-964, 2019.
Han, X. et al., "Strategies for the discovery of oral PROTAC degraders aimed at cancer therapy," Cell Reports Physical Science, 3(101062):1-22, 2022.
Hayama, M. et al., "Taking the next step in double refractory disease: current and future treatment strategies for chronic lymphocytic leukemia," Onco Targets and Therapy, 17:181-198, 2024.
Humphries, L. A. et al., "Tec Kinases Mediate Sustained Calcium Influx via Site-specific Tyrosine Phosphorylation of the Phospholipase Cgamma Src Homology 2-Src Homology 3 Linker," J. Biol. Chem., 279(36): 37651-37661, 2004.
Jarusiewicz, J. A. et al., "Phenyl dihodrouracil: an alternative cereblon binder for PROTAC design," ACS Medicial Chemstry Letters, 14:141-145, 2023.
Kargbo, Robert B., "PROTAC molecules for the treatment of autoimmune disorders," ACS Medicinal Chemistry Letters, 10:276-277, 2019.
Khan, W. N., "Regulation of B lymphocyte development and activation by Bruton's tyrosine kinase," Immunol. Res., 23(213):147-156, 2001.
Komander, D. et al., "The Ubiquitin Code," Annu. Rev. Biochem., 81:30 pages, 2012.
Kronke, J. et al., "Lenalidomide induces ubiquitination and degradation of CK1alpha in del (95q) MDS," Nature, 523:20 pages, 2015.
Lebraud, H. et al., "Protein degradation: a validated therapeutic strategy with exciting prospects," Essays Biochem., 61(5):517-527, 2017.
Li, B. et al., "3D based generative PROTAC linker design with reinforcement learning," Briefings in Bioinformatics, 24(5):1-13, 2023.
Li, W. et al., "Bruton's tyrosine kinase inhibitors with distinct binding modes reveal differential functional impact on B-cell receptor signaling," Molecular Cancer Therapeutics, 23:35-46, 2024.
Li, X. et al., "A patent review of the ubiquitin ligase system: 2015-2018," Expert Opinion on Therapeutic Patents, 28(12):919-937, 2018.
Liu, S. et al., "Targeted selective degradation of Bruton's tyrosine kinase by PROTACs," Medicinal Chemistry Research, 29:802-808, 2020.
Lu, J. et al., "Hijacking the E3 Ubiquitin ligase cereblon to efficiently target BRD4," Chemistry and Biology, 22(6):755-763, 2015.
Lu, M. et al., "Discovery of a Keap1-dependent peptide PROTAC to knockdown Tau by ubiquitination-proteasome degradation pathway," European Journal of Medicinal Chemistry, 146:251-259, 2018.
Min, J. et al., "Phenyl-glutarimides: Alternative cereblon binders for the design of PROTACs," Angewandte Chemie, 60:26633-26670, 2021.
Moon, S. et al., "Chemically induced cellular proteolysis: an emerging therapeutic strategy for undruggable targets," Molecules and Cells, 41(11): 933-942, 2018.
Neklesa, T. K. et al., "Targeted protein degradation by PROTACs," Pharmacology & Therapeutics, 174:138-144, 2017.
Nowak, R. P. et al., "Plasticity in binding confers selectivity in ligand-induced protein degradation," Nature chemical biology, 14:706-714, 2018.
Ottis, P. et al., "Assessing Different E3 Ligases for Small Molecule Induced Protein Ubiquitination and Degradation," ACS Chem. Biol., 12(10):2570-2578, 2017.
Ottis, P. et al., "Proteolysis-Targeting Chimeras: Induced Protein Degradation as a Therapeutic Strategy," ACS Chem. Biol., 12(4):892-898, 2017.
Plaintiff AbbVie Inc.'s Opposition to Defendants' Motion to Dismiss, citation: Civil Action 1:24-cv-08167 filed on Jan. 24, 2025, 44 pages.
Takayama, T. et al., "Ring-fused pyrazole derivatives as potent inhibitors of lymphocyte-specific kinase (Lck): Structure, synthesis, and SAR," Bioorganic & Medicinal Chemistry Letters, Jan. 2010, vol. 20, No. 1, pp. 112-116.

DEGRADATION OF BRUTON'S TYROSINE KINASE (BTK) BY CONJUGATION OF BTK INHIBITORS WITH E3 LIGASE LIGAND AND METHODS OF USE

CROSS-REFERENCE TO RELATED APPLICATION

This application is a Section 371 of International Application No. PCT/CN2021/142801 filed Dec. 30, 2021, which was published in the English language Jul. 7, 2022, under International Publication No. WO 2022/143856 A1, which claims priority to International Patent Application No. PCT/CN2020/142567 filed Dec. 31, 2020, the disclosures of which are incorporated herein by reference in their entireties.

FIELD OF THE INVENTION

Disclosed herein are novel bifunctional compounds formed by conjugating BTK inhibitor moieties with E3 ligase Ligand moieties, which function to recruit targeted proteins to E3 ubiquitin ligase for degradation, and methods of preparation and uses thereof.

BACKGROUND OF THE INVENTION

Proteolysis-targeting chimera (PROTAC) is a novel strategy for selective knockdown of target proteins by small molecules (Sakamoto K M et al., *Proc Natl Acad Sci* 2001, 98:8554-9.; Sakamoto K. M. et al., *Methods Enzymol.* 2005; 399:833-847.). PROTAC utilizes the ubiquitin-protease system to target a specific protein and induce its degradation in the cell (Zhou P. et al., *Mol Cell.* 2000; 6(3):751-756; Neklesa T. K. et al., *Pharmacol Ther.* 2017; 174:138-144; Lu M. et al., *Eur J Med Chem.* 2018; 146:251-259). The normal physiological function of the ubiquitin-protease system is responsible for clearing denatured, mutated, or harmful proteins in cells. The normal physiological function of the ubiquitin-protease system is responsible for clearing denatured, mutated, or harmful proteins in cells. The ubiquitin-proteasome system (UPS), also known as the ubiquitin-proteasome pathway (UPP), is a common posttranslational regulation mechanism that is responsible for protein degradation in normal and pathological states (Ardley H. et al., *Essays Biochem.* 2005, 41, 15-30; Komander D. et al., *Biochem.* 2012, 81, 203-229; Grice G. L. et al., *Cell Rep.* 2015, 12, 545-553; Swatek K. N. et al., *Cell Res.* 2016, 26, 399-422). Ubiquitin, which is highly conserved in eukaryotic cells, is a modifier molecule, composed of 76 amino acids, that covalently binds to and labels target substrates via a cascade of enzymatic reactions involving E1, E2, and E3 enzymes. Subsequently, the modified substrate is recognized by the 26S proteasome complex for ubiquitination-mediated degradation. So far, two E1 enzymes have been discovered, which are termed UBA1 and UBA6. On the other hand, there are about 40 E2 enzymes and more than 600 E3 enzymes that offer the functional diversity to govern the activity of many downstream protein substrates. However, only a limited number of E3 ubiquitin ligases have been successfully hijacked for use by small-molecule PROTAC technology: the Von Hippel-Lindau disease tumor suppressor protein (VHL), the Mouse Double Minute 2 homologue (MDM2), the Cellular Inhibitor of Apoptosis (cIAP), and cereblon (Philipp O. et al., *Chem. Biol.* 2017, 12, 2570-2578).

Bifunctional compounds composed of a target protein-binding moiety and an E3 ubiquitin ligase-binding moiety have been shown to induce proteasome-mediated degradation of selected proteins. These drug-like molecules offer the possibility of temporal control over protein expression and could be useful as biochemical reagents for the treatment of diseases. In recent years, this newly developed method has been widely used in antitumor studies (Lu J. et al., *Chem Biol.* 2015; 22(6):755-763; Ottis P. et al., *Chem Biol.* 2017; 12(4):892-898.; Crews C. M. et al., *J Med Chem.* 2018; 61(2):403-404; Neklesa T. K. et al., *Pharmacol Ther.* 2017, 174:138-144.; Cermakova K. et al., *Molecules,* 2018.23(8).; An S. et al., *EBioMedicine,* 2018.; Lebraud H. et al., *Essays Biochem.* 2017; 61(5): 517-527.; Sun Y. H. et al., *Cell Res.* 2018; 28:779-81; Toure M. et al., *Angew Chem Int Ed Engl.* 2016; 55(6):1966-1973; Yonghui Sun et al., *Leukemia, volume* 33, pages2105-2110(2019); Shaodong Liu et al., *Medicinal Chemistry Research, volume* 29, pages802-808 (2020); Shenxin Z. et al., *European Journal of Medicinal Chemistry,* 2020, doi.org/10.1016/j.ejmech.2020.112981) and has been disclosed or discussed in patent publications, e.g., US20160045607, US20170008904, US20180050021, US20180072711, WO2002020740, WO2014108452, WO2016146985, WO2016149668, WO2016149989, WO2016197032, WO2016197114, WO2017011590, WO2017030814, WO2017079267, WO2017182418, WO2017197036, WO2017197046, WO2017197051, WO2017197056, WO2017201449, WO2017211924, WO2018033556, WO2018071606, US 20200297725, US20200239430, WO 2020142228, WO2020163823, WO2020198711, WO2020201080, et al.

Bruton's tyrosine kinase (Btk) belongs to the Tec tyrosine kinase family (Vetrie et al., *Nature* 361: 226-233, 1993; Bradshaw, *Cell Signal.* 22: 1175-84, 2010). Btk is primarily expressed in most hematopoietic cells such as B cells, mast cells and macrophages (Smith et al., *J. Immunol.* 152: 557-565, 1994) and is localized in bone marrow, spleen and lymph node tissue. Btk plays important roles in B-cell receptor (BCR) and FcR signaling pathways, which involve in B-cell development, differentiation (Khan, *Immunol. Res.* 23: 147, 2001). Btk is activated by upstream Src-family kinases. Once activated, Btk in turn phosphorylates PLC gamma, leading to effects on B-cell function and survival (Humphries et al., *J. Biol. Chem.* 279: 37651, 2004). These signaling pathways must be precisely regulated. Mutations in the gene encoding Btk cause an inherited B-cell specific immunodeficiency disease in humans, known as X-linked agammaglobulinemia (XLA) (Conley et al., *Annu. Rev. Immunol.* 27: 199-227, 2009). Aberrant BCR-mediated signaling may result in dysregulated B-cell activation leading to a number of autoimmune and inflammatory diseases. Preclinical studies show that Btk deficient mice are resistant to developing collagen-induced arthritis. Moreover, clinical studies of Rituxan, a CD20 antibody to deplete mature B-cells, reveal the key role of B-cells in a number of inflammatory diseases such as rheumatoid arthritis, systemic lupus erythematosus and multiple sclerosis (Gurcan et al., *Int. Immunopharmacol.* 9: 10-25, 2009). Therefore, Btk inhibitors can be used to treat autoimmune and/or inflammatory diseases.

Inhibition of BTK has been shown to affect cancer development (B cell malignancies) and cell viability, and improve autoimmune diseases (e.g., rheumatoid arthritis and lupus). Inhibition of BTK has also been reported via alternative strategies, such as through degradation of BTK (Alexandru D. et al., *Biochemistry* 2018, 57, 26, 3564-3575; Adelajda Z. et al., *PNAS* 2018 115 (31); Dennis D., et al., *Blood,* 2019, 133:952-961; Yonghui S. et al., *Cell Research,* 2018, 28, 779-781; Yonghui S. et al., *Leukemia,* 2019, Degradation of Bruton's tyrosine kinase mutants by PROTACs for potential treatment of ibrutinib-resistant non-Hodgkin lymphomas) and has been disclosed or discussed in patent publications, e.g. US20190276459, WO2019186343, WO2019186358, WO2019148150, WO2019177902, WO2019127008, and WO2020239103.

There is a need of new BTK inhibitors or degrader which are more potent than known inhibitors of BTK and inhibit BTK via alternative strategies, such as through degradation of BTK. The present application addresses the need.

SUMMARY OF THE INVENTION

The following aspects or embodiments are parts of the instant invention. However, the instant invention is not limited thereto.

Aspect 1. A compound of Formula (I):

(I)

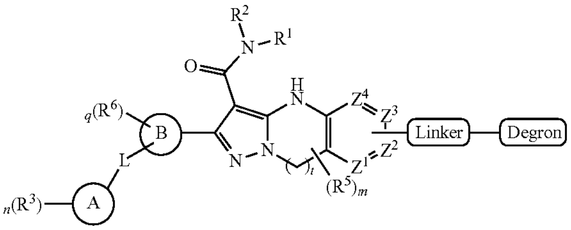

or a pharmaceutically acceptable salt thereof, or a stereoisomer thereof, wherein:

ring A and B are each independently an aromatic ring comprising 0-3 heteroatoms selected from nitrogen, sulfur and oxygen as ring member(s);

$Z^1$, $Z^2$, $Z^3$ and $Z^4$ are each independently N or $CR^z$;

L is independently a bond, —$C_{1-8}$alkylene-, —$N(R^4)$—, —O—, —S—, $*^L$—$C_{1-8}$alkylene-O—$**^L$, $*^L$—O—$C_{1-8}$alkylene-$**^L$, $*^L$—$N(R^4)CO$—$**^L$, $*^L$—$CON(R^4)$—$**^L$, $*^L$—$N(R^4)CO$—$C_{1-8}$alkylene-$**^L$, $*^L$—$CON(R^4)$—$C_{1-8}$alkylene-$**^L$, $*^L$—$N(R^4)$—$C_{1-8}$alkylene-$**^L$, $*^L$—$C_{1-8}$alkylene-$N(R^4)$—$**^L$, -heterocyclene-, or -heteroarylene-, wherein each of said —$C_{1-8}$alkylene-, $*^L$—$C_{1-8}$alkylene-O—$**^L$, $*^L$—O—$C_{1-8}$alkylene-$**^L$, $*^L$—$N(R^4)CO$—$C_{1-8}$alkylene-$**^L$, $*^L$—$CON(R^4)$—$C_{1-8}$alkylene-$**^L$, $*^L$—$N(R^4)$—$C_{1-8}$alkylene-$**^L$, $*^L$—$C_{1-8}$alkylene-$N(R^4)$—$**^L$, -heterocyclene- and -heteroarylene- is optionally substituted with at least one substituent $R^L$;

wherein $*^L$ refers to the position attached to ring A, and $**^L$ refers to the position attached to ring B;

m, n and q are each independently 0, 1, 2, 3 or 4;

t is 0, 1 or 2;

$R^1$, $R^2$, and $R^4$ are each independently hydrogen, —$C_{1-8}$alkyl, —$C_{2-8}$alkenyl, —$C_{2-8}$alkynyl, cycloalkyl, heterocyclyl, aryl, or heteroaryl, wherein each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkyoxy, cycloalkyl, heterocyclyl, aryl, or heteroaryl;

$R^L$, $R^3$, $R^5$ and $R^6$ are each independently hydrogen, halogen, —$C_{1-8}$alkyl, —$C_{2-8}$alkenyl, —$C_{2-8}$alkynyl, cycloalkyl, heterocyclyl, aryl, heteroaryl, —CN, —$NO_2$, —$OR^a$, —$SO_2R^a$, —$COR^a$, —$CO_2R^a$, —$CONR^aR^b$, —$C(=NR^a)NR^bR^c$, —$NR^aR^b$, —$NR^aCOR^b$, —$NR^aCONR^bR^c$, —$NR^aCO_2R^b$, —$NR^aSONR^bR^c$, —$NR^aSO_2NR^bR^c$, or —$NR^aSO_2R^b$, wherein each of said —$C_{1-8}$alkyl, —$C_{2-8}$alkenyl, —$C_{2-8}$alkynyl, cycloalkyl, heterocyclyl, aryl, or heteroaryl is optionally substituted with at least one halogen, hydroxy, —$C_{1-8}$alkyl, —$C_{1-8}$alkyoxy, cycloalkyl, heterocyclyl, aryl, or heteroaryl;

$R^z$ is selected from the bond between

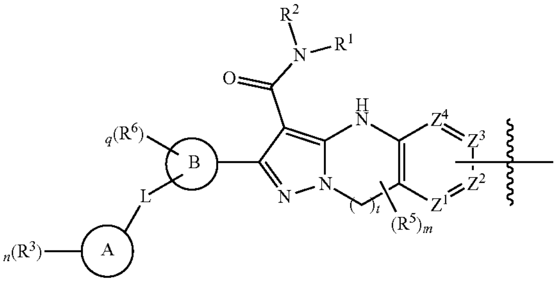

moiety and

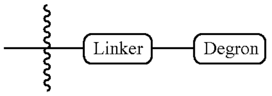

moiety, hydrogen, halogen, —$C_{1-8}$alkyl, —$C_{2-8}$alkenyl, —$C_{2-8}$alkynyl, cycloalkyl, heterocyclyl, aryl, heteroaryl, —CN, —$NO_2$, —$OR^a$, —$SO_2R^a$, —$COR^a$, —$CO_2R^a$, —$CONR^aR^b$, —$C(=NR^a)NR^bR^c$, —$NR^aR^b$, —$NR^aCOR^b$, —$NR^aCONR^bR^c$, —$NR^aCO_2R^b$, —$NR^aSONR^bR^c$, —$NR^aSO_2NR^bR^c$, or —$NR^aSO_2R^b$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one halogen, hydroxy, —$C_{1-8}$alkyl, —$C_{1-8}$alkyoxy, cycloalkyl, heterocyclyl, aryl, or heteroaryl; $R^a$, $R^b$, and $R^c$ are each independently hydrogen, —$C_{1-8}$alkyl, —$C_{2-8}$alkenyl, —$C_{2-8}$alkynyl, cycloalkyl, heterocyclyl, aryl, or heteroaryl;

or two $R^L$, together with the atom(s) to which they are attached, form a 3- to 12-membered ring, said ring comprising 0, 1 or 2 additional heteroatoms independently selected from nitrogen, oxygen or optionally oxidized sulfur as ring member(s), said ring is optionally substituted with at least one substituent independently selected from halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO_2$, —$OR^{3f}$, —$SO_2R^{3f}$, —$SO_2NR^{3f}R^{3g}$, —$COR^{3f}$, —$CO_2R^{3f}$, —$CONR^{3f}R^{3g}$, —$C(=NR^{3f})NR^{3g}R^{3h}$, —$NR^{3f}R^{3g}$, —$NR^{3f}COR^{3g}$, —$NR^{3f}CONR^{3g}R^{3h}$, —$NR^{3f}CO_2R^{3f}$, —$NR^{3f}SONR^{3f}R^{3g}$, —$NR^{3f}SO_2NR^{3g}R^{3h}$, or —$NR^{3f}SO_2R^{3g}$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituent selected from halogen, —$C_{1-8}$alkyl, —$OR^{3L}$, —$NR^{3i}R^{3j}$, cycloalkyl, heterocyclyl, aryl, or heteroaryl; or two $R^3$, together with the atoms to which they are attached, form a 3- to 12-membered ring, said ring comprising 0, 1 or 2 additional heteroatoms independently selected from nitrogen, oxygen or optionally oxidized sulfur as ring member(s), said ring is optionally substituted with at least one substituent independently selected from halogen, $-C_{1-8}$alkyl, $-C_{2-8}$alkenyl, $-C_{2-8}$alkynyl, cycloalkyl, heterocyclyl, aryl, heteroaryl, oxo, —CN, $-NO_2$, $-OR^{3f}$, $-SO_2R^{3f}$, $-SO_2NR^{3f}R^{3g}$, $-COR^{3f}$, $-CO_2R^{3f}$, $-CONR^{3f}R^{3g}$, $-C(=NR^{3f})NR^{3g}R^{3h}$, $-NR^{3f}R^{3g}$, $-NR^{3f}COR^{3g}$, $-NR^{3f}CONR^{3g}R^{3h}$, $-NR^{3f}CO_2R^{3f}$, $-NR^{3f}SONR^{3f}R^{3g}$, $-NR^{3f}SO_2NR^{3g}R^{3h}$, or $-NR^{3f}SO_2R^{3g}$, each of said $-C_{1-8}$alkyl, $-C_{2-8}$alkenyl, $-C_{2-8}$alkynyl, cycloalkyl, heterocyclyl, aryl, or heteroaryl is optionally substituted with at least one substituent selected from halogen, $-C_{1-8}$alkyl, $-OR^{3i}$, $-NR^{3i}R^{3j}$, cycloalkyl, heterocyclyl, aryl, or heteroaryl;

or $R^4$ and one of $R^3$, together with the atoms to which they are attached, form a 3- to 12-membered ring, said ring comprising 0, 1 or 2 additional heteroatoms independently selected from nitrogen, oxygen or optionally oxidized sulfur as ring member(s), said ring is optionally substituted with at least one substituent independently selected from halogen, $-C_{1-8}$alkyl, $-C_{2-8}$alkenyl, $-C_{2-8}$alkynyl, cycloalkyl, heterocyclyl, aryl, heteroaryl, oxo, —CN, $-NO_2$, $-OR^{3f}$, $-SO_2R^{3f}$, $-SO_2NR^{3f}R^{3g}$, $-COR^{3f}$, $-CO_2R^{3f}$, $-CONR^{3f}R^{3g}$, $-C(=NR^{3f})NR^{3g}R^{3h}$, $-NR^{3f}R^{3g}$, $-NR^{3f}COR^{3g}$, $-NR^{3f}CONR^{3g}R^{3h}$, $-NR^{3f}CO_2R^{3f}$, $-NR^{3f}SONR^{3f}R^{3g}$, $-NR^{3f}SO_2NR^{3g}R^{3h}$, or $-NR^{3f}SO_2R^{3g}$, each of said $-C_{1-8}$alkyl, $-C_{2-8}$alkenyl, $-C_{2-8}$alkynyl, cycloalkyl, heterocyclyl, aryl, or heteroaryl is optionally substituted with at least one substituent selected from halogen, $-C_{1-8}$alkyl, $-OR^{3i}$, $-NR^{3i}R^{3j}$, cycloalkyl, heterocyclyl, aryl, or heteroaryl;

$R^{3f}$, $R^{3g}$, $R^{3h}$, $R^{3i}$, and $R^{3j}$ are each independently hydrogen, $-C_{1-8}$alkyl, $C_{1-8}$alkoxy-$C_{1-8}$alkyl-, $-C_{2-8}$alkenyl, $-C_{2-8}$alkynyl, cycloalkyl, heterocyclyl, aryl, or heteroaryl;

the Linker is a bond or a divalent linking group, and the Degron is an E3 Ubiquitin ligase moiety.

Aspect 2. The compound according to Aspect 1, wherein the Degron moiety is selected from Formulas D1 D2 or D3:

D1

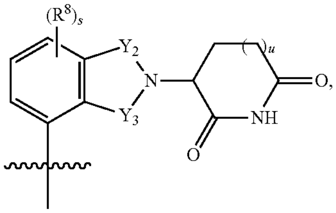

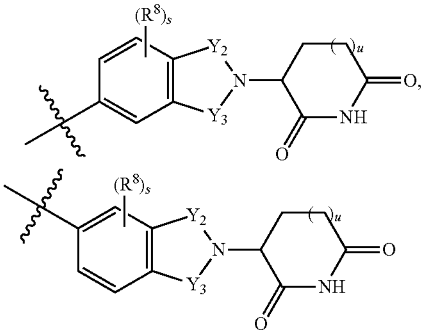

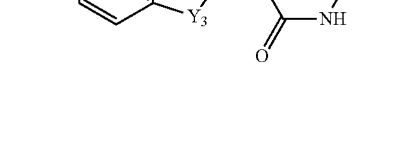

or

-continued

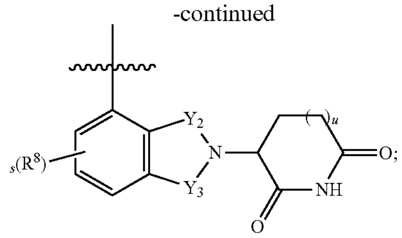

or

D2

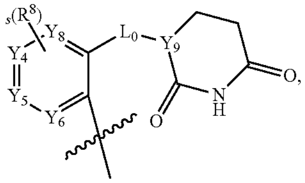

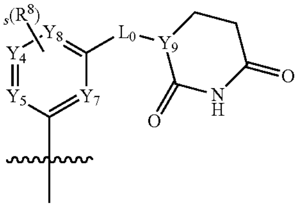

or

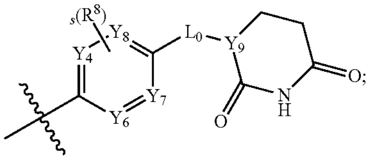

D3

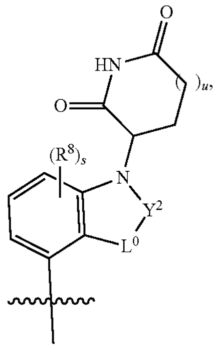

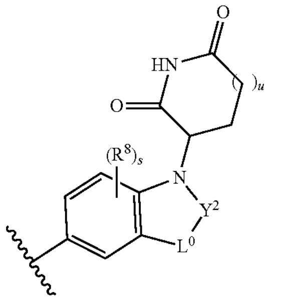

or

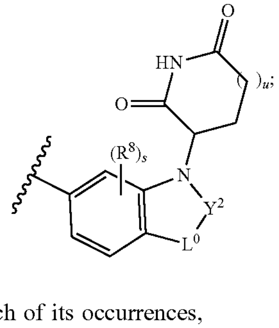

wherein, at each of its occurrences, $Y_2$ and $Y_3$ are each independently $-CH_2-$, —NH— or —C(O)—;

$L_0$ is selected from a bond, $-CH_2-$, —O—, —NH— and —S—; wherein each of $Y^2$, $Y^3$ and $L^0$ is independently optionally substituted with at least one substituent selected from hydrogen, halogen, $-C_{1-8}$alkyl, $-C_{2-8}$alkenyl, $-C_{2-8}$alkynyl, cycloalkyl, heterocyclyl, aryl, heteroaryl, —CN;

$Y_4$, $Y_5$, $Y_6$, $Y_7$ and $Y_8$ are each independently CH or N;

$Y_9$ is CH or N;

s is 0, 1, 2, 3, or 4;

u is 0, 1, or 2;

$R^8$ is each independently hydrogen, halogen, —$C_{1-8}$alkyl, —$C_{2-8}$alkenyl, —$C_{2-8}$alkynyl, cycloalkyl, heterocyclyl, aryl, heteroaryl, —CN, —$NO_2$, —$OR^{8a}$, —$SO_2R^{8a}$, —$COR^{8a}$, —$CO_2R^{8a}$, —$CONR^{8a}R^{8b}$, —C(=$NR^{8a}$)$NR^{8b}R^{8c}$, —$NR^{8a}R^{8b}$, —$NR^{8a}COR^{8b}$, —$NR^{8a}CONR^{8b}R^{8c}$, —$NR^{8a}CO_2R^{8b}$, —$NR^{8a}SONR^{8b}R^{8c}$, —$NR^{8a}SO_2NR^{8b}R^{8c}$, or —$NR^{8a}SO_2R^{8b}$, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkyoxy, cycloalkyl, heterocyclyl, aryl, or heteroaryl; and $R^{8a}$, $R^{8b}$, and $R^{8c}$ are each independently hydrogen, —$C_{1-8}$alkyl, —$C_{2-8}$alkenyl, —$C_{2-8}$alkynyl, cycloalkyl, heterocyclyl, aryl, or heteroaryl.

Aspect 3. The compound according to Aspect 2, wherein Formula D1 is selected from

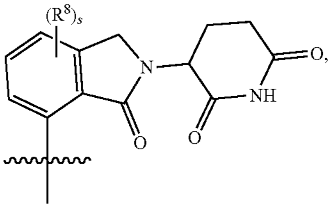

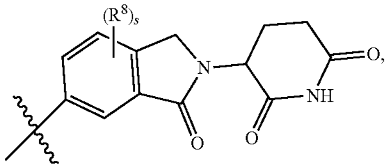

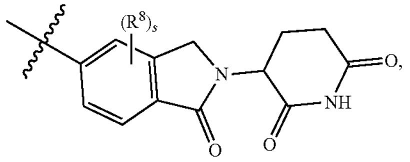

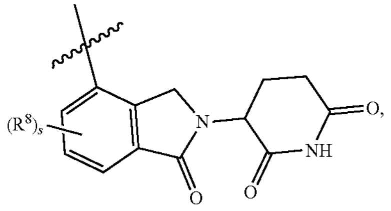

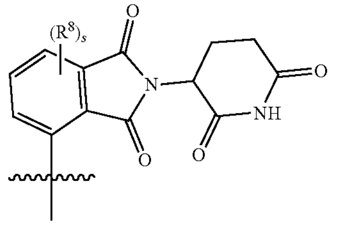

or

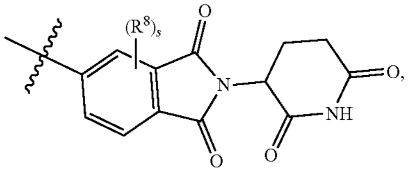

wherein $R^8$ is defined as above.

Aspect 4. The compound according to Aspect 2, wherein Formula D1 is selected from

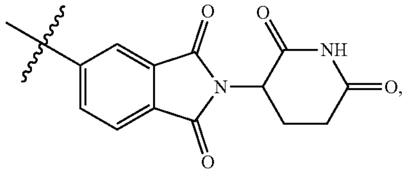

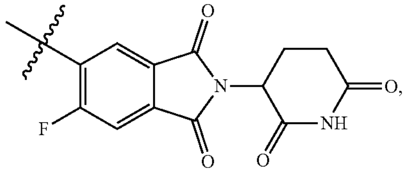

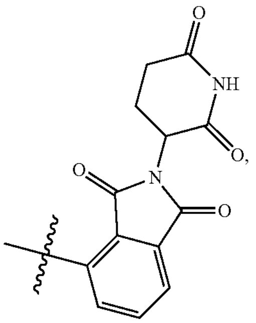

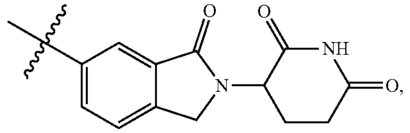

or

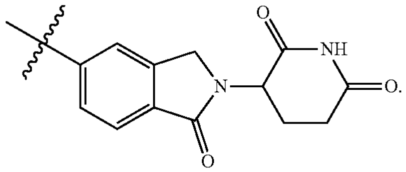

Aspect 5. The compound according to Aspect 2, wherein Formula D2 is selected from

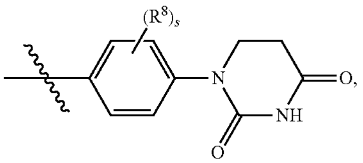

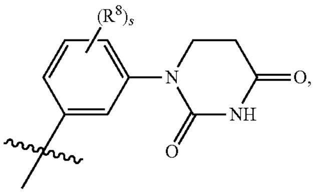

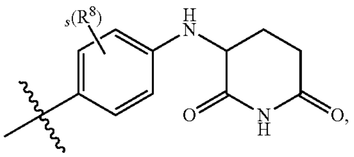

-continued
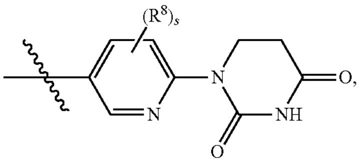
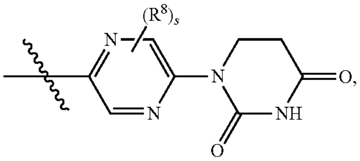
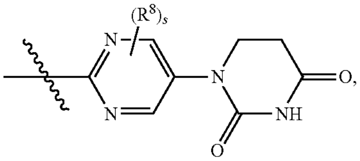
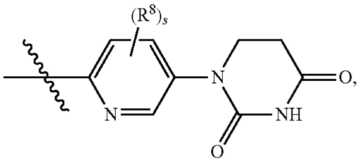
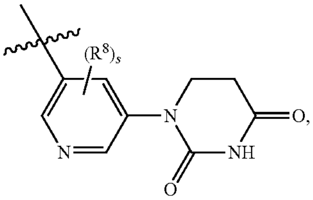
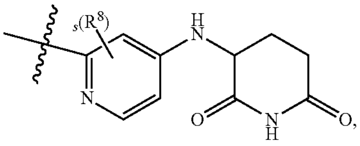
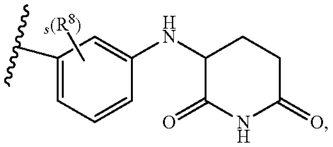
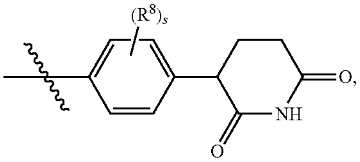
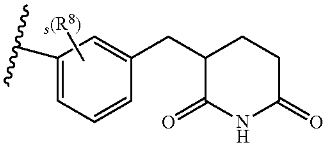
or
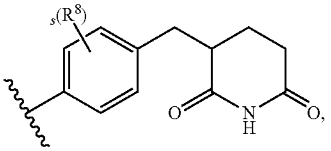
wherein $R^8$ is defined as above.
Aspect 6. The compound according to Aspect 2, wherein Formula D2 is selected from
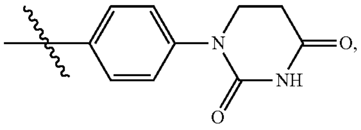
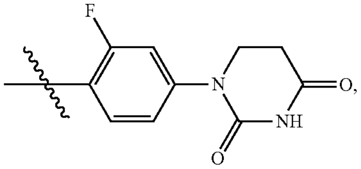
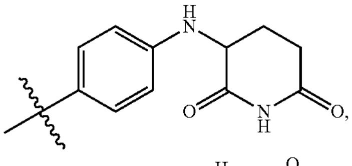
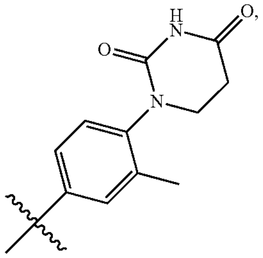
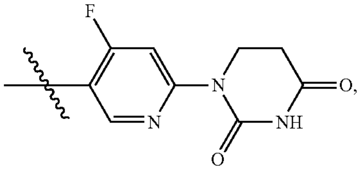
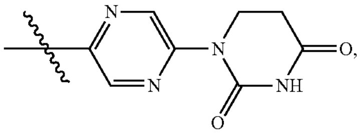
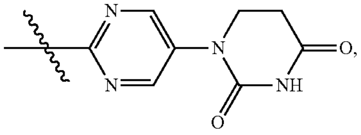
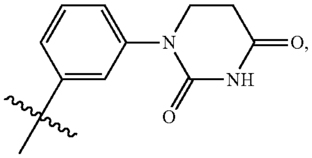
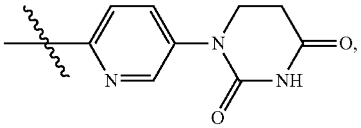
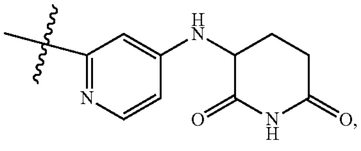
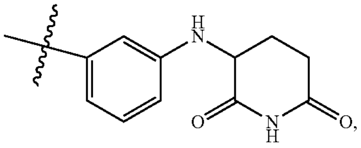

-continued

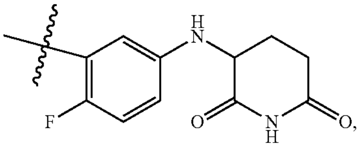

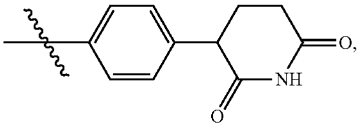

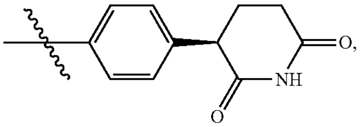

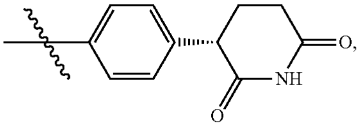

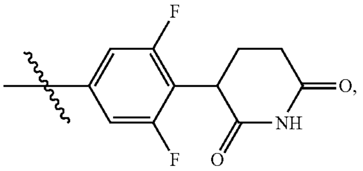

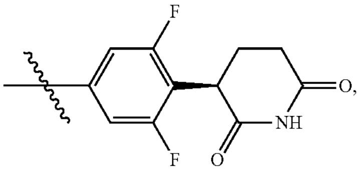

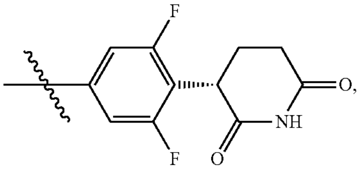

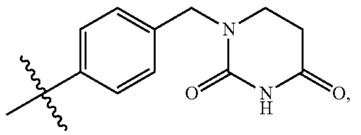

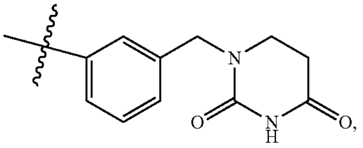

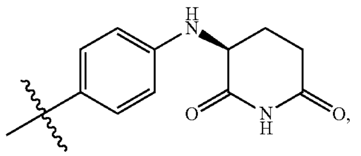

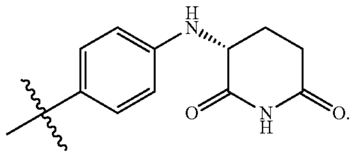

Aspect 7. The compound according to Aspect 2, wherein Formula D3 is selected from

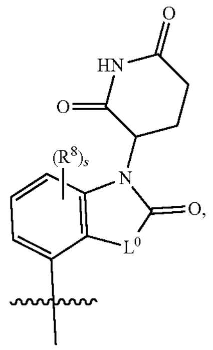

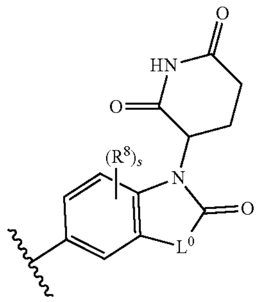

or

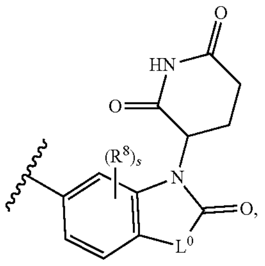

wherein $R^8$ is defined as above;

$L^0$ is selected from a bond, —$CH_2$—, —O—, —NH— and —S—; wherein $L^0$ is independently optionally substituted with at least one substituent selected from hydrogen, F, Cl, Br, I, —$CH_3$, —$C_2H_5$, —$C_3H_7$, —$C_4H_9$, —$C_5H_{11}$, —$C_{2-8}$alkenyl, —$C_{2-8}$alkynyl, cyclopropyl, cyclobutyl, cyclopentyl, cyclohexyl, cycloheptyl, cyclooctyl, heterocyclyl, aryl, heteroaryl or —CN.

Aspect 8. The compound according to Aspect 2, wherein Formula D3 is selected from

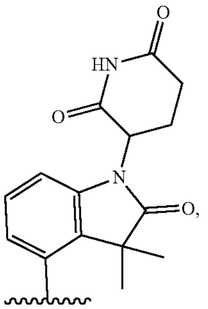

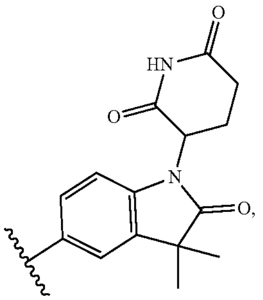

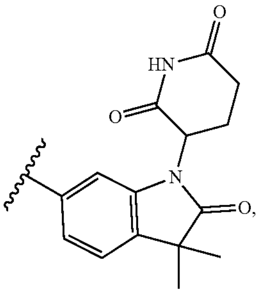

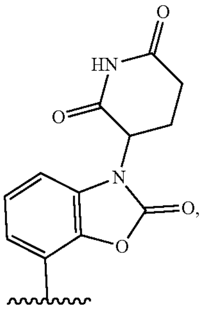

-continued

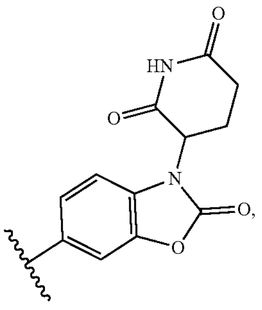

or

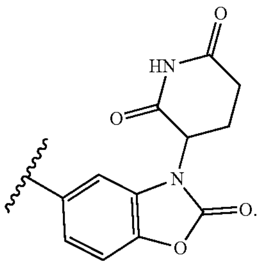

Aspect 9. The compound according to any one of Aspects 1-8, wherein L is a bond, —$CH_2$—, —$C_2H_4$—, —$C_3H_6$—, —$C_4H_8$—, —$C_5H_{10}$—, —O—, —NH—, $*^L$—$NHCH_2$—$**^L$, $*^L$—$NHC_2H_4$—$**^L$, $*^L$—$NHC_3H_6$—$**^L$, $*^L$—$NHC_4H_8$—$**^L$, $*^L$—$NHC_5H_{10}$—$**^L$, $*^L$—$OCH_2$—$**^L$, $*^L$—$OC_2H_4$—$**^L$, $*^L$—$OC_3H_6$—$**^L$, $*^L$—$OC_4H_8$—$**^L$, $*^L$—$OC_5H_{10}$$**^L$, $*^L$$CH_2O$—$**^L$, $*^L$—$C_2H_4O$—$**^L$, $*^L$—$C_3H_6O$—$**^L$, $*^L$—$C_4H_6O$—$**^L$, $*^L$—$C_5H_{10}$—$**^L$, $*^L$—CONH—$**^L$, $*^L$—NHCO—$**^L$, $*^L$—$CONHCH_2$—$**^L$, $*^L$—$CONHC_2H_4$—$**^L$, $*^L$—$CONHC_3H_6$—$**^L$, $*^L$—$CONHC_4H_8$—$**^L$, $*^L$—$CONHC_5H_{10}$$**^L$,

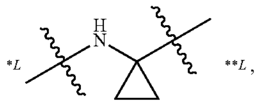 [SMILES: *NC1(*)CC1]

3- to 8-membered -heterocyclene- or 5- to 6-membered -heteroarylene-; wherein each of said —$CH_2$—, —$C_2H_4$—, —$C_3H_6$—, —$C_4H_8$—, —$C_5H_{10}$—, —O—, —NH—, $*^L$—$NHCH_2$—$**^L$, $*^L$—$NHC_2H_4$—$**^L$, $*^L$—$NHC_3H_6$—$**^L$, $*^L$—$NHC_4H_8$—$**^L$, $*^L$—$NHC_5H_{10}$—$**^L$, $*^L$—$OC_2$—$**^L$, $*^L$—$OC_2H_4$—$**^L$, $*^L$—$OC_3H_6$—$**^L$, $*^L$—$OC_4H_8$—$**^L$, $*^L$—$OC_5H_{10}$$**^L$, $*^L$$CH_2O$—$**^L$, $*^L$—$C_2H_4O$—$**^L$, $*^L$—$C_3H_6O$—$**^L$, $*^L$—$C_4H_8O$—$**^L$, $*^L$—$C_5H_{10}O$—$**^L$, $*^L$—CONH—$**^L$, $*^L$—NHCO—$**^L$, $*^L$—$CONHCH_2$—$**^L$, $*^L$—$CONHC_2H_4$—$**^L$, $*^L$—$CONHC_3H_6$—$**^L$, $*^L$—$CONHC_4H_8$—$**^L$, $*^L$—$CONHC_5H_{10}$—$**^L$,

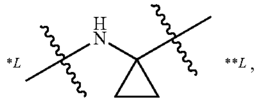 [SMILES: *NC1(*)CC1]

3- to 8-membered -heterocyclene- and 5- to 6-membered -heteroarylene- is optionally substituted with at least one substituent $R^L$; wherein $R^L$ is defined as above.

Aspect 10. The compound according to any one of Aspects 1-9, wherein L is a bond, —O—, $*^L$—$OCH_2$—$**^L$, $*^L$—$CH_2O$—$**^L$, —NH—, $*^L$—CONH—$**^L$, $*^L$—NHCO—$**^L$, $*^L$—$CONHCH_2$—$**^L$, $*^L$—$CONHCH_2CH_2$—$**^L$, $*^L$—$CONHCH_2CH_2CH_2$—$**^L$, $*^L$—$CONHCH(CH_3)$—$**^L$, $*^L$—$CONHCH(C_2H_5)$—$**^L$, $*^L$—$NHCH_2$—$**^L$, $*^L$—$NHCH_2CH_2$—$**^L$, $*^L$—$NHCH_2CH_2CH_2$—$**^L$, $*^L$—$NHCH(CH_3)$—$**^L$, $*^L$—$NHCH(C_2H_5)$—$**^L$,

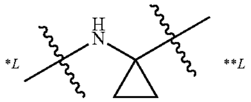

or

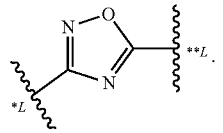

Aspect 11. The compound according to any one of Aspects 1-10, wherein L is $*^L$—$N(R^4)CO$—$**^L$, $R^3$ and $R^4$, together with the atoms to which they are attached, form a 5-, 6- or 7-membered ring, said ring comprising 0, 1 or 2 additional heteroatoms independently selected from nitrogen, oxygen or optionally oxidized sulfur as ring member(s), said ring is optionally substituted with at least one substituent independently selected from —F, —Cl, —Br, —I, —$CH_3$, —$C_2H_5$, —$C_3H_7$, —$C_4H_9$, —$C_5H_{11}$, cycloalkyl, heterocyclyl, aryl, heteroaryl, or oxo.

Aspect 12. The compound according to any one of Aspects 1-11, wherein the

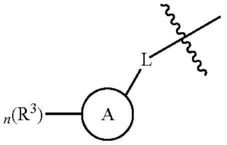

moiety is

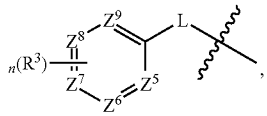

,

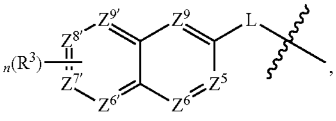

,

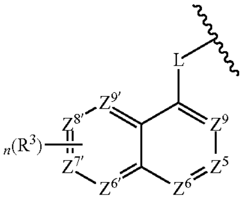

,

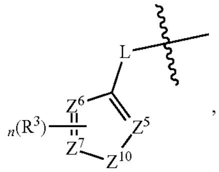

,

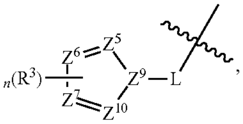

,

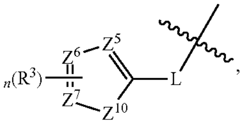

,

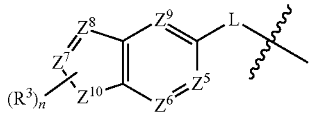

or

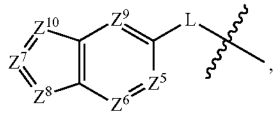

, wherein $Z^5$, $Z^6$, $Z^7$, $Z^8$, $Z^9$, $Z^{6'}$, $Z^{7'}$, $Z^{8'}$ and $Z^{9'}$ are each independently N or C(H); $Z^{10}$ is N(H), O or S.

Aspect 13. The compound according to any one of Aspects 1-12, wherein ring A is a 5- to 6-membered aromatic ring comprising 0-3 heteroatoms selected from nitrogen, sulfur and oxygen as ring member(s).

Aspect 14. The compound according to any one of Aspects 1-12, wherein ring A is phenyl, naphthalenyl, quinoxalinyl, pyridinyl, pyridazinyl, pyrimidinyl, imidazolyl, thiazolyl, oxazolyl, oxadiazole, pyridyl, pyrazinyl, pyridazinyl, pyrrolyl, imidazolyl, pyrazolyl, triazolyl, furanyl, pyrimidinyl, pyrazinyl or pyrrolopyridinyl.

Aspect 15. The compound according to any one of Aspects 1-14, wherein the

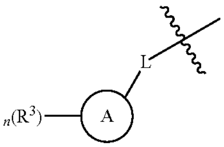

moiety is

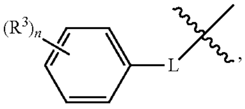,
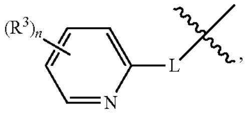,
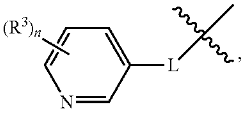,
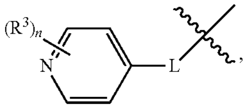,
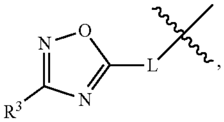,
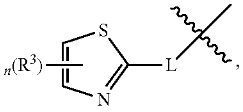,
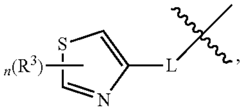,
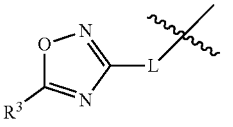,
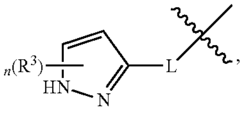,
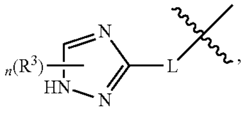,
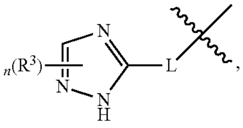,
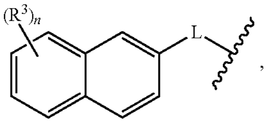,
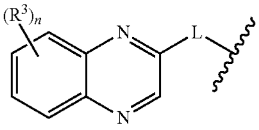,
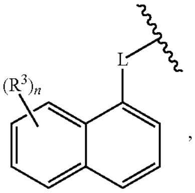,
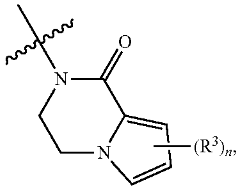,
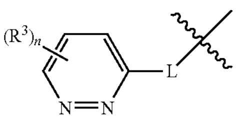, -continued

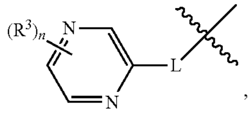,
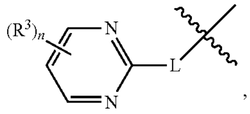,
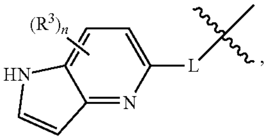,
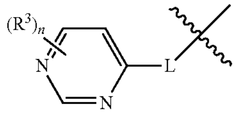,
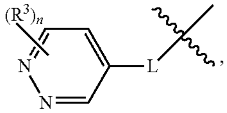,
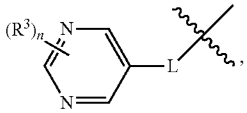,
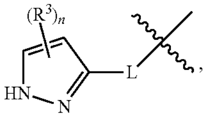,
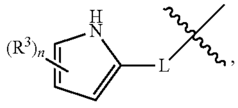,
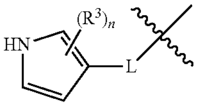
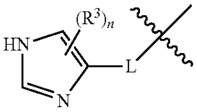
or
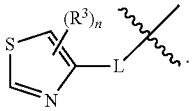.

Aspect 16. The compound according to any one of Aspects 1-15, wherein $R^3$ is hydrogen, —F, —Cl, —Br, —I, $—CH_3$, $—C_2H_5$, $—C_3H_7$, $—C_4H_9$, $—C_5H_{11}$, $—OCH_3$, $—OC_2H_5$, $—OC_3H_7$, $—OC_4H_9$, $—OC_5H_{11}$, cyclopropyl, cyclobutyl, cyclopentyl, tetrahydropyrrolyl or phenyl, wherein each of said $—CH_3$, $—C_2H_5$, $—C_3H_7$, $—C_4H_9$, $—C_5H_{11}$, $—OCH_3$, $—OC_2H_5$, $—OC_3H_7$, $—OC_4H_9$, $—OC_5H_{11}$, cyclopropyl, cyclobutyl, cyclopentyl, tetrahydropyrrolyl or phenyl is optionally substituted with at least one —F, —Cl, —Br, —I, $—CH_3$, $—C_2H_5$, $—C_3H_7$, $—C_4H_9$, $—C_5H_{11}$, $—OCH_3$, $—OC_2H_5$, $—OC_3H_7$, $—OC_4H_9$, $—OC_5H_{11}$, —OH, cyclopropyl, cyclobutyl or cyclopentyl.

Aspect 17. The compound according to any one of Aspects 1-16, wherein $R^3$ is hydrogen, —F, —Cl, —Br, —I, methyl, ethyl, n-propyl, iso-propyl, n-butyl, iso-butyl, sec-butyl, tert-butyl, trifluoromethyl, difluoromethyl, fluoromethyl, —OMe, —OEt, —OPr, —OBu, cyclopropyl, cyclobutyl, tetrahydropyrrolyl or phenyl.

Aspect 18. The compound according to any one of Aspects 1-17, wherein two $R^3$, together with the atoms to which they are attached, form a 4-, 5-, 6-, 7- or 8-membered ring, said ring comprising 0, 1 or 2 additional heteroatoms independently selected from nitrogen, oxygen or optionally oxidized sulfur as ring member(s), said ring is optionally substituted with at least one substituent independently selected from —F, —Cl, —Br, —I, $—CH_3$, $—C_2H_5$, $—C_3H_7$, $—C_4H_9$, $—C_5H_{11}$, $—OCH_3$, $—OC_2H_5$, $—OC_3H_7$, $—OC_4H_9$, $—OC_5H_{11}$, —OH, —CN, cyclopropyl, cyclobutyl or cyclopentyl.

Aspect 19. The compound according to any one of Aspects 1-18, wherein

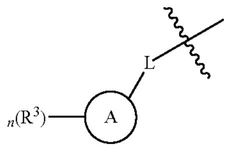
moiety is
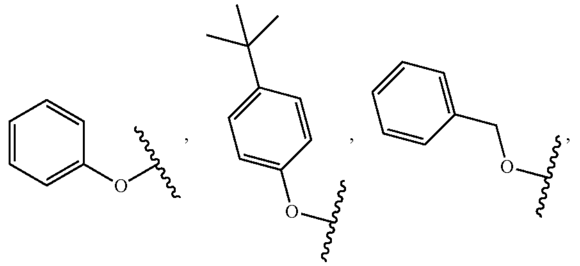
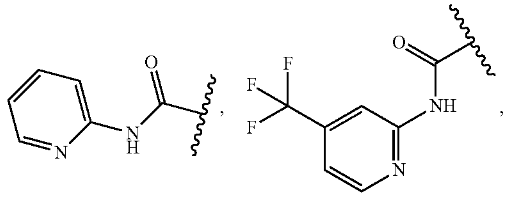
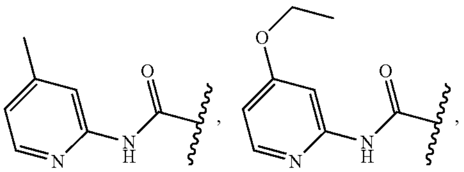
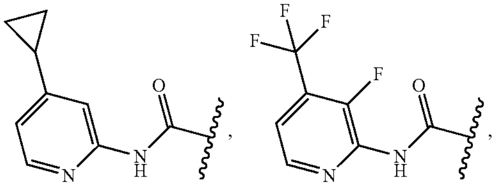
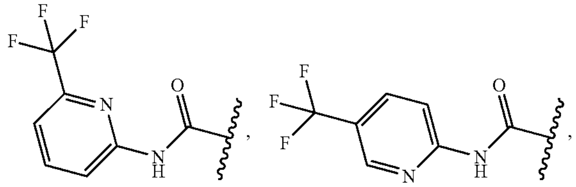
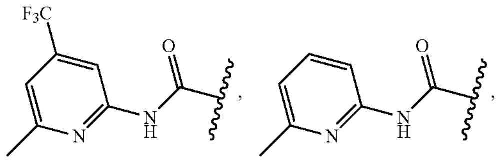
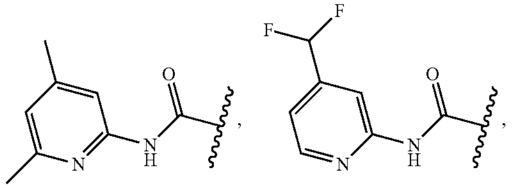
-continued
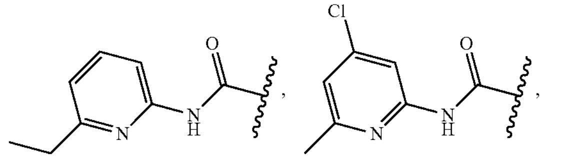
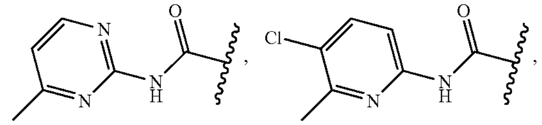
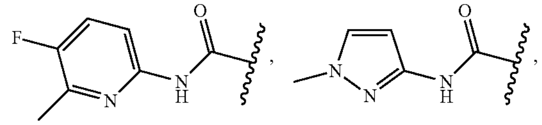
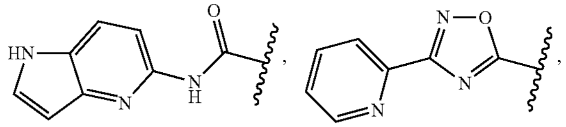
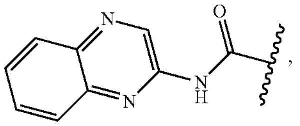
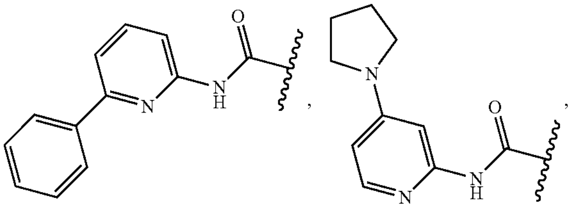
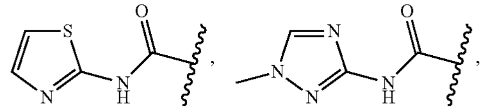
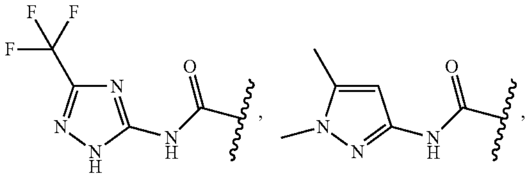
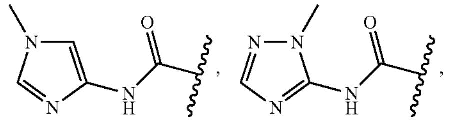
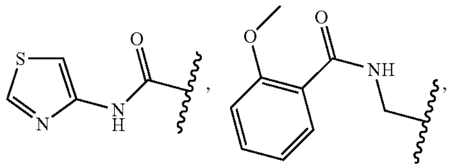
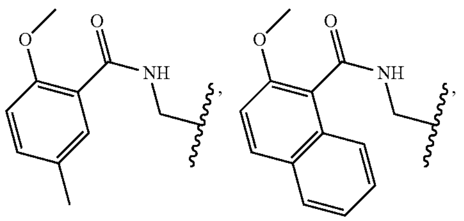

-continued
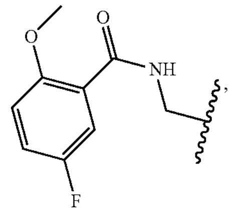,
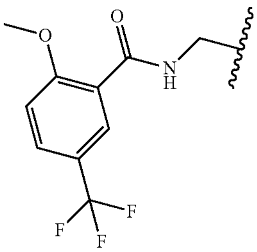,
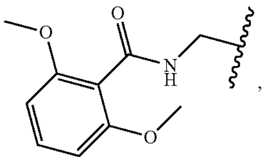,
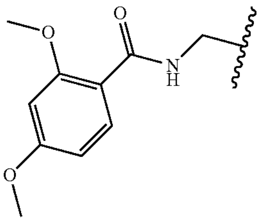,
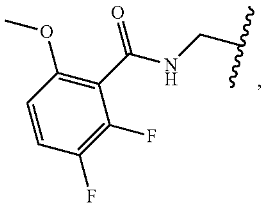,
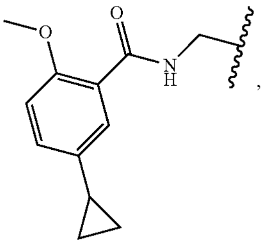,
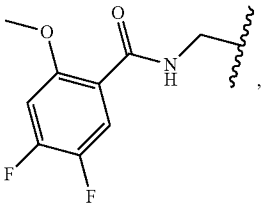,
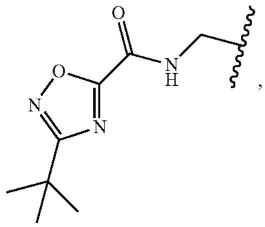,
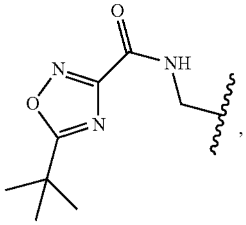,
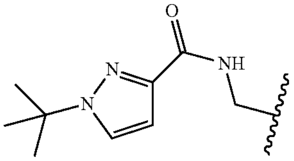,
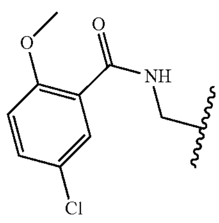,
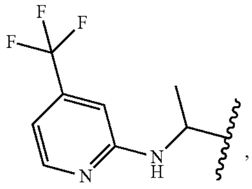,
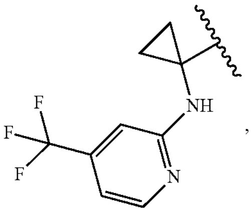,
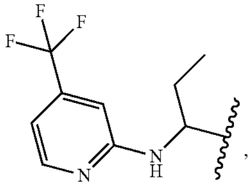,
-continued
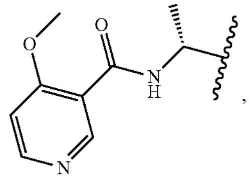,
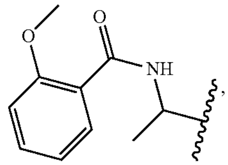,
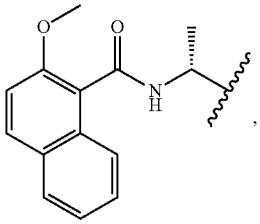,
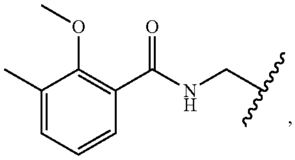,
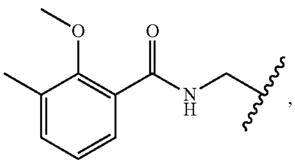,
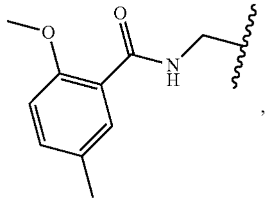,
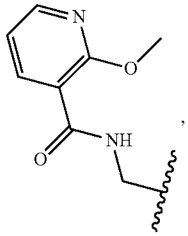,
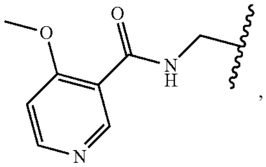,
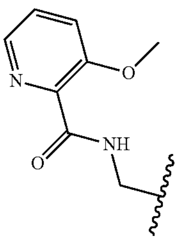,
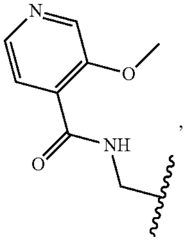,
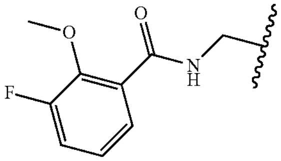,
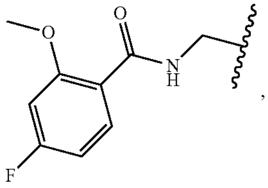,
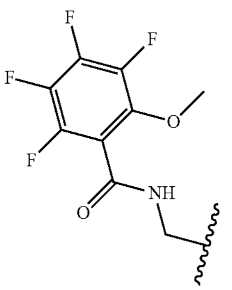
or
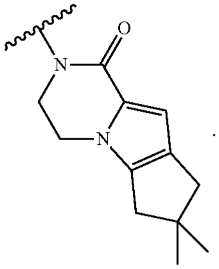.
Aspect 20. The compound according to any one of Aspects 1-19, wherein the

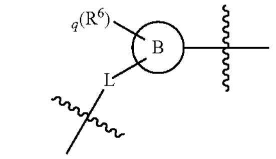

moiety is

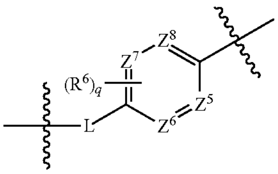

or

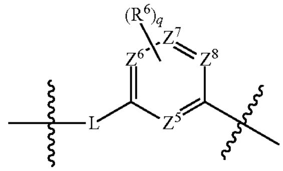

, wherein $Z^5$, $Z^6$, $Z^7$ and $Z^8$ are defined as above.

Aspect 21. The compound according to any one of Aspects 1-20, wherein the

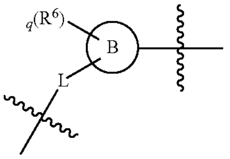

moiety is

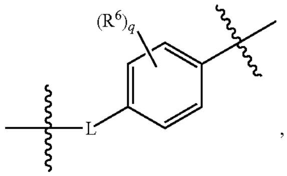

,

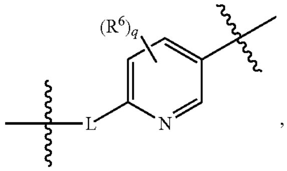

,

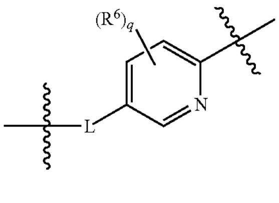

or

-continued

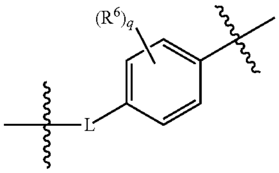

.

Aspect 22. The compound according to any one of Aspects 1-21, wherein ring B is phenyl, pyridinyl, imidazolyl, thiazolyl, oxazolyl, pyridyl, pyrimidinyl, pyrazinyl, pyridazinyl, pyrrolyl, imidazolyl, pyrazolyl, thiazolyl, oxazolyl, triazolyl, thiophenyl, furanyl, pyrimidinyl or pyrazinyl, each of which is optionally substituted with $(R^6)_q$.

Aspect 23. The compound according to any one of Aspects 1-22, wherein $R^6$ is hydrogen, —F, —Cl, —Br, —I, $—CH_3$, $—C_2H_5$, $—C_3H_7$, $—C_4H_9$, $—C_5H_{11}$, —CN, $—OCH_3$, $—OC_2H_5$, $—OC_3H_7$, $—OC_4H_9$ or $—OC_5H_{11}$, wherein each of said $—CH_3$, $—C_2H_5$, $—C_3H_7$, $—C_4H_9$, $—C_5H_{11}$, $—OCH_3$, $—OC_2H_5$, $—OC_3H_7$, $—OC_4H_9$ or $—OC_5H_{11}$ is optionally substituted with —F, —Cl, —Br, —I, hydroxy, $—C_{1-8}$alkyoxy, cycloalkyl, heterocyclyl, aryl, or heteroaryl.

Aspect 24. The compound according to any one of Aspects 1-23, wherein

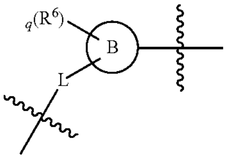

moiety is

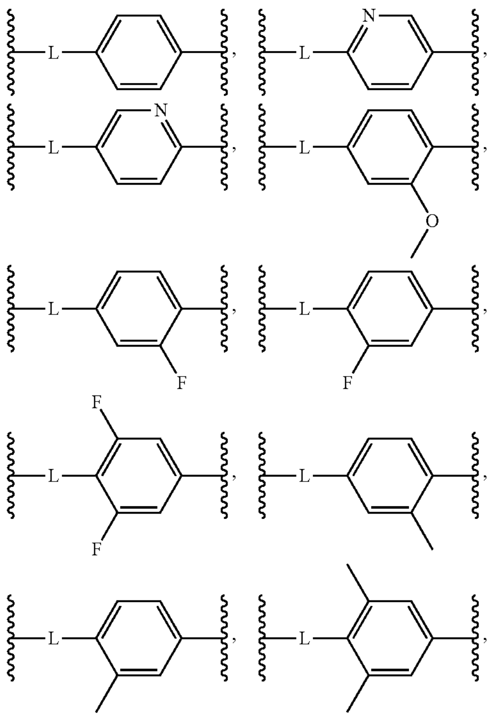

-continued

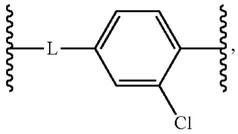, 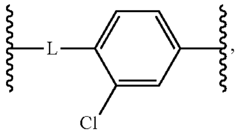,

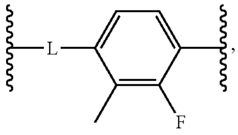, 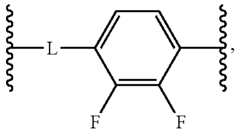,

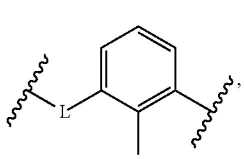, 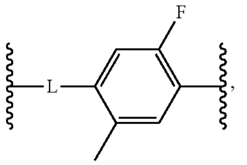,

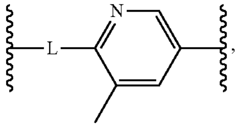, 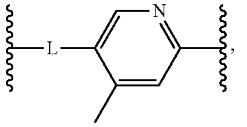,

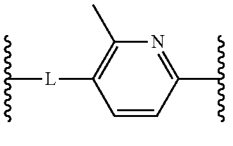 or 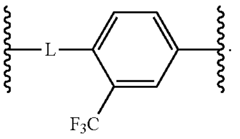.

Aspect 25. The compound according to any one of Aspects 1-24, wherein

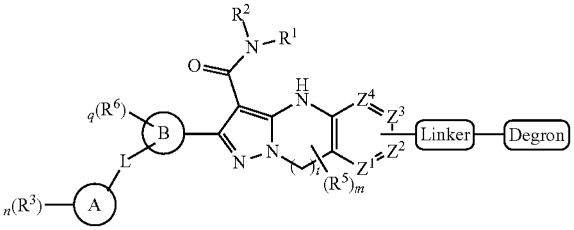

is

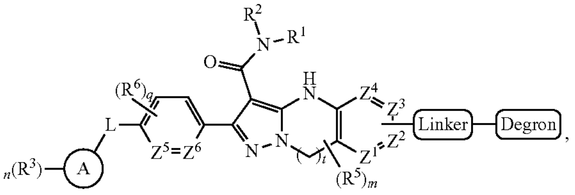, preferably is

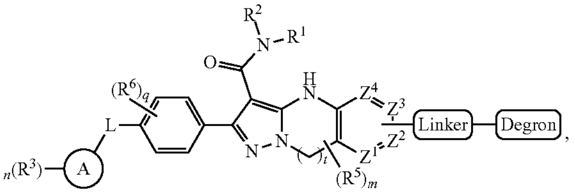,

-continued

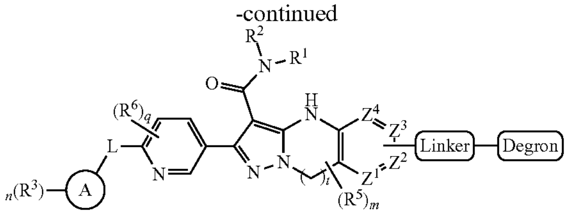

or

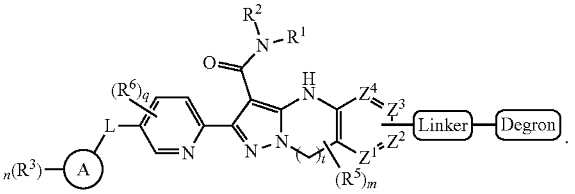.

Aspect 26. The compound according to any one of Aspects 1-25, wherein $R^1$ and $R^2$ are each independently hydrogen, —$CH_3$, —$C_2H_5$, —$C_3H_7$, —$C_4H_9$, —$C_5H_{11}$, —$C_{2-8}$alkenyl, —$C_{2-8}$alkynyl or aryl.

Aspect 27. The compound according to any one of Aspects 1-26, wherein $R^1$ and $R^2$ are both H.

Aspect 28. The compound according to any one of Aspects 1-27, wherein $R^5$ is independently hydrogen, —F, —Cl, —Br, —I, —$CH_3$, —$C_2H_5$, —$C_3H_7$, —$C_4H_9$, —$C_5H_{11}$, —$C_{2-8}$alkenyl, —$C_{2-8}$alkynyl or aryl.

Aspect 29. The compound according to any one of Aspects 1-28, wherein $R^z$ is independently the bond between

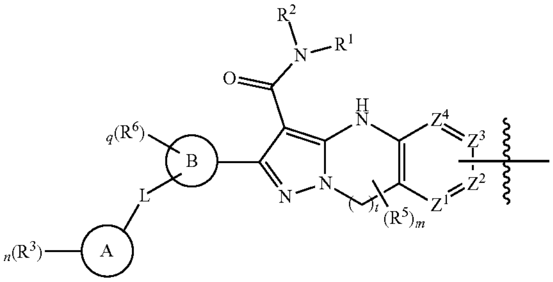

moiety and

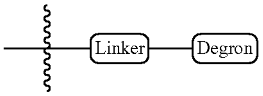

moiety, hydrogen, —F, —Cl, —Br, —I, —$CH_3$, —$C_2H_5$, —$C_3H_7$, —$C_4H_9$ or —$C_5H_{11}$.

Aspect 30. The compound according to any one of Aspects 1-29, wherein

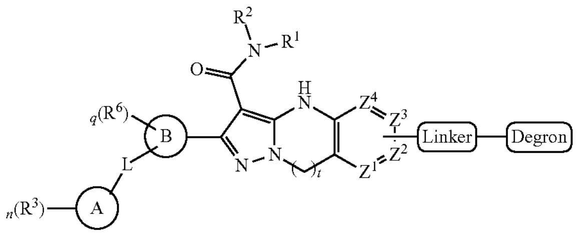

-continued
is
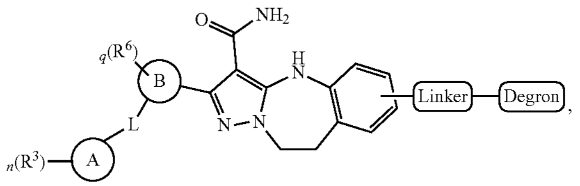
preferably
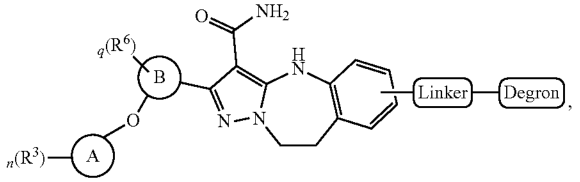
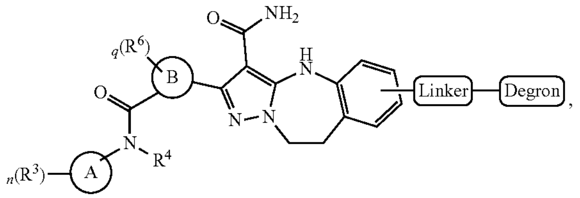
or
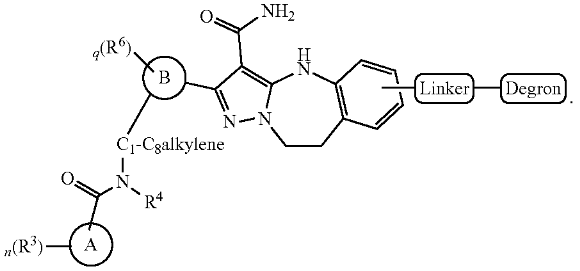
Aspect 31. The compound according to any one of Aspects 1-30, wherein the
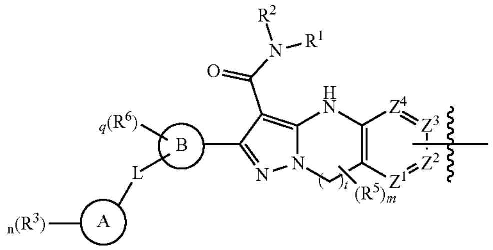
moiety is
-continued
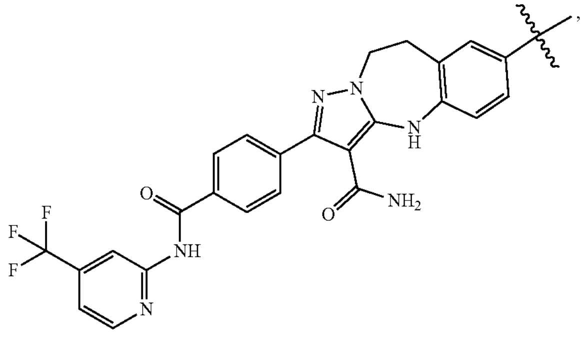
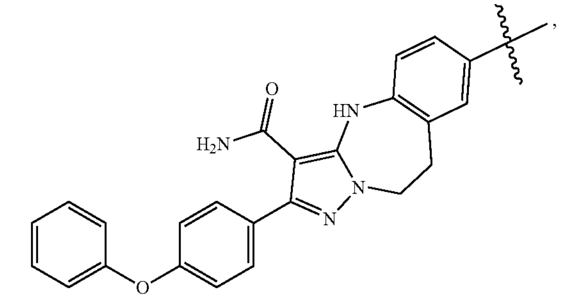
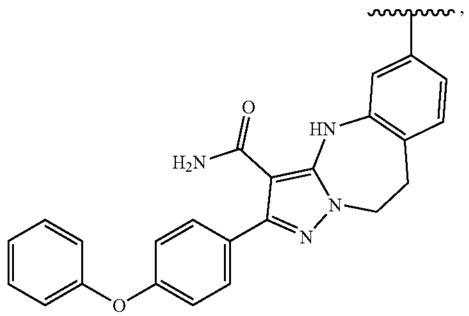
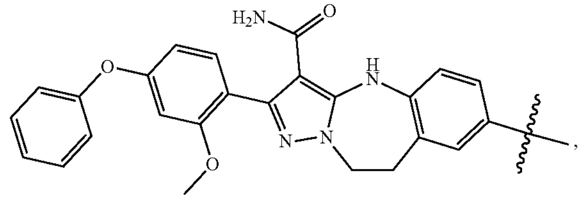
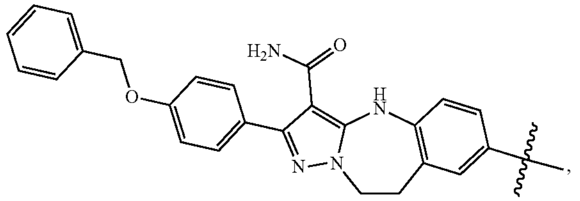
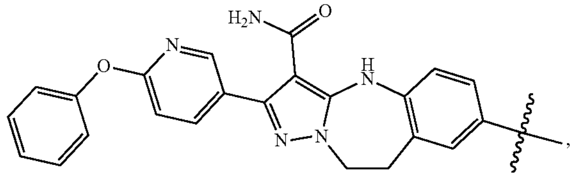
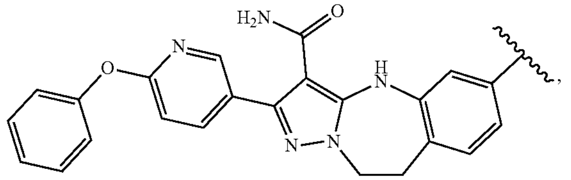

-continued
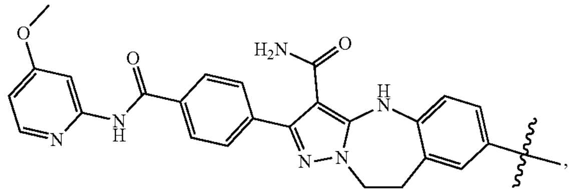
,
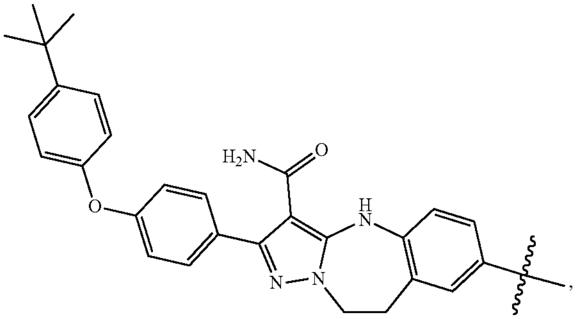
,
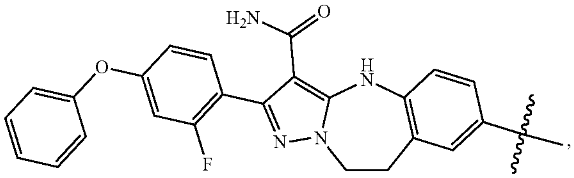
,
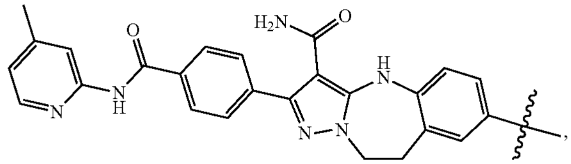
,
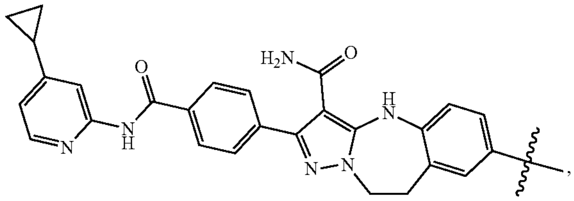
,
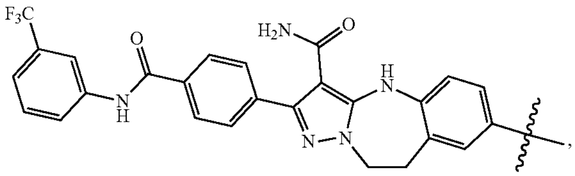
,
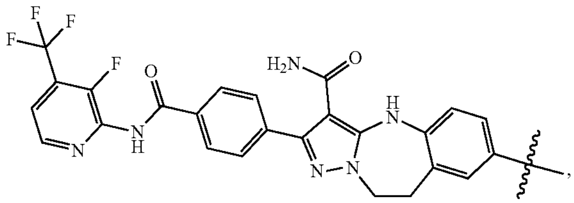
,
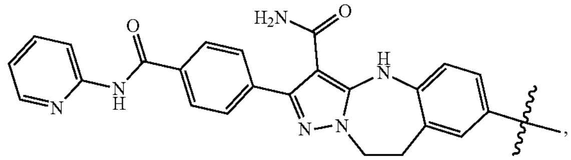
,
-continued
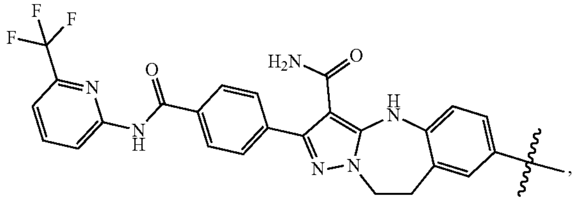
,
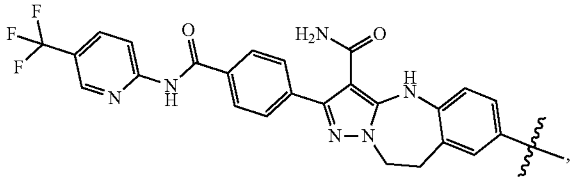
,
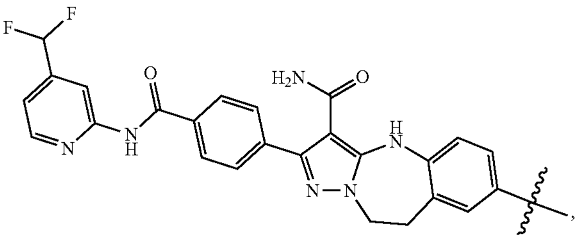
,
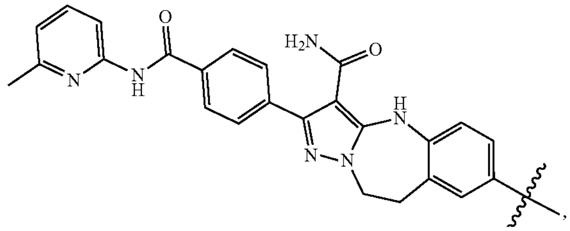
,
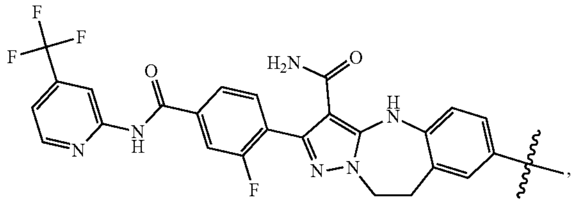
,
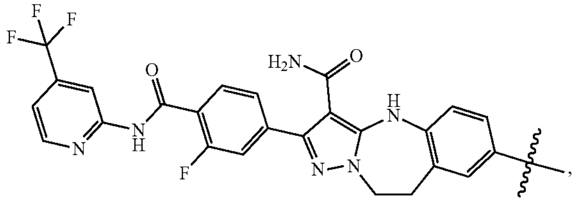
,
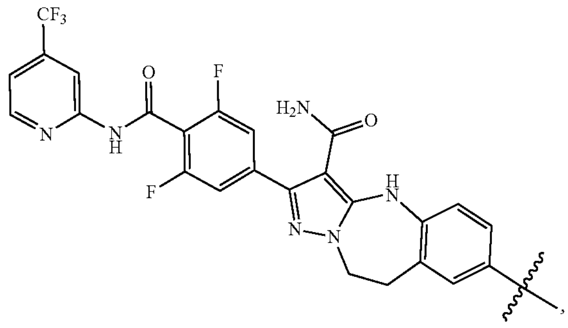
, -continued
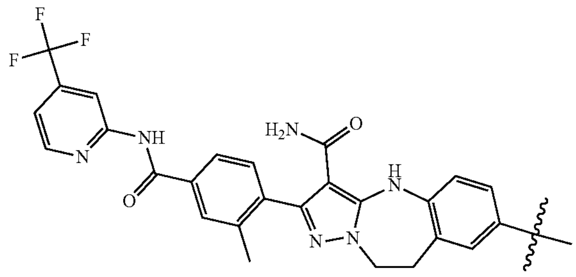,
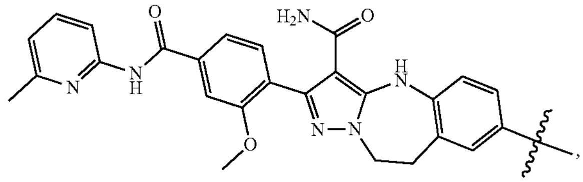,
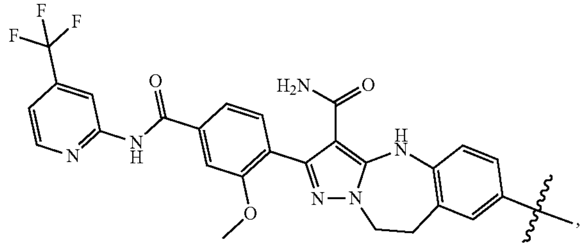,
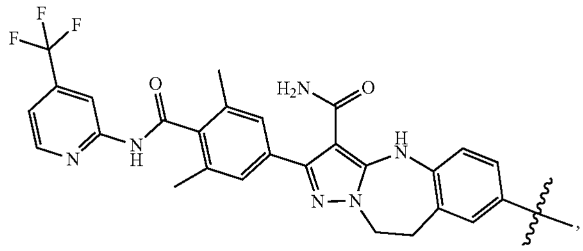,
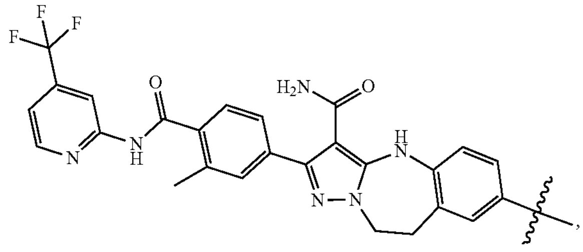,
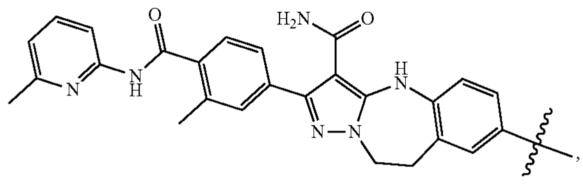,
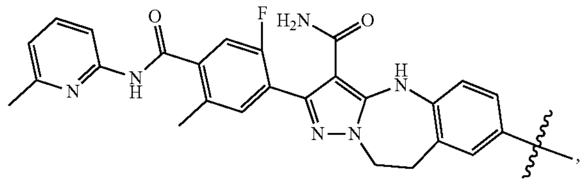,
-continued
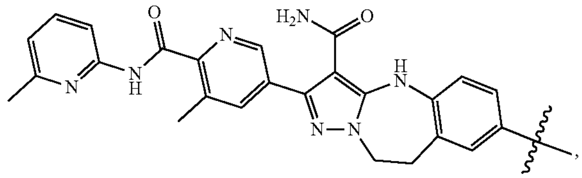,
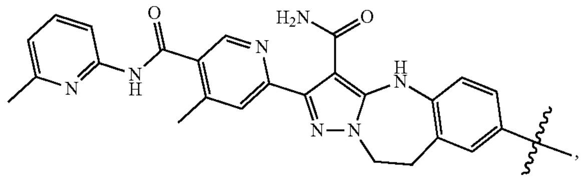,
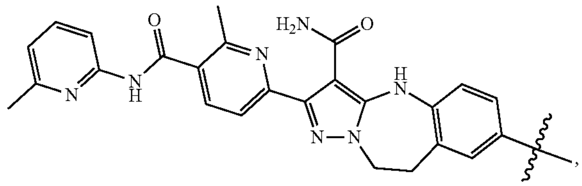,
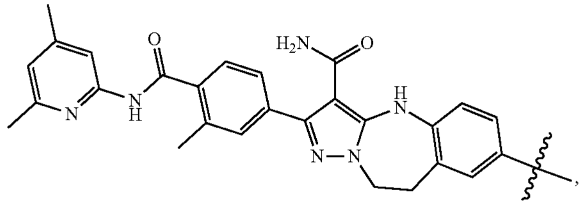,
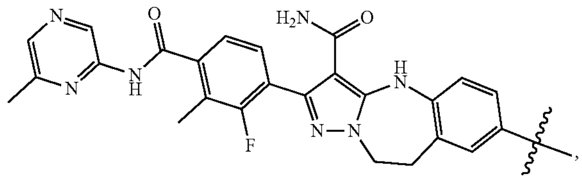,
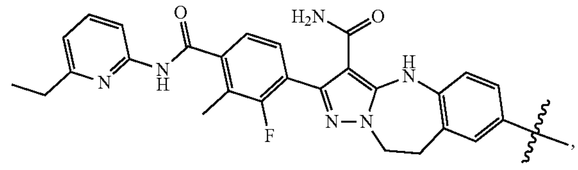,
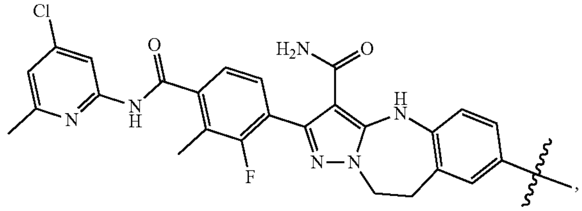,
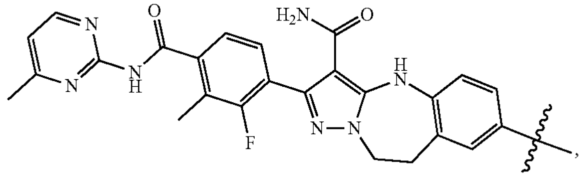,
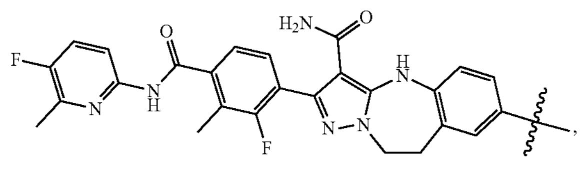, -continued
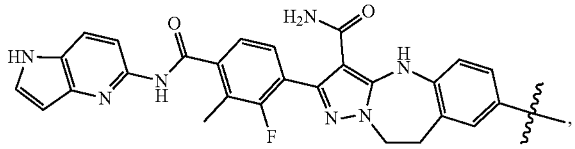
,
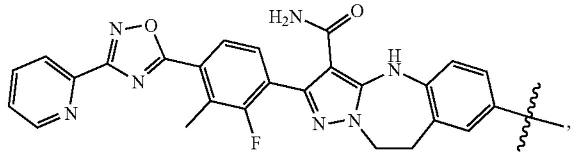
,
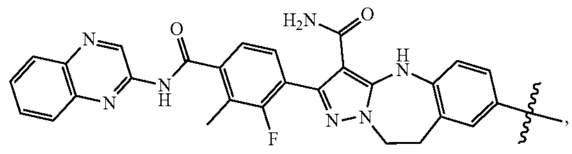
,
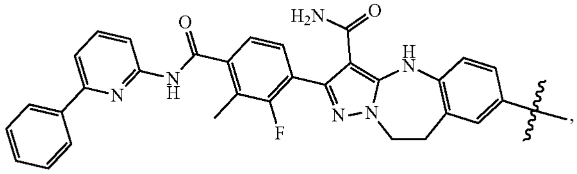
,
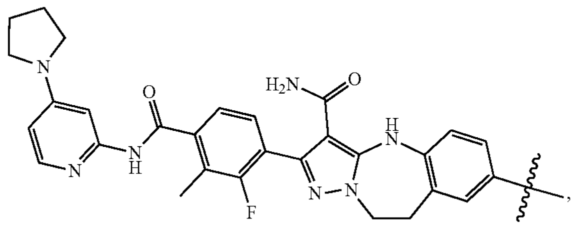
,
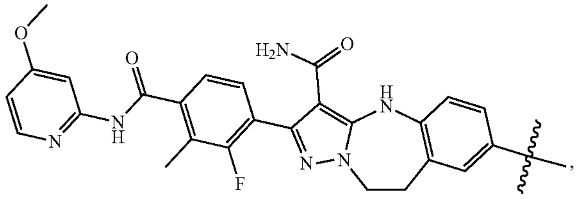
,
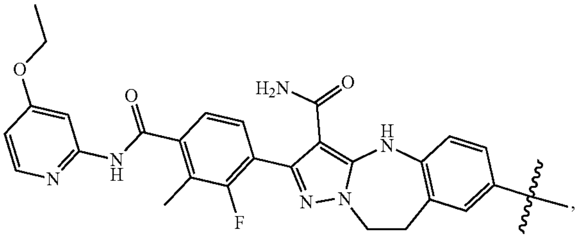
,
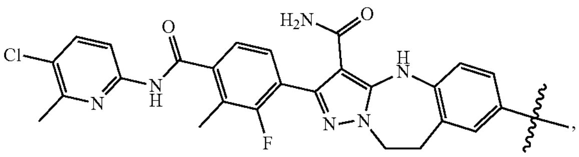
,
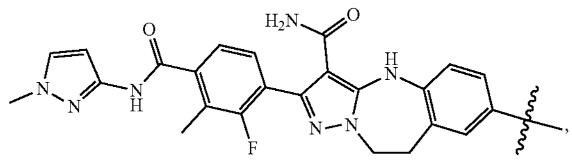
,
-continued
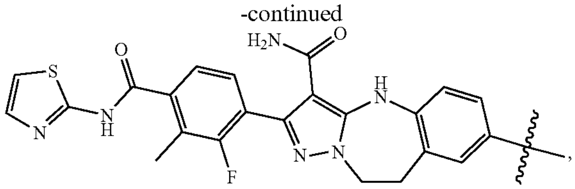
,
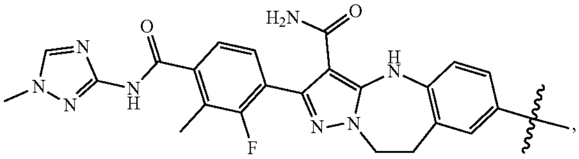
,
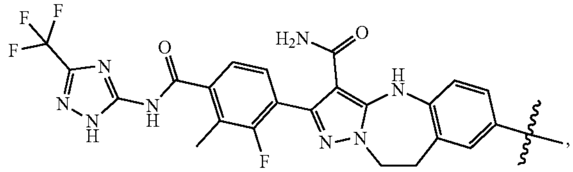
,
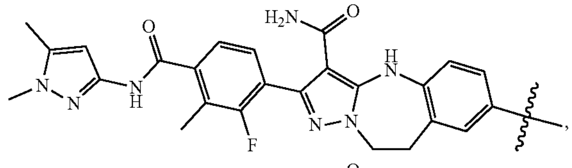
,
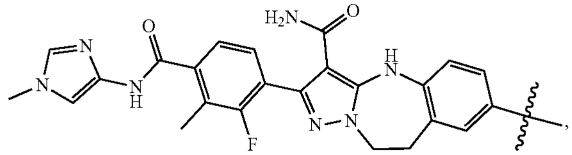
,
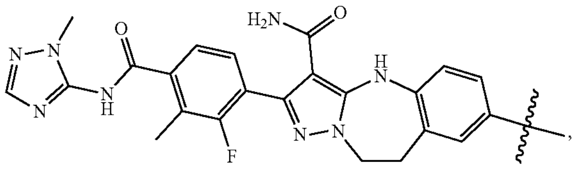
,
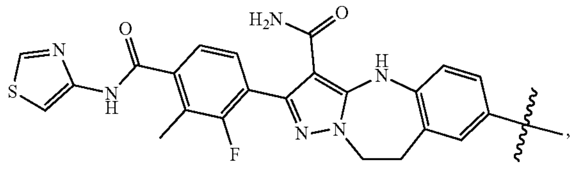
,
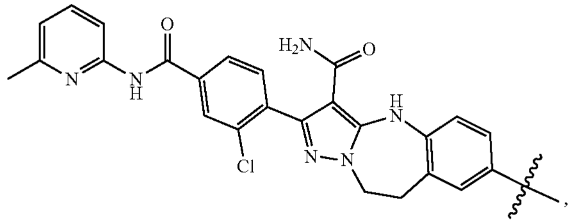
,
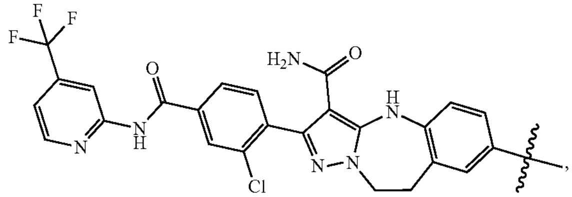
,
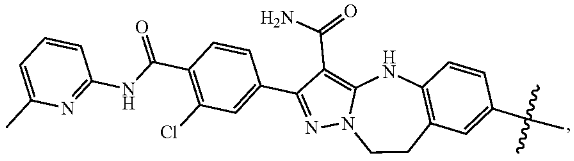
, -continued
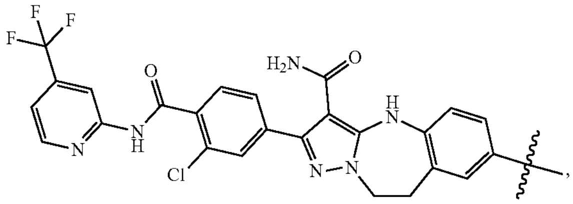,
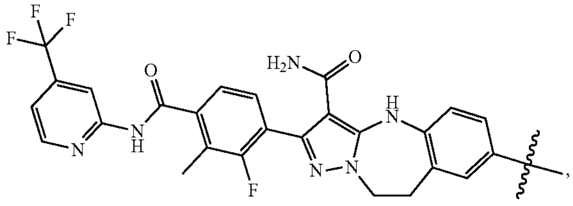,
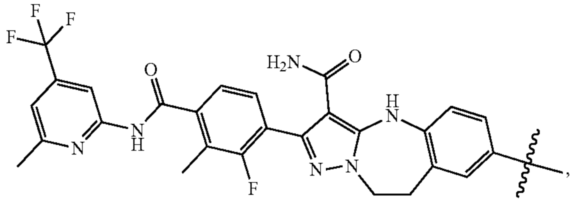,
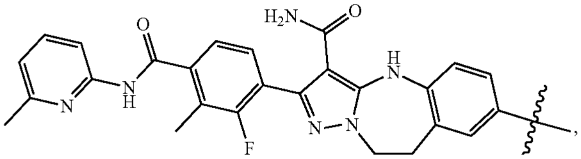,
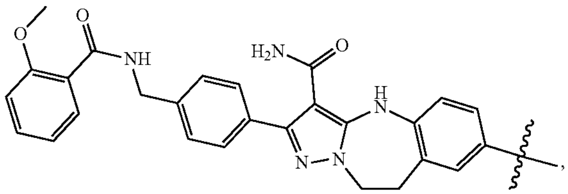,
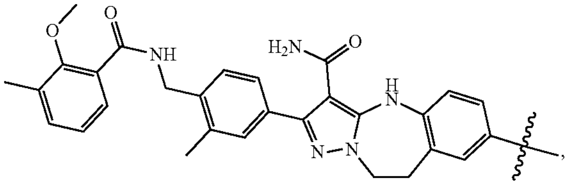,
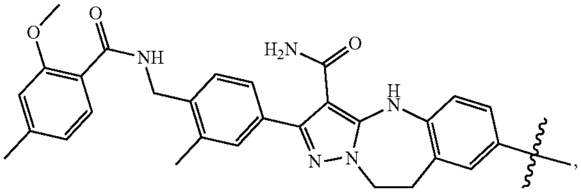,
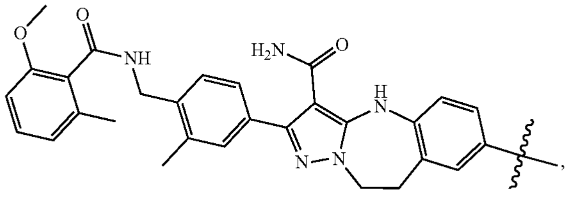,
-continued
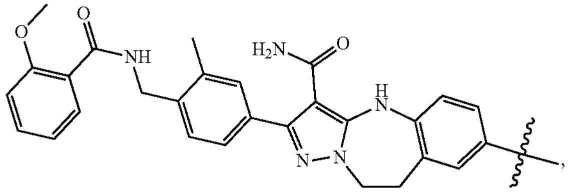,
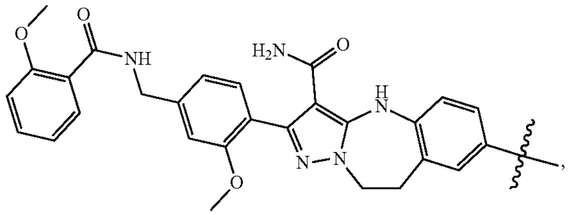,
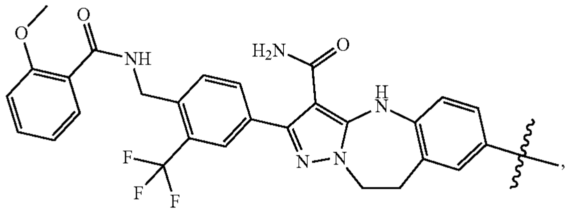,
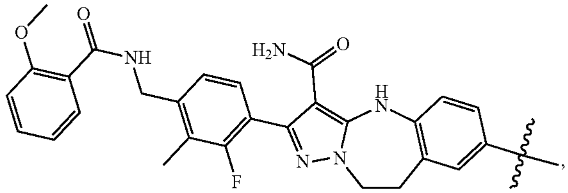,
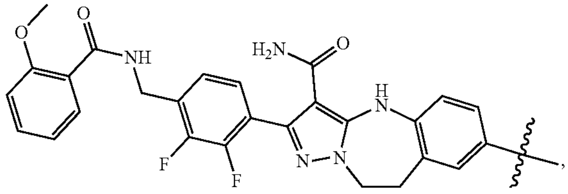,
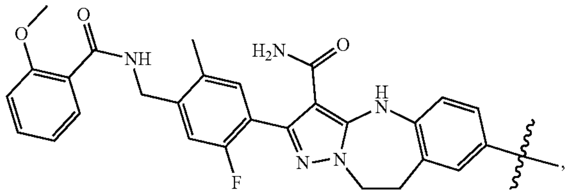,
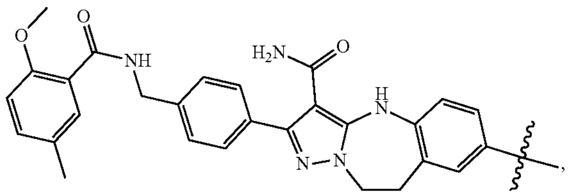,
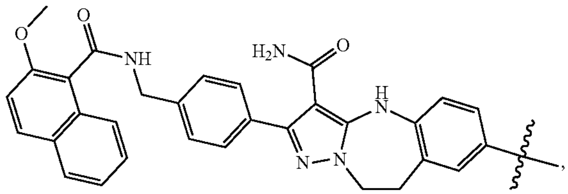, -continued
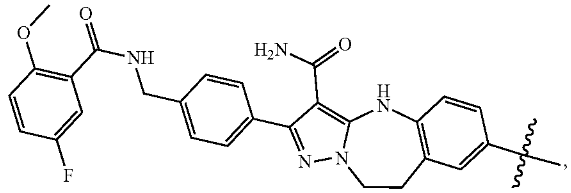,
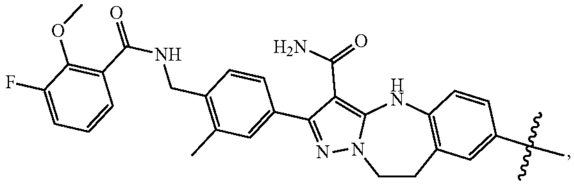,
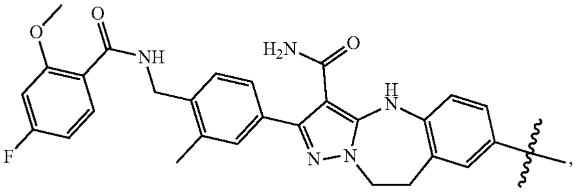,
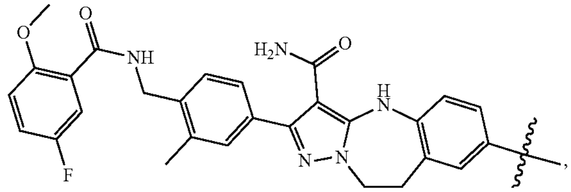,
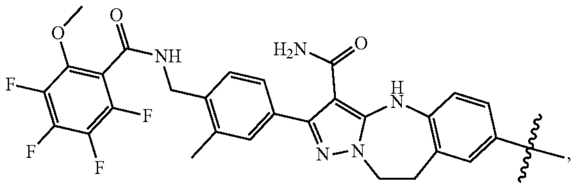,
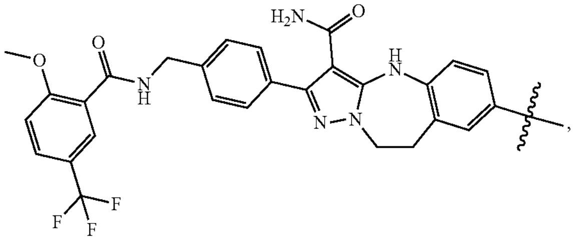,
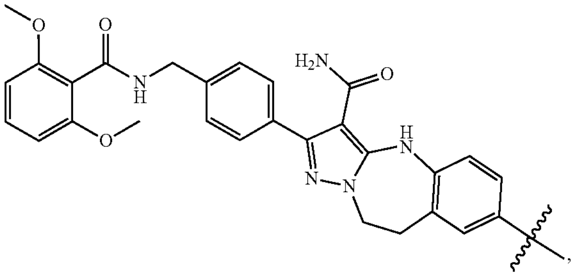,
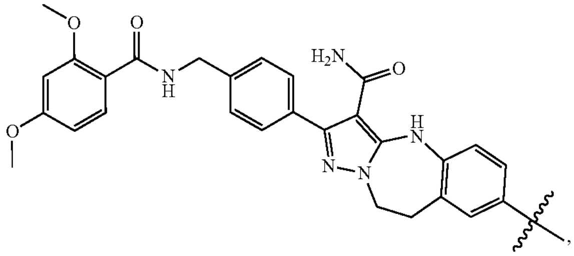,
-continued
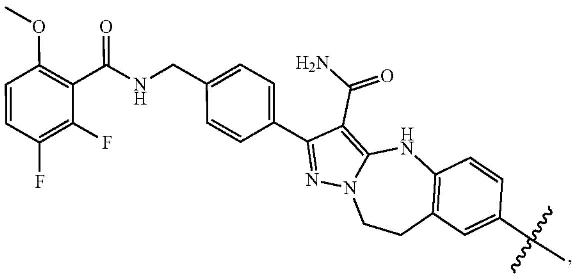,
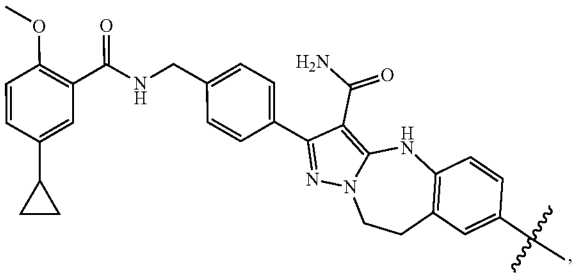,
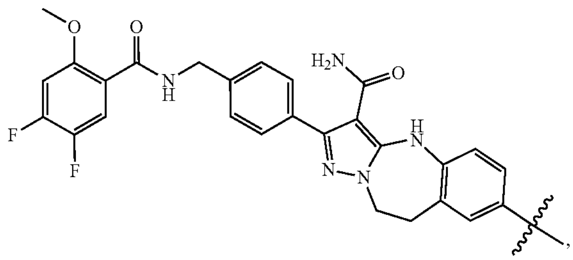,
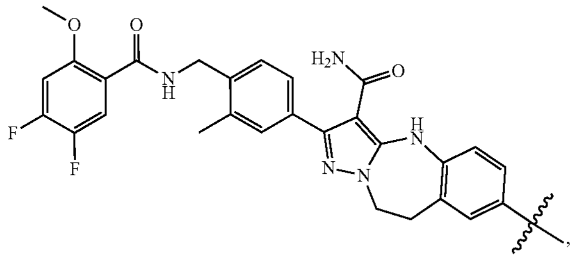,
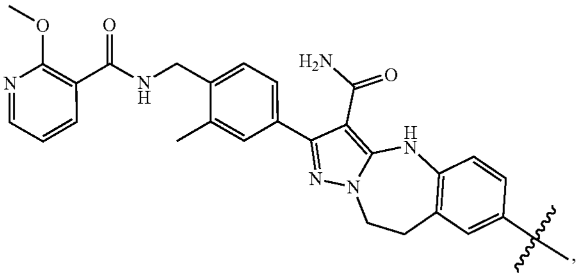,
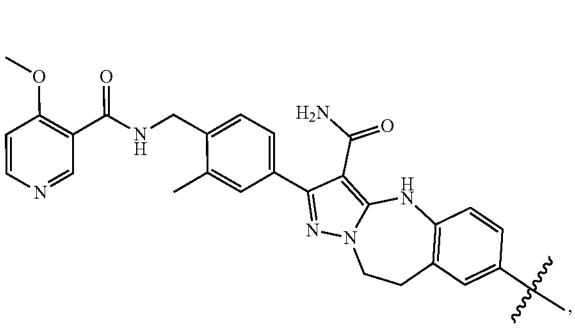, -continued
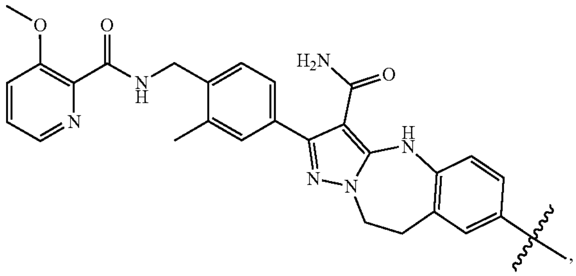
,
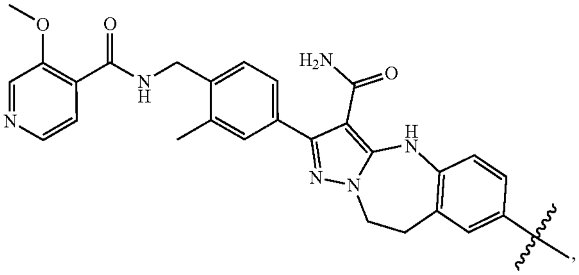
,
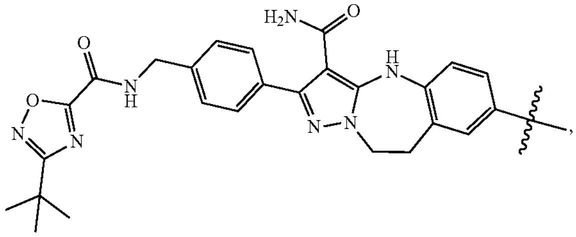
,
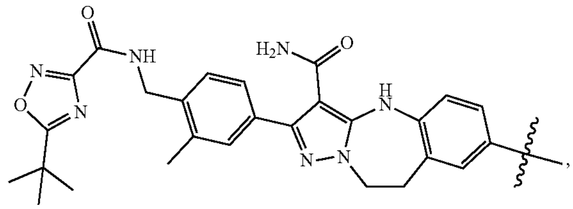
,
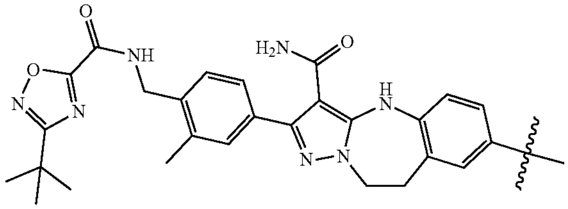
,
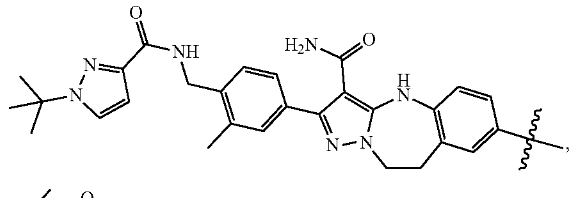
,
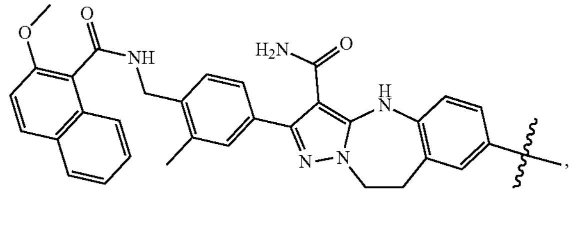
,
-continued
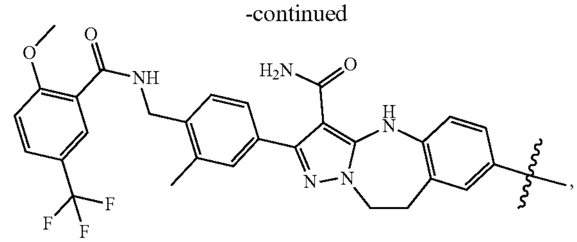
,
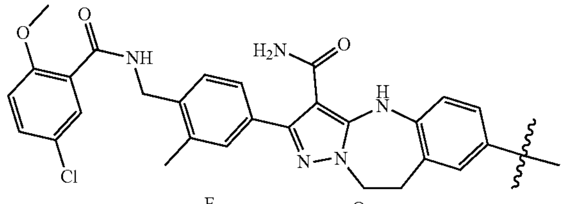
,
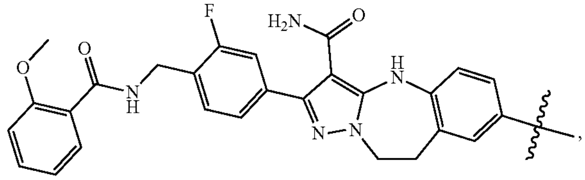
,
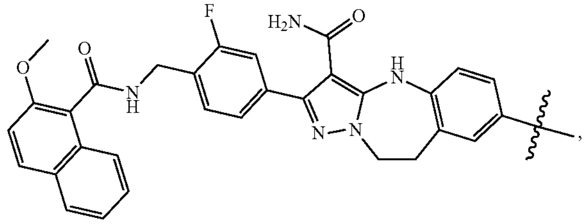
,
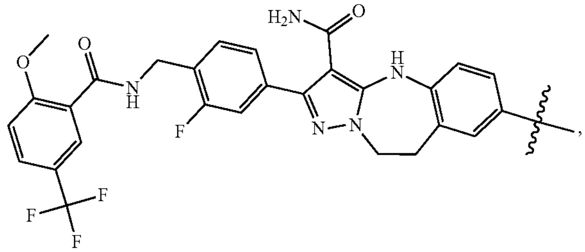
,
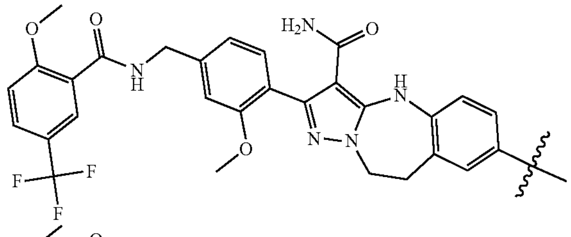
,
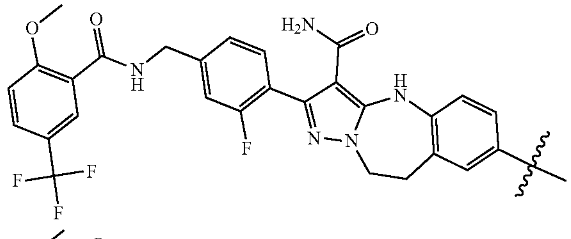
,
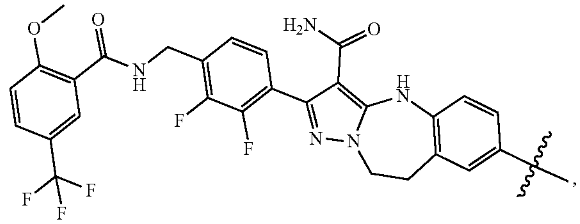
, -continued
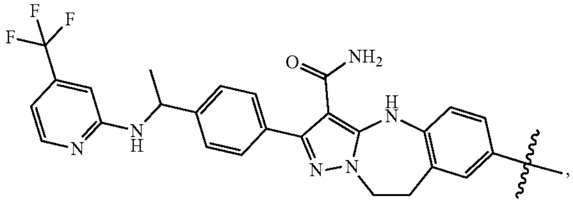
,
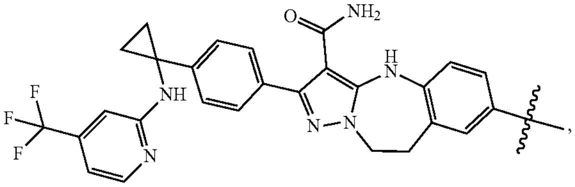
,
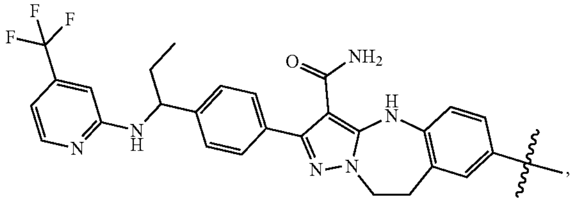
,
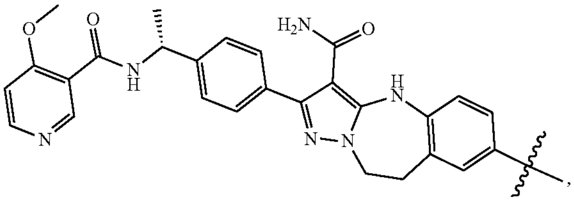
,
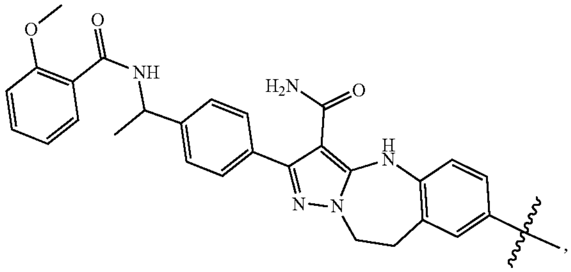
,
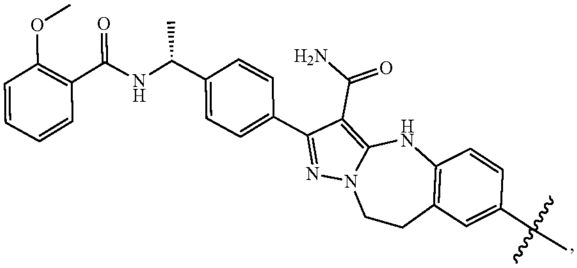
,
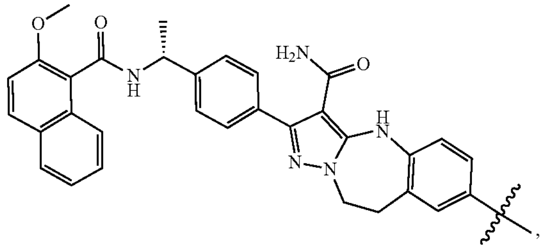
, or
-continued
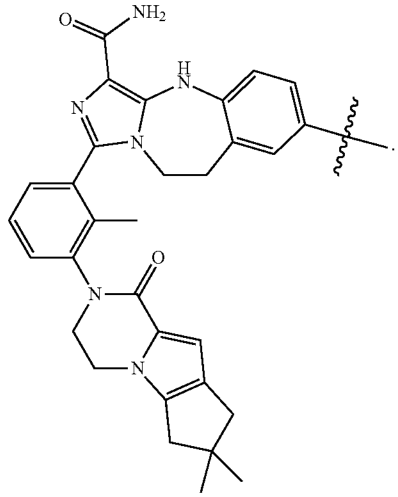
.
Aspect 32. The compound according to any one of Aspects 1-31, wherein the
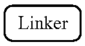
moiety is
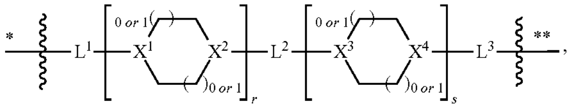
,
wherein * refers to the position attached to the
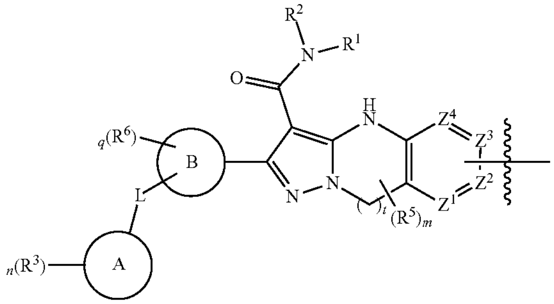
moiety, and ** refers to the position attached to the
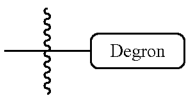

moiety;

$X^1$, $X^2$, $X^3$ and $X^4$ are each independently selected from CH or N;

r and s are each independently 0 or 1;

$L^1$ is a single bond, —O—, —$SO_2$—, —C(O)—, —$NR^{L1a}$—, —$C_3$-$C_8$cycloalkylene-, $*^{L1}$—O—$C_{1-8}$alkylene-$**^{L1}$, $*^{L1}$—$C_{1-8}$alkylene-O—$**^{L1}$, $*^{L1}$—$SO_2$—$C_{1-8}$alkylene-$**^{L1}$, $*^{L1}$—$C_{1-8}$alkylene-$SO_2$—$**^{L1}$, $*^{L1}$—C(O)—$C_{1-8}$alkylene-$**^{L1}$, $*^{L1}$—$C_{1-8}$alkylene-C(O)—$**^{L1}$, $*^{L1}$—$NR^{L1a}$—$C_{1-8}$alkylene-$**^{L1}$, $*^{L1}$—$C_{1-8}$ alkylene-$NR^{L1a}$—$**^{L}$, $*^{L}$—$NR^{L1a}$C(O)$**^{L1}$, $*^{L1}$—C(O)$NR^{L1a}$—$**^{L1}$, $*^{L1}$—$NR^{L1a}$C(O)$C_{1-8}$alkylene-$**^{L1}$, $*^{L1}$—C(O)$NR^{L1a}$—$C_{1-8}$alkylene-$**^{L1}$, $*^{L1}$—$C_{1-8}$alkylene$NR^{L1a}$C(O)—$**^{L1}$, $*^{L1}$—$C_{1-8}$alkyleneC(O)$NR^{L1a}$—$**^{L1}$, —$C_{1-8}$alkylene-, —$C_{2-8}$alkenylene-, —$C_{2-8}$alkynylene-, —$[O(CR^{L1a}R^{L1b})_{u1}]_{v1}$—;

each of said —$C_3$-$C_8$cycloalkylene-, $*^{L}$—O—$C_{1-8}$alkylene-$**^{L1}$, $*^{L1}$—$C_{1-8}$alkylene-O—$**^{L1}$, $*^{L1}$—$SO_2$—$C_{1-8}$alkylene-$**^{L}$, $*^{L}$—$C_{1-8}$alkylene-$SO_2$—$**^{L1}$, $*^{L1}$—C(O)—$C_{1-8}$alkylene-$**^{L1}$, $*^{L1}$—$C_{1-8}$alkylene-C(O)—$**^{L1}$, $*^{L1}$—$NR^{L1a}$—$C_{1-8}$alkylene-$**^{L1}$, $*^{L1}$—$C_{1-8}$alkylene-$NR^{L1a}$—$**^{L}$, $*^{L1}$—$NR^{L1a}$C(O)$C_{1-8}$alkylene-$**^{L1}$, $*^{L1}$—C(O)$NR^{L1a}C_{1-8}$alkylene-$**^{L1}$, $*^{L1}$—$C_{1-8}$alkylene$NR^{L1a}$C(O)—$**^{L1}$, $*^{L1}$—$C_{1-8}$alkyleneC(O)$NR^{L1a}$—$**^{L1}$, —$C_{1-8}$alkylene-, —$C_{2-8}$alkenylene- or —$C_{2-8}$alkynylene- are optionally substituted with at least one $R^{L1c}$;

u1 and v1 are each independently selected from 1, 2, 3, 4, 5, 6, 7 or 8;

wherein $*^{L1}$ refers to the position attached to the

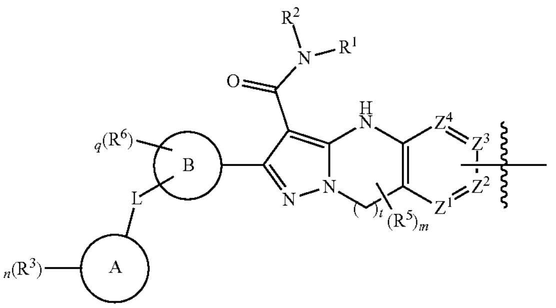

moiety and $**^{L1}$ refers to the position attached to the

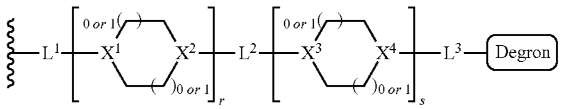

moiety;

$L^2$ is selected from a single bond, —O—, —$SO_2$—, —CO—, —$NR^{L2a}$—, —$C_3$-$C_8$cycloalkylene-, $*^{L}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$N^{RL2a}$—$C_{1-8}$alkylene-$**^{L2}$, $*^{L2}$—$C_{1-8}$alkylene-$NR^{L2a}$—$**^{L2}$, $*^{L2}$—$NR^{L2a}$C(O)—$**^{L2}$, $*^{L}$C(O)$NR^{L2a}$—$**^{L2}$, $*^{L}$—$NR^{L2a}$C(O)$C_{1-8}$alkylene-$**^{L}$, $*^{L2}$—C(O)$NR^{L2a}C_{1-8}$alkylene-$**^{L2}$, $*^{L2}$—$C_{1-8}$alkylene$NR^{L2a}$C(O)—$**^{L2}$, $*^{L}$—$C_{1-8}$alkyleneC(O)$NR^{L2a}$—$**^{L}$, —$C_{1-8}$alkylene-, —$C_{2-8}$alkenylene-, —$C_{2-8}$alkynylene- or —$[O(CR^{L2a}R^{L2b})_{u2}]_{v2}$—;

each of said —$C_3$-$C_8$cycloalkylene-, $*^{L}$—O—$C_{1-8}$alkylene-$**^{L2}$, $*^{L}$—$C_{1-8}$alkylene-O—$**^{L2}$, $*^{L}$—$SO_2$—$C_{1-8}$alkylene-$**^{L2}$, $*^{L}$—$C_{1-8}$alkylene-$SO_2$—$**^{L2}$, $*^{L}$—CO—$C_{1-8}$alkylene-$**^{L2}$, $*^{L}$—$C_{1-8}$alkylene-CO—$**^{L}$, $*^{L2}$—$NR^{L2a}$—$C_{1-8}$alkylene-$**^{L2}$, $*^{L2}$—$C_{1-8}$alkylene-$NR^{L2a}$—$**^{L2}$, $*^{L2}$—$NR^{L2a}$C(O)$C_{1-8}$alkylene-$**^{L2}$, $*^{L}$—C(O)$NR^{L2a}C_{1-8}$alkylene-$**^{L2}$, $*^{L2}$—$C_{1-8}$alkylene$NR^{L2a}$C(O)—$**^{L2}$, $*^{L2}$—$C_{1-8}$alkyleneC(O)$NR^{L2a}$—$**^{L}$, —$C_{1-8}$alkylene-, —$C_{2-8}$alkenylene- or —$C_{2-8}$alkynylene- are optionally substituted with at least one substituent $R^{L2c}$;

u2 and v2 are each independently selected from 1, 2, 3, 4, 5, 6, 7 or 8;

wherein $*^{L2}$ refers to the position attached to the

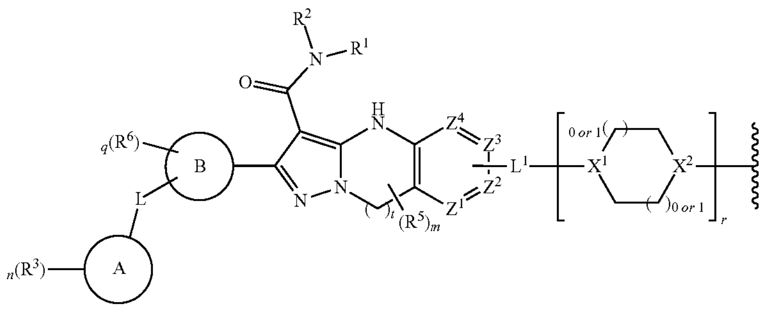

moiety, and $**^{L2}$ refers to the position attached to the

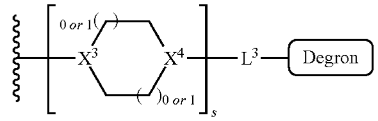

moiety;

$L_3$ is selected from a single bond, —O—, —$SO_2$—, —CO—, —$NR^{L3a}$—, —$C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$, $*^{L3}$—$NR^{L3a}$C(O)—$**^{L3}$, $*^{L3}$—C(O)$NR^{L3a}$—$**^{L3}$, $*^{L3}$—$NR^{L3a}$C(O)$C_{1-8}$alkylene-$**^{L3}$, $*^{L3}$—C(O)$NR^{L3a}C_{1-8}$alkylene-$**^{L3}$, $*^{L3}$—$C_{1-8}$alkylene$NR^{L3a}$C(O)—$**^{L3}$, $*^{L3}$—$C_{1-8}$alkyleneC(O)$NR^{L3a}$—$**^{L3}$, —$C_{1-8}$alkylene-, —$C_{2-8}$alkenylene-, —$C_{2-8}$alkynylene- or —[O$(CR^{L3a}R^{L3b})_{u3}]_{v3}$—; each of said —$C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$, $*^{L3}$—$NR^{L3a}$C(O)$C_{1-8}$alkylene-$**^{L3}$, $*^{L3}$—C(O)$NR^{L3a}C_{1-8}$alkylene-$**^{L3}$, $*^{L3}$—$C_{1-8}$ alkylene$NR^{L3a}$C(O)—$^{L3}$, $*^{L3}$—$C_{1-8}$alkyleneC(O) $NR^{L3a}$—$**^{L3}$, —$C_{1-8}$alkylene-, —$C_{2-8}$alkenylene-, —$C_{2-8}$alkynylene-, are optionally substituted with at least one substituent $R^{L3c}$;

u3 and v3 are each independently selected from 1, 2, 3, 4, 5, 6, 7 or 8;

wherein $*^{L3}$ refers to the position attached to the

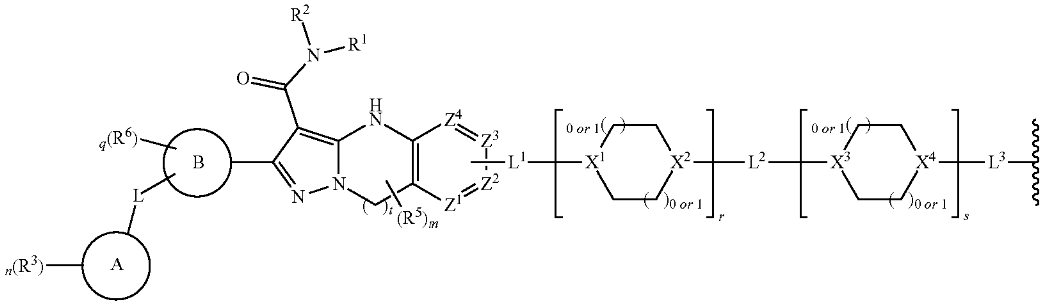

moiety, and $**^{L3}$ refers to the position attached to the

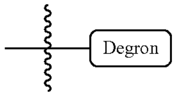

moiety;

$R^{L1a}$, $R^{L1b}$, $R^{L2a}$, $R^{L2b}$, $R^{L3a}$ and $R^{L3b}$ are each independently selected from hydrogen, —$C_{1-8}$alkyl, —$C_{2-8}$alkenyl, —$C_{2-8}$alkynyl, cycloalkyl, heterocyclyl, aryl or heteroaryl, wherein each of said —$C_{1-8}$alkyl, —$C_{2-8}$alkenyl, —$C_{2-8}$alkynyl, cycloalkyl, heterocyclyl, aryl or membered heteroaryl is optionally substituted with at least one substituent $R^{L3d}$; $R^{L3d}$ is halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl.

Aspect 33. The compound according to any one of Aspects 1-32, wherein the

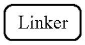

moiety is

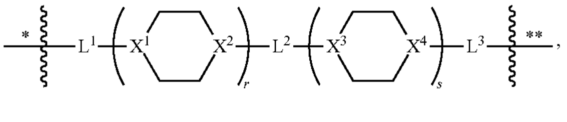

wherein * refers to the position attached to the

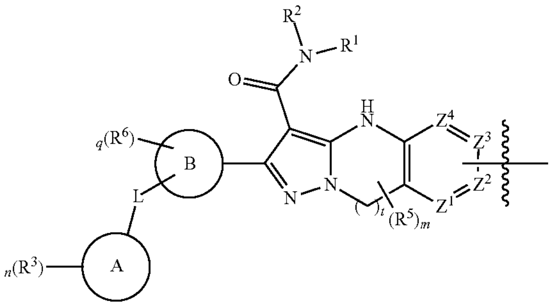

moiety, and ** refers to the position attached to the

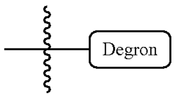

moiety;

$X^1$, $X^2$, $X^3$ and $X^4$ are each independently selected from CH or N;

r and s are each independently 0 or 1;

$L^1$ is a single bond, —O—, —$SO_2$—, —C(O)—, —$NR^{L1a}$—, —$C_3$-$C_8$cycloalkylene-, $*^{L1}$—O—$C_{1-8}$alkylene-$**^{L}$, $*^{L1}$—$C_{1-8}$alkylene-O—$**^{L1}$, $*^{L1}$—$SO_2$—$C_{1-8}$alkylene-$**^{L}$, $*^{L1}$—$C_{1-8}$alkylene-$SO_2$—$**^{L1}$, $*^{L1}$—C(O)—$C_{1-8}$alkylene-$**^{L}$, $*^{L1}$—$C_{1-8}$alkylene-C (O)—**$^{L}$, *$^{L}$—NR$^{L1a}$—C$_{1-8}$alkylene-**$^{L}$, *$^{L1}$—C$_{1-8}$alkylene-NR$^{L1a}$—**$^{L}$, *$^{L1}$—NR$^{L1a}$C(O)—**$^{L}$, *$^{L}$C(O)NR$^{L1a}$—**$^{L1}$, *$^{L1}$—NR$^{L1a}$C(O)C$_{1-8}$alkylene-**$^{L}$, *$^{L}$—C(O)NR$^{L1a}$—C$_{1-8}$alkylene-**$^{L}$, *$^{L1}$—C$_{1-8}$alkyleneNR$^{L1a}$C(O)—**$^{L}$, *$^{L1}$—C$_{1-8}$alkyleneC(O)NR$^{L1a}$—**$^{L1}$, —C$_{1-8}$alkylene-, —C$_{2-8}$alkenylene-, —C$_{2-8}$alkynylene-, —[O(CR$^{L1a}$R$^{L1b}$)$_{u1}$]$_{v1}$—;

each of said —C$_3$-C$_8$cycloalkylene-, *$^{L1}$—O—C$_{1-8}$alkylene-**$^{L}$, *$^{L}$—C$_{1-8}$alkylene-O—**$^{L}$, *$^{L1}$—SO$_2$—C$_{1-8}$alkylene-**$^{L}$, *$^{L1}$—C$_{1-8}$alkylene-SO$_2$—**$^{L}$, *$^{L1}$—C(O)—C$_{1-8}$alkylene-**$^{L}$, *$^{L1}$—C$_{1-8}$alkylene-C(O)—**$^{L1}$, *$^{L1}$—NR$^{L1a}$—C$_{1-8}$alkylene-**$^{L}$, *$^{L1}$—C$_{1-8}$alkylene-NR$^{L1a}$—**$^{L1}$, *$^{L1}$—NR$^{L1a}$C(O)C$_{1-8}$alkylene-**$^{L}$, *$^{L}$—C(O)NR$^{L1a}$C$_{1-8}$alkylene-**$^{L}$, *$^{L}$—C$_{1-8}$alkyleneNR$^{L1a}$C(O)—**$^{L}$, *$^{L}$—C$_{1-8}$alkyleneC(O)NR$^{L1a}$—**$^{L}$, —C$_{1-8}$alkylene-, —C$_{2-8}$alkenylene- or —C$_{2-8}$alkynylene- are optionally substituted with at least one R$^{L1c}$;

u1 and v1 are each independently selected from 1, 2, 3, 4, 5, 6, 7 or 8;

wherein *$^{L1}$ refers to the position attached to the

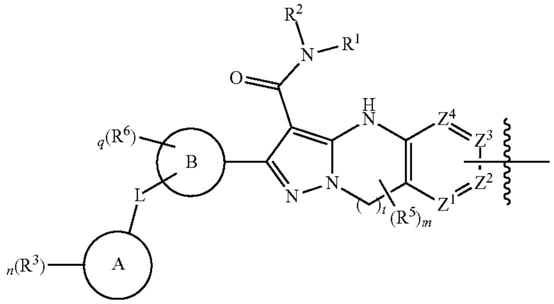

moiety, and **$^{L1}$ refers to the position attached to the

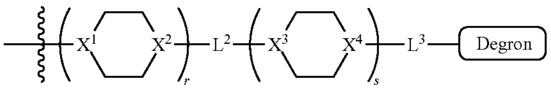

moiety;

L$^2$ is selected from a single bond, —O—, —SO$_2$—, —CO—, —NR$^{L2a}$—, —C$_3$-C$_8$cycloalkylene-, *$^{L2}$—O—C$_{1-8}$alkylene-**$^{L2}$, *$^{L2}$—C$_{1-8}$alkylene-O—**$^{L2}$, *$^{L2}$—SO$_2$—C$_{1-8}$alkylene-**$^{L2}$, *$^{L2}$—C$_{1-8}$alkylene-SO$_2$—**$^{L2}$, *$^{L}$—CO—C$_{1-8}$alkylene-**$^{L2}$, *$^{L}$—C$_{1-8}$alkylene-CO—**$^{L2}$, *$^{L2}$—NR$^{L2a}$—C$_{1-8}$alkylene-**$^{L2}$, *$^{L2}$—C$_{1-8}$alkylene-NR$^{L2a}$—**$^{L2}$, *$^{L2}$—NR$^{L2a}$C(O)—**$^{L2}$, *$^{L2}$—C(O)NR$^{L2a}$—**$^{L2}$, *$^{L2}$—NR$^{L2a}$C(O)C$_{1-8}$alkylene-**$^{L2}$, *$^{L2}$—C(O)NR$^{L2a}$C$_{1-8}$alkylene-**$^{L2}$, *$^{L2}$—C$_{1-8}$alkyleneNR$^{L2a}$C(O)—**$^{L2}$*$^{L2}$—C$_{1-8}$alkyleneC(O)NR$^{L2a}$—**$^{L2}$—C$_{1-8}$alkylene-, —C$_{2-8}$alkenylene-, —C$_{2-8}$alkynylene- or —[O(CR$^{L2a}$R$^{L2b}$)$_{u2}$]$_{v2}$—;

each of said —C$_3$-C$_8$cycloalkylene-, *$^{L2}$—O—C$_{1-8}$alkylene-**$^{L2}$, *$^{L2}$—C$_{1-8}$alkylene-O—**$^{L2}$*$^{L2}$—SO$_2$—C$_{1-8}$alkylene-**$^{L2}$, *$^{L2}$—C$_{1-8}$alkylene-SO$_2$—**$^{L2}$, *$^{L2}$—CO—C$_{1-8}$alkylene-**$^{L2}$, *$^{L2}$—C$_{1-8}$alkylene-CO—**$^{L2}$, *$^{L2}$—NR$^{L2a}$—C$_{1-8}$alkylene-**$^{L2}$, *$^{L2}$—C$_{1-8}$alkylene-NR$^{L2a}$—**$^{L2}$, *$^{L2}$—NR$^{L2a}$C(O)C$_{1-8}$alkylene-**$^{L2}$, *$^{L2}$—C(O)NR$^{L2a}$C$_{1-8}$alkylene-**$^{L2}$, *$^{L2}$—C$_{1-8}$alkyleneNR$^{L2a}$C(O)—**$^{L2}$, *$^{L2}$—C$_{1-8}$alkyleneC(O)NR$^{L2a}$—**$^{L2}$—C$_{1-8}$alkylene-, —C$_{2-8}$alkenylene- or —C$_{2-8}$alkynylene- are optionally substituted with at least one substituent R$^{L2c}$;

u2 and v2 are each independently selected from 1, 2, 3, 4, 5, 6, 7 or 8;

wherein *$^{L2}$ refers to the position attached to the

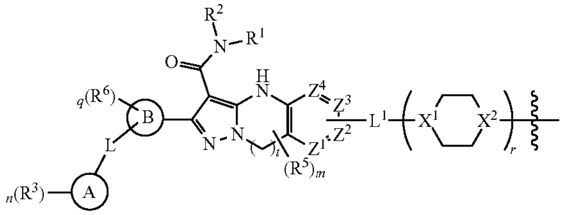

moiety, and **$^{L2}$ refers to the position attached to the

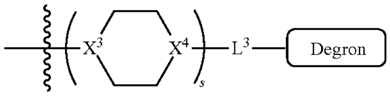

moiety;

L$_3$ is selected from a single bond, —O—, —SO$_2$—, —CO—, —NR$^{L3a}$—, —C$_3$-C$_8$cycloalkylene-, *$^{L3}$—O—C$_{1-8}$alkylene-**$^{L3}$, *$^{L3}$—C$_{1-8}$alkylene-O—**$^{L3}$, *$^{L3}$—SO$_2$—C$_{1-8}$alkylene-**$^{L3}$, *$^{L3}$—C$_{1-8}$alkylene-SO$_2$—**$^{L3}$, *$^{L3}$—CO—C$_{1-8}$alkylene-**$^{L3}$, *$^{L3}$—C$_{1-8}$alkylene-CO—**$^{L3}$, *$^{L3}$—NR$^{L3a}$—C$_{1-8}$alkylene-**$^{L3}$, *$^{L3}$—C$_{1-8}$alkylene-NR$^{L3a}$—**$^{L3}$, *$^{L3}$—NR$^{L3a}$—C(O)—**$^{L3}$, *$^{L3}$—C(O)NR$^{L3a}$—**$^{L3}$, *$^{L3}$—NR$^{L3a}$C(O)C$_{1-8}$alkylene-**$^{L3}$, *$^{L3}$—C(O)NR$^{L3a}$C$_{1-8}$alkylene-**$^{L3}$, *$^{L3}$—C$_{1-8}$alkyleneNR$^{L3a}$C(O)—**$^{L3}$, *$^{L3}$—C$_{1-8}$alkyleneC(O)NR$^{L3a}$—**$^{L3}$, —C$_{1-8}$alkylene-, —C$_{2-8}$alkenylene-, —C$_{2-8}$alkynylene- or —[O(CR$^{L3a}$R$^{L3b}$)$_{u3}$]$_{v3}$—; each of said —C$_3$-C$_8$cycloalkylene-, *$^{L3}$—O—C$_{1-8}$alkylene-**$^{L3}$, *$^{L3}$—C$_{1-8}$alkylene-O—**$^{L3}$, *$^{L3}$—SO$_2$—C$_{1-8}$alkylene-**$^{L3}$, *$^{L3}$—C$_{1-8}$alkylene-SO$_2$—**$^{L3}$, *$^{L3}$—CO—C$_{1-8}$alkylene-**$^{L3}$, *$^{L3}$—C$_{1-8}$alkylene-CO—**$^{L3}$, *$^{L3}$—NR$^{L3a}$—C$_{1-8}$alkylene-**$^{L3}$, *$^{L3}$—C$_{1-8}$alkylene-NR$^{L3a}$—**$^{L3}$, *$^{L3}$—NR$^{L3a}$C(O)C$_{1-8}$alkylene-**$^{L3}$, *$^{L3}$—C(O)NR$^{L3a}$C$_{1-8}$alkylene-**$^{L3}$, *$^{L3}$—C$_{1-8}$alkyleneNR$^{L3a}$C(O—$^{L3}$, *$^{L3}$—C$_{1-8}$alkyleneC(O)NR$^{L3a}$—**$^{L3}$, —C$_{1-8}$alkylene-, —C$_{2-8}$alkenylene-, —C$_{2-8}$alkynylene-, are optionally substituted with at least one substituent R$^{L3c}$;

u3 and v3 are each independently selected from 1, 2, 3, 4, 5, 6, 7 or 8;

wherein $*^{L3}$ refers to the position attached to the

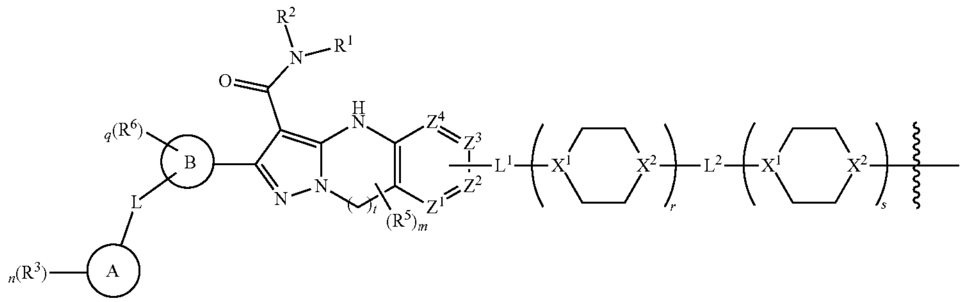

moiety, and $**^{L3}$ refers to the position attached to the

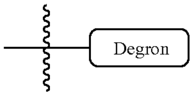

moiety;

$R^{L1a}$, $R^{L1b}$, $R^{L2a}$, $R^{L2b}$, $R^{L3a}$ and $R^{L3b}$ are each independently selected from hydrogen, —$C_{1-8}$alkyl, —$C_{2-8}$alkenyl, —$C_{2-8}$alkynyl, cycloalkyl, heterocyclyl, aryl or heteroaryl, wherein each of said —$C_{1-8}$alkyl, —$C_{2-8}$alkenyl, —$C_{2-8}$alkynyl, cycloalkyl, heterocyclyl, aryl or membered heteroaryl is optionally substituted with at least one substituent $R^{L3d}$; $R^{L3d}$ is halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl.

Aspect 34. The compound according to any one of Aspects 1-33, wherein $L^1$ is a single bond, —O—, —$SO_2$—, —C(O)—, —NH—, —$N(CH_3)$—, —$N(C_2H_5)$—, —$N(C_3H_7)$—, $*^{L1}$—O—$CH_2$—$**^{L1}$, $*^{L1}$—O—$C_2H_4$—$**^{L1}$, $*^{L1}$—O—$C_3H_6$—$**^{L1}$, $*^{L1}$, $*^{L1}$—$CH_2$—O—$**^{L1}$, $*^{L1}$—$C_2H_4$—O—$**^{L1}$, $*^{L1}$—$C_3H_6$—O—$**^{L1}$, $*^{L1}$—$C_4H_8$—O—$**^{L1}$, $*^{L1}$—$SO_2$—$CH_2$—$**^{L1}$, $*^{L1}$—$SO_2$—$C_2H_4$—$**^{L1}$, $*^{L1}$—$SO_2$—$C_3H_6$—$**^{L1}$, $*^{L1}$—$SO_2$—$C_4H_8$—$**^{L1}$, $*^{L1}$—$CH_2$—$SO_2$—$**^{L1}$, $*^{L1}$—$C_2H_4$—$SO_2$—$**^{L1}$, $*^{L1}$—$C_3H_6$—$SO_2$—$**^{L1}$, $*^{L1}$—$C_4H_8$—$SO_2$—$**^{L1}$, $*^{L1}$—C(O)—$CH_2$—$**^{L1}$, $*^{L1}$—C(O)—$C_2H_4$—$**^{L1}$, $*^{L1}$—C(O)—$C_3H_6$—$**^{L1}$, $*^{L1}$—C(O)—$C_4H_8$—$**^{L1}$, $*^{L1}$—$CH_2$—C(O)—$**^{L1}$, $*^{L1}$—$C_2H_4$—C(O)—$**^{L1}$, $*^{L1}$—$C_3H_6$—C(O)—$**^{L1}$, $*^{L1}$—$C_4H_8$—C(O)—$**^{L1}$, $*^{L1}$—NH—$CH_2$—$**^{L1}$, $*^{L1}$—NH—$C_2H_4$—$**^{L1}$, $*^{L1}$—NH—$C_3H_8$—$**^{L1}$, $*^{L1}$—NH—$C_4H_8$—$**^{L1}$, $*^{L1}$—$CH_2$—NH—$**^{L1}$, $*^{L1}$—$C_2H_4$—NH—$**^{L1}$, $*^{L1}$—$C_3H_6$—NH—$**^{L1}$, $*^{L1}$—$C_4H_8$—NH—$**^{L1}$, $*^{L1}$—NHC(O)—$**^{L1}$, $*^{L1}$—C(O)NH—$**^{L1}$, $*^{L1}$—$N(CH_3)C(O)$—$**^{L1}$, $*^{L1}$—C(O)N$(CH_3)$—$**^{L1}$, $*^{L1}$—$N(C_2H_5)C(O)$—$**^{L1}$, $*^{L1}$—C(O)N$(C_2H_5)$—$**^{L1}$, $*^{L1}$—$N(C_3H_7)C(O)$—$**^{L1}$, $*^{L1}$—C(O)N$(C_3H_7)$—$**^{L1}$, $*^{L1}$—NHC(O)$CH_2$—$**^{L1}$, $*^{L1}$—NHC(O)$C_2H_4$—$**^{L1}$, $*^{L1}$—NHC(O)$C_3H_6$—$**^{L1}$, $*^{L1}$—NHC(O)$C_4H_8$—$**^{L1}$, $*^{L1}$—C(O)NH$CH_2$—$**^{L1}$, $*^{L1}$—C(O)NH$C_2H_4$—$**^{L1}$, $*^{L1}$—C(O)NH$C_3H_6$—$**^{L1}$, $*^{L1}$—C(O)NH$C_4H_8$—$**^{L1}$, $*^{L1}$—$CH_2$NHC(O)—$**^{L1}$, $*^{L1}$—$C_2H_4$NHC(O)—$**^{L1}$, $*^{L1}$—$C_3H_6$NHC(O)—$**^{L1}$, $*^{L1}$—$C_4H_8$NHC(O)—$**^{L1}$, $*^{L1}$—$CH_2$C(O)NH—$**^{L1}$, $*^{L1}$—$C_2H_4$C(O)NH—$**^{L1}$, $*^{L1}$—$C_3H_6$C(O)NH—$**^{L1}$, $*^{L1}$—$C_4H_8$C(O)NH—$**^{L1}$, —$CH_2$—, —$C_2H_4$—, —$C_3H_6$—, —$C_4H_8$—, —$O(CH_2)_2$—, —$[O(CH_2)_2]_2$—, —$[O(CH_2)_2]_3$—, —$[O(CH_2)_2]_4$— or —$[O(CH_2)_2]_5$—.

Aspect 35. The compound according to any one of Aspects 1-34, wherein $L^2$ is a single bond, —O—, —$SO_2$—, —C(O)—, —NH—, —$N(CH_3)$—, —$N(C_2H_5)$—, —$N(C_3H_7)$—, $*^{L2}$—O—$CH_2$—$**^{L2}$, $*^{L2}$—O—$C_2H_4$—$**^{L2}$, $*^{L2}$—O—$C_3H_6$—$**^{L2}$, $*^{L2}$—O—$C_4H_8$—$**^{L2}$, $*^{L2}$—$CH_2$—O—$**^{L2}$, $*^{L2}$—$C_2H_4$—O—$**^{L2}$, $*^{L2}$—$C_3H_6$—O—$**^{L2}$, $*^{L2}$—$C_4H_8$—O—$**^{L2}$, $*^{L2}$—$SO_2$—$CH_2$—$**^{L2}$, $*^{L2}$—$SO_2$—$C_2H_4$—$**^{L2}$, $*^{L2}$—$SO_2$—$C_3H_6$—$**^{L2}$, $*^{L2}$—$SO_2$—$C_4H_8$—$**^{L2}$, $*^{L2}$—$CH_2$—$SO_2$—$**^{L2}$, $*^{L2}$—$C_2H_4$—$SO_2$—$**^{L2}$, $*^{L2}$—$C_3H_6$—$SO_2$—$**^{L2}$, $*^{L2}$—$C_4H_8$—$SO_2$—$**^{L2}$, $*^{L2}$—C(O)—$CH_2$—$**^{L2}$, $*^{L2}$—C(O)—$C_2H_4$—$**^{L2}$, $*^{L2}$—C(O)—$C_3H_6$—$**^{L2}$, $*^{L2}$—C(O)—$C_4H_8$—$**^{L2}$, $*^{L2}$—$CH_2$—C(O)—$**^{L2}$, $*^{L2}$, $*^{L2}$—$C_2H_4$—C(O)—$**^{L2}$, $*^{L2}$—$C_3H_6$—C(O)—$**^{L2}$, $*^{L2}$—$C_4H_8$—C(O)—$**^{L2}$, $*^{L2}$—NH—$CH_2$—$**^{L2}$, $*^{L2}$—NH—$C_2H_4$—$**^{L2}$, $*^{L2}$—NH—$C_3H_6$—$**^{L2}$, $*^{L2}$—NH—$C_4H_8$—$**^{L2}$, $*^{L2}$—$CH_2$—NH—$**^{L2}$, $*^{L2}$—$C_2H_4$—NH—$**^{L2}$, $*^{L2}$—$C_3H_6$—NH—$**^{L2}$, $*^{L2}$—$C_4H_8$—NH—$**^{L2}$, $*^{L2}$—NHC(O)—$**^{L2}$, $*^{L2}$—C(O)NH—$**^{L2}$, $*^{L2}$—$N(CH_3)C(O)$—$**^{L2}$, $*^{L2}$—C(O)N$(CH_3)$—$**^{L2}$, $*^{L2}$—$N(C_2H_5)C(O)$—$**^{L2}$, $*^{L2}$—C(O)N$(C_2H_5)$—$**^{L2}$, $*^{L2}$—$N(C_3H_7)C(O)$—$**^{L2}$, $*^{L2}$—C(O)N$(C_3H_7)$—$**^{L2}$, $*^{L2}$—NHC(O)$CH_2$—$**^{L2}$, $*^{L2}$—NHC(O)$C_2H_4$—$**^{L2}$, $*^{L2}$—NHC(O)$C_3H_6$—$**^{L2}$, $*^{L2}$—NHC(O)$C_4H_8$—$**^{L2}$, $*^{L2}$—C(O)NH$CH_2$—$**^{L2}$, $*^{L2}$—C(O)NH$C_2H_4$—$**^{L2}$, $*^{L2}$—C(O)NH$C_3H_6$—$**^{L2}$, $*^{L2}$—C(O)NH$C_4H_8$—$**^{L2}$, $*^{L2}$—$CH_2$NHC(O)—$**^{L2}$, $*^{L2}$—$C_2H_4$NHC(O)—$**^{L2}$, $*^{L2}$—$C_3H_6$NHC(O)—$**^{L2}$, $*^{L2}$—$C_4H_8$NHC(O)—$**^{L2}$, $*^{L2}$—$CH_2$C(O)NH—$**^{L2}$, $*^{L2}$—$C_2H_4$C(O)NH—$**^{L2}$, $*^{L2}$—$C_3H_6$C(O)NH—$**^{L2}$, $*^{L2}$—$C_4H_8$C(O)NH—$**^{L2}$, —$CH_2$—, —$C_2H_4$—, —$C_3H_6$—, —$C_4H_8$—, —$O(CH_2)_2$—, —$[O(CH_2)_2]_2$—, —$[O(CH_2)_2]_3$—, —$[O(CH_2)_2]_4$— or —$[O(CH_2)_2]_5$—.

Aspect 36. The compound according to any one of Aspects 1-35, wherein $L^3$ is a single bond, —O—, —$SO_2$—, —C(O)—, —NH—, —$N(CH_3)$—, —$N(C_2H_5)$—, —$N(C_3H_7)$—, $*^{L3}$—O—$CH_2$—$**^{L3}$, $*^{L3}$—O—$C_2H_4$—$**^{L3}$, $*^{L3}$—O—$C_3H_6$—$**^{L3}$, $*^{L3}$—O—$C_4H_8$—$**^{L3}$, $*^{L3}$—$CH_2$—O—$**^{L3}$, $*^{L3}$—$C_2H_4$—O—$**^{L3}$, $*^{L3}$—$C_3H_6$—O—$**^{L3}$, $*^{L3}$—$C_4H_8$—O—$**^{L3}$, $*^{L3}$—$SO_2$—$CH_2$—$**^{L3}$, $*^{L3}$—$SO_2$—$C_2H_4$—$**^{L3}$, $*^{L3}$—$SO_2$—$C_3H_6$—$**^{L3}$, $*^{L3}$—$SO_2$—$C_4H_8$—$**^{L3}$, $*^{L3}$—$CH_2$—$SO_2$—$**^{L3}$, $*^{L3}$—$C_2H_4$—$SO_2$—$**^{L3}$, $*^{L3}$—$C_3H_6$—$SO_2$—$**^{L3}$, $*^{L3}$—$C_4H_8$—$SO_2$—$**^{L3}$, $*^{L3}$, $*^{L3}$—C(O)—$CH_2$—$**^{L3}$, $*^{L3}$—C(O)—$C_2H_4$—$**^{L3}$, $*^{L3}$—C(O)—$C_3H_6$—$**^{L3}$, $*^{L3}$—C(O)—$C_4H_8$—$**^{L3}$, $*^{L3}$—$CH_2$—C(O)—$**^{L3}$, $*^{L3}$—$C_2H_4$—C(O)—$**^{L3}$, $*^{L3}$—$C_3H_6$—C(O)—$**^{L3}$, $*^{L3}$—$C_4H_8$—C(O)—$**^{L3}$, $*^{L3}$—NH—$CH_2$—$**^{L3}$, $*^{L3}$—NH—$C_2H_4$—$**^{L3}$, $*^{L3}$—NH—$C_3H_6$—$**^{L3}$, $*^{L3}$—NH—$C_4H_8$—$**^{L3}$, $*^{L3}$—$CH_2$—NH—$**^{L3}$, $*^{L3}$—$C_2H_4$—NH—$**^{L3}$, $*^{L3}$—$C_3H_6$—NH—$**^{L3}$, $*^{L3}$—$C_4H_8$—NH—$**^{L3}$, $*^{L3}$—NHC(O)—$**^{L3}$, $*^{L3}$—C(O)NH—$**^{L3}$, $*^{L3}$—$N(CH_3)C(O)$—$**^{L3}$, $*^{L3}$—C(O)N $(CH_3)$—$**^{L3}$, $*^{L3}$—$N(C_2H_5)C(O)$—$**^{L3}$, $*^{L3}$—$C(O)N(C_2H_5)$—$**^{L3}$, $*^{L3}$—$N(C_3H_7)C(O)$—$**^{L3}$, $*^{L3}$—$C(O)N(C_3H_7)$—$**^{L3}$, $*^{L3}$—$NHC(O)CH_2$—$**^{L3}$, $*^{L3}$—$NHC(O)C_2H_4$—$**^{L3}$, $*^{L3}$—$NHC(O)C_3H_6$—$**^{L3}$, $*^{L3}$—$NHC(O)C_4H_8$—$**^{L3}$, $*^{L3}$—$C(O)NHCH_2$—$**^{L3}$, $*^{L3}$—$C(O)NHC_2H_4$—$**^{L3}$, $*^{L3}$—$C(O)NHC_3H_6$—$**^{L3}$, $*^{L3}$—$C(O)NHC_4H_8$—$**^{L3}$, $*^{L3}$—$CH_2NHC(O)$—$**^{L3}$, $*^{L3}$—$C_2H_4NHC(O)$—$**^{L3}$, $*^{L3}$—$C_3H_6NHC(O)$—$**^{L3}$, $*^{L3}$—$C_4H_8NHC(O)$—$**^{L3}$, $*^{L3}$—$CH_2C(O)NH$—$**^{L3}$, $*^{L3}$—$C_2H_4C(O)NH$—$**^{L3}$, $*^{L3}$—$C_3H_6C(O)NH$—$**^{L3}$, $*^{L3}$—$C_4H_8C(O)NH$—$**^{L3}$, —$CH_2$—, —$C_2H_4$—, —$C_3H_6$—, —$C_4H_8$—, —$O(CH_2)_2$—, —$[O(CH_2)_2]_2$—, —$[O(CH_2)_2]_3$—, —$[O(CH_2)_2]_4$— or —$[O(CH_2)_2]_5$—.

Aspect 37. The compound according to any one of Aspects 1-36, wherein the

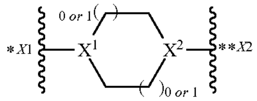

moiety is independently selected from

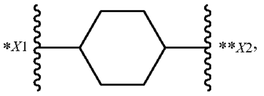
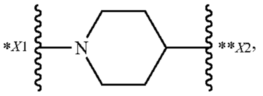
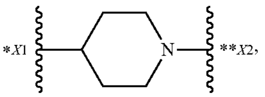
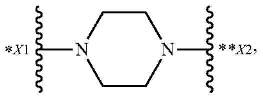
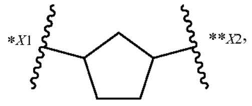
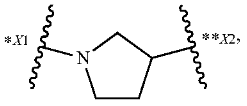
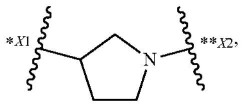
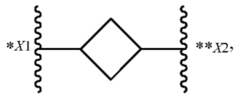
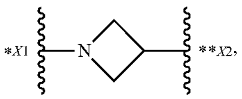
or
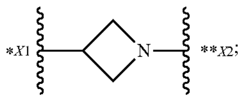

wherein $*^{X1}$ refers to the position attached to the

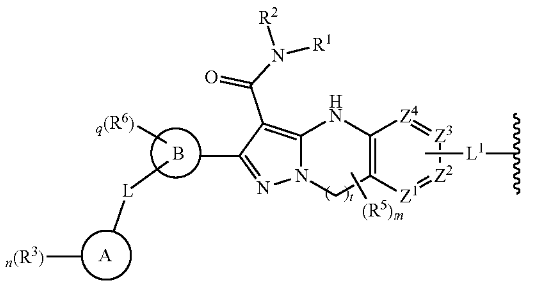

moiety, and $**^{X2}$ refers to the position attached to the

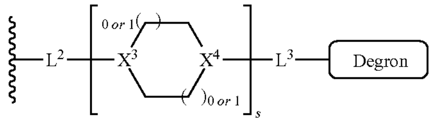

moiety.

Aspect 38. The compound according to any one of Aspects 1-37, wherein the

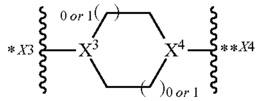

moiety is independently selected from

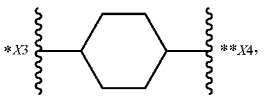
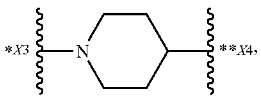
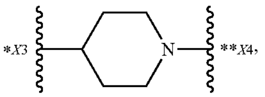
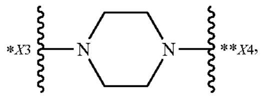
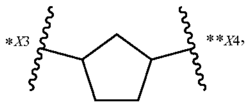
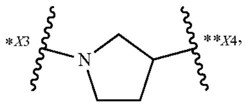
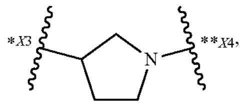
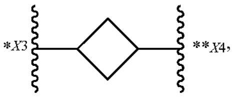
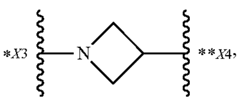
or
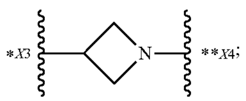

wherein *[X3] refers to the position attached to the
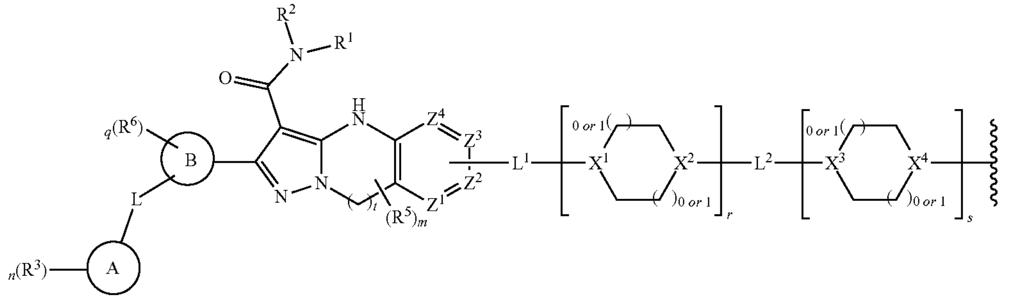
moiety, and **[L4] refers to the position attached to the
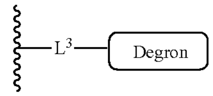
moiety.
Aspect 39. The compound according to any one of Aspects 1-38, wherein the
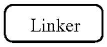
moiety is
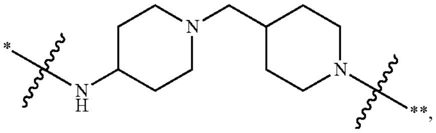
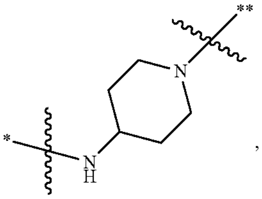
,
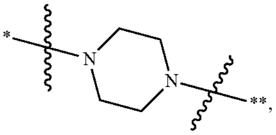
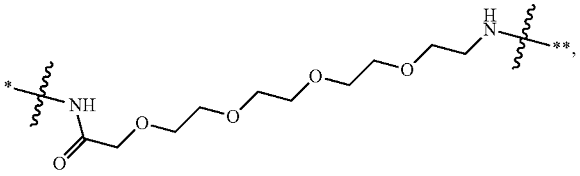
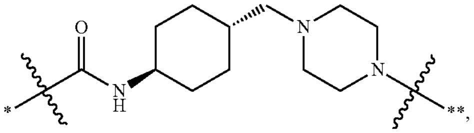
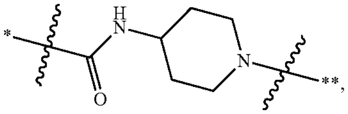
-continued
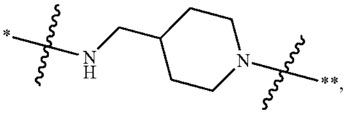
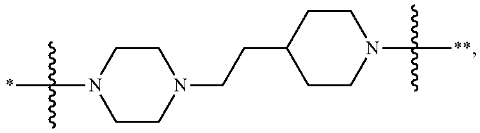
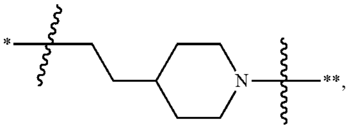
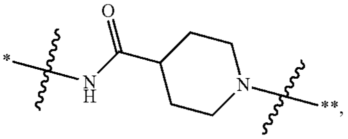
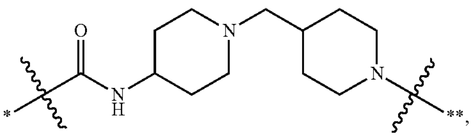
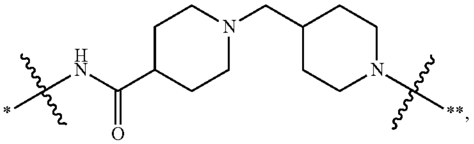
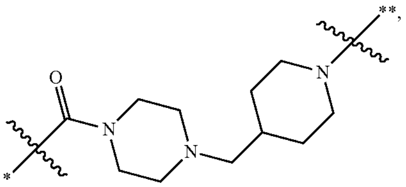
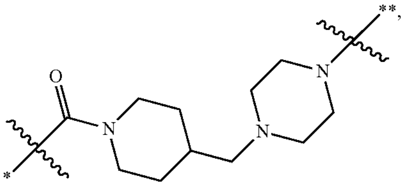

-continued
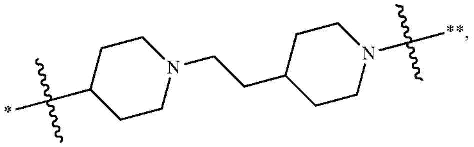
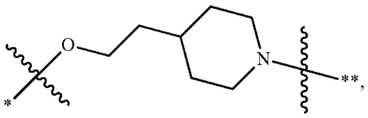
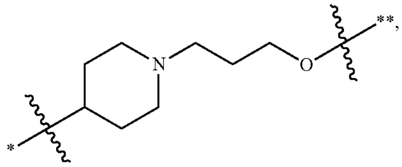
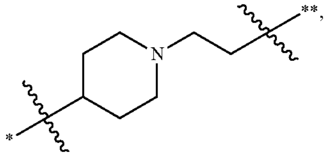
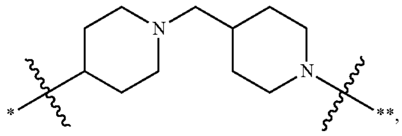
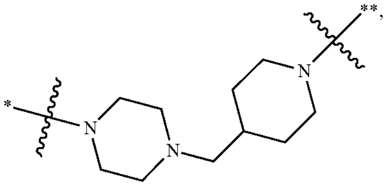
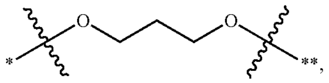
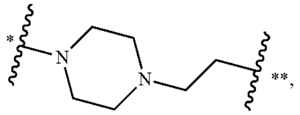
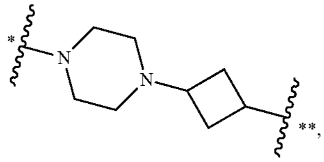
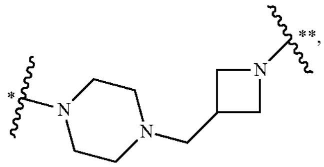
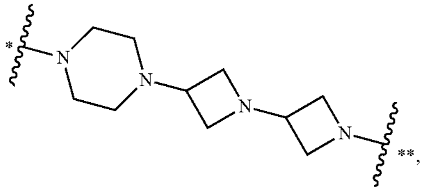
-continued
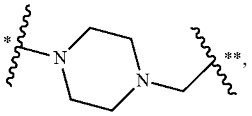
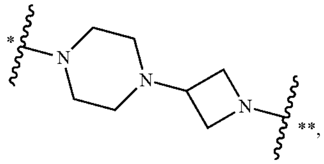
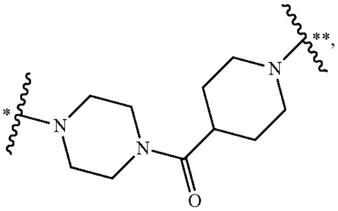
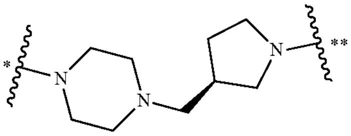
or
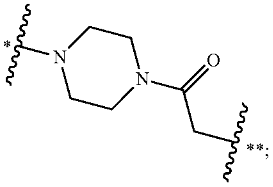
wherein * refers to the position attached to the
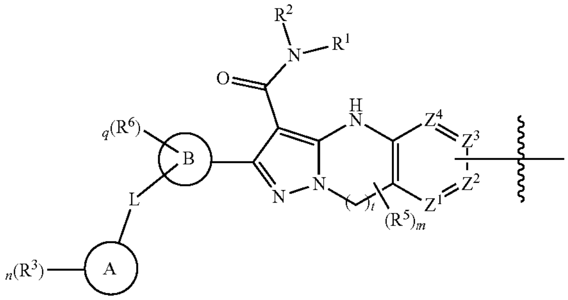
moiety, and ** refers to the position attached to the
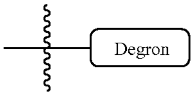
moiety.
Aspect 40. The compound according to any one of Aspects 1-39, wherein the compound is selected from 1 A4
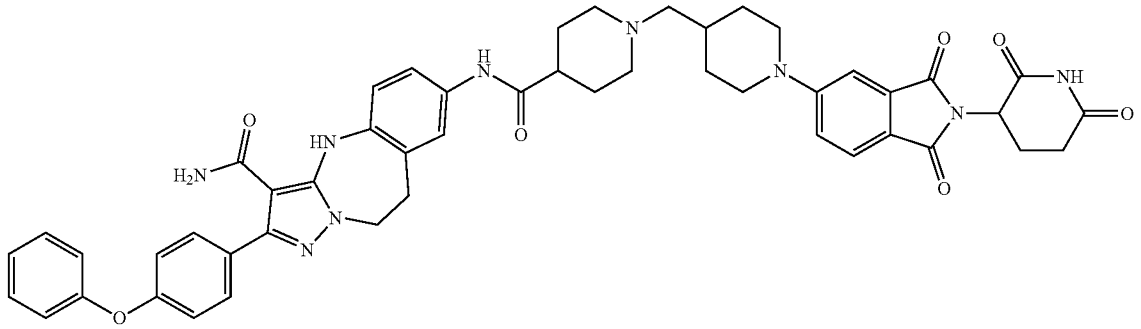
2 A5
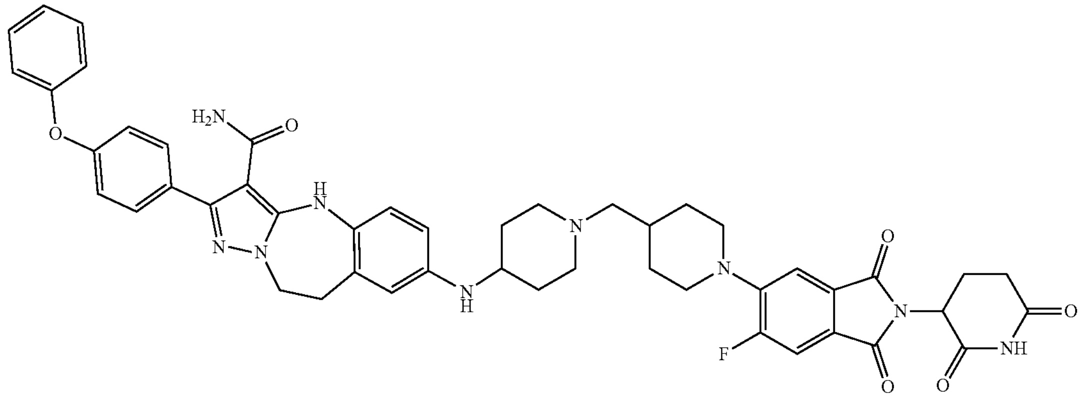
3 A6
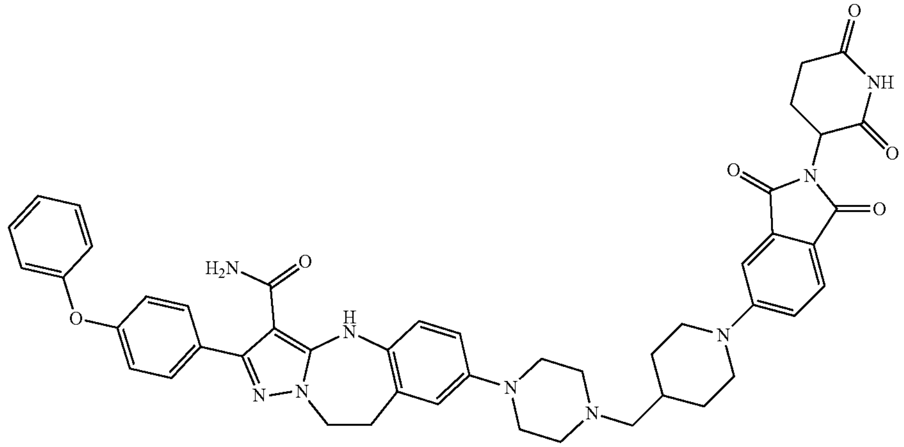
4 A3
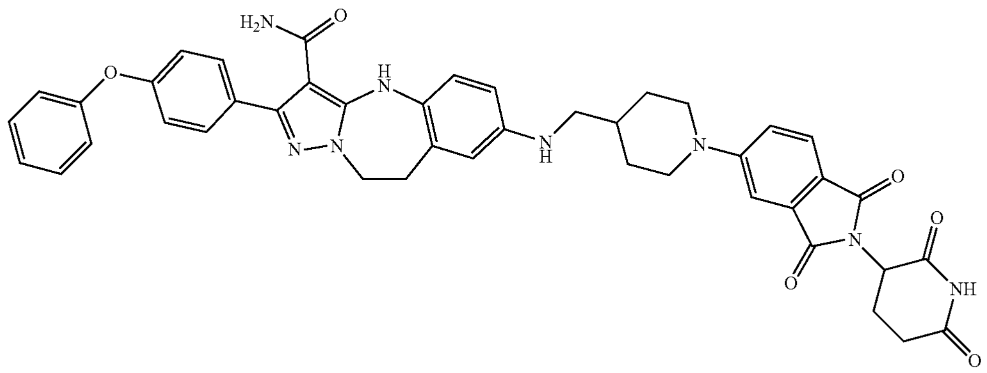

-continued
5 A8
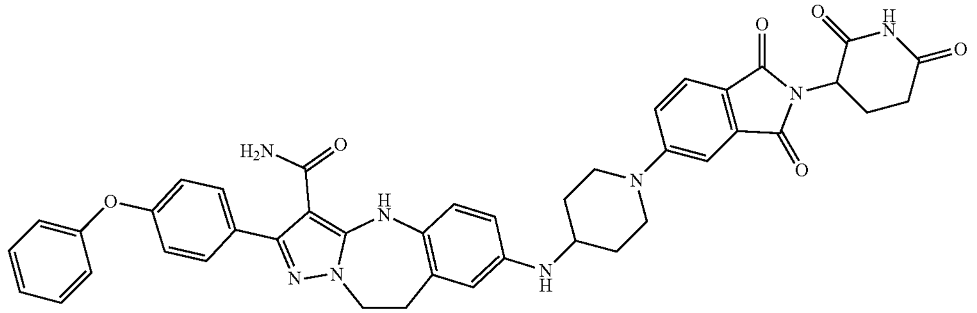
6 A7
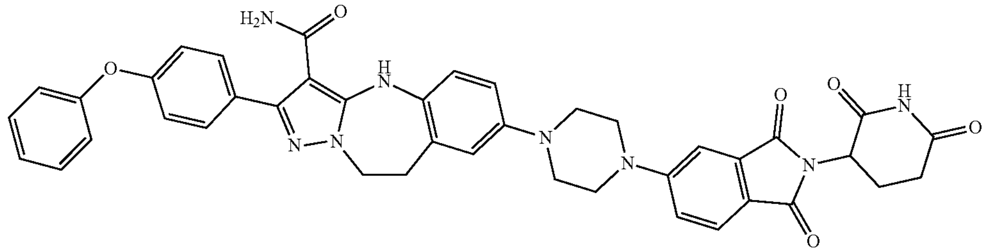
7 A2
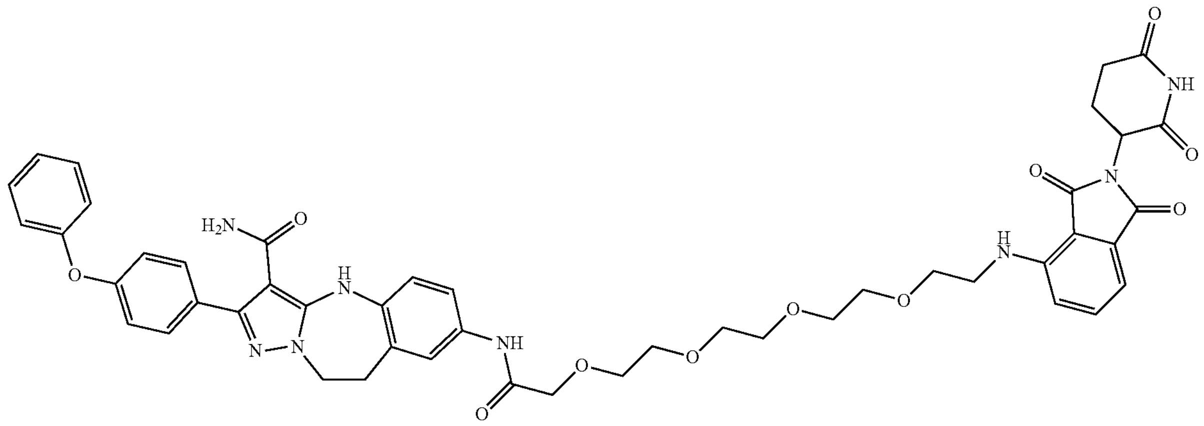
8 A10
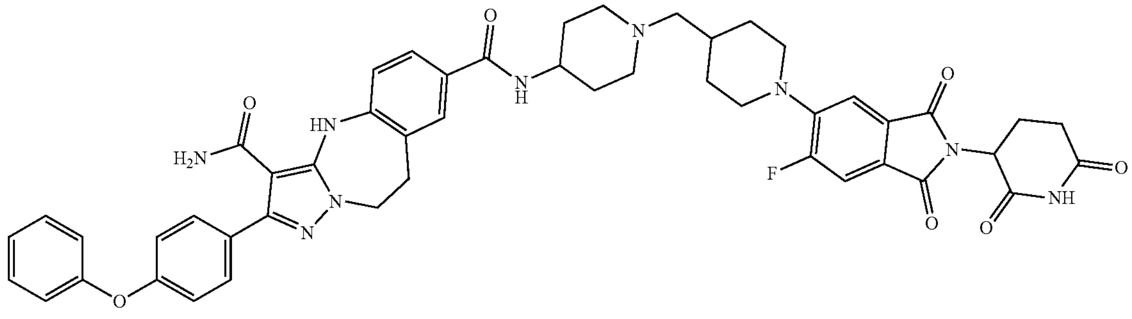

-continued
9 A12
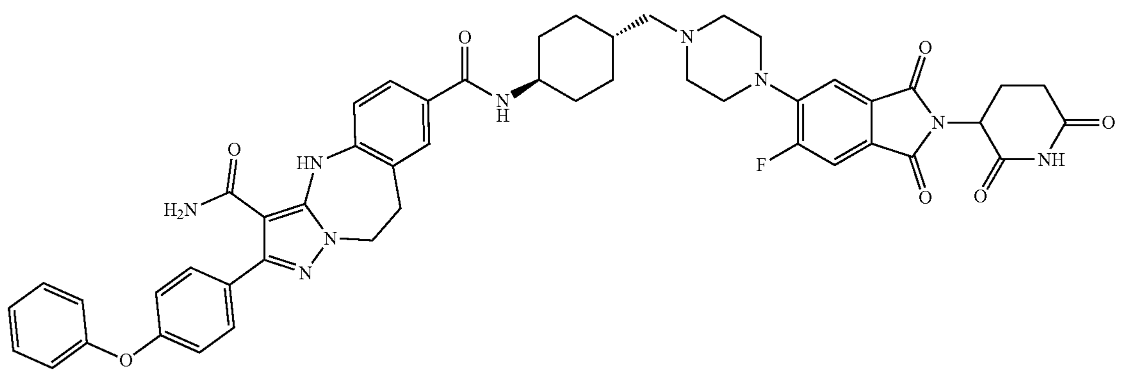
10 A13
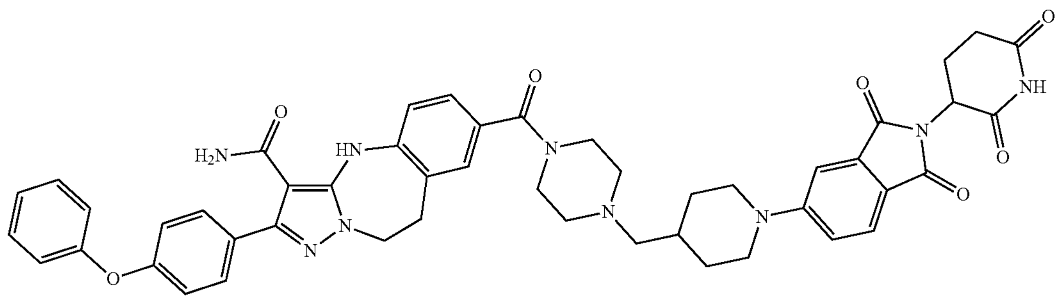
11 A14
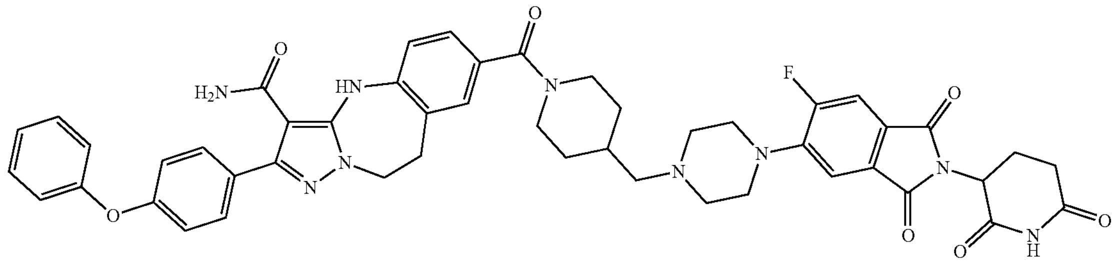
12 A9
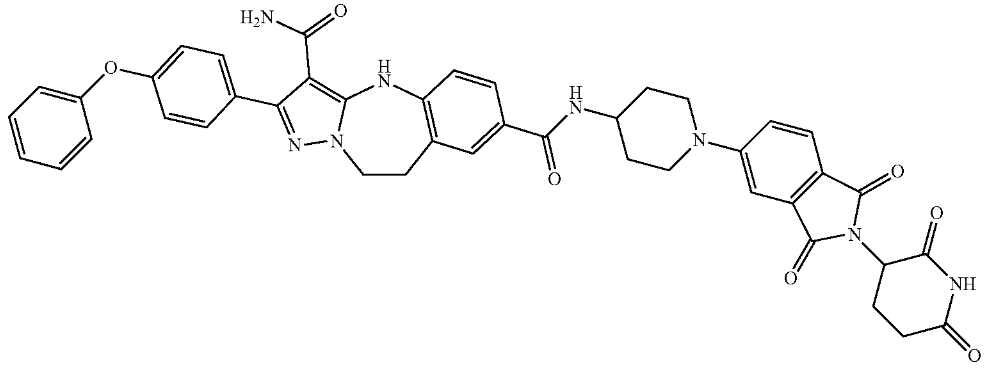

-continued
13 A1
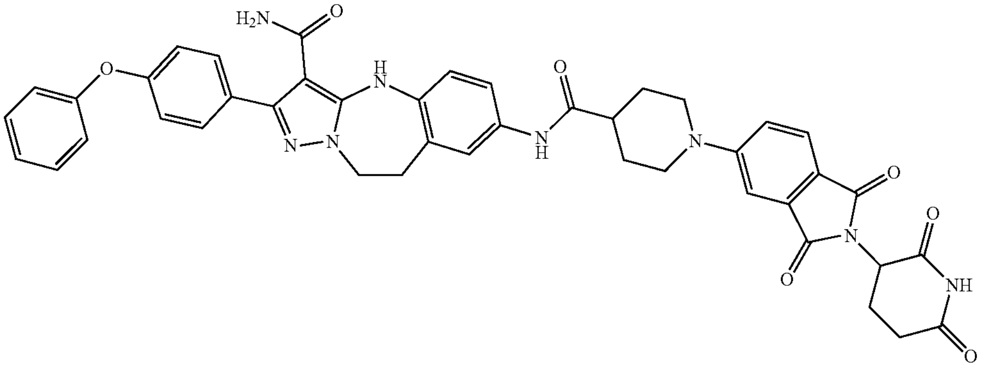
14 A11
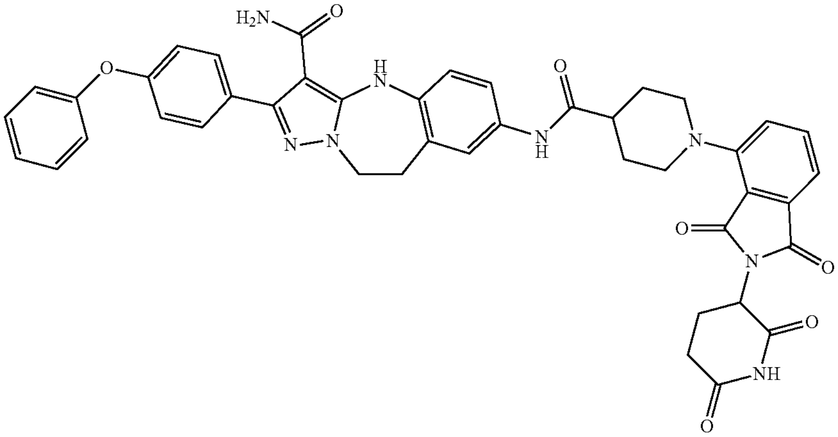
15 A16
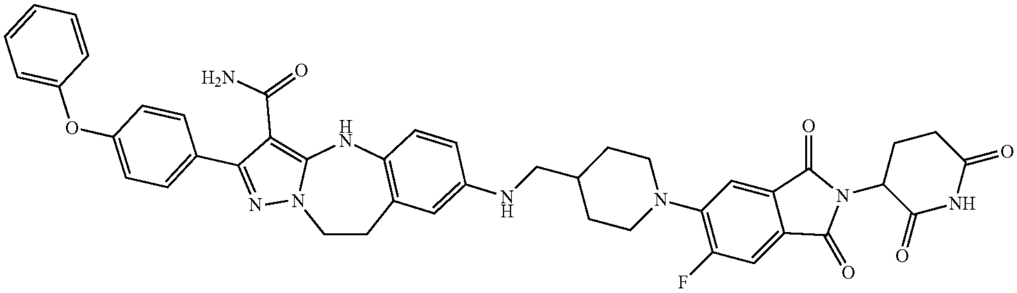
16 A21
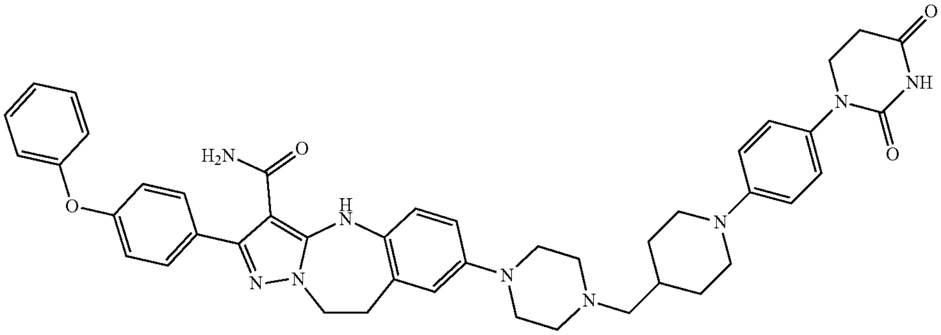
17 A22
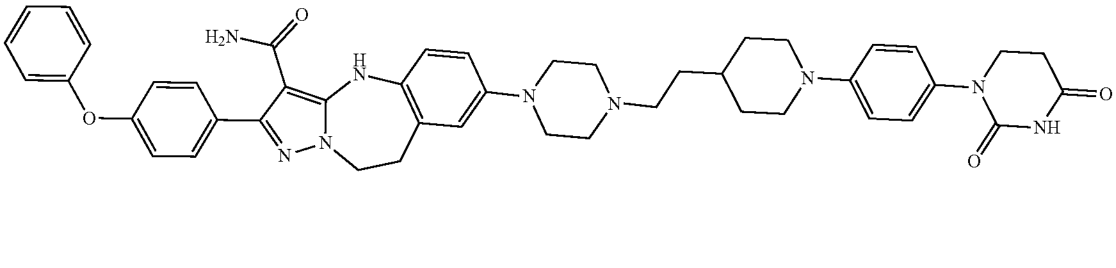

-continued
18 A24
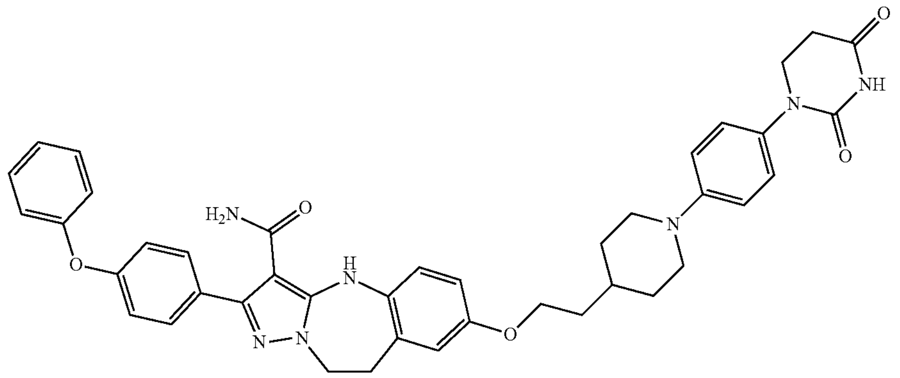
19 A28
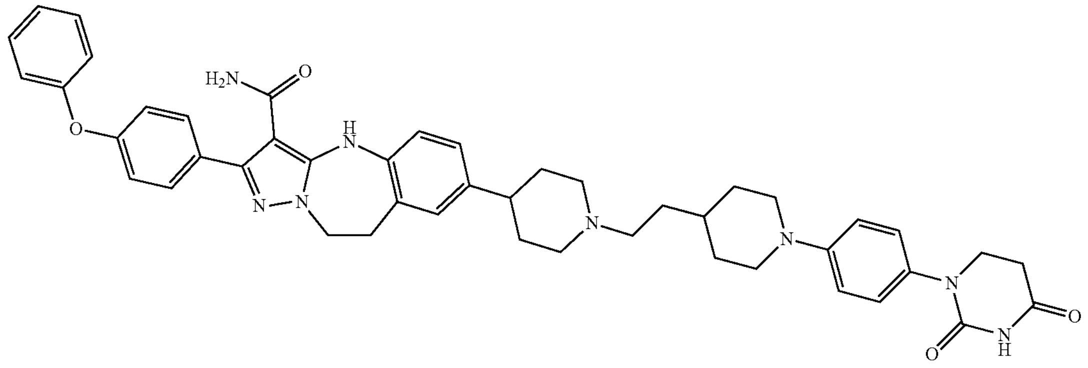
20 A30
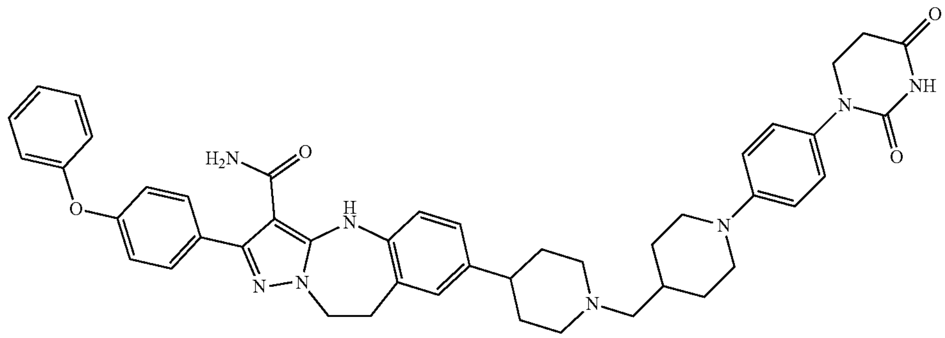
21 A26
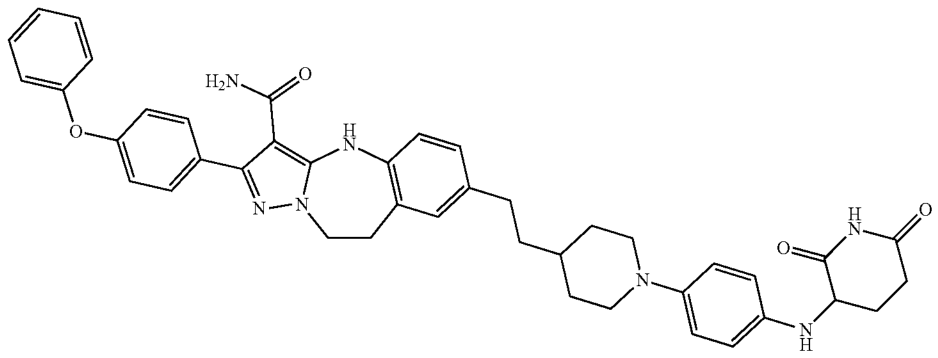

-continued
22
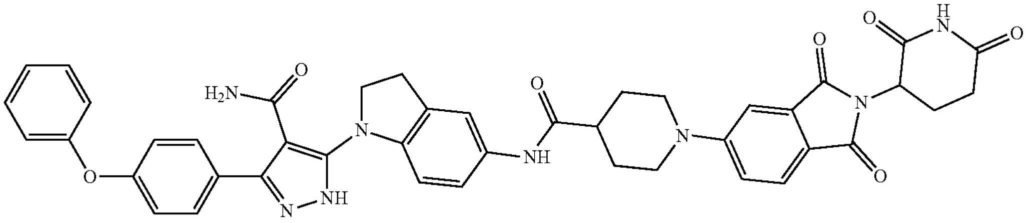
23 A29
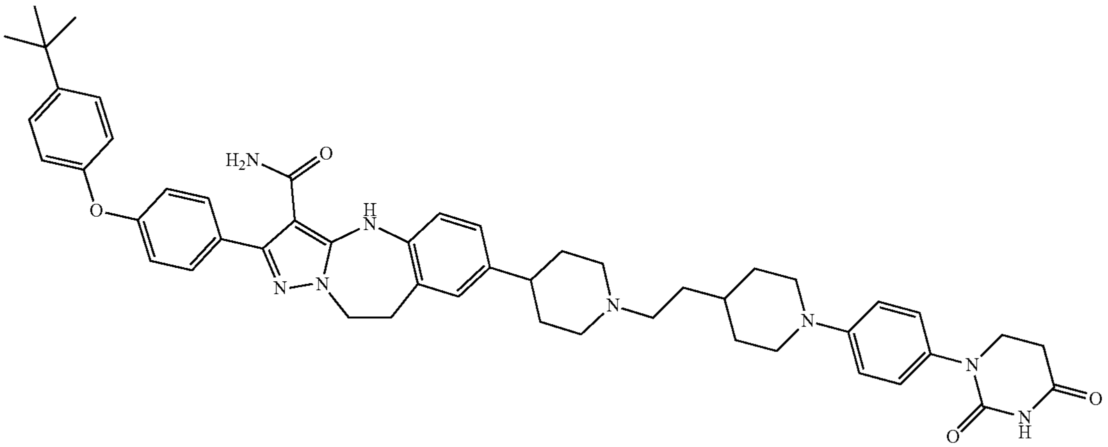
24 A31
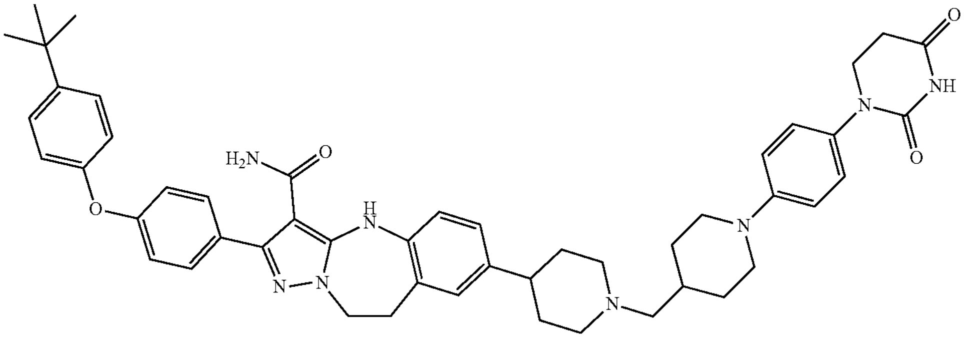
25 A17
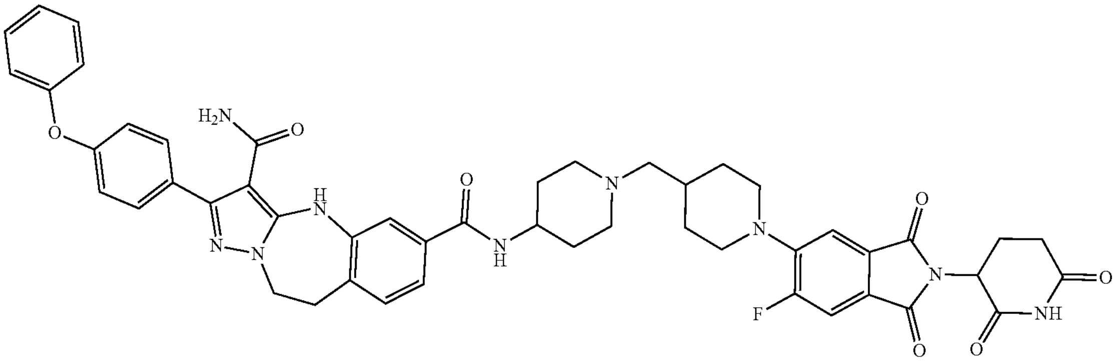

-continued
26 A18
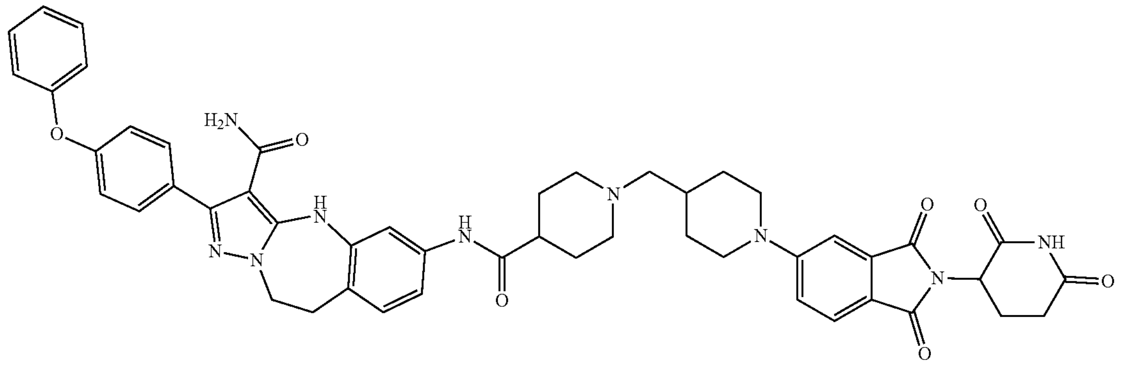
27 A19
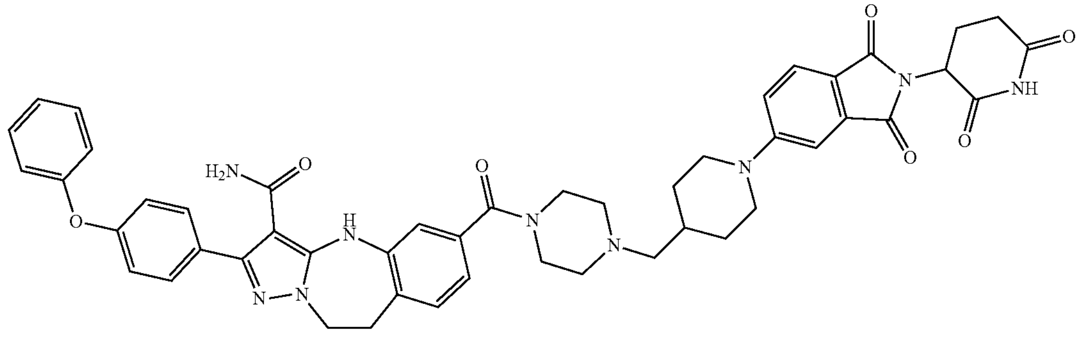
28 A20
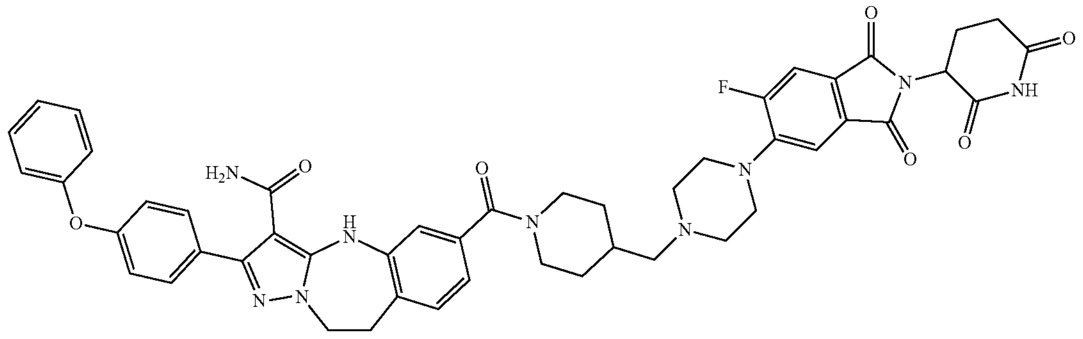
29 A15
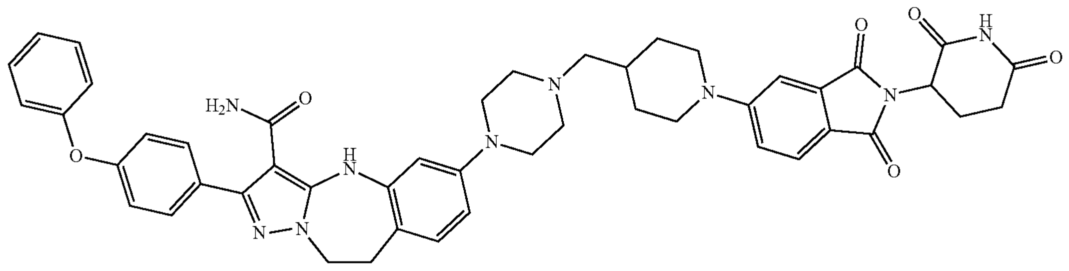

-continued
30 A23
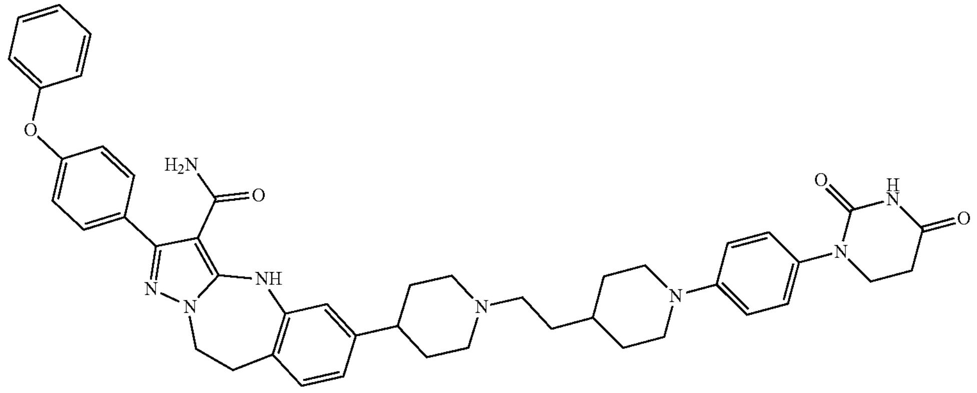
31 A27
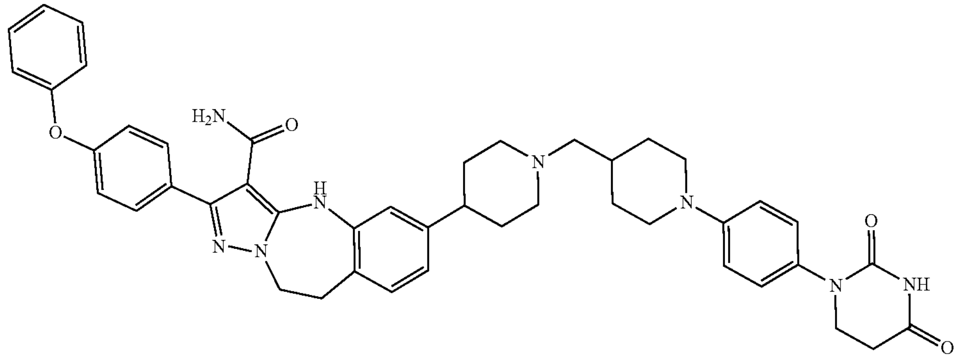
32 A25
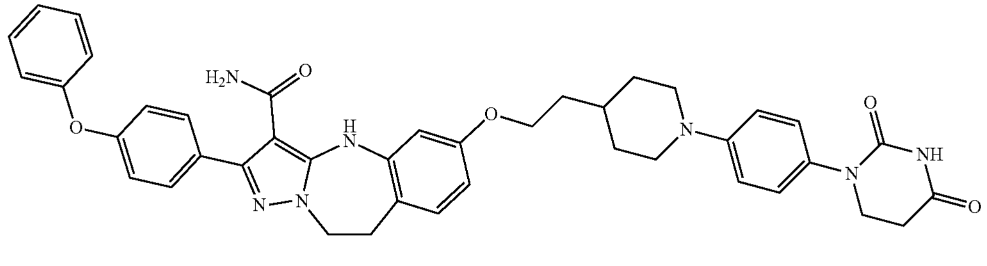
33 A32
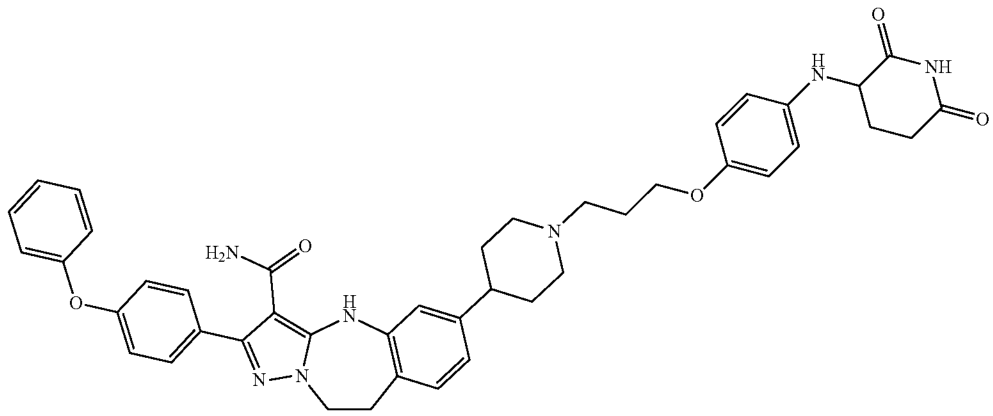

-continued
34 A33
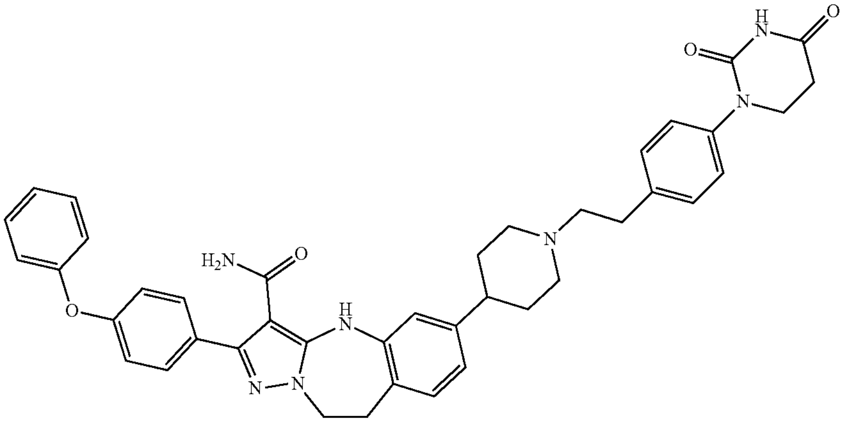
35 A34
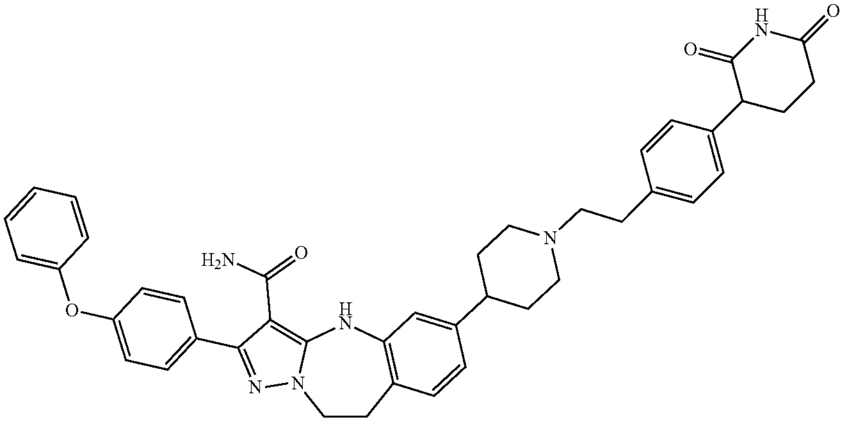
36 A35
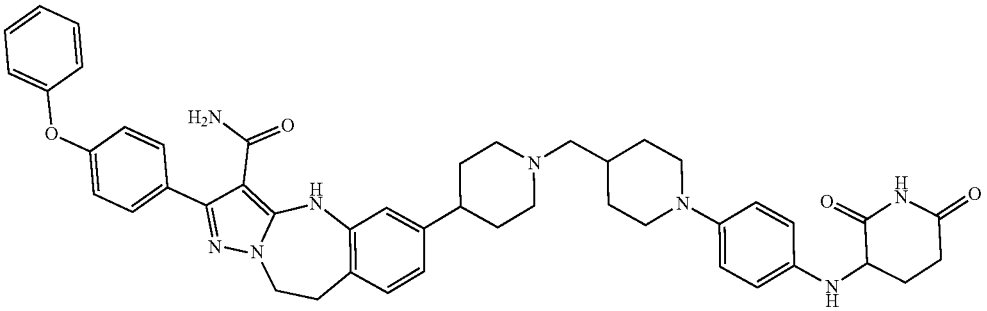
37
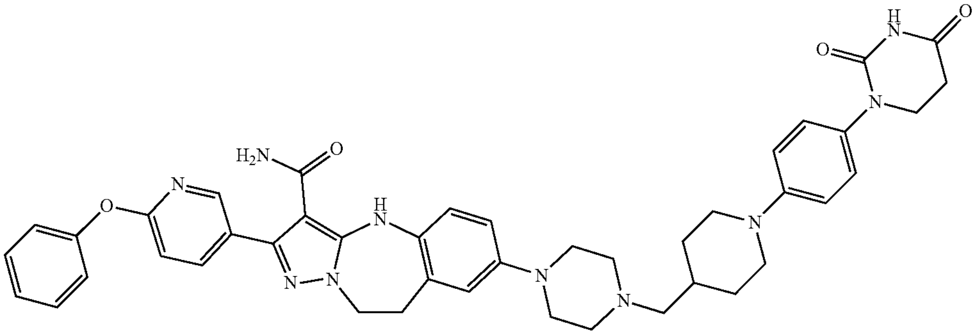

-continued
38 A36
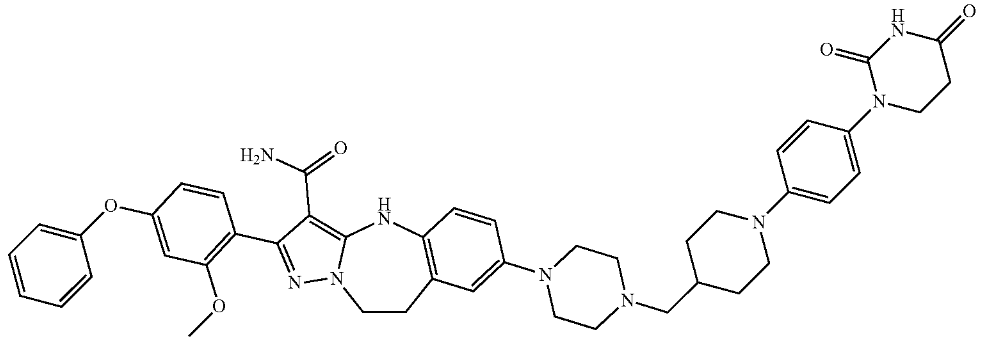
39 A37
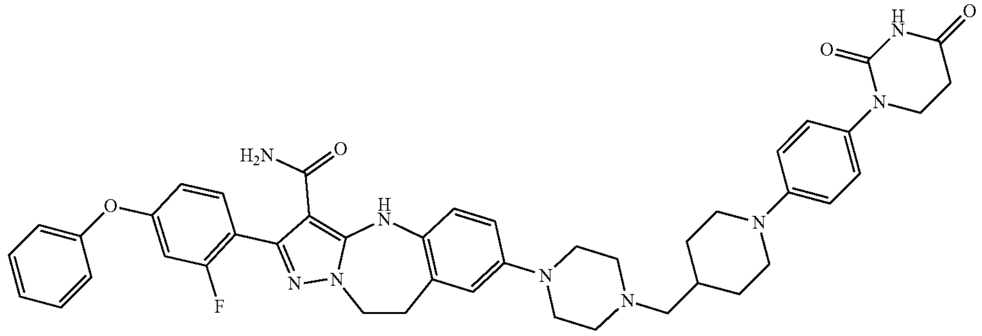
40 A38
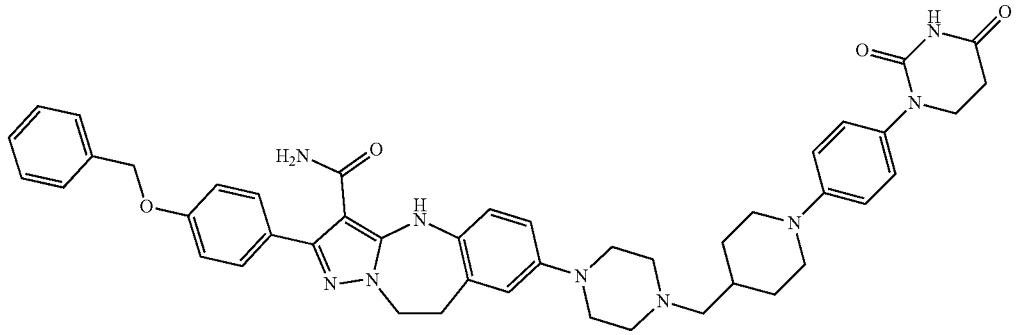
41 B1
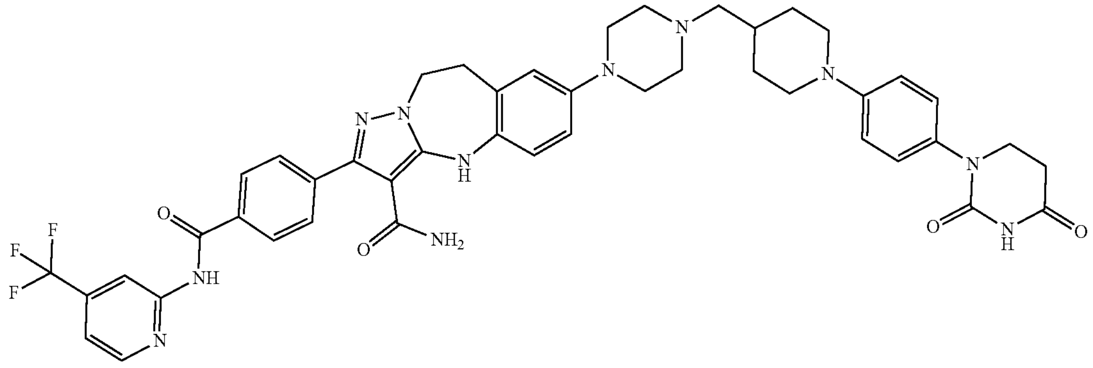

-continued
42 B3
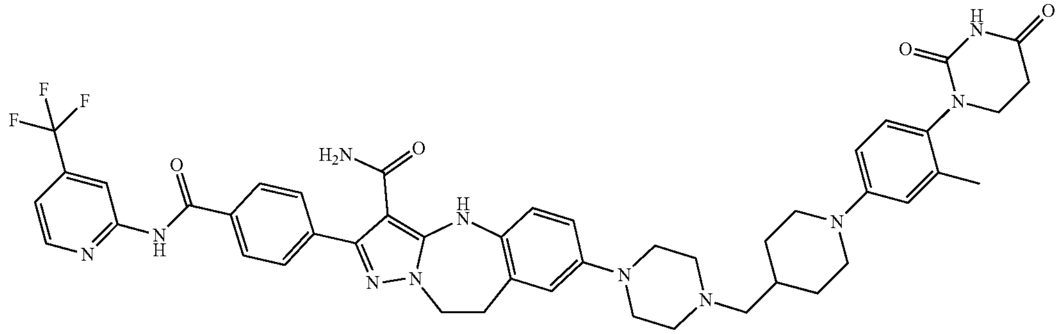
43 B9
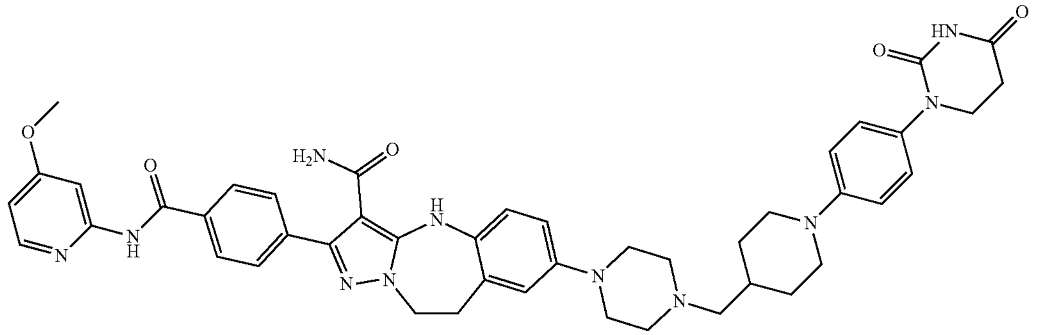
44 B10
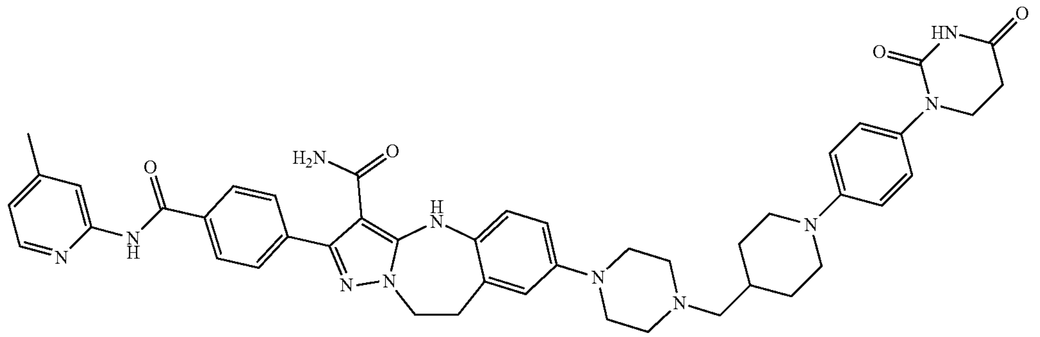
45 B11
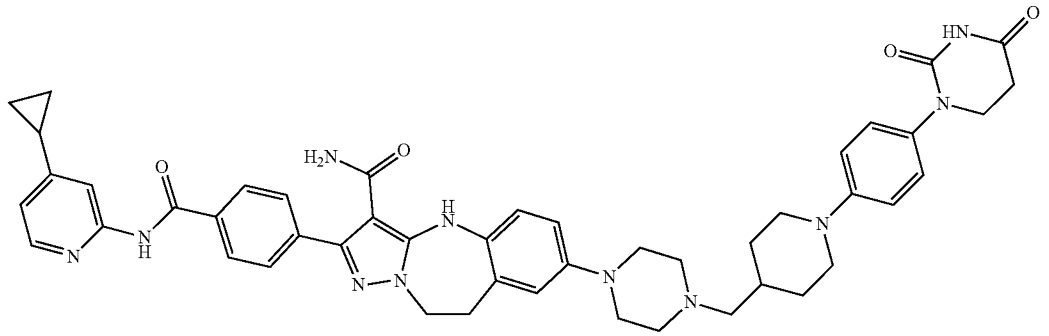

-continued
46 B12
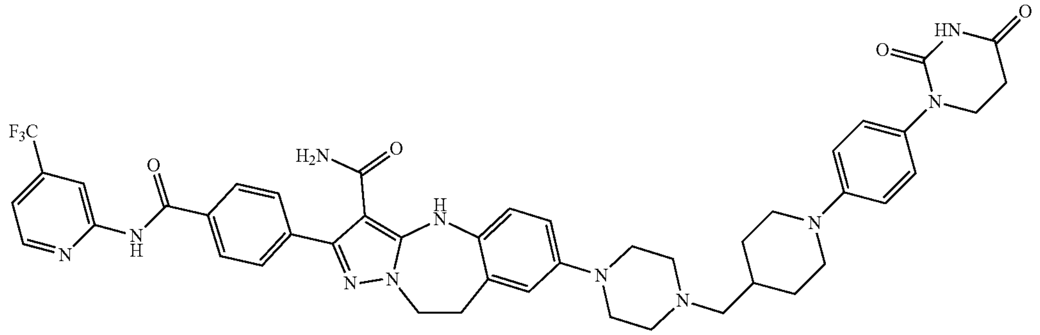
47 B13
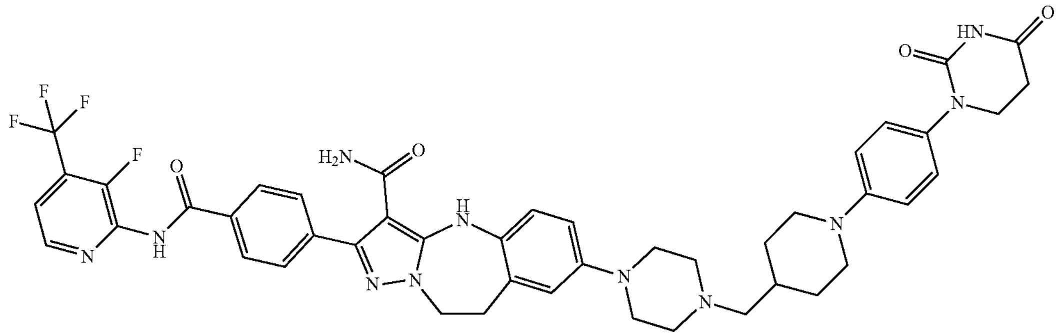
48 B4
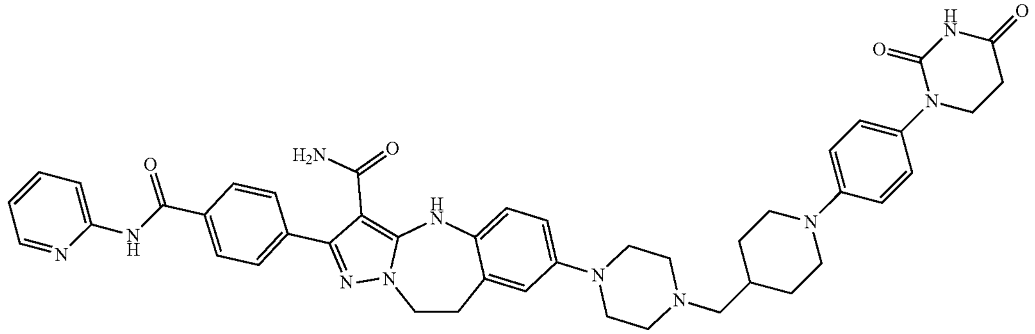
49 B16
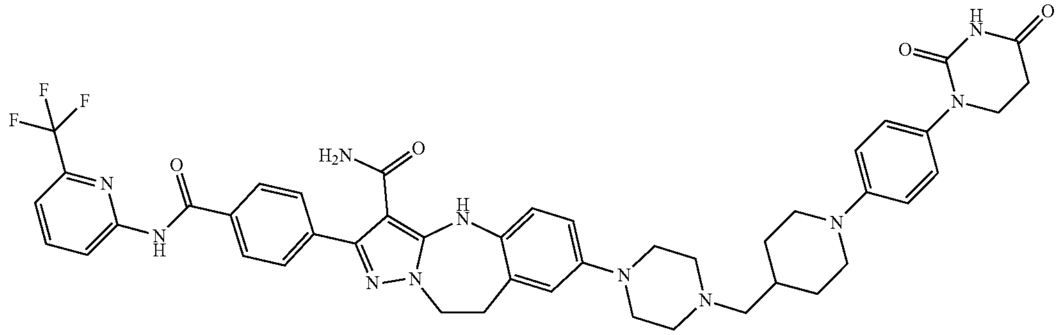

-continued
50 B17
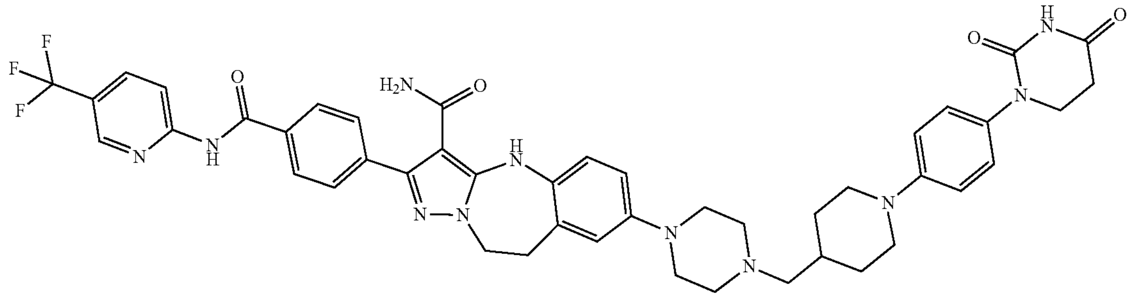
51 B18
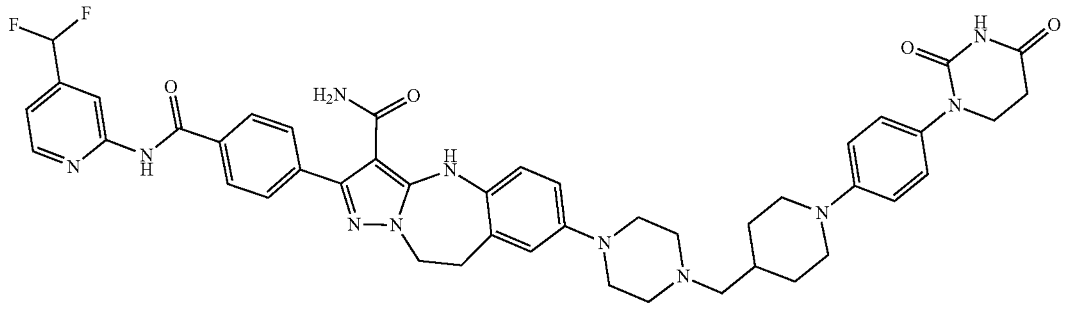
52 B19
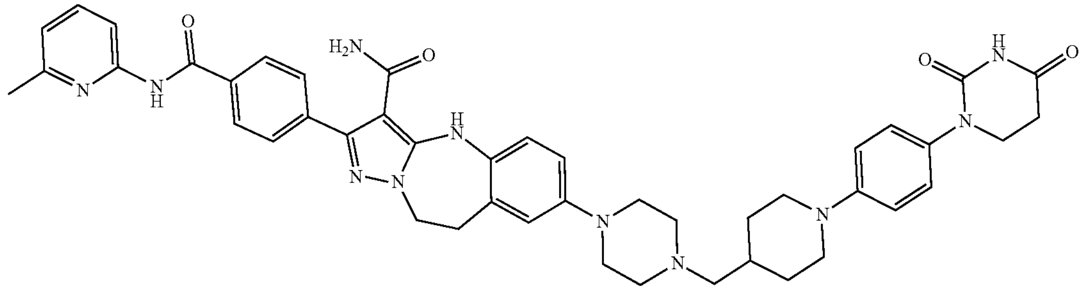
53 B2
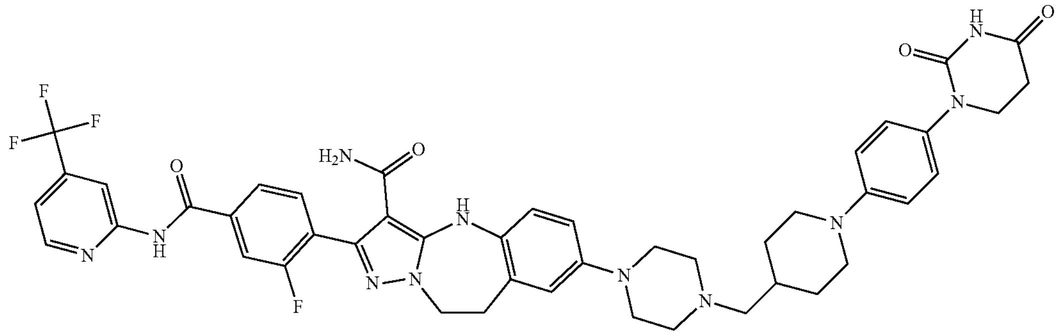
54 B8
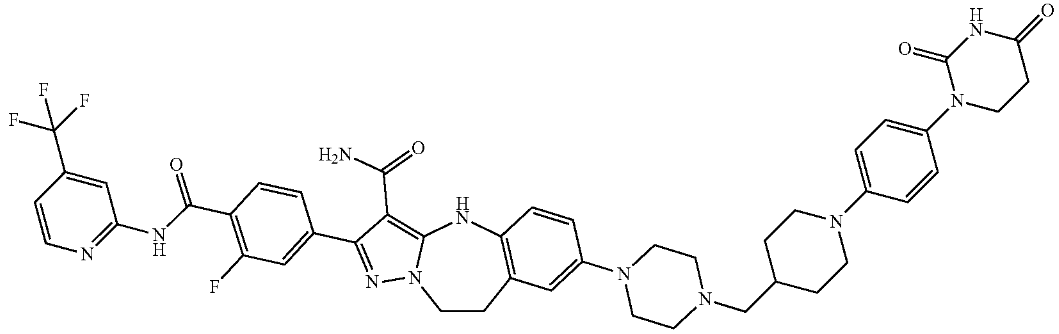

-continued
55 B14
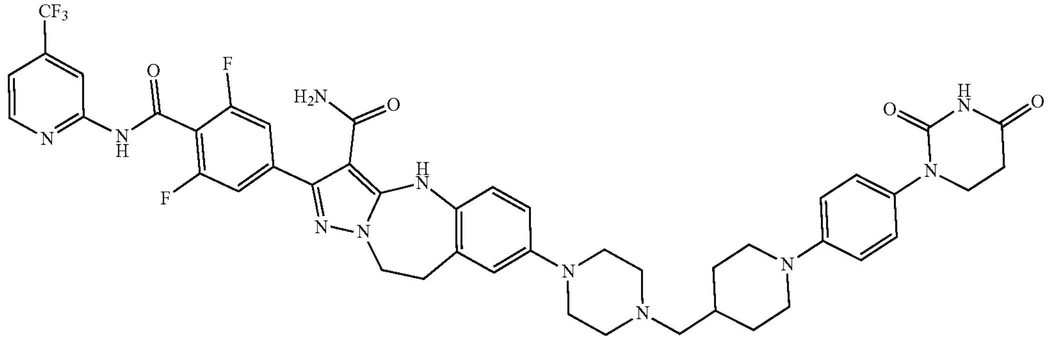
56 B6
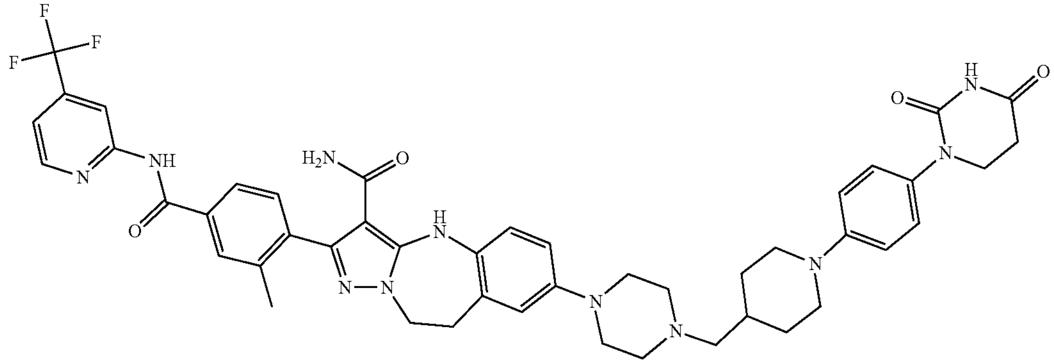
57 B22
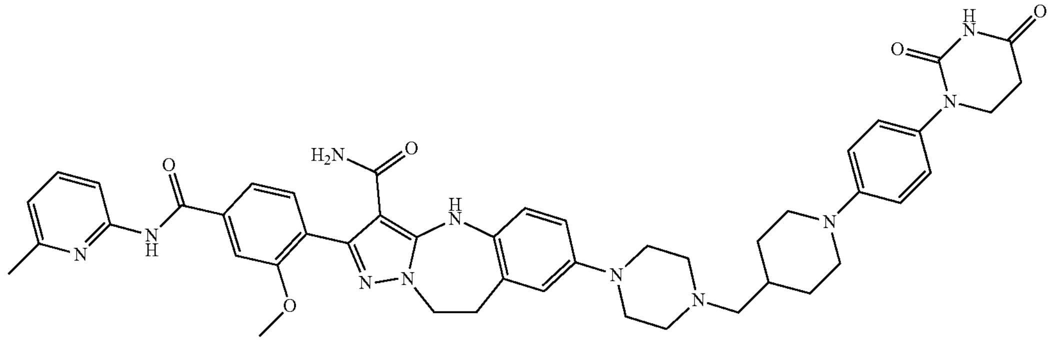
58 B27
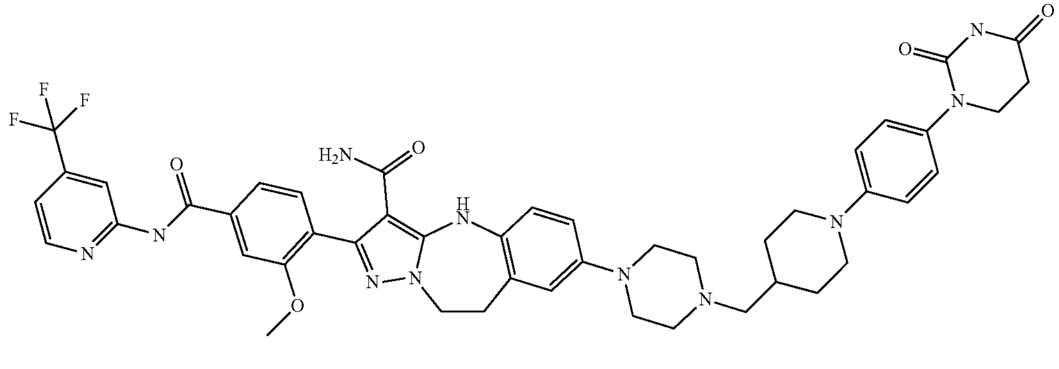

-continued
59 B7
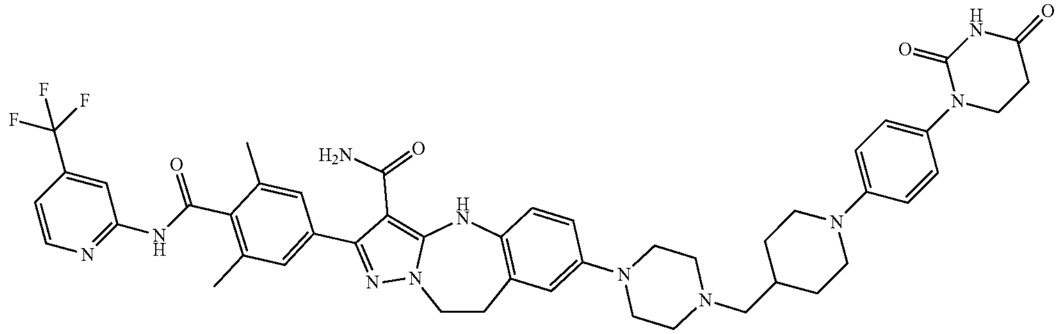
60 B5
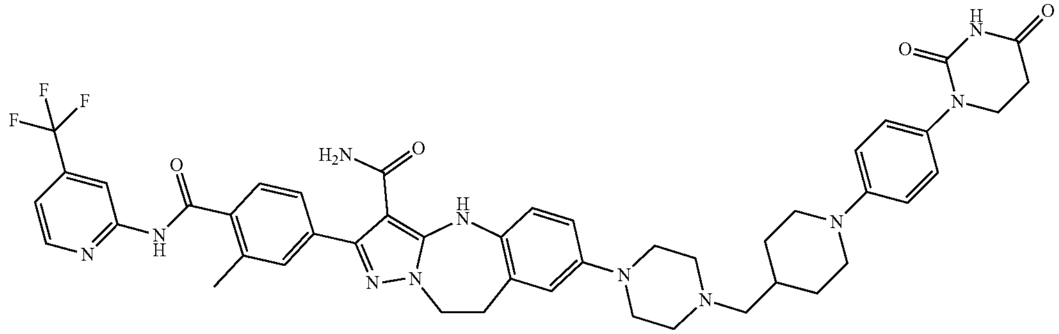
61 21
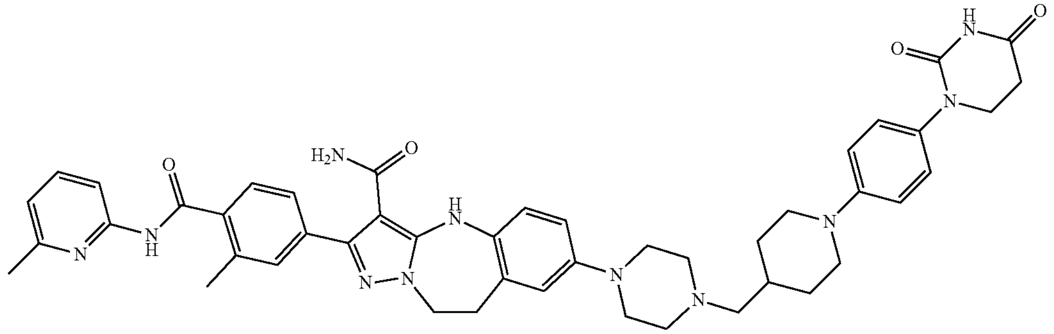
62 B23
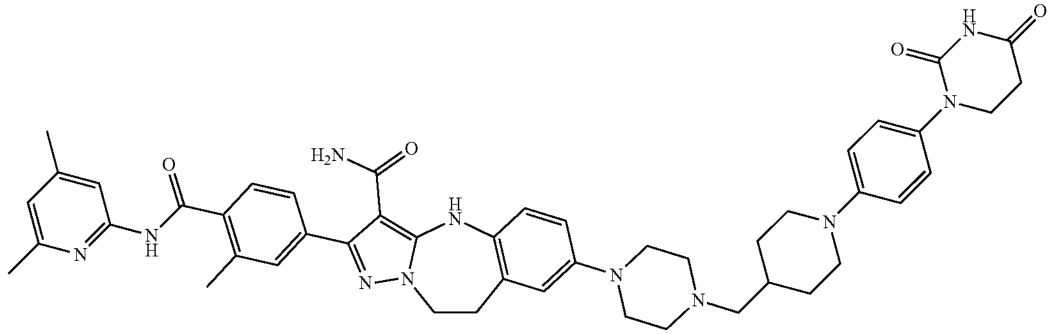

-continued
63 B20
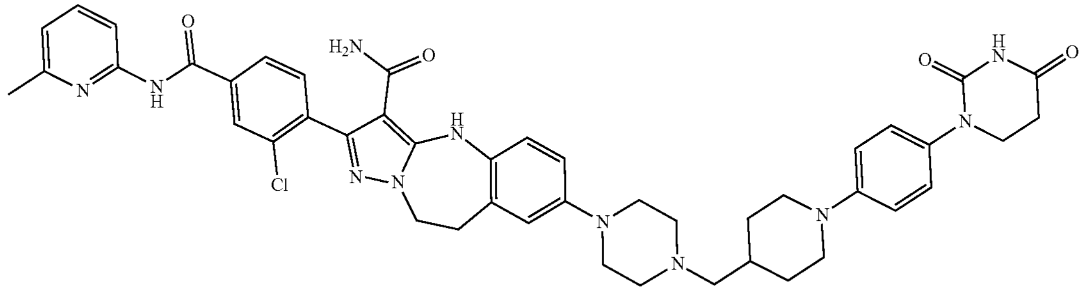
64 B24
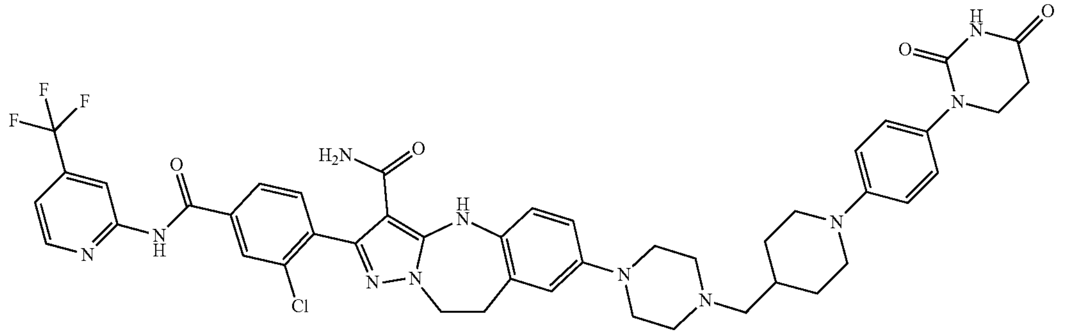
65 B25
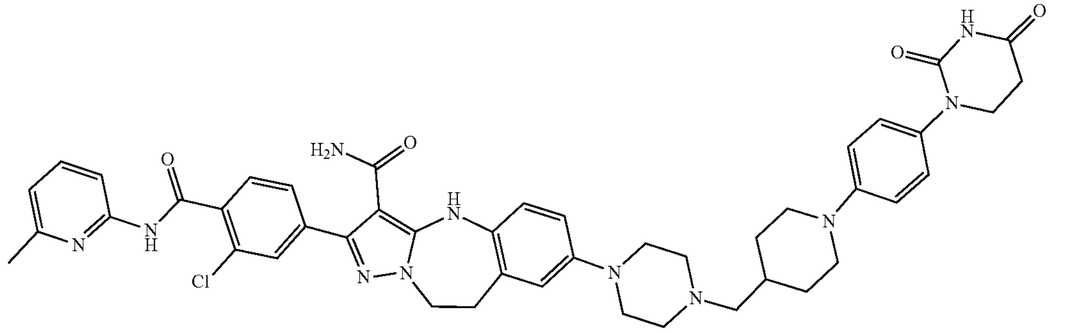
66 B26
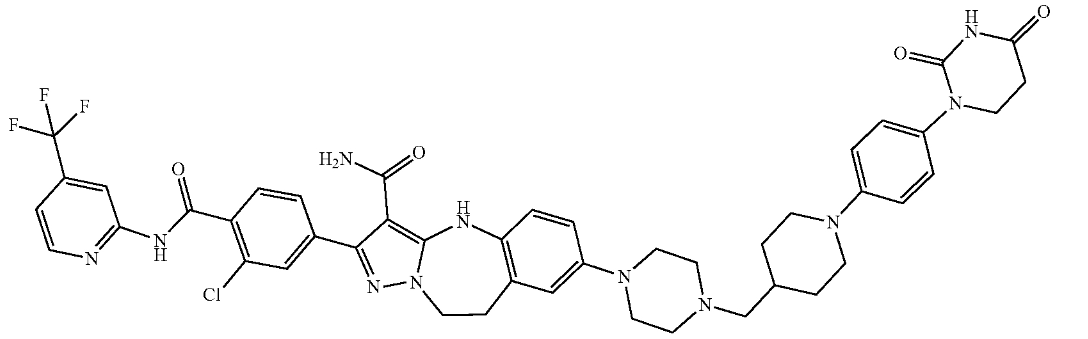

-continued
67 B15
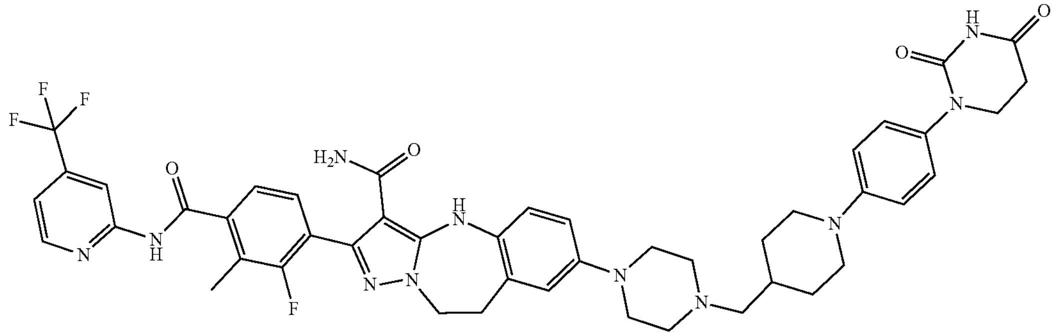
68 B28
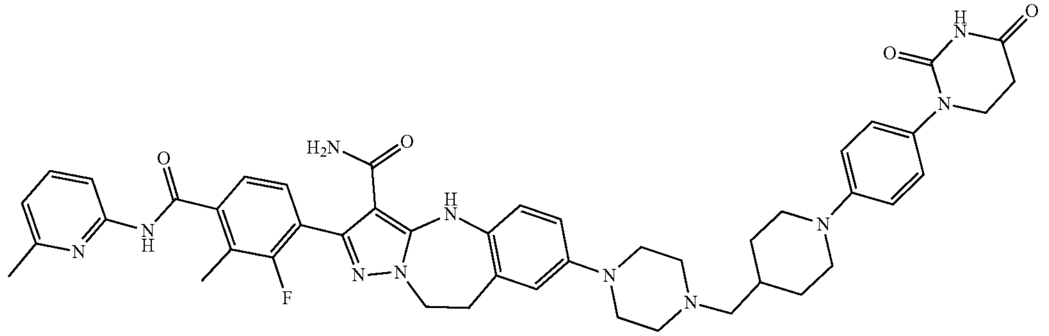
69 C1
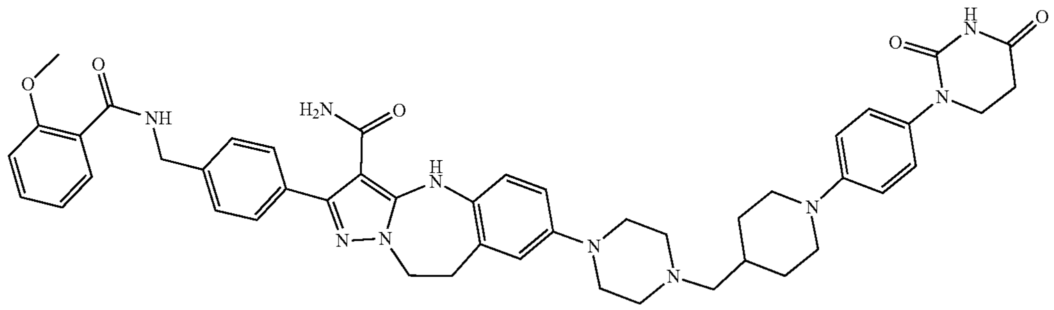
70 C2
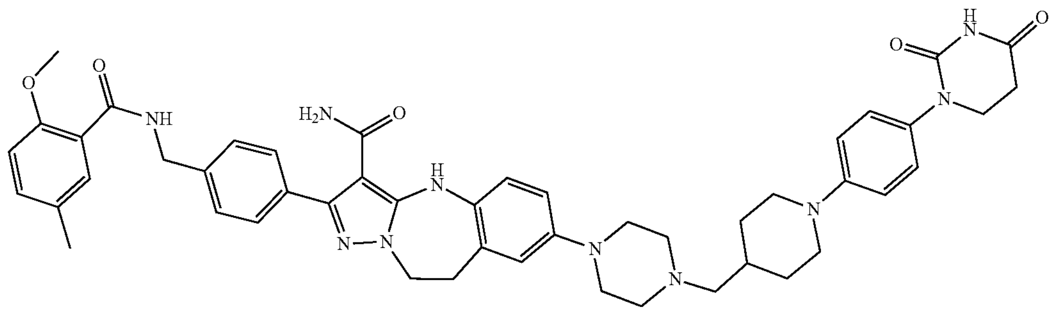
71 C4
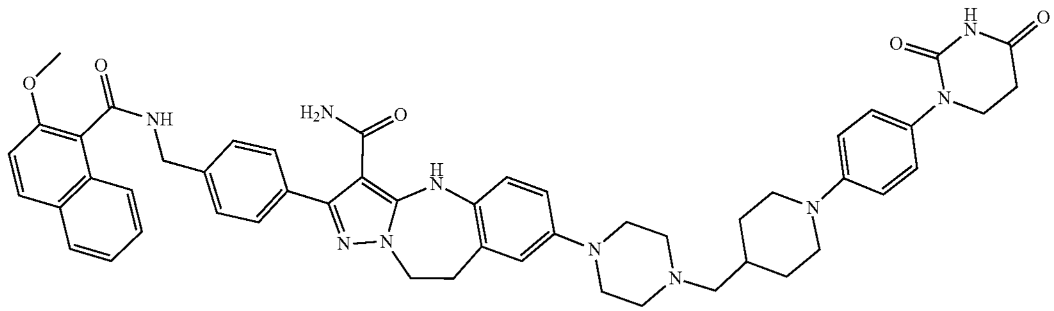

-continued
72 C3
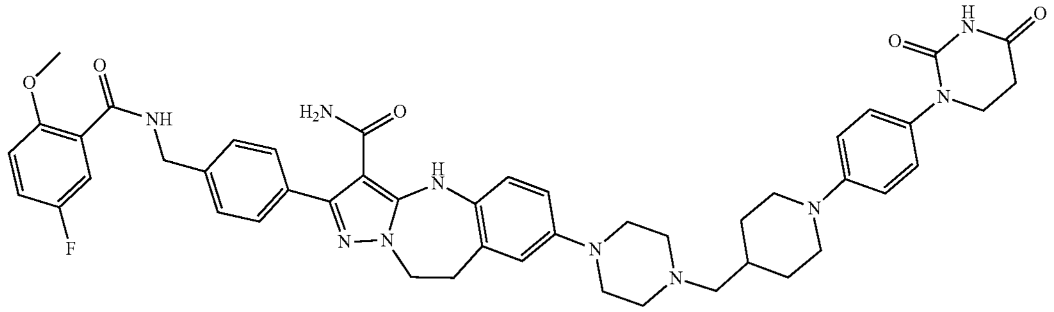
73 C21
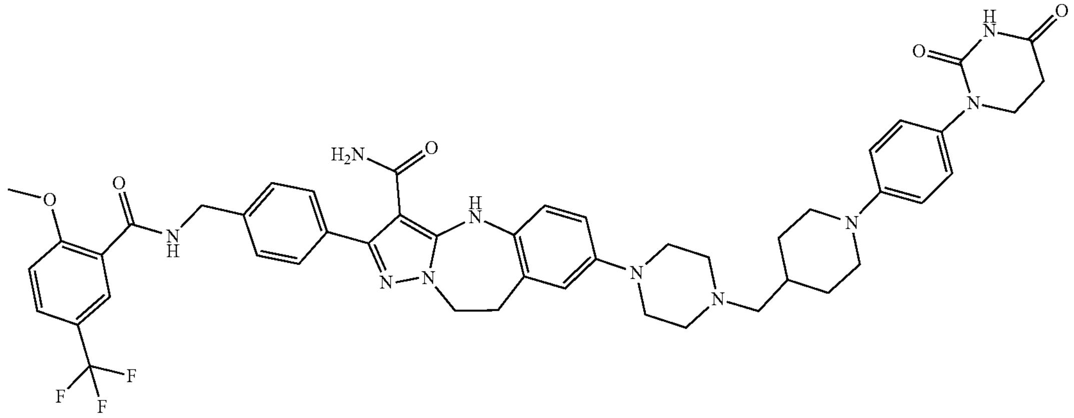
74 C22
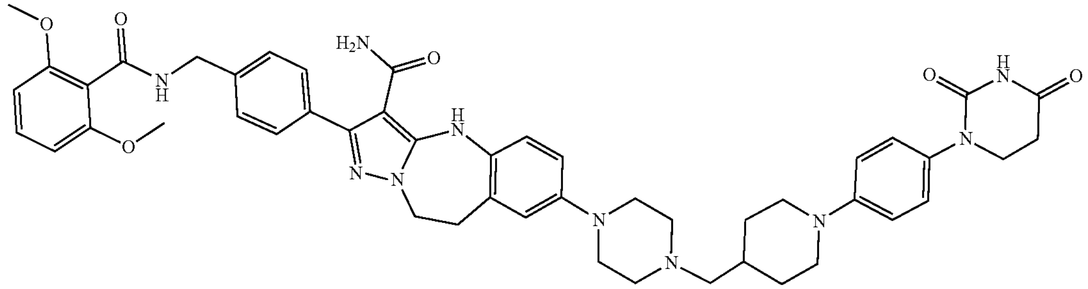
75 C23
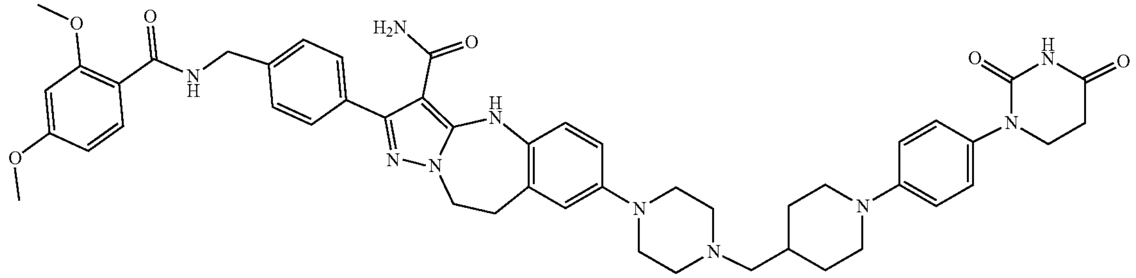
76 C25
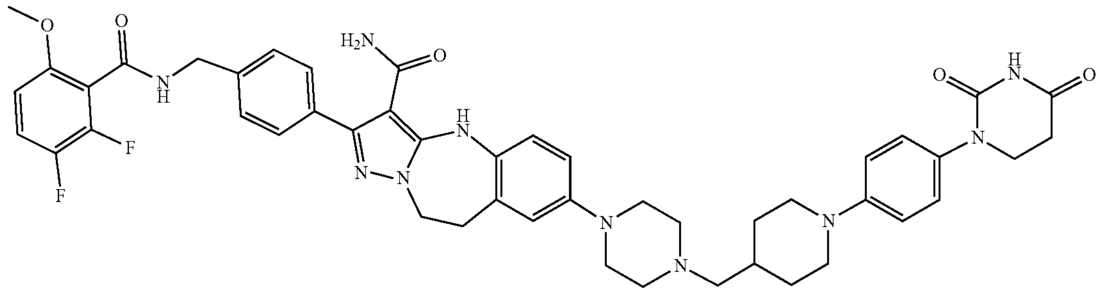

-continued
77 C29
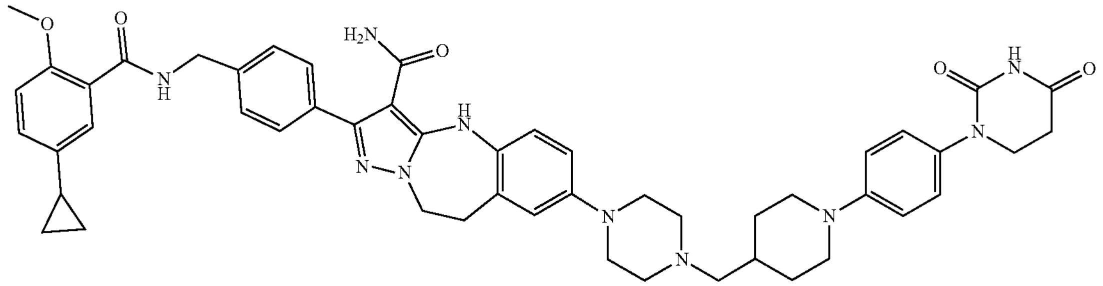
78 C30
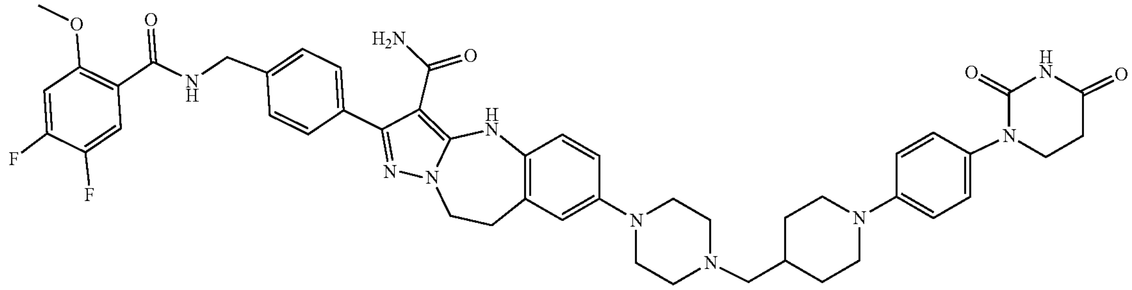
79 C12
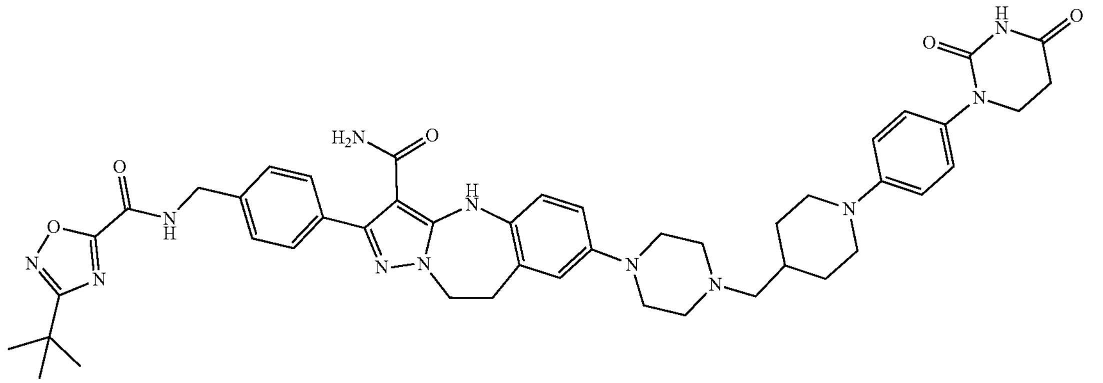
80 C7
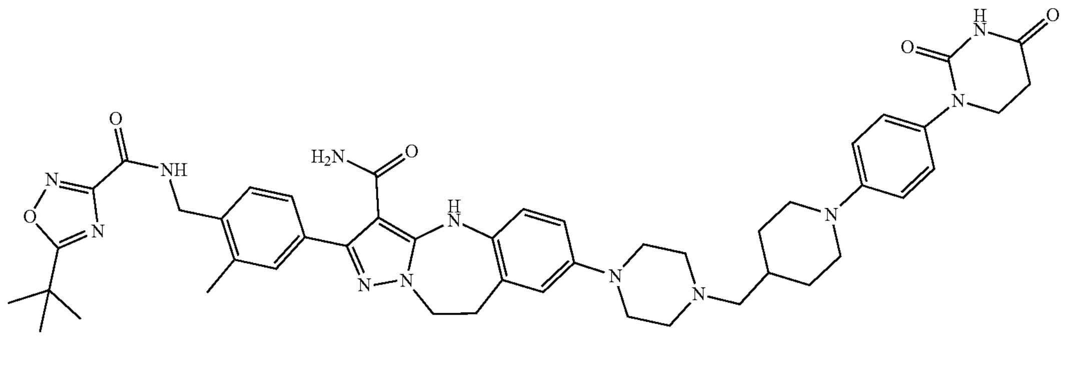

-continued
81 C8
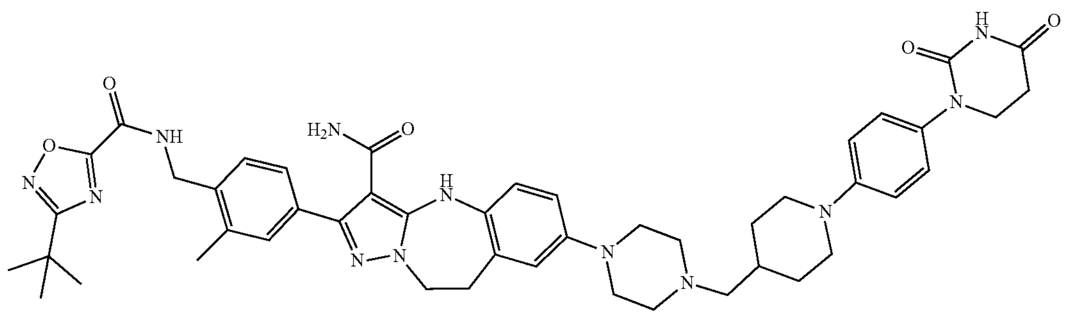
82 C9
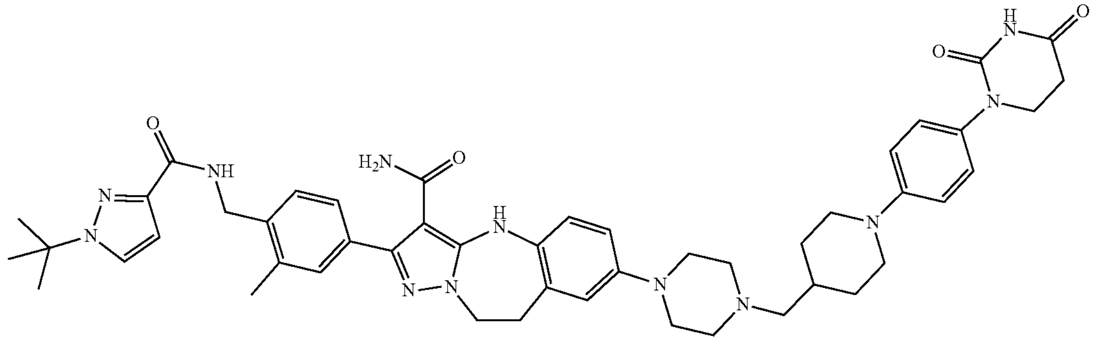
83 C10
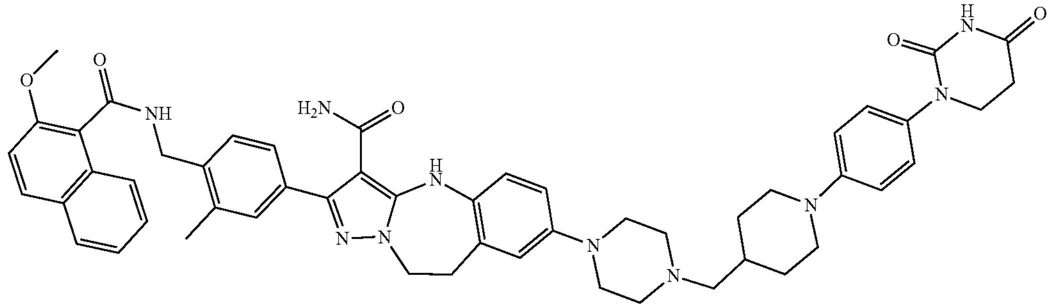
84 C11
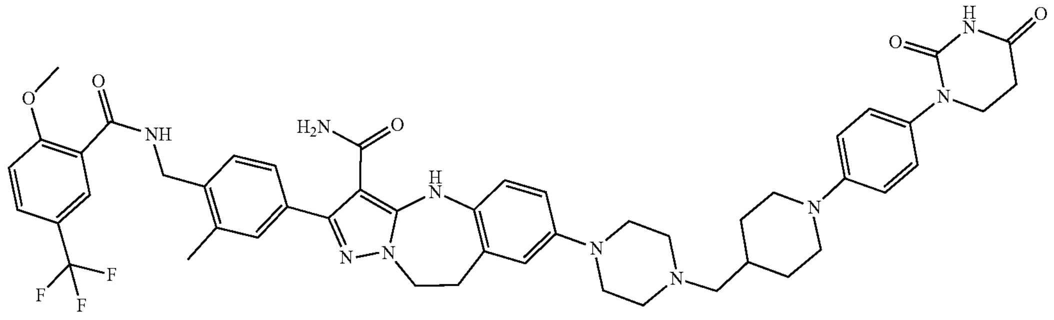
85 C6
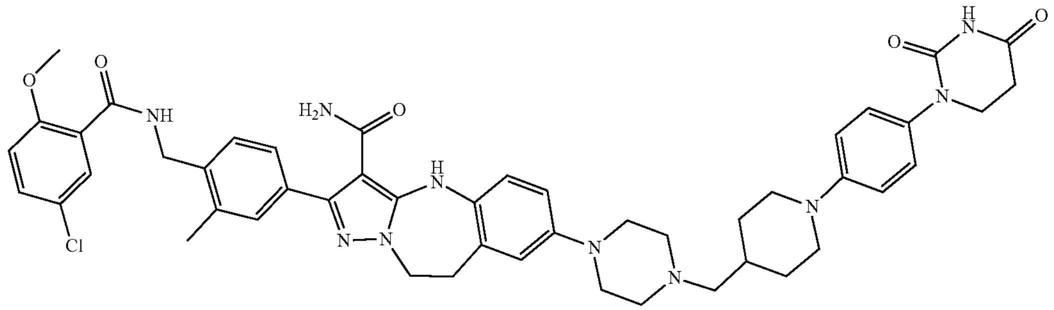

-continued
86 C19
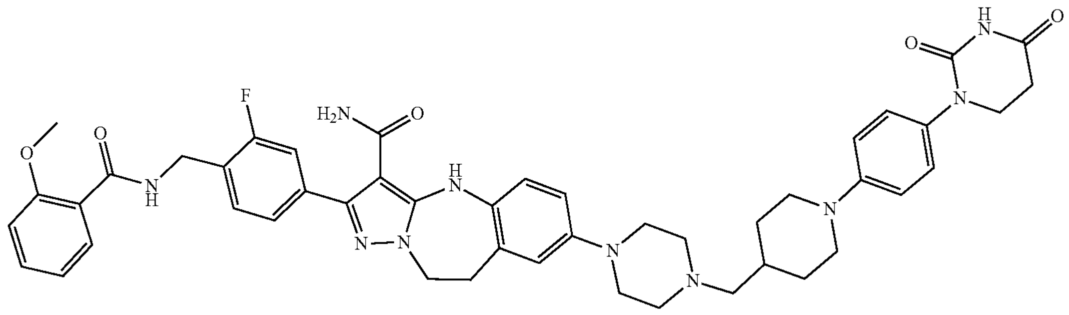
87 C20
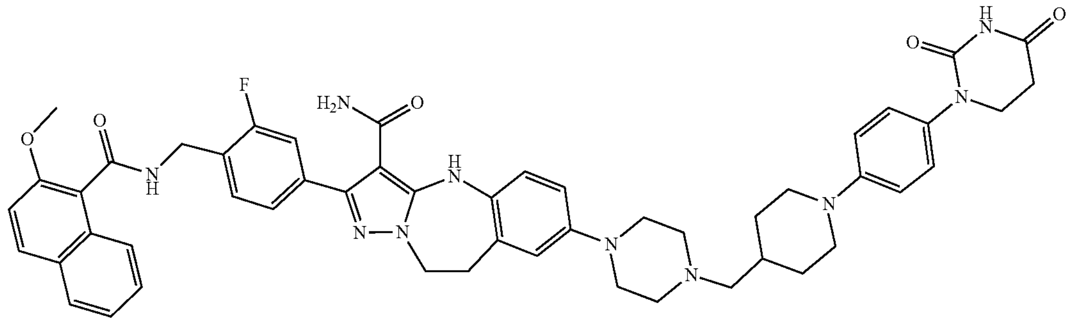
88 C26
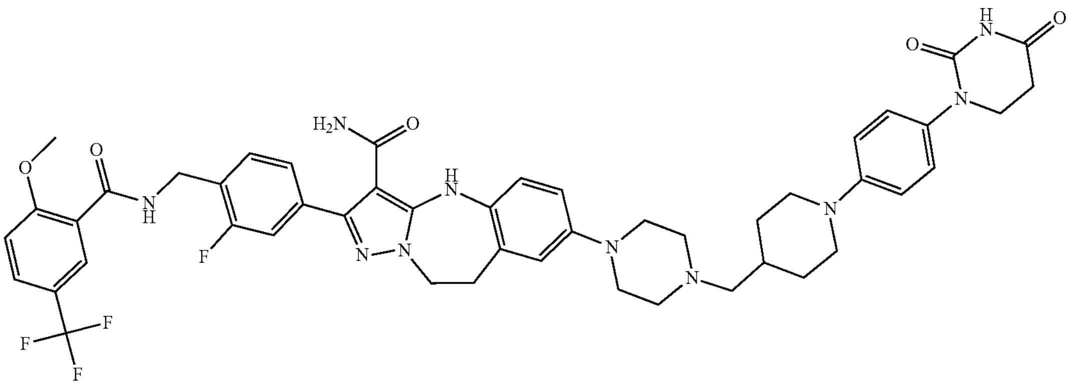
89 C27
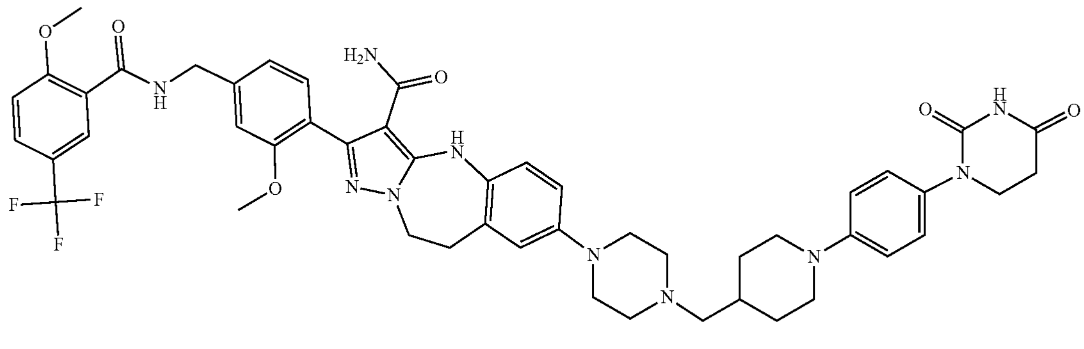

-continued
90 C24
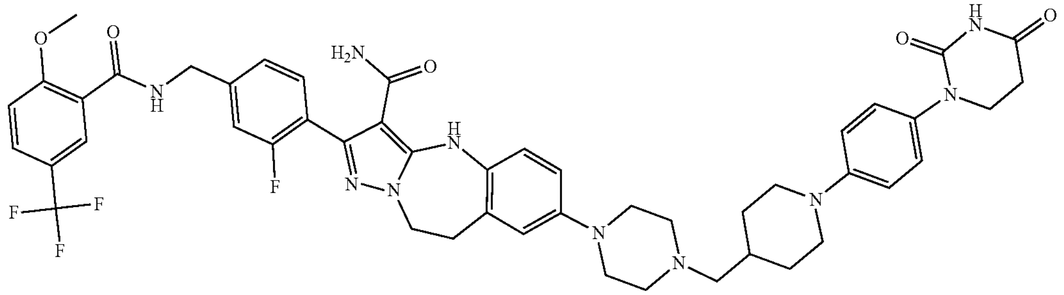
91 C28
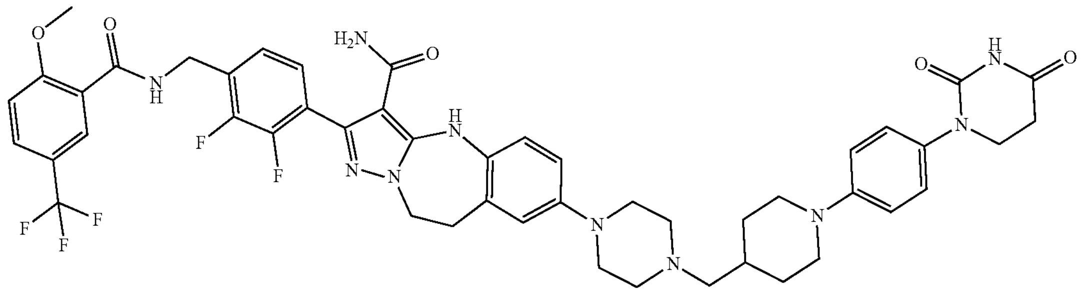
92 C15
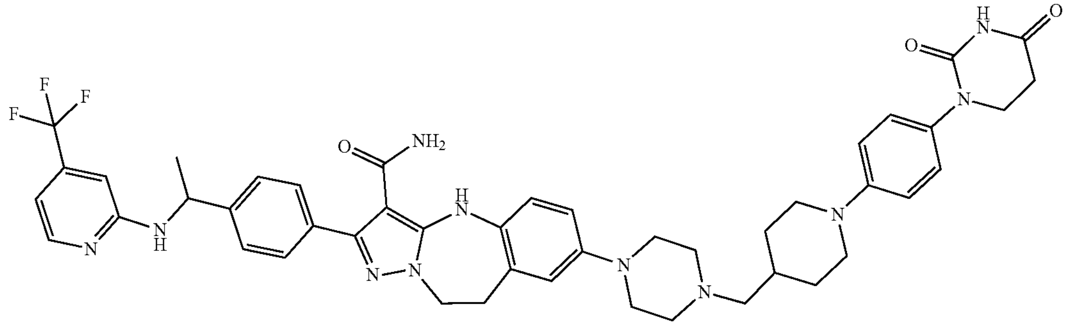
93 C16
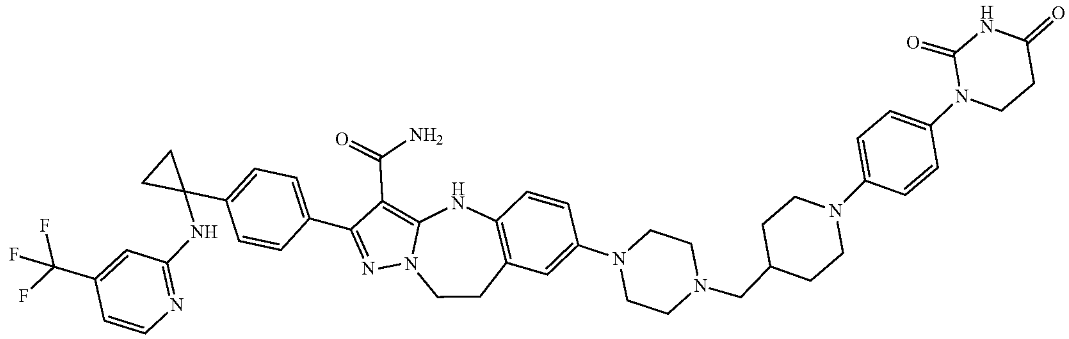
94 C17
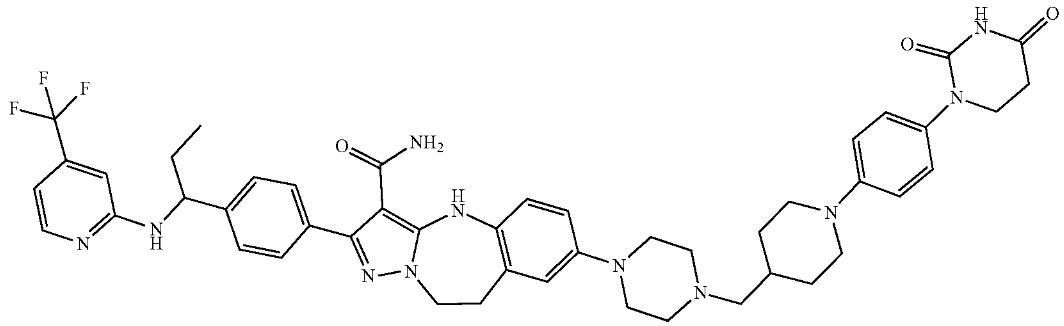

-continued
95 C18
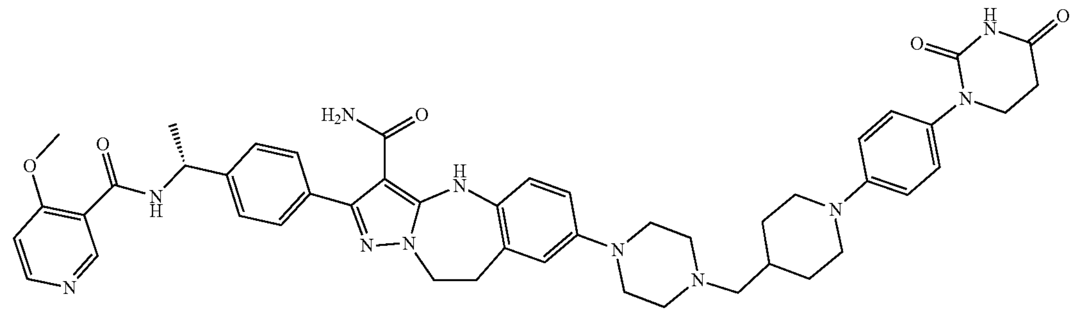
96 C5
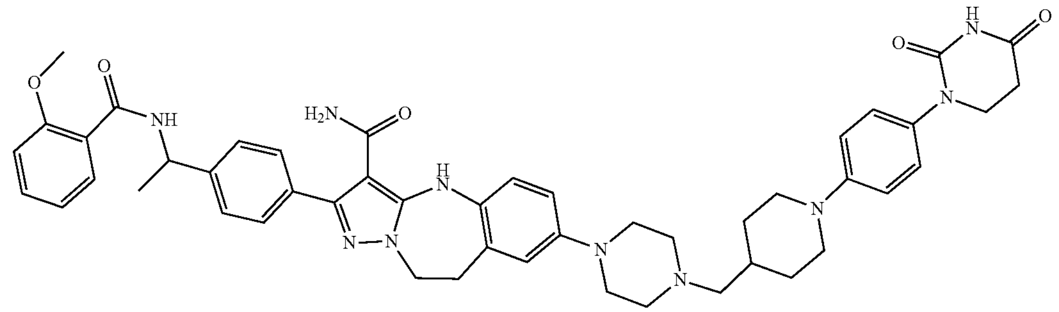
97 C14
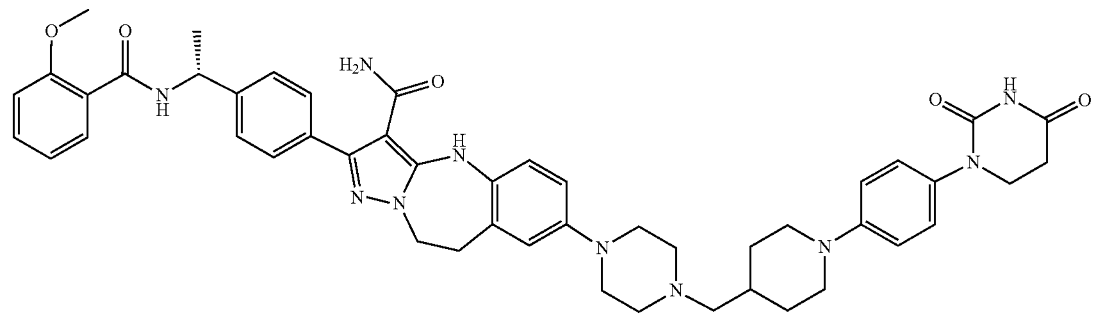
98 C13
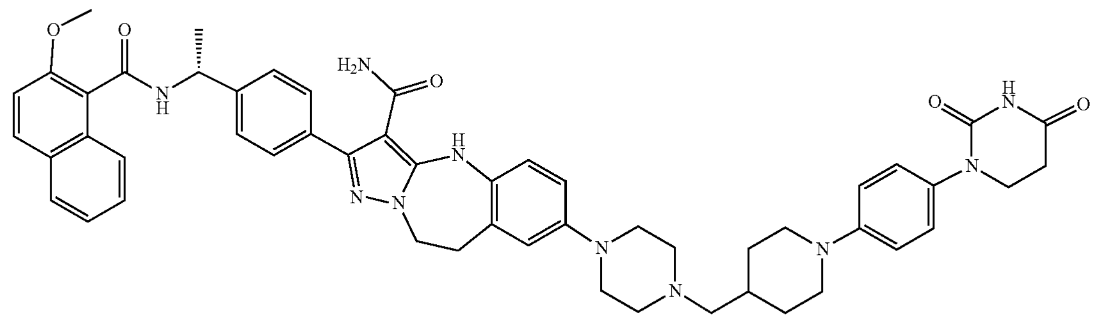

-continued
99
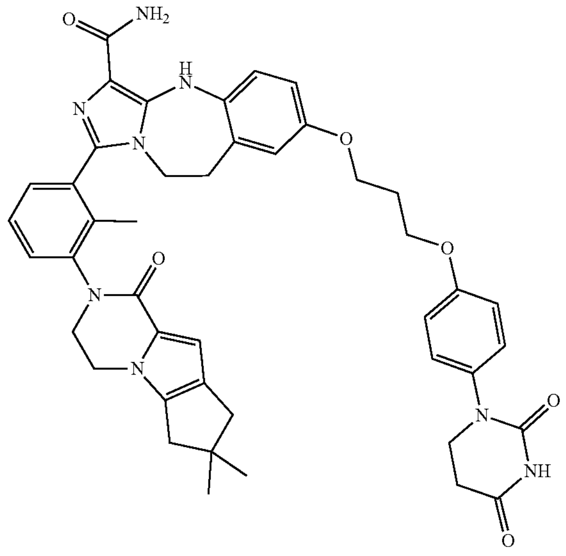
100 B30
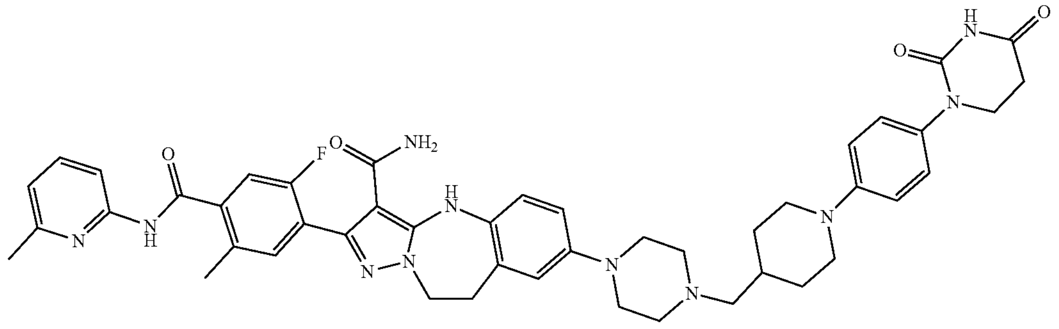
101 B31
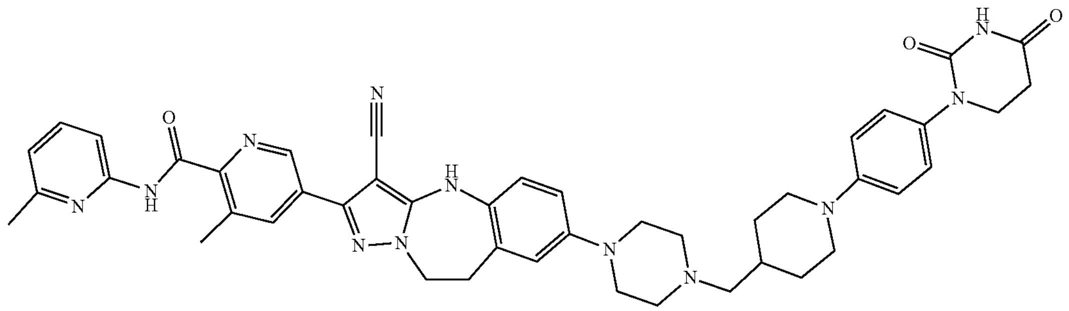
102 B32
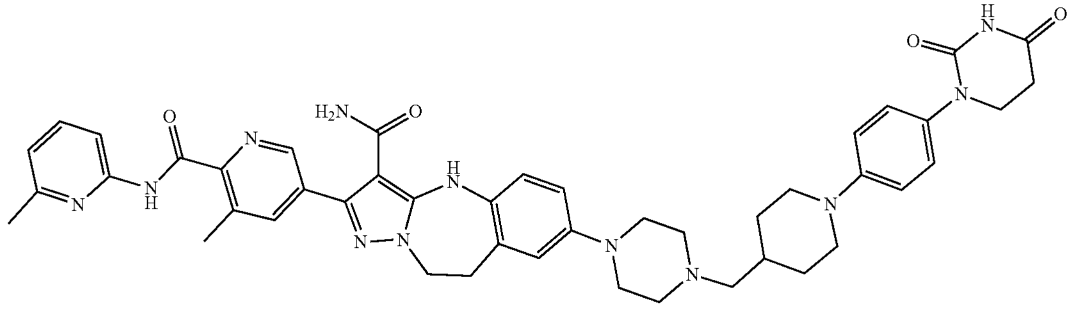

-continued
103 B33
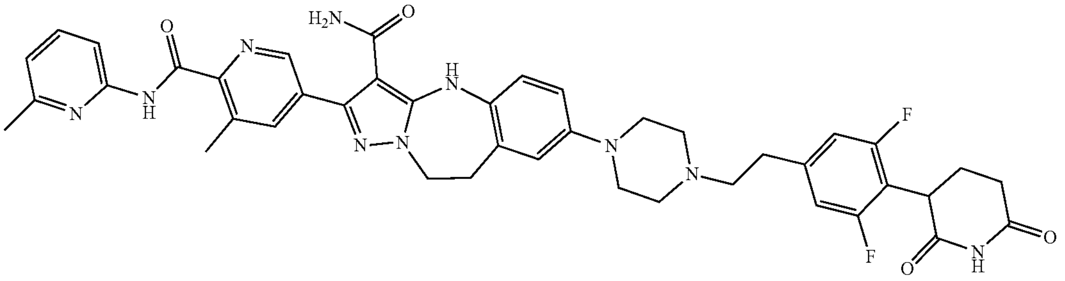
104 B34
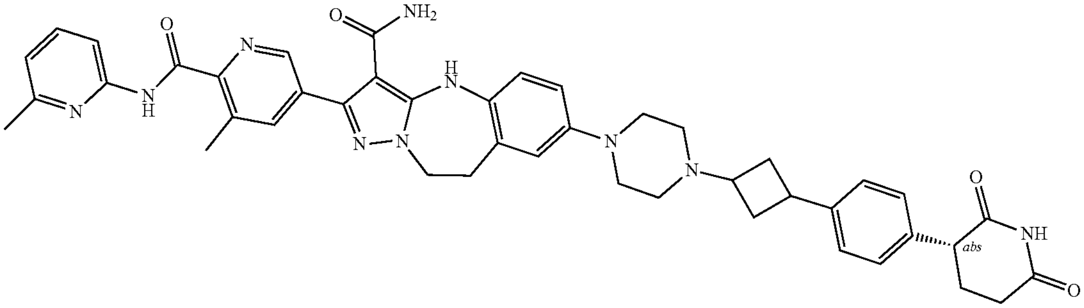
105 B35
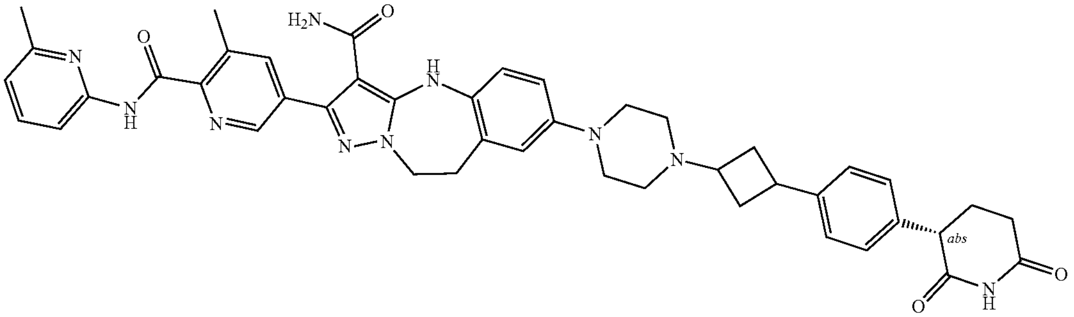
106 B36
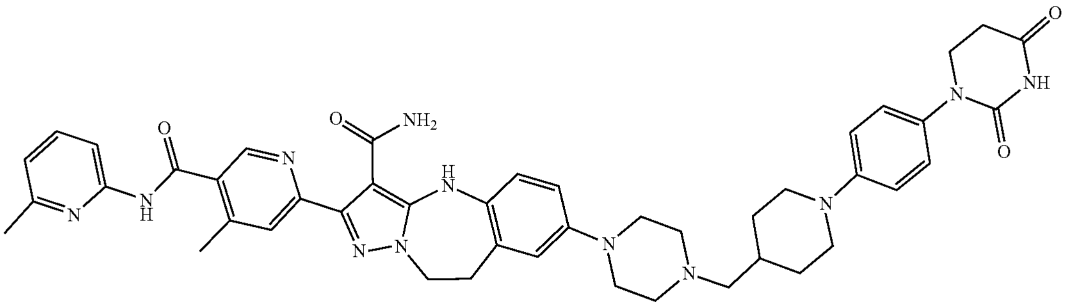
107 B37
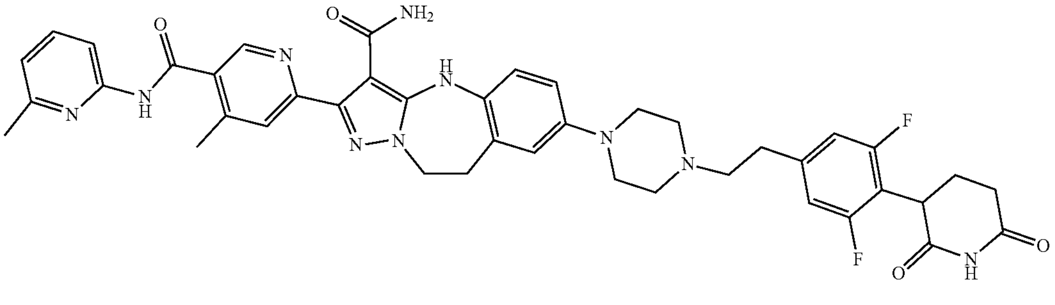

-continued
108 B38
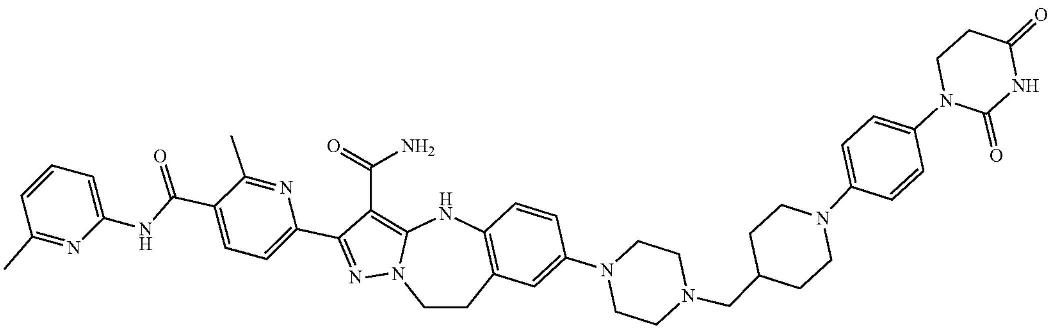
109 B39
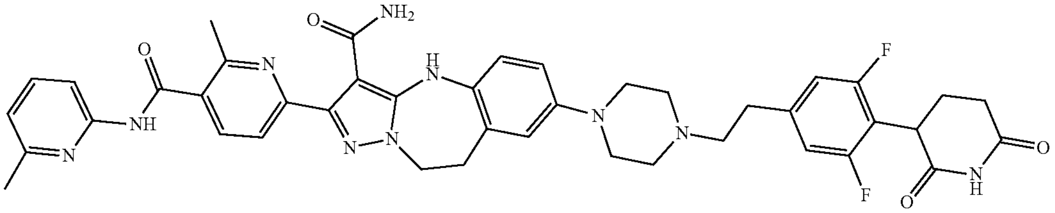
110 B40
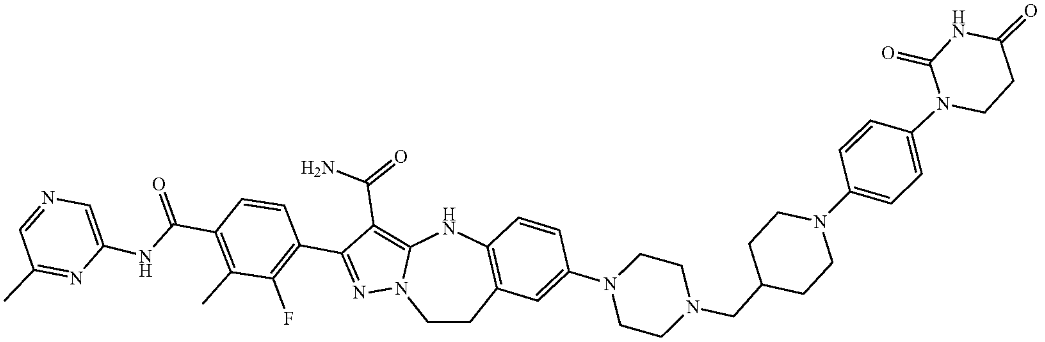
111 B41
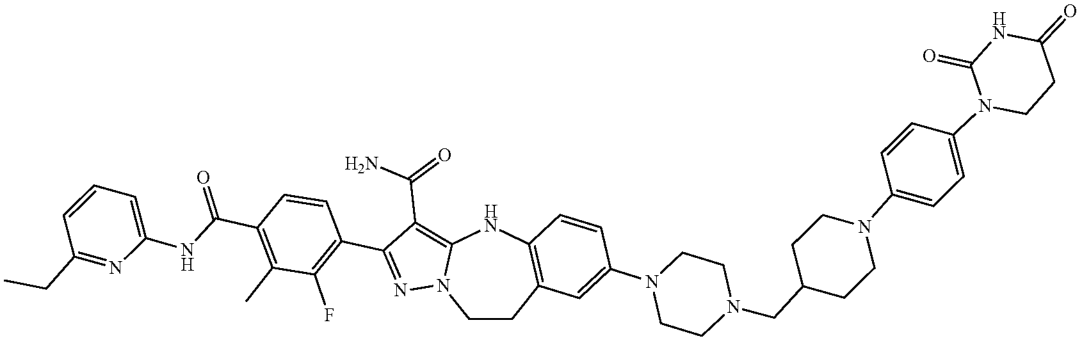
112 B42
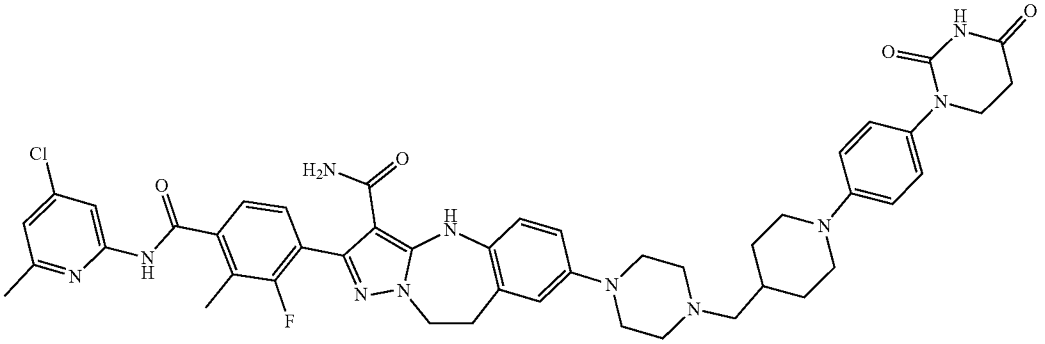

-continued
113 B43
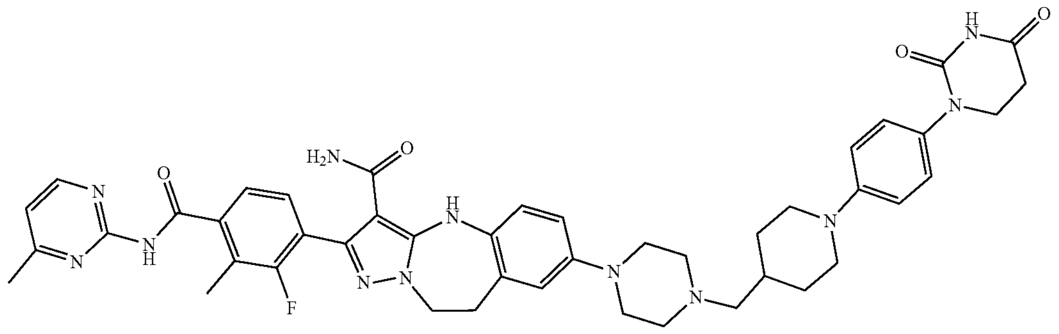
114 B44
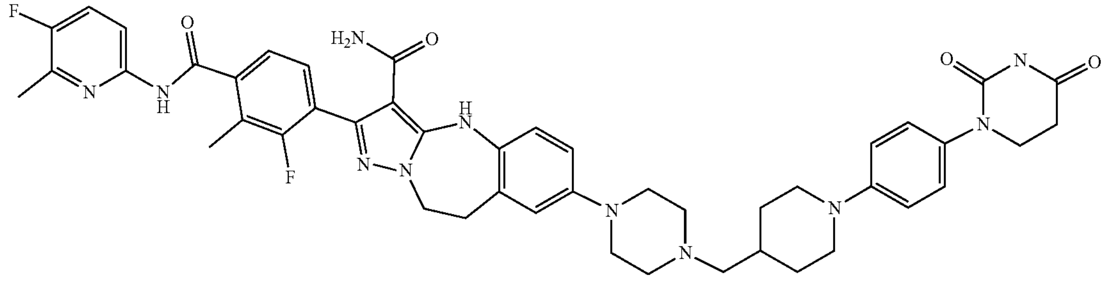
115 B45
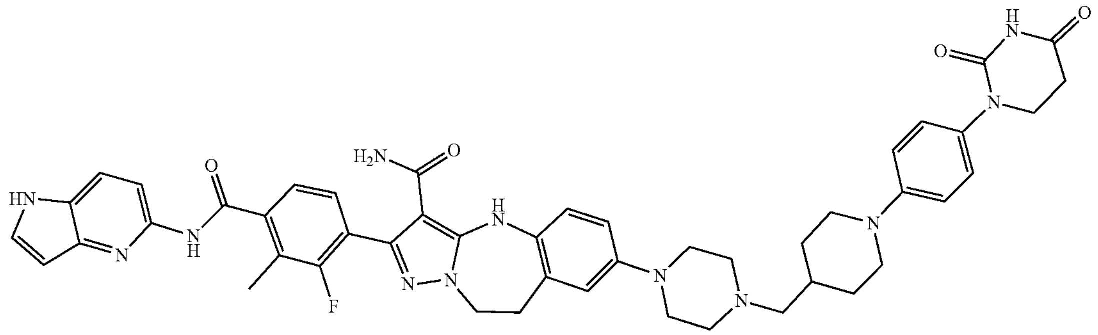
116 B46
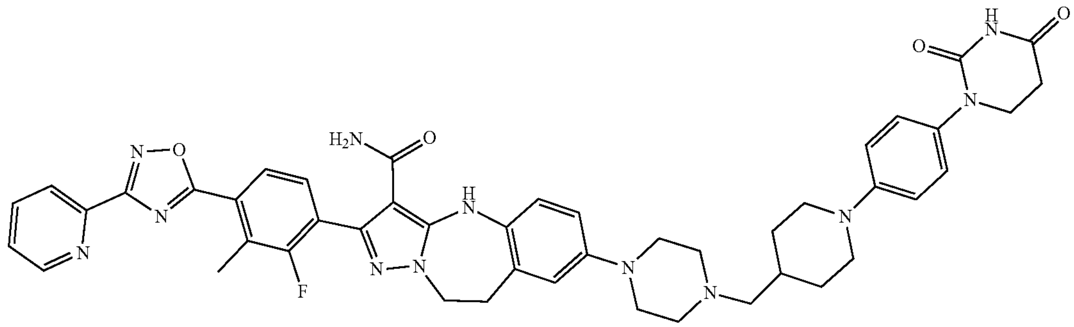

-continued
117 B47
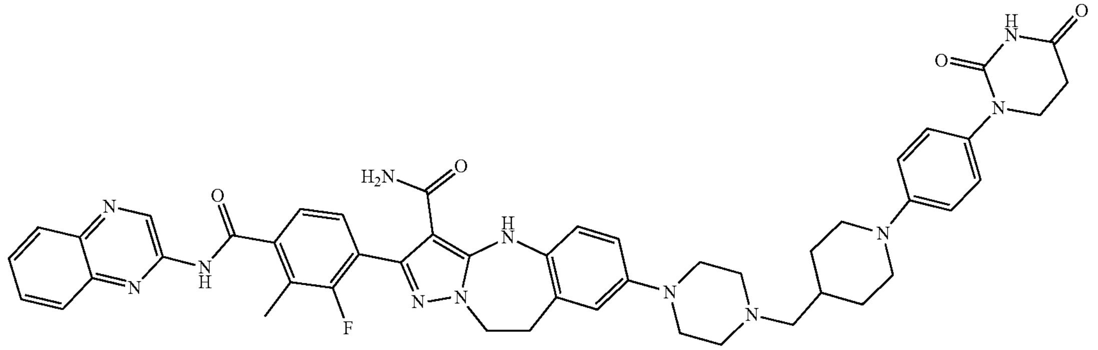
118 B48
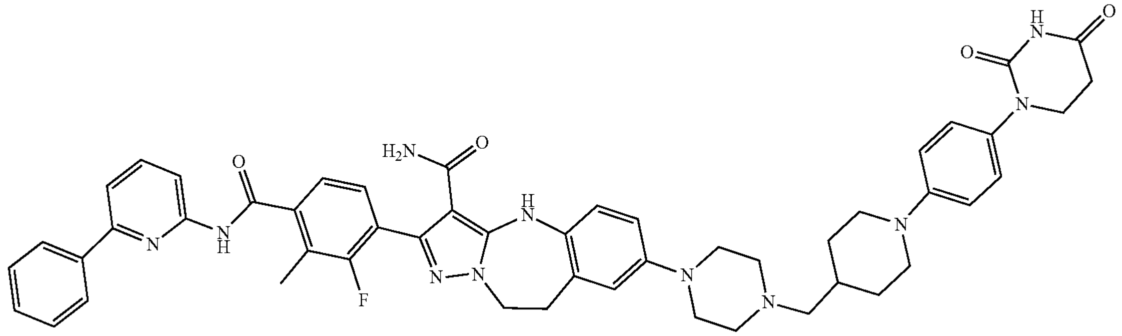
119 B49
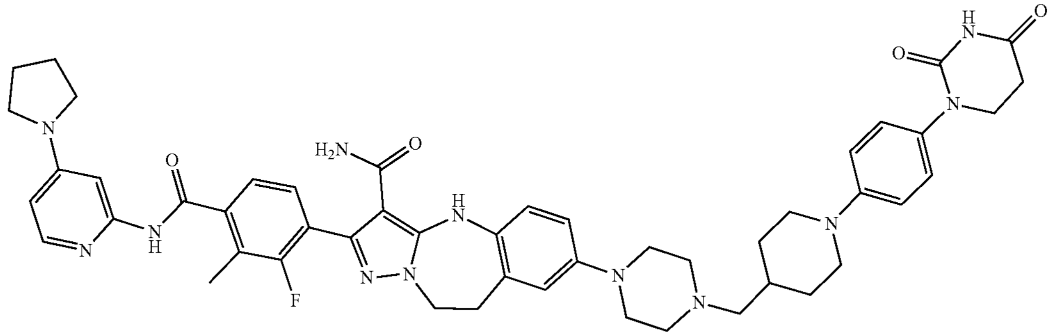
120 B50
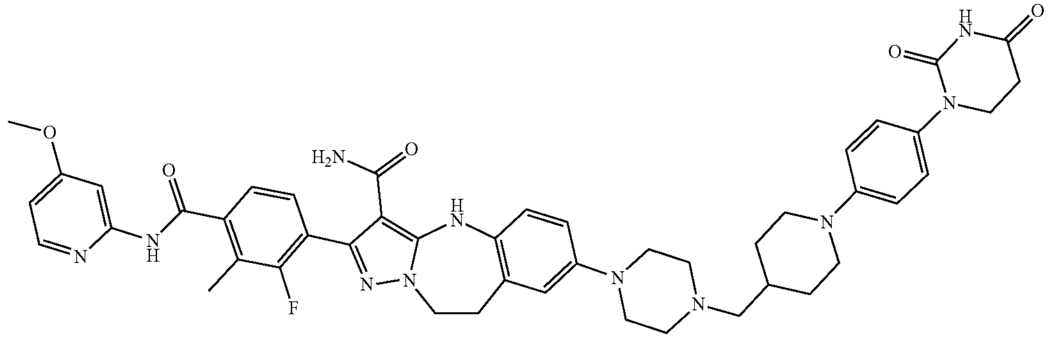

-continued
121 B51
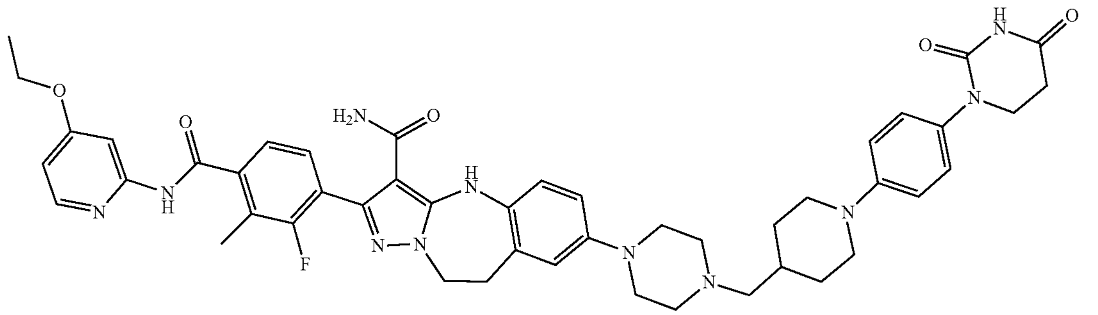
122 B52
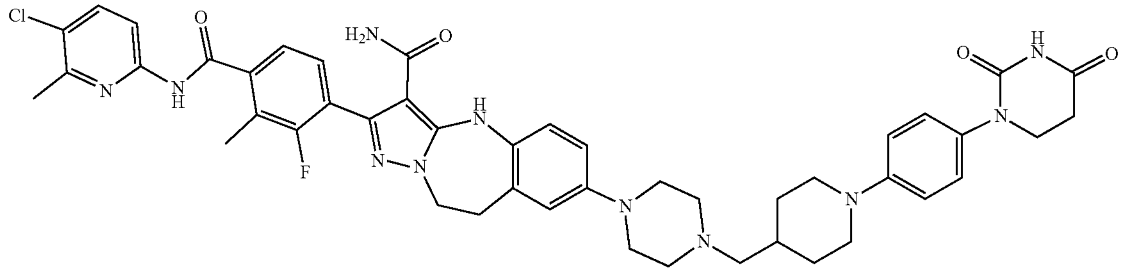
123 B53
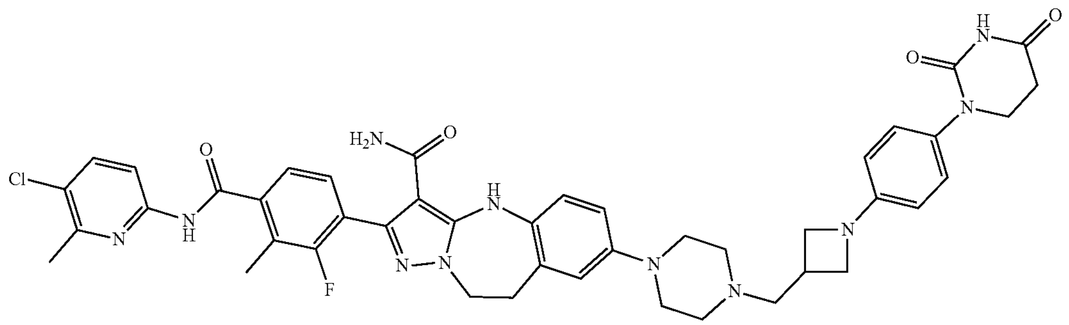
124 B54
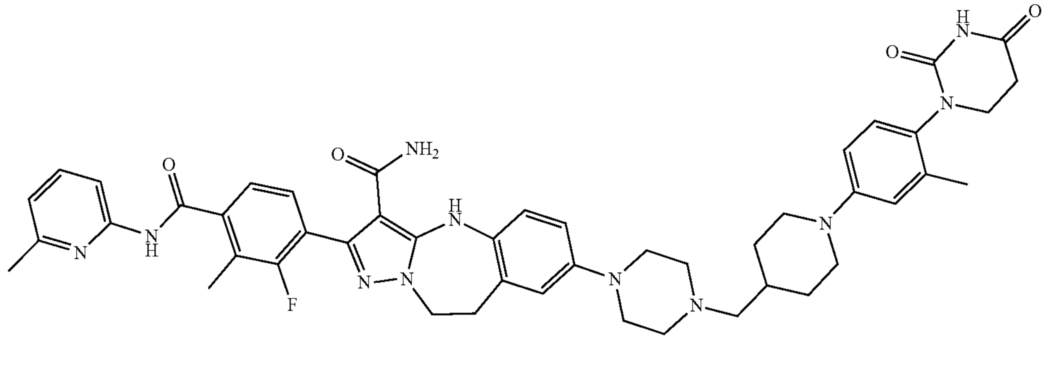
125 B55
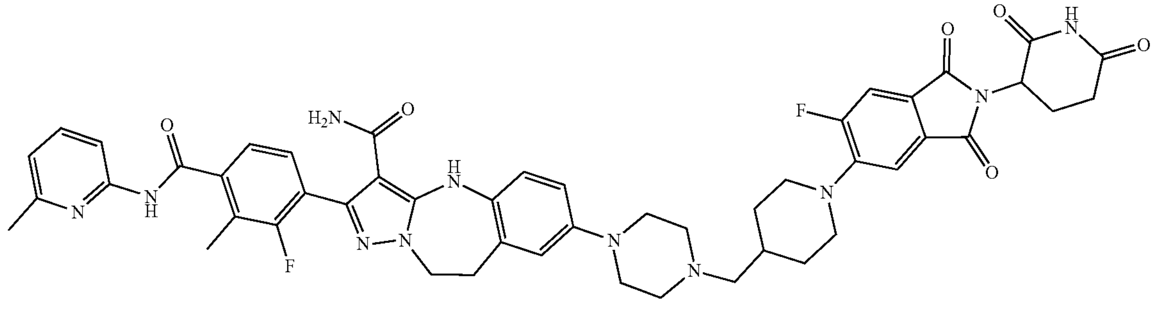

-continued
126 B56
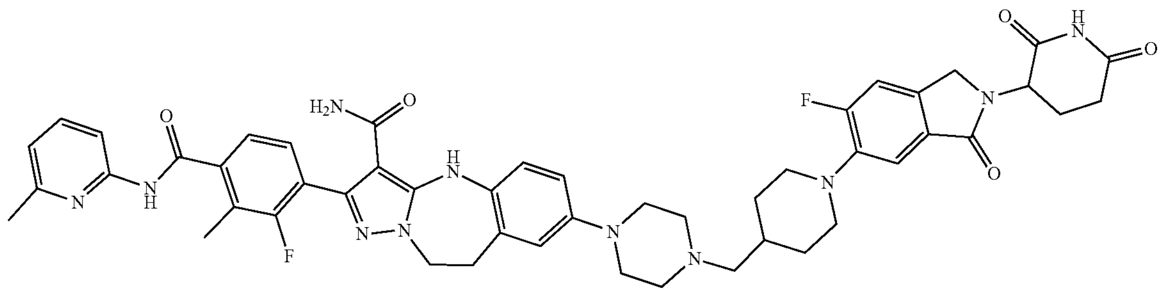
127 B57
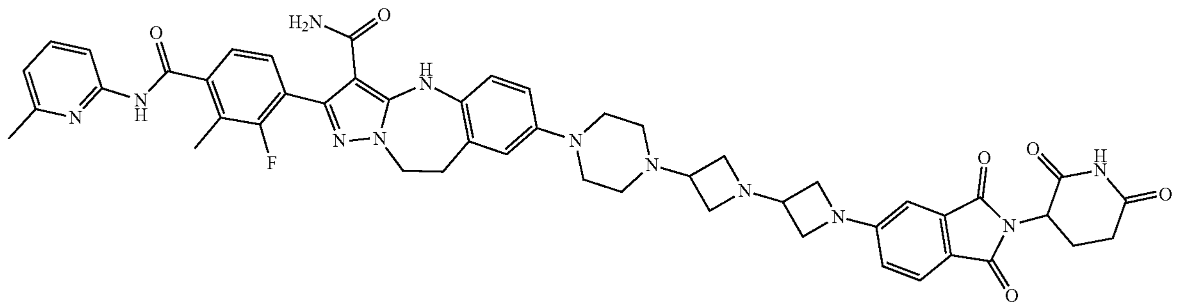
128 B58
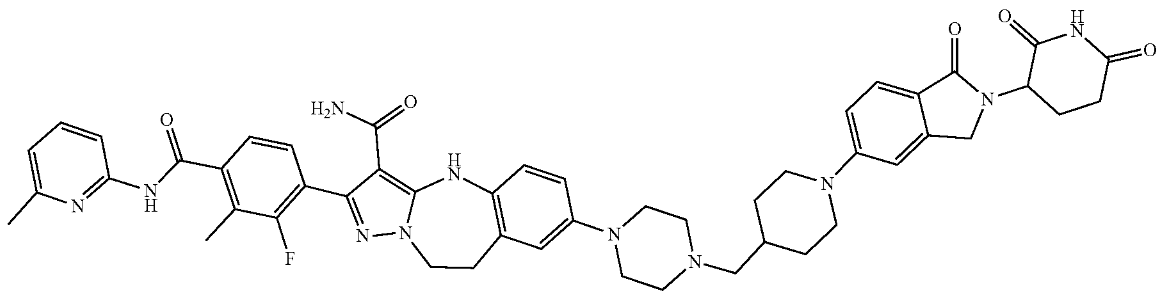
129 B59
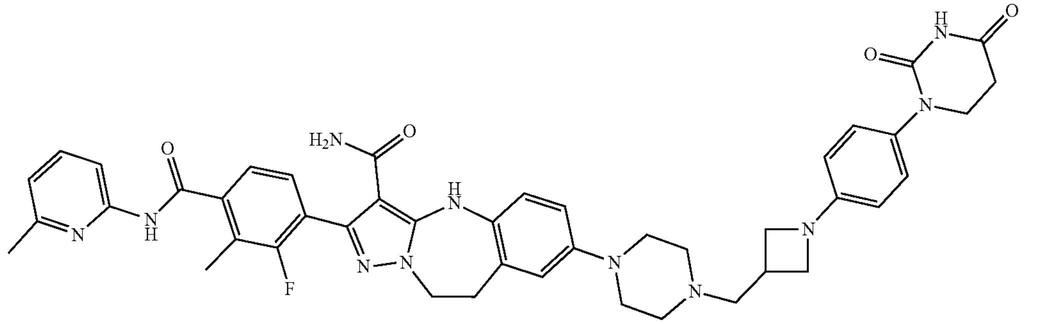
130 B60
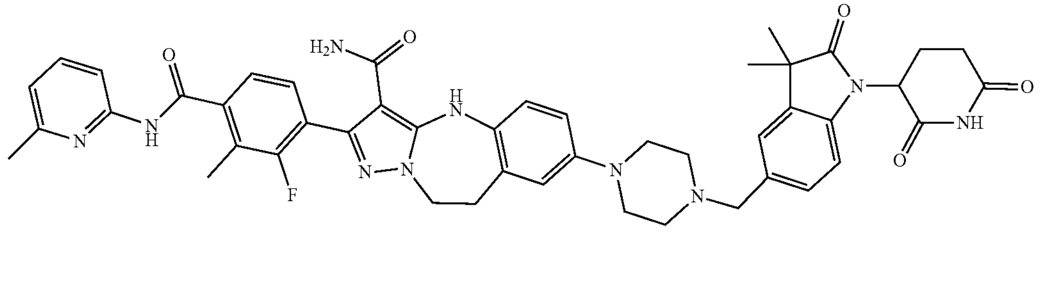

-continued
131 B61
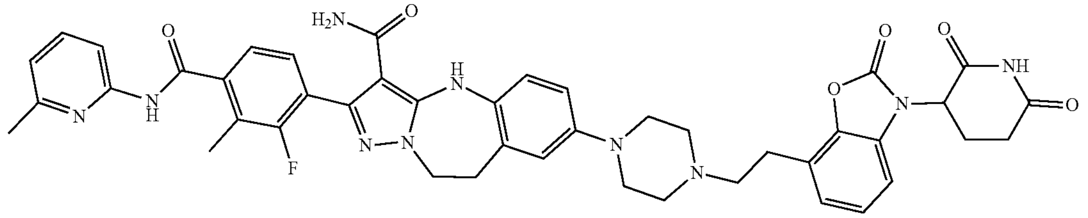
132 B62
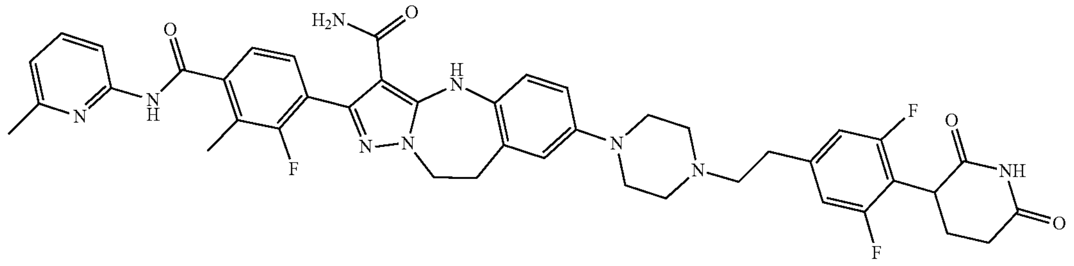
133 B63
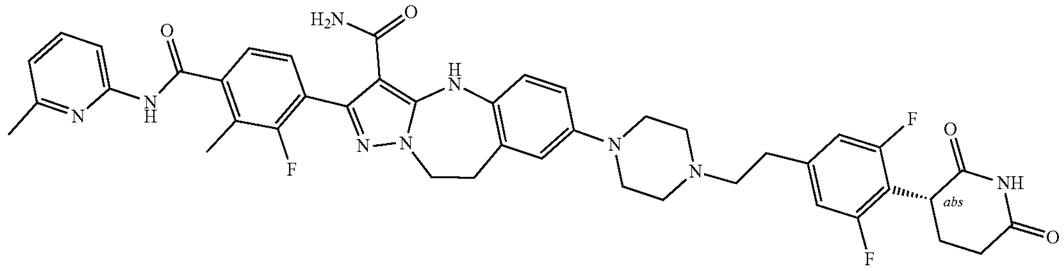
134 B64
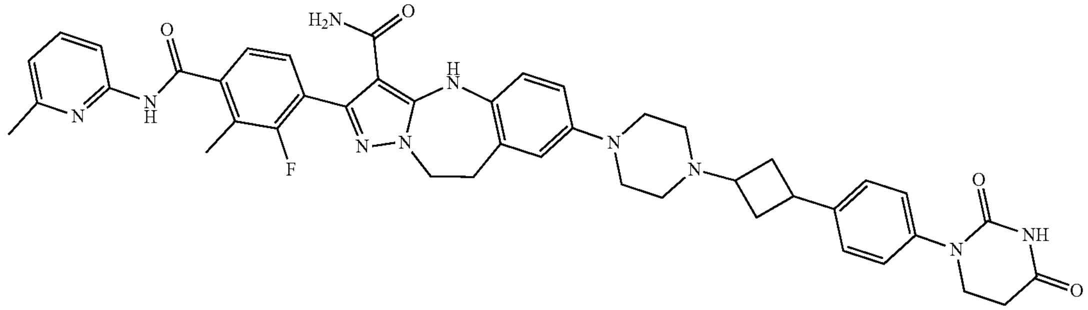
135 B65
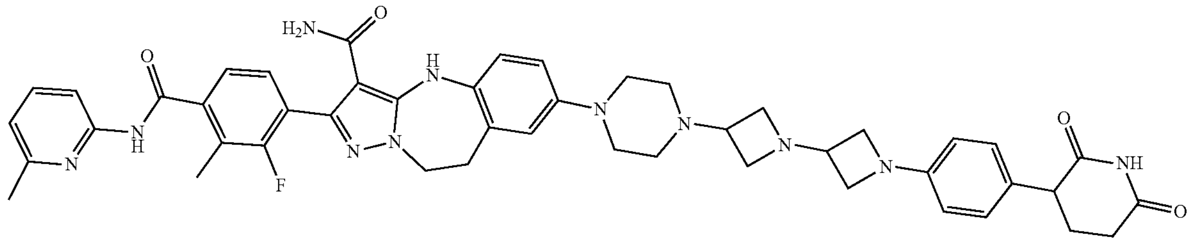

-continued
136 B66
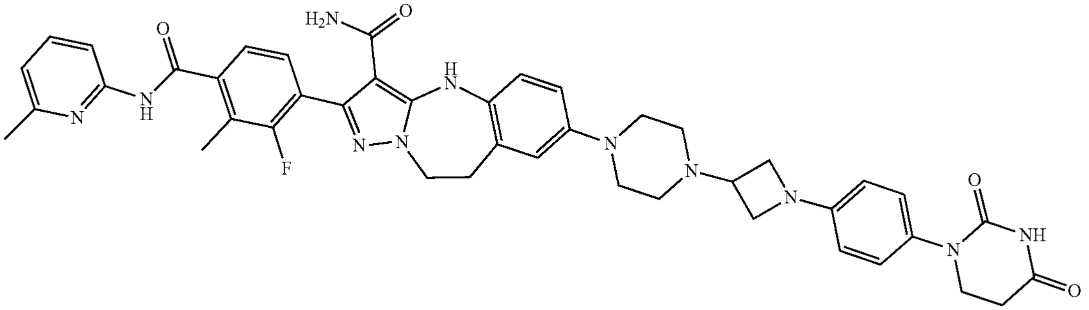
137 B67
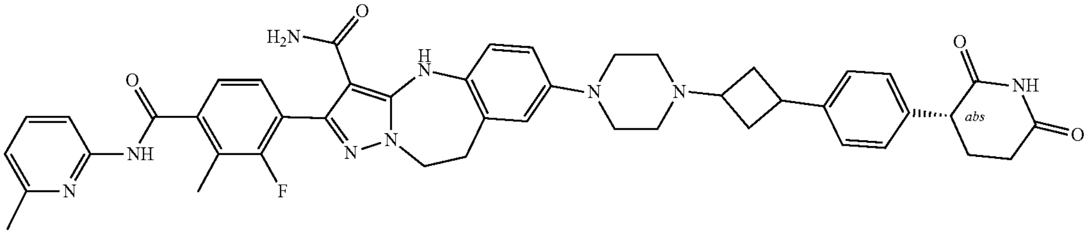
138 B68
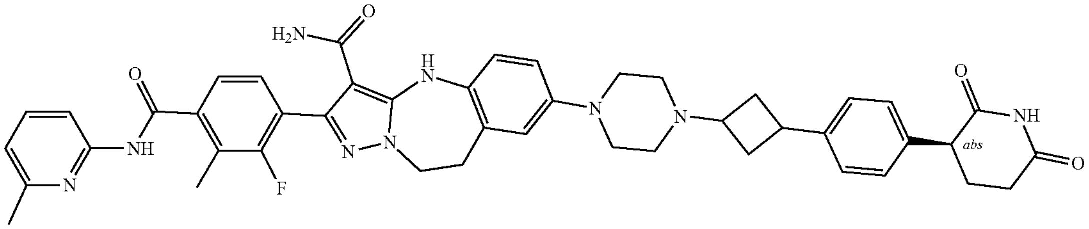
139 B69
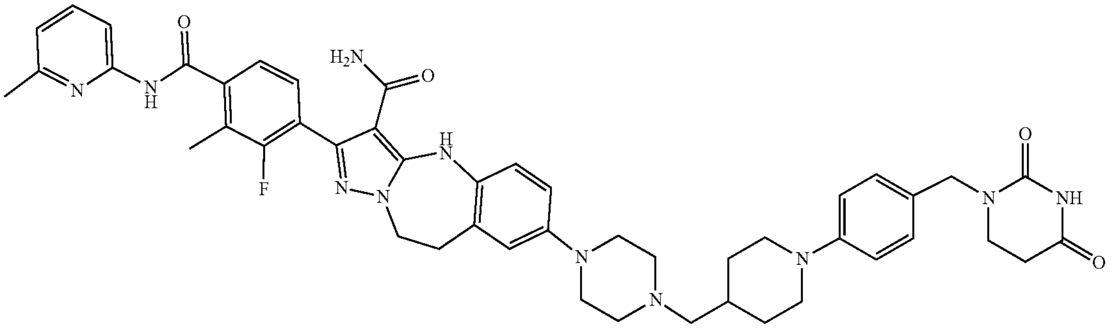
140 B70
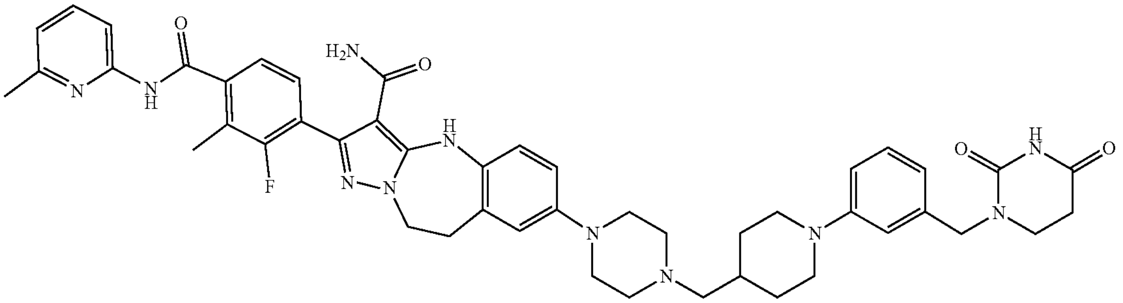

141 B71
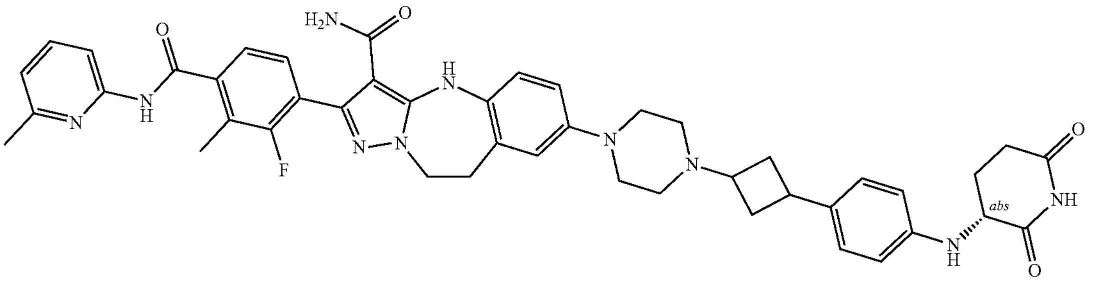
142 B72
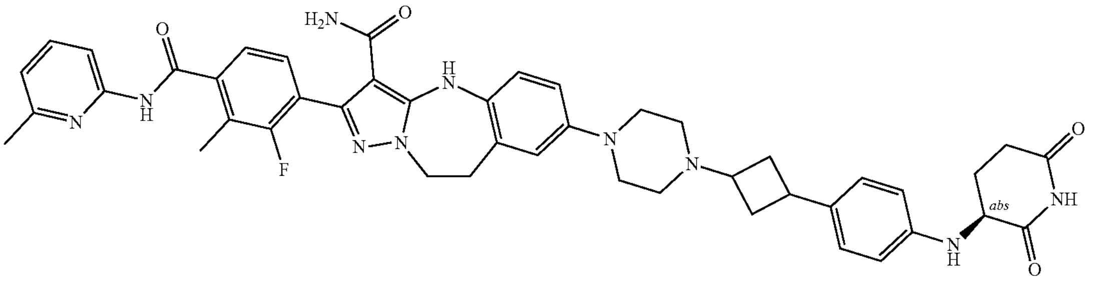
143 B73
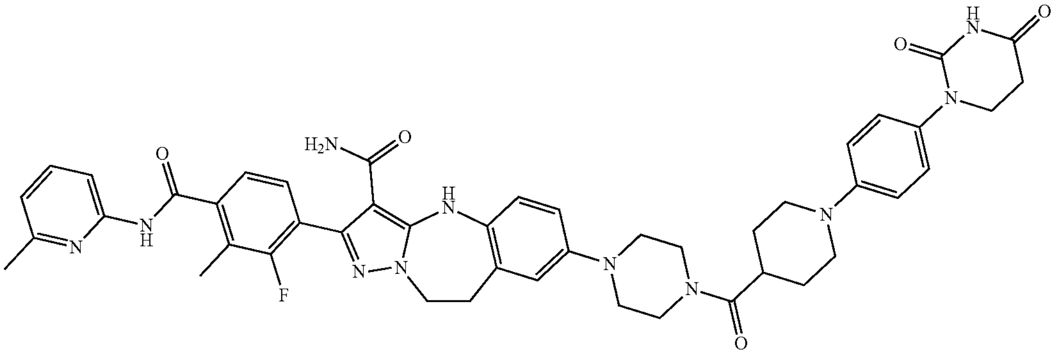
144 B74
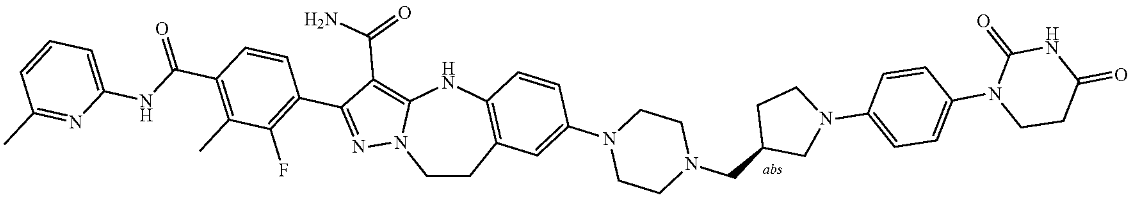
145 B75
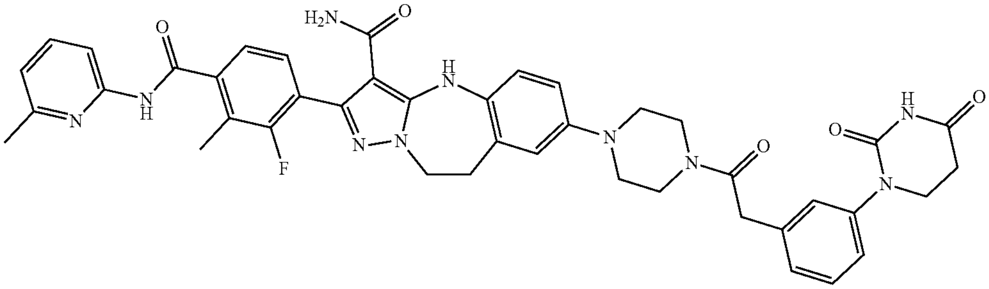

-continued
152 B82
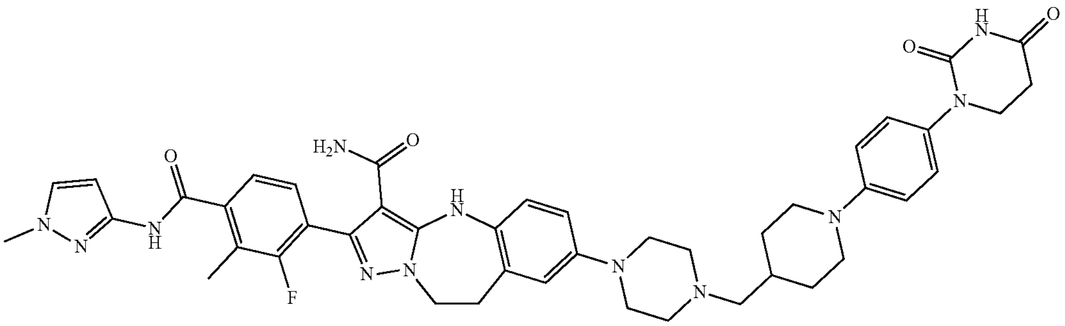
153 B83
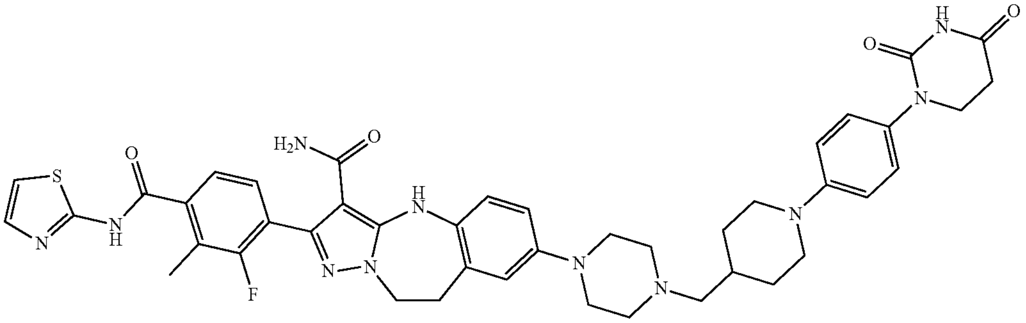
154 B84
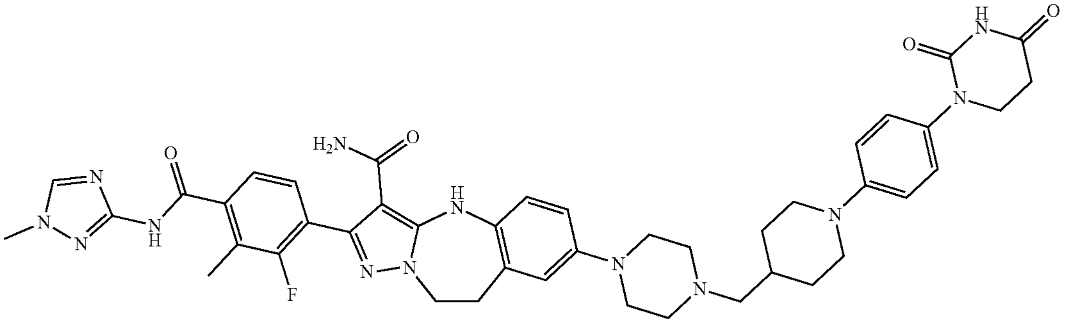
155 B85
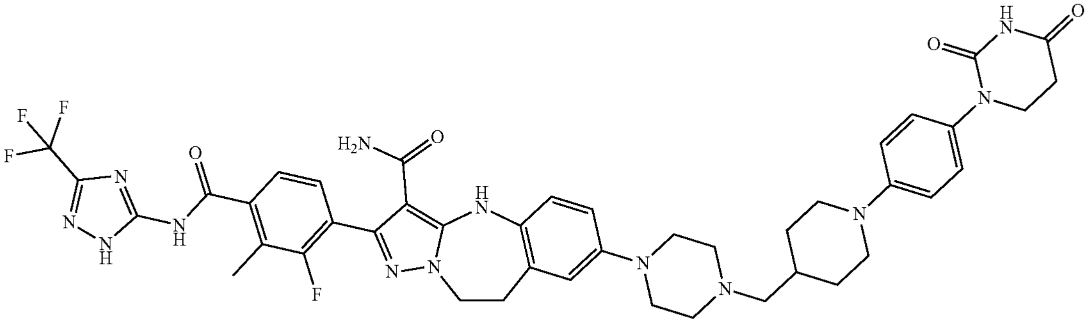

-continued
156 B86
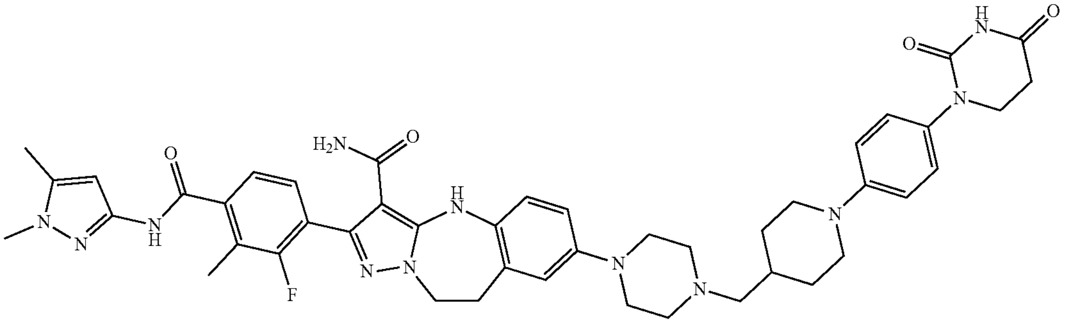
157 B87
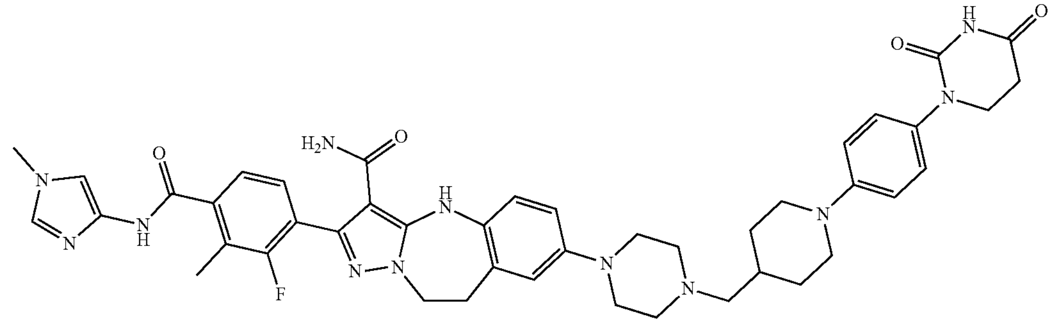
158 B88
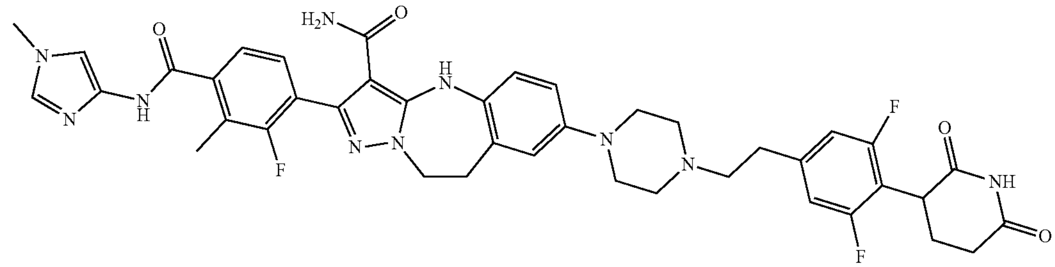
159 B89
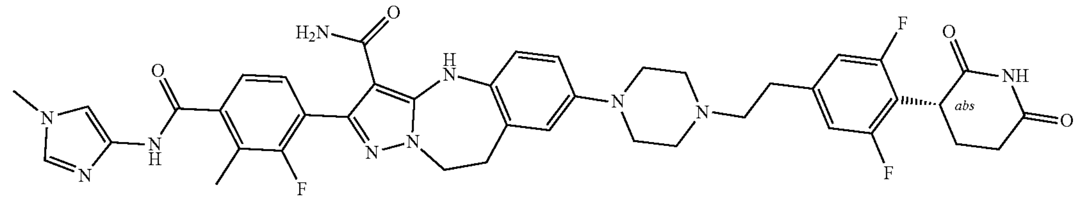
160 B90
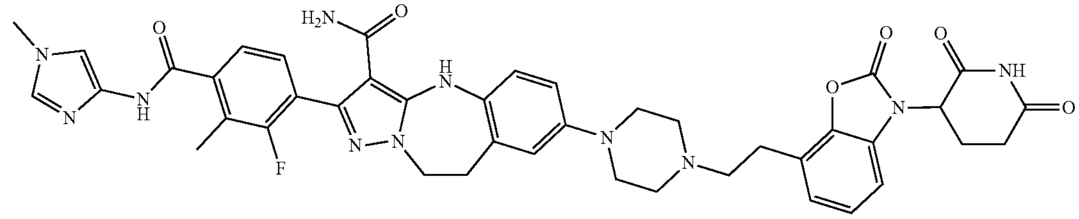

-continued
161 B91
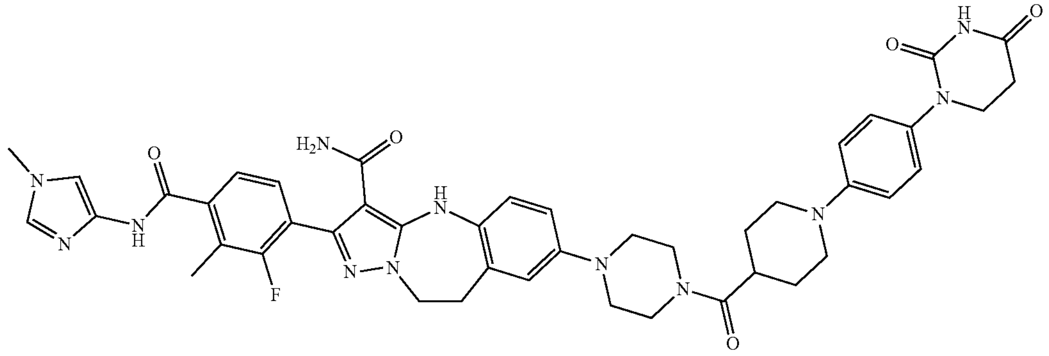
162 B92
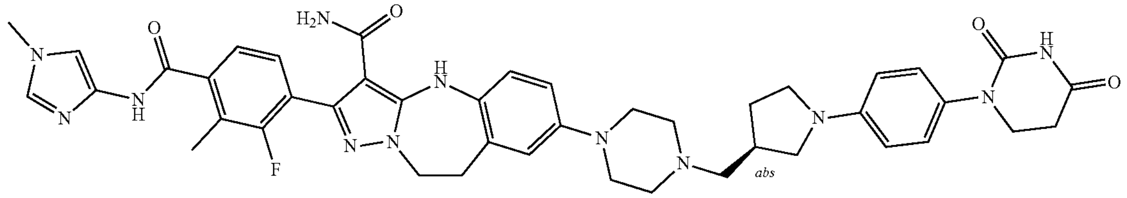
163 B93
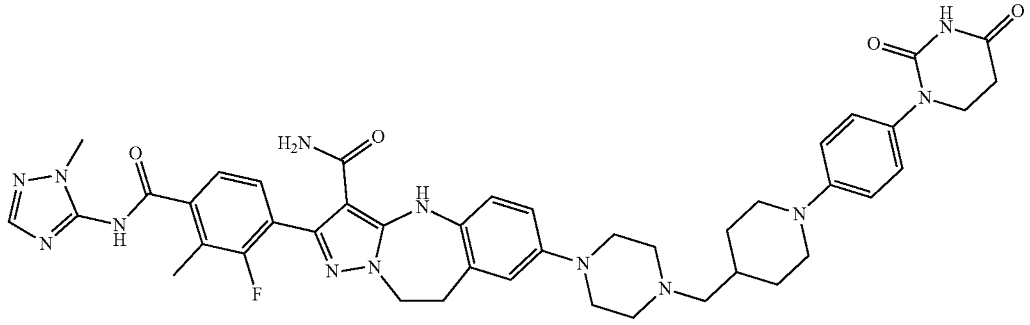
164 B94
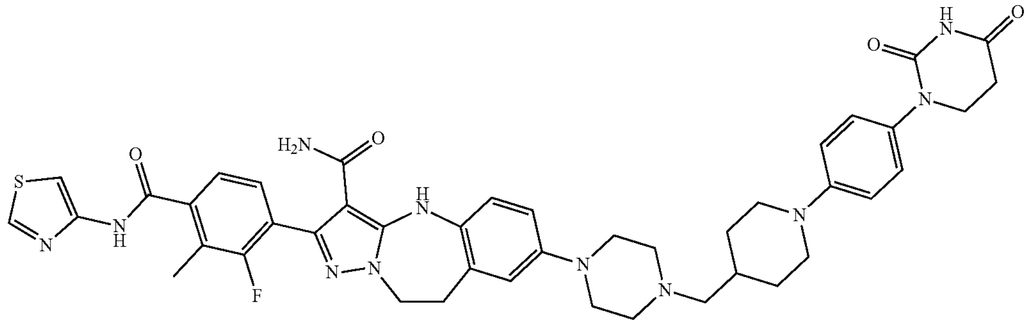
165 B95
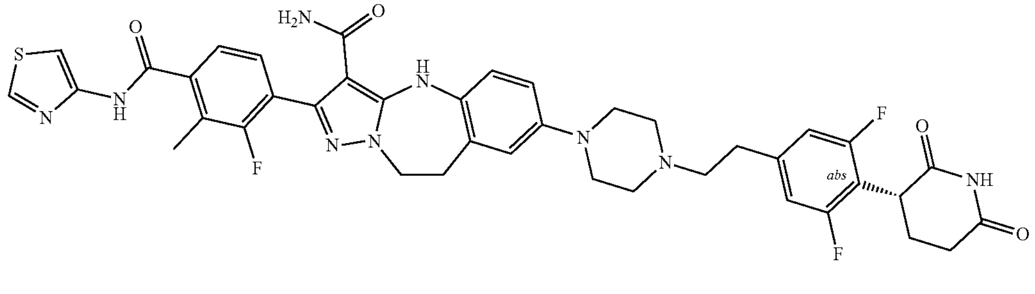

-continued
166 B96
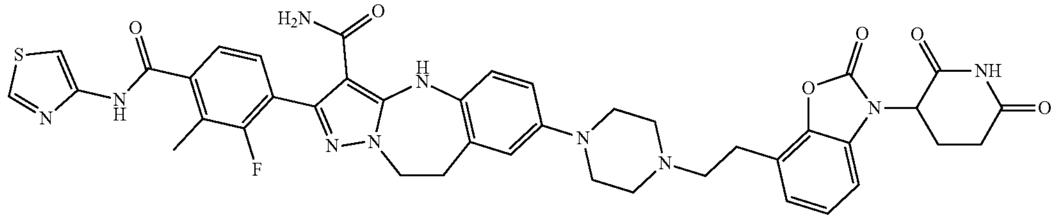
167 B97
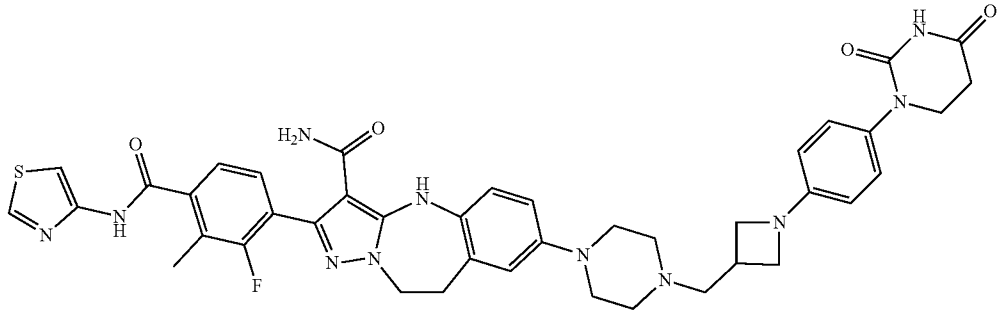
168 B98
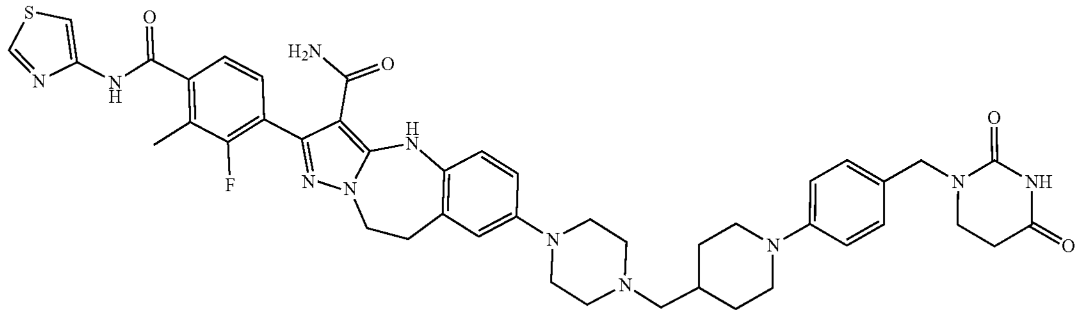
169 B99
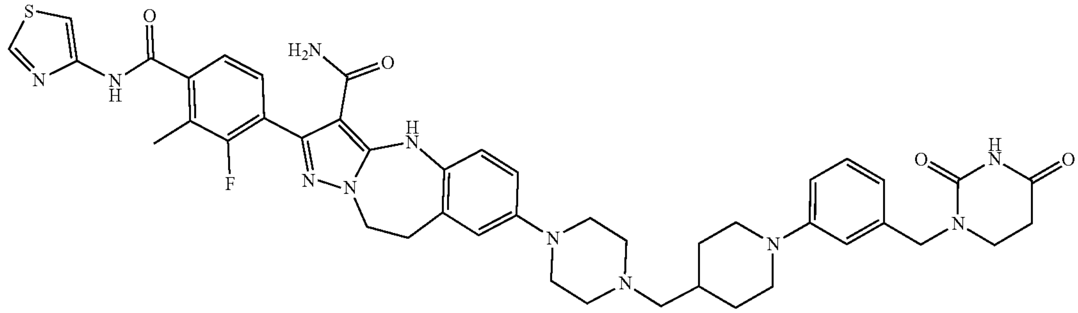
170 B100
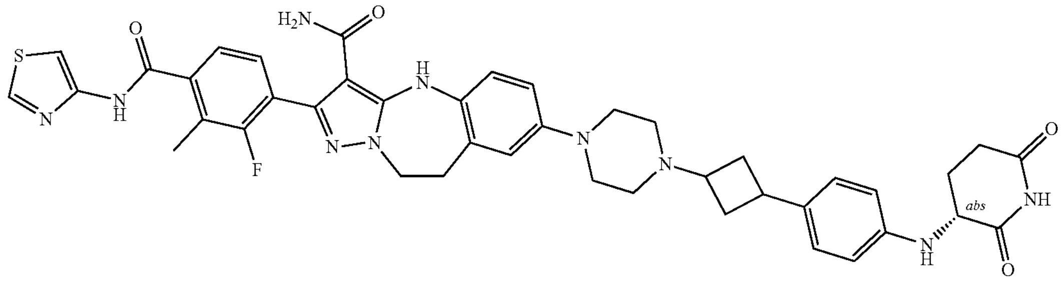

-continued
171 B101
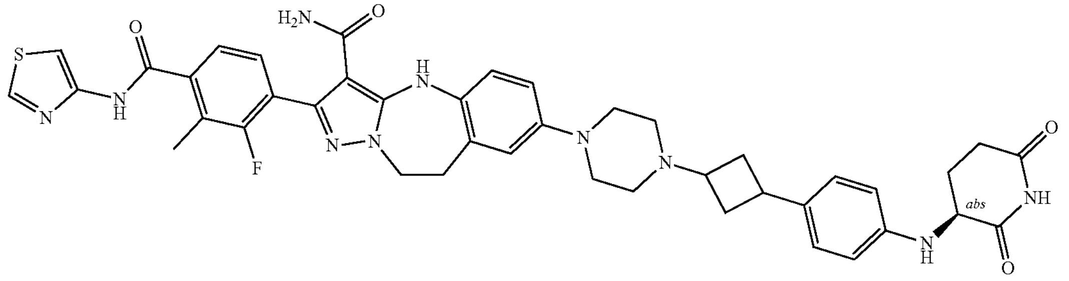
172 B102
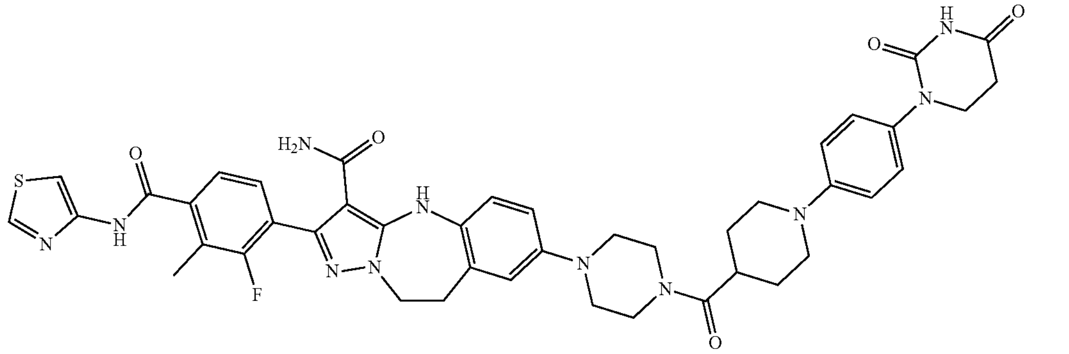
173 B103
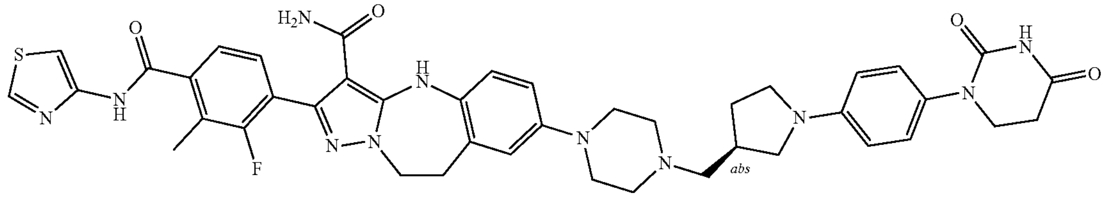
174 C31
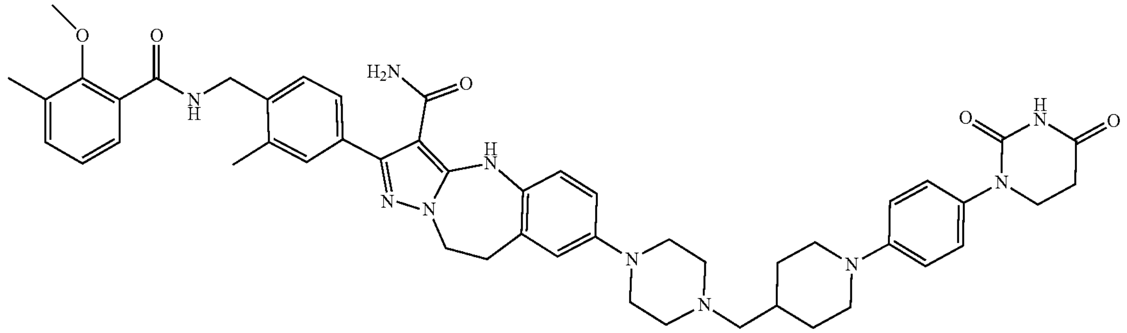
175 C32
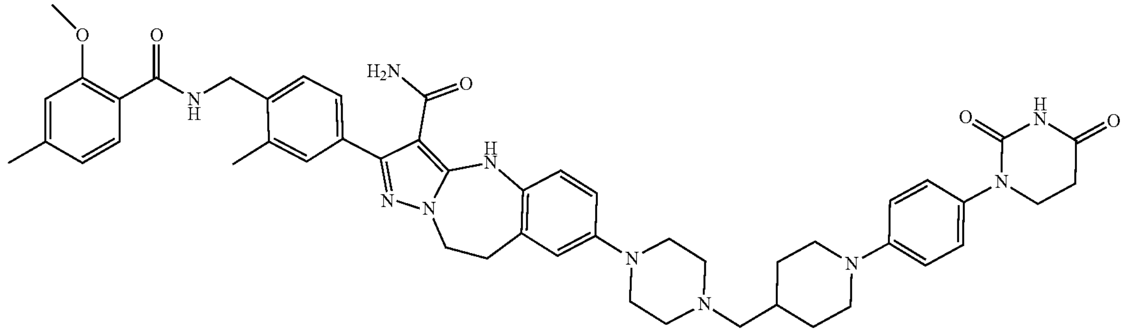

-continued
176 C33
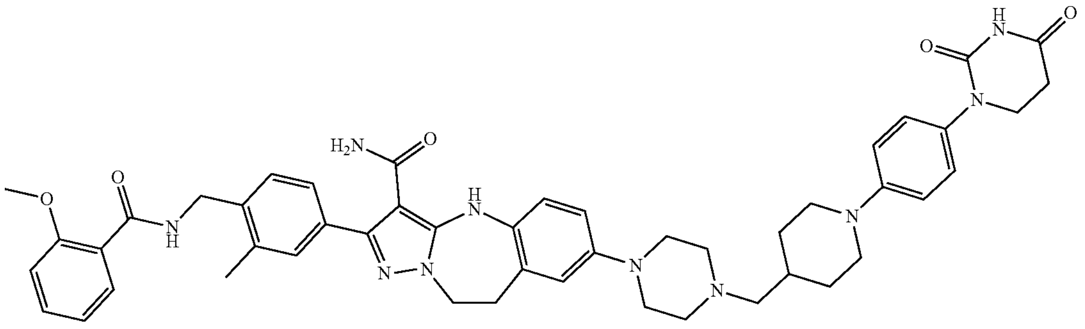
177 C34
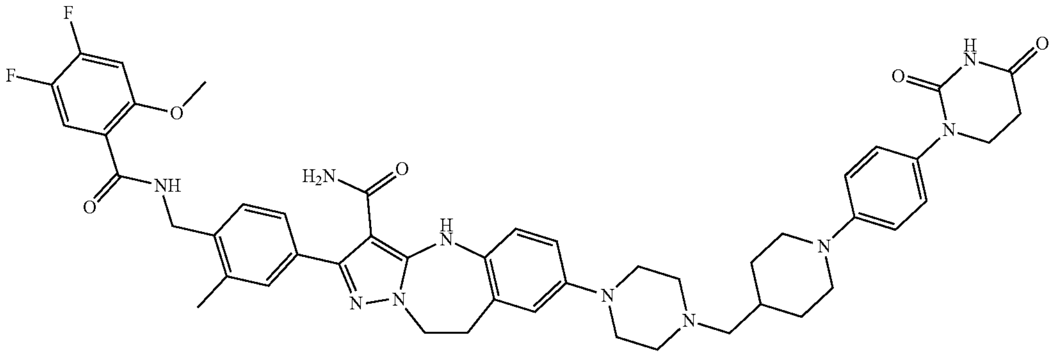
178 C35
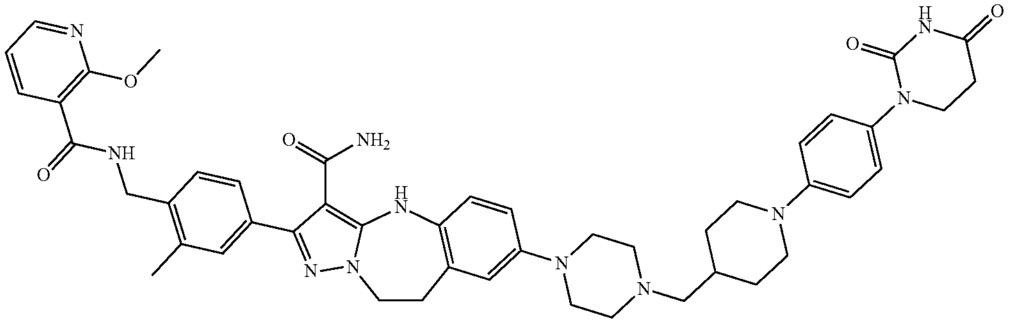
179 C36
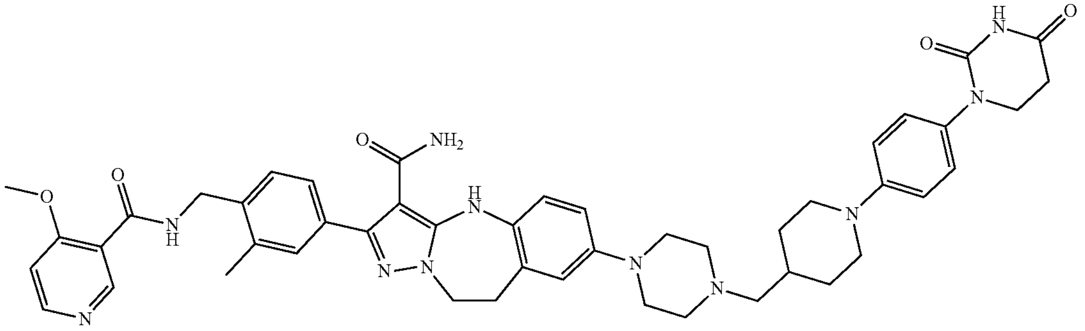

-continued
180 C37
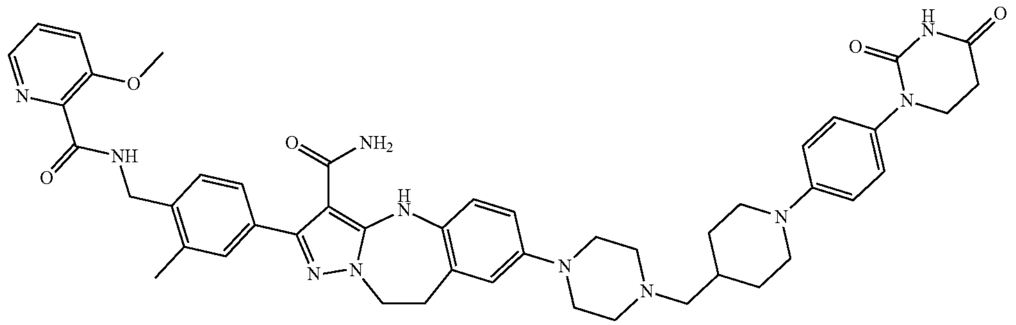
181 C38
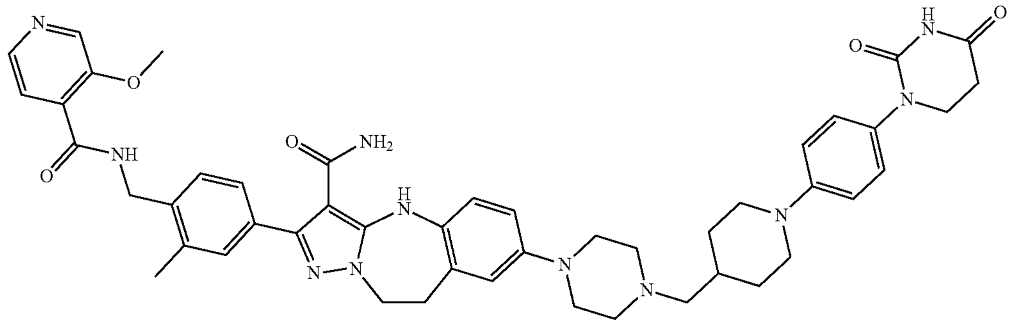
182 C39
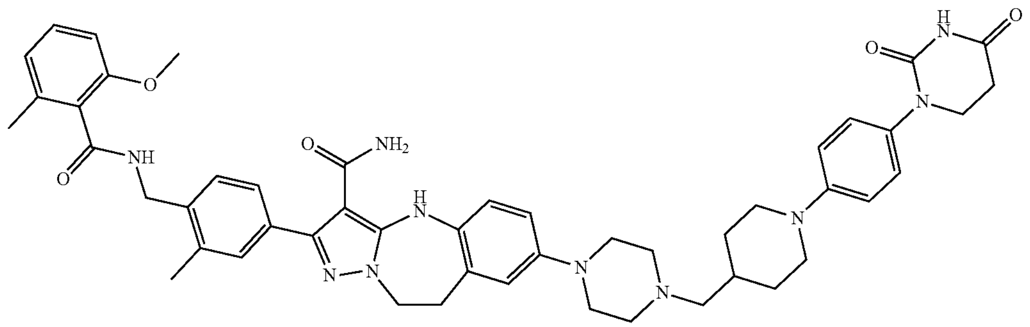
183 C40
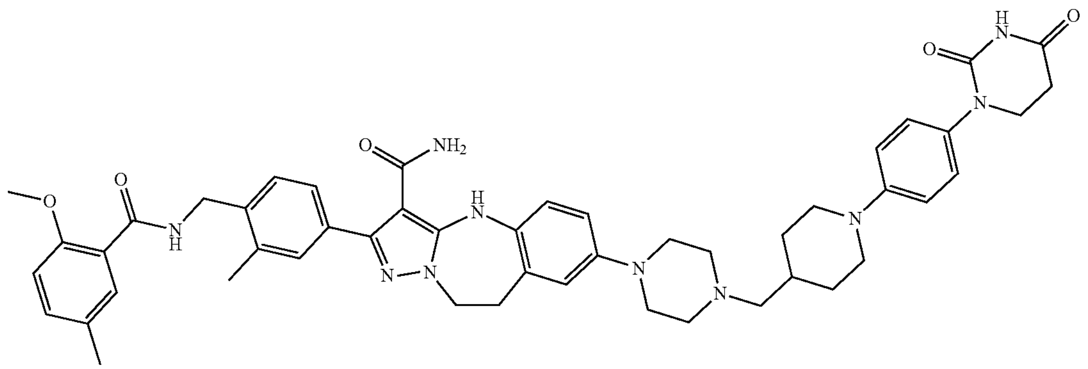

-continued
184 C41
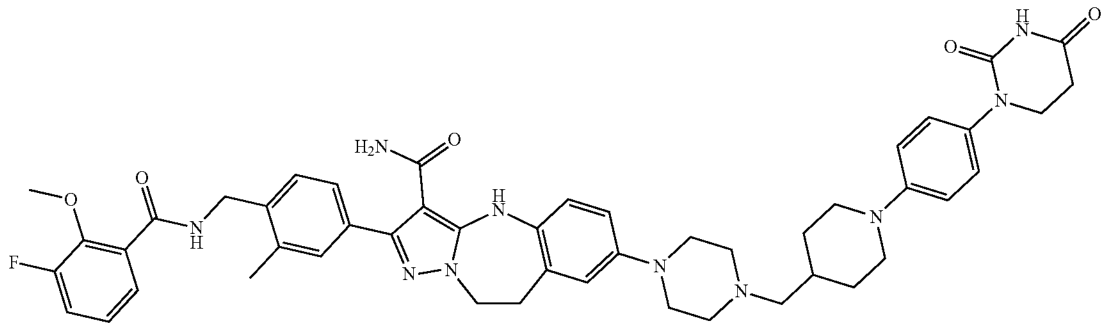
185 C42
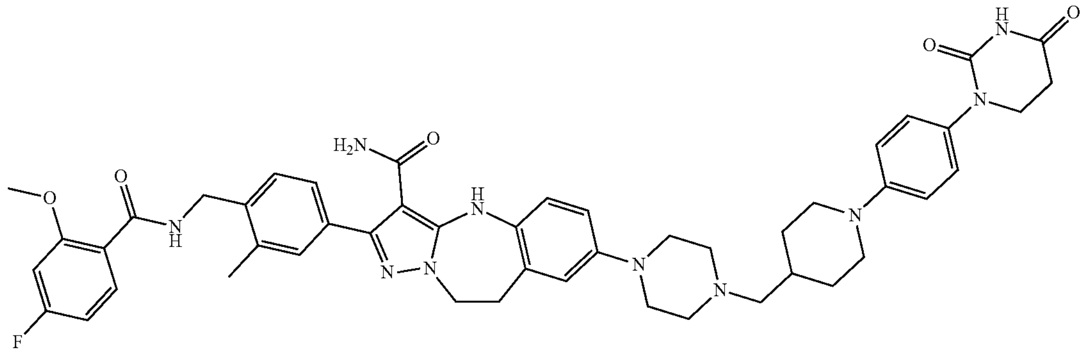
186 C43
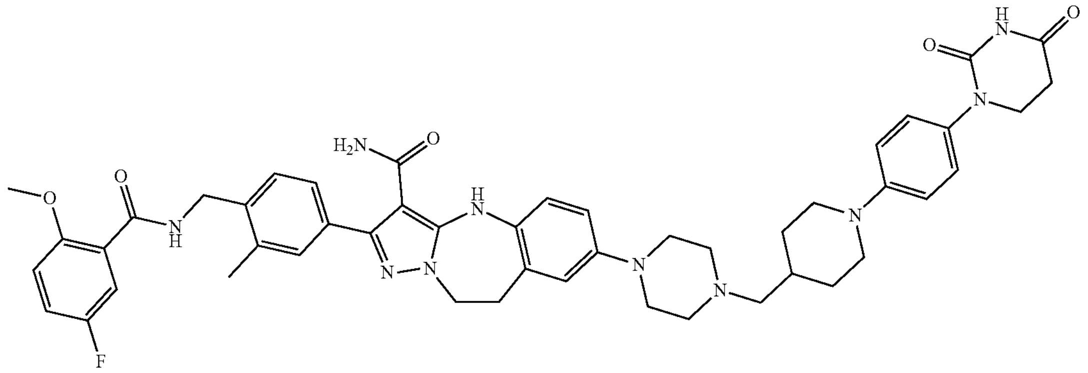
187 C44
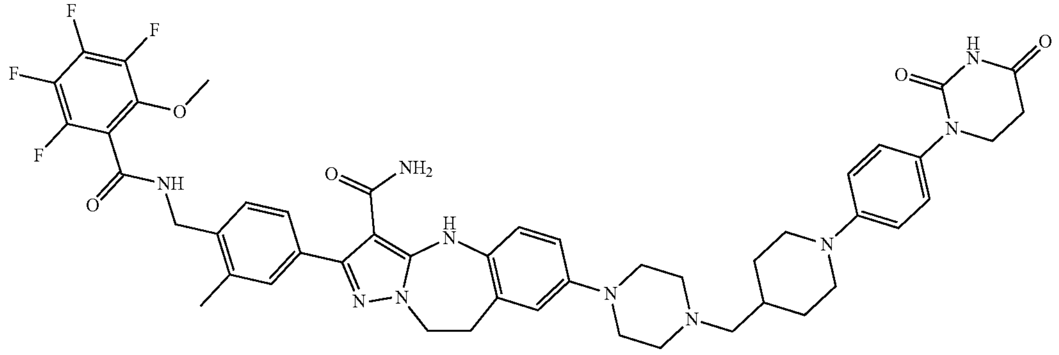

-continued
188 C45
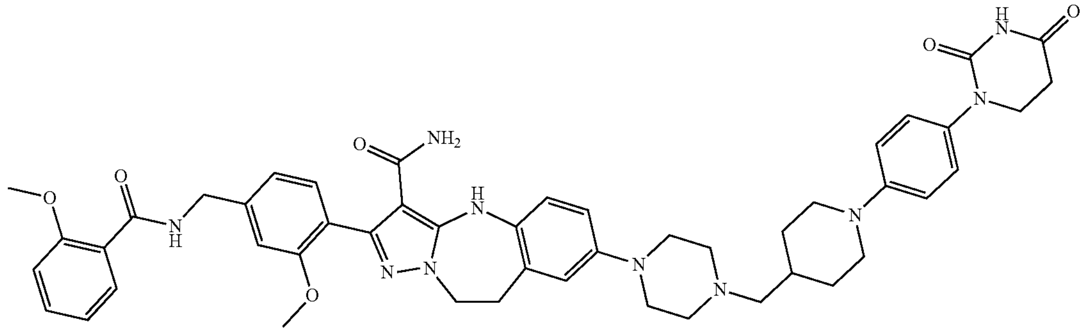
189 C46
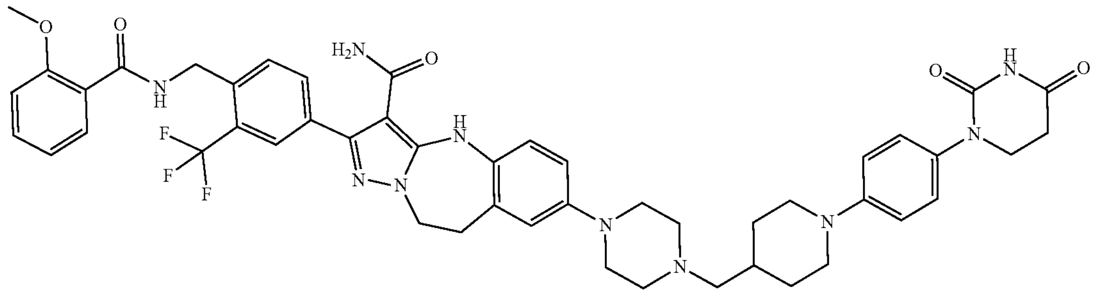
190 C47
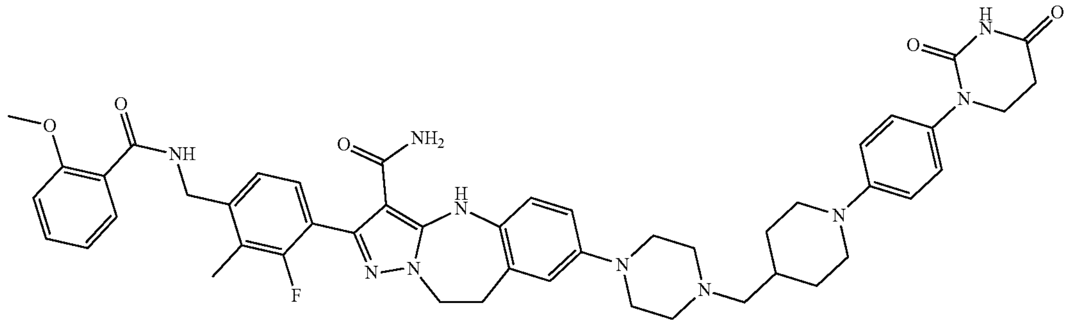
191 C48
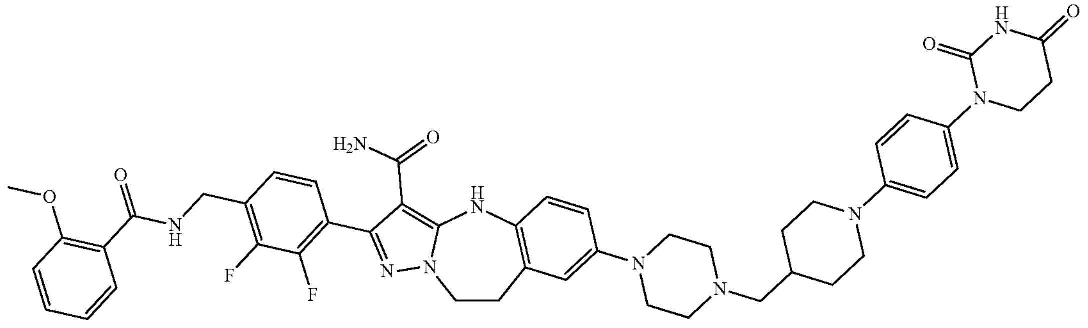
192 C49
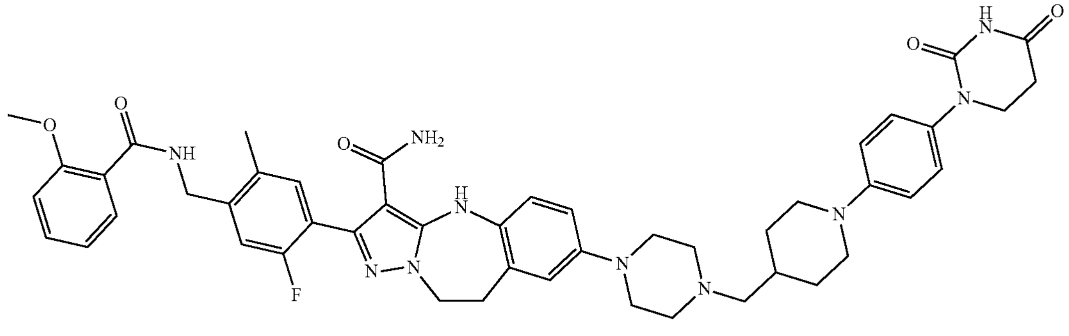
or -continued

193 B29

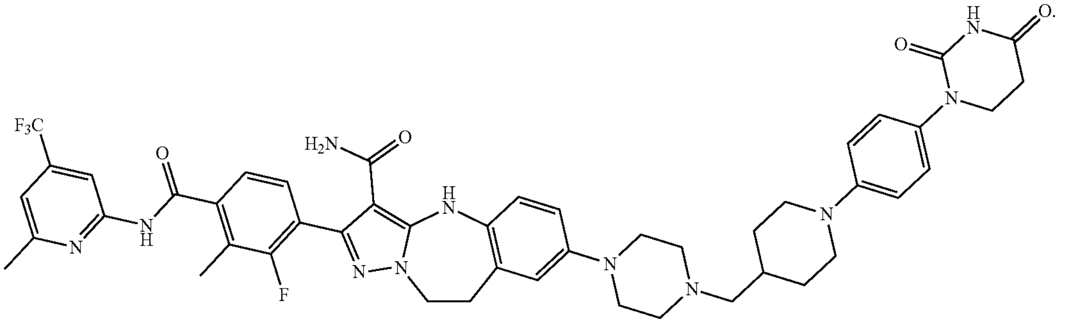

Aspect 41. A prodrug of the compound according to any one of aspects 1-40, wherein an N atom of the compound is substituted with $R^{pro}$, $R^{pro}$ is —$C_{1-8}$alkyl, —$C_{2-8}$alkenyl, —$C_{2-8}$alkynyl, cycloalkyl, heterocyclyl, aryl, or heteroaryl, wherein each of said —$C_{1-8}$alkyl, —$C_{2-8}$alkenyl, —$C_{2-8}$alkynyl, cycloalkyl, heterocyclyl, aryl, or heteroaryl is optionally substituted with $R^{proa}$; $R^{proa}$ is independently selected from hydrogen, halogen, —$C_{1-8}$alkyl, —$C_{2-8}$alkenyl, —$C_{2-8}$alkynyl, cycloalkyl, heterocyclyl, aryl, heteroaryl, —CN, —$NO_2$, —$OR^{prob}$, —$OCOR^{prob}$, —$COR^{prob}$, —$CO_2R^{prob}$, —$CONR^{prob}R^{proc}$, —$NR^{prob}R^{proc}$, —$NR^{prob}COR^{proc}$, —$NR^{prob}CONR^{proc}R^{prod}$, —$NR^{prob}CO_2R^{proc}$ wherein $R^{prob}$, $R^{proc}$, and $R^{prod}$ is each independently selected from —$C_{1-8}$alkyl, —$C_{2-8}$alkenyl, —$C_{2-8}$alkynyl, cycloalkyl, heterocyclyl, aryl, heteroaryl, cycloalkyl-$C_{1-8}$alkyl-, heterocyclyl-$C_{1-8}$alkyl-, aryl-$C_{1-8}$alkyl-, or heteroaryl-$C_{1-8}$alkyl-.

Aspect 41a. A prodrug of Aspect 41, wherein an N atom within the Degron moiety of the compound is substituted with $R^{pro}$.

Aspect 41b. A prodrug of Aspect 41, wherein the N atom of the lactam group within the Degron moiety of the compound is substituted with $R^{pro}$.

Aspect 41c. A prodrug of Aspect 41b, wherein the N atom of lactam group within the Degron moiety is the nitrogen atom which has a free hydrogen in the following moiety:

D1

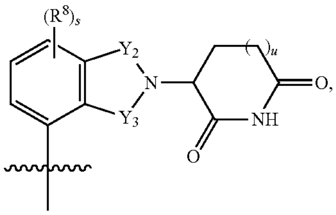

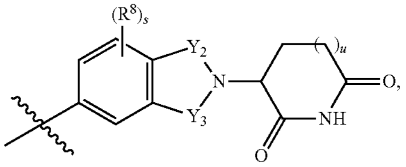

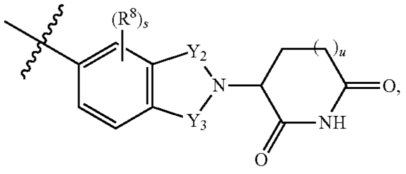

-continued

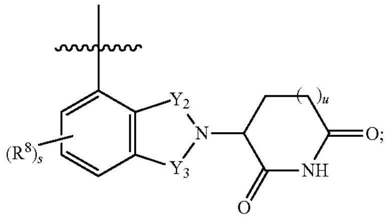

or

D2

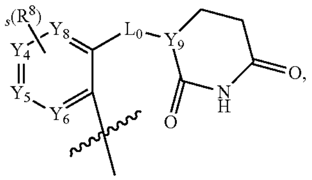

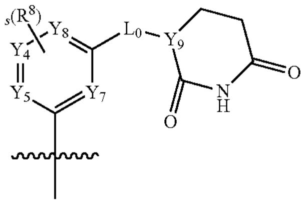

or

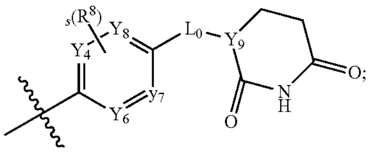

D3

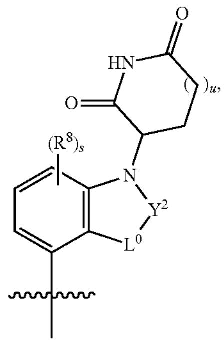

-continued
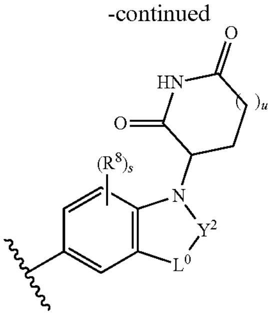
or
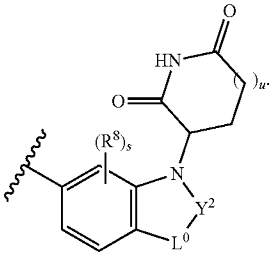
Aspect 42. The prodrug of Aspect 41, wherein $R^{pro}$ is
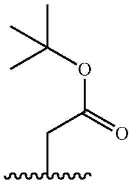
or
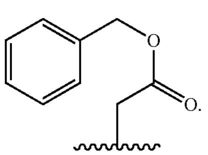
Aspect 43. The prodrug of any one of Aspects 41-42, the prodrug is selected from
146 B76
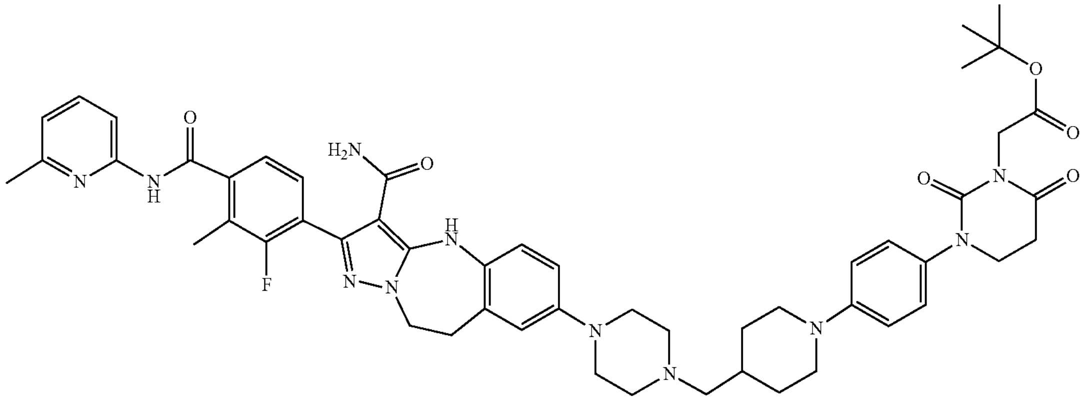
147 B77
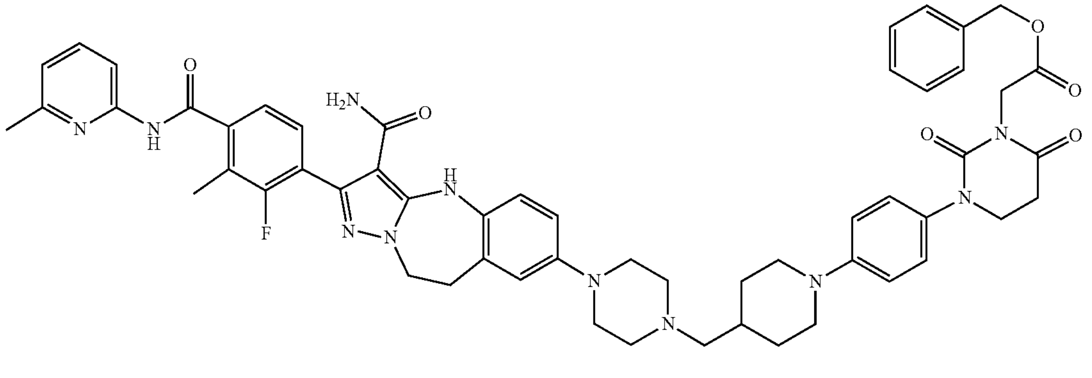

-continued
148 B78
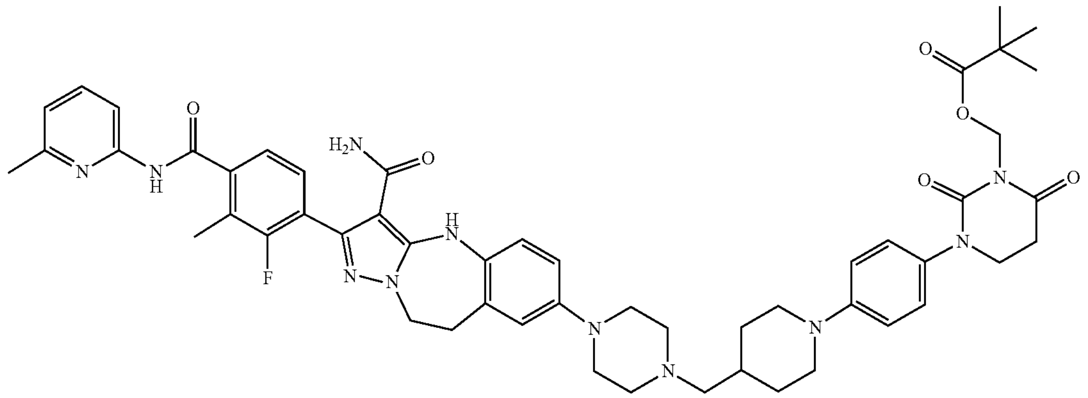
149 B79
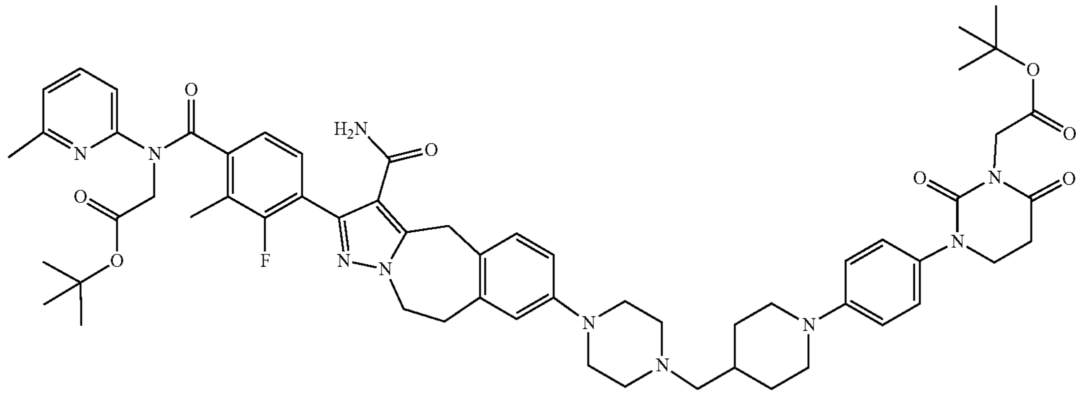
150 B80
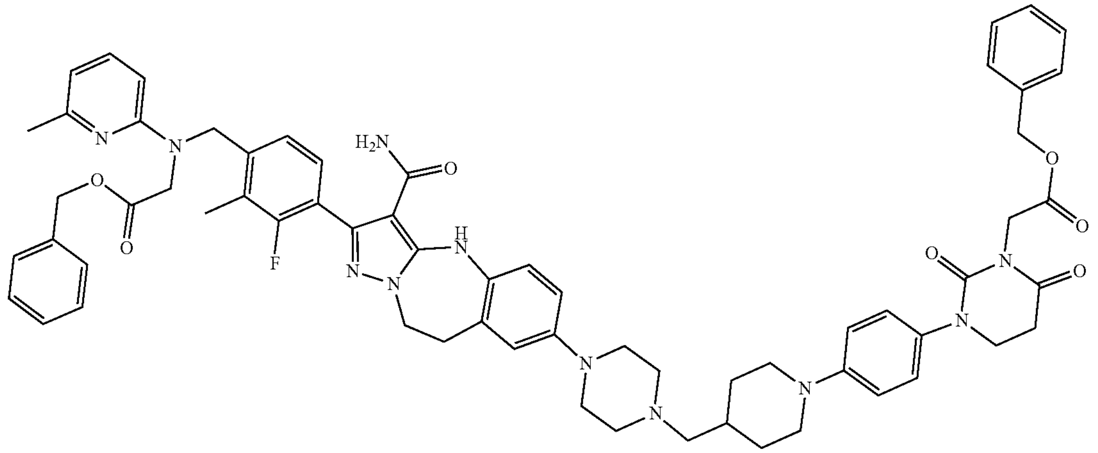
or

-continued

151 B81

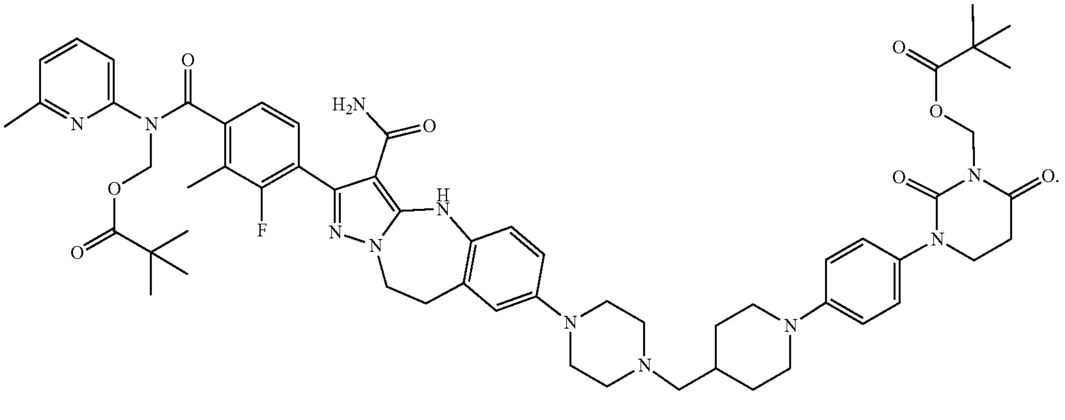

Aspect 44. A pharmaceutical composition comprising the compound according to any one of Aspects 1-40 or the prodrug according to any one of Aspects 41-43, or a pharmaceutically acceptable salt thereof, and at least one pharmaceutically acceptable carrier or excipient.

Aspect 45. A method of inhibiting BTK activity, which comprises administering to an individual the compound according to any one of Aspects 1-40 or the prodrug according to any one of Aspects 41-43, or a pharmaceutically acceptable salt thereof, including the compound of formula (I) or the specific compounds exemplified herein.

Aspect 46. A method of treating a disease or disorder in a patient comprising administering to the patient in need thereof a therapeutically effective amount of the compound according to any one of Aspects 1-40 or the prodrug according to any one of Aspects 41-43, or a pharmaceutically acceptable salt thereof as an BTK kinase inhibitor, wherein the disease or disorder is associated with inhibition of BTK, preferably, the disease or disorder is cancer.

DETAILED DESCRIPTION OF THE INVENTION

Definitions

The following terms have the indicated meaning throughout the specification:

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

The term "alkyl" refers to a hydrocarbon group selected from linear and branched, saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include without limitation to methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1, 1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2, 3-dimethyl-2-butyl and 3, 3-dimethyl-2-butyl groups.

The term "propyl" refers to 1-propyl or n-propyl ("n-Pr"), 2-propyl or isopropyl ("i-Pr").

The term "butyl" refers to 1-butyl or n-butyl ("n-Bu"), 2-methyl-1-propyl or isobutyl ("i-Bu"), 1-methylpropyl or s-butyl ("s-Bu"), 1, 1-dimethylethyl or t-butyl ("t-Bu").

The term "pentyl" refers to 1-pentyl, 2-pentyl, 3-pentyl, 2-methyl-2-butyl, 3-methyl-2-butyl, 3-methyl-1-butyl, 2-methyl-1-butyl.

The term "hexyl" refers to 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2, 3-dimethyl-2-butyl and 3, 3-dimethyl-2-butyl.

The term "halogen" refers to fluoro (F), chloro (Cl), bromo (Br) and iodo (I).

The term "haloalkyl" refers to an alkyl group in which one or more hydrogens are replaced by one or more halogen atoms such as fluoro, chloro, bromo, and iodo. Examples of the haloalkyl include without limitation to halo$C_{1-8}$alkyl, halo$C_{1-6}$alkyl or halo $C_{1-4}$alkyl, such as $-CF_3$, $-CH_2Cl$, $-CH_2CF_3$, $-CHCl_2$, $-CF_3$, and the like.

The term "alkenyl" refers to a hydrocarbon group selected from linear and branched hydrocarbon groups comprising at least one C=C double bond and from 2 to 18, such as from 2 to 8, further such as from 2 to 6, carbon atoms. Examples of the alkenyl group, e.g., $C_{2-6}$ alkenyl, include without limitation to ethenyl or vinyl, prop-1-enyl, prop-2-enyl, 2-methylprop-1-enyl, but-1-enyl, but-2-enyl, but-3-enyl, buta-1, 3-dienyl, 2-methylbuta-1, 3-dienyl, hex-1-enyl, hex-2-enyl, hex-3-enyl, hex-4-enyl, and hexa-1, 3-dienyl groups.

The term "alkynyl" refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include without limitation to ethynyl, 1-propynyl, 2-propynyl (propargyl), 1-butynyl, 2-butynyl, and 3-butynyl groups.

The term "cycloalkyl" refers to a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. In particular, examples of the saturated monocyclic cycloalkyl group, e.g., $C_{3-8}$cycloalkyl, include without limitation to cyclopropyl, cyclobutyl, cyclopentyl, cyclohexyl, cycloheptyl, and cyclooctyl groups. In a preferred embodiment, the cycloalkyl is a monocyclic ring comprising 3 to 6 carbon atoms (abbreviated as $C_{3-6}$ cycloalkyl), including but not limited to cyclopropyl, cyclobutyl, cyclopentyl, and cyclohexyl. Examples of the bicyclic cycloalkyl groups include those having from 7 to 12 ring atoms arranged as a fused bicyclic ring selected from [4, 4], [4, 5], [5, 5], [5, 6] and [6, 6] ring systems, or as a bridged bicyclic ring selected from bicyclo[2.2.1]heptane, bicyclo[2.2.2]octane, and bicyclo[3.2.2]nonane. Further examples of the bicyclic cycloalkyl groups include those arranged as a bicyclic ring selected from [5, 6] and [6, 6] ring systems.

The term "spiro cycloalkyl" refers to a cyclic structure which contains carbon atoms and is formed by at least two rings sharing one atom. The term "7 to 12 membered spiro cycloalkyl" refers to a cyclic structure which contains 7 to 12 carbon atoms and is formed by at least two rings sharing one atom.

The term "fused cycloalkyl" refers to a bicyclic cycloalkyl group as defined herein which is saturated and is formed by two or more rings sharing two adjacent atoms.

The term "bridged cycloalkyl" refers to a cyclic structure which contains carbon atoms and is formed by two rings sharing two atoms which are not adjacent to each other. The term "7 to 10 membered bridged cycloalkyl" refers to a cyclic structure which contains 7 to 12 carbon atoms and is formed by two rings sharing two atoms which are not adjacent to each other.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, 1-cyclopent-1-enyl, 1-cyclopent-2-enyl, 1-cyclopent-3-enyl, 1-cyclohex-1-enyl, 1-cyclohex-2-enyl, 1-cyclohex-3-enyl, cyclohexadienyl, preferably cyclohexenyl.

The term "fused cycloalkenyl" refers to a bicyclic cycloalkyl group as defined herein which contain at least one double bond and is formed by two or more rings sharing two adjacent atoms.

The term "cycloalkynyl" refers to non-aromatic cycloalkyl groups of from 5 to 10 carbon atoms having single or multiple rings and having at least one triple bond.

The term "fused cycloalkynyl" refers to a bicyclic cycloalkyl group as defined herein which contains at least one triple bond and is formed by two or more rings sharing two adjacent atoms.

The term a "benzo fused cycloalkyl" is a bicyclic fused cycloalkyl in which a 4- to 8-membered monocyclic cycloalkyl ring fused to a benzene ring. For example, a benzo fused cycloalkyl is

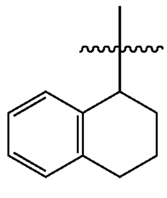

or

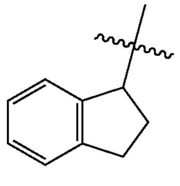

wherein the wavy lines indicate the points of attachment.

The term a "benzo fused cycloalkenyl" is a bicyclic fused cycloalkenyl in which a 4- to 8-membered monocyclic cycloalkenyl ring fused to a benzene ring.

The term a "benzo fused cycloalkynyl" is a bicyclic fused cycloalkynyl in which a 4- to 8-membered monocyclic cycloalkynyl ring fused to a benzene ring.

Examples of fused cycloalkyl, fused cycloalkenyl, or fused cycloalkynyl include but are not limited to bicyclo [1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$ cycloalkenyl, 2, 3-dihydro-1H-indenyl, 1H-indenyl, 1, 2, 3, 4-tetralyl, 1, 4-dihydronaphthyl, etc. Preferred embodiments are 8 to 9 membered fused rings, which refer to cyclic structures containing 8 to 9 ring atoms within the above examples.

The term "aryl" used alone or in combination with other terms refers to a group selected from:

a) 5- and 6-membered carbocyclic aromatic rings, e.g., phenyl;
b) bicyclic ring systems such as 7 to 12 membered bicyclic ring systems, wherein at least one ring is carbocyclic and aromatic, e.g., naphthyl and indanyl; and,
c) tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring include without limitation to phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

Specifically, the term "bicyclic fused aryl" refers to a bicyclic aryl ring as defined herein. The typical bicyclic fused aryl is naphthalene.

The term "heteroaryl" refers to a group selected from:

a) 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
b) 7- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and
c) 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

Specifically, the term "bicyclic fused heteroaryl" refers to a 7- to 12-membered, preferably 7- to 10-membered, more preferably 9- or 10-membered fused bicyclic heteroaryl ring as defined herein. Typically, a bicyclic fused heteroaryl is 5-membered/5-membered, 5-membered/6-membered, 6-membered/6-membered, or 6-membered/7-membered bicyclic. The group can be attached to the remainder of the molecule through either ring.

Representative examples of bicyclic fused heteroaryl include without limitation to the following groups: benzisoxazolyl, benzodiazolyl, benzofuranyl, benzofurazanyl, benzofuryl, benzoimidazolyl, benzoisothiazolyl, benzothiadiazolyl, benzothiazolyl, benzothienyl, benzothiophenyl, benzotriazolyl, benzoxadiazolyl, benzoxazolyl, furopyridinyl, furopyrrolyl, imidazopyridinyl, imidazopyridyl, imidazothiazolyl, indazolyl, indolizinyl, indolyl, isobenzofuryl, isoindolyl, isoquinolinyl (or isoquinolyl), naphthyridinyl, phthalazinyl, pteridinyl, purinyl, pyrazinopyridazinyl, pyrazolopyridinyl, pyrazolopyrimidinyl, pyrazolopyridyl, pyrazolotriazinyl, pyridazolopyridyl, pyrrolopyridinyl, quinazolinyl, quinolinyl (or quinolyl), quinoxalinyl, thiazolopyridyl, thienopyrazinyl, thienopyrazolyl, thienopyridyl, thienopyrrolyl, thienothienyl, or triazolopyridyl.

The term a "benzo fused heteroaryl" is a bicyclic fused heteroaryl in which a 5- to 7-membered (preferably, 5- or 6-membered) monocyclic heteroaryl ring as defined herein fused to a benzene ring.

The terms "aromatic heterocyclic ring" and "heteroaryl" are used interchangeably throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is an 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2, 4-pyrimidinyl, 3, 5-pyrimidinyl, 2, 4-imidazolyl, imidazopyridinyl, isoxazolyl, oxazolyl, thiazolyl, isothiazolyl, thiadiazolyl (such as 1, 2, 3-thiadiazolyl, 1, 2, 4-thiadiazolyl, or 1, 3, 4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, oxadiazolyl (such as 1, 2, 3-oxadiazolyl, 1, 2, 4-oxadiazolyl, or 1, 3, 4-oxadiazolyl), phthalazinyl, pyrazinyl, pyridazinyl, pyrrolyl, triazolyl (such as 1, 2, 3-triazolyl, 1, 2, 4-triazolyl, or 1, 3, 4-triazolyl), quinolinyl, isoquinolinyl, pyrazolyl, pyrrolopyridinyl (such as 1H-pyrrolo[2, 3-b]pyridin-5-yl), pyrazolopyridinyl (such as 1H-pyrazolo[3, 4-b]pyridin-5-yl), benzoxazolyl (such as benzo[d]oxazol-6-yl), pteridinyl, purinyl, 1-oxa-2, 3-diazolyl, 1-oxa-2, 4-diazolyl, 1-oxa-2, 5-diazolyl, 1-oxa-3, 4-diazolyl, 1-thia-2, 3-diazolyl, 1-thia-2, 4-diazolyl, 1-thia-2, 5-diazolyl, 1-thia-3, 4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), and indazolyl (such as 1H-indazol-5-yl).

"Aromatic ring" refers to aromatic carbocycles (e.g., the above-mentioned aryl) and aromatic heterocycles (e.g., the above-mentioned heteroaryl).

"Heterocyclyl", "heterocycle" or "heterocyclic" are interchangeable and refer to a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "optionally oxidized sulfur" used herein refers to S, SO or $SO_2$.

The term "monocyclic heterocyclyl" refers to monocyclic groups in which at least one ring member (e.g., 1-3 heteroatoms, 1 or 2 heteroatom(s)) is a heteroatom selected from nitrogen, oxygen or optionally oxidized sulfur. A heterocycle may be saturated or partially saturated.

Exemplary monocyclic 4 to 9-membered heterocyclyl groups include without limitation to pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2, 5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1, 2-dithietanyl, 1, 3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1, 4-oxathianyl, 1, 4-dioxepanyl, 1, 4-oxathiepanyl, 1, 4-oxaazepanyl, 1, 4-dithiepanyl, 1, 4-thiazepanyl and 1, 4-diazepanyl, 1, 4-dithianyl, 1, 4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1, 4-dioxanyl, 1, 3-dioxolanyl, pyrazolinyl, pyrazolidinyl, dithianyl, dithiolanyl, pyrazolidinyl, imidazolinyl, pyrimidinonyl, or 1, 1-dioxo-thiomorpholinyl.

The term "spiro heterocyclyl" refers to a 5 to 20-membered polycyclic heterocyclyl with rings connected through one common carbon atom (called a spiro atom), comprising one or more heteroatoms selected from nitrogen, oxygen or optionally oxidized sulfur as ring members, with the remaining ring members being carbon. One or more rings of a spiro heterocyclyl group may contain one or more double bonds, but none of the rings has a completely conjugated pi-electron system. Preferably a spiro heterocyclyl is 6 to 14-membered, and more preferably 7 to 12-membered. According to the number of common spiro atoms, a spiro heterocyclyl could be mono-spiro heterocyclyl, di-spiro heterocyclyl, or poly-spiro heterocyclyl, and preferably refers to mono-spiro heterocyclyl or di-spiro heterocyclyl, and more preferably 4-membered/3-membered, 4-membered/4-membered, 3-membered/5-membered, 4-membered/5-membered, 4-membered/6-membered, 5-membered/5-membered, or 5-membered/6-membered mono-spiro heterocyclyl. Representative examples of spiro heterocyclyls include without limitation to the following groups: 2, 3-dihydrospiro[indene-1, 2'-pyrrolidine] (e.g., 2, 3-dihydrospiro[indene-1, 2'-pyrrolidine]-1'-yl), 1, 3-dihydrospiro[indene-2, 2'-pyrrolidine] (e.g., 1, 3-dihydrospiro [indene-2, 2'-pyrrolidine]-1'-yl), azaspiro[2.4]heptane (e.g., 5-azaspiro[2.4]heptane-5-yl), 2-oxa-6-azaspiro[3.3]heptane (e.g., 2-oxa-6-azaspiro[3.3]heptan-6-yl), azaspiro[3.4]octane (e.g., 6-azaspiro[3.4]octane-6-yl), 2-oxa-6-azaspiro [3.4]octane (e.g., 2-oxa-6-azaspiro[3.4]octane-6-yl), azaspiro[3.4]octane (e.g., 6-azaspiro[3.4]octan-6-yl), azaspiro[3.4]octane (e.g., 6-azaspiro[3.4]octan-6-yl), 1, 7-dioxaspiro[4.5]decane, 2-oxa-7-aza-spiro[4.4]nonane (e.g., 2-oxa-7-aza-spiro[4.4]non-7-yl), 7-oxa-spiro[3.5] nonyl and 5-oxa-spiro[2.4]heptyl.

The term "fused heterocyclyl" refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from nitrogen, oxygen or optionally oxidized sulfur as ring members, with the remaining ring members being carbon. One or more rings of a fused heterocyclic group may contain one or more double bonds, but the fused heterocyclic group does not have a completely conjugated pi-electron system. Preferably, a fused heterocyclyl is 6 to 14-membered, and more preferably 7 to 12-membered, or 7- to 10-membered. According to the number of membered rings, a fused heterocyclyl could be bicyclic, tricyclic, tetracyclic, or polycyclic fused heterocyclyl. The group can be attached to the remainder of the molecule through either ring.

Specifically, the term "bicyclic fused heterocyclyl" refers to a 7 to 12-membered, preferably 7- to 10-membered, more preferably 9- or 10-membered fused heterocyclyl as defined herein comprising two fused rings and comprising 1 to 4 heteroatoms selected from nitrogen, oxygen or optionally oxidized sulfur as ring members. Typically, a bicyclic fused heterocyclyl is 5-membered/5-membered, 5-membered/6-membered, 6-membered/6-membered, or 6-membered/7-membered bicyclic fused heterocyclyl. Representative examples of (bicyclic) fused heterocycles include without limitation to the following groups: octahydrocyclopenta[c] pyrrole, octahydropyrrolo[3, 4-c]pyrrolyl, octahydroisoindolyl, isoindolinyl, octahydro-benzo[b][1, 4]dioxin, indolinyl, isoindolinyl, benzopyranyl, dihydrothiazolopyrimidinyl, tetrahydroquinolyl, tetrahydroisoquinolyl (or tetrahydroisoquinolinyl), dihydrobenzofuranyl, dihydrobenzoxazinyl, dihydrobenzoimidazolyl, tetrahydrobenzothienyl, tetrahydrobenzofuranyl, benzodioxolyl, benzodioxonyl, chromanyl, chromenyl, octahydrochromenyl, dihydrobenzodioxynyl, dihydrobenzoxezinyl, dihydrobenzodioxepinyl, dihydrothienodioxynyl, dihydrobenzooxazepinyl, tetrahydrobenzooxazepinyl, dihydrobenzoazepinyl, tetrahydrobenzoazepinyl, isochromanyl, chromanyl, or tetrahydropyrazolopyrimidinyl (e.g., 4, 5, 6, 7-tetrahydropyrazolo[1,5-a]pyrimidin-3-yl).

The term a "benzo fused heterocyclyl" is a bicyclic fused heterocyclyl in which a monocyclic 4 to 9-membered heterocyclyl as defined herein (preferably 5- or 6-membered) is fused to a benzene ring.

The term "bridged heterocyclyl" refers to a 5- to 14-membered polycyclic heterocyclic alkyl group, wherein every two rings in the system share two disconnected atoms, comprising one or more heteroatoms selected from nitrogen, oxygen or optionally oxidized sulfur as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl could be bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include without limitation to the following groups: 2-azabicyclo [2.2.1]heptyl, azabicyclo[3.1.0]hexyl, 2-azabicyclo[2.2.2] octyl and 2-azabicyclo[3.3.2]decyl.

The term "at least one substituent" disclosed herein includes, for example, from 1 to 4, such as from 1 to 3, further as 1 or 2, substituents, provided that the theory of valence is met. For example, "at least one substituent $R^{6d}$" disclosed herein includes from 1 to 4, such as from 1 to 3, further as 1 or 2, substituents selected from the list of $R^{6d}$ as disclosed herein.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclic ring system, substituents found on such ring system may adopt cis and trans formations. Cis formation means that both substituents are found on the upper side of the 2 substituent placements on the carbon, while trans would mean that they were on opposing sides. For example, the di-substituted cyclic ring system may be cyclohexyl or cyclobutyl ring.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refer to stereoisomers of a compound with two or more chiral centers but which are not mirror images of one another. Diastereomeric mixtures can be separated into their individual diastereomers on the basis of their physical or chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers and diastereomers can also be separated by the use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H, et al. "*Chromatographic resolution of enantiomers: Selective review.*" *J. Chromatogr.,* 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W, Ed. *Drug Stereochemistry: Analytical Methods and Pharmacology*. New York: Marcel Dekker, Inc., 1993.

"Pharmaceutically acceptable salts" refer to those salts which are, within the scope of sound medical judgment, suitable for use in contact with the tissues of humans and animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" includes salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic agent, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined herein, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical route to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc., a filler such as starch, sucrose, etc., a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, an aromatic, a sweetener, a dye and etc.

The term “disease” refers to any disease, discomfort, illness, symptoms or indications, and can be interchangeable with the term “disorder” or “condition”.

Throughout this specification and the claims which follow, unless the context requires otherwise, the term “comprise”, and variations such as “comprises” and “comprising” are intended to specify the presence of the features thereafter, but do not exclude the presence or addition of one or more other features. When used herein the term “comprising” can be substituted with the term “containing”, “including” or sometimes “having”.

Throughout this specification and the claims which follow, the term “Cn-m” indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

General Reaction Scheme for Compound Preparation

The subject compounds and pharmaceutically acceptable salts thereof, can be prepared from (a) commercially available starting materials (b) known starting materials which may be prepared as described in literature procedures (c) new intermediates described in the schemes and experimental procedures herein. In making the compounds of the invention, the order of synthetic steps may be varied to increase the yield of the desired product. Some of the compounds in this invention may be generated by the methods as shown in the following reaction schemes and the description thereof.

Scheme A

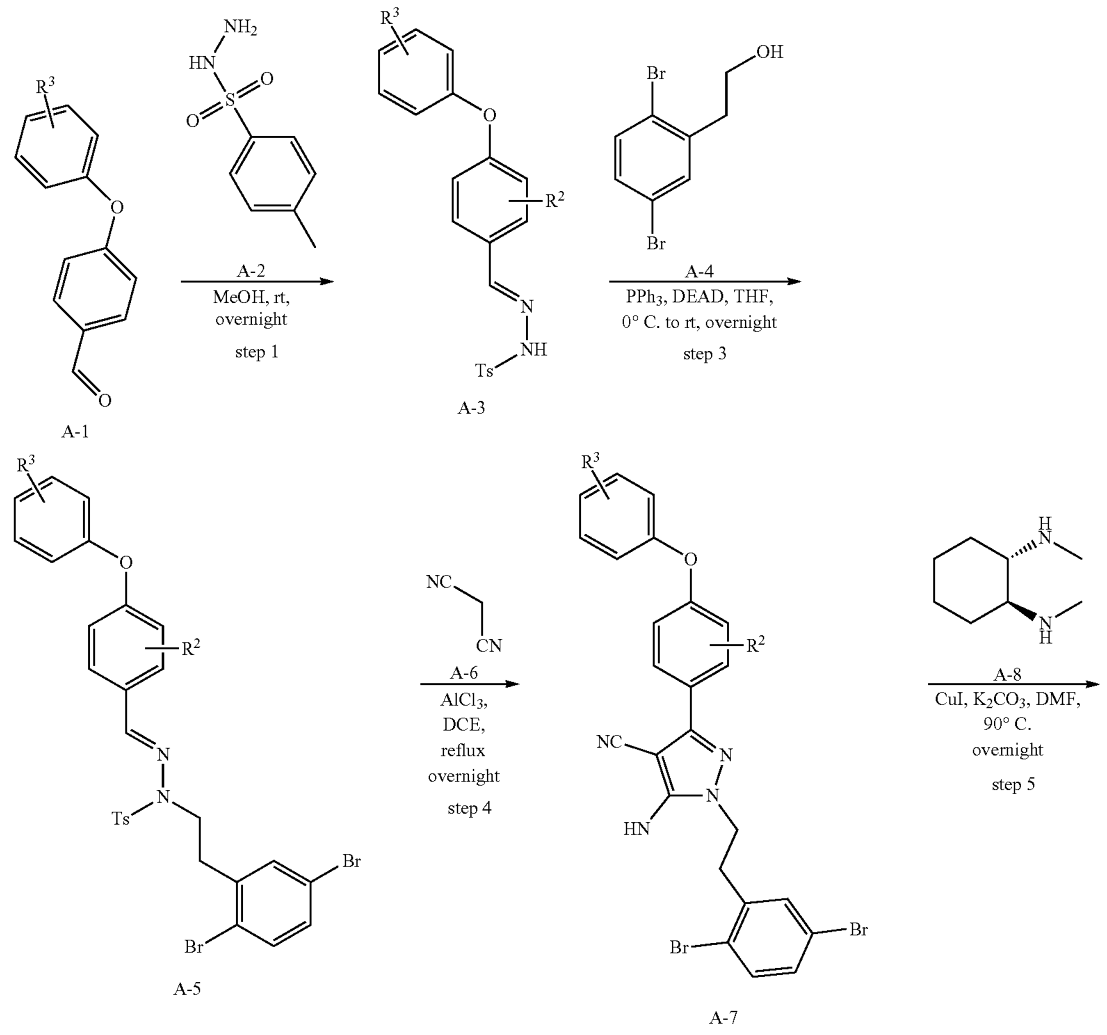

-continued
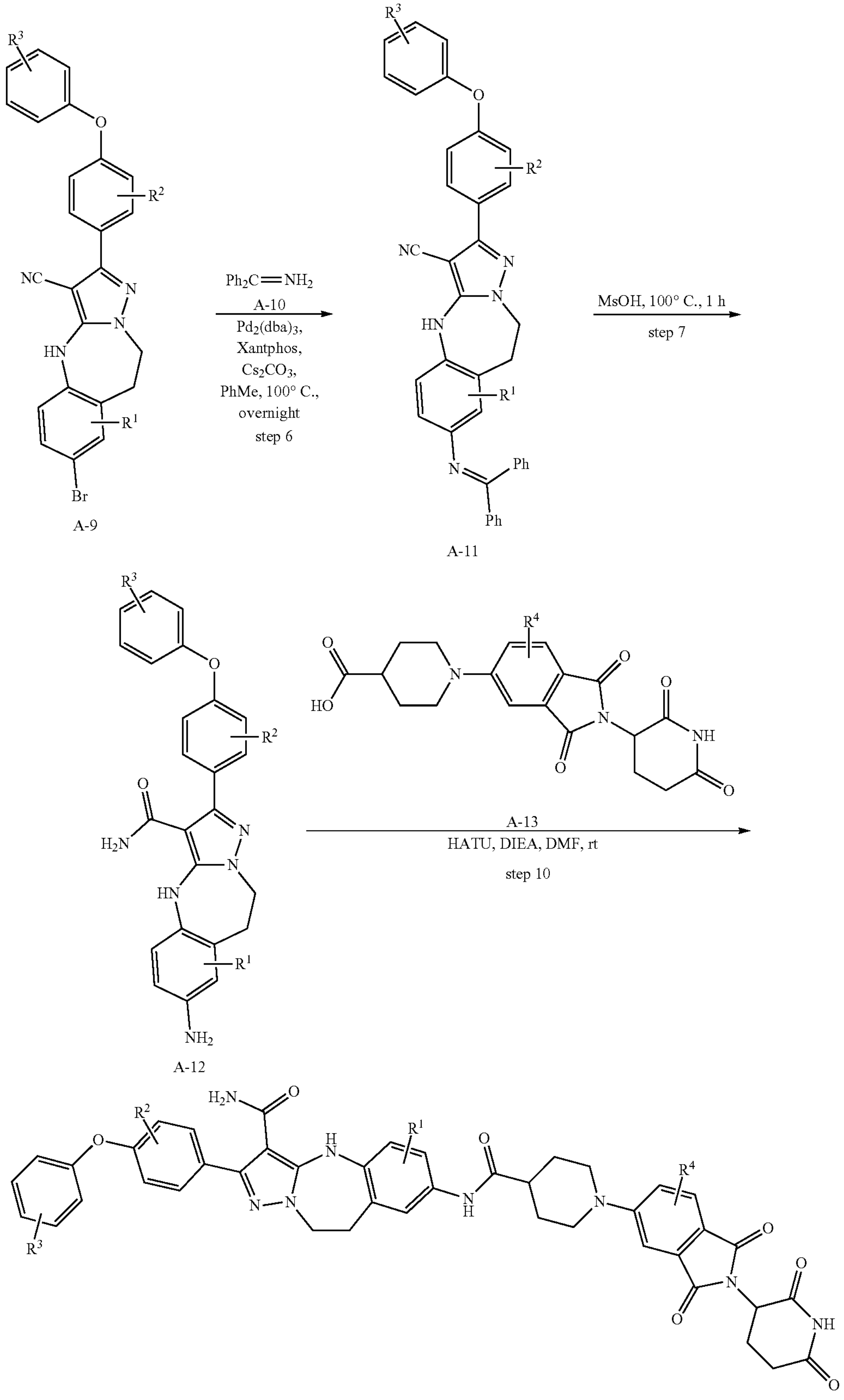
A-9
A-11
A-12
A

Wherein $R^1$, $R^2$, $R^3$ and $R^4$ are defined as described herein. A-3 can be synthesized from A-1 and 4-methylbenzenesulfonohydrazide in methanol, which was coupled with A-4 in the Mitsunobu reaction condition to form A-5. A-7 was synthesized from A-5 and A-6 by acid with a catalyst, to form A-9 by intramolecular cyclization with copper catalyst. A-9 was coupled with A-10 by Pd2(dba)2 as a catalyst to form A-11, and the protecting group was removed in acid to give A-12. Final product A was prepared from intermediate amine (A-12) and an acid (A-13).

Scheme B

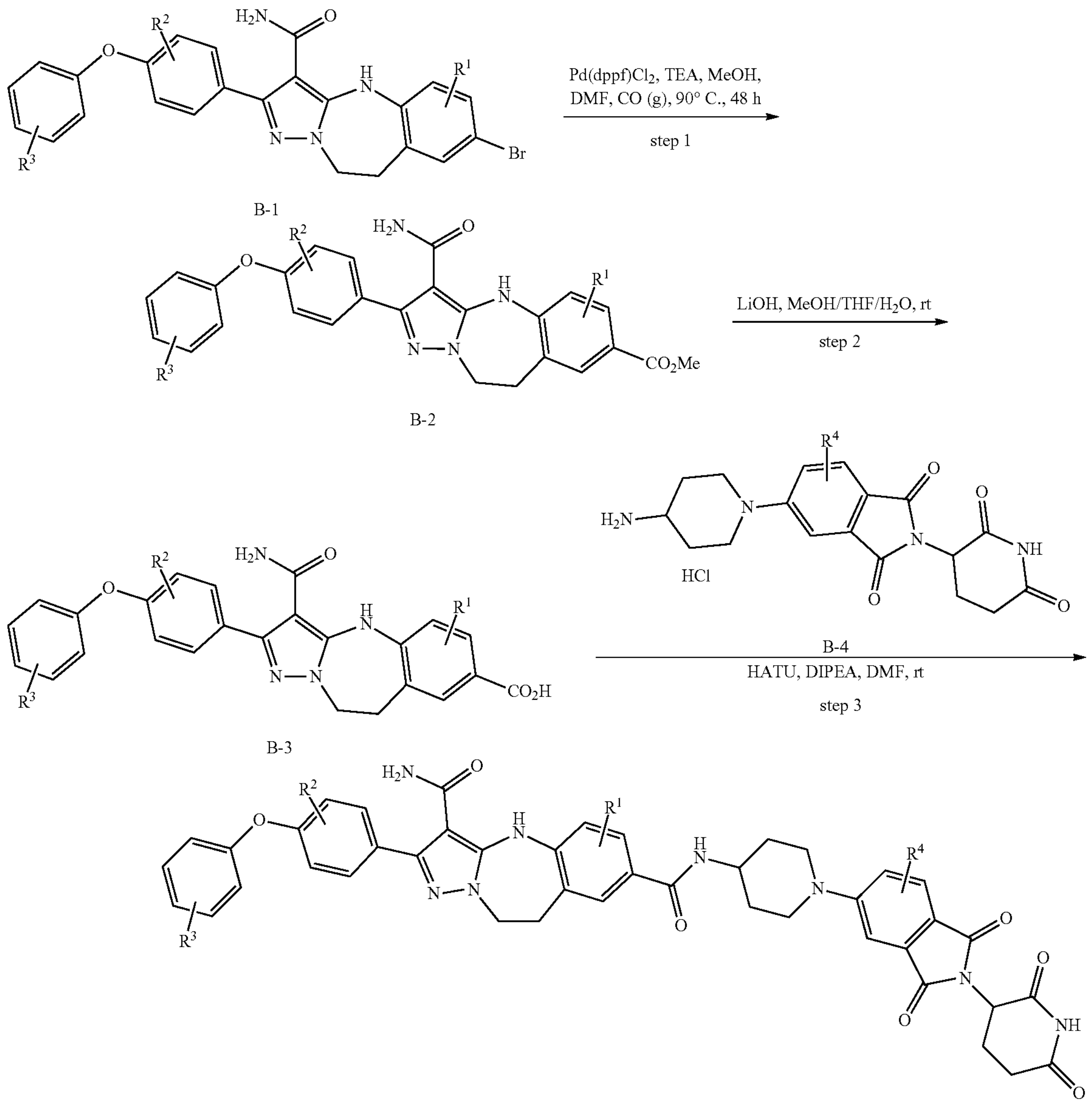

B

Wherein $R^1$, $R^2$, $R^3$ and $R^4$ are defined as described herein. B-2 can be synthesized from B-1 by using Pd as a catalyst, B-2 was hydrolyzed with LiOH to form acid (B-3). B-3 and B-4 were coupled in the presence of a coupling reagent, such as HATU, PyBOP, and so on to give the final product B.

Scheme C
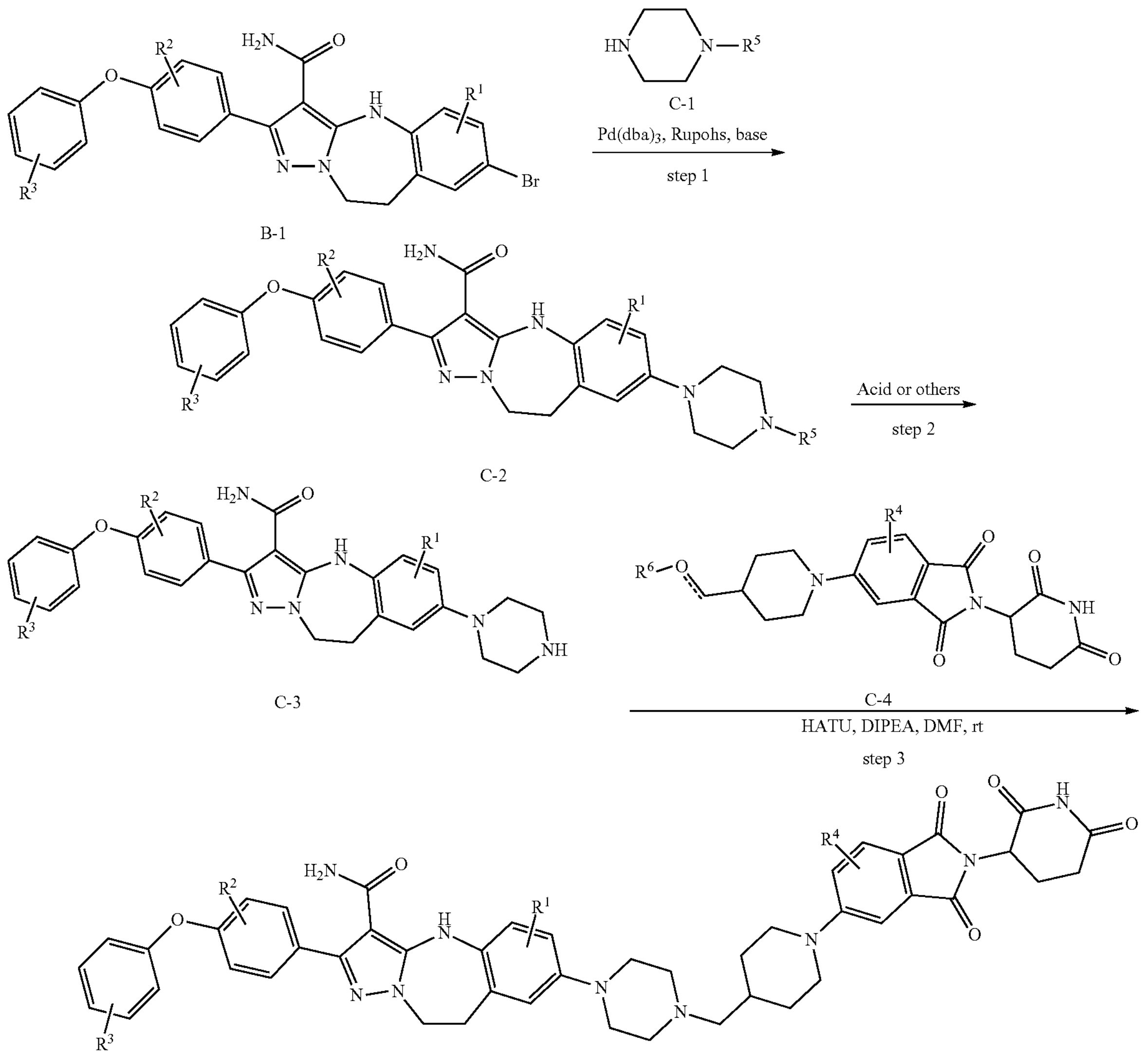
C
Wherein $R^1$, $R^2$, $R^3$, $R^4$, $R^5$ and $R^6$ are defined as described herein. C-2 can be synthesized from B-1 by using Pd as a catalyst, and $R^5$ was removed with an acid or other condition to form C-3, which was coupled with C-4 to give the final product C.
Scheme D
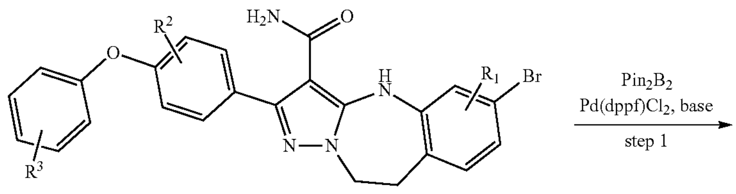
D-1

-continued

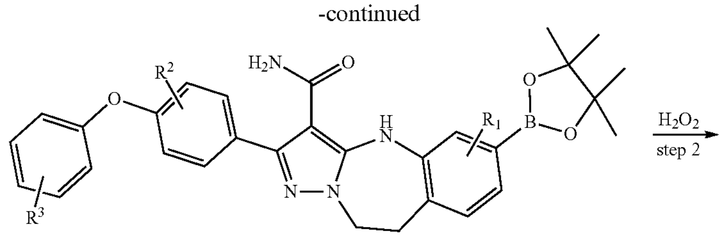

D-2

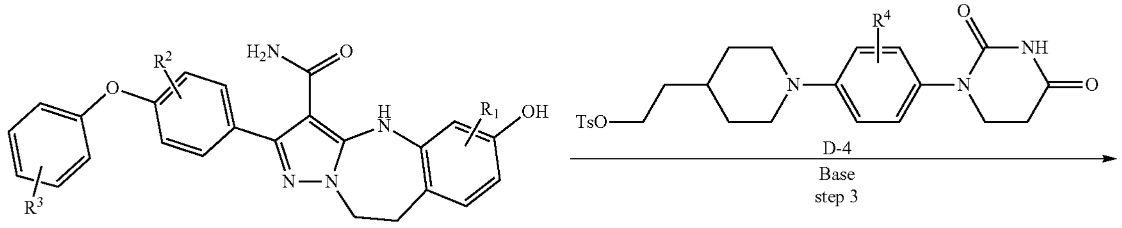

D-3

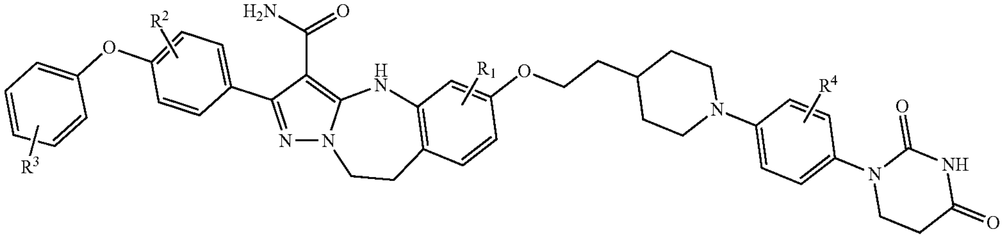

D

Wherein $R^1$, $R^2$, $R^3$ and $R^4$ are defined as described herein. D-1 was made from a similar method in Scheme A. D-2 can be synthesized from D-1 by using Pd as a catalyst, and a hydroxy compound D-3 was obtained from oxidation of intermediate borate (D-2) by $H_2O_2$ or other oxidation reagents. The final compound D was formed from D-3 and D-4 in the presence of a base or other conditions.

Scheme E

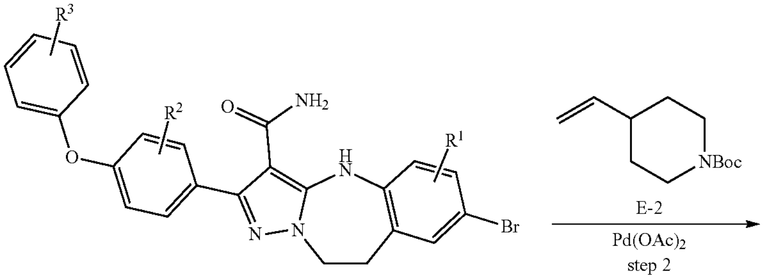

E-1

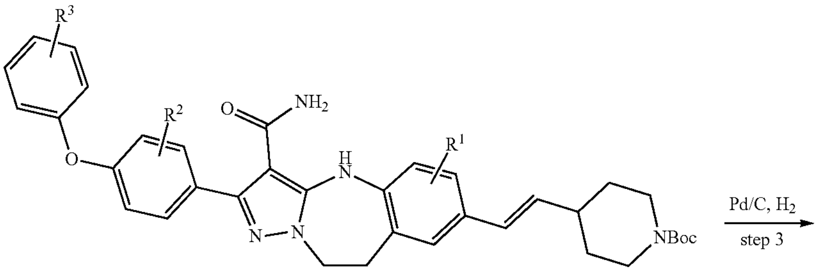

E-3

-continued
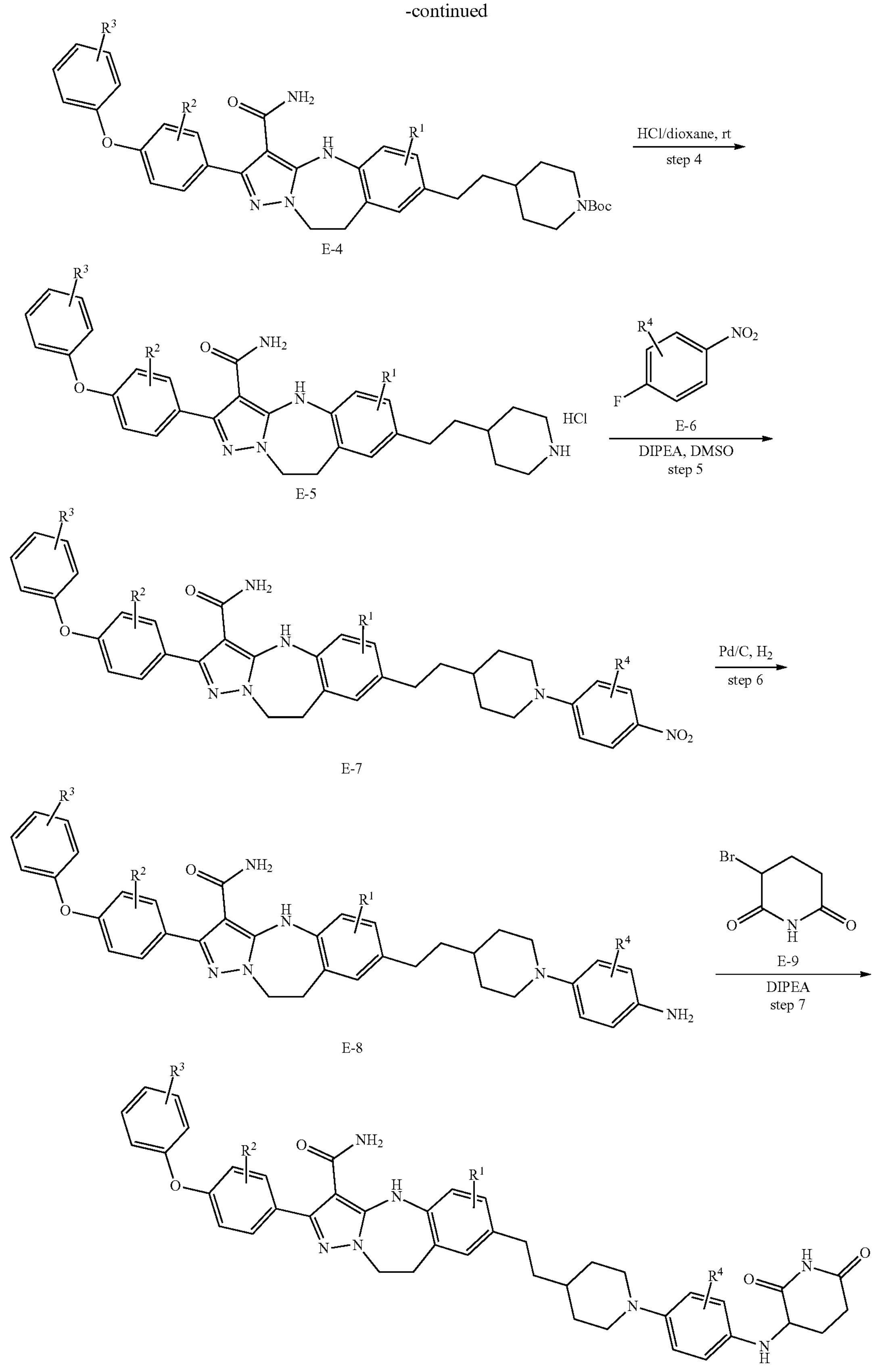
E

Wherein $R^1$, $R^2$, $R^3$ and $R^4$ are defined as described herein. E-1 was made from a similar method in Scheme A. E-2 can be synthesized from E-1 by using Pd as a catalyst, and E-3 was hydrogenated with Pd/C to form intermediate E-4. Boc group in E-4 was removed in acid condition to give E-5, which was coupled with E-6 in the presence of a base to form E-7. And the nitro group was reduced in the presence of hydrogen to form Intermediate amine (E-8), which was reacted with E-9 in a basic condition to give the final compound E.

Scheme F

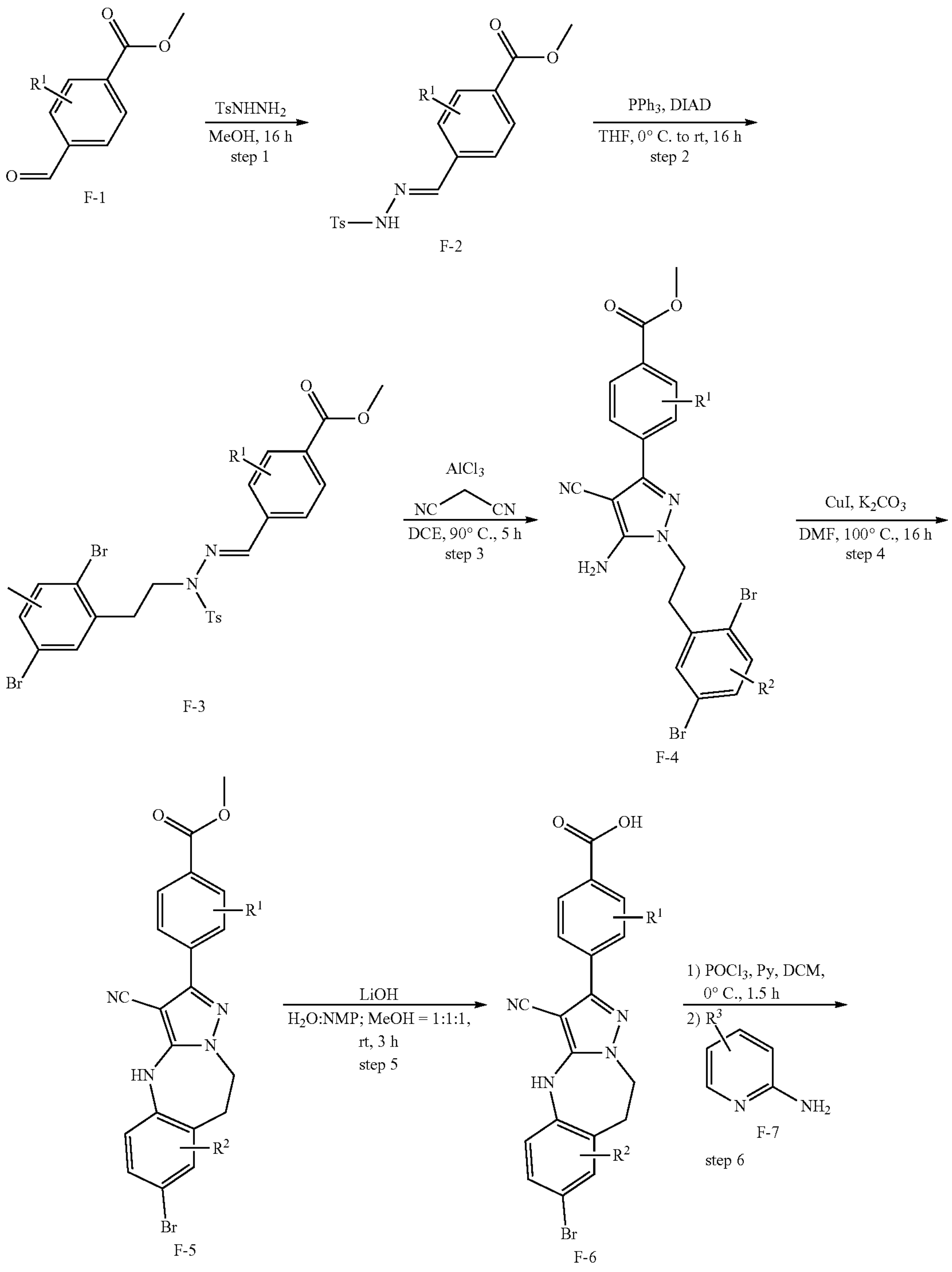

-continued

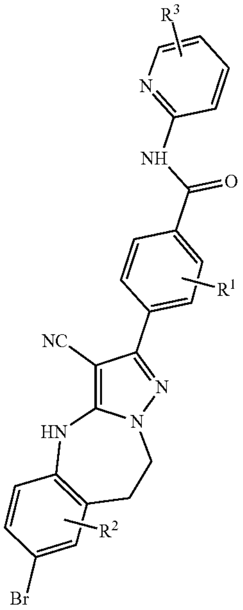

F-8

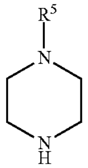

F-9

$Pd_2(dba)_3$, LiHMDS, BrettPhos

THF, 70° C., 5 h step 7

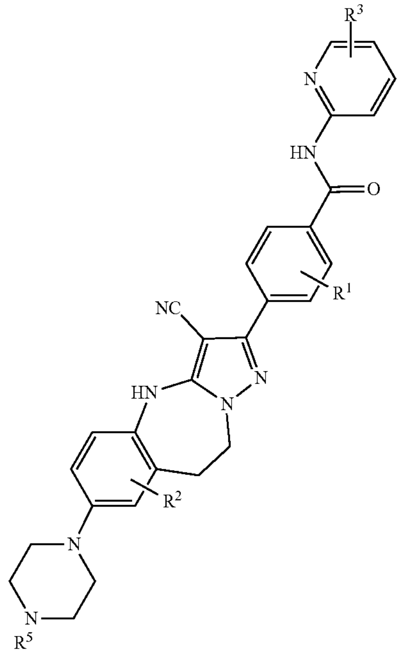

F-10

MsOH, 100° C., 3 h step 8

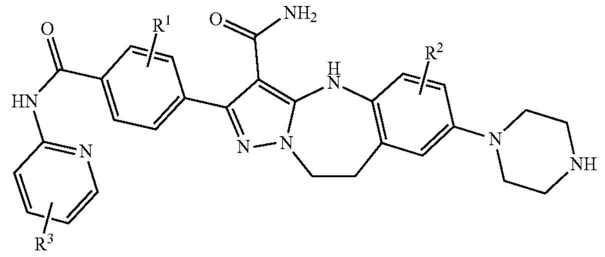

F-11

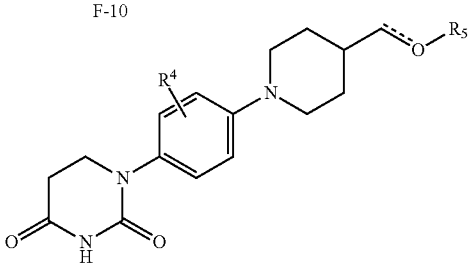

F-12 step 9

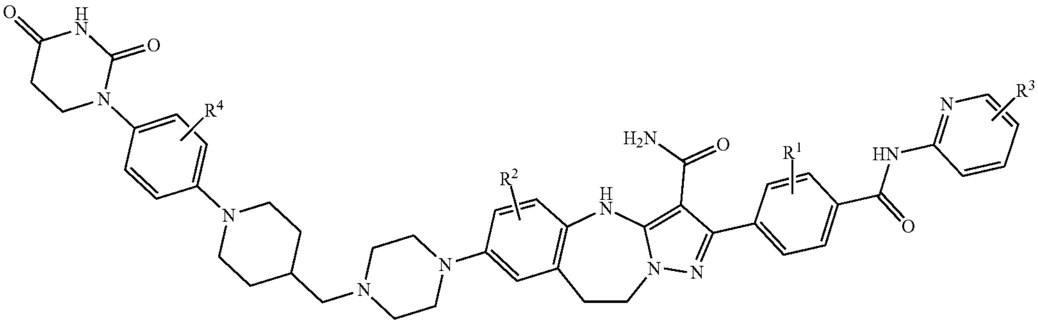

F

Wherein $R^1$, $R^2$, $R^3$, $R^4$ and $R^5$ are defined as described herein. F-2 was made from F-1 and 4-methylbenzenesulfonohydrazide, and F-2 was coupled with an alcohol in the $PPh_3$/DIAD condition to form intermediate F-3. And F-4 was made from F-3 and malononitrile by using $AlCl_3$ as a catalyst, then an intramolecular ring formed with a copper catalyst to form Intermediate F-5. The ester group in F-5 was hydrolyzed in a basic condition to form Intermediate acid (F-6). F-8 was synthesized from F-6 and F-7 through two steps, and F-8 was coupled with F-9 with Pd as a catalyst to form Intermediate F-10. F-11 and F-12 were coupled by reductive amination or $SN_2$ reaction to form the final compound F.

Scheme G
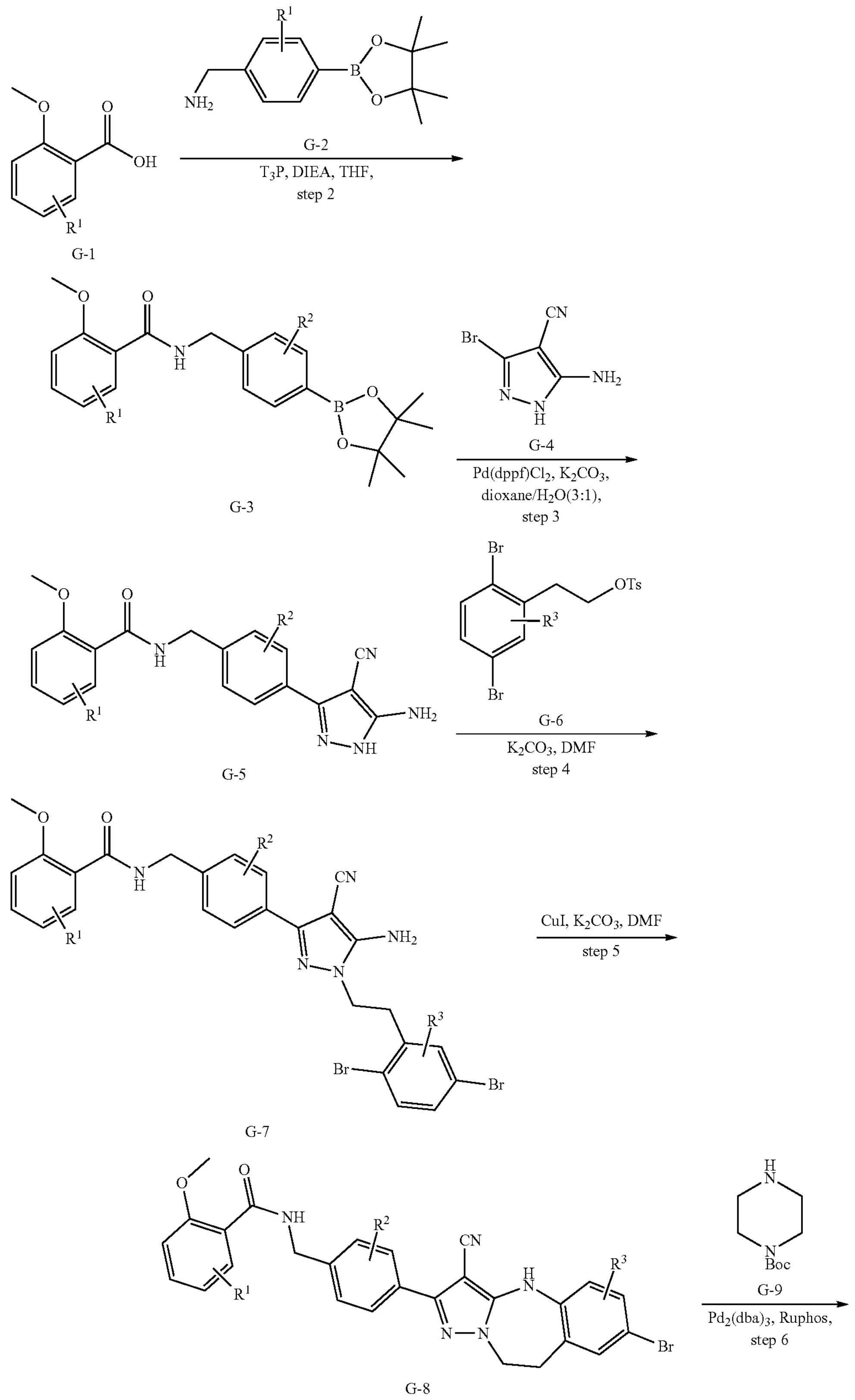

-continued

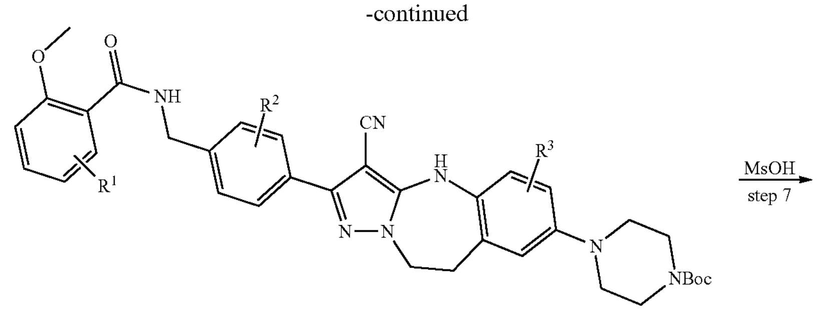

G-10

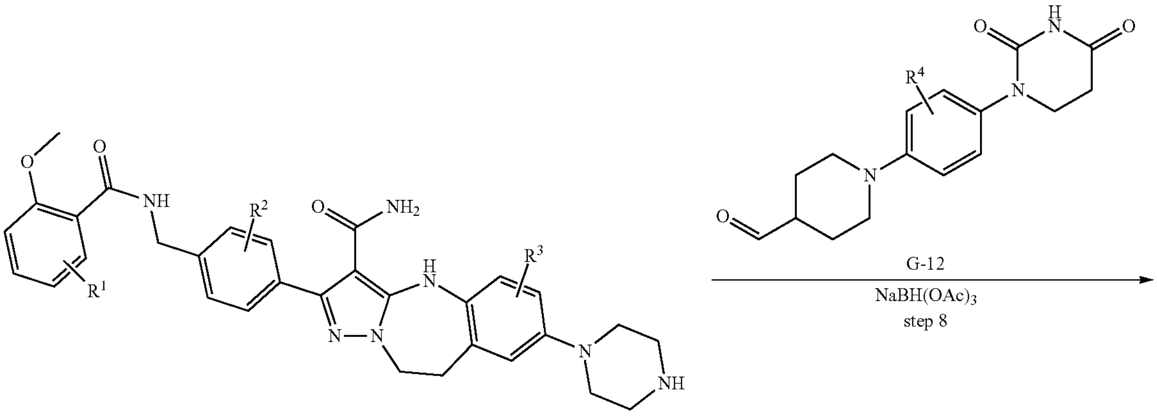

G-11

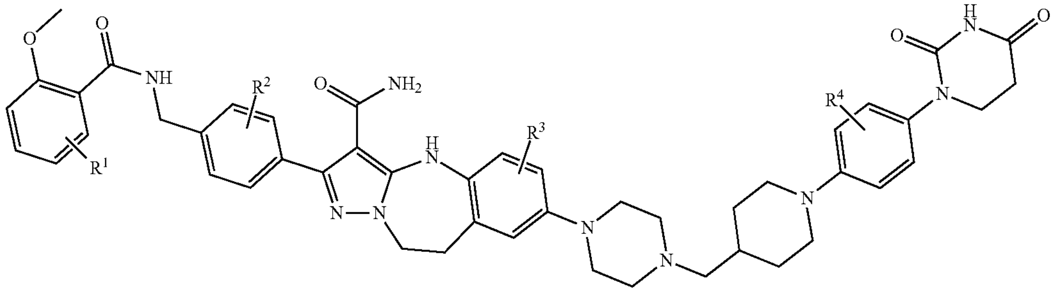

G

Wherein $R^1$, $R^2$, $R^3$, and $R^4$ are defined as described herein. G-1 was coupled with G-2 to form G-3, which was reacted with G-4 in the $Pd(dppf)Cl_2$/base condition to form Intermediate G-5. G-7 was made from G-5 and G-6 in a basic condition, and an intramolecular ring formed in intermediate G-8 by using CuI as a catalyst. G-10 was formed from G-8 and G-9 with Pd as a catalyst, and the cyan group was hydrolyzed into an amide group in G-11 in an acid condition. The final compound G was synthesized from G-11 and G-12 by a reductive amination reaction.

Scheme H
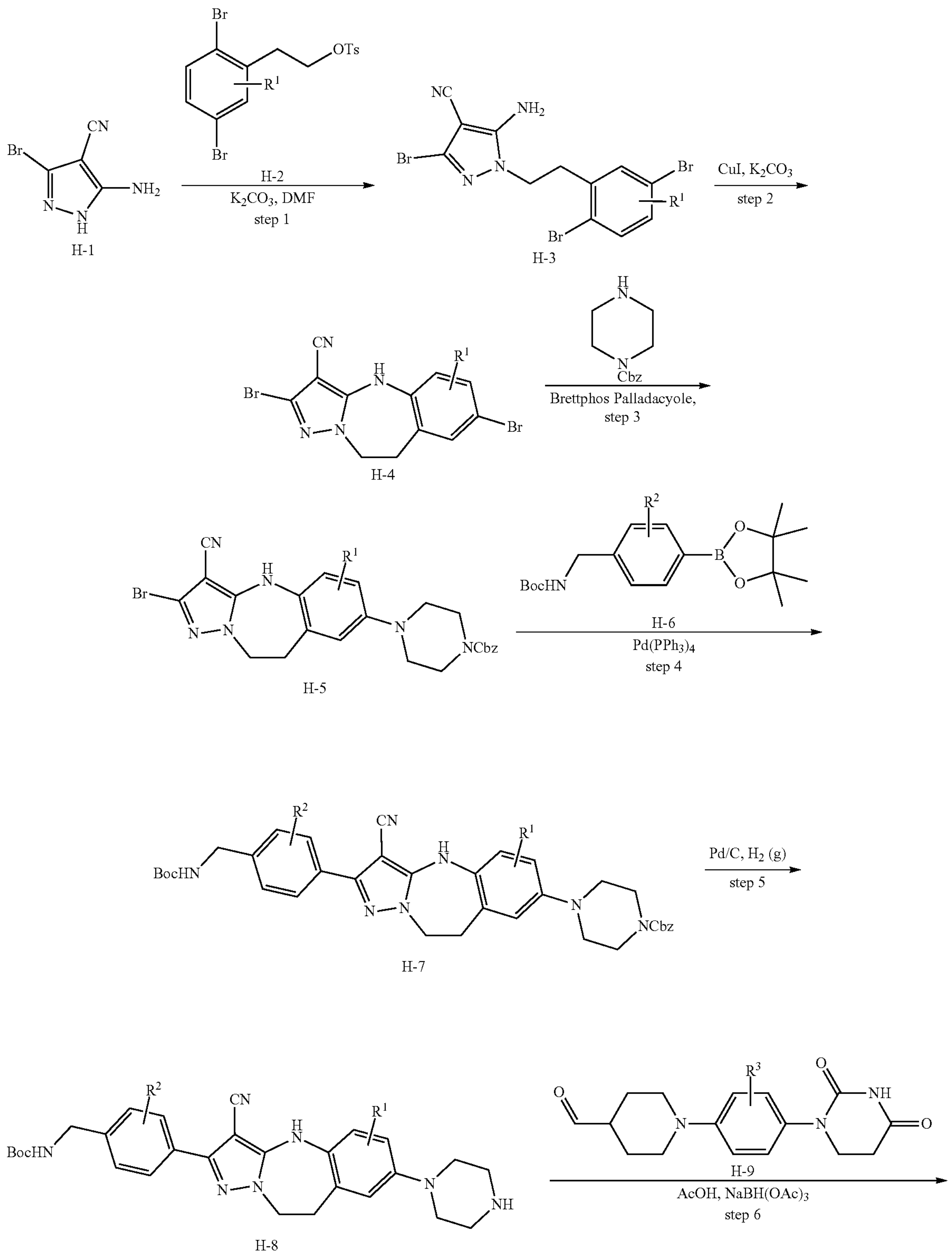
H-1 H-3 H-4 H-5 H-7 H-8

-continued

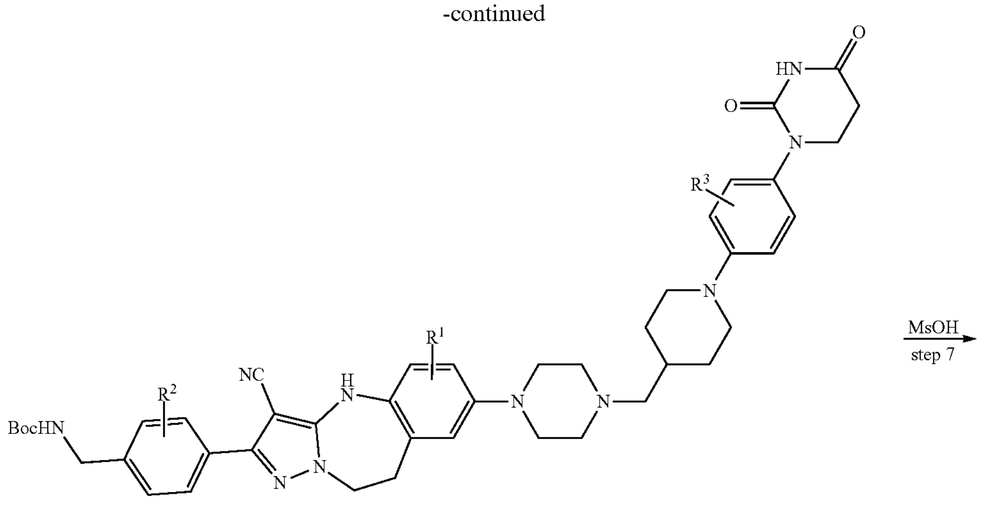

H-10

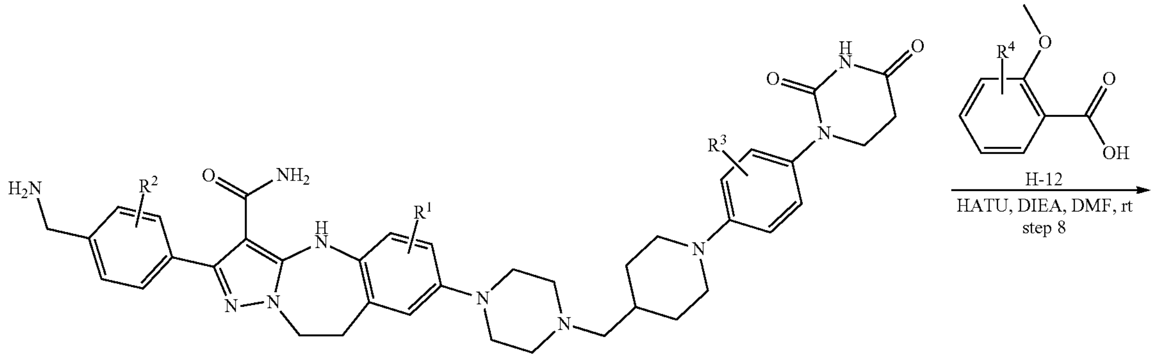

H-11

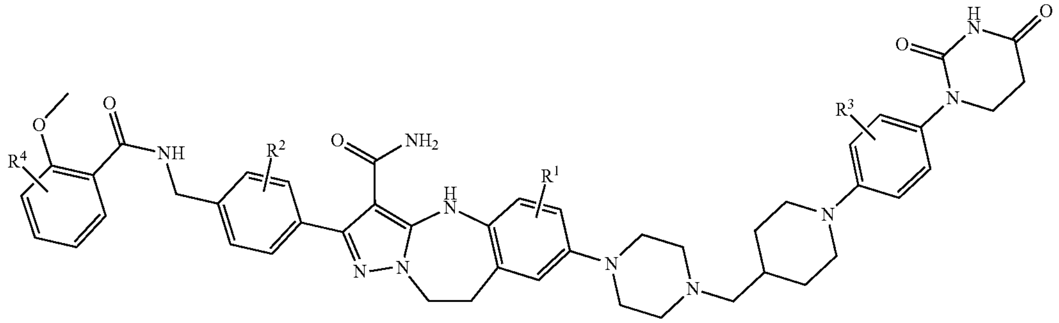

H

Wherein $R^1$, $R^2$, $R^3$, and $R^4$ are defined as described herein. H-3 was synthesized from H-1 and H-2 in the basic condition, and H-3 was subject to cyclization to form H-4 by using CuI as a catalyst. H-4 was coupled with benzyl piperazine-1-carboxylate to form H-5. H-5 and H-6 were reacted in the $Pd(PPh_3)_4$ as a catalyst to form H-7, and the Cbz group in H-7 was removed by Pd/C in the presence of $H_2$ to form H-8. Reductive amination reaction between H-8 and H-9 to give Intermediate H-10. And the cyan group in H-10 was converted into an amide group in H-11 by using MsOH, and the Boc group was also removed in this condition. Another amide bond was formed in the final compound H by coupling between H-11 and H-12 with a coupling reagent, such as HATU, PyBop, and so on.

Scheme I

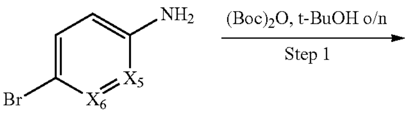

I-1

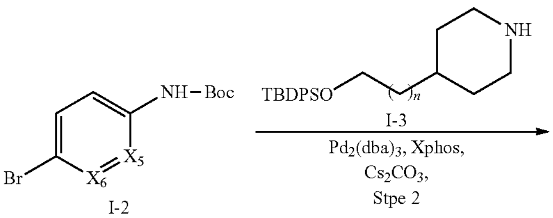

I-2

-continued

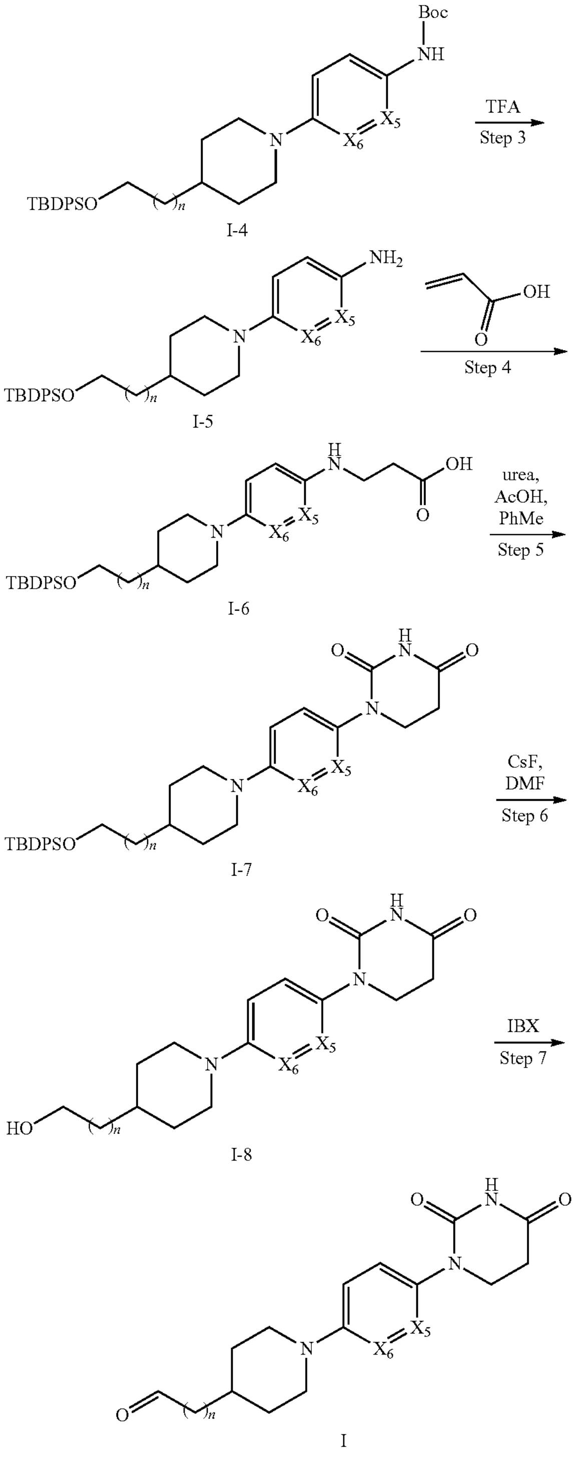

I-4

I-5

I-6

I-7

I-8

I

Wherein n, $X_5$ and $X_6$ are defined as described herein. I-2 was synthesized from I-1 and $(BOC)_2O$, then 1-2 and 1-3 were coupled with Pd as a catalyst to give Intermediate 1-4. Boc group was removed in acid condition to form 1-5, which was mixed with acrylic acid and heated to give 1-6. 1-7 was synthesized from 1-6 and urea in a heated condition, and then the TBS group in 1-7 was removed by TBAF or CsF to give Intermediate 1-8, which was oxidized to Intermediate I by using oxidation reagent, such as IBX and so on.

Scheme J

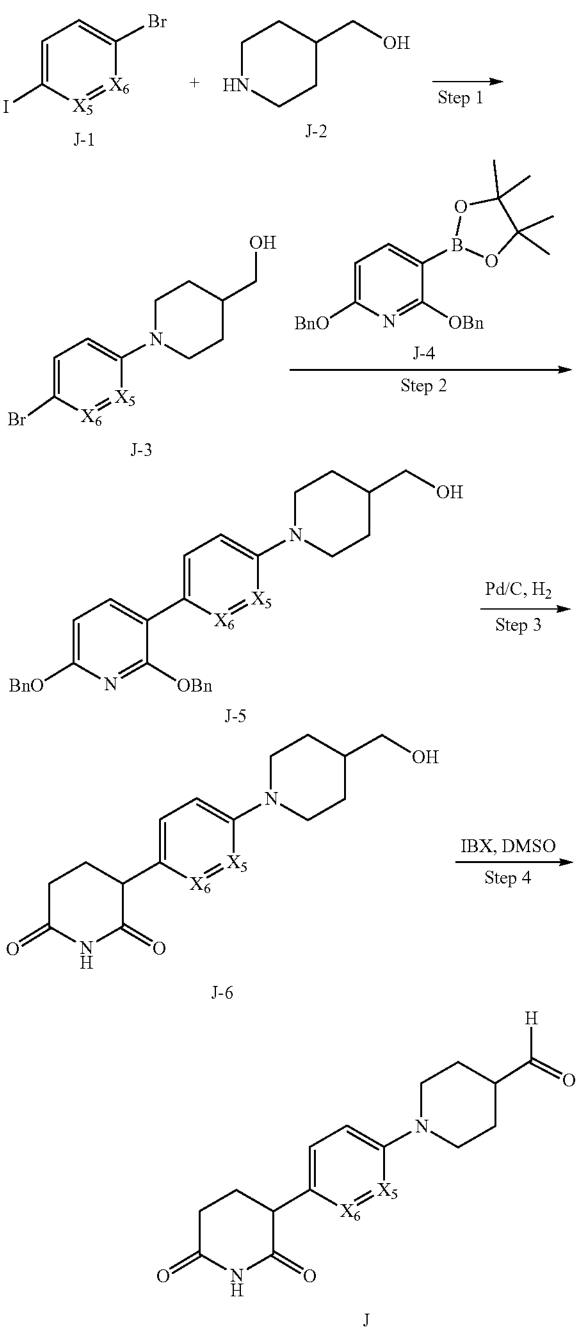

J-1

J-2

J-3

J-4

J-5

J-6

J

Wherein $X_3$ and $X_4$ are defined as described herein. J-1 and J-2 were coupled in the metal catalyst (CuI, Pd and so on) to give J-3, which was coupled with J-4 by using Pd as a catalyst to give J-5. The bis(benzyloxy)pyridine group in J-5 was reduced to piperidine-2,6-dione in J-6 by hydrogen $(H_2)$ with Pd/C as a catalyst, then the final intermediate J was obtained by oxidization with an oxidation reagent, such as IBX and so on.

EXAMPLES

The examples below are intended to be purely exemplary and should not be considered to be limiting in any way.

Efforts have been made to ensure accuracy with respect to numbers used (for example, amounts, temperature, etc.), but some experimental errors and deviations should be accounted for. Unless indicated otherwise, the temperature is in degrees Centigrade. Reagents were purchased from commercial suppliers such as Sigma-Aldrich, Alfa Aesar, or TCI, and were used without further purification unless indicated otherwise. Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

$^1$H NMR spectra were recorded on an Agilent instrument operating at 400 MHz.

$^1$HNMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_3CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz).

LCMS-1: LC-MS spectrometer (Agilent 1260 Infinity) Detector: MWD (190-400 nm), Mass detector: 6120 SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.8 mL/min Time (min) A (%) B (%)

| Time (min) | A(%) | B(%) |
|---|---|---|
| 0.00 | 95 | 5 |
| 1.5 | 5 | 95 |
| 2.0 | 5 | 95 |
| 2.1 | 95 | 5 |
| 3.0 | 95 | 5 |

LCMS, LCMS-3: LC-MS spectrometer (Agilent 1260 Infinity II) Detector: MWD (190-400 nm), Mass detector: G6125C SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.8 mL/min Time (min) A(%) B (%)

| Time (min) | A(%) | B(%) |
|---|---|---|
| 0.00 | 95 | 5 |
| 1.5 | 5 | 95 |
| 2.0 | 5 | 95 |
| 2.1 | 95 | 5 |
| 3.0 | 95 | 5 |

LCMS-2: LC-MS spectrometer (Agilent 1290 Infinity II) Detector: MWD (190-400 nm), Mass detector: G6125C SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.2 mL/min mL/min Time (min) A(%) B (%)

| Time (min) | A(%) | B(%) |
|---|---|---|
| 0.00 | 90 | 10 |
| 1.5 | 5 | 95 |
| 2.0 | 5 | 95 |
| 2.1 | 90 | 10 |
| 3.0 | 90 | 10 |

Preparative HPLC was conducted on any commercially available column (e.g., 150×21.2 mm ID, 5 pm, Gemini NXC 18, Waters Xselect CSH C18, or Waters Xbridge C18) at a flow rate of 20 ml/min, injection volume of 2 ml, at room temperature and UV Detection at 214 nm and 254 nm. Mobile phase A is ACN (optionally with 0.1% FA); Mobile phase B is water (optionally with 0.1% FA or 0.03% $NH_3{\cdot}H_2O$). Gradient Table: Mobile Phase A (20%-90%, 30%-90%, 40%-90% or 50%-90%), Time (min): 0-15 min, 0-17 min, or 0-20 min.

In the following examples, the abbreviations below are used:

| | |
|---|---|
| AcOH | Acetic acid |
| AcOK | Potassium acetate |
| Aq | Aqueous |
| ACN | Acetonitrile |
| Brine | Saturated aqueous sodium chloride solution |
| Bn | Benzyl |
| BnBr | Benzyl Bromide |
| Boc | Tert-butyloxycarbonyl |
| $(Bpin)_2$ | 4,4,4',4',5,5,5',5'-octamethyl-2,2'-bi(1,3,2-dioxaborolane) |
| BPO | Dibenzoyl peroxide |
| BINAP | (±)-2,2'-Bis(diphenylphosphino)-1,1'-binaphthalene |
| Cbz | benzyloxycarbonyl |
| $CH_2Cl_2$ | Dichloromethane |
| $CoCl_2$ | Cobalt chloride |
| DCE | dichloroethane |
| DMF | N,N-Dimethylformamide |
| Dppf | 1,1''-bis(diphenylphosphino)ferrocene |
| DBU | 1,8-diazabicyclo[5.4.0]undec-7-ene |
| DCM | Dichloromethane |
| DIAD | Diisopropyl azodicarboxylate |
| DIEA or DIPEA | N,N-diisopropylethylamine |
| DIBAL-H | Diisobutylaluminium hydride |
| DMAP | 4-N,N-dimethylaminopyridine |
| DMF | N,N-dimethylformamide |
| DMSO | Dimethyl sulfoxide |
| EA or EtOAc | Ethyl acetate |
| EtOH | Ethanol |
| $Et_2O$ or ether | Diethyl ether |
| FA | Formic acid |
| g | Grams |
| h or hr | Hour |
| HATU | O-(7-Azabenzotriazol-1-yl)-N,N,N',N'-tetramethyluronium hexafluorophosphate |
| HBTU | 2-(1H-Benzotriazole-1-yl)-1,1,3,3-tetramethylaminium hexafluorophosphate |
| HCl | Hydrochloric acid |
| Hex | Hexane |
| HPLC | High-performance liquid chromatography |
| IBX | 2-iodoxybenzoic acid |
| IPA | 2-propanol |
| i-PrOH | Isopropyl alcohol |
| LiHMDS | lithium bis(trimethylsilyl)azanide |
| mg | Milligrams |
| mL | Milliliters |
| Mmol | Millimole |
| MeCN | Acetonitrile |
| MeOH | Methanol |
| Min | Minutes |
| ms or MS | Mass spectrum |
| MsCl | methanesulfonyl chloride |
| MsOH | Methanesulfonic acid |
| $Na_2SO_4$ | Sodium sulfate |
| NBS | N-Bromosuccinimide |

-continued

| | |
|---|---|
| NMP | N-Methyl pyrrolidone |
| PE | Petroleum ether |
| $Ph_3PO$ | Triphenyl phosphorus oxide |
| PhMe | Toluene |
| $PPh_3$ | triphenylphosphine |
| PPA | Polyphosphoric acid |
| PIN | pinacol |
| Rt | Retention time |
| R.T. or r.t. | Room temperature |
| Ruphos | 2-Dicyclohexylphosphino-2',6'-diisopropoxybiphenyl |
| SM | Starting material |
| STAB | Sodium triacetoxyborohydride |
| $T_3P$ | Propylphosphonic anhydride |
| TBAF | Tetra-butyl ammonium fluoride |
| TBSCl | tert-Butyldimethylsilyl chloride |
| TEA | Triethanolamine |
| TFA | Trifluoroacetic acid |
| $Tf_2O$ | Triflic anhydride |
| THF | Tetrahydrofuran |
| TLC | thin layer chromatography |
| TMSOK | trimethyl(potassiooxy)silane |
| Ts | para-toluenesulfonyl |
| Ts Cl | p-Toluenesulfonyl chloride |
| TsOH | 4-toluene sulfonic acid |
| TBS | tert-butyldimethylsilyl |
| µL | Microliters |
| Brettphos | Dicyclohexyl[3,6-dimethoxy-2',4',6'-tris(1-methylethyl)[1,1'-biphenyl]-2-yl]phosphine |
| $Pd_2(dba)_2$ | Di(dibenzylideneacetone)dipalladium |
| Prep-HPLC | preparative high performance liquid chromatography |
| Prep-TLC | preparative thin layer chromatography |

Example A1: 7-(1-(2-(2,6-dioxopiperidin-3-yl)-1,3-dioxoisoindolin-5-yl)piperidine-4-carboxamido)-2-(4-phenoxyphenyl)-9,10-dihydro-4H-benzo[d]pyrazolo[1,5-a][1,3]diazepine-3-carboxamide Step 1: (E)-4-methyl-N'-(4-phenoxybenzylidene) benzenesulfonohydrazide

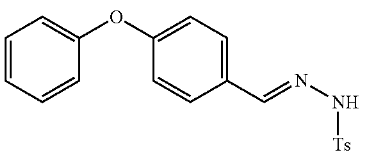 [SMILES: Cc1ccc(S(=O)(=O)N/N=C/c2ccc(Oc3ccccc3)cc2)cc1]

A mixture of 4-phenoxybenzaldehyde (65.0 g, 0.328 mol) and 4-methylbenzenesulfonohydrazide (61.0 g, 0.328 mol) in MeOH (2.0 L) was stirred at room temperature overnight. The solid was filtered, washed with MeOH (2.0 L) and dried to give the product (108.0 g, 90%). $^1H$ NMR (400 MHz, DMSO) δ 11.35 (s, 1H), 7.89 (s, 1H), 7.75 (d, J=8.1 Hz, 2H), 7.56 (d, J=8.6 Hz, 2H), 7.41 (t, J=7.9 Hz, 4H), 7.19 (t, J=7.4 Hz, 1H), 7.04 (d, J=8.2 Hz, 2H), 6.98 (d, J=8.6 Hz, 2H), 2.36 (s, 3H); $[M+H]^+$=366.9.

Step 2: 2-(2,5-dibromophenyl)ethan-1-ol

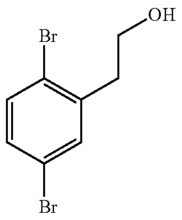 [SMILES: OCCc1cc(Br)ccc1Br]

A mixture of 2-(2,5-dibromophenyl)acetic acid (44.0 g, 0.15 mol) in 1,4-dioxane (500 mL) was added dropwise borane tetrahydrofuran complex solution (195.0 mL, 0.195 mol, 1.0 M in THF) at 0° C. The mixture was stirred in a round bottom flask at room temperature overnight. Then the mixture was treated with 1 M aqueous hydrochloric acid solution, extracted with dichloromethane (3×300 mL), and washed with brine (500 mL). The organic phase was dried over anhydrous sodium sulfate, filtered, and concentrated under reduced pressure to afford the product (43.0 g, 100%). $^1H$ NMR (400 MHz, DMSO) δ 7.53 (dt, J=8.8, 3.8 Hz, 2H), 7.35 (dd, J=8.5, 2.2 Hz, 1H), 4.77 (s, 1H), 3.61 (t, J=6.7 Hz, 2H), 2.85 (dd, J=12.1, 5.5 Hz, 2H); $[M+H—OH]^+$=262.7.

Step 3: (E)-N-(2,5-dibromophenethyl)-4-methyl-N'-(4-phenoxybenzylidene)benzenesulfonohydrazide

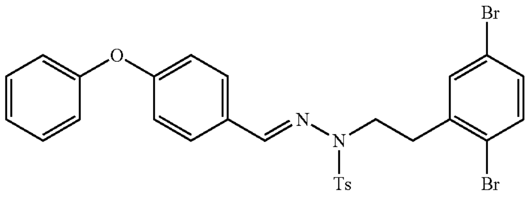 [SMILES: Cc1ccc(S(=O)(=O)N(CCc2cc(Br)ccc2Br)/N=C/c2ccc(Oc3ccccc3)cc2)cc1]

A mixture of (E)-4-methyl-N'-(4-phenoxybenzylidene) benzenesulfonohydrazide (62.0 g, 0.17 mol), 2-(2,5-dibromophenyl)ethan-1-ol (47.0 g, 0.17 mol) and triphenylphosphine (66.8 g, 0.255 mol) in dry THE (800 mL) was added dropwise diisopropylazodiformate (51.5 g, 0.255 mol) at 0° C. The mixture was stirred in a round bottom flask at room temperature overnight. Then the mixture was treated with water (1 L), extracted with EA (3×500 mL). The organic phase was dried over anhydrous sodium sulfate, filtered and concentrated under reduced pressure to afford the crude product, which was purified with silica gel column chromatography (PE:EA=100:0~50:50 gradient elution) to give the product (80.0 g, 74.9%). $^1H$ NMR (400 MHz, DMSO) δ 8.10 (s, 1H), 7.71 (dd, J=12.7, 8.4 Hz, 4H), 7.61 (d, J=2.2 Hz, 1H), 7.56 (d, J=8.5 Hz, 1H), 7.42 (dt, J=16.5, 8.3 Hz, 5H), 7.21 (t, J=7.4 Hz, 1H), 7.07 (dd, J=12.0, 8.6 Hz, 4H), 3.91 (t, J=7.0 Hz, 2H), 2.97 (t, J=7.0 Hz, 2H), 2.37 (s, 3H); $[M+H]^+$=628.6.

Step 4: 5-amino-1-(2,5-dibromophenethyl)-3-(4-phenoxyphenyl)-1H-pyrazole-4-carbonitrile

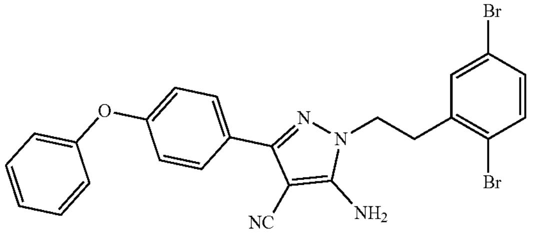 [SMILES: N#Cc1c(-c2ccc(Oc3ccccc3)cc2)nn(CCc2cc(Br)ccc2Br)c1N]

To a solution of (E)-N-(2,5-dibromophenethyl)-4-methyl-N'-(4-phenoxybenzylidene)benzenesulfonohydrazide (85.0 g, 135.8 mmol) was added malononitrile (22.4 g, 0.34 mol) and aluminum trichloride (45.2 g, 0.34 mol) in 1,2-dichlorethan (1 L). The mixture was stirred at 90° C. for 30 h and then treated with water (1 L), extracted with dichloromethane (3×300 mL), and washed with brine (500 mL). The organic phase was dried over anhydrous sodium sulfate, filtered and concentrated under reduced pressure to afford the crude product, which was purified with silica gel column chromatography (DCM:MeOH=100:0~90:10 gradient elution) to give the product (30.0 g, 41.2%). $^1H$ NMR (400 MHz, DMSO) δ 7.74 (d, J=8.3 Hz, 2H), 7.55 (d, J=10.9 Hz, 2H), 7.49-7.34 (m, 3H), 7.18 (t, J=7.4 Hz, 1H), 7.12-7.03 (m, 4H), 6.75 (s, 2H), 4.18 (t, J=6.8 Hz, 2H), 3.13 (t, J=6.8 Hz, 2H); $[M+H]^+$=536.6.

Step 5: 7-bromo-2-(4-phenoxyphenyl)-9,10-dihydro-4H-benzo[d]pyrazolo[1,5-a][1,3]diazepine-3-carbonitrile

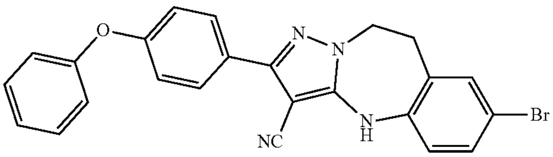 [SMILES: N#Cc1c(-c2ccc(Oc3ccccc3)cc2)nn2c1Nc1ccc(Br)cc1CC2]

A mixture of 5-amino-1-(2,5-dibromophenethyl)-3-(4-phenoxyphenyl)-1H-pyrazole-4-carbonitrile (25.0 g, 46.6 mmol), (1S,2S)—$N^1$,$N^2$-dimethylcyclohexane-1,2-diamine (994 mg, 7.0 mmol), copper (I) iodide (1.3 g, 7.0 mmol), potassium carbonate (19.3 g, 140.0 mmol) in DMF (300.0 mL) was stirred at 90° C. overnight under nitrogen. The mixture was evaporated in vacuum to give the crude product, which was purified with silica gel column chromatography (PE:EA=80:20~50:50 gradient elution) to give the product (16.0 g, 75.1%). $^1H$ NMR (400 MHz, DMSO) δ 9.77 (s, 1H), 7.83 (d, J=8.5 Hz, 2H), 7.48-7.36 (m, 4H), 7.29 (d, J=8.7 Hz, 1H), 7.19 (t, J=7.4 Hz, 1H), 7.10 (dd, J=7.8, 5.3 Hz, 4H), 4.40 (d, J=4.5 Hz, 2H), 3.22-3.08 (m, 2H); $[M+H]^+$=456.8.

Step 6: 7-((diphenylmethylene)amino)-2-(4-phenoxyphenyl)-9,10-dihydro-4H-benzo[d]pyrazolo[1,5-a][1,3]diazepine-3-carbonitrile

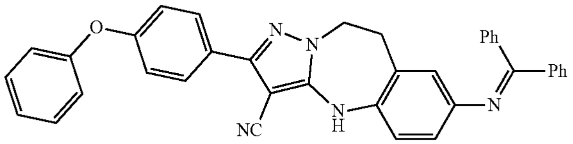 [SMILES: N#Cc1c(-c2ccc(Oc3ccccc3)cc2)nn2c1Nc1ccc(N=C(c3ccccc3)c3ccccc3)cc1CC2]

A mixture of 7-bromo-2-(4-phenoxyphenyl)-9,10-dihydro-4H-benzo[d]pyrazolo[1,5-a][1,3]diazepine-3-carbonitrile (1.0 g, 2.2 mmol), diphenylmethanimine (494.0 mg, 2.74 mmol), tris(dibenzylideneacetone)dipalladium (302.0 mg, 0.33 mmol), 4,5-bis(diphenylphosphino)-9,9-diMethylxanthene (381.5 mg, 0.66 mmol), cesium carbonate (2.15 g, 6.6 mmol) in toluene (20.0 mL) was stirred at 110° C. overnight under nitrogen. The mixture was evaporated in vacuum to give the crude product, which was purified with silica gel column chromatography (DCM:MeOH=100:0~90:10 gradient elution) to give the product (0.4 g, 32.8%). $^1H$ NMR (400 MHz, DMSO) δ 9.43 (s, 1H), 7.82 (d, J=8.7 Hz, 2H), 7.65 (d, J=7.1 Hz, 2H), 7.56-7.50 (m, 1H), 7.50-7.40 (m, 4H), 7.36 (d, J=3.3 Hz, 3H), 7.18 (dd, J=14.1, 6.8 Hz, 4H), 7.08 (t, J=8.8 Hz, 5H), 6.65 (d, J=1.3 Hz, 1H), 6.51 (d, J=8.2 Hz, 1H), 4.40-4.19 (m, 2H), 3.04-2.92 (m, 2H); $[M+H]^+$=557.9.

Step 7: 7-amino-2-(4-phenoxyphenyl)-9,10-dihydro-4H-benzo[d]pyrazolo[1,5-a][1,3]diazepine-3-carboxamide

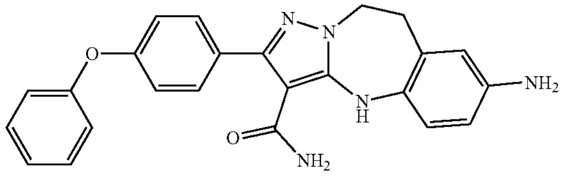 [SMILES: NC(=O)c1c(-c2ccc(Oc3ccccc3)cc2)nn2c1Nc1ccc(N)cc1CC2]

A mixture of 7-((diphenylmethylene)amino)-2-(4-phenoxyphenyl)-9,10-dihydro-4H-benzo[d]pyrazolo[1,5-a][1,3]diazepine-3-carbonitrile (0.4 g, 0.72 mmol) in methanesulfonic acid (10 mL) was stirred at 100° C. for 3 hours. The mixture was then cooled and alkalified basified with aqueous sodium carbonate solution to pH 8 and extracted with dichloromethane (3×20 mL). The organic phase was dried over anhydrous sodium sulfate, filtered and concentrated under reduced pressure to afford the product (0.2 g, 67.6%). $^1H$ NMR (400 MHz, DMSO) δ 9.58 (s, 1H), 7.74 (d, J=7.2 Hz, 2H), 7.68 (d, J=7.4 Hz, 1H), 7.57 (t, J=7.6 Hz, 2H), 7.51 (d, J=8.5 Hz, 1H), 7.43 (t, J=7.9 Hz, 2H), 7.19 (d, J=7.5 Hz, 1H), 7.09 (t, J=9.2 Hz, 2H), 6.67 (d, J=8.5 Hz, 1H), 6.45 (d, J=7.6 Hz, 2H), 4.85 (s, 2H), 4.29 (s, 2H), 3.03 (s, 2H); $[M+H]^+$=411.9.

Step 8: tert-butyl 1-(2-(2,6-dioxopiperidin-3-yl)-1,3-dioxoisoindolin-5-yl)piperidine-4-carboxylate

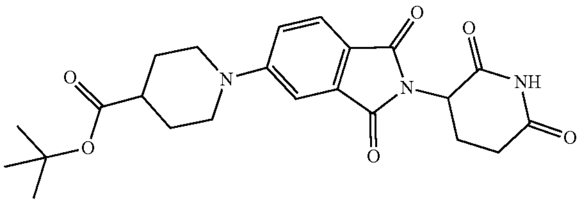 [SMILES: CC(C)(C)OC(=O)C1CCN(c2ccc3c(c2)C(=O)N(C2CCC(=O)NC2=O)C3=O)CC1]

A mixture of 2-(2,6-dioxopiperidin-3-yl)-5-fluoroisoindoline-1,3-dione (2 g, 7.24 mmol), tert-butyl piperidine-4-carboxylate hydrochloride (1.61 g, 7.24 mmol) and DIPEA (2.8 g, 21.72 mmol) in DMSO (50.0 mL) was stirred in a round bottom flask at 100° C. overnight. The mixture was quenched with water (150 mL) and filtered to afford the product (2.3 g, 72%). $^1$H NMR (400 MHz, DMSO) δ 11.06 (s, 1H), 7.64 (d, J=8.5 Hz, 1H), 7.31 (s, 1H), 7.23 (d, J=8.6 Hz, 1H), 5.05 (dd, J=12.9, 5.3 Hz, 1H), 3.95 (d, J=13.3 Hz, 2H), 3.05 (t, J=11.4 Hz, 2H), 2.93-2.80 (m, 1H), 2.56 (d, J=15.6 Hz, 2H), 2.00 (d, J=5.4 Hz, 1H), 1.85 (d, J=10.9 Hz, 2H), 1.54 (d, J=10.2 Hz, 2H), 1.38 (s, 9H); [M+H]$^+$=441.9.

Step 9: 1-(2-(2,6-dioxopiperidin-3-yl)-1,3-dioxoisoindolin-5-yl)piperidine-4-carboxylic acid

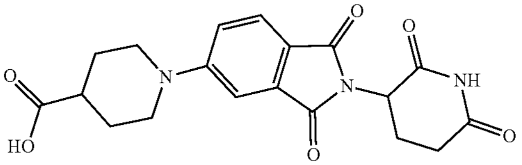 [SMILES: O=C1CCC(N2C(=O)c3ccc(N4CCC(C(=O)O)CC4)cc3C2=O)C(=O)N1]

A mixture of tert-butyl 1-(2-(2,6-dioxopiperidin-3-yl)-1,3-dioxoisoindolin-5-yl)piperidine-4-carboxylate (2.3 g, 5.2 mmol) in 2,2,2-trifluoroacetic acid (10 mL) and DCM (20 mL) was stirred in a round bottom flask at room temperature overnight. The mixture was evaporated in vacuum, washed with EA and filtered to afford the product (1.5 g, 75%). $^1$H NMR (400 MHz, DMSO) δ 12.19 (s, 1H), 11.08 (s, 1H), 7.66 (d, J=7.7 Hz, 1H), 7.40-7.16 (m, 2H), 5.07 (d, J=8.5 Hz, 1H), 3.99 (t, J=16.4 Hz, 2H), 3.09 (t, J=11.2 Hz, 2H), 2.87 (d, J=13.6 Hz, 1H), 2.58 (d, J=22.5 Hz, 3H), 1.99 (s, 1H), 1.90 (d, J=11.2 Hz, 2H), 1.60 (d, J=10.5 Hz, 2H); [M+H]$^+$=385.8.

Step 10: 7-(1-(2-(2,6-dioxopiperidin-3-yl)-1,3-dioxoisoindolin-5-yl)piperidine-4-carboxamido)-2-(4-phenoxyphenyl)-9,10-dihydro-4H-benzo[d]pyrazolo[1,5-a][1,3]diazepine-3-carboxamide

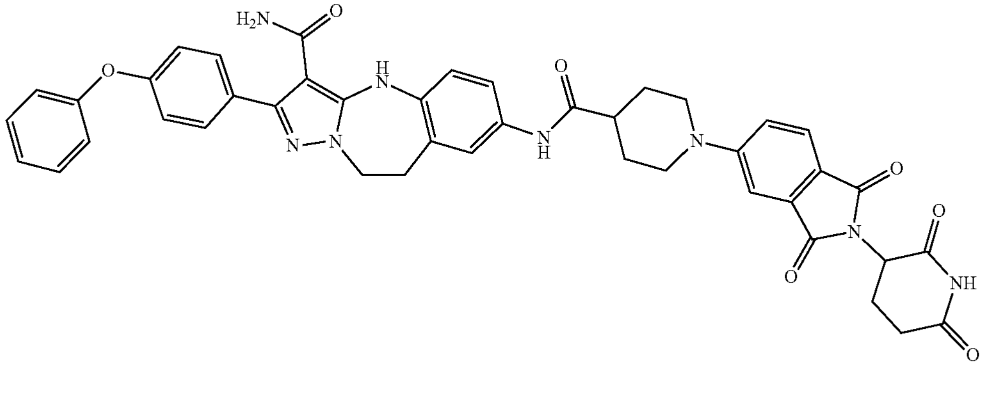 [SMILES: NC(=O)c1c(-c2ccc(Oc3ccccc3)cc2)nn2c1Nc1ccc(NC(=O)C3CCN(c4ccc5c(c4)C(=O)N(C4CCC(=O)NC4=O)C5=O)CC3)cc1CC2]

A mixture of 7-amino-2-(4-phenoxyphenyl)-9,10-dihydro-4H-benzo[d]pyrazolo[1,5-a][1,3]diazepine-3-carboxamide (0.1 g, 0.243 mmol), 1-(2-(2,6-dioxopiperidin-3-yl)-1,3-dioxoisoindolin-5-yl)piperidine-4-carboxylic acid (103.0 mg, 0.267 mmol), HATU (277.0 mg, 0.73 mmol) and DIPEA (94.2 mg, 0.73 mmol) in DMF (10 mL) was stirred in a round bottom flask at room temperature overnight. Then the mixture was evaporated in vacuum to afford the crude product, which was purified by prep-TLC (DCM:MeOH=7:1) to give the product (62 mg, 32.8%). $^1$H NMR (400 MHz, DMSO) δ 11.08 (s, 1H), 9.91 (d, J=20.2 Hz, 2H), 7.68 (d, J=8.2 Hz, 1H), 7.52 (d, J=8.0 Hz, 3H), 7.43 (t, J=7.0 Hz, 3H), 7.37 (s, 1H), 7.28 (d, J=8.2 Hz, 1H), 7.19 (s, 1H), 7.10 (t, J=8.2 Hz, 4H), 6.92 (d, J=8.3 Hz, 1H), 6.09-5.43 (m, 1H), 5.08 (d, J=8.1 Hz, 1H), 4.35 (s, 2H), 4.13 (d, J=12.2 Hz, 2H), 3.15 (s, 2H), 3.06 (t, J=12.1 Hz, 2H), 2.89 (t, J=13.6 Hz, 1H), 2.58 (d, J=22.4 Hz, 3H), 2.02 (d, J=10.6 Hz, 1H), 1.89 (d, J=11.9 Hz, 2H), 1.70 (d, J=11.3 Hz, 2H); [M+H]$^+$=779.8.

Example A2: 7-(14-((2-(2,6-dioxopiperidin-3-yl)-1,3-dioxoisoindolin-4-yl)amino)-3,6,9,12-tetraoxatetradecanamido)-2-(4-phenoxyphenyl)-9,10-dihydro-4H-benzo[d]pyrazolo[1,5-a][1,3]diazepine-3-carboxamide

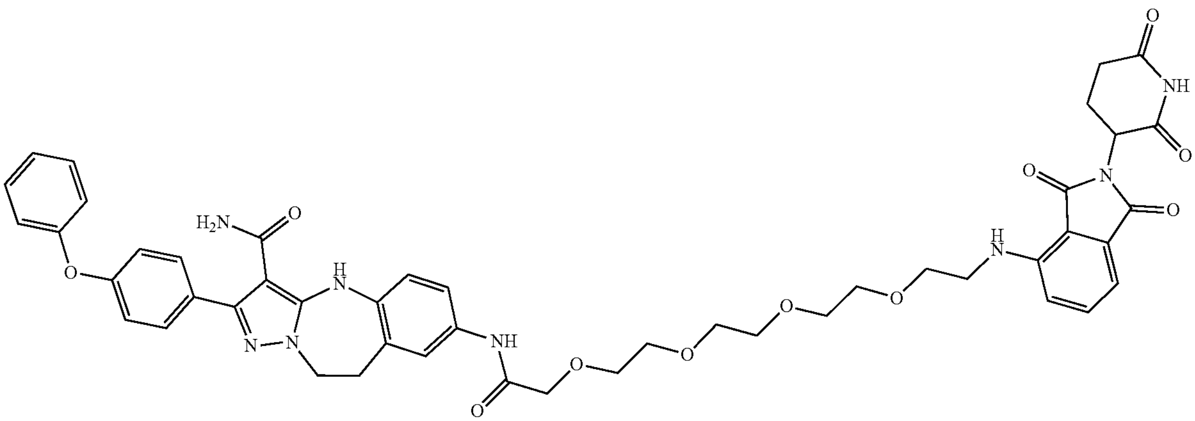 [SMILES: NC(=O)c1c(-c2ccc(Oc3ccccc3)cc2)nn2c1Nc1ccc(NC(=O)COCCOCCOCCOCCNc3cccc4c3C(=O)N(C3CCC(=O)NC3=O)C4=O)cc1CC2]

The titled compound was synthesized in the procedures similar to Example A1. $^1$H NMR (400 MHz, DMSO) δ 11.10 (s, 1H), 9.95 (s, 1H), 9.52 (s, 1H), 7.61-7.41 (m, 7H), 7.23-7.01 (m, 7H), 6.94 (d, J=8.1 Hz, 1H), 6.60 (s, 1H), 5.04 (s, 1H), 4.36 (s, 2H), 4.05 (s, 2H), 3.68-3.52 (m, 14H), 3.45 (s, 2H), 3.15 (s, 2H), 3.12-2.68 (m, 2H), 2.64 (d, J=27.8 Hz, 1H), 2.33 (s, 1H), 2.03 (s, 1H). $[M+H]^+$=901.8.

Example A3:7-(((1-(2-(2,6-dioxopiperidin-3-yl)-1,3-dioxoisoindolin-5-yl)piperidin-4-yl)methyl)amino)-2-(4-phenoxyphenyl)-9,10-dihydro-4H-benzo[d]pyrazolo[1,5-a][1,3]diazepine-3-carboxamide

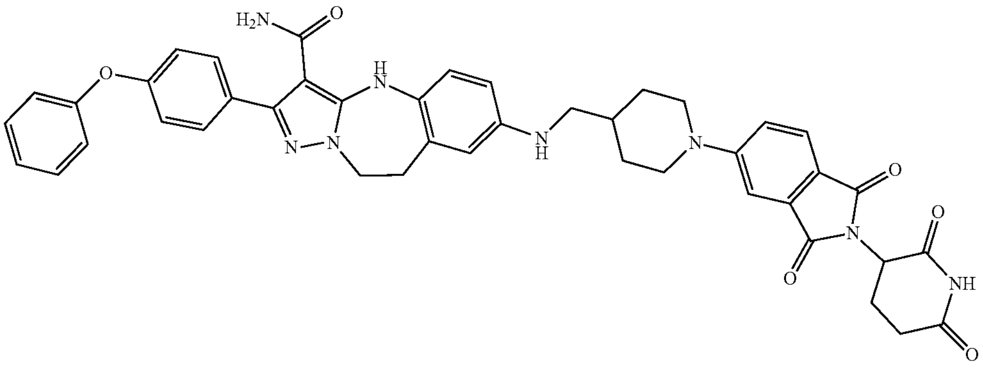 [SMILES: NC(=O)c1c(-c2ccc(Oc3ccccc3)cc2)nn2c1Nc1ccc(NCC3CCN(c4ccc5c(c4)C(=O)N(C4CCC(=O)NC4=O)C5=O)CC3)cc1CC2]

A mixture of 7-amino-2-(4-phenoxyphenyl)-9,10-dihydro-4H-benzo[d]pyrazolo[1,5-a][1,3]diazepine-3-carboxamide (100 mg, 0.243 mmol), (1-(2-(2,6-dioxopiperidin-3-yl)-1,3-dioxoisoindolin-5-yl)piperidin-4-yl)methyl 4-methylbenzenesulfonate (280 mg, 0.533 mmol, made by procedures similar to step 8 in example A1) and DIPEA (188 mg, 1.46 mmol) in DMSO (20 mL) was stirred in a round bottom flask at 50° C. overnight and then 80° C. for 3 hours. The mixture was extracted with dichloromethane (3×20 mL) and washed with brine (3×20 mL). The organic phase was dried over anhydrous sodium sulfate, filtered and concentrated under reduced pressure to afford crude product, which was purified by prep-TLC (DCM:MeOH=7:1) to give the product (22 mg, 11.8%). $^1$H NMR (400 MHz, DMSO) δ 11.07 (s, 1H), 9.60 (s, 1H), 7.64 (d, J=8.4 Hz, 1H), 7.51 (d, J=8.5 Hz, 2H), 7.43 (s, 2H), 7.18 (t, J=7.8 Hz, 1H), 7.09 (t, J=9.1 Hz, 4H), 6.93 (s, 1H), 6.82 (d, J=8.2 Hz, 1H), 6.74 (s, 1H), 6.50 (s, 2H), 5.44 (s, 1H), 5.05 (d, J=7.5 Hz, 1H), 4.30 (s, 2H), 3.67 (s, 1H), 3.52 (s, 1H), 3.39 (d, J=7.5 Hz, 1H), 3.08 (s, 5H), 2.87 (d, J=13.3 Hz, 1H), 2.68-2.55 (m, 2H), 2.46-2.38 (m, 1H), 2.21 (s, 1H), 2.00 (d, J=6.8 Hz, 2H), 1.72 (d, J=7.8 Hz, 4H); $[M+H]^+$=764.8.

Example A4: 7-(1-((1-(2-(2,6-dioxopiperidin-3-yl)-1,3-dioxoisoindolin-5-yl)piperidin-4-yl)methyl)piperidine-4-carboxamido)-2-(4-phenoxyphenyl)-9,10-dihydro-4H-benzo[d]pyrazolo[1,5-a][1,3]diazepine-3-carboxamide Step 1: 1-((1-(2-(2,6-dioxopiperidin-3-yl)-1,3-dioxoisoindolin-5-yl)piperidin-4-yl)methyl)piperidine-4-carboxylic acid

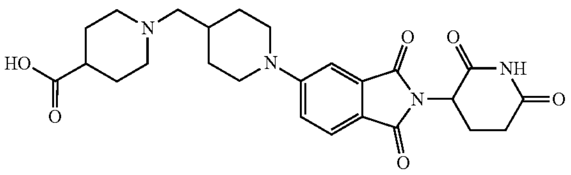 [SMILES: O=C1CCC(N2C(=O)c3ccc(N4CCC(CN5CCC(C(=O)O)CC5)CC4)cc3C2=O)C(=O)N1]

A mixture of 1-(2-(2,6-dioxopiperidin-3-yl)-1,3-dioxoisoindolin-5-yl)piperidine-4-carbaldehyde (200 mg, 0.54 mmol, made by procedures similar to step 8 in example A1), piperidine-4-carboxylic acid (66.4 mg, 0.51 mmol) and AcOH (0.02 mL) in MeOH was stirred at rt for 1 h. Then, $NaBH_3CN$ (50.8 mg, 0.81 mmol) was added to the mixture above. The resulting mixture was stirred at rt for 16 h. The mixture was evaporated in vacuum to afford the crude product, which was further purified by reverse phase chromatography (ACN: $H_2O$=0:100~60:40 gradient elution) to give the product (45 mg, 17.2%). $[M+H]^+$=483.2.

Step 2: 7-(1-((1-(2-(2,6-dioxopiperidin-3-yl)-1,3-dioxoisoindolin-5-yl)piperidin-4-yl)methyl)piperidine-4-carboxamido)-2-(4-phenoxyphenyl)-9,10-dihydro-4H-benzo[d]pyrazolo[1,5-a][1,3]diazepine-3-carboxamide

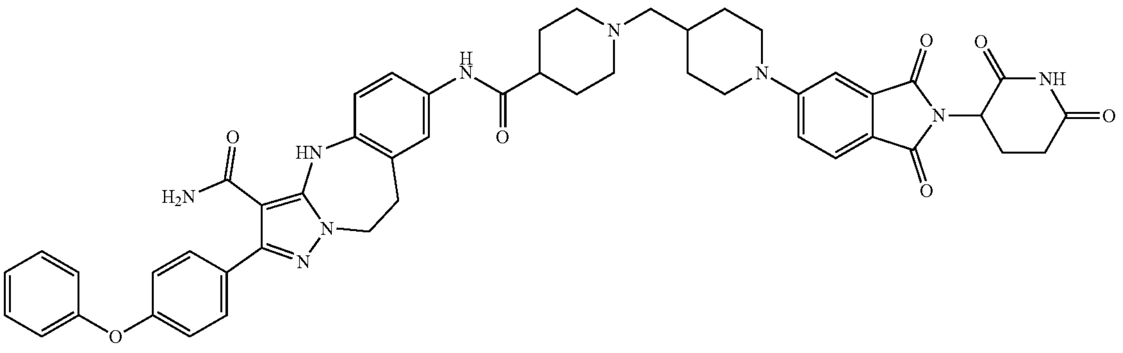 [SMILES: NC(=O)c1c(-c2ccc(Oc3ccccc3)cc2)nn2c1Nc1ccc(NC(=O)C3CCN(CC4CCN(c5ccc6c(c5)C(=O)N(C5CCC(=O)NC5=O)C6=O)CC4)CC3)cc1CC2]

A mixture of 1-((1-(2-(2,6-dioxopiperidin-3-yl)-1,3-dioxoisoindolin-5-yl)piperidin-4-yl)methyl)piperidine-4-carboxylic acid (45 mg, 0.093 mmol), HATU (37.2 mg, 0.098 mmol) and DIEA (36.1 mg, 0.28 mmol) in DMF (5 mL) was stirred at rt for 15 min, followed by addition of 7-amino-2-(4-phenoxyphenyl)-9,10-dihydro-4H-benzo[d]pyrazolo[1,5-a][1,3]diazepine-3-carboxamide (38.4 mg, 0.093 mmol). The resulting mixture was stirred at rt overnight. The mixture was diluted with water (50 mL) and extracted with EA (3×50 mL). The combined organic layers were dried over $Na_2SO_4$, filtered and concentrated under vacuum. The residue was purified by silica gel column chromatography, eluted with MeOH/DCM (1:10) to afford the product (31.82 mg, 38.9%). $^1$H NMR (400 MHz, DMSO) δ 11.07 (s, 1H), 9.93 (s, 1H), 9.78 (s, 1H), 7.65 (d, J=8.0 Hz, 1H), 7.58-7.38 (m, 6H), 7.34-7.15 (m, 3H), 7.09 (t, J=8.0 Hz, 4H), 6.91 (d, J=8.0 Hz, 1H), 5.12-4.99 (m, 1H), 4.41-4.29 (m, 2H), 4.15-3.98 (m, 2H), 3.2-2.8 (m, 11H), 2.35-1.96 (m, 6H), 1.83-1.58 (m, 6H), 1.23-1.01 (m, 3H); $[M+H]^+$=876.4.

Example A5: 7-((1-((1-(2-(2,6-dioxopiperidin-3-yl)-6-fluoro-1,3-dioxoisoindolin-5-yl)piperidin-4-yl)methyl)piperidin-4-yl)amino)-2-(4-phenoxyphenyl)-9,10-dihydro-4H-benzo[d]pyrazolo[1,5-a][1,3]diazepine-3-carboxamide Step 1: 5-(4-((1,4-dioxa-8-azaspiro[4.5]decan-8-yl)methyl)piperidin-1-yl)-2-(2,6-dioxopiperidin-3-yl)-6-fluoroisoindoline-1,3-dione

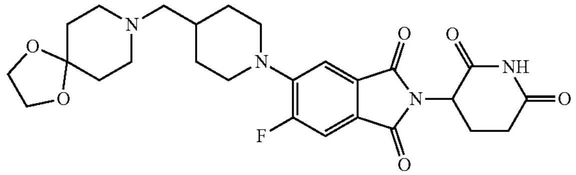 [SMILES: O=C1CCC(N2C(=O)c3cc(F)c(N4CCC(CN5CCC6(CC5)OCCO6)CC4)cc3C2=O)C(=O)N1]

A mixture of 2-(2,6-dioxopiperidin-3-yl)-5,6-difluoroisoindoline-1,3-dione (294 mg, 1 mmol), 8-(piperidin-4-ylmethyl)-1-oxa-4,8-diazaspiro[4.5]decane (600 mg, 2.5 mmol) and DIEA (258 mg, 2 mmol) in DMSO was stirred at 100° C. for 2 h. The mixture was diluted with water (100 mL) and extracted with EA (3×100 mL). The combined organic layers were dried over $Na_2SO_4$, filtered and concentrated under vacuum to afford the product (500 mg, 97.2%). $[M+H]^+$=515.2.

Step 2: 2-(2,6-dioxopiperidin-3-yl)-5-fluoro-6-(4-((4-oxopiperidin-1-yl)methyl)piperidin-1-yl)isoindoline-1,3-dione

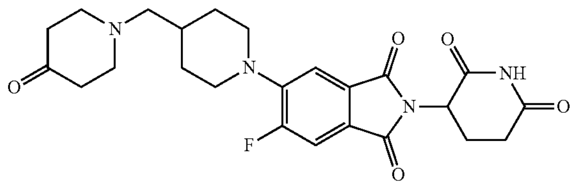 [SMILES: O=C1CCN(CC2CCN(c3cc4c(cc3F)C(=O)N(C3CCC(=O)NC3=O)C4=O)CC2)CC1]

A solution of 5-(4-((1,4-dioxa-8-azaspiro[4.5]decan-8-yl)methyl)piperidin-1-yl)-2-(2,6-dioxopiperidin-3-yl)-6-fluoroisoindoline-1,3-dione (200 mg, 0.39 mmol) in 6.0 M HCl in THF (10 mL) was stirred at rt for 16 h. The mixture was adjusted to pH=8 with saturated $NaHCO_3$ solution and extracted with EA (3×100 mL). The combined organic layers were dried over $Na_2SO_4$, filtered and concentrated under vacuum to afford the product (170 mg, crude), which was used in the next step directly. $[M+H]^+$=471.2.

Step 3: 7-((1-((1-(2-(2,6-dioxopiperidin-3-yl)-6-fluoro-1,3-dioxoisoindolin-5-yl)piperidin-4-yl)methyl)piperidin-4-yl)amino)-2-(4-phenoxyphenyl)-9,10-dihydro-4H-benzo[d]pyrazolo[1,5-a][1,3]diazepine-3-carboxamide

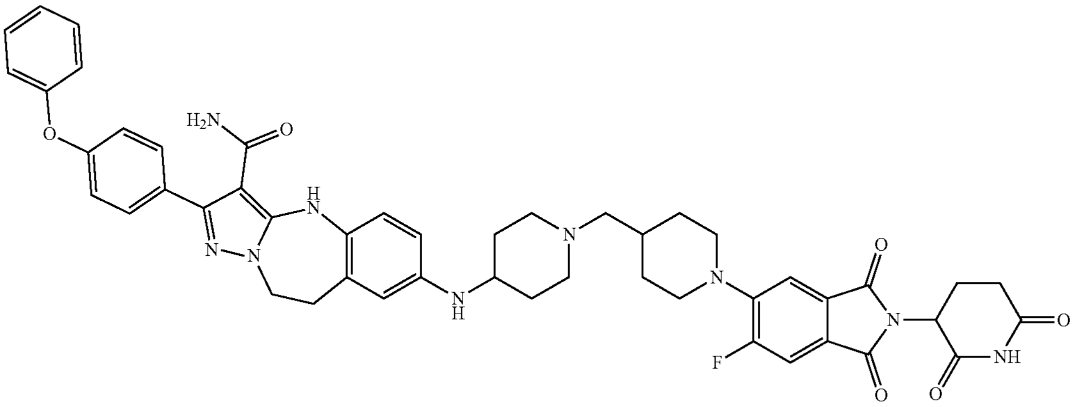 [SMILES: NC(=O)c1c(-c2ccc(Oc3ccccc3)cc2)nn2c1Nc1ccc(NC3CCN(CC4CCN(c5cc6c(cc5F)C(=O)N(C5CCC(=O)NC5=O)C6=O)CC4)CC3)cc1CC2]

A mixture of 2-(2,6-dioxopiperidin-3-yl)-5-fluoro-6-(4-((4-oxopiperidin-1-yl)methyl)piperidin-1-yl)isoindoline-1,3-dione (170 mg, 0.36 mmol), 7-amino-2-(4-phenoxyphenyl)-9,10-dihydro-4H-benzo[d]pyrazolo[1,5-a][1,3]diazepine-3-carboxamide (133 mg, 0.32 mmo) and titanium ethoxide (0.02 mL) in MeOH was refluxed for 16 h. Then, $NaBH_3CN$ (45.2 mg, 0.72 mmol) was added to the mixture above. The resulting mixture was stirred at rt for 5 h. The mixture was evaporated in vacuum to afford the crude product, which was further purified with silica gel column chromatography, MeOH/DCM (1:9) to afford the product (28.18 mg, 9%). $^1$H NMR (400 MHz, DMSO) δ 11.10 (s, 1H), 9.58 (s, 1H), 7.70 (d, J=12.0 Hz, 1H), 7.64-7.37 (m, 5H), 7.22-7.03 (m, 5H), 6.72 (d, J=8.0 Hz, 1H), 6.50-6.44 (m, 2H), 5.21 (d, J=8.0 Hz, 1H), 5.13-5.05 (m, 1H), 4.33-4.26 (m, 2H), 3.60 (d, J=12.0 Hz, 2H), 3.21-2.75 (m, 11H), 2.22-2.14 (m, 2H), 2.09-1.96 (m, 3H), 1.95-1.71 (m, 5H), 1.45-1.19 (m, 5H); $[M+H]^+$=866.2.

Example A6: 7-(4-((1-(2-(2,6-dioxopiperidin-3-yl)-1,3-dioxoisoindolin-5-yl)piperidin-4-yl)methyl)piperazin-1-yl)-2-(4-phenoxyphenyl)-9,10-dihydro-4H-benzo[d]pyrazolo[1,5-a][1,3]diazepine-3-carboxamide Step 1: 2-(4-phenoxyphenyl)-7-(piperazin-1-yl)-9,10-dihydro-4H-benzo[d]pyrazolo[1,5-a][1,3]diazepine-3-carboxamide

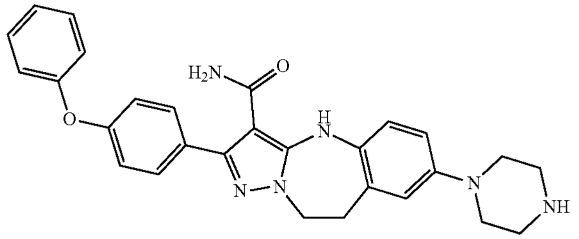 [SMILES: NC(=O)c1c(-c2ccc(Oc3ccccc3)cc2)nn2c1Nc1ccc(N3CCNCC3)cc1CC2]

A mixture of 7-bromo-2-(4-phenoxyphenyl)-9,10-dihydro-4H-benzo[d]pyrazolo[1,5-a][1,3]diazepine-3-carboxamide (100.0 mg, 0.211 mmol), piperazine (54.4 mg, 0.633 mmol), tris(dibenzylideneacetone)dipalladium (19.3 mg, 0.0211 mmol), 2-dicyclohexylphosphino-2',6'-di-i-propoxy-1,1'-biphenyl (21.0 mg, 0.0422 mmol) and sodium tert-butoxide (60.8 mg, 0.0.633 mmol) in PhMe (15.0 mL) was stirred in a round bottom flask at 110° C. overnight under nitrogen. The mixture was evaporated in vacuum to give the crude product, which was purified with silica gel column chromatography (DCM:MeOH=100:0~90:10 gradient elution) to give the product (50.0 mg, crude). $[M+H]^+$=480.9.

Step 2: 7-(4-((1-(2-(2,6-dioxopiperidin-3-yl)-1,3-dioxoisoindolin-5-yl)piperidin-4-yl)methyl)piperazin-1-yl)-2-(4-phenoxyphenyl)-9,10-dihydro-4H-benzo[d]pyrazolo[1,5-a][1,3]diazepine-3-carboxamide

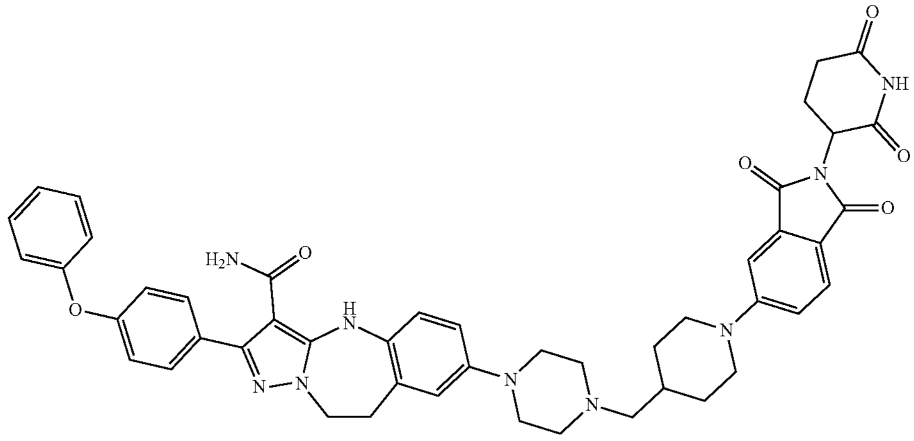 [SMILES: NC(=O)c1c(-c2ccc(Oc3ccccc3)cc2)nn2c1Nc1ccc(N3CCN(CC4CCN(c5ccc6c(c5)C(=O)N(C5CCC(=O)NC5=O)C6=O)CC4)CC3)cc1CC2]

To a solution of 2-(4-phenoxyphenyl)-7-(piperazin-1-yl)-9,10-dihydro-4H-benzo[d]pyrazolo[1,5-a][1,3]diazepine-3-carboxamide (50.0 mg, 0.104 mmol), (1-(2-(2,6-dioxopiperidin-3-yl)-1,3-dioxoisoindolin-5-yl)piperidin-4-yl)methyl 4-methylbenzenesulfonate (82.0 mg, 0.156 mmol) and DIPEA (40.0 mg, 0.312 mmol) in DMSO (15 mL) was stirred in a round bottom flask at 80° C. for 2 hours. The mixture was extracted with dichloromethane (3×20 mL) and washed with brine (3×20 mL). The organic phase was dried over anhydrous sodium sulfate, filtered and concentrated under reduced pressure to afford crude product, which was purified by prep-HPLC (Anal. Column: Waters Xselect CSH C18, Column Temp.: Room temperature, Mobile Phase A: ACN, Mobile Phase B: $H_2O$(0.03% $NH_3 \cdot H_2O$), Gradient Table: Mobile Phase A (42%-90%), Time (min):0-17 min) to give the product (5 mg, 5.8%). $^1H$ NMR (400 MHz, DMSO) δ 11.07 (s, 1H), 9.78-9.63 (m, 3H), 7.65 (s, 1H), 7.52 (d, J=8.1 Hz, 2H), 7.43 (t, J=7.5 Hz, 2H), 7.23-7.17 (m, 2H), 7.09 (t, J=8.3 Hz, 4H), 6.95-6.78 (m, 4H), 5.06 (d, J=8.0 Hz, 1H), 4.34 (s, 2H), 4.06 (d, J=10.9 Hz, 1H), 3.86-3.46 (m, 4H), 3.15-2.85 (m, 12H), 2.05-1.98 (m, 2H), 1.78-1.60 (m, 2H), 1.28-1.12 (m, 4H); $[M+H]^+$=833.9.

Example A7: 7-(4-(2-(2,6-dioxopiperidin-3-yl)-1,3-dioxoisoindolin-5-yl)piperazin-1-yl)-2-(4-phenoxyphenyl)-9,10-dihydro-4H-benzo[d]pyrazolo[1,5-a][1,3]diazepine-3-carboxamide

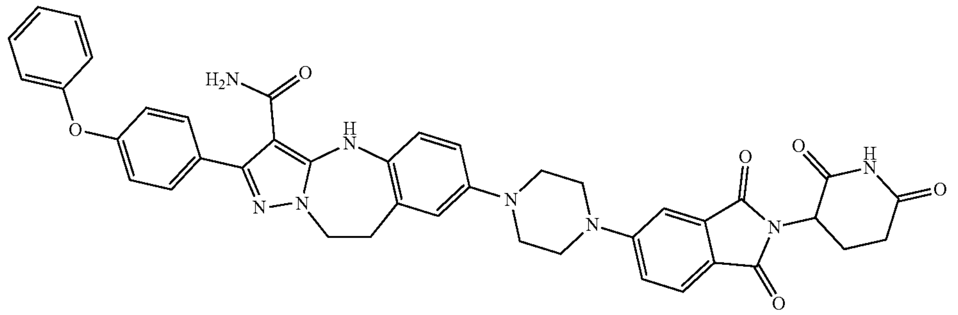 [SMILES: NC(=O)c1c(-c2ccc(Oc3ccccc3)cc2)nn2c1Nc1ccc(N3CCN(c4ccc5c(c4)C(=O)N(C4CCC(=O)NC4=O)C5=O)CC3)cc1CC2]

A mixture of 2-(4-phenoxyphenyl)-7-(piperazin-1-yl)-9,10-dihydro-4H-benzo[d]pyrazolo[1,5-a][1,3]diazepine-3-carboxamide (80.0 mg, 0.167 mmol), 2-(2,6-dioxopiperidin-3-yl)-5-fluoroisoindoline-1,3-dione (55.0 mg, 0.2 mmol) and DIPEA (108.0 mg, 0.83 mmol) in DMSO (15.0 mL) was stirred in a round bottom flask at 100° C. overnight. The mixture was extracted with dichloromethane (3×20 mL) and washed with brine (3×20 mL). The organic phase was dried over anhydrous sodium sulfate, filtered and concentrated under reduced pressure to afford crude product, which was purified by prep-HPLC to give the product (5 mg, 4.1%). $^1$H NMR (400 MHz, DMSO) δ 11.06 (s, 1H), 9.81 (s, 1H), 7.71 (d, J=8.3 Hz, 1H), 7.52 (d, J=8.3 Hz, 2H), 7.46-7.39 (m, 3H), 7.33 (d, J=7.8 Hz, 1H), 7.19 (t, J=7.4 Hz, 1H), 7.09 (t, J=9.0 Hz, 4H), 6.92 (d, J=16.3 Hz, 3H), 5.05-4.92 (m, 1H), 4.41-4.31 (m, 2H), 3.61 (s, 4H), 3.25 (s, 3H), 3.19-3.15 (m, 3H), 3.03-2.97 (m, 2H), 2.86-2.74 (m, 1H); [M+H]$^+$=737.7.

Example A8:7-((1-(2-(2,6-dioxopiperidin-3-yl)-1,3-dioxoisoindolin-5-yl)piperidin-4-yl)amino)-2-(4-phenoxyphenyl)-9,10-dihydro-4H-benzo[d]pyrazolo[1,5-a][1,3]diazepine-3-carboxamide Step 1: 2-(2,6-dioxopiperidin-3-yl)-5-(1,4-dioxa-8-azaspiro[4.5]decan-8-yl)isoindoline-1,3-dione

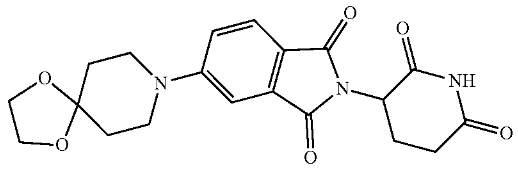 [SMILES: O=C1CCC(N2C(=O)c3ccc(N4CCC5(CC4)OCCO5)cc3C2=O)C(=O)N1]

A mixture of 2-(2,6-dioxopiperidin-3-yl)-5-fluoroisoindoline-1,3-dione (3.0 g, 10.87 mmol), 1,4-dioxa-8-azaspiro[4.5]decane (1.55 g, 10.87 mmol) and DIPEA (4.2 g, 32.6 mmol) in DMSO (80 mL) was stirred at 100° C. overnight. The mixture was extracted with EA (3×100 mL) and washed with brine (3×100 mL). The organic phase was dried over anhydrous sodium sulfate, filtered and concentrated under reduced pressure to afford crude product (4.0 g, 93.0%). $^1$H NMR (400 MHz, DMSO) δ 11.08 (s, 1H), 7.66 (d, J=8.5 Hz, 1H), 7.36 (s, 1H), 7.27 (d, J=8.4 Hz, 1H), 5.07 (dd, J=12.8, 5.2 Hz, 1H), 3.93 (s, 4H), 3.58 (s, 4H), 3.49-3.40 (m, 1H), 2.95-2.83 (m, 1H), 2.59 (d, J=16.7 Hz, 1H), 1.69 (s, 4H); [M+H]$^+$=399.9.

Step 2: 2-(2,6-dioxopiperidin-3-yl)-5-(4-oxopiperidin-1-yl)isoindoline-1,3-dione

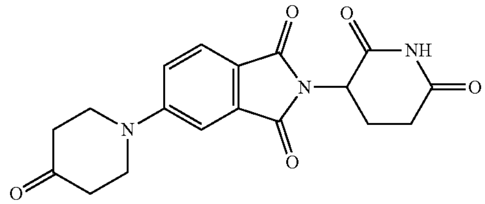 [SMILES: O=C1CCN(c2ccc3c(c2)C(=O)N(C2CCC(=O)NC2=O)C3=O)CC1]

A mixture of 2-(2,6-dioxopiperidin-3-yl)-5-(1,4-dioxa-8-azaspiro[4.5]decan-8-yl)isoindoline-1,3-dione (3.7 g, 9.27 mmol) and 6 M aqueous hydrochloric acid solution (100.0 mL) in THE (30 mL) was stirred at room temperature overnight. The mixture was acidified with aqueous sodium bicarbonate solution to pH 8 and extracted with DCM (3×50 mL) and washed with brine (3×50 mL). The organic phase was dried over anhydrous sodium sulfate, filtered and concentrated under reduced pressure to afford crude product (2.0 g, 66.9%). $^1$H NMR (400 MHz, DMSO) δ 11.08 (s, 1H), 7.71 (d, J=8.5 Hz, 1H), 7.38 (s, 1H), 7.29 (d, J=7.9 Hz, 1H), 5.08 (dd, J=12.7, 5.1 Hz, 1H), 3.85 (d, J=5.4 Hz, 4H), 2.88 (dd, J=22.1, 9.5 Hz, 1H), 2.59 (d, J=20.7 Hz, 2H), 2.50 (d, J=4.4 Hz, 4H), 2.02 (d, J=11.5 Hz, 1H); [M+H]+=355.9.

Step 3: 7-((1-(2-(2,6-dioxopiperidin-3-yl)-1,3-dioxoisoindolin-5-yl)piperidin-4-yl)amino)-2-(4-phenoxyphenyl)-9,10-dihydro-4H-benzo[d]pyrazolo[1,5-a][1,3]diazepine-3-carboxamide

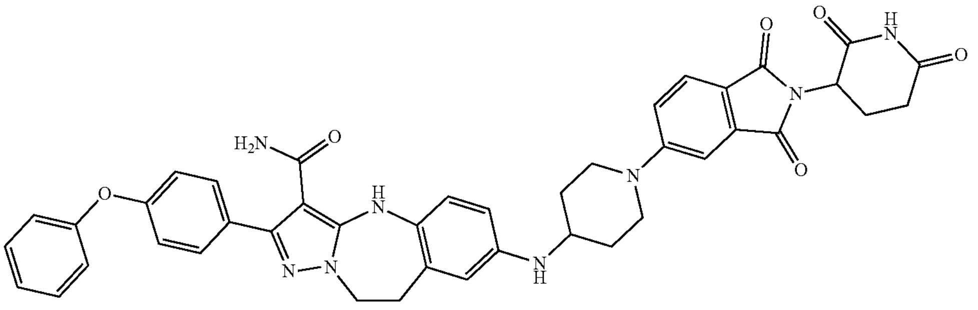 [SMILES: NC(=O)c1c(-c2ccc(Oc3ccccc3)cc2)nn2c1Nc1ccc(NC3CCN(c4ccc5c(c4)C(=O)N(C4CCC(=O)NC4=O)C5=O)CC3)cc1CC2]

A mixture of 7-amino-2-(4-phenoxyphenyl)-9,10-dihydro-4H-benzo[d]pyrazolo[1,5-a][1,3]diazepine-3-carboxamide (0.1 g, 0.243 mmol), 2-(2,6-dioxopiperidin-3-yl)-5-(4-oxopiperidin-1-yl)isoindoline-1,3-dione (103.6 mg, 0.292 mmol) and titanium ethoxide (0.4 mL) in MeOH (10.0 mL) and DCE (10.0 mL) was stirred at 65° C. overnight. The mixture was then cooled, added sodium triacetoxyborohydride (257.6 mg, 1.215 mmol), and stirred at room temperature overnight. The mixture was treated with water (20 mL), extracted with dichloromethane (3×30.0 mL), and washed with brine (50 mL). The organic phase was dried over anhydrous sodium sulfate, filtered and concentrated under reduced pressure to afford the crude product, which was purified by prep-HPLC to give the product (10.0 mg, 5.5%). $^1$H NMR (400 MHz, DMSO) δ 11.10 (s, 1H), 9.83 (s, 1H), 7.69 (d, J=8.3 Hz, 1H), 7.52 (d, J=7.9 Hz, 2H), 7.43 (t, J=7.7 Hz, 2H), 7.38 (s, 1H), 7.29 (d, J=9.0 Hz, 1H), 7.22-7.16 (m, 1H), 7.10 (t, J=8.0 Hz, 4H), 6.98-6.72 (m, 3H), 5.08 (dd, J=13.3, 6.0 Hz, 1H), 4.35 (s, 2H), 4.17-4.01 (m, 2H), 3.20-3.03 (m, 6H), 2.97-2.83 (m, 2H), 2.09-1.91 (m, 3H), 1.60-1.42 (m, 2H); [M+H]$^+$=751.7.

Example A9: N7-(1-(2-(2,6-dioxopiperidin-3-yl)-1,3-dioxoisoindolin-5-yl)piperidin-4-yl)-2-(4-phenoxyphenyl)-9,10-dihydro-4H-benzo[d]pyrazolo[1,5-a][1,3]diazepine-3,7-dicarboxamide Step 1: methyl 3-carbamoyl-2-(4-phenoxyphenyl)-9,10-dihydro-4H-benzo[d]pyrazolo[1,5-a][1,3]diazepine-7-carboxylate

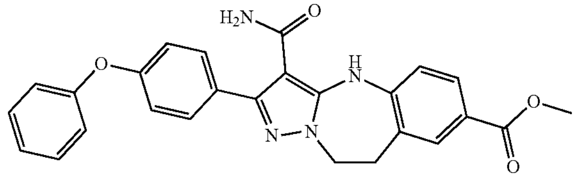 [SMILES: COC(=O)c1ccc2c(c1)CCn1nc(-c3ccc(Oc4ccccc4)cc3)c(C(N)=O)c1N2]

A mixture of 7-bromo-2-(4-phenoxyphenyl)-9,10-dihydro-4H-benzo[d]pyrazolo[1,5-a][1,3]diazepine-3-carboxamide (2.0 g, 4.22 mmol), Pd(dppf)Cl$_2$ (618.0 mg, 0.844 mmol) and TEA (1.28 g, 12.66 mmol) in DMF (15 mL) and MeOH (30 mL) was stirred in a round bottom flask at 100° C. for 48 hours under CO/10 PMa. The mixture was evaporated in vacuum to give the crude product, which was purified with silica gel column chromatography (DCM: MeOH=100:0~90:10 gradient elution) to give the product (1.7 g, 89.0%). $^1$H NMR (400 MHz, DMSO) δ 10.42 (s, 1H), 7.86 (s, 1H), 7.79 (d, J=8.1 Hz, 1H), 7.54 (d, J=8.4 Hz, 2H), 7.43 (t, J=7.8 Hz, 2H), 7.19 (t, J=7.3 Hz, 1H), 7.10 (t, J=8.0 Hz, 5H), 4.41 (s, 2H), 3.83 (s, 3H), 3.28 (s, 2H); [M+H]$^+$=455.4.

Step 2: 3-carbamoyl-2-(4-phenoxyphenyl)-9,10-dihydro-4H-benzo[d]pyrazolo[1,5-a][1,3]diazepine-7-carboxylic acid

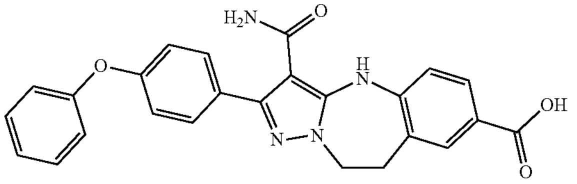 [SMILES: NC(=O)c1c(-c2ccc(Oc3ccccc3)cc2)nn2c1Nc1ccc(C(=O)O)cc1CC2]

A mixture of methyl 3-carbamoyl-2-(4-phenoxyphenyl)-9,10-dihydro-4H-benzo[d]pyrazolo[1,5-a][1,3]diazepine-7-carboxylate (1.5 g, 3.3 mmol), lithium hydroxide monohydrate (1.38 g, 33.0 mmol) in $H_2O$ (30.0 mL), THE (20.0 mL) and MeOH (10.0 mL) was stirred in a round bottom flask at room temperature overnight. The mixture was acidified with 6 M aqueous hydrochloric acid solution to pH 3 and extracted with dichloromethane (3×30 mL). The organic phase was dried over anhydrous sodium sulfate, filtered and concentrated under reduced pressure to afford the product (1.2 g, 82.7%). $^1$H NMR (400 MHz, DMSO) δ 12.61 (s, 1H), 10.38 (s, 1H), 7.83 (s, 1H), 7.77 (d, J=8.4 Hz, 1H), 7.54 (d, J=8.3 Hz, 2H), 7.43 (t, J=7.7 Hz, 2H), 7.19 (t, J=7.3 Hz, 1H), 7.13-7.03 (m, 5H), 5.76 (s, 1H), 4.41 (s, 2H), 3.27 (s, 2H); [M+H]$^+$=441.4.

Step 3: tert-butyl (1-(2-(2,6-dioxopiperidin-3-yl)-1,3-dioxoisoindolin-5-yl)piperidin-4-yl)carbamate

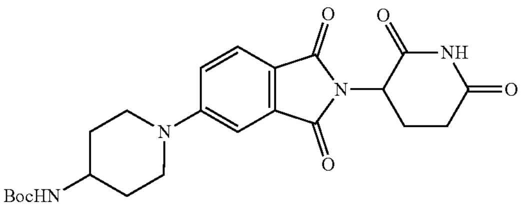 [SMILES: CC(C)(C)OC(=O)NC1CCN(c2ccc3c(c2)C(=O)N(C2CCC(=O)NC2=O)C3=O)CC1]

A mixture of 2-(2,6-dioxopiperidin-3-yl)-5-fluoroisoindoline-1,3-dione (1.0 g, 3.62 mmol), tert-butyl piperidin-4-ylcarbamate (725 mg, 3.62 mmol) and DIPEA (1.4 g, 10.87 mmol) in DMSO (30 mL) was stirred in a round bottom flask at 100° C. overnight. The mixture was washed with water (50 mL) and extracted with EA (3×30 mL). The organic phase was dried over anhydrous sodium sulfate, filtered and concentrated under reduced pressure to afford the product (1.6 g, 97.0%). $^1$H NMR (400 MHz, DMSO) δ 11.07 (s, 1H), 7.65 (d, J=8.5 Hz, 1H), 7.31 (s, 1H), 7.23 (d, J=8.3 Hz, 1H), 6.87 (d, J=7.4 Hz, 1H), 5.06 (dd, J=12.8, 5.3 Hz, 1H), 4.00 (dd, J=20.2, 10.5 Hz, 3H), 3.53 (s, 1H), 3.05 (t, J=12.1 Hz, 2H), 2.88 (s, 1H), 2.63-2.52 (m, 2H), 2.02 (d, J=5.3 Hz, 1H), 1.80 (d, J=11.3 Hz, 2H), 1.39 (s, 11H); [M+H]$^+$=456.9.

Step 4: 5-(4-aminopiperidin-1-yl)-2-(2,6-dioxopiperidin-3-yl)isoindoline-1,3-dione hydrochloride

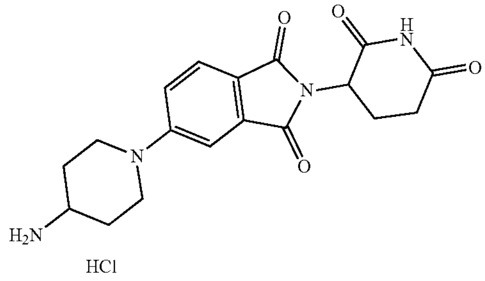 [SMILES: NC1CCN(c2ccc3c(c2)C(=O)N(C2CCC(=O)NC2=O)C3=O)CC1 ; Cl]

A mixture of tert-butyl (1-(2-(2,6-dioxopiperidin-3-yl)-1,3-dioxoisoindolin-5-yl)piperidin-4-yl)carbamate (1.6 g, 3.51 mmol) in HCl/1,4-dioxane (50.0 mL, 6 N) was stirred in a round bottom flask at room temperature for 3 hours. The mixture was filtered to afford the product (1.3 g, 94.5%). $^1$H NMR (400 MHz, DMSO) δ 11.09 (s, 1H), 8.21 (s, 3H), 7.69 (d, J=8.6 Hz, 1H), 7.38 (s, 1H), 7.28 (d, J=8.5 Hz, 1H), 5.08 (dd, J=12.9, 5.3 Hz, 1H), 4.11 (d, J=13.1 Hz, 2H), 3.57 (s, 1H), 3.31 (s, 1H), 3.05 (t, J=12.5 Hz, 2H), 2.95-2.82 (m, 1H), 2.63-2.55 (m, 1H), 2.01 (t, J=10.9 Hz, 3H), 1.57 (q, J=10.2 Hz, 2H); [M+H]$^+$=356.9.

Step 5: N7-(1-(2-(2,6-dioxopiperidin-3-yl)-1,3-dioxoisoindolin-5-yl)piperidin-4-yl)-2-(4-phenoxyphenyl)-9,10-dihydro-4H-benzo[d]pyrazolo[1,5-a][1,3]diazepine-3,7-dicarboxamide

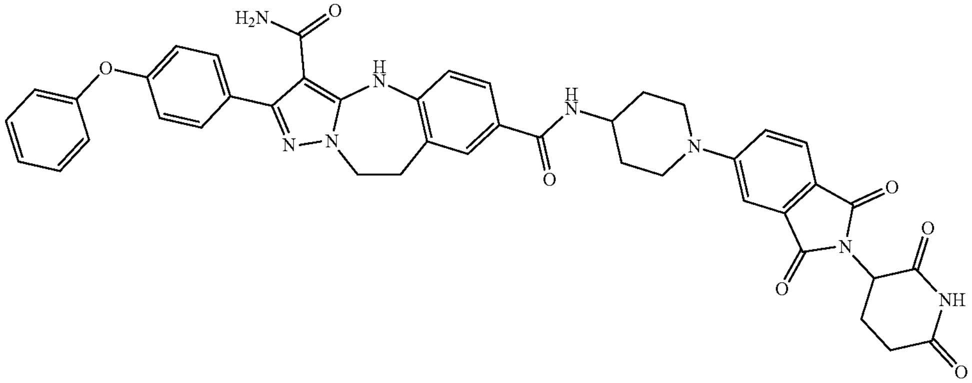 [SMILES: NC(=O)c1c(-c2ccc(Oc3ccccc3)cc2)nn2c1Nc1ccc(C(=O)NC3CCN(c4ccc5c(c4)C(=O)N(C4CCC(=O)NC4=O)C5=O)CC3)cc1CC2]

A mixture of 3-carbamoyl-2-(4-phenoxyphenyl)-9,10-dihydro-4H-benzo[d]pyrazolo[1,5-a][1,3]diazepine-7-carboxylic acid (0.15 g, 0.341 mmol), 5-(4-aminopiperidin-1-yl)-2-(2,6-dioxopiperidin-3-yl)isoindoline-1,3-dione hydrochloride (0.147 g, 0.375 mmol), HATU (0.194 g, 0.511 mmol) and DIPEA (0.132 g, 1.023 mmol) in DMF (10.0 mL) was stirred in a round bottom flask at room temperature overnight. The mixture was evaporated in vacuum to give the crude product, which was purified with silica gel column chromatography (DCM:MeOH=100:0~90:10 gradient elution) to give the product (31 mg, 11.7%). $^1$H NMR (400 MHz, DMSO) δ 11.09 (s, 1H), 10.26 (s, 1H), 8.15 (d, J=6.9 Hz, 1H), 7.80-7.65 (m, 3H), 7.53 (d, J=8.0 Hz, 2H), 7.42 (d, J=7.5 Hz, 2H), 7.38 (s, 1H), 7.30 (d, J=7.9 Hz, 1H), 7.20 (d, J=6.9 Hz, 1H), 7.15-7.00 (m, 5H), 5.08 (d, J=8.2 Hz, 1H), 4.40 (s, 2H), 4.11 (d, J=11.7 Hz, 3H), 3.24 (s, 2H), 3.15 (t, J=12.1 Hz, 2H), 2.89 (s, 1H), 2.59 (d, J=20.5 Hz, 2H), 2.04 (s, 1H), 1.87 (s, 2H), 1.60 (d, J=10.6 Hz, 2H); [M+H]$^+$=779.7.

Example A10: N[7]-(1-((1-(2-(2,6-dioxopiperidin-3-yl)-6-fluoro-1,3-dioxoisoindolin-5-yl)piperidin-4-yl)methyl)piperidin-4-yl)-2-(4-phenoxyphenyl)-9,10-dihydro-4H-benzo[d]pyrazolo[1,5-a][1,3]diazepine-3,7-dicarboxamide

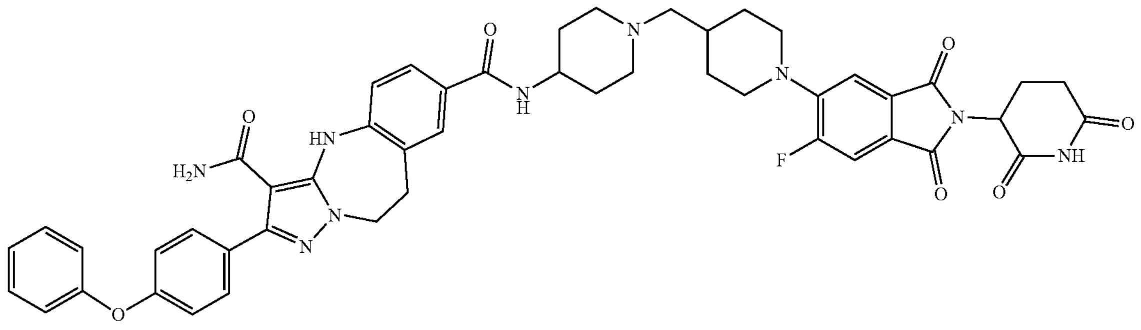 [SMILES: NC(=O)c1c(-c2ccc(Oc3ccccc3)cc2)nn2c1Nc1ccc(C(=O)NC3CCN(CC4CCN(c5cc6c(cc5F)C(=O)N(C5CCC(=O)NC5=O)C6=O)CC4)CC3)cc1CC2]

A mixture of 3-carbamoyl-2-(4-phenoxyphenyl)-9,10-dihydro-4H-benzo[d]pyrazolo[1,5-a][1,3]diazepine-7-carboxylic acid (0.15 g, 0.341 mmol), 5-(4-((4-aminopiperidin-1-yl)methyl)piperidin-1-yl)-2-(2,6-dioxopiperidin-3-yl)-6-fluoroisoindoline-1,3-dione hydrochloride (0.190 g, 0.375 mmol, made by procedures similar to step 8 in example A1), HATU (0.194 g, 0.511 mmol) and DIPEA (0.132 g, 1.023 mmol) in DMF (10.0 mL) was stirred in a round bottom flask at room temperature overnight. The mixture was evaporated in vacuum to give the crude product, which was purified with silica gel column chromatography (DCM:MeOH=100:0~90:10 gradient elution) and prep-TLC to give the product (12 mg, 4.0%). $^1$H NMR (400 MHz, DMSO) δ 11.12 (s, 1H), 10.28 (s, 1H), 9.90 (s, 1H), 8.43 (s, 1H), 7.76 (dd, J=23.0, 11.3 Hz, 3H), 7.54 (d, J=8.0 Hz, 2H), 7.49-7.39 (m, 3H), 7.22-7.17 (m, 1H), 7.09 (dd, J=18.0, 10.6 Hz, 5H), 5.11 (dd, J=12.4, 5.0 Hz, 1H), 4.41 (s, 2H), 4.13-3.90 (m, 1H), 3.77-3.50 (m, 5H), 3.15-2.82 (m, 7H), 2.71-2.56 (m, 2H), 2.26-1.75 (m, 8H), 1.52-1.31 (m, 3H); $[M+H]^+$=894.8.

Example A11:7-(1-(2-(2,6-dioxopiperidin-3-yl)-1,3-dioxoisoindolin-4-yl)piperidine-4-carboxamido)-2-(4-phenoxyphenyl)-9,10-dihydro-4H-benzo[d]pyrazolo[1,5-a][1,3]diazepine-3-carboxamide Step 1: tert-butyl 1-(2-(2,6-dioxopiperidin-3-yl)-1,3-dioxoisoindolin-4-yl)piperidine-4-carboxylate

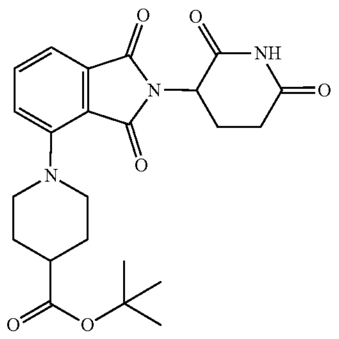 [SMILES: CC(C)(C)OC(=O)C1CCN(c2cccc3c2C(=O)N(C2CCC(=O)NC2=O)C3=O)CC1]

A mixture of 2-(2,6-dioxopiperidin-3-yl)-4-fluoroisoindoline-1,3-dione (1.0 g, 3.62 mmol), tert-butyl piperidine-4-carboxylate hydrochloride (888.0 mg, 4.0 mmol) and DIPEA (1.4 g, 10.86 mmol) in DMSO (20.0 mL) was stirred in a round bottom flask at 100° C. overnight. The mixture was quenched with water (150 mL) at 5-10° C. and filtered to afford the product (0.6 g, 37.5%). $^1$H NMR (400 MHz, DMSO) δ 11.09 (s, 1H), 7.68 (t, J=7.8 Hz, 1H), 7.34 (d, J=7.8 Hz, 2H), 5.09 (d, J=8.0 Hz, 1H), 3.62 (d, J=11.4 Hz, 2H), 2.98-2.83 (m, 3H), 2.59 (d, J=17.6 Hz, 1H), 2.43 (s, 1H), 2.04 (s, 1H), 1.91 (d, J=11.8 Hz, 2H), 1.73 (d, J=11.1 Hz, 2H), 1.42 (s, 9H); $[M+H]^+$=441.9.

Step 2: 1-(2-(2,6-dioxopiperidin-3-yl)-1,3-dioxoisoindolin-4-yl)piperidine-4-carboxylic acid

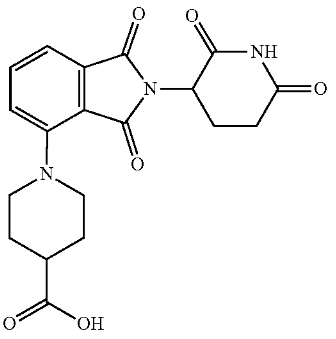 [SMILES: O=C1CCC(N2C(=O)c3cccc(N4CCC(C(=O)O)CC4)c3C2=O)C(=O)N1]

A mixture of tert-butyl 1-(2-(2,6-dioxopiperidin-3-yl)-1,3-dioxoisoindolin-4-yl)piperidine-4-carboxylate (0.6 g, 1.36 mmol) in 2,2,2-trifluoroacetic acid (10.0 mL) was stirred in a round bottom flask at room temperature overnight. The mixture was evaporated in vacuum to afford the crude product (174 mg). $[M+H]^+$=385.9.

Step 3: 7-(1-(2-(2,6-dioxopiperidin-3-yl)-1,3-dioxoisoindolin-4-yl)piperidine-4-carboxamido)-2-(4-phenoxyphenyl)-9,10-dihydro-4H-benzo[d]pyrazolo[1,5-a][1,3]diazepine-3-carboxamide

-

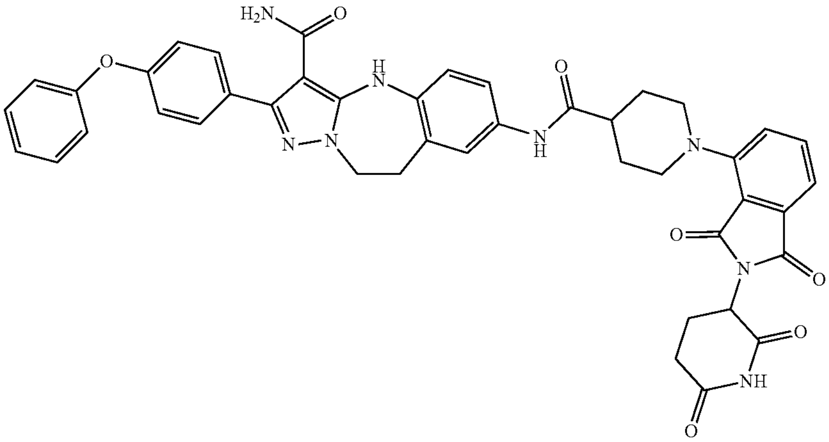 [SMILES: NC(=O)c1c(-c2ccc(Oc3ccccc3)cc2)nn2c1Nc1ccc(NC(=O)C3CCN(c4cccc5c4C(=O)N(C4CCC(=O)NC4=O)C5=O)CC3)cc1CC2]

A mixture of 7-amino-2-(4-phenoxyphenyl)-9,10-dihydro-4H-benzo[d]pyrazolo[1,5-a][1,3]diazepine-3-carboxamide (0.12 g, 0.3 mmol), 1-(2-(2,6-dioxopiperidin-3-yl)-1,3-dioxoisoindolin-4-yl)piperidine-4-carboxylic acid (0.174 g, 0.45 mmol), HATU (0.171 g, 0.45 mmol) and DIPEA (0.116 g, 0.9 mmol) in DMF (10.0 mL) was stirred in a round bottom flask at room temperature overnight. Then the mixture was evaporated in vacuum to afford the crude product, which was purified by prep-TLC (DCM:MeOH=7:1) to give the product (63 mg, 26.9%). $^1$H NMR (400 MHz, DMSO) δ 11.09 (s, 1H), 9.92 (d, J=16.8 Hz, 2H), 7.70 (t, J=7.8 Hz, 1H), 7.53 (d, J=8.8 Hz, 3H), 7.48-7.39 (m, 3H), 7.39-7.33 (m, 2H), 7.19 (t, J=7.3 Hz, 1H), 7.10 (t, J=8.5 Hz, 4H), 6.93 (d, J=8.7 Hz, 1H), 5.11 (dd, J=12.8, 5.3 Hz, 1H), 4.35 (d, J=5.6 Hz, 2H), 3.78 (d, J=11.0 Hz, 2H), 3.70-3.55 (m, 1H), 3.15 (d, J=2.4 Hz, 2H), 3.02-2.83 (m, 3H), 2.64-2.53 (m, 3H), 2.10-1.98 (m, 1H), 1.96-1.83 (m, 3H); $[M+H]^+$ =779.7.

Example A12: $N^7$-((1r,4r)-4-((4-(2-(2,6-dioxopiperidin-3-yl)-6-fluoro-1,3-dioxoisoindolin-5-yl)piperazin-1-yl)methyl)cyclohexyl)-2-(4-phenoxyphenyl)-9,10-dihydro-4H-benzo[d]pyrazolo[1,5-a][1,3]diazepine-3,7-dicarboxamide

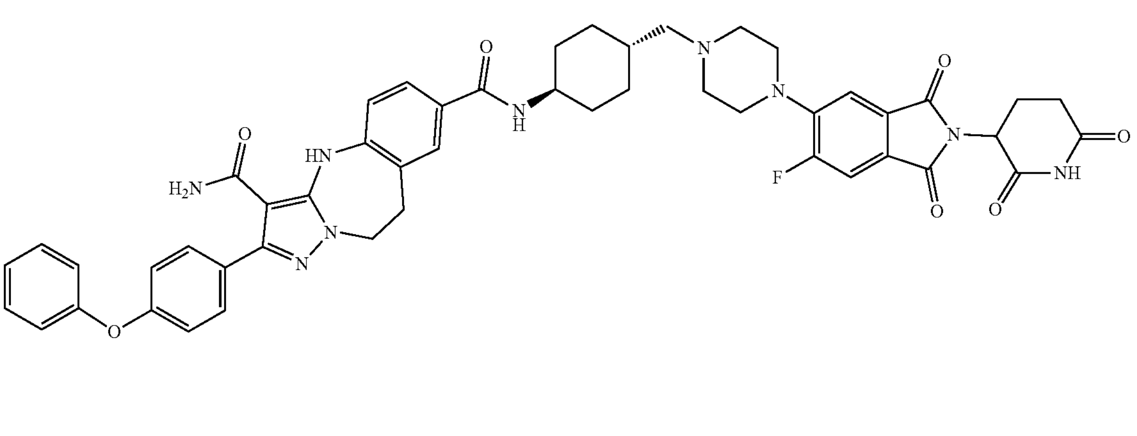 [SMILES: NC(=O)c1c(-c2ccc(Oc3ccccc3)cc2)nn2c1Nc1ccc(C(=O)N[C@H]3CC[C@H](CN4CCN(c5cc6c(cc5F)C(=O)N(C5CCC(=O)NC5=O)C6=O)CC4)CC3)cc1CC2]

A mixture of 3-carbamoyl-2-(4-phenoxyphenyl)-9,10-dihydro-4H-benzo[d]pyrazolo[1,5-a][1,3]diazepine-7-carboxylic acid (0.15 g, 0.341 mmol), 5-(4-(((1r,4r)-4-aminocyclohexyl)methyl)piperazin-1-yl)-2-(2,6-dioxopiperidin-3-yl)-6-fluoroisoindoline-1,3-dione hydrochloride (0.190 g, 0.375 mmol, made by procedures similar to step 8 in example A1), HATU (0.194 g, 0.511 mmol) and DIPEA (0.132 g, 1.023 mmol) in DMF (10.0 mL) was stirred in a round bottom flask at room temperature overnight. The mixture was evaporated in vacuum to give the crude product, which was purified by prep-TLC (DCM:MeOH=7:1) to give the product (42 mg, 13.8%). $^1$H NMR (400 MHz, DMSO) δ 11.15 (s, 1H), 10.26 (s, 1H), 9.00 (s, 1H), 8.18-8.10 (m, 1H), 7.85-7.69 (m, 3H), 7.62-7.48 (m, 3H), 7.43 (t, J=7.9 Hz, 2H), 7.19 (t, J=7.3 Hz, 1H), 7.10 (t, J=7.8 Hz, 3H), 7.04 (d, J=8.3 Hz, 1H), 5.12 (dd, J=13.2, 5.1 Hz, 1H), 4.40 (d, J=7.7 Hz, 2H), 3.77 (dd, J=27.8, 12.5 Hz, 2H), 3.67-3.41 (m, 5H), 3.29-3.19 (m, 4H), 3.18-3.07 (m, 4H), 2.95-2.82 (m, 2H), 2.60 (dd, J=34.9, 13.7 Hz, 3H), 2.05 (dd, J=13.0, 5.6 Hz, 1H), 1.95-1.82 (m, 4H), 1.39 (dd, J=16.8, 9.8 Hz, 2H); [M+H]$^+$=894.9.

Example A13:7-(4-((1-(2-(2,6-dioxopiperidin-3-yl)-1,3-dioxoisoindolin-5-yl)piperidin-4-yl)methyl)piperazine-1-carbonyl)-2-(4-phenoxyphenyl)-9,10-dihydro-4H-benzo[d]pyrazolo[1,5-a][1,3]diazepine-3-carboxamide Step 1: tert-butyl 4-((1-((benzyloxy)carbonyl)piperidin-4-yl)methyl)piperazine-1-carboxylate

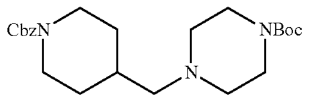 [SMILES: CC(C)(C)OC(=O)N1CCN(CC2CCN(C(=O)OCc3ccccc3)CC2)CC1]

A mixture of benzyl 4-formylpiperidine-1-carboxylate (10.0 g, 40.5 mmol) and tert-butyl piperazine-1-carboxylate (7.5 g, 40.5 mmol) in DCM (300 mL) was stirred in a round bottom flask at room temperature for 3 hours. Then sodium triacetoxyborohydride (9.4 g, 44.55 mmol) was added, and the mixture was stirred in a round bottom flask at room temperature overnight. The mixture was quenched with water (500 mL) at 5-10° C. and extracted with EA (3×300 mL). The organic phase was dried over anhydrous sodium sulfate, filtered and concentrated under reduced pressure to afford the product (17.0 g, 100.0%). [M+H]$^+$=418.0.

Step 2: tert-butyl 4-(piperidin-4-ylmethyl)piperazine-1-carboxylate

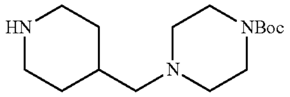 [SMILES: CC(C)(C)OC(=O)N1CCN(CC2CCNCC2)CC1]

A mixture of tert-butyl 4-((1-((benzyloxy)carbonyl)piperidin-4-yl)methyl)piperazine-1-carboxylate (5.0 g, 12.0 mmol) and palladium hydroxide (1.0 g) in ethanol (50 mL) was stirred in a round bottom flask at room temperature overnight. The mixture was filtered and evaporated in vacuum to afford the product (3.4 g, 100.0%). $^1$H NMR (400 MHz, DMSO) δ 4.29-3.84 (m, 3H), 3.28 (s, 4H), 2.97 (d, J=11.5 Hz, 2H), 2.62-2.48 (m, 1H), 2.25 (s, 4H), 2.09 (d, J=6.1 Hz, 2H), 1.73-1.53 (m, 3H), 1.39 (s, 9H), 1.12-0.93 (m, 2H). [M+H]$^+$=283.9.

Step 3: tert-butyl 4-((1-(2-(2,6-dioxopiperidin-3-yl)-1,3-dioxoisoindolin-5-yl)piperidin-4-yl)methyl)piperazine-1-carboxylate

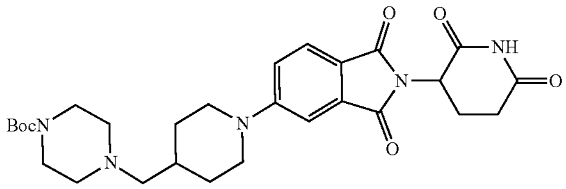 [SMILES: CC(C)(C)OC(=O)N1CCN(CC2CCN(c3ccc4c(c3)C(=O)N(C3CCC(=O)NC3=O)C4=O)CC2)CC1]

A mixture of 2-(2,6-dioxopiperidin-3-yl)-5-fluoroisoindoline-1,3-dione (552.0 mg, 2.0 mmol), tert-butyl 4-(piperidin-4-ylmethyl)piperazine-1-carboxylate (620.4 mg, 2.2 mmol) and DIPEA (774.0 mg, 6.0 mmol) in DMSO (15.0 mL) was stirred in a round bottom flask at 100° C. overnight. The mixture was filtered and the solid was washed with water (50 mL) to afford the product (670.0 mg, 62.1%). [M+H]$^+$=539.9.

Step 4: 2-(2,6-dioxopiperidin-3-yl)-5-(4-(piperazin-1-ylmethyl)piperidin-1-yl)isoindoline-1,3-dione hydrochloride

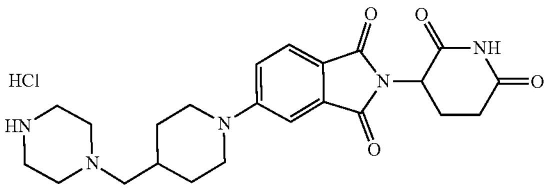 [SMILES: Cl ; O=C1CCC(N2C(=O)c3ccc(N4CCC(CN5CCNCC5)CC4)cc3C2=O)C(=O)N1]

A mixture of tert-butyl 4-((1-(2-(2,6-dioxopiperidin-3-yl)-1,3-dioxoisoindolin-5-yl)piperidin-4-yl)methyl)piperazine-1-carboxylate (0.67 g, 1.243 mmol) in HCl/1,4-dioxane (20.0 mL, 6 N) and DCM (20.0 mL) was stirred in a round bottom flask at room temperature for 3 hours. The solid was filtered to afford the product (0.55 g, 100.0%). $^1$H NMR (400 MHz, DMSO) δ 11.50 (s, 1H), 11.08 (s, 1H), 9.83 (d, J=52.5 Hz, 2H), 7.67 (d, J=8.6 Hz, 1H), 7.36 (s, 1H), 7.27 (d, J=8.4 Hz, 1H), 6.75 (s, 4H), 5.07 (dd, J=12.8, 5.3 Hz, 1H), 4.08 (d, J=13.0 Hz, 2H), 3.71 (s, 2H), 3.51 (s, 3H), 3.29 (s, 2H), 3.08 (d, J=5.0 Hz, 2H), 2.98 (t, J=12.3 Hz, 3H), 2.89 (s, 1H), 2.63-2.53 (m, 2H), 2.17 (s, 1H), 1.99 (d, J=11.1 Hz, 3H), 1.27 (d, J=10.8 Hz, 2H); [M+H]$^+$=439.9.

Step 5: 7-(4-((1-(2-(2,6-dioxopiperidin-3-yl)-1,3-dioxoisoindolin-5-yl)piperidin-4-yl)methyl)piperazine-1-carbonyl)-2-(4-phenoxyphenyl)-9,10-dihydro-4H-benzo[d]pyrazolo[1,5-a][1,3]diazepine-3-carboxamide

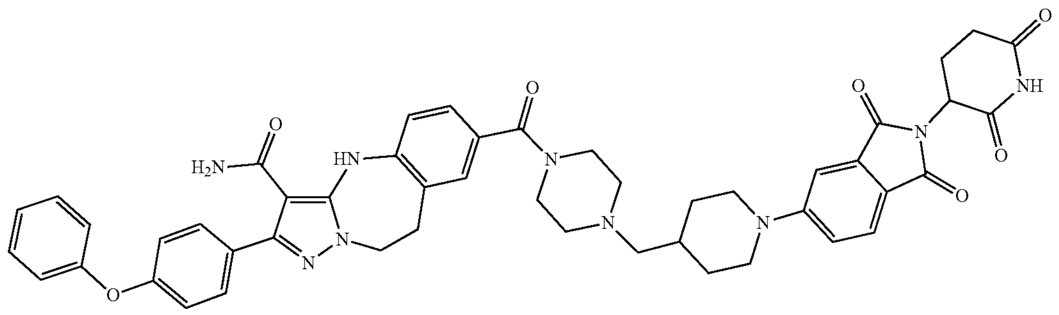 [SMILES: NC(=O)c1c(-c2ccc(Oc3ccccc3)cc2)nn2c1Nc1ccc(C(=O)N3CCN(CC4CCN(c5ccc6c(c5)C(=O)N(C5CCC(=O)NC5=O)C6=O)CC4)CC3)cc1CC2]

A mixture of 3-carbamoyl-2-(4-phenoxyphenyl)-9,10-dihydro-4H-benzo[d]pyrazolo[1,5-a][1,3]diazepine-7-carboxylic acid (0.15 g, 0.341 mmol), 2-(2,6-dioxopiperidin-3-yl)-5-(4-(piperazin-1-ylmethyl)piperidin-1-yl)isoindoline-1,3-dione hydrochloride (0.178 g, 0.375 mmol), HATU (0.194 g, 0.511 mmol) and DIPEA (0.132 g, 1.023 mmol) in DMF (5.0 mL) was stirred in a round bottom flask at room temperature overnight. The mixture was evaporated in vacuum to give the crude product, which was purified by prep-TLC to give the product (43 mg, 14.6%). $^1$H NMR (400 MHz, DMSO) δ 11.08 (s, 1H), 10.22 (s, 1H), 7.65 (d, J=8.5 Hz, 1H), 7.54 (d, J=8.5 Hz, 2H), 7.43 (t, J=7.9 Hz, 2H), 7.32 (d, J=4.0 Hz, 2H), 7.24 (t, J=9.2 Hz, 2H), 7.19 (t, J=7.5 Hz, 1H), 7.10 (t, J=8.1 Hz, 4H), 7.02 (d, J=8.2 Hz, 1H), 5.06 (dd, J=13.3, 5.6 Hz, 1H), 4.40 (d, J=1.8 Hz, 2H), 4.04 (d, J=12.1 Hz, 2H), 3.54 (dt, J=15.9, 9.6 Hz, 4H), 3.23 (d, J=4.8 Hz, 2H), 2.96 (t, J=11.9 Hz, 2H), 2.87 (d, J=8.4 Hz, 1H), 2.63-2.52 (m, 2H), 2.44-2.30 (m, 4H), 2.18 (d, J=5.5 Hz, 2H), 2.02 (d, J=6.1 Hz, 1H), 1.81 (d, J=12.0 Hz, 3H), 1.29-1.09 (m, 3H); [M+H]$^+$=862.9.

Example A14: 7-(4-((4-(2-(2,6-dioxopiperidin-3-yl)-6-fluoro-1,3-dioxoisoindolin-5-yl)piperazin-1-yl)methyl)piperidine-1-carbonyl)-2-(4-phenoxyphenyl)-9,10-dihydro-4H-benzo[d]pyrazolo[1,5-a][1,3]diazepine-3-carboxamide Step 1: tert-butyl 4-((4-(2-(2,6-dioxopiperidin-3-yl)-6-fluoro-1,3-dioxoisoindolin-5-yl)piperazin-1-yl)methyl)piperidine-1-carboxylate

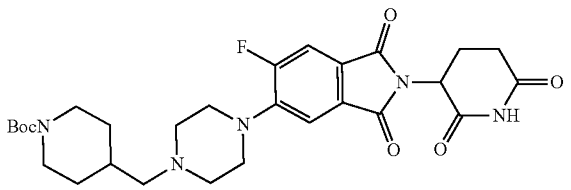 [SMILES: CC(C)(C)OC(=O)N1CCC(CN2CCN(c3cc4c(cc3F)C(=O)N(C3CCC(=O)NC3=O)C4=O)CC2)CC1]

A mixture of 2-(2,6-dioxopiperidin-3-yl)-5,6-difluoroisoindoline-1,3-dione (0.6 g, 2.0 mmol), tert-butyl 4-(piperazin-1-ylmethyl)piperidine-1-carboxylate (577.6 mg, 2.0 mmol) and DIPEA (774.0 mg, 6.0 mmol) in DMSO (20.0 mL) was stirred in a round bottom flask at 100° C. overnight. The mixture was filtered and the solid was washed with water (50 mL) to afford the product (1.0 g, 89.8%). [M+H]$^+$=557.9.

Step 2: 2-(2,6-dioxopiperidin-3-yl)-5-fluoro-6-(4-(piperidin-4-ylmethyl)piperazin-1-yl)isoindoline-1,3-dione hydrochloride

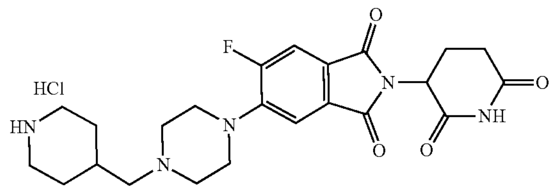 [SMILES: O=C1CCC(N2C(=O)c3cc(F)c(N4CCN(CC5CCNCC5)CC4)cc3C2=O)C(=O)N1 ; Cl]

A mixture of tert-butyl 4-((4-(2-(2,6-dioxopiperidin-3-yl)-6-fluoro-1,3-dioxoisoindolin-5-yl)piperazin-1-yl)methyl)piperidine-1-carboxylate (1.0 g, 1.8 mmol) in HCl/1,4-dioxane (20.0 mL, 6 N) and DCM (5.0 mL) was stirred in a round bottom flask at room temperature for 2 hours. The solid was filtered to afford the product (0.85 g, 100.0%). [M+H]$^+$=457.9.

Step 3: 7-(4-((4-(2-(2,6-dioxopiperidin-3-yl)-6-fluoro-1,3-dioxoisoindolin-5-yl)piperazin-1-yl)methyl)piperidine-1-carbonyl)-2-(4-phenoxyphenyl)-9,10-dihydro-4H-benzo[d] pyrazolo[1,5-a][1,3]diazepine-3-carboxamide

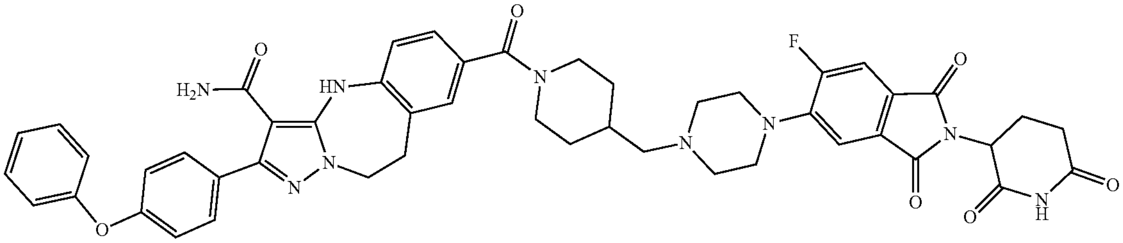 [SMILES: NC(=O)c1c(-c2ccc(Oc3ccccc3)cc2)nn2c1Nc1ccc(C(=O)N3CCC(CN4CCN(c5cc6c(cc5F)C(=O)N(C5CCC(=O)NC5=O)C6=O)CC4)CC3)cc1CC2]

A mixture of 3-carbamoyl-2-(4-phenoxyphenyl)-9,10-dihydro-4H-benzo[d]pyrazolo[1,5-a][1,3]diazepine-7-carboxylic acid (0.16 g, 0.364 mmol), 2-(2,6-dioxopiperidin-3-yl)-5-fluoro-6-(4-(piperidin-4-ylmethyl)piperazin-1-yl)isoindoline-1,3-dione hydrochloride (0.215 g, 0.437 mmol), HATU (207.5 mg, 0.546 mmol) and DIPEA (234.8 mg, 1.82 mmol) in DMF (5.0 mL) was stirred in a round bottom flask at room temperature overnight. The mixture was evaporated in vacuum to give the crude product, which was purified with silica gel column chromatography (DCM:MeOH=100:0~90:10 gradient elution) and prep-TLC (DCM:MeOH=7:1) to give the product (60 mg, 18.7%). $^1$H NMR (400 MHz, DMSO) δ 11.11 (s, 1H), 10.21 (s, 1H), 7.83-7.68 (m, 1H), 7.54 (d, J=8.2 Hz, 2H), 7.43 (t, J=7.8 Hz, 3H), 7.31 (s, 1H), 7.25 (d, J=7.7 Hz, 1H), 7.19 (t, J=7.3 Hz, 1H), 7.10 (t, J=7.6 Hz, 4H), 7.02 (d, J=7.6 Hz, 1H), 5.11 (dd, J=13.0, 5.3 Hz, 1H), 4.40 (d, J=3.9 Hz, 2H), 3.88-3.56 (m, 1H), 3.29-3.06 (m, 8H), 2.96-2.82 (m, 2H), 2.59 (d, J=18.1 Hz, 2H), 2.23 (dt, J=16.4, 8.3 Hz, 2H), 2.10-2.00 (m, 1H), 1.93-1.70 (m, 2H), 1.29-1.11 (m, 6H); $[M+H]^+$=880.8.

Example A15: 6-(4-((1-(2-(2,6-dioxopiperidin-3-yl)-1,3-dioxoisoindolin-5-yl)piperidin-4-yl)methyl)piperazin-1-yl)-2-(4-phenoxyphenyl)-9,10-dihydro-4H-benzo[d]pyrazolo[1,5-a][1,3]diazepine-3-carboxamide Step 1: tert-butyl 4-(3-cyano-2-(4-phenoxyphenyl)-9,10-dihydro-4H-benzo[d]pyrazolo[1,5-a][1,3]diazepin-6-yl)piperazine-1-carboxylate

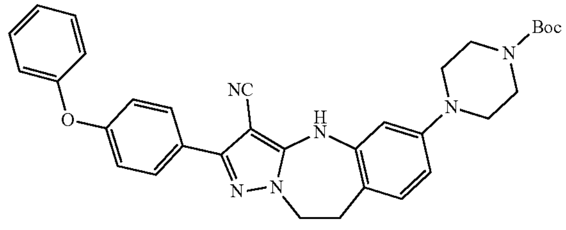 [SMILES: CC(C)(C)OC(=O)N1CCN(c2ccc3c(c2)Nc2c(C#N)c(-c4ccc(Oc5ccccc5)cc4)nn2CC3)CC1]

A mixture of 6-bromo-2-(4-phenoxyphenyl)-9,10-dihydro-4H-benzo[d]pyrazolo[1,5-a][1,3]diazepine-3-carbonitrile (250 mg, 0.55 mmol), tert-butyl piperazine-1-carboxylate (122.4 mg, 0.65 mmol), $Pd_2(dba)_3$ (50 mg, 0.05 mmol), Ruphos (51 mg, 0.11 mmol) and t-BuONa (131.6 mg, 1.37 mmol) in toluene (10 mL) was stirred at 110° C. overnight under nitrogen atmosphere. The mixture was concentrated under vacuum. The residue was purified by silica gel column chromatography, eluted with EA/PE (1:1) to afford the product (120 mg, 39%). $[M+H]^+$=563.3.

Step 2: 2-(4-phenoxyphenyl)-6-(piperazin-1-yl)-9,10-dihydro-4H-benzo[d]pyrazolo[1,5-a][1,3]diazepine-3-carboxamide

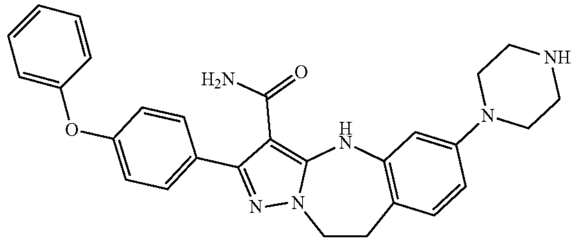 [SMILES: NC(=O)c1c(-c2ccc(Oc3ccccc3)cc2)nn2c1Nc1cc(N3CCNCC3)ccc1CC2]

A solution of tert-butyl 4-(3-cyano-2-(4-phenoxyphenyl)-9,10-dihydro-4H-benzo[d]pyrazolo[1,5-a][1,3]diazepin-6-yl)piperazine-1-carboxylate (120 mg, 0.21 mmol) in MsOH (5 mL) was stirred at 100° C. for 1 h. The mixture was added dropwise to saturated $NaHCO_3$ aqueous solution and extracted with DCM (3×100 mL). The combined organic layers were dried over $Na_2SO_4$, filtered and concentrated under vacuum to afford the desired product (110 mg, crude), which was used in the next step directly. $[M+H]^+$=481.2.

Step 3: 6-(4-((1-(2-(2,6-dioxopiperidin-3-yl)-1,3-dioxoisoindolin-5-yl)piperidin-4-yl)methyl)piperazin-1-yl)-2-(4-phenoxyphenyl)-9,10-dihydro-4H-benzo[d]pyrazolo[1,5-a][1,3]diazepine-3-carboxamide

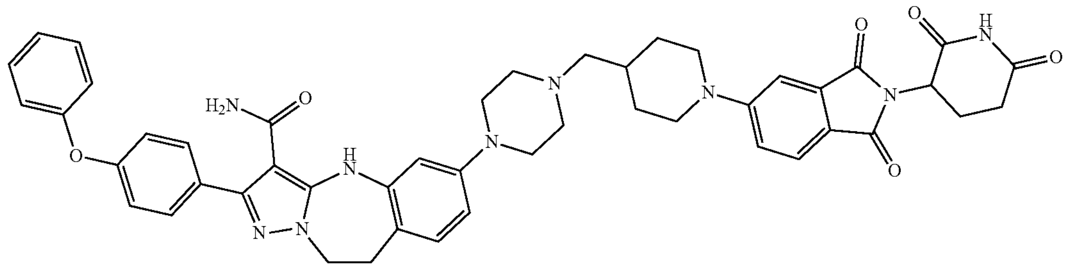 [SMILES: NC(=O)c1c(-c2ccc(Oc3ccccc3)cc2)nn2c1Nc1cc(N3CCN(CC4CCN(c5ccc6c(c5)C(=O)N(C5CCC(=O)NC5=O)C6=O)CC4)CC3)ccc1CC2]

A mixture of 2-(4-phenoxyphenyl)-6-(piperazin-1-yl)-9,10-dihydro-4H-benzo[d]pyrazolo[1,5-a][1,3]diazepine-3-carboxamide (60 mg, 0.12 mmol), (1-(2-(2,6-dioxopiperidin-3-yl)-1,3-dioxoisoindolin-5-yl)piperidin-4-yl)methyl 4-methylbenzenesulfonate (85.3 mg, 0.16 mmol) and DIEA (48.4 mg, 0.37 mmol) in DMSO (5 mL) was stirred at 70° C. overnight. The mixture was diluted with water (50 mL) and extracted with EA (3×50 mL). The combined organic layers were dried over $Na_2SO_4$, filtered and concentrated under vacuum. The residue was purified by Prep-HPLC to afford the product (10.95 mg, 10.5%). $^1H$ NMR (400 MHz, DMSO) δ 11.06 (s, 1H), 9.90 (s, 1H), 7.64 (d, J=8.0 Hz, 1H), 7.52 (d, J=8.0 Hz, 2H), 7.43 (t, J=8.0 Hz, 2H), 7.23-7.02 (m, 6H), 6.91 (s, 1H), 6.81 (d, J=8.0 Hz, 1H), 6.61-6.52 (m, 1H), 6.49-6.41 (m, 1H), 5.10-5.00 (m, 1H), 4.35-4.26 (m, 2H), 3.72-3.46 (m, 4H), 3.20-3.00 (m, 9H), 2.94-2.81 (m, 3H), 2.41-2.31 (m, 3H), 2.25-2.12 (m, 2H), 2.06-1.92 (m, 2H), 1.76-1.57 (m, 4H); $[M+H]^+$=834.3.

Example A16: 7-(((1-(2-(2,6-dioxopiperidin-3-yl)-6-fluoro-1,3-dioxoisoindolin-5-yl)piperidin-4-yl)methyl)amino)-2-(4-phenoxyphenyl)-9,10-dihydro-4H-benzo[d]pyrazolo[1,5-a][1,3]diazepine-3-carboxamide Step 1: 2-(2,6-dioxopiperidin-3-yl)-5-fluoro-6-(4-(hydroxymethyl)piperidin-1-yl)isoindoline-1,3-dione

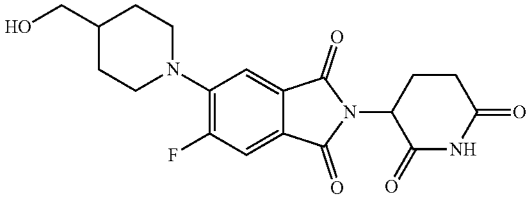 [SMILES: O=C1CCC(N2C(=O)c3cc(F)c(N4CCC(CO)CC4)cc3C2=O)C(=O)N1]

A mixture of 2-(2,6-dioxopiperidin-3-yl)-5,6-difluoroisoindoline-1,3-dione (2.94 g, 10 mmol), piperidin-4-ylmethanol (1.15 g, 10 mmol) and DIEA (2.58 g, 20 mmol) in DMSO (20 mL) was stirred at 100° C. for 2 h. The mixture was diluted with water (100 mL) and extracted with EA (3×100 mL). The combined organic layers were dried over $Na_2SO_4$, filtered and concentrated under vacuum to afford the product (3.5 g, 89.9%), which was used in the next step directly. $[M+H]^+$=390.1.

Step 2: 1-(2-(2,6-dioxopiperidin-3-yl)-6-fluoro-1,3-dioxoisoindolin-5-yl)piperidine-4-carbaldehyde

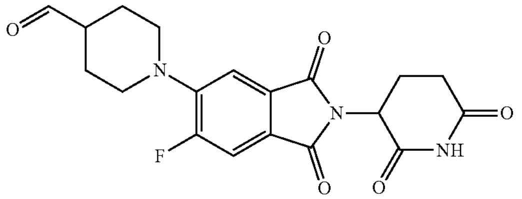 [SMILES: O=CC1CCN(c2cc3c(cc2F)C(=O)N(C2CCC(=O)NC2=O)C3=O)CC1]

To a solution of 2-(2,6-dioxopiperidin-3-yl)-5-fluoro-6-(4-(hydroxymethyl)piperidin-1-yl)isoindoline-1,3-dione (3.5 g, 9 mmol) in DMSO (30 mL) was added IBX (6.3 g, 22.5 mmol). The mixture was stirred at rt for 16 h. The mixture was diluted with water (100 mL) and extracted with EA (3×100 mL). The combined organic layers were dried over $Na_2SO_4$, filtered and concentrated under vacuum. The residue was purified by silica gel column chromatography, eluted with EA/PE (1:2) to afford the product (3 g, 86.2%). $[M+H]^+$=388.1.

Step 3: 7-(((1-(2-(2,6-dioxopiperidin-3-yl)-6-fluoro-1,3-dioxoisoindolin-5-yl)piperidin-4-yl)methyl)amino)-2-(4-phenoxyphenyl)-9,10-dihydro-4H-benzo[d]pyrazolo[1,5-a][1,3]diazepine-3-carboxamide

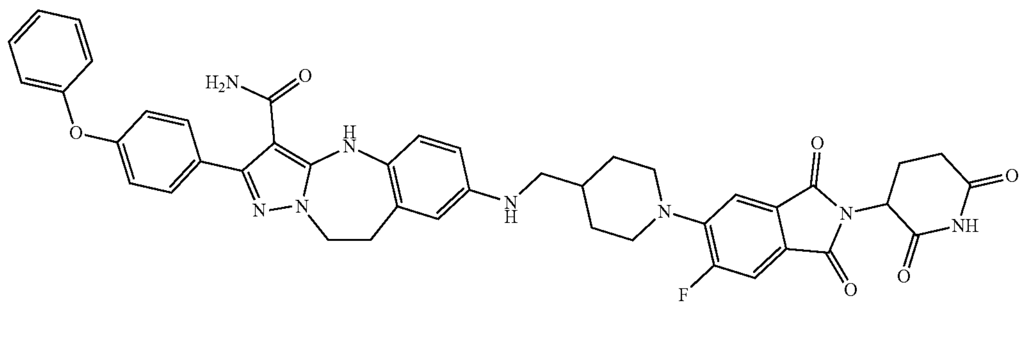 [SMILES: NC(=O)c1c(-c2ccc(Oc3ccccc3)cc2)nn2c1Nc1ccc(NCC3CCN(c4cc5c(cc4F)C(=O)N(C4CCC(=O)NC4=O)C5=O)CC3)cc1CC2]

A mixture of 1-(2-(2,6-dioxopiperidin-3-yl)-6-fluoro-1,3-dioxoisoindolin-5-yl)piperidine-4-carbaldehyde (100 mg, 0.258 mmol), 7-amino-2-(4-phenoxyphenyl)-9,10-dihydro-4H-benzo[d]pyrazolo[1,5-a][1,3]diazepine-3-carboxamide (106 mg, 0.258 mmol) and AcOH (0.02 mL) in MeOH was stirred at rt for 16 h. Then, $NaBH_3CN$ (24.3 mg, 0.38 mmol) was added to the mixture above. The mixture was stirred at rt for 5 h. The mixture was concentrated under vacuum. The residue was purified by Prep-HPLC with the following conditions: Anal. Column: Waters Xselect CSH C18, Column Temp.: Room temperature, Mobile Phase A: ACN, Mobile Phase B: $H_2O$ (0.03% $NH_3$·H2O), Gradient Table: Mobile Phase A (55-90%), Time (min):0-17 min to afford the product (8.92 mg, 4.4%). $^1$H NMR (400 MHz, DMSO) δ 11.11 (s, 1H), 9.59 (s, 1H), 7.71 (d, J=12.0 Hz, 1H), 7.56-7.37 (m, 5H), 7.23-7.03 (m, 5H), 6.77-6.69 (m, 1H), 6.53-6.46 (m, 2H), 5.56-5.47 (m, 1H), 5.15-5.05 (m, 1H), 4.36-4.25 (m, 2H), 3.70-3.59 (m, 2H), 3.15-2.79 (m, 9H), 2.10-1.67 (m, 5H), 1.43-1.29 (m, 2H); $[M+H]^+$=783.3.

Example A17: $N^6$-(1-((1-(2-(2,6-dioxopiperidin-3-yl)-6-fluoro-1,3-dioxoisoindolin-5-yl)piperidin-4-yl)methyl)piperidin-4-yl)-2-(4-phenoxyphenyl)-9,10-dihydro-4H-benzo[d]pyrazolo[1,5-a][1,3]diazepine-3,6-dicarboxamide Step 1: 2-(2,4-dibromophenyl)ethan-1-ol

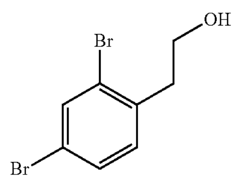 [SMILES: OCCc1ccc(Br)cc1Br]

To a solution of 2-(2,4-dibromophenyl)acetic acid (20 g, 68.5 mmol) in THE was added $BH_3$-THF (88.7 mL, 89 mmol) at 0° C. The mixture was stirred at rt for 16 h. The mixture was quenched by 1.0 N HCl solution and extracted with DCM (3×300 mL). The combined organic layers were dried over $Na_2SO_4$, filtered and concentrated under vacuum to afford the product (19 g, 99%). $[M+H—OH]^+$=263.1.

Step 2: (E)-4-methyl-N'-(4-phenoxybenzylidene)benzenesulfonohydrazide

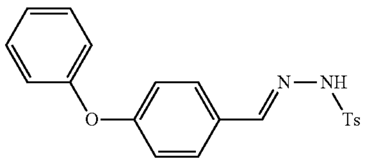 [SMILES: Cc1ccc(S(=O)(=O)N/N=C/c2ccc(Oc3ccccc3)cc2)cc1]

A mixture of 4-phenoxybenzaldehyde (20 g, 0.1 mol) and 4-methylbenzenesulfonohydrazide (18.6 g, 0.1 mmol) in MeOH was stirred at rt for 5 h. The mixture was filtered and the solids were washed with hexane and dried under vacuum to afford the product (30 g, 81.9%). $[M+H]^+$=367.0.

Step 3: (E)-N-(2,4-dibromophenethyl)-4-methyl-N'-(4-phenoxybenzylidene)benzenesulfonohydrazide

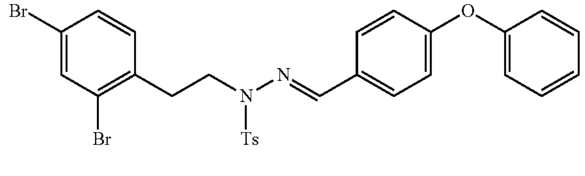 [SMILES: Cc1ccc(S(=O)(=O)N(CCc2ccc(Br)cc2Br)/N=C/c2ccc(Oc3ccccc3)cc2)cc1]

To a mixture of 2-(2,4-dibromophenyl)ethan-1-ol (35 g, 0.126 mol) in THE were added (E)-4-methyl-N'-(4-phenoxybenzylidene)benzenesulfonohydrazide (46.1 g, 0.126 mol) and $PPh_3$ (49.5 g, 0.189 mol) at rt. Then, DIEA (38.2 g, 0.189 mol) was added dropwise to the mixture at 0° C. under nitrogen atmosphere. The mixture was stirred at rt for 16 h. The mixture was diluted with water (500 mL) and extracted with EA (3×500 mL). The combined organic layers were dried over $Na_2SO_4$, filtered and concentrated under vacuum. The residue was purified by silica gel column chromatography, eluted with EA/PE (1:4) to afford the product (50 g, 63.3%). $[M+H]^+$=627.0.

Step 4: 5-amino-1-(2,4-dibromophenethyl)-3-(4-phenoxyphenyl)-1H-pyrazole-4-carbonitrile

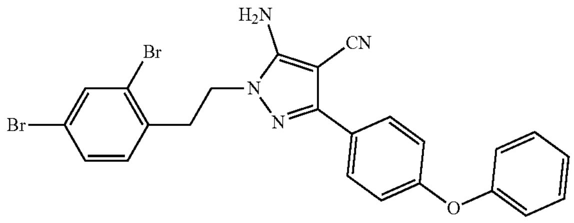 [SMILES: N#Cc1c(-c2ccc(Oc3ccccc3)cc2)nn(CCc2ccc(Br)cc2Br)c1N]

To a mixture of (E)-N-(2,4-dibromophenethyl)-4-methyl-N'-(4-phenoxybenzylidene)benzenesulfonohydrazide (50 g, 79.8 mmol) and malononitrile (13.2 g, 0.2 mol) was added $AlCl_3$ (26.6 g, 0.2 mol). The mixture was refluxed for 16 h under nitrogen atmosphere. The mixture was quenched by water (500 mL) and extracted with DCM (3×500 mL). The combined organic layers were dried over $Na_2SO_4$, filtered and concentrated under vacuum. The residue was purified by silica gel column chromatography, eluted with EA/PE (1:1) to afford product (30 g, 70.1%). $[M+H]^+$=537.0.

Step 5: 6-bromo-2-(4-phenoxyphenyl)-9,10-dihydro-4H-benzo[d]pyrazolo[1,5-a][1,3]diazepine-3-carbonitrile

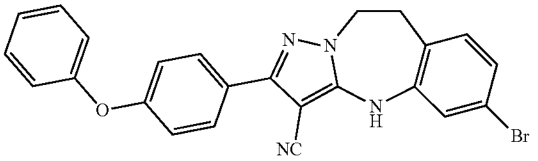 [SMILES: N#Cc1c(-c2ccc(Oc3ccccc3)cc2)nn2c1Nc1cc(Br)ccc1CC2]

A mixture of 5-amino-1-(2,4-dibromophenethyl)-3-(4-phenoxyphenyl)-1H-pyrazole-4-carbonitrile (32 g, 59.7 mmol), (1R,2R)—N1,N2-dimethylcyclohexane-1,2-diamine (1.7 g, 11.9 mmol), CuI (2.27 g, 11.9 mmol) and $K_2CO_3$ (16.7 g, 121 mmol) in DMF (100 mL) was stirred at 100° C. for 16 h under nitrogen atmosphere. The mixture was concentrated under vacuum. The residue was purified by silica gel column chromatography, eluted with EA/PE (1:1) to afford product (15 g, 55.1%). $[M+H]^+$=457.1.

Step 6: 6-bromo-2-(4-phenoxyphenyl)-9,10-dihydro-4H-benzo[d]pyrazolo[1,5-a][1,3]diazepine-3-carboxamide

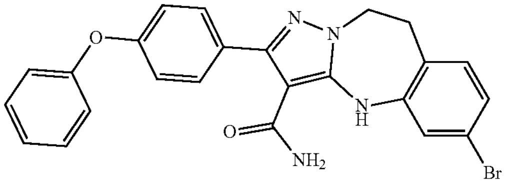 [SMILES: NC(=O)c1c(-c2ccc(Oc3ccccc3)cc2)nn2c1Nc1cc(Br)ccc1CC2]

A mixture of 6-bromo-2-(4-phenoxyphenyl)-9,10-dihydro-4H-benzo[d]pyrazolo[1,5-a][1,3]diazepine-3-carbonitrile (2 g, 4.38 mmol) in MsOH (10 mL) was stirred at 100° C. for 1 h. The mixture was added to saturated $NaHCO_3$ aqueous solution and extracted with DCM (3×100 mL). The combined organic layers were dried over $Na_2SO_4$, filtered and concentrated under vacuum to afford the product (2 g, crude). $[M+H]^+$=475.1.

Step 7: methyl 3-carbamoyl-2-(4-phenoxyphenyl)-9,10-dihydro-4H-benzo[d]pyrazolo[1,5-a][1,3]diazepine-6-carboxylate

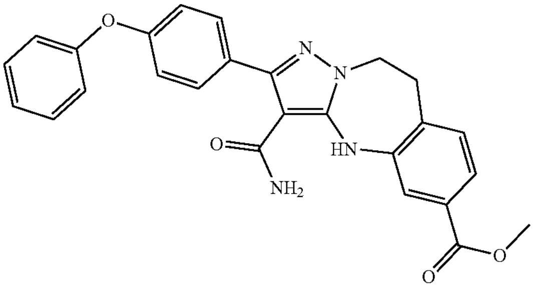 [SMILES: COC(=O)c1ccc2c(c1)Nc1c(C(N)=O)c(-c3ccc(Oc4ccccc4)cc3)nn1CC2]

A mixture of 6-bromo-2-(4-phenoxyphenyl)-9,10-dihydro-4H-benzo[d]pyrazolo[1,5-a][1,3]diazepine-3-carboxamide (2 g, 4.29 mmol), Pd(dppf)$Cl_2$ (617 mg, 0.84 mmol) and TEA (1.28 g, 12.6 mmol) in MeOH (20 mL) and DMF (2 mL) was stirred at 90° C. under CO atmosphere. The mixture was concentrated under vacuum. The residue was purified by silica gel column chromatography, eluted with EA/PE (1:1) to afford product (1.3 g, 67.7%). [M+H]+ =455.2.

Step 8: 3-carbamoyl-2-(4-phenoxyphenyl)-9,10-dihydro-4H-benzo[d]pyrazolo[1,5-a][1,3]diazepine-6-carboxylic acid

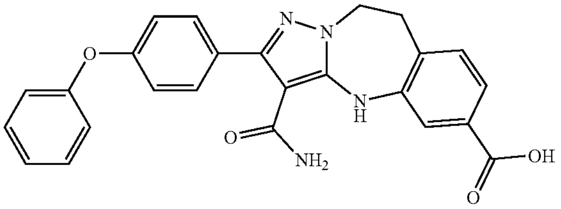 [SMILES: NC(=O)c1c(-c2ccc(Oc3ccccc3)cc2)nn2c1Nc1cc(C(=O)O)ccc1CC2]

To a solution of methyl 3-carbamoyl-2-(4-phenoxyphenyl)-9,10-dihydro-4H-benzo[d]pyrazolo[1,5-a][1,3]diazepine-6-carboxylate (1.3 g, 2.86 mmol) in MeOH (10 mL) and THE (10 mL) was added 2 N LiOH (aq., 7.2 mL, 14.3 mmol). The mixture was stirred at 60° C. for 5 h. The mixture was concentrated under vacuum. The residue was dissolved in water (10 mL) and adjusted to pH=6 with 1 N HCl aqueous solution. The mixture was filtered and the solids were collected and dried under vacuum to afford the product (700 mg, 55.5%). $[M+H]^+$=441.1.

Step 9: N[6]-(1-((1-(2-(2,6-dioxopiperidin-3-yl)-6-fluoro-1,3-dioxoisoindolin-5-yl)piperidin-4-yl)methyl)piperidin-4-yl)-2-(4-phenoxyphenyl)-9,10-dihydro-4H-benzo[d]pyrazolo-[1,5-a][1,3]diazepine-3,6-dicarboxamide

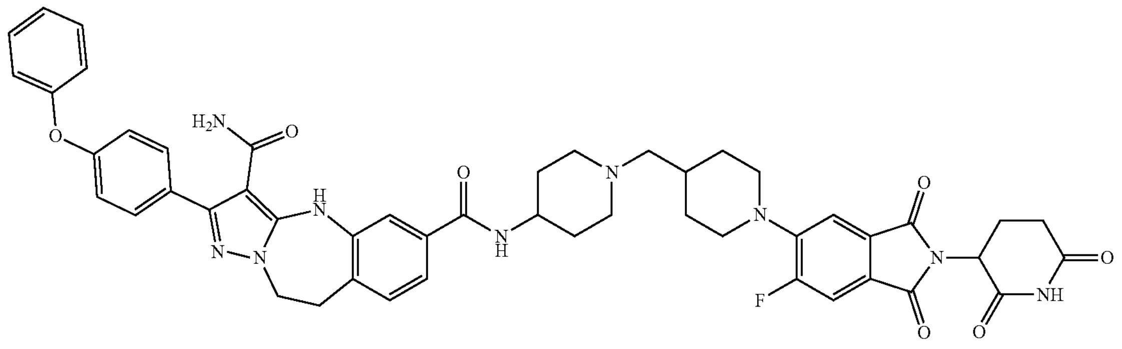 [SMILES: NC(=O)c1c(-c2ccc(Oc3ccccc3)cc2)nn2c1Nc1cc(C(=O)NC3CCN(CC4CCN(c5cc6c(cc5F)C(=O)N(C5CCC(=O)NC5=O)C6=O)CC4)CC3)ccc1CC2]

To a mixture of 3-carbamoyl-2-(4-phenoxyphenyl)-9,10-dihydro-4H-benzo[d]pyrazolo[1,5-a][1,3]diazepine-6-carboxylic acid (44 mg, 0.1 mmol) in DMF (3 mL) were added HATU (41.8 mg, 0.11 mmol) and DIEA (64.5 mg, 0.5 mmol). After stirring for 10 min, 5-(4-((4-aminopiperidin-1-yl)methyl)piperidin-1-yl)-2-(2,6-dioxopiperidin-3-yl)-6-fluoroisoindoline-1,3-dione (47.1 mg, 0.1 mmol) was added to the mixture above. The resulting mixture was stirred at rt for 16 h. The mixture was diluted with water (50 mL) and extracted with EA (3×50 mL). The combined organic layers were dried over $Na_2SO_4$, filtered and concentrated under vacuum. The residue was purified by silica gel column chromatography, eluted with MeOH/DCM (1:11) to afford to afford product (24.3 mg, 27.2%). $^1H$ NMR (400 MHz, DMSO) δ 11.12 (s, 1H), 10.17 (s, 1H), 7.72 (d, J=12.0 Hz, 1H), 7.59-7.38 (m, 7H), 7.37-7.30 (m, 1H), 7.23-7.05 (m, 5H), 5.16-5.06 (m, 1H), 4.42-4.33 (m, 2H), 3.70-3.54 (m, 3H), 2.28-2.20 (m, 2H), 3.18-2.80 (m, 9H), 2.12-1.67 (m, 9H), 1.31-1.16 (m, 6H); $[M+H]^+$=894.4.

Example A18:6-(1-((1-(2-(2,6-dioxopiperidin-3-yl)-1,3-dioxoisoindolin-5-yl)piperidin-4-yl)methyl)piperidine-4-carboxamido)-2-(4-phenoxyphenyl)-9,10-dihydro-4H-benzo[d]pyrazolo[1,5-a][1,3]diazepine-3-carboxamide A mixture of 6-amino-2-(4-phenoxyphenyl)-9,10-dihydro-4H-benzo[d]pyrazolo[1,5-a][1,3]diazepine-3-carboxamide (50 mg, 0.12 mmol, made by procedures similar to step 8 in example A1), HATU (49.4 mg, 0.13 mmol) and DIEA (47.1 mg, 0.36 mmol) in DMF (5 mL) was stirred at rt for 10 min. Then, 1-((1-(2-(2,6-dioxopiperidin-3-yl)-1,3-dioxoisoindolin-5-yl)piperidin-4-yl)methyl)piperidine-4-carboxylic acid (64.5 mg, 0.13 mmol) was added and the mixture was stirred at rt overnight. The mixture was diluted with water (50 mL) and extracted with EA (3×50 mL). The combined organic layers were dried over $Na_2SO_4$, filtered and concentrated under vacuum. The residue was purified by Prep-HPLC with the following conditions: Anal. Column: Waters Xselect CSH C18, Column Temp.: Room temperature, Mobile Phase A: ACN, Mobile Phase B: $H_2O$ (0.03% $NH_3$·H2O), Gradient Table: Mobile Phase A (45-90%), Time (min):0-17 min to afford the product (25.34 mg, 23.8%). $^1H$ NMR (400 MHz, DMSO) δ 11.09 (s, 1H), 10.05 (s, 1H), 9.87 (s, 1H), 7.65 (d, J=8.0 Hz, 1H), 7.53 (d, J=12.0 Hz, 2H), 7.48-7.39 (m, 3H), 7.31 (s, 1H), 7.26-7.04 (m, 9H), 5.11-5.02 (m, 1H), 4.43-4.28 (m, 2H), 4.11-4.00 (m, 2H), 3.18-3.10 (m, 2H), 3.05-2.82 (m, 6H), 2.35-2.10 (m, 3H), 2.06-1.57 (m, 12H), 1.21-1.06 (m, 2H); $[M+H]^+$=876.3.

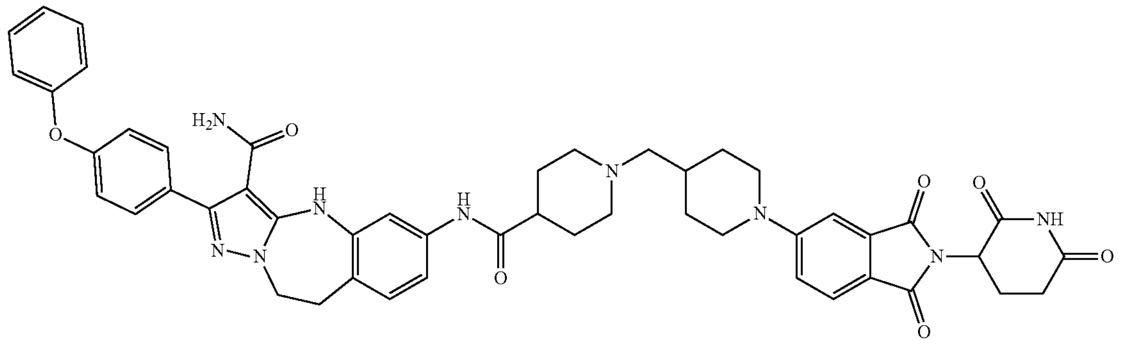 [SMILES: NC(=O)c1c(-c2ccc(Oc3ccccc3)cc2)nn2c1Nc1cc(NC(=O)C3CCN(CC4CCN(c5ccc6c(c5)C(=O)N(C5CCC(=O)NC5=O)C6=O)CC4)CC3)ccc1CC2]

Example A19:6-(4-((1-(2-(2,6-dioxopiperidin-3-yl)-1,3-dioxoisoindolin-5-yl)piperidin-4-yl)methyl)piperazine-1-carbonyl)-2-(4-phenoxyphenyl)-9,10-dihydro-4H-benzo[d]pyrazolo[1,5-a][1,3]diazepine-3-carboxamide Step 1: tert-butyl 4-((1-(2-(2,6-dioxopiperidin-3-yl)-1,3-dioxoisoindolin-5-yl)piperidin-4-yl)methyl)piperazine-1-carboxylate

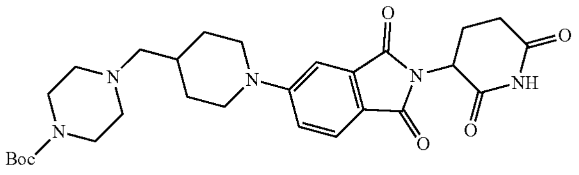 [SMILES: CC(C)(C)OC(=O)N1CCN(CC2CCN(c3ccc4c(c3)C(=O)N(C3CCC(=O)NC3=O)C4=O)CC2)CC1]

A mixture of tert-butyl 4-(piperidin-4-ylmethyl)piperazine-1-carboxylate (700 mg, 2.47 mmol), 2-(2,6-dioxopiperidin-3-yl)-5-fluoroisoindoline-1,3-dione (682 mg, 2.47 mmol) and DIEA (638 mg, 4.94 mmol) in DMSO was stirred at 100° C. for 2 h. The mixture was diluted with water (100 mL) and extracted with EA (3×150 mL). The combined organic layers were dried over $Na_2SO_4$, filtered and concentrated under vacuum to afford the product (1.1 g, 82.7%). $[M+H]^+$=540.3.

Step 2: 2-(2,6-dioxopiperidin-3-yl)-5-(4-(piperazin-1-ylmethyl)piperidin-1-yl)isoindoline-1,3-dione hydrochloride

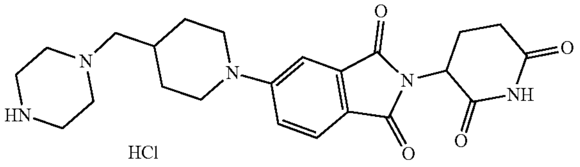 [SMILES: O=C1CCC(N2C(=O)c3ccc(N4CCC(CN5CCNCC5)CC4)cc3C2=O)C(=O)N1 ; Cl]

A mixture of tert-butyl 4-((1-(2-(2,6-dioxopiperidin-3-yl)-1,3-dioxoisoindolin-5-yl)piperidin-4-yl)methyl)piperazine-1-carboxylate (200 mg, 0.37 mmol) in 4.0 N HCl in dioxane (5 mL) was stirred at rt for 2 h. The mixture was concentrated under vacuum to afford the product (160 mg, crude), which was used in the next step directly. $[M+H]^+$=440.2.

Step 3: 6-(4-((1-(2-(2,6-dioxopiperidin-3-yl)-1,3-dioxoisoindolin-5-yl)piperidin-4-yl)methyl)piperazine-1-carbonyl)-2-(4-phenoxyphenyl)-9,10-dihydro-4H-benzo[d]pyrazolo[1,5-a][1,3]diazepine-3-carboxamide m

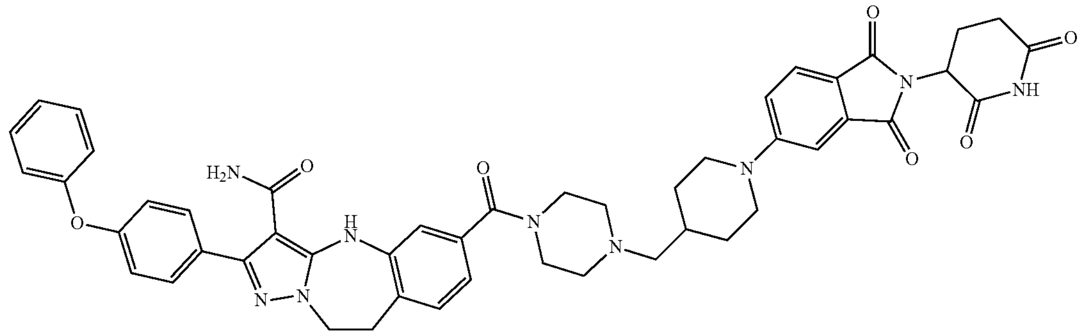 [SMILES: NC(=O)c1c(-c2ccc(Oc3ccccc3)cc2)nn2c1Nc1cc(C(=O)N3CCN(CC4CCN(c5ccc6c(c5)C(=O)N(C5CCC(=O)NC5=O)C6=O)CC4)CC3)ccc1CC2]

To a mixture of 3-carbamoyl-2-(4-phenoxyphenyl)-9,10-dihydro-4H-benzo[d]pyrazolo[1,5-a][1,3]diazepine-6-carboxylic acid (50 mg, 0.11 mmol) in DMF (5 mL) were added HATU (43.2 mg, 0.11 mmol) and DIEA (44 mg, 0.34 mmol). After stirring for 10 min, 2-(2,6-dioxopiperidin-3-yl)-5-(4-(piperazin-1-ylmethyl)piperidin-1-yl)isoindoline-1,3-dione hydrochloride (55 mg, 0.12 mmol) was added. The mixture was stirred at rt for 16 h. The mixture was diluted with water (50 mL) and extracted with EA (3×50 mL). The combined organic layers were dried over $Na_2SO_4$, filtered and concentrated under vacuum. The residue was purified by silica gel column chromatography, eluted with MeOH/DCM (1:9) to afford the product (4.81 mg, 4.9%). $^1H$ NMR (400 MHz, DMSO) δ 11.08 (s, 1H), 10.12 (s, 1H), 7.65 (d, J=8.0 Hz, 1H), 7.53 (d, J=8.0 Hz, 2H), 7.43 (t, J=8.0 Hz, 2H), 7.34-7.15 (m, 5H), 7.10 (t, J=8.0 Hz, 4H), 6.99-6.89 (m, 2H), 5.11-5.01 (m, 1H), 4.42-4.33 (m, 2H), 4.10-3.98 (m, 2H), 3.67-3.53 (m, 2H), 3.03-2.79 (m, 5H), 2.44-2.26 (m, 5H), 2.23-1.93 (m, 5H), 1.90-1.68 (m, 4H), 1.25-1.07 (m, 3H); $[M+H]^+$=862.3.

Example A20:6-(4-((4-(2-(2,6-dioxopiperidin-3-yl)-6-fluoro-1,3-dioxoisoindolin-5-yl)piperazin-1-yl)methyl)piperidine-1-carbonyl)-2-(4-phenoxyphenyl)-9,10-dihydro-4H-benzo[d]pyrazolo[1,5-a][1,3]diazepine-3-carboxamide

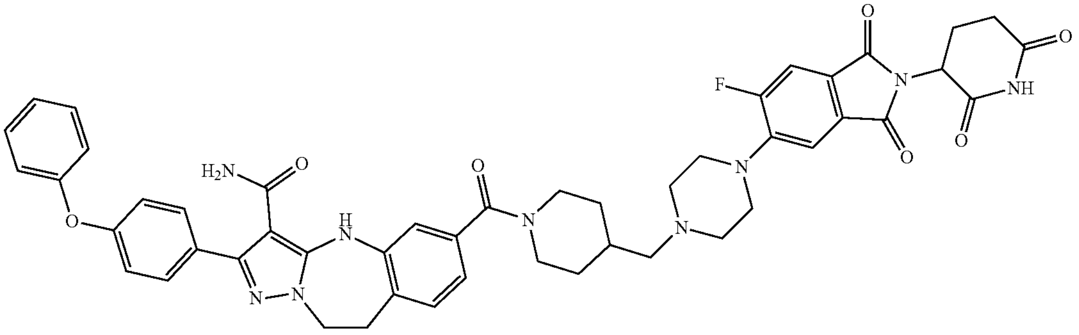 [SMILES: NC(=O)c1c(-c2ccc(Oc3ccccc3)cc2)nn2c1Nc1cc(C(=O)N3CCC(CN4CCN(c5cc6c(cc5F)C(=O)N(C5CCC(=O)NC5=O)C6=O)CC4)CC3)ccc1CC2]

A mixture of 3-carbamoyl-2-(4-phenoxyphenyl)-9,10-dihydro-4H-benzo[d]pyrazolo[1,5-a][1,3]diazepine-6-carboxylic acid (50 mg, 0.11 mmol), HATU (50.1 mg, 0.13 mmol) and DIEA (56.7 mg, 0.44 mmol) in DMF was stirred at rt for 10 min. 2-(2,6-dioxopiperidin-3-yl)-5-fluoro-6-(4-(piperidin-4-ylmethyl)piperazin-1-yl)isoindoline-1,3-dione hydrochloride (57.1 mg, 0.12 mmol) was added to the mixture above. The mixture was stirred at rt for 16 h. The mixture was diluted with water (50 mL) and extracted with EA (3×50 mL). The combined organic layers were dried over $Na_2SO_4$, filtered and concentrated under vacuum. The residue was purified by Prep-HPLC with the following conditions: Anal. Column: Waters Xselect CSH C18, Column Temp.: Room temperature, Mobile Phase A: ACN, Mobile Phase B: $H_2O$ (0.03% $NH_3$·H2O), Gradient Table: Mobile Phase A (45-90%), Time (min):0-17 min to afford the product (10.93 mg, 11%). $^1$H NMR (400 MHz, DMSO) $\delta_H$ 11.12 (s, 1H), 10.12 (s, 1H), 7.73 (d, J=8.0 Hz, 1H), 7.74 (d, J=12.0 Hz, 2H), 7.48-7.39 (m, 3H), 7.30 (d, J=12.0 Hz, 1H), 7.22-7.05 (m, 5H), 6.98-6.89 (m, 2H), 5.15-5.06 (m, 1H), 4.51-4.33 (m, 2H), 3.71-3.61 (m, 2H), 3.03-2.73 (m, 10H), 2.28-2.17 (m, 3H), 2.10-1.61 (m, 9H), 1.17-1.01 (m, 3H); $[M+H]^+$=880.3.

Example A21:7-(4-((1-(4-(2,4-dioxotetrahydropyrimidin-1(2H)-yl)phenyl)piperidin-4-yl)methyl)piperazin-1-yl)-2-(4-phenoxyphenyl)-9,10-dihydro-4H-benzo[d]pyrazolo[1,5-a][1,3]diazepine-3-carboxamide Step 1: tert-butyl 4-(4-(4,4,5,5-tetramethyl-1,3,2-dioxaborolan-2-yl)phenyl)piperidine-1-carboxylate

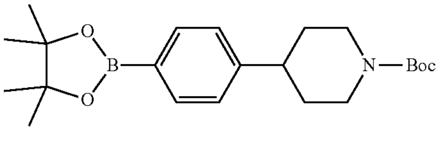 [SMILES: CC(C)(C)OC(=O)N1CCC(c2ccc(B3OC(C)(C)C(C)(C)O3)cc2)CC1]

A mixture of tert-butyl 4-(4-bromophenyl)piperidine-1-carboxylate (10 g, 29.4 mmol), 4,4,4',4',5,5,5',5'-octamethyl-2,2'-bi(1,3,2-dioxaborolane) (9 g, 5.0 mmol), Pd(dppf)$Cl_2$ (2.12 g, 10.6 mmol) and KOAc (4.55 g, 22.75 mmol) in 1,4-dioxane (200 mL) was stirred in a round bottom flask at 100° C. overnight. The mixture was evaporated in vacuum to afford the crude product, which was further purified with silica gel column chromatography (PE:EA=100:0~90:10 gradient elution) to give the title product (11 g, 90%). $[M+H]^+$=388.0.

Step 2: (1-(4-nitrophenyl)piperidin-4-yl)methanol

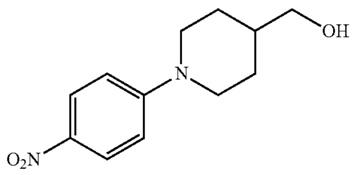 [SMILES: O=[N+]([O-])c1ccc(N2CCC(CO)CC2)cc1]

To a solution of 1-fluoro-4-nitrobenzene (100.0 g, 710.0 mmol) and 4-piperidinemethanol (98.0 g, 85.0 mmol) in DMF (1400.0 mL) was added $K_2CO_3$ (196.0 g) at 25° C. The mixture reaction was stirred at 80° C. for 15 h. Reaction was monitored by HPLC. The reaction was cooled to room temperature, the mixture was poured into ice-water (6000.0 mL) and stirred for 20 mins. The solid was filtered and washed with water (500.0 mL×2), dried to give the product (140.0 g, 83.8%). $^1$H NMR (400 MHz, DMSO) $\delta_H$ 8.03 (d, J=9.4 Hz, 2H), 7.01-6.98 (m, 2H), 4.54 (t, J=5.3 Hz, 1H), 4.07-4.04 (m, 2H), 3.29-3.26 (m, 2H), 3.00-2.93 (m, 2H), 1.76-1.67 (m, 3H), 1.21-1.11 (m, 2H); $[M+H]^+$=237.2.

Step 3: (1-(4-aminophenyl)piperidin-4-yl)methanol

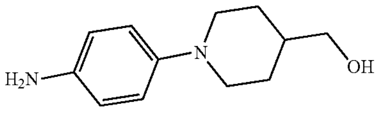 [SMILES: Nc1ccc(N2CCC(CO)CC2)cc1]

Under $N_2$, to a solution of (1-(4-nitrophenyl)piperidin-4-yl)methanol (140.0 g, 592.7 mmol) in MeOH (1680.0 mL) was added 10% Pd/C (28.0 g) at 25° C. And then the mixture was exchanged with $H_2$ two times and stirred under $H_2$ atmosphere at 25° C. for 15 h. Reaction was monitored by HPLC. The mixture was filtered through a pad of Celite and washed with MeOH (140.0 mL). The filtrate was concentrated under vacuum to obtain the product (113.0 g, 92.0%). $^1$H NMR (400 MHz, DMSO) $\delta_H$ 6.77-6.61 (m, 2H), 6.54-6.38 (m, 2H), 4.53 (brs, 2H), 4.45 (t, J=5.3 Hz, 1H), 3.32-3.27 (m, 2H), 2.46-2.41 (m, 2H), 1.76-1.62 (m, 2H), 1.50-1.31 (m, 1H), 1.27-1.08 (m, 2H); [M+H]$^+$=207.2.

Step 4 and 5: (1-(4-(2,4-dioxotetrahydropyrimidin-1(2H)-yl)phenyl)piperidin-4-yl)methyl acetate

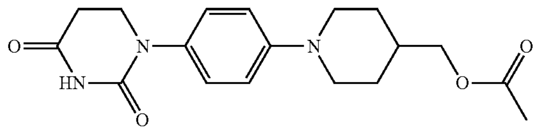 [SMILES: CC(=O)OCC1CCN(c2ccc(N3CCC(=O)NC3=O)cc2)CC1]

To a solution of (1-(4-aminophenyl)piperidin-4-yl)methanol (25.0 g, 121.2 mmol) in PhMe (183.0 mL) was added acrylic acid (13.0 g, 181.8 mmol) at 25° C. The mixture was stirred at 90° C. for 15 h. Reaction was monitored by HPLC. The reaction was cooled to 25° C., then HOAc (183.0 mL) and urea (36.4 g, 606.2 mmol) were added. The mixture was stirred at 110° C. for 24 h. Reaction was monitored by HPLC. The reaction was cooled to 25° C. and concentrated under vacuum. The residue was dissolved with EtOAc (500.0 mL) and then adjusted to pH=7 with sat. $NaHCO_3$. The resulting solution was extracted with 2×200.0 mL of EtOAc and the organic layers were combined. The organic layer was dried over anhydrous sodium sulfate and concentrated under vacuum, and the residual was purified on silica gel to give the product (17.5 g, 74%). $^1$H NMR (400 MHz, DMSO) $\delta_H$ 10.32 (s, 1H), 7.20 (d, J=8.9 Hz, 2H), 6.99 (d, J=9.0 Hz, 2H), 3.98 (d, J=6.2 Hz, 2H), 3.80-3.66 (m, 4H), 2.74-2.72 (m, 4H), 2.09 (s, 3H), 1.80 (d, J=13.8 Hz, 4H), 1.37 (dd, J=12.1, 2.8 Hz, 3H); [M+H]$^+$=346.2.

Step 6: 1-(4-(4-(hydroxymethyl)piperidin-1-yl)phenyl)dihydropyrimidine-2,4(1H,3H)-dione

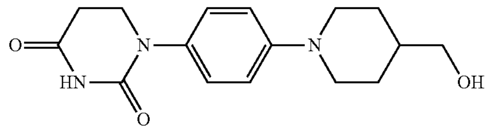 [SMILES: O=C1CCN(c2ccc(N3CCC(CO)CC3)cc2)C(=O)N1]

(1-(4-(2,4-Dioxotetrahydropyrimidin-1(2H)-yl)phenyl)piperidin-4-yl)methyl acetate (35.0 g, 121.2 mmol) was added into 2N HCl (260.0 mL) at 25° C. The mixture was stirred at 100° C. for 15 h. Reaction was monitored by HPLC. The reaction was cooled to 10° C. and then adjusted to pH=7 with sat. $NaHCO_3$. The solid was collected by filtrated, washed by water (50.0 mL), and dried to obtain the product (16.9 g, 55%). $^1$H NMR (400 MHz, DMSO) $\delta_H$ 10.26 (s, 1H), 7.13 (d, J=8.9 Hz, 2H), 6.92 (d, J=9.0 Hz, 2H), 4.49 (s, 1H), 3.78-3.61 (m, 4H), 3.30-3.28 (m, 2H), 2.70-2.66 (m, 4H), 1.75-1.72 (m, 2H), 1.52-1.49 (m, 1H), 1.28-1.18 (m, 2H); [M+H]$^+$=304.2.

Step 7: 1-(4-(2,4-dioxotetrahydropyrimidin-1(2H)-yl)phenyl)piperidine-4-carbaldehyde

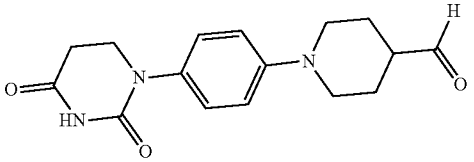 [SMILES: O=CC1CCN(c2ccc(N3CCC(=O)NC3=O)cc2)CC1]

To a solution of 1-(4-(4-(hydroxymethyl)piperidin-1-yl)phenyl)dihydropyrimidine-2,4(1H,3H)-dione (15.0 g, 46.8 mmol) in DMSO (120.0 mL) was added IBX (32.7 g, 117.1 mmol) in portions at 25° C. (caution: exothermal to 40° C.). The mixture was stirred at 25° C. for 15 h. Reaction was monitored by HPLC. Water (300.0 mL) was added to the reaction at 25° C. The solid was filtered and washed with water (100.0 mL) and then EtOAc (100.0 mL). The resulting solution was extracted with 4×200.0 mL of EtOAc. The combined organic layer was dried over $Na_2SO_4$ and concentrated under vacuum to afford a crude residue. The crude product was purified by column chromatography to afford the product (3.1 g, 22.1%). $^1$H NMR (300 MHz, DMSO) $\delta_H$ 10.26 (s, 1H), 9.63 (s, 1H), 7.15-7.10 (m, 2H), 6.95-6.89 (m, 2H), 3.71-3.51 (m, 4H), 2.86-2.57 (m, 4H), 1.94-1.91 (m, 1H), 1.77-1.73 (m, 1H), 1.64-1.51 (m, 2H), 1.38-1.30 (m, 1H); [M+H]$^+$=302.1.

Step 8: 7-(4-((1-(4-(2,4-dioxotetrahydropyrimidin-1(2H)-yl)phenyl)piperidin-4-yl)methyl)piperazin-1-yl)-2-(4-phenoxyphenyl)-9,10-dihydro-4H-benzo[d]pyrazolo[1,5-a][1,3]diazepine-3-carboxamide

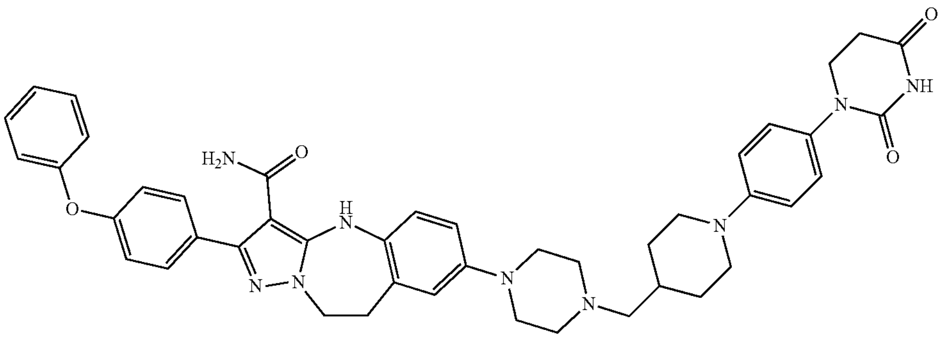 [SMILES: NC(=O)c1c(-c2ccc(Oc3ccccc3)cc2)nn2c1Nc1ccc(N3CCN(CC4CCN(c5ccc(N6CCC(=O)NC6=O)cc5)CC4)CC3)cc1CC2]

A mixture of 2-(4-phenoxyphenyl)-7-(piperazin-1-yl)-9,10-dihydro-4H-benzo[d]pyrazolo[1,5-a][1,3]diazepine-3-carboxamide (96.0 mg, 0.2 mmol), 1-(4-(2,4-dioxotetrahydropyrimidin-1(2H)-yl)phenyl)piperidine-4-carbaldehyde (60.0 g, 0.2 mmol) and titanium ethoxide (0.1 mL) in MeOH (5.0 mL) and DCM (15.0 mL) was stirred at room temperature overnight, and then sodium triacetoxyborohydride (85.0 mg, 0.4 mmol) was added and stirred at room temperature for 3 hours. The mixture was treated with water (20 mL), extracted with dichloromethane (3×20 mL), and washed with brine (20.0 mL). The organic phase was dried over anhydrous sodium sulfate, filtered and concentrated under reduced pressure to afford the crude product, which was purified by prep-HPLC to give the product (3.0 mg, 2.0%). $^1$H NMR (400 MHz, DMSO) δ 10.25 (s, 1H), 9.77 (s, 1H), 7.52 (d, J=8.0 Hz, 2H), 7.43 (t, J=7.5 Hz, 2H), 7.19 (s, 1H), 7.11 (dd, J=18.9, 9.2 Hz, 6H), 6.93 (d, J=8.5 Hz, 2H), 6.84 (d, J=7.9 Hz, 3H), 4.33 (s, 2H), 3.68 (d, J=7.0 Hz, 4H), 3.11 (d, J=24.1 Hz, 8H), 2.67 (dd, J=14.4, 8.8 Hz, 5H), 2.22 (d, J=6.1 Hz, 2H), 1.81 (d, J=12.3 Hz, 2H), 1.71 (s, 1H), 1.22 (d, J=10.3 Hz, 3H); [M+H]$^+$=766.8.

Example A22: 7-(4-(2-(1-(4-(2,4-dioxotetrahydropyrimidin-1(2H)-yl)phenyl)piperidin-4-yl)ethyl)piperazin-1-yl)-2-(4-phenoxyphenyl)-9,10-dihydro-4H-benzo[d]pyrazolo[1,5-a][1,3]diazepine-3-carboxamide Step 1: 2-(1-(4-(2,4-dioxotetrahydropyrimidin-1(2H)-yl)phenyl)piperidin-4-yl)acetaldehyde

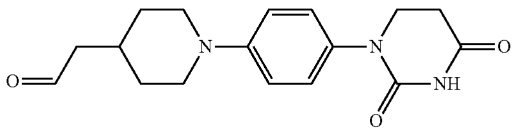 [SMILES: O=CCC1CCN(c2ccc(N3CCC(=O)NC3=O)cc2)CC1]

A mixture of 1-(4-(4-(2-hydroxyethyl)piperidin-1-yl)phenyl)dihydropyrimidine-2,4(1H,3H)-dione (0.5 g, 1.58 mmol, the procedure was similar to example A21 step 1-7) and IBX (884.8 mg, 3.16 mmol) in DMSO (15.0 mL) was stirred in a round bottom flask at room temperature overnight. The mixture was washed with EA (3*30 mL), filtered, and then the organic layer was extraction with water (3*30 mL). The organic layer was evaporated in vacuum to give the crude product, which was purified with silica gel column chromatography (DCM:MeOH=100:0~90:10 gradient elution) to give the product (0.5 g, 100.0%). [M+H]$^+$=316.0.

Step 2: 7-(4-(2-(1-(4-(2,4-dioxotetrahydropyrimidin-1(2H)-yl)phenyl)piperidin-4-yl)ethyl)piperazin-1-yl)-2-(4-phenoxyphenyl)-9,10-dihydro-4H-benzo[d]pyrazolo[1,5-a][1,3]diazepine-3-carboxamide

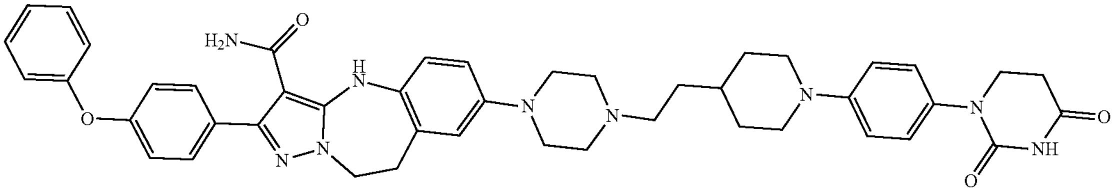 [SMILES: NC(=O)c1c(-c2ccc(Oc3ccccc3)cc2)nn2c1Nc1ccc(N3CCN(CCC4CCN(c5ccc(N6CCC(=O)NC6=O)cc5)CC4)CC3)cc1CC2]

A mixture of 2-(4-phenoxyphenyl)-7-(piperazin-1-yl)-9,10-dihydro-4H-benzo[d]pyrazolo[1,5-a][1,3]diazepine-3-carboxamide (0.1 g, 0.21 mmol), 2-(1-(4-(2,4-dioxotetrahydropyrimidin-1(2H)-yl)phenyl)piperidin-4-yl)acetaldehyde (99.0 mg, 0.315 mmol) and titanium ethoxide (0.2 mL) in MeOH (5.0 mL) and DCM (15.0 mL) was stirred at room temperature overnight, and then sodium triacetoxyborohydride (89.0 mg, 0.42 mmol) was added and stirred at room temperature for 3 hours. The mixture was treated with water (20 mL), extracted with dichloromethane (3×20 mL), and washed with brine (20 mL). The organic phase was dried over anhydrous sodium sulfate, filtered, concentrated under reduced pressure to afford the crude product, which was purified by prep-HPLC to give the product (9.0 mg, 5.5%). $^1$H NMR (400 MHz, DMSO) δ 10.27 (s, 1H), 9.77 (s, 1H), 8.28 (s, 1H), 7.52 (d, J=8.2 Hz, 2H), 7.43 (t, J=7.5 Hz, 2H), 7.19 (d, J=7.4 Hz, 1H), 7.10 (dd, J=18.1, 8.8 Hz, 6H), 6.92 (d, J=8.1 Hz, 2H), 6.84 (d, J=8.4 Hz, 3H), 4.33 (s, 2H), 3.74-3.62 (m, 5H), 3.11 (d, J=28.4 Hz, 8H), 2.64 (dd, J=19.8, 8.9 Hz, 5H), 2.37 (s, 2H), 1.77 (d, J=12.3 Hz, 2H), 1.45 (s, 3H), 1.26 (d, J=10.1 Hz, 2H); [M+H]$^+$=780.8.

Example A23:6-(1-(2-(1-(4-(2,4-dioxotetrahydropyrimidin-1(2H)-yl)phenyl)piperidin-4-yl)ethyl)piperidin-4-yl)-2-(4-phenoxyphenyl)-9,10-dihydro-4H-benzo[d]pyrazolo[1,5-a] [1,3]diazepine-3-carboxamide

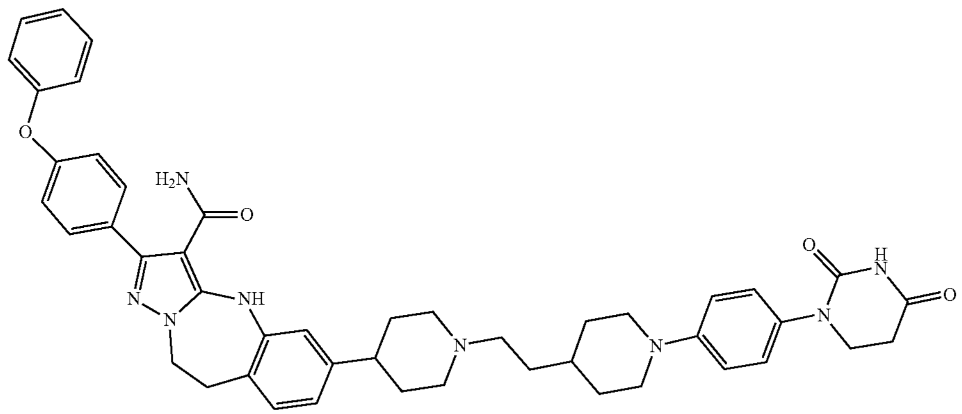 [SMILES: NC(=O)c1c(-c2ccc(Oc3ccccc3)cc2)nn2c1Nc1cc(C3CCN(CCC4CCN(c5ccc(N6CCC(=O)NC6=O)cc5)CC4)CC3)ccc1CC2]

The titled compound was synthesized in the procedures similar to Example A22. $^1$H NMR (400 MHz, DMSO) δ 10.27 (s, 1H), 10.02 (s, 1H), 7.53 (d, J=12.0 Hz, 2H), 7.43 (t, J=8.0 Hz, 2H), 7.25-7.04 (m, 8H), 6.93 (d, J=8.0 Hz, 2H), 6.87-6.80 (m, 2H), 4.38-4.32 (m, 2H), 3.74-3.62 (m, 4H), 3.23-3.11 (m, 4H), 2.71-2.58 (m, 7H), 2.41-2.23 (m, 2H), 1.87-1.68 (m, 6H), 1.52-1.42 (m, 3H), 1.33-1.21 (m, 2H); $[M+H]^+$=779.2.

Example A24: 7-(2-(1-(4-(2,4-dioxotetrahydropyrimidin-1(2H)-yl)phenyl)piperidin-4-yl)ethoxy)-2-(4-phenoxyphenyl)-9,10-dihydro-4H-benzo[d]pyrazolo[1,5-a][1,3]diazepine-3-carboxamide Step 1: 2-(2-bromo-5-methoxyphenyl)ethan-1-ol

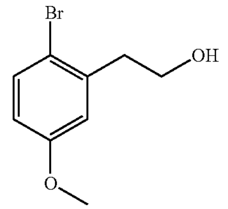

A mixture of 2-(3-methoxyphenyl)ethan-1-ol (15.2 g, 0.1 mol) and NBS (17.8 g, 0.1 mol) in acetonitrile (300.0 mL) was stirred in a round bottom flask at room temperature for 12 hours. The mixture was evaporated in vacuum to afford the crude product, which was purified with silica gel column chromatography (PE:EA=100:0~50:50 gradient elution) to afford the product (23.0 g, 76.7%). $^1$H NMR (400 MHz, DMSO) δ 7.45 (d, J=8.8 Hz, 1H), 6.93 (d, J=2.5 Hz, 1H), 6.75 (dd, J=8.8, 2.8 Hz, 1H), 4.74 (t, J=5.3 Hz, 1H), 3.74 (s, 3H), 3.59 (dd, J=12.6, 7.0 Hz, 2H), 2.81 (t, J=7.1 Hz, 2H); $[M-OH+H]^+$=215.

Step 2: (E)-N-(2-bromo-5-methoxyphenethyl)-4-methyl-N'-(4-phenoxybenzylidene)benzenesulfonohydrazide

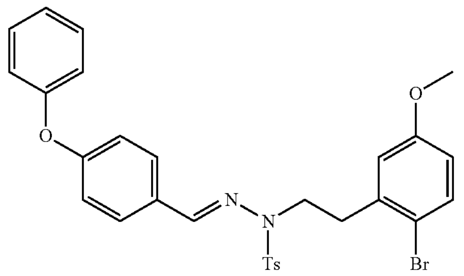 [SMILES: COc1ccc(Br)c(CCN(/N=C/c2ccc(Oc3ccccc3)cc2)S(=O)(=O)c2ccc(C)cc2)c1]

A mixture of (E)-4-methyl-N'-(4-phenoxybenzylidene) benzenesulfonohydrazide (36.6 g, 0.1 mol), 2-(2-bromo-5-methoxyphenyl)ethan-1-ol (23.0 g, 0.1 mol) and triphenylphosphine (39.45 g, 0.15 mol) in dry THE (350.0 mL) was added dropwise diisopropylazodiformate (30.3 g, 0.15 mol) at 0° C. The mixture was stirred in a round bottom flask at room temperature overnight. Then the mixture was treated with water (0.6 L) and extracted with EA (3×300 mL). The organic phase was dried over anhydrous sodium sulfate, filtered and concentrated under reduced pressure to afford the crude product, which was washed with ethanol (1.0 L) and filtered to give the product (45.0 g, 77.8%). $^1$H NMR (400 MHz, DMSO) δ 8.09 (s, 1H), 7.75 (s, 2H), 7.69 (d, J=8.6 Hz, 2H), 7.54-7.37 (m, 5H), 7.21 (t, J=7.4 Hz, 1H), 7.07 (dd, J=12.6, 8.4 Hz, 4H), 6.97 (d, J=2.7 Hz, 1H), 6.80 (dd, J=8.8, 2.7 Hz, 1H), 3.89 (t, J=7.3 Hz, 2H), 3.74 (s, 3H), 2.93 (t, J=7.2 Hz, 2H), 2.37 (s, 3H); $[M+H]^+$=579.3.

Step 3: 5-amino-1-(2-bromo-5-methoxyphenethyl)-3-(4-phenoxyphenyl)-1H-pyrazole-4-carbonitrile

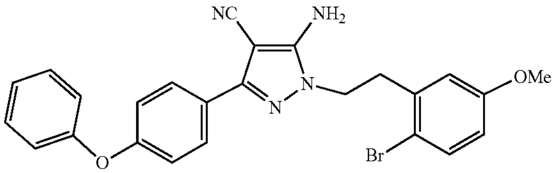 [SMILES: COc1ccc(Br)c(CCn2nc(-c3ccc(Oc4ccccc4)cc3)c(C#N)c2N)c1]

A mixture of (E)-N-(2-bromo-5-methoxyphenethyl)-4-methyl-N'-(4-phenoxybenzylidene)benzenesulfonohydrazide (10.0 g, 17.3 mmol), malononitrile (2.85 g, 43.25 mmol) and aluminum trichloride (5.75 g, 43.25 mmol) in 1,2-dichlorethan (200 mL) was stirred at 85° C. overnight and then treated with water (300 mL), extracted with dichloromethane (3×200 mL), and washed with brine (300 mL). The organic phase was dried over anhydrous sodium sulfate, filtered and concentrated under reduced pressure to afford the crude product, which was purified with silica gel column chromatography (DCM:MeOH=100:0~90:10 gradient elution) to give the product (3.5 g, 45.0%). $[M+H]^+$=489.0.

Step 4: 7-methoxy-2-(4-phenoxyphenyl)-9,10-dihydro-4H-benzo[d]pyrazolo[1,5-a][1,3]diazepine-3-carbonitrile

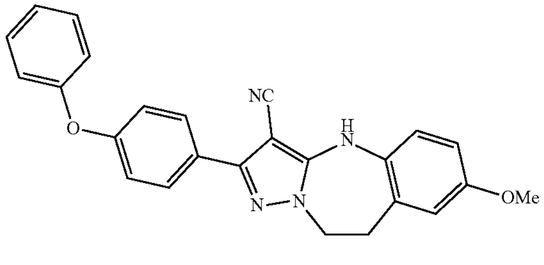 [SMILES: COc1ccc2c(c1)CCn1nc(-c3ccc(Oc4ccccc4)cc3)c(C#N)c1N2]

A mixture of 5-amino-1-(2-bromo-5-methoxyphenethyl)-3-(4-phenoxyphenyl)-1H-pyrazole-4-carbonitrile (3.0 g, 6.15 mmol), tris(dibenzylideneacetone)dipalladium (340.0 mg, 0.37 mmol), BINAP (0.23 g, 0.37 mmol), cesium carbonate (4.0 g, 12.3 mmol) in diglyme (30.0 mL) was stirred at 160° C. for 2 hours under nitrogen. The mixture was concentrated in vacuum to give the crude product, which was purified with silica gel column chromatography (DCM:MeOH=100:0~80:20 gradient elution) to give the product (2.4 g, 96.0%). $^1$H NMR (400 MHz, DMSO) δ 9.42 (s, 1H), 7.83 (d, J=8.6 Hz, 2H), 7.43 (t, J=7.9 Hz, 2H), 7.27-7.17 (m, 2H), 7.13-7.05 (m, 4H), 6.83 (d, J=9.1 Hz, 2H), 4.37 (s, 2H), 3.73 (s, 3H), 3.14 (s, 2H); $[M+H]^+$=409.0.

Step 5: 7-hydroxy-2-(4-phenoxyphenyl)-9,10-dihydro-4H-benzo[d]pyrazolo[1,5-a][1,3]diazepine-3-carboxamide

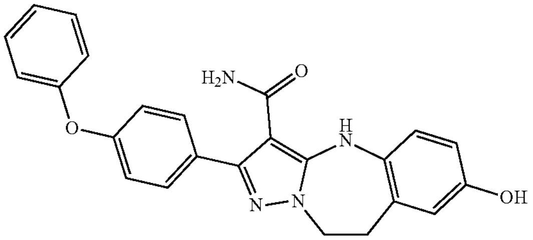 [SMILES: NC(=O)c1c(-c2ccc(Oc3ccccc3)cc2)nn2c1Nc1ccc(O)cc1CC2]

A mixture of 7-methoxy-2-(4-phenoxyphenyl)-9,10-dihydro-4H-benzo[d]pyrazolo[1,5-a][1,3]diazepine-3-carbonitrile (1.0 g, 2.45 mmol) in methanesulfonic acid (15.0 mL) was stirred at 100° C. overnight. The mixture was then cooled and alkalified with aqueous sodium carbonate solution to pH 8 and extracted with dichloromethane (3×20 mL). The organic phase was dried over anhydrous sodium sulfate, filtered and concentrated under reduced pressure to afford the product (0.5 g, 50.0%). $[M+H]^+$=413.3.

Step 6: 7-(2-(1-(4-(2,4-dioxotetrahydropyrimidin-1(2H)-yl)phenyl)piperidin-4-yl)ethoxy)-2-(4-phenoxyphenyl)-9,10-dihydro-4H-benzo[d]pyrazolo[1,5-a][1,3]diazepine-3-carboxamide

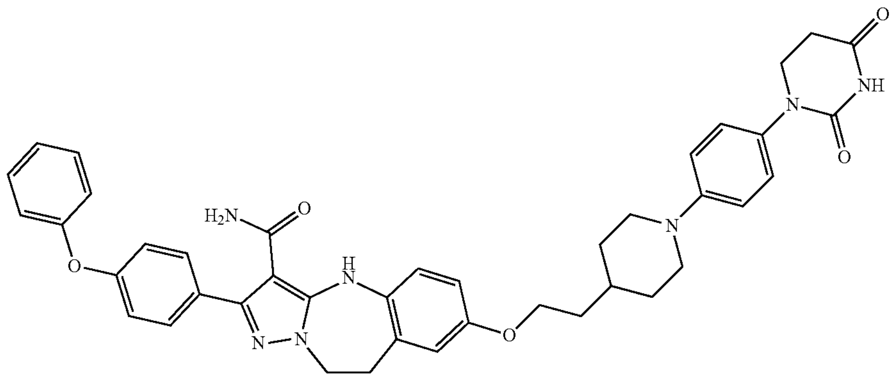 [SMILES: NC(=O)c1c(-c2ccc(Oc3ccccc3)cc2)nn2c1Nc1ccc(OCCC3CCN(c4ccc(N5CCC(=O)NC5=O)cc4)CC3)cc1CC2]

A mixture of 7-hydroxy-2-(4-phenoxyphenyl)-9,10-dihydro-4H-benzo[d]pyrazolo[1,5-a][1,3]diazepine-3-carboxamide (80.0 mg, 0.2 mmol), 2-(1-(4-(2,4-dioxotetrahydropyrimidin-1(2H)-yl)phenyl)piperidin-4-yl)ethyl 4-methylbenzenesulfonate (104.0 mg, 0.22 mmol) and $K_2CO_3$ (55.2 mg, 0.4 mmol) in DMF (8.0 mL) was stirred in a round bottom flask at 50° C. overnight. The mixture was treated with water (20 mL), extracted with dichloromethane (3×20 mL), and washed with brine (30 mL). The organic phase was dried over anhydrous sodium sulfate, filtered and concentrated under reduced pressure to afford the crude product, which was purified by prep-HPLC (DCM: MeOH=7: 1) to give the product (5 mg, 3.5%). $^1H$ NMR (400 MHz, DMSO) δ 8.09 (s, 1H), 7.75 (s, 2H), 7.69 (d, J=8.6 Hz, 2H), 7.54-7.37 (m, 5H), 7.21 (t, J=7.4 Hz, 1H), 7.07 (dd, J=12.6, 8.4 Hz, 4H), 6.97 (d, J=2.7 Hz, 1H), 6.80 (dd, J=8.8, 2.7 Hz, 1H), 3.89 (t, J=7.3 Hz, 2H), 3.74 (s, 3H), 2.93 (t, J=7.2 Hz, 2H), 2.37 (s, 3H); $[M+H]^+$=712.6.

Example A25:6-(2-(1-(4-(2,4-dioxotetrahydropyrimidin-1(2H)-yl)phenyl)piperidin-4-yl)ethoxy)-2-(4-phenoxyphenyl)-9,10-dihydro-4H-benzo[d]pyrazolo[1,5-a][1,3]diazepine-3-carboxamide Step 1: 2-(1-(4-(2,4-dioxotetrahydropyrimidin-1(2H)-yl)phenyl)piperidin-4-yl)ethyl 4-methylbenzenesulfonate

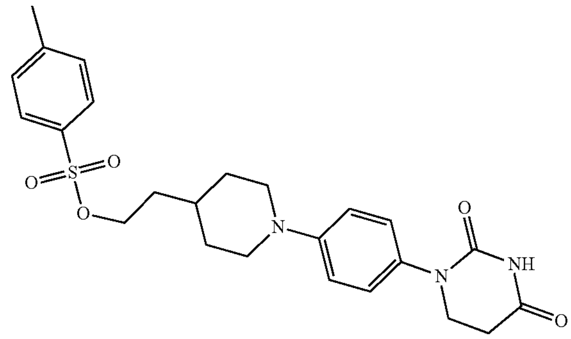 [SMILES: Cc1ccc(S(=O)(=O)OCCC2CCN(c3ccc(N4CCC(=O)NC4=O)cc3)CC2)cc1]

To a solution of 1-(4-(4-(2-hydroxyethyl)piperidin-1-yl)phenyl)dihydropyrimidine-2,4(1H,3H)-dione (300 mg, 0.95 mmol) in pyridine (10 mL) was added 4-methylbenzenesulfonyl chloride (270 mg, 1.42 mmol). The mixture was stirred at rt overnight. The mixture was concentrated under vacuum. The residue was purified by silica gel column chromatography, eluted with EtOAc/PE (0-100%) to afford the desired product (250 mg, 56%). $[M+H]^+$=472.2.

Step 2: 2-(4-phenoxyphenyl)-6-(4,4,5,5-tetramethyl-1,3,2-dioxaborolan-2-yl)-9,10-dihydro-4H-benzo[d]pyrazolo[1,5-a][1,3]diazepine-3-carbonitrile

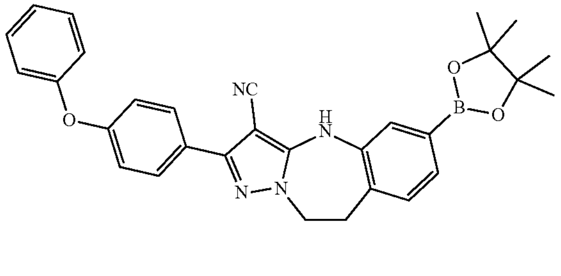 [SMILES: CC1(C)OB(c2ccc3c(c2)Nc2c(C#N)c(-c4ccc(Oc5ccccc5)cc4)nn2CC3)OC1(C)C]

A mixture of 6-bromo-2-(4-phenoxyphenyl)-9,10-dihydro-4H-benzo[d]pyrazolo[1,5-a][1,3]diazepine-3-carbonitrile (2 g, 4.38 mmol), 4,4,4',4',5,5,5',5'-octamethyl-2,2'-bi(1,3,2-dioxaborolane) (2.23 g, 8.77 mmol), Pd(dppf)$Cl_2$ (160 mg, 0.22 mmol) and KOAc (429 mg, 4.38 mmol) in dioxane (15 mL) was stirred at 100° C. overnight under nitrogen atmosphere. The mixture was concentrated under vacuum. The residue was purified by silica gel column chromatography, eluted with EtOAc/PE (1/2) to afford the desired product (1.9 g, 85.6%). $[M+H]^+$=505.2.

Step 3: 6-hydroxy-2-(4-phenoxyphenyl)-9,10-dihydro-4H-benzo[d]pyrazolo[1,5-a][1,3]diazepine-3-carbonitrile

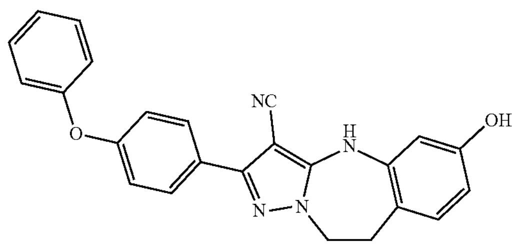 [SMILES: N#Cc1c(-c2ccc(Oc3ccccc3)cc2)nn2c1Nc1cc(O)ccc1CC2]

To a solution of 2-(4-phenoxyphenyl)-6-(4,4,5,5-tetramethyl-1,3,2-dioxaborolan-2-yl)-9,10-dihydro-4H-benzo[d]pyrazolo[1,5-a][1,3]diazepine-3-carbonitrile (1.9 g, 3.77 mmol) in MeOH (15 mL) and $H_2O$ (15 mL) was added $H_2O_2$(20 mL). The mixture was stirred at rt overnight. The mixture was filtered and the solids were collected and dried under vacuum to afford the product (1.3 g, 87.8%). $[M+H]^+$=395.1.

Step 4: 6-hydroxy-2-(4-phenoxyphenyl)-9,10-dihydro-4H-benzo[d]pyrazolo[1,5-a][1,3]diazepine-3-carboxamide

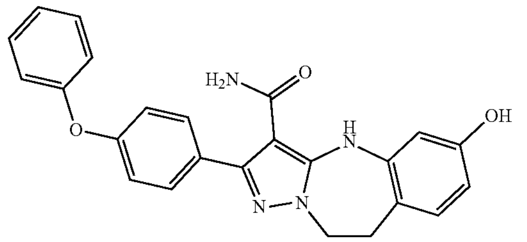 [SMILES: NC(=O)c1c(-c2ccc(Oc3ccccc3)cc2)nn2c1Nc1cc(O)ccc1CC2]

A mixture of 6-hydroxy-2-(4-phenoxyphenyl)-9,10-dihydro-4H-benzo[d]pyrazolo[1,5-a][1,3]diazepine-3-carbonitrile (1.5 g, 3.8 mmol) in MsOH (10 mL) was stirred at 100° C. for 2 h. The mixture was added dropwise to saturated $NaHCO_3$ aqueous solution and extracted with DCM (3×100 mL). The combined organic layers were dried over $Na_2SO_4$, filtered and concentrated under vacuum to afford the desired product (800 mg, crude), which was used in the next step directly. $[M+H]^+$=413.1.

Step 5: 6-(2-(1-(4-(2,4-dioxotetrahydropyrimidin-1(2H)-yl)phenyl)piperidin-4-yl)ethoxy)-2-(4-phenoxyphenyl)-9,10-dihydro-4H-benzo[d]pyrazolo[1,5-a][1,3]diazepine-3-carboxamide

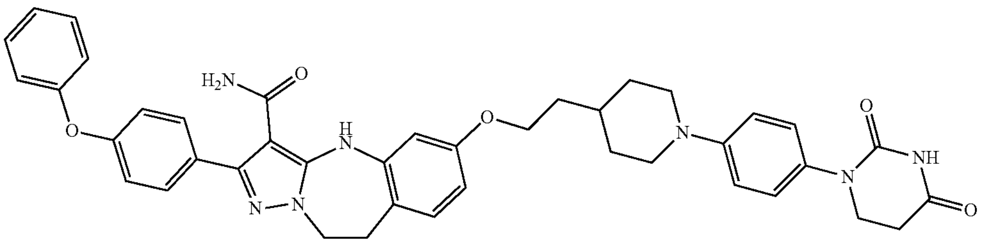 [SMILES: NC(=O)c1c(-c2ccc(Oc3ccccc3)cc2)nn2c1Nc1cc(OCCC3CCN(c4ccc(N5CCC(=O)NC5=O)cc4)CC3)ccc1CC2]

A mixture of 6-hydroxy-2-(4-phenoxyphenyl)-9,10-dihydro-4H-benzo[d]pyrazolo[1,5-a][1,3]diazepine-3-carboxamide (60 mg, 0.15 mmol), 2-(1-(4-(2,4-dioxotetrahydropyrimidin-1(2H)-yl)phenyl)piperidin-4-yl)ethyl 4-methylbenzenesulfonate (82.3 mg, 0.17 mmol) and $K_2CO_3$ (41 mg, 0.29 mmol) in DMF was stirred at 80° C. for 16 h. The mixture was diluted with water (50 mL), extracted with EA (3×50 mL). The combined organic layers were dried over $Na_2SO_4$, filtered and concentrated under vacuum. The residue was purified by Prep-HPLC with the following conditions: Anal. Column: Waters Xselect CSH C18, Column Temp.: Room temperature, Mobile Phase A: ACN, Mobile Phase B: $H_2O$ (0.03% $NH_3 \cdot H_2O$), Gradient Table: Mobile Phase A (45-90%), Time (min):0-17 min to afford the product (13.54 mg, 13%). $^1H$ NMR (400 MHz, DMSO) δ 10.25 (s, 1H), 9.98 (s, 1H), 7.53 (d, J=8.0 Hz, 2H), 7.43 (t, J=8.0 Hz, 2H), 7.23-7.04 (m, 4H), 6.93 (d, J=8.0 Hz, 2H), 6.60-5.51 (m, 2H), 4.40-4.27 (m, 2H), 4.10-4.00 (m, 2H), 3.75-3.63 (m, 4H), 3.18-3.07 (m, 2H), 2.76-2.60 (m, 6H), 1.88-1.61 (m, 6H), 1.40-1.21 (m, 3H); $[M+H]^+$=712.1.

Example A26: 7-(2-(1-(4-((2,6-dioxopiperidin-3-yl)amino)phenyl)piperidin-4-yl)ethyl)-2-(4-phenoxyphenyl)-9,10-dihydro-4H-benzo[d]pyrazolo[1,5-a][1,3] diazepine-3-carboxamide Step 1: 7-bromo-2-(4-phenoxyphenyl)-9,10-dihydro-4H-benzo[d]pyrazolo[1,5-a][1,3]diazepine-3-carboxamide

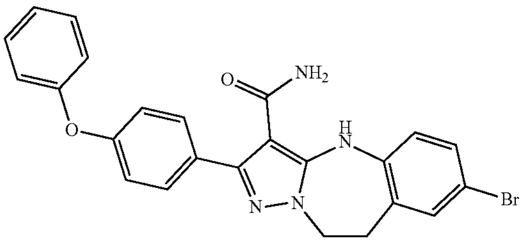 [SMILES: NC(=O)c1c(-c2ccc(Oc3ccccc3)cc2)nn2c1Nc1ccc(Br)cc1CC2]

A mixture of 7-bromo-2-(4-phenoxyphenyl)-9,10-dihydro-4H-benzo[d]pyrazolo[1,5-a][1,3]diazepine-3-carbonitrile (6.0 g, 13.16 mmol), in methanesulfonic acid (50.0 mL) was stirred at 100° C. overnight. The mixture was then cooled, alkalified with aqueous sodium carbonate solution to pH 8 and filtered to afford the product (5.0 g, 80.6%). $[M+H]^+$=475.3.

Step 2: tert-butyl (E)-4-(2-(3-carbamoyl-2-(4-phenoxyphenyl)-9,10-dihydro-4H-benzo[d]pyrazolo[1,5-a][1,3]diazepin-7-yl vinyl)piperidine-1-carboxylate

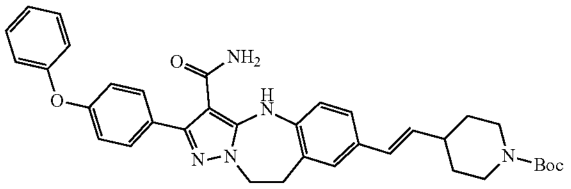 [SMILES: CC(C)(C)OC(=O)N1CCC(/C=C/c2ccc3c(c2)CCn2nc(-c4ccc(Oc5ccccc5)cc4)c(C(N)=O)c2N3)CC1]

A mixture of 7-bromo-2-(4-phenoxyphenyl)-9,10-dihydro-4H-benzo[d]pyrazolo[1,5-a][1,3]diazepine-3-carboxamide (3.5 g, 7.38 mmol), tert-butyl 4-vinylpiperidine-1-carboxylate (2.8 g, 13.17 mmol), $Pd(OAc)_2$ (760.0 mg, 0.738 mmol) and $P(o\text{-}Tol)_3$ (1.5 g, 4.93 mmol) in TEA (30 mL) and MeCN (40 mL) was stirred in a round bottom flask at 100° C. overnight under nitrogen. The mixture was evaporated in vacuum to give the crude product, which was purified with silica gel column chromatography (DCM:MeOH=100:0~90:10 gradient elution) to give the product (1.0 g, 22.4%). $[M+H]^+$=606.0.

Step 3: tert-butyl 4-(2-(3-carbamoyl-2-(4-phenoxyphenyl)-9,10-dihydro-4H-benzo[d]pyrazolo[1,5-a][1,3]diazepin-7-yl)ethyl)piperidine-1-carboxylate

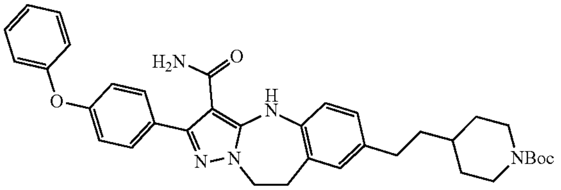 [SMILES: CC(C)(C)OC(=O)N1CCC(CCc2ccc3c(c2)CCn2nc(-c4ccc(Oc5ccccc5)cc4)c(C(N)=O)c2N3)CC1]

A mixture of tert-butyl (E)-4-(2-(3-carbamoyl-2-(4-phenoxyphenyl)-9,10-dihydro-4H-benzo[d]pyrazolo[1,5-a][1,3]diazepin-7-yl)vinyl)piperidine-1-carboxylate (1.0 g, 1.65 mmol) and Pd/C (0.3 g) in methanol (10.0 mL) and THF (10.0 mL) was stirred in a round bottom flask at room temperature overnight under $H_2$. The mixture was filtered and evaporated in vacuum to afford the product (0.5 g); $[M+H]^+$=608.0.

Step 4: 2-(4-phenoxyphenyl)-7-(2-(piperidin-4-yl)ethyl)-9,10-dihydro-4H-benzo[d]pyrazolo[1,5-a][1,3]diazepine-3-carboxamide hydrochloride

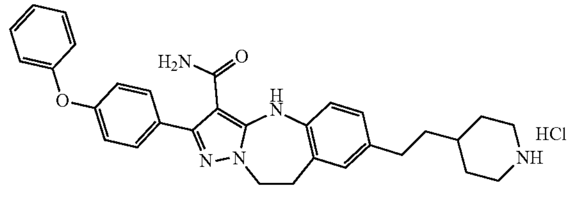 [SMILES: NC(=O)c1c(-c2ccc(Oc3ccccc3)cc2)nn2c1Nc1ccc(CCC3CCNCC3)cc1CC2 ; Cl]

A mixture of tert-butyl 4-(2-(3-carbamoyl-2-(4-phenoxyphenyl)-9,10-dihydro-4H-benzo[d]pyrazolo[1,5-a][1,3]diazepin-7-yl)ethyl)piperidine-1-carboxylate (0.5 g, 0.82 mmol) in HCl/1,4-dioxane (20.0 mL, 6 N) and DCM (5.0 mL) was stirred in a round bottom flask at room temperature for 2 hours. The mixture was filtered to afford the product (0.55 g, 100.0%); $[M+H]^+$=508.0.

Step 5: 7-(2-(1-(4-nitrophenyl)piperidin-4-yl)ethyl)-2-(4-phenoxyphenyl)-9,10-dihydro-4H-benzo[d]pyrazolo[1,5-a][1,3]diazepine-3-carboxamide

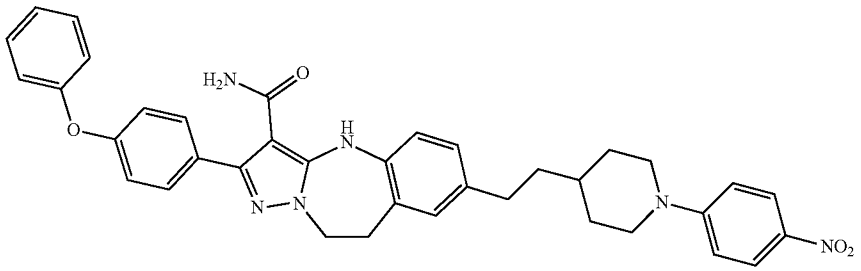 [SMILES: NC(=O)c1c(-c2ccc(Oc3ccccc3)cc2)nn2c1Nc1ccc(CCC3CCN(c4ccc([N+](=O)[O-])cc4)CC3)cc1CC2]

A mixture of 2-(4-phenoxyphenyl)-7-(2-(piperidin-4-yl)ethyl)-9,10-dihydro-4H-benzo[d]pyrazolo[1,5-a][1,3]diazepine-3-carboxamide hydrochloride (550.0 mg, 1.0 mmol), 1-fluoro-4-nitrobenzene (141.0 mg, 1.0 mmol) and DIPEA (645.0 mg, 5.0 mmol) in DMSO (15.0 mL) was stirred in a round bottom flask at 100° C. for 2 hours. The mixture was filtered and the solid was washed with water (50 mL) to afford the product (550.0 mg, 87.4%). $[M+H]^+$=629.0.

Step 6: 7-(2-(1-(4-aminophenyl)piperidin-4-yl)ethyl)-2-(4-phenoxyphenyl)-9,10-dihydro-4H-benzo[d]pyrazolo[1,5-a][1,3]diazepine-3-carboxamide

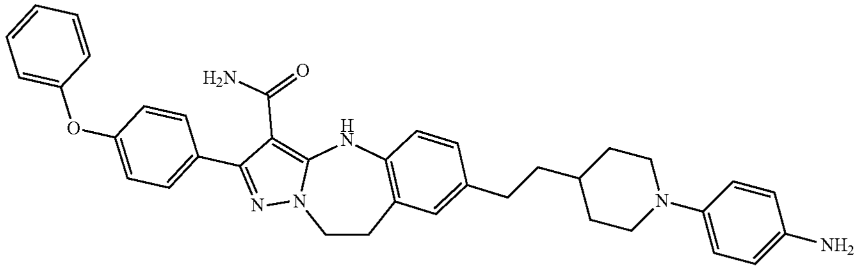

A mixture of 7-(2-(1-(4-nitrophenyl)piperidin-4-yl)ethyl)-2-(4-phenoxyphenyl)-9,10-dihydro-4H-benzo[d]pyrazolo[1,5-a][1,3]diazepine-3-carboxamide (0.5 g, 0.8 mmol) and Pd/C (0.2 g) in methanol (10.0 mL) and THE (20.0 mL) was stirred in a round bottom flask at room temperature overnight under $H_2$. The mixture was filtered and evaporated in vacuum to afford the product (0.45 g, 94.1%); $[M+H]^+$=599.0.

Step 7: 7-(2-(1-(4-((2,6-dioxopiperidin-3-yl)amino)phenyl)piperidin-4-yl)ethyl)-2-(4-phenoxyphenyl)-9,10-dihydro-4H-benzo[d]pyrazolo[1,5-a][1,3]diazepine-3-carboxamide

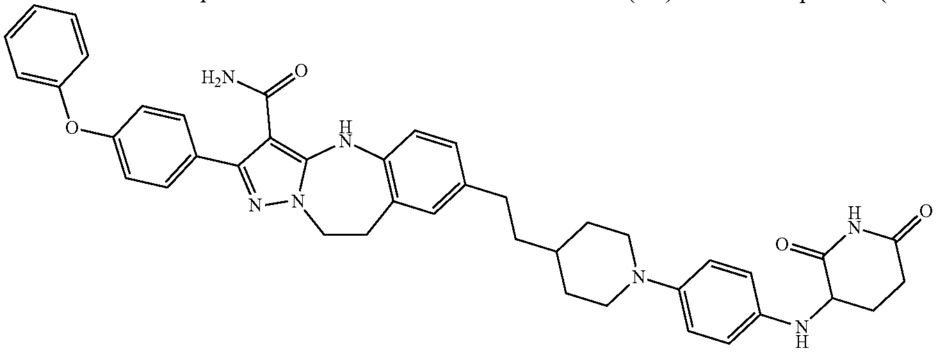

A mixture of 7-(2-(1-(4-aminophenyl)piperidin-4-yl)ethyl)-2-(4-phenoxyphenyl)-9,10-dihydro-4H-benzo[d]pyrazolo[1,5-a][1,3]diazepine-3-carboxamide (0.15 mg, 0.25 mmol), 3-bromopiperidine-2,6-dione (57.6 mg, 0.3 mmol) and DIPEA (64.5 mg, 0.5 mmol) in DMSO (5.0 mL) was stirred in a round bottom flask at 80° C. for 3 hours. The mixture was washed with water (20 mL) and filtered to afford the crude product, which was purified by prep-TLC (DCM:MeOH=7:1) to give the product (16.0 mg, 9.0%); $^1H$ NMR (400 MHz, DMSO) δ 10.70 (s, 1H), 9.89 (s, 1H), 7.46 (d, J=7.7 Hz, 2H), 7.41-7.31 (m, 2H), 7.16-7.09 (m, 1H), 7.09-6.93 (m, 6H), 6.88-6.79 (m, 1H), 6.75-6.62 (m, 2H), 6.58-6.47 (m, 2H), 5.68 (s, 1H), 5.42-5.18 (m, 1H), 4.29 (s, 2H), 4.21-4.02 (m, 1H), 3.11 (s, 3H), 2.78-2.47 (m, 5H), 2.15-1.95 (m, 1H), 1.87-1.63 (m, 3H), 1.54-1.39 (m, 2H), 1.37-1.08 (m, 5H); $[M+H]^+$=710.5.

Example A27: 6-(1-((1-(4-(2,4-dioxotetrahydropyrimidin-1(2H)-yl)phenyl)piperidin-4-yl)methyl)piperidin-4-yl)-2-(4-phenoxyphenyl)-9,10-dihydro-4H-benzo[d]pyrazolo[1,5-a][1,3]diazepine-3-carboxamide Step 1: tert-butyl 4-(3-cyano-2-(4-phenoxyphenyl)-9,10-dihydro-4H-benzo[d]pyrazolo[1,5-a][1,3]diazepin-6-yl)-3,6-dihydropyridine-1(2H)-carboxylate

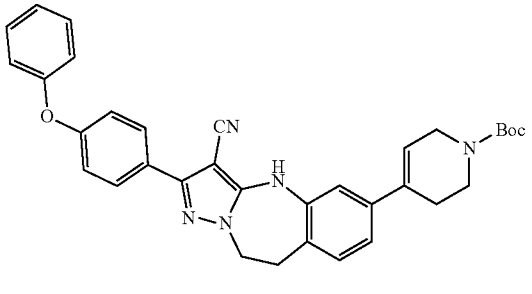 [SMILES: CC(C)(C)OC(=O)N1CC=C(c2ccc3c(c2)Nc2c(C#N)c(-c4ccc(Oc5ccccc5)cc4)nn2CC3)CC1]

A mixture of 6-bromo-2-(4-phenoxyphenyl)-9,10-dihydro-4H-benzo[d]pyrazolo[1,5-a][1,3]diazepine-3-carbonitrile (1 g, 2.19 mmol), tert-butyl 4-(4,4,5,5-tetramethyl-1,3,2-dioxaborolan-2-yl)-3,6-dihydropyridine-1(2H)-carboxylate (813 mg, 2.63 mmol), $Pd(dppf)Cl_2$ (160 mg, 0.22 mmol) and $K_2CO_3$ (908 mg, 6.57 mmol) in DMF (15 mL) and $H_2O$ (3 mL) was stirred at 80° C. overnight under nitrogen atmosphere. The mixture was diluted with water (100 mL) and extracted with DCM (3×100 mL). The combined organic layers were dried over $Na_2SO_4$, filtered and concentrated under vacuum. The residue was purified by silica gel column chromatography, eluted with EtOAc/PE (1:1) to afford the product (910 mg, 74.1%). $[M+H]^+$=560.2.

Step 2: 2-(4-phenoxyphenyl)-6-(1,2,3,6-tetrahydropyridin-4-yl)-9,10-dihydro-4H-benzo[d]pyrazolo[1,5-a][1,3]diazepine-3-carboxamide

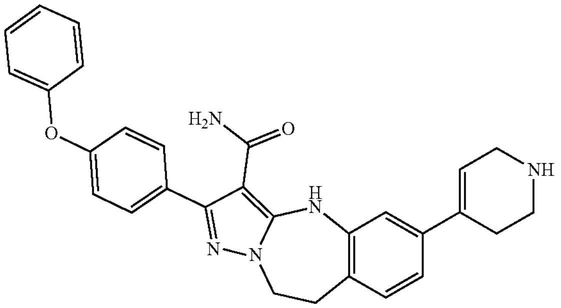 [SMILES: NC(=O)c1c(-c2ccc(Oc3ccccc3)cc2)nn2c1Nc1cc(C3=CCNCC3)ccc1CC2]

A mixture of tert-butyl 4-(3-cyano-2-(4-phenoxyphenyl)-9,10-dihydro-4H-benzo[d]pyrazolo[1,5-a][1,3]diazepin-6-yl)-3,6-dihydropyridine-1(2H)-carboxylate (910 mg, 1.6 mmol) in MsOH (10 mL) was stirred at 100° C. for 2 h. The mixture was added dropwise to saturated $NaHCO_3$ aqueous solution and extracted with DCM (3×100 mL). The combined organic layers were dried over $Na_2SO_4$, filtered and concentrated under vacuum to afford the desired product (650 mg, crude), which was used in the next step directly. $[M+H]^+$=478.2.

-

Step 3: 2-(4-phenoxyphenyl)-6-(piperidin-4-yl)-9,10-dihydro-4H-benzo[d]pyrazolo[1,5-a][1,3]diazepine-3-carboxamide

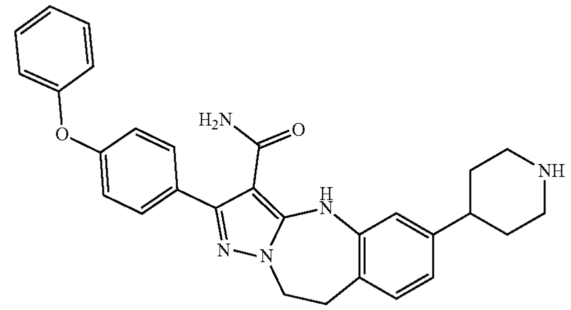 [SMILES: NC(=O)c1c(-c2ccc(Oc3ccccc3)cc2)nn2c1Nc1cc(C3CCNCC3)ccc1CC2]

To a solution of 2-(4-phenoxyphenyl)-6-(1,2,3,6-tetrahydropyridin-4-yl)-9,10-dihydro-4H-benzo[d]pyrazolo[1,5-a][1,3]diazepine-3-carboxamide (650 mg, 1.36 mmol) in EtOH (10 mL) and THE (10 mL) was added Pd/C (200 mg). The mixture was stirred at rt overnight under hydrogen atmosphere. The mixture was filtered and the filtrate was concentrated under vacuum to afford the product (550 mg, 84.2%). $[M+H]^+$=480.2.

Step 4: 6-(1-((1-(4-(2,4-dioxotetrahydropyrimidin-1(2H)-yl)phenyl)piperidin-4-yl)methyl)piperidin-4-yl)-2-(4-phenoxyphenyl)-9,10-dihydro-4H-benzo[d]pyrazolo[1,5-a][1,3]diazepine-3-carboxamide

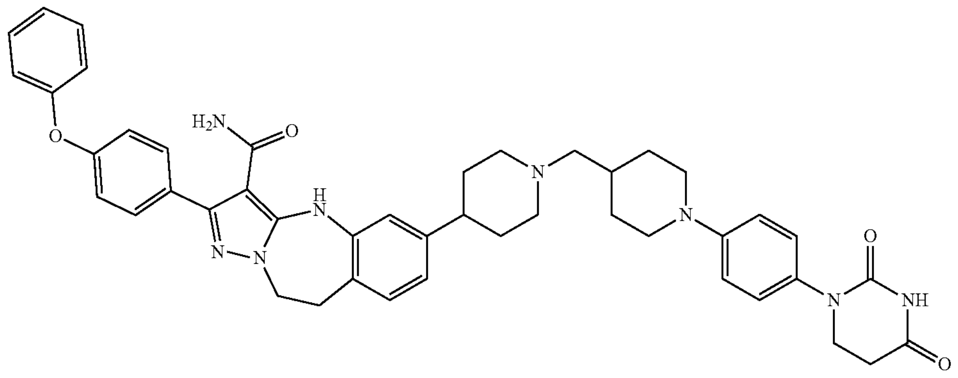 [SMILES: NC(=O)c1c(-c2ccc(Oc3ccccc3)cc2)nn2c1Nc1cc(C3CCN(CC4CCN(c5ccc(N6CCC(=O)NC6=O)cc5)CC4)CC3)ccc1CC2]

A mixture of 2-(4-phenoxyphenyl)-6-(piperidin-4-yl)-9,10-dihydro-4H-benzo[d]pyrazolo[1,5-a][1,3]diazepine-3-carboxamide (80 mg, 0.17 mmol), 1-(4-(2,4-dioxotetrahydropyrimidin-1(2H)-yl)phenyl)piperidine-4-carbaldehyde (75.4 mg, 0.25 mmol) and AcOH (one drop) in MeOH (5 mL) and DCM (5 mL) was stirred at rt for 16 h. Then, STAB (71 mg, 0.34 mmol) was added to the mixture above and stirred at rt for 5 h. The mixture was diluted with water (50 mL) and extracted with DCM (3×100 mL). The combined organic layers were dried over $Na_2SO_4$, filtered and concentrated under vacuum. The residue was purified by Prep-HPLC to afford the product (15.31 mg, 12%). $^1H$ NMR (400 MHz, DMSO) δ 10.26 (s, 1H), 10.00 (s, 1H), 7.53 (d, J=8.0 Hz, 2H), 7.43 (t, J=8.0 Hz, 2H), 7.23-7.04 (m, 8H), 6.92 (d, J=8.0 Hz, 2H), 6.87-6.78 (m, 2H), 4.39-4.29 (m, 2H), 3.73-3.61 (m, 4H), 3.20-3.11 (m, 2H), 3.01-2.89 (m, 3H), 2.72-2.59 (m, 5H), 2.23-2.17 (m, 2H), 2.03-1.91 (m, 2H), 1.87-1.58 (m, 8H), 1.26-1.14 (m, 2H); $[M+H]^+$=765.4.

Example A28 and A29:7-(1-(2-(1-(4-(2,4-dioxotetrahydropyrimidin-1(2H)-yl)phenyl)piperidin-4-yl)ethyl)piperidin-4-yl)-2-(4-phenoxyphenyl)-9,10-dihydro-4H-benzo[d]pyrazolo[1,5-a][1,3]diazepine-3-carboxamide and 2-(4-(4-(tert-butyl)phenoxy)phenyl)-7-(1-(2-(1-(4-(2,4-dioxotetrahydropyrimidin-1(2H)-yl)phenyl)piperidin-4-yl)ethyl)piperidin-4-yl)-9,10-dihydro-4H-benzo[d]pyrazolo[1,5-a][1,3]diazepine-3-carboxamide

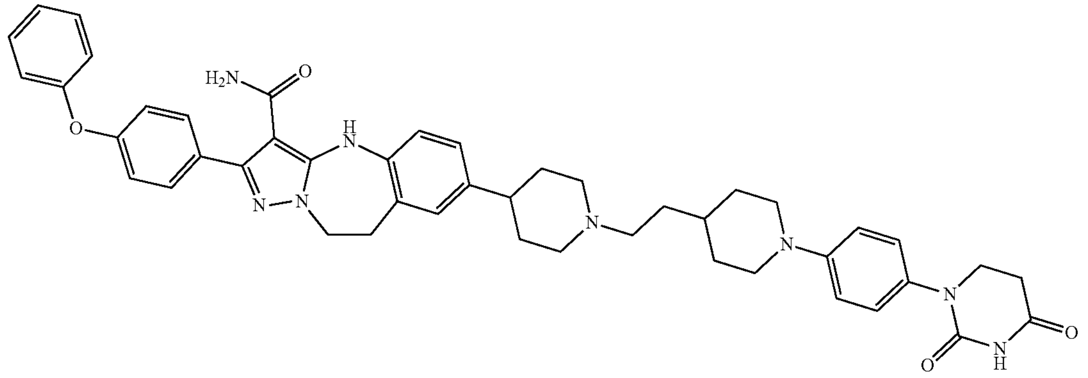

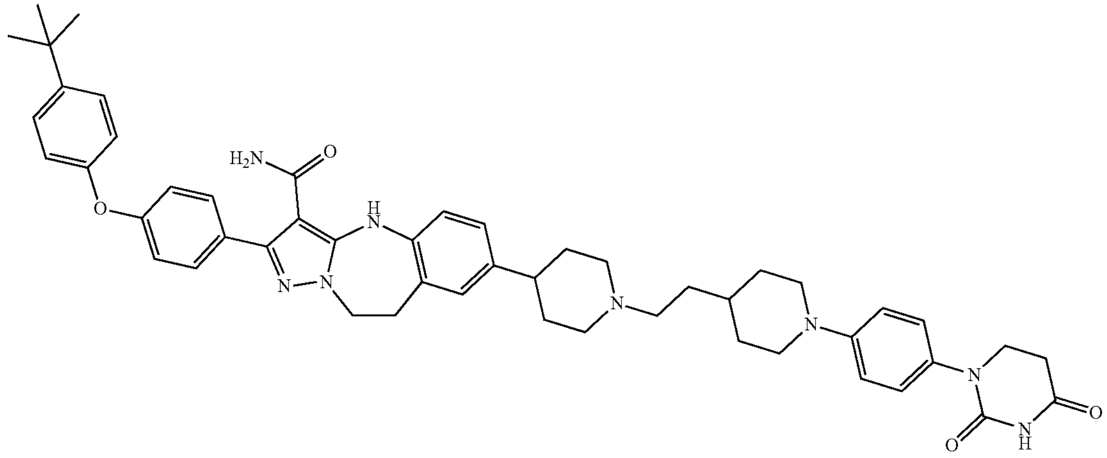

A mixture of 2-(4-phenoxyphenyl)-7-(piperidin-4-yl)-9,10-dihydro-4H-benzo[d]pyrazolo[1,5-a][1,3]diazepine-3-carboxamide and 2-(4-(4-(tert-butyl)phenoxy)phenyl)-7-(piperidin-4-yl)-9,10-dihydro-4H-benzo[d]pyrazolo[1,5-a][1,3]diazepine-3-carboxamide (0.1 g, 2.1 mmol), 2-(1-(4-(2,4-dioxotetrahydropyrimidin-1(2H)-yl)phenyl)piperidin-4-yl)acetaldehyde (79 mg, 0.25 mmol) and titanium ethoxide (0.2 mL) in MeOH (3.0 mL) and DCM (10.0 mL) was stirred at room temperature overnight, and then sodium triacetoxyborohydride (222.6 mg, 1.05 mmol) was added and stirred at room temperature for 2 hours. The mixture was treated with water (20 mL), extracted with dichloromethane (3×20 mL), and washed with brine (20 mL). The organic phase was dried over anhydrous sodium sulfate, filtered and concentrated under reduced pressure to afford the crude product, which was purified by prep-HPLC (Anal. Column: Phenomenex gemini C18, Column Temp.: Room temperature, Mobile Phase A: CAN (0.1% FA), Mobile Phase B: $H_2O$ (0.1% FA), Gradient Table: Mobile Phase A (25-90%), Time (min):0-17 min) to give the two products (5.0 mg and 22 mg). $^1H$ NMR of example A28 (400 MHz, DMSO) δ 10.26 (s, 1H), 9.96 (s, 1H), 8.35 (s, 1H), 7.52 (d, J=8.5 Hz, 2H), 7.43 (t, J=7.9 Hz, 2H), 7.19 (t, J=7.8 Hz, 1H), 7.16-7.05 (m, 8H), 6.98-6.85 (m, 3H), 4.35 (dd, J=6.5, 3.1 Hz, 2H), 3.68 (dd, J=14.6, 7.9 Hz, 4H), 3.20-3.14 (m, 2H), 2.98 (d, J=9.9 Hz, 2H), 2.65 (dd, J=24.3, 9.0 Hz, 5H), 2.39-2.29 (m, 3H), 1.95 (t, J=10.6 Hz, 2H), 1.74 (t, J=13.7 Hz, 4H), 1.68-1.59 (m, 2H), 1.49-1.37 (m, 3H), 1.31-1.20 (m, 2H); $[M+H]^+$=779.6. $^1H$ NMR of example A29 (400 MHz, DMSO) δ 10.27 (s, 1H), 9.97 (s, 1H), 8.30 (s, 1H), 7.51 (d, J=8.5 Hz, 2H), 7.44 (d, J=8.5 Hz, 2H), 7.16-7.00 (m, 8H), 6.91 (dd, J=14.0, 8.7 Hz, 3H), 4.35 (d, J=4.9 Hz, 2H), 3.68 (dd, J=14.3, 8.1 Hz, 4H), 3.17 (d, J=8.6 Hz, 2H), 2.98 (d, J=7.2 Hz, 2H), 2.72-2.59 (m, 5H), 2.41-2.30 (m, 3H), 1.96 (t, J=13.4 Hz, 2H), 1.75 (t, J=13.3 Hz, 3H), 1.68-1.56 (m, 2H), 1.50-1.39 (m, 3H), 1.29 (s, 9H), 1.24 (t, J=9.3 Hz, 2H); $[M+H]^+$=835.7.

Example A30 and A31:7-(1-((1-(4-(2,4-dioxotetrahydropyrimidin-1(2H)-yl)phenyl)piperidin-4-yl)methyl)piperidin-4-yl)-2-(4-phenoxyphenyl)-9,10-dihydro-4H-benzo[d]pyrazolo[1,5-a][1,3]diazepine-3-carboxamide and 2-(4-(4-(tert-butyl)phenoxy)phenyl)-7-(1-((1-(4-(2,4-dioxotetrahydropyrimidin-1(2H)-yl)phenyl)piperidin-4-yl)methyl)piperidin-4-yl)-9,10-dihydro-4H-benzo[d]pyrazolo[1,5-a][1,3]diazepine-3-carboxamide Step 1: tert-butyl 4-(3-cyano-2-(4-phenoxyphenyl)-9,10-dihydro-4H-benzo[d]pyrazolo[1,5-a][1,3]diazepin-7-yl)-3,6-dihydropyridine-1(2H)-carboxylate

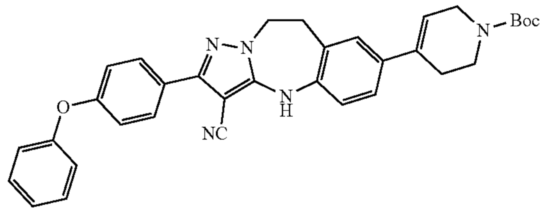 [SMILES: CC(C)(C)OC(=O)N1CC=C(c2ccc3c(c2)CCn2nc(-c4ccc(Oc5ccccc5)cc4)c(C#N)c2N3)CC1]

A mixture of 7-bromo-2-(4-phenoxyphenyl)-9,10-dihydro-4H-benzo[d]pyrazolo[1,5-a][1,3]diazepine-3-carbonitrile (2.0 g, 4.4 mmol), tert-butyl 4-(4,4,5,5-tetramethyl-1,3,2-dioxaborolan-2-yl)-3,6-dihydropyridine-1(2H)-carboxylate (1.63 g, 5.28 mmol), Pd(dppf)$Cl_2$ (322.0 mg, 0.44 mmol) and $K_2CO_3$ (1.82 g, 13.2 mmol) in DMF (30.0 mL) was stirred in a round bottom flask at 80° C. overnight under nitrogen. The mixture was evaporated in vacuum to give the crude product, which was purified with silica gel column chromatography (DCM: MeOH=100:0~90:10 gradient elution) to give the product (2.6 g, 100.0%). $[M+H]^+$=560.0.

Step 2: 2-(4-phenoxyphenyl)-7-(1,2,3,6-tetrahydropyridin-4-yl)-9,10-dihydro-4H-benzo[d]pyrazolo[1,5-a][1,3]diazepine-3-carboxamide and 2-(4-(4-(tert-butyl)phenoxy)phenyl)-7-(1,2,3,6-tetrahydropyridin-4-yl)-9,10-dihydro-4H-benzo[d]pyrazolo[1,5-a][1,3]diazepine-3-carboxamide

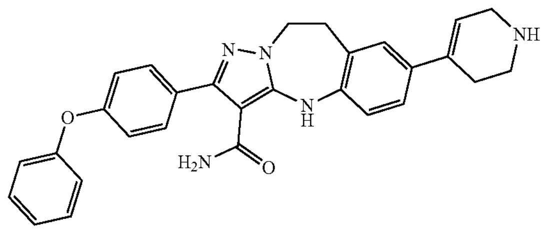

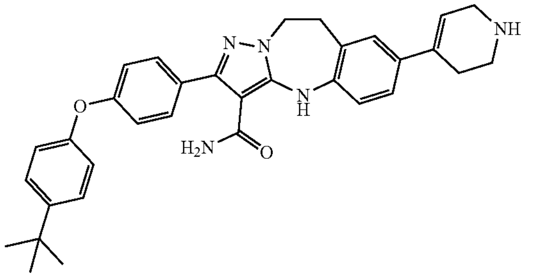

A mixture of tert-butyl 4-(3-cyano-2-(4-phenoxyphenyl)-9,10-dihydro-4H-benzo[d]pyrazolo[1,5-a][1,3]diazepin-7-yl)-3,6-dihydropyridine-1(2H)-carboxylate (2.5 g, 44.7 mmol) in methanesulfonic acid (25.0 mL) was stirred at 50° C. overnight. The mixture was then cooled and alkalified with aqueous sodium carbonate solution to pH 8 and filtered to afford the crude product, which was purified with silica gel column chromatography (DCM:MeOH=100:0~90:10 gradient elution) to give the two products (1.0 g). $[M+H]^+$=478.5/534.5.

Step 3: 2-(4-phenoxyphenyl)-7-(piperidin-4-yl)-9,10-dihydro-4H-benzo[d]pyrazolo[1,5-a][1,3]diazepine-3-carboxamide and 2-(4-(4-(tert-butyl)phenoxy)phenyl)-7-(piperidin-4-yl)-9,10-dihydro-4H-benzo[d]pyrazolo[1,5-a][1,3]diazepine-3-carboxamide

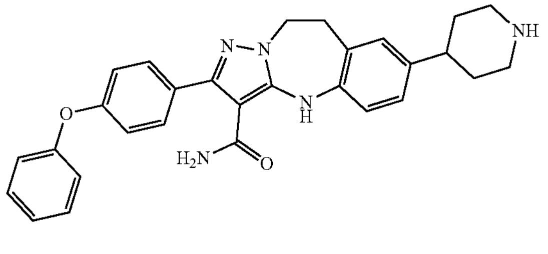

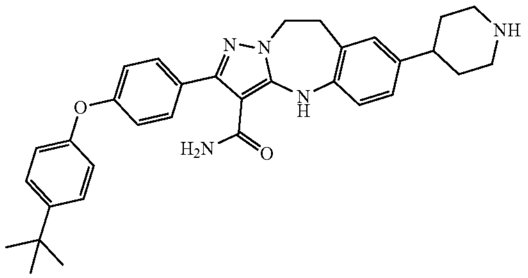

A mixture of 2-(4-phenoxyphenyl)-7-(1,2,3,6-tetrahydropyridin-4-yl)-9,10-dihydro-4H-benzo[d]pyrazolo[1,5-a][1,3]diazepine-3-carboxamide and 2-(4-(4-(tert-butyl)phenoxy)phenyl)-7-(1,2,3,6-tetrahydropyridin-4-yl)-9,10-dihydro-4H-benzo[d]pyrazolo[1,5-a][1,3]diazepine-3-carboxamide (1.0 g) and Pd/C (0.5 g) in methanol (5.0 mL) and THF (15.0 mL) was stirred in a round bottom flask at room temperature overnight under $H_2$. The mixture was filtered and evaporated in vacuum to afford the two products (0.4 g); $[M+H]^+$=480.4/536.4.

Step 4: 7-(1-((1-(4-(2,4-dioxotetrahydropyrimidin-1(2H)-yl)phenyl)piperidin-4-yl)methyl)piperidin-4-yl)-2-(4-phenoxyphenyl)-9,10-dihydro-4H-benzo[d]pyrazolo[1,5-a][1,3]diazepine-3-carboxamide and 2-(4-(4-(tert-butyl)phenoxy)phenyl)-7-(1-((1-(4-(2,4-dioxotetrahydropyrimidin-1(2H)-yl)phenyl)piperidin-4-yl)methyl)piperidin-4-yl)-9,10-dihydro-4H-benzo[d]pyrazolo[1,5-a][1,3]diazepine-3-carboxamide

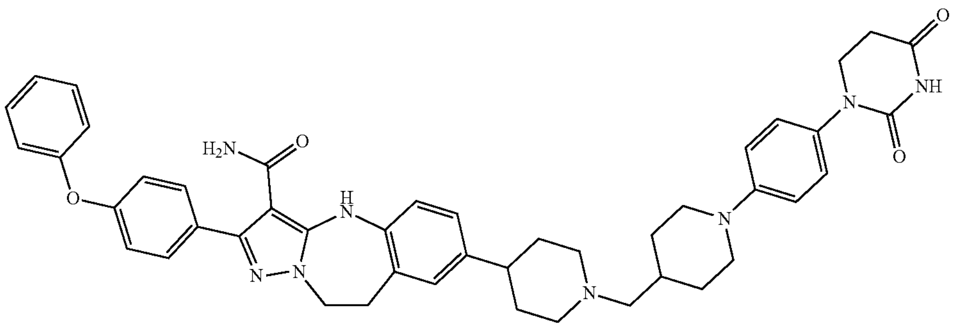

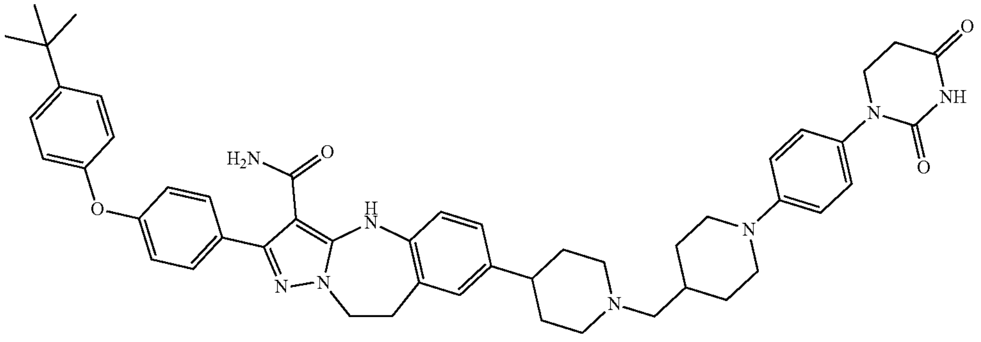

A mixture of 2-(4-phenoxyphenyl)-7-(piperidin-4-yl)-9,10-dihydro-4H-benzo[d]pyrazolo[1,5-a][1,3]diazepine-3-carboxamide and 2-(4-(4-(tert-butyl)phenoxy)phenyl)-7-(piperidin-4-yl)-9,10-dihydro-4H-benzo[d]pyrazolo[1,5-a][1,3]diazepine-3-carboxamide (0.1 g, 2.1 mmol), 1-(4-(2,4-dioxotetrahydropyrimidin-1(2H)-yl)phenyl)piperidine-4-carbaldehyde (75 mg, 0.25 mmol) and titanium ethoxide (0.2 mL) in MeOH (3.0 mL) and DCM (10.0 mL) was stirred at room temperature overnight, and then sodium triacetoxyborohydride (222.6 mg, 1.05 mmol) was added and stirred at room temperature for 2 hours. The mixture was treated with water (20 mL), extracted with dichloromethane (3×20 mL), and washed with brine (20 mL). The organic phase was dried over anhydrous sodium sulfate, filtered and concentrated under reduced pressure to afford the crude product, which was purified by prep-HPLC (Anal. Column: Phenomenex gemini C18, Column Temp.: Room temperature, Mobile Phase A: ACN(0.1% FA), Mobile Phase B: $H_2O$ (0.1% FA), Gradient Table: Mobile Phase A (25-90%), Time (min):0-17 min) to give the two products (6.0 mg and 15 mg). $^1H$ NMR of example 30 (400 MHz, DMSO) δ 10.27 (s, 1H), 9.97 (s, 1H), 7.53 (d, J=8.4 Hz, 2H), 7.43 (s, 2H), 7.21-7.16 (m, 1H), 7.14-7.07 (m, 8H), 6.95-6.88 (m, 3H), 4.36 (s, 2H), 3.72-3.64 (m, 4H), 3.18 (s, 2H), 2.95 (d, J=9.5 Hz, 2H), 2.68 (t, J=6.7 Hz, 4H), 2.43 (s, 1H), 2.19 (d, J=6.7 Hz, 2H), 1.97 (t, J=10.7 Hz, 2H), 1.80 (d, J=12.6 Hz, 2H), 1.67 (dd, J=24.7, 11.8 Hz, 5H), 1.21 (d, J=11.9 Hz, 2H); $[M+H]^+$=765.6. $^1H$ NMR of example 31 (400 MHz, DMSO) δ 10.27 (s, 1H), 9.97 (s, 1H), 7.51 (d, J=8.5 Hz, 2H), 7.44 (d, J=8.6 Hz, 2H), 7.14-7.02 (m, 8H), 6.91 (dd, J=14.7, 8.5 Hz, 3H), 4.36 (s, 2H), 3.72-3.64 (m, 4H), 3.18 (s, 2H), 2.95 (d, J=9.5 Hz, 2H), 2.68 (t, J=6.7 Hz, 4H), 2.43 (s, 1H), 2.19 (d, J=6.7 Hz, 2H), 1.97 (t, J=10.7 Hz, 2H), 1.80 (d, J=12.6 Hz, 2H), 1.67 (dd, J=24.7, 11.8 Hz, 5H), 1.29 (s, 9H), 1.21 (d, J=11.9 Hz, 2H); $[M+H]^+$=821.7.

Example A32: 6-(1-(3-(4-((2,6-dioxopiperidin-3-yl) amino)phenoxy)propyl)piperidin-4-yl)-2-(4-phenoxyphenyl)-9,10-dihydro-4H-benzo[d]pyrazolo[1,5-a] [1,3]diazepine-3-carboxamide

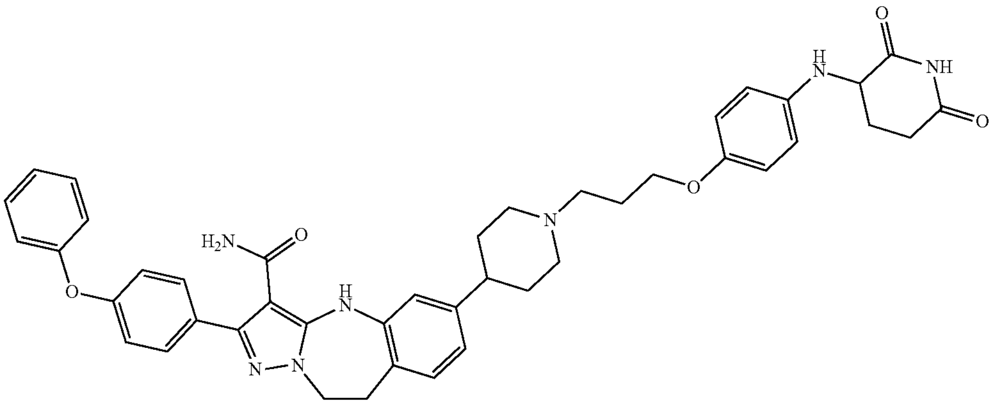 [SMILES: NC(=O)c1c(-c2ccc(Oc3ccccc3)cc2)nn2c1Nc1cc(C3CCN(CCCOc4ccc(NC5CCC(=O)NC5=O)cc4)CC3)ccc1CC2]

A mixture of 2-(4-phenoxyphenyl)-6-(piperidin-4-yl)-9,10-dihydro-4H-benzo[d]pyrazolo[1,5-a][1,3]diazepine-3-carboxamide (134.5 mg, 0.28 mmol), 3-(4-((2,6-dioxopiperidin-3-yl)amino)phenoxy)propyl methanesulfonate (120 mg, 0.34 mmol) and DIEA (181 mg, 1.4 mmol) in DMSO (5 mL) was stirred at 80° C. overnight. The mixture was diluted with water (100 mL) and extracted with EA (3×100 mL). The combined organic layers were dried over $Na_2SO_4$, filtered and concentrated under vacuum. The residue was purified by silica gel column chromatography, eluted with MeOH/DCM (1:8) to afford the product (52.5 mg, 25.2%). $^1$H NMR (400 MHz, DMSO) δ 10.76 (s, 1H), 10.00 (s, 1H), 7.53 (d, J=8.0 Hz, 2H), 7.43 (t, J=12.0 Hz, 2H), 7.26-7.02 (m, 7H), 6.88-6.77 (m, 3H), 6.76-6.69 (m, 2H), 6.68-6.59 (m, 2H), 5.48-5.37 (m, 1H), 4.40-4.31 (m, 2H), 4.26-4.15 (m, 2H), 3.96-3.82 (m, 1H), 3.20-3.12 (m, 2H), 3.06-2.85 (m, 4H), 2.77-2.65 (m, 2H), 2.16-1.60 (m, 11H); $[M+H]^+$ =740.3.

Example A33:6-(1-(4-(2,4-dioxotetrahydropyrimidin-1(2H)-yl)phenethyl)piperidin-4-yl)-2-(4-phenoxyphenyl)-9,10-dihydro-4H-benzo[d]pyrazolo[1,5-a][1,3]diazepine-3-carboxamide Step 1: 2-(4-(2,4-dioxotetrahydropyrimidin-1(2H)-yl)phenyl)acetaldehyde

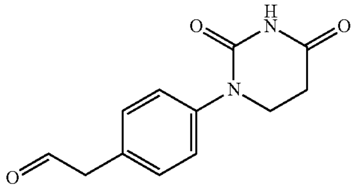 [SMILES: O=CCc1ccc(N2CCC(=O)NC2=O)cc1]

1-(4-(2-hydroxyethyl)phenyl)dihydropyrimidine-2,4(1H,3H)-dione (50 mg, 0.21 mmol, the procedure was similar to example A21 step 1-7) was placed in toluene/DMSO (3 mL, 1:1). IBX (120 mg, 0.42 mmol) was added to the solution in one portion at room temperature. The mixture was stirred at room temperature for 16 h until TLC indicated all the starting material was consumed. The resulting mixture was diluted with water and extracted with EtOAc for 3 times. The combined organic layer was washed with water and brine, dried over $Na_2SO_4$ and concentrated to provide crude product (47 mg, crude) which was used directly without further purification.

Step 2: 6-(1-(4-(2,4-dioxotetrahydropyrimidin-1(2H)-yl)phenethyl)piperidin-4-yl)-2-(4-phenoxyphenyl)-9,10-dihydro-4H-benzo[d]pyrazolo[1,5-a][1,3]diazepine-3-carboxamide

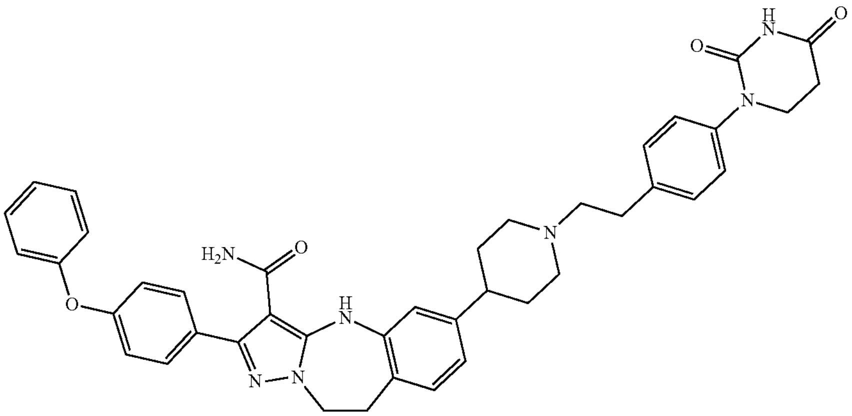 [SMILES: NC(=O)c1c(-c2ccc(Oc3ccccc3)cc2)nn2c1Nc1cc(C3CCN(CCc4ccc(N5CCC(=O)NC5=O)cc4)CC3)ccc1CC2]

The fresh prepared 2-(4-(2,4-dioxotetrahydropyrimidin-1(2H)-yl)phenyl)acetaldehyde (47 mg, 0.21 mmol), 2-(4-phenoxyphenyl)-6-(piperidin-4-yl)-9,10-dihydro-4H-benzo[d]pyrazolo[1,5-a][1,3]diazepine-3-carboxamide (47.9 mg, 0.1 mmol) and 0.02 mL AcOH were placed in DCM/MeOH (5 mL, 9:1). The mixture was stirred at room temperature for 1 h, and $NaBH(OAc)_3$ (212 mg, 1.0 mmol) was added to the mixture in one portion. The resulting mixture was stirred at room temperature for another 1 h until LC-MS indicated all the starting material was consumed. The mixture was concentrated and purified with $SiO_2$-gel column (eluted with DCM/MeOH=10:1) to provide desired product (11 mg, 15.8%). $^1$H NMR (400 MHz, DMSO) δ 10.35 (s, 1H), 10.01 (s, 1H), 7.51 (d, J=8.0 Hz, 2H), 7.43-7.41 (m, 4H), 7.32-7.24 (m, 2H), 7.17-7.07 (m, 4H), 6.86-6.83 (m, 2H), 4.37-4.34 (m, 2H), 3.76-3.75 (m, 2H), 3.32-3.30 (m, 2H), 3.16-3.10 (m, 4H), 2.75-2.70 (m, 2H), 2.65-2.63 (m, 2H), 2.50-2.49 (m, 1H), 2.33-2.25 (m, 2H), 1.83-1.79 (m, 2H), 1.78-1.68 (m, 2H); $[M+H]^+$=696.5.

Example A34: 6-(1-(4-(2,6-dioxopiperidin-3-yl)phenethyl)piperidin-4-yl)-2-(4-phenoxyphenyl)-9,10-dihydro-4H-benzo[d]pyrazolo[1,5-a][1,3]diazepine-3-carboxamide

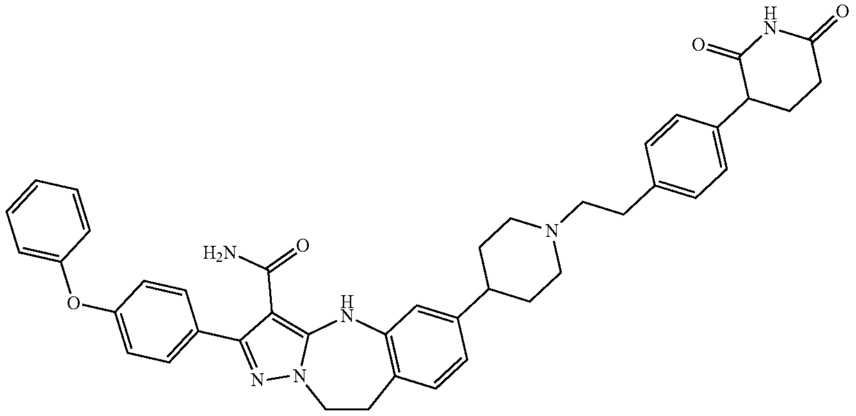 [SMILES: NC(=O)c1c(-c2ccc(Oc3ccccc3)cc2)nn2c1Nc1cc(C3CCN(CCc4ccc(C5CCC(=O)NC5=O)cc4)CC3)ccc1CC2]

The titled compound was synthesized in the procedures similar to Example A33. $^1$H NMR (400 MHz, DMSO) δ 10.83 (s, 1H), 10.00 (s, 1H), 7.53 (d, J=8.0 Hz, 2H), 7.43 (t, J=12.0 Hz, 2H), 7.40-7.01 (m, 10H), 6.89-6.78 (m, 2H), 4.41-4.29 (m, 2H), 3.87-3.76 (m, 1H), 3.20-3.11 (m, 2H), 3.10-3.00 (m, 2H), 2.84-2.56 (m, 5H), 2.25-1.97 (m, 5H), 1.85-1.55 (m, 5H); $[M+H]^+$=695.3.

Example A35: 6-(1-((1-(4-((2,6-dioxopiperidin-3-yl)amino)phenyl)piperidin-4-yl)methyl)piperidin-4-yl)-2-(4-phenoxyphenyl)-9,10-dihydro-4H-benzo[d]pyrazolo[1,5-a][1,3]diazepine-3-carboxamide Step 1: (1-(4-nitrophenyl)piperidin-4-yl)methanol

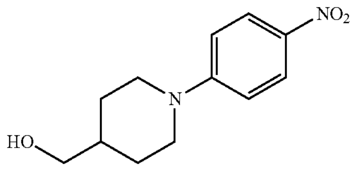 [SMILES: O=[N+]([O-])c1ccc(N2CCC(CO)CC2)cc1]

A mixture of 1-fluoro-4-nitrobenzene (5 g, 35.5 mmol), piperidin-4-ylmethanol (4.89 g, 42.5 mmol) and DIEA (9.15 g, 70.9 mmol) in DMSO (30 mL) was stirred at 100° C. for 2 h. The mixture was poured into water (200 mL), and yellow solids were precipitated, washed with water and dried under vacuum to afford the product (10 g, crude), which was used in the next step directly. $[M+H]^+$=237.1.

Step 2: 1-(4-nitrophenyl)piperidine-4-carbaldehyde

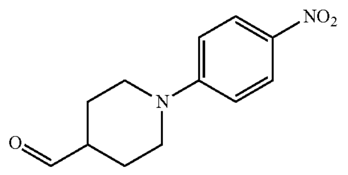 [SMILES: O=CC1CCN(c2ccc([N+](=O)[O-])cc2)CC1]

A mixture of (1-(4-nitrophenyl)piperidin-4-yl)methanol (500 mg, 2.12 mmol) and IBX (1.18 g, 4.23 mmol) in DMSO (10 mL) was stirred at rt for 16 h. The mixture was diluted with water (100 mL), extracted with EA (3×100 mL). The combined organic layers were dried over $Na_2SO_4$, filtered and concentrated under vacuum. The residue was purified by silica gel column chromatography, eluted with EtOAc/PE (1/1) to afford the desired product (300 mg, 60.5%). $[M+H]^+$=235.1.

Step 3: 6-(1-((1-(4-nitrophenyl)piperidin-4-yl)methyl)piperidin-4-yl)-2-(4-phenoxyphenyl)-9,10-dihydro-4H-benzo[d]pyrazolo[1,5-a][1,3]diazepine-3-carboxamide

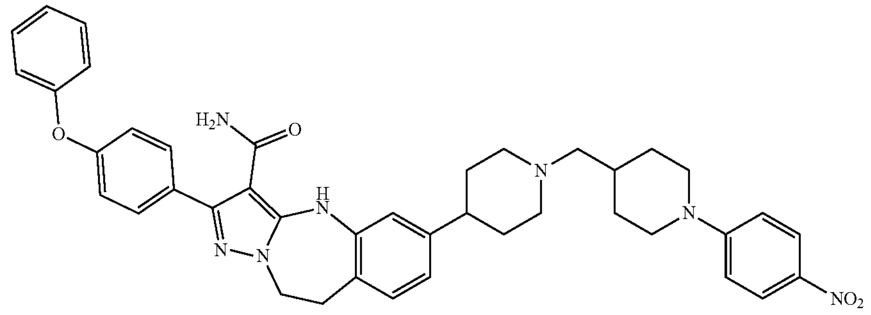 [SMILES: NC(=O)c1c(-c2ccc(Oc3ccccc3)cc2)nn2c1Nc1cc(C3CCN(CC4CCN(c5ccc([N+](=O)[O-])cc5)CC4)CC3)ccc1CC2]

A mixture of 2-(4-phenoxyphenyl)-6-(piperidin-4-yl)-9,10-dihydro-4H-benzo[d]pyrazolo[1,5-a][1,3]diazepine-3-carboxamide (100 mg, 0.21 mmol), 1-(4-nitrophenyl)piperidine-4-carbaldehyde (58.6 mg, 0.25 mmol) and AcOH (0.02 mL) in MeOH (5 mL) and DCM (5 mL) was stirred at rt for 16 h. Then, sodium triacetoxyborohydride (88.5 mg, 0.42 mmol) was added to the mixture above and the mixture was stirred at rt for 5 h. The mixture was quenched by water (50 mL), extracted with DCM (3×100 mL). The combined organic layers were dried over $Na_2SO_4$, filtered and concentrated under vacuum. The residue was purified by silica gel column chromatography, eluted with MeOH/DCM (1/11) to afford the desired product (85 mg, 57.3%). $[M+H]^+$=698.3.

Step 4: 6-(1-((1-(4-aminophenyl)piperidin-4-yl)methyl)piperidin-4-yl)-2-(4-phenoxyphenyl)-9,10-dihydro-4H-benzo[d]pyrazolo[1,5-a][1,3]diazepine-3-carboxamide

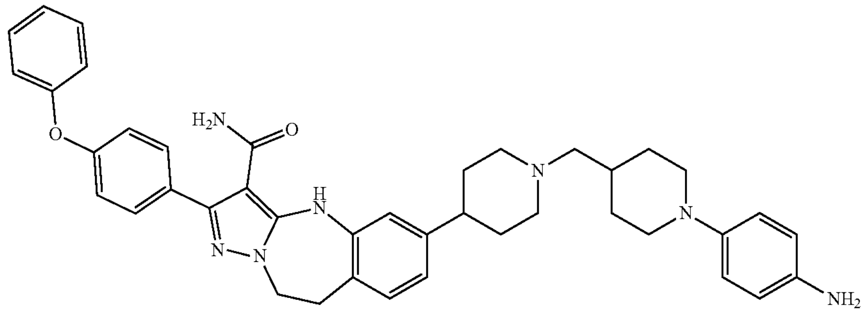

To a solution of 6-(1-((1-(4-nitrophenyl)piperidin-4-yl)methyl)piperidin-4-yl)-2-(4-phenoxyphenyl)-9,10-dihydro-4H-benzo[d]pyrazolo[1,5-a][1,3]diazepine-3-carboxamide (85 mg, 0.12 mmol) in MeOH (5 mL) and THE (5 mL) was added Pd/C (40 mg). The mixture was stirred at rt overnight under hydrogen atmosphere. The mixture was filtered and the filtrate was concentrated under vacuum to afford the product (75 mg, 92.2%), which was used in the next step directly. $[M+H]^+$=668.3.

Step 4: 6-(1-((1-(4-((2,6-dioxopiperidin-3-yl)amino)phenyl)piperidin-4-yl)methyl)piperidin-4-yl)-2-(4-phenoxyphenyl)-9,10-dihydro-4H-benzo[d]pyrazolo[1,5-a][1,3]diazepine-3-carboxamide

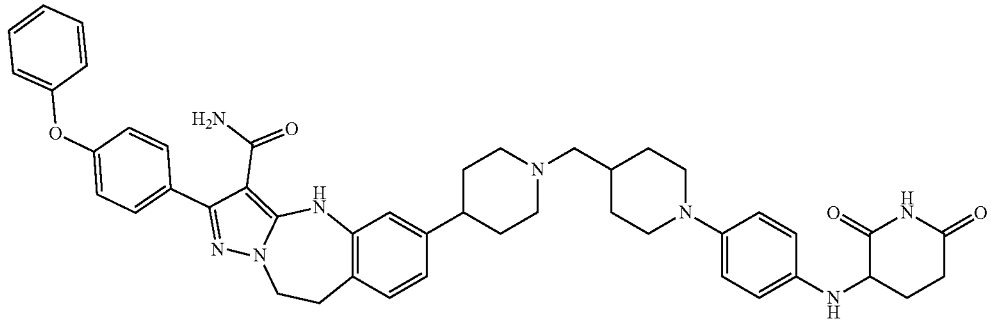 [SMILES: NC(=O)c1c(-c2ccc(Oc3ccccc3)cc2)nn2c1Nc1cc(C3CCN(CC4CCN(c5ccc(NC6CCC(=O)NC6=O)cc5)CC4)CC3)ccc1CC2]

A mixture of 6-(1-((1-(4-aminophenyl)piperidin-4-yl)methyl)piperidin-4-yl)-2-(4-phenoxyphenyl)-9,10-dihydro-4H-benzo[d]pyrazolo[1,5-a][1,3]diazepine-3-carboxamide (65 mg, 0.09 mmol), 3-bromopiperidine-2,6-dione (18.6 mg, 0.09 mmol) and DIEA (25.1 mg, 0.19 mmol) in DMSO (3 mL) was stirred at 80° C. for 4 h. The mixture was diluted with water (50 mL) and extracted with EA (3×100 mL). The combined organic layers were dried over $Na_2SO_4$, filtered and concentrated under vacuum. The residue was purified by Prep-HPLC with the following conditions: Anal. Column: Phenomenex gemini C18, Column Temp.: Room temperature, Mobile Phase A: ACN, Mobile Phase B: $H_2O$ (0.1% FA), Gradient Table: Mobile Phase A (20-90%), Time (min): 0-17 min to afford the product (4.84 mg, 6.4%). $^1H$ NMR (400 MHz, DMSO) δ 10.76 (s, 1H), 10.03 (s, 1H), 7.53 (d, J=8.0 Hz, 2H), 7.43 (t, J=8.0 Hz, 2H), 7.26-7.04 (m, 7H), 6.90-6.72 (m, 5H), 6.64-6.56 (m, 2H), 5.41-5.34 (m, 1H), 4.40-4.32 (m, 2H), 4.23-4.13 (m, 1H), 3.43-3.36 (m, 2H), 3.22-3.11 (m, 4H), 3.09-2.82 (m, 7H), 2.15-2.05 (m, 2H), 1.87-1.74 (m, 7H), 1.37-1.18 (m, 4H); $[M+H]^+$=779.4.

Example A36: 7-(4-((1-(4-(2,4-dioxotetrahydropyrimidin-1(2H)-yl)phenyl)piperidin-4-yl)methyl)piperazin-1-yl)-2-(2-methoxy-4-phenoxyphenyl)-9,10-dihydro-4H-benzo[d]pyrazolo[1,5-a][1,3]diazepine-3-carboxamide

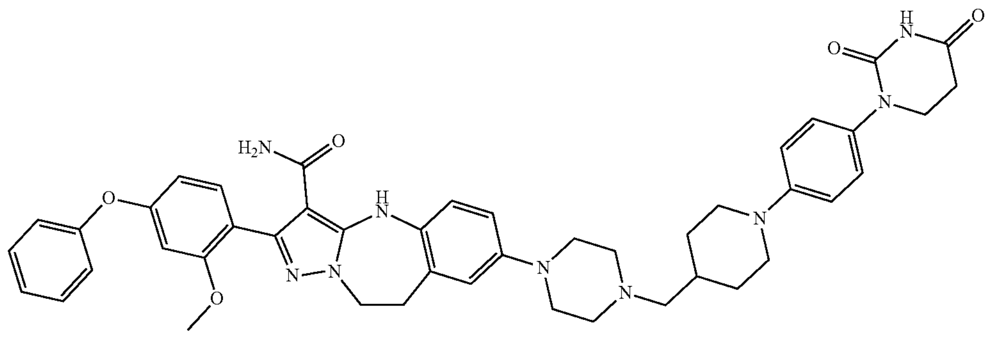 [SMILES: COc1cc(Oc2ccccc2)ccc1-c1nn2c(c1C(N)=O)Nc1ccc(N3CCN(CC4CCN(c5ccc(N6CCC(=O)NC6=O)cc5)CC4)CC3)cc1CC2]

The titled compound was synthesized in the procedures similar to Example A35. $^1H$ NMR (400 MHz, DMSO) δ 10.27 (s, 1H), 9.73 (s, 1H), 7.44 (d, J=8.0 Hz, 2H), 7.31-7.08 (m, 7H), 6.99-6.79 (m, 7H), 6.55 (d, J=8.0 Hz, 1H), 4.37-4.26 (m, 2H), 3.77-3.65 (m, 7H), 3.20-3.03 (m, 7H), 2.75-2.62 (m, 5H), 2.26-2.15 (m, 2H), 1.90-1.75 (m, 3H), 1.45-1.10 (m, 4H); $[M+H]^+$=796.4.

Example A37: 7-(4-((1-(4-(2,4-dioxotetrahydropyrimidin-1(2H)-yl)phenyl)piperidin-4-yl)methyl)piperazin-1-yl)-2-(2-fluoro-4-phenoxyphenyl)-9,10-dihydro-4H-benzo[d]pyrazolo[1,5-a][1,3]diazepine-3-carboxamide

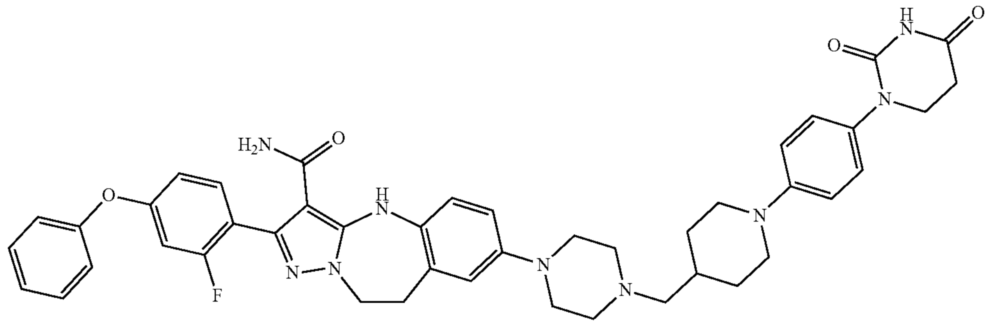 [SMILES: NC(=O)c1c(-c2ccc(Oc3ccccc3)cc2F)nn2c1Nc1ccc(N3CCN(CC4CCN(c5ccc(N6CCC(=O)NC6=O)cc5)CC4)CC3)cc1CC2]

The titled compound was synthesized in the procedures similar to Example A35. $^1H$ NMR (400 MHz, DMSO) δ 10.27 (s, 1H), 9.65 (s, 1H), 7.51-7.40 (m, 3H), 7.22-7.07 (m, 6H), 6.95-6.78 (m, 8H), 4.40-4.31 (m, 2H), 3.75-3.65 (m, 5H), 3.19-3.05 (m, 6H), 2.72-2.64 (m, 5H), 2.25-2.20 (m, 1H), 1.95-1.75 (m, 4H), 1.35-1.16 (m, 4H); $[M+H]^+$=784.4.

Example A38:2-(4-(benzyloxy)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

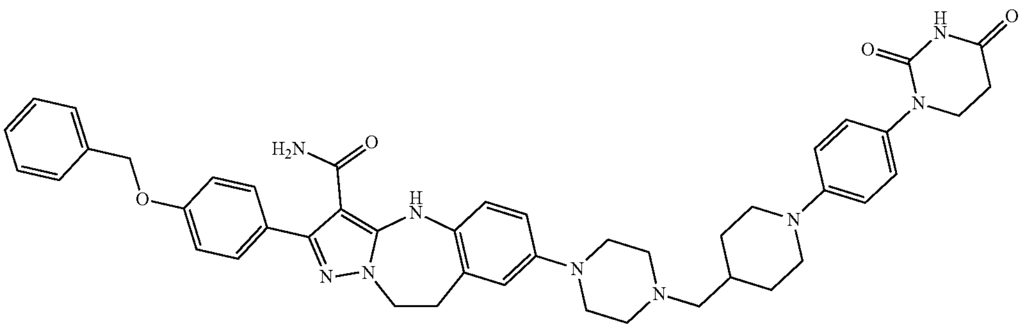 [SMILES: NC(=O)c1c(-c2ccc(OCc3ccccc3)cc2)nn2c1Nc1ccc(N3CCN(CC4CCN(c5ccc(N6CCC(=O)NC6=O)cc5)CC4)CC3)cc1CC2]

The titled compound was synthesized in the procedures similar to Example A35. $^1$H NMR (400 MHz, DMSO) δ 10.25 (s, 1H), 9.78 (s, 1H), 7.56-7.31 (m, 7H), 7.18-7.10 (m, 4H), 6.97-6.90 (m, 2H), 6.88-6.79 (m, 3H), 5.16 (s, 2H), 4.36-4.29 (m, 2H), 3.76-3.61 (m, 5H), 3.19-3.03 (m, 7H), 2.73-2.62 (m, 5H), 2.27-2.18 (m, 2H), 1.88-1.65 (m, 4H), 1.30-1.17 (m, 3H); $[M+H]^+$=780.4.

Example B1:7-(4-((1-(4-(2,4-dioxotetrahydropyrimidin-1(2H)-yl)phenyl)piperidin-4-yl)methyl)piperazin-1-yl)-2-(4-((4-(trifluoromethyl)pyridin-2-yl)carbamoyl)phenyl)-9,10-dihydro-4H-benzo[d]pyrazolo[1,5-a][1,3]diazepine-3-carboxamide Step 1: methyl 4-((2-tosylhydrazineylidene)methyl)benzoate

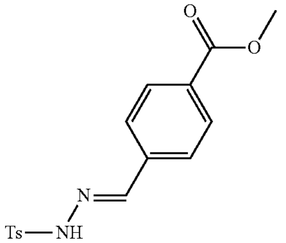 [SMILES: COC(=O)c1ccc(/C=N/NS(=O)(=O)c2ccc(C)cc2)cc1]

To a solution of compound 4-methylbenzenesulfonohydrazide (9.30 g, 50 mmol) dissolved in MeOH (150 mL) was added methyl 4-formylbenzoate (8.20 g, 50 mmol). The mixture was stirred at room temperature for 3 h. Then the mixture was filtered and concentrated to dryness to afford the product (7.0 g, 42%). $[M+H]^+$=333.1.

Step 2: methyl 4-((2-(2,5-dibromophenethyl)-2-tosylhydrazineylidene)methyl)benzoate

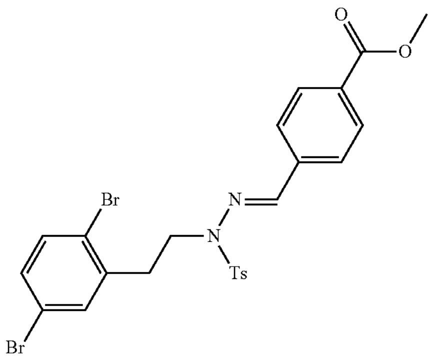 [SMILES: COC(=O)c1ccc(/C=N/N(CCc2cc(Br)ccc2Br)S(=O)(=O)c2ccc(C)cc2)cc1]

To a mixture of methyl 4-((2-tosylhydrazineylidene)methyl)benzoate (7.0 g, 21.08 mmol) and $PPh_3$ (11.05 g, 42.16 mmol) dissolved in THE (200 mL) was dropwise added DIAD (8.52 g, 42.16 mmol) at 0° C. The mixture was stirred at rt for 1 h. Then, 2-(2,5-dibromophenyl)ethan-1-ol (5.90 g, 21.08 mmol) in THE was added to the mixture at 0° C. The reaction was stirred at 0° C. for 2 h and stirred at room temperature overnight. The solvent was removed by reduced pressure. The residue was purified by slurring in EtOH. The mixture was filtered to afford the product (5.6 g, 45%). $[M+H]^+$=594.1.

Step 3: methyl 4-(5-amino-4-cyano-1-(2,5-dibromophenethyl)-1H-pyrazol-3-yl)benzoate

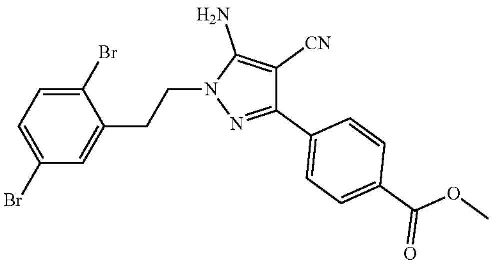 [SMILES: COC(=O)c1ccc(-c2nn(CCc3cc(Br)ccc3Br)c(N)c2C#N)cc1]

To a solution of methyl 4-((2-(2,5-dibromophenethyl)-2-tosylhydrazineylidene)methyl)benzoate (5.6 g, 9.44 mmol) and malononitrile (829 mg, 12.55 mmol) in DCE (100 mL) was added aluminum chloride (3.14 g, 23.6 mmol). The mixture was stirred at 90° C. for 5 h. Then, the reaction was cooled down to room temperature. The mixture was washed by water and filtered. The filtered cake was purified by slurring in EtOH. The mixture was filtered to afford the product (3.43 g, 72%). $[M+H]^+$=505.1.

Step 4: methyl 4-(7-bromo-3-cyano-9,10-dihydro-4H-benzo[d]pyrazolo[1,5-a][1,3]diazepin-2-yl)benzoate

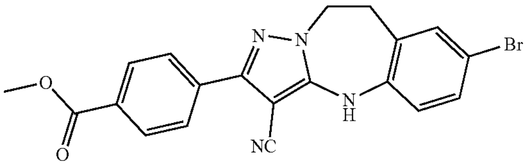 [SMILES: COC(=O)c1ccc(-c2nn3c(c2C#N)Nc2ccc(Br)cc2CC3)cc1]

To a mixture of methyl 4-(5-amino-4-cyano-1-(2,5-dibromophenethyl)-1H-pyrazol-3-yl)benzoate (3.43 g, 6.79 mmol), CuI (258 mg, 1.36 mmol) and $K_2CO_3$ (1.87 g, 13.58 mmol) dissolved in DMF (50 ml) was dropwise added (1S,2S)—N,N'-dimethyl-1,2-cyclohexanediamine (145 mg, 1.02 mmol). And the mixture was stirred at 100° C. overnight. Then the mixture was washed by water and filtered. The filtered cake was purified by slurring in EtOH. The mixture was filtered to afford the product (2.4 g, 84%). $[M+H]^+$=423.1.

Step 5: 4-(7-bromo-3-cyano-9,10-dihydro-4H-benzo[d]pyrazolo[1,5-a][1,3]diazepin-2-yl)benzoic acid

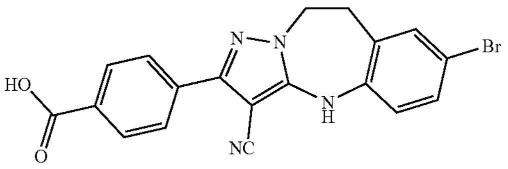 [SMILES: N#Cc1c(-c2ccc(C(=O)O)cc2)nn2c1Nc1ccc(Br)cc1CC2]

To a mixture of methyl 4-(7-bromo-3-cyano-9,10-dihydro-4H-benzo[d]pyrazolo[1,5-a][1,3]diazepin-2-yl)benzoate (1.5 g, 3.55 mmol) dissolved in NMP (15 mL)/THF (10 mL)/$H_2O$ (15 mL) was added $LiOH{\cdot}H_2O$ (1.1 g, 26.2 mmol). The mixture was stirred at room temperature for 3 h. Then, the mixture was washed by water. The mixture pH value was adjusted to 3 by 1 N HCl. The solid was filtered to afford the product (280 mg, 20%). $[M+H]^+$=409.3.

Step 6: 4-(7-bromo-3-cyano-9,10-dihydro-4H-benzo[d]pyrazolo[1,5-a][1,3]diazepin-2-yl)-N-(4-(trifluoromethyl)pyridin-2-1)benzamide

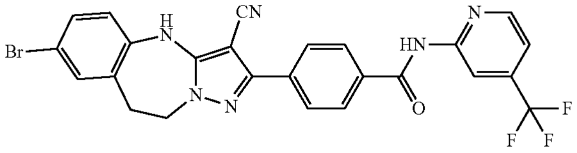 [SMILES: N#Cc1c(-c2ccc(C(=O)Nc3cc(C(F)(F)F)ccn3)cc2)nn2c1Nc1ccc(Br)cc1CC2]

To a mixture of 4-(7-bromo-3-cyano-9,10-dihydro-4H-benzo[d]pyrazolo[1,5-a][1,3]diazepin-2-yl)benzoic acid (280 mg, 0.69 mmol) dissolved in DCM (5 mL) was dropwise added $POCl_3$ (317 mg, 2.07 mmol) and pyridine (273 mg, 3.45 mmol) at 0° C. The mixture was stirred at 0° C. for 2 h. Then, 4-(trifluoromethyl)pyridin-2-amine (112 mg, 0.69 mmol) in DCM (3 mL). The mixture was stirred at room temperature overnight. Then the mixture was washed by water and extracted with DCM. The organic layers were combined and dried over $Na_2SO_4$. The mixture was filtered. The filtrate was concentrated in vacuum. The residue was purified by silica gel column chromatography (PE: EtOAc=1:1) to afford the product (50 mg, 14%). $[M+H]^+$=553.1.

Step 7: tert-butyl 4-(3-cyano-2-(4-((4-(trifluoromethyl)pyridin-2-yl)carbamoyl)phenyl)-9,10-dihydro-4H-benzo[d]pyrazolo[1,5-a][1,3]diazepin-7-yl)piperazine-1-carboxylate

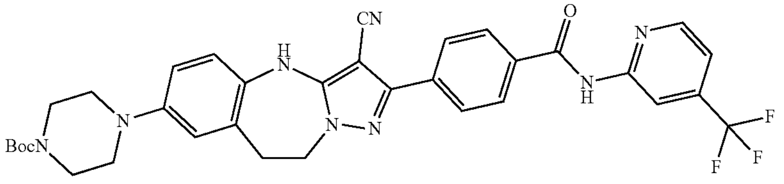 [SMILES: CC(C)(C)OC(=O)N1CCN(c2ccc3c(c2)CCn2nc(-c4ccc(C(=O)Nc5cc(C(F)(F)F)ccn5)cc4)c(C#N)c2N3)CC1]

To a mixture of 4-(7-bromo-3-cyano-9,10-dihydro-4H-benzo[d]pyrazolo[1,5-a][1,3]diazepin-2-yl)-N-(4-(trifluoromethyl)pyridin-2-yl)benzamide (50 mg, 0.09 mmol), $Pd_2dba_3$ (8.2 mg, 0.009 mmol), N-Boc-piperazine (17 mg, 0.09 mmol) and Brettphos (9.7 mg, 0.018 mmol) dissolved in THE (2 mL) was dropwise added LiHMDS (1 N) (0.27 mL, 0.27 mmol). The mixture was stirred at 70° C. for 5 h in sealed tube. Then, the mixture was cooled down to room temperature. The solvent was removed by reduced pressure. The residue was purified by silica gel column chromatography (PE: EtOAc=1:3) to afford the product (20 mg, 34%). $[M+H]^+$=659.1.

Step 8: 7-(piperazin-1-yl)-2-(4-((4-(trifluoromethyl)pyridin-2-yl)carbamoyl)phenyl)-9,10-dihydro-4H-benzo[d]pyrazolo[1,5-a][1,3]diazepine-3-carboxamide

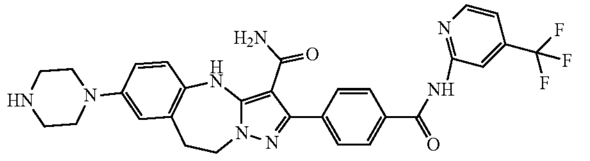 [SMILES: NC(=O)c1c(-c2ccc(C(=O)Nc3cc(C(F)(F)F)ccn3)cc2)nn2c1Nc1ccc(N3CCNCC3)cc1CC2]

To a mixture of tert-butyl 4-(3-cyano-2-(4-((4-(trifluoromethyl)pyridin-2-yl)carbamoyl)phenyl)-9,10-dihydro-4H-benzo[d]pyrazolo[1,5-a][1,3]diazepin-7-yl)piperazine-1-carboxylate (20 mg, 0.034 mmol) dissolved in MsOH (3 mL) was stirred at 100° C. for 3 h. Then, the mixture was cooled down to room temperature. The mixture was washed by water and extracted with EtOAc. The aqueous phase pH value was adjusted to 10 by saturated $NaHCO_3$ (aq.). The mixture was extracted with DCM. The organic layers were combined and dried over $Na_2SO_4$. The mixture was filtered and the filtrate was concentrated in vacuum to afford the product (10 mg, 57%). $[M+H]^+$=577.2.

Step 9: 7-(4-((1-(4-(2,4-dioxotetrahydropyrimidin-1(2H)-yl)phenyl)piperidin-4-yl)methyl)piperazin-1-yl)-2-(4-((4-(trifluoromethyl)pyridin-2-yl)carbamoyl)phenyl)-9,10-dihydro-4H-benzo[d]pyrazolo[1,5-a][1,3]diazepine-3-carboxamide

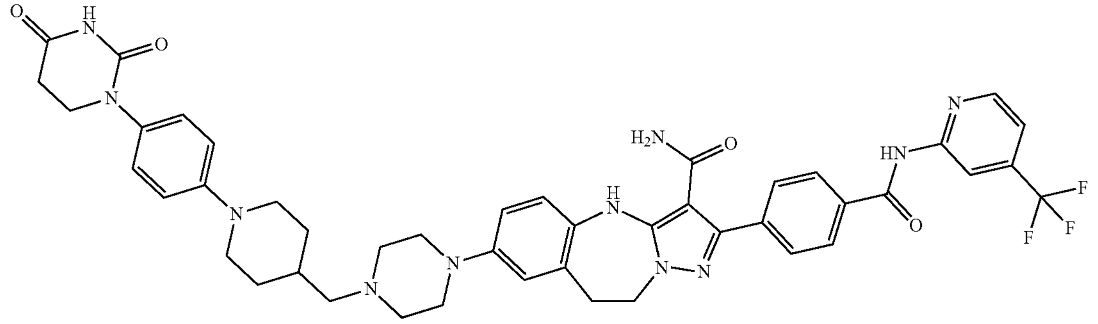 [SMILES: NC(=O)c1c(-c2ccc(C(=O)Nc3cc(C(F)(F)F)ccn3)cc2)nn2c1Nc1ccc(N3CCN(CC4CCN(c5ccc(N6CCC(=O)NC6=O)cc5)CC4)CC3)cc1CC2]

To a mixture of 7-(piperazin-1-yl)-2-(4-((4-(trifluoromethyl)pyridin-2-yl)carbamoyl)phenyl)-9,10-dihydro-4H-benzo[d]pyrazolo[1,5-a][1,3]diazepine-3-carboxamide (10 mg, 0.017 mmol) and 1-(4-(2,4-dioxotetrahydropyrimidin-1(2H)-yl)phenyl)piperidine-4-carbaldehyde (5.2 mg, 0.017 mmol) dissolved in DCM (3 mL) and MeOH (1 mL) was dropwise added AcOH (0.05 mL). The mixture was stirred at room temperature for 2 h. Then, $NaBH(OAc)_3$ (15 mg, 0.068 mmol) was added to the reaction. The mixture was stirred at room temperature for 0.5 h. The mixture was concentrated in vacuum. The residue was purified by Prep-HPLC to afford the product (2.2 mg, 15%). $^1H$ NMR (400 MHz, DMSO) δ 11.39 (s, 1H), 10.28 (s, 1H), 9.72 (s, 1H), 8.72 (d, J=10.1 Hz, 1H), 8.58 (s, 1H), 8.16 (d, J=8.2 Hz, 2H), 7.70 (d, J=8.5 Hz, 2H), 7.57 (s, 1H), 7.15 (d, J=8.5 Hz, 2H), 6.97-6.83 (m, 5H), 4.38 (s, 2H), 3.69 (dt, J=14.2, 7.3 Hz, 4H), 3.33 (s, 3H), 3.14 (d, J=25.1 Hz, 7H), 2.69 (d, J=6.0 Hz, 5H), 2.58 (s, 3H), 2.23 (dd, J=6.5, 3.4 Hz, 2H), 1.87-1.68 (m, 3H), 1.30-1.19 (m, 3H); $[M+H]^+$=862.4.

Example B2: 7-(4-((1-(4-(2,4-dioxotetrahydropyrimidin-1(2H)-yl)phenyl)piperidin-4-yl)methyl)piperazin-1-yl)-2-(2-fluoro-4-((4-(trifluoromethyl)pyridin-2-yl)carbamoyl)phenyl)-9,10-dihydro-4H-benzo[d]pyrazolo[1,5-a][1,3]diazepine-3-carboxamide

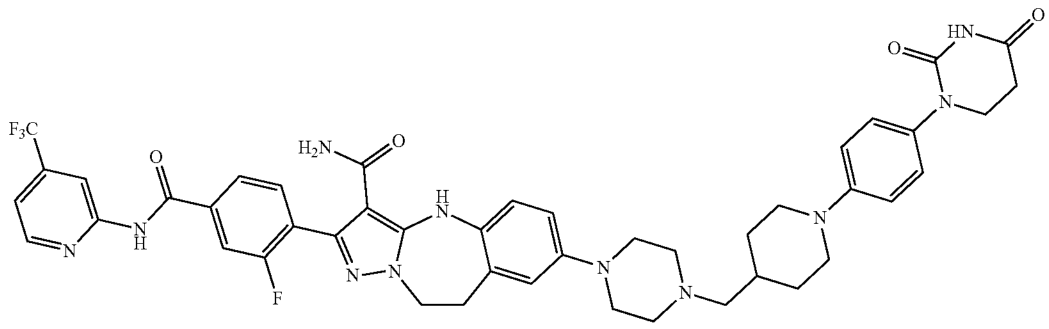 [SMILES: NC(=O)c1c(-c2ccc(C(=O)Nc3cc(C(F)(F)F)ccn3)cc2F)nn2c1Nc1ccc(N3CCN(CC4CCN(c5ccc(N6CCC(=O)NC6=O)cc5)CC4)CC3)cc1CC2]

The titled compound was synthesized in the procedures similar to Example B1. $^1$H NMR (400 MHz, DMSO) δ 11.47 (s, 1H), 10.26 (s, 1H), 9.61 (s, 1H), 8.71 (s, 1H), 8.57-8.53 (m, 1H), 7.99 (t, J=8.0 Hz, 2H), 7.68-7.55 (m, 2H), 7.13 (d, J=8.0 Hz, 2H), 6.98-6.80 (m, 6H), 4.43-4.34 (m, 2H), 3.75-3.64 (m, 4H), 3.22-2.90 (m, 8H), 2.74-2.62 (m, 5H), 2.29-2.18 (m, 2H), 1.88-1.64 (m, 3H), 1.30-1.13 (m, 4H); $[M+H]^+$=880.3.

Example B3:7-(4-((1-(4-(2,4-dioxotetrahydropyrimidin-1(2H)-yl)-3-methylphenyl)piperidin-4-yl)methyl)piperazin-1-yl)-2-(4-((4-(trifluoromethyl)pyridin-2-yl)carbamoyl)phenyl)-9,10-dihydro-4H-benzo[d]pyrazolo[1,5-a][1,3]diazepine-3-carboxamide

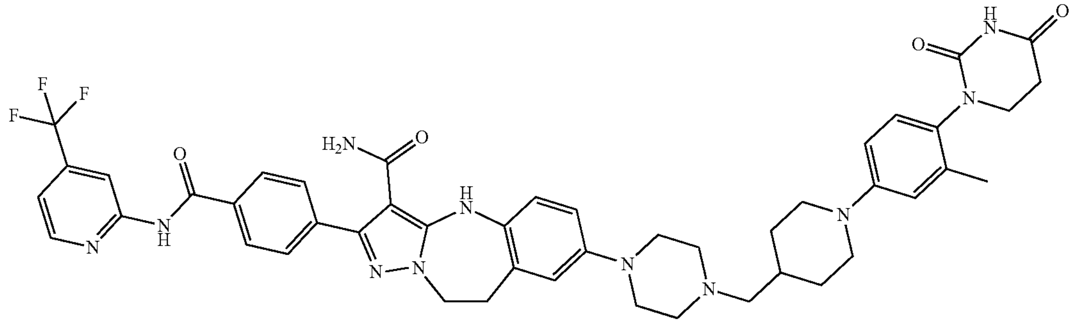 [SMILES: Cc1cc(N2CCC(CN3CCN(c4ccc5c(c4)CCn4nc(-c6ccc(C(=O)Nc7cc(C(F)(F)F)ccn7)cc6)c(C(N)=O)c4N5)CC3)CC2)ccc1N1CCC(=O)NC1=O]

The titled compound was synthesized in the procedures similar to Example B1. $^1$H NMR (400 MHz, DMSO) δ 11.38 (s, 1H), 10.25 (s, 1H), 9.71 (s, 1H), 8.70 (s, 1H), 8.56 (s, 1H), 8.14 (d, J=7.9 Hz, 2H), 7.69 (d, J=7.8 Hz, 2H), 7.59-7.52 (m, 1H), 7.04 (d, J=8.5 Hz, 1H), 6.92-6.74 (m, 6H), 4.38 (s, 2H), 3.68 (ddd, J=14.3, 10.8, 6.4 Hz, 3H), 3.46 (dq, J=7.1, 4.7 Hz, 1H), 3.13 (d, J=29.1 Hz, 7H), 2.79-2.60 (m, 5H), 2.22 (dd, J=4.2, 2.5 Hz, 2H), 2.12 (s, 3H), 1.86-1.66 (m, 4H), 1.30-1.15 (m, 4H); $[M+H]^+$=876.7.

Example B4: 7-(4-((1-(4-(2,4-dioxotetrahydropyrimidin-1(2H)-yl)phenyl)piperidin-4-yl)methyl)piperazin-1-yl)-2-(4-(pyridin-2-ylcarbamoyl)phenyl)-9,10-dihydro-4H-benzo[d]pyrazolo[1,5-a][1,3]diazepine-3-carboxamide Step 1: 7-(piperazin-1-yl)-2-(4-(pyridin-2-ylcarbamoyl)phenyl)-9,10-dihydro-4H-benzo[d]pyrazolo[1,5-a][1,3]diazepine-3-carboxamide

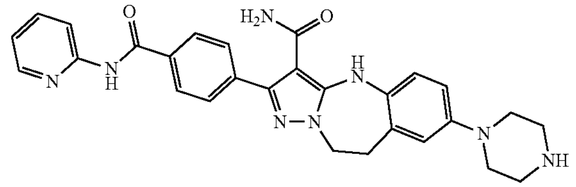 [SMILES: NC(=O)c1c(-c2ccc(C(=O)Nc3ccccn3)cc2)nn2c1Nc1ccc(N3CCNCC3)cc1CC2]

A mixture of tert-butyl 4-(3-cyano-2-(4-(pyridin-2-ylcarbamoyl)phenyl)-9,10-dihydro-4H-benzo[d]pyrazolo[1,5-a][1,3]diazepin-7-yl)piperazine-1-carboxylate (100 mg, 0.17 mmol, made by procedures similar to B1) in methanesulfonic acid (6.0 mL) was stirred at 60° C. for 3 hours. The mixture was then cooled, acidified with aqueous sodium hydroxide solution to pH 12 and filtered to afford the crude product, which was purified with silica gel column chromatography (DCM:MeOH=100:0~85:15 gradient elution) to give the product (80 mg, crude). $[M+H]^+=509.0$.

Step 2: 7-(4-((1-(4-(2,4-dioxotetrahydropyrimidin-1(2H)-yl)phenyl)piperidin-4-yl)methyl)piperazin-1-yl)-2-(4-(pyridin-2-ylcarbamoyl)phenyl)-9,10-dihydro-4H-benzo[d]pyrazolo[1,5-a][1,3]diazepine-3-carboxamide

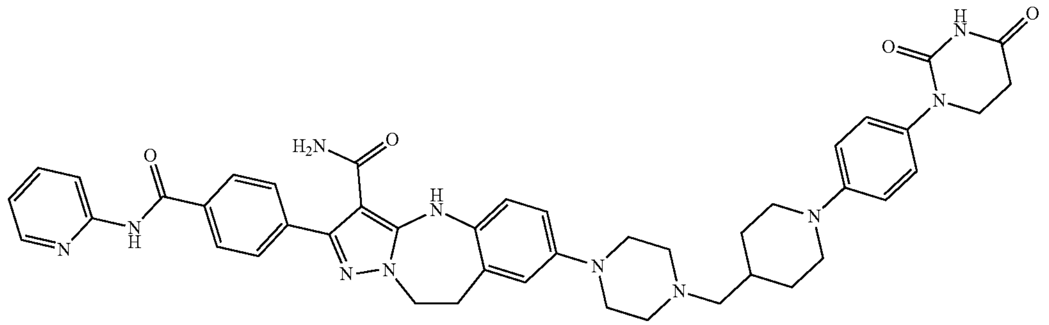 [SMILES: NC(=O)c1c(-c2ccc(C(=O)Nc3ccccn3)cc2)nn2c1Nc1ccc(N3CCN(CC4CCN(c5ccc(N6CCC(=O)NC6=O)cc5)CC4)CC3)cc1CC2]

A mixture of 7-(piperazin-1-yl)-2-(4-(pyridin-2-ylcarbamoyl)phenyl)-9,10-dihydro-4H-benzo[d]pyrazolo[1,5-a][1,3]diazepine-3-carboxamide (60 mg, 0.12 mmol) and 1-(4-(2,4-dioxotetrahydropyrimidin-1(2H)-yl)phenyl)piperidine-4-carbaldehyde (54 mg, 0.18 mmol) in MeOH (3.0 mL), DCM (10.0 mL) and acetic acid (1.0 mL) was stirred at room temperature overnight, and then $NaBH(OAc)_3$ (254.4 mg, 1.2 mmol) was added and stirred at room temperature for 2 hours. The mixture was treated with water (20 mL), extracted with dichloromethane (3×20 mL), and washed with brine (30 mL). The organic phase was dried over anhydrous sodium sulfate, filtered and concentrated under reduced pressure to afford the crude product, which was purified by prep-HPLC (Anal. Column: Waters Xbridge C18, Column Temp.: Room temperature, Mobile Phase A: CAN (0.1% FA), Mobile Phase B: $H_2O$ (0.1% FA), Gradient Table: Mobile Phase A (20-90%), Time (min):0-17 min) to give the product (2.5 mg, 2.6%). $^1H$ NMR (400 MHz, DMSO) δ 10.87 (s, 1H), 10.27 (s, 1H), 9.73 (s, 1H), 8.41 (s, 1H), 8.21 (d, J=8.1 Hz, 1H), 8.14 (s, 2H), 7.86 (s, 1H), 7.67 (d, J=7.5 Hz, 2H), 7.13 (s, 3H), 6.95 (s, 5H), 4.38 (s, 2H), 3.69 (s, 4H), 3.13 (d, J=34.1 Hz, 7H), 2.68 (s, 7H), 2.33 (s, 1H), 2.22 (s, 1H), 1.81 (s, 2H), 1.24 (s, 3H); $[M+H]^+=794.0$.

Example B5: 7-(4-((1-(4-(2,4-dioxotetrahydropyrimidin-1(2H)-yl)phenyl)piperidin-4-yl)methyl)piperazin-1-yl)-2-(3-methyl-4-((4-(trifluoromethyl)pyridin-2-yl)carbamoyl)phenyl)-9,10-dihydro-4H-benzo[d]pyrazolo[1,5-a][1,3]diazepine-3-carboxamide Step 1: methyl 4-formyl-2-methylbenzoate

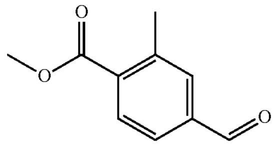

To a solution of methyl 4-bromo-2-methylbenzoate (13.80 g, 60.5 mmol), $PdCl_2(PPh_3)_2$ (2.12 g, 3.03 mmol), HCOONa (6.17 g, 90.8 mmol) dissolved in DMF (180 mL) was added $PPh_3$ (1.59 g, 6.05 mmol). The mixture was stirred at 110° C. for 6 h under CO atmosphere. The mixture was washed by water and extracted with EtOAc. The organic layers were combined and washed by brine. The mixture was dried over $Na_2SO_4$ and filtered. The filtrate was concentrated in vacuum. The residue was purified by silica gel column chromatography (PE: EtOAc=9:1) to afford the product (3.30 g, 31%). $^1H$ NMR (400 MHz, $CDCl_3$) δ 10.05 (s, 1H), 8.03 (d, J=8.2 Hz, 1H), 7.75 (s, 2H), 3.94 (s, 3H), 2.66 (s, 3H).

Step 2: methyl 2-methyl-4-((2-tosylhydrazineylidene)methyl)benzoate

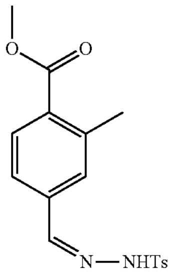

To a solution of methyl 4-formyl-2-methylbenzoate (3.30 g, 18.5 mmol) dissolved in MeOH (70 mL) was added 4-methylbenzenesulfonhydrazide (3.45 g, 18.5 mmol). The mixture was stirred at room temperature for 3 h. The mixture was filtered and concentrated to dryness to afford the product (5.7 g, 89%). $[M+H]^+$=347.1.

Step 3: methyl 4-((2-(2,5-dibromophenethyl)-2-tosylhydrazineylidene)methyl)-2-methylbenzoate

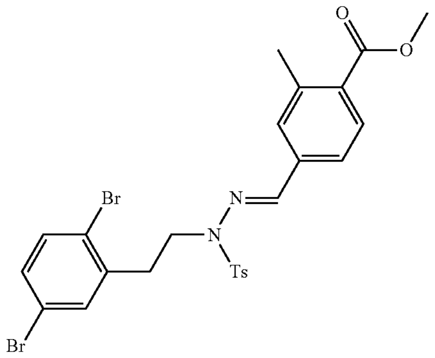 [SMILES: COC(=O)c1ccc(/C=N/N(CCc2cc(Br)ccc2Br)S(=O)(=O)c2ccc(C)cc2)cc1C]

To a mixture of methyl 2-methyl-4-((2-tosylhydrazineylidene)methyl)benzoate (5.7 g, 16.5 mmol) and $PPh_3$ (8.64 g, 33.0 mmol) dissolved in THE (200 mL) was dropwise added DIAD (6.67 g, 33.0 mmol) at 0° C. The mixture was stirred at rt for 1 h. Then, 2-(2,5-dibromophenyl)ethan-1-ol (4.62 g, 16.5 mmol) in THE was added to mixture at 0° C. The reaction was stirred at 0° C. for 2 h and stirred at room temperature overnight. The solvent was removed by reduced pressure. The residue was purified by slurring in EtOH. The mixture was filtered to afford the product (3.0 g, 30%). $[M+H]^+$=609.1.

Step 4: methyl 4-(5-amino-4-cyano-1-(2,5-dibromophenethyl)-1H-pyrazol-3-yl)-2-methylbenzoate

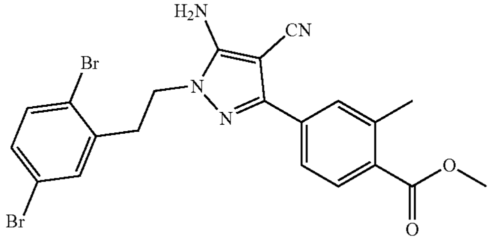 [SMILES: COC(=O)c1ccc(-c2nn(CCc3cc(Br)ccc3Br)c(N)c2C#N)cc1C]

To a solution of methyl 4-((2-(2,5-dibromophenethyl)-2-tosylhydrazineylidene)methyl)-2-methylbenzoate (3.0 g, 4.93 mmol) and malononitrile (436 mg, 6.60 mmol) in DCE (50 mL) was added aluminum chloride (1.64 g, 12.3 mmol). The mixture was stirred at 90° C. for 5 h. Then, the reaction was cooled down to room temperature. The mixture was washed by water and filtered. The filtered cake was purified by slurring in EtOH. The mixture was filtered to afford the product (2.0 g, 78%). $[M+H]^+$=519.1.

Step 5: methyl 4-(7-bromo-3-cyano-9,10-dihydro-4H-benzo[d]pyrazolo[1,5-a][1,3]diazepin-2-yl)-2-methylbenzoate

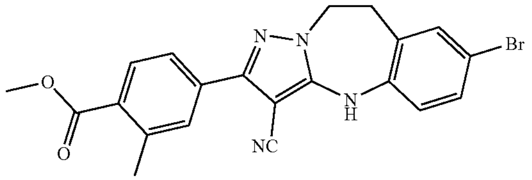 [SMILES: COC(=O)c1ccc(-c2nn3c(c2C#N)Nc2ccc(Br)cc2CC3)cc1C]

To a mixture of methyl 4-(5-amino-4-cyano-1-(2,5-dibromophenethyl)-1H-pyrazol-3-yl)-2-methylbenzoate (2.0 g, 3.86 mmol), CuI (147 mg, 0.77 mmol) and $K_2CO_3$ (1.07 g, 7.72 mmol) dissolved in DMF (40 mL) was dropwise added (1S,2S)—N,N'-dimethyl-1,2-cyclohexanediamine (82 mg, 0.58 mmol). And the mixture was stirred at 100° C. overnight. Then the mixture was washed by water and filtered. The filtered cake was purified by slurring in EtOH. The mixture was filtered to afford the product (1.6 g, 95%). $[M+H]^+$=437.1.

Step 6: 4-(7-bromo-3-cyano-9,10-dihydro-4H-benzo[d]pyrazolo[1,5-a][1,3]diazepin-2-yl)-2-methyl-N-(4-(trifluoromethyl)pyridin-2-yl)benzamide

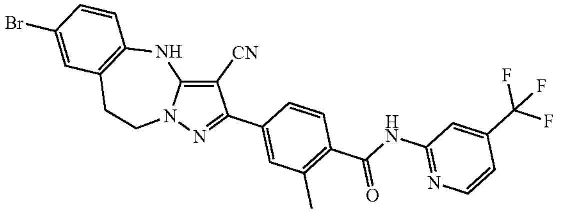 [SMILES: Cc1cc(-c2nn3c(c2C#N)Nc2ccc(Br)cc2CC3)ccc1C(=O)Nc1cc(C(F)(F)F)ccn1]

To a mixture of methyl 4-(7-bromo-3-cyano-9,10-dihydro-4H-benzo[d]pyrazolo[1,5-a][1,3]diazepin-2-yl)-2-methylbenzoate (600 mg, 1.38 mmol), 4-(trifluoromethyl)pyridine-2-amine (224 mg, 1.38 mmol) dissolved in THE (15 mL) was dropwise added LiHMDS (1 N) (3.45 mL, 3.45 mmol). The mixture was stirred at 70° C. for 3 h. Then the mixture was washed by water and extracted with DCM. The organic layers were combined and dried over $Na_2SO_4$. The mixture was filtered. The filtrate was concentrated in vacuum. The residue was purified by silica gel column chromatography (PE: EtOAc=1:1) to afford the product (600 mg, 77%). $[M+H]^+$=567.2.

Step 7: tert-butyl 4-(3-cyano-2-(3-methyl-4-((4-(trifluoromethyl)pyridin-2-yl)carbamoyl)phenyl)-9,10-dihydro-4H-benzo[d]pyrazolo[1,5-a][1,3]diazepin-7-yl)piperazine-1-carboxylate

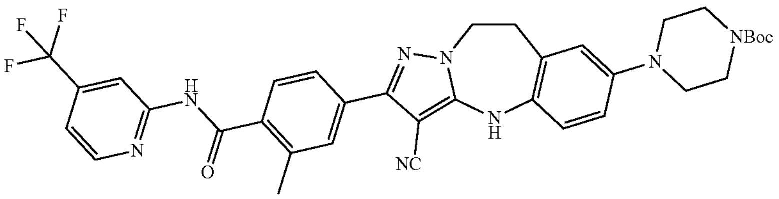 [SMILES: Cc1cc(-c2nn3c(c2C#N)Nc2ccc(N4CCN(C(=O)OC(C)(C)C)CC4)cc2CC3)ccc1C(=O)Nc1cc(C(F)(F)F)ccn1]

To a mixture of 4-(7-bromo-3-cyano-9,10-dihydro-4H-benzo[d]pyrazolo[1,5-a][1,3]diazepin-2-yl)-2-methyl-N-(4-(trifluoromethyl)pyridin-2-yl)benzamide (305 mg, 0.54 mmol), Pd(Brettphos)$Cl_2$(40 mg, 0.05 mmol), BOC-piperazine (100 mg, 0.54 mmol) and Brettphos (53.7 mg, 0.1 mmol) dissolved in THE (2 mL) was dropwise added LiHMDS (1 N) (1.62 mL, 1.62 mmol). The mixture was stirred at 70° C. for 3 h in sealed tube. Then, the mixture was cooled down to room temperature. The solvent was removed by reduced pressure. The residue was purified by silica gel column chromatography (PE: EtOAc=1:3) to afford the product (200 mg, 55%). $[M+H]^+$=673.1.

Step 8: 2-(3-methyl-4-((4-(trifluoromethyl)pyridin-2-yl)carbamoyl)phenyl)-7-(piperazin-1-yl)-9,10-dihydro-4H-benzo[d]pyrazolo[1,5-a][1,3]diazepine-3-carboxamide

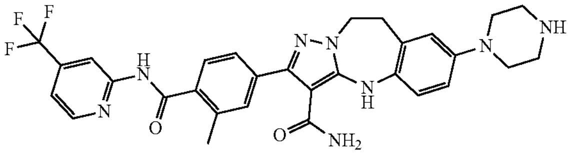 [SMILES: Cc1cc(-c2nn3c(c2C(N)=O)Nc2ccc(N4CCNCC4)cc2CC3)ccc1C(=O)Nc1cc(C(F)(F)F)ccn1]

To a mixture of tert-butyl 4-(3-cyano-2-(3-methyl-4-((4-(trifluoromethyl)pyridin-2-yl)carbamoyl)phenyl)-9,10-dihydro-4H-benzo[d]pyrazolo[1,5-a][1,3]diazepin-7-yl)piperazine-1-carboxylate (200 mg, 0.30 mmol) dissolved in MsOH (5 mL) was stirred at 100° C. for 3 h. Then, the mixture was cooled down to room temperature. The mixture was washed by water and extracted with EtOAc. The aqueous phase pH value was adjusted to 10 by saturated $NaHCO_3$ (aq.). The mixture was extracted with DCM. The organic layers were combined and dried over $Na_2SO_4$. The mixture was filtered and the filtrate was concentrated in vacuum to afford the product (100 mg, 56%). $[M+H]^+$=591.1.

Step 9: 7-(4-((1-(4-(2,4-dioxotetrahydropyrimidin-1(2H)-yl)phenyl)piperidin-4-yl)methyl)piperazin-1-yl)-2-(3-methyl-4-((4-(trifluoromethyl)pyridin-2-yl)carbamoyl)phenyl)-9,10-dihydro-4H-benzo[d]pyrazolo[1,5-a][1,3]diazepine-3-carboxamide

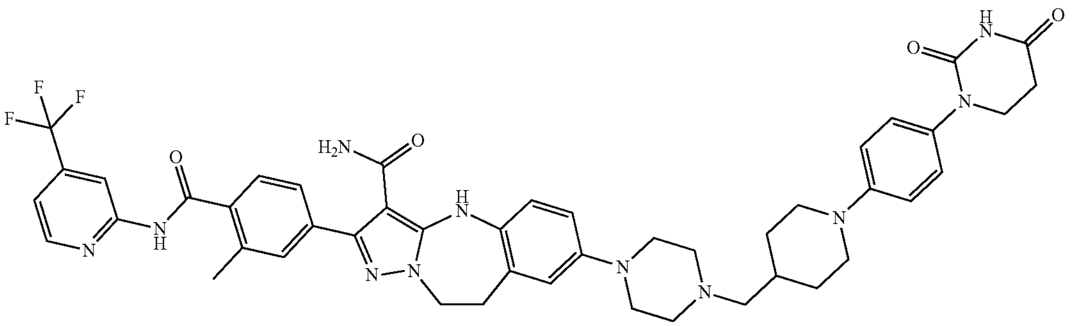 [SMILES: Cc1cc(-c2nn3c(c2C(N)=O)Nc2ccc(N4CCN(CC5CCN(c6ccc(N7CCC(=O)NC7=O)cc6)CC5)CC4)cc2CC3)ccc1C(=O)Nc1cc(C(F)(F)F)ccn1]

To a mixture of 2-(3-methyl-4-((4-(trifluoromethyl)pyridin-2-yl)carbamoyl)phenyl)-7-(piperazin-1-yl)-9,10-dihydro-4H-benzo[d]pyrazolo[1,5-a][1,3]diazepine-3-carboxamide (100 mg, 0.17 mmol) and 1-(4-(2,4-dioxotetrahydropyrimidin-1(2H)-yl)phenyl)piperidine-4-carbaldehyde (52 mg, 0.17 mmol) dissolved in DCM (6 mL) and MeOH (1 mL) was dropwise added AcOH (0.2 mL). The mixture was stirred at room temperature for 2 h. Then, $NaBH(OAc)_3$ (144 mg, 0.68 mmol) was added to the reaction. The mixture was stirred at room temperature for 0.5 h. The mixture was concentrated in vacuum. The residue was purified by Prep-HPLC (Column: Waters Xbridge C18, Column Temp.: Room temperature, Mobile Phase A: CAN, Mobile Phase B: $H_2O$ (0.1% TFA), Gradient Table: Mobile Phase A (30-90%), Time (min):0-17 min) to afford the product (25.1 mg, 17%). $^1H$ NMR (400 MHz, DMSO) δ 11.35 (s, 1H), 10.26 (s, 1H), 9.78 (s, 1H), 8.66 (s, 1H), 8.56 (s, 1H), 7.62 (d, J=8.4 Hz, 1H), 7.55 (s, 1H), 7.47-7.44 (m, 2H), 7.13 (d, J=8.6 Hz, 2H), 6.94-6.90 (m, 2H), 6.87-6.75 (m, 4H), 4.36 (s, 2H), 3.69-3.60 (m, 5H), 3.12-3.01 (m, 8H), 2.71-2.63 (m, 5H), 2.45 (s, 3H), 2.25-2.19 (m, 2H), 1.91 (d, J=2.4 Hz, 1H), 1.85-1.78 (m, 2H), 1.27-1.19 (m, 3H); $[M+H]^+$=876.5.

Example B6: 7-(4-((1-(4-(2,4-dioxotetrahydropyrimidin-1(2H)-yl)phenyl)piperidin-4-yl)methyl)piperazin-1-yl)-2-(2-methyl-4-((4-(trifluoromethyl)pyridin-2-yl)carbamoyl)phenyl)-9,10-dihydro-4H-benzo[d]pyrazolo[1,5-a][1,3]diazepine-3-carboxamide

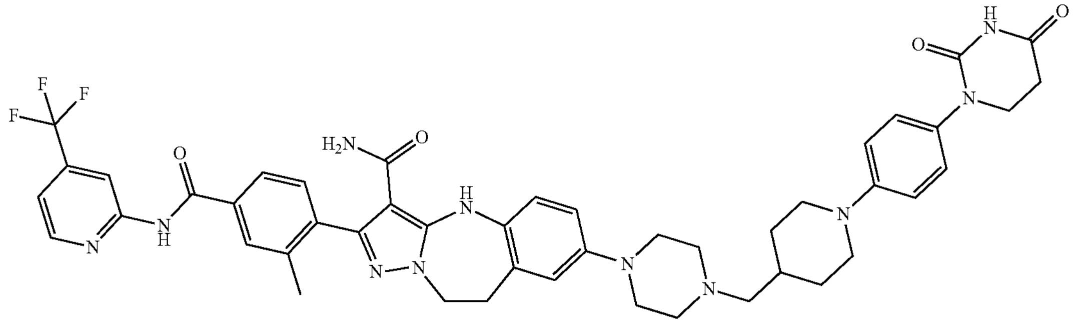 [SMILES: Cc1cc(C(=O)Nc2cc(C(F)(F)F)ccn2)ccc1-c1nn2c(c1C(N)=O)Nc1ccc(N3CCN(CC4CCN(c5ccc(N6CCC(=O)NC6=O)cc5)CC4)CC3)cc1CC2]

The titled compound was synthesized in the procedures similar to Example B5. $^1H$ NMR (400 MHz, DMSO) δ 11.35 (s, 1H), 10.27 (s, 1H), 9.78 (s, 1H), 8.70 (s, 1H), 8.56 (s, 1H), 8.06 (s, 1H), 7.95 (d, J=7.1 Hz, 1H), 7.56 (s, 1H), 7.45 (d, J=7.7 Hz, 1H), 7.13 (d, J=8.0 Hz, 2H), 6.98-6.75 (m, 6H), 4.36 (s, 2H), 3.76-3.64 (m, 4H), 3.12-3.01 (m, 7H), 2.74-2.61 (m, 5H), 2.31-2.17 (m, 5H), 1.77-1.61 (m, 3H), 1.30-1.15 (m, 3H); $[M+H]^+$=876.4.

Example B7: 2-(3,5-dimethyl-4-((4-(trifluoromethyl)pyridin-2-yl)carbamoyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

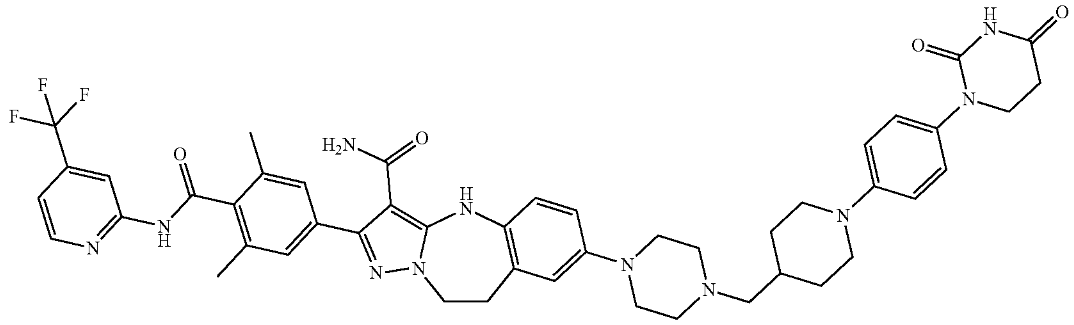 [SMILES: Cc1cc(-c2nn3c(c2C(N)=O)Nc2ccc(N4CCN(CC5CCN(c6ccc(N7CCC(=O)NC7=O)cc6)CC5)CC4)cc2CC3)cc(C)c1C(=O)Nc1cc(C(F)(F)F)ccn1]

The titled compound was synthesized in the procedures similar to Example 5. H NMR (400 MHz, DMSO) δ 11.44 (s, 1H), 10.26 (s, 1H), 9.83 (s, 1H), 8.62 (d, J=21.9 Hz, 2H), 7.59-7.53 (m, 1H), 7.26 (s, 2H), 7.13 (d, J=8.1 Hz, 2H), 6.96-6.81 (m, 5H), 4.35 (s, 2H), 3.68 (d, J=6.7 Hz, 4H), 3.20-3.04 (m, 8H), 2.72-2.61 (m, 7H), 2.32 (s, 6H), 2.22 (s, 2H), 1.80-1.65 (m, 3H), 1.29-1.16 (m, 3H); $[M+H]^+$=890.5.

Example B8:7-(4-((1-(4-(2,4-dioxotetrahydropyrimidin-1(2H)-yl)phenyl)piperidin-4-yl)methyl)piperazin-1-yl)-2-(3-fluoro-4-((4-(trifluoromethyl)pyridin-2-yl)carbamoyl)phenyl)-9,10-dihydro-4H-benzo[d]pyrazolo[1,5-a][1,3]diazepine-3-carboxamide

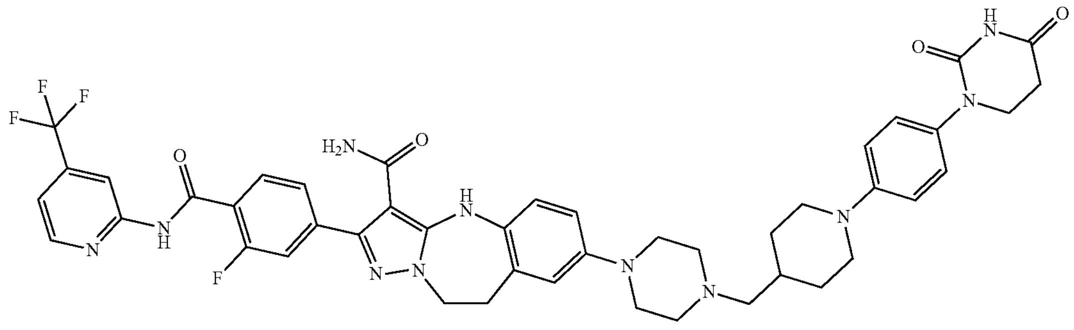 [SMILES: NC(=O)c1c(-c2ccc(C(=O)Nc3cc(C(F)(F)F)ccn3)c(F)c2)nn2c1Nc1ccc(N3CCN(CC4CCN(c5ccc(N6CCC(=O)NC6=O)cc5)CC4)CC3)cc1CC2]

The titled compound was synthesized in the procedures similar to Example B5. $^1$H NMR (400 MHz, DMSO) δ 11.36 (s, 1H), 10.28 (s, 1H), 9.72 (s, 1H), 9.48 (s, 1H), 8.67 (s, 1H), 8.53 (s, 1H), 7.81 (s, 1H), 7.58 (s, 1H), 7.48 (d, J=10.5 Hz, 2H), 7.14 (s, 2H), 6.98-6.90 (m, 5H), 4.40 (s, 2H), 3.72-3.61 (m, 8H), 3.22-3.04 (m, 9H), 2.69 (s, 4H), 1.86 (s, 2H), 1.36 (s, 3H); $[M+H]^+$=880.5.

Example B9:7-(4-((1-(4-(2,4-dioxotetrahydropyrimidin-1(2H)-yl)phenyl)piperidin-4-yl)methyl)piperazin-1-yl)-2-(4-((4-methoxypyridin-2-yl)carbamoyl)phenyl)-9,10-dihydro-4H-benzo[d]pyrazolo[1,5-a][1,3]diazepine-3-carboxamide Step 1: tert-butyl 4-(3-cyano-2-(4-(methoxycarbonyl)phenyl)-9,10-dihydro-4H-benzo[d]pyrazolo[1,5-a][1,3]diazepin-7-yl)piperazine-1-carboxylate

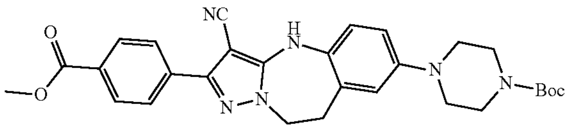 [SMILES: COC(=O)c1ccc(-c2nn3c(c2C#N)Nc2ccc(N4CCN(C(=O)OC(C)(C)C)CC4)cc2CC3)cc1]

A mixture of methyl 4-(7-bromo-3-cyano-9,10-dihydro-4H-benzo[d]pyrazolo[1,5-a][1,3]diazepin-2-yl)benzoate (1.5 g, 3.55 mmol), tert-butyl piperazine-1-carboxylate (793 mg, 4.26 mmol), $Pd_2(dba)_3$ (325 mg, 0.36 mmol), Ruphos (331 mg, 0.71 mmol) and $Cs_2CO_3$ (3.5 g, 10.65 mmol) in dioxane (20 mL) was stirred at 105° C. overnight under nitrogen atmosphere. The mixture was concentrated under vacuum. The residue was purified by silica gel column chromatography, eluted with EA/PE (3/1) to afford the product (1 g, 53.2%). $[M+H]^+$=529.2.

Step 2: tert-butyl 4-(3-cyano-2-(4-((4-methoxypyridin-2-yl)carbamoyl)phenyl)-9,10-dihydro-4H-benzo[d]pyrazolo[1,5-a][1,3]diazepin-7-yl)piperazine-1-carboxylate

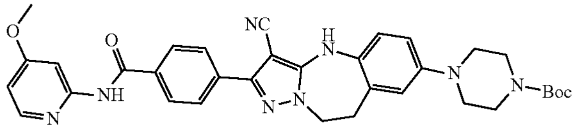 [SMILES: COc1ccnc(NC(=O)c2ccc(-c3nn4c(c3C#N)Nc3ccc(N5CCN(C(=O)OC(C)(C)C)CC5)cc3CC4)cc2)c1]

To a mixture of tert-butyl 4-(3-cyano-2-(4-(methoxycarbonyl)phenyl)-9,10-dihydro-4H-benzo[d]pyrazolo[1,5-a][1,3]diazepin-7-yl)piperazine-1-carboxylate (80 mg, 0.15 mmol) and 4-methoxypyridin-2-amine (19 mg, 0.15 mmol) in THE (5 mL) was added 1 N LiHMDS (0.45 mL, 0.45 mmol). The mixture was stirred at 75° C. for 3 h. The mixture was diluted with water (50 mL) and extracted with EA (3×100 mL). The combined organic layers were dried over $Na_2SO_4$, filtered and concentrated under vacuum. The residue was purified by silica gel column chromatography, eluted with EA/PE (100%) to afford the product (57 mg, 60.6%). $[M+H]^+$=621.3.

Step 3: 2-(4-((4-methoxypyridin-2-yl)carbamoyl)phenyl)-7-(piperazin-1-yl)-9,10-dihydro-4H-benzo[d]pyrazolo[1,5-a][1,3]diazepine-3-carboxamide

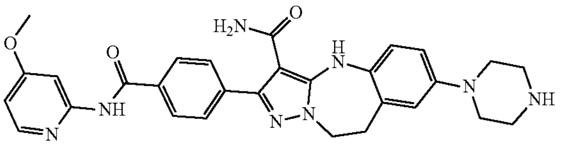 [SMILES: COc1ccnc(NC(=O)c2ccc(-c3nn4c(c3C(N)=O)Nc3ccc(N5CCNCC5)cc3CC4)cc2)c1]

A mixture of tert-butyl 4-(3-cyano-2-(4-((4-methoxypyridin-2-yl)carbamoyl)phenyl)-9,10-dihydro-4H-benzo[d]pyrazolo[1,5-a][1,3]diazepin-7-yl)piperazine-1-carboxylate (57 mg, 0.09 mmol) in MsOH was stirred at 100° C. for 1 h. The mixture was added dropwise to saturated $NaHCO_3$ aqueous solution and extracted with DCM (3×100 mL). The combined organic layers were dried over $Na_2SO_4$, filtered and concentrated under vacuum to afford the desired product (30 mg, crude), which was used in the next step directly. $[M+H]^+$=539.2.

Step 4: 7-(4-((1-(4-(2,4-dioxotetrahydropyrimidin-1(2H)-yl)phenyl)piperidin-4-yl)methyl)piperazin-1-yl)-2-(4-((4-methoxypyridin-2-yl)carbamoyl)phenyl)-9,10-dihydro-4H-benzo[d]pyrazolo[1,5-a][1,3]diazepine-3-carboxamide

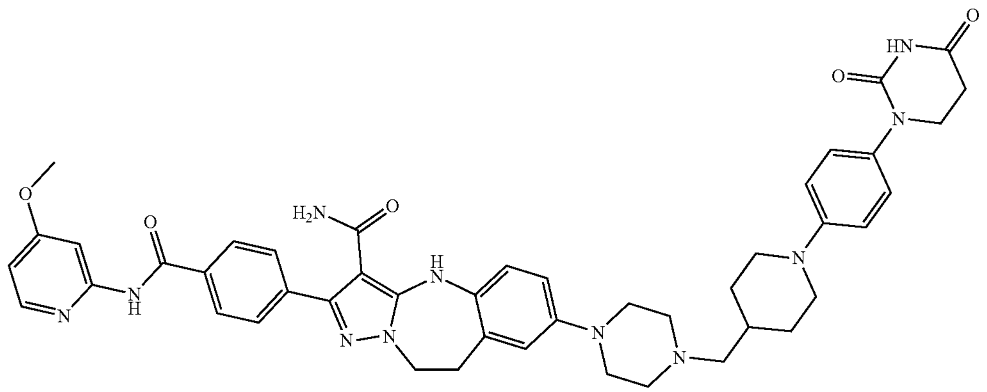 [SMILES: COc1ccnc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)cc2)c1]

A mixture of 2-(4-((4-methoxypyridin-2-yl)carbamoyl)phenyl)-7-(piperazin-1-yl)-9,10-dihydro-4H-benzo[d]pyrazolo[1,5-a][1,3]diazepine-3-carboxamide (30 mg, 0.06 mmol), 1-(4-(2,4-dioxotetrahydropyrimidin-1(2H)-yl)phenyl)piperidine-4-carbaldehyde (21.8 mg, 0.07 mmol) and AcOH (one drop) in MeOH (5 mL) and DCM (5 mL) was stirred at rt overnight. Then, sodium triacetoxyborohydride (24 mg, 0.12 mmol) was added to the mixture above and the mixture was stirred at rt for 5 h. The mixture was diluted with water (50 mL) and extracted with DCM (3×50 mL). The combined organic layers were dried over $Na_2SO_4$, filtered and concentrated under vacuum. The residue was purified by silica gel column chromatography, eluted with MeOH/DCM (1/10) to afford the product (15.57 mg, 33.9%). $^1$H NMR (400 MHz, DMSO) δ 10.81 (s, 1H), 10.26 (s, 1H), 9.71 (s, 1H), 8.21 (s, 1H), 8.11 (d, J=8.0 Hz, 2H), 7.91-7.83 (m, 1H), 7.71-7.63 (m, 2H), 7.17-7.10 (m, 2H), 6.97-6.78 (m, 7H), 4.41-4.33 (m, 2H), 3.90-3.85 (m, 3H), 3.73-3.65 (m, 4H), 3.20-3.01 (m, 8H), 2.72-2.61 (m, 5H), 2.26-2.18 (m, 2H), 1.86-1.77 (m, 2H), 1.75-1.67 (m, 1H), 1.23-1.16 (m, 4H); $[M+H]^+$=824.4.

Example B10:7-(4-((1-(4-(2,4-dioxotetrahydropyrimidin-1(2H)-yl)phenyl)piperidin-4-yl)methyl)piperazin-1-yl)-2-(4-((4-methylpyridin-2-yl)carbamoyl)phenyl)-9,10-dihydro-4H-benzo[d]pyrazolo[1,5-a][1,3]diazepine-3-carboxamide

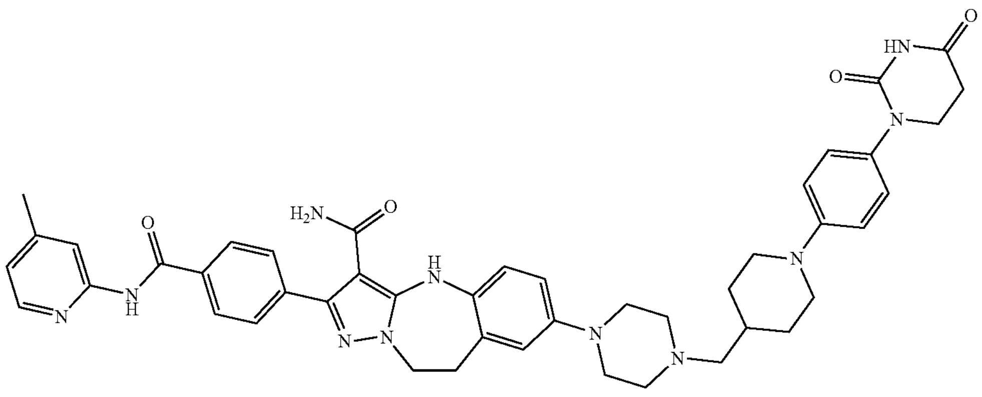 [SMILES: Cc1ccnc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)cc2)c1]

The titled compound was synthesized in the procedures similar to Example B9. $^1$H NMR (400 MHz, DMSO) δ 10.77 (s, 1H), 10.27 (s, 1H), 9.71 (s, 1H), 8.25 (d, J=4.0 Hz, 1H), 8.10 (t, J=12.0 Hz, 3H), 7.66 (d, J=8.0 Hz, 2H), 7.13 (d, J=8.0 Hz, 2H), 7.02 (d, J=4.0 Hz, 1H), 6.95-6.81 (m, 5H), 4.41-4.33 (m, 2H), 3.73-3.65 (m, 4H), 3.21-2.96 (m, 8H), 2.72-2.62 (m, 5H), 2.37 (s, 3H), 2.26-2.18 (m, 2H), 1.86-1.77 (m, 2H), 1.70 (brs, 1H), 1.29-1.77 (m, 3H); $[M+H]^+$ =808.4.

Example B11:2-(4-((4-cyclopropylpyridin-2-yl)carbamoyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

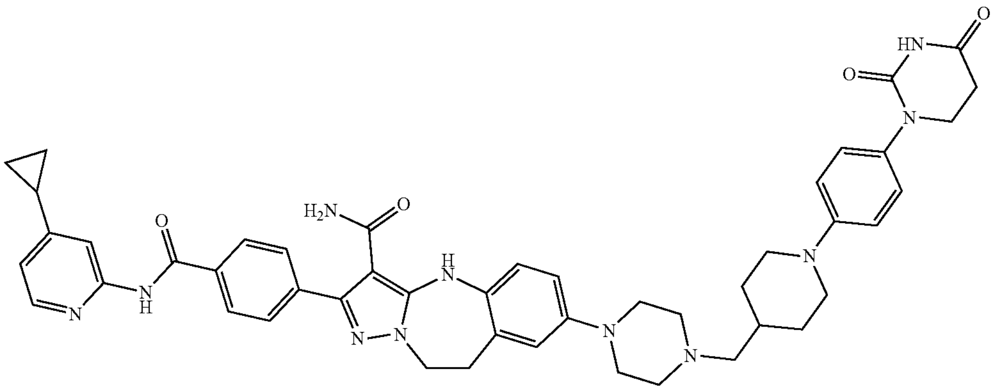 [SMILES: NC(=O)c1c(-c2ccc(C(=O)Nc3cc(C4CC4)ccn3)cc2)nn2c1Nc1ccc(N3CCN(CC4CCN(c5ccc(N6CCC(=O)NC6=O)cc5)CC4)CC3)cc1CC2]

The titled compound was synthesized in the procedures similar to Example B9. $^1$H NMR (400 MHz, DMSO) δ 10.80 (s, 1H), 10.26 (s, 1H), 9.71 (s, 1H), 8.43 (s, 1H), 8.29 (d, J=8.0 Hz, 1H), 8.18-8.09 (m, 3H), 7.66 (d, J=8.0 Hz, 2H), 7.22-7.18 (m, 1H), 7.13 (d, J=8.0 Hz, 2H), 6.97-6.80 (m, 6H), 6.53-6.44 (m, 1H), 4.41-4.32 (m, 2H), 3.73-3.63 (m, 4H), 3.20-3.05 (m, 8H), 2.71-2.63 (m, 5H), 2.25-2.18 (m, 2H), 1.98-1.87 (m, 2H), 1.86-1.68 (m, 3H), 1.32-1.14 (m, 5H); $[M+H]^+$=834.4.

Example B12: 7-(4-((1-(4-(2,4-dioxotetrahydropyrimidin-1(2H)-yl)phenyl)piperidin-4-yl)methyl)piperazin-1-yl)-2-(4-((4-(trifluoromethyl)pyridin-2-yl)carbamoyl)phenyl)-9,10-dihydro-4H-benzo[d]pyrazolo[1,5-a][1,3]diazepine-3-carboxamide

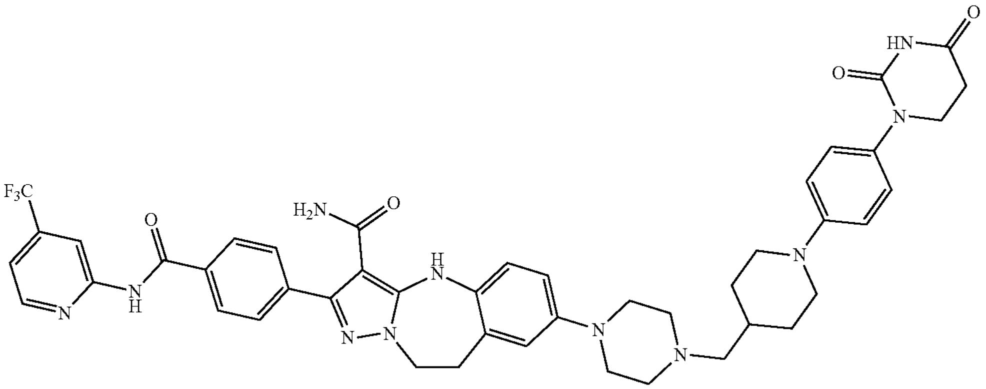 [SMILES: NC(=O)c1c(-c2ccc(C(=O)Nc3cc(C(F)(F)F)ccn3)cc2)nn2c1Nc1ccc(N3CCN(CC4CCN(c5ccc(N6CCC(=O)NC6=O)cc5)CC4)CC3)cc1CC2]

The titled compound was synthesized in the procedures similar to Example B9. $^1H$ NMR (400 MHz, DMSO) δ 10.65 (s, 1H), 10.26 (s, 1H), 9.72 (s, 1H), 8.29 (s, 1H), 8.08 (d, J=12.0 Hz, 2H), 7.72 (d, J=8.0 Hz, 2H), 7.62 (t, J=8.0 Hz, 1H), 7.47 (d, J=8.0 Hz, 2H), 7.13 (d, J=8.0 Hz, 2H), 6.97-6.80 (m, 6H), 4.42-4.34 (m, 2H), 3.74-3.63 (m, 5H), 3.20-3.04 (m, 7H), 2.73-2.62 (m, 5H), 2.27-2.17 (m, 2H), 1.86-1.67 (m, 3H), 1.30-1.16 (m, 3H); $[M+H]^+$=862.3.

Example B13:7-(4-((1-(4-(2,4-dioxotetrahydropyrimidin-1(2H)-yl)phenyl)piperidin-4-yl)methyl)piperazin-1-yl)-2-(4-((3-fluoro-4-(trifluoromethyl)pyridin-2-yl)carbamoyl)phenyl)-9,10-dihydro-4H-benzo[d]pyrazolo[1,5-a][1,3]diazepine-3-carboxamide

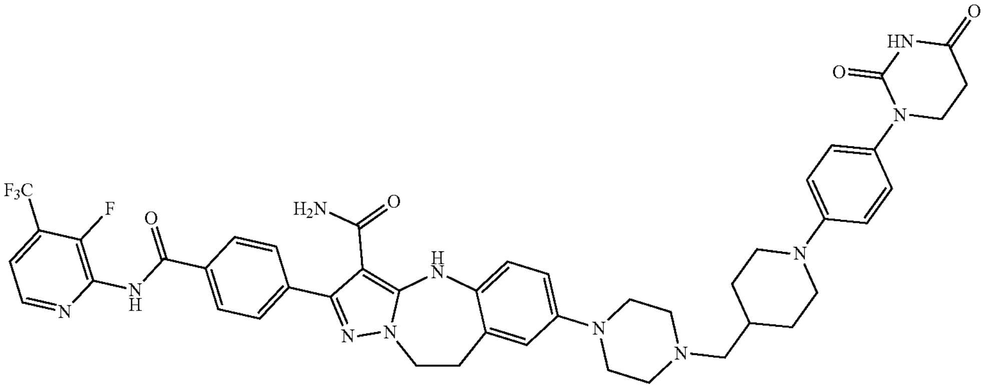 [SMILES: NC(=O)c1c(-c2ccc(C(=O)Nc3nccc(C(F)(F)F)c3F)cc2)nn2c1Nc1ccc(N3CCN(CC4CCN(c5ccc(N6CCC(=O)NC6=O)cc5)CC4)CC3)cc1CC2]

The titled compound was synthesized in the procedures similar to Example B9. $^1H$ NMR (400 MHz, DMSO) δ 11.19 (s, 1H), 10.22 (s, 1H), 9.66 (s, 1H), 8.54 (s, 1H), 8.08 (d, J=8.0 Hz, 2H), 7.76 (s, 1H), 7.67 (d, J=8.0 Hz, 2H), 7.85 (d, J=12.0 Hz, 2H), 6.92-6.75 (m, 5H), 4.37-4.30 (m, 2H), 3.68-3.60 (m, 4H), 3.17-2.95 (m, 8H), 2.68-2.58 (m, 5H), 2.21-2.14 (m, 2H), 1.80-1.63 (m, 3H), 1.26-1.10 (m, 3H); $[M+H]^+$=880.3.

Example B14: 2-(3,5-difluoro-4-((4-(trifluoromethyl)pyridin-2-yl)carbamoyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

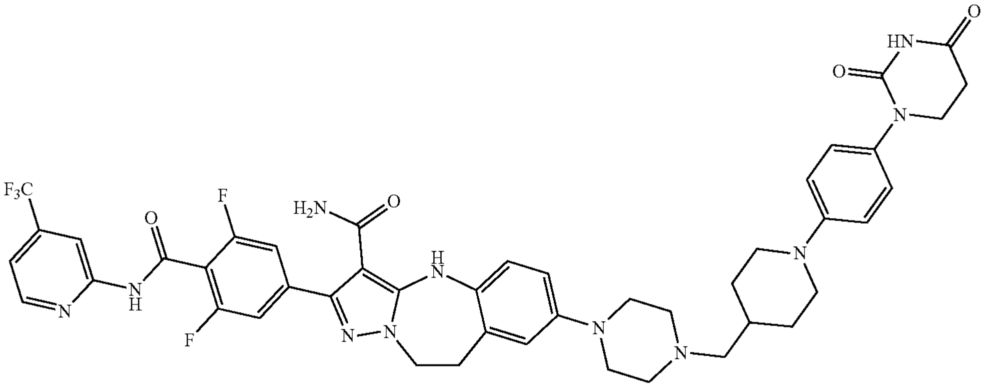 [SMILES: NC(=O)c1c(-c2cc(F)c(C(=O)Nc3cc(C(F)(F)F)ccn3)c(F)c2)nn2c1Nc1ccc(N3CCN(CC4CCN(c5ccc(N6CCC(=O)NC6=O)cc5)CC4)CC3)cc1CC2]

The titled compound was synthesized in the procedures similar to Example B9. $^{1}H$ NMR (400 MHz, DMSO) δ 11.84 (s, 1H), 10.25 (s, 1H), 9.62 (s, 1H), 8.68 (s, 1H), 8.50 (s, 1H), 7.60 (t, J=8.0 Hz, 1H), 7.37 (t, J=8.0 Hz, 2H), 7.13 (t, J=8.0 Hz, 2H), 6.97-6.80 (m, 6H), 4.41-4.34 (m, 2H), 3.72-3.65 (m, 4H), 3.19-3.06 (m, 8H), 2.72-2.63 (m, 5H), 2.26-2.18 (m, 2H), 1.85-1.67 (m, 3H), 1.22-1.18 (m, 4H); $[M+H]^{+}$=898.3.

Example B15: 7-(4-((1-(4-(2,4-dioxotetrahydropyrimidin-1(2H)-yl)phenyl)piperidin-4-yl)methyl)piperazin-1-yl)-2-(2-fluoro-3-methyl-4-((4-(trifluoromethyl)pyridin-2-yl)carbamoyl)phenyl)-9,10-dihydro-4H-benzo[d]pyrazolo[1,5-a][1,3]diazepine-3-carboxamide Step 1: 4-bromo-2-fluoro-3-methylaniline

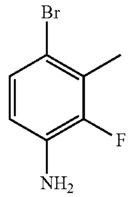

To a solution of 2-fluoro-3-methylaniline (11.5 g, 92 mmol) dissolved in ACN (170 mL) was added NBS (19.7 g, 110.4 mmol) at 0° C. The mixture was stirred at room temperature for 3 h. The mixture was washed by water and extracted with DCM. The organic layers were combined and dried over $Na_2SO_4$ and filtered. The filtrate was concentrated in vacuum. The residue was purified by silica gel column chromatography (PE: EtOAc=9:1) to afford the product (14.6 g, 78%). $[M+H]^{+}$=204.1.

Step 2: methyl 4-amino-3-fluoro-2-methylbenzoate

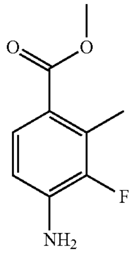

To a solution of 4-bromo-2-fluoro-3-methylaniline (10.2 g, 50 mmol), $Pd(dppf)Cl_2$ (1.83 g, 2.50 mmol) dissolved in MeOH (140 mL) was dropwise added $Et_3N$ (10.1 g, 100 mmol). The mixture was stirred at 90° C. for 16 h under CO atmosphere. The mixture was concentrated in vacuum. The mixture was washed by water and extracted with EtOAc. The organic layers were combined and dried over $Na_2SO_4$ and filtered. The filtrate was concentrated in vacuum. The residue was purified by silica gel column chromatography (PE: EtOAc=4:1) to afford the product (2.53 g, 28%). $[M+H]^{+}$=184.1.

Step 3: methyl 3-fluoro-2-methyl-4-(4,4,5,5-tetramethyl-1,3,2-dioxaborolan-2-yl)benzoate

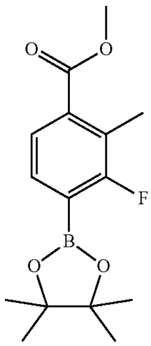 [SMILES: COC(=O)c1ccc(B2OC(C)(C)C(C)(C)O2)c(F)c1C]

To a solution of methyl 4-amino-3-fluoro-2-methylbenzoate (2.53 g, 13.8 mmol), tert-butyl nitrite (2.84 g, 27.6 mmol) and BPO (334 mg, 1.38 mmol) dissolved in ACN (70 mL) was added $(Bpin)_2$ (3.86 g, 15.2 mmol). The mixture was stirred at room temperature for 16 h. The mixture was concentrated in vacuum. The mixture was washed by water and extracted with EtOAc. The organic layers were combined, dried over $Na_2SO_4$ and filtered. The filtrate was concentrated in vacuum. The residue was purified by silica gel column chromatography (PE: EtOAc=12:1) to afford the product (1.83 g, 45%). $^{1}H$ NMR (500 MHz, $CDCl_3$) δ 7.67-7.53 (m, 2H), 3.90 (s, 3H), 2.47 (d, J=2.1 Hz, 3H), 1.37 (s, 12H).

Step 4: 4-(7-(4-((benzyloxy)carbonyl)piperazin-1-yl)-3-cyano-9,10-dihydro-4H-benzo[d]pyrazolo[1,5-a][1,3]diazepin-2-yl)-3-fluoro-2-methylbenzoic acid

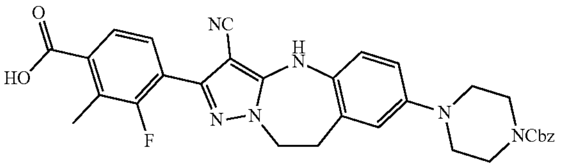 [SMILES: Cc1c(C(=O)O)ccc(-c2nn3c(c2C#N)Nc2ccc(N4CCN(C(=O)OCc5ccccc5)CC4)cc2CC3)c1F]

To a mixture of methyl 3-fluoro-2-methyl-4-(4,4,5,5-tetramethyl-1,3,2-dioxaborolan-2-yl)benzoate (300 mg, 1.02 mmol), benzyl 4-(2-bromo-3-cyano-9,10-dihydro-4H-benzo[d]pyrazolo[1,5-a][1,3]diazepin-6-yl)piperazine-1-carboxylate (506 mg, 1.02 mmol, made by the similar method of B5 step 7) and $Pd(PPh_3)_4$(116 mg, 0.1 mmol) dissolved in dioxane (20 mL)/$H_2O$ (8 mL) was added $Na_2CO_3$ (216 mg, 2.04 mmol). The mixture was stirred at 100° C. for 16 h. The mixture was washed by water and extracted with EtOAc. The organic layers were combined and dried over $Na_2SO_4$ and filtered. The filtrate was concentrated in vacuum. The residue was purified by silica gel column chromatography (PE: EtOAc=2:1) to afford the product (130 mg, 22%). $[M+H]^{+}$=581.1.

Step 5: benzyl 4-(3-cyano-2-(2-fluoro-3-methyl-4-((4-(trifluoromethyl)pyridin-2-yl)carbamoyl)phenyl)-9,10-dihydro-4H-benzo[d]pyrazolo[1,5-a][1,3]diazepin-7-yl)piperazine-1-carboxylate

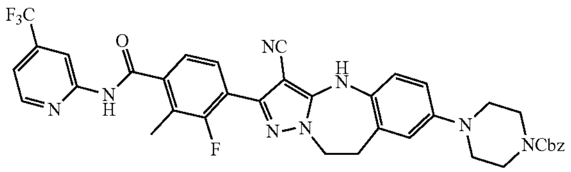 [SMILES: Cc1c(C(=O)Nc2cc(C(F)(F)F)ccn2)ccc(-c2nn3c(c2C#N)Nc2ccc(N4CCN(C(=O)OCc5ccccc5)CC4)cc2CC3)c1F]

To a mixture of 4-(7-(4-((benzyloxy)carbonyl)piperazin-1-yl)-3-cyano-9,10-dihydro-4H-benzo[d]pyrazolo[1,5-a][1,3]diazepin-2-yl)-3-fluoro-2-methylbenzoic acid (130 mg, 0.22 mmol) dissolved in DCM (5 mL) was dropwise added $POCl_3$ (168.3 mg, 1.1 mmol) and pyridine (174 mg, 2.2 mmol) at 0° C. The mixture was stirred at 0° C. for 2 h. Then, 4-(trifluoromethyl)pyridin-2-amine (36.3 mg, 0.22 mmol) in DCM (3 mL) was added. The mixture was stirred at room temperature overnight. Then the mixture was washed by water and extracted with DCM. The organic layers were combined and dried over $Na_2SO_4$. The mixture was filtered. The filtrate was concentrated in vacuum. The residue was purified by silica gel column chromatography (PE: EtOAc=1:3) to afford the product (60 mg, 38%). $[M+H]^+$=725.3.

Step 6: 4-(3-cyano-7-(piperazin-1-yl)-9,10-dihydro-4H-benzo[d]pyrazolo[1,5-a][1,3]diazepin-2-yl)-3-fluoro-2-methyl-N-(4-(trifluoromethyl)pyridin-2-yl)benzamide

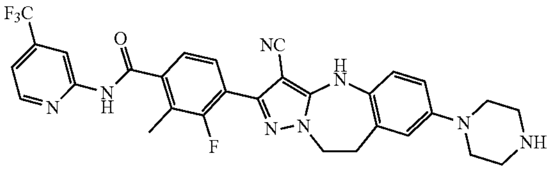 [SMILES: Cc1c(C(=O)Nc2cc(C(F)(F)F)ccn2)ccc(-c2nn3c(c2C#N)Nc2ccc(N4CCNCC4)cc2CC3)c1F]

A mixture of benzyl 4-(3-cyano-2-(2-fluoro-3-methyl-4-((4-(trifluoromethyl)pyridin-2-yl)carbamoyl)phenyl)-9,10-dihydro-4H-benzo[d]pyrazolo[1,5-a][1,3]diazepin-7-yl)piperazine-1-carboxylate (60 mg, 0.083 mmol) dissolved in MsOH (5 mL) was stirred at 100° C. for 3 h. Then, the mixture was cooled down to room temperature. The mixture was washed by water and extracted with EtOAc. The aqueous phase pH value was adjusted to 10 by saturated $NaHCO_3$ (aq.). The mixture was extracted with DCM. The organic layers were combined and dried over $Na_2SO_4$. The mixture was filtered and the filtrate was concentrated in vacuum to afford the product (25 mg, 51%). $[M+H]^+$=591.3.

Step 7: 7-(4-((1-(4-(2,4-dioxotetrahydropyrimidin-1(2H)-yl)phenyl)piperidin-4-yl)methyl)piperazin-1-yl)-2-(2-fluoro-3-methyl-4-((4-(trifluoromethyl)pyridin-2-yl)carbamoyl)phenyl)-9,10-dihydro-4H-benzo[d]pyrazolo[1,5-a][1,3]diazepine-3-carboxamide

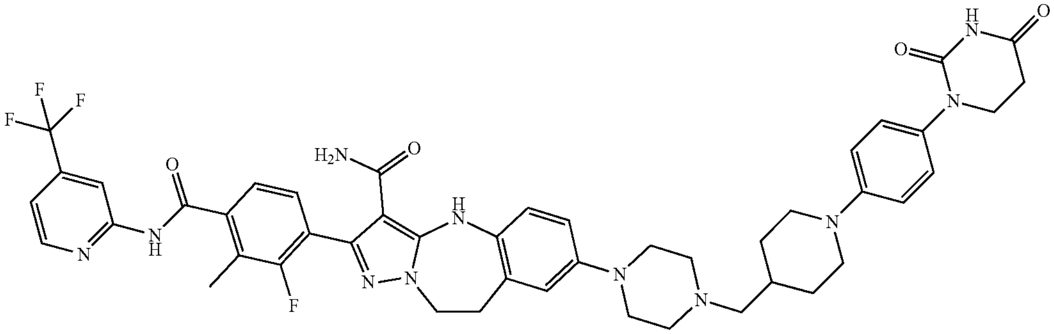 [SMILES: Cc1c(C(=O)Nc2cc(C(F)(F)F)ccn2)ccc(-c2nn3c(c2C(N)=O)Nc2ccc(N4CCN(CC5CCN(c6ccc(N7CCC(=O)NC7=O)cc6)CC5)CC4)cc2CC3)c1F]

To a mixture of 4-(3-cyano-7-(piperazin-1-yl)-9,10-dihydro-4H-benzo[d]pyrazolo[1,5-a][1,3]diazepin-2-yl)-3-fluoro-2-methyl-N-(4-(trifluoromethyl)pyridin-2-yl)benzamide (25 mg, 0.043 mmol) and 1-(4-(2,4-dioxotetrahydropyrimidin-1(2H)-yl)phenyl)piperidine-4-carbaldehyde (12.8 mg, 0.043 mmol) dissolved in DCM (6 mL) and MeOH (1 mL) was dropwise added AcOH (0.2 mL). The mixture was stirred at room temperature for 2 h. Then, $NaBH(OAc)_3$ (36 mg, 0.17 mmol) was added to the reaction. The mixture was stirred at room temperature for 0.5 h. The mixture was concentrated in vacuum. The residue was purified by Prep-HPLC to afford the product (25.1 mg, 17%). $^1H$ NMR (500 MHz, DMSO) δ 11.44 (s, 1H), 10.25 (s, 1H), 9.69 (s, 1H), 8.67 (s, 1H), 8.54 (s, 1H), 7.56 (s, 1H), 7.42 (d, J=17.3 Hz, 3H), 7.13 (d, J=8.7 Hz, 3H), 6.89 (dd, J=27.6 Hz, 10.5 Hz, 7H), 4.36 (s, 3H), 3.69 (d, J=6.8 Hz, 6H), 3.13 (d, J=27.7 Hz, 5H), 2.69 (d, J=7.0 Hz, 5H), 2.33 (s, 3H), 2.22 (s, 2H), 1.81 (d, J=12.7 Hz, 2H), 0.88 (d, J=23.5 Hz, 5H); $[M+H]^+$=894.8.

Example B16: 7-(4-((1-(4-(2,4-dioxotetrahydropyrimidin-1(2H)-yl)phenyl)piperidin-4-yl)methyl)piperazin-1-yl)-2-(4-((6-(trifluoromethyl)pyridin-2-yl)carbamoyl)phenyl)-9,10-dihydro-4H-benzo[d]pyrazolo[1,5-a][1,3]diazepine-3-carboxamide Step 1: tert-butyl 4-(3-cyano-2-(4-((6-(trifluoromethyl)pyridin-2-yl)carbamoyl)phenyl)-9,10-dihydro-4H-benzo[d]pyrazolo[1,5-a][1,3]diazepin-7-yl)piperazine-1-carboxylate

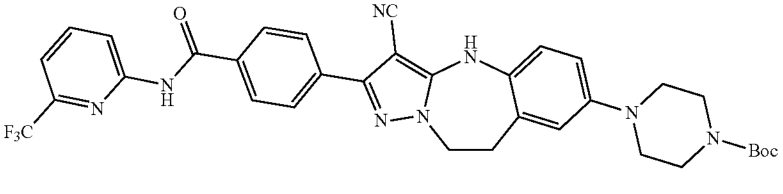 [SMILES: CC(C)(C)OC(=O)N1CCN(c2ccc3c(c2)CCn2nc(-c4ccc(C(=O)Nc5cccc(C(F)(F)F)n5)cc4)c(C#N)c2N3)CC1]

A mixture of tert-butyl 4-(3-cyano-2-(4-(methoxycarbonyl)phenyl)-9,10-dihydro-4H-benzo[d]pyrazolo[1,5-a][1,3]diazepin-7-yl)piperazine-1-carboxylate (0.2 g, 0.38 mmol), 6-(trifluoromethyl)pyridin-2-amine (123 mg, 0.76 mmol) and LiHMDS (1.9 mL, 1.9 mmol, 1.0 M) in THE (10 mL) was stirred at 78° C. for 5 hours in sealed tube under $N_2$. Then the mixture was extracted with dichloromethane (3×30 mL) and water (3×30 mL). The organic phase was dried over anhydrous sodium sulfate, filtered and concentrated under reduced pressure to afford the crude product, which was purified with silica gel column chromatography (PE:EA=80:20~50:50 gradient elution) to give the product (240 mg, 96.0%). $[M+H]^+$=659.6.

Step 2: 7-(piperazin-1-yl)-2-(4-((6-(trifluoromethyl)pyridin-2-yl)carbamoyl)phenyl)-9,10-dihydro-4H-benzo[d]pyrazolo[1,5-a][1,3]diazepine-3-carboxamide

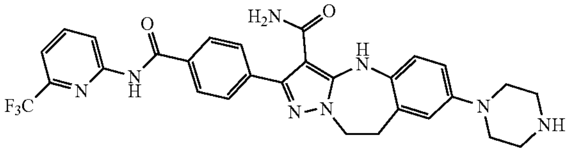 [SMILES: NC(=O)c1c(-c2ccc(C(=O)Nc3cccc(C(F)(F)F)n3)cc2)nn2c1Nc1ccc(N3CCNCC3)cc1CC2]

A mixture of tert-butyl 4-(3-cyano-2-(4-((6-(trifluoromethyl)pyridin-2-yl)carbamoyl)phenyl)-9,10-dihydro-4H-benzo[d]pyrazolo[1,5-a][1,3]diazepin-7-yl)piperazine-1-carboxylate (0.24 g, 0.365 mmol) in methanesulfonic acid (10.0 mL) was stirred at 100° C. for 1 hour. The mixture was then cooled, acidified with aqueous sodium hydroxide solution to pH 12 and extracted with dichloromethane (3×30 mL) and water (3×30 mL). The organic phase was dried over anhydrous sodium sulfate, filtered and concentrated under reduced pressure to afford the product (200 mg, crude). $[M+H]^+$=577.3.

Step 3: 7-(4-((1-(4-(2,4-dioxotetrahydropyrimidin-1(2H)-yl)phenyl)piperidin-4-yl)methyl)piperazin-1-yl)-2-(4-((6-(trifluoromethyl)pyridin-2-yl)carbamoyl)phenyl)-9,10-dihydro-4H-benzo[d]pyrazolo[1,5-a][1,3]diazepine-3-carboxamide

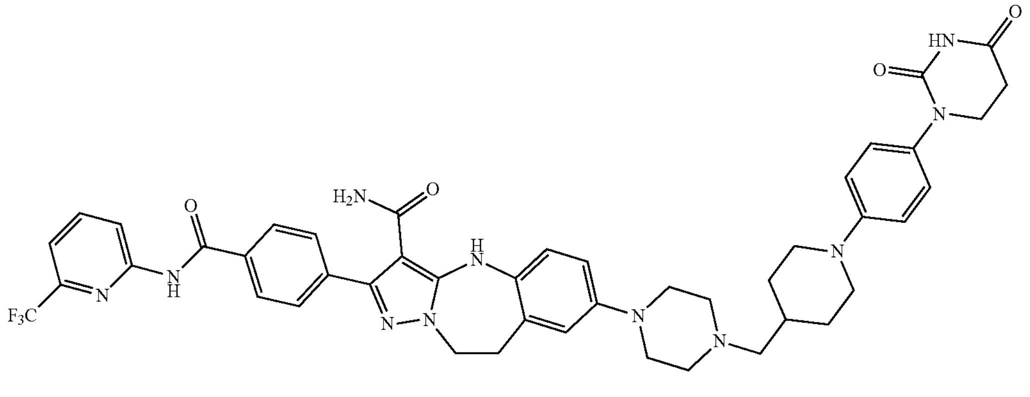 [SMILES: NC(=O)c1c(-c2ccc(C(=O)Nc3cccc(C(F)(F)F)n3)cc2)nn2c1Nc1ccc(N3CCN(CC4CCN(c5ccc(N6CCC(=O)NC6=O)cc5)CC4)CC3)cc1CC2]

A mixture of 7-(piperazin-1-yl)-2-(4-((6-(trifluoromethyl)pyridin-2-yl)carbamoyl)phenyl)-9,10-dihydro-4H-benzo[d]pyrazolo[1,5-a][1,3]diazepine-3-carboxamide (200 mg, 0.35 mmol) and 1-(4-(2,4-dioxotetrahydropyrimidin-1(2H)-yl)phenyl)piperidine-4-carbaldehyde (158 mg, 0.525 mmol) in MeOH (4.0 mL), DCM (16.0 mL) and acetic acid (0.3 mL) was stirred at room temperature for 16 hours, and then $NaBH(OAc)_3$ (371 mg, 1.75 mmol) was added and stirred at room temperature for 1 hours. The mixture was treated with water (30 mL), extracted with dichloromethane (3×30 mL), and washed with brine (30 mL). The organic phase was dried over anhydrous sodium sulfate, filtered and concentrated under reduced pressure to afford the crude product, which was purified with silica gel column chromatography (DCM: MeOH=100:0~85:15 gradient elution) to give the product (60 mg, 19.9%). $^1H$ NMR (400 MHz, DMSO) δ 11.29 (s, 1H), 10.26 (s, 1H), 9.71 (s, 1H), 8.47 (d, J=8.6 Hz, 1H), 8.14 (d, J=8.2 Hz, 3H), 7.67 (d, J=7.7 Hz, 3H), 7.13 (d, J=8.7 Hz, 2H), 6.86 (ddd, J=16.3, 14.7, 7.8 Hz, 5H), 4.38 (d, J=3.9 Hz, 2H), 3.74-3.65 (m, 4H), 3.17 (d, J=3.8 Hz, 2H), 3.08 (d, J=5.2 Hz, 4H), 2.67 (dd, J=13.7, 9.0 Hz, 4H), 2.51 (m, 4H), 2.22 (d, J=6.0 Hz, 2H), 1.81 (d, J=12.3 Hz, 2H), 1.73 (d, J=9.4 Hz, 1H), 1.23 (dd, J=22.2, 10.6 Hz, 2H); $[M+H]^+$=862.7.

Example B17: 7-(4-((1-(4-(2,4-dioxotetrahydropyrimidin-1(2H)-yl)phenyl)piperidin-4-yl)methyl)piperazin-1-yl)-2-(4-((5-(trifluoromethyl)pyridin-2-yl)carbamoyl)phenyl)-9,10-dihydro-4H-benzo[d]pyrazolo[1,5-a][1,3]diazepine-3-carboxamide

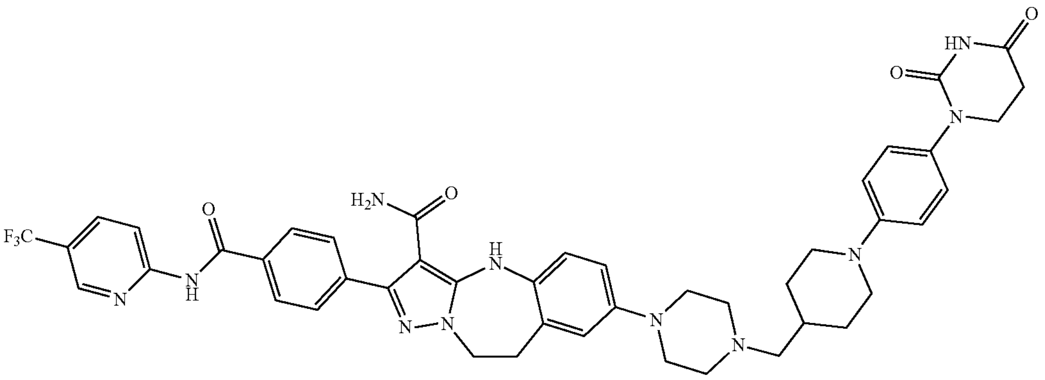 [SMILES: NC(=O)c1c(-c2ccc(C(=O)Nc3ccc(C(F)(F)F)cn3)cc2)nn2c1Nc1ccc(N3CCN(CC4CCN(c5ccc(N6CCC(=O)NC6=O)cc5)CC4)CC3)cc1CC2]

The titled compound was synthesized in the procedures similar to Example B16. $^1H$ NMR (400 MHz, DMSO) δ 11.35 (s, 1H), 10.26 (s, 1H), 9.70 (s, 1H), 8.80 (s, 1H), 8.43 (d, J=8.5 Hz, 1H), 8.27 (d, J=8.9 Hz, 1H), 8.14 (d, J=8.0 Hz, 2H), 7.69 (d, J=8.1 Hz, 2H), 7.13 (d, J=8.5 Hz, 2H), 6.89 (dd, J=30.0, 11.1 Hz, 5H), 4.38 (d, J=8.7 Hz, 2H), 3.69 (d, J=5.9 Hz, 4H), 3.17 (d, J=4.3 Hz, 2H), 3.13-3.06 (m, 4H), 2.79-2.55 (m, 8H), 2.25-2.19 (m, 2H), 1.82 (dd, J=17.8, 4.2 Hz, 2H), 1.75-1.66 (m, 1H), 1.25 (m, 2H); $[M+H]^+$=862.8.

Example B18:2-(4-((4-(difluoromethyl)pyridin-2-yl)carbamoyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

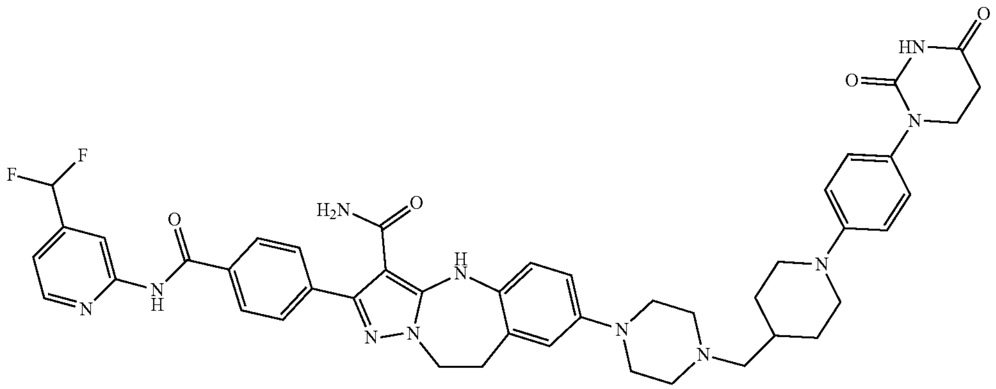 [SMILES: NC(=O)c1c(-c2ccc(C(=O)Nc3cc(C(F)F)ccn3)cc2)nn2c1Nc1ccc(N3CCN(CC4CCN(c5ccc(N6CCC(=O)NC6=O)cc5)CC4)CC3)cc1CC2]

The titled compound was synthesized in the procedures similar to Example B16. $^{1}H$ NMR (400 MHz, DMSO) δ 11.16 (s, 1H), 10.25 (s, 1H), 9.71 (s, 1H), 8.57 (d, J=4.8 Hz, 1H), 8.43 (s, 1H), 8.14 (d, J=8.3 Hz, 2H), 7.68 (d, J=8.3 Hz, 2H), 7.36 (d, J=4.7 Hz, 1H), 7.19-7.09 (m, 3H), 6.94-6.81 (m, 5H), 4.37 (s, 2H), 3.69 (t, J=6.6 Hz, 5H), 3.17 (d, J=2.3 Hz, 2H), 3.09 (d, J=0.7 Hz, 4H), 2.67 (dd, J=13.2, 9.6 Hz, 4H), 2.58-2.54 (m, 4H), 2.22 (d, J=6.1 Hz, 2H), 1.81 (d, J=12.5 Hz, 2H), 1.76-1.65 (m, 1H), 1.28-1.15 (m, 2H); $[M+H]^+$=844.7.

Example B19:7-(4-((1-(4-(2,4-dioxotetrahydropyrimidin-1(2H)-yl)phenyl)piperidin-4-yl)methyl)piperazin-1-yl)-2-(4-((6-methylpyridin-2-yl)carbamoyl)phenyl)-9,10-dihydro-4H-benzo[d]pyrazolo[1,5-a][1,3]diazepine-3-carboxamide

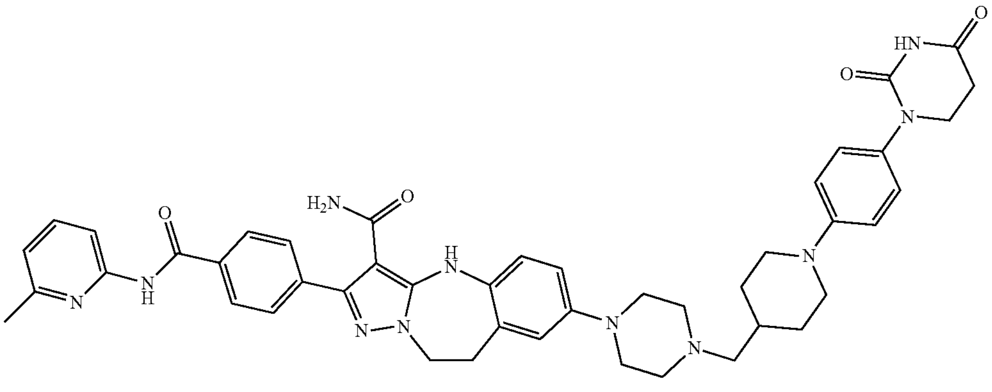 [SMILES: Cc1cccc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)cc2)n1]

The titled compound was synthesized in the procedures similar to Example B16. $^{1}H$ NMR (400 MHz, DMSO) δ 10.76 (s, 1H), 10.25 (s, 1H), 9.71 (s, 1H), 8.12 (d, J=8.1 Hz, 2H), 8.02 (d, J=8.2 Hz, 1H), 7.73 (t, J=7.8 Hz, 1H), 7.65 (d, J=8.0 Hz, 2H), 7.13 (d, J=8.6 Hz, 2H), 7.04 (d, J=7.6 Hz, 1H), 6.93 (d, J=9.0 Hz, 2H), 6.85 (q, J=8.7 Hz, 3H), 4.37 (d, J=7.6 Hz, 2H), 3.69 (t, J=6.4 Hz, 4H), 3.16 (d, J=7.8 Hz, 2H), 3.09 (d, J=0.7 Hz, 4H), 2.72-2.63 (m, 4H), 2.60-2.51 (m, 4H), 2.46 (s, 3H), 2.22 (d, J=6.6 Hz, 2H), 1.81 (d, J=11.2 Hz, 2H), 1.72 (t, J=11.1 Hz, 1H), 1.27-1.17 (m, 2H); $[M+H]^+$=808.7.

Example B20:2-(2-chloro-4-((6-methylpyridin-2-yl)carbamoyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

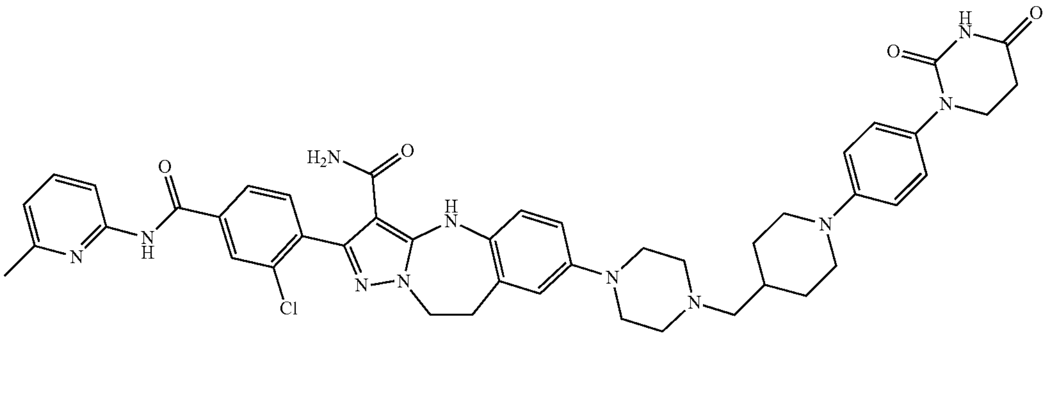 [SMILES: Cc1cccc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)c(Cl)c2)n1]

The titled compound was synthesized in the procedures similar to Example B16. $^1$H NMR (500 MHz, DMSO) 10.97 (d, J=3.1 Hz, 1H), 10.28 (d, J=3.4 Hz, 1H), 9.73 (d, J=2.9 Hz, 1H), 8.23 (d, J=1.9 Hz, 1H), 8.06 (dd, J=7.9, 2.0 Hz, 1H), 8.01 (dd, J=8.1, 3.1 Hz, 1H), 7.75 (td, J=8.0, 3.7 Hz, 1H), 7.60 (dd, J=7.9, 3.7 Hz, 1H), 7.14 (dd, J=8.8, 3.5 Hz, 2H), 7.06 (dd, J=7.5, 3.2 Hz, 1H), 6.93 (dd, J=8.8, 3.3 Hz, 2H), 6.91-6.86 (m, 2H), 6.84 (d, J=8.3 Hz, 1H), 4.37 (d, J=4.8 Hz, 2H), 3.69 (dd, J=6.7, 3.6 Hz, 4H), 3.17 (d, J=4.3 Hz, 2H), 3.10 (s, 4H), 2.71-2.61 (m, 4H), 2.53-2.49 (m, 4H), 2.47 (d, J=3.4 Hz, 3H), 2.22 (d, J=3.8 Hz, 2H), 1.81 (d, J=12.5 Hz, 2H), 1.73 (dd, J=17.4, 10.2 Hz, 1H), 1.23 (q, J=12.0 Hz, 2H); $[M+H]^+$=842.8.

Example B21:7-(4-((1-(4-(2,4-dioxotetrahydropyrimidin-1(2H)-yl)phenyl)piperidin-4-yl)methyl)piperazin-1-yl)-2-(3-methyl-4-((6-methylpyridin-2-yl)carbamoyl)phenyl)-9,10-dihydro-4H-benzo[d]pyrazolo[1,5-a][1,3]diazepine-3-carboxamide

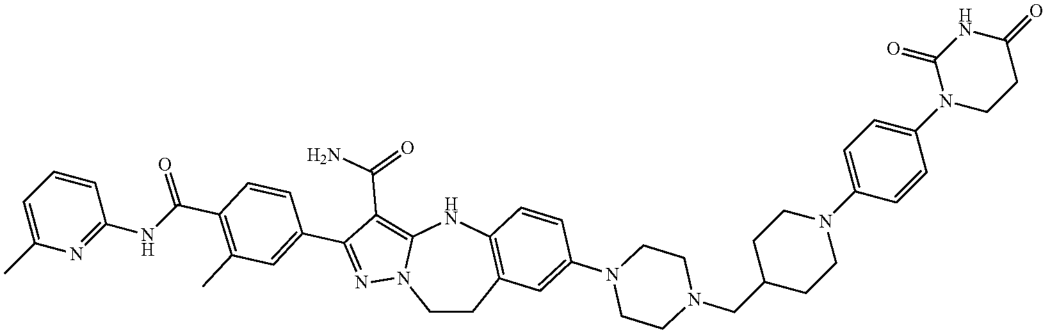

The titled compound was synthesized in the procedures similar to Example B16. $^1$H NMR (500 MHz, DMSO) δ 10.73 (s, 1H), 10.27 (s, 1H), 9.81 (s, 1H), 8.02 (d, J=7.5 Hz, 1H), 7.73 (t, J=7.5 Hz, 1H), 7.55 (d, J=7.4 Hz, 1H), 7.42 (s, 1H), 7.38 (d, J=6.9 Hz, 1H), 7.13 (d, J=8.0 Hz, 2H), 7.03 (d, J=7.2 Hz, 1H), 6.93 (d, J=8.1 Hz, 2H), 6.87 (s, 2H), 6.83 (d, J=7.5 Hz, 1H), 4.36 (d, J=2.1 Hz, 2H), 3.69 (d, J=7.0 Hz, 4H), 3.16 (d, J=3.9 Hz, 2H), 3.09 (s, 4H), 2.71-2.63 (m, 5H), 2.40 (d, J=17.5 Hz, 8H), 2.22 (d, J=5.9 Hz, 2H), 1.81 (d, J=12.6 Hz, 2H), 1.74-1.68 (m, 1H), 1.22 (dd, J=23.4, 12.9 Hz, 2H); $[M+H]^+$=822.5.

Example B22: 7-(4-((1-(4-(2,4-dioxotetrahydropyrimidin-1(2H)-yl)phenyl)piperidin-4-yl)methyl)piperazin-1-yl)-2-(2-methoxy-4-((6-methylpyridin-2-yl)carbamoyl)phenyl)-9,10-dihydro-4H-benzo[d]pyrazolo[1,5-a][1,3]diazepine-3-carboxamide

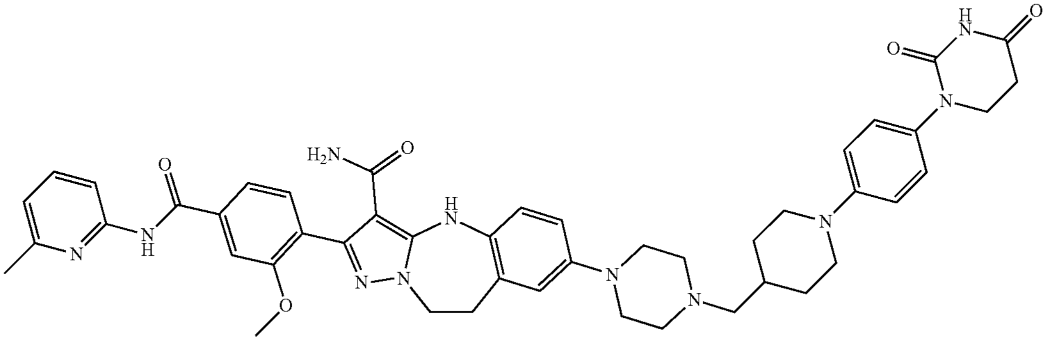 [SMILES: COc1cc(C(=O)Nc2cccc(C)n2)ccc1-c1nn2c(c1C(N)=O)Nc1ccc(N3CCN(CC4CCN(c5ccc(N6CCC(=O)NC6=O)cc5)CC4)CC3)cc1CC2]

The titled compound was synthesized in the procedures similar to Example B16. $^1H$ NMR (500 MHz, DMSO) δ 10.92 (s, 1H), 10.28 (s, 1H), 9.73 (s, 1H), 8.04 (d, J=8.2 Hz, 1H), 7.79 (s, 1H), 7.75 (t, J=7.9 Hz, 1H), 7.69 (d, J=8.6 Hz, 1H), 7.39 (d, J=7.8 Hz, 1H), 7.13 (d, J=8.8 Hz, 2H), 7.05 (d, J=7.5 Hz, 1H), 6.93 (d, J=8.9 Hz, 2H), 6.87 (d, J=8.2 Hz, 2H), 6.83 (d, J=8.6 Hz, 1H), 4.38-4.28 (m, 2H), 3.87 (s, 3H), 3.69 (t, J=6.7 Hz, 4H), 3.21-3.13 (m, 2H), 3.09 (s, 4H), 2.67 (dd, J=16.2, 9.4 Hz, 4H), 2.50 (s, 4H), 2.47 (s, 3H), 2.22 (d, J=6.8 Hz, 2H), 1.81 (d, J=11.7 Hz, 2H), 1.71 (dt, J=10.7, 6.1 Hz, 1H), 1.23 (t, J=16.3 Hz, 2H); $[M+H]^+$=838.9.

Example B23:2-(4-((4,6-dimethylpyridin-2-yl)carbamoyl)-3-methylphenyl)-7-(4-((1-(4-(2,4-dioxotetrahydropyrimidin-1(2H$_1$)-yl)phenyl)piperidin-4-yl)methyl)piperazin-1-yl)-9,10-dihydro-4H-benzo[d]pyrazolo[1,5a][1,3]diazepine-3-carboxamide

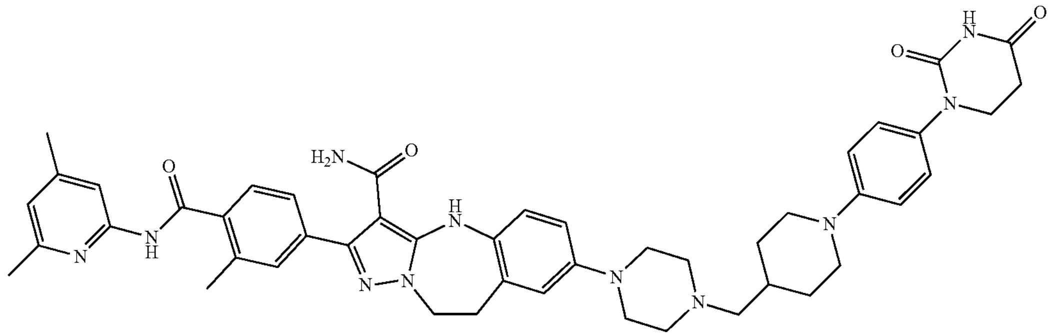 [SMILES: Cc1cc(C)nc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)cc2C)c1]

The titled compound was synthesized in the procedures similar to Example B16. $^1H$ NMR (500 MHz, DMSO) δ 10.65 (s, 1H), 10.27 (s, 1H), 9.81 (s, 1H), 7.90 (s, 1H), 7.53 (d, J 7.8 Hz, 1H), 7.42 (s, 1H), 7.38 (d, J=7.7 Hz, 1H), 7.13 (d, J=8.7 Hz, 2H), 6.93 (d, J=8.8 Hz, 2H), 6.87 (s, 3H), 6.84 (s, 1H)), 4.39-4.33 (m, 2H), 3.69 (t, J=6.7 Hz, 4H), 3.18-3.14 (m, 2H), 3.09 (s, 4H), 2.69-2.64 (m, 4H), 2.57-2.54 (i, 4H), 2.42 (s, 3H), 2.37 (s, 3H), 2.32 (s, 3H), 2.25-2.19 (i, 2H), 1.84-1.78 (i, 2H), 1.75-1.67 (m, 1H), 1.27-1.17 (m, 2H); [M+H], =836.6.

Example B24: 2-(2-chloro-4-((4-(trifluoromethyl)pyridin-2-yl)carbamoyl)phenyl)-7-(4-((1-(4-(2,4-dioxotetrahydropyrimidin-1(2H)-yl)phenyl)piperidin-4-yl)methyl)piperazin-1-yl)-9,10-dihydro-4-benzo[d]pyrazolo[1,5-a][1,3]diazepine-3-carboxamide

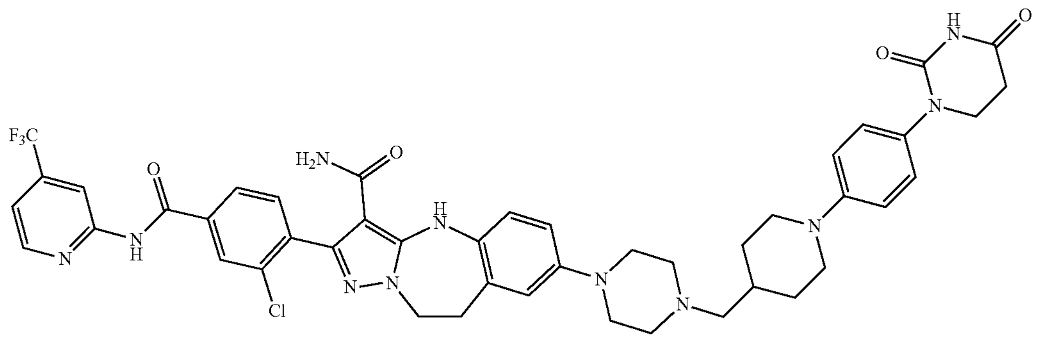 [SMILES: NC(=O)c1c(-c2ccc(C(=O)Nc3cc(C(F)(F)F)ccn3)cc2Cl)nn2c1Nc1ccc(N3CCN(CC4CCN(c5ccc(N6CCC(=O)NC6=O)cc5)CC4)CC3)cc1CC2]

The titled compound was synthesized in the procedures similar to Example B16. $^1$H NMR (500 MHz, DMSO) δ 11.53 (s, 1H), 10.27 (s, 1H), 9.72 (s, 1H), 8.71 (d, J=5.1 Hz, 1H), 8.54 (s, 1H), 8.26 (s, 1H), 8.08 (d, J=8.8 Hz, 1H), 7.64 (d, J=7.9 Hz, 1H), 7.58 (d, J=4.8 Hz, 1H), 7.13 (d, J=8.7 Hz, 2H), 6.93 (d, J=8.9 Hz, 2H), 6.89 (d, J=8.7 Hz, 2H), 6.84 (d, J=8.2 Hz, 1H), 4.42-4.33 (m, 2H), 3.69 (t, J=6.6 Hz, 4H), 3.22-3.15 (m, 2H), 3.09 (s, 4H), 2.67 (dd, J=15.9, 9.2 Hz, 4H), 2.51 (s, 4H), 2.22 (d, J=6.7 Hz, 2H), 1.81 (d, J=12.2 Hz, 2H), 1.76-1.69 (m, 1H), 1.28-1.17 (m, 2H); [M+H]$^+$=896.4.

Example B25:2-(3-chloro-4-((6-methylpyridin-2-yl)carbamoyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

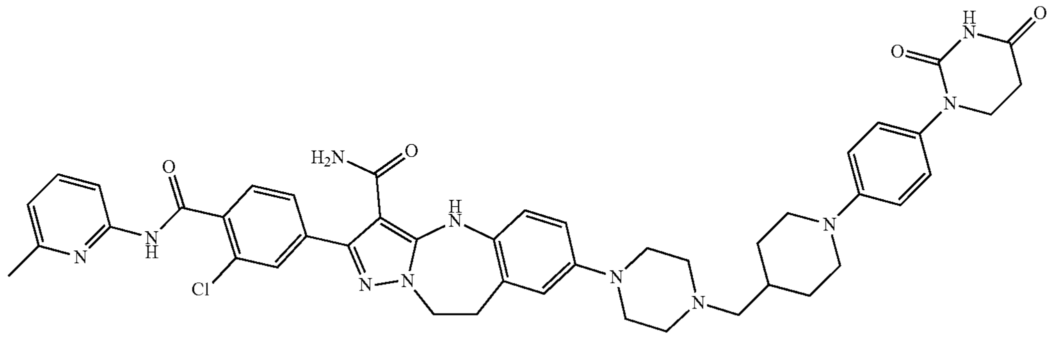 [SMILES: Cc1cccc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)cc2Cl)n1]

The titled compound was synthesized in the procedures similar to Example B16. $^1$H NMR (500 MHz, DMSO) δ 10.93 (s, 1H), 10.27 (s, 1H), 9.68 (s, 1H), 8.02 (d, J=7.2 Hz, 1H), 7.74 (t, J=7.8 Hz, 1H), 7.63 (d, J=7.1 Hz, 2H), 7.54 (d, J=8.1 Hz, 1H), 7.13 (d, J=8.8 Hz, 2H), 7.05 (d, J=7.5 Hz, 1H), 6.93 (d, J=8.9 Hz, 2H), 6.88 (d, J=8.8 Hz, 2H), 6.84-6.81 (m, 1H), 4.40-4.31 (m, 2H), 3.69 (t, J=6.7 Hz, 4H), 3.15 (d, J=4.1 Hz, 2H), 3.09 (s, 4H), 2.67 (dd, J=16.0, 9.3 Hz, 4H), 2.53-2.49 (m, 4H), 2.42 (s, 3H), 2.22 (d, J=7.0 Hz, 2H), 1.81 (d, J=11.5 Hz, 2H), 1.72 (d, J=9.6 Hz, 1H), 1.22 (dd, J=23.6, 12.4 Hz, 2H); [M+H]$^+$=842.4.

Example B26: 2-(3-chloro-4-((4-(trifluoromethyl)pyridin-2-yl)carbamoyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

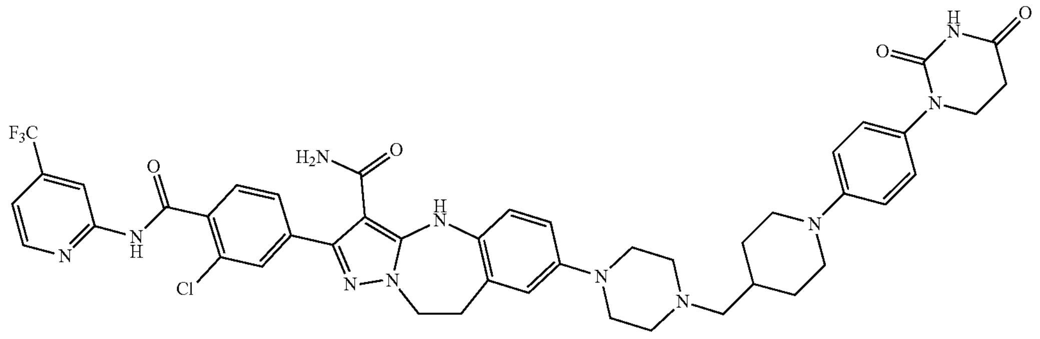 [SMILES: NC(=O)c1c(-c2ccc(C(=O)Nc3cc(C(F)(F)F)ccn3)c(Cl)c2)nn2c1Nc1ccc(N3CCN(CC4CCN(c5ccc(N6CCC(=O)NC6=O)cc5)CC4)CC3)cc1CC2]

The titled compound was synthesized in the procedures similar to Example B16. $^1$H NMR (500 MHz, DMSO) δ 11.55 (s, 1H), 10.26 (s, 1H), 9.68 (d, J=30.6 Hz, 1H), 8.67 (d, J=5.1 Hz, 1H), 8.53 (s, 1H), 7.71 (d, J=8.0 Hz, 1H), 7.67 (s, 1H), 7.59 (dd, J=11.2, 6.4 Hz, 2H), 7.14 (s, 2H), 6.94 (d, J=2.7 Hz, 6H), 4.38 (s, 2H), 3.69 (t, J=6.6 Hz, 4H), 3.16 (s, 4H), 3.09 (d, J=2.6 Hz, 2H), 2.72-2.65 (m, 4H), 2.53-2.49 (m, 5H), 2.22 (s, 1H), 1.81 (d, J=11.3 Hz, 2H), 1.72 (s, 1H), 1.26 (t, J=30.1 Hz, 2H); $[M+H]^+$=895.6.

Example B27: 7-(4-((1-(4-(2,4-dioxotetrahydropyrimidin-1(2H)-yl)phenyl)piperidin-4-yl)methyl)piperazin-1-yl)-2-(2-methoxy-4-((4-(trifluoromethyl)pyridin-2-yl)carbamoyl)phenyl)-9,10-dihydro-4H-benzo[d]pyrazolo[1,5-a][1,3]diazepine-3-carboxamide

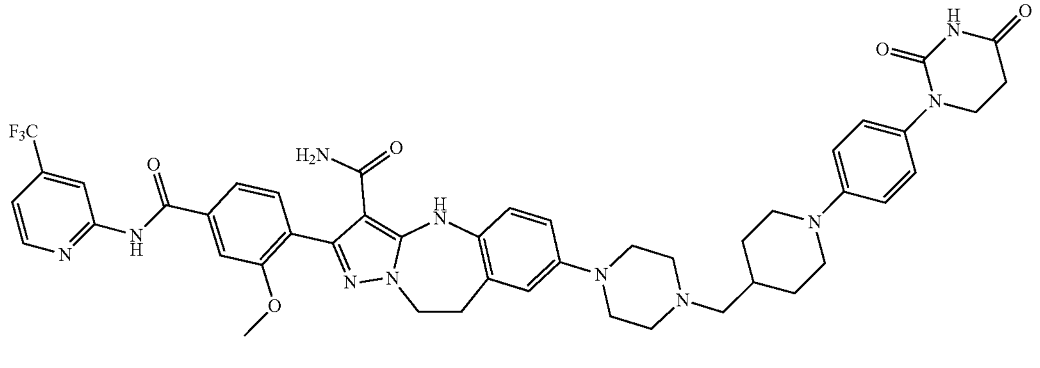 [SMILES: COc1cc(C(=O)Nc2cc(C(F)(F)F)ccn2)ccc1-c1nn2c(c1C(N)=O)Nc1ccc(N3CCN(CC4CCN(c5ccc(N6CCC(=O)NC6=O)cc5)CC4)CC3)cc1CC2]

The titled compound was synthesized in the procedures similar to Example B16. H NMR (500 MHz, DMSO) δ 11.47 (s, 1H), 10.26 (s, 1H), 9.72 (s, 1H), 8.70 (d, J=5.0 Hz, 1H), 8.57 (s, 1H), 7.82 (s, 1H), 7.72 (d, J=8.2 Hz, 1H), 7.57 (d, J=4.6 Hz, 1H), 7.43 (d, J=7.8 Hz, 1H), 7.13 (d, J=8.7 Hz, 2H), 6.93 (d, J=8.8 Hz, 2H), 6.87 (d, J=5.1 Hz, 2H), 6.83 (d, J=8.3 Hz, 1H), 4.34 (d, J=4.6 Hz, 2H), 3.87 (s, 3H), 3.69 (t, J=6.6 Hz, 4H), 3.19-3.14 (m, 2H), 3.08 (d, J=7.2 Hz, 4H), 2.67 (dd, J=15.4, 8.8 Hz, 4H), 2.53-2.49 (m, 4H), 2.22 (d, J=6.9 Hz, 2H), 1.81 (d, J=12.2 Hz, 2H), 1.71 (dt, J=15.8, 8.0 Hz, 1H), 1.22 (q, J=11.7 Hz, 2H); $[M+H]^+$=891.7.

Example B28:7-(4-((1-(4-(2,4-dioxotetrahydropyrimidin-1(2H)-yl)phenyl)piperidin-4-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

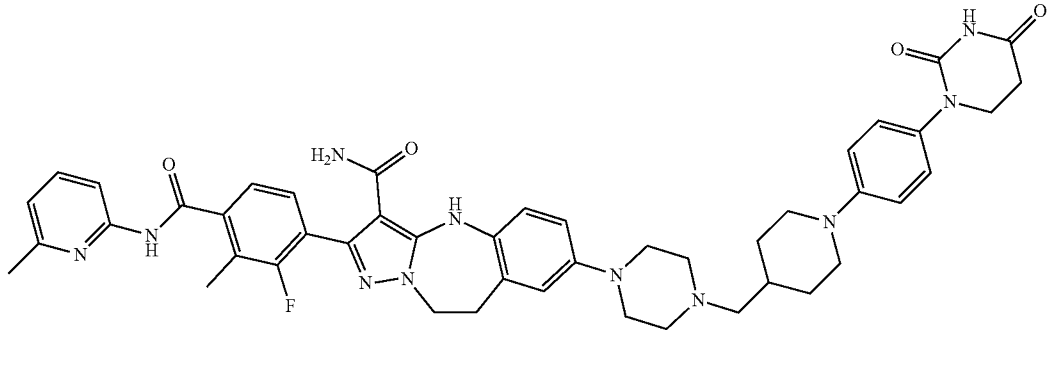 [SMILES: Cc1cccc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)c(F)c2C)n1]

The titled compound was synthesized in the procedures similar to Example B16. $^1$H NMR (500 MHz, DMSO) δ 10.84 (s, 1H), 10.27 (s, 1H), 9.72 (s, 1H), 8.02 (d, J=8.0 Hz, 1H), 7.74 (t, J=7.9 Hz, 1H), 7.40-7.32 (m, 2H), 7.13 (d, J=8.8 Hz, 2H), 7.05 (d, J=7.5 Hz, 1H), 6.93 (d, J=8.9 Hz, 2H), 6.88 (d, J=8.6 Hz, 2H), 6.83 (d, J=8.5 Hz, 1H), 4.44-4.32 (m, 2H), 3.69 (t, J=6.7 Hz, 4H), 3.17 (d, J=5.2 Hz, 2H), 3.12-3.04 (m, 4H), 2.69-2.64 (m, 4H), 2.55-2.51 (m, 4H), 2.42 (s, 3H), 2.30 (s, 3H), 2.22 (d, J=6.8 Hz, 2H), 1.81-1.79 (m, 2H) 1.76-1.69 (m, 1H), 1.25-1.19 (m, 2H); [M+H]$^+$=840.6.

Example B29:7-(4-((1-(4-(2,4-dioxotetrahydropyrimidin-1(2H)-yl)phenyl)piperidin-4-yl)methyl)piperazin-1-yl)-2-(2-fluoro-3-methyl-4-((6-methyl-4-(trifluoromethyl)pyridin-2-yl)carbamoyl)phenyl)-9,10-dihydro-4H-benzo[d]pyrazolo[1,5-a][1,3]diazepine-3-carboxamide

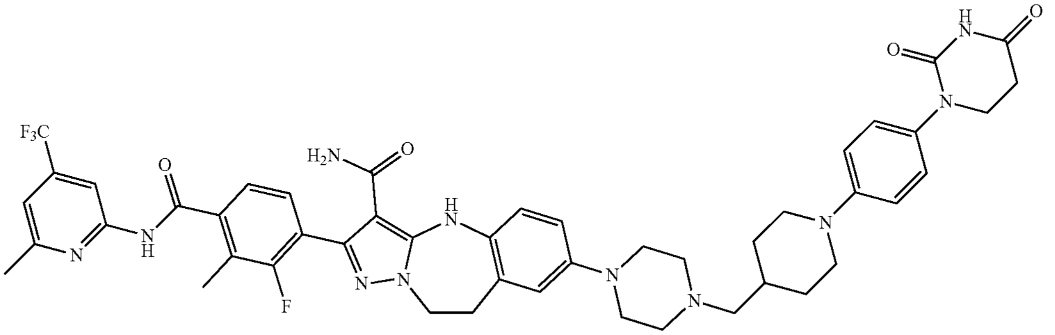 [SMILES: Cc1cc(C(F)(F)F)cc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)c(F)c2C)n1]

The titled compound was synthesized in the procedures similar to Example B16. $^1$H NMR (500 MHz, DMSO) δ 11.27 (s, 1H), 10.18 (s, 1H), 9.63 (s, 1H), 8.29 (s, 1H), 7.39 (s, 1H), 7.35 (d, J=7.9 Hz, 1H), 7.33-7.28 (m, 1H), 7.06 (d, J=8.9 Hz, 2H), 6.86 (d, J=9.1 Hz, 2H), 6.82 (d, J=8.8 Hz, 2H), 6.79-6.75 (m, 1H), 4.34-4.26 (m, 2H), 3.63-3.60 (m, 4H), 3.13-3.08 (m, 2H), 3.06-2.96 (m, 4H), 2.62-2.57 (m, 3H), 2.47 (s, 3H), 2.45-2.41 (m, 5H), 2.25 (s, 3H), 2.19-2.12 (m, 2H), 1.78-1.70 (m, 2H), 1.68-1.60 (m, 1H), 1.19-1.12 (m, 2H); [M+H]$^+$=908.5.

Example C1:7-(4-((1-(4-(2,4-dioxotetrahydropyrimidin-1(2H)-yl)phenyl)piperidin-4-yl)methyl)piperazin-1-yl)-2-(4-((2-methoxybenzamido)methyl)phenyl)-9,10-dihydro-4H-benzo[d]pyrazolo[1,5-a][1,3]diazepine-3-carboxamide Step 1: 2,5-dibromophenethyl 4-methylbenzenesulfonate

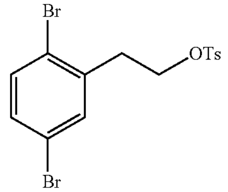 [SMILES: Cc1ccc(S(=O)(=O)OCCc2cc(Br)ccc2Br)cc1]

A mixture of 2-(2,5-dibromophenyl)ethan-1-ol (33.0 g, 118.7 mmol), 4-methylbenzenesulfonyl chloride (190.0 g, 178.0 mmol) and TEA (60.0 g, 593.5 mmol) in DCM (600 mL) was stirred in a round bottom flask at room temperature overnight. The mixture was treated with water (800 mL), extracted with dichloromethane (3×40 mL) and washed with brine (50 mL). The organic phase was dried over anhydrous sodium sulfate, filtered and concentrated under reduced pressure to afford the crude product, which was purified with silica gel column chromatography (PE:EA=100:0~60:40 gradient elution) to give the product (40.0 g, 78.1%). $^1$H NMR (400 MHz, DMSO) δ 7.63 (d, J=8.3 Hz, 2H), 7.50-7.45 (m, 2H), 7.40 (s, 1H), 7.38 (s, 1H), 7.36 (dd, J=8.5, 2.5 Hz, 1H), 4.27 (t, J=6.3 Hz, 2H), 3.01 (t, J=6.3 Hz, 2H), 2.41 (s, 3H).

Step 2: 2-methoxy-N-(4-(4,4,5,5-tetramethyl-1,3,2-dioxaborolan-2-yl)benzyl)benzamide

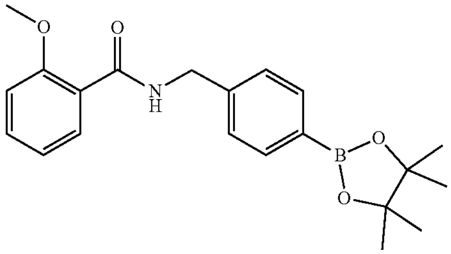

A mixture of (4-(4,4,5,5-tetramethyl-1,3,2-dioxaborolan-2-yl)phenyl)methanamine (2.56 g, 11.0 mmol), 2-methoxybenzoic acid (1.52 g, 10 mmol), T3P (4.77 g, 15.0 mmol) and DIPEA (6.45 g, 50.0 mmol) in THF (50.0 mL) was stirred in a round bottom flask at 70° C. for 14 hours. The mixture was treated with water (80 mL), extracted with dichloromethane (3×30 mL) and washed with brine (50 mL). The organic phase was dried over anhydrous sodium sulfate, filtered and concentrated under reduced pressure to afford the crude product, which was purified with silica gel column chromatography (PE:EA=100:0~60:40 gradient elution) to give the product (2.3 g, 62.6%). [M+H]$^+$=368.0.

Step 3: N-(4-(5-amino-4-cyano-1H-pyrazol-3-yl) benzyl)-2-methoxybenzamide

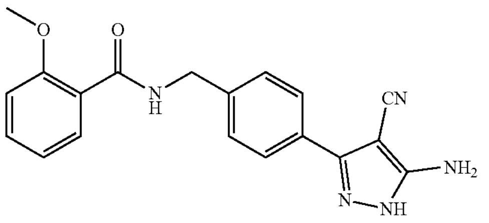 [SMILES: COc1ccccc1C(=O)NCc1ccc(-c2n[nH]c(N)c2C#N)cc1]

A mixture of 2-methoxy-N-(4-(4,4,5,5-tetramethyl-1,3,2-dioxaborolan-2-yl)benzyl)benzamide (2.3 g, 6.3 mmol), 5-amino-3-bromo-1H-pyrazole-4-carbonitrile (11.18 g, 6.3 mmol), Pd(dppf)$Cl_2$·DCM (514.0 mg, 0.63 mmol) and $K_2CO_3$ (1.74 g, 12.6 mmol) in 1,4-dioxane (30 mL) and $H_2O$ (10 mL) was stirred in a round bottom flask at 115° C. overnight under nitrogen. The mixture was evaporated in vacuum to give the crude product, which was purified with silica gel column chromatography (PE:EA=80:40~50:50 gradient elution) to give the product (1.0 g, 45.4%). $[M+H]^+$ =348.0.

Step 4: N-(4-(5-amino-4-cyano-1-(2,5-dibromophenethyl)-1H-pyrazol-3-yl)benzyl)-2-methoxybenzamide NC

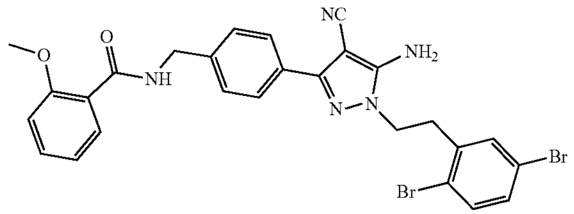 [SMILES: COc1ccccc1C(=O)NCc1ccc(-c2nn(CCc3cc(Br)ccc3Br)c(N)c2C#N)cc1]

A mixture of N-(4-(5-amino-4-cyano-1H-pyrazol-3-yl) benzyl)-2-methoxybenzamide (1.0 g, 2.9 mmol), 2,5-dibromophenethyl 4-methylbenzenesulfonate (1.9 g, 4.5 mmol) and potassium carbonate (1.2 g, 8.7 mmol) in DMF (20.0 mL) was stirred at 80° C. overnight under nitrogen. The mixture was evaporated in vacuum to give the crude product, which was purified with silica gel column chromatography (PE:EA=80:20~40:60 gradient elution) to give the product (1.1 g, 66.2%). $[M+H]^+$=608.0.

Step 5: N-(4-(7-bromo-3-cyano-9,10-dihydro-4H-benzo[d]pyrazolo[1,5-a][1,3]diazepin-2-yl)benzyl)-2-methoxybenzamide

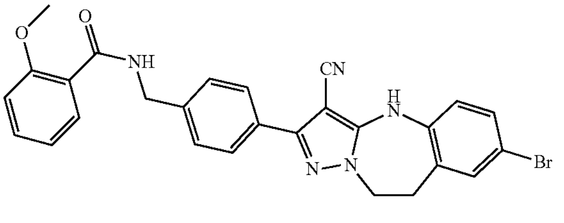 [SMILES: COc1ccccc1C(=O)NCc1ccc(-c2nn3c(c2C#N)Nc2ccc(Br)cc2CC3)cc1]

A mixture of N-(4-(5-amino-4-cyano-1-(2,5-dibromophenethyl)-1H-pyrazol-3-yl)benzyl)-2-methoxybenzamide (1.1 g, 1.8 mmol), (1S,2S)—N1,N2-dimethylcyclohexane-1,2-diamine (38 mg, 0.27 mmol), copper(I) iodide (51.3 mg, 0.27 mmol), potassium carbonate (745 mg, 5.4 mmol) in DMF (20.0 mL) was stirred at 90° C. overnight under nitrogen. The mixture was evaporated in vacuum to give the crude product, which was purified with silica gel column chromatography (PE:EA=80:20~40:60 gradient elution) to give the product (630 mg, 66.4%). $[M+H]^+$=528.0.

Step 6: tert-butyl 4-(3-cyano-2-(4-((2-methoxybenzamido)methyl)phenyl)-9,10-dihydro-4H-benzo[d] pyrazolo[1,5-a][1,3]diazepin-7-yl)piperazine-1-carboxylate

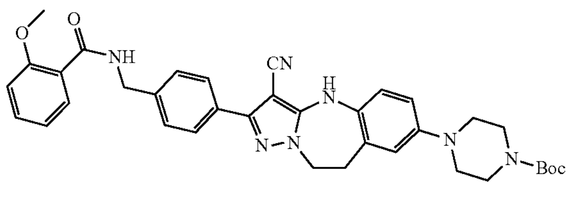 [SMILES: COc1ccccc1C(=O)NCc1ccc(-c2nn3c(c2C#N)Nc2ccc(N4CCN(C(=O)OC(C)(C)C)CC4)cc2CC3)cc1]

A mixture of N-(4-(7-bromo-3-cyano-9,10-dihydro-4H-benzo[d]pyrazolo[1,5-a][1,3]diazepin-2-yl)benzyl)-2-methoxybenzamide (630.0 mg, 1.2 mmol), tert-butyl piperazine-1-carboxylate (268 mg, 1.44 mmol), tris (dibenzylideneacetone)dipalladium (110 mg, 0.12 mmol), 2-dicyclohexylphosphino-2',6'-di-i-propoxy-1,1'-biphenyl (112.0 mg, 0.24 mmol) and sodium tert-butoxide (345.6 mg, 3.6 mmol) in PhMe (20.0 mL) was stirred in a round bottom flask at 110° C. overnight under nitrogen. The mixture was evaporated in vacuum to give the crude product, which was purified with silica gel column chromatography PE:EA=80:20~40:60 gradient elution) to give the product (420.0 mg, 55.3%). $[M+H]^+$=634.6.

Step 7: 2-(4-((2-methoxybenzamido)methyl)phenyl)-7-(piperazin-1-yl)-9,10-dihydro-4H-benzo[d] pyrazolo[1,5-al 1,3]diazepine-3-carboxamide

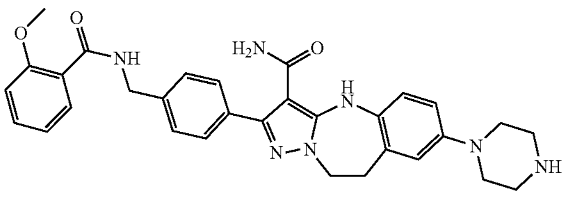 [SMILES: COc1ccccc1C(=O)NCc1ccc(-c2nn3c(c2C(N)=O)Nc2ccc(N4CCNCC4)cc2CC3)cc1]

A mixture of tert-butyl 4-(3-cyano-2-(4-((2-methoxybenzamido)methyl)phenyl)-9,10-dihydro-4H-benzo[d]pyrazolo [1,5-a][1,3]diazepin-7-yl)piperazine-1-carboxylate (420 mg, 0.66 mmol) in methanesulfonic acid (15.0 mL) was stirred at 70° C. for 2 hours. The mixture was then cooled, alkalified with aqueous sodium carbonate solution to pH 9 and the solid was filtered to afford the product (0.3 g, 82.5%). $[M+H]^+$=552.0.

Step 8: 7-(4-((1-(4-(2,4-dioxotetrahydropyrimidin-1(2H)-yl)phenyl)piperidin-4-yl)methyl)piperazin-1-yl)-2-(4-((2-methoxybenzamido)methyl)phenyl)-9,10-dihydro-4H-benzo[d]pyrazolo[1,5-a][1,3]diazepine-3-carboxamide

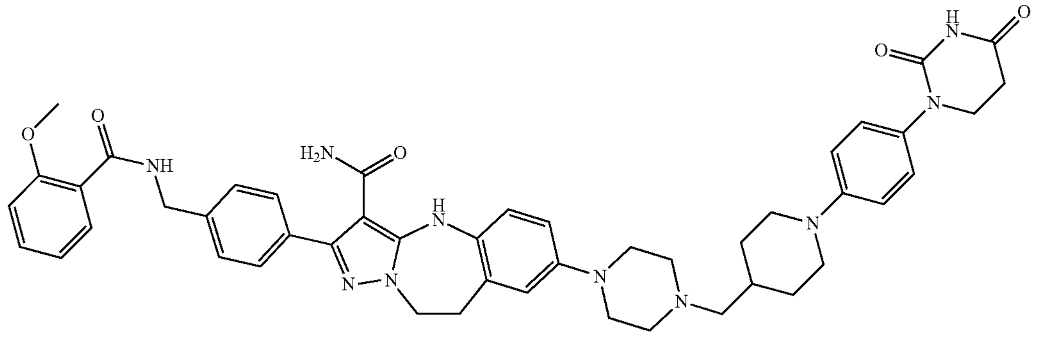 [SMILES: COc1ccccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1]

A mixture of 2-(4-((2-methoxybenzamido)methyl)phenyl)-7-(piperazin-1-yl)-9,10-dihydro-4H-benzo[d]pyrazolo[1,5-a][1,3]diazepine-3-carboxamide (0.22 g, 0.4 mmol) and 1-(4-(2,4-dioxotetrahydropyrimidin-1(2H)-yl)phenyl)piperidine-4-carbaldehyde (240.8 mg, 0.8 mmol) in MeOH/DCM(10.0/20.0 mL) and acetic acid (1.0 mL) was stirred at room temperature to 40° C. overnight, and then NaBH$(OAc)_3$ (424 mg, 2.0 mmol) was added and stirred at room temperature for 2 hours. The mixture was treated with water (50 mL), extracted with dichloromethane (3×40 mL), and washed with brine (50 mL). The organic phase was dried over anhydrous sodium sulfate, filtered and concentrated under reduced pressure to afford the crude product, which was purified by prep-HPLC (Anal. Column: Waters Xbridge C18, Column Temp.: Room temperature, Mobile Phase A: CAN (0.1% FA), Mobile Phase B: $H_2O$ (0.1% FA), Gradient Table: Mobile Phase A (20-90%), Time (min):0-17 min) to give the product (35 mg, 10.4%). $^1H$ NMR (400 MHz, DMSO) δ 10.26 (s, 1H), 9.77 (s, 1H), 8.77 (s, 1H), 7.76 (d, J=7.0 Hz, 1H), 7.46 (d, J=9.8 Hz, 5H), 7.17-7.10 (m, 3H), 7.04 (s, 1H), 6.93 (d, J=7.9 Hz, 2H), 6.86 (s, 3H), 4.57 (s, 2H), 4.34 (s, 2H), 3.90 (s, 3H), 3.69 (s, 4H), 3.12 (d, J=23.8 Hz, 7H), 2.68 (s, 6H), 2.23 (s, 2H), 1.81 (d, J=13.1 Hz, 4H), 1.24 (s, 2H); $[M+H]^+$=837.6.

Example C2: 7-(4-((1-(4-(2,4-dioxotetrahydropyrimidin-1(2H)-yl)phenyl)piperidin-4-yl)methyl)piperazin-1-yl)-2-(4-((2-methoxy-5-methylbenzamido)methyl)phenyl)-9,10-dihydro-4H-benzo[d]pyrazolo[1,5-a][1,3]diazepine-3-carboxamide Step 1: tert-butyl (4-bromobenzyl)carbamate

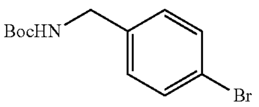 [SMILES: CC(C)(C)OC(=O)NCc1ccc(Br)cc1]

A mixture of (4-bromophenyl)methanamine (25.0 g, 134.4 mmol), di-tert-butyl dicarbonate (32.2 g, 147.9 mmol) and TEA (15.0 g, 147.9 mmol) in DCM (400 mL) was stirred at room temperature overnight. The mixture was treated with water (500 mL), extracted with dichloromethane (3×300 mL), and washed with brine (500 mL). The organic phase was dried over anhydrous sodium sulfate, filtered and concentrated under reduced pressure to afford the product (38.0 g, 99.2%). $^1H$ NMR (400 MHz, DMSO) δ 7.51 (d, J=8.3 Hz, 2H), 7.44 (d, J=6.1 Hz, 1H), 7.19 (d, J=8.3 Hz, 2H), 4.08 (d, J=6.2 Hz, 2H), 1.39 (s, 9H); [M-56]=229.9.

Step 2: tert-butyl (4-(4,455-tetramethyl-13,2-dioxaborolan-21)benzyl)carbamate

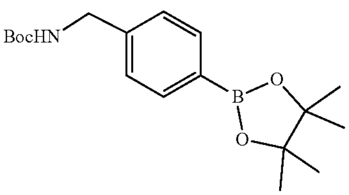 [SMILES: CC(C)(C)OC(=O)NCc1ccc(B2OC(C)(C)C(C)(C)O2)cc1]

A mixture of tert-butyl (4-bromobenzyl)carbamate (5.0 g, 17.5 mmol), 4,4,4',4',5,5,5',5'-octamethyl-2,2'-bi(1,3,2-dioxaborolane) (5.33 g, 21 mmol), Pd(dppf)$Cl_2$ (0.64 g, 0.875 mmol) and AcOK (5.1 g, 52.5 mmol) in 1,4-dioxane (30 mL) was stirred in a round bottom flask at 90° C. overnight under nitrogen. The mixture was evaporated in vacuum to give the crude product, which was purified with silica gel column chromatography (PE:EA=100:0~60:40 gradient elution) to give the product (5.2 g, 89.2%). $^1H$ NMR (400 MHz, DMSO) δ 7.77 (d, J=7.8 Hz, 2H), 7.33-7.22 (m, 2H), 4.33 (s, 2H), 1.46 (s, 9H), 1.34 (s, 12H); [M-56]+=278.0.

Step 3: tert-butyl (4-(5-amino-4-cyano-1H-pyrazol-3-yl)benzyl)carbamate

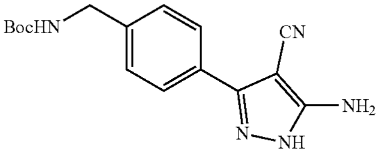 [SMILES: CC(C)(C)OC(=O)NCc1ccc(-c2n[nH]c(N)c2C#N)cc1]

A mixture of tert-butyl (4-(4,4,5,5-tetramethyl-1,3,2-dioxaborolan-2-yl)benzyl)carbamate (5.2 g, 15.6 mmol), 5-amino-3-bromo-1H-pyrazole-4-carbonitrile (2.92 g, 15.6 mmol), Pd(dppf)$Cl_2$·DCM (637.0 mg, 0.78 mmol) and $K_2CO_3$ (4.3 g, 31.2 mmol) in 1,4-dioxane (100 mL) and $H_2O$ (20 mL) was stirred in a round bottom flask at 100° C. overnight under nitrogen. The mixture was evaporated in vacuum to give the crude product, which was purified with silica gel column chromatography (PE:EA=80:40~50:50 gradient elution) to give the product (2.2 g, 45.1%). $[M+H]^+$ =314.0.

Step 4: tert-butyl (4-(5-amino-4-cyano-1-(2,5-dibromophenethyl)-1H-pyrazol-3-yl)benzyl)carbamate

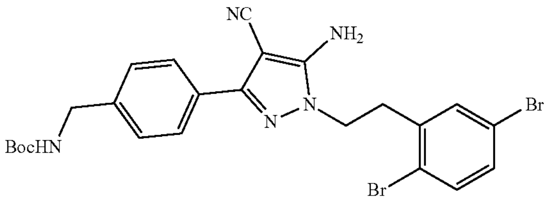 [SMILES: CC(C)(C)OC(=O)NCc1ccc(-c2nn(CCc3cc(Br)ccc3Br)c(N)c2C#N)cc1]

A mixture of tert-butyl (4-(5-amino-4-cyano-1H-pyrazol-3-yl)benzyl)carbamate (2.2 g, 7.03 mmol), 2,5-dibromophenethyl 4-methylbenzenesulfonate (4.55 g, 10.5 mmol) and $K_2CO_3$ (2.42 g, 17.6 mmol) in DMF (50.0 mL) was stirred at 80° C. overnight. The mixture was treated with water (80 mL), extracted with dichloromethane (3×40 mL), and washed with brine (50 mL). The organic phase was dried over anhydrous sodium sulfate, filtered and concentrated under reduced pressure to afford the crude product, which was purified with silica gel column chromatography (PE: EA=100:0~60:40 gradient elution) to give the product (2.5 g, 62.0%). $^1H$ NMR (400 MHz, DMSO) δ 7.66 (d, J=7.7 Hz, 2H), 7.55 (d, J=8.6 Hz, 2H), 7.44 (s, 1H), 7.38 (d, J=8.5 Hz, 1H), 7.30 (d, J=7.7 Hz, 2H), 6.75 (s, 2H), 4.17 (dd, J=15.1, 6.8 Hz, 4H), 3.13 (t, J=6.8 Hz, 2H), 1.40 (s, 9H); $[M+H]^+$ =574.0.

Step 5: tert-butyl (4-(7-bromo-3-cyano-9,10-dihydro-4H-benzo[d]pyrazolo[1,5-a][1,3]diazepin-2-yl)benzyl)carbamate

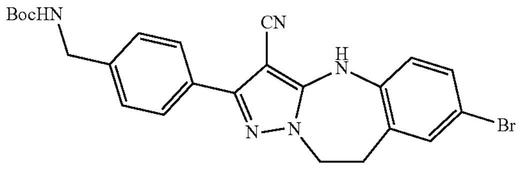 [SMILES: CC(C)(C)OC(=O)NCc1ccc(-c2nn3c(c2C#N)Nc2ccc(Br)cc2CC3)cc1]

A mixture of tert-butyl (4-(5-amino-4-cyano-1-(2,5-dibromophenethyl)-1H-pyrazol-3-yl)benzyl)carbamate (2.5 g, 4.4 mmol), (1S,2S)—N1,N2-dimethylcyclohexane-1,2-diamine (94 mg, 0.66 mmol), copper(I) iodide (125.4 mg, 0.66 mmol), potassium carbonate (1.8 g, 13.2 mmol) in DMF (30 mL) was stirred at 90° C. overnight under nitrogen. The mixture was evaporated in vacuum to give the crude product, which was purified with silica gel column chromatography (PE:EA=80:20~40:60 gradient elution) to give the product (1.8 g, 82.9%). $[M+H]^+$=494.0.

Step 6: 2-(4-(aminomethyl)phenyl)-7-bromo-9,10-dihydro-4H-benzo[d]pyrazolo[1,5-a][1,3]diazepine-3-carbonitrile hydrochloride

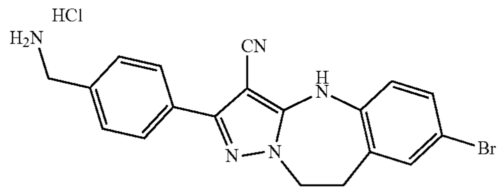 [SMILES: Cl ; N#Cc1c(-c2ccc(CN)cc2)nn2c1Nc1ccc(Br)cc1CC2]

A mixture of tert-butyl (4-(7-bromo-3-cyano-9,10-dihydro-4H-benzo[d]pyrazolo[1,5-a][1,3]diazepin-2-yl)benzyl)carbamate (1.8 g, 3.64 mmol) in HCl/1,4-dioxane (20.0 mL, 6 N) and DCM (10.0 mL) was stirred in a round bottom flask at room temperature for 2 hours. The solid was filtered to afford the product (1.5 g, 96.1%). $[M+H]^+$=394.0.

Step 7: N-(4-(7-bromo-3-cyano-9,10-dihydro-4H-benzo[d]pyrazolo[1,5-a][1,3]diazepin-2-yl)benzyl)-2-methoxy-5-methylbenzamide

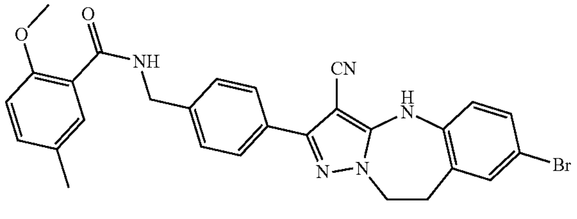 [SMILES: COc1ccc(C)cc1C(=O)NCc1ccc(-c2nn3c(c2C#N)Nc2ccc(Br)cc2CC3)cc1]

A mixture of 2-(4-(aminomethyl)phenyl)-7-bromo-9,10-dihydro-4H-benzo[d]pyrazolo[1,5-a][1,3]diazepine-3-carbonitrile hydrochloride (0.36 mg, 0.84 mmol), 2-methoxy-5-methylbenzoic acid (166 mg, 1.0 mmol), HATU (478.8 mg, 1.26 mmol) and DIPEA (325 mg, 2.52 mmol) in DMF (20.0 mL) was stirred in a round bottom flask at room temperature overnight. Then the mixture was evaporated in vacuum to afford the crude product, which was washed with MeOH to give the product (0.3 g, 66.0%). $^1H$ NMR (400 MHz, DMSO) δ 9.75 (s, 1H), 8.72 (s, 1H), 7.78 (d, J=7.6 Hz, 2H), 7.57 (s, 1H), 7.41 (dd, J=17.6, 9.0 Hz, 4H), 7.29 (d, J=8.3 Hz, 2H), 7.04 (d, J=8.2 Hz, 1H), 4.54 (s, 2H), 4.41 (s, 2H), 3.87 (s, 3H), 3.17 (s, 2H), 2.27 (s, 3H); $[M+H]^+$=542.0.

Step 8: tert-butyl 4-(3-cyano-2-(4-((2-methoxy-5-methylbenzamido)methyl)phenyl)-9,10-dihydro-4H-benzo[d]pyrazolo[1,5-a][1,3]diazepin-7-yl)piperazine-1-carboxylate

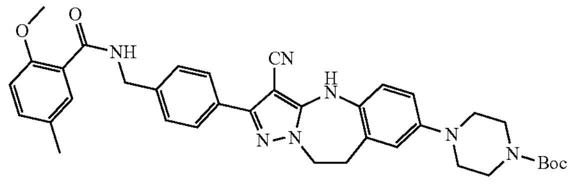 [SMILES: COc1ccc(C)cc1C(=O)NCc1ccc(-c2nn3c(c2C#N)Nc2ccc(N4CCN(C(=O)OC(C)(C)C)CC4)cc2CC3)cc1]

A mixture of N-(4-(7-bromo-3-cyano-9,10-dihydro-4H-benzo[d]pyrazolo[1,5-a][1,3]diazepin-2-yl)benzyl)-2-methoxy-5-methylbenzamide (0.3 g, 0.555 mmol), tert-butylpiperazine-1-carboxylate (154.8 mg, 0.834 mmol), BrettPhos Pd G4 (44.4 mg, 0.0555 mmol), BrettPhos (29.8 mg, 0.0555 mmol) and LiHMDS (1.4 mL, 2.775 mmol, 2.0 M) in THE (5.0 mL) was stirred at 75° C. for 3 hours in sealed tube. Then the mixture was evaporated in vacuum to afford the crude product, which was purified with silica gel column chromatography (PE:EA=80:20~30:70 gradient elution) to give the product (0.28 g, 78%). $[M+H]^+$=648.0.

Step 9: 2-(4-((2-methoxy-5-methylbenzamido)methyl)phenyl)-7-(piperazin-1-yl)-9,10-dihydro-4H-benzo[d]pyrazolo[1,5-a][1,3]diazepine-3-carboxamide

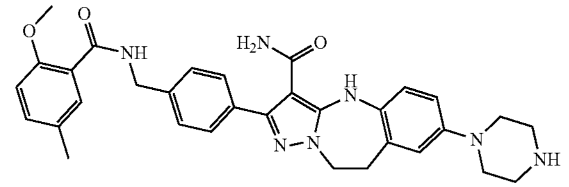 [SMILES: COc1ccc(C)cc1C(=O)NCc1ccc(-c2nn3c(c2C(N)=O)Nc2ccc(N4CCNCC4)cc2CC3)cc1]

A mixture of tert-butyl 4-(3-cyano-2-(4-((2-methoxy-5-methylbenzamido)methyl)phenyl)-9,10-dihydro-4H-benzo[d]pyrazolo[1,5-a][1,3]diazepin-7-yl)piperazine-1-carboxylate (0.28 g, 0.433 mmol) in methanesulfonic acid (15.0 mL) was stirred at 100° C. for 1.5 hours. The mixture was then cooled, acidified with aqueous sodium hydroxide solution to pH 12 and filtered to afford the product (0.22 g, 90%). $[M+H]^+$=566.6.

Step 10: 7-(4-((1-(4-(2,4-dioxotetrahydropyrimidin-1(2H)-yl)phenyl)piperidin-4-yl)methyl)piperazin-1-yl)-2-(4-((2-methoxy-5-methylbenzamido)methyl)phenyl)-9,10-dihydro-4H-benzo[d]pyrazolo[1,5-a][1,3]diazepine-3-carboxamide

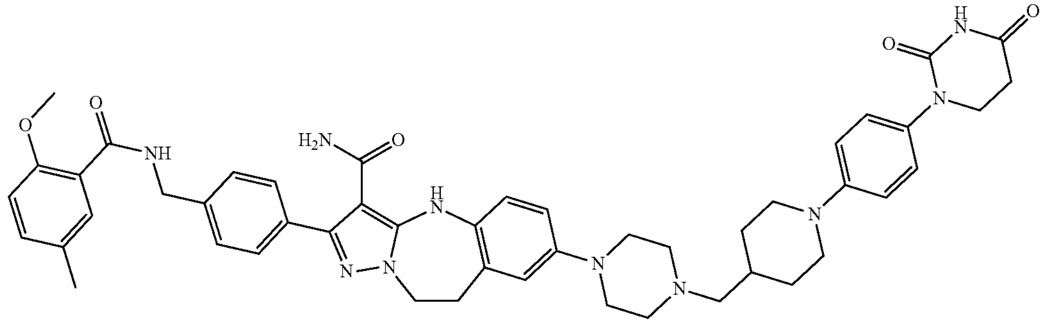 [SMILES: COc1ccc(C)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1]

A mixture of 2-(4-((2-methoxy-5-methylbenzamido)methyl)phenyl)-7-(piperazin-1-yl)-9,10-dihydro-4H-benzo[d]pyrazolo[1,5-a][1,3]diazepine-3-carboxamide (0.2 g, 0.354 mmol) and 1-(4-(2,4-dioxotetrahydropyrimidin-1(2H)-yl)phenyl)piperidine-4-carbaldehyde (128 mg, 0.425 mmol) in MeOH (4.0 mL), DCM (16.0 mL) and acetic acid (1.0 mL) was stirred at room temperature for 2 hours, and then $NaBH(OAc)_3$ (315 mg, 1.77 mmol) was added and stirred at room temperature for 2 hours. The mixture was treated with water (30 mL), extracted with dichloromethane (3×30 mL), and washed with brine (30 mL). The organic phase was dried over anhydrous sodium sulfate, filtered and concentrated under reduced pressure to afford the crude product, which was purified with silica gel column chromatography (DCM:MeOH=100:0~90:10 gradient elution), washed with MeOH and filtered to give the product (70 mg, 23.2%). $^1$H NMR (400 MHz, DMSO) δ 10.26 (s, 1H), 9.77 (s, 1H), 8.74 (s, 1H), 7.58 (s, 1H), 7.45 (d, J=12.1 Hz, 4H), 7.28 (d, J=7.4 Hz, 1H), 7.13 (d, J=8.6 Hz, 2H), 7.04 (d, J=8.3 Hz, 1H), 6.93 (d, J=8.4 Hz, 2H), 6.84 (d, J=10.7 Hz, 3H), 4.56 (s, 2H), 4.33 (s, 2H), 3.86 (s, 3H), 3.68 (d, J=6.7 Hz, 4H), 3.11 (d, J=23.1 Hz, 6H), 2.67 (d, J=5.6 Hz, 4H), 2.27 (s, 3H), 2.21 (s, 2H), 1.81 (d, J=12.0 Hz, 2H), 1.71 (s, 1H), 1.22 (d, J=11.1 Hz, 2H); $[M+H]^+$=851.0.

Example C3:7-(4-((1-(4-(2,4-dioxotetrahydropyrimidin-1(2H)-yl)phenyl)piperidin-4-yl)methyl)piperazin-1-yl)-2-(4-((5-fluoro-2-methoxybenzamido)methyl)phenyl)-9,10-dihydro-4H-benzo[d]pyrazolo[1,5-a][1,3]diazepine-3-carboxamide

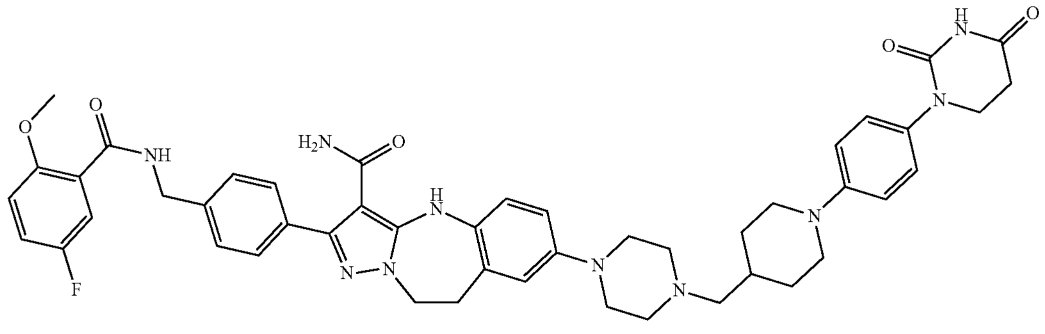 [SMILES: COc1ccc(F)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1]

The titled compound was synthesized in the procedures similar to Example C2. $^1$H NMR (400 MHz, DMSO) δ 10.26 (s, 1H), 9.77 (s, 1H), 8.87 (s, 1H), 7.46 (d, J=11.5 Hz, 5H), 7.35 (s, 1H), 7.19 (s, 1H), 7.13 (d, J=7.5 Hz, 2H), 6.93 (d, J=7.8 Hz, 2H), 6.86 (s, 3H), 4.57 (s, 2H), 4.34 (s, 2H), 3.89 (s, 3H), 3.70 (s, 4H), 3.14 (s, 2H), 3.09 (s, 4H), 2.68 (s, 4H), 2.52 (s, 4H), 2.22 (s, 2H), 1.81 (d, J=10.4 Hz, 2H), 1.71 (s, 1H), 1.22 (d, J=11.1 Hz, 2H); $[M+H]^+$=855.5.

Example C4: 7-(4-((1-(4-(2,4-dioxotetrahydropyrimidin-1(2H)-yl)phenyl)piperidin-4-yl)methyl)piperazin-1-yl)-2-(4-((2-methoxy-1-naphthamido)methyl)phenyl)-9,10-dihydro-4H-benzo[d]pyrazolo[1,5-a][1,3]diazepine-3-carboxamide

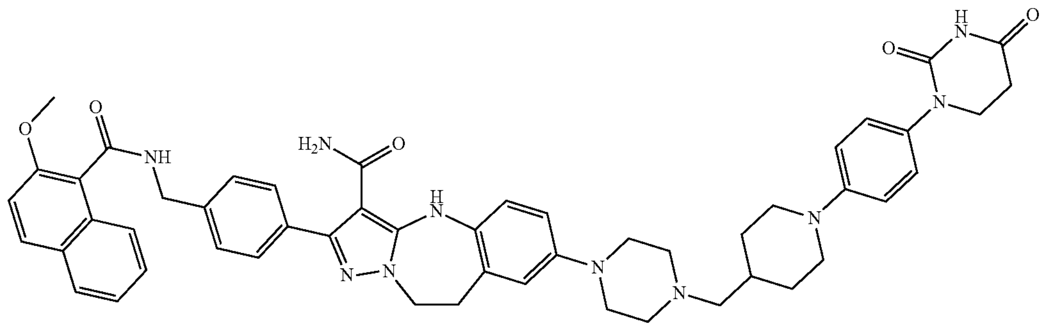 [SMILES: COc1ccc2ccccc2c1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1]

The titled compound was synthesized in the procedures similar to Example C2. $^1$H NMR (400 MHz, DMSO) δ 10.27 (s, 1H), 9.80 (s, 1H), 8.97 (s, 1H), 8.00 (d, J=9.6 Hz, 1H), 7.89 (s, 1H), 7.64 (s, 1H), 7.56 (s, 6H), 7.38 (s, 1H), 7.13 (d, J=7.8 Hz, 2H), 6.94 (s, 2H), 6.87 (s, 3H), 4.61 (s, 2H), 4.35 (s, 2H), 3.94 (s, 3H), 3.69 (s, 4H), 3.16 (s, 2H), 3.09 (s, 4H), 2.67 (s, 4H), 2.52 (s, 4H), 2.22 (s, 2H), 1.80 (s, 2H), 1.75-1.67 (m, 1H), 1.24 (s, 2H); $[M+H]^+$=887.6.

Example C5: 7-(4-((1-(4-(2,4-dioxotetrahydropyrimidin-1(2H)-yl)phenyl)piperidin-4-yl)methyl)piperazin-1-yl)-2-(4-(1-(2-methoxybenzamido)ethyl)phenyl)-9,10-dihydro-4H-benzo[d]pyrazolo[1,5-a][1,3]diazepine-3-carboxamide

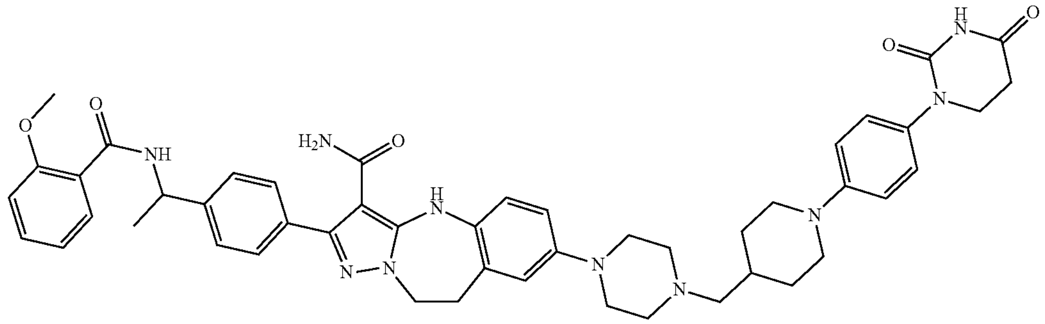 [SMILES: COc1ccccc1C(=O)NC(C)c1ccc(-c2nn3c(c2C(N)=O)Nc2ccc(N4CCN(CC5CCN(c6ccc(N7CCC(=O)NC7=O)cc6)CC5)CC4)cc2CC3)cc1]

The titled compound was synthesized in the procedures similar to Example C2. $^1$H NMR (400 MHz, DMSO) δ 10.27 (s, 1H), 9.78 (s, 1H), 8.54 (s, 1H), 7.63 (s, 1H), 7.51 (s, 5H), 7.14 (s, 3H), 7.03 (s, 1H), 6.91 (d, J=25.0 Hz, 5H), 5.20 (s, 1H), 4.34 (s, 2H), 3.90 (s, 3H), 3.69 (s, 4H), 3.12 (d, J=25.8 Hz, 6H), 2.68 (s, 5H), 2.22 (s, 1H), 1.84 (s, 2H), 1.50 (s, 3H), 1.23 (s, 6H); $[M+H]^+$=851.7.

Example C6: 2-(4-((5-chloro-2-methoxybenzamido)methyl)-3-methylphenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide Step 1:5-amino-3-bromo-1-(2,5-dibromophenethyl)-1H-pyrazole-4-carbonitrile

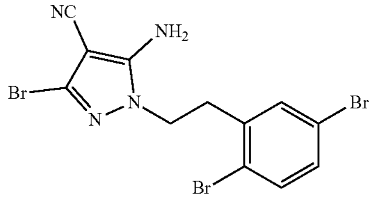 [SMILES: N#Cc1c(Br)nn(CCc2cc(Br)ccc2Br)c1N]

A mixture of 5-amino-3-bromo-1H-pyrazole-4-carbonitrile (20.0 g, 107 mmol), 2,5-dibromophenethyl 4-methylbenzenesulfonate (60.1 g, 139.2 mmol) and $K_2CO_3$ (29.6 g, 214 mmol) in DMF (300.0 mL) was stirred at 80° C. overnight. The mixture was treated with water (500 mL), extracted with dichloromethane (3×30 mL), and washed with brine (500 mL). The organic phase was dried over anhydrous sodium sulfate, filtered and concentrated under reduced pressure to afford the crude product, which was purified with silica gel column chromatography (DCM: MeOH=100:0~93:7 gradient elution) to give the product (8.0 g, 16.8%). $[M+H]^+$=448.0.

Step 2: 2,7-dibromo-9,10-dihydro-4H-benzo[d]pyrazolo[1,5-a][1,3]diazepine-3-carbonitrile

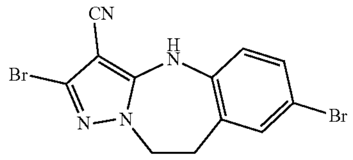 [SMILES: N#Cc1c(Br)nn2c1Nc1ccc(Br)cc1CC2]

A mixture of 5-amino-3-bromo-1-(2,5-dibromophenethyl)-1H-pyrazole-4-carbonitrile (8.0 g, 18 mmol), (1S,2S)—N1,N2-dimethylcyclohexane-1,2-diamine (383.4 mg, 2.7 mmol), copper(I) iodide (513 mg, 2.7 mmol), potassium carbonate (7.45 g, 54 mmol) in DMF (100 mL) was stirred at 95° C. overnight under nitrogen. The mixture was treated with water (300 mL) and filtered to give the crude product, which was purified with silica gel column chromatography (PE:EA=80:20~50:50 gradient elution) to give the product (2.2 g, 33.3%). $^1$H NMR (400 MHz, DMSO) δ 10.00 (s, 1H), 7.44 (s, 1H), 7.39 (d, J=8.5 Hz, 1H), 7.23 (d, J=8.4 Hz, 1H), 4.33 (s, 2H), 3.13 (s, 2H); $[M+H]^+$=367.0.

Step 3: benzyl 4-(2-bromo-3-cyano-9,10-dihydro-4H-benzo[d]pyrazolo[1,5-a][1,3]diazepin-7-yl)piperazine-1-carboxylate

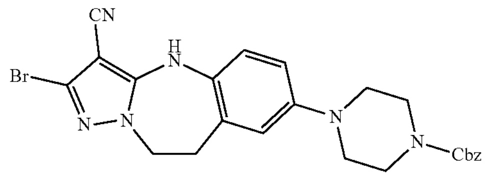 [SMILES: N#Cc1c(Br)nn2c1Nc1ccc(N3CCN(C(=O)OCc4ccccc4)CC3)cc1CC2]

A mixture of 2,7-dibromo-9,10-dihydro-4H-benzo[d]pyrazolo[1,5-a][1,3]diazepine-3-carbonitrile (1.6 g, 4.37 mmol), tert-butyl piperazine-1-carboxylate (1.44 g, 6.56 mmol), BrettPhos Pd G4 (349 mg, 0.437 mmol), BrettPhos (235 mg, 0.437 mmol) and LiHMDS (11 mL, 22 mmol, 2.0 M) in THE (10.0 mL) was stirred at 75° C. for 6 hours in sealed tube. Then the mixture was evaporated in vacuum to afford the crude product, which was purified with silica gel column chromatography (PE:EA=80:20~50:50 gradient elution) to give the product (350 mg, 15.9%). $^1$H NMR (400 MHz, DMSO) δ 9.64 (s, 1H), 7.35 (d, J=15.9 Hz, 5H), 7.15 (d, J=8.8 Hz, 1H), 6.84 (d, J=13.2 Hz, 2H), 5.11 (s, 2H), 4.28 (s, 2H), 3.53 (s, 4H), 3.06 (s, 6H); $[M+H]^+$=507.0.

Step 4: benzyl 4-(2-(4-(((tert-butoxycarbonyl) amino)methyl)-3-methylphenyl)-3-cyano-9,10-dihydro-4H-benzo[d]pyrazolo[1,5-a][1,3]diazepin-7-yl)piperazine-1-carboxylate

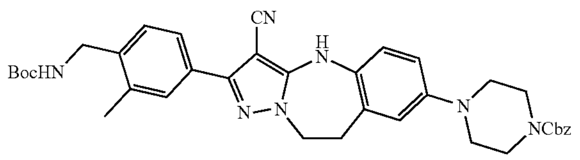 [SMILES: Cc1cc(-c2nn3c(c2C#N)Nc2ccc(N4CCN(C(=O)OCc5ccccc5)CC4)cc2CC3)ccc1CNC(=O)OC(C)(C)C]

A mixture of benzyl 4-(2-bromo-3-cyano-9,10-dihydro-4H-benzo[d]pyrazolo[1,5-a][1,3]diazepin-7-yl)piperazine-1-carboxylate (0.35 mg, 0.7 mmol), tert-butyl (2-methyl-4-(4,4,5,5-tetramethyl-1,3,2-dioxaborolan-2-yl)benzyl) carbamate (486 mg, 1.4 mmol), $Pd(PPh_3)_4$ (162.0 mg, 0.14 mmol) and $Na_2CO_3$ (1.75 mL, 3.5 mmol, 2 M) in 1,4-dioxane (15.0 mL) was stirred in a round bottom flask at 100° C. overnight under nitrogen. The mixture was evaporated in vacuum to give the crude product, which was purified with silica gel column chromatography (PE:EA=80:40~20:80 gradient elution) to give the product (445 mg, 98.4%). $[M+H]^+$=648.4.

Step 5: tert-butyl (4-(3-cyano-7-(piperazin-1-yl)-9,10-dihydro-4H-benzo[d]pyrazolo[1,5-a][1,3]diazepin-2-yl)-2-methylbenzyl)carbamate

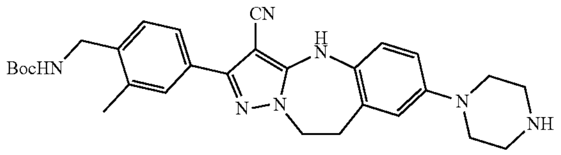 [SMILES: Cc1cc(-c2nn3c(c2C#N)Nc2ccc(N4CCNCC4)cc2CC3)ccc1CNC(=O)OC(C)(C)C]

A mixture of benzyl 4-(2-(4-(((tert-butoxycarbonyl) amino)methyl)-3-methylphenyl)-3-cyano-9,10-dihydro-4H-benzo[d]pyrazolo[1,5-a][1,3]diazepin-7-yl)piperazine-1-carboxylate (445 mg, 0.7 mmol) and Pd/C (0.1 g) in THE (20.0 mL) was stirred in a round bottom flask at room temperature overnight under $H_2$. The mixture was filtered and evaporated in vacuum to afford the product (0.24 g, 66.8%). $[M+H]^+$=514.0.

Step 6: tert-butyl (4-(3-cyano-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepin-2-yl)-2-methylbenzyl)carbamate

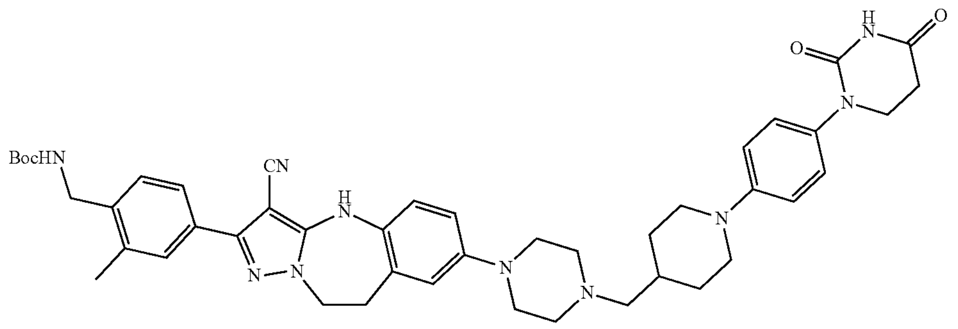 [SMILES: Cc1cc(-c2nn3c(c2C#N)Nc2ccc(N4CCN(CC5CCN(c6ccc(N7CCC(=O)NC7=O)cc6)CC5)CC4)cc2CC3)ccc1CNC(=O)OC(C)(C)C]

A mixture of tert-butyl (4-(3-cyano-7-(piperazin-1-yl)-9,10-dihydro-4H-benzo[d]pyrazolo[1,5-a][1,3]diazepin-2-yl)-2-methylbenzyl)carbamate (0.24 g, 0.47 mmol) and 1-(4-(2,4-dioxotetrahydropyrimidin-1(2H)-yl)phenyl)piperidine-4-carbaldehyde (212 mg, 0.7 mmol) in MeOH (5.0 mL), DCM (20.0 mL) and acetic acid (0.3 mL) was stirred at room temperature for 16 hours, and then $NaBH(OAc)_3$ (0.5 g, 2.35 mmol) was added and stirred at room temperature for 2 hours. The mixture was treated with water (30 mL), extracted with dichloromethane (3×30 mL), and washed with brine (30 mL). The organic phase was dried over anhydrous sodium sulfate, filtered and concentrated under reduced pressure to afford the crude product, which was purified with silica gel column chromatography (DCM:MeOH=100:0~90:10 gradient elution) to give the product (350 mg, 93.3%). $[M+H]^+$=799.8.

Step 7: 2-(4-(aminomethyl)-3-methylphenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

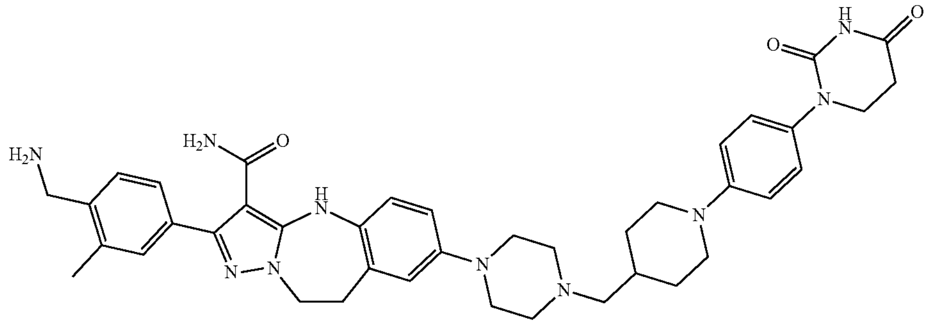 [SMILES: Cc1cc(-c2nn3c(c2C(N)=O)Nc2ccc(N4CCN(CC5CCN(c6ccc(N7CCC(=O)NC7=O)cc6)CC5)CC4)cc2CC3)ccc1CN]

A mixture of tert-butyl (4-(3-cyano-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepin-2-yl)-2-methylbenzyl)carbamate (0.35 g, 0.44 mmol) in methanesulfonic acid (10.0 mL) was stirred at 100° C. for 1 hour. The mixture was then cooled, alkalified with aqueous sodium carbonate solution to pH 9, extracted with dichloromethane (3×30 mL), and washed with brine (30 mL). The organic phase was dried over anhydrous sodium sulfate, filtered and concentrated under reduced pressure to afford the product (300 mg, 94.9%). $[M+H]^+$=717.0.

Step 8: 2-(4-((5-chloro-2-methoxybenzamido)methyl)-3-methylphenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

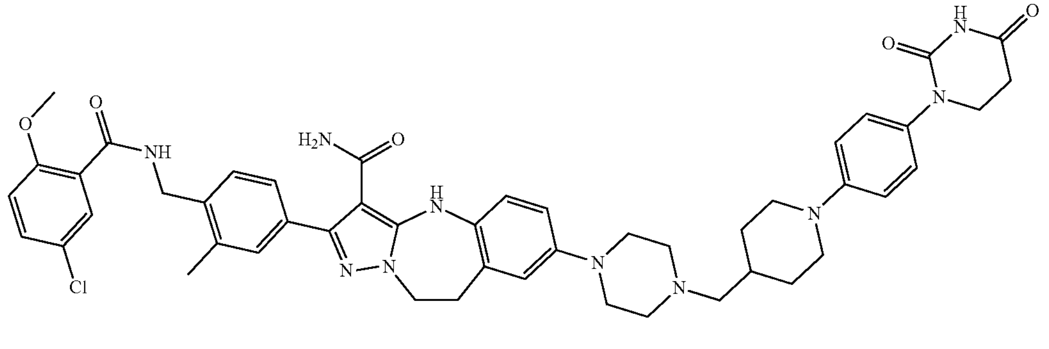 [SMILES: COc1ccc(Cl)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

A mixture of 2-(4-(aminomethyl)-3-methylphenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide (50 mg, 0.07 mmol), 5-chloro-2-methoxybenzoic acid (15.6 mg, 0.084 mmol), HATU (40 mg, 0.105 mmol) and DIPEA (27 mg, 0.21 mmol) in DMF (5.0 mL) was stirred in a round bottom flask at room temperature overnight. The mixture was evaporated in vacuum to afford the crude product, which was purified by prep-TLC (DCM:MeOH=7:1) to give the product (8 mg, 12.9%). $^1$H NMR (400 MHz, DMSO) δ 10.29 (s, 1H), 9.82 (s, 1H), 8.77 (s, 1H), 7.69 (s, 1H), 7.55 (s, 1H), 7.35 (s, 3H), 7.19 (d, J=33.0 Hz, 3H), 6.92 (d, J=29.7 Hz, 5H), 4.53 (s, 2H), 4.36 (s, 2H), 3.92 (s, 3H), 3.72 (s, 4H), 3.16 (s, 6H), 2.65 (d, J=43.2 Hz, 8H), 2.39 (s, 5H), 1.83 (s, 3H), 1.23-1.16 (m, 2H); $[M+H]^+$=885.5.

Example C7: 5-(tert-butyl)-N-(4-(3-carbamoyl-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepin-2-yl)-2-methylbenzyl)-1,2,4-oxadiazole-3-carboxamide

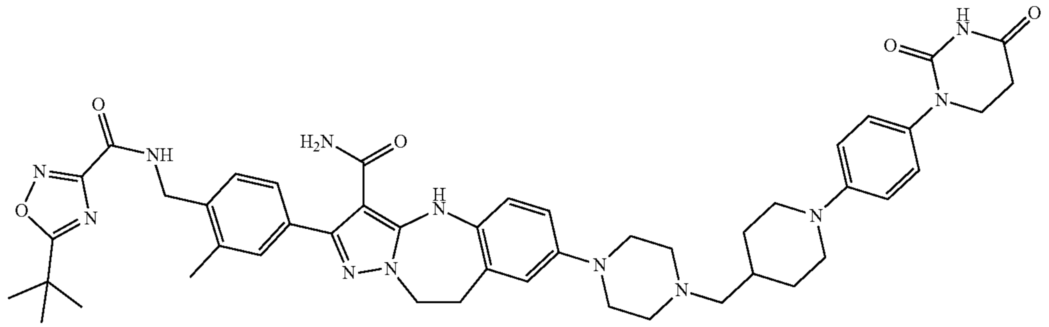 [SMILES: Cc1cc(-c2nn3c(c2C(N)=O)Nc2ccc(N4CCN(CC5CCN(c6ccc(N7CCC(=O)NC7=O)cc6)CC5)CC4)cc2CC3)ccc1CNC(=O)c1noc(C(C)(C)C)n1]

The titled compound was synthesized in the procedures similar to Example C6. $^1$H NMR (400 MHz, DMSO) δ 10.26 (s, 1H), 9.79 (s, 1H), 9.44 (s, 1H), 7.33 (s, 3H), 7.13 (d, J=8.2 Hz, 2H), 6.93 (d, J=7.7 Hz, 2H), 6.86 (s, 3H), 4.50 (s, 2H), 4.33 (s, 2H), 3.69 (s, 4H), 3.14 (s, 2H), 3.08 (s, 4H), 2.68 (s, 4H), 2.52 (s, 4H), 2.37 (s, 3H), 2.22 (s, 2H), 1.81 (d, J=12.1 Hz, 2H), 1.72 (s, 1H), 1.43 (s, 9H), 1.24 (s, 2H); $[M+H]^+$=869.8.

Example C8:3-(tert-butyl)-N-(4-(3-carbamoyl-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepin-2-yl)-2-methylbenzyl)-1,2,4-oxadiazole-5-carboxamide

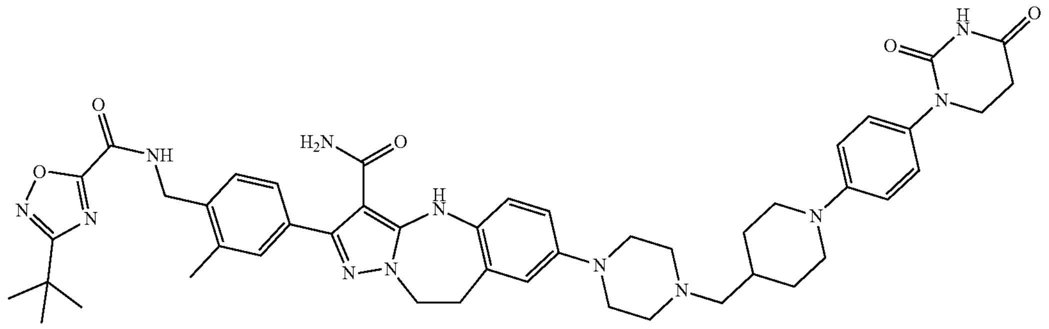 [SMILES: Cc1cc(-c2nn3c(c2C(N)=O)Nc2ccc(N4CCN(CC5CCN(c6ccc(N7CCC(=O)NC7=O)cc6)CC5)CC4)cc2CC3)ccc1CNC(=O)c1nc(C(C)(C)C)no1]

The titled compound was synthesized in the procedures similar to Example C6. $^1$H NMR (400 MHz, DMSO) δ 10.27 (s, 1H), 9.83 (s, 1H), 9.78 (s, 1H), 7.34 (s, 3H), 7.13 (s, 2H), 6.94 (s, 2H), 6.86 (s, 3H), 4.50 (s, 2H), 4.33 (s, 2H), 3.69 (s, 4H), 3.12 (d, J=16.0 Hz, 6H), 2.67 (s, 4H), 2.52 (s, 4H), 2.37 (s, 3H), 2.23 (s, 2H), 1.80 (s, 2H), 1.75-1.66 (m, 1H), 1.37 (s, 9H), 1.26 (s, 2H); [M+H]$^+$=869.5.

-

Example C9:2-(4-((1-(tert-butyl)-1H-pyrazole-3-carboxamido)methyl)-3-methylphenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

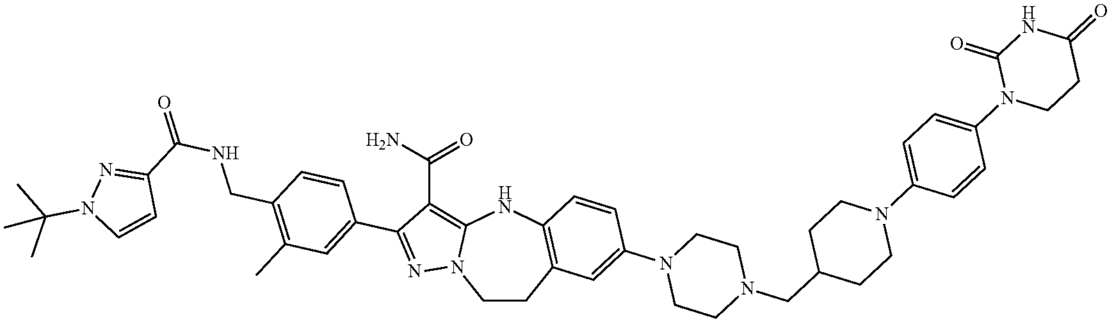 [SMILES: Cc1cc(-c2nn3c(c2C(N)=O)Nc2ccc(N4CCN(CC5CCN(c6ccc(N7CCC(=O)NC7=O)cc6)CC5)CC4)cc2CC3)ccc1CNC(=O)c1ccn(C(C)(C)C)n1]

The titled compound was synthesized in the procedures similar to Example C6. $^1$H NMR (400 MHz, DMSO) δ 10.23 (s, 1H), 9.75 (s, 1H), 8.44 (s, 1H), 7.89 (s, 1H), 7.28 (s, 3H), 7.10 (s, 2H), 6.85 (d, J=27.9 Hz, 5H), 6.64 (s, 1H), 4.44 (s, 2H), 4.30 (s, 2H), 3.66 (s, 4H), 3.09 (s, 6H), 2.64 (s, 8H), 2.34 (s, 5H), 1.77 (s, 3H), 1.53 (s, 9H), 1.31 (s, 2H); [M+H]$^+$=867.5.

Example C10:7-(4-((1-(4-(2,4-dioxotetrahydropyrimidin-1(2H)-yl)phenyl)piperidin-4-yl)methyl)piperazin-1-yl)-2-(4-((2-methoxy-1-naphthamido)methyl)-3-methylphenyl)-9,10-dihydro-4H-benzo[d]pyrazolo[1,5-a][1,3]diazepine-3-carboxamide

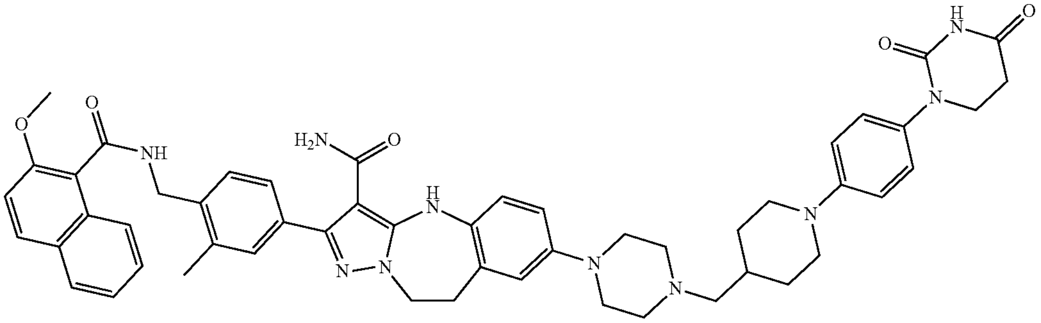 [SMILES: COc1ccc2ccccc2c1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

The titled compound was synthesized in the procedures similar to Example C6. $^1$H NMR (400 MHz, DMSO) δ 10.25 (s, 1H), 9.81 (s, 1H), 8.86 (s, 1H), 7.99 (s, 1H), 7.90 (s, 1H), 7.59 (s, 3H), 7.49 (s, 2H), 7.35 (s, 3H), 7.12 (s, 2H), 6.89 (d, J=23.6 Hz, 4H), 4.56 (s, 2H), 4.34 (s, 3H), 3.93 (s, 4H), 3.68 (s, 6H), 3.14 (s, 6H), 2.67 (s, 5H), 2.41 (s, 5H), 1.81 (s, 3H), 1.44 (s, 2H); [M+H]$^+$=901.6.

Example C11:7-(4-((1-(4-(2,4-dioxotetrahydropyrimidin-1(2H)-yl)phenyl)piperidin-4-yl)methyl)piperazin-1-yl)-2-(4-((2-methoxy-5-(trifluoromethyl)benzamido)methyl)-3-methylphenyl)-9,10-dihydro-4H-benzo[d]pyrazolo[1,5-a][1,3]diazepine-3-carboxamide

-

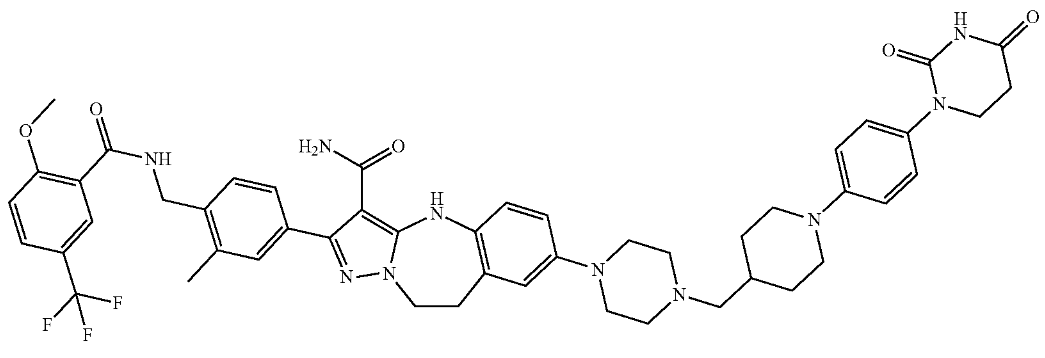 [SMILES: COc1ccc(C(F)(F)F)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

The titled compound was synthesized in the procedures similar to Example C6. $^1H$ NMR (400 MHz, DMSO) δ 10.26 (s, 1H), 9.79 (s, 1H), 8.80 (s, 1H), 7.98 (s, 1H), 7.85 (s, 1H), 7.36 (d, J=15.4 Hz, 4H), 7.13 (d, J=6.8 Hz, 2H), 6.93 (d, J=7.4 Hz, 2H), 6.86 (s, 3H), 4.53 (s, 2H), 4.33 (s, 2H), 3.98 (s, 3H), 3.70 (s, 4H), 3.14 (s, 2H), 3.09 (s, 4H), 2.68 (s, 7H), 2.38 (s, 4H), 2.22 (s, 2H), 1.81 (d, J=11.4 Hz, 2H), 1.75-1.67 (m, 1H), 1.23-1.17 (m, 2H); $[M+H]^+$=919.8.

Example C12: 3-(tert-butyl)-N-(4-(3-carbamoyl-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepin-2-yl)benzyl)-1,2,4-oxadiazole-5-carboxamide

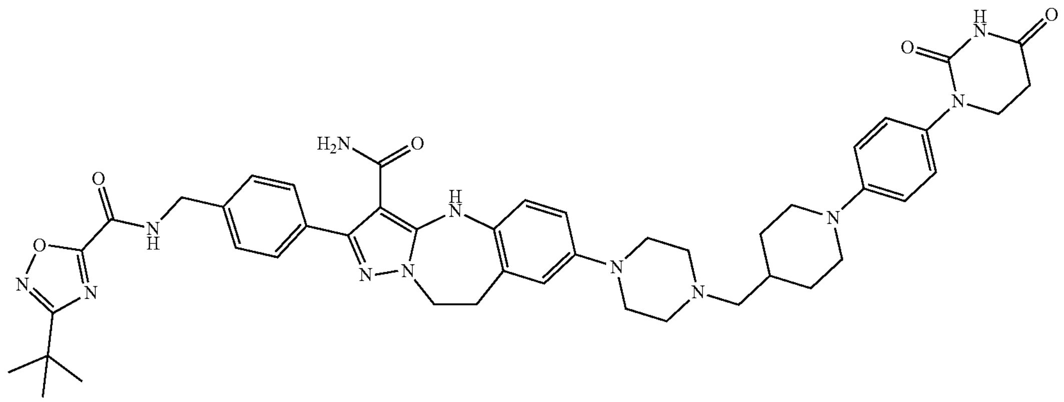 [SMILES: CC(C)(C)c1noc(C(=O)NCc2ccc(-c3nn4c(c3C(N)=O)Nc3ccc(N5CCN(CC6CCN(c7ccc(N8CCC(=O)NC8=O)cc7)CC6)CC5)cc3CC4)cc2)n1]

The titled compound was synthesized in the procedures similar to Example C6. $^1H$ NMR (400 MHz, DMSO) δ 10.26 (s, 1H), 9.91 (s, 1H), 9.74 (s, 1H), 8.05 (s, 1H), 7.45 (dd, J=19.2, 8.4 Hz, 4H), 7.11 (d, J=8.9 Hz, 2H), 6.91 (d, J=9.0 Hz, 2H), 6.85 (s, 3H), 4.50 (d, J=5.7 Hz, 2H), 4.32 (s, 2H), 3.69-3.65 (m, 1H), 3.10 (d, J=27.3 Hz, 6H), 2.66 (t, J=6.6 Hz, 4H), 2.24 (dd, J=27.5, 20.2 Hz, 4H), 2.01-1.95 (m, 3H), 1.77 (s, 2H), 1.43 (s, 3H), 1.34 (s, 9H), 1.22 (s, 2H); $[M+H]^+$=855.6.

Example C13: (R)-7-(4-((1-(4-(2,4-dioxotetrahydro-pyrimidin-1(2H)-yl)phenyl)piperidin-4-yl)methyl) piperazin-1-yl)-2-(4-(1-(2-methoxy-1-naphthamido) ethyl)phenyl)-9,10-dihydro-4H-benzo[d]pyrazolo[1,5-a][1,3]diazepine-3-carboxamide

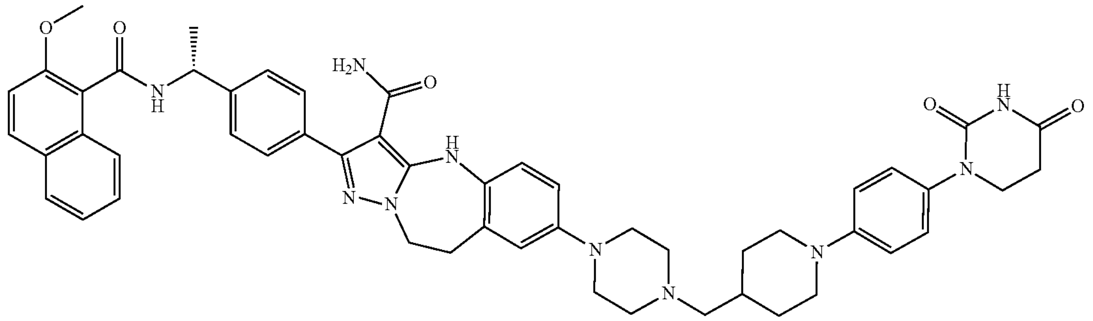 [SMILES: COc1ccc2ccccc2c1C(=O)N[C@H](C)c1ccc(-c2nn3c(c2C(N)=O)Nc2ccc(N4CCN(CC5CCN(c6ccc(N7CCC(=O)NC7=O)cc6)CC5)CC4)cc2CC3)cc1]

The titled compound was synthesized in the procedures similar to Example C6. $^1$H NMR (400 MHz, DMSO) δ 10.25 (s, 1H), 9.77 (s, 1H), 8.90 (s, 1H), 7.97 (d, J=8.7 Hz, 1H), 7.87 (s, 1H), 7.57 (s, 2H), 7.53-7.46 (m, 3H), 7.35 (s, 1H), 7.10 (s, 2H), 6.92 (s, 2H), 6.85 (s, 3H), 6.64 (s, 1H), 5.29 (s, 3H), 4.33 (s, 2H), 3.90 (s, 3H), 3.67 (s, 3H), 3.14 (s, 2H), 3.07 (s, 3H), 2.65 (s, 5H), 2.18 (d, J=13.4 Hz, 4H), 1.77 (s, 2H), 1.47 (s, 4H), 1.36 (d, J=5.6 Hz, 3H); $[M+H]^+$=901.8.

Example C14: (R)-7-(4-((1-(4-(2,4-dioxotetrahydro-pyrimidin-1(2H)-yl)phenyl)piperidin-4-yl)methyl) piperazin-1-yl)-2-(4-(1-(2-methoxybenzamido)ethyl) phenyl)-9,10-dihydro-4H-benzo[d]pyrazolo[1,5-a][1,3]diazepine-3-carboxamide

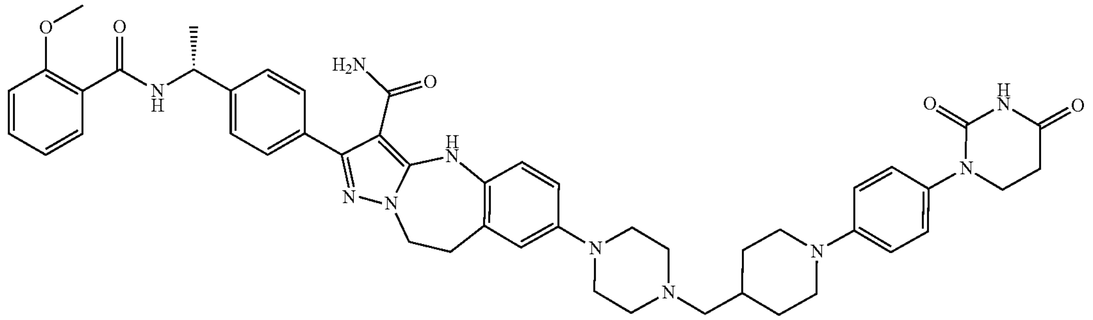 [SMILES: COc1ccccc1C(=O)N[C@H](C)c1ccc(-c2nn3c(c2C(N)=O)Nc2ccc(N4CCN(CC5CCN(c6ccc(N7CCC(=O)NC7=O)cc6)CC5)CC4)cc2CC3)cc1]

The titled compound was synthesized in the procedures similar to Example C6. $^1$H NMR (400 MHz, DMSO) δ 10.25 (s, 1H), 9.75 (s, 1H), 8.53 (d, J=8.1 Hz, 1H), 7.61 (dd, J=7.6, 1.9 Hz, 1H), 7.50-7.44 (m, 4H), 7.12 (dd, J=8.2, 6.0 Hz, 3H), 7.00 (d, J=7.3 Hz, 1H), 6.91 (d, J=9.0 Hz, 2H), 6.85 (s, 4H), 5.22-5.15 (m, 1H), 4.32 (s, 2H), 3.88 (s, 3H), 3.67 (t, J=6.8 Hz, 4H), 3.12 (s, 2H), 3.06 (s, 4H), 2.68-2.64 (m, 4H), 2.55-2.52 (m, 2H), 2.43 (d, J=1.8 Hz, 2H), 2.31 (d, J=1.9 Hz, 1H), 2.21 (s, 2H), 1.78 (s, 2H), 1.46 (s, 2H), 1.33 (s, 3H); [M+H]+=851.8.

Example C15: 7-(4-((1-(4-(2,4-dioxotetrahydropyrimidin-1(2H)-yl)phenyl)piperidin-4-yl)methyl)piperazin-1-yl)-2-(4-(1-((4-(trifluoromethyl)pyridin-2-yl)amino)ethyl)phenyl)-9,10-dihydro-4H-benzo[d]pyrazolo[1,5-a][1,3]diazepine-3-carboxamide Step 1: N-(1-(4-bromophenyl)ethyl)-4-(trifluoromethyl)pyridin-2-amine

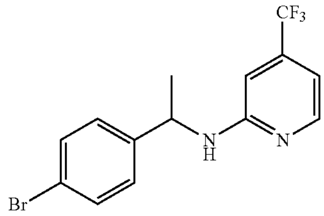 [SMILES: CC(Nc1cc(C(F)(F)F)ccn1)c1ccc(Br)cc1]

A mixture of 1-(4-bromophenyl)ethan-1-amine (3 g, 15 mmol), 2-fluoro-4-(trifluoromethyl)pyridine (2.97 g, 18 mmol) and $Cs_2CO_3$ (9.7 g, 30 mmol) in DMSO (20 mL) was stirred at 120° C. for 16 h under nitrogen atmosphere. The mixture was diluted with water (200 mL) and extracted with EA (3×150 mL). The combined organic layers were dried over $Na_2SO_4$, filtered and concentrated under vacuum. The residue was purified by silica gel column chromatography, eluted with EA/PE (1/3) to afford the product (1.6 g, 30.7%). $[M+H]^+$=345.1.

Step 2: N-(1-(4-(4,4,5,5-tetramethyl-1,3,2-dioxaborolan-2-yl)phenyl)ethyl)-4-(trifluoromethyl)pyridin-2-amine

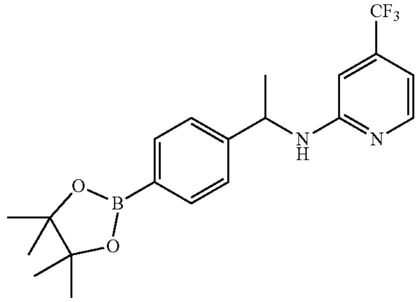 [SMILES: CC(Nc1cc(C(F)(F)F)ccn1)c1ccc(B2OC(C)(C)C(C)(C)O2)cc1]

A mixture of N-(1-(4-bromophenyl)ethyl)-4-(trifluoromethyl)pyridin-2-amine (1.6 g, 4.65 mmol), 4,4,4',4',5,5,5',5'-octamethyl-2,2'-bi(1,3,2-dioxaborolane) (1.3 g, 5.11 mmol), $Pd(dppf)Cl_2$ (170 mg, 0.23 mmol) and KOAc (911 mg, 9.3 mmol) in dioxane (15 mL) was stirred in a round bottom flask at 100° C. overnight under nitrogen atmosphere. The mixture was concentrated under vacuum. The residue was purified by silica gel column chromatography, eluted with EA/PE (1:3) to afford the product (1.8 g, 98.9%). $[M+H]^+$=393.2.

Step 3: benzyl 4-(2-bromo-3-carbamoyl-9,10-dihydro-4H-benzo[d]pyrazolo[1,5-a][1,3]diazepin-7-yl)piperazine-1-carboxylate

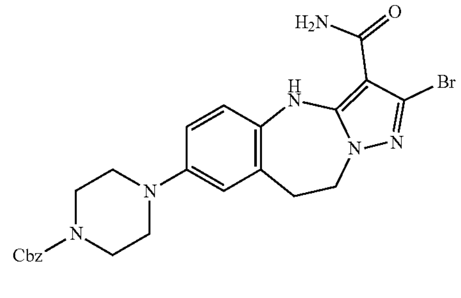 [SMILES: NC(=O)c1c(Br)nn2c1Nc1ccc(N3CCN(C(=O)OCc4ccccc4)CC3)cc1CC2]

To a solution of benzyl 4-(2-bromo-3-cyano-9,10-dihydro-4H-benzo[d]pyrazolo[1,5-a][1,3]diazepin-7-yl)piperazine-1-carboxylate (200 mg, 0.39 mmol) in DMSO (5 mL) were added $H_2O_2$ (78.8 mg, 1.97 mmol) and NaOH (79 mg, 1.97 mmol). The mixture was stirred at rt for 1 h. The mixture was diluted with water (50 mL) and extracted with EA (3×50 mL). The combined organic layers were dried over $Na_2SO_4$, filtered and concentrated under vacuum. The residue was purified by silica gel column chromatography, eluted with EA/PE (100%) to afford the product (140 mg, 67.6%). $[M+H]^+$=525.1.

Step 4: benzyl 4-(3-carbamoyl-2-(4-(1-((4-(trifluoromethyl)pyridin-2-yl)amino)ethyl)phenyl)-9,10-dihydro-4H-benzo[d]pyrazolo[1,5-a][1,3]diazepin-7-yl)piperazine-1-carboxylate

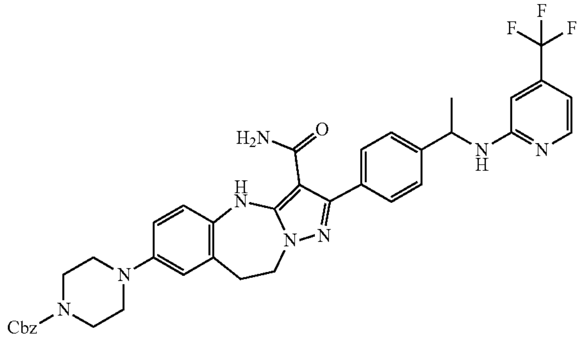 [SMILES: CC(Nc1cc(C(F)(F)F)ccn1)c1ccc(-c2nn3c(c2C(N)=O)Nc2ccc(N4CCN(C(=O)OCc5ccccc5)CC4)cc2CC3)cc1]

A mixture of benzyl 4-(2-bromo-3-carbamoyl-9,10-dihydro-4H-benzo[d]pyrazolo[1,5-a][1,3]diazepin-7-yl)piperazine-1-carboxylate (70 mg, 0.13 mmol), N-(1-(4-(4,4,5,5-tetramethyl-1,3,2-dioxaborolan-2-yl)phenyl)ethyl)-4-(trifluoromethyl)pyridin-2-amine (63 mg, 0.16 mmol), $Pd(PPh_3)_4$ (30.8 mg, 0.026 mmol) and 2.0 N $Na_2CO_3$ (aq., 0.3 mL, 0.67 mmol) in dioxane (10 mL) was stirred at 100° C. overnight under nitrogen atmosphere. The mixture was concentrated under vacuum. The residue was purified by silica gel column chromatography, eluted with EA/PE (0-100%) to afford the product (85 mg, 89.5%). $[M+H]^+$=711.3.

Step 5: 7-(piperazin-1-yl)-2-(4-(1-((4-(trifluoromethyl)pyridin-2-yl)amino)ethyl)phenyl)-9,10-dihydro-4H-benzo[d]pyrazolo[1,5-a][1,3]diazepine-3-carboxamide

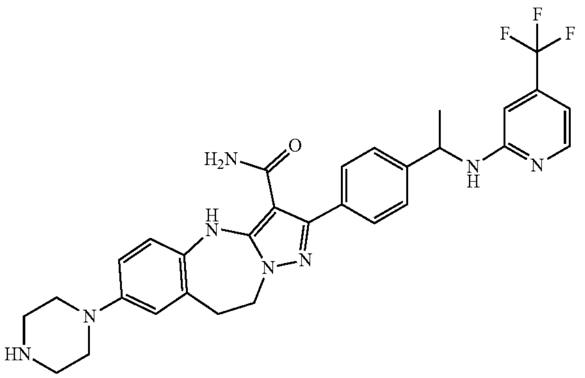 [SMILES: CC(Nc1cc(C(F)(F)F)ccn1)c1ccc(-c2nn3c(c2C(N)=O)Nc2ccc(N4CCNCC4)cc2CC3)cc1]

To a solution of benzyl 4-(3-carbamoyl-2-(4-(1-((4-(trifluoromethyl)pyridin-2-yl)amino)ethyl)phenyl)-9,10-dihydro-4H-benzo[d]pyrazolo[1,5-a][1,3]diazepin-7-yl)piperazine-1-carboxylate (50 mg, 0.07 mmol) in MeOH (10 mL) was added Pd/C (15 mg, 10%). The mixture was stirred at rt overnight under hydrogen atmosphere. The mixture was filtered and the filtrate was concentrated under vacuum to afford the product (40 mg, 58.1%). $[M+H]^+$=577.3.

Step 6: 7-(4-((1-(4-(2,4-dioxotetrahydropyrimidin-1(2H)-yl)phenyl)piperidin-4-yl)methyl)piperazin-1-yl)-2-(4-(1-((4-(trifluoromethyl)pyridin-2-yl)amino)ethyl)phenyl)-9,10-dihydro-4H-benzo[d]pyrazolo[1,5-a][1,3]diazepine-3-carboxamide

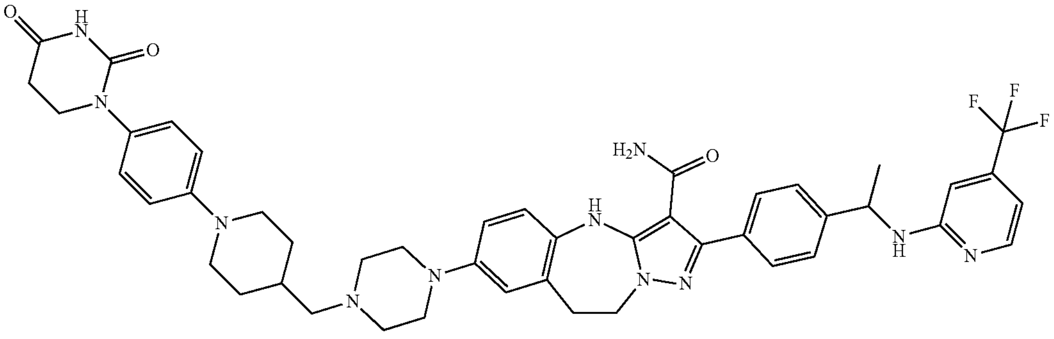 [SMILES: CC(Nc1cc(C(F)(F)F)ccn1)c1ccc(-c2nn3c(c2C(N)=O)Nc2ccc(N4CCN(CC5CCN(c6ccc(N7CCC(=O)NC7=O)cc6)CC5)CC4)cc2CC3)cc1]

A mixture of 7-(piperazin-1-yl)-2-(4-(1-((4-(trifluoromethyl)pyridin-2-yl)amino)ethyl)phenyl)-9,10-dihydro-4H-benzo[d]pyrazolo[1,5-a][1,3]diazepine-3-carboxamide (40 mg, 0.07 mmol), 1-(4-(2,4-dioxotetrahydropyrimidin-1(2H)-yl)phenyl)piperidine-4-carbaldehyde (25 mg, 0.08 mmol) and AcOH (0.02 mL) in MeOH (5 mL) and DCM (5 mL) was stirred at rt overnight. After sodium triacetoxyborohydride (29.2 mg, 0.138 mmol) was added, the mixture was stirred at rt for 5 h. The mixture was concentrated under vacuum. The residue was purified by Prep-TLC (DCM/MeOH=9:1) to afford the product (2.16 mg, 3.6%). $^1H$ NMR (400 MHz, DMSO) δ 10.25 (s, 1H), 9.73 (s, 1H), 8.11 (t, J=8.0 Hz, 1H), 7.64-7.58 (m, 1H), 7.49-7.40 (m, 4H), 7.14-7.07 (m, 2H), 6.96-6.75 (m, 6H), 6.70-6.64 (m, 1H), 5.18-5.09 (m, 1H), 4.32-4.26 (m, 2H), 3.71-3.62 (m, 4H), 3.15-3.01 (m, 5H), 2.71-2.58 (m, 4H), 2.24-2.15 (m, 2H), 1.83-1.72 (m, 2H), 1.50-1.39 (m, 3H), 1.23-1.15 (m, 6H), 0.92-0.75 (m, 2H); $[M+H]^+$=862.4.

Example C16: 7-(4-((1-(4-(2,4-dioxotetrahydropyrimidin-1(2H)-yl)phenyl)piperidin-4-yl)methyl)piperazin-1-yl)-2-(4-(1-((4-(trifluoromethyl)pyridin-2-yl)amino)cyclopropyl)phenyl)-9,10-dihydro-4H-benzo[d]pyrazolo[1,5-a][1,3]diazepine-3-carboxamide

-

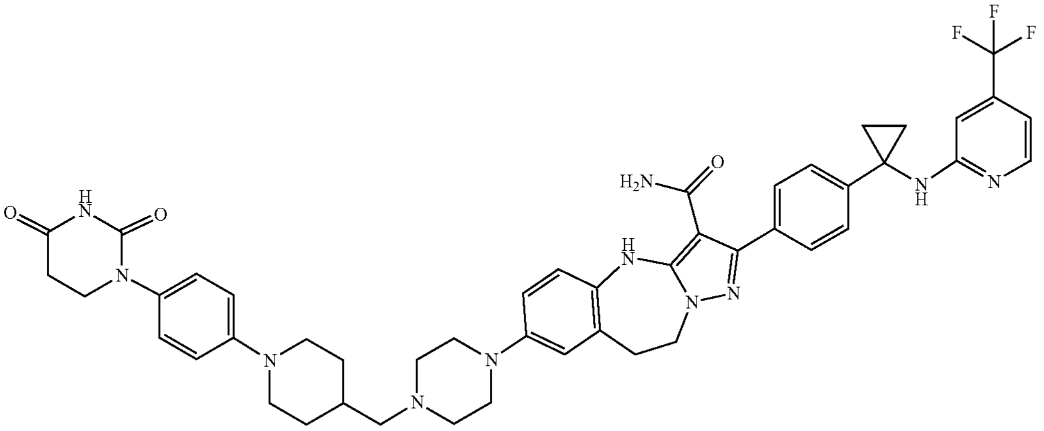 [SMILES: NC(=O)c1c(-c2ccc(C3(Nc4cc(C(F)(F)F)ccn4)CC3)cc2)nn2c1Nc1ccc(N3CCN(CC4CCN(c5ccc(N6CCC(=O)NC6=O)cc5)CC4)CC3)cc1CC2]

The titled compound was synthesized in the procedures similar to Example C15. $^1$H NMR (400 MHz, DMSO) δ 10.25 (s, 1H), 9.74 (s, 1H), 8.21 (t, J=4.0 Hz, 1H), 8.08 (s, 1H), 7.39 (t, J=8.0 Hz, 2H), 7.39 (t, J=8.0 Hz, 2H), 7.24 (t, J=8.0 Hz, 2H), 7.11 (t, J=8.0 Hz, 2H), 6.94-6.88 (m, 2H), 6.86-6.74 (m, 4H), 4.33-4.25 (m, 2H), 3.71-3.62 (m, 4H), 3.14-3.02 (m, 6H), 2.71-2.60 (m, 5H), 2.55-2.53 (m, 2H), 2.23-2.17 (m, 2H), 1.82-1.65 (m, 5H), 1.42-1.37 (m, 2H), 1.28-1.17 (m, 4H); $[M+H]^+$=874.4.

Example C17: 7-(4-((1-(4-(2,4-dioxotetrahydropyrimidin-1(2H)-yl)phenyl)piperidin-4-yl)methyl)piperazin-1-yl)-2-(4-(1-((4-(trifluoromethyl)pyridin-2-yl)amino)propyl)phenyl)-9,10-dihydro-4H-benzo[d]pyrazolo[1,5-a][1,3]diazepine-3-carboxamide

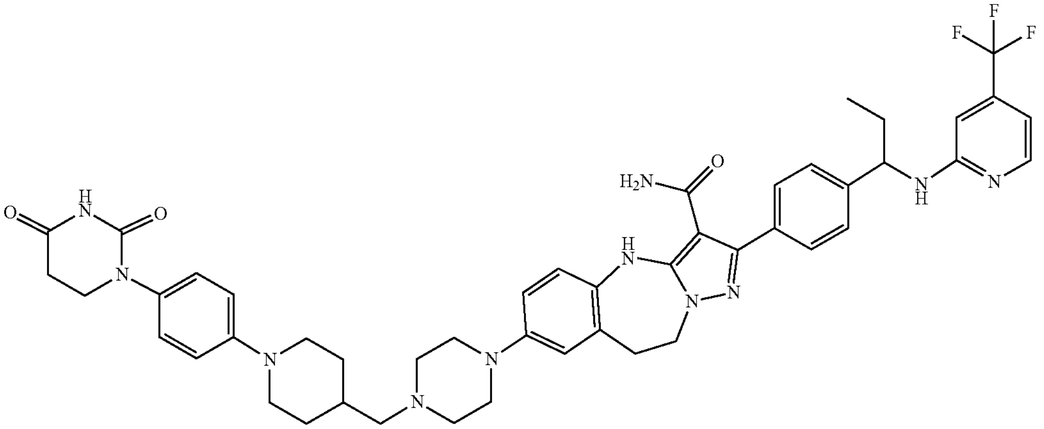 [SMILES: CCC(Nc1cc(C(F)(F)F)ccn1)c1ccc(-c2nn3c(c2C(N)=O)Nc2ccc(N4CCN(CC5CCN(c6ccc(N7CCC(=O)NC7=O)cc6)CC5)CC4)cc2CC3)cc1]

The titled compound was synthesized in the procedures similar to Example C15. $^1$H NMR (400 MHz, DMSO) δ 10.25 (s, 1H), 9.72 (s, 1H), 8.11 (t, J=4.0 Hz, 1H), 7.43 (t, J=8.0 Hz, 2H), 7.17-7.08 (m, 4H), 6.91 (t, J=12.0 Hz, 2H), 6.86-6.77 (m, 4H), 6.52-6.44 (m, 1H), 4.34-4.27 (m, 2H), 3.71-3.63 (m, 4H), 3.18-2.98 (m, 7H), 2.71-2.60 (m, 5H), 2.56-2.50 (m, 2H), 2.23-2.16 (m, 2H), 1.86-1.64 (m, 4H), 1.63-1.52 (m, 4H), 1.28-1.14 (m, 4H); $[M+H]^+$=876.4.

Example C18: (R)-7-(4-((1-(4-(2,4-dioxotetrahydropyrimidin-1(2H)-yl)phenyl)piperidin-4-yl)methyl)piperazin-1-yl)-2-(4-(1-(4-methoxynicotinamido)ethyl)phenyl)-9,10-dihydro-4H-benzo[d]pyrazolo[1,5-a][1,3]diazepine-3-carboxamide

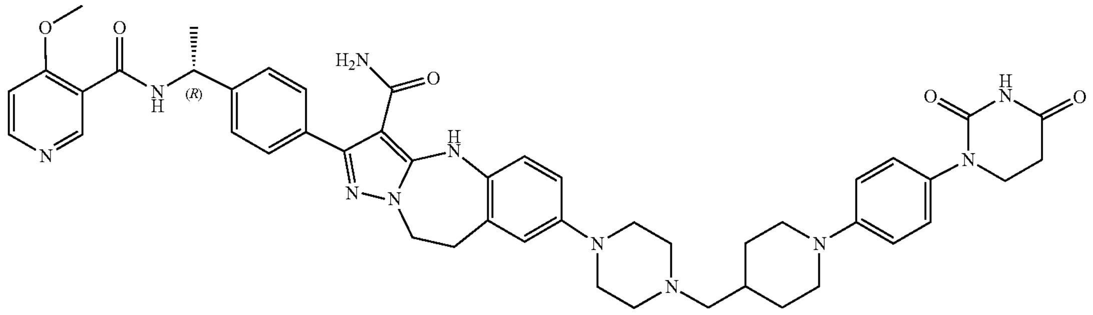

The titled compound was synthesized in the procedures similar to Example C6. $^{1}H$ NMR (400 MHz, DMSO) δ 10.27 (s, 1H), 9.78 (s, 1H), 8.64 (s, 1H), 8.59-8.55 (m, 2H), 7.53-7.49 (m, 4H), 7.15-7.11 (m, 3H), 6.91 (d, J=28.9 Hz, 5H), 5.23-5.19 (m, 1H), 4.37-4.33 (m, 2H), 3.94 (s, 3H), 3.72-3.68 (m, 5H), 3.17-3.13 (m, 6H), 2.70-2.66 (m, 8H), 2.34-2.30 (m, 2H), 1.81 (s, 3H), 1.51-1.47 (m, 3H), 1.27-1.23 (m, 2H); $[M+H]^{+}$=852.8.

Example C19:7-(4-((1-(4-(2,4-dioxotetrahydropyrimidin-1(2H)-yl)phenyl)piperidin-4-yl)methyl)piperazin-1-yl)-2-(3-fluoro-4-((2-methoxybenzamido)methyl)phenyl)-9,10-dihydro-4H-benzo[d]pyrazolo[1,5-a][1,3]diazepine-3-carboxamide

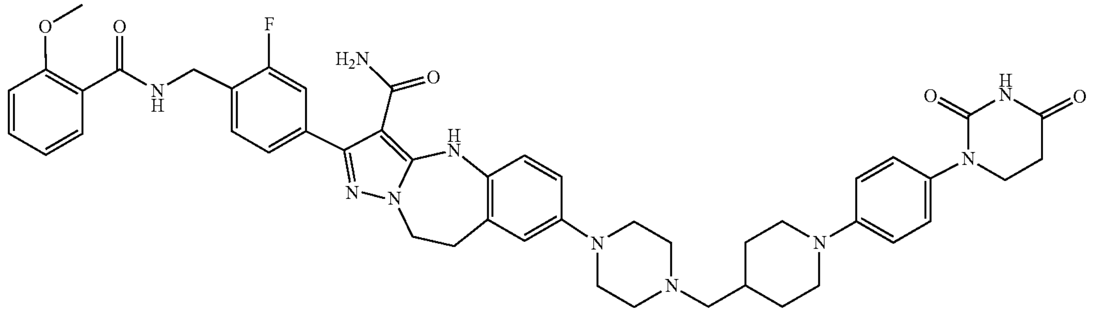 [SMILES: COc1ccccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1F]

The titled compound was synthesized in the procedures similar to Example C6. $^{1}H$ NMR (400 MHz, DMSO) δ 10.28 (s, 1H), 9.75 (s, 1H), 8.76 (s, 1H), 7.77-7.73 (m, 1H), 7.49-7.45 (m, 2H), 7.33 (d, J=14.1 Hz, 2H), 7.15 (d, J=8.6 Hz, 3H), 7.07-7.03 (m, 1H), 6.96-6.92 (m, 5H), 4.61-4.57 (m, 2H), 4.38-4.34 (m, 2H), 3.91 (s, 3H), 3.72-3.68 (m, 4H), 3.18-3.14 (m, 4H), 3.08-3.02 (m, 2H), 2.70-2.66 (m, 6H), 2.54-2.50 (m, 3H), 2.08-1.94 (m, 1H), 1.84-1.80 (m, 2H), 1.28 (d, J=32.5 Hz, 3H); $[M+H]^{+}$=855.8.-

Example C20:7-(4-((1-(4-(2,4-dioxotetrahydropyrimidin-1(2H)-yl)phenyl)piperidin-4-yl)methyl)piperazin-1-yl)-2-(3-fluoro-4-((2-methoxy-1-naphthamido)methyl)phenyl)-9,10-dihydro-4H-benzo[d]pyrazolo[1,5-a][1,3]diazepine-3-carboxamide

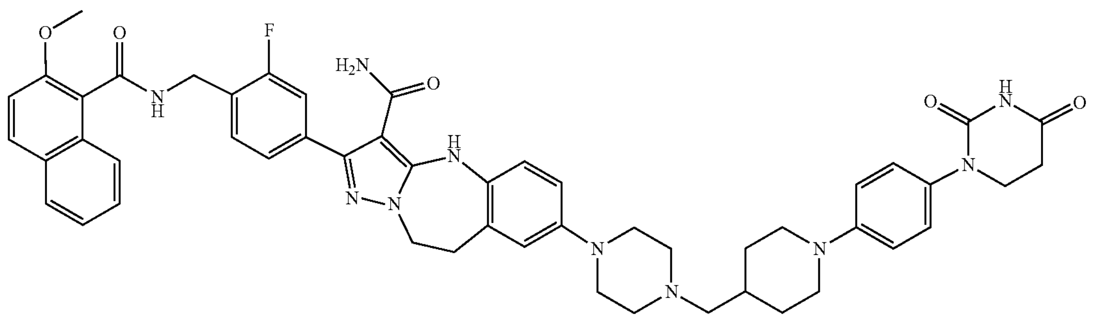 [SMILES: COc1ccc2ccccc2c1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1F]

The titled compound was synthesized in the procedures similar to Example C6. $^1$H NMR (400 MHz, DMSO) δ 10.21 (s, 1H), 9.70 (s, 1H), 8.91 (s, 1H), 7.96 (d, J=7.8 Hz, 1H), 7.88-7.84 (m, 1H), 7.64-7.60 (m, 2H), 7.51-7.26 (m, 5H), 7.10-7.06 (m, 2H), 6.90-6.86 (m, 5H), 4.60-4.56 (m, 2H), 4.34-4.30 (m, 2H), 3.89 (s, 3H), 3.66-3.62 (m, 4H), 3.14-3.10 (m, 4H), 3.05-2.99 (m, 2H), 2.65-2.61 (m, 5H), 2.49-2.45 (m, 4H), 1.81-1.77 (m, 2H), 1.26 (d, J=59.3 Hz, 3H); $[M+H]^+$=905.8.

Example C21:7-(4-((1-(4-(2,4-dioxotetrahydropyrimidin-1(2H)-yl)phenyl)piperidin-4-yl)methyl)piperazin-1-yl)-2-(4-((2-methoxy-5-(trifluoromethyl)benzamido)methyl)phenyl)-9,10-dihydro-4H-benzo[d]pyrazolo[1,5-a][1,3]diazepine-3-carboxamide

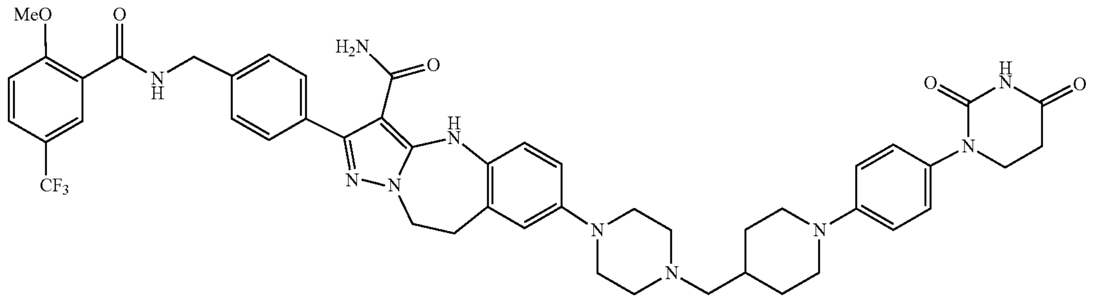 [SMILES: COc1ccc(C(F)(F)F)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1]

The titled compound was synthesized in the procedures similar to Example C6. $^1$H NMR (400 MHz, DMSO) δ 10.27 (s, 1H), 9.77 (s, 1H), 8.92 (s, 1H), 8.01 (s, 1H), 7.86 (d, J=8.0 Hz, 1H), 7.47 (d, J=10.0 Hz, 4H), 7.37 (d, J=9.0 Hz, 1H), 7.15-7.11 (m, 2H), 6.96-6.92 (m, 3H), 6.89-6.85 (m, 2H), 4.60-4.56 (m, 2H), 4.36-4.32 (m, 2H), 3.98 (s, 3H), 3.71-3.67 (m, 4H), 3.11 (d, J=23.5 Hz, 8H), 2.70-2.66 (m, 6H), 2.20 (d, J=12.7 Hz, 3H), 1.81-1.77 (m, 2H), 1.75-1.66 (m, 1H), 1.26-1.22 (m, 3H); $[M+H]^+$=905.8.

Example C22: 2-(4-((2,6-dimethoxybenzamido) methyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

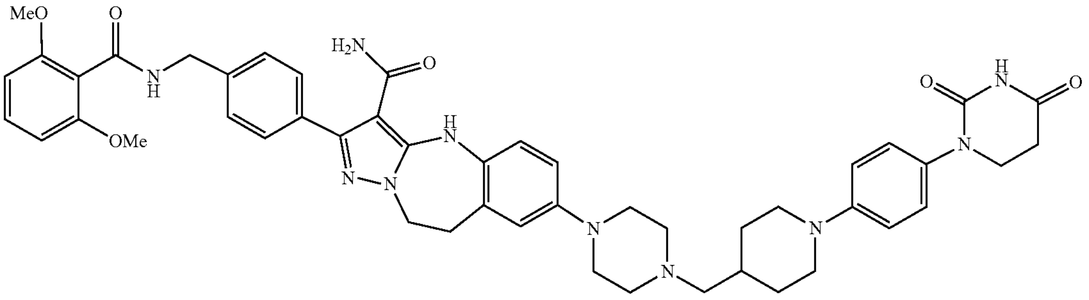 [SMILES: COc1cccc(OC)c1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1]

The titled compound was synthesized in the procedures similar to Example C6. $^1$H NMR (400 MHz, DMSO) δ 10.26 (s, 1H), 9.79 (s, 1H), 8.63 (s, 1H), 7.52-7.48 (m, 3H), 7.30 (d, J=8.5 Hz, 1H), 7.13 (d, J=7.9 Hz, 2H), 6.96-6.92 (m, 3H), 6.88-6.84 (m, 3H), 6.70 (d, J=8.5 Hz, 2H), 4.49-4.45 (m, 2H), 4.37-4.33 (m, 2H), 3.77 (s, 6H), 3.69 (d, J=6.7 Hz, 4H), 3.17-3.13 (m, 3H), 3.11-3.07 (m, 5H), 2.70-2.66 (m, 7H), 2.24-2.20 (m, 2H), 1.85-1.81 (m, 2H), 1.76-1.65 (m, 1H), 1.26-1.22 (m, 3H); $[M+H]^+$=867.9.

Example C23:2-(4-((2,4-dimethoxybenzamido) methyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

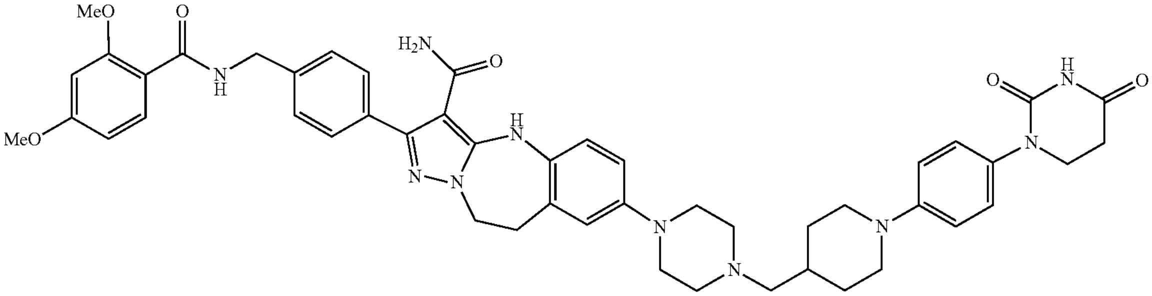 [SMILES: COc1ccc(C(=O)NCc2ccc(-c3nn4c(c3C(N)=O)Nc3ccc(N5CCN(CC6CCN(c7ccc(N8CCC(=O)NC8=O)cc7)CC6)CC5)cc3CC4)cc2)c(OC)c1]

The titled compound was synthesized in the procedures similar to Example C6. $^1$H NMR (400 MHz, DMSO) δ 10.25 (s, 1H), 9.77 (s, 1H), 8.63-8.59 (m, 1H), 7.84 (d, J=8.5 Hz, 1H), 7.44 (d, J=13.9 Hz, 3H), 7.13 (d, J=8.0 Hz, 2H), 6.90 (d, J=31.9 Hz, 6H), 6.69-6.60 (m, 2H), 4.59-4.55 (m, 2H), 4.36-4.32 (m, 2H), 3.92 (s, 3H), 3.83 (s, 3H), 3.71-3.67 (m, 4H), 3.11 (d, J=22.5 Hz, 8H), 2.70-2.66 (m, 7H), 2.24-2.20 (m, 2H), 1.85-1.81 (m, 2H), 1.75-1.64 (m, 1H), 1.27-1.23 (m, 3H); $[M+H]^+$=867.8.

Example C24: 7-(4-((1-(4-(2,4-dioxotetrahydropyrimidin-1(2H)-yl)phenyl)piperidin-4-yl)methyl)piperazin-1-yl)-2-(2-fluoro-4-((2-methoxy-5-(trifluoromethyl)benzamido)methyl)phenyl)-9,10-dihydro-4H-benzo[d]pyrazolo[1,5-a][1,3]diazepine-3-carboxamide Step 1: benzyl 4-(2-(4-(aminomethyl)-2-fluorophenyl)-3-cyano-9,10-dihydro-4H-benzo[d]pyrazolo[1,5-a][1,3]diazepin-7-yl)piperazine-1-carboxylate hydrochloride

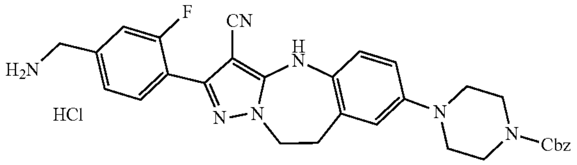 [SMILES: N#Cc1c(-c2ccc(CN)cc2F)nn2c1Nc1ccc(N3CCN(C(=O)OCc4ccccc4)CC3)cc1CC2 ; Cl]

A mixture of benzyl 4-(2-(4-(((tert-butoxycarbonyl)amino)methyl)-2-fluorophenyl)-3-cyano-9,10-dihydro-4H-benzo[d]pyrazolo[1,5-a][1,3]diazepin-7-yl)piperazine-1-carboxylate (0.14 g, 0.22 mmol, made by procedure similar to example C6 step 4) in HCl/1,4-dioxane (5.0 mL, 6 N) and DCM (3.0 mL) was stirred in a round bottom flask at room temperature for 10 min. The mixture was filtered to afford the product (126 mg, 100.0%); $[M-NH_2+H]^+=535.0$.

Step 2: benzyl 4-(3-cyano-2-(2-fluoro-4-((2-methoxy-5-(trifluoromethyl)benzamido)methyl)phenyl)-9,10-dihydro-4H-benzo[d]pyrazolo[1,5-a][1,3]diazepin-7-yl)piperazine-1-carboxylate

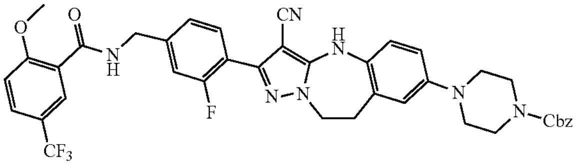 [SMILES: COc1ccc(C(F)(F)F)cc1C(=O)NCc1ccc(-c2nn3c(c2C#N)Nc2ccc(N4CCN(C(=O)OCc5ccccc5)CC4)cc2CC3)c(F)c1]

A mixture of benzyl 4-(2-(4-(aminomethyl)-2-fluorophenyl)-3-cyano-9,10-dihydro-4H-benzo[d]pyrazolo[1,5-a][1,3]diazepin-7-yl)piperazine-1-carboxylate hydrochloride (126 mg, 0.22 mmol), 2-methoxy-5-(trifluoromethyl)benzoic acid (72.6 mg, 0.33 mmol), HATU (125.4 mg, 0.33 mmol) and DIPEA (142 mg, 1.1 mmol) in DMF (8.0 mL) was stirred in a round bottom flask at room temperature overnight. Then the mixture was evaporated in vacuum to afford the crude product, which was purified with silica gel column chromatography (DCM: MeOH=100:0~90:10 gradient elution) to give the product (170 mg). $[M+H]^+=754.3$.

Step 3: 2-(2-fluoro-4-((2-methoxy-5-(trifluoromethyl)benzamido)methyl)phenyl)-7-(piperazin-1-yl)-9,10-dihydro-4H-benzo[d]pyrazolo[1,5-a][1,3]diazepine-3-carboxamide

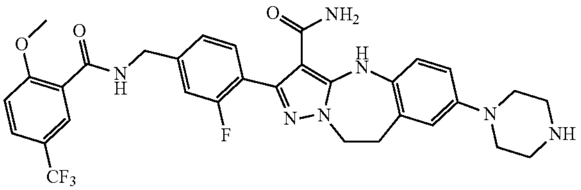 [SMILES: COc1ccc(C(F)(F)F)cc1C(=O)NCc1ccc(-c2nn3c(c2C(N)=O)Nc2ccc(N4CCNCC4)cc2CC3)c(F)c1]

A mixture of benzyl 4-(3-cyano-2-(2-fluoro-4-((2-methoxy-5-(trifluoromethyl)benzamido)methyl)phenyl)-9,10-dihydro-4H-benzo[d]pyrazolo[1,5-a][1,3]diazepin-7-yl)piperazine-1-carboxylate (170 mg, 0.226 mmol) in methanesulfonic acid (10.0 mL) was stirred at 100° C. for 1 hour. The mixture was then cooled, alkalified with aqueous sodium carbonate solution to pH 12, extracted with dichloromethane (3×30 mL), and washed with brine (30 mL). The organic phase was dried over anhydrous sodium sulfate, filtered and concentrated under reduced pressure to afford the product (140 mg). $[M+H]^+=638.0$.

Step 4: 7-(4-((1-(4-(2,4-dioxotetrahydropyrimidin-1(2H)-yl)phenyl)piperidin-4-yl)methyl)piperazin-1-yl)-2-(2-fluoro-4-((2-methoxy-5-(trifluoromethyl)benzamido)methyl)phenyl)-9,10-dihydro-4H-benzo[d]pyrazolo[1,5-a][1,3]diazepine-7-yl)piperazine-1-carboxylate

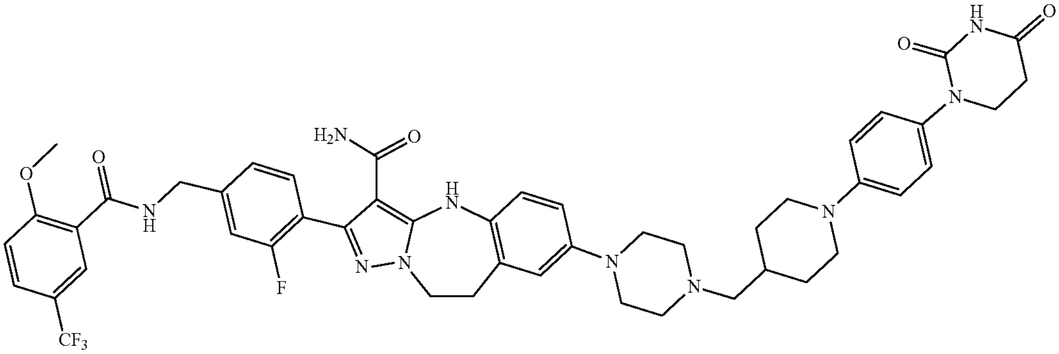 [SMILES: COc1ccc(C(F)(F)F)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)c(F)c1]

A mixture of 2-(2-fluoro-4-((2-methoxy-5-(trifluoromethyl)benzamido)methyl)phenyl)-7-(piperazin-1-yl)-9,10-dihydro-4H-benzo[d]pyrazolo[1,5-a][1,3]diazepine-3-carboxamide (140 mg, 0.422 mmol) and 1-(4-(2,4-dioxotetrahydropyrimidin-1(2H)-yl)phenyl)piperidine-4-carbaldehyde (99 mg, 0.33 mmol) in MeOH (4.0 mL), DCM (16.0 mL) and acetic acid (0.3 mL) was stirred at room temperature for 16 hours, and then $NaBH(OAc)_3$ (0.5 g, 2.35 mmol) was added and stirred at room temperature for 1 hour. The mixture was treated with water (30 mL), extracted with dichloromethane (3x30.0 mL), and washed with brine (30 mL). The organic phase was dried over anhydrous sodium sulfate, filtered and concentrated under reduced pressure to afford the crude product, which was purified with silica gel column chromatography (DCM:MeOH=100:0~90:10 gradient elution) and prep-TLC (DCM:MeOH=7:1) to give the product (17 mg, 8.4%). $^1H$ NMR (400 MHz, DMSO) δ 10.25 (s, 1H), 9.72 (s, 1H), 8.89 (s, 1H), 8.00 (s, 1H), 7.88-7.84 (m, 1H), 7.50-7.46 (m, 1H), 7.34 (d, J=20.7 Hz, 3H), 7.15-7.11 (m, 2H), 6.90 (d, J=30.2 Hz, 5H), 4.63-4.59 (m, 2H), 4.37-4.33 (m, 2H), 3.99 (s, 3H), 3.71-3.67 (m, 4H), 3.11 (d, J=21.4 Hz, 8H), 2.70-2.66 (m, 5H), 2.35-2.31 (m, 1H), 2.23-2.19 (m, 2H), 1.82-1.78 (m, 3H), 1.27-1.23 (m, 2H); $[M+H]^+$=923.7.

Example C25:2-(4-((2,3-difluoro-6-methoxybenzamido)methyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a] [1,3]diazepine-3-carboxamide

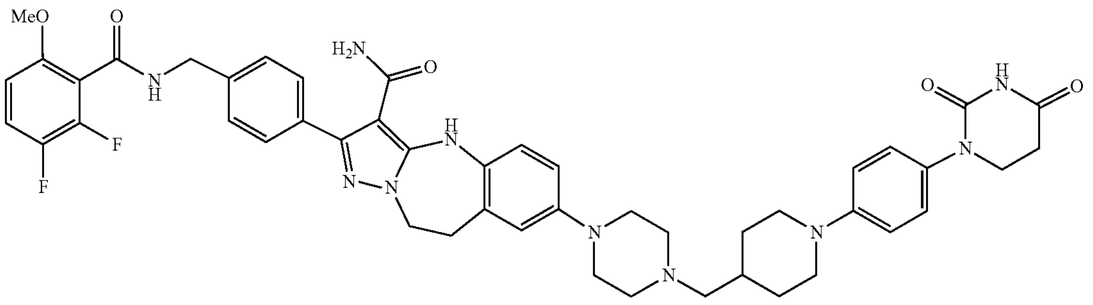 [SMILES: COc1ccc(F)c(F)c1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1]

The titled compound was synthesized in the procedures similar to Example C24. $^1H$ NMR (400 MHz, DMSO) δ 10.26 (s, 1H), 9.84 (s, 1H), 9.13-9.08 (m, 1H), 7.48 (d, J=11.7 Hz, 5H), 7.16-7.12 (m, 2H), 6.95-6.91 (m, 6H), 4.54-4.50 (m, 2H), 4.38-4.34 (m, 2H), 3.81 (s, 3H), 3.72-3.68 (m, 2H), 3.63-3.58 (m, 2H), 3.18-3.14 (m, 8H), 2.70-2.66 (m, 5H), 2.35-2.31 (m, 2H), 1.97-1.93 (m, 3H), 1.32-1.28 (m, 2H); $[M+H]^+$=873.7.

Example C26: 7-(4-((1-(4-(2,4-dioxotetrahydropyrimidin-1(2H)-yl)phenyl)piperidin-4-yl)methyl)piperazin-1-yl)-2-(3-fluoro-4-((2-methoxy-5-(trifluoromethyl)benzamido)methyl)phenyl)-9,10-dihydro-4H-benzo[d]pyrazolo[1,5-a][1,3]diazepine-3-carboxamide

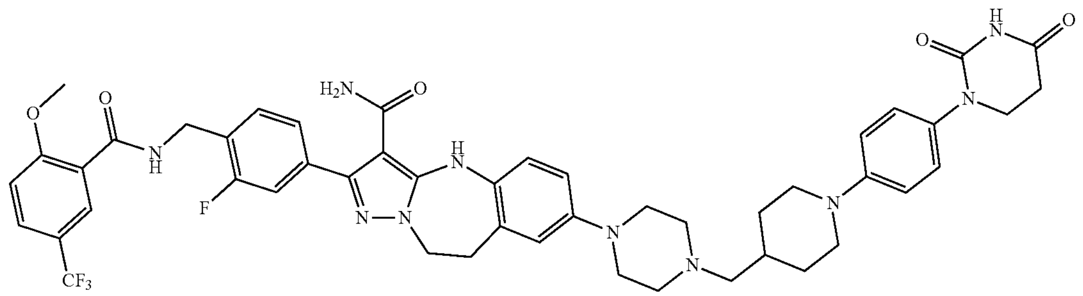 [SMILES: COc1ccc(C(F)(F)F)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1F]

The titled compound was synthesized in the procedures similar to Example C24. $^1H$ NMR (400 MHz, DMSO) δ 10.24 (s, 1H), 9.71 (s, 1H), 8.88 (s, 1H), 8.00 (s, 1H), 7.86 (d, J=7.4 Hz, 1H), 7.48 (s, 1H), 7.36 (s, 3H), 7.12 (s, 2H), 6.96-6.82 (m, 5H), 4.60 (s, 2H), 4.34 (s, 2H), 3.99 (s, 3H), 3.69 (s, 4H), 3.15 (s, 6H), 2.68 (s, 7H), 1.82 (s, 3H), 1.25 (d, J=11.7 Hz, 5H); $[M+H]^+$=923.7.

Example C27: 7-(4-((1-(4-(2,4-dioxotetrahydropyrimidin-1(2H)-yl)phenyl)piperidin-4-yl)methyl)piperazin-1-yl)-2-(2-methoxy-4-((2-methoxy-5-(trifluoromethyl)benzamido)methyl)phenyl)-9,10-dihydro-4H-benzo[d]pyrazolo[1,5-a][1,3]diazepine-3-carboxamide

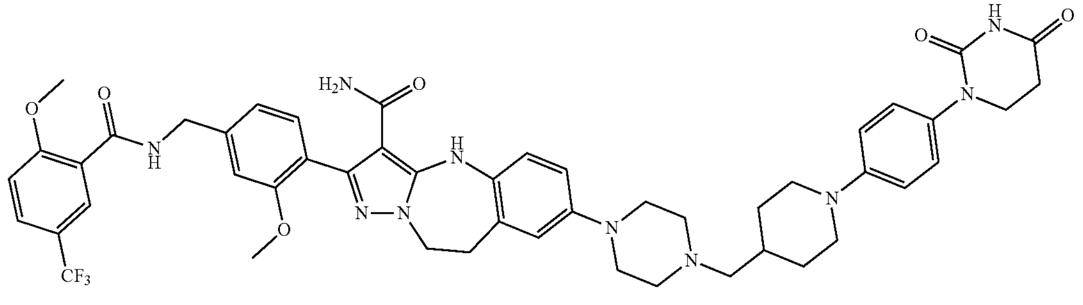 [SMILES: COc1ccc(C(F)(F)F)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)c(OC)c1]

The titled compound was synthesized in the procedures similar to Example C24. $^1H$ NMR (400 MHz, DMSO) δ 10.24 (s, 1H), 9.72 (s, 1H), 8.89 (t, J=4.9 Hz, 1H), 7.99 (s, 1H), 7.85 (d, J=8.6 Hz, 1H), 7.37 (d, J=8.7 Hz, 1H), 7.24 (d, J=7.5 Hz, 1H), 7.14 (d, J=9.2 Hz, 3H), 7.03 (d, J=7.5 Hz, 1H), 6.93 (d, J=8.3 Hz, 2H), 6.84 (dd, J=16.6, 3.9 Hz, 3H), 4.58 (d, J=5.0 Hz, 2H), 4.31 (d, J=3.2 Hz, 2H), 3.98 (s, 3H), 3.75 (s, 3H), 3.72-3.65 (m, 4H), 3.20-3.04 (m, 6H), 2.68 (t, J=6.3 Hz, 5H), 2.30-2.14 (m, 2H), 1.91-1.72 (m, 3H), 1.26-1.22 (m, 5H); $[M+H]^+$=935.8.

Example C28:2-(2,3-difluoro-4-((2-methoxy-5-(trifluoromethyl)benzamido)methyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide Step 1: 3,5-dibromo-1H-pyrazole-4-carbonitrile

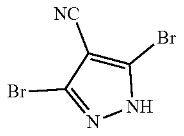

To a solution of 1H-pyrazole-4-carbonitrile (50.0 g, 538 mmol) and sodium acetate (308.8 g, 3.766 mol) in EtOH (1.0 L) and $H_2O$ (1.5 L) was added dropwise bromine (344 g, 2.15 mol). The mixture was stirred at room temperature overnight. The mixture was extracted with dichloromethane (2×1.0 L) and washed with anhydrous sodium hyposulfite (1.0 L). The organic phase was dried over anhydrous sodium sulfate, filtered and concentrated under reduced pressure to afford the crude product, which was purified by recrystallization (PE:EA=6:1) to give the product (100.0 g, 74.6%). $[M+H]^+$=249.0.

Step 2: 2-(5-fluoro-2-nitrophenyl)ethan-1-ol

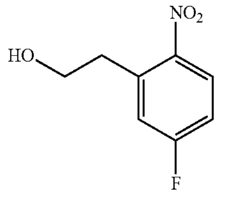 [SMILES: O=[N+]([O-])c1ccc(F)cc1CCO]

To a solution of 2-(5-fluoro-2-nitrophenyl)acetic acid (75.0 g, 377 mmol) in dry THF (1.0 L) was added borane-THF (566 mL, 566 mmol, 1.0 M in THF) at 0° C. The mixture was stirred at room temperature overnight. The mixture was treated with hydrochloric acid (1.0 L, 3 N in water), extracted with dichloromethane (3×800 mL) and washed with brine (1.0 L). The organic phase was dried over anhydrous sodium sulfate, filtered and concentrated under reduced pressure to afford the product (71 g, 100%). $[M-OH]^+$=168.0.

Step 3: benzyl 4-(3-(2-hydroxyethyl)-4-nitrophenyl)piperazine-1-carboxylate

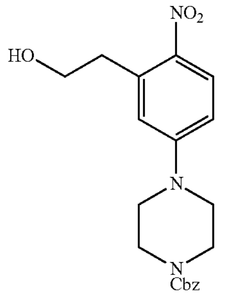 [SMILES: O=C(OCc1ccccc1)N1CCN(c2ccc([N+](=O)[O-])c(CCO)c2)CC1]

A mixture of 2-(5-fluoro-2-nitrophenyl)ethan-1-ol (71.0 g, 383.8 mmol), benzyl piperazine-1-carboxylate (101.3 g, 460.56 mmol) and $K_2CO_3$ (106.0 g, 767.6 mmol) in DMSO (800 mL) was stirred at 110° C. overnight. The mixture was treated with water (1.0 L), extracted with dichloromethane (3×500 mL) and washed with brine (800 mL). The organic phase was dried over anhydrous sodium sulfate, filtered and concentrated under reduced pressure to afford the crude product, which was purified with silica gel column chromatography (PE:EA=100:0~80:20 gradient elution) to give the product (125 g, 84.4%). $[M+H]^+$=386.0.

Step 4: benzyl 4-(4-nitro-3-(2-(tosyloxy)ethyl)phenyl)piperazine-1-carboxylate

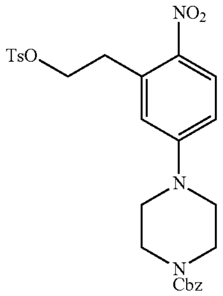 [SMILES: Cc1ccc(S(=O)(=O)OCCc2cc(N3CCN(C(=O)OCc4ccccc4)CC3)ccc2[N+](=O)[O-])cc1]

To a solution of benzyl 4-(3-(2-hydroxyethyl)-4-nitrophenyl)piperazine-1-carboxylate (152.0 g, 394.8 mmol) and TEA (179 g, 1.77 mol) in DCM (1.2 L) was added tosyl chloride (112.2 g, 590.7 mmol) at 0° C. The mixture was stirred at room temperature overnight. The mixture was extracted with water (3×800 mL) and washed with brine (500 mL). The organic phase was dried over anhydrous sodium sulfate, filtered and concentrated under reduced pressure to afford the crude product, which was purified with silica gel column chromatography (PE:EA=100:0~80:20 gradient elution) to give the product (173.0 g, 81.3%). $[M+H]^+$=540.0.

Step 5: benzyl 4-(3-(2-(3,5-dibromo-4-cyano-1H-pyrazol-1-yl)ethyl)-4-nitrophenyl)piperazine-1-carboxylate

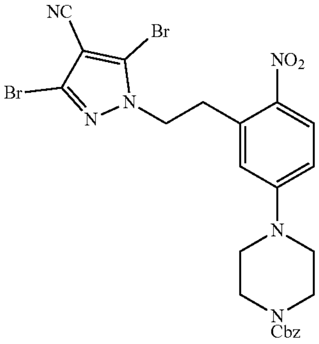 [SMILES: N#Cc1c(Br)nn(CCc2cc(N3CCN(C(=O)OCc4ccccc4)CC3)ccc2[N+](=O)[O-])c1Br]

A mixture of benzyl 4-(4-nitro-3-(2-(tosyloxy)ethyl)phenyl)piperazine-1-carboxylate (97.0 g, 0.18 mol), 3,5-dibromo-1H-pyrazole-4-carbonitrile (47 g, 0.189 mol) and $K_2CO_3$ (49.7 g, 0.36 mmol) in MeCN (1.2 L) was stirred at 90° C. overnight. The mixture was treated with water (1.5 L), extracted with dichloromethane (3×800 mL) and washed with brine (800 mL). The organic phase was dried over anhydrous sodium sulfate, filtered and concentrated under reduced pressure to afford the crude product, which was purified with silica gel column chromatography (PE:EA=75:25~25:75 gradient elution) to give the product (80 g, 72.1%). $[M+H]^+$=617.3.

Step 6: benzyl 4-(4-amino-3-(2-(3,5-dibromo-4-cyano-1H-pyrazol-1-yl)ethyl)phenyl)piperazine-1-carboxylate

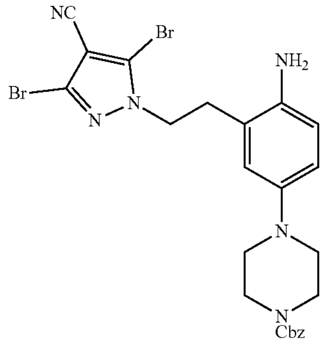 [SMILES: N#Cc1c(Br)nn(CCc2cc(N3CCN(C(=O)OCc4ccccc4)CC3)ccc2N)c1Br]

To a solution of benzyl 4-(3-(2-(3,5-dibromo-4-cyano-1H-pyrazol-1-yl)ethyl)-4-nitrophenyl)piperazine-1-carboxylate (80.0 g, 0.13 mol) and sodium hydrosulfite (135.7 g, 0.78 mol, in 0.6 L of water) in MeOH (1.2 L) and DCM (0.6 L) was added ammonium hydroxide (20.0 mL) at 0° C. The mixture was stirred at room temperature for 30 min, filtered and extracted with dichloromethane (3×300 mL) and water (3×500 mL). The organic phase was dried over anhydrous sodium sulfate and filtered to give the crude product, which was purified with silica gel column chromatography (PE:EA=60:40~10:90 gradient elution) to give the product (78 g, 100%). $[M+H]^+$=587.0.

Step 7: benzyl 4-(2-bromo-3-cyano-9,10-dihydro-4H-benzo[d]pyrazolo[1,5-a][1,3]diazepin-7-yl)piperazine-1-carboxylate

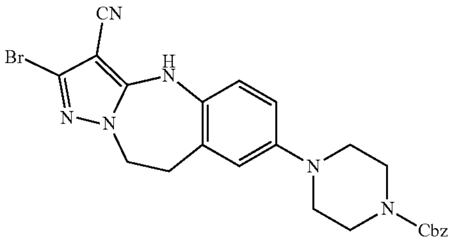 [SMILES: N#Cc1c(Br)nn2c1Nc1ccc(N3CCN(C(=O)OCc4ccccc4)CC3)cc1CC2]

A mixture of benzyl 4-(4-amino-3-(2-(3,5-dibromo-4-cyano-1H-pyrazol-1-yl)ethyl)phenyl)piperazine-1-carboxylate (10.0 g, 17.06 mmol), N1,N2-bis(4-hydroxy-2,6-dimethylphenyl)oxalamide (560 mg, 1.706 mmol), copper(I) iodide (324 mg, 1.706 mmol), potassium carbonate (4.7 g, 34.16 mmol) in DMSO (80.0 mL) was stirred at 80° C. overnight under nitrogen. The mixture was treated with water (200 mL), extracted with dichloromethane (3×100 mL) and washed with brine (200 mL). The organic phase was dried over anhydrous sodium sulfate, filtered and concentrated under reduced pressure to afford the crude product, which was purified with silica gel column chromatography (PE:EA=60:40~30:70 gradient elution) to give the product (3.7 g, 43.0%). $[M+H]^+$=507.0.

Step 8: benzyl 4-(2-(4-(((tert-butoxycarbonyl)amino)methyl)-2,3-difluorophenyl)-3-cyano-9,10-dihydro-4H-benzo[d]pyrazolo[1,5-a][1,3]diazepin-7-yl)piperazine-1-carboxylate

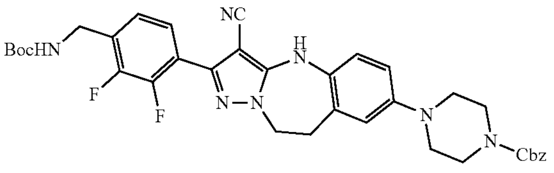 [SMILES: CC(C)(C)OC(=O)NCc1ccc(-c2nn3c(c2C#N)Nc2ccc(N4CCN(C(=O)OCc5ccccc5)CC4)cc2CC3)c(F)c1F]

A mixture of benzyl 4-(2-bromo-3-cyano-9,10-dihydro-4H-benzo[d]pyrazolo[1,5-a][1,3]diazepin-7-yl)piperazine-1-carboxylate (300 mg, 0.6 mmol), tert-butyl (2,3-difluoro-4-(4,4,5,5-tetramethyl-1,3,2-dioxaborolan-2-yl)benzyl) carbamate (442.8 mg, 1.2 mmol, made by procedure similar to example C2 step 2), $Pd(PPh_3)_4$ (138.6 mg, 0.12 mmol) and $Na_2CO_3$ (1.5 mL, 3 mmol, 2 M) in 1,4-dioxane (30.0 mL) was stirred in a round bottom flask at 100° C. overnight under nitrogen. The mixture was evaporated in vacuum to give the crude product, which was purified with silica gel column chromatography (PE:EA=80:40~20:80 gradient elution) to give the product (300 mg, 74.8%). $[M+H]^+$=670.3.

Step 9: benzyl 4-(2-(4-(aminomethyl)-2,3-difluorophenyl)-3-cyano-9,10-dihydro-4H-benzo[d]pyrazolo[1,5-a][1,3]diazepin-7-yl)piperazine-1-carboxylate hydrochloride

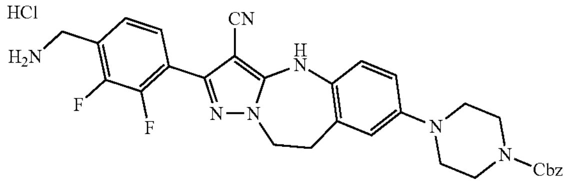 [SMILES: Cl ; N#Cc1c(-c2ccc(CN)c(F)c2F)nn2c1Nc1ccc(N3CCN(C(=O)OCc4ccccc4)CC3)cc1CC2]

A mixture of benzyl 4-(2-(4-(((tert-butoxycarbonyl)amino)methyl)-2,3-difluorophenyl)-3-cyano-9,10-dihydro-4H-benzo[d]pyrazolo[1,5-a][1,3]diazepin-7-yl)piperazine-1-carboxylate (0.3 g, 0.45 mmol) in HCl/1,4-dioxane (20.0 mL, 6 N) and DCM (5.0 mL) was stirred in a round bottom flask at room temperature for 1 hour. The mixture was filtered to afford the product (270 mg, 99.0%). $[M-NH_2+H]^+$=570.2.

Step 10: benzyl 4-(3-cyano-2-(2,3-difluoro-4-((2-methoxy-5-(trifluoromethyl)benzamido)methyl)phenyl)-9,10-dihydro-4H-benzo[d]pyrazolo[1,5-a][1,3]diazepin-7-yl)piperazine-1-carboxylate

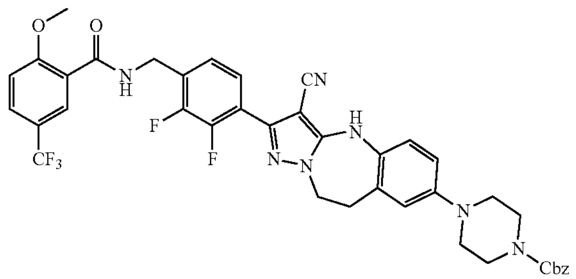 [SMILES: COc1ccc(C(F)(F)F)cc1C(=O)NCc1ccc(-c2nn3c(c2C#N)Nc2ccc(N4CCN(C(=O)OCc5ccccc5)CC4)cc2CC3)c(F)c1F]

A mixture of benzyl 4-(2-(4-(aminomethyl)-2,3-difluorophenyl)-3-cyano-9,10-dihydro-4H-benzo[d]pyrazolo[1,5-a][1,3]diazepin-7-yl)piperazine-1-carboxylate hydrochloride (270 mg, 0.382 mmol), 2-methoxy-5-(trifluoromethyl)benzoic acid (126 mg, 0.574 mmol), HATU (218 mg, 0.574 mmol) and DIPEA (148 mg, 1.146 mmol) in DMF (20.0 mL) was stirred in a round bottom flask at room temperature overnight. The mixture was evaporated in vacuum to afford the crude product, which was purified with silica gel column chromatography (PE:EA=80:40~20:80 gradient elution) to give the product (400 mg, crude). $[M+H]^+$=772.2.

Step 11: 2-(2,3-difluoro-4-((2-methoxy-5-(trifluoromethyl)benzamido)methyl)phenyl)-7-(piperazin-1-yl)-9,10-dihydro-4H-benzo[d]pyrazolo[1,5-a][1,3]diazepine-3-carboxamide

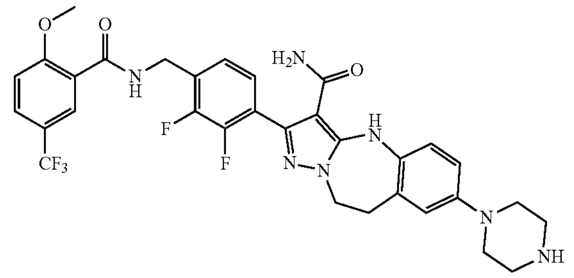 [SMILES: COc1ccc(C(F)(F)F)cc1C(=O)NCc1ccc(-c2nn3c(c2C(N)=O)Nc2ccc(N4CCNCC4)cc2CC3)c(F)c1F]

A mixture of benzyl 4-(3-cyano-2-(2,3-difluoro-4-((2-methoxy-5-(trifluoromethyl)benzamido)methyl)phenyl)-9,10-dihydro-4H-benzo[d]pyrazolo[1,5-a][1,3]diazepin-7-yl)piperazine-1-carboxylate (0.4 g, 0.52 mmol) in methanesulfonic acid (20.0 mL) was stirred at 100° C. for 1 hour. The mixture was then cooled, alkalified with aqueous sodium hydride solution to pH 12, extracted with dichloromethane (3×30.0 mL) and washed with brine (30.0 mL). The organic phase was dried over anhydrous sodium sulfate, filtered and concentrated under reduced pressure to afford the product (370 mg, crude). $[M+H]^+$=656.4.

Step 12: 2-(2,3-difluoro-4-((2-methoxy-5-(trifluoromethyl)benzamido)methyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

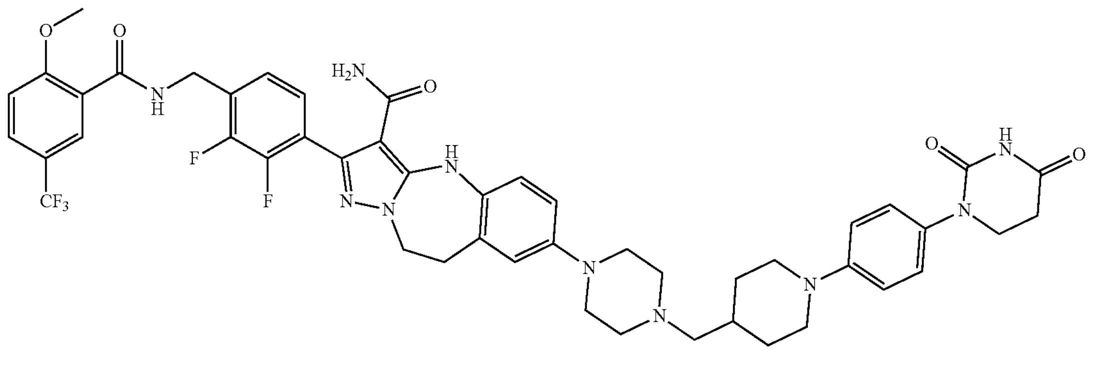 [SMILES: COc1ccc(C(F)(F)F)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)c(F)c1F]

A mixture of 2-(2,3-difluoro-4-((2-methoxy-5-(trifluoromethyl)benzamido)methyl)phenyl)-7-(piperazin-1-yl)-9,10-dihydro-4H-benzo[d]pyrazolo[1,5-a][1,3]diazepine-3-carboxamide (0.37 g, 0.565 mmol) and 1-(4-(2,4-dioxotetrahydropyrimidin-1(2H)-yl)phenyl)piperidine-4-carbaldehyde (170 mg, 0.847 mmol) in MeOH (5.0 mL), DCM (20.0 mL) and acetic acid (1.0 mL) was stirred at room temperature for 16 hours, and then sodium triacetoxyborohydride (0.6 g, 2.825 mmol) was added and stirred at room temperature for 1 hour. The mixture was treated with water (30.0 mL), extracted with dichloromethane (3×30.0 mL), and washed with brine (30.0 mL). The organic phase was dried over anhydrous sodium sulfate, filtered, concentrated under reduced pressure to afford the crude product, which was purified with silica gel column chromatography (DCM: MeOH=100:0~90:10 gradient elution) and washed with MeOH (30.0 mL) to give the product (80 mg, 15.1%). $^1H$ NMR (400 MHz, DMSO) δ 10.26 (s, 1H), 9.63 (s, 1H), 8.94 (t, J=6.0 Hz, 1H), 8.00 (d, J=2.1 Hz, 1H), 7.87 (dd, J=8.9, 2.4 Hz, 1H), 7.37 (d, J=8.8 Hz, 1H), 7.32-7.24 (m, 2H), 7.13 (d, J=8.9 Hz, 2H), 6.93 (d, J=9.0 Hz, 2H), 6.85 (q, J=8.7 Hz, 3H), 4.63 (d, J=5.6 Hz, 2H), 4.39-4.32 (m, 2H), 3.99 (s, 3H), 3.69 (t, J=6.7 Hz, 4H), 3.18-3.14 (m, 2H), 3.11-3.07 (m, 4H), 2.67 (dd, J=14.8, 8.2 Hz, 4H), 2.53-2.49 (m, 4H), 2.22 (d, J=6.6 Hz, 2H), 1.81 (d, J=11.9 Hz, 2H), 1.75-1.64 (m, 1H), 1.22 (dd, J=22.4, 12.1 Hz, 2H); $[M+H]^+$=941.8.

Example C29:2-(4-((5-cyclopropyl-2-methoxybenzamido)methyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

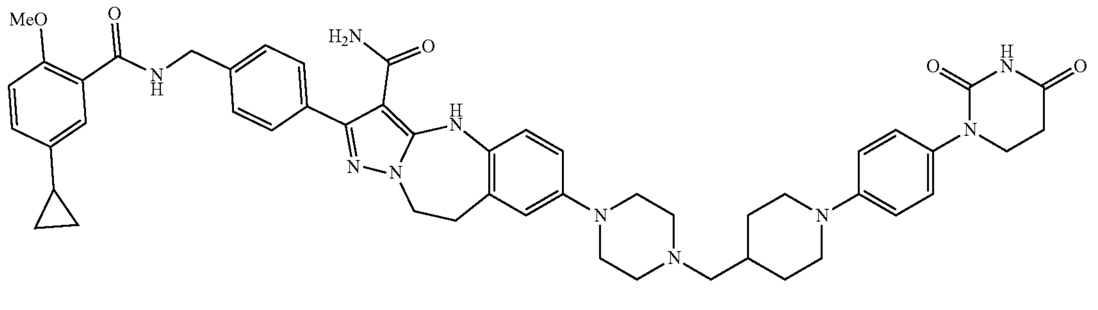 [SMILES: COc1ccc(C2CC2)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1]

The titled compound was synthesized in the procedures similar to Example C28. $^1$H NMR (500 MHz, DMSO) δ 10.19 (s, 1H), 9.72 (s, 1H), 8.67 (s, 1H), 7.41 (d, J=5.5 Hz, 3H), 7.36 (d, J=6.1 Hz, 2H), 7.12 (d, J=8.3 Hz, 1H), 7.07 (d, J=7.6 Hz, 2H), 6.97 (d, J=8.2 Hz, 1H), 6.87 (d, J=7.3 Hz, 2H), 6.81 (s, 3H), 4.48 (s, 2H), 4.27 (s, 2H), 3.79 (s, 3H), 3.64-3.60 (m, 4H), 3.12-2.99 (m, 6H), 2.63-2.59 (m, 5H), 2.49-2.45 (m, 3H), 1.87 (d, J=20.6 Hz, 2H), 1.75 (d, J=11.2 Hz, 3H), 1.17 (s, 3H), 0.84 (d, J=6.8 Hz, 2H), 0.53 (s, 2H); $[M+H]^+$=877.7.

Example C30:2-(4-((4,5-difluoro-2-methoxybenzamido)methyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

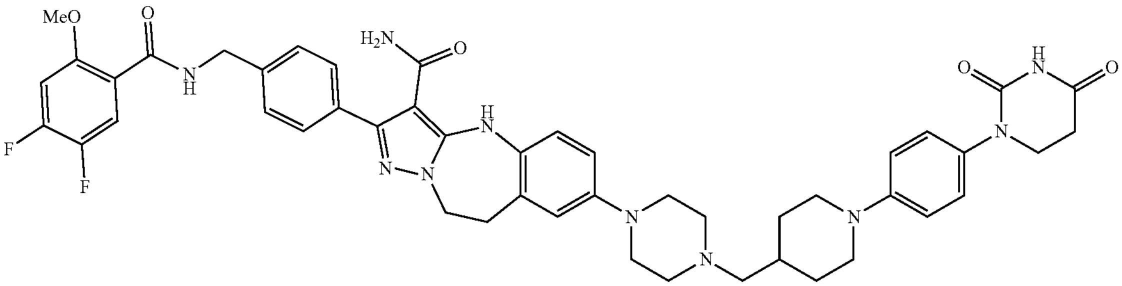 [SMILES: COc1cc(F)c(F)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1]

The titled compound was synthesized in the procedures similar to Example C28. $^1$H NMR (500 MHz, DMSO) δ 10.19 (s, 1H), 9.73 (s, 1H), 8.75 (s, 1H), 7.70 (t, J=10.3 Hz, 1H), 7.44-7.33 (m, 4H), 7.32-7.27 (m, 1H), 7.07 (d, J=8.1 Hz, 2H), 6.91-6.75 (m, 6H), 4.49 (d, J=4.1 Hz, 2H), 4.27 (d, J=0.6 Hz, 2H), 3.84 (s, 3H), 3.63 (s, 4H), 3.12-2.97 (m, 6H), 2.68-2.59 (m, 5H), 2.47 (s, 4H), 1.80-1.70 (m, 3H), 1.27-1.13 (m, 3H); $[M+H]^+$=873.7.

Example B30:7-(4-((1-(4-(2,4-dioxotetrahydropyrimidin-1(2H)-yl)phenyl)piperidin-4-yl)methyl)piperazin-1-yl)-2-(2-fluoro-5-methyl-4-((6-methylpyridin-2-yl)carbamoyl)phenyl)-9,10-dihydro-4H-benzo[d]pyrazolo[1,5-a][1,3]diazepine-3-carboxamide Step 1: 4-bromo-5-fluoro-2-methyl-N-(6-methylpyridin-2-yl)benzamide

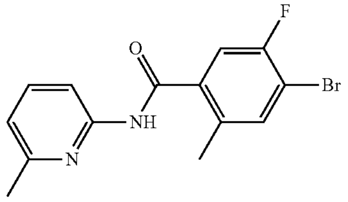 [SMILES: Cc1cccc(NC(=O)c2cc(F)c(Br)cc2C)n1]

A mixture of methyl 4-bromo-5-fluoro-2-methylbenzoate (1 g, 0.00406 mol) and 6-methylpyridin-2-amine (0.44 g, 0.00406 mol) in THE (30 mL) was stirred at 0° C.-5° C. for 5 mins, then LiHMDS (6.2 mL, 0.00812 mol, 1.3 M) was added dropwise. The mixture was stirred at room temperature overnight. Then the mixture was quenched by $NH_4Cl$ solution, extracted with EA (3×50 mL) and washed with brine (100 mL). The organic phase was dried over anhydrous $Na_2SO_4$, filtered, and concentrated under reduced pressure to afford the product (1.67 g, crude). $[M+H]^+$=323.0.

Step 2: 5-fluoro-2-methyl-N-(6-methylpyridin-2-yl)-4-(4,4,5,5-tetramethyl-1,3,2-dioxaborolan-2-yl)benzamide

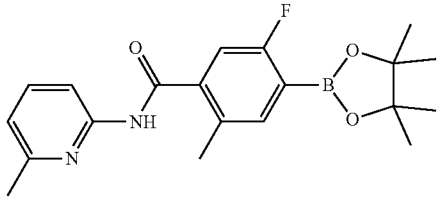 [SMILES: Cc1cccc(NC(=O)c2cc(F)c(B3OC(C)(C)C(C)(C)O3)cc2C)n1]

A mixture of 4-bromo-5-fluoro-2-methyl-N-(6-methylpyridin-2-yl)benzamide (1.5 g, 0.00467 mol), 4,4,4',4',5,5,5',5'-octamethyl-2,2'-bi(1,3,2-dioxaborolane) (1.78 g, 0.00700 mol), Pd(dppf)$Cl_2$ (170 mg, 0.000233 mol) and KOAc (915 mg, 0.00934 mol) in dioxane (30.0 mL) was stirred at 93° C. overnight under $N_2$. The mixture was cooled down to room temperature, and concentrated under reduced pressure. The residue was purified by silica gel column chromatography PE:EA=100%:0%~50%:50% to afford the product (530 mg, 31%). $[M+H]^+$=371.0.

Step 3: benzyl 4-(3-cyano-2-(2-fluoro-5-methyl-4-((6-methylpyridin-2-yl)carbamoyl)phenyl)-9,10-dihydro-4H-benzo[d]pyrazolo[1,5-a][1,3]diazepin-7-yl)piperazine-1-carboxylate

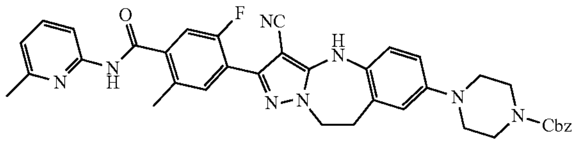 [SMILES: Cc1cccc(NC(=O)c2cc(F)c(-c3nn4c(c3C#N)Nc3ccc(N5CCN(C(=O)OCc6ccccc6)CC5)cc3CC4)cc2C)n1]

A mixture of benzyl 4-(2-bromo-3-cyano-9,10-dihydro-4H-benzo[d]pyrazolo[1,5-a][1,3]diazepin-7-yl)piperazine-1-carboxylate (725 mg, 1.43 mmol), 5-fluoro-2-methyl-N-(6-methylpyridin-2-yl)-4-(4,4,5,5-tetramethyl-1,3,2-dioxaborolan-2-yl)benzamide (530 mg, 1.43 mmol), $Na_2CO_3$ (303 mg, 1.86 mmol) and $Pd(PPh_3)_4$ (165 mg, 0.143 mmol) in dioxane/water (20 mL/4 mL) was stirred at 95° C. overnight under $N_2$. The mixture was cooled down to room temperature, and concentrated under reduced pressure. The residue was purified by silica gel column chromatography PE:EA=100%:0%~0%:100% to afford the desired product (347 mg, 36%). $[M+H]^+$=671.0.

Step 4: 2-(2-fluoro-5-methyl-4-((6-methylpyridin-2-yl)carbamoyl)phenyl)-7-(piperazin-1-yl)-9,10-dihydro-4H-benzo[d]pyrazolo[1,5-a][1,3]diazepine-3-carboxamide

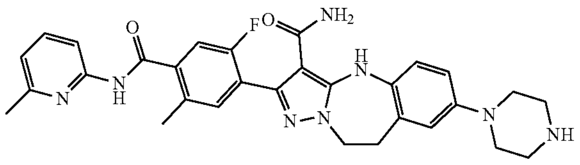 [SMILES: Cc1cccc(NC(=O)c2cc(F)c(-c3nn4c(c3C(N)=O)Nc3ccc(N5CCNCC5)cc3CC4)cc2C)n1]

A mixture of benzyl 4-(3-cyano-2-(2-fluoro-5-methyl-4-((6-methylpyridin-2-yl)carbamoyl)phenyl)-9,10-dihydro-4H-benzo[d]pyrazolo[1,5-a][1,3]diazepin-7-yl)piperazine-1-carboxylate (347 mg, 0.517 mmol) in methanesulfonic acid (10.0 mL) was stirred at 100° C. for 30 mins. The mixture was then cooled, basified with aqueous sodium hydroxide solution to pH 12, extracted with dichloromethane (3×30 mL) and washed with water (3×30 mL). The organic phase was dried over anhydrous sodium sulfate, filtered, and concentrated under reduced pressure to afford the product (225 mg, crude).

Step 5: 7-(4-((1-(4-(2,4-dioxotetrahydropyrimidin-1(2H)-yl)phenyl)piperidin-4-yl)methyl)piperazin-1-yl)-2-(2-fluoro-5-methyl-4-((6-methylpyridin-2-yl)carbamoyl)phenyl)-9,10-dihydro-4H-benzo[d]pyrazolo[1,5-a][1,3]diazepine-3-carboxamide

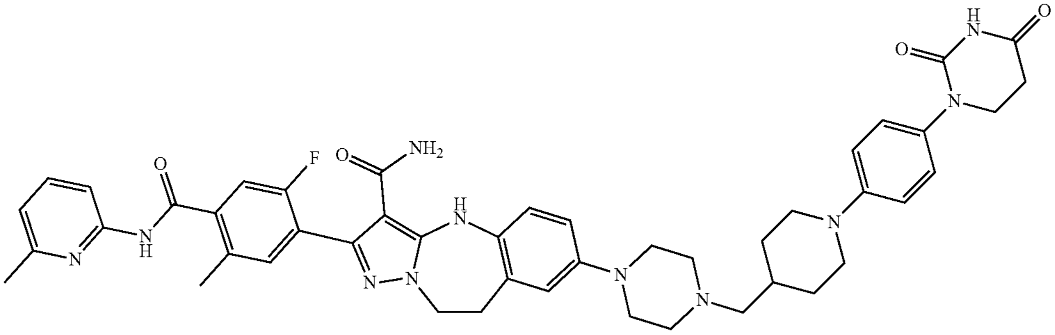 [SMILES: Cc1cccc(NC(=O)c2cc(F)c(-c3nn4c(c3C(N)=O)Nc3ccc(N5CCN(CC6CCN(c7ccc(N8CCC(=O)NC8=O)cc7)CC6)CC5)cc3CC4)cc2C)n1]

A mixture of 2-(2-fluoro-5-methyl-4-((6-methylpyridin-2-yl)carbamoyl)phenyl)-7-(piperazin-1-yl)-9,10-dihydro-4H-benzo[d]pyrazolo[1,5-a][1,3]diazepine-3-carboxamide (100 mg, crude), 1-(4-(2,4-dioxotetrahydropyrimidin-1(2H)-yl)phenyl)piperidine-4-carbaldehyde (70 mg, 0.234 mmol) in dichloromethane (5 mL) and MeOH (5 mL) was stirred at room temperature for 5 mins. Then HOAc (0.06 mL) was added. The mixture was stirred at room temperature overnight. Then $NaBH(OAc)_3$ (191 mg, 0.90 mmol) was added and stirred at room temperature for 2 hours. The reaction mixture was concentrated in vacuum, and the residue was purified by silica gel column chromatography (DCM:MeOH=100%: 0%~90%: 10% gradient elution) to give crude product, which was further purified by prep-TLC (DCM:MeOH=10:1) to afford desired product (9.28 mg, 6%). $^1H$ NMR (400 MHz, DMSO) δ 10.82 (s, 1H), 10.27 (s, 1H), 9.70 (s, 1H), 8.02 (d, J=8.0 Hz, 1H), 7.74 (t, J=8.0 Hz, 1H), 7.41 (dd, J=20.0, 8.0 Hz, 2H), 7.13 (d, J=8.0 Hz, 2H), 7.04 (d, J=8.0 Hz, 1H), 6.93 (d, J=8.0 Hz, 2H), 6.90-6.86 (m, 2H), 6.83 (d, J=8.0 Hz, 1H), 4.40-4.32 (m, 2H), 3.73-3.64 (m, 4H), 3.20-3.13 (m, 2H), 3.09 (s, 4H), 2.71-2.62 (m, 4H), 2.53-2.51 (m, 6H), 2.42 (s, 3H), 2.37 (s, 3H), 2.22 (d, J=8.0 Hz, 2H), 1.81 (d, J=12.0 Hz, 2H), 1.72 (s, 1H), 1.28-1.16 (m, 2H); $[M+H]^+$=840.5.

Example B31 and Example B32: 5-(3-cyano-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepin-2-yl)-3-methyl-N-(6-methylpyridin-2-yl)picolinamide and 7-(4-((1-(4-(2,4-dioxotetrahydropyrimidin-1(2H)-yl)phenyl)piperidin-4-yl)methyl)piperazin-1-yl)-2-(5-methyl-6-((6-methylpyridin-2-yl)carbamoyl)pyridin-3-yl)-9,10-dihydro-4H-benzo[d]pyrazolo[1,5-a][1,3]diazepine-3-carboxamide Step 1: 5-bromo-3-methyl-N-(6-methylpyridin-2-yl)picolinamide

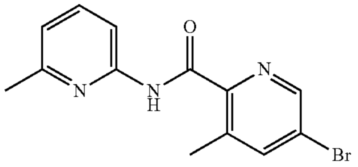 [SMILES: Cc1cccc(NC(=O)c2ncc(Br)cc2C)n1]

To a mixture of 5-bromo-3-methylpicolinic acid (2.16 g, 10.0 mmol) in DMF (20 mL) were added 6-methylpyridin-2-amine (1.08 g, 10.0 mmol), HATU (3.80 g, 10.0 mmol) and DIPEA (2.58 g, 20.0 mmol). The mixture was stirred at 80° C. for 18 hours. LCMS showed the reaction was completed. The reaction was poured into water (100 mL), filtered, and washed with water (20 mL) to get the product (2.96 g, 97%). $[M+H]^+$=306.0.

Step 2: 3-methyl-N-(6-methylpyridin-2-yl)-5-(4,4,5,5-tetramethyl-1,3,2-dioxaborolan-2-yl)picolinamide

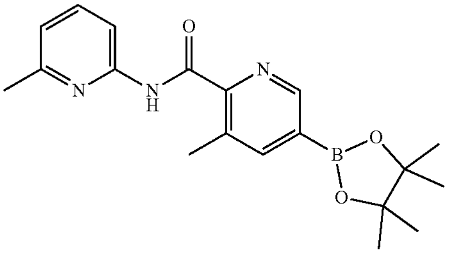

To a mixture of 5-bromo-3-methyl-N-(6-methylpyridin-2-yl)picolinamide (2.96 g, 9.6 mmol) in dioxane (50 mL) were added 4,4,4',4',5,5,5',5'-octamethyl-2,2'-bi(1,3,2-dioxaborolane) (2.54 g, 10.0 mmol), Pd(dppf)$Cl_2$ (731 mg, 1.0 mmol) and potassium acetate (1.44 g, 7.5 mmol). The mixture was stirred at 105° C. for 18 hours. The mixture was evaporated in vacuum to afford the crude product, which was further purified with silica gel column chromatography (PE:EA=100:1~30:70 gradient elution) to give the product (3.0 g, 87%). $[M-C_6H_{10}+H]^+$=272.1.

Step 3: benzyl 4-(3-cyano-2-(5-methyl-6-((6-methylpyridin-2-yl)carbamoyl)pyridin-3-yl)-9,10-dihydro-4H-benzo[d]pyrazolo[1,5-a][1,3]diazepin-7-yl)piperazine-1-carboxylate

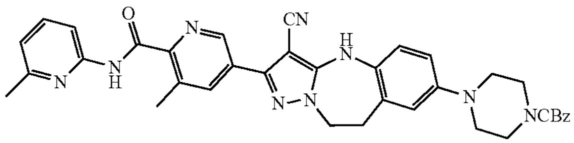

A mixture of 3-methyl-N-(6-methylpyridin-2-yl)-5-(4,4,5,5-tetramethyl-1,3,2-dioxaborolan-2-yl)picolinamide (353 mg, 1.0 mmol), benzyl 4-(2-bromo-3-cyano-9,10-dihydro-4H-benzo[d]pyrazolo[1,5-a][1,3]diazepin-7-yl)piperazine-1-carboxylate (506 mg, 1.0 mmol), $Pd(PPh_3)_4$ (115 mg, 0.1 mmol) and $K_2CO_3$ (276 mg, 2.0 mmol) in 1,4-dioxane (10 mL) and $H_2O$ (2 mL) was stirred in a round bottom flask at 100° C. for 18 hours. The mixture was evaporated in vacuum to afford the crude product, which was further purified with silica gel column chromatography (PE:EA=3:1) to give the product (360 mg, 55%). $[M+H]^+$=654.4.

Step 4: 5-(3-cyano-7-(piperazin-1-yl)-9,10-dihydro-4H-benzo[d]pyrazolo[1,5-a][1,3]diazepin-2-yl)-3-methyl-N-(6-methylpyridin-2-yl)picolinamide and 2-(5-methyl-6-((6-methylpyridin-2-yl)carbamoyl)pyridin-3-yl)-7-(piperazin-1-yl)-9,10-dihydro-4H-benzo[d]pyrazolo[1,5-a][1,3]diazepine-3-carboxamide

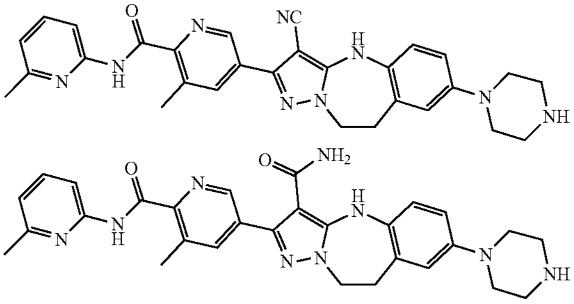

A mixture of benzyl 4-(3-cyano-2-(5-methyl-6-((6-methylpyridin-2-yl)carbamoyl)pyridin-3-yl)-9,10-dihydro-4H-benzo[d]pyrazolo[1,5-a][1,3]diazepin-7-yl)piperazine-1-carboxylate (360 mg, 0.55 mmol) in methylsulfonic acid (20 mL) was stirred in a round bottom flask at 100° C. for 0.5 hour. The mixture was cooled down to room temperature and poured into 1 N NaOH solution. To the mixture was added 1N HCl to adjust PH to 7-8. The mixture was filtered and evaporated in vacuum to afford the crude product (322 mg, mixture), which was used for next step without further purification. $[M+H]^+$=538.4.

Step 5: 5-(3-cyano-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepin-2-yl)-3-methyl-N-(6-methylpyridin-2-yl)picolinamide and 7-(4-((1-(4-(2,4-dioxotetrahydropyrimidin-1(2H)-yl)phenyl)piperidin-4-yl)methyl)piperazin-1-yl)-2-(5-methyl-6-((6-methylpyridin-2-yl)carbamoyl)pyridin-3-yl)-9,10-dihydro-4H-benzo[d]pyrazolo[1,5-][1,3]diazepine-3-carboxamide Example B31

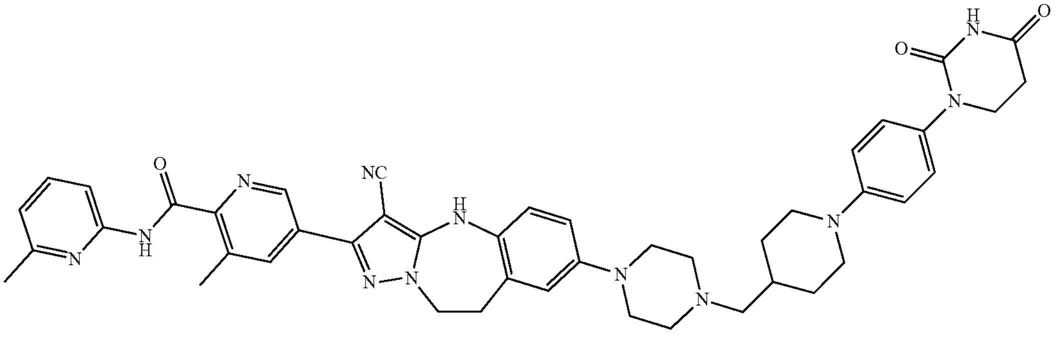

-continued

Example B32

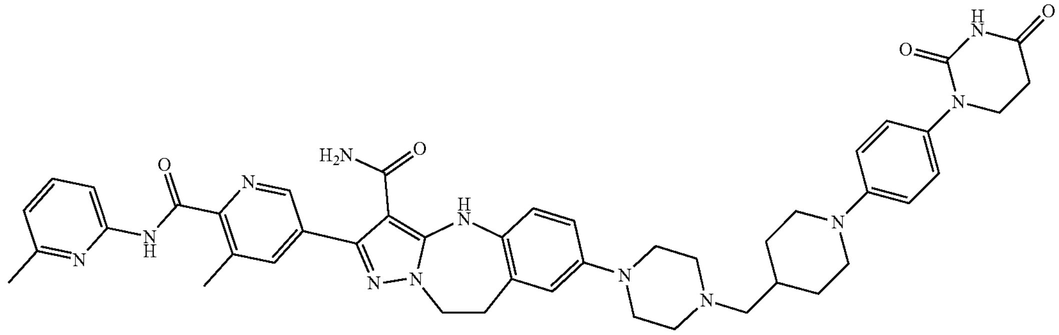

A mixture of the previous residue (102 mg, crude) and 1-(4-(2,4-dioxotetrahydropyrimidin-1(2H)-yl)phenyl)piperidine-4-carbaldehyde (120 mg, 0.4 mmol) in DCM (20 mL), MeOH (1 mL) and acetic acid (0.06 mL) was stirred in a round bottom flask at room temperature for 1 hour. To the mixture was added $NaBH(OAc)_3$ (424 mg, 2.0 mmol) and stirred at room temperature for 18 hours. Then the mixture was purified with Pre-TLC (DCM: MeOH=8:1) to give example B31 (4 mg, 5%) and example B32 (18 mg, 10%). Example B31: $^1H$ NMR (400 MHz, DMSO) δ 10.57 (s, 1H), 10.25 (s, 1H), 9.54 (s, 1H), 8.96 (s, 1H), 8.19 (s, 1H), 8.07 (d, J=8.0 Hz, 1H), 7.77 (t, J=7.8 Hz, 1H), 7.21 (d, J=8.5 Hz, 1H), 7.13 (d, J=8.8 Hz, 2H), 7.05 (d, J=7.5 Hz, 1H), 6.93 (d, J=9.0 Hz, 2H), 6.88-6.82 (m, 2H), 4.47-4.40 (m, 2H), 3.73-3.64 (m, 4H), 3.30-3.28 (m, 3H), 3.18-3.13 (m, 2H), 3.12-3.05 (m, 4H), 2.72 (s, 3H), 2.70-2.64 (m, 4H), 2.44 (s, 3H), 2.22 (d, J=7.0 Hz, 2H), 1.81 (d, J=12.5 Hz, 2H), 1.76-1.67 (m, 1H), 1.29-1.17 (m, 3H); $[M+H]^+$=804.9. Example B32: $^1H$ NMR (500 MHz, DMSO) δ 10.57 (s, 1H), 10.25 (s, 1H), 9.63 (s, 1H), 8.68 (d, J=1.5 Hz, 1H), 8.08 (d, J=8.0 Hz, 1H), 7.98 (d, J=1.5 Hz, 1H), 7.77 (t, J=8.0 Hz, 1H), 7.13 (d, J=9.0 Hz, 2H), 7.05 (d, J=7.5 Hz, 1H), 7.00-6.75 (m, 6H), 4.39 (d, J=4.5 Hz, 2H), 3.69 (t, J=6.5 Hz, 4H), 3.16 (s, 2H), 3.09 (s, 4H), 2.72 (s, 3H), 2.69-2.65 (m, 4H), 2.50-2.48 (m, 5H), 2.44 (s, 3H), 2.22 (d, J=7.0 Hz, 2H), 1.81 (d, J=12.5 Hz, 2H), 1.22 (m, 3H); $[M+H]^+$=823.7.

Example B33:7-(4-(4-(2,6-dioxopiperidin-3-yl)-3,5-difluorophenethyl)piperazin-1-yl)-2-(5-methyl-6-((6-methylpyridin-2-yl)carbamoyl)pyridin-3-yl)-9,10-dihydro-4H-benzo[d]pyrazolo[1,5-a][1,3]diazepine-3-carboxamide Step 1: 7-(4-(4-(2,6-dioxopiperidin-3-yl)-3,5-difluorophenethyl)piperazin-1-yl)-2-(5-methyl-6-((6-methylpyridin-2-yl)carbamoyl)pyridin-3-yl)-9,10-dihydro-4H-benzo[d]pyrazolo[1,5-a][1,3]diazepine-3-carboxamide

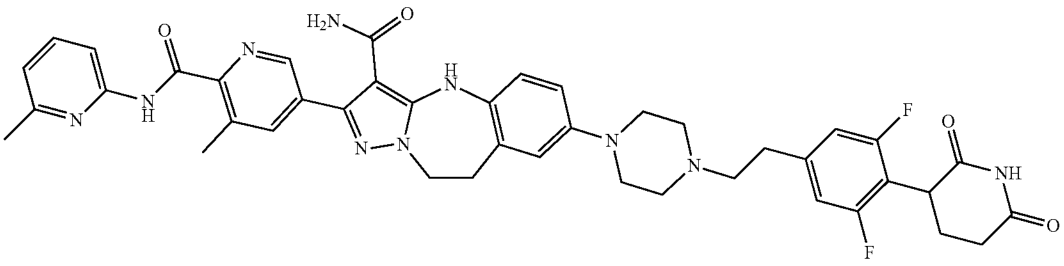 [SMILES: Cc1cccc(NC(=O)c2ncc(-c3nn4c(c3C(N)=O)Nc3ccc(N5CCN(CCc6cc(F)c(C7CCC(=O)NC7=O)c(F)c6)CC5)cc3CC4)cc2C)n1]

A mixture of 2-(5-methyl-6-((6-methylpyridin-2-yl)carbamoyl)pyridin-3-yl)-7-(piperazin-1-yl)-9,10-dihydro-4H-benzo[d]pyrazolo[1,5-a][1,3]diazepine-3-carboxamide (60 mg, 0.11 mmol) and 2-(4-(2,6-dioxopiperidin-3-yl)-3,5-difluorophenyl)acetaldehyde (30 mg, 0.11 mmol) in DCM (6 mL) and MeOH (1 mL) was stirred in a round bottom flask at room temperature for 2 hours. To the mixture was added $NaBH_3CN$ (64 mg, 1.0 mmol) and stirred at room temperature for 18 hours. Then the mixture was purified with Pre-TLC (DCM:MeOH=9:1) to give the product (14 mg, 18%). $^1H$ NMR (500 MHz, DMSO) δ 10.94 (s, 1H), 10.57 (s, 1H), 9.63 (s, 1H), 8.68 (s, 1H), 8.08 (d, J=8.5 Hz, 1H), 7.98 (s, 1H), 7.77 (t, J=7.5 Hz, 1H), 7.09-7.01 (m, 3H), 6.91-6.82 (m, 3H), 4.47-4.33 (m, 2H), 4.25-4.15 (m, 1H), 3.29 (s, 2H), 3.19-3.14 (m, 2H), 3.13-3.03 (m, 4H), 2.88-2.76 (m, 3H), 2.72 (s, 3H), 2.62-2.56 (m, 5H), 2.45-2.41 (m, 4H), 2.19-2.07 (m, 1H), 2.04-1.95 (m, 1H), 1.28-1.18 (m, 1H); $[M+H]^+$=788.7.

Example B34: (R)-7-(4-(3-(4-(2,6-dioxopiperidin-3-yl)phenyl)cyclobutyl)piperazin-1-yl)-2-(5-methyl-6-((6-methylpyridin-2-yl)carbamoyl)pyridin-3-yl)-9,10-dihydro-4H-benzo[d]pyrazolo[1,5-a][1,3]diazepine-3-carboxamide Step 1: (R)-7-(4-(3-(4-(2,6-dioxopiperidin-3-yl)phenyl)cyclobutyl)piperazin-1-yl)-2-(5-methyl-6-((6-methylpyridin-2-yl)carbamoyl)pyridin-3-yl)-9,10-dihydro-4H-benzo[d]pyrazolo[1,5-a][1,3]diazepine-3-carboxamide

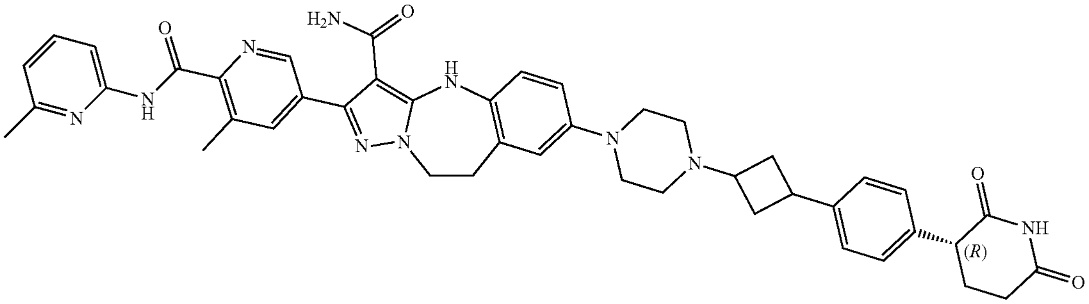

A mixture of 2-(5-methyl-6-((6-methylpyridin-2-yl)carbamoyl)pyridin-3-yl)-7-(piperazin-1-yl)-9,10-dihydro-4H-benzo[d]pyrazolo[1,5-a][1,3]diazepine-3-carboxamide (53 mg, 0.10 mmol) and (R)-3-(4-(3-oxocyclobutyl)phenyl)piperidine-2,6-dione (30 mg, 0.11 mmol) in DCM (6 mL) and MeOH (1 mL) was stirred in a round bottom flask at room temperature for 18 hours. To the mixture was added $NaBH_3CN$ (64 mg, 1.0 mmol) and stirred at room temperature for 2 hours. Then the mixture was purified with Pre-TLC (DCM:MeOH=10:1) to give the product (9 mg, 11%). $^1$H NMR (500 MHz, DMSO) δ 10.82 (s, 1H), 10.57 (s, 1H), 9.64 (s, 1H), 8.68 (s, 1H), 8.07 (s, 1H), 7.98 (s, 1H), 7.77 (s, 1H), 7.25-7.11 (m, 3H), 7.05 (d, J=7.5 Hz, 1H), 6.95-6.81 (m, 3H), 4.49-4.35 (m, 2H), 3.88-3.70 (m, 2H), 3.52-3.36 (m, 1H), 3.23-2.98 (m, 7H), 2.72 (s, 3H), 2.70-2.61 (m, 2H), 2.48-2.39 (m, 10H), 2.18 (d, J=11.5 Hz, 1H), 2.07-1.97 (m, 1H), 1.98-1.76 (m, 1H), 1.34-1.11 (m, 2H); $[M+H]^+$=779.5.

Example B35: (S)-7-(4-(3-(4-(2,6-dioxopiperidin-3-yl)phenyl)cyclobutyl)piperazin-1-yl)-2-(5-methyl-6-((6-methylpyridin-2-yl)carbamoyl)pyridin-3-yl)-9,10-dihydro-4H-benzo[d]pyrazolo[1,5-a][1,3]diazepine-3-carboxamide Step 1: (S)-7-(4-(3-(4-(2,6-dioxopiperidin-3-yl)phenyl)cyclobutyl)piperazin-1-yl)-2-(5-methyl-6-((6-methylpyridin-2-yl)carbamoyl)pyridin-3-yl)-9,10-dihydro-4H-benzo[d]pyrazolo[1,5-a][1,3]diazepine-3-carboxamide

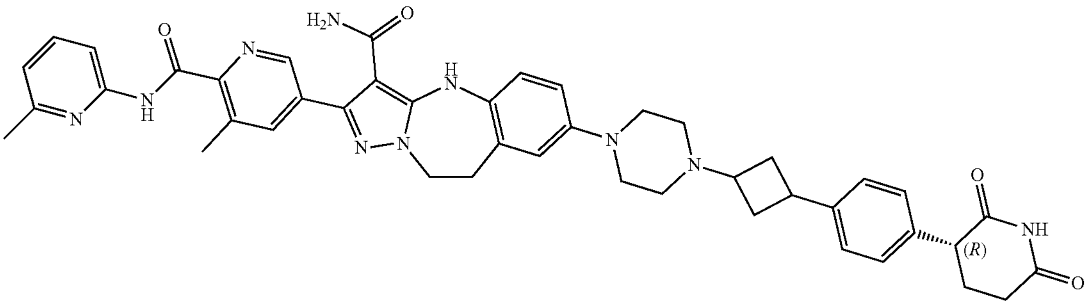

A mixture of 2-(5-methyl-6-((6-methylpyridin-2-yl)carbamoyl)pyridin-3-yl)-7-(piperazin-1-yl)-9,10-dihydro-4H-benzo[d]pyrazolo[1,5-a][1,3]diazepine-3-carboxamide (53 mg, 0.10 mmol) and (S)-3-(4-(3-oxocyclobutyl)phenyl)piperidine-2,6-dione (30 mg, 0.11 mmol) in DCM (6 mL) and MeOH (1 mL) was stirred in a round bottom flask at room temperature for 18 hours. To the mixture was added $NaBH_3CN$ (64 mg, 1.0 mmol) and stirred at room temperature for 2 hours. Then the mixture was purified with Pre-TLC (DCM:MeOH=9:1) to give the product (16 mg, 20%). $^1H$ NMR (500 MHz, DMSO) δ 10.82 (s, 1H), 10.57 (s, 1H), 9.64 (s, 1H), 8.68 (d, J=1.5 Hz, 1H), 8.08 (d, J=8.0 Hz, 1H), 7.98 (d, J=1.5 Hz, 1H), 7.77 (t, J=7.5 Hz, 1H), 7.30-7.19 (m, 2H), 7.18-7.11 (m, 2H), 7.07-7.03 (m, 1H), 6.92-6.81 (m, 3H), 4.46-4.33 (m, 2H), 3.82 (dd, J=11.5, 5.0 Hz, 1H), 3.19-3.06 (m, 6H), 2.72 (s, 3H), 2.70-2.62 (m, 2H), 2.49-2.45 (m, 8H), 2.45-2.41 (m, 4H), 2.22-2.13 (m, 1H), 2.06-1.98 (m, 1H), 1.93-1.81 (m, 2H), 1.31-1.20 (m, 1H); $[M+H]^+$ =779.5.

Example B36: 7-(4-((1-(4-(2,4-dioxotetrahydropyrimidin-1(2H)-yl)phenyl)piperidin-4-yl)methyl)piperazin-1-yl)-2-(4-methyl-5-((6-methylpyridin-2-yl)carbamoyl)pyridin-2-yl)-9,10-dihydro-4H-benzo[d]pyrazolo[1,5-a][1,3]diazepine-3-carboxamide Step 1: 6-chloro-4-methyl-N-(6-methylpyridin-2-yl)nicotinamide

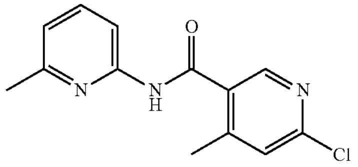 [SMILES: Cc1cccc(NC(=O)c2cnc(Cl)cc2C)n1]

To a mixture of 6-chloro-4-methylnicotinic acid (5.10 g, 30.0 mmol) in DMF (45 mL) were added 6-methylpyridin-2-amine (3.24 g, 30.0 mmol), HATU (11.40 g, 30.0 mmol) and DIPEA (7.74 g, 60.0 mmol). The mixture was stirred at 40° C. for 18 hours. LCMS showed the reaction was completed. The reaction was poured into water (100 mL), filtered, and washed with water (20 mL) to get the crude product, which was further purified with silica gel column chromatography (PE:EA=100:1~50:50 gradient elution) to give the product (4.0 g, 76%). $[M+H]^+$=261.8.

Step 2: tert-butyl 4-(3-cyano-2-(4-methyl-5-((6-methylpyridin-2-yl)carbamoyl)pyridin-2-yl)-9,10-dihydro-4H-benzo[d]pyrazolo[1,5-a][1,3]diazepin-7-yl)piperazine-1-carboxylate

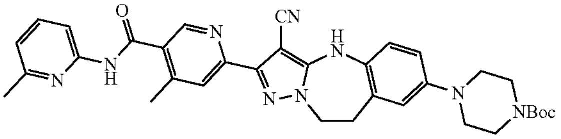 [SMILES: Cc1cccc(NC(=O)c2cnc(-c3nn4c(c3C#N)Nc3ccc(N5CCN(C(=O)OC(C)(C)C)CC5)cc3CC4)cc2C)n1]

To a mixture of 6-chloro-4-methyl-N-(6-methylpyridin-2-yl)nicotinamide (526 mg, 2.0 mmol) in dry dioxane (20 mL) were added tert-butyl 4-(2-bromo-3-cyano-9,10-dihydro-4H-benzo[d]pyrazolo[1,5-a][1,3]diazepin-7-yl)piperazine-1-carboxylate (the compound was synthesized through the similar way of benzyl 4-(2-bromo-3-cyano-9,10-dihydro-4H-benzo[d]pyrazolo[1,5-a][1,3]diazepin-7-yl)piperazine-1-carboxylate described in example B15) (944 mg, 2.0 mmol), 1,1,1,2,2,2-hexamethyldistannane (850 mg, 2.6 mmol) and $Pd(PPh_3)_4$ (231 mg, 0.2 mmol). The mixture was stirred at 120° C. for 18 hours. The mixture was evaporated in vacuum to afford the crude product, which was further purified with silica gel column chromatography (PE:EA=100:1~1:100 gradient elution) to give the product (760 mg, crude). $[M+H]^+$=620.4.

Step 3: 2-(4-methyl-5-((6-methylpyridin-2-yl)carbamoyl)pyridin-2-yl)-7-(piperazin-1-yl)-9,10-dihydro-4H-benzo[d]pyrazolo[1,5-a][1,3]diazepine-3-carboxamide

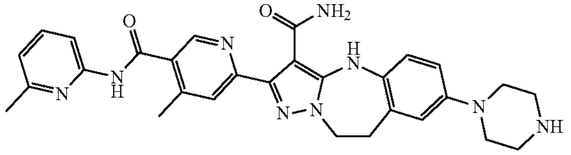 [SMILES: Cc1cccc(NC(=O)c2cnc(-c3nn4c(c3C(N)=O)Nc3ccc(N5CCNCC5)cc3CC4)cc2C)n1]

A mixture of tert-butyl 4-(3-cyano-2-(4-methyl-5-((6-methylpyridin-2-yl)carbamoyl)pyridin-2-yl)-9,10-dihydro-4H-benzo[d]pyrazolo[1,5-a][1,3]diazepin-7-yl)piperazine-1-carboxylate (760 mg, 1.2 mmol) in methylsulfonic acid (20 mL) was stirred in a round bottom flask at 100° C. for 0.5 hour. The mixture was cooled down to room temperature and poured into 1 N NaOH solution. To the mixture was added 1N HCl to adjust PH to 7-8. The mixture was extracted with DCM/MeOH (20:1, 100 mL×3). Combined organic layers were evaporated in vacuum to afford the crude product, which was further purified with silica gel column chromatography (PE:EA=100:1~1:100 gradient elution) to give the product (760 mg, crude). $[M+H]^+$=538.4.

Step 4: 7-(4-((1-(4-(2,4-dioxotetrahydropyrimidin-1(2H)-yl)phenyl)piperidin-4-yl)methyl)piperazin-1-yl)-2-(4-methyl-5-((6-methylpyridin-2-yl)carbamoyl)pyridin-2-yl)-9,10-dihydro-4H-benzo[d]pyrazolo[1,5-a] [1,3]diazepine-3-carboxamide

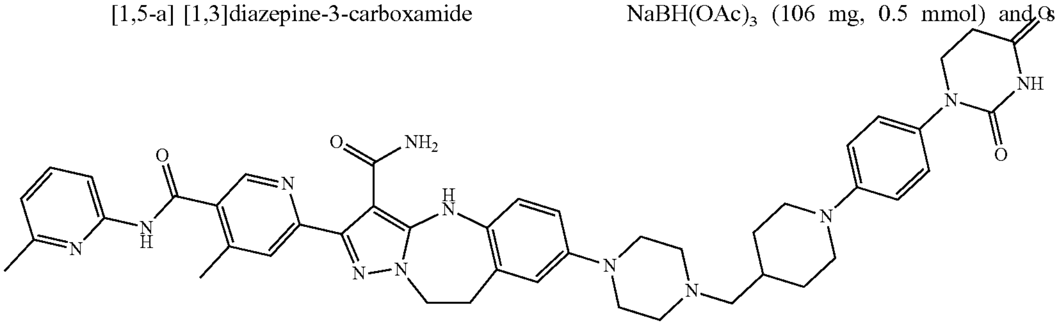

A mixture of 2-(4-methyl-5-((6-methylpyridin-2-yl)carbamoyl)pyridin-2-yl)-7-(piperazin-1-yl)-9,10-dihydro-4H-benzo[d]pyrazolo[1,5-a][1,3]diazepine-3-carboxamide (100 mg, 0.1 mmol) and 1-(4-(2,4-dioxotetrahydropyrimidin-1(2H)-yl)phenyl)piperidine-4-carbaldehyde (60 mg, 0.2 mmol) in DCM (5 mL) and MeOH (1 mL) was stirred in a round bottom flask at room temperature for 2 hours. To the mixture was added $NaBH(OAc)_3$ (106 mg, 0.5 mmol) and stirred at room temperature for 2 hours. Then the mixture was purified with Pre-TLC (DCM:MeOH=9:1) to give the product (8 mg, 10%). $^1H$ NMR (500 MHz, DMSO) δ 11.07 (s, 1H), 10.91-10.78 (m, 1H), 10.69 (s, 1H), 10.28 (s, 1H), 8.68 (s, 1H), 8.03 (d, J=6.0 Hz, 2H), 7.75 (t, J=8.0 Hz, 1H), 7.41 (s, 1H), 7.13 (d, J=8.5 Hz, 2H), 7.05 (d, J=7.5 Hz, 1H), 6.93 (d, J=8.0 Hz, 2H), 6.86 (d, J=8.0 Hz, 2H), 4.53-4.40 (m, 2H), 3.77-3.65 (m, 4H), 3.22-3.16 (m, 2H), 3.14-3.02 (m, 4H), 2.74-2.63 (m, 4H), 2.48 (s, 3H), 2.43 (s, 3H), 2.34-2.11 (m, 2H), 1.89-1.74 (m, 2H), 1.54-1.36 (m, 1H), 1.26-1.22 (m, 5H), 0.89-0.74 (m, 1H); $[M+H]^+$=823.6.

Example B37: 7-(4-(4-(2,6-dioxopiperidin-3-yl)-3,5-difluorophenethyl)piperazin-1-yl)-2-(4-methyl-5-((6-methylpyridin-2-yl)carbamoyl)pyridin-2-yl)-9,10-dihydro-4H-benzo[d]pyrazolo[1,5-a][1,3]diazepine-3-carboxamide Step 1: 7-(4-(4-(2,6-dioxopiperidin-3-yl)-3,5-difluorophenethyl)piperazin-1-yl)-2-(4-methyl-5-((6-methylpyridin-2-yl)carbamoyl)pyridin-2-yl)-9,10-dihydro-4H-benzo[d]pyrazolo[1,5-a][1,3]diazepine-3-carboxamide

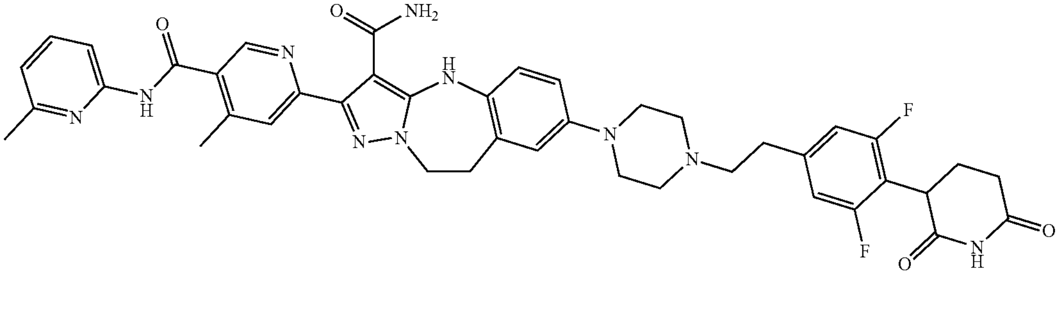 [SMILES: Cc1cccc(NC(=O)c2cnc(-c3nn4c(c3C(N)=O)Nc3ccc(N5CCN(CCc6cc(F)c(C7CCC(=O)NC7=O)c(F)c6)CC5)cc3CC4)cc2C)n1]

A mixture of 2-(4-methyl-5-((6-methylpyridin-2-yl)carbamoyl)pyridin-2-yl)-7-(piperazin-1-yl)-9,10-dihydro-4H-benzo[d]pyrazolo[1,5-a][1,3]diazepine-3-carboxamide (100 mg, 0.1 mmol) and 2-(4-(2,6-dioxopiperidin-3-yl)-3,5-difluorophenyl)acetaldehyde (51 mg, 0.2 mmol) in DCM (5 mL) and MeOH (1 mL) was stirred in a round bottom flask at room temperature for 2 hours. To the mixture was added $NaBH(OAc)_3$ (106 mg, 0.5 mmol) and stirred at room temperature for 2 hours. Then the mixture was purified with Pre-TLC (DCM: MeOH=9:1) to give the product (8 mg, 10%). $^1H$ NMR (500 MHz, DMSO) δ 11.07 (s, 1H), 10.97 (s, 1H), 10.80 (s, 1H), 10.69 (s, 1H), 8.68 (s, 1H), 8.09-7.98 (m, 2H), 7.75 (t, J=8.0 Hz, 1H), 7.41 (s, 1H), 7.24 (s, 1H), 7.10-7.03 (m, 3H), 6.89-6.83 (m, 2H), 4.49-4.39 (m, 2H), 4.25-4.17 (m, 1H), 3.33-3.29 (m, 1H), 3.20-3.14 (m, 2H), 3.13-3.03 (m, 4H), 2.87-2.76 (m, 3H), 2.65-2.56 (m, 4H), 2.48 (s, 3H), 2.43 (s, 3H), 2.18-2.08 (m, 1H), 2.04-1.97 (m, 1H), 1.25-1.21 (m, 2H); $[M+H]^+$=789.5.

Example B38:7-(4-((1-(4-(2,4-dioxotetrahydropyrimidin-1(2H)-yl)phenyl)piperidin-4-yl)methyl)piperazin-1-yl)-2-(6-methyl-5-((6-methylpyridin-2-yl)carbamoyl)pyridin-2-yl)-9,10-dihydro-4H-benzo[d]pyrazolo[1,5-a][1,3]diazepine-3-carboxamide Step 1: 6-chloro-2-methyl-N-(6-methylpyridin-2-yl)nicotinamide

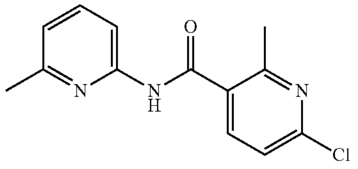 [SMILES: Cc1cccc(NC(=O)c2ccc(Cl)nc2C)n1]

To a mixture of 6-chloro-2-methylnicotinic acid (3.42 g, 20.0 mmol) in DMF (20 mL) were added 6-methylpyridin-2-amine (2.16 g, 20.0 mmol), HATU (7.60 g, 20.0 mmol) and DIPEA (5.16 g, 40.0 mmol). The mixture was stirred at 40° C. for 18 hours. LCMS showed the reaction was completed. The reaction was poured into water (200 mL), filtered, and washed with water (20 mL) to get the crude, which was further purified with silica gel column chromatography (PE:EA=100:1~50:50 gradient elution) to give the product (2.5 g, 48%). $[M+H]^+$=262.3.

Step 2: tert-butyl 4-(3-cyano-2-(6-methyl-5-((6-methylpyridin-2-yl)carbamoyl)pyridin-2-yl)-9,10-dihydro-4H-benzo[d]pyrazolo[1,5-a][1,3]diazepin-7-yl)piperazine-1-carboxylate

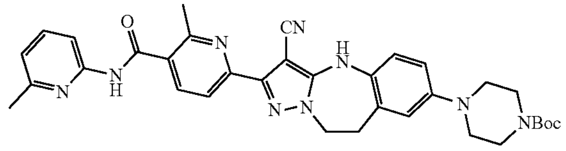 [SMILES: Cc1cccc(NC(=O)c2ccc(-c3nn4c(c3C#N)Nc3ccc(N5CCN(C(=O)OC(C)(C)C)CC5)cc3CC4)nc2C)n1]

To a mixture of 6-chloro-2-methyl-N-(6-methylpyridin-2-yl)nicotinamide (524 mg, 2.0 mmol) in dry dioxane (20 mL) were added tert-butyl 4-(2-bromo-3-cyano-9,10-dihydro-4H-benzo[d]pyrazolo[1,5-a][1,3]diazepin-7-yl)piperazine-1-carboxylate (944 mg, 2.0 mmol), 1,1,1,2,2,2-hexamethyldistannane (850 mg, 2.6 mmol) and $Pd(PPh_3)_4$ (231 mg, 0.2 mmol). The mixture was stirred at 120° C. for 18 hours. The mixture was evaporated in vacuum to afford the crude product, which was further purified with silica gel column chromatography (PE:EA=100:1~1:100 gradient elution) to give the product (550 mg, crude). $[M+H]^+$=620.4.

Step 3: 2-(6-methyl-5-((6-methylpyridin-2-yl)carbamoyl)pyridin-2-yl)-7-(piperazin-1-yl)-9,10-dihydro-4H-benzo[d]pyrazolo[1,5-a][1,3]diazepine-3-carboxamide

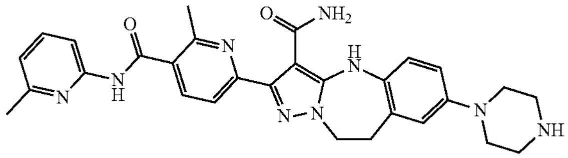 [SMILES: Cc1cccc(NC(=O)c2ccc(-c3nn4c(c3C(N)=O)Nc3ccc(N5CCNCC5)cc3CC4)nc2C)n1]

A mixture of tert-butyl 4-(3-cyano-2-(6-methyl-5-((6-methylpyridin-2-yl)carbamoyl)pyridin-2-yl)-9,10-dihydro-4H-benzo[d]pyrazolo[1,5-a][1,3]diazepin-7-yl)piperazine-1-carboxylate (550 mg, 0.8 mmol) in methylsulfonic acid (20 mL) was stirred in a round bottom flask at 100° C. for 3 hours. The mixture was cooled down to room temperature and poured into 1 N NaOH solution. To the mixture was added 1 N HCl to adjust PH to 7-8. The mixture was filtered and washed with water to give the product (343 mg, crude). $[M+H]^+$=538.4.

Step 4: 7-(4-((1-(4-(2,4-dioxotetrahydropyrimidin-1(2H)-yl)phenyl)piperidin-4-yl)methyl)piperazin-1-yl)-2-(6-methyl-5-((6-methylpyridin-2-yl)carbamoyl)pyridin-2-yl)-9,10-dihydro-4H-benzo[d]pyrazolo[1,5-a][1,3]diazepine-3-carboxamide

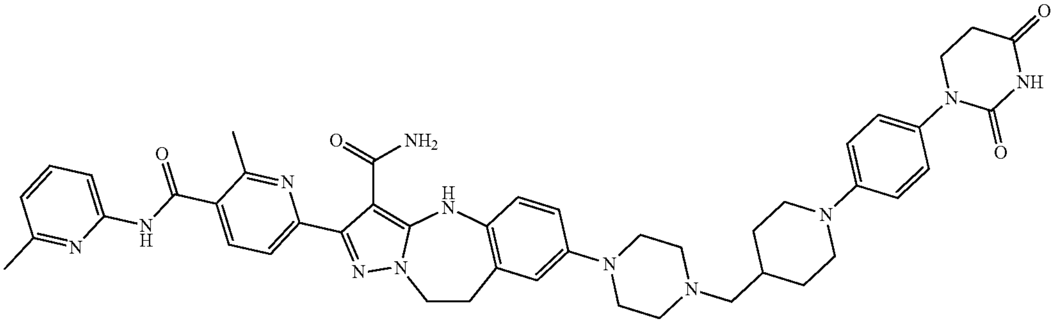 [SMILES: Cc1cccc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)nc2C)n1]

A mixture of 2-(6-methyl-5-((6-methylpyridin-2-yl)carbamoyl)pyridin-2-yl)-7-(piperazin-1-yl)-9,10-dihydro-4H-benzo[d]pyrazolo[1,5-a][1,3]diazepine-3-carboxamide (80 mg, 0.1 mmol) and 1-(4-(2,4-dioxotetrahydropyrimidin-1(2H)-yl)phenyl)piperidine-4-carbaldehyde (60 mg, 0.2 mmol) in DCM (5 mL) and MeOH (1 mL) was stirred in a round bottom flask at room temperature for 2 hours. To the mixture was added $NaBH(OAc)_3$ (106 mg, 0.5 mmol) and stirred at room temperature for 18 hours. Then the mixture was purified with Pre-TLC (DCM:MeOH=8:1) to give the product (17 mg, 21%). $^1H$ NMR (500 MHz, DMSO) δ 11.03 (d, J=6.5 Hz, 2H), 10.80 (s, 1H), 10.32-10.24 (m, 1H), 8.13-7.94 (m, 3H), 7.75 (t, J=8.0 Hz, 1H), 7.40 (s, 1H), 7.13 (d, J=8.5 Hz, 2H), 7.05 (d, J=7.5 Hz, 1H), 6.93 (d, J=9.0 Hz, 2H), 6.89-6.80 (m, 3H), 4.51-4.38 (m, 2H), 3.78-3.64 (m, 4H), 3.22-3.14 (m, 2H), 3.09 (s, 4H), 2.72-2.65 (m, 4H), 2.61 (s, 3H), 2.55-2.51 (m, 3H), 2.43 (s, 3H), 2.29-2.14 (m, 3H), 1.86-1.78 (m, 2H), 1.76-1.67 (m, 1H), 1.52-1.42 (m, 1H), 0.89-0.81 (m, 1H); $[M+H]^+$=823.6.

Example B39:7-(4-(4-(2,6-dioxopiperidin-3-yl)-3,5-difluorophenethyl)piperazin-1-yl)-2-(6-methyl-5-((6-methylpyridin-2-yl)carbamoyl)pyridin-2-yl)-9,10-dihydro-4H-benzo[d]pyrazolo[1,5-a][1,3]diazepine-3-carboxamide Step 1: 7-(4-(4-(2,6-dioxopiperidin-3-yl)-3,5-difluorophenethyl)piperazin-1-yl)-2-(6-methyl-5-((6-methylpyridin-2-yl)carbamoyl)pyridin-2-yl)-9,10-dihydro-4H-benzo[d]pyrazolo[1,5-a][1,3]diazepine-3-carboxamide

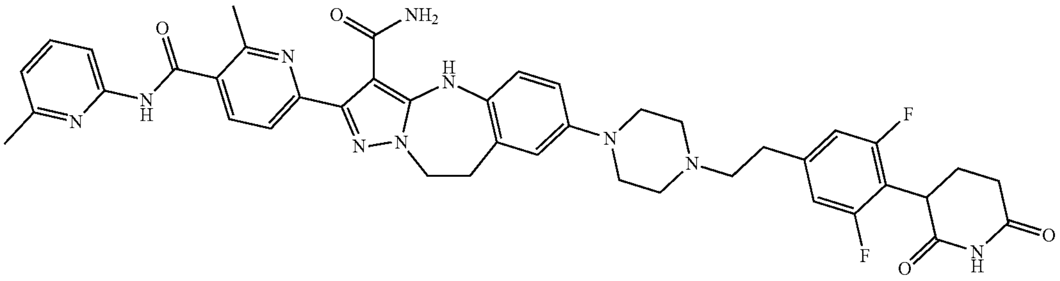 [SMILES: Cc1cccc(NC(=O)c2ccc(-c3nn4c(c3C(N)=O)Nc3ccc(N5CCN(CCc6cc(F)c(C7CCC(=O)NC7=O)c(F)c6)CC5)cc3CC4)nc2C)n1]

A mixture of 2-(6-methyl-5-((6-methylpyridin-2-yl)carbamoyl)pyridin-2-yl)-7-(piperazin-1-yl)-9,10-dihydro-4H-benzo[d]pyrazolo[1,5-a][1,3]diazepine-3-carboxamide (80 mg, 0.1 mmol) and 2-(4-(2,6-dioxopiperidin-3-yl)-3,5-difluorophenyl)acetaldehyde (52 mg, 0.2 mmol) in DCM (5 mL) and MeOH (1 mL) was stirred in a round bottom flask at room temperature for 2 hours. To the mixture was added $NaBH(OAc)_3$ (106 mg, 0.5 mmol) and stirred at room temperature for 18 hours. Then the mixture was purified with Pre-TLC (DCM: MeOH=8:1) to give the product (17 mg, 21%). $^1H$ NMR (500 MHz, DMSO) δ 11.09-10.99 (m, 2H), 10.97 (s, 1H), 10.81 (s, 1H), 8.14-7.89 (m, 3H), 7.75 (t, J=7.5 Hz, 1H), 7.40 (s, 1H), 7.12-7.00 (m, 3H), 6.95-6.78 (m, 3H), 4.51-4.38 (m, 2H), 4.26-4.14 (m, 1H), 3.21-3.15 (m, 2H), 3.13-2.91 (m, 5H), 2.86-2.73 (m, 3H), 2.70-2.53 (m, 9H), 2.43 (s, 3H), 2.18-2.08 (m, 1H), 2.03-1.96 (m, 1H); $[M+H]^+$=789.6.

Example B40:7-(4-((1-(4-(2,4-dioxotetrahydropyrimidin-1(2H)-yl)phenyl)piperidin-4-yl)methyl)piperazin-1-yl)-2-(2-fluoro-3-methyl-4-((6-methylpyrazin-2-yl)carbamoyl)phenyl)-9,10-dihydro-4H-benzo[d]pyrazolo[1,5-a][1,3]diazepine-3-carboxamide

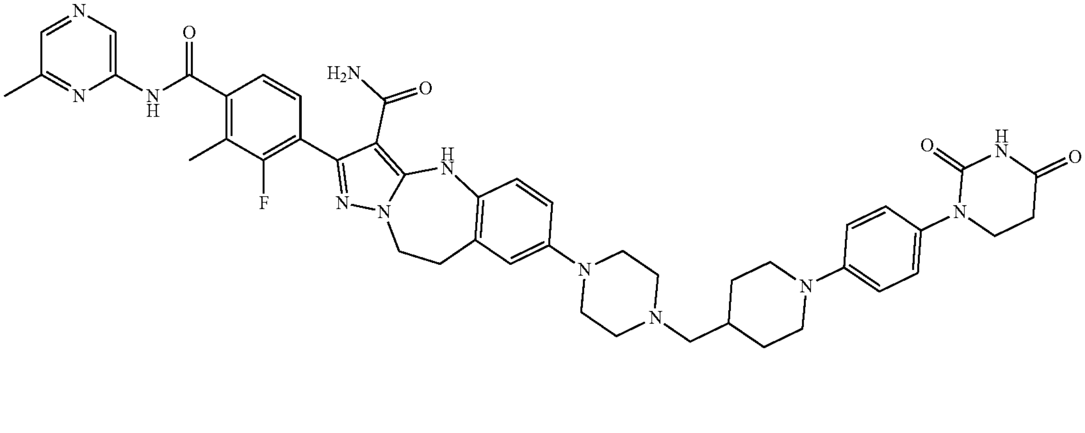 [SMILES: Cc1cncc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)c(F)c2C)n1]

The titled compound was synthesized in the procedures similar to Example B39. $^1H$ NMR (500 MHz, DMSO) δ 11.20 (s, 1H), 10.25 (s, 1H), 9.70 (s, 1H), 9.26 (s, 1H), 8.34 (s, 1H), 7.40 (d, J=23.8 Hz, 2H), 7.13 (d, J=5.9 Hz, 2H), 7.04-6.79 (m, 5H), 4.45-4.31 (m, 2H), 3.78-3.62 (m, 4H), 3.22-3.14 (m, 2H), 3.13-3.00 (m, 4H), 2.75-2.62 (m, 4H), 2.59-2.53 (m, 4H), 2.47-2.41 (m, 3H), 2.33 (s, 3H), 2.27-2.16 (m, 2H), 1.87-1.76 (m, 2H), 1.76-1.64 (m, 1H), 1.22-1.15 (m, 2H); $[M+H]^+$=841.6.

Example B41:7-(4-((1-(4-(2,4-dioxotetrahydropyrimidin-1(2H)-yl)phenyl)piperidin-4-yl)methyl)piperazin-1-yl)-2-(4-((6-ethylpyridin-2-yl)carbamoyl)-2-fluoro-3-methylphenyl)-9,10-dihydro-4H-benzo[d]pyrazolo[1,5-a][1,3]diazepine-3-carboxamide

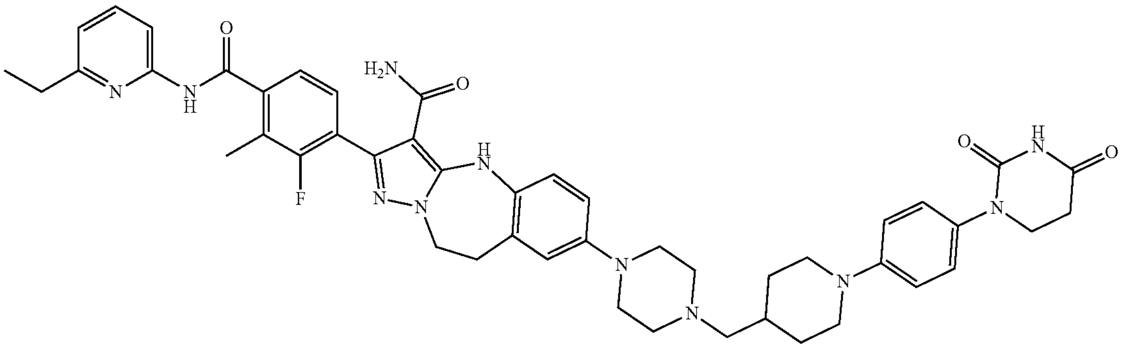 [SMILES: CCc1cccc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)c(F)c2C)n1]

The titled compound was synthesized in the procedures similar to Example B39. $^1H$ NMR (500 MHz, DMSO) δ 10.79 (s, 1H), 10.25 (s, 1H), 9.73 (s, 1H), 8.03 (d, J=7.4 Hz, 1H), 7.77 (t, J=7.9 Hz, 1H), 7.39-7.32 (m, 2H), 7.13 (d, J=8.9 Hz, 2H), 7.06 (d, J=7.5 Hz, 1H), 6.93 (d, J=9.0 Hz, 2H), 6.88 (d, J=8.7 Hz, 2H), 6.83 (d, J=8.6 Hz, 1H), 4.41-4.32 (m, 2H), 3.72-3.66 (m, 4H), 3.21-3.13 (m, 2H), 3.13-3.06 (m, 4H), 2.73-2.62 (m, 6H), 2.58-2.55 (m, 4H), 2.30 (d, J=1.8 Hz, 3H), 2.25-2.18 (m, 2H), 1.84-1.78 (m, 2H), 1.75-1.67 (m, 1H), 1.27-1.18 (m, 5H); $[M+H]^+$=854.5.

Example B42: 2-(4-((4-chloro-6-methylpyridin-2-yl)carbamoyl)-2-fluoro-3-methylphenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

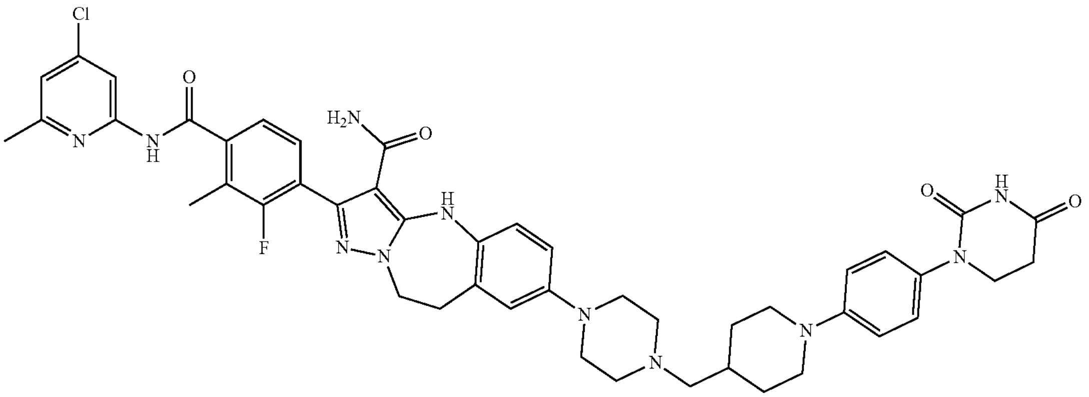 [SMILES: Cc1cc(Cl)cc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)c(F)c2C)n1]

The titled compound was synthesized in the procedures similar to Example B39. $^1$H NMR (500 MHz, DMSO) δ 11.08 (s, 1H), 10.18 (s, 1H), 9.64 (s, 1H), 8.06 (s, 1H), 7.34-7.26 (m, 2H), 7.16 (s, 1H), 7.06 (d, J=8.8 Hz, 2H), 6.86 (d, J=8.9 Hz, 2H), 6.81 (d, J=8.8 Hz, 2H), 6.76 (d, J=8.6 Hz, 1H), 4.33-4.26 (m, 2H), 3.64-3.59 (m, 4H), 3.13-3.08 (m, 2H), 3.06-2.98 (m, 4H), 2.64-2.56 (m, 4H), 2.50-2.44 (m, 4H), 2.36 (s, 3H), 2.23 (d, J=1.7 Hz, 3H), 2.19-2.13 (m, 2H), 1.78-1.70 (m, 2H), 1.68-1.61 (m, 1H), 1.19-1.11 (m, 2H); [M+H]$^+$=874.7.

Example B43:7-(4-((1-(4-(2,4-dioxotetrahydropyrimidin-1(2H)-yl)phenyl)piperidin-4-yl)methyl)piperazin-1-yl)-2-(2-fluoro-3-methyl-4-((4-methylpyrimidin-2-yl)carbamoyl)phenyl)-9,10-dihydro-4H-benzo[d]pyrazolo[1,5-a][1,3]diazepine-3-carboxamide

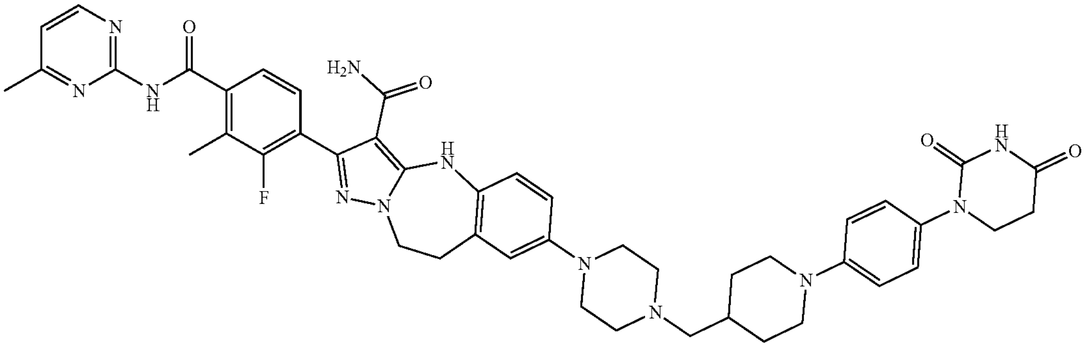 [SMILES: Cc1ccnc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)c(F)c2C)n1]

The titled compound was synthesized in the procedures similar to Example B39. $^1$H NMR (500 MHz, DMSO) δ 11.02 (s, 1H), 10.25 (s, 1H), 9.69 (s, 1H), 8.50 (d, J=5.0 Hz, 1H), 7.36-7.28 (m, 2H), 7.12 (dd, J=10.2, 7.0 Hz, 3H), 6.93 (d, J=9.0 Hz, 2H), 6.88 (d, J=8.8 Hz, 2H), 6.83 (d, J=8.5 Hz, 1H), 4.37-4.35 (m, 2H), 3.70-3.68 (m, 4H), 3.18-3.14 (m, 2H), 3.11-3.06 (m, 4H), 2.69-2.64 (m, 5H), 2.53-2.51 (m, 3H), 2.39 (s, 3H), 2.28 (d, J=1.5 Hz, 3H), 2.22 (d, J=6.9 Hz, 2H), 1.84-1.78 (m, 2H), 1.76-1.67 (m, 1H), 1.27-1.18 (m, 2H); [M+H]$^+$=841.7.

Example B44: 7-(4-((1-(4-(2,4-dioxotetrahydropyrimidin-1(2H)-yl)phenyl)piperidin-4-yl)methyl)piperazin-1-yl)-2-(2-fluoro-4-((5-fluoro-6-methylpyridin-2-yl)carbamoyl)-3-methylphenyl)-9,10-dihydro-4H-pyrazolo[1,5-a]pyrido[3,2-d][1,3]diazepine-3-carboxamide

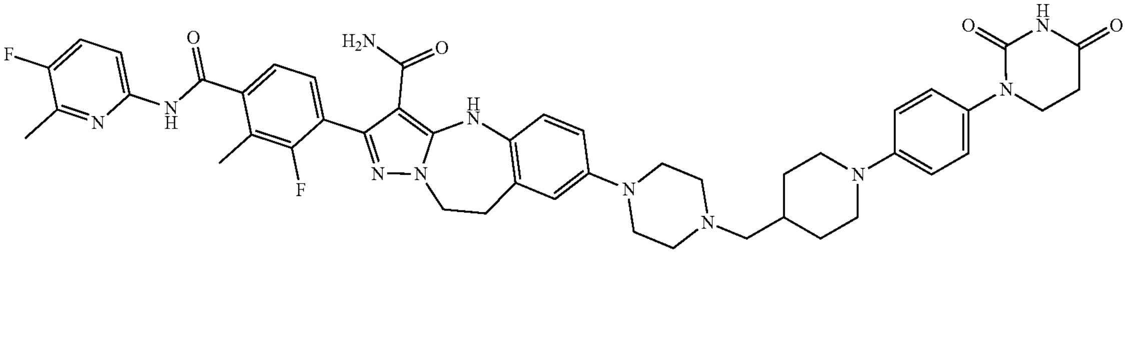 [SMILES: Cc1nc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)c(F)c2C)ccc1F]

The titled compound was synthesized in the procedures similar to Example B39. $^1$H NMR (500 MHz, DMSO) δ 10.89 (s, 1H), 10.20 (s, 1H), 9.71 (s, 1H), 8.00 (d, J=6.4 Hz, 1H), 7.65 (t, J=9.0 Hz, 1H), 7.31-2.27 (m, 2H), 7.09 (s, 2H), 6.93-6.82 (m, 5H), 4.35-4.27 (m, 2H), 3.74-3.60 (m, 5H), 3.59-3.53 (m, 2H), 3.16-3.04 (m, 6H), 3.01-2.93 (m, 2H), 2.70-2.65 (m, 2H), 2.63-2.60 (m, 2H), 2.34 (d, J=2.7 Hz, 3H), 2.24 (d, J=2.0 Hz, 3H), 2.02-1.93 (m, 1H), 1.82-1.75 (m, 2H), 1.34-1.24 (m, 2H); [M+H]$^+$=858.7.

Example B45: 2-(4-((1H-pyrrolo[3,2-b]pyridin-5-yl)carbamoyl)-2-fluoro-3-methylphenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

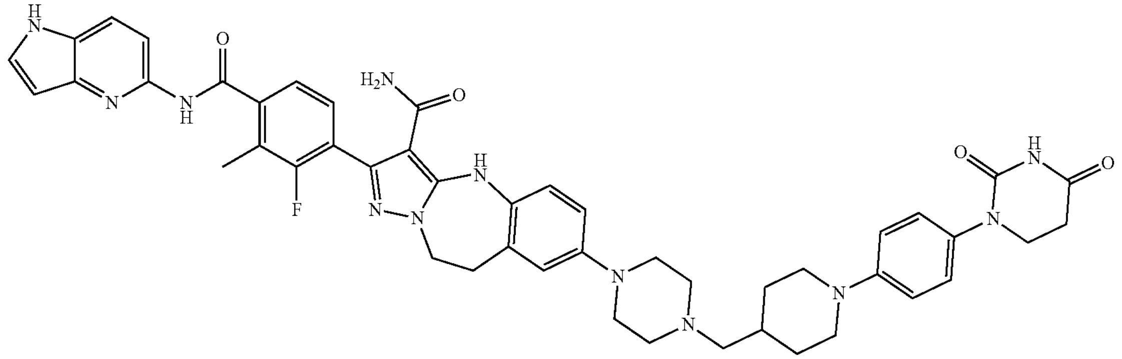 [SMILES: Cc1c(C(=O)Nc2ccc3[nH]ccc3n2)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B39. $^1$H NMR (500 MHz, DMSO) δ 11.33 (s, 1H), 10.68 (s, 1H), 10.25 (s, 1H), 9.73 (s, 1H), 7.99 (d, J=7.8 Hz, 1H), 7.85 (d, J=8.8 Hz, 1H), 7.65-7.60 (m, 1H), 7.44-7.33 (m, 2H), 7.13 (d, J=8.8 Hz, 2H), 6.93 (d, J=8.9 Hz, 2H), 6.89 (d, J=8.7 Hz, 2H), 6.87-6.81 (m, 1H), 6.44 (s, 1H), 4.42-4.34 (m, 2H), 3.71-3.68 (m, 4H), 3.21-3.15 (m, 2H), 3.14-3.05 (m, 4H), 2.72-2.62 (m, 4H), 2.60-2.54 (m, 4H), 2.34 (d, J=1.6 Hz, 3H), 2.27-2.16 (m, 2H), 1.86-1.78 (m, 2H), 1.77-1.66 (m, 1H), 1.36-1.27 (m, 2H); [M+H]$^+$=865.6.

Example B46: 7-(4-((1-(4-(2,4-dioxotetrahydropyrimidin-1(2H)-yl)phenyl)piperidin-4-yl)methyl)piperazin-1-yl)-2-(2-fluoro-3-methyl-4-(3-(pyridin-2-yl)-1,2,4-oxadiazol-5-yl)phenyl)-9,10-dihydro-4H-benzo[d]pyrazolo[1,5-a][1,3]diazepine-3-carboxamide

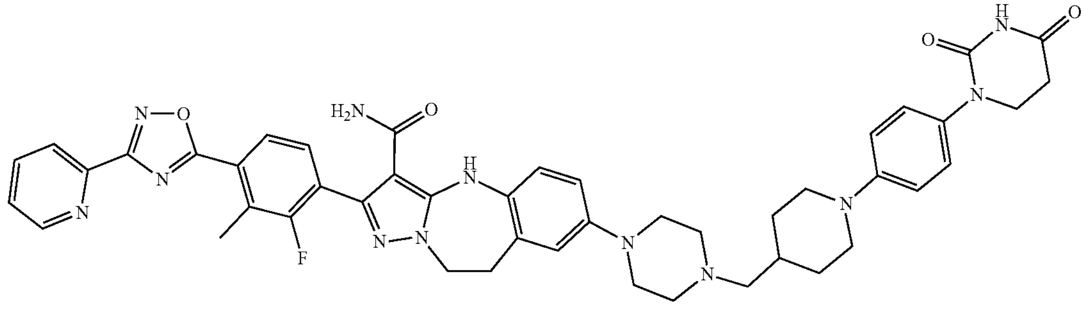 [SMILES: Cc1c(-c2nc(-c3ccccn3)no2)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B39. $^1$H NMR (500 MHz, DMSO) δ 10.25 (s, 1H), 9.65 (s, 1H), 8.83 (s, 1H), 8.21 (d, J=7.6 Hz, 1H), 8.15-8.02 (m, 2H), 7.72-7.62 (m, 1H), 7.63-7.55 (m, 1H), 7.19-7.11 (m, 2H), 7.02-6.81 (m, 5H), 4.51-4.31 (m, 2H), 3.77-3.63 (m, 4H), 3.18-3.06 (m, 6H), 2.89-2.61 (m, 8H), 2.35-2.13 (m, 3H), 2.12-1.88 (m, 2H), 1.88-1.66 (m, 3H), 1.53-1.43 (m, 2H); [M+H]$^+$=851.5.

Example B47: 7-(4-((1-(4-(2,4-dioxotetrahydropyrimidin-1(2H)-yl)phenyl)piperidin-4-yl)methyl)piperazin-1-yl)-2-(2-fluoro-3-methyl-4-(quinoxalin-2-ylcarbamoyl)phenyl)-9,10-dihydro-4H-benzo[d]pyrazolo[1,5-a][1,3]diazepine-3-carboxamide

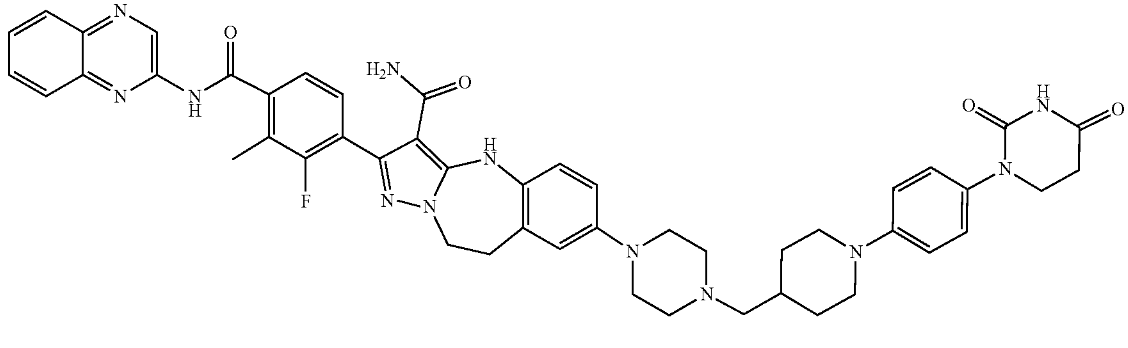 [SMILES: Cc1c(C(=O)Nc2cnc3ccccc3n2)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B30. $^1$H NMR (500 MHz, DMSO) δ 11.63 (s, 1H), 10.26 (s, 1H), 9.70 (d, J=4.7 Hz, 2H), 8.10 (d, J=8.3 Hz, 1H), 7.96-7.90 (m, 1H), 7.87-7.81 (m, 1H), 7.81-7.76 (m, 1H), 7.53 (d, J=7.8 Hz, 1H), 7.42 (t, J=7.3 Hz, 1H), 7.13 (d, J=8.9 Hz, 2H), 6.93 (d, J=9.0 Hz, 2H), 6.89 (t, J=6.4 Hz, 2H), 6.83 (dd, J=8.7, 2.2 Hz, 1H), 4.43-4.31 (m, 2H), 3.73-3.64 (m, 4H), 3.21-3.14 (m, 2H), 3.13-3.04 (m, 4H), 2.72-2.62 (m, 4H), 2.56-2.53 (m, 2H), 2.39 (d, J=2.0 Hz, 3H), 2.22 (d, J=6.9 Hz, 2H), 1.86-1.76 (m, 2H), 1.76-1.66 (m, 1H), 1.28-1.16 (m, 2H); [M+H]$^+$=877.6.

Example B48:7-(4-((1-(4-(2,4-dioxotetrahydropyrimidin-1(2H)-yl)phenyl)piperidin-4-yl)methyl)piperazin-1-yl)-2-(2-fluoro-3-methyl-4-((6-phenylpyridin-2-yl)carbamoyl)phenyl)-9,10-dihydro-4H-benzo[d]pyrazolo[1,5-a][1,3]diazepine-3-carboxamide

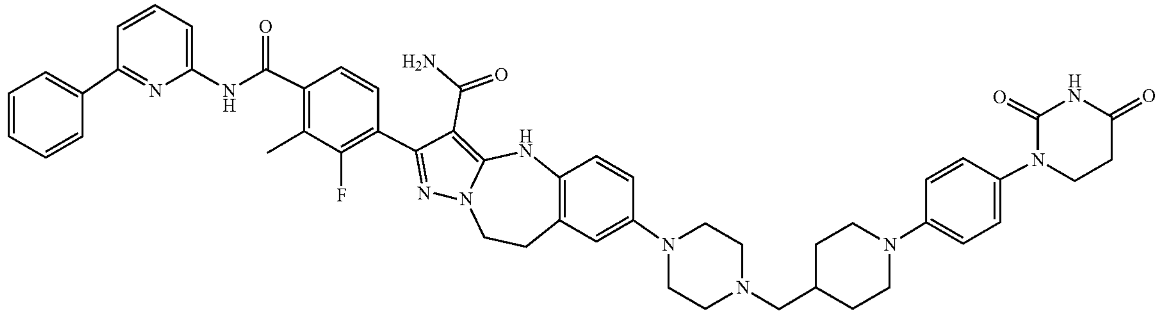 [SMILES: Cc1c(C(=O)Nc2cccc(-c3ccccc3)n2)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B39. $^1$H NMR (500 MHz, DMSO) δ 10.95 (s, 1H), 10.29 (s, 1H), 9.79 (s, 1H), 8.16 (d, J=6.9 Hz, 1H), 8.10 (d, J=7.1 Hz, 2H), 7.96 (t, J=7.9 Hz, 1H), 7.76 (d, J=7.8 Hz, 1H), 7.53-7.42 (m, 4H), 7.39 (t, J=7.2 Hz, 1H), 7.19 (d, J=8.7 Hz, 2H), 7.02 (d, J=8.3 Hz, 2H), 6.94 (dt, J=10.6, 5.4 Hz, 3H), 4.45-4.34 (m, 2H), 3.82-3.68 (m, 6H), 3.64 (d, J=11.0 Hz, 2H), 3.25-3.12 (m, 6H), 3.09-3.01 (m, 2H), 2.84-2.75 (m, 2H), 2.69 (t, J=6.7 Hz, 2H), 2.35 (d, J=1.6 Hz, 3H), 2.11-2.02 (m, 1H), 1.91-1.83 (m, 2H), 1.43-1.33 (m, 2H); $[M+H]^+$=902.7.

Example B49:7-(4-((1-(4-(2,4-dioxotetrahydropyrimidin-1(2H)-yl)phenyl)piperidin-4-yl)methyl)piperazin-1-yl)-2-(2-fluoro-3-methyl-4-((4-(pyrrolidin-1-yl)pyridin-2-yl)carbamoyl)phenyl)-9,10-dihydro-4H-benzo[d]pyrazolo[1,5-a][1,3]diazepine-3-carboxamide

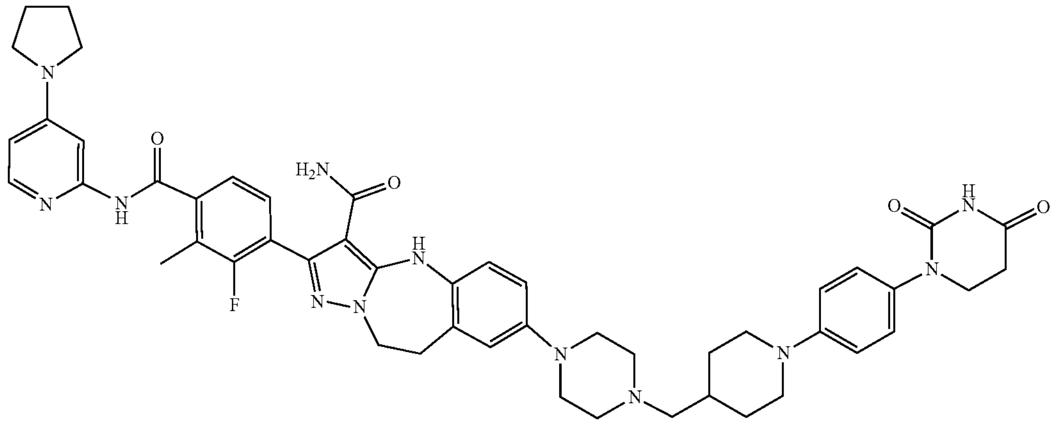 [SMILES: Cc1c(C(=O)Nc2cc(N3CCCC3)ccn2)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B39. $^1$H NMR (500 MHz, DMSO) δ 11.87 (s, 1H), 10.27 (s, 1H), 9.70 (s, 1H), 7.99 (d, J=7.3 Hz, 1H), 7.57 (d, J=7.9 Hz, 1H), 7.49 (t, J=7.2 Hz, 1H), 7.16 (d, J=8.7 Hz, 2H), 7.02-6.89 (m, 5H), 6.75 (dd, J=7.1, 1.8 Hz, 1H), 6.57 (d, J=1.2 Hz, 1H), 4.43-4.36 (m, 2H), 3.78-3.68 (m, 5H), 3.66-3.60 (m, 2H), 3.57-3.37 (m, 5H), 3.25-3.10 (m, 6H), 3.09-2.99 (m, 2H), 2.79-2.72 (m, 2H), 2.69 (t, J=6.7 Hz, 2H), 2.40 (s, 3H), 2.10-1.98 (m, 5H), 1.91-1.81 (m, 2H), 1.41-1.31 (m, 2H); $[M+H]^+$=895.7.-

Example B50:7-(4-((1-(4-(2,4-dioxotetrahydropyrimidin-1(2H)-yl)phenyl)piperidin-4-yl)methyl)piperazin-1-yl)-2-(2-fluoro-4-((4-methoxypyridin-2-yl)carbamoyl)-3-methylphenyl)-9,10-dihydro-4H-benzo[d]pyrazolo[1,5-a][1,3]diazepine-3-carboxamide

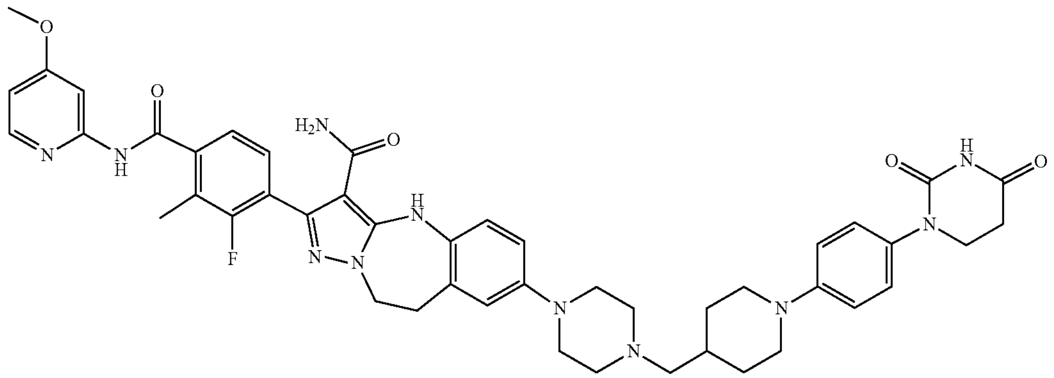 [SMILES: COc1ccnc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)c(F)c2C)c1]

The titled compound was synthesized in the procedures similar to Example B39. $^1$H NMR (500 MHz, DMSO) δ 11.16 (s, 1H), 10.23 (s, 1H), 9.68 (s, 1H), 8.17 (d, J=6.1 Hz, 1H), 7.61 (d, J=1.9 Hz, 1H), 7.40-7.30 (m, 2H), 7.14 (d, J=8.8 Hz, 2H), 6.98 (d, J=8.8 Hz, 2H), 6.92-6.81 (m, 4H), 4.34-4.29 (m, 2H), 3.84 (s, 3H), 3.73-3.62 (m, 8H), 3.17-3.05 (m, 6H), 3.03-2.92 (m, 2H), 2.76 (t, J=11.5 Hz, 2H), 2.63 (t, J=6.7 Hz, 2H), 2.27 (d, J=1.8 Hz, 3H), 2.05-1.96 (m, 1H), 1.85-1.76 (m, 2H), 1.38-1.26 (m, 2H); $[M+H]^+$=856.7.

Example B51:7-(4-((1-(4-(2,4-dioxotetrahydropyrimidin-1(2H)-yl)phenyl)piperidin-4-yl)methyl)piperazin-1-yl)-2-(4-((4-ethoxypyridin-2-yl)carbamoyl)-2-fluoro-3-methylphenyl)-9,10-dihydro-4H-benzo[d]pyrazolo[1,5-a][1,3]diazepine-3-carboxamide

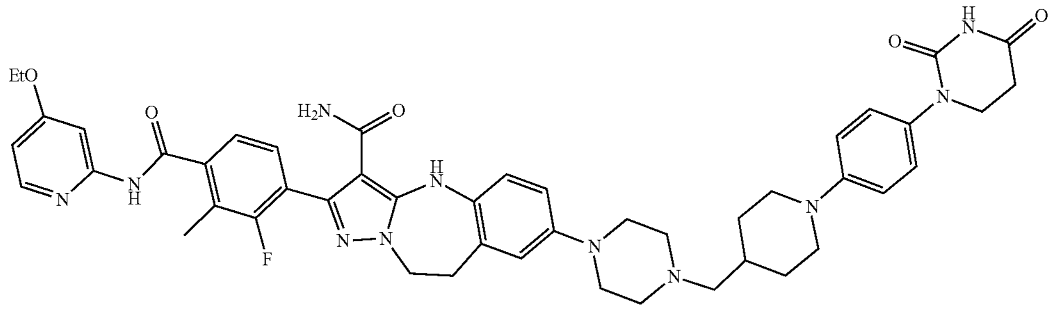 [SMILES: CCOc1ccnc(NC(=O)c2ccc(-c3nn4c(c3C(N)=O)Nc3ccc(N5CCN(CC6CCN(c7ccc(N8CCC(=O)NC8=O)cc7)CC6)CC5)cc3CC4)c(F)c2C)c1]

The titled compound was synthesized in the procedures similar to Example B39. $^1$H NMR (400 MHz, DMSO) δ 10.87 (s, 1H), 10.28 (s, 1H), 9.77 (s, 1H), 9.60 (s, 1H), 8.16 (d, J=5.7 Hz, 1H), 7.82 (s, 1H), 7.37-7.34 (m, 2H), 7.15 (d, J=8.6 Hz, 2H), 6.98-6.90 (m, 4H), 6.78-6.76 (m, 1H), 4.40-4.35 (m, 2H), 4.17-4.12 (m, 2H), 3.77-3.67 (m, 6H), 3.65-3.59 (m, 2H), 3.22-3.07 (m, 8H), 2.75-2.65 (m, 4H), 2.31 (s, 3H), 2.10-1.99 (m, 1H), 1.92-1.83 (m, 2H), 1.40-1.31 (m, 5H); $[M+H]^+$=870.6.

Example B52: 2-(4-((5-chloro-6-methylpyridin-2-yl) carbamoyl)-2-fluoro-3-methylphenyl)-7-(4-((1-(4-(2, 4-dioxotetrahydropyrimidin-1(2H)-yl)phenyl)piperidin-4-yl)methyl)piperazin-1-yl)-9,10-dihydro-4H-pyrazolo[1,5-a]pyrido[3,2-d][1,3]diazepine-3-carboxamide

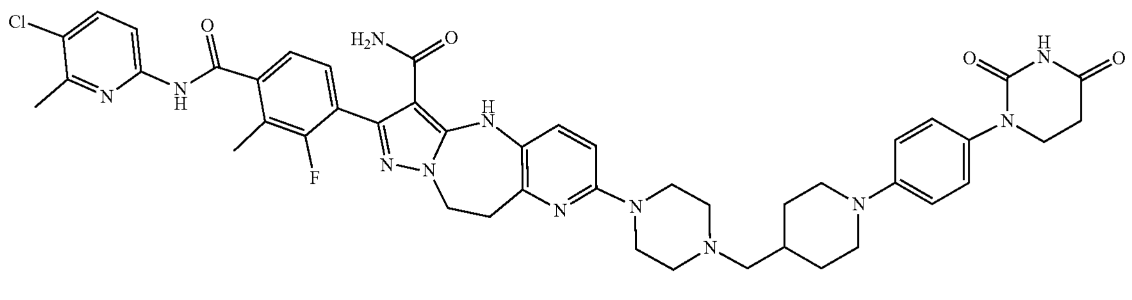 [SMILES: Cc1nc(NC(=O)c2ccc(-c3nn4c(c3C(N)=O)Nc3ccc(N5CCN(CC6CCN(c7ccc(N8CCC(=O)NC8=O)cc7)CC6)CC5)nc3CC4)c(F)c2C)ccc1Cl]

The titled compound was synthesized in the procedures similar to Example B39. $^1$H NMR (500 MHz, DMSO) δ 11.05 (s, 1H), 10.28 (s, 1H), 9.78 (s, 1H), 8.09 (d, J=8.6 Hz, 1H), 7.91 (d, J=8.7 Hz, 1H), 7.40 (d, J=7.9 Hz, 1H), 7.38-7.32 (m, 1H), 7.18 (d, J=8.8 Hz, 2H), 7.01 (d, J=8.8 Hz, 2H), 6.98-6.91 (m, 3H), 4.45-4.34 (m, 2H), 3.84-3.71 (m, 5H), 3.69-3.62 (m, 5H), 3.24-3.12 (m, 6H), 3.05 (t, J=11.8 Hz, 2H), 2.78 (t, J=11.8 Hz, 2H), 2.69 (t, J=6.7 Hz, 2H), 2.30 (d, J=1.8 Hz, 3H), 2.10-2.05 (m, 1H), 1.91-1.82 (m 2H), 1.42-1.32 (m, 2H); $[M+H]^+$=874.5.

Example B53:2-(4-((5-chloro-6-methylpyridin-2-yl) carbamoyl)-2-fluoro-3-methylphenyl)-7-(4-((1-(4-(2, 4-dioxotetrahydropyrimidin-1(2H)-yl)phenyl)azetidin-3-yl)methyl)piperazin-1-yl)-9,10-dihydro-4H-benzo[d]pyrazolo[1,5-a][1,3]diazepine-3-carboxamide

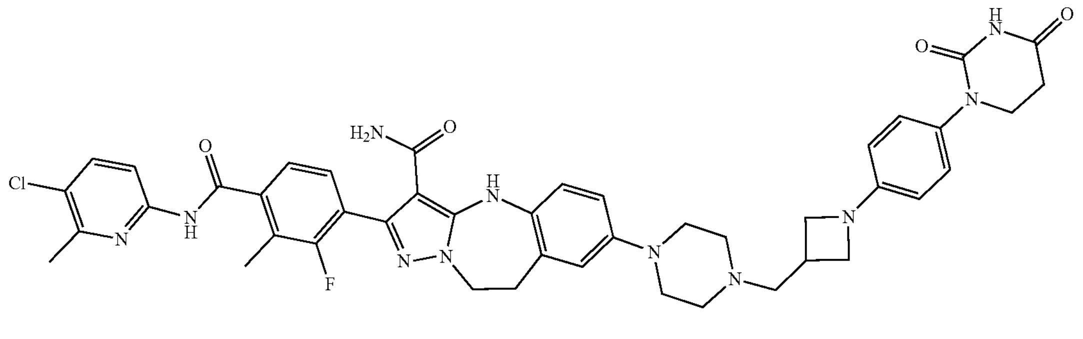 [SMILES: Cc1nc(NC(=O)c2ccc(-c3nn4c(c3C(N)=O)Nc3ccc(N5CCN(CC6CN(c7ccc(N8CCC(=O)NC8=O)cc7)C6)CC5)cc3CC4)c(F)c2C)ccc1Cl]

The titled compound was synthesized in the procedures similar to Example B39. $^1$H NMR (500 MHz, DMSO) δ 11.00 (s, 1H), 10.16 (s, 1H), 9.70 (s, 1H), 8.02 (d, J=8.7 Hz, 1H), 7.85 (d, J=8.7 Hz, 1H), 7.35-7.24 (m, 2H), 7.00-6.91 (m, 2H), 6.89-6.77 (m, 3H), 6.56-6.50 (m, 2H), 4.33-4.24 (m, 3H), 4.11-4.04 (m, 2H), 3.66-3.61 (m, 2H), 3.59-3.54 (m, 4H), 3.44-3.38 (m, 2H), 3.25-3.16 (m, 3H), 3.14-3.02 (m, 4H), 2.62-2.58 (m, 4H), 2.51-2.45 (m, 2H), 2.23 (s, 3H); $[M+H]^+$=846.5.

Example B54: 7-(4-((1-(4-(2,4-dioxotetrahydropyrimidin-1(2H)-yl)-3-methylphenyl)piperidin-4-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide Step 1: 1-(4-(2,4-dioxotetrahydropyrimidin-1(2H)-yl)-3-methylphenyl)piperidine-4-carbaldehyde

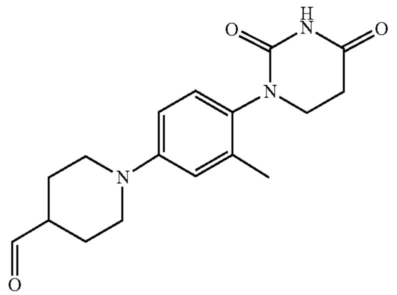 [SMILES: Cc1cc(N2CCC(C=O)CC2)ccc1N1CCC(=O)NC1=O]

To a mixture of 1-(4-(4-(hydroxymethyl)piperidin-1-yl)-2-methylphenyl)dihydropyrimidine-2,4(1H,3H)-dione (95.1 mg, 0.30 mmol) in DMSO (5 mL) was added IBX (109 mg, 0.39 mmol). The reaction was stirred at rt for 16 hours. Then the mixture was washed by water and extracted with dichloromethane (3×60 mL). The organic phase was combined and washed by brine. The mixture was dried over anhydrous sodium sulfate, filtered, and concentrated under reduced pressure to afford the crude product, which was purified with silica gel column chromatography (PE:EA=80:20~30:70 gradient elution) to give the product (40 mg, 42%). $[M+H]^+$=315.2.

Step 2: 7-(4-((1-(4-(2,4-dioxotetrahydropyrimidin-1(2H)-yl)-3-methylphenyl)piperidin-4-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

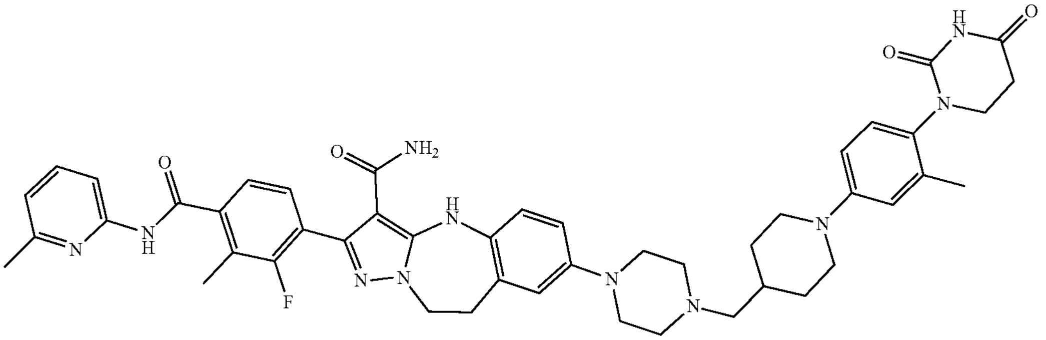 [SMILES: Cc1cccc(NC(=O)c2ccc(-c3nn4c(c3C(N)=O)Nc3ccc(N5CCN(CC6CCN(c7ccc(N8CCC(=O)NC8=O)c(C)c7)CC6)CC5)cc3CC4)c(F)c2C)n1]

A mixture of 1-(4-(2,4-dioxotetrahydropyrimidin-1(2H)-yl)-3-methylphenyl)piperidine-4-carbaldehyde (40 mg, 0.13 mmol) and 2-(2-fluoro-3-methyl-4-((6-methylpyridin-2-yl)carbamoyl)phenyl)-7-(piperazin-1-yl)-9,10-dihydro-4H-benzo[d]pyrazolo[1,5-a][1,3]diazepine-3-carboxamide (the compound was synthesized through the similar way of the intermediate in B30) (70 mg, 0.13 mmol) in MeOH (2.0 mL), DCM (6.0 mL) and acetic acid (0.1 mL) was stirred at room temperature for 16 hours, and then $NaBH(OAc)_3$ (110 mg, 0.52 mmol) was added and stirred at room temperature for 1 hour. The mixture was treated with water (30 mL), extracted with dichloromethane (3×30 mL), and washed with brine (30 mL). The organic phase was dried over anhydrous sodium sulfate, filtered, and concentrated under reduced pressure to afford the crude product, which was purified with silica gel column chromatography (DCM:MeOH=100:0~90:10 gradient elution) to give the product (14 mg, 16%). $^1H$ NMR (400 MHz, DMSO) δ 10.85 (s, 1H), 10.30 (s, 1H), 9.72 (s, 1H), 8.02 (d, J=8.5 Hz, 1H), 7.75 (t, J=7.9 Hz, 1H), 7.36 (q, J=7.9 Hz, 2H), 7.12-7.00 (m, 4H), 6.91-6.80 (m, 3H), 4.41-4.33 (m, 2H), 3.71 (t, J=6.7 Hz, 2H), 3.20-3.00 (m, 9H), 2.64 (dt, J=23.7, 9.2 Hz, 6H), 2.42 (s, 3H), 2.33-2.20 (m, 8H), 1.88-1.79 (m, 2H), 1.77-1.63 (m, 1H), 1.36-1.19 (m, 4H); $[M+H]^+$=854.7.

Example B55: 7-(4-((1-(2-(2,6-dioxopiperidin-3-yl)-6-fluoro-1,3-dioxoisoindolin-5-yl)piperidin-4-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide Step 1: 7-(4-((1-(2-(2,6-dioxopiperidin-3-yl)-6-fluoro-1,3-dioxoisoindolin-5-yl)piperidin-4-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

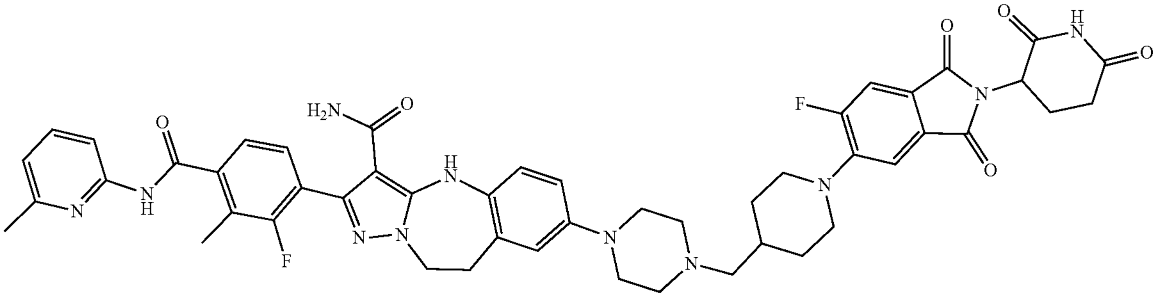 [SMILES: Cc1cccc(NC(=O)c2ccc(-c3nn4c(c3C(N)=O)Nc3ccc(N5CCN(CC6CCN(c7cc8c(cc7F)C(=O)N(C7CCC(=O)NC7=O)C8=O)CC6)CC5)cc3CC4)c(F)c2C)n1]

A mixture of 2-(2-fluoro-3-methyl-4-((6-methylpyridin-2-yl)carbamoyl)phenyl)-7-(piperazin-1-yl)-9,10-dihydro-4H-benzo[d]pyrazolo[1,5-a][1,3]diazepine-3-carboxamide (200 mg, 0.361 mmol), 2-(2,6-dioxopiperidin-3-yl)-5-fluoro-6-(4-(hydroxymethyl)piperidin-1-yl)isoindoline-1,3-dione (281 mg, 0.722 mmol), (cyanomethyl)trimethylphosphonium iodide (263 mg, 1.083 mmol) and DIEA (186 mg, 1.444 mmol) in MeCN (15 mL) was stirred at 100° C. for 16 h under $N_2$ atmosphere. The mixture was cooled and concentrated under reduced pressure. The mixture was purified with $SiO_2$-gel column (DCM:MeOH=10:1) and prep-HPLC to afford the product (50 mg, 15%). $^1$H NMR (500 MHz, DMSO) δ 11.02 (s, 1H), 10.75 (s, 1H), 9.69 (s, 1H), 7.95 (d, J=8.0 Hz, 1H), 7.68 (t, J=7.8 Hz, 1H), 7.54 (d, J=12.6 Hz, 1H), 7.33-7.25 (m, 2H), 6.99 (dd, J=11.3, 7.6 Hz, 2H), 6.88-6.78 (m, 3H), 5.00 (dd, J=12.8, 5.3 Hz, 1H), 4.34-4.26 (m, 2H), 3.70-3.63 (m, 1H), 3.62-3.48 (m, 3H), 3.22-3.15 (m, 4H), 3.15-3.06 (m, 5H), 2.87-2.75 (m, 4H), 2.57-2.45 (m, 2H), 2.35 (s, 3H), 2.26-2.17 (m, 4H), 2.12-2.04 (m, 1H), 1.98-1.91 (m, 1H), 1.74-1.65 (m, 2H), 1.63-1.55 (m, 1H); $[M+H]^+$=926.6.

Example B56: 7-(4-((1-(2-(2,6-dioxopiperidin-3-yl)-6-fluoro-3-oxoisoindolin-5-yl)piperidin-4-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

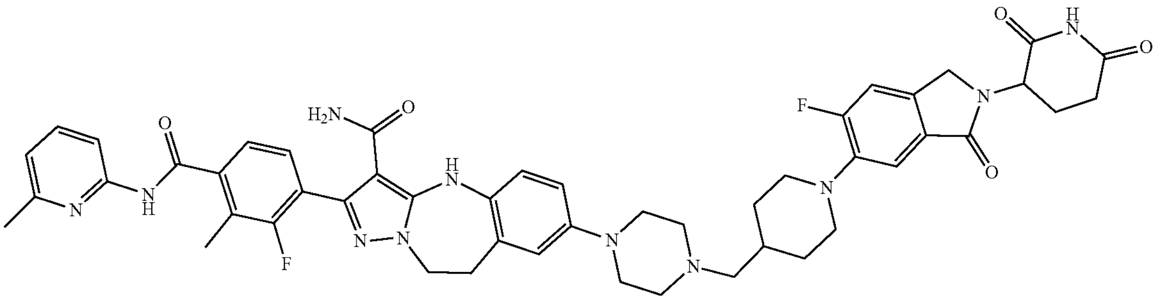 [SMILES: Cc1cccc(NC(=O)c2ccc(-c3nn4c(c3C(N)=O)Nc3ccc(N5CCN(CC6CCN(c7cc8c(cc7F)CN(C7CCC(=O)NC7=O)C8=O)CC6)CC5)cc3CC4)c(F)c2C)n1]

The titled compound was synthesized in the procedures similar to Example B55. $^1$H NMR (400 MHz, DMSO) δ 10.91 (s, 1H), 10.78 (s, 1H), 9.65 (s, 1H), 7.95 (d, J=8.2 Hz, 1H), 7.68 (t, J=7.8 Hz, 1H), 7.32-7.25 (m, 3H), 6.98 (d, J=7.6 Hz, 1H), 6.88 (d, J=8.3 Hz, 1H), 6.83-6.75 (m, 3H), 5.01 (dd, J=13.1, 5.0 Hz, 1H), 4.33-4.27 (m, 2H), 4.24 (d, J=17.1 Hz, 1H), 4.11 (d, J=17.0 Hz, 1H), 3.51-3.41 (m, 2H), 3.41-3.31 (m, 3H), 3.13-3.06 (m, 2H), 3.06-2.97 (m, 4H), 2.90-2.76 (m, 1H), 2.56-2.52 (m, 1H), 2.49-2.46 (m, 2H), 2.41-2.27 (m, 6H), 2.23 (s, 3H), 2.21-2.15 (m, 1H), 2.09-2.00 (m, 1H), 1.95-1.87 (m, 1H), 1.62-1.49 (m, 3H); $[M+H]^+$ =912.7.

Example B57: 7-(4-(1'-(2-(2,6-dioxopiperidin-3-yl)-1,3-dioxoisoindolin-5-yl)-[1,3'-biazetidin]-3-yl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide Step 1: 7-(4-(1'-(2-(2,6-dioxo-1-((2-(trimethylsilyl)ethoxy)methyl)piperidin-3-yl)-1,3-dioxoisoindolin-5-yl)-[1,3'-biazetidin]-3-yl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

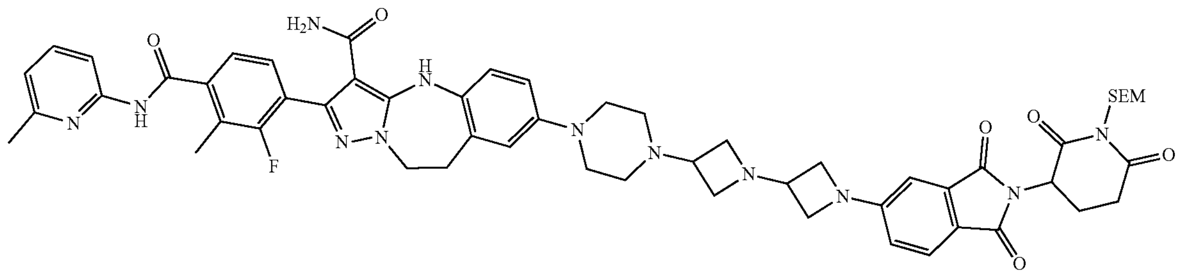 [SMILES: Cc1cccc(NC(=O)c2ccc(-c3nn4c(c3C(N)=O)Nc3ccc(N5CCN(C6CN(C7CN(c8ccc9c(c8)C(=O)N(C8CCC(=O)N(COCC[Si](C)(C)C)C8=O)C9=O)C7)C6)CC5)cc3CC4)c(F)c2C)n1]

2-(2-Fluoro-3-methyl-4-((6-methylpyridin-2-yl)carbamoyl)phenyl)-7-(piperazin-1-yl)-9,10-dihydro-4H-benzo[d]pyrazolo[1,5-a][1,3]diazepine-3-carboxamide (200 mg, 0.361 mmol) and 2-(2,6-dioxo-1-((2-(trimethylsilyl)ethoxy)methyl)piperidin-3-yl)-5-(3-oxo-[1,3'-biazetidin]-1'-yl)isoindoline-1,3-dione (the compound was synthesized through the similar way of the intermediate in WO2021219070A1)(222 mg, 0.433 mmol) were dissolved in DCM/HOAc (15 mL/1 mL). The mixture was stirred at room temperature for 16 h. To the mixture was added sodium triacetoxyborohydride (230 mg, 1.08 mmol) and stirred at room temperature for 1 h. To the resulting mixture was added water (25 mL) and extracted with DCM (3×20 mL). The combined organic layers were washed with sat. NaCl (25 mL) and dried over anhydrous $Na_2SO_4$. After filtration, the filtrate was concentrated under reduced pressure. The resulting residue was purified by silica gel column chromatography, eluted with DCM/MeOH (10:1) to afford the product (210 mg, 56%); $[M+H]^+$=1051.4.

Step 2: 7-(4-(1'-(2-(2,6-dioxopiperidin-3-yl)-1,3-dioxoisoindolin-5-yl)-[1,3'-biazetidin]-3-yl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

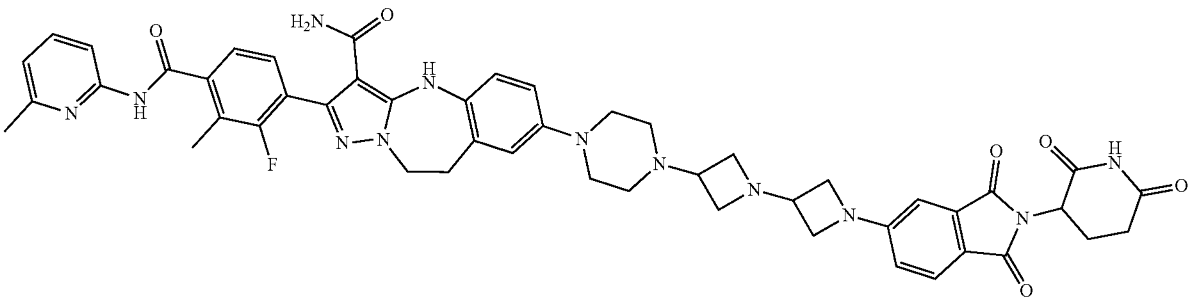 [SMILES: Cc1cccc(NC(=O)c2ccc(-c3nn4c(c3C(N)=O)Nc3ccc(N5CCN(C6CN(C7CN(c8ccc9c(c8)C(=O)N(C8CCC(=O)NC8=O)C9=O)C7)C6)CC5)cc3CC4)c(F)c2C)n1]

A solution of 7-(4-(1'-(2-(2,6-dioxo-1-((2-(trimethylsilyl)ethoxy)methyl)piperidin-3-yl)-1,3-dioxoisoindolin-5-yl)-[1,3'-biazetidin]-3-yl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide (210 mg, 0.2 mmol) in TFA (15 mL) was stirred at room temperature for 1 h. The mixture was concentrated in vacuo. The resulting mixture was dissolved in 10 mL of THF. $NH_3 \cdot H_2O$ (5 mL) was added at 5° C. and stirred for 5 min at room temperature. To the resulting mixture was added water (25 mL) and extracted with DCM (3×20 mL). The combined organic layers were washed with sat. NaCl (25 mL) and dried over anhydrous $Na_2SO_4$. After filtration, the filtrate was concentrated under reduced pressure. The resulting residue was purified by silica gel column chromatography, eluted with DCM/MeOH (10:1) and prep-HPLC to afford the product (25 mg, 14%). $^1$H NMR (500 MHz, DMSO) δ 11.00 (s, 1H), 10.75 (s, 1H), 9.65 (s, 1H), 7.95 (d, J=8.0 Hz, 1H), 7.67 (t, J=7.9 Hz, 1H), 7.57 (d, J=8.3 Hz, 1H), 7.31-7.26 (m, 2H), 6.97 (d, J=7.6 Hz, 1H), 6.82-6.72 (m, 4H), 6.59 (dd, J=8.4, 1.9 Hz, 1H), 4.99 (dd, J=12.8, 5.4 Hz, 1H), 4.34-4.26 (m, 2H), 3.97 (t, J=7.8 Hz, 2H), 3.74-3.72 (m, 2H), 3.61-3.53 (m, 1H), 3.43-3.30 (m, 4H), 3.13-3.07 (m, 2H), 3.05-2.96 (m, 4H), 2.94-2.87 (m, 3H), 2.86-2.75 (m, 1H), 2.57-2.45 (m, 1H), 2.39-2.29 (m, 6H), 2.23 (d, J=2.0 Hz, 3H), 2.00-1.89 (m, 1H); $[M+H]^+$=921.6.

Example B58:7-(4-((1-(2-(2,6-dioxopiperidin-3-yl)-1-oxoisoindolin-5-yl)piperidin-4-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

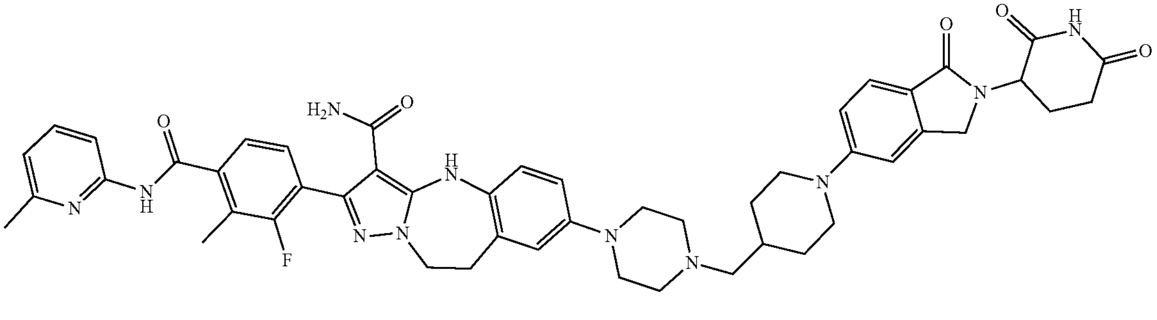 [SMILES: Cc1cccc(NC(=O)c2ccc(-c3nn4c(c3C(N)=O)Nc3ccc(N5CCN(CC6CCN(c7ccc8c(c7)CN(C7CCC(=O)NC7=O)C8=O)CC6)CC5)cc3CC4)c(F)c2C)n1]

The titled compound was synthesized in the procedures similar to Example B57. $^1H$ NMR (500 MHz, DMSO) δ 10.86 (s, 1H), 10.75 (s, 1H), 9.65 (s, 1H), 7.95 (d, J=7.6 Hz, 1H), 7.68 (t, J=7.9 Hz, 1H), 7.42 (d, J=9.0 Hz, 1H), 7.34-7.25 (m, 2H), 6.98 (d, J=7.5 Hz, 1H), 6.82-6.76 (m, 3H), 6.55 (d, J=7.2 Hz, 2H), 4.97-4.94 (m, 1H), 4.32-4.27 (m, 2H), 4.23 (d, J=16.4 Hz, 1H), 4.11 (d, J=16.4 Hz, 1H), 3.47-3.44 (m, 1H), 3.13-3.02 (m, 8H), 2.94-2.87 (m, 2H), 2.87-2.79 (m, 2H), 2.56-2.50 (m, 4H), 2.35 (s, 3H), 2.33-2.17 (m, 6H), 2.13-2.08 (m, 1H), 1.89-1.86 (m, 1H), 1.63-1.57 (m, 3H); $[M+H]^+$=894.6.

Example B59:7-(4-((1-(4-(2,4-dioxotetrahydropyrimidin-1(2H)-yl)phenyl)azetidin-3-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

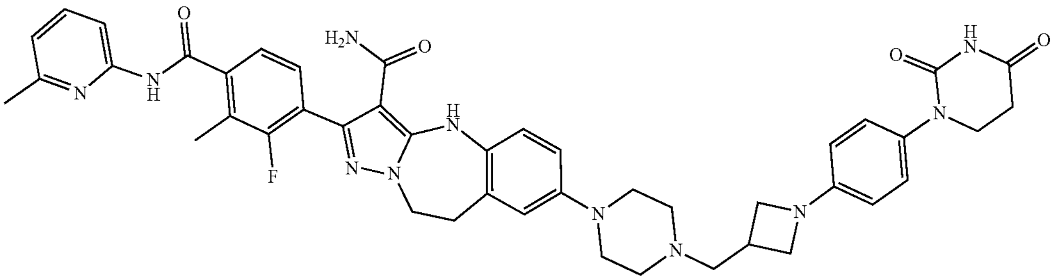 [SMILES: Cc1cccc(NC(=O)c2ccc(-c3nn4c(c3C(N)=O)Nc3ccc(N5CCN(CC6CN(c7ccc(N8CCC(=O)NC8=O)cc7)C6)CC5)cc3CC4)c(F)c2C)n1]

The titled compound was synthesized in the procedures similar to Example B57. $^1H$ NMR (500 MHz, DMSO) δ 10.83 (s, 1H), 10.25 (s, 1H), 9.79 (s, 1H), 8.02 (d, J=7.9 Hz, 1H), 7.75 (t, J=7.9 Hz, 1H), 7.41-7.31 (m, 2H), 7.14 (d, J=8.6 Hz, 2H), 7.05 (d, J=7.5 Hz, 1H), 6.94 (q, J=8.6 Hz, 3H), 6.46 (d, J=8.7 Hz, 2H), 4.43-4.35 (m, 2H), 4.06-4.03 (m, 2H), 3.82-3.75 (m, 2H), 3.67 (t, J=6.7 Hz, 2H), 3.65-3.60 (m, 2H), 3.59-3.49 (m, 3H), 3.28-3.12 (m, 5H), 2.99-2.95 (m, 2H), 2.68 (t, J=6.7 Hz, 2H), 2.54 (s, 1H), 2.43 (s, 3H), 2.31 (d, J=1.5 Hz, 3H); $[M+H]^+$=812.5.

Example B60:7-(4-((1-(2,6-dioxopiperidin-3-yl)-3,3-dimethyl-2-oxoindolin-5-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide Step 1: 7-(4-((1-(2,6-dioxopiperidin-3-yl)-3,3-dimethyl-2-oxoindolin-5-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

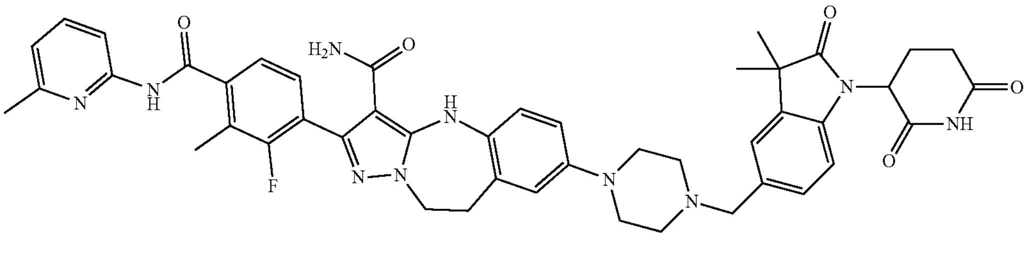 [SMILES: Cc1cccc(NC(=O)c2ccc(-c3nn4c(c3C(N)=O)Nc3ccc(N5CCN(Cc6ccc7c(c6)C(C)(C)C(=O)N7C6CCC(=O)NC6=O)CC5)cc3CC4)c(F)c2C)n1]

A solution of 2-(2-fluoro-3-methyl-4-((6-methylpyridin-2-yl)carbamoyl)phenyl)-7-(piperazin-1-yl)-9,10-dihydro-4H-benzo[d]pyrazolo[1,5-a][1,3]diazepine-3-carboxamide (150 mg, 0.270 mmol) and 1-(2,6-dioxopiperidin-3-yl)-3,3-dimethyl-2-oxoindoline-5-carbaldehyde (the compound was synthesized through the similar way of the intermediate in WO2021219070A)(81 mg, 0.270 mmol) in dichloromethane (5 mL) and MeOH (5 mL) was stirred at room temperature for 5 mins. Then HOAc (0.06 mL) was added. The mixture was stirred at room temperature overnight. Then NaBH $(OAc)_3$ (286 mg, 1.35 mmol) was added and stirred at room temperature overnight. Then $NaBH_3CN$ (85 mg, 1.35 mmol) was added and stirred at room temperature overnight. The reaction mixture was concentrated in vacuum, and the residue was purified by silica gel column chromatography (DCM:MeOH=100%: 0%~90%: 10% gradient elution) to give crude product, which was further purified by prep-HPLC to afford desired product (11.98 mg, 5%). $^1H$ NMR (500 MHz, DMSO) δ 11.00 (s, 1H), 10.75 (s, 1H), 9.64 (s, 1H), 7.95 (d, J=8.0 Hz, 1H), 7.67 (t, J=8.0 Hz, 1H), 7.33-7.23 (m, 3H), 7.12 (d, J=8.0 Hz, 1H), 6.97 (d, J=8.0 Hz, 1H), 6.92-6.72 (m, 4H), 5.17 (s, 1H), 4.30 (s, 2H), 3.43 (s, 4H), 3.10 (s, 2H), 3.03 (s, 3H), 2.86-2.77 (m, 1H), 2.72-2.63 (m, 2H), 2.61-2.54 (m, 4H), 2.53-2.51 (m, 2H), 2.35 (s, 3H), 2.23 (s, 3H), 1.94-1.86 (m, 1H), 1.23 (s, 6H); $[M+H]^+$=839.5.

Example B61:7-(4-(2-(3-(2,6-dioxopiperidin-3-yl)-2-oxo-2,3-dihydrobenzo[d]oxazol-7-yl)ethyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

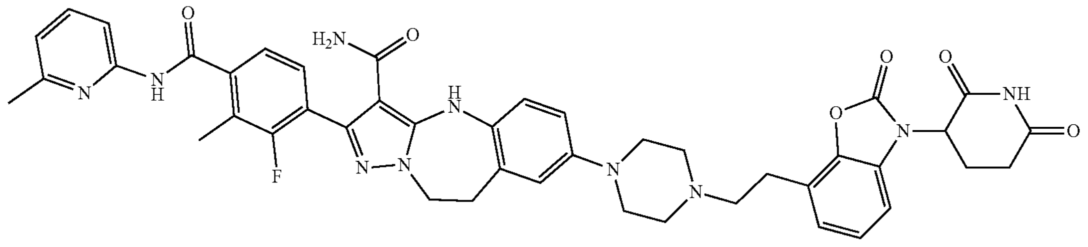 [SMILES: Cc1cccc(NC(=O)c2ccc(-c3nn4c(c3C(N)=O)Nc3ccc(N5CCN(CCc6cccc7c6oc(=O)n7C6CCC(=O)NC6=O)CC5)cc3CC4)c(F)c2C)n1]

The titled compound was synthesized in the procedures similar to Example B60. $^1H$ NMR (500 MHz, DMSO) δ 11.21 (s, 1H), 10.82 (s, 1H), 9.72 (s, 1H), 8.02 (d, J=8.1 Hz, 1H), 7.74 (t, J=7.9 Hz, 1H), 7.40-7.32 (m, 2H), 7.13 (dt, J=15.9, 7.7 Hz, 3H), 7.04 (d, J=7.5 Hz, 1H), 6.86 (dd, J=20.4, 8.5 Hz, 3H), 5.36 (dd, J=12.8, 5.2 Hz, 1H), 4.42-4.30 (m, 2H), 3.21-3.14 (m, 2H), 3.14-3.06 (m, 4H), 2.98-2.83 (m, 3H), 2.76-2.57 (m, 8H), 2.42 (s, 3H), 2.30 (s, 3H), 2.20-2.12 (m, 1H); $[M+H]^+$=827.5.

Example B62: 7-(4-(4-(2,6-dioxopiperidin-3-yl)-3,5-difluorophenethyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a] [1,3] diazepine-3-carboxamide

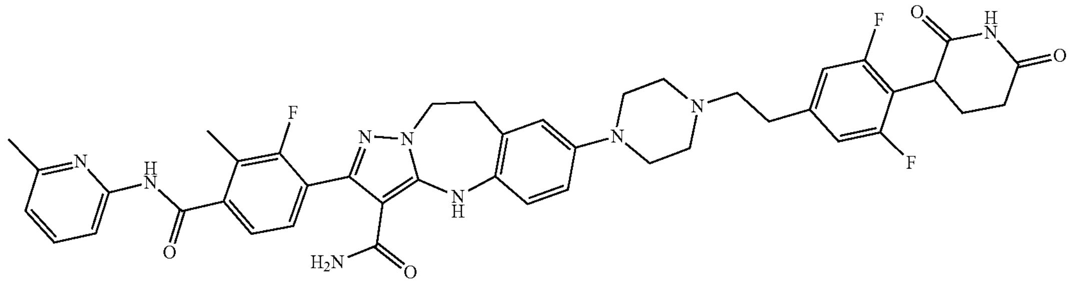 [SMILES: Cc1cccc(NC(=O)c2ccc(-c3nn4c(c3C(N)=O)Nc3ccc(N5CCN(CCc6cc(F)c(C7CCC(=O)NC7=O)c(F)c6)CC5)cc3CC4)c(F)c2C)n1]

The titled compound was synthesized in the procedures similar to Example B54. $^1$H NMR (500 MHz, DMSO) δ 10.95 (s, 1H), 10.82 (s, 1H), 9.72 (s, 1H), 8.02 (d, J=8.0 Hz, 1H), 7.74 (t, J=7.9 Hz, 1H), 7.42-7.30 (m, 2H), 7.05 (dd, J=8.6, 6.5 Hz, 3H), 6.93-6.80 (m, 3H), 4.45-4.32 (m, 2H), 4.22-4.18 (m, 1H), 3.30-3.26 (m, 2H), 3.19-3.14 (m, 2H), 3.13-3.05 (m, 4H), 2.85-2.77 (m, 3H), 2.65-2.51 (m, 7H), 2.42 (s, 3H), 2.30 (d, J=1.9 Hz, 3H), 2.17-2.08 (m, 1H), 2.03-1.96 (m, 1H); $[M+H]^+$=806.5.

Example B63: (R)-7-(4-(4-(2,6-dioxopiperidin-3-yl)-3,5-difluorophenethyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

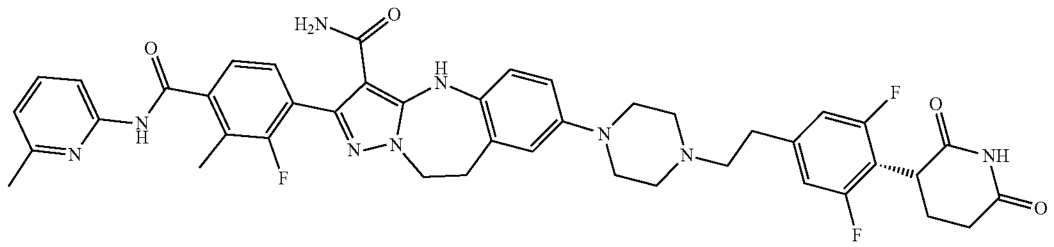

The titled compound was synthesized in the procedures similar to Example B54. $^1$H NMR (500 MHz, DMSO) δ 10.98 (s, 1H), 10.82 (s, 1H), 9.79 (s, 1H), 8.02 (d, J=8.1 Hz, 1H), 7.75 (t, J=7.9 Hz, 1H), 7.40-7.32 (m, 2H), 7.14 (d, J=9.8 Hz, 2H), 7.05 (d, J=7.5 Hz, 1H), 6.98-6.91 (m, 3H), 4.41-4.36 (m, 2H), 4.24 (dd, J=12.6, 5.0 Hz, 1H), 3.84-3.77 (m, 2H), 3.69-3.62 (m, 2H), 3.57-2.48 (m, 2H), 3.25-3.15 (m, 4H), 3.11-3.06 (m, 2H), 3.02-2.94 (m, 2H), 2.88-2.77 (m, 1H), 2.58-2.52 (m, 1H), 2.43 (s, 3H), 2.31 (d, J=1.7 Hz, 3H), 2.18-2.10 (m, 1H), 2.04-1.97 (m, 1H); $[M+H]^+$=806.6.

Example B64: 7-(4-(3-(4-(2,4-dioxotetrahydropyrimidin-1(2H)-yl)phenyl)cyclobutyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide Step 1: 3-(4-(4,4,5,5-tetramethyl-1,3,2-dioxaborolan-2-yl)phenyl)cyclobutan-1-one

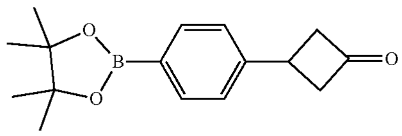 [SMILES: CC1(C)OB(c2ccc(C3CC(=O)C3)cc2)OC1(C)C]

A mixture of 3-(4-bromophenyl)cyclobutan-1-one (4.5 g, 0.02 mol), 4,4,4',4',5,5,5',5'-octamethyl-2,2'-bi(1,3,2-dioxaborolane) (7.62 g, 0.03 mol), Pd(dppf)$Cl_2$ (0.731 g, 0.001 mol) and KOAc (3.92 g, 0.04 mol) in dioxane (200 mL) was stirred for 16 h at 100° C. under nitrogen atmosphere. The mixture was allowed to cool down to room temperature and concentrated under reduced pressure. The residue was purified by silica gel column chromatography, eluted with PE/EtOAc (100%:0% to 80%:20%) to afford the product (3.9 g, 71%). $[M+H]^+$=273.4.

Step 2: (4-(3-oxocyclobutyl)phenyl)boronic acid

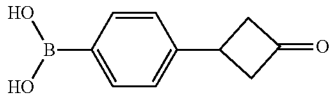 [SMILES: O=C1CC(c2ccc(B(O)O)cc2)C1]

A solution of 3-(4-(4,4,5,5-tetramethyl-1,3,2-dioxaborolan-2-yl)phenyl)cyclobutan-1-one (3.9 g, 0.0143 mol) and $NaIO_4$ (6.13 g, 0.0286 mol) in THF/water (40 mL/10 mL) was stirred at rt for 20 mins. Then HCl (2 M, 10 mL) was added. The mixture was stirred at room temperature overnight. The mixture was extracted with EA, washed with brine, dried over $Na_2SO_4$, and concentrated in vacuo. The residue was purified by silica gel column chromatography, eluted with DCM/MeOH (100%:0% to 90%:10%) to afford the product (1.6 g, 58%). $[M+H]^+$=191.4.

Step 3: 1-(4-(3-oxocyclobutyl)phenyl)-3-((2-(trimethylsilyl)ethoxy)methyl)pyrimidine-2,4(1H,3H)-dione

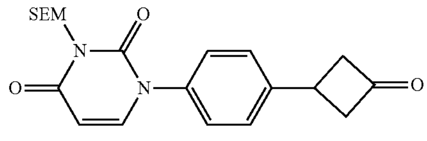 [SMILES: C[Si](C)(C)CCOCn1c(=O)ccn(-c2ccc(C3CC(=O)C3)cc2)c1=O]

A mixture of (4-(3-oxocyclobutyl)phenyl)boronic acid (1.6 g, 8.42 mmol), 3-((2-(trimethylsilyl)ethoxy)methyl)pyrimidine-2,4(1H,3H)-dione (2 g, 8.42 mmol), $Cu(OAc)_2$ (4.57 g, 25.26 mmol), pyridine (3.32 g, 42.9 mmol) and 4A MS in DMA (30 mL) was stirred at 80° C. for 2 h under oxygen. The mixture was allowed to cool down to room temperature. The resulting mixture was extracted with EA (100 mL*3), washed with brine (150 mL), dried over $Na_2SO_4$, and concentrated under reduced pressure. The residue was purified by silica gel column chromatography, eluted with PE/EA (100%:0%~0%:100%) to afford the product (700 mg, 21%). $[M+H]^+$=387.5.

Step 4: 1-(4-(3-oxocyclobutyl)phenyl)-3-((2-(trimethylsilyl)ethoxy)methyl)dihydropyrimidine-2,4(1H,3H)-dione

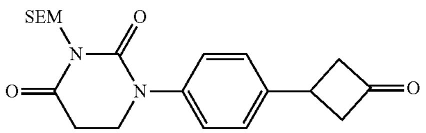 [SMILES: C[Si](C)(C)CCOCN1C(=O)CCN(c2ccc(C3CC(=O)C3)cc2)C1=O]

To a solution of 1-(4-(3-oxocyclobutyl)phenyl)-3-((2-(trimethylsilyl)ethoxy)methyl)pyrimidine-2,4(1H,3H)-dione (700 mg, 1.81 mmol) and Pd/C (350 mg) in THE (20 mL), HCl (2 M) was added. The mixture was stirred at room temperature overnight under 4 atm of hydrogen. The mixture was filtered, and the filtration was concentrated in vacuo to give the product (400 mg, crude). $[M+H]^+$=389.5.

Step 5: 1-(4-(3-oxocyclobutyl)phenyl)dihydropyrimidine-2,4(1H,3H)-dione

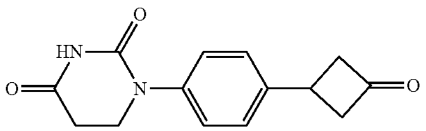 [SMILES: O=C1CC(c2ccc(N3CCC(=O)NC3=O)cc2)C1]

To a suspension of 1-(4-(3-oxocyclobutyl)phenyl)-3-((2-(trimethylsilyl)ethoxy)methyl)dihydropyrimidine-2,4(1H,3H)-dione (400 mg, 1.03 mmol) in DCM, TFA (10 mL) was added. The mixture was stirred at room temperature for 6 h and concentrated in vacuo. The residue was diluted with DCM (1 mL), and $NH_3 \cdot H_2O$ (3 mL) was added. The mixture was stirred at room temperature for 2 h. The mixture was concentrated in vacuo and the residue was purified by silica gel column chromatography, eluted with DCM/MeOH (100%:0% to 95%:5%) to afford the product (120 mg, 46%). $[M+H]^+$=259.5.

Step 6: 7-(4-(3-(4-(2,4-dioxotetrahydropyrimidin-1(2H)-yl)phenyl)cyclobutyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

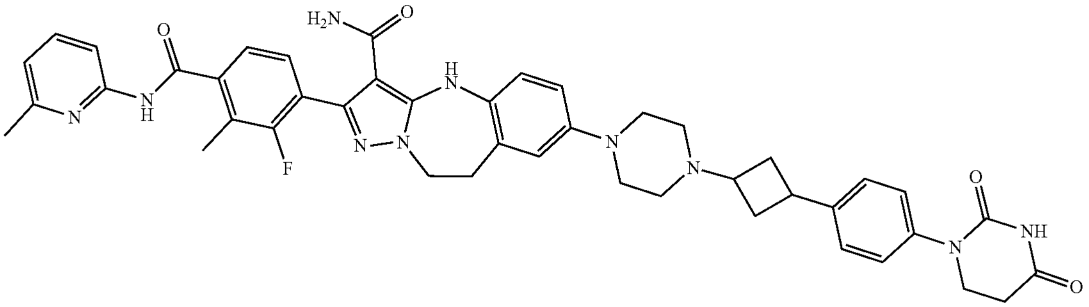 [SMILES: Cc1cccc(NC(=O)c2ccc(-c3nn4c(c3C(N)=O)Nc3ccc(N5CCN(C6CC(c7ccc(N8CCC(=O)NC8=O)cc7)C6)CC5)cc3CC4)c(F)c2C)n1]

A solution of 2-(2-fluoro-3-methyl-4-((6-methylpyridin-2-yl)carbamoyl)phenyl)-7-(piperazin-1-yl)-9,10-dihydro-4H-benzo[d]pyrazolo[1,5-a][1,3]diazepine-3-carboxamide (150 mg, 0.270 mmol) and 1-(4-(3-oxocyclobutyl)phenyl) dihydropyrimidine-2,4(1H,3H)-dione (45 mg, 0.175 mmol) in dichloromethane (5 mL) and MeOH (5 mL) was stirred at room temperature for 5 mins. Then HOAc (0.06 mL) was added. The mixture was stirred at room temperature overnight. Then $NaBH(OAc)_3$ (286 mg, 1.35 mmol) was added and stirred at room temperature overnight. The reaction mixture was concentrated in vacuum, and the residue was purified by silica gel column chromatography (DCM: MeOH=100%: 0%~90%: 10% gradient elution) to give crude product, which was further purified by prep-HPLC to afford desired product (6.08 mg, 4%). $^1H$ NMR (500 MHz, DMSO) δ 10.82 (s, 1H), 10.33 (s, 1H), 9.72 (s, 1H), 8.02 (d, J=4.0 Hz, 1H), 7.74 (t, J=8.0 Hz, 1H), 7.44-7.31 (m, 2H), 7.29-7.22 (m, 4H), 7.04 (d, J=4.0 Hz, 1H), 6.91-6.79 (m, 3H), 4.45-4.31 (m, 2H), 3.76 (t, J=5.0 Hz, 2H), 3.17 (dd, J=15.0, 10.0 Hz, 4H), 3.14-3.04 (m, 5H), 2.80-2.73 (m, 1H), 2.70 (t, J=10.0 Hz, 2H), 2.48-2.44 (m, 5H), 2.42 (s, 3H), 2.30 (s, 3H), 1.88 (dd, J=20.0, 10.0 Hz, 2H); $[M+H]^+$=797.6.

Example B65: 7-(4-(1'-(4-(2,6-dioxopiperidin-3-yl)phenyl)-[1,3'-biazetidin]-3-yl)piperazin-1-yl)-2-(2-fluoro-3-methyl-4-((6-methylpyridin-2-yl)carbamoyl)phenyl)-9,10-dihydro-4H-benzo[d]pyrazol[1,5-a][1,3]diazepine-carboxamide

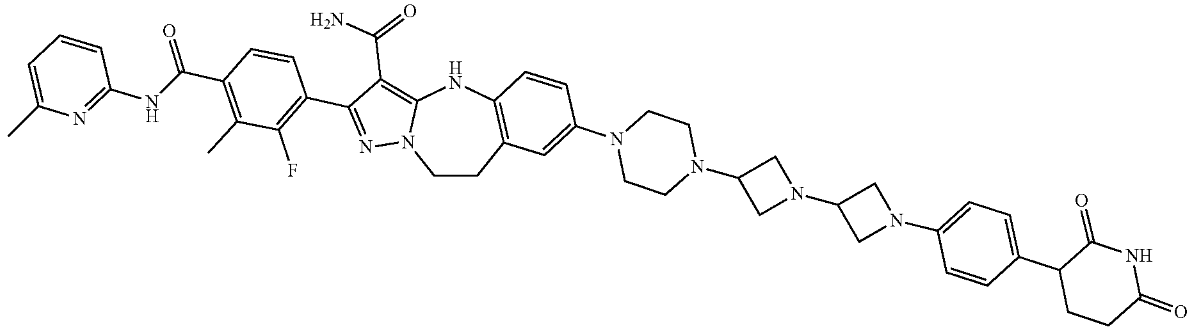 [SMILES: Cc1cccc(NC(=O)c2ccc(-c3nn4c(c3C(N)=O)Nc3ccc(N5CCN(C6CN(C7CN(c8ccc(C9CCC(=O)NC9=O)cc8)C7)C6)CC5)cc3CC4)c(F)c2C)n1]

The titled compound was synthesized in the procedures similar to Example B64. $^1H$ NMR (500 MHz, DMSO) δ 10.83 (s, 1H), 10.77 (s, 1H), 9.76 (s, 1H), 8.01 (d, J=8.1 Hz, 1H), 7.78-7.72 (m, 1H), 7.42-7.32 (m, 2H), 7.06 (dd, J=7.9, 6.1 Hz, 3H), 6.94-6.87 (m, 3H), 6.48 (d, J=8.5 Hz, 2H), 4.42-4.35 (m, 2H), 4.33-4.19 (m, 3H), 4.18-4.09 (m, 2H), 4.04-4.00 (m, 2H), 3.87-3.82 (m, 2H), 3.74-3.72 (m, 2H), 3.26-3.11 (m, 6H), 2.81-2.68 (m, 3H), 2.66-2.60 (m, 2H), 2.49-2.44 (m, 1H), 2.43 (s, 3H), 2.30 (d, J=2.0 Hz, 3H), 2.17-2.08 (m, 1H), 2.02-1.95 (m, 1H); $[M+H]^+$=852.6.

Example B66: 7-(4-(1-(4-(2,4-dioxotetrahydropyrimidin-1(2H)-yl)phenyl)azetidin-3-yl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide Step 1: 3,3'-((4-hydroxyphenyl)azanediyl)dipropionic acid

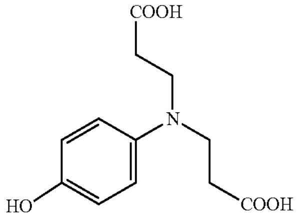 [SMILES: O=C(O)CCN(CCC(=O)O)c1ccc(O)cc1]

A solution of 4-aminophenol (250 g, 2.29 mol) and acrylic acid (363 g, 5.04 mol) in water (1.25 L) was stirred at 80~85° C. for 16 hrs. TLC indicated starting material was consumed. The mixture was cooled to 20~25° C. The reaction mixture was filtered, and the filter cake was washed with $H_2O$ (2.00 L). The filter cake was concentrated in vacuum to give the titled product (552 g, 95%). $^1H$NMR (400 MHz, DMSO) δ 12.18 (brs, 2H), 8.67 (brs, 1H), 6.48-6.88 (m, 4H), 3.38 (s, 5H), 2.36 (t, J=7.06 Hz, 4H).

Step 2: 1-(4-hydroxyphenyl)dihydropyrimidine-2,4(1H,3H)-dione

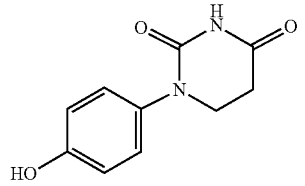 [SMILES: O=C1CCN(c2ccc(O)cc2)C(=O)N1]

To a solution of 3,3'-((4-hydroxyphenyl)azanediyl)dipropionic acid (300 g, 1.18 mol) in AcOH (1.50 L) was added urea (106 g, 1.76 mol) at 20~30° C. After addition, the mixture was stirred at 120~130° C. for 12 hrs. LCMS showed the starting material was consumed completely and desired product was observed. 10.0% HCl (1.00 L) was added to the reactor at 120~130° C. After addition, the mixture was stirred at 120~130° C. for 1 hr. The reaction mixture was cooled to 10~20° C. and filtered. The filter cake was rinsed with petroleum ether (2.00 L) to give the titled product (185 g, crude). $^1H$NMR (400 MHz, DMSO) δ 10.3 (s, 1H), 9.45 (s, 1H), 7.00-7.26 (m, 2H), 6.67-6.86 (m, 2H), 3.67 (t, J=6.72 Hz, 2H), 2.67 (t, J=6.72 Hz, 2H).

Step 3: 1-(4-((tert-butyldimethylsilyl)oxy)phenyl)dihydropyrimidine-2,4(1H,3H)-dione

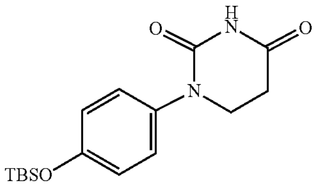 [SMILES: CC(C)(C)[Si](C)(C)Oc1ccc(N2CCC(=O)NC2=O)cc1]

To a solution of 1-(4-hydroxyphenyl)dihydropyrimidine-2,4(1H,3H)-dione (80.0 g, 0.380 mol) and imidazole (52.8 g, 0.770 mol) in DCM (400 mL) was added TBSCl (64.3 g, 0.420 mol) at 10-15° C. Then the mixture was stirred at 25° C. for 12 hrs. TLC indicated starting material was consumed. The reaction mixture was partitioned between DCM (400 mL) and water (500 mL). The aqueous layer was extracted with DCM (200 mL). The combined organic layers were washed with brine (200 mL), dried with anhydrous $Na_2SO_4$, and concentrated in vacuo to give the titled product (120 g, 96%). $^1$HNMR (400 MHz, DMSO) δ 10.31 (s, 1H), 7.07-7.40 (m, 2H), 6.67-6.95 (m, 2H), 3.72 (t, J=6.73 Hz, 2H), 2.68 (t, J=6.73 Hz, 2H), 0.95 (s, 9H), 0.20 (s, 6H).

Step 4: 1-(4-((tert-butyldimethylsilyl)oxy)phenyl)-3-((2-(trimethylsilyl)ethoxy)methyl)dihydropyrimidine-2,4(1H,3H)-dione

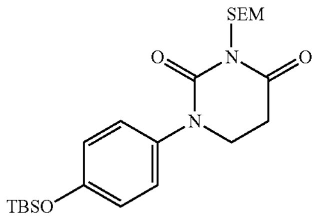 [SMILES: CC(C)(C)[Si](C)(C)Oc1ccc(N2CCC(=O)N(COCC[Si](C)(C)C)C2=O)cc1]

To a solution of 1-(4-((tert-butyldimethylsilyl)oxy)phenyl)dihydropyrimidine-2,4(1H,3H)-dione (85.0 g, 0.260 mol) and DIEA (137 g, 1.06 mol) in ACN (425 mL) was added SEMCl (88.4 g, 0.530 mol) at 20-25° C. Then the mixture was stirred at 80-85° C. for 12 hrs. TLC indicated starting material was consumed. The reaction mixture was cooled to 20-25° C. and put into water (500 mL). The mixture was filtered and concentrated in reduced pressure at 45° C. The residue was purified by activated carbon, then adsorption by silica gel to give the product (124 g, 69%). $^1$HNMR (400 MHz, $CDCl_3$) δ 7.03-7.21 (m, 2H), 6.85 (d, J=8.60 Hz, 2H), 5.29 (s, 2H), 3.78 (t, J=6.62 Hz, 2H), 3.61-3.72 (m, 2H), 2.89 (t, J=6.62 Hz, 2H), 0.98 (s, 9H), 0.72-0.93 (m, 1H), 0.20 (s, 5H), 0.04-0.03 (m, 10H). Step 5: 1-(4-hydroxyphenyl)-3-((2-(trimethylsilyl)ethoxy)methyl)dihydropyrimidine-2,4(1H,3H)-dione

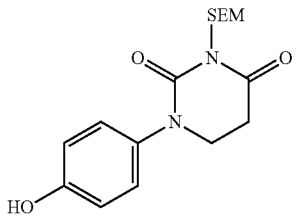 [SMILES: C[Si](C)(C)CCOCN1C(=O)CCN(c2ccc(O)cc2)C1=O]

A solution of 1-(4-((tert-butyldimethylsilyl)oxy)phenyl)-3-((2-(trimethylsilyl)ethoxy)methyl)dihydropyrimidine-2,4(1H,3H)-dione (124 g, 0.270 mol) and $NH_4F$ (20.3 g, 0.550 mol) in MeOH (620 mL) was stirred at 15-20° C. for 1 hr. TLC indicated starting material was consumed. The mixture was filtered and concentrated in reduced pressure at 45° C. The crude product was triturated with petroleum ether: ethyl acetate=10:1 (200 mL) at 15° C. for 45 mins, to give target product (65.0 g, 69%). $^1$HNMR (400 MHz, DMSO) δ 6.96-7.15 (m, 2H), 6.63-6.84 (m, 2H), 5.31 (s, 2H), 5.93 (s, 1H), 3.76 (t, J=6.80 Hz, 2H), 3.66-3.73 (m, 2H), 2.90 (t, J=6.58 Hz, 2H), 0.87-1.16 (m, 2H), 0.02 (s, 9H).

Step 6: 4-(2,4-dioxo-3-((2-(trimethylsilyl)ethoxy)methyl)tetrahydropyrimidin-1(2H)-yl)phenyl trifluoromethanesulfonate

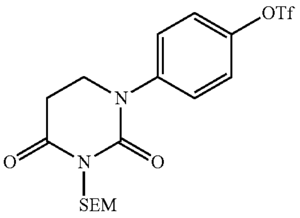 [SMILES: C[Si](C)(C)CCOCN1C(=O)CCN(c2ccc(OS(=O)(=O)C(F)(F)F)cc2)C1=O]

To a mixture of 1-(4-hydroxyphenyl)-3-((2-(trimethylsilyl)ethoxy)methyl)dihydropyrimidine-2,4(1H,3H)-dione (4 g, 11.9 mmol) and pyridine (1.88 g, 23.8 mmol) in DCM (30 mL) was added $Tf_2O$ (4.03 g, 14.28 mmol) dropwise at 0° C. The mixture was stirred at rt for 3 h. The mixture was diluted with water (100 mL) and extracted with DCM (3×100 mL). The combined organic layers were dried over $Na_2SO_4$, filtered and concentrated under vacuum. The residue was purified by silica gel column chromatography, eluted with EA/PE (2:3) to afford the product (5.1 g, 92%). $[M+H]^+$=469.1.

Step 7: 1-(4-(3-hydroxyazetidin-1-yl)phenyl)-3-((2-(trimethylsilyl)ethoxy)methyl)dihydropyrimidine-2,4(1H,3H)-dione

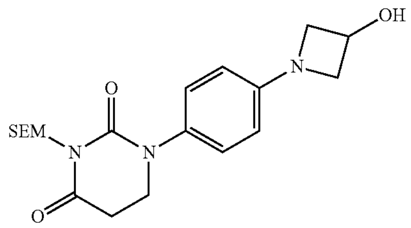 [SMILES: C[Si](C)(C)CCOCN1C(=O)CCN(c2ccc(N3CC(O)C3)cc2)C1=O]

A mixture of 4-(2,4-dioxo-3-((2-(trimethylsilyl)ethoxy)methyl)tetrahydropyrimidin-1(2H)-yl)phenyl trifluoromethanesulfonate (1.25 g, 0.00267 mol), azetidin-3-ol hydrochloride (582 mg, 0.00534 mol), $Pd_2(dba)_3$ (250 mg, 0.00267 mol), RuPhos (125 mg, 0.00027 mol) and $Cs_2CO_3$ (2.6 g, 0.00810 mol) in 1,4-dioxane (20 mL) was stirred in a round bottom flask at 100° C. overnight under nitrogen. The mixture was evaporated in vacuum to afford the crude product, which was further purified with silica gel column chromatography (PE:EA=100:0~0:100 gradient elution) to give the titled product (600 mg, 57%). $[M+H]^+$=392.3.

Step 8: 1-(4-(3-oxoazetidin-1-yl)phenyl)-3-((2-(trimethylsilyl)ethoxy)methyl)dihydropyrimidine-24 (1H,3H)-dione

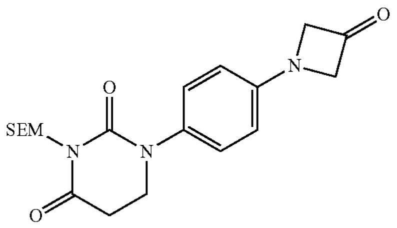 [SMILES: C[Si](C)(C)CCOCN1C(=O)CCN(c2ccc(N3CC(=O)C3)cc2)C1=O]

To a solution of $(COCl)_2$ (2.76 mL, 1.38 mmol, 1M in DCM) in DCM (10 mL), DMSO (430 mg, 5.52 mmol, dissolved in 2 mL DCM) was added dropwise at −60° C. The mixture was stirred at −60° C. for 1 hour. Then 1-(4-(3-hydroxyazetidin-1-yl)phenyl)-3-((2-(trimethylsilyl)ethoxy)methyl)dihydropyrimidine-2,4(1H,3H)-dione (540 mg, 1.38 mmol, dissolved in 2 mL DCM) was added. The mixture was stirred at −60° C. for 1 hour. Then triethylamine (836 mg, 8.28 mmol) was added, and the mixture was stirred from −60° C. to room temperature. The mixture was evaporated in vacuum to afford the crude product, which was further purified with silica gel column chromatography (PE:EA=100:0~90:10 gradient elution) to give the titled product (400 mg, 74%). $[M+H]^+$=390.0.

Step 9: 7-(4-(1-(4-(2,4-dioxo-3-((2-(trimethylsilyl)ethoxy)methyl)tetrahydropyrimidin-1(2H)-yl)phenyl)azetidin-3-yl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

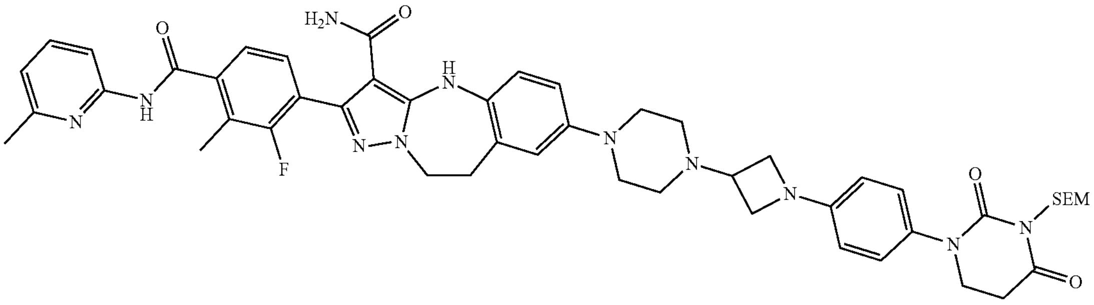 [SMILES: Cc1cccc(NC(=O)c2ccc(-c3nn4c(c3C(N)=O)Nc3ccc(N5CCN(C6CN(c7ccc(N8CCC(=O)N(COCC[Si](C)(C)C)C8=O)cc7)C6)CC5)cc3CC4)c(F)c2C)n1]

A mixture of 2-(2-fluoro-3-methyl-4-((6-methylpyridin-2-yl)carbamoyl)phenyl)-7-(piperazin-1-yl)-9,10-dihydro-4H-benzo[d]pyrazolo[1,5-a][1,3]diazepine-3-carboxamide (150 mg, crude), 1-(4-(3-oxoazetidin-1-yl)phenyl)-3-((2-(trimethylsilyl)ethoxy)methyl)dihydropyrimidine-2,4(1H,3H)-dione (108 mg, 0.280 mmol) in dichloromethane (5 mL) and MeOH (5 mL) was stirred at room temperature for 5 mins. Then HOAc (0.06 mL) was added. The mixture was stirred at room temperature overnight. Then $NaBH(OAc)_3$ (296 mg, 1.4 mmol) was added and stirred at room temperature for 2 hours. The reaction mixture was concentrated in vacuum, and the residue was purified by silica gel column chromatography (DCM:MeOH=100%: 0%~90%: 10% gradient elution) to give the product (95 mg, 38%). $[M+H]^+$=928.0.

Step 10: 7-(4-(1-(4-(2,4-dioxotetrahydropyrimidin-1(2H)-yl)phenyl)azetidin-3-yl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

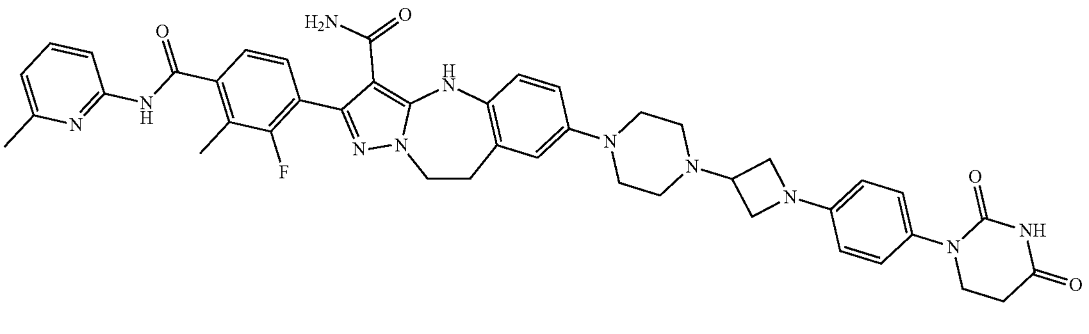 [SMILES: Cc1cccc(NC(=O)c2ccc(-c3nn4c(c3C(N)=O)Nc3ccc(N5CCN(C6CN(c7ccc(N8CCC(=O)NC8=O)cc7)C6)CC5)cc3CC4)c(F)c2C)n1]

To a solution of 7-(4-(1-(4-(2,4-dioxo-3-((2-(trimethylsilyl)ethoxy)methyl)tetrahydropyrimidin-1(2H)-yl)phenyl)azetidin-3-yl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide (100 mg, 0.097 mmol) in dichloromethane (5 mL), TFA (4 mL) was added. The mixture was stirred at room temperature for 1.5 h. The reaction mixture was concentrated in vacuum, and the residue was diluted with MeOH (5 mL). $NH_3$ in MeOH (7 M, 0.1 mL) was added dropwise, and the mixture was stirred at room temperature for 15 mins. Then the mixture was concentrated in vacuo and the residue was purified by prep-TLC (DCM:MeOH=10:1) to afford desired product (10.3 mg, 12%). $^1H$ NMR (500 MHz, DMSO) δ 10.75 (s, 1H), 10.16 (s, 1H), 9.65 (s, 1H), 7.94 (d, J=5.0 Hz, 1H), 7.67 (t, J=5.0 Hz, 1H), 7.32-7.25 (m, 2H), 7.05 (d, J=4.0 Hz, 2H), 6.98 (d, J=4.0 Hz, 1H), 6.90-6.72 (m, 3H), 6.38 (d, J=8.0 Hz, 2H), 4.29 (s, 2H), 3.88 (t, J=4.0 Hz, 2H), 3.63-3.54 (m, 4H), 3.34 (s, 6H), 3.13-3.00 (m, 6H), 2.63-2.58 (m, 2H), 2.47 (s, 3H), 2.35 (s, 3H), 2.23 (s, 3H); $[M+H]^+$=798.5.

Example B67 and example B68: (R)-7-(4-(3-(4-(2,6-dioxopiperidin-3-yl)phenyl)cyclobutyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide and (S)-7-(4-(3-(4-(2,6-dioxopiperidin-3-yl)phenyl)cyclobutyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide Step 1: 2,6-bis(benzyloxy)-3-(4,4,5,5-tetramethyl-1,3,2-dioxaborolan-2-yl)pyridine

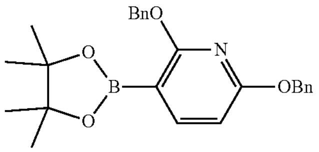 [SMILES: CC1(C)OB(c2ccc(OCc3ccccc3)nc2OCc2ccccc2)OC1(C)C]

To a solution of 2,6-bis(benzyloxy)-3-bromopyridine (40.00 g, 108.036 mmol) and 4,4,5,5-tetramethyl-2-(tetramethyl-1,3,2-dioxaborolan-2-yl)-1,3,2-dioxaborolane (41.15 g, 162.054 mmol) in dioxane (800.00 mL) were added KOAc (31.81 g, 324.109 mmol) and $Pd(dppf)Cl_2$ (6.32 g, 8.643 mmol). After stirring for 16 h at 100° C. under nitrogen atmosphere, the resulting mixture was concentrated under reduced pressure. The reaction mixture was used in next step directly. $[M+H]^+$=418.1.

Step 2: 3-(4-(2,6-bis(benzyloxy)pyridin-3-yl)phenyl)cyclobutan-1-one

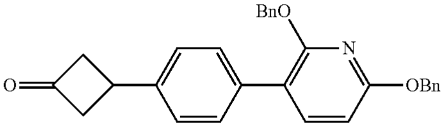 [SMILES: O=C1CC(c2ccc(-c3ccc(OCc4ccccc4)nc3OCc3ccccc3)cc2)C1]

To a solution of 3-(4-bromophenyl)cyclobutan-1-one (22.50 g, 99.962 mmol) and 2,6-bis(benzyloxy)-3-(4,4,5,5-tetramethyl-1,3,2-dioxaborolan-2-yl)pyridine (37.54 g, 89.966 mmol) in dioxane (200 mL) and water (40 mL) were added $K_2CO_3$ (16.58 g, 119.955 mmol) and $Pd(dppf)Cl_2$ (7.31 g, 9.996 mmol). After stirring for 16 h at 90° C. under nitrogen atmosphere, the resulting mixture was concentrated under reduced pressure. The residue was purified by silica gel column chromatography, eluted with 1-20% EtOAc in PE to afford the product (30.1 g, 39%). $[M+H]^+$=436.1.

Step 3: 3-(4-(5,8-dioxaspiro[3.4]octan-2-yl)phenyl)-2,6-bis(benzyloxy)pyridine

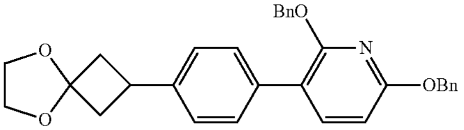 [SMILES: c1ccc(COc2ccc(-c3ccc(C4CC5(C4)OCCO5)cc3)c(OCc3ccccc3)n2)cc1]

To a solution of 3-(4-(2,6-bis(benzyloxy)pyridin-3-yl)phenyl)cyclobutan-1-one (26.00 g, 59.698 mmol) in toluene (500.00 mL) were added 4-methylbenzene-1-sulfonic acid hydrate (1.14 g, 5.970 mmol) and 2-dihydroxyethane (14.82 g, 238.793 mmol) under nitrogen atmosphere. The mixture was refluxed for 16 h through a Dean Stark to separate the water. The resulting mixture was concentrated under reduced pressure and dissolved in EtOAc (500 mL). The mixture was washed with aqueous $NaHCO_3$ (3×200 mL) and dried over anhydrous $Na_2SO_4$. After filtration, the filtrate was concentrated under reduced pressure. The residue was purified by silica gel column chromatography, eluted with 1~40% EtOAc in PE to afford the product (25.2 g, 88%). $[M+H]^+$=480.1.

Step 4: 3-(4-(5,8-dioxaspiro[3.4]octan-2-yl)phenyl) piperidine-2,6-dione

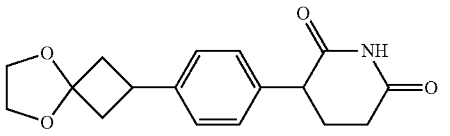 [SMILES: O=C1CCC(c2ccc(C3CC4(C3)OCCO4)cc2)C(=O)N1]

To a solution of 3-(4-(5,8-dioxaspiro[3.4]octan-2-yl)phenyl)-2,6-bis(benzyloxy)pyridine (25.00 g, 52.129 mmol) in THF (600.00 mL) and EtOH (200.00 mL) was added Pd/C (5.55 g) under nitrogen atmosphere. The mixture was stirred for 16 h under hydrogen atmosphere using a hydrogen tire. The resulting mixture was filtered through a Celite pad, and the filter cake was washed with MeOH (3×20 mL). The filtrate was concentrated under reduced pressure. The residue was purified by silica gel column chromatography, eluted with 10~40% EtOAc in PE to afford the product (14.4 g, 92%). $[M+H]^+$=302.2.

Step 5: 3-(4-(3-oxocyclobutyl)phenyl)piperidine-2,6-dione

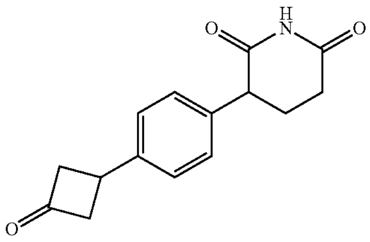

To a stirred solution of 3-(4-(5,8-dioxaspiro[3.4]octan-2-yl)phenyl)piperidine-2,6-dione (13.5 g, 44.8 mmol) in THE (100 mL) and water (80 mL) was added 2 M HCl (20 mL) at room temperature. The resulting mixture was stirred for 4 h at 55° C. under nitrogen atmosphere. Desired product could be detected by LCMS. The reaction was quenched with aqueous $NaHCO_3$ (10 mL) at 0° C. The resulting mixture was extracted with EtOAc (3×100 mL). The combined organic layers were washed with brine (3×100 mL) and dried over anhydrous $Na_2SO_4$. After filtration, the filtrate was concentrated under reduced pressure. The residue was purified by silica gel column chromatography, eluted with 10-60% EtOAc in PE to afford the product (8.2 g, 72%). $[M+H]^+$=258.1.

Step 6: (R)-3-(4-(3-oxocyclobutyl)phenyl)piperidine-2,6-dione and (S)-3-(4-(3-oxocyclobutyl)phenyl)piperidine-2,6-dione

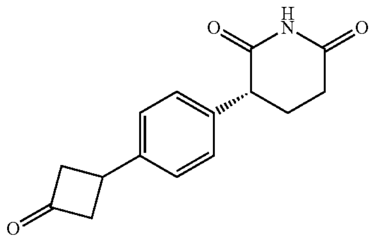 [SMILES: O=C1CC(c2ccc(C3CCC(=O)NC3=O)cc2)C1]

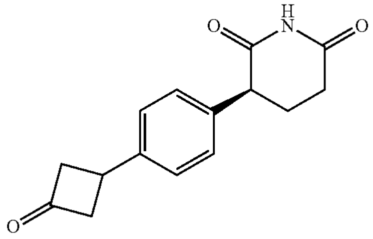

3-(4-(3-oxocyclobutyl)phenyl)piperidine-2,6-dione (8.20 g, 31.9 mmol) was separated by Prep-Chiral-SFC with the following conditions: Column: CHIRALPAK IH, 5*25 cm, 5 um; Mobile Phase A: $CO_2$, Mobile Phase B: MeOH; Flow rate:200 mL/min; Gradient:50% B; Back Pressure: 100 bar; Detector: 220 nm; $RT_1$: 3.99 min; $RT_2$: 5.53 min; Injection Volume: 5 mL; Number Of Runs: 30; (R)-3-(4-(3-oxocyclobutyl)phenyl)piperidine-2,6-dione (3.30 g, 40%) was obtained at 3.99 min. $^1H$ NMR (400 MHz, DMSO) δ 10.84 (s, 1H), 7.36-7.32 (m, 2H), 7.21-7.19 (m, 2H), 3.86 (dd, J=11.6, 5.2 Hz, 1H), 3.84-3.83 (m, 1H), 3.47-3.40 (m, 2H), 3.34-3.18 (m, 2H), 2.70-2.62 (m, 1H), 2.52-2.47 (m, 1H), 2.20-2.17 (m, 1H), 2.05-2.01 (m, 1H); $[M+H]^+$=258.1. (S)-3-(4-(3-oxocyclobutyl)phenyl)piperidine-2,6-dione (3.23 g, 40%) was obtained at 5.53 min. $^1H$ NMR (400 MHz, DMSO) δ 10.84 (s, 1H), 7.38-7.31 (m, 2H), 7.23-7.13 (m, 2H), 3.85 (dd, J=11.6, 4.8 Hz, 1H), 3.71-3.58 (m, 1H), 3.50-3.37 (m, 2H), 3.28-3.21 (m, 2H), 2.70-2.62 (m, 1H), 2.52-2.47 (m, 1H), 2.22-2.18 (m, 1H), 2.05-2.01 (m, 1H); $[M+H]^+$=258.1.

Step 7: (R)-7-(4-(3-(4-(2,6-dioxopiperidin-3-yl)phenyl)cyclobutyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

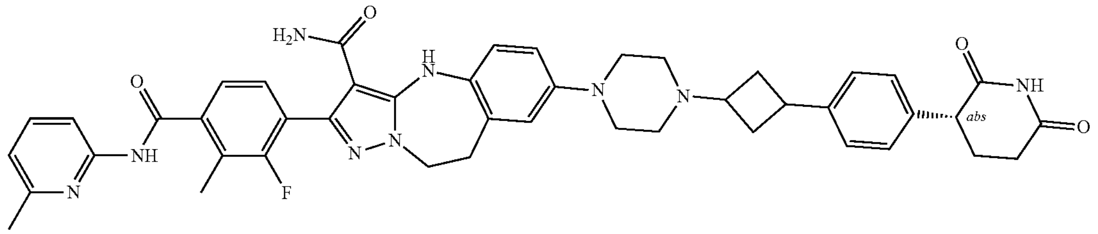 [SMILES: Cc1cccc(NC(=O)c2ccc(-c3nn4c(c3C(N)=O)Nc3ccc(N5CCN(C6CC(c7ccc([C@H]8CCC(=O)NC8=O)cc7)C6)CC5)cc3CC4)c(F)c2C)n1]

A solution of 2-(2-fluoro-3-methyl-4-((6-methylpyridin-2-yl)carbamoyl)phenyl)-7-(piperazin-1-yl)-9,10-dihydro-4H-benzo[d]pyrazolo[1,5-a][1,3]diazepine-3-carboxamide (150 mg, crude) and (R)-3-(4-(3-oxocyclobutyl)phenyl)piperidine-2,6-dione (76 mg, 0.297 mmol) in dichloromethane (5 mL) and MeOH (5 mL) was stirred at room temperature for 5 mins. Then HOAc (0.06 mL) was added. The mixture was stirred at room temperature overnight. Then NaBH $(OAc)_3$ was added (286 mg, 1.35 mmol) and stirred at room temperature overnight. Then $NaBH_3CN$ (85 mg, 1.35 mmol) was added and stirred at room temperature overnight. The reaction mixture was concentrated in vacuum, and the residue was purified by silica gel column chromatography (DCM:MeOH=100%: 0%~90%: 10% gradient elution) to give crude product, which was further purified by prep-TLC (DCM:MeOH=10:1) to afford desired product (56.37 mg, 26%). $^1$H NMR (500 MHz, DMSO) δ 10.82 (s, 1H), 9.72 (s, 1H), 8.02 (d, J=5.0 Hz, 1H), 7.74 (t, J=5.0 Hz, 1H), 7.40-7.31 (m, 2H), 7.30-7.18 (m, 1H), 7.17-7.13 (m, 1H), 7.04 (d, J=5.0 Hz, 1H), 6.90-6.86 (m, 2H), 6.86-6.81 (m, 1H), 4.40-4.32 (m, 2H), 3.82 (dd, J=12.0, 4.0 Hz, 1H), 3.20-3.05 (m, 7H), 2.75 (s, 1H), 2.70-2.60 (m, 2H), 2.48-2.43 (m, 6H), 2.42 (s, 4H), 2.30 (s, 1H), 2.22-2.12 (m, 2H), 2.07-1.97 (m, 1H), 1.94-1.82 (m, 2H); $[M+H]^+$=796.5.

Step 8: (S)-7-(4-(3-(4-(2,6-dioxopiperidin-3-yl)phenyl)cyclobutyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

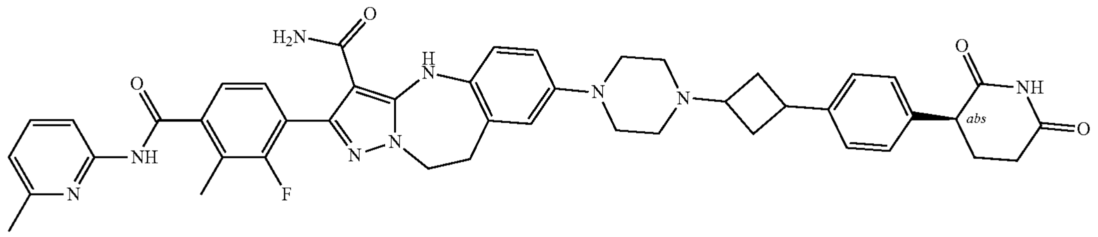 [SMILES: Cc1cccc(NC(=O)c2ccc(-c3nn4c(c3C(N)=O)Nc3ccc(N5CCN(C6CC(c7ccc([C@@H]8CCC(=O)NC8=O)cc7)C6)CC5)cc3CC4)c(F)c2C)n1]

A solution of 2-(2-fluoro-3-methyl-4-((6-methylpyridin-2-yl)carbamoyl)phenyl)-7-(piperazin-1-yl)-9,10-dihydro-4H-benzo[d]pyrazolo[1,5-a][1,3]diazepine-3-carboxamide (150 mg, crude) and (S)-3-(4-(3-oxocyclobutyl)phenyl)piperidine-2,6-dione (76 mg, 0.297 mmol) in dichloromethane (5 mL) and MeOH (5 mL) was stirred at room temperature for 5 mins. Then HOAc (0.06 mL) was added. The mixture was stirred at room temperature overnight. Then NaBH $(OAc)_3$ (286 mg, 1.35 mmol) was added and stirred at room temperature overnight. Then $NaBH_3CN$ (85 mg, 1.35 mmol) was added and stirred at room temperature overnight. The reaction mixture was concentrated in vacuum, and the residue was purified by silica gel column chromatography (DCM:MeOH=100%: 0%~90%: 10% gradient elution) to give crude product, which was further purified by prep-TLC (DCM:MeOH=10:1) to afford desired product (43.08 mg, 20%). $^1$H NMR (500 MHz, DMSO) δ 10.82 (s, 1H), 9.72 (s, 1H), 8.02 (d, J=8.0 Hz, 1H), 7.74 (t, J=8.0 Hz, 1H), 7.40-7.31 (m, 2H), 7.30-7.19 (m, 2H), 7.19-7.13 (m, 2H), 7.04 (d, J=4.0 Hz, 1H), 6.91-6.81 (m, 3H), 4.40-4.32 (m, 1H), 3.82 (dd, J=12.0, 4.0 Hz, 1H), 3.20-3.06 (m, 7H), 2.75 (s, 1H), 2.70-2.60 (m, 2H), 2.49-2.44 (m, 5H), 2.43-2.35 (m, 5H), 2.30 (s, 3H), 2.23-2.13 (m, 2H), 2.06-1.98 (m, 1H), 1.93-1.82 (m, 1H); $[M+H]^+$=796.5.

Example B69:7-(4-((1-(4-((2,4-dioxotetrahydropyrimidin-1(2H)-yl)methyl)phenyl)piperidin-4-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

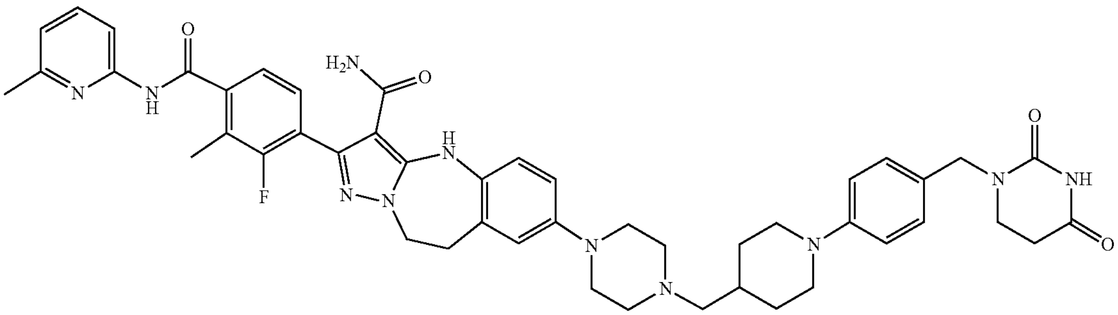 [SMILES: Cc1cccc(NC(=O)c2ccc(-c3nn4c(c3C(N)=O)Nc3ccc(N5CCN(CC6CCN(c7ccc(CN8CCC(=O)NC8=O)cc7)CC6)CC5)cc3CC4)c(F)c2C)n1]

The titled compound was synthesized in the procedures similar to Example B66. $^1$H NMR (500 MHz, DMSO) δ 10.84 (s, 1H), 10.17 (s, 1H), 9.78 (s, 1H), 8.01 (s, 1H), 7.75 (s, 1H), 7.43-7.30 (m, 2H), 7.20 (d, J=6.1 Hz, 2H), 7.04 (s, 3H), 6.95 (s, 3H), 4.47-4.34 (m, 4H), 3.66-3.40 (m, 6H), 3.34-3.10 (m, 10H), 3.10-2.98 (m, 2H), 2.90-2.76 (m, 2H), 2.43 (s, 3H), 2.31 (s, 3H), 2.12-2.02 (m, 1H), 1.94-1.83 (m, 2H), 1.45-1.33 (m, 2H); $[M+H]^+$=854.1.

Example B70:7-(4-((1-(3-((2,4-dioxotetrahydropyrimidin-1(2H)-yl)methyl)phenyl)piperidin-4-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

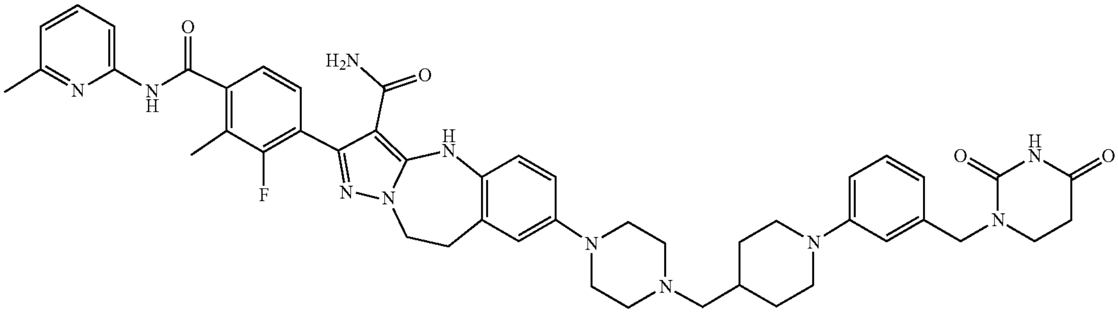 [SMILES: Cc1cccc(NC(=O)c2ccc(-c3nn4c(c3C(N)=O)Nc3ccc(N5CCN(CC6CCN(c7cccc(CN8CCC(=O)NC8=O)c7)CC6)CC5)cc3CC4)c(F)c2C)n1]

The titled compound was synthesized in the procedures similar to Example B66. R NMR (500 MHz, DMSO) δ 10.83 (s, 1H), 10.19 (s, 1H), 9.79 (s, 1H), 8.02 (d, J=7.9 Hz, 1H), 7.75 (t, J=7.8 Hz, 1H), 7.41-7.31 (m, 2H), 7.21 (t, J=7.8 Hz, 1H), 7.05 (d, J=7.5 Hz, 1H), 6.94 (dt, J=16.5, 8.3 Hz, 5H), 6.74 (d, J=7.2 Hz, 1H), 4.47 (s, 2H), 4.42-4.35 (m, 2H), 3.80-3.69 (m, 6H), 3.28 (t, J=6.8 Hz, 2H), 3.23-3.11 (m, 6H), 3.04 (t, J=11.8 Hz, 2H), 2.78 (t, J=11.7 Hz, 2H), 2.57-2.51 (m, 2H), 2.43 (s, 3H), 2.31 (s, 3H), 2.10-2.00 (m, 1H), 1.91-1.82 (m, 2H), 1.41-1.30 (m, 2H); $[M+H]^+$=854.1.

Example B71: (R)-7-(4-(3-(4-((2,6-dioxopiperidin-3-yl)amino)phenyl)cyclobutyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

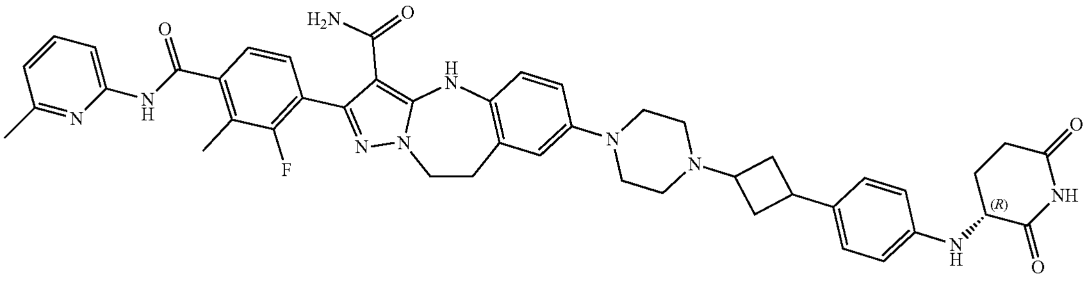

The titled compound was synthesized in the procedures similar to Example B66. $^1$H NMR (500 MHz, DMSO) δ 10.83 (s, 1H), 10.78 (s, 1H), 9.83 (s, 1H), 9.79 (s, 1H), 8.02 (d, J=8.0 Hz, 1H), 7.75 (t, J=7.9 Hz, 1H), 7.41-7.31 (m, 2H), 7.06 (dt, J=7.6, 4.0 Hz, 3H), 6.98-6.91 (m, 3H), 6.67 (t, J=8.8 Hz, 2H), 4.42-4.36 (m, 2H), 4.31 (dd, J=11.4, 4.7 Hz, 1H), 3.85-3.78 (m, 2H), 3.77-3.70 (m, 1H), 3.67-3.60 (m, 2H), 3.22-3.17 (m, 2H), 3.11-3.01 (m, 3H), 2.98-2.90 (m, 2H), 2.79-2.69 (m, 1H), 2.66-2.55 (m, 3H), 2.43 (s, 3H), 2.37-2.21 (m, 5H), 2.13-2.06 (m, 1H), 1.92-1.83 (m, 1H); $[M+H]^+$=811.0.

Example B72: (S)-7-(4-(3-(4-((2,6-dioxopiperidin-3-yl)amino)phenyl)cyclobutyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

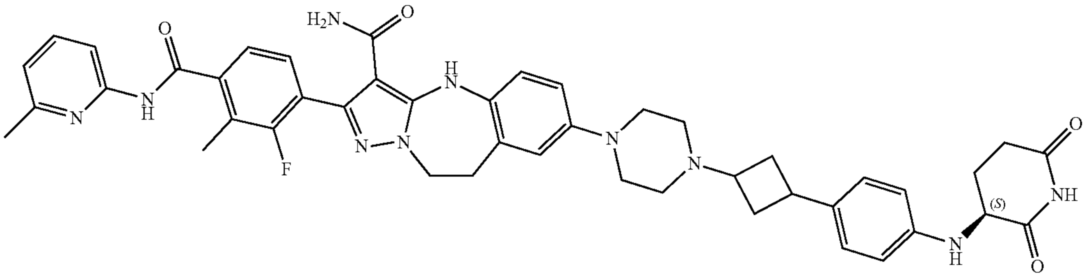

The titled compound was synthesized in the procedures similar to Example B66. $^1$H NMR (500 MHz, DMSO) δ 10.83 (s, 1H), 10.78 (s, 1H), 9.85 (s, 1H), 9.79 (s, 1H), 8.02 (d, J=8.1 Hz, 1H), 7.75 (t, J=7.9 Hz, 1H), 7.40-7.32 (m, 2H), 7.06 (dt, J=7.5, 3.6 Hz, 3H), 6.99-6.91 (m, 3H), 6.67 (t, J=9.0 Hz, 2H), 4.42-4.35 (m, 2H), 4.31 (dd, J=11.3, 4.7 Hz, 1H), 3.86-3.78 (m, 3H), 3.77-3.73 (m, 2H), 3.22-3.18 (m, 2H), 3.11-3.01 (m, 3H), 2.98-2.90 (m, 2H), 2.78-2.70 (m, 1H), 2.67-2.55 (m, 3H), 2.43 (s, 3H), 2.38-2.21 (m, 5H), 2.13-2.06 (m, 1H), 1.93-1.83 (m, 1H); $[M+H]^+$=811.0.

Example B73:7-(4-(1-(4-(2,4-dioxotetrahydropyrimidin-1(2H)-yl)phenyl)piperidine-4-carbonyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide Step 1: 7-(4-(1-(4-(2,4-dioxotetrahydropyrimidin-1(2H)-yl)phenyl)piperidine-4-carbonyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

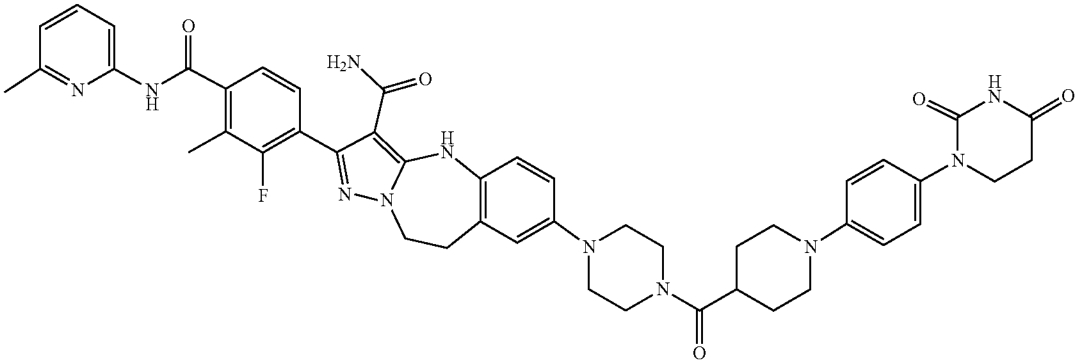 [SMILES: Cc1cccc(NC(=O)c2ccc(-c3nn4c(c3C(N)=O)Nc3ccc(N5CCN(C(=O)C6CCN(c7ccc(N8CCC(=O)NC8=O)cc7)CC6)CC5)cc3CC4)c(F)c2C)n1]

A mixture of 2-(2-fluoro-3-methyl-4-((6-methylpyridin-2-yl)carbamoyl)phenyl)-7-(piperazin-1-yl)-9,10-dihydro-4H-benzo[d]pyrazolo[1,5-a][1,3]diazepine-3-carboxamide (55 mg, 0.1 mmol), 1-(4-(2,4-dioxotetrahydropyrimidin-1(2H)-yl)phenyl)piperidine-4-carboxylic acid 2,2,2-trifluoroacetic acid (the compound was synthesized through the similar way of the intermediate in WO2021219070A) (50 mg, 0.12 mmol), HATU (57 mg, 0.15 mmol) and DIPEA (38.7 mg, 0.3 mmol) in DMF (6.0 mL) was stirred in a round bottom flask at room temperature overnight. Then the mixture was evaporated in vacuum to afford the crude product, which was purified by prep-HPLC to give the product (34 mg, 40%). $^1$H NMR (500 MHz, DMSO) δ 10.85 (s, 1H), 10.35 (s, 1H), 9.78 (s, 1H), 8.01 (d, J=8.1 Hz, 1H), 7.76 (t, J=7.9 Hz, 1H), 7.41-7.33 (m, 2H), 7.29 (s, 2H), 7.22 (s, 2H), 7.06 (d, J=7.5 Hz, 1H), 6.94 (d, J=12.4 Hz, 3H), 4.41-4.37 (m, 2H), 3.80-3.68 (m, 6H), 3.68-3.62 (m, 2H), 3.23-3.13 (m, 5H), 3.12-3.06 (m, 3H), 3.02-2.93 (m, 1H), 2.70 (t, J=6.7 Hz, 2H), 2.43 (s, 3H), 2.31 (d, J=1.7 Hz, 3H), 1.91-1.77 (m, 4H); $[M+H]^+$=854.0.

Example B74: (R)-7-(4-((1-(4-(2,4-dioxotetrahydropyrimidin-1(2H)-yl)phenyl)pyrrolidin-3-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

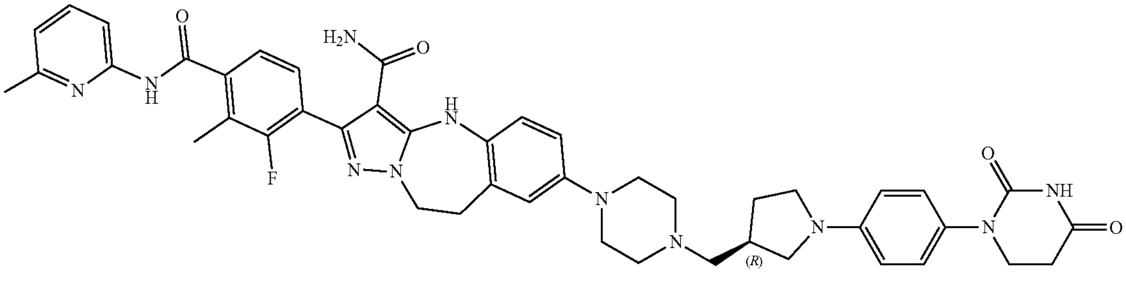

The titled compound was synthesized in the procedures similar to Example B73. $^1$H NMR (500 MHz, DMSO) δ 10.83 (s, 1H), 10.23 (s, 1H), 9.79 (s, 1H), 8.02 (d, J=8.1 Hz, 1H), 7.75 (t, J=7.9 Hz, 1H), 7.41-7.30 (m, 2H), 7.13 (d, J=8.8 Hz, 2H), 7.05 (d, J=7.5 Hz, 1H), 6.95 (q, J=8.6 Hz, 3H), 6.55 (d, J=8.9 Hz, 2H), 4.43-4.35 (m, 2H), 3.68-3.65 (m, 5H), 3.57-3.51 (m, 2H), 3.41-3.33 (m, 3H), 3.31-3.15 (m, 5H), 3.10-2.98 (m, 3H), 2.83 (dt, J=14.2, 7.2 Hz, 1H), 2.69 (t, J=6.7 Hz, 2H), 2.43 (s, 3H), 2.31 (d, J=1.8 Hz, 3H), 2.28-2.22 (m, 1H), 1.84-1.77 (m, 1H); $[M+H]^+$=826.0.

Example B75:7-(4-(2-(3-(2,4-dioxotetrahydropyrimidin-1(2H)-yl)phenyl)acetyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide

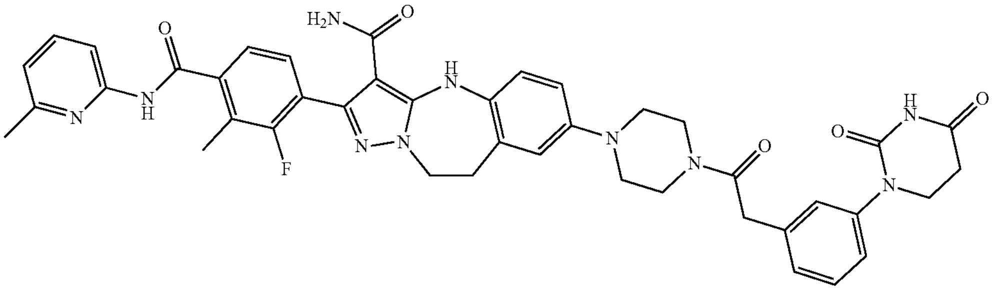 [SMILES: Cc1cccc(NC(=O)c2ccc(-c3nn4c(c3C(N)=O)Nc3ccc(N5CCN(C(=O)Cc6cccc(N7CCC(=O)NC7=O)c6)CC5)cc3CC4)c(F)c2C)n1]

The titled compound was synthesized in the procedures similar to Example B73. $^1$H NMR (500 MHz, DMSO) δ 10.83 (s, 1H), 10.36 (s, 1H), 9.75 (s, 1H), 8.01 (d, J=8.3 Hz, 1H), 7.75 (t, J=7.8 Hz, 1H), 7.40-7.31 (m, 3H), 7.23-7.18 (m, 2H), 7.12 (d, J=7.5 Hz, 1H), 7.05 (d, J=7.5 Hz, 1H), 6.88 (q, J=8.6 Hz, 3H), 4.40-4.33 (m, 2H), 3.82-3.75 (m, 4H), 3.68-3.61 (m, 4H), 3.19-3.14 (m, 2H), 3.08-2.98 (m, 4H), 2.70 (t, J=6.7 Hz, 2H), 2.42 (s, 3H), 2.30 (d, J=1.7 Hz, 3H); $[M+H]^+$=785.1.

Example B76 and example B77: tert-butyl 2-(3-(4-(4-((4-(3-carbamoyl-2-(2-fluoro-3-methyl-4-((6-methylpyridin-2-yl)carbamoyl)phenyl)-9,10-dihydro-4H-benzo[d]pyrazolo[1,5-a][1,3]diazepin-7-yl)piperazin-1-yl)methyl)piperidin-1-yl)phenyl)-2,6-dioxotetrahydropyrimidin-1(2H)-yl)acetate and tert-butyl 2-(3-(4-(4-((4-(2-(4-((2-(tert-butoxy)-2-oxoethyl)(6-methylpyridin-2-yl)carbamoyl)-2-fluoro-3-methylphenyl)-3-carbamoyl-9,10-dihydro-4H-benzo[d]pyrazolo[1,5-a][1,3]diazepin-7-yl)piperazin-1-yl)methyl)piperidin-1-yl)phenyl)-2,6-dioxotetrahydropyrimidin-1(2H)-yl)acetate The titled compounds was synthesized in the procedures similar to Example B78 and Example B79. Example B76: $^1$H NMR (500 MHz, DMSO) δ 10.84 (s, 1H), 9.79 (s, 1H), 8.02 (d, J=7.9 Hz, 1H), 7.75 (t, J=7.9 Hz, 1H), 7.41-7.31 (m, 2H), 7.20 (d, J=8.3 Hz, 2H), 7.05 (t, J=8.1 Hz, 3H), 6.94 (q, J=8.6 Hz, 3H), 4.43-4.36 (m, 2H), 4.29 (s, 2H), 3.76-3.72 (m, 6H), 3.65-3.62 (m, 2H), 3.23-3.12 (m, 6H), 3.05 (t, J=11.9 Hz, 2H), 2.88 (t, J=6.6 Hz, 2H), 2.80 (t, J=11.5 Hz, 2H), 2.43 (s, 3H), 2.31 (d, J=1.9 Hz, 3H), 2.11-2.03 (m, 1H), 1.91-1.84 (m, 2H), 1.43-1.34 (m, 11H); $[M+H]^+$=954.0. Example B77: $^1$H NMR (500 MHz, DMSO) δ 9.71 (s, 1H), 9.29 (s, 1H), 7.54 (s, 1H), 7.18 (d, J=8.7 Hz, 3H), 7.01 (d, J=6.5 Hz, 4H), 6.93 (q, J=8.7 Hz, 3H), 4.63-4.54 (m, 2H), 4.37-4.33 (m, 2H), 4.28 (s, 2H), 3.80-3.72 (m, 8H), 3.21-3.12 (m, 6H), 3.03 (t, J=11.8 Hz, 2H), 2.88 (t, J=6.7 Hz, 2H), 2.77 (t, J=11.5 Hz, 2H), 2.33 (s, 3H), 2.25 (d, J=1.8 Hz, 3H), 2.09-2.01 (m, 1H), 1.89-1.83 (m, 2H), 1.47-1.34 (m, 20H); $[M+H]^+$=1068.2.

Example B76

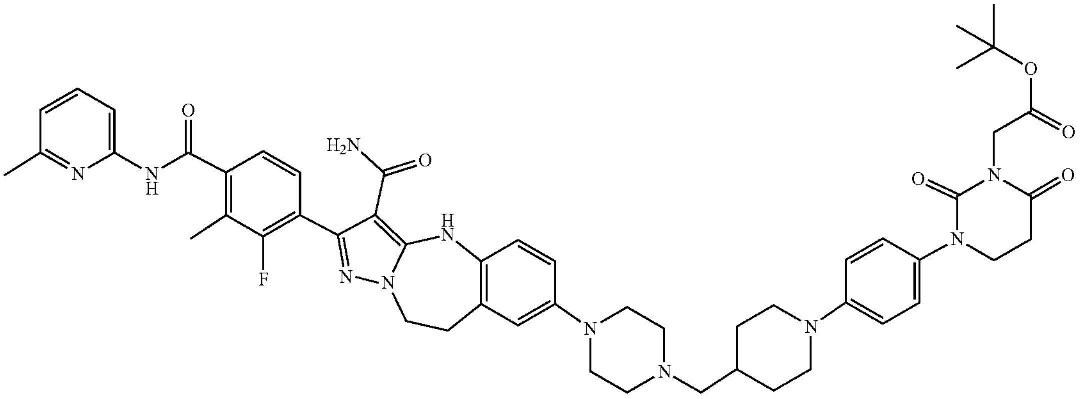

Example B77

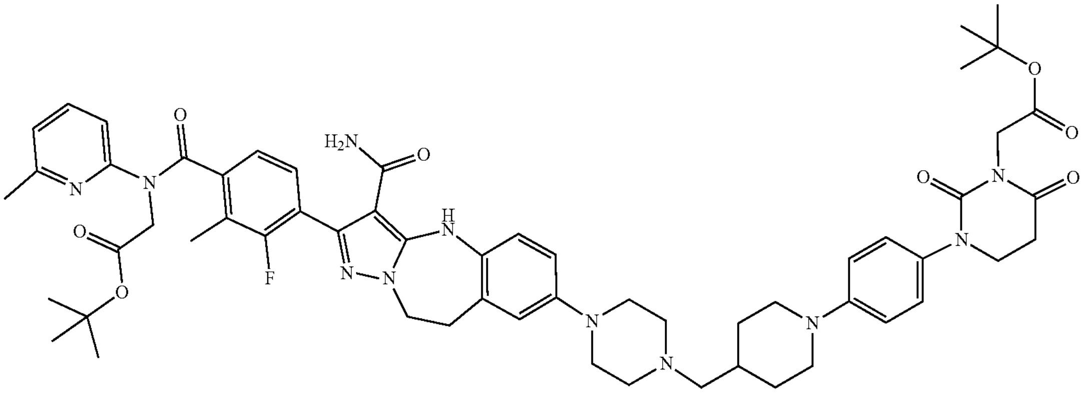

Example B78 and example B79: (3-(4-(4-((4-(3-carbamoyl-2-(2-fluoro-3-methyl-4-((6-methylpyridin-2-yl)carbamoyl)phenyl)-9,10-dihydro-4H-benzo[d]pyrazolo[1,5-a][1,3]diazepin-7-yl)piperazin-1-yl)methyl)piperidin-1-yl)phenyl)-2,6-dioxotetrahydropyrimidin-1(2H)-yl)methyl pivalate and (3-(4-(4-((4-(3-carbamoyl-2-(2-fluoro-3-methyl-4-((6-methylpyridin-2-yl)((pivaloyloxy)methyl)carbamoyl)phenyl)-9,10-dihydro-4H-benzo[d]pyrazolo[1,5-a][1,3]diazepin-7-yl)piperazin-1-yl)methyl)piperidin-1-yl)phenyl)-2,6-dioxotetrahydropyrimidin-1(2H)-yl)methyl pivalate Step 1: (3-(4-(4-((4-(3-carbamoyl-2-(2-fluoro-3-methyl-4-((6-methylpyridin-2-yl)carbamoyl)phenyl)-9,10-dihydro-4H-benzo[d]pyrazolo[1,5-a][1,3]diazepin-7-yl)piperazin-1-yl)methyl)piperidin-1-yl)phenyl)-2,6-dioxotetrahydropyrimidin-1(2H)-yl)methyl pivalate and (3-(4-(4-((4-(3-carbamoyl-2-(2-fluoro-3-methyl-4-((6-methylpyridin-2-yl)((pivaloyloxy)methyl)carbamoyl)phenyl)-9,10-dihydro-4H-benzo[d]pyrazolo[1,5-a][1,3]diazepin-7-yl)piperazin-1-yl)methyl)piperidin-1-yl)phenyl)-2,6-dioxotetrahydropyrimidin-1(2H)-yl)methyl pivalate A mixture of 7-(4-((1-(4-(2,4-dioxotetrahydropyrimidin-1(2H)-yl)phenyl)piperidin-4-yl)methyl)piperazin-1-yl)-2-(2-fluoro-3-methyl-4-((6-methylpyridin-2-yl)carbamoyl)phenyl)-9,10-dihydro-4H-benzo[d]pyrazolo[1,5-a][1,3]diazepine-3-carboxamide (170 mg, 0.203 mmol), chloromethyl pivalate (304 mg, 2.03 mmol), tetrabutylammonium iodide (37.4 mg, 0.106 mmol) and $Cs_2CO_3$ (331 mg, 1.015 mmol) in DMF (20 mL) was stirred at room temperature for 16 h under $N_2$ atmosphere. To the mixture was added water (50 mL) and filtered. The solid was purified by prep-HPLC to afford example B78 (19 mg, 10%) and example B79 (4 mg, 2%). Example B78: $^1$H NMR (500 MHz, DMSO) δ 10.83 (s, 1H), 9.78 (s, 1H), 8.02 (d, J=8.1 Hz, 1H), 7.75 (t, J=7.9 Hz, 1H), 7.41-7.32 (m, 2H), 7.20 (d, J=8.7 Hz, 2H), 7.05 (d, J=7.5 Hz, 1H), 7.02 (d, J=8.6 Hz, 2H), 6.94 (q, J=8.7 Hz, 3H), 5.66 (s, 2H), 4.43-4.35 (m, 2H), 3.76-3.72 (m, 6H), 3.65-3.62 (m, 2H), 3.23-3.11 (m, 6H), 3.07-3.02 (m, 2H), 2.92 (t, J=6.6 Hz, 2H), 2.78 (t, J=11.8 Hz, 2H), 2.43 (s, 3H), 2.31 (d, J=1.6 Hz, 3H), 2.09-2.03 (m, 1H), 1.86 (d, J=11.8 Hz, 2H), 1.39-1.32 (m, 2H), 1.12 (s, 9H); $[M+H]^+$=954.8. Example B79: $^1$H NMR (500 MHz, DMSO) δ 9.71 (s, 1H), 7.65 (t, J=7.7 Hz, 1H), 7.19 (d, J=8.7 Hz, 3H), 7.08 (dd, J=18.1, 7.7 Hz, 3H), 7.00 (d, J=8.6 Hz, 2H), 6.93 (q, J=8.7 Hz, 3H), 5.87 (s, 2H), 5.66 (s, 2H), 4.37-3.32 (m, 2H), 3.76-3.71 (m, 6H), 3.64-3.59 (m, 2H), 3.20-3.10 (m, 6H), 3.06-3.01 (m, 2H), 2.92 (t, J=6.6 Hz, 2H), 2.75 (t, J=11.7 Hz, 2H), 2.32 (s, 3H), 2.25 (s, 3H), 2.07-2.01 (m, 1H), 1.85 (d, J=11.6 Hz, 2H), 1.38-1.31 (m, 2H), 1.13-1.09 (m, 18H); $[M+H]^+$=1068.9.

Example B78

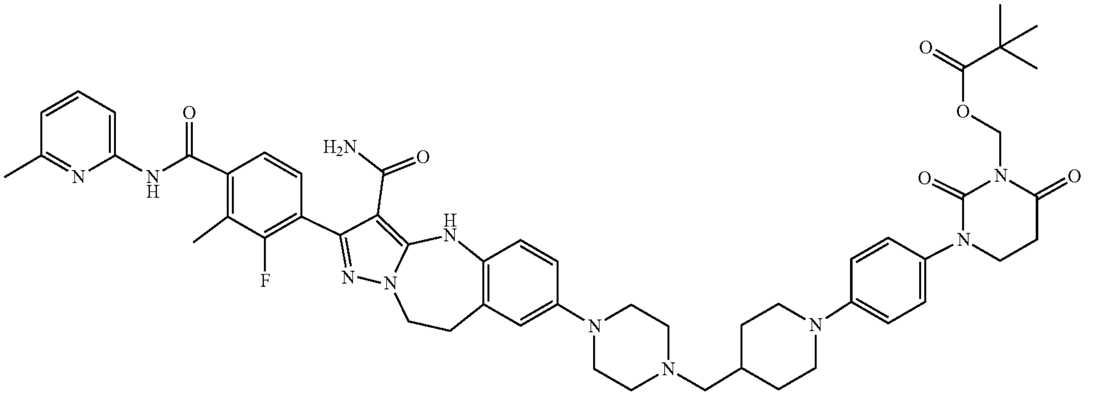

Example B79

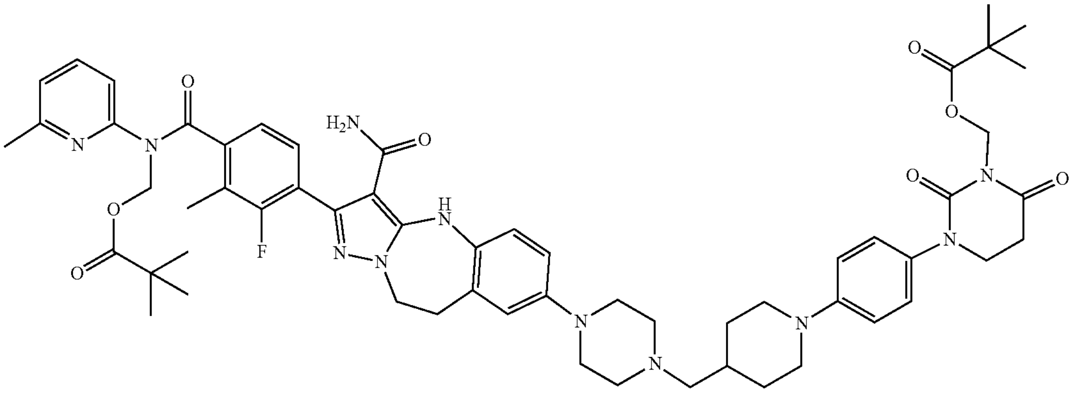

Example B80 and example B81: benzyl 2-(3-(4-(4-((4-(3-carbamoyl-2-(2-fluoro-3-methyl-4-((6-methylpyridin-2-yl)carbamoyl)phenyl)-9,10-dihydro-4H-benzo[d]pyrazolo[1,5-a][1,3]diazepin-7-yl)piperazin-1-yl)methyl)piperidin-1-yl)phenyl)-2,6-dioxotetrahydropyrimidin-1(2H)-yl)acetate and benzyl 2-(3-(4-(4-((4-(2-(4-((2-(benzyloxy)-2-oxoethyl)(6-methylpyridin-2-yl)carbamoyl)-2-fluoro-3-methylphenyl)-3-carbamoyl-9,10-dihydro-4H-benzo[d]pyrazolo[1,5-a][1,3]diazepin-7-yl)piperazin-1-yl)methyl)piperidin-1-yl)phenyl)-2,6-dioxotetrahydropyrimidin-1(2H)-yl)acetate

-

Example B80

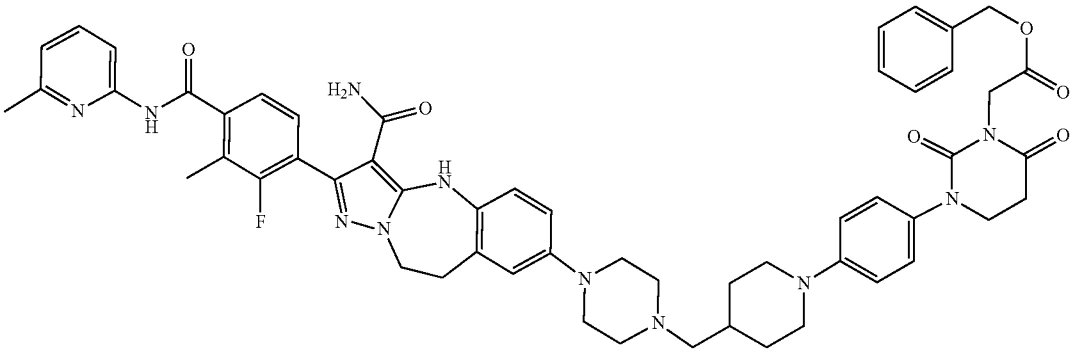

Example B81

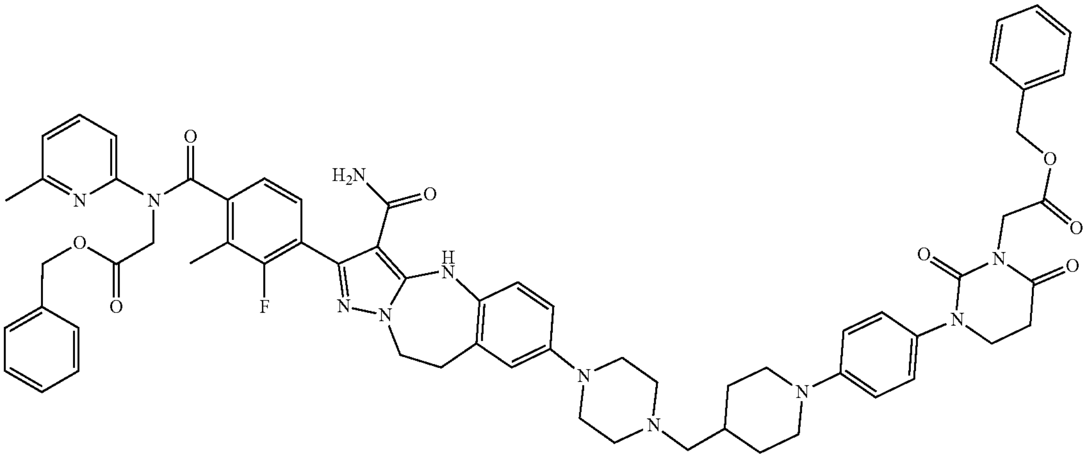

The titled compounds was synthesized in the procedures similar to Example B78 and Example B79. Example B80: $^{1}H$ NMR (500 MHz, DMSO) δ 10.82 (s, 1H), 9.72 (s, 1H), 8.02 (d, J=7.9 Hz, 1H), 7.74 (t, J=7.9 Hz, 1H), 7.42-7.32 (m, 7H), 7.13 (d, J=8.8 Hz, 2H), 7.05 (d, J=7.5 Hz, 1H), 6.94 (d, J=9.0 Hz, 2H), 6.88 (d, J=8.8 Hz, 2H), 6.84 (d, J=8.4 Hz, 1H), 5.16 (s, 2H), 4.47 (s, 2H), 4.39-4.33 (m, 2H), 3.74-3.68 (m, 4H), 3.19-3.14 (m, 2H), 3.13-3.06 (m, 4H), 2.88 (t, J=6.6 Hz, 2H), 2.72-2.63 (m, 2H), 2.57-2.52 (m, 4H), 2.42 (s, 3H), 2.30 (s, 3H), 2.25-2.20 (m, 2H), 1.85-1.78 (m, 2H), 1.76-1.69 (m, 1H), 1.27-1.19 (m, 2H); $[M+H]^+$=988.3. Example B81: $^{1}H$ NMR (500 MHz, DMSO) δ 9.64 (s, 1H), 7.53 (s, 1H), 7.42-7.32 (m, 11H), 7.20-7.09 (m, 3H), 7.01 (d, J=7.5 Hz, 1H), 6.94 (d, J=9.0 Hz, 3H), 6.84 (q, J=8.7 Hz, 3H), 5.21 (s, 2H), 5.16 (s, 2H), 4.78 (s, 2H), 4.47 (s, 2H), 4.36-4.30 (m, 2H), 3.74-3.66 (m, 4H), 3.15-3.12 (m, 2H), 3.11-3.02 (m, 4H), 2.88 (t, J=6.6 Hz, 2H), 2.70-2.63 (m, 2H), 2.56-2.52 (m, 4H), 2.31 (s, 3H), 2.25-2.15 (m, 5H), 1.85-1.77 (m, 2H), 1.75-1.68 (m, 1H), 1.27-1.16 (m, 2H); $[M+H]^+$=1136.3.

Example B82: 7-(4-((1-(4-(2,4-dioxotetrahydropyrimidin-1(2H)-yl)phenyl)piperidin-4-yl)methyl)piperazin-1-yl)-2-(2-fluoro-3-methyl-4-((1-methyl-1H-pyrazol-3-yl)carbamoyl)phenyl)-9,10-dihydro-4H-benzo[d]pyrazolo[1,5-a][1,3]diazepine-3-carboxamide

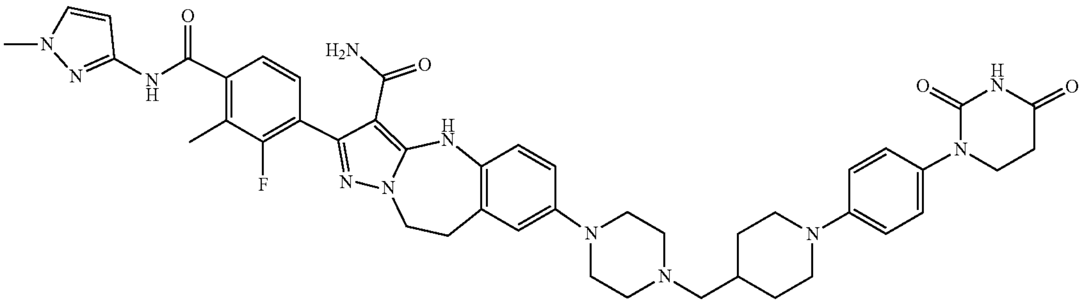 [SMILES: Cc1c(C(=O)Nc2ccn(C)n2)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B66. $^{1}$H NMR (500 MHz, DMSO) δ 10.79 (s, 1H), 10.22 (s, 1H), 9.68 (s, 1H), 7.55 (d, J=2.0 Hz, 1H), 7.31-7.26 (m, 2H), 7.12 (d, J=8.8 Hz, 2H), 6.96 (d, J=8.7 Hz, 2H), 6.90-6.84 (m, 3H), 6.52 (d, J=2.2 Hz, 1H), 4.33-4.27 (m, 3H), 3.70 (s, 3H), 3.69-3.61 (m, 6H), 3.60-3.53 (m, 2H), 3.17-3.05 (m, 6H), 3.03-2.93 (m, 2H), 2.78-2.69 (m, 2H), 2.66-2.59 (m, 2H), 2.23 (d, J=2.0 Hz, 3H), 2.05-1.96 (m, 1H), 1.84-1.76 (m, 2H), 1.37-1.26 (m, 2H); $[M+H]^{+}$=829.6.

Example B83:7-(4-((1-(4-(2,4-dioxotetrahydropyrimidin-1(2H)-yl)phenyl)piperidin-4-yl)methyl)piperazin-1-yl)-2-(2-fluoro-3-methyl-4-(thiazol-2-ylcarbamoyl)phenyl)-9,10-dihydro-4H-benzo[d]pyrazolo[1,5-a][1,3]diazepine-3-carboxamide

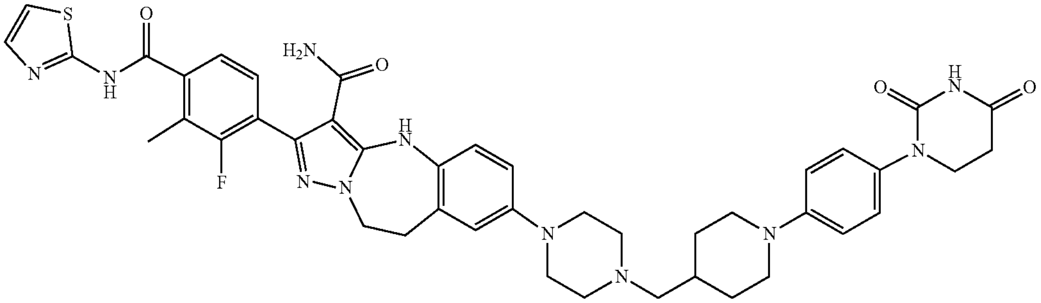 [SMILES: Cc1c(C(=O)Nc2nccs2)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B66. $^{1}$H NMR (500 MHz, DMSO) δ 12.68 (s, 1H), 10.27 (s, 1H), 9.73 (s, 1H), 7.56 (d, J=3.6 Hz, 1H), 7.49 (d, J=7.9 Hz, 1H), 7.40 (t, J=7.3 Hz, 1H), 7.33 (d, J=3.5 Hz, 1H), 7.17 (d, J=8.8 Hz, 2H), 7.02-6.90 (m, 5H), 4.42-4.36 (m, 2H), 3.78-3.67 (m, 6H), 3.66-3.60 (m, 2H), 3.22-3.11 (m, 6H), 3.04 (t, J=11.7 Hz, 2H), 2.75 (t, J=11.5 Hz, 2H), 2.69 (t, J=6.7 Hz, 2H), 2.33 (d, J=1.8 Hz, 3H), 2.10-1.99 (m, 1H), 1.88-1.82 (m, 2H), 1.40-1.31 (m, 2H); $[M+H]^{+}$=832.5.

Example B84: 7-(4-((1-(4-(2,4-dioxotetrahydropyrimidin-1(2H)-yl)phenyl)piperidin-4-yl)methyl)piperazin-1-yl)-2-(2-fluoro-3-methyl-4-((1-methyl-1H-1,2,4-triazol-3-yl)carbamoyl)phenyl)-9,10-dihydro-4H-benzo[d]pyrazolo[1,5-a][1,3]diazepine-3-carboxamide

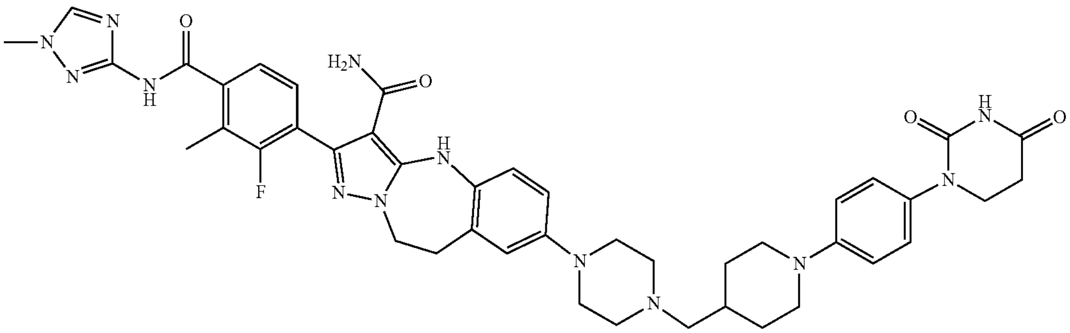 [SMILES: Cc1c(C(=O)Nc2ncn(C)n2)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B66. $^1$H NMR (500 MHz, DMSO) δ 10.79 (s, 1H), 10.25 (s, 1H), 9.68 (s, 1H), 8.35 (s, 1H), 7.35 (s, 2H), 7.13 (d, J=8.8 Hz, 2H), 6.94-6.80 (m, 5H), 4.38-4.34 (m, 2H), 3.83 (s, 3H), 3.72-3.65 (m, 4H), 3.19-3.14 (m, 2H), 3.12-3.05 (m, 4H), 2.71-2.62 (m, 4H), 2.58-2.53 (m, 4H), 2.30 (s, 3H), 2.25-2.20 (m, 2H), 1.85-1.78 (m, 2H), 1.75-1.66 (m, 1H), 1.29-1.26 (m, 2H); $[M+H]^+$=830.5.

Example B85:7-(4-((1-(4-(2,4-dioxotetrahydropyrimidin-1(2H)-yl)phenyl)piperidin-4-yl)methyl)piperazin-1-yl)-2-(2-fluoro-3-methyl-4-((3-(trifluoromethyl)-1H-1,2,4-triazol-5-yl)carbamoyl)phenyl)-9,10-dihydro-4H-benzo[d]pyrazolo[1,5-a][1,3]diazepine-3-carboxamide

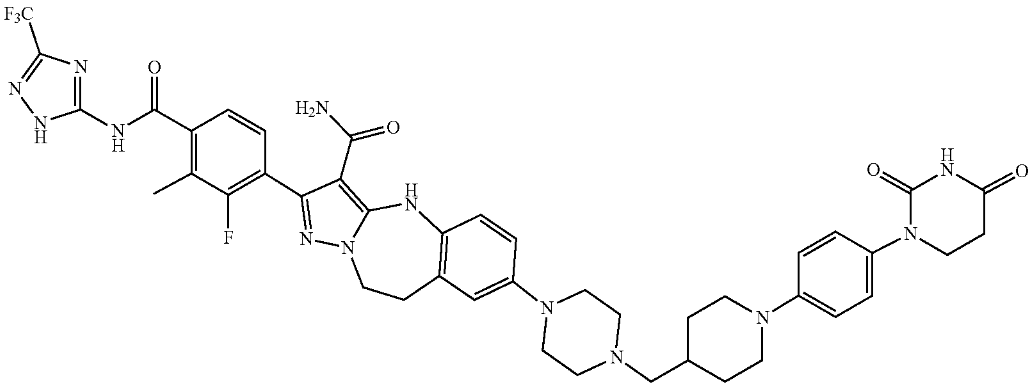 [SMILES: Cc1c(C(=O)Nc2nc(C(F)(F)F)n[nH]2)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B66. $^1$H NMR (500 MHz, DMSO) δ 12.42 (s, 1H), 10.25 (s, 1H), 9.66 (s, 1H), 7.52 (d, J=7.9 Hz, 1H), 7.43 (t, J=7.3 Hz, 1H), 7.14 (d, J=8.9 Hz, 2H), 6.93 (d, J=8.9 Hz, 2H), 6.90 (d, J=8.9 Hz, 2H), 6.88-6.85 (m, 2H), 4.36 (d, J=4.9 Hz, 2H), 3.76-3.63 (m, 4H), 3.20-3.14 (m, 2H), 3.14-3.02 (m, 4H), 2.72-2.62 (m, 5H), 2.58-2.51 (m, 4H), 2.36 (d, J=1.8 Hz, 3H), 2.32-2.13 (m, 2H), 1.85-1.78 (m, 2H), 1.78-1.66 (m, 1H), 1.30-1.17 (m, 2H); $[M+H]^+$=884.5.

Example B86: 2-(4-((1,5-dimethyl-1H-pyrazol-3-yl)carbamoyl)-2-fluoro-3-methylphenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

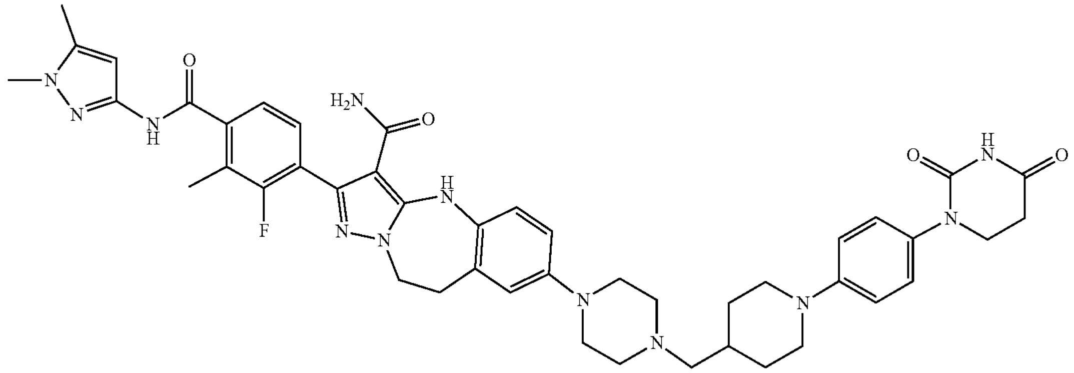 [SMILES: Cc1c(C(=O)Nc2cc(C)n(C)n2)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B66. $^1$H NMR (500 MHz, DMSO) δ 10.72 (s, 1H), 10.25 (s, 1H), 9.69 (s, 1H), 7.34 (q, J=7.8 Hz, 2H), 7.13 (d, J=8.9 Hz, 2H), 6.93 (d, J=9.0 Hz, 2H), 6.88 (d, J=8.7 Hz, 2H), 6.83 (d, J=8.7 Hz, 1H), 6.43 (s, 1H), 4.40-4.31 (m, 2H), 3.72-3.66 (m, 4H), 3.64 (s, 3H), 3.19-3.13 (m, 2H), 3.12-3.06 (m, 4H), 2.71-2.63 (m, 4H), 2.55-2.50 (m, 4H), 2.28 (d, J=1.9 Hz, 3H), 2.25 (s, 3H), 2.30-2.19 (m, 2H), 1.84-1.78 (m, 2H), 1.75-1.67 (m, 1H), 1.26-1.18 (m, 2H); $[M+H]^+$=843.7.

Example B87: 7-(4-((1-(4-(2,4-dioxotetrahydropyrimidin-1(2H)-yl)phenyl)piperidin-4-yl)methyl)piperazin-1-yl)-2-(2-fluoro-3-methyl-4-((1-methyl-1H-imidazol-4-yl)carbamoyl)phenyl)-9,10-dihydro-4H-benzo[d]pyrazolo[1,5-a][1,3]diazepine-3-carboxamide Step 1: benzyl 4-(3-cyano-2-(2-fluoro-4-(methoxycarbonyl)-3-methylphenyl)-9,10-dihydro-4H-benzo [d]pyrazolo 1,5-al 1,3 diazepin-7-yl)piperazine-1-carboxylate

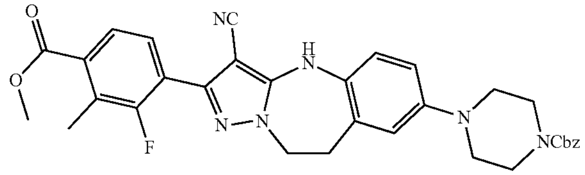 [SMILES: COC(=O)c1ccc(-c2nn3c(c2C#N)Nc2ccc(N4CCN(C(=O)OCc5ccccc5)CC4)cc2CC3)c(F)c1C]

A mixture of benzyl 4-(2-bromo-3-cyano-9,10-dihydro-4H-benzo[d]pyrazolo[1,5-a][1,3]diazepin-7-yl)piperazine-1-carboxylate (0.84 g, 1.66 mmol), methyl 3-fluoro-2-methyl-4-(4,4,5,5-tetramethyl-1,3,2-dioxaborolan-2-yl) benzoate (0.636 g, 2.16 mmol), $Pd(dppf)Cl_2$ (0.124 g, 0.17 mmol) and $Na_2CO_3$ (0.352 g, 3.32 mmol) in dioxane (25 mL) and $H_2O$ (3 mL) was stirred at 95° C. for 16 hours under $N_2$. Then the mixture was washed by water and extracted with dichloromethane (3×60 mL). The organic phase was dried over anhydrous sodium sulfate, filtered, and concentrated under reduced pressure to afford the crude product, which was purified with silica gel column chromatography (PE:EA=80:20~50:50 gradient elution) to give the product (345 mg, 35%). $[M+H]^+$=595.3.

Step 2: benzyl 4-(3-cyano-2-(2-fluoro-3-methyl-4-((1-methyl-1H-imidazol-4-yl)carbamoyl)phenyl)-9,10-dihydro-4H-benzo[d]pyrazolo[1,5-a][1,3]diazepin-7-yl)piperazine-1-carboxylate

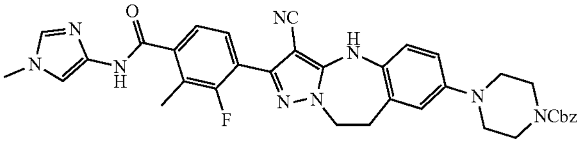 [SMILES: Cc1c(C(=O)Nc2cn(C)cn2)ccc(-c2nn3c(c2C#N)Nc2ccc(N4CCN(C(=O)OCc5ccccc5)CC4)cc2CC3)c1F]

To a mixture of benzyl 4-(3-cyano-2-(2-fluoro-4-(methoxycarbonyl)-3-methylphenyl)-9,10-dihydro-4H-benzo[d]pyrazolo[1,5-a][1,3]diazepin-7-yl)piperazine-1-carboxylate (0.345 g, 0.581 mmol) and 1-methyl-1H-imidazol-4-amine hydrochloride (0.077 g, 0.581 mmol) in THE (8.0 mL) was added LiHMDS (1.74 mL, 1 M) dropwise. The reaction was stirred at 60° C. for 2 hours and then cooled. The mixture was washed with water and extracted with dichloromethane (3×30 mL). The organic phase was dried over anhydrous sodium sulfate, filtered, and concentrated under reduced pressure to afford the product (365 mg, 95%). $[M+H]^+$=660.2.

Step 3: 2-(2-fluoro-3-methyl-4-((1-methyl-1H-imidazol-4-yl)carbamoyl)phenyl)-7-(piperazin-1-yl)-9,10-dihydro-4H-benzo[d]pyrazolo[1,5-a][1,3]diazepine-3-carboxamide

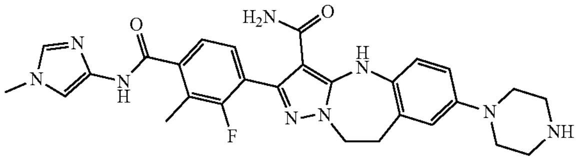 [SMILES: Cc1c(C(=O)Nc2cn(C)cn2)ccc(-c2nn3c(c2C(N)=O)Nc2ccc(N4CCNCC4)cc2CC3)c1F]

A mixture of benzyl 4-(3-cyano-2-(2-fluoro-3-methyl-4-((1-methyl-1H-imidazol-4-yl)carbamoyl)phenyl)-9,10-dihydro-4H-benzo[d]pyrazolo[1,5-a][1,3]diazepin-7-yl)piperazine-1-carboxylate (0.36 g, 0.55 mmol) in methanesulfonic acid (10.0 mL) was stirred at 100° C. for 1 hour. The mixture was then cooled, acidified with aqueous sodium hydroxide solution to pH 12 and extracted with dichloromethane (3×30 mL) and water (3×30 mL). The organic phase was dried over anhydrous sodium sulfate, filtered, and concentrated under reduced pressure to afford the product (290 mg, 97%). $[M+H]^+$=544.1.

Step 4: 7-(4-((1-(4-(2,4-dioxotetrahydropyrimidin-1(2H)-yl)phenyl)piperidin-4-yl)methyl)piperazin-1-yl)-2-(2-fluoro-3-methyl-4-((1-methyl-1H-imidazol-4-yl)carbamoyl)phenyl)-9,10-dihydro-4H-benzo[d]pyrazolo[1,5-a][1,3]diazepine-3-carboxamide

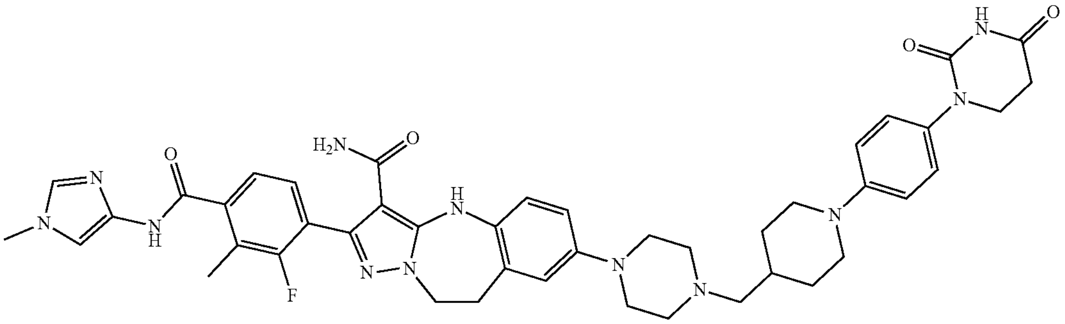 [SMILES: Cc1c(C(=O)Nc2cn(C)cn2)ccc(-c2nn3c(c2C(N)=O)Nc2ccc(N4CCN(CC5CCN(c6ccc(N7CCC(=O)NC7=O)cc6)CC5)CC4)cc2CC3)c1F]

A mixture of 2-(2-fluoro-3-methyl-4-((1-methyl-1H-imidazol-4-yl)carbamoyl)phenyl)-7-(piperazin-1-yl)-9,10-dihydro-4H-benzo[d]pyrazolo[1,5-a][1,3]diazepine-3-carboxamide (140 mg, 0.26 mmol) and 1-(4-(2,4-dioxotetrahydropyrimidin-1(2H)-yl)phenyl)piperidine-4-carbaldehyde (78 mg, 0.26 mmol) in MeOH (2.0 mL), DCM (6.0 mL) and acetic acid (0.1 mL) was stirred at room temperature for 16 hours, and then $NaBH(OAc)_3$ (220 mg, 1.04 mmol) was added and stirred at room temperature for 1 hour. The mixture was treated with water (30 mL), extracted with dichloromethane (3×30 mL), and washed with brine (30 mL). The organic phase was dried over anhydrous sodium sulfate, filtered, and concentrated under reduced pressure to afford the crude product, which was purified with silica gel column chromatography (DCM: MeOH=100:0~85:15 gradient elution) to give the product (120 mg, 56%). $^1H$ NMR (500 MHz, DMSO) δ 10.76 (s, 1H), 10.25 (s, 1H), 9.69 (s, 1H), 7.43 (s, 1H), 7.38 (s, 1H), 7.33 (s, 2H), 7.13 (d, J=8.8 Hz, 2H), 6.93 (d, J=8.9 Hz, 2H), 6.88 (d, J=8.5 Hz, 2H), 6.83 (d, J=8.4 Hz, 1H), 4.39-4.33 (m, 2H), 3.75-3.61 (m, 8H), 3.33 (d, J=1.5 Hz, 3H), 3.19-3.14 (m, 2H), 3.11-3.03 (m, 4H), 2.69-2.62 (m, 5H), 2.28 (d, J=1.6 Hz, 3H), 2.25-2.19 (m, 2H), 1.84-1.78 (m, 2H), 1.76-1.66 (m, 1H), 1.30-1.16 (m, 3H); $[M+H]^+$=829.6.

Example B88:7-(4-(4-(2,6-dioxopiperidin-3-yl)-3,5-difluorophenethyl)piperazin-1-yl)-2-(2-fluoro-3-methyl-4-((1-methyl-1H-imidazol-4-yl)carbamoyl)phenyl)-9,10-dihydro-4H-benzo[d]pyrazolo[1,5-a][1,3]diazepine-3-carboxamide

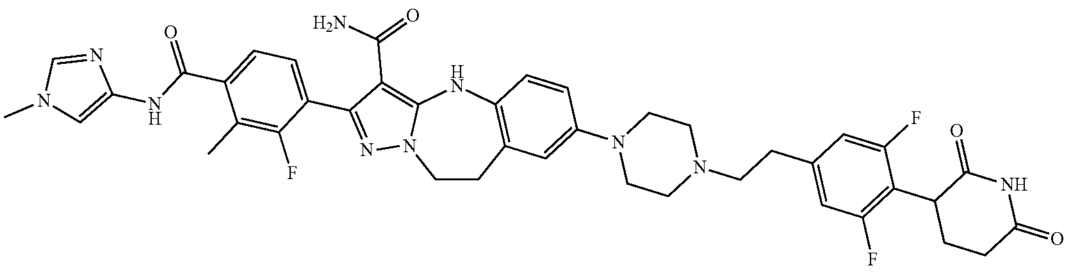 [SMILES: Cc1c(C(=O)Nc2cn(C)cn2)ccc(-c2nn3c(c2C(N)=O)Nc2ccc(N4CCN(CCc5cc(F)c(C6CCC(=O)NC6=O)c(F)c5)CC4)cc2CC3)c1F]

The titled compound was synthesized in the procedures similar to Example B87. $^1$H NMR (500 MHz, DMSO) δ 10.94 (s, 1H), 10.75 (s, 1H), 9.69 (s, 1H), 7.43 (s, 1H), 7.38 (d, J=1.4 Hz, 1H), 7.33 (d, J=4.1 Hz, 2H), 7.06 (d, J=10.0 Hz, 2H), 6.86-6.82 (m, 3H), 4.38-4.31 (m, 2H), 4.23-4.17 (m, 1H), 3.66 (s, 3H), 3.29 (s, 3H), 3.19-3.14 (m, 2H), 3.12-3.06 (m, 4H), 2.85-2.75 (m, 3H), 2.65-2.53 (m, 7H), 2.38-2.35 (m, 1H), 2.28 (d, J=2.1 Hz, 3H), 2.17-2.08 (m, 1H), 2.03-1.96 (m, 1H), 1.28-1.20 (m, 1H); $[M+H]^+$=795.5.

Example B89: (R)-7-(4-(4-(2,6-dioxopiperidin-3-yl)-3,5-difluorophenethyl)piperazin-1-yl)-2-(2-fluoro-3-methyl-4-((1-methyl-1H-imidazol-4-yl)carbamoyl)phenyl)-9,10-dihydro-4H-benzo[d]pyrazolo[1,5-a][1,3]diazepine-3-carboxamide

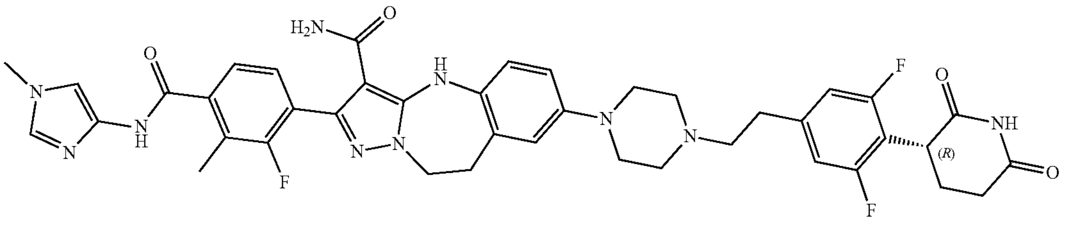

The titled compound was synthesized in the procedures similar to Example B87. $^1$H NMR (500 MHz, DMSO) δ 10.95 (s, 1H), 10.75 (s, 1H), 9.69 (s, 1H), 7.43 (s, 1H), 7.38 (d, J=1.1 Hz, 1H), 7.35-7.31 (m, 2H), 7.06 (d, J=10.0 Hz, 2H), 6.88 (d, J=8.4 Hz, 2H), 6.86-6.82 (m, 1H), 4.40-4.32 (m, 2H), 4.20 (dd, J=12.5, 4.9 Hz, 1H), 3.66 (s, 3H), 3.19-3.14 (m, 2H), 3.12-3.06 (m, 4H), 2.85-2.77 (m, 3H), 2.65-2.53 (m, 7H), 2.28 (d, J=2.0 Hz, 3H), 2.18-2.08 (m, 1H), 2.04-1.97 (m, 1H); $[M+H]^+$=795.5.

Example B90:7-(4-(2-(3-(2,6-dioxopiperidin-3-yl)-2-oxo-2,3-dihydrobenzo[d]oxazol-7-yl)ethyl)piperazin-1-yl)-2-(2-fluoro-3-methyl-4-((1-methyl-1H-imidazol-4-yl)carbamoyl)phenyl)-9,10-dihydro-4H-benzo[d]pyrazolo[1,5-a][1,3]diazepine-3-carboxamide

-

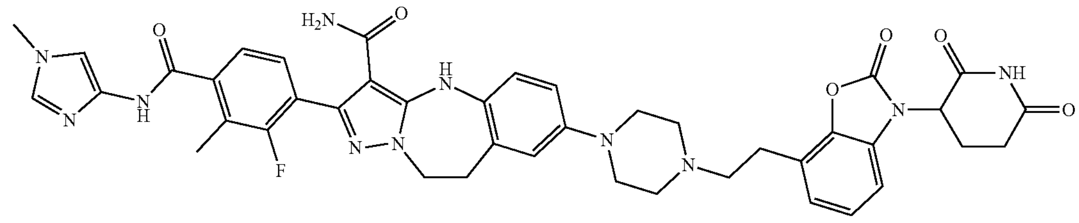 [SMILES: Cc1c(C(=O)Nc2cn(C)cn2)ccc(-c2nn3c(c2C(N)=O)Nc2ccc(N4CCN(CCc5cccc6c5oc(=O)n6C5CCC(=O)NC5=O)CC4)cc2CC3)c1F]

The titled compound was synthesized in the procedures similar to Example 7. H NMR (500 MHz, DMSO) δ 11.21 (s, 1H), 10.76 (s, 1H), 9.69 (s, 1H), 7.43 (s, 1H), 7.38 (s, 1H), 7.35-7.31 (m, 2H), 7.13 (dt, J=14.5, 7.7 Hz, 3H), 6.88 (d, J=8.2 Hz, 2H), 6.84 (d, J=8.8 Hz, 1H), 5.36 (dd, J=12.9, 5.3 Hz, 1H), 4.40-4.32 (m, 2H), 3.66 (s, 3H), 3.19-3.14 (m, 2H), 3.13-3.07 (m, 4H), 2.95-2.83 (m, 3H), 2.75-2.56 (m, 8H), 2.28 (d, J=1.8 Hz, 3H), 2.20-2.12 (m, 1H); $[M+H]^+$=816.5.

Example B91:7-(4-(1-(4-(2,4-dioxotetrahydropyrimidin-1(2H)-yl)phenyl)piperidine-4-carbonyl)piperazin-1-yl)-2-(2-fluoro-3-methyl-4-((1-methyl-1H-imidazol-4-yl)carbamoyl)phenyl)-9,10-dihydro-4H-benzo[d]pyrazolo[1,5-a][1,3]diazepine-3-arboxamide

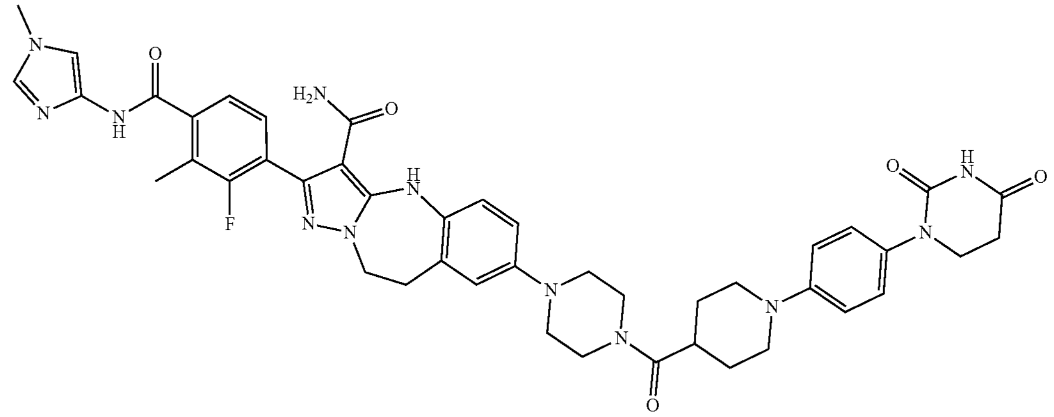 [SMILES: Cc1c(C(=O)Nc2cn(C)cn2)ccc(-c2nn3c(c2C(N)=O)Nc2ccc(N4CCN(C(=O)C5CCN(c6ccc(N7CCC(=O)NC7=O)cc6)CC5)CC4)cc2CC3)c1F]

The titled compound was synthesized in the procedures similar to Example B87. $^1$H NMR (500 MHz, DMSO) δ 11.24 (s, 1H), 10.31 (s, 1H), 9.71 (s, 1H), 8.35 (s, 1H), 7.56 (s, 1H), 7.46-7.38 (m, 2H), 7.24 (d, J=8.2 Hz, 2H), 7.11 (s, 2H), 6.91 (dd, J=13.4, 8.3 Hz, 3H), 4.39-4.36 (m, 2H), 3.79 (s, 3H), 3.75-3.67 (m, 6H), 3.66-3.58 (m, 2H), 3.22-3.04 (m, 6H), 3.02-2.90 (m, 3H), 2.69 (t, J=6.7 Hz, 2H), 2.33 (d, J=1.5 Hz, 3H), 1.84-1.72 (m, 4H); $[M+H]^+$=843.0.

-

Example B92: (R)-7-(4-((1-(4-(2,4-dioxotetrahydropyrimidin-1(2H)-yl)phenyl)pyrrolidin-3-yl)methyl)piperazin-1-yl)-2-(2-fluoro-3-methyl-4-((1-methyl-1H-imidazol-4-yl)carbamoyl)phenyl)-9,10-dihydro-4H-benzo[d]pyrazolo[1,5-a][1,3]diazepine-3-carboxamide

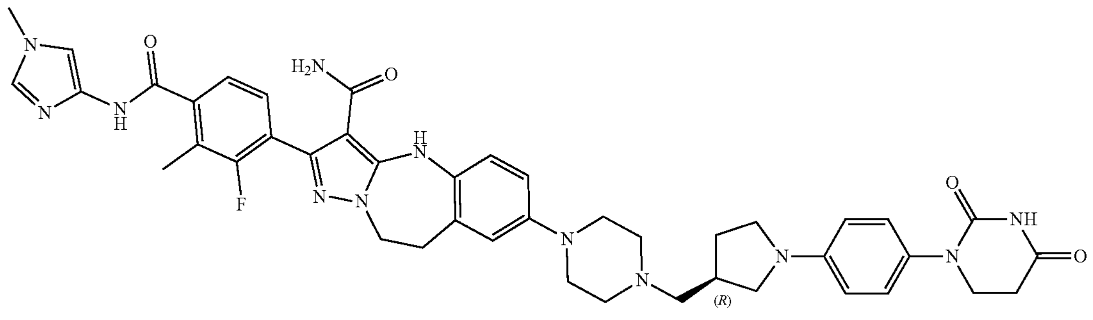

The titled compound was synthesized in the procedures similar to Example B87. $^{1}$H NMR (500 MHz, DMSO) δ 11.02 (d, J=31.5 Hz, 1H), 10.22 (s, 1H), 9.74 (s, 1H), 7.95 (s, 1H), 7.48 (d, J=9.5 Hz, 1H), 7.38 (d, J=3.6 Hz, 2H), 7.13 (d, J=8.8 Hz, 2H), 6.95 (q, J=8.5 Hz, 3H), 6.55 (d, J=8.9 Hz, 2H), 4.47-4.33 (m, 2H), 3.83-3.76 (m, 2H), 3.75-3.71 (m, 4H), 3.70-3.64 (m, 4H), 3.29-3.14 (m, 8H), 3.08-2.98 (m, 3H), 2.87-2.77 (m, 1H), 2.69 (t, J=6.7 Hz, 2H), 2.31 (s, 3H), 2.28-2.21 (m, 1H), 1.85-1.76 (m, 1H); [M+H]$^{+}$=815.2.

Example B93:7-(4-((1-(4-(2,4-dioxotetrahydropyrimidin-1(2H)-yl)phenyl)piperidin-4-yl)methyl)piperazin-1-yl)-2-(2-fluoro-3-methyl-4-((1-methyl-1H-1,2,4-triazol-5-yl)carbamoyl)phenyl)-9,10-dihydro-4H-benzo[d]pyrazolo[1,5-a][1,3]diazepine-3-carboxamide

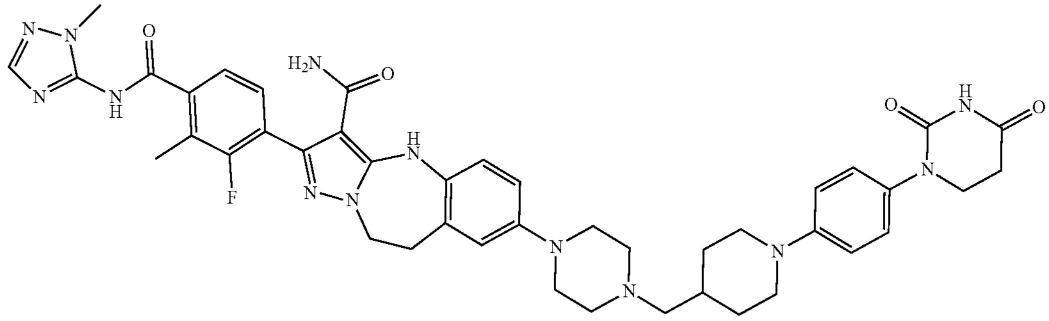 [SMILES: Cc1c(C(=O)Nc2ncnn2C)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B87. $^{1}$H NMR (500 MHz, DMSO) δ 11.13 (s, 1H), 10.25 (s, 1H), 9.65 (s, 1H), 7.90 (s, 1H), 7.54 (s, 1H), 7.43 (t, J=7.3 Hz, 1H), 7.13 (d, J=8.9 Hz, 2H), 6.93 (d, J=9.0 Hz, 2H), 6.88 (d, J=8.9 Hz, 2H), 6.83 (d, J=8.6 Hz, 1H), 4.41-4.31 (m, 2H), 3.76 (s, 3H), 3.72-3.65 (m, 5H), 3.20-3.14 (m, 2H), 3.12-3.06 (m, 4H), 2.71-2.62 (m, 5H), 2.47-2.43 (m, 1H), 2.40-2.35 (m, 4H), 2.25-2.20 (m, 2H), 1.84-1.78 (m, 2H), 1.75-1.67 (m, 1H), 1.27-1.18 (m, 2H); [M+H]$^{+}$=830.1.

Example B94: 7-(4-((1-(4-(2,4-dioxotetrahydropyrimidin-1(2H)-yl)phenyl)piperidin-4-yl)methyl)piperazin-1-yl)-2-(2-fluoro-3-methyl-4-(thiazol-4-ylcarbamoyl)phenyl)-9,10-dihydro-4H-benzo[d]pyrazolo[1,5-a][1,3]diazepine-3-carboxamide

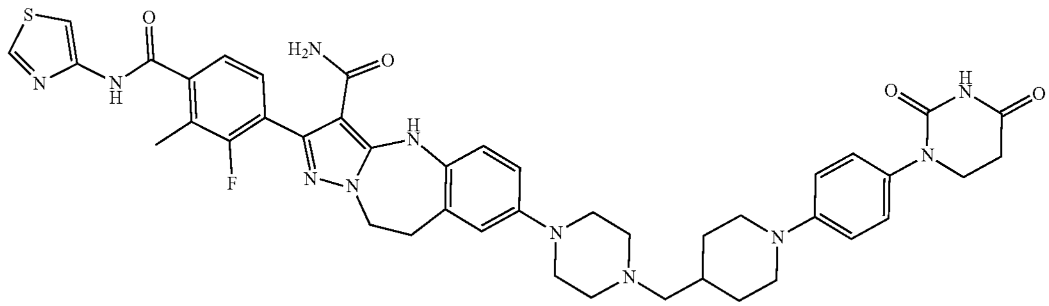 [SMILES: Cc1c(C(=O)Nc2cscn2)ccc(-c2nn3c(c2C(N)=O)Nc2ccc(N4CCN(CC5CCN(c6ccc(N7CCC(=O)NC7=O)cc6)CC5)CC4)cc2CC3)c1F]

The titled compound was synthesized in the procedures similar to Example B87. $^1$H NMR (500 MHz, DMSO) δ 11.45 (s, 1H), 10.19 (s, 1H), 9.62 (s, 1H), 8.95 (d, J=2.2 Hz, 1H), 7.77 (d, J=2.1 Hz, 1H), 7.34-7.29 (m, 2H), 7.06 (d, J=8.9 Hz, 2H), 6.85 (d, J=9.1 Hz, 2H), 6.81 (t, J=6.5 Hz, 2H), 6.76 (dd, J=8.7, 2.3 Hz, 1H), 4.30-4.28 (m, 2H), 3.63-3.59 (m, 4H), 3.10-3.08 (m, 2H), 3.55-2.97 (m, 4H), 2.62-2.57 (m, 4H), 2.48-2.45 (m, 4H), 2.25 (d, J=1.9 Hz, 3H), 2.19-2.10 (m, 2H), 1.78-1.69 (m, 2H), 1.68-1.59 (m, 1H), 1.19-1.10 (m, 2H); $[M+H]^+$=832.7.

Example B95: (R)-7-(4-(4-(2,6-dioxopiperidin-3-yl)-3,5-difluorophenethyl)piperazin-1-yl)-2-(2-fluoro-3-methyl-4-(thiazol-4-ylcarbamoyl)phenyl)-9,10-dihydro-4H-benzo[d]pyrazolo[1,5-a] [1,3] diazepine-3-carboxamide

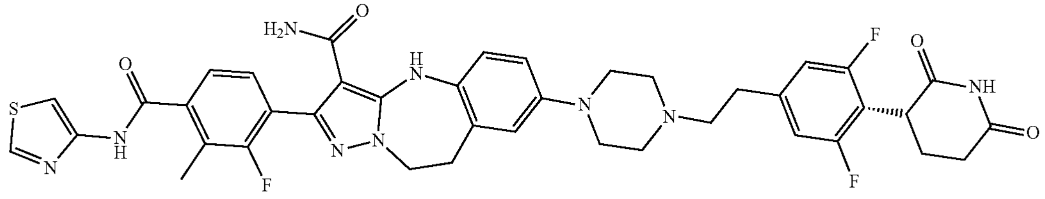

The titled compound was synthesized in the procedures similar to Example B87. $^1$H NMR (500 MHz, DMSO) δ 11.52 (s, 1H), 10.98 (s, 1H), 9.76 (s, 1H), 9.03 (d, J=2.1 Hz, 1H), 7.84 (d, J=2.1 Hz, 1H), 7.44-7.35 (m, 2H), 7.13 (d, J=9.8 Hz, 2H), 6.99-6.90 (m, 3H), 4.43-4.35 (m, 2H), 4.24 (dd, J=12.7, 5.0 Hz, 1H), 3.85-3.75 (m, 2H), 3.69-3.61 (m, 2H), 3.51-3.44 (m, 2H), 3.26-3.14 (m, 4H), 3.09-3.06 (m, 2H), 3.04-2.94 (m, 2H), 2.87-2.77 (m, 1H), 2.58-2.52 (m, 1H), 2.32 (d, J=1.7 Hz, 3H), 2.18-2.10 (m, 1H), 2.04-1.97 (m, 1H); $[M+H]^+$=797.8.

Example B96: 7-(4-(2-(3-(2,6-dioxopiperidin-3-yl)-2-oxo-2,3-dihydrobenzo[d]oxazol-7-yl)ethyl)piperazin-1-yl)-2-(2-fluoro-3-methyl-4-(thiazol-4-ylcarbamoyl)phenyl)-9,10-dihydro-4H-benzo[d]pyrazolo[1,5-a][1,3]diazepine-3-carboxamide

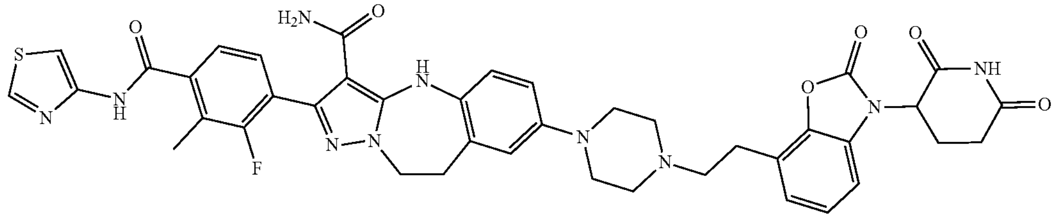 [SMILES: Cc1c(C(=O)Nc2cscn2)ccc(-c2nn3c(c2C(N)=O)Nc2ccc(N4CCN(CCc5cccc6c5oc(=O)n6C5CCC(=O)NC5=O)CC4)cc2CC3)c1F]

The titled compound was synthesized in the procedures similar to Example B87. $^{1}H$ NMR (500 MHz, DMSO) δ 11.52 (s, 1H), 11.21 (s, 1H), 9.68 (s, 1H), 9.02 (d, J=1.9 Hz, 1H), 7.84 (s, 1H), 7.39 (q, J=7.6 Hz, 2H), 7.13 (dt, J=14.5, 7.6 Hz, 3H), 6.86 (dd, J=21.6, 8.2 Hz, 3H), 5.40-5.33 (m, 1H), 4.41-4.31 (m, 2H), 3.19-3.14 (m, 2H), 3.13-3.05 (m, 4H), 2.97-2.83 (m, 3H), 2.74-2.56 (m, 8H), 2.32 (s, 3H), 2.21-2.12 (m, 1H); $[M+H]^{+}$=819.6.

Example B97: 7-(4-((1-(4-(2,4-dioxotetrahydropyrimidin-1(2H)-yl)phenyl)azetidin-3-yl)methyl)piperazin-1-yl)-2-(2-fluoro-3-methyl-4-(thiazol-4-ylcarbamoyl)phenyl)-9,10-dihydro-4H-benzo[d]pyrazolo[1,5-a][1,3]diazepine-3-carboxamide

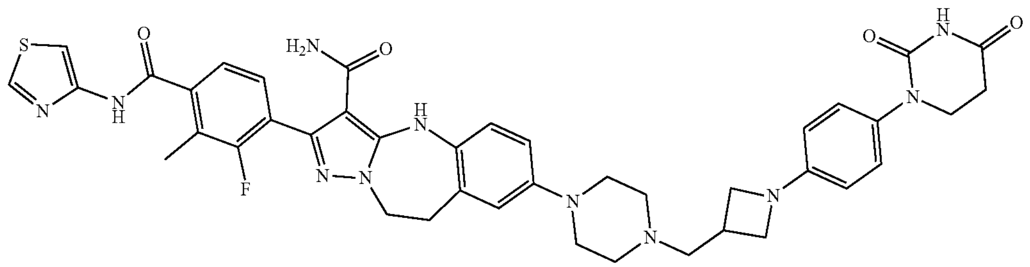 [SMILES: Cc1c(C(=O)Nc2cscn2)ccc(-c2nn3c(c2C(N)=O)Nc2ccc(N4CCN(CC5CN(c6ccc(N7CCC(=O)NC7=O)cc6)C5)CC4)cc2CC3)c1F]

The titled compound was synthesized in the procedures similar to Example B87. $^{1}H$ NMR (500 MHz, DMSO) δ 11.52 (s, 1H), 10.23 (s, 1H), 9.69 (s, 1H), 9.02 (d, J=2.1 Hz, 1H), 7.84 (d, J=2.0 Hz, 1H), 7.43-7.35 (m, 2H), 7.10 (d, J=8.7 Hz, 2H), 6.88 (d, J=8.8 Hz, 2H), 6.85-6.81 (m, 1H), 6.42 (d, J=8.7 Hz, 2H), 4.40-4.33 (m, 2H), 3.95 (t, J=7.4 Hz, 2H), 3.67 (t, J=6.7 Hz, 2H), 3.47 (t, J=6.4 Hz, 2H), 3.19-3.14 (m, 2H), 3.12-3.05 (m, 4H), 2.99-2.92 (m, 1H), 2.67 (t, J=6.7 Hz, 2H), 2.63 (d, J=7.3 Hz, 2H), 2.57-2.51 (m, 4H), 2.32 (d, J=1.6 Hz, 3H); $[M+H]^{+}$=804.4.

Example B98:7-(4-((1-(4-((2,4-dioxotetrahydropyrimidin-1(2H)-yl)methyl)phenyl)piperidin-4-yl)methyl)piperazin-1-yl)-2-(2-fluoro-3-methyl-4-(thiazol-4-ylcarbamoyl)phenyl)-9,10-dihydro-4H-benzo[d]pyrazolo[1,5-a][1,3]diazepine-3-carboxamide

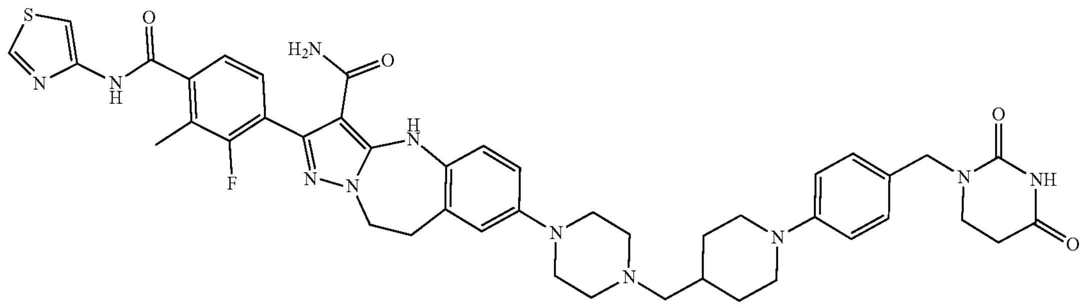 [SMILES: Cc1c(C(=O)Nc2cscn2)ccc(-c2nn3c(c2C(N)=O)Nc2ccc(N4CCN(CC5CCN(c6ccc(CN7CCC(=O)NC7=O)cc6)CC5)CC4)cc2CC3)c1F]

The titled compound was synthesized in the procedures similar to Example B87. $^{1}H$ NMR (500 MHz, DMSO) δ 11.52 (s, 1H), 10.17 (s, 1H), 9.75 (s, 1H), 9.03 (d, J=2.0 Hz, 1H), 7.84 (d, J=2.0 Hz, 1H), 7.44-7.35 (m, 2H), 7.17 (d, J=8.4 Hz, 2H), 7.03-6.90 (m, 5H), 4.41-4.37 (m, 4H), 3.80-3.68 (m, 4H), 3.66-3.62 (m, 2H), 3.22-3.11 (m, 2H), 3.17 (d, J=17.7 Hz, 6H), 3.04 (t, J=11.8 Hz, 2H), 2.77 (t, J=11.5 Hz, 2H), 2.54-2.52 (m, 2H), 2.32 (d, J=1.4 Hz, 3H), 2.09-2.03 (m, 1H), 1.90-1.82 (m, 2H), 1.43-1.31 (m, 2H); $[M+H]^{+}$=845.9.

Example B99:7-(4-((1-(3-((2,4-dioxotetrahydropyrimidin-1(2H)-yl)methyl)phenyl)piperidin-4-yl)methyl)piperazin-1-yl)-2-(2-fluoro-3-methyl-4-(thiazol-4-ylcarbamoyl)phenyl)-9,10-dihydro-4H-benzo[d]pyrazolo[1,5-a][1,3]diazepine-3-carboxamide

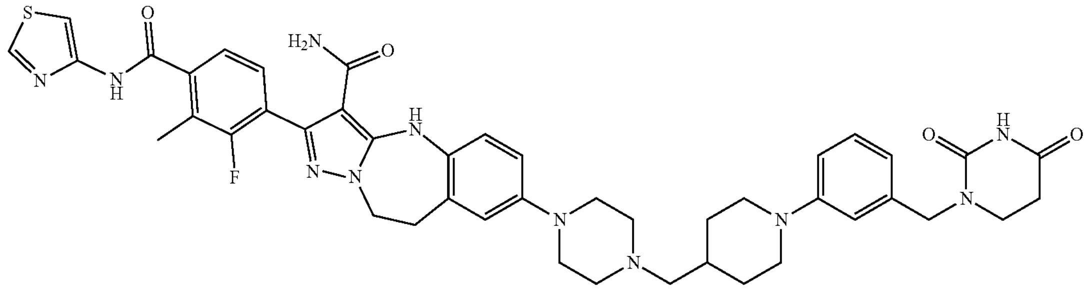 [SMILES: Cc1c(C(=O)Nc2cscn2)ccc(-c2nn3c(c2C(N)=O)Nc2ccc(N4CCN(CC5CCN(c6cccc(CN7CCC(=O)NC7=O)c6)CC5)CC4)cc2CC3)c1F]

The titled compound was synthesized in the procedures similar to Example B87. $^{1}H$ NMR (500 MHz, DMSO) δ 11.52 (s, 1H), 10.19 (s, 1H), 9.75 (s, 1H), 9.03 (d, J=2.1 Hz, 1H), 7.84 (d, J=2.1 Hz, 1H), 7.44-7.35 (m, 2H), 7.21 (t, J=7.8 Hz, 1H), 6.99-6.86 (m, 5H), 6.73 (d, J=7.4 Hz, 1H), 4.46 (s, 2H), 4.42-4.34 (m, 2H), 3.81-3.69 (m, 4H), 3.67-3.60 (m, 2H), 3.28 (t, J=6.8 Hz, 2H), 3.24-3.11 (m, 6H), 3.04 (t, J=11.8 Hz, 2H), 2.77 (t, J=11.3 Hz, 2H), 2.53 (dd, J=11.9, 5.0 Hz, 2H), 2.32 (d, J=1.6 Hz, 3H), 2.10-2.00 (m, 1H), 1.89-1.82 (m, 2H), 1.41-1.31 (m, 2H); $[M+H]^{+}$=846.1.

-

Example B100: (R)-7-(4-(3-(4-((2,6-dioxopiperidin-3-yl)amino)phenyl)cyclobutyl)piperazin-1-yl)-2-(2-fluoro-3-methyl-4-(thiazol-4-ylcarbamoyl)phenyl)-9,10-dihydro-4H-benzo[d]pyrazolo[1,5-a][1,3]diazepine-3-carboxamide

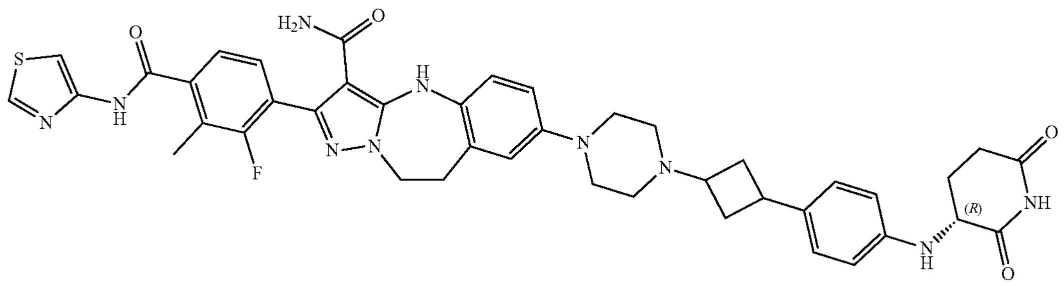

The titled compound was synthesized in the procedures similar to Example B87. H NMR (500 MHz, DMSO) δ 11.52 (s, 1H), 10.78 (s, 1H), 9.96 (s, 1H), 9.76 (s, 1H), 9.03 (d, J=2.1 Hz, 1H), 7.84 (d, J=2.0 Hz, 1H), 7.44-7.33 (m, 2H), 7.06 (d, J=8.4 Hz, 2H), 6.95 (q, J=8.5 Hz, 3H), 6.66 (t, J=9.7 Hz, 2H), 4.43-4.35 (m, 2H), 4.31 (dd, J=11.3, 4.7 Hz, 1H), 3.81 (d, J=12.1 Hz, 2H), 3.77-3.69 (m, 1H), 3.61 (d, J=5.7 Hz, 2H), 3.23-3.17 (m, 2H), 3.06 (dd, J=17.5, 8.2 Hz, 3H), 2.95 (t, J=11.8 Hz, 2H), 2.75 (ddd, J=17.4, 12.1, 5.3 Hz, 1H), 2.58 (dd, J=18.2, 14.4 Hz, 3H), 2.40-2.22 (m, 5H), 2.14-2.06 (m, 1H), 1.88 (qd, J=12.5, 4.6 Hz, 1H); $[M+H]^+$=802.9.

Example B101: (S)-7-(4-(3-(4-((2,6-dioxopiperidin-3-yl)amino)phenyl)cyclobutyl)piperazin-1-yl)-2-(2-fluoro-3-methyl-4-(thiazol-4-ylcarbamoyl)phenyl)-9,10-dihydro-4H-benzo[d]pyrazolo[1,5-a][1,3]diazepine-3-carboxamide

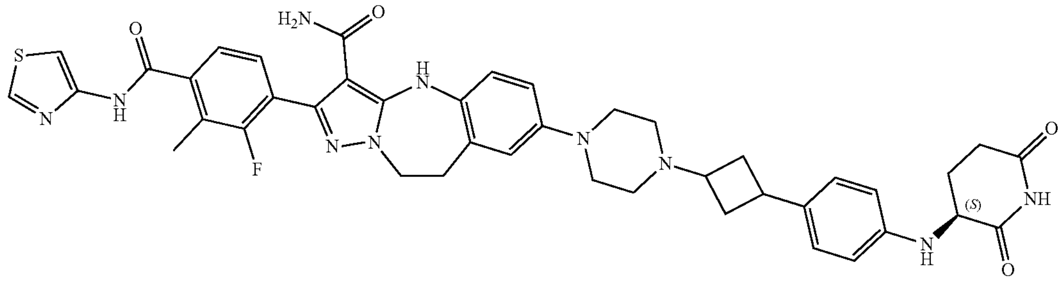

The titled compound was synthesized in the procedures similar to Example B87. $^1$H NMR (500 MHz, DMSO) δ 11.52 (s, 1H), 10.78 (s, 1H), 9.88 (s, 1H), 9.75 (s, 1H), 9.02 (d, J=2.0 Hz, 1H), 7.84 (d, J=2.0 Hz, 1H), 7.44-7.34 (m, 2H), 7.10-7.04 (m, 2H), 6.95 (q, J=8.7 Hz, 3H), 6.67 (t, J=9.1 Hz, 2H), 4.43-4.35 (m, 2H), 4.31 (dd, J=11.3, 4.7 Hz, 1H), 3.85-3.78 (m, 2H), 3.77-3.71 (m, 1H), 3.67-3.59 (m, 2H), 3.22-3.17 (m, 2H), 3.11-3.02 (m, 3H), 2.99-2.90 (m, 2H), 2.79-2.71 (m, 1H), 2.67-2.53 (m, 3H), 2.39-2.20 (m, 5H), 2.15-2.06 (m, 1H), 1.92-1.82 (m, 1H); $[M+H]^+$=802.9.

Example B102: 7-(4-(1-(4-(2,4-dioxotetrahydropyrimidin-1(2H)-yl)phenyl)piperidine-4-carbonyl)piperazin-1-yl)-2-(2-fluoro-3-methyl-4-(thiazol-4-ylcarbamoyl)phenyl)-9,10-dihydro-4H-benzo[d]pyrazolo[1,5-a][1,3]diazepine-3-carboxamide

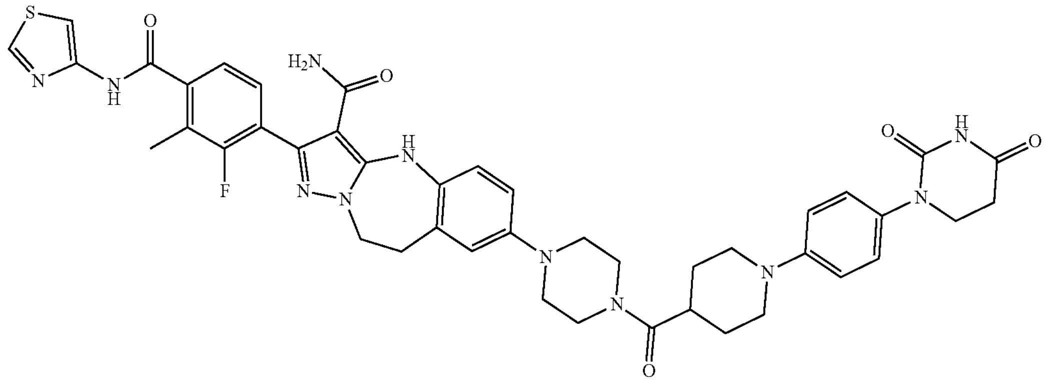 [SMILES: Cc1c(C(=O)Nc2cscn2)ccc(-c2nn3c(c2C(N)=O)Nc2ccc(N4CCN(C(=O)C5CCN(c6ccc(N7CCC(=O)NC7=O)cc6)CC5)CC4)cc2CC3)c1F]

The titled compound was synthesized in the procedures similar to Example B87. $^1H$ NMR (500 MHz, DMSO) δ 11.52 (s, 1H), 10.32 (s, 1H), 9.74 (s, 1H), 9.02 (d, J=2.0 Hz, 1H), 7.84 (d, J=1.9 Hz, 1H), 7.43-7.34 (m, 2H), 7.26 (s, 2H), 7.14 (s, 2H), 6.92 (dd, J=12.5, 8.5 Hz, 3H), 4.41-4.35 (m, 2H), 3.75-3.68 (m, 6H), 3.67-3.59 (m, 2H), 3.21-3.02 (m, 7H), 3.01-2.90 (m, 2H), 2.69 (t, J=6.6 Hz, 2H), 2.32 (s, 3H), 1.87-1.74 (m, 4H); $[M+H]^+$=846.0.

Example B103: (R)-7-(4-((1-(4-(2,4-dioxotetrahydropyrimidin-1(2H)-yl)phenyl)pyrrolidin-3-yl)methyl)piperazin-1-yl)-2-(2-fluoro-3-methyl-4-(thiazol-4-ylcarbamoyl)phenyl)-9,10-dihydro-4H-benzo[d]pyrazolo[1,5-a][1,3]diazepine-3-carboxamide

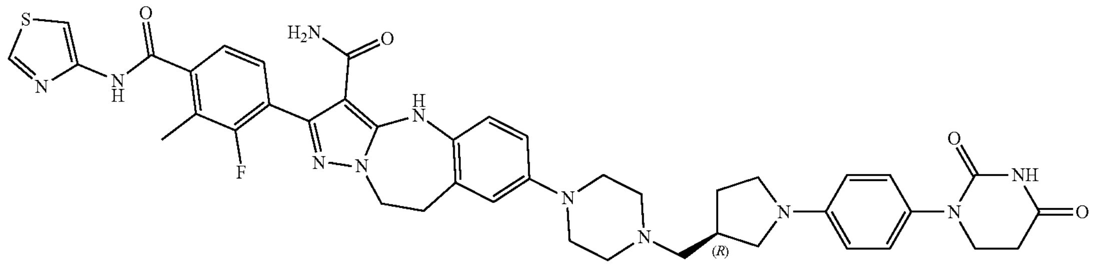

The titled compound was synthesized in the procedures similar to Example B87. $^1H$ NMR (500 MHz, DMSO) δ 11.52 (s, 1H), 10.22 (s, 1H), 9.76 (s, 1H), 9.03 (d, J=2.2 Hz, 1H), 7.84 (d, J=2.1 Hz, 1H), 7.44-7.35 (m, 2H), 7.13 (d, J=8.8 Hz, 2H), 6.94 (dt, J=10.8, 5.2 Hz, 3H), 6.55 (d, J=8.9 Hz, 2H), 4.43-4.35 (m, 2H), 3.82-3.75 (m, 2H), 3.76-3.63 (m, 4H), 3.58-3.52 (m, 1H), 3.31-3.15 (m, 8H), 3.10-2.99 (m, 3H), 2.87-2.78 (m, 1H), 2.69 (t, J=6.7 Hz, 2H), 2.32 (d, J=1.8 Hz, 3H), 2.28-2.22 (m, 1H), 1.86-1.76 (m, 1H); $[M+H]^+$=818.1.

Example C31:7-(4-((1-(4-(2,4-dioxotetrahydropyrimidin-1(2H)-yl)phenyl)piperidin-4-yl)methyl)piperazin-1-yl)-2-(4-((2-methoxy-4-methylbenzamido)methyl)-3-methylphenyl)-9,10-dihydro-4H-benzo[d]pyrazolo[1,5-a][1,3]diazepine-3-carboxamide Step 1: 7-(4-((1-(4-(2,4-dioxotetrahydropyrimidin-1(2H)-yl)phenyl)piperidin-4-yl)methyl)piperazin-1-yl)-2-(4-((2-methoxy-4-methylbenzamido)methyl)-3-methylphenyl)-9,10-dihydro-4H-benzo[d]pyrazolo[1,5-a][1,3]diazepine-3-carboxamide

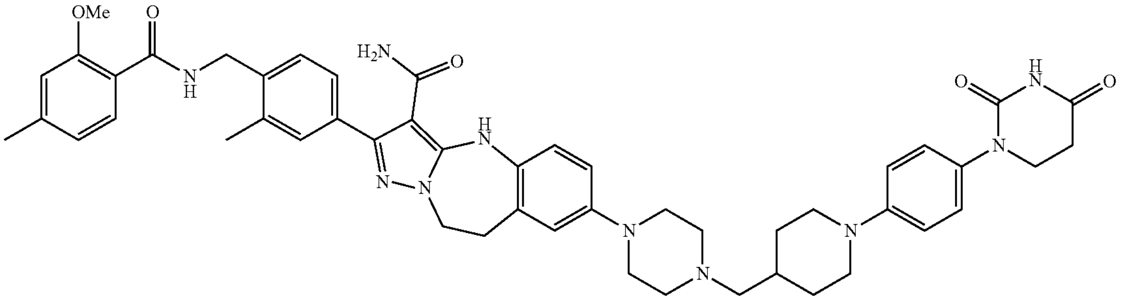 [SMILES: COc1cc(C)ccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

A mixture of 2-(4-((2-methoxy-4-methylbenzamido)methyl)-3-methylphenyl)-7-(piperazin-1-yl)-9,10-dihydro-4H-benzo[d]pyrazolo[1,5-a][1,3]diazepine-3-carboxamide (the compound was synthesized through the similar way of the intermediate in example C28) (0.84 g, 1.45 mmol) and 1-(4-(2,4-dioxotetrahydropyrimidin-1(2H)-yl)phenyl)piperidine-4-carbaldehyde (the compound was synthesized through the similar way of the intermediate in WO2021219070A) (437 mg, 1.45 mmol) in DCM (30.0 mL) and acetic acid (1.0 mL) was stirred at room temperature overnight. Then $NaBH(OAc)_3$ (922 mg, 4.35 mmol) was added and stirred at room temperature for 1 hour. The mixture was treated with water (100.0 mL), extracted with dichloromethane (3×50.0 mL), and washed with brine (50.0 mL). The organic phase was dried over anhydrous sodium sulfate, filtered and concentrated under reduced pressure to afford the crude product, which was purified by prep-HPLC to give the product (133 mg, 11%). $^1H$ NMR (500 MHz, DMSO) δ 10.14 (s, 1H), 9.72 (s, 1H), 8.50 (t, J=5.9 Hz, 1H), 7.63 (d, J=7.8 Hz, 1H), 7.31-7.21 (m, 3H), 7.06 (d, J=8.8 Hz, 2H), 6.92 (s, 1H), 6.85 (d, J=8.9 Hz, 2H), 6.81-6.72 (m, 4H), 4.45 (d, J=5.7 Hz, 2H), 4.29-4.20 (m, 2H), 3.83 (s, 3H), 3.82-3.80 (m, 1H), 3.63-3.56 (m, 4H), 3.07-3.05 (m, 2H), 3.04-2.95 (m, 4H), 2.61-2.56 (m, 4H), 2.47-2.43 (m, 2H), 2.30-2.27 (m, 7H), 2.17-2.12 (m, 2H), 1.74-1.70 (m, 2H), 1.66-1.58 (m, 1H), 1.20-1.10 (m, 2H); $[M+H]^+$=865.6.

Example C32: 7-(4-((1-(4-(2,4-dioxotetrahydropyrimidin-1(2H)-yl)phenyl)piperidin-4-yl)methyl)piperazin-1-yl)-2-(4-((2-methoxybenzamido)methyl)-3-methylphenyl)-9,10-dihydro-4H-benzo[d]pyrazolo[1,5-a][1,3]diazepine-3-carboxamide

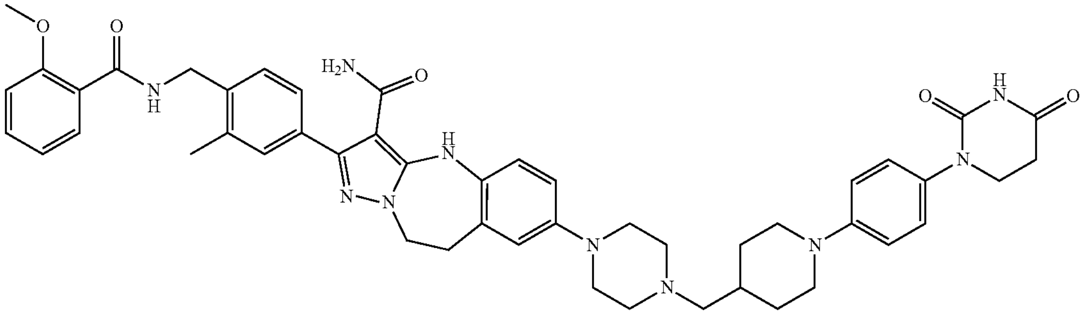 [SMILES: COc1ccccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

The titled compound was synthesized in the procedures similar to Example C31. $^1H$ NMR (500 MHz, DMSO) δ 10.15 (s, 1H), 9.72 (s, 1H), 8.55 (t, J=5.8 Hz, 1H), 7.68 (d, J=7.6 Hz, 1H), 7.41 (t, J=7.8 Hz, 1H), 7.32 (d, J=7.8 Hz, 1H), 7.28-7.22 (m, 2H), 7.07 (dd, J=14.1, 8.6 Hz, 3H), 6.97 (t, J=7.5 Hz, 1H), 6.85 (d, J=8.8 Hz, 2H), 6.79-6.72 (m, 3H), 4.46 (d, J=5.8 Hz, 2H), 4.29-4.20 (m, 2H), 3.83 (s, 3H), 3.63-3.59 (m, 4H), 3.10-3.05 (m, 2H), 3.03-2.97 (m, 4H), 2.64-2.55 (m, 4H), 2.48-2.45 (m, 4H), 2.31 (s, 3H), 2.18-2.12 (m, 2H), 1.77-1.70 (m, 2H), 1.68-1.60 (m, 1H), 1.20-1.11 (m, 2H); $[M+H]^+$=852.6.

Example C33:2-(4-((4,5-difluoro-2-methoxybenzamido)methyl)-3-methylphenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide Step 1: 4,5-difluoro-2-methoxy-N-(2-methyl-4-(4,4,5,5-tetramethyl-1,3,2-dioxaborolan-2-yl)benzyl)benzamide

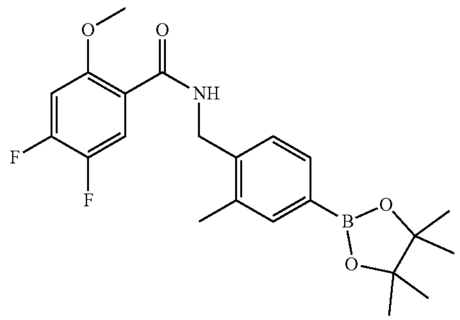 [SMILES: COc1cc(F)c(F)cc1C(=O)NCc1ccc(B2OC(C)(C)C(C)(C)O2)cc1C]

To a stirred solution of 4,5-difluoro-2-methoxybenzoic acid (1.5 g, 9.487 mmol) in DCM (20 mL) were added (2-methyl-4-(4,4,5,5-tetramethyl-1,3,2-dioxaborolan-2-yl)phenyl)methanamine hydrochloride (2.47 g, 8.770 mmol), $T_3P$ (5.07 g, 15.946 mmol) and DIEA (2.06 g, 15.946 mmol) dropwise at room temperature. The resulting mixture was stirred for 30 min at room temperature and extracted with EtOAc (3×200 mL). The combined organic layers were washed with brine (3×100 mL) and dried over anhydrous $Na_2SO_4$. After filtration, the filtrate was concentrated under reduced pressure. The residue was purified by silica gel column chromatography, eluted with 1-60% EtOAc in PE to afford the product (2.7297 g, 82%). $^1H$ NMR (400 MHz, $CDCl_3$) δ 8.14 (dd, J=11.6, 9.6 Hz, 1H), 7.94-7.90 (m, 1H), 7.68-7.65 (m, 2H), 7.33 (d, J=7.6 Hz, 1H), 6.81 (dd, J=11.6, 6.0 Hz, 1H), 4.68 (d, J=5.4 Hz, 2H), 3.89 (s, 3H), 2.39 (s, 3H), 1.37 (s, 12H); $[M+H]^+$=418.2.

Step 2: tert-butyl 4-(3-cyano-2-(4-((4,5-difluoro-2-methoxybenzamido)methyl)-3-methylphenyl)-9,10-dihydro-4H-benzo[d]pyrazolo[1,5-a][1,3]diazepin-7-yl)piperazine-1-carboxylate

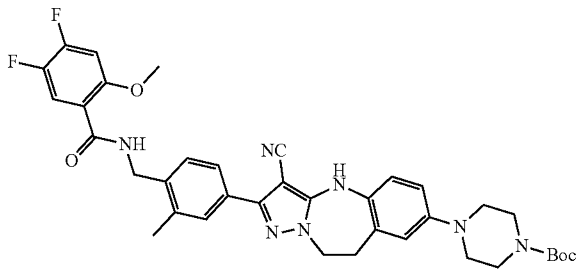 [SMILES: COc1cc(F)c(F)cc1C(=O)NCc1ccc(-c2nn3c(c2C#N)Nc2ccc(N4CCN(C(=O)OC(C)(C)C)CC4)cc2CC3)cc1C]

A mixture of 4,5-difluoro-2-methoxy-N-(2-methyl-4-(4,4,5,5-tetramethyl-1,3,2-dioxaborolan-2-yl)benzyl)benzamide (0.451 g, 1.081 mmol), tert-butyl 4-(2-bromo-3-cyano-9,10-dihydro-4H-benzo[d]pyrazolo[1,5-a][1,3]diazepin-7-yl)piperazine-1-carboxylate (0.5 g, 0.985 mmol), $Pd_2(dba)_3$ (0.046 g, 0.05 mmol), tricyclohexylphosphane (0.056 g, 0.2 mmol) and $K_3PO_4$ (0.416 g, 2 mmol) in isopropanol (16 mL) and $H_2O$ (4 mL) was stirred in a round bottom flask at 90° C. overnight. The mixture was evaporated in vacuum to afford the crude product, which was further purified with silica gel column chromatography (PE:EA=100:0~10:90 gradient elution) to give the product (0.41 g, 57%). $[M+H]^+$=684.3.

Step 3: 2-(4-((4,5-difluoro-2-methoxybenzamido)methyl)-3-methylphenyl)-7-(piperazin-1-yl)-9,10-dihydro-4H-benzo[d]pyrazolo[1,5-a][1,3]diazepine-3-carboxamide

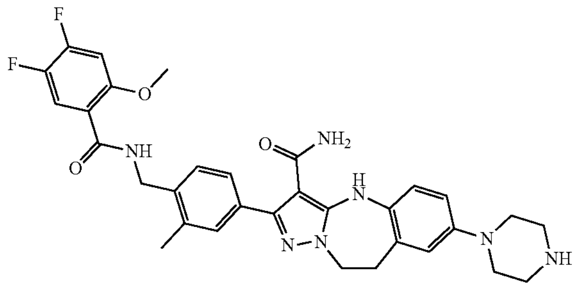 [SMILES: COc1cc(F)c(F)cc1C(=O)NCc1ccc(-c2nn3c(c2C(N)=O)Nc2ccc(N4CCNCC4)cc2CC3)cc1C]

A mixture of tert-butyl 4-(3-cyano-2-(4-((4,5-difluoro-2-methoxybenzamido)methyl)-3-methylphenyl)-9,10-dihydro-4H-benzo[d]pyrazolo[1,5-a][1,3]diazepin-7-yl)piperazine-1-carboxylate (0.41 g, 0.601 mmol) in methanesulfonic acid (10.0 mL) was stirred at 100° C. for 0.5 hour. The mixture was then cooled, basified with aqueous sodium hydroxide solution to pH 12 and extracted with dichloromethane (3×30 mL) and water (3×30 mL). The organic phase was dried over anhydrous sodium sulfate, filtered, and concentrated under reduced pressure to afford the product (160 mg, crude). $[M+H]^+$=602.3.

Step 4: 2-(4-((4,5-difluoro-2-methoxybenzamido)methyl)-3-methylphenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a][1,3]diazepine-3-carboxamide

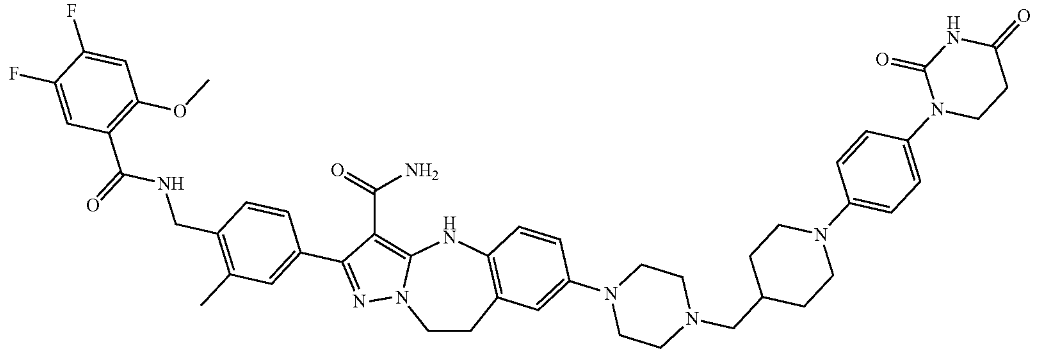 [SMILES: COc1cc(F)c(F)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

A mixture of 2-(4-((4,5-difluoro-2-methoxybenzamido)methyl)-3-methylphenyl)-7-(piperazin-1-yl)-9,10-dihydro-4H-benzo[d]pyrazolo[1,5-a][1,3]diazepine-3-carboxamide (0.06 g, 0.1 mmol) and 1-(4-(2,4-dioxotetrahydropyrimidin-1(2H)-yl)phenyl)piperidine-4-carbaldehyde (0.034 g, 0.11 mmol) in 1,2-dichloroethane (5 mL) and HOAc (25 mg) was stirred in a round bottom flask at room temperature for 0.5 hour. To the mixture was added $NaBH(OAc)_3$ (0.032 g, 0.15 mmol) and stirred at room temperature for 12 hours. Then the mixture was evaporated in vacuum to afford the crude product, which was purified by pre-HPLC to afford the product (58.3 mg, 66%). $^1$H NMR (500 MHz, DMSO) δ 10.25 (s, 1H), 9.79 (s, 1H), 8.70 (t, J=5.9 Hz, 1H), 8.20 (s, 1H), 7.74 (dd, J=11.1, 9.5 Hz, 1H), 7.34 (ddd, J=20.8, 11.5, 7.1 Hz, 4H), 7.13 (d, J=8.9 Hz, 2H), 6.92 (d, J=9.0 Hz, 2H), 6.83 (dd, J=16.0, 6.7 Hz, 3H), 4.51 (d, J=5.8 Hz, 2H), 4.36-4.26 (m, 2H), 3.90 (s, 3H), 3.69 (t, J=6.7 Hz, 4H), 3.22-2.95 (m, 8H), 2.67 (dd, J=15.7, 8.9 Hz, 4H), 2.41-2.32 (m, 5H), 2.22 (d, J=7.0 Hz, 2H), 1.77 (t, J=26.6 Hz, 3H), 1.22 (dd, J=21.0, 11.5 Hz, 2H); $[M+H]^+$=887.6.

Example C34: 7-(4-((1-(4-(2,4-dioxotetrahydropyrimidin-1(2H)-yl)phenyl)piperidin-4-yl)methyl)piperazin-1-yl)-2-(4-((2-methoxynicotinamido)methyl)-3-methylphenyl)-9,10-dihydro-4H-benzo[d]pyrazolo[1,5-a][1,3]diazepine-3-carboxamide Step 1: N-(4-bromo-2-methylbenzyl)-2-methoxynicotinamide

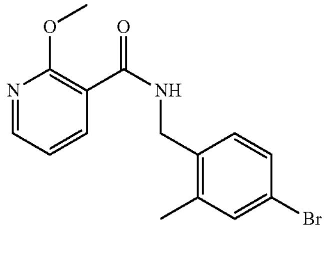 [SMILES: COc1ncccc1C(=O)NCc1ccc(Br)cc1C]

To a stirred solution of 2-methoxypyridine-3-carboxylic acid (2 g, 13.060 mmol) and HATU (5.96 g, 15.672 mmol) in DMF (40 mL) was added DIEA (9.1 mL, 52.240 mmol) at rt under nitrogen atmosphere. The mixture was stirred for 5 min at room temperature under nitrogen atmosphere. Then 1-(4-bromo-2-methylphenyl)methanamine hydrochloride (3.71 g, 15.672 mmol) was added to the mixture. The resulting mixture was stirred for 16 h at room temperature under nitrogen atmosphere and diluted with water (300 mL). The resulting mixture was extracted with EtOAc (3×200 mL). The combined organic layers were washed with brine (2×100 mL) and dried over anhydrous $Na_2SO_4$. After filtration, the filtrate was concentrated under reduced pressure. The residue was purified by silica gel column chromatography, eluted with 1-30% EtOAc in petroleum ether to afford the product (4.3 g, 98%). $[M+H]^+$=334.9.

Step 2: 2-methoxy-N-(2-methyl-4-(4,4,5,5-tetramethyl-1,3,2-dioxaborolan-2-yl)benzyl)nicotinamide

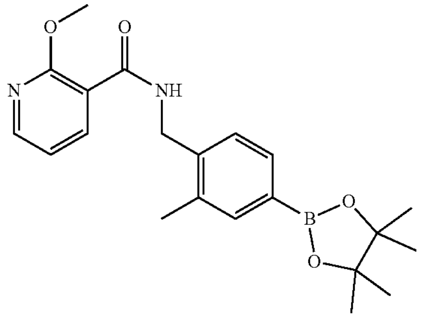 [SMILES: COc1ncccc1C(=O)NCc1ccc(B2OC(C)(C)C(C)(C)O2)cc1C]

To a stirred mixture of N-(4-bromo-2-methylbenzyl)-2-methoxynicotinamide (4.3 g, 12.828 mmol) and 4,4,5,5-tetramethyl-2-(tetramethyl-1,3,2-dioxaborolan-2-yl)-1,3,2-dioxaborolane (4.89 g, 19.242 mmol) in dioxane (80 mL) were added KOAc (2.52 g, 25.656 mmol) and $Pd(dppf)Cl_2$ (939 mg, 1.283 mmol) at room temperature under nitrogen atmosphere. The resulting mixture was stirred for 16 h at 80° C. under nitrogen atmosphere. The resulting mixture was filtered, and the filter cake was washed with EtOAc (3×500 mL). The filtrate was concentrated under reduced pressure.

The residue was purified by silica gel column chromatography, eluted with 5%-35% EtOAc in petroleum ethers to afford the product (3.12 g, 64%). $^1$H NMR (400 MHz, $CDCl_3$) δ 8.61-8.54 (m, 1H), 8.31-8.28 (m, 1H), 8.11 (s, 1H), 7.67 (d, J=7.2 Hz, 2H), 7.35 (d, J=7.6 Hz, 1H), 7.11-7.08 (m, 1H), 4.71 (d, J=5.2 Hz, 2H), 4.07 (s, 3H), 2.41 (s, 3H), 1.39-1.35 (m, 12H); $[M+H]^+$=383.1.

Step 3: tert-butyl 4-(3-cyano-2-(4-((2-methoxynicotinamido)methyl)-3-methylphenyl)-9,10-dihydro-4H-benzo[d]pyrazolo[1,5-a][1,3]diazepin-7-yl)piperazine-1-carboxylate

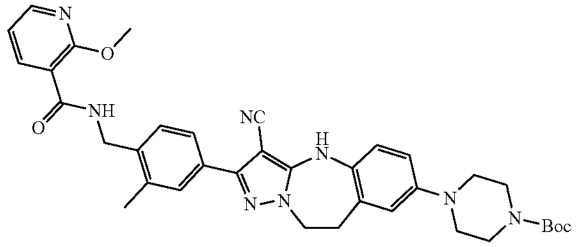 [SMILES: COc1ncccc1C(=O)NCc1ccc(-c2nn3c(c2C#N)Nc2ccc(N4CCN(C(=O)OC(C)(C)C)CC4)cc2CC3)cc1C]

A mixture of 2-methoxy-N-(2-methyl-4-(4,4,5,5-tetramethyl-1,3,2-dioxaborolan-2-yl)benzyl)nicotinamide (0.413 g, 1.081 mmol), tert-butyl 4-(2-bromo-3-cyano-9,10-dihydro-4H-benzo[d]pyrazolo[1,5-a][1,3]diazepin-7-yl)piperazine-1-carboxylate (0.5 g, 0.985 mmol), $Pd_2(dba)_3$ (0.046 g, 0.05 mmol), tricyclohexylphosphane (0.056 g, 0.2 mmol) and $K_3PO_4$ (0.416 g, 2 mmol) in isopropanol (16 mL) and $H_2O$ (4 mL) was stirred in a round bottom flask at 90° C. overnight. The mixture was evaporated in vacuum to afford the crude product, which was further purified with silica gel column chromatography (PE:EA=100:0~10:90 gradient elution) to give the product (0.46 g, 72%). $[M+H]^+$=649.3.

Step 4: 2-(4-((2-methoxynicotinamido)methyl)-3-methylphenyl)-7-(piperazin-1-yl)-9,10-dihydro-4H-benzo[d]pyrazolo[1,5-a][1,3]diazepine-3-carboxamide

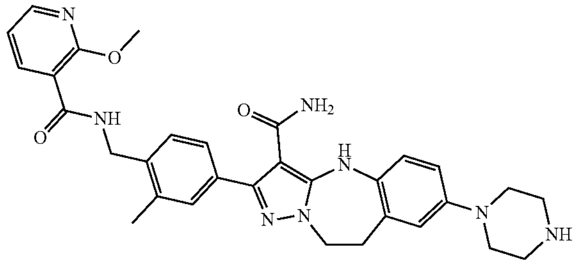 [SMILES: COc1ncccc1C(=O)NCc1ccc(-c2nn3c(c2C(N)=O)Nc2ccc(N4CCNCC4)cc2CC3)cc1C]

A mixture of tert-butyl 4-(3-cyano-2-(4-((2-methoxynicotinamido)methyl)-3-methylphenyl)-9,10-dihydro-4H-benzo[d]pyrazolo[1,5-a][1,3]diazepin-7-yl)piperazine-1-carboxylate (0.46 g, 0.71 mmol) in methanesulfonic acid (10.0 mL) was stirred at 100° C. for 0.5 hour. The mixture was then cooled, basified with aqueous sodium hydroxide solution to pH 12 and extracted with dichloromethane (3×30 mL), then the organic phase was washed with water (3×30 mL). The organic phase was dried over anhydrous sodium sulfate, filtered, and concentrated under reduced pressure to afford the product (200 mg, crude). $[M+H]^+$=567.3.

Step 5: 7-(4-((1-(4-(2,4-dioxotetrahydropyrimidin-1(2H)-yl)phenyl)piperidin-4-yl)methyl)piperazin-1-yl)-2-(4-((2-methoxynicotinamido)methyl)-3-methylphenyl)-9,10-dihydro-4H-benzo[d]pyrazolo[1,5-a][1,3]diazepine-3-carboxamide

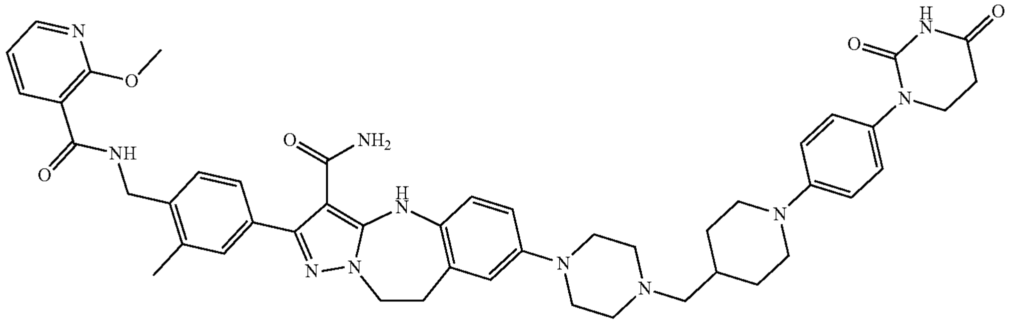 [SMILES: COc1ncccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

A mixture of 2-(4-((2-methoxynicotinamido)methyl)-3-methylphenyl)-7-(piperazin-1-yl)-9,10-dihydro-4H-benzo[d]pyrazolo[1,5-a][1,3]diazepine-3-carboxamide (0.06 g, 0.106 mmol) and 1-(4-(2,4-dioxotetrahydropyrimidin-1(2H)-yl)phenyl)piperidine-4-carbaldehyde (0.036 g, 0.12 mmol) in 1,2-dichloroethane (5 mL) and HOAc (25 mg) was stirred in a round bottom flask at room temperature for 0.5 hour. To the mixture was added $NaBH(OAc)_3$ (0.034 g, 0.16 mmol) and stirred at room temperature for 12 hours. Then the mixture was evaporated in vacuum to afford the crude product, which was purified by pre-HPLC to afford the product (46.47 mg, 51%). $^1$H NMR (500 MHz, DMSO) δ 10.25 (s, 1H), 9.79 (s, 1H), 8.75 (s, 1H), 8.35-8.29 (m, 1H), 8.14 (d, J=7.4 Hz, 1H), 7.41-7.29 (m, 3H), 7.13 (d, J=6.7 Hz, 3H), 6.93 (d, J=7.5 Hz, 2H), 6.84 (dd, J=18.5, 6.7 Hz, 3H), 4.53 (d, J=5.2 Hz, 2H), 4.33 (s, 2H), 3.99 (d, J=1.4 Hz, 3H), 3.69 (t, J=6.5 Hz, 4H), 3.48-3.35 (m, 4H), 3.21-3.05 (m, 6H), 2.67 (dd, J=14.9, 9.4 Hz, 4H), 2.38 (s, 3H), 2.22 (d, J=6.2 Hz, 2H), 1.85-1.65 (m, 3H), 1.28-1.17 (m, 2H); $[M+H]^+$=852.6.

Example C35: 7-(4-((1-(4-(2,4-dioxotetrahydropyrimidin-1(2H)-yl)phenyl)piperidin-4-yl)methyl)piperazin-1-yl)-2-(4-((4-methoxynicotinamido)methyl)-3-methylphenyl)-9,10-dihydro-4H-benzo[d]pyrazolo[1,5-a][1,3]diazepine-3-carboxamide

-

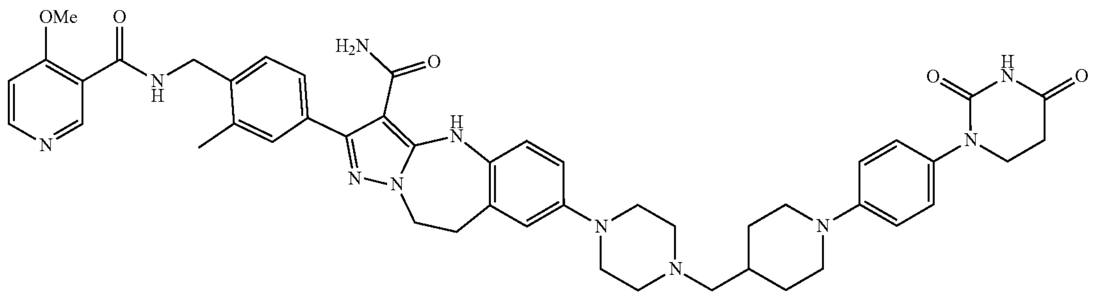 [SMILES: COc1ccncc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

The titled compound was synthesized in the procedures similar to Example C34. $^1H$ NMR (500 MHz, DMSO) δ 10.25 (d, J=2.9 Hz, 1H), 9.80 (s, 1H), 8.73-8.65 (m, 2H), 8.57-8.52 (m, 1H), 7.40-7.38 (m, 1H), 7.35-7.30 (m, 2H), 7.21-7.19 (m, 1H), 7.16-7.11 (m, 2H), 6.96-6.91 (m, 2H), 6.89-6.80 (m, 3H), 4.54-4.50 (m, 2H), 4.35-4.31 (m, 2H), 3.95 (d, J=3.4 Hz, 3H), 3.72-3.65 (m, 4H), 3.33-3.31 (m, 4H), 3.17-3.12 (m, 2H), 3.12-3.06 (m, 4H), 2.70-2.63 (m, 4H), 2.38 (d, J=2.6 Hz, 3H), 2.25-2.19 (m, 2H), 1.85-1.78 (m, 2H), 1.75-1.67 (m, 1H), 1.28-1.18 (m, 2H); $[M+H]^+$ =852.6.

Example C36: 7-(4-((1-(4-(2,4-dioxotetrahydropyrimidin-1(2H)-yl)phenyl)piperidin-4-yl)methyl)piperazin-1-yl)-2-(4-((3-methoxynicotinamido)methyl)-3-methylphenyl)-9,10-dihydro-4H-benzo[d]pyrazolo[1,5-a][1,3]diazepine-3-carboxamide

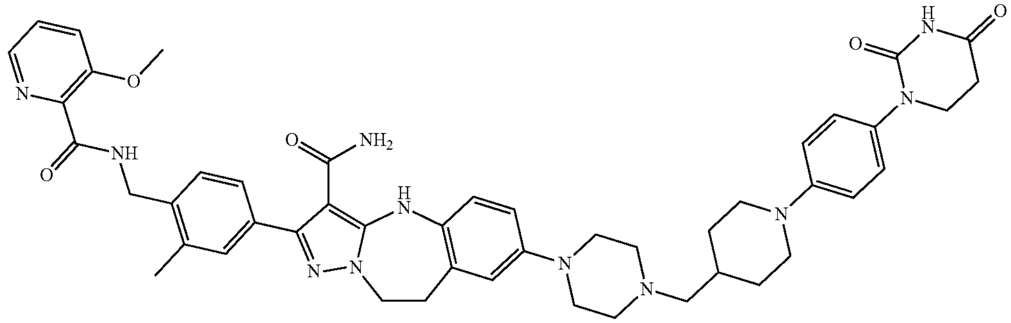

The titled compound was synthesized in the procedures similar to Example C34. $^1H$ NMR (400 MHz, DMSO) δ 10.27 (s, 1H), 9.80 (s, 1H), 8.83 (t, J=5.9 Hz, 1H), 8.16 (d, J=4.6 Hz, 1H), 7.59 (d, J=8.4 Hz, 1H), 7.51-7.42 (m, 2H), 7.32 (d, J=5.4 Hz, 2H), 7.13 (d, J=8.9 Hz, 2H), 6.93 (d, J=9.0 Hz, 2H), 6.84 (dd, J=13.7, 6.9 Hz, 3H), 4.46 (d, J=5.7 Hz, 2H), 4.34 (s, 2H), 3.84 (s, 3H), 3.69 (t, J=6.7 Hz, 4H), 3.48-3.32 (m, 4H), 3.18-3.05 (m, 6H), 2.67 (dd, J=15.5, 9.0 Hz, 4H), 2.37 (s, 3H), 2.22 (d, J=6.7 Hz, 2H), 1.85-1.65 (m, 3H), 1.29-1.16 (m, 2H); $[M+H]^+$=852.7.

-

Example C37: 7-(4-((1-(4-(2,4-dioxotetrahydropyrimidin-1(2H)-yl)phenyl)piperidin-4-yl)methyl)piperazin-1-yl)-2-(4-((3-methoxyisonicotinamide)methyl)-3-methylphenyl)-9,10-dihydro-4H-benzo[d]pyrazolo[1,5-a][1,3]diazepine-3-carboxamide

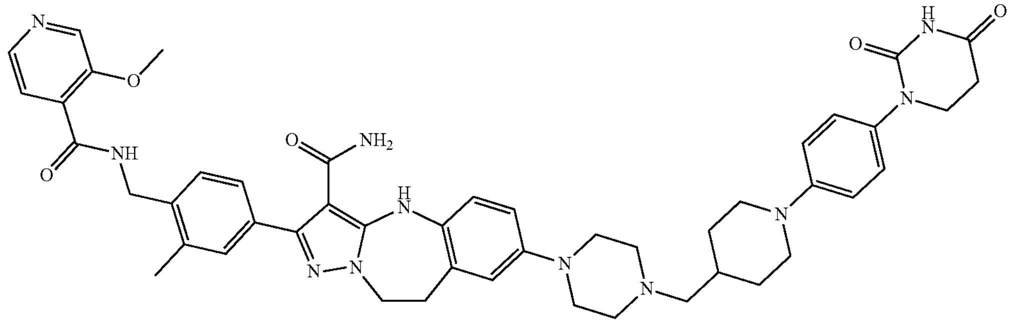 [SMILES: COc1cnccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

The titled compound was synthesized in the procedures similar to Example C34. $^{1}H$ NMR (400 MHz, DMSO) δ 10.27 (s, 1H), 9.79 (s, 1H), 8.83 (t, J=5.7 Hz, 1H), 8.55 (s, 1H), 8.31 (d, J=4.7 Hz, 1H), 7.54 (d, J=4.7 Hz, 1H), 7.36 (q, J=7.8 Hz, 3H), 7.13 (d, J=8.9 Hz, 2H), 6.93 (d, J=9.0 Hz, 2H), 6.84 (dd, J=13.7, 6.9 Hz, 3H), 4.51 (d, J=5.4 Hz, 2H), 4.33 (s, 2H), 3.99 (s, 3H), 3.69 (t, J=6.7 Hz, 4H), 3.48-3.21 (m, 4H), 3.18-3.05 (m, 6H), 2.67 (dd, J=15.3, 8.7 Hz, 4H), 2.37 (s, 3H), 2.22 (d, J=7.2 Hz, 2H), 1.85-1.65 (m, 3H), 1.22 (d, J=9.1 Hz, 2H); $[M+H]^{+}$=852.6.

Example C38:7-(4-((1-(4-(2,4-dioxotetrahydropyrimidin-1(2H)-yl)phenyl)piperidin-4-yl)methyl)piperazin-1-yl)-2-(4-((2-methoxy-6-methylbenzamido)methyl)-3-methylphenyl)-9,10-dihydro-4H-benzo[d]pyrazolo[1,5-a][1,3]diazepine-3-carboxamide

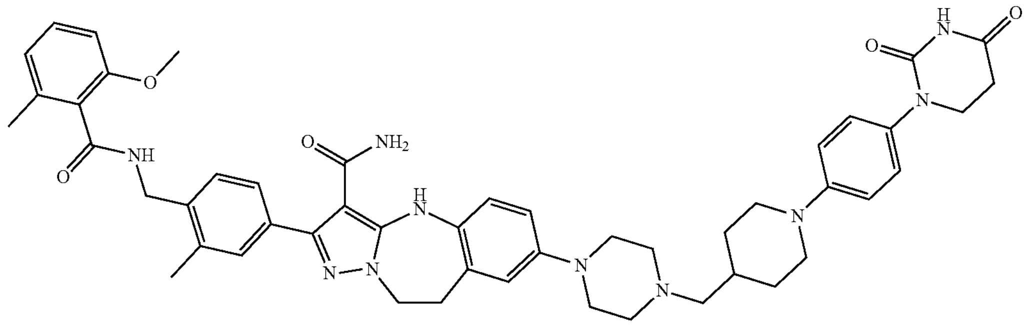 [SMILES: COc1cccc(C)c1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

The titled compound was synthesized in the procedures similar to Example C34. $^{1}H$ NMR (400 MHz, DMSO) δ 10.27 (s, 1H), 9.80 (s, 1H), 8.67 (t, J=5.8 Hz, 1H), 7.53 (d, J=7.7 Hz, 1H), 7.33 (d, J=8.6 Hz, 2H), 7.24 (t, J=7.9 Hz, 1H), 7.13 (d, J=8.8 Hz, 2H), 6.87 (ddd, J=23.6, 16.2, 8.3 Hz, 8H), 4.44 (d, J=5.4 Hz, 2H), 4.34 (s, 2H), 3.77 (s, 3H), 3.69 (t, J=6.6 Hz, 4H), 3.45-3.25 (m, 4H), 3.18-3.05 (m, 6H), 2.67 (dd, J=15.2, 8.6 Hz, 4H), 2.37 (s, 3H), 2.25-2.14 (m, 5H), 1.85-1.65 (m, 3H), 1.23 (t, J=10.7 Hz, 2H); $[M+H]^{+}$=865.8.

Example C39:7-(4-((1-(4-(2,4-dioxotetrahydropyrimidin-1(2H)-yl)phenyl)piperidin-4-yl)methyl)piperazin-1-yl)-2-(4-((2-methoxy-5-methylbenzamido)methyl)-3-methylphenyl)-9,10-dihydro-4H-benzo[d]pyrazolo[1,5-a][1,3]diazepine-3-carboxamide

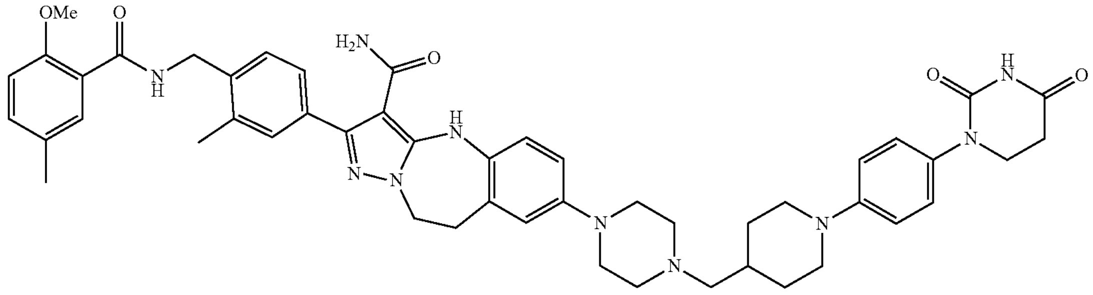 [SMILES: COc1ccc(C)cc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

The titled compound was synthesized in the procedures similar to Example C34. $^1$H NMR (500 MHz, DMSO) δ 10.25 (s, 1H), 9.79 (s, 1H), 8.61 (t, J=5.9 Hz, 1H), 7.57 (d, J=2.1 Hz, 1H), 7.36 (d, J=7.8 Hz, 1H), 7.35-7.26 (m, 3H), 7.13 (d, J=8.8 Hz, 2H), 7.05 (d, J=8.4 Hz, 1H), 6.93 (d, J=8.9 Hz, 2H), 6.87-6.80 (m, 3H), 4.51 (d, J=5.9 Hz, 2H), 4.33-4.31 (m, 2H), 3.86 (s, 3H), 3.70-3.67 (m, 4H), 3.30-3.27 (m, 4H), 3.15-3.13 (m, 2H), 3.11-3.05 (m, 4H), 2.69-2.64 (m, 4H), 2.37 (s, 3H), 2.27 (s, 3H), 2.25-2.19 (m, 2H), 1.82-1.79 (m, 2H), 1.74-1.68 (m, 1H), 1.26-1.18 (m, 2H); $[M+H]^+$ =865.6.

Example C40:7-(4-((1-(4-(2,4-dioxotetrahydropyrimidin-1(2H)-yl)phenyl)piperidin-4-yl)methyl)piperazin-1-yl)-2-(4-((3-fluoro-2-methoxybenzamido)methyl)-3-methylphenyl)-9,10-dihydro-4H-benzo[d]pyrazolo[1,5-a][1,3]diazepine-3-carboxamide

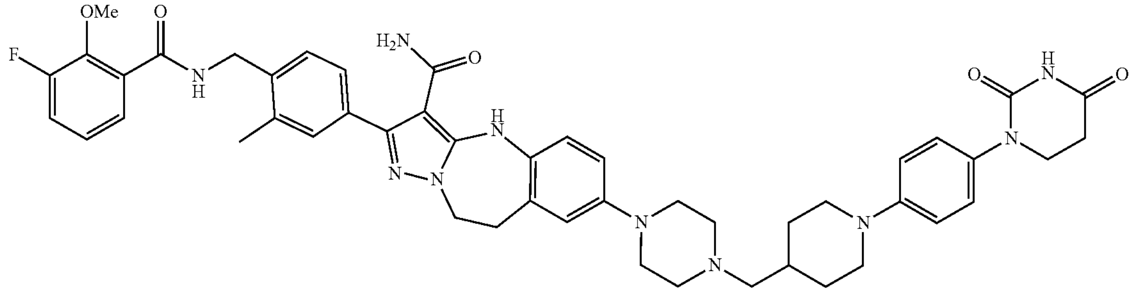 [SMILES: COc1c(F)cccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

The titled compound was synthesized in the procedures similar to Example C34. $^1$H NMR (400 MHz, DMSO) δ 10.27 (s, 1H), 9.79 (s, 1H), 8.78 (t, J=5.7 Hz, 1H), 7.44-7.30 (m, 5H), 7.22-7.10 (m, 3H), 6.93 (d, J=9.0 Hz, 2H), 6.89-6.79 (m, 3H), 4.50 (d, J=5.5 Hz, 2H), 4.35-4.31 (m, 2H), 3.89-3.87 (m, 3H), 3.71-3.67 (m, 4H), 3.33 (s, 4H), 3.16-3.12 (m, 2H), 3.11-3.05 (m, 4H), 2.70-2.62 (m, 4H), 2.38 (s, 3H), 2.23-2.22 (m, 2H), 1.84-1.77 (m, 2H), 1.75-1.67 (m, 1H), 1.25-1.16 (m, 2H); $[M+H]^+$=869.6.

Example C41:7-(4-((1-(4-(2,4-dioxotetrahydropyrimidin-1(2H)-yl)phenyl)piperidin-4-yl)methyl)piperazin-1-yl)-2-(4-((4-fluoro-2-methoxybenzamido)methyl)-3-methylphenyl)-9,10-dihydro-4H-benzo[d]pyrazolo[1,5-a][1,3]diazepine-3-carboxamide

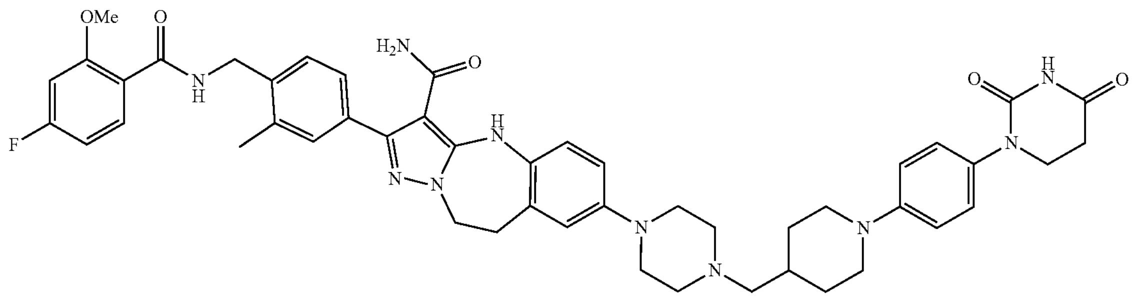 [SMILES: COc1cc(F)ccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

The titled compound was synthesized in the procedures similar to Example C34. $^1$H NMR (500 MHz, DMSO) δ 10.25 (s, 1H), 9.79 (s, 1H), 8.60 (t, J=5.9 Hz, 1H), 7.80 (dd, J=8.6, 7.2 Hz, 1H), 7.38-7.27 (m, 3H), 7.13 (d, J=8.8 Hz, 2H), 7.08 (dd, J=11.4, 2.3 Hz, 1H), 6.93 (d, J=9.0 Hz, 2H), 6.90-6.80 (m, 4H), 4.51 (d, J=5.7 Hz, 2H), 4.33-4.31 (m, 2H), 3.91 (s, 3H), 3.70-3.67 (m, 4H), 3.30-3.27 (m, 4H), 3.15-3.13 (m, 2H), 3.11-3.04 (m, 4H), 2.69-2.63 (m, 4H), 2.37 (s, 3H), 2.24-2.19 (m, 2H), 1.84-1.77 (m, 2H), 1.74-1.67 (m, 1H), 1.27-1.18 (m, 2H); [M+H]$^+$=869.6.

Example C42: 7-(4-((1-(4-(2,4-dioxotetrahydropyrimidin-1(2H)-yl)phenyl)piperidin-4-yl)methyl)piperazin-1-yl)-2-(4-((5-fluoro-2-methoxybenzamido)methyl)-3-methylphenyl)-9,10-dihydro-4H-benzo[d]pyrazolo[1,5-a][1,3]diazepine-3-carboxamide

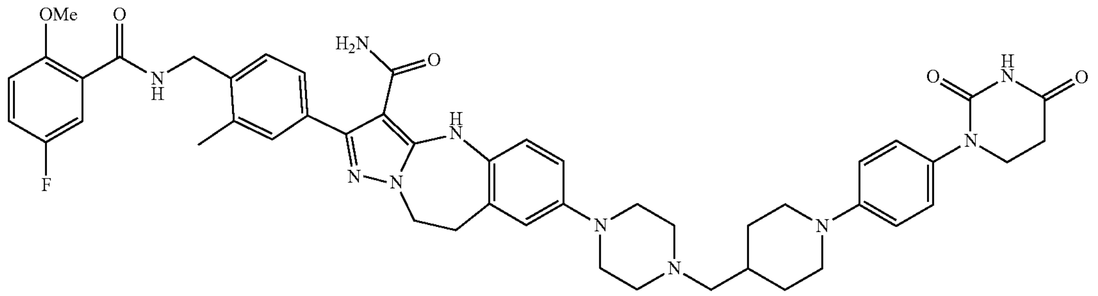

The titled compound was synthesized in the procedures similar to Example C34. $^1$H NMR (500 MHz, DMSO) δ 10.25 (s, 1H), 9.79 (s, 1H), 8.74 (t, J=5.9 Hz, 1H), 7.50 (dd, J=9.1, 3.3 Hz, 1H), 7.38-7.30 (m, 4H), 7.19 (dd, J=9.2, 4.3 Hz, 1H), 7.13 (d, J=8.8 Hz, 2H), 6.93 (d, J=8.9 Hz, 2H), 6.84 (m, 3H), 4.52 (d, J=5.8 Hz, 2H), 4.36-4.30 (m, 2H), 3.89 (s, 3H), 3.70-3.65 (m, 4H), 3.31-3.29 (m, 4H), 3.17-3.12 (m, 2H), 3.11-3.04 (m, 4H), 2.70-2.63 (m, 4H), 2.37 (s, 3H), 2.24-2.19 (m, 2H), 1.84-1.78 (m, 2H), 1.75-1.68 (m, 1H), 1.27-1.18 (m, 2H); [M+H]$^+$=869.6.

Example C43:7-(4-((1-(4-(2,4-dioxotetrahydropyrimidin-1(2H)-yl)phenyl)piperidin-4-yl)methyl)piperazin-1-yl)-2-(3-methyl-4-((2,3,4,5-tetrafluoro-6-methoxybenzamido)methyl)phenyl)-9,10-dihydro-4H-benzo[d]pyrazolo[1,5-a][1,3]diazepine-3-carboxamide Step 1: 2,3,4,5-tetrafluoro-6-methoxybenzoic acid

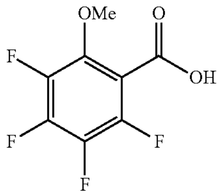

A mixture of pentafluorobenzoic acid (3.0 g, 14.146 mmol) and magnesium methoxide (3.0 g, 35.365 mmol) in toluene (60 mL) was stirred for 16 h at 110° C. The mixture was allowed to cool down to room temperature and concentrated under reduced pressure. The residue was acidified to pH 5 with HCl (1 M). The resulting mixture was extracted with EtOAc (3×200 mL). The combined organic layers were washed with brine (200 mL) and dried over anhydrous $Na_2SO_4$. After filtration, the filtrate was concentrated under reduced pressure. This resulted in the product (3.1 g, crude).

Step 2: 2,3,4,5-tetrafluoro-6-methoxy-N-(2-methyl-4-(4,4,5,5-tetramethyl-1,3,2-dioxaborolan-2-yl)benzyl)benzamide

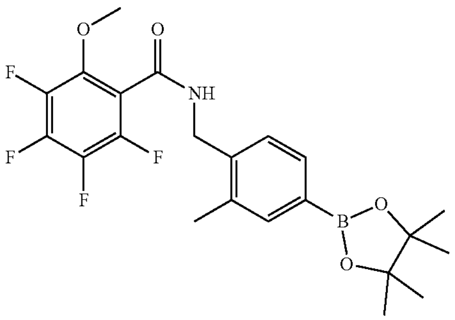 [SMILES: COc1c(F)c(F)c(F)c(F)c1C(=O)NCc1ccc(B2OC(C)(C)C(C)(C)O2)cc1C]

To a stirred solution of 2,3,4,5-tetrafluoro-6-methoxybenzoic acid (2.5 g, 11.155 mmol) and HATU (5.1 g, 13.386 mmol) in DMF (50 mL) was added DIEA (5.8 g, 44.620 mmol) at room temperature. The resulting mixture was stirred for 10 mins at room temperature. To the above mixture was added 1-[2-methyl-4-(4,4,5,5-tetramethyl-1,3,2-dioxaborolan-2-yl)phenyl]methanamine hydrochloride (3.8 g, 13.399 mmol) at room temperature. The resulting mixture was stirred for additional 1 h at room temperature. To the resulting mixture was added water (200 mL) and extracted with EtOAc (2×200 mL). The combined organic layers were washed with brine (3×100 mL) and dried over anhydrous $Na_2SO_4$. After filtration, the filtrate was concentrated under reduced pressure. The residue was purified by silica gel column chromatography, eluted with EtOAc in PE (10%-20%) to afford the product (1.13 g, 22%). $^1H$ NMR (400 MHz, $CDCl_3$) δ 7.68-7.64 (m, 2H), 7.34 (d, J=7.5 Hz, 1H), 6.13-6.11 (m, 1H), 4.67 (d, J=5.5 Hz, 2H), 3.98 (d, J=1.8 Hz, 3H), 2.40 (s, 3H), 1.37 (s, 12H); $[M+H]^+$=454.3.

Step 3: tert-butyl 4-(3-cyano-2-(3-methyl-4-((2,3,4,5-tetrafluoro-6-methoxybenzamido)methyl)phenyl)-9,10-dihydro-4H-benzo[d]pyrazolo[1,5-a][1,3]diazepin-7-yl)piperazine-1-carboxylate

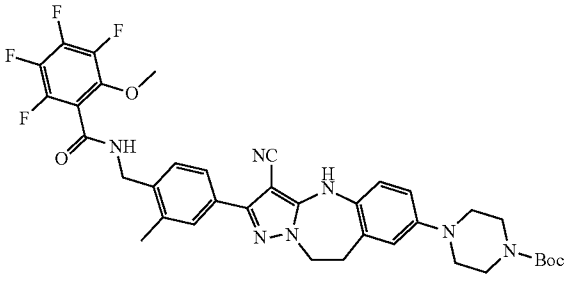 [SMILES: COc1c(F)c(F)c(F)c(F)c1C(=O)NCc1ccc(-c2nn3c(c2C#N)Nc2ccc(N4CCN(C(=O)OC(C)(C)C)CC4)cc2CC3)cc1C]

A mixture of 2,3,4,5-tetrafluoro-6-methoxy-N-(2-methyl-4-(4,4,5,5-tetramethyl-1,3,2-dioxaborolan-2-yl)benzyl)benzamide (0.58 g, 1.28 mmol), tert-butyl 4-(2-bromo-3-cyano-9,10-dihydro-4H-benzo[d]pyrazolo[1,5-a][1,3]diazepin-7-yl)piperazine-1-carboxylate (0.5 g, 0.985 mmol), $Pd_2(dba)_3$ (0.046 g, 0.05 mmol), tricyclohexylphosphane (0.056 g, 0.2 mmol) and $K_3PO_4$ (0.417 g, 2 mmol) in isopropanol (16 mL) and $H_2O$ (4 mL) was stirred in a round bottom flask at 90° C. overnight. The mixture was evaporated in vacuum to afford the crude product, which was further purified with silica gel column chromatography (PE:EA=100:0~10:90 gradient elution) to give the product (0.49 g, 64%). $[M+H]^+$=720.3.

Step 4: 2-(3-methyl-4-((2,3,4,5-tetrafluoro-6-methoxybenzamido)methyl)phenyl)-7-(piperazin-1-yl)-9,10-dihydro-4H-benzo[d]pyrazolo[1,5-a][1,3]diazepine-3-carboxamide

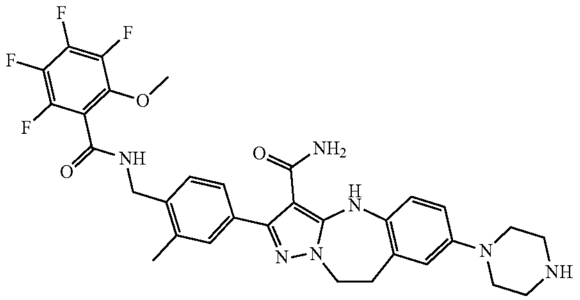 [SMILES: COc1c(F)c(F)c(F)c(F)c1C(=O)NCc1ccc(-c2nn3c(c2C(N)=O)Nc2ccc(N4CCNCC4)cc2CC3)cc1C]

A mixture of tert-butyl 4-(3-cyano-2-(3-methyl-4-((2,3,4,5-tetrafluoro-6-methoxybenzamido)methyl)phenyl)-9,10-dihydro-4H-benzo[d]pyrazolo[1,5-a][1,3]diazepin-7-yl)piperazine-1-carboxylate (0.49 g, 0.681 mmol) in methanesulfonic acid (10.0 mL) was stirred at 100° C. for 0.5 hour. The mixture was then cooled, basified with aqueous sodium hydroxide solution to pH 12 and extracted with dichloromethane (3×30 mL) and water (3×30 mL). The organic phase was dried over anhydrous sodium sulfate, filtered, and concentrated under reduced pressure to afford the product (230 mg, crude). $[M+H]^+$=638.2.

Step 5: 7-(4-((1-(4-(2,4-dioxotetrahydropyrimidin-1(2H)-yl)phenyl)piperidin-4-yl)methyl)piperazin-1-yl)-2-(3-methyl-4-((2,3,4,5-tetrafluoro-6-methoxybenzamido)methyl)phenyl)-9,10-dihydro-4H-benzo[d]pyrazolo[1,5-a][1,3]diazepine-3-carboxamide

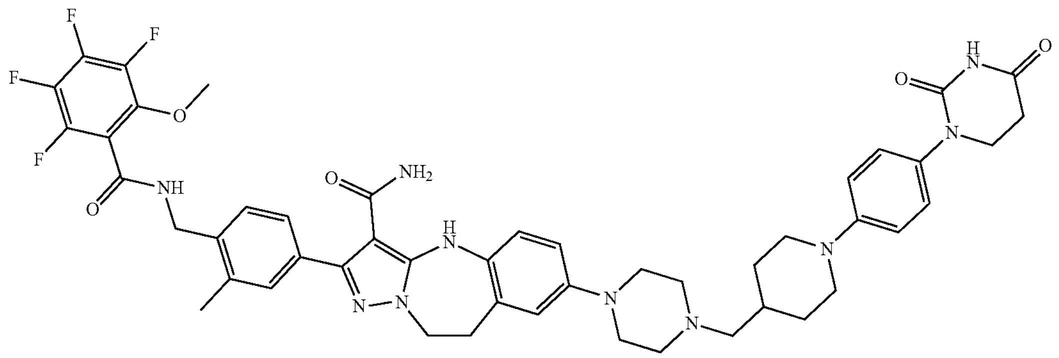 [SMILES: COc1c(F)c(F)c(F)c(F)c1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

A mixture of 2-(3-methyl-4-((2,3,4,5-tetrafluoro-6-methoxybenzamido)methyl)phenyl)-7-(piperazin-1-yl)-9,10-dihydro-4H-benzo[d]pyrazolo[1,5-a][1,3]diazepine-3-carboxamide (0.1 g, 0.157 mmol) and 1-(4-(2,4-dioxotetrahydropyrimidin-1(2H)-yl)phenyl)piperidine-4-carbaldehyde (0.054 g, 0.173 mmol) in 1,2-dichloroethane (5 mL) and HOAc (25 mg) was stirred in a round bottom flask at room temperature for 0.5 hour. To the mixture was added $NaBH(OAc)_3$ (0.05 g, 0.235 mmol) and stirred at room temperature for 12 hours. Then the mixture was evaporated in vacuum to afford the crude product, which was purified by pre-HPLC to afford the product (93.68 mg, 65%). $^1H$ NMR (500 MHz, DMSO) δ 10.25 (s, 1H), 9.79 (s, 1H), 9.17 (t, J=5.7 Hz, 1H), 7.42 (d, J=7.8 Hz, 1H), 7.35 (d, J=7.5 Hz, 2H), 7.13 (d, J=8.9 Hz, 2H), 6.93 (d, J=9.1 Hz, 2H), 6.88-6.77 (m, 3H), 4.51 (d, J=5.5 Hz, 2H), 4.37-4.31 (m, 2H), 3.91 (s, 3H), 3.69 (dd, J=12.0, 5.2 Hz, 4H), 3.45-3.31 (m, 4H), 3.16-3.12 (m, 2H), 3.09 (s, 4H), 2.67 (dd, J=15.2, 8.5 Hz, 4H), 2.37 (s, 3H), 2.22 (d, J=7.1 Hz, 2H), 1.81 (d, J=12.1 Hz, 2H), 1.71 (s, 1H), 1.22 (q, J=11.3 Hz, 2H); $[M+H]^+$=923.3.

Example C44: 7-(4-((1-(4-(2,4-dioxotetrahydropyrimidin-1(2H)-yl)phenyl)piperidin-4-yl)methyl)piperazin-1-yl)-2-(2-methoxy-4-((2-methoxybenzamido)methyl)phenyl)-9,10-dihydro-4H-benzo[d]pyrazolo[1,5-a][1,3]diazepine-3-carboxamide

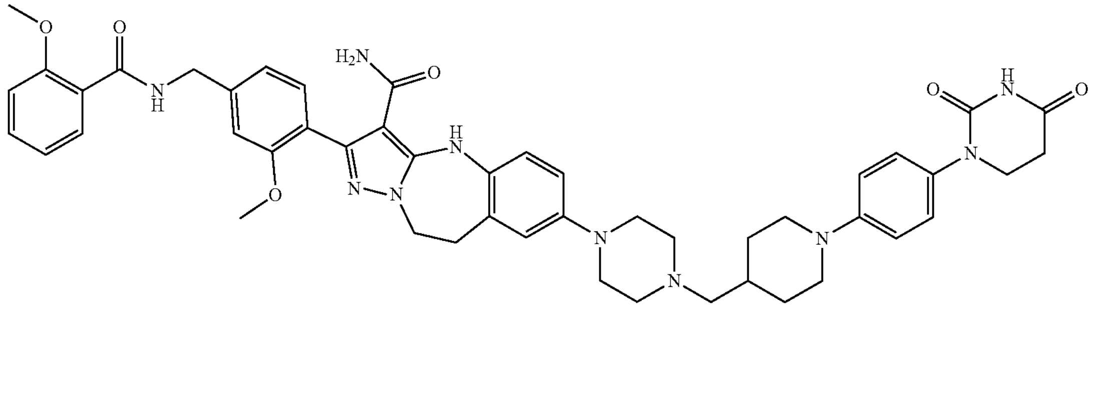 [SMILES: COc1ccccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)c(OC)c1]

The titled compound was synthesized in the procedures similar to Example C43. $^1$H NMR (500 MHz, DMSO) δ 10.27 (s, 1H), 9.78 (s, 1H), 8.75 (t, J=6.1 Hz, 1H), 7.74 (dd, J=7.6, 1.5 Hz, 1H), 7.48 (dd, J=11.2, 4.5 Hz, 1H), 7.23 (d, J=7.6 Hz, 1H), 7.16 (dd, J=8.9, 4.0 Hz, 4H), 7.04 (dd, J=14.2, 7.3 Hz, 2H), 6.99 (d, J=8.6 Hz, 2H), 6.92 (t, J=9.6 Hz, 3H), 4.57 (d, J=6.0 Hz, 2H), 4.39-4.28 (m, 2H), 3.90 (s, 3H), 3.78-3.68 (m, 9H), 3.66-3.59 (m, 2H), 3.22-3.11 (m, 6H), 3.08-2.99 (m, 2H), 2.76 (t, J=11.4 Hz, 2H), 2.69 (t, J=6.7 Hz, 2H), 2.09-2.01 (m, 1H), 1.89-1.81 (m, 2H), 1.41-1.31 (m, 2H); $[M+H]^+$=867.7.

Example C45: 7-(4-((1-(4-(2,4-dioxotetrahydropyrimidin-1(2H)-yl)phenyl)piperidin-4-yl)methyl)piperazin-1-yl)-2-(4-((2-methoxybenzamido)methyl)-3-(trifluoromethyl)phenyl)-9,10-dihydro-4H-benzo[d]pyrazolo[1,5-a][1,3]diazepine-3-carboxamide

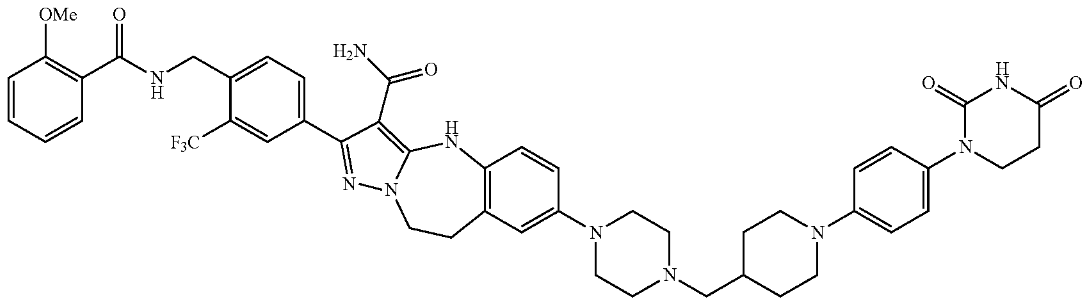 [SMILES: COc1ccccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C(F)(F)F]

The titled compound was synthesized in the procedures similar to Example C43. $^1$H NMR (500 MHz, DMSO) δ 10.25 (s, 1H), 9.59 (s, 1H), 8.85 (t, J=6.0 Hz, 1H), 7.84 (d, J=8.6 Hz, 2H), 7.78 (dd, J=7.6, 1.7 Hz, 1H), 7.66 (d, J=7.8 Hz, 1H), 7.54-7.49 (m, 1H), 7.19 (d, J=8.4 Hz, 1H), 7.13 (d, J=8.8 Hz, 2H), 7.06 (t, J=7.5 Hz, 1H), 6.92 (d, J=8.9 Hz, 2H), 6.87 (d, J=8.7 Hz, 2H), 6.82 (d, J=8.5 Hz, 1H), 4.76-4.71 (m, 2H), 4.40-4.31 (m, 2H), 3.93 (s, 3H), 3.70-3.66 (m, 4H), 3.34-3.26 (m, 3H), 3.15-3.13 (m, 2H), 3.11-3.05 (m, 5H), 2.69-2.64 (m, 4H), 2.22-2.21 (m, 2H), 1.81-1.79 (m, 2H), 1.74-1.68 (m, 1H), 1.25-1.19 (m, 2H); $[M+H]^+$=905.6.

Example C46: 7-(4-((1-(4-(2,4-dioxotetrahydropyrimidin-1(2H)-yl)phenyl)piperidin-4-yl)methyl)piperazin-1-yl)-2-(2-fluoro-4-((2-methoxybenzamido)methyl)-3-methylphenyl)-9,10-dihydro-4H-benzo[d]pyrazolo[1,5-a][1,3]diazepine-3-carboxamide

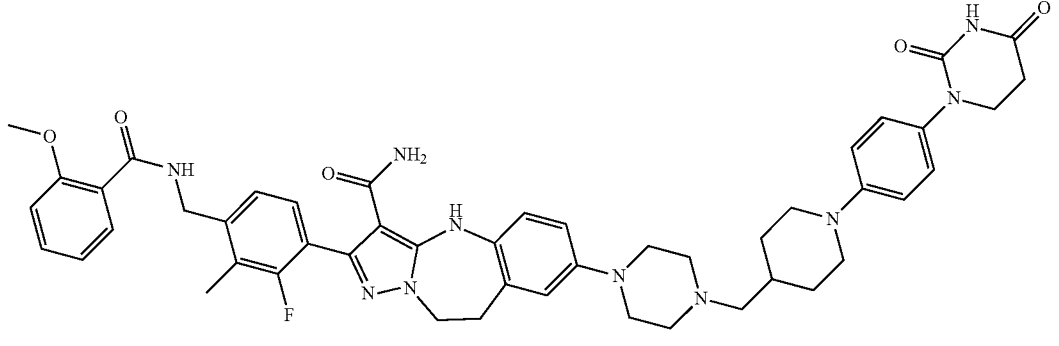 [SMILES: COc1ccccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)c(F)c1C]

The titled compound was synthesized in the procedures similar to Example C43. $^1$H NMR (400 MHz, DMSO) δ 10.27 (s, 1H), 9.68 (s, 1H), 8.70 (t, J=6.0 Hz, 1H), 7.73 (dd, J=8.0, 2.0 Hz, 1H), 7.54-7.44 (m, 1H), 7.31-7.21 (m, 2H), 7.18-7.10 (m, 3H), 7.04 (t, J=8.0 Hz, 1H), 6.97-6.79 (m, 5H), 4.55 (d, J=6.0 Hz, 2H), 4.40-4.24 (m, 2H), 3.90 (s, 3H), 3.74-3.64 (m, 4H), 3.17-3.12 (m, 2H), 3.09 (s, 4H), 2.72-2.61 (m, 4H), 2.54-2.50 (m, 6H), 2.28 (s, 3H), 2.22 (d, J=8.0 Hz, 2H), 1.81 (d, J=12.0 Hz, 2H), 1.71 (s, 1H), 1.22 (q, J=12.0 Hz, 2H); $[M+H]^+$=869.6.

Example C47: 2-(2,3-difluoro-4-((2-methoxybenzamido)methyl)phenyl)-7-(4-((1-(4-(2,4-dioxotetrahydropyrimidin-1(2H)-yl)phenyl)piperidin-4-yl)methyl)piperazin-1-yl)-9,10-dihydro-4H-benzo[d]pyrazolo[1,5-a] [1,3]diazepine-3-carboxamide

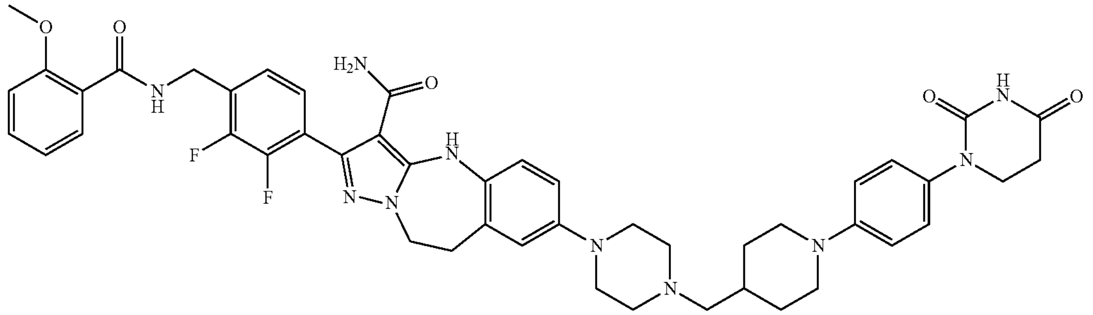 [SMILES: COc1ccccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)c(F)c1F]

The titled compound was synthesized in the procedures similar to Example C43. $^1$H NMR (500 MHz, DMSO) δ 10.18 (s, 1H), 9.56 (s, 1H), 8.73 (t, J=6.0 Hz, 1H), 7.69 (dd, J=7.6, 1.7 Hz, 1H), 7.46-7.40 (m, 1H), 7.24-7.17 (m, 2H), 7.10 (d, J=8.3 Hz, 1H), 7.06 (d, J=8.9 Hz, 2H), 6.98 (t, J=7.4 Hz, 1H), 6.85 (d, J=9.0 Hz, 2H), 6.80 (d, J=8.9 Hz, 2H), 6.75 (d, J=8.6 Hz, 1H), 4.56 (d, J=5.8 Hz, 2H), 4.35-4.22 (m, 2H), 3.84 (s, 3H), 3.64-3.58 (m, 4H), 3.12-3.05 (m, 2H), 3.05-2.96 (m, 4H), 2.62-2.56 (m, 4H), 2.49-2.45 (m, 4H), 2.18-2.10 (m, 2H), 1.78-1.70 (m, 2H), 1.68-1.58 (m, 1H), 1.19-1.11 (m, 2H); $[M+H]^+$=873.6.

Example C48:7-(4-((1-(4-(2,4-dioxotetrahydropyrimidin-1(2H)-yl)phenyl)piperidin-4-yl)methyl)piperazin-1-yl)-2-(2-fluoro-4-((2-methoxybenzamido)methyl)-5-methylphenyl)-9,10-dihydro-4H-benzo[d]pyrazolo[1,5-a][1,3]diazepine-3-carboxamide Step 1: benzyl 4-(3-cyano-2-(2-fluoro-4-((2-methoxybenzamido)methyl)-5-methylphenyl)-9,10-dihydro-4H-benzo[d]pyrazolo[1,5-a][1,3]diazepin-7-yl)piperazine-1-carboxylate

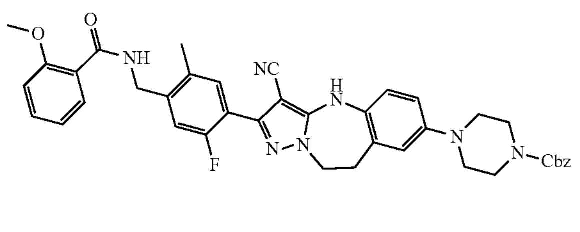 [SMILES: COc1ccccc1C(=O)NCc1cc(F)c(-c2nn3c(c2C#N)Nc2ccc(N4CCN(C(=O)OCc5ccccc5)CC4)cc2CC3)cc1C]

A mixture of benzyl 4-(2-bromo-3-cyano-9,10-dihydro-4H-benzo[d]pyrazolo[1,5-a][1,3]diazepin-7-yl)piperazine-1-carboxylate (506 mg, 1 mmol), N-(5-fluoro-2-methyl-4-(4,4,5,5-tetramethyl-1,3,2-dioxaborolan-2-yl)benzyl)-2-methoxybenzamide (400 mg, 1 mmol), $Na_2CO_3$ (212 mg, 2 mmol) and $Pd(PPh_3)_4$ (115 mg, 0.1 mmol) in dioxane/water (20 mL/4 mL) was stirred at 95° C. overnight under $N_2$. The mixture was cooled down to room temperature, and concentrated under reduced pressure. The residue was purified by silica gel column chromatography PE:EA=100%:0% 0%:100% to afford the desired product (494 mg, 70%). $[M+H]^+$=700.0.

Step 2: 2-(2-fluoro-4-((2-methoxybenzamido)methyl)-5-methylphenyl)-7-(piperazin-1-yl)-9,10-dihydro-4H-benzo[d]pyrazolo[1,5-a][1,3]diazepine-3-carboxamide

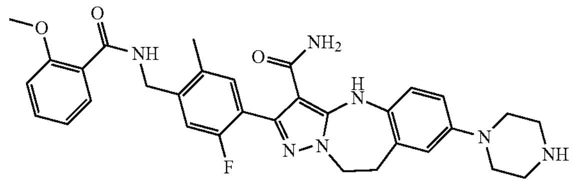 [SMILES: COc1ccccc1C(=O)NCc1cc(F)c(-c2nn3c(c2C(N)=O)Nc2ccc(N4CCNCC4)cc2CC3)cc1C]

A mixture of benzyl 4-(3-cyano-2-(2-fluoro-4-((2-methoxybenzamido)methyl)-5-methylphenyl)-9,10-dihydro-4H-benzo[d]pyrazolo[1,5-a][1,3]diazepin-7-yl)piperazine-1-carboxylate (494 mg, 0.706 mmol) in methanesulfonic acid (10.0 mL) was stirred at 100° C. for 30 mins. The mixture was then cooled, basified with aqueous sodium hydroxide solution to pH 12 and extracted with dichloromethane (3×30 mL) and water (3×30 mL). The organic phase was dried over anhydrous sodium sulfate, filtered, and concentrated under reduced pressure to afford the product (380 mg, 92%). $[M+H]^+$=584.0.

Step 3: 7-(4-((1-(4-(2,4-dioxotetrahydropyrimidin-1(2H)-yl)phenyl)piperidin-4-yl)methyl)piperazin-1-yl)-2-(2-fluoro-4-((2-methoxybenzamido)methyl)-5-methylphenyl)-9,10-dihydro-4H-benzo[d]pyrazolo[1,5-a][1,3]diazepine-3-carboxamide

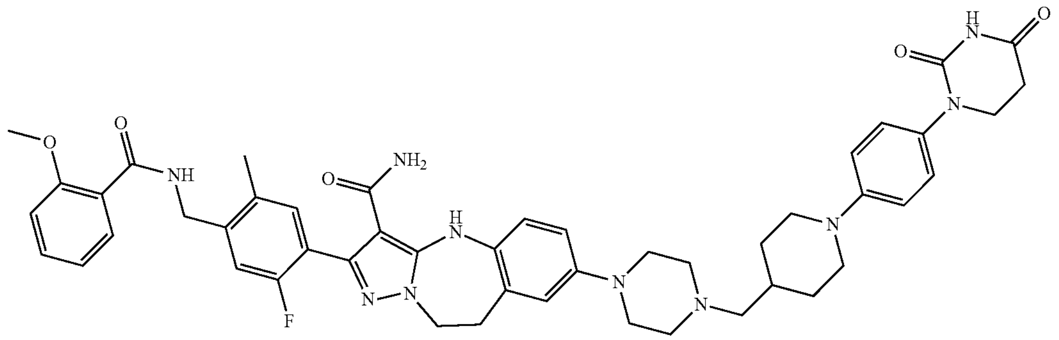 [SMILES: COc1ccccc1C(=O)NCc1cc(F)c(-c2nn3c(c2C(N)=O)Nc2ccc(N4CCN(CC5CCN(c6ccc(N7CCC(=O)NC7=O)cc6)CC5)CC4)cc2CC3)cc1C]

A mixture of 2-(2-fluoro-4-((2-methoxybenzamido)methyl)-5-methylphenyl)-7-(piperazin-1-yl)-9,10-dihydro-4H-benzo[d]pyrazolo[1,5-a][1,3]diazepine-3-carboxamide (100 mg, 0.176 mmol) and 1-(4-(2,4-dioxotetrahydropyrimidin-1(2H)-yl)phenyl)piperidine-4-carbaldehyde (67 mg, 0.223 mmol) in MeOH (5.0 mL), DCM (5.0 mL) and acetic acid (0.06 mL) was stirred at room temperature for 16 hours. Then $NaBH(OAc)_3$ (186.5 mg, 0.88 mmol) was added and stirred at room temperature for 2 hours. The reaction mixture was concentrated in vacuum, and the residue was purified by silica gel column chromatography (DCM:MeOH=100%: 0%~90%: 10% gradient elution) to give crude product, which was further purified by prep-TLC (DCM:MeOH=10:1) to afford desired product (23.44 mg, 16%). $^1H$ NMR (400 MHz, DMSO) δ 10.27 (s, 1H), 9.65 (s, 1H), 8.73 (t, J=6.0 Hz, 1H), 7.70 (dd, J=8.0, 2.0 Hz, 1H), 7.55-7.43 (m, 1H), 7.30 (d, J=8.0 Hz, 1H), 7.24-7.10 (m, 4H), 7.05 (t, J=8.0 Hz, 1H), 6.93 (d, J=8.0 Hz, 2H), 6.89-6.77 (m, 3H), 4.50 (d, J=4.0 Hz, 2H), 4.40-4.28 (m, 2H), 3.91 (s, 3H), 3.75-3.63 (m, 4H), 3.20-3.13 (m, 2H), 3.08 (s, 4H), 2.71-2.61 (m, 4H), 2.54-2.49 (m, 6H), 2.33 (s, 3H), 2.21 (d, J=4.0 Hz, 2H), 1.81 (d, J=12.0 Hz, 2H), 1.71 (s, 1H), 1.22 (q, J=12.0 Hz, 2H); $[M+H]^+$=869.6.

Example C49:7-(4-((1-(4-(2,4-dioxotetrahydropyrimidin-1(2H)-yl)phenyl)piperidin-4-yl)methyl)piperazin-1-yl)-2-(4-((2-methoxy-3-methylbenzamido)methyl)-3-methylphenyl)-9,10-dihydro-4H-benzo[d]pyrazolo[1,5-a][1,3]diazepine-3-carboxamide The titled compound was synthesized in the procedures similar to Example C31. $^1H$ NMR (500 MHz, DMSO) δ 10.26 (s, 1H), 9.81 (s, 1H), 8.69 (t, J=5.4 Hz, 1H), 7.43 (d, J=7.6 Hz, 1H), 7.39 (d, J=7.5 Hz, 1H), 7.33-7.31 (m, 3H), 7.13-7.08 (m, 3H), 6.92 (d, J=8.5 Hz, 2H), 6.88-6.78 (m, 3H), 4.50 (d, J=5.0 Hz, 2H), 4.35-3.31 (m, 2H), 3.69-3.59 (m, 8H), 3.16-3.12 (m, 2H), 3.09-3.05 (m, 5H), 2.68-2.63 (m, 5H), 2.39 (s, 3H), 2.27 (s, 3H), 2.24-2.12 (m, 3H), 1.83-1.77 (m, 2H), 1.72-1.68 (m, 1H), 1.25-1.17 (m, 2H); $[M+H]^+$=865.7.

Cell Degradation

Cell Treatment

TMVD-8 cells were seeded at 20000 cells/well at a volume of 15 μl/well in cell culture medium [RPMI1640 (Gibco, phenol red free, Cat #11835-030), 10% heat-inactive FBS, 1% PS(Gibco, Cat #10378)] in Corning 96 well plate (Cat #3799). TMD-8 cells were treated with compounds diluted in 0.2% DMSO, dilution was done according to the following protocol: (1) making 500× stock solution in DMSO from 1 mM by 6-fold dilution, total 8 doses were included; (2) making 2× solution in cell culture medium by transferring 0.5 μl 500× stock solution into 125 μl medium; (3) adding 15 μl of 2× solution to cells for incubation of 6 h.

HTFR Assay

After 6 h treatment, 10 μl 14×lysis buffer was added to each well; the plate was sealed and incubated for 30 min at room temperature on a plate shaker; Once the cells was lysed, 16 μL of cell lysate were transferred to a PE 384-well

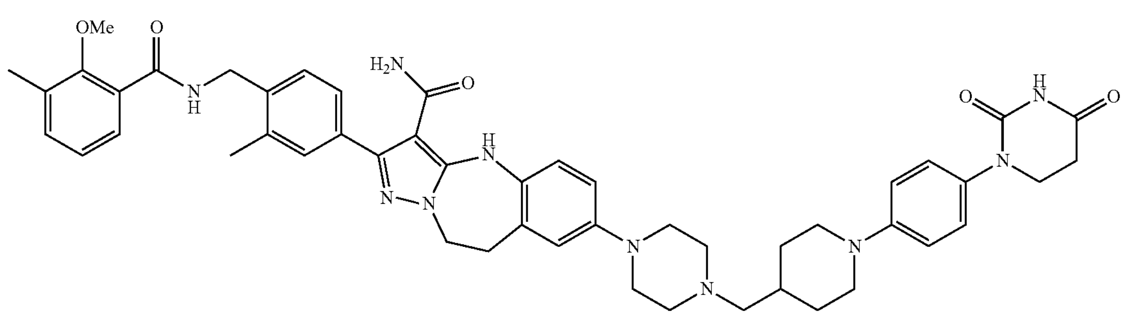 [SMILES: COc1c(C)cccc1C(=O)NCc1ccc(-c2nn3c(c2C(N)=O)Nc2ccc(N4CCN(CC5CCN(c6ccc(N7CCC(=O)NC7=O)cc6)CC5)CC4)cc2CC3)cc1C]

HTRF detection plate; 4 μL of pre-mixed HTRF antibodies were added to each well; the plate was covered with a plate sealer, and then spinned at 1000 rpm for 1 min, then incubated overnight at room temperature; the results were read on BMG PheraStar with HTRF protocol (337 nm-665 nm-620 nm).

The inhibition (degradation) percentage of the compound was calculated by the following equation: Inhibition percentage of Compound=100−100×(Signal-low control)/(High control-low control), wherein signal=each test compound group Low control=only lysis buffer without cells, indicating that BTK is completely degraded;

High control=Cell group with added DMSO and without compound, indicating microplate readings without BTK degradation;

Dmax is the maximum percentage of inhibition (degradation).

The $IC_{50}$ ($DC_{50}$) value of a compound can be obtained by fitting the following equation $$Y=\text{Bottom}+(\text{TOP}-\text{Bottom})/(1+((IC_{50}/X)^\wedge\text{hillslope}))$$

wherein, X and Y are known values, and $IC_{50}$, Hillslope, Top and Bottom are the parameters obtained by fitting with software. Y is the inhibition percentage (calculated from the equation), X is the concentration of the compound; $IC_{50}$ is the concentration of the compound when the 50% inhibition is reached. The smaller the $IC_{50}$ value is, the stronger the inhibitory ability of the compound is. Vice versa, the higher the $IC_{50}$ value is, the weaker the ability the inhibitory ability of the compound is; Hillslope represents the slope of the fitted curve, generally around 1*; Bottom represents the minimum value of the curve obtained by data fitting, which is generally 0%±20%; Top represents the maximum value of the curve obtained by data fitting, which is generally 100%±20%. The experimental data were fitted by calculating and analyzing with Dotmatics data analysis software.

HEK-293 Cell Treatment

HEK-293 cells were seeded at 2000 cells/well at a volume of 50 ul/well in cell culture medium [DMEM (Gibco, Cat #11965-092), 10% heat-inactive FBS(Gibco, Cat #10099), 1% PS(Gibco, Cat #10378)] in Corning 96 well plate (Cat #3903), and then incubated overnight. HEK-293 cells were treated with compounds diluted in 0.2% DMSO, dilution was done according to the following protocol: (1) making 500× stock solution in DMSO from 5 mM by 4-fold dilution, total 8 doses were included; (2) making 2× solution in cell culture medium by transferring 0.5 ul 500× stock solution into 125 ul medium; (3) adding 50 ul of 2× solution to cells for incubation of 72 h.

Cytotoxicity Detection

25 μl of the CellTiter-Glo®Reagent [(Promega)—Cat No. G7572] was added to each well in the 96-well plate. The contents were mixed for 2 minutes on an orbital shaker to induce cell lysis. The plate was then allowed to incubate at room temperature for 10 minutes to stabilize luminescent signal. Luminescence was recorded on BMG PheraStar with luminescence protocol.

IC50 Calculation

The inhibition percentage of the compound was calculated by the following equation: Inhibition percentage of Compound=100−100×(Signal-low control)/(High control-low control), wherein signal=each test compound group Low control=only medium group (without cells), indicating that cells proliferation is completely inhibited;

High control=Cell group with added DMSO and without compound, indicating cells proliferation with no inhibition;

Imax is the maximum percentage of inhibition.

The IC50 value of a compound can be obtained by fitting the following equation $$Y=\text{Bottom}+(\text{TOP}-\text{Bottom})/\left(1+\left(IC50/X\right)\wedge\text{hillslope}\right)$$

Wherein, X and Y are known values, and IC50, Hillslope, Top and Bottom are the parameters obtained by fitting with software. Y is the inhibition percentage (calculated from the equation), X is the concentration of the compound; IC50 is the concentration of the compound when the 50% inhibition is reached. The smaller the IC50 value is, the stronger the inhibitory ability of the compound is. Vice versa, the higher the IC50 value is, the weaker the ability the inhibitory ability of the compound is; Hillslope represents the slope of the fitted curve, generally around 1*; Bottom represents the minimum value of the curve obtained by data fitting, which is generally 0%±20%; Top represents the maximum value of the curve obtained by data fitting, which is generally 100%±20%. The experimental data were fitted by calculating and analyzing with Dotmatics data analysis software.

TABLE 1

Degradation and HEK293 result for Example A1 to Example Example A38

| Example | HEK293 (nM) | DC50 (nM) |
|---|---|---|
| A1 | 417 | 3 |
| A2 | 557 | 1.85 |
| A3 | >10000.0 | 20.6 |
| A4 | 78.1 | 1.26 |
| A5 | 83.3 | 1.45 |
| A6 | 163 | 3.42 |
| A7 | 178 | 2.51 |
| A8 | 280 | 2.97 |
| A9 | 65.6 | 2.26 |
| A10 | 121 | 1.75 |
| A11 | 826 | 5.71 |
| A12 | 396.00 | 4.58 |
| A13 | 167.00 | 2.79 |
| A14 | 509.00 | 3.22 |
| A15 | ND | 27.9 |
| A16 | ND | 9.71 |
| A17 | ND | 14.4 |
| A18 | 2510 | 9.62 |
| A19 | ND | 17.9 |
| A20 | >10000.0 | 13.4 |
| A21 | 62.1 | 1.51 |
| A22 | ND | 1.31 |
| A23 | 445 | 9.23 |
| A24 | 235 | 9.26 |
| A25 | >10000.0 | 24.9 |
| A26 | 283 | 16.04 |
| A27 | 317.00 | 6.73 |
| A28 | 81.08 | 2.01 |
| A29 | ND | 16.3 |
| A30 | 28.67 | 1.58 |
| A31 | 555.6 | 11.85 |
| A32 | 416.6 | 6.03 |
| A33 | 313.7 | >2000.0 |
| A34 | 337 | 11.9 |
| A35 | 241 | 69.14 |
| A36 | 147.7 | 3.6 |
| A37 | 69.95 | 4.71 |
| A38 | 184.74 | 1.12 |

TABLE 2

| Table 1. Degradation and HEK293 result for Example B1 to Example Example B103 | | |
|---|---|---|
| Example B | HEK293 (nM) | DC50 (nM) |
| B1 | >10000.0 | 0.561 |
| B2 | >10000.0 | 0.842 |
| B3 | 88.82 | 0.534 |
| B4 | >10000.0 | 0.704 |
| B5 | >10000.0 | 1.46 |
| B6 | >10000.0 | 2.22 |
| B7 | >10000.0 | 5.37 |
| B8 | 301.3 | 1.82 |
| B9 | >10000.0 | 6.14 |
| B10 | >10000.0 | 4.69 |
| B11 | >10000.0 | 0.387 |
| B12 | >10000.0 | 5.82 |
| B13 | 179.5 | 0.408 |
| B14 | 75.42 | 1.61 |
| B15 | 184.7 | 1.13 |
| B16 | 232 | 1.32 |
| B17 | >10000.0 | 2.19 |
| B18 | >10000.0 | 0.378 |
| B19 | >10000.0 | 0.284 |
| B20 | >10000.0 | 0.469 |
| B21 | >10000.0 | 0.602 |
| B22 | >10000.0 | 0.338 |
| B23 | >10000.0 | 0.594 |
| B24 | >10000.0 | 1.51 |
| B25 | >10000.0 | 0.415 |
| B26 | >10000.0 | 0.928 |
| B27 | >10000.0 | 0.849 |
| B28 | >10000.0 | 0.726 |
| B29 | >10000.0 | 2.44 |
| B30 | >10000.0 | 2.53 |
| B31 | 133.2 | >2000 |
| B32 | 331.9 | 8.86 |
| B33 | 400.3 | 17.64 |
| B34 | 167.7 | 57.8 |
| B35 | 97.37 | 10.64 |
| B36 | >10000.0 | 47.24 |
| B37 | >10000.0 | 15.24 |
| B38 | >10000.0 | 4.89 |
| B39 | >10000.0 | 5.66 |
| B40 | >10000.0 | 5.69 |
| B41 | >10000.0 | 9.26 |
| B42 | >10000.0 | 3.67 |
| B43 | >10000.0 | 0.543 |
| B44 | >10000.0 | 2.33 |
| B45 | >10000.0 | 1.69 |
| B46 | >10000.0 | 15 |
| B47 | >10000.0 | 1.9 |
| B48 | >10000.0 | 4.2 |
| B49 | >10000.0 | 13.5 |
| B50 | >10000.0 | 2.16 |
| B51 | 290.4 | 7.39 |
| B52 | >10000.0 | 4.06 |
| B53 | >10000.0 | 18.64 |
| B54 | >10000.0 | 3.75 |
| B55 | >10000.0 | 2.42 |
| B56 | >10000.0 | 4.31 |
| B57 | >10000.0 | 0.526 |
| B58 | >10000.0 | 2.01 |
| B59 | >10000.0 | 1.47 |
| B60 | >10000.0 | 4.97 |
| B61 | >10000.0 | 1.09 |
| B62 | >10000.0 | 1.7 |
| B63 | >10000.0 | 2.32 |
| B64 | >10000.0 | 4.85 |
| B65 | 98.83 | 1.78 |
| B66 | >10000.0 | 1.35 |
| B67 | 96.78 | 0.622 |
| B68 | 104.7 | 2.56 |
| B69 | — | 8.05 |
| B70 | — | 8.66 |
| B71 | >10000.0 | 7.45 |
| B72 | >10000.0 | 6.23 |
| B73 | >10000.0 | 2.18 |
| B74 | >10000.0 | 7.15 |
| B75 | >10000.0 | 30.06 |
| B76 | >10000.0 | >2000 |
| B77 | 38.34 | >2000 |
| B78 | >10000.0 | 6.27 |
| B79 | >10000.0 | 3.68 |
| B80 | >10000.0 | >2000 |
| B81 | 56.81 | >2000 |
| B82 | >10000.0 | 4.1 |
| B83 | >10000.0 | 2.9 |
| B84 | >10000.0 | 2.32 |
| B85 | >10000.0 | 1.87 |
| B86 | >10000.0 | 4.37 |
| B87 | >10000.0 | 0.591 |
| B88 | >10000.0 | 1.63 |
| B89 | >10000.0 | 0.414 |
| B90 | >10000.0 | 0.706 |
| B91 | >10000.0 | 1.36 |
| B92 | >10000.0 | 1.86 |
| B93 | >10000.0 | 3.77 |
| B94 | >10000.0 | 0.378 |
| B95 | 26.78 | 1.7 |
| B96 | 116.1 | 0.586 |
| B97 | >10000.0 | 2.11 |
| B98 | >10000.0 | 1.1 |
| B99 | >10000.0 | 2.72 |
| B100 | 34.07 | 2.14 |
| B101 | 32.31 | 2.42 |
| B102 | >10000.0 | 1.1 |
| B103 | >10000.0 | 3.3 |

TABLE 3

| Degradation and HEK293 result for Example C1 to Example Example C49 | | |
|---|---|---|
| Example C | HEK293 (nM) | DC50 (nM) |
| C1 | >10000.0 | 0.758 |
| C2 | >10000.0 | 0.52 |
| C3 | >10000.0 | 0.343 |
| C4 | >10000.0 | 0.282 |
| C5 | >10000.0 | 3.82 |
| C6 | >10000.0 | 3.4 |
| C7 | >10000.0 | 22.72 |
| C8 | >10000.0 | 15.58 |
| C9 | >10000.0 | 54.18 |
| C10 | >10000.0 | 10.1 |
| C11 | >10000.0 | 3.36 |
| C12 | >10000.0 | 1.82 |
| C13 | >10000.0 | 11.55 |
| C14 | >10000.0 | 2.76 |
| C15 | 8854.9 | 14.58 |
| C16 | >10000 | 60.1 |
| C17 | >10000.0 | 55.1 |
| C18 | >10000.0 | 12.49 |
| C19 | 142.5 | 0.848 |
| C20 | >10000.0 | 0.956 |
| C21 | >10000.0 | 0.703 |
| C22 | >10000.0 | 2.12 |
| C23 | >10000.0 | 2 |
| C24 | >10000.0 | 2.11 |
| C25 | >10000.0 | 0.611 |
| C26 | 108.5 | 1.79 |
| C27 | 208.8 | 1.76 |
| C28 | >10000.0 | 1.15 |
| C29 | >10000.0 | 1.56 |
| C30 | >10000.0 | 0.786 |
| C31 | >10000.0 | 7.02 |
| C32 | >10000.0 | 3.1 |
| C33 | >10000.0 | 9.19 |
| C34 | >10000.0 | 3.91 |
| C35 | >10000.0 | 1.1 |
| C36 | >10000.0 | 6.66 |

TABLE 3-continued

| Degradation and HEK293 result for Example C1 to Example Example C49 | | |
|---|---|---|
| Example C | HEK293 (nM) | DC50 (nM) |
| C37 | >10000.0 | 12.45 |
| C38 | >10000.0 | 7.96 |
| C39 | >10000.0 | 8.52 |
| C40 | >10000.0 | 10.5 |
| C41 | >10000.0 | 9.74 |
| C42 | >10000.0 | 5.36 |
| C43 | 978.8 | 29.43 |
| C44 | 642.5 | 3.8 |
| C45 | >10000.0 | 56.4 |
| C46 | >10000.0 | 4.38 |
| C47 | 221.6 | 4.64 |
| C48 | >10000.0 | 3.52 |
| C49 | >10000.0 | 9.8 |

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

It is to be understood that, if any prior art publication is referred to herein, such reference does not constitute an admission that the publication forms a part of the common general knowledge in the art in any country.

What is claimed is:

1. A compound of Formula (I):

(I)

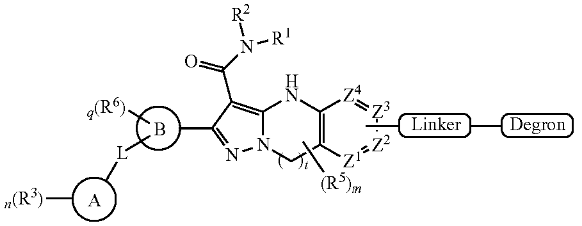

or a pharmaceutically acceptable salt thereof, or a stereoisomer thereof, wherein:

ring A and B are each independently an aromatic ring comprising 0-3 heteroatoms selected from nitrogen, sulfur and oxygen as ring member(s);

$Z^1$, $Z^2$, $Z^3$ and $Z^4$ are each independently N or $CR^z$;

L is independently a bond, —$C_{1-8}$alkylene-, —N($R^4$)—, —O—, —S—, $*^L$—$C_{1-8}$alkylene-O—$**^L$, $*^L$—O—$C_{1-8}$alkylene-$**^L$, $*^L$—N($R^4$)CO—$**^L$, $*^L$—CON($R^4$)—$**^L$, $*^L$—N($R^4$)CO—$C_{1-8}$alkylene-$**^L$, $*^L$—CON($R^4$)—$C_{1-8}$alkylene-$**^L$, $*^L$—N($R^4$)—$C_{1-8}$alkylene-$**^L$, $*^L$—$C_{1-8}$alkylene-N($R^4$)—$**^L$, -heterocyclene-, or -heteroarylene-, wherein each of said —$C_{1-8}$alkylene-, $*^L$—$C_{1-8}$alkylene-O—$**^L$, $*^L$—O—$C_{1-8}$alkylene-$**^L$, $*^L$—N($R^4$)CO—$C_{1-8}$alkylene-$**^L$, $*^L$—CON($R^4$)—$C_{1-8}$alkylene-$**^L$, $*^L$—N($R^4$)—$C_{1-8}$alkylene-$**^L$, $*^L$—$C_{1-8}$alkylene-N($R^4$)—$**^L$, -heterocyclene- and -heteroarylene- is optionally substituted with at least one substituent $R^L$;

wherein $*^L$ refers to the position attached to ring A, and $**^L$ refers to the position attached to ring B;

m, n and q are each independently 0, 1, 2, 3 or 4;

t is 0, 1 or 2;

$R^1$, $R^2$, and $R^4$ are each independently hydrogen, —$C_{1-8}$alkyl, —$C_{2-8}$alkenyl, —$C_{2-8}$alkynyl, cycloalkyl, heterocyclyl, aryl, or heteroaryl, wherein each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkyoxy, cycloalkyl, heterocyclyl, aryl, or heteroaryl;

$R^L$, $R^3$, $R^5$ and $R^6$ are each independently hydrogen, halogen, —$C_{1-8}$alkyl, —$C_{2-8}$alkenyl, —$C_{2-8}$alkynyl, cycloalkyl, heterocyclyl, aryl, heteroaryl, —CN, —$NO^2$, —$OR^a$, —$SO_2R^a$, —$COR^a$, —$CO^2R^a$, —$CONR^aR^b$, —C(=$NR^a$)$NR^bR^c$, —$NR^aR^b$, —$NR^aCOR^b$, —$NR^aCONR^bR^c$, —$NR^aCO_2R^b$, —$NR^aSONR^bR^c$, —$NR^aSO_2NR^bR^c$, or —$NR^aSO_2R^b$, wherein each of said —$C_{1-8}$alkyl, —$C_{2-8}$alkenyl, —$C_{2-8}$alkynyl, cycloalkyl, heterocyclyl, aryl, or heteroaryl is optionally substituted with at least one halogen, hydroxy, —$C_{1-8}$alkyl, —$C_{1-8}$alkyoxy, cycloalkyl, heterocyclyl, aryl, or heteroaryl;

$R^z$ is selected from the bond between

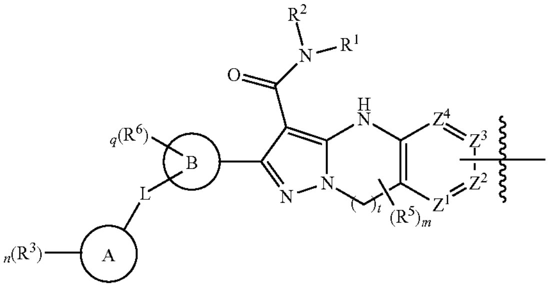

moiety and

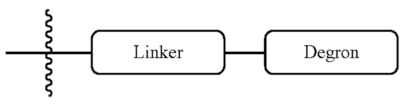

moiety, hydrogen, halogen, —$C_{1-8}$alkyl, —$C_{2-8}$alkenyl, —$C_{2-8}$alkynyl, cycloalkyl, heterocyclyl, aryl, heteroaryl, —CN, —$NO^2$, —$OR^a$, —$SO_2R^a$, —$COR^a$, —$CO^2R^a$, —$CONR^aR^b$, —C(=$NR^a$)$NR^bR^c$, —$NR^aR^b$, —$NR^aCOR^b$, —$NR^aCONR^bR^c$, —$NR^aCO_2R^b$, —$NR^aSONR^bR^c$, —$NR^aSO_2NR^bR^c$, or —$NR^aSO_2R^b$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one halogen, hydroxy, —$C_{1-8}$alkyl, —$C_{1-8}$alkyoxy, cycloalkyl, heterocyclyl, aryl, or heteroaryl;

$R^a$, $R^b$, and $R^c$ are each independently hydrogen, —$C_{1-8}$alkyl, —$C_{2-8}$alkenyl, —$C_{2-8}$alkynyl, cycloalkyl, heterocyclyl, aryl, or heteroaryl;

or two $R^L$, together with the atom(s) to which they are attached, form a 3- to 12-membered ring, said ring comprising 0, 1 or 2 additional heteroatoms independently selected from nitrogen, oxygen or optionally oxidized sulfur as ring member(s), said ring is optionally substituted with at least one substituent independently selected from halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO^2$, —$OR^{3f}$, —$SO_2R^{3f}$, —$SO_2NR^{3f}R^{3g}$, —$COR^{3f}$, —$CO_2R^{3f}$, —$CONR^{3f}R^{3g}$, —C(=$NR^{3f}$) $NR^{3g}R^{3h}$, —$NR^{3f}R^{3g}$, —$NR^{3f}COR^{3g}$, —$NR^{3f}CONR^{3g}R^{3h}$, —$NR^{3f}CO_2R^{3f}$, —$NR^{3f}SONR^{3f}R^{3g}$, —$NR^{3f}SO_2NR^{3g}R^{3h}$, or —$NR^{3f}SO_2R^{3g}$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituent selected from halogen, —$C_{1-8}$alkyl, —$OR^{3i}$, —$NR^{3i}R^{3j}$, cycloalkyl, heterocyclyl, aryl, or heteroaryl;

or two $R^3$, together with the atoms to which they are attached, form a 3- to 12-membered ring, said ring comprising 0, 1 or 2 additional heteroatoms independently selected from nitrogen, oxygen or optionally oxidized sulfur as ring member(s), said ring is optionally substituted with at least one substituent independently selected from halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO_2$, —$OR^{3f}$, —$SO_2R^{3f}$, —$SO_2NR^{3f}R^{3g}$, —$COR^{3f}$, —$CO_2R^{3f}$, —$CONR^{3f}R^{3g}$, —C(=$NR^{3f}$)$NR^{3g}R^{3h}$, —$NR^{3f}R^{3g}$, —$NR^{3f}COR^{3g}$, —$NR^3CONR^{3g}R^{3h}$, —$NR^{3f}CO_2R^{3f}$, —$NR^{3f}SONR^{3f}R^{3g}$, —$NR^{3f}SO_2NR^{3g}R^{3h}$, or —$NR^{3f}SO_2R^{3g}$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituent selected from halogen, —$C_{1-8}$alkyl, —$OR^{3i}$, —$NR^{3i}R^{3j}$, cycloalkyl, heterocyclyl, aryl, or heteroaryl;

or $R^4$ and one of $R^3$, together with the atoms to which they are attached, form a 3- to 12-membered ring, said ring comprising 0, 1 or 2 additional heteroatoms independently selected from nitrogen, oxygen or optionally oxidized sulfur as ring member(s), said ring is optionally substituted with at least one substituent independently selected from halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO^2$, —$OR^{3f}$, —$SO_2R^{3f}$, —$SO_2NR^{3f}R^{3g}$, —$COR^{3f}$, —$CO_2R^{3f}$, —$CONR^{3f}R_{3g}$, —C(=$NR^{3f}$) $NR^{3g}R^{3h}$, —$NR^{3f}R^{3g}$, —$NR^{3f}COR^{3g}$, —$NR^{3f}CONR^{3g}R^{3h}$, —$NR^{3f}CO_2R^{3f}$, —$NR^{3f}SONR^{3f}R_{3g}$, —$NR^{3f}SO_2NR^{3g}R^{3h}$, or —$NR^{3f}SO_2R^{3g}$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituent selected from halogen, —$C_{1-8}$alkyl, —$OR^{3i}$, —$NR^{3i}R^{3j}$, cycloalkyl, heterocyclyl, aryl, or heteroaryl;

$R^{3f}$, $R^{3g}$, $R^{3h}$, $R^{3i}$, and $R^{3j}$ are each independently hydrogen, —$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl, or heteroaryl;

the Linker is a bond or a divalent linking group, and the Degron is an E3 Ubiquitin ligase moiety.

2. The compound according to claim 1, wherein the Degron moiety is selected from Formulas D1, D2 or D3:

D1

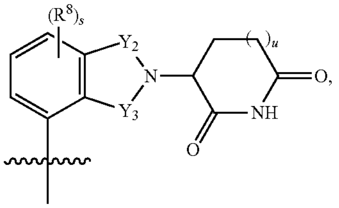

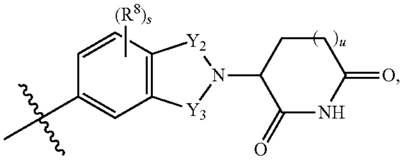

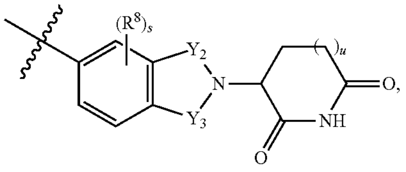

or

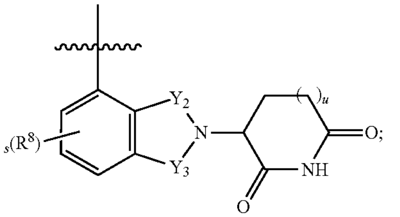

or

D2

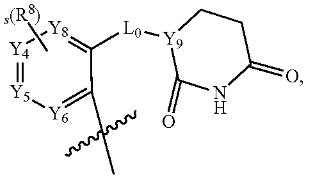

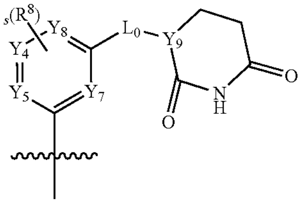

or

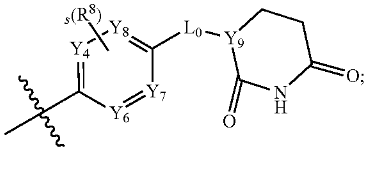

D3

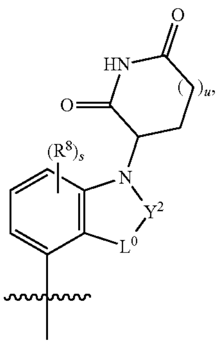

-continued

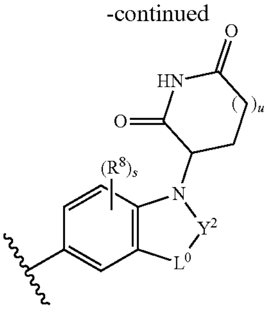

or

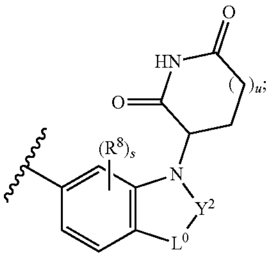

wherein, at each of its occurrences, $Y_2$ and $Y_3$ are each independently —$CH_2$—, —NH— or —C(O)—;

$L_0$ is selected from a bond, —$CH_2$—, —O—, —NH— and —S—; wherein each of $Y_2$, $Y_3$ and $L_0$ is independently optionally substituted with at least one substituent selected from hydrogen, halogen, —$C_{1-8}$alkyl, —$C_{2-8}$alkenyl, —$C_{2-8}$alkynyl, cycloalkyl, heterocyclyl, aryl, heteroaryl, —CN;

$Y_4$, $Y_5$, $Y_6$, $Y_7$ and $Y_8$ are each independently CH or N;

$Y_9$ is CH or N;

s is 0, 1, 2, 3, or 4;

u is 0, 1, or 2;

$R^8$ is each independently hydrogen, halogen, —$C_{1-8}$alkyl, —$C_{2-8}$alkenyl, —$C_{2-8}$alkynyl, cycloalkyl, heterocyclyl, aryl, heteroaryl, —CN, —$NO^2$, —$OR^{8a}$, —$SO_2R^{8a}$, —$COR^{8a}$, —$CO_2R^{8a}$, —$CONR^{8a}R^{8b}$, —C(=$NR^{8a}$)$NR^{8b}R^{8c}$, —$NR^{8a}R^{8b}$, —$NR^{8a}COR^{8b}$, —$NR^{8a}CONR^{8b}R^{8c}$, —$NR^{8a}CO_2R^{8b}$, —$NR^{8a}SONR^{8b}R^{8c}$, —$NR^{8a}SO_2NR^{8b}R^{8c}$, or —$NR^{8a}SO_2R^{8b}$, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkyoxy, cycloalkyl, heterocyclyl, aryl, or heteroaryl; and $R^{8a}$, $R^{8b}$, and $R^{8c}$ are each independently hydrogen, —$C_{1-8}$alkyl, —$C_{2-8}$alkenyl, —$C_{2-8}$alkynyl, cycloalkyl, heterocyclyl, aryl, or heteroaryl.

3. The compound according to claim 2, wherein (a) Formula D1 is selected from

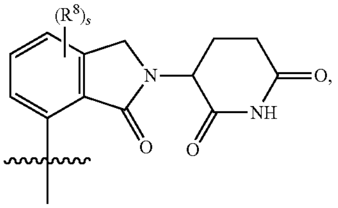

-continued

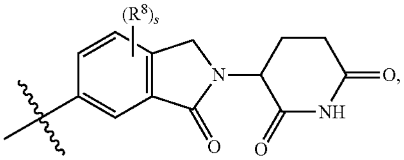

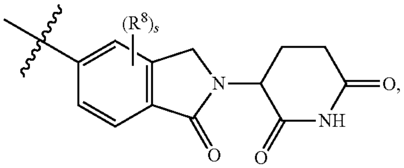

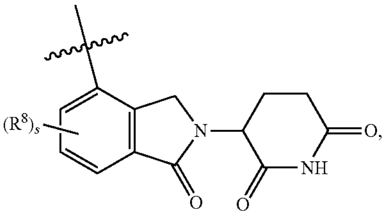

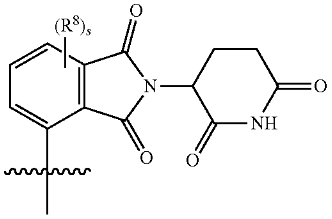

or

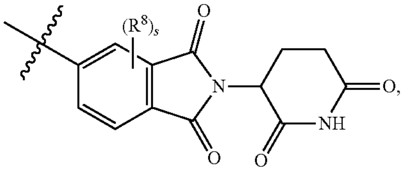

wherein $R^8$ is defined as in claim 2; or (b) Formula D1 is selected from

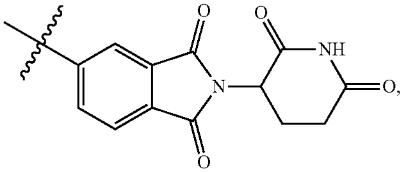

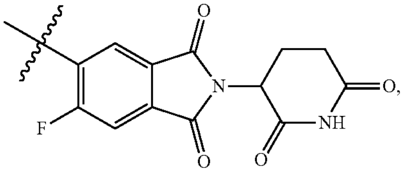

-continued
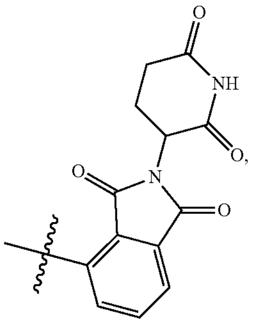
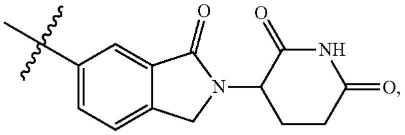
or
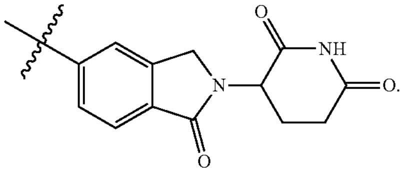
4. The compound according to claim 2, wherein (a) Formula D2 is selected from
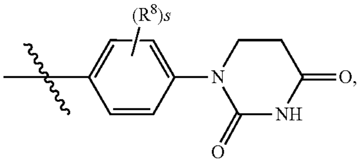
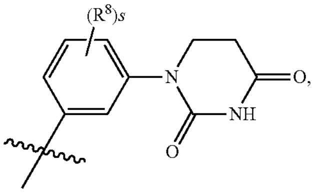
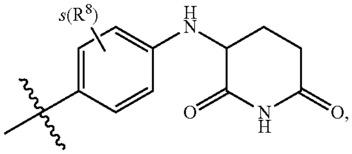
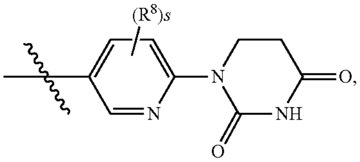
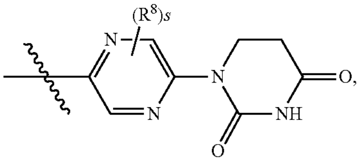
-continued
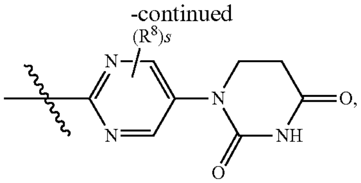
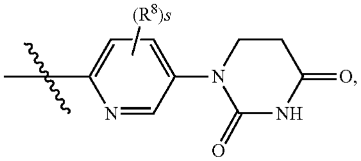
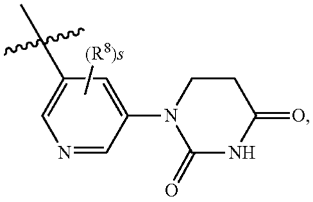
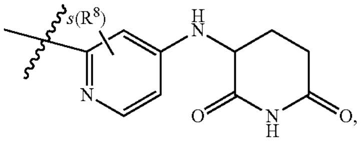
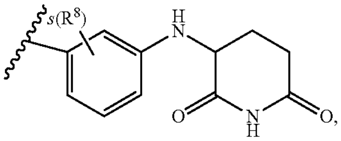
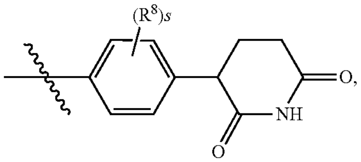
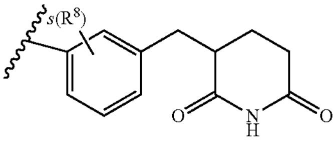
or
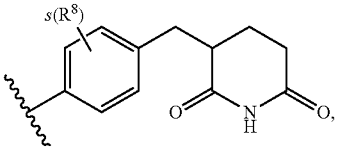
wherein $R^8$ is defined as in claim 2; or (b) Formula D2 is selected from
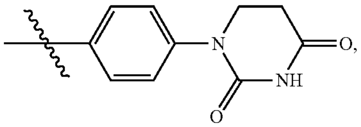
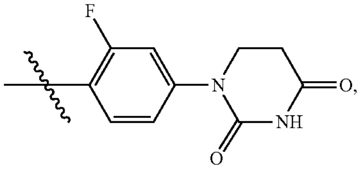

-continued
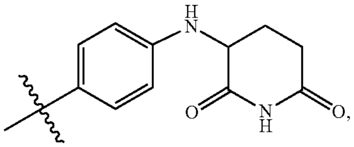
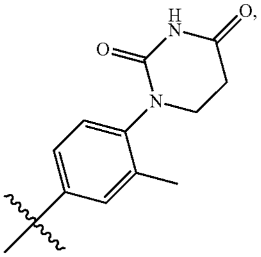
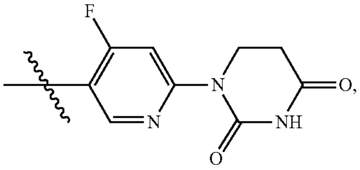
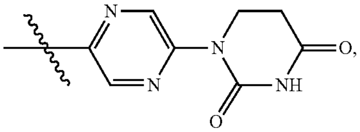
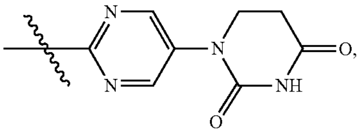
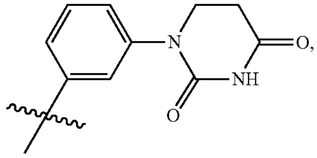
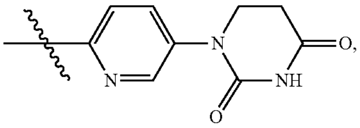
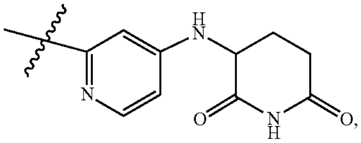
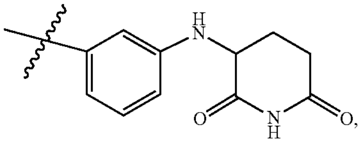
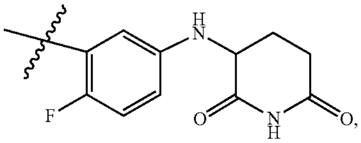
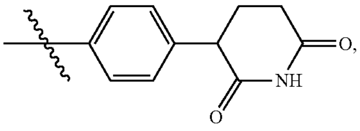
-continued
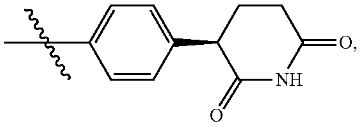
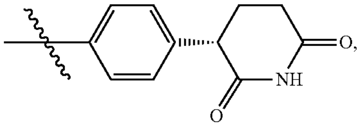
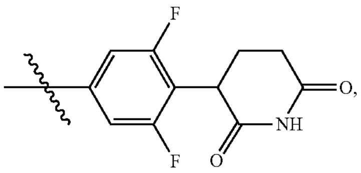
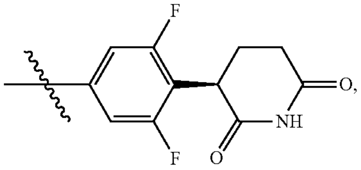
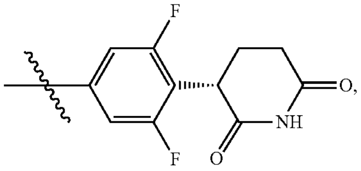
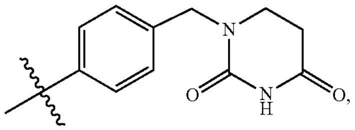
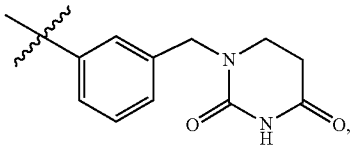
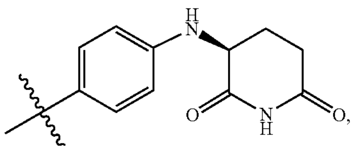
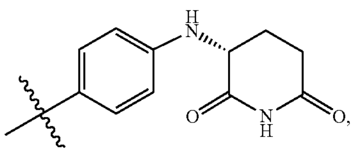

5. The compound according to claim 2, wherein (a) Formula D3 is selected from

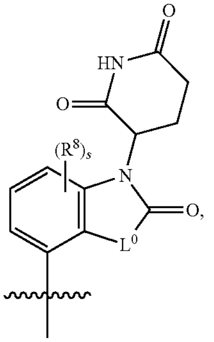

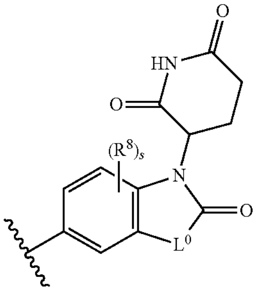

or

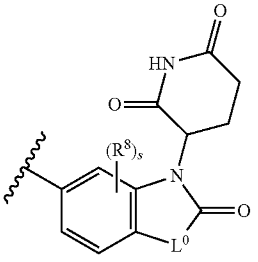

wherein $R^8$ is defined as above;

$L^0$ is selected from a bond, —$CH_2$—, —O—, —NH— and —S—; wherein $L^0$ is independently optionally substituted with at least one substituent selected from hydrogen, F, Cl, Br, I, —$CH_3$, —$C_2H_5$, —$C_3H_7$, —$C_4H_9$, —$C_5H_{11}$, —$C_{2-8}$alkenyl, —$C_{2-8}$alkynyl, cyclopropyl, cyclobutyl, cyclopentyl, cyclohexyl, cycloheptyl, cyclooctyl, heterocyclyl, aryl, heteroaryl or —CN; or (b) Formula D3 is selected from

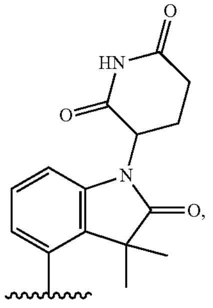

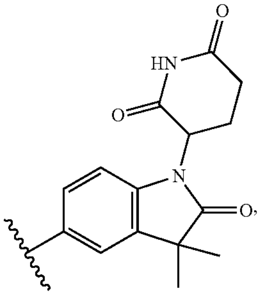

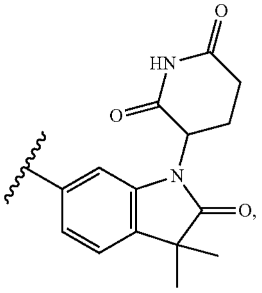

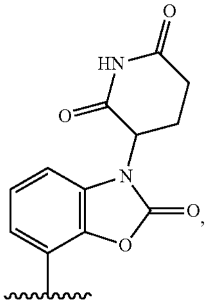

-continued

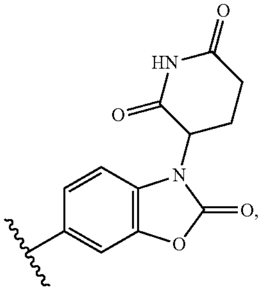

or

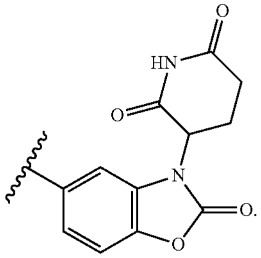

6. The compound according to claim 1, wherein (a) L is a bond, —$CH_2$—, —$C_2H_4$—, —$C_3H_6$—, —$C_4H_8$—, —$C_5H_{10}$—, —O—, —NH—, $*^L$—$NHCH_2$—$**^L$, $*^L$—$NHC_2H_4$—$**^L$, $*^L$—$NHC_3H_6$—$**^L$, $*^L$—$NHC_4H_8$—$**^L$, $*^L$—$NHC_5H_{10}$—$**^L$, $*^L$—$OCH_2$—$**^L$, $*^L$—$OC_2H_4$—$**^L$, $*^L$—$OC_3H_6$—$**^L$, $*^L$—$OC_4H_8$—$**^L$, $*^L$—$OCH_{10}$—$**^L$, $*^L$—$CH_2O$—$**^L$, $*^L$—$C_2H_4O$—$**^L$, $*^L$—$C_3H_6O$—$**^L$, $*^L$—$C_4H_8O$—$**^L$, $*^L$—$C_5H_{10}O$—$**^L$, $*^L$—CONH—$**^L$, $*^L$—NHCO—$**^L$, $*^L$—$CONHCH_2$—$**^L$, $*^L$—$CONHC_2H_4$—$**^L$, $*^L$—$CONHC_3H_6$—$**^L$, $*^L$—$CONHC_4H_8$—$**^L$, $*^L$—$CONHC_5H_{10}$—$**^L$,

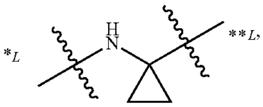 [SMILES: *NC1(*)CC1]

3- to 8-membered-heterocyclene- or 5- to 6-membered-heteroarylene-; wherein each of said —$CH_2$—, —$C_2H_4$—, —$C_3H_6$—, —$C_4H_8$—, —$C_5H_{10}$—, —O—, —NH—, $*^L$—$NHCH_2$—$**^L$, $*^L$—$NHC_2H_4$—$**^L$, $*^L$—$NHC_3H_6$—$**^L$, $*^L$—$NHC_4H_8$—$**^L$, $*^L$—$NHC_5H_{10}$—$**^L$, $*^L$—$OCH_2$—$**^L$, $*^L$—$OCH_4$—$**^L$, $*^L$—$OC_3H_6$—$**^L$, $*^L$—$OC_4H_8$—$**^L$, $*^L$—$OCH_{10}$—$**^L$, $*^L$—$CH_2O$—$**^L$, $*^L$—$C_2H_4O$—$**^L$, $*^L$—$C_3H_6O$—$**^L$, $*^L$—$C_4H_8O$—$**^L$, $*^L$—$C_5H_{10}O$—$**^L$, $*^L$—CONH—$**^L$, $*^L$—NHCO—$**^L$, $*^L$—$CONHCH_2$—$**^L$, $*^L$—$CONHC_2H_4$—$**^L$, $*^L$—$CONHC_3H_6$—$**^L$, $*^L$—$CONHC_4H_8$—$**^L$, $*^L$—$CONHC_5H_{10}$—$**^L$,

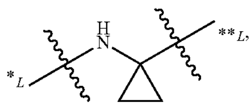 [SMILES: *NC1(*)CC1]

3- to 8-membered-heterocyclene-and 5- to 6-membered-heteroarylene- is optionally substituted with at least one substituent $R^L$; wherein $R^L$ is defined as in claim 1; or (b) L is a bond, —O—, $*^L$—$OCH_2$—$**^L$, $*^L$—$CH_2O$—$**^L$, —NH—, $*^L$—CONH—$**^L$, $*^L$—NHCO—$**^L$, $*^L$—$CONHCH_2$—$**^L$, $*^L$—$CONHCH_2CH_2$—$**^L$, $*^L$—$CONHCH_2CH_2CH_2$—$**^L$, $*^L$—CONHCH$(CH_3)$—$**^L$, $*^L$—CONHCH$(C_2H_5)$—$**^L$, $*^L$—$NHCH_2$—$**^L$, $*^L$—$NHCH_2CH_2$—$**^L$, $*^L$—$NHCH_2CH_2CH_2$—$**^L$, $*^L$—NHCH$(CH_3)$—$**^L$, $*^L$—NHCH$(C_2H_5)$—$**^L$,

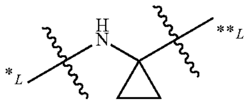 or

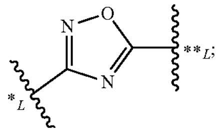

or (c) L is $*^L$—N($R^4$)CO—$**^L$, $R^3$ and $R^4$, together with the atoms to which they are attached, form a 5-, 6- or 7-membered ring, said ring comprising 0, 1 or 2 additional heteroatoms independently selected from nitrogen, oxygen or optionally oxidized sulfur as ring member(s), said ring is optionally substituted with at least one substituent independently selected from —F, —Cl, —Br, —I, —$CH_3$, —$C_2H_5$, —$C_3H_7$, —$C_4H_9$, —$C_5H_{11}$, cycloalkyl, heterocyclyl, aryl, heteroaryl, or oxo.

7. The compound according to claim 1, wherein (a)

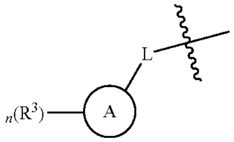

moiety is

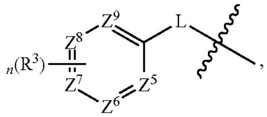,

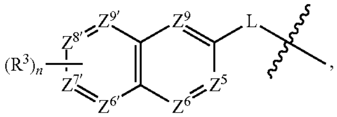,

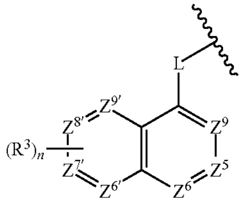, 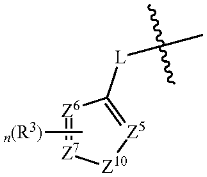,

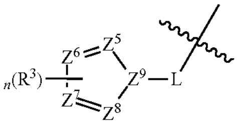, 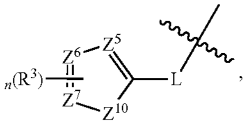,

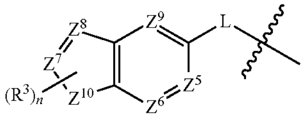 or

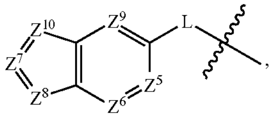, wherein $Z^5$, $Z^6$, $Z^7$, $Z^8$, $Z^9$, $Z^{6'}$, $Z^{7'}$, $Z^{8'}$ and $Z^{9'}$ are each independently N or C(H); $Z^{10}$ is N(H), O or S;

optionally wherein ring A is a 5- to 6-membered aromatic ring comprising 0-3 heteroatoms selected from nitrogen, sulfur and oxygen as ring member(s);

further optionally wherein ring A is phenyl, naphthalenyl, quinoxalinyl, pyridinyl, pyridazinyl, pyrimidinyl, imidazolyl, thiazolyl, oxazolyl, oxadiazole, pyridyl, pyrazinyl, pyridazinyl, pyrrolyl, imidazolyl, pyrazolyl, triazolyl, furanyl, pyrimidinyl, pyrazinyl or pyrrolopyridinyl; or (b) the

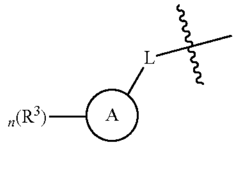

moiety is

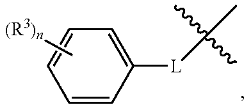,

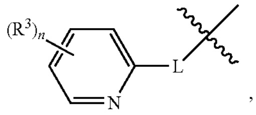,

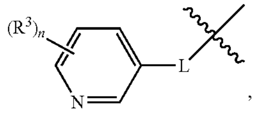,

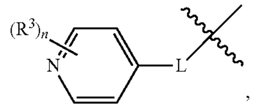,

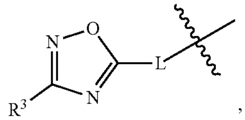,

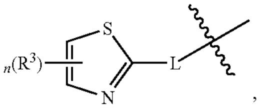,

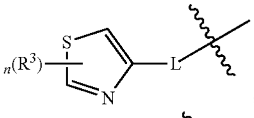,

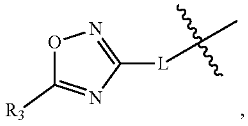,

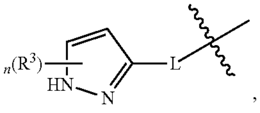,

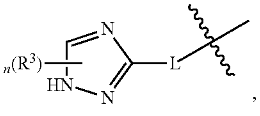,

-continued

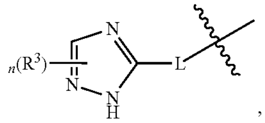

,

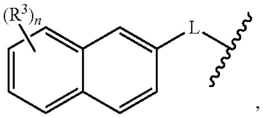

,

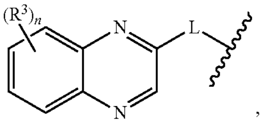

,

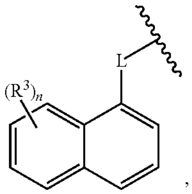

,

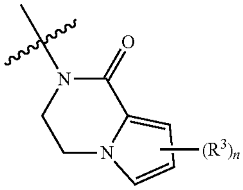

,

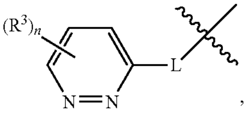

,

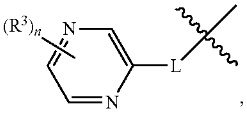

,

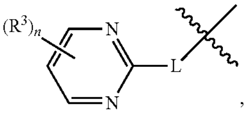

,

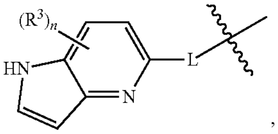

,

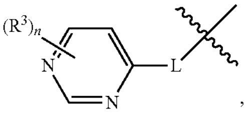

,

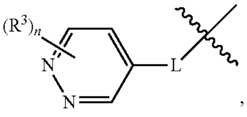

,

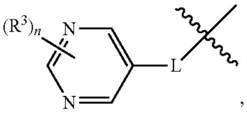

,

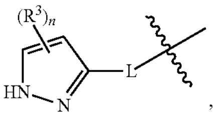

,

-continued

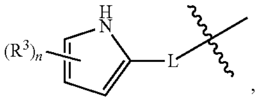

,

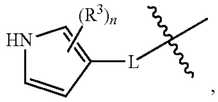

,

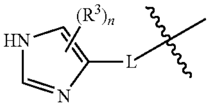

or

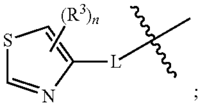

;

optionally wherein $R^3$ is hydrogen, —F, —Cl, —Br, —I, $—CH_3$, $—C_2H_5$, $—C_3H_7$, $—C_4H_9$, $—C_5H_{11}$, $—OCH_3$, $—OCH_5$, $—OC_3H_7$, $—OC_4H_9$, $—OCH_{11}$, cyclopropyl, cyclobutyl, cyclopentyl, tetrahydropyrrolyl or phenyl, wherein each of said $—CH_3$, $—C_2H_5$, $—C_3H_7$, $—C_4H_9$, $—C_5H_{11}$, $—OCH_3$, $—OCH_5$, $—OC_3H_7$, $—OC_4H_9$, $—OCH_{11}$, cyclopropyl, cyclobutyl, cyclopentyl, tetrahydropyrrolyl or phenyl, is optionally substituted with at least one —F, —Cl, —Br, —I, $—CH_3$, $—C_2H_5$, $—C_3H_7$, $—C_4H_9$, $—C_5H_{11}$, $—OCH_3$, $—OC_2H_5$, $—OC_3H_7$, $—OC_4H_9$, $—OCH_{11}$, —OH, cyclopropyl, cyclobutyl or cyclopentyl;

further optionally wherein $R^3$ is hydrogen, —F, —Cl, —Br, —I, methyl, ethyl, n-propyl, iso-propyl, n-butyl, iso-butyl, sec-butyl, tert-butyl, trifluoromethyl, difluoromethyl, fluoromethyl, —OMe, —OEt, —OPr, —OBu, cyclopropyl, cyclobutyl, tetrahydropyrrolyl or phenyl;

or optionally wherein two $R^3$, together with the atoms to which they are attached, form a 4-, 5-6-, 7- or 8-membered ring, said ring comprising 0, 1 or 2 additional heteroatoms independently selected from nitrogen, oxygen or optionally oxidized sulfur as ring member(s), said ring is optionally substituted with at least one substituent independently selected from —F, —Cl, —Br, —I, $—CH_3$, $—C_2H_5$, $—C_3H_7$, $—C_4H_9$, $—C_5H_{11}$, $—OCH_3$, $—OCH_5$, $—OCH_7$, $—OCH_9$, $—OCH_{11}$, —OH, —CN, cyclopropyl, cyclobutyl or cyclopentyl; or (c) the

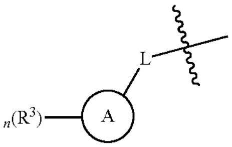

moiety is
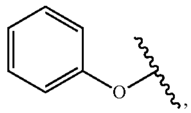,
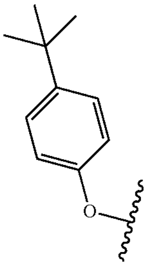,
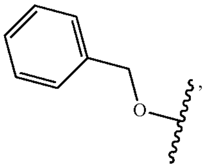,
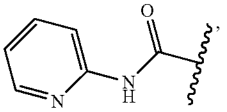,
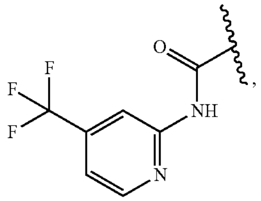,
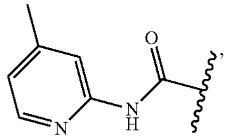,
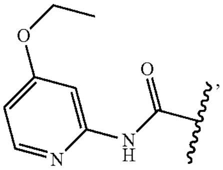,
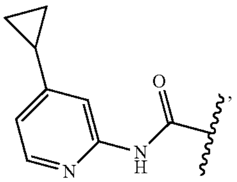,
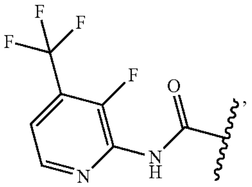,
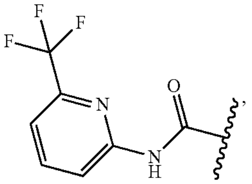,
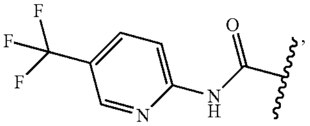,
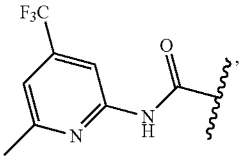,
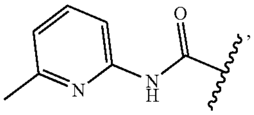,
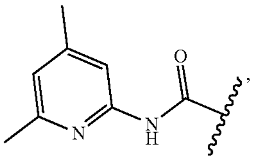,
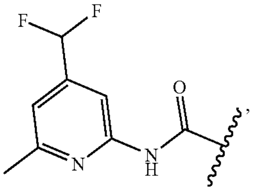,
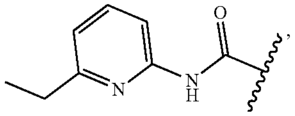,
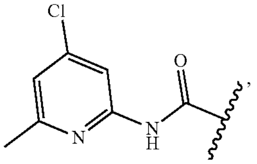,
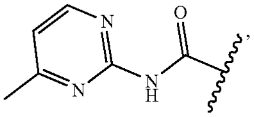,
-continued
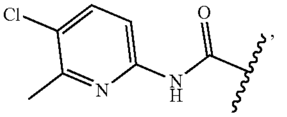,
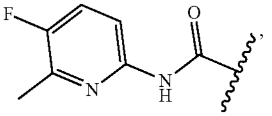,
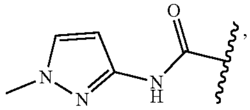,
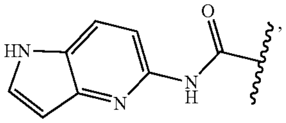,
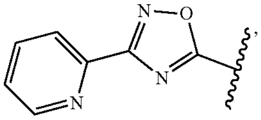,
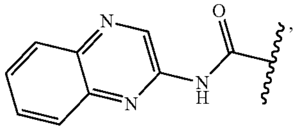,
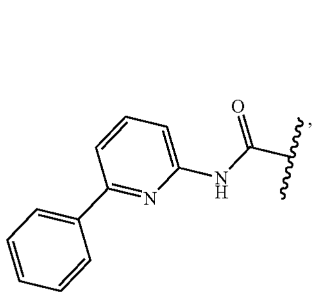,
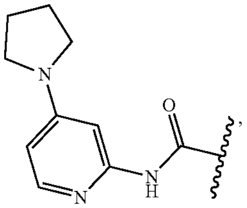,
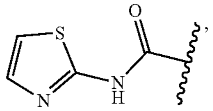,
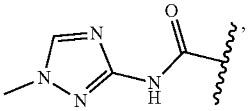,
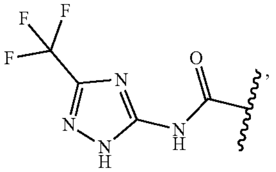,
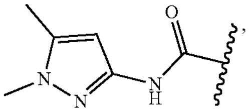,
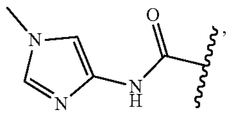,
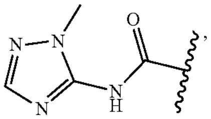,
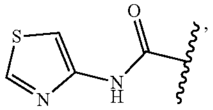,
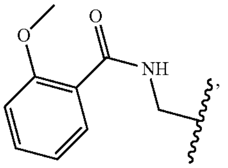,
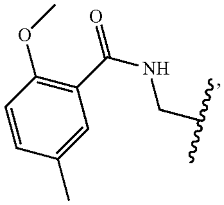,
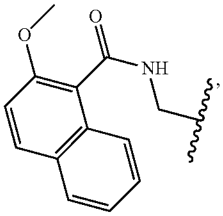,
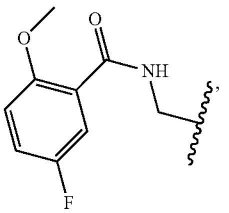,
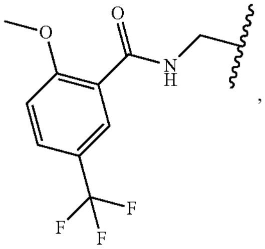, -continued
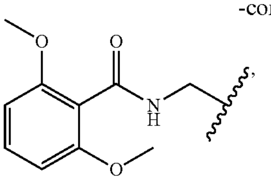
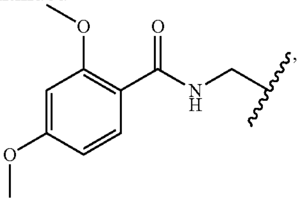
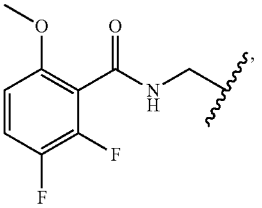
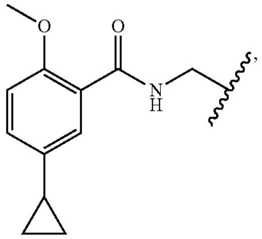
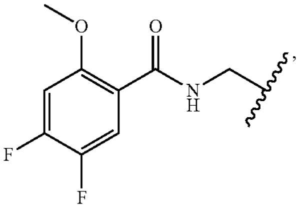
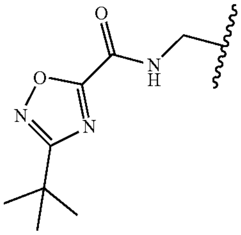
,
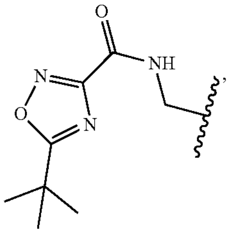
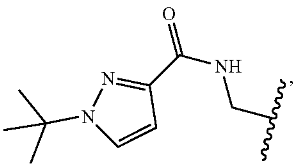
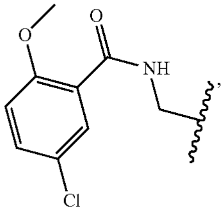
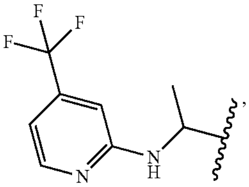
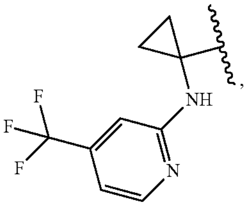
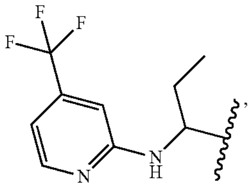
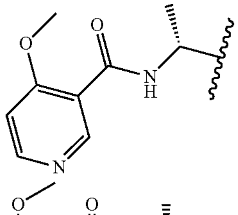
,
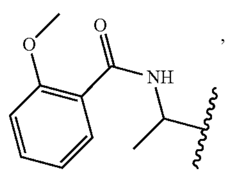
,
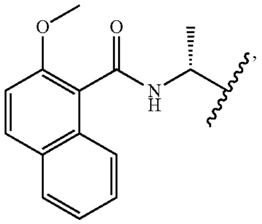
-continued
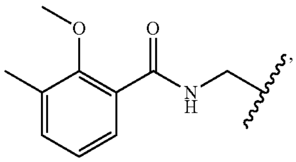
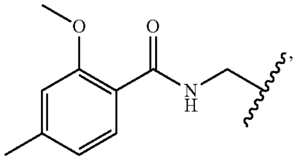
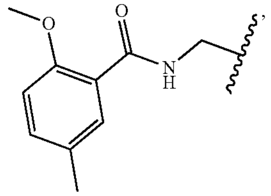
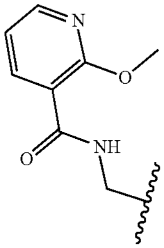
,
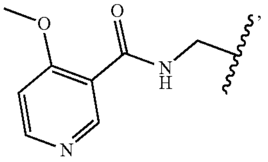
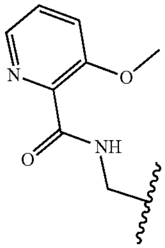
,
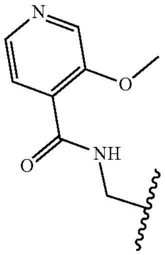
,
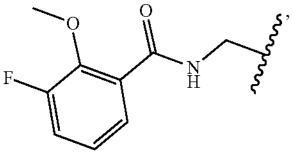
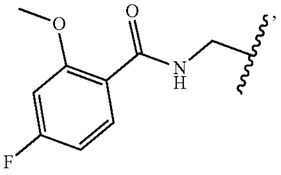
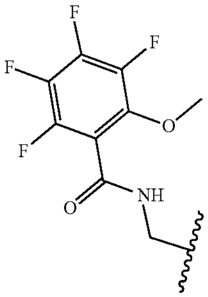
or
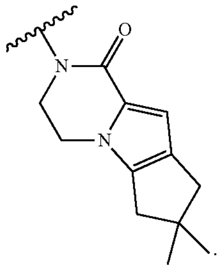

8. The compound according to claim 7, wherein
(a) the
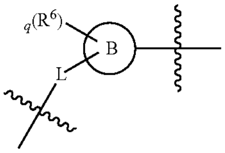
moiety is
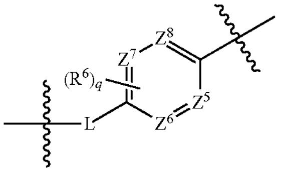
or
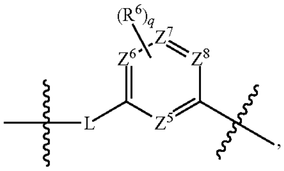
,
wherein $Z^5$, $Z^6$, $Z^7$ and $Z^8$ are defined as in claim 7; or
(b) the
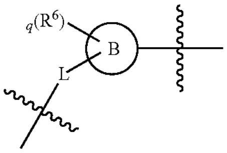
moiety is
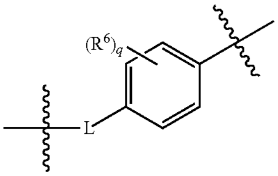
,
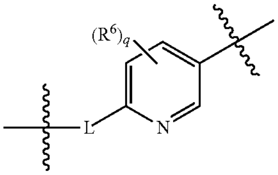
,
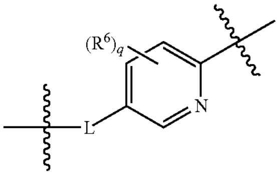
or
-continued
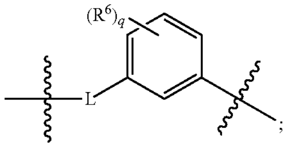
;
or
(c) the
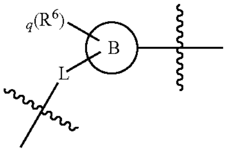
moiety is
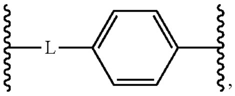
,
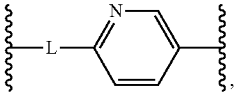
,
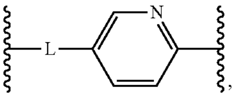
,
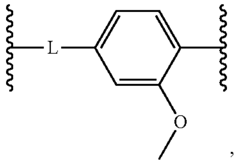
,
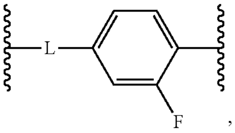
,
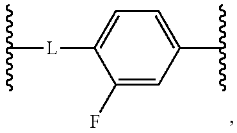
,
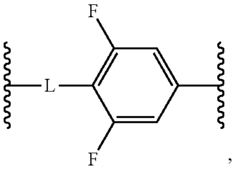
,
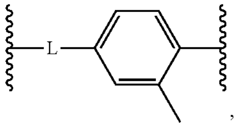
,
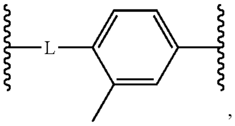
,
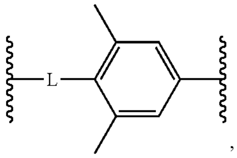
,
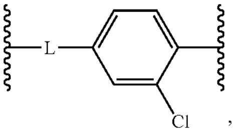
,
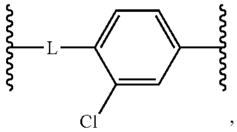
,
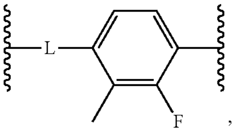
,
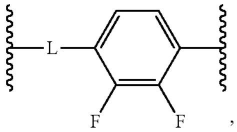
,
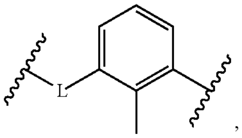
,
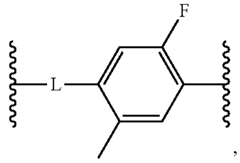
, -continued

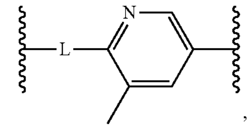,
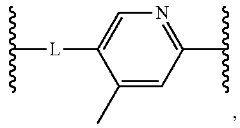,
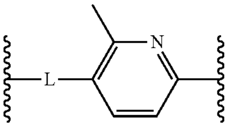 or 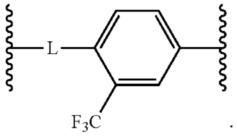.

9. The compound according to claim 1, wherein ring B is phenyl, pyridinyl, imidazolyl, thiazolyl, oxazolyl, pyridyl, pyrimidinyl, pyrazinyl, pyridazinyl, pyrrolyl, imidazolyl, pyrazolyl, thiazolyl, oxazolyl, triazolyl, thiophenyl, furanyl, pyrimidinyl or pyrazinyl, each of which is optionally substituted with $(R^6)_q$.

10. The compound according to claim 1, wherein $R^6$ is hydrogen, —F, —Cl, —Br, —I, —$CH_3$, —$C_2H_5$, —$C_3H_7$, —$C_4H_9$, —$C_5H_{11}$, —CN, —$OCH_3$, —$OC_2H_5$, —$OC_3H_7$, —$OC_4H_9$ or —$OCH_{11}$, wherein each of said —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$ or —$OCH_{11}$ is optionally substituted with —F, —Cl, —Br, —I, hydroxy, —$C_{1-8}$alkyoxy, cycloalkyl, heterocyclyl, aryl, or heteroaryl.

11. The compound according to claim 1, wherein

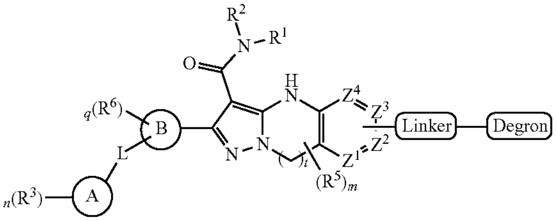

is

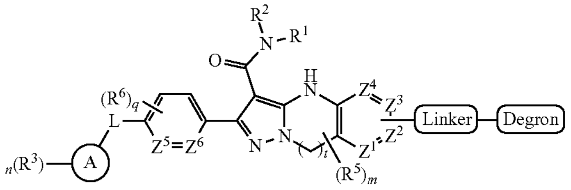

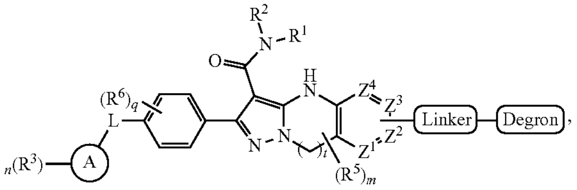

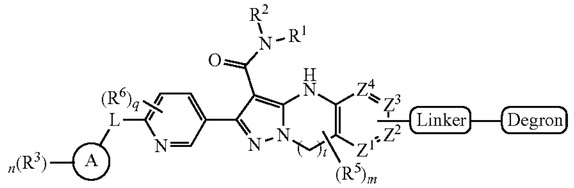

or

-continued

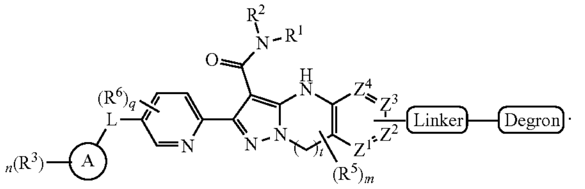.

12. The compound according to claim 1, wherein (a) $R^1$ and $R^2$ are each independently hydrogen, —$CH_3$, —$C_2H_5$, —$C_3H_7$, —$C_4H_9$, —$C_5H_{11}$, —$C_{2-8}$alkenyl, —$C_{2-8}$alkynyl or aryl; optionally wherein $R^1$ and $R^2$ are both H;

and/or (b) $R^5$ is independently hydrogen, —F, —Cl, —Br, —I, —$CH_3$, —$C_2H_5$, —$C_3H_7$, —$C_4H_9$, —$C_5H_{11}$, —$C_{2-8}$alkenyl, —$C_{2-8}$alkynyl or aryl;

and/or (c) $R^z$ is independently the bond between

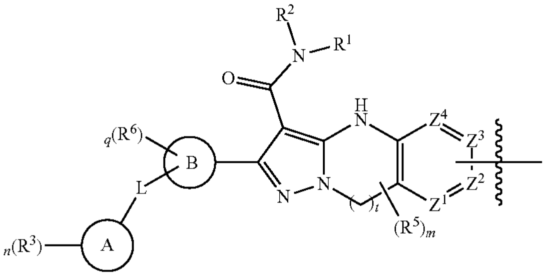

moiety and

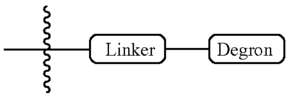

moiety, hydrogen, —F, —Cl, —Br, —I, —$CH_3$, —$C_2H_5$, —$C_3H_7$, —$C_4H_9$ or —$C_5H_{11}$.

13. The compound according to claim 1, wherein

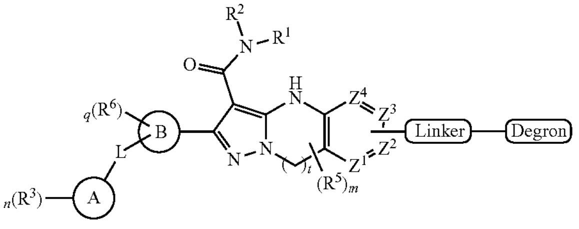

is

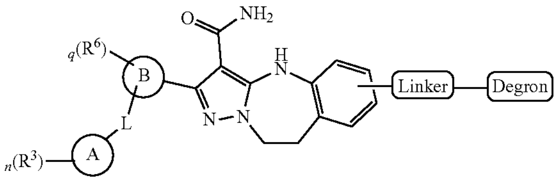
,
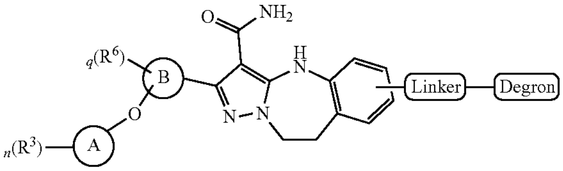
,
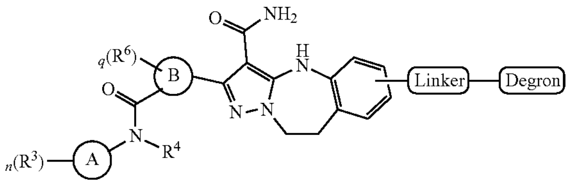
or
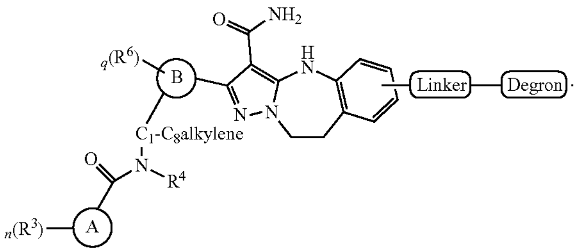
.
14. The compound according to claim 1, wherein the
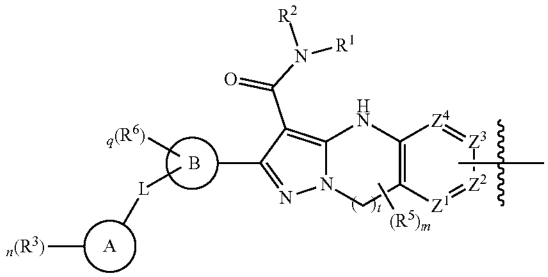
moiety is
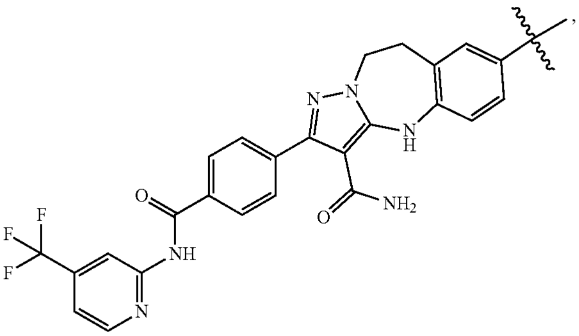
,
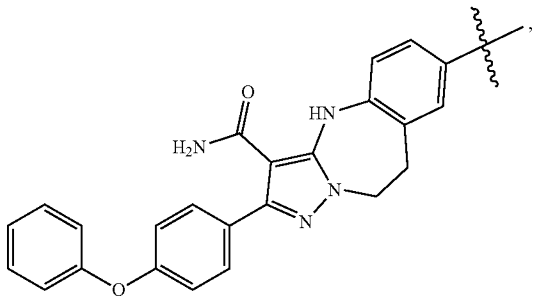
,
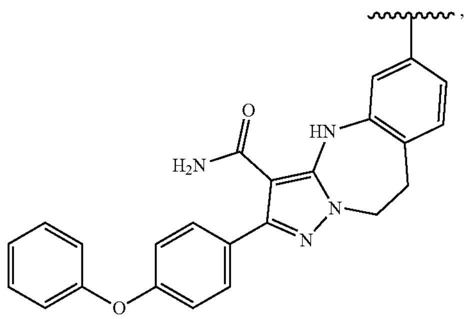
,
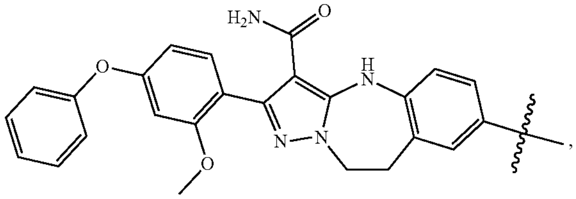
,
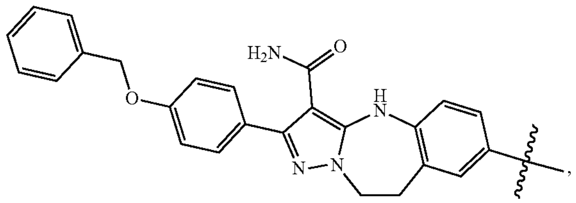
,
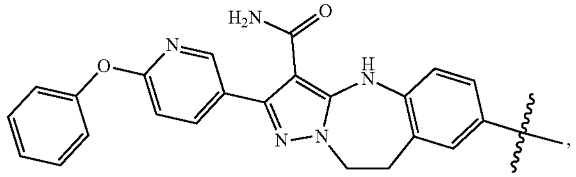
, -continued
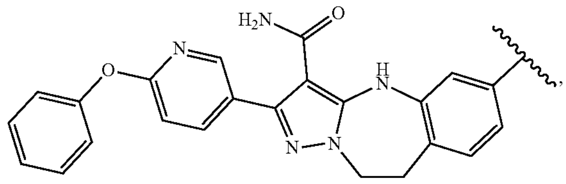,
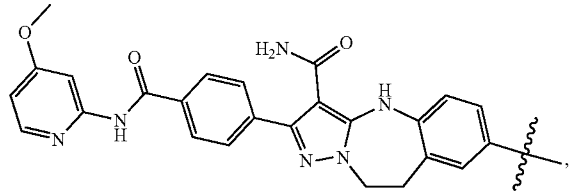,
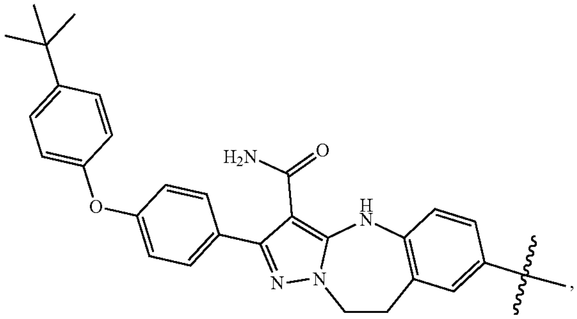,
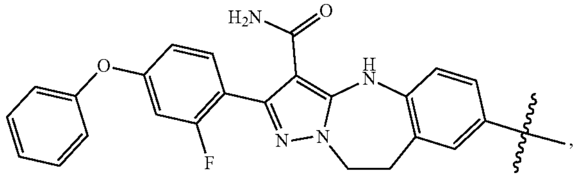,
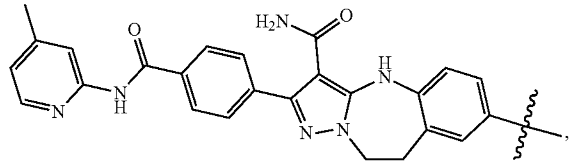,
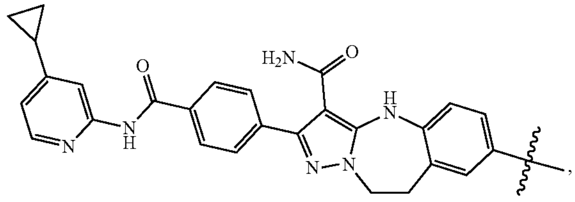,
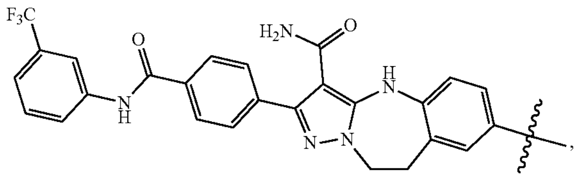,
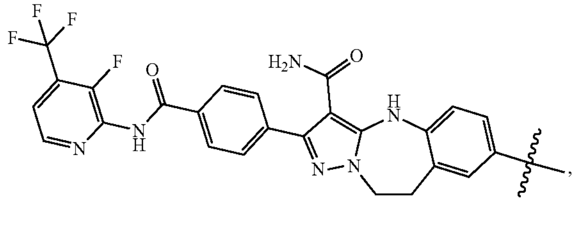,
-continued
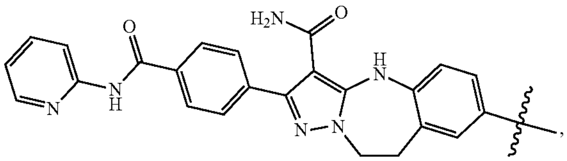,
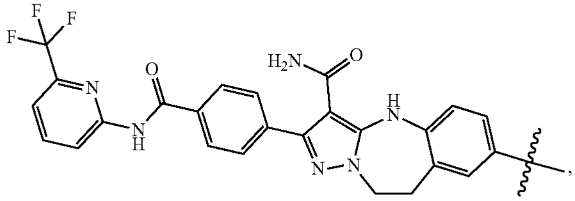,
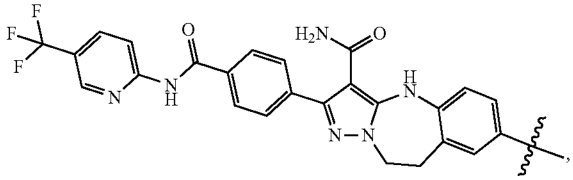,
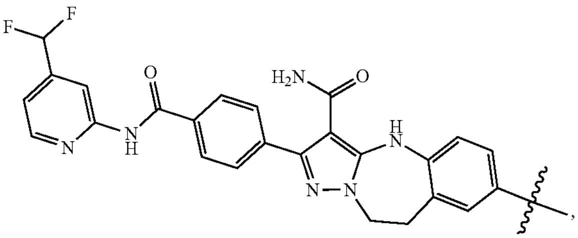,
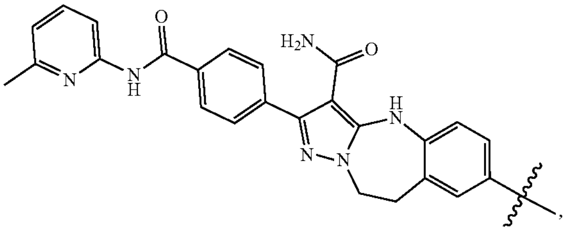,
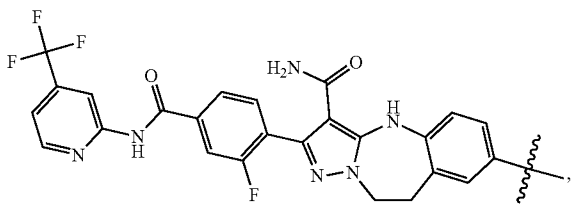,
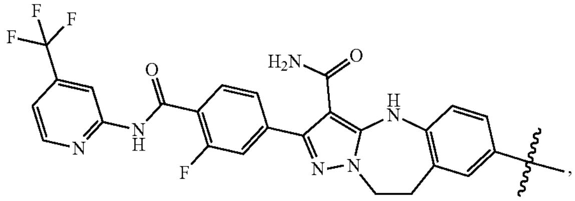, -continued
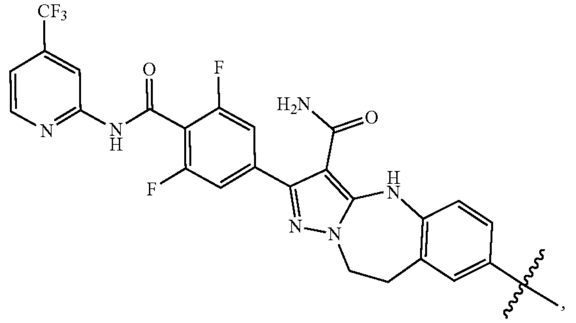
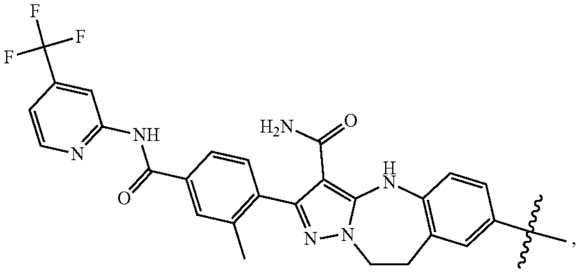
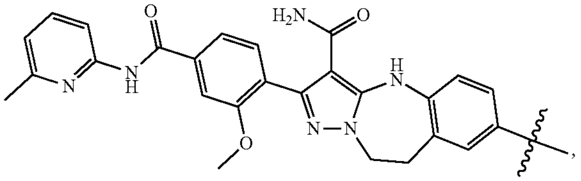
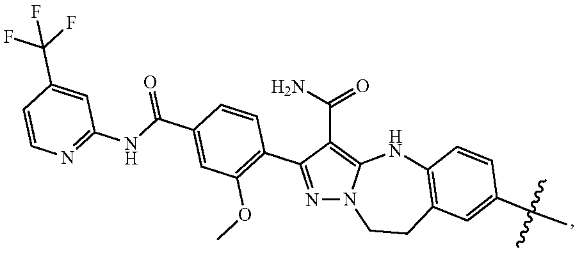
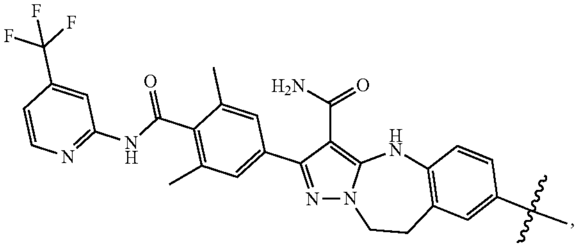
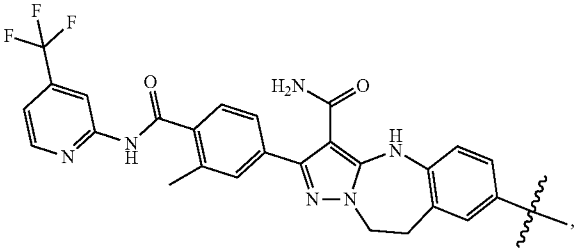
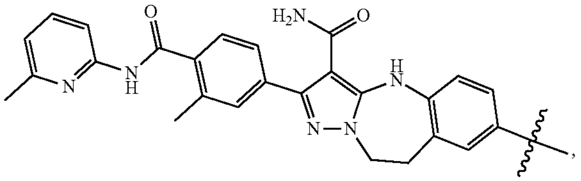
-continued
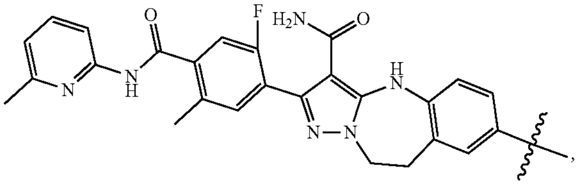
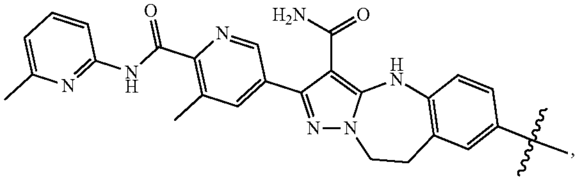
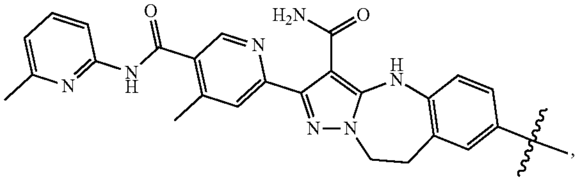
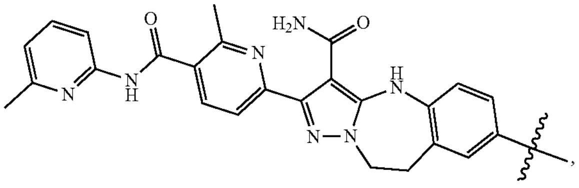
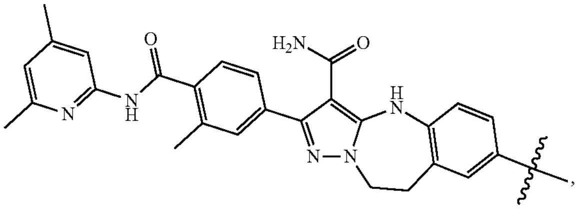
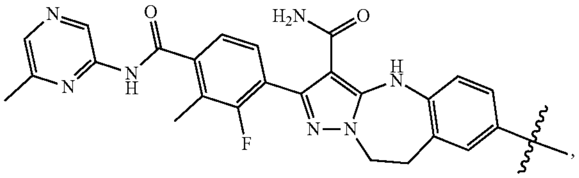
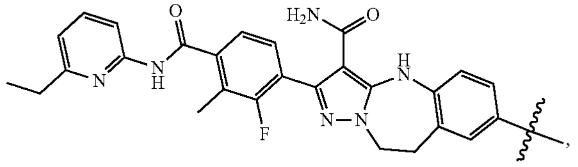
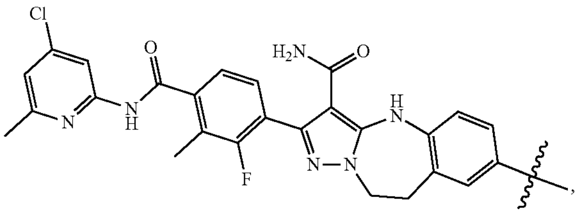
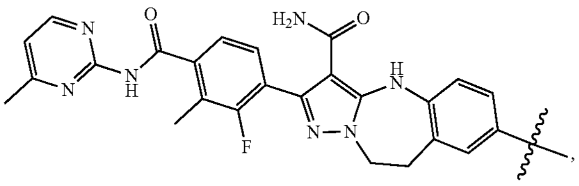

-continued
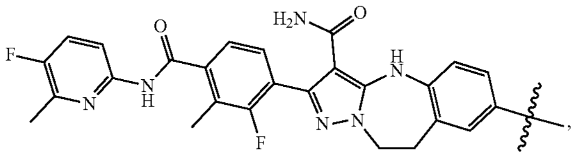
,
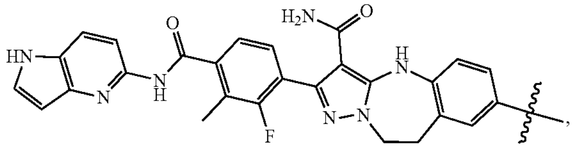
,
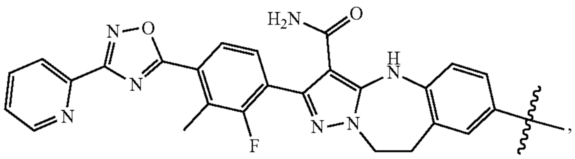
,
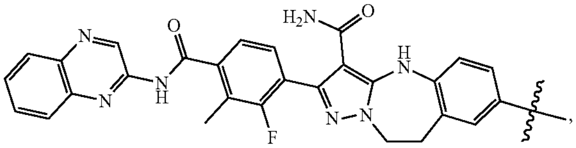
,
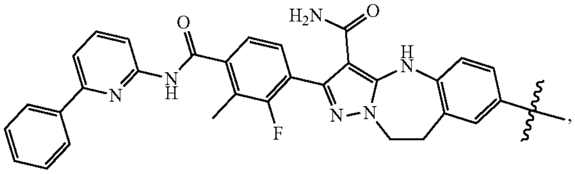
,
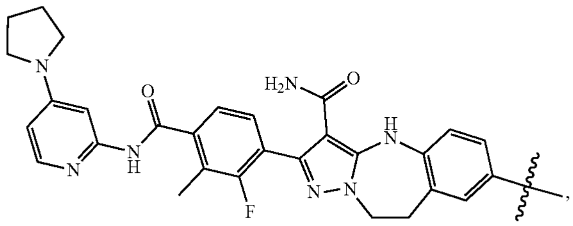
,
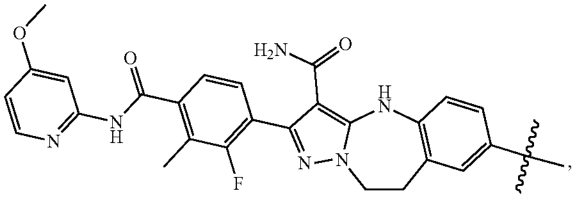
,
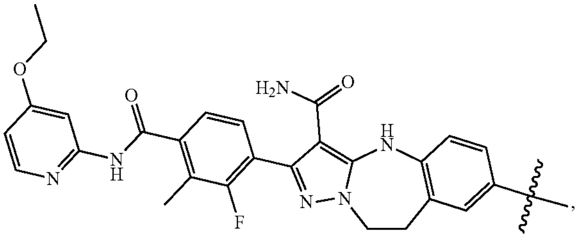
,
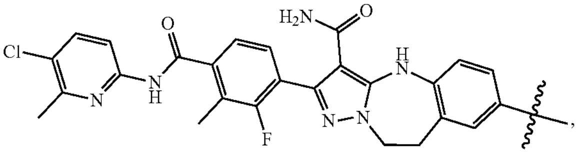
,
-continued
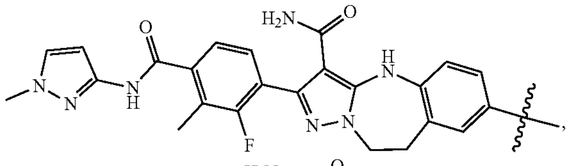
,
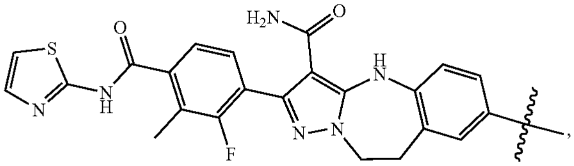
,
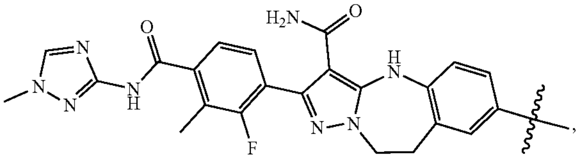
,
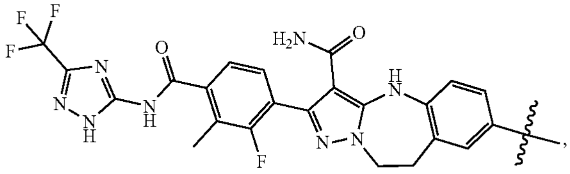
,
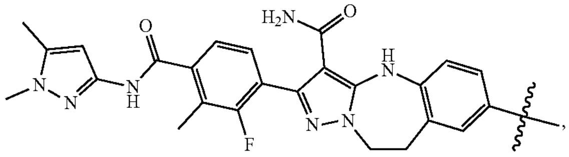
,
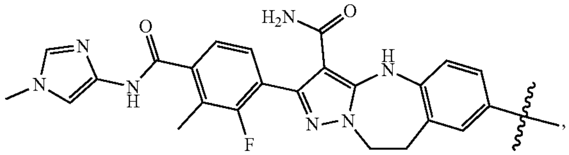
,
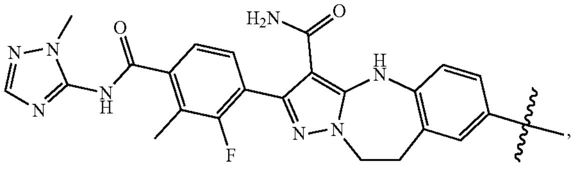
,
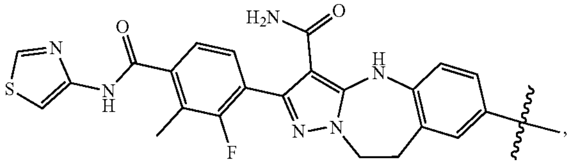
,
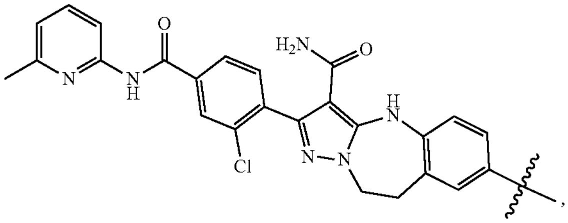
,
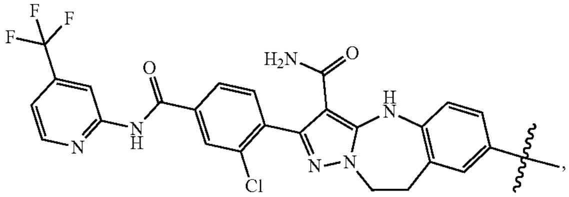
, -continued
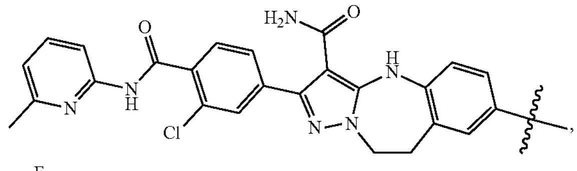,
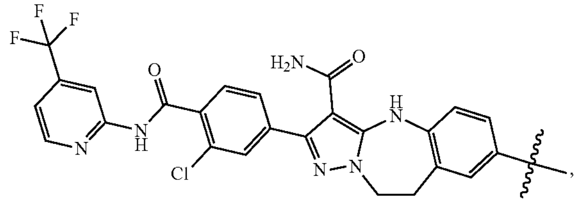,
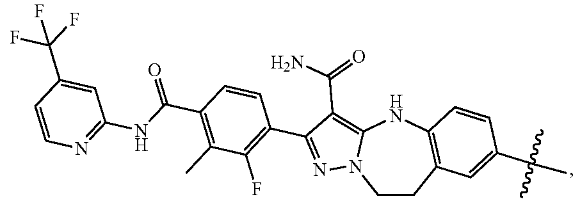,
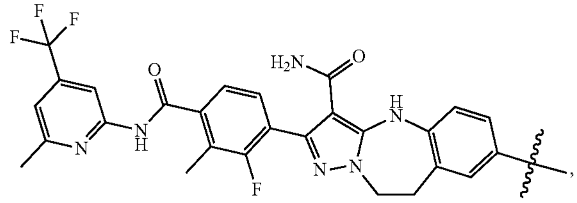,
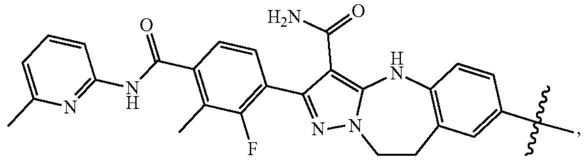,
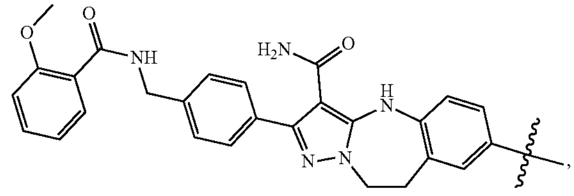,
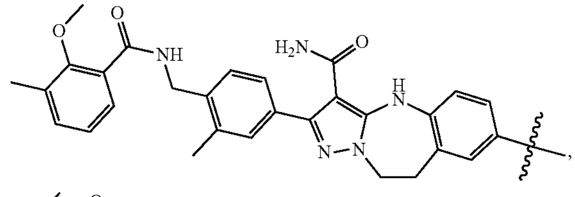,
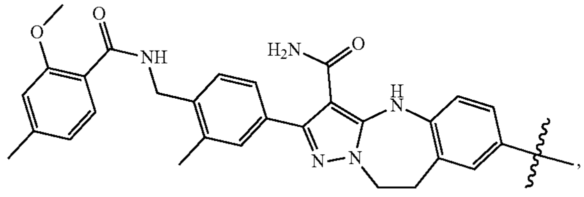,
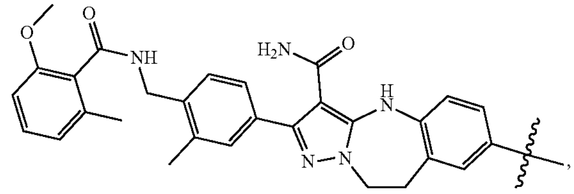,
-continued
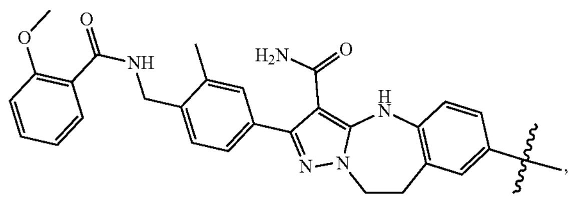,
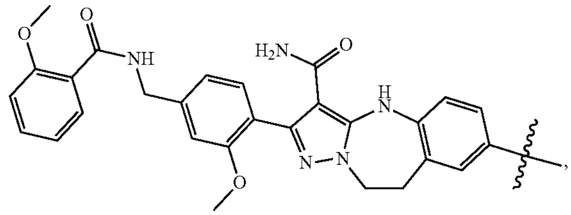,
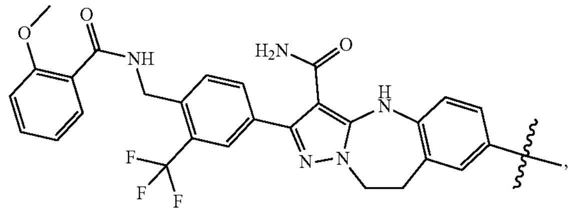,
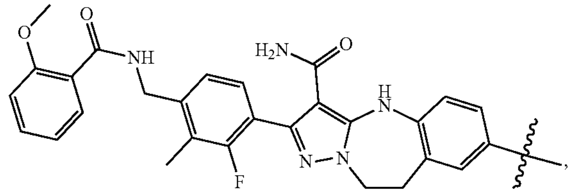,
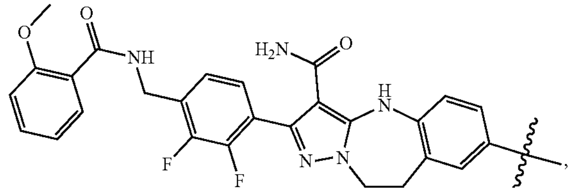,
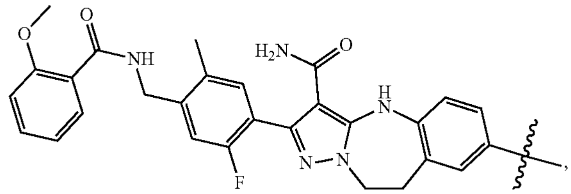,
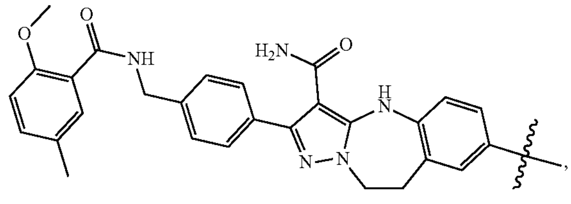,
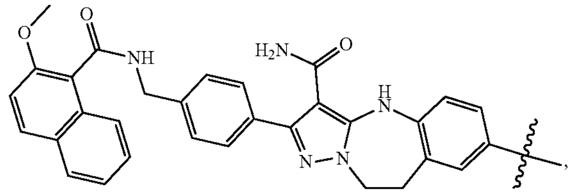, -continued
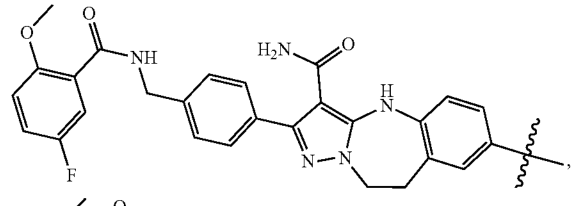,
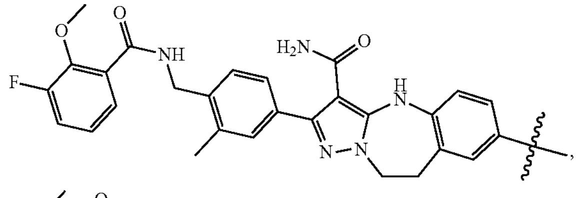,
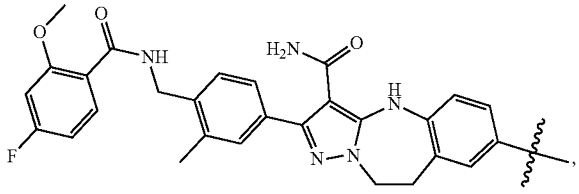,
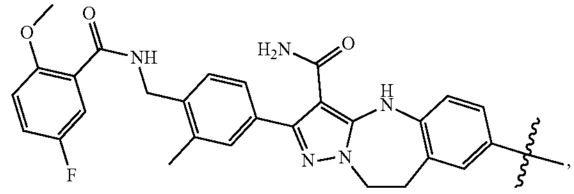,
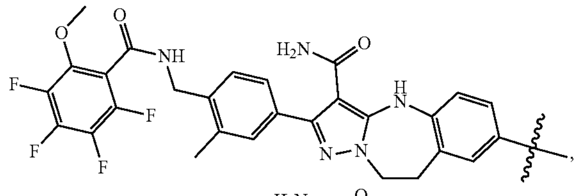,
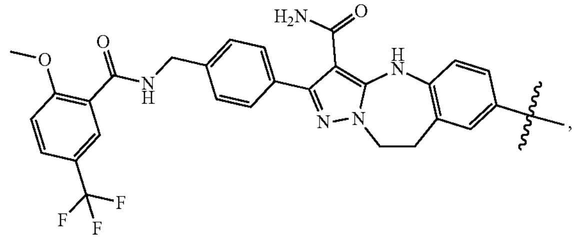,
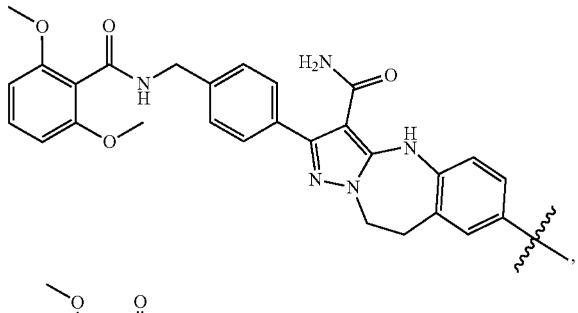,
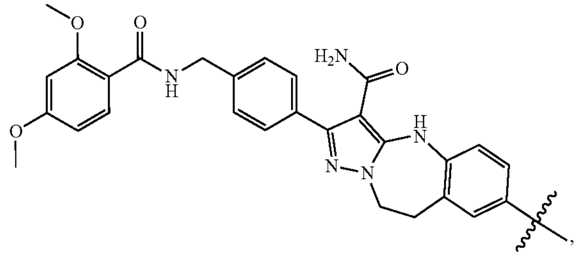,
-continued
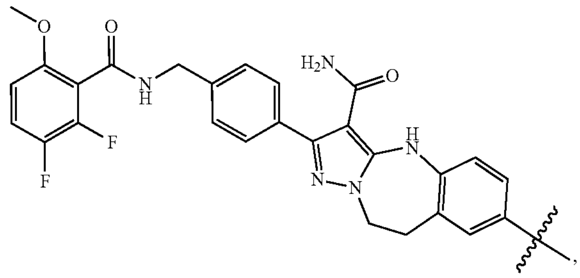,
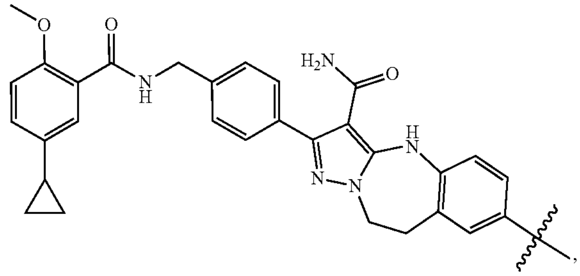,
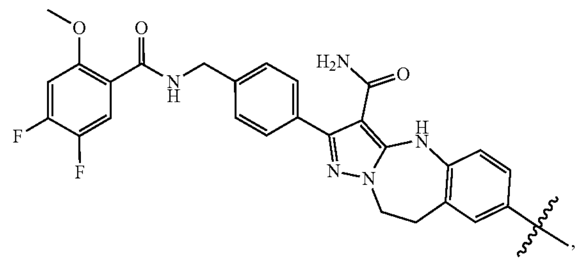,
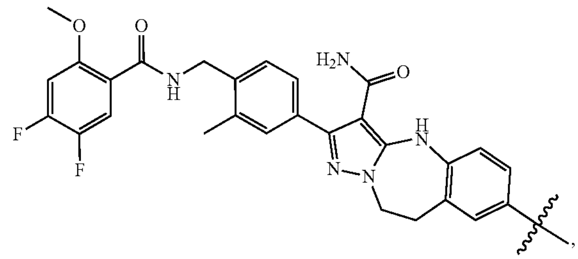,
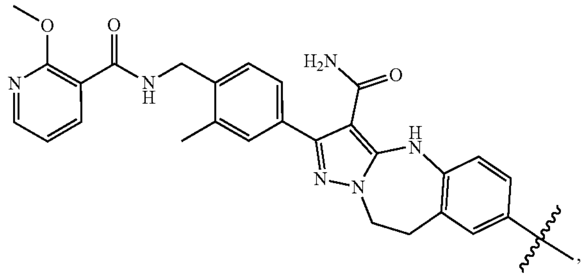,
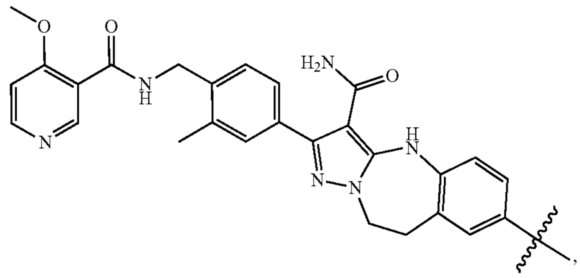, -continued
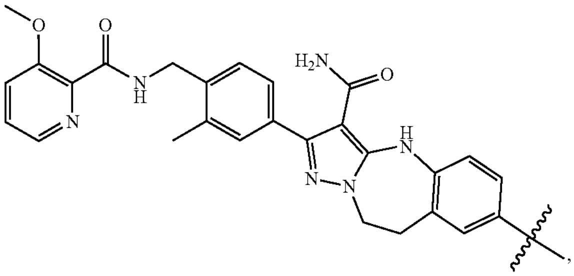
,
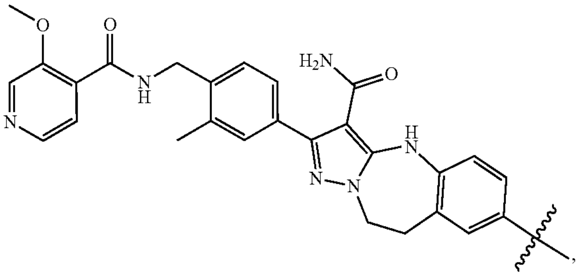
,
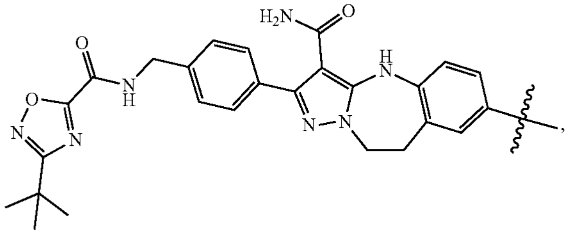
,
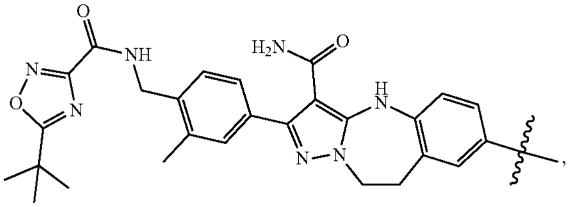
,
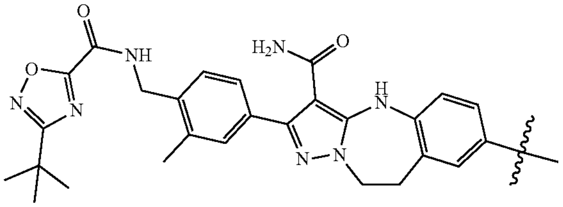
,
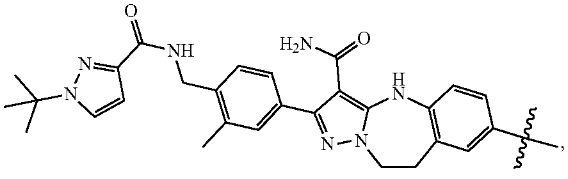
,
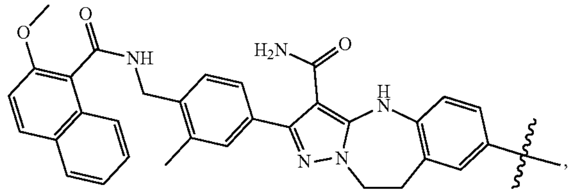
,
-continued
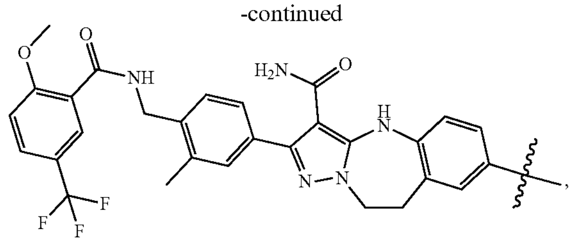
,
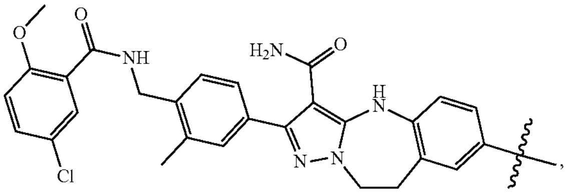
,
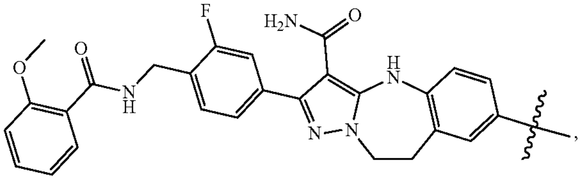
,
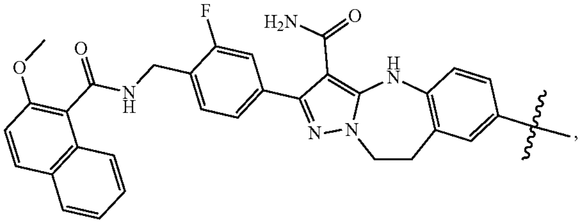
,
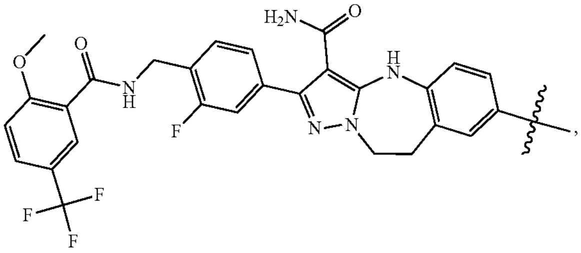
,
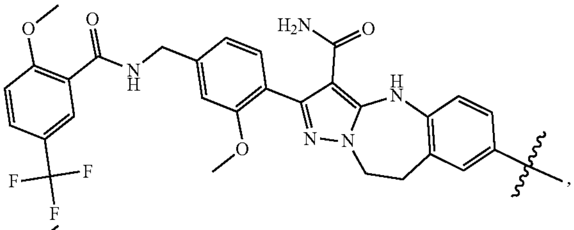
,
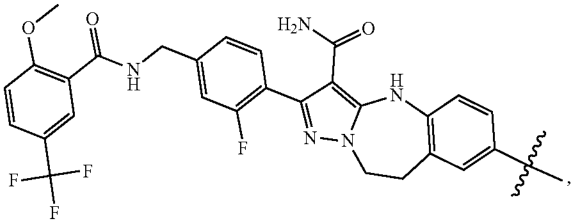
,
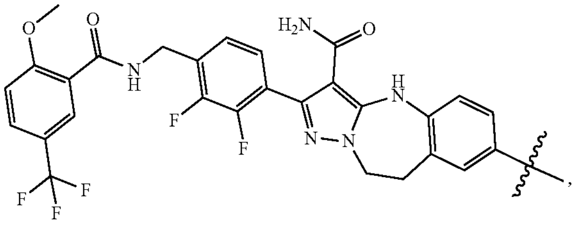
, -continued

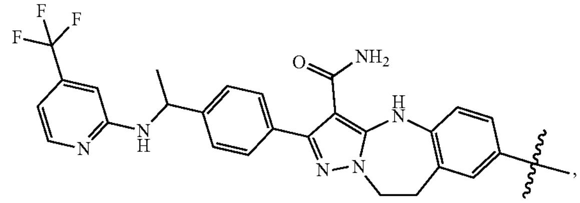
,

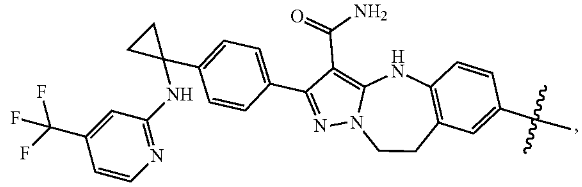
,

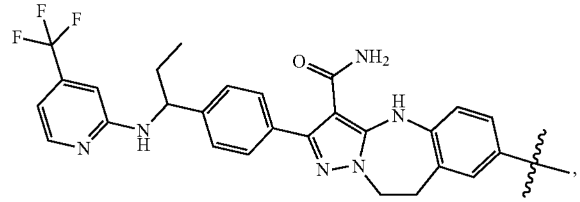
,

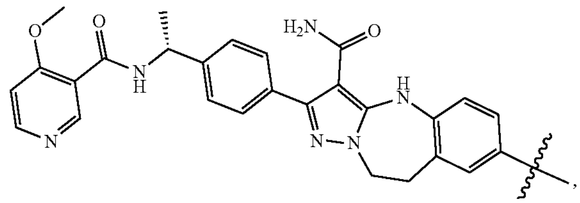
,

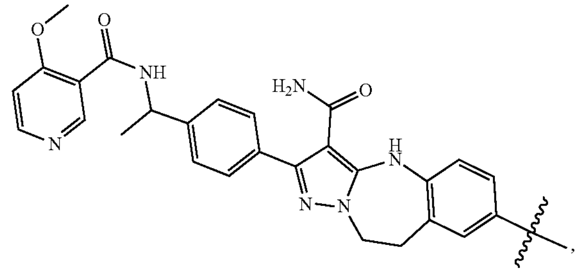
,

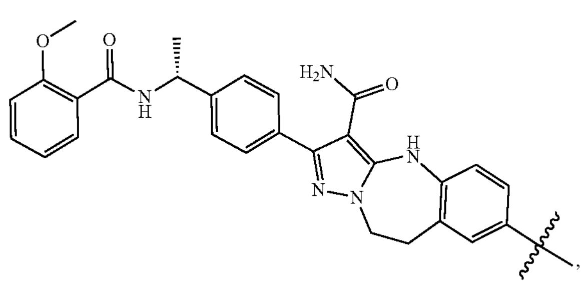
,

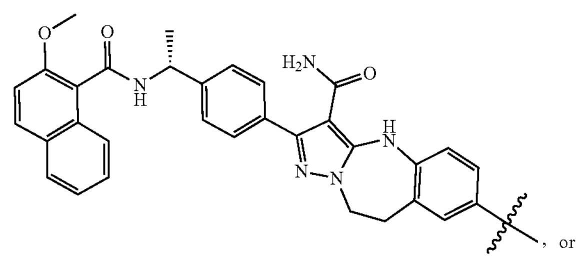
, or

-continued

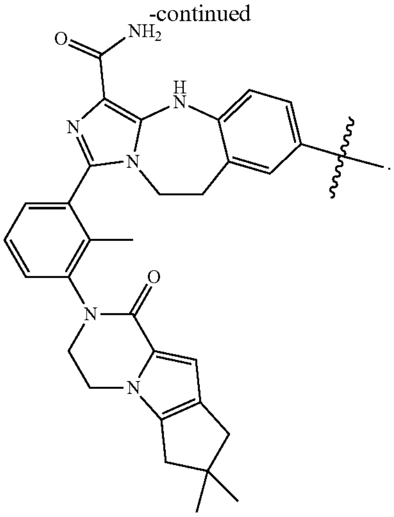
.

15. The compound according to claim 1, wherein the

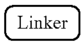

moiety is

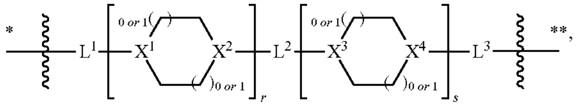
, wherein * refers to the position attached to the

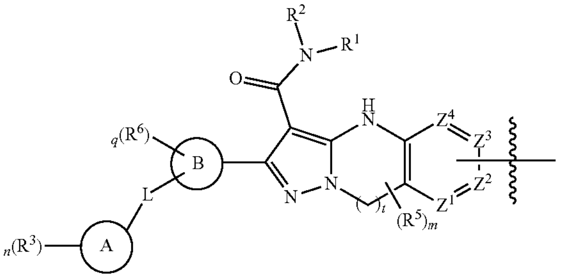

moiety, and ** refers to the position attached to the

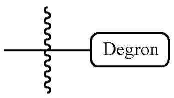

moiety;

$X^1$, $X^2$, $X^3$ and $X_4$ are each independently selected from CH or N;

r and s are each independently 0 or 1;

$L^1$ is a single bond, —O—, —$SO_2$—, —C(O)—, —$NR^{L1a}$—, —$C_3$-$C_8$cycloalkylene-, $*^{L1}$—O—$C_{1-8}$alkylene-$**^{L1}$, $*^{L1}$—$C_{1-8}$alkylene-O—$**^{L1}$, $*^{L1}$—$SO_2$—$C_{1-8}$alkylene-$**^{L1}$, $*^{L1}$—$C_{1-8}$alkylene-$SO_2$—$**^{L1}$, $*^{L1}$—C(O)—$C_{1-8}$alkylene-$**^{L1}$, $*^{L1}$-$C_{1-8}$alkylene-C(O)—$**^{L1}$, $*^{L1}$—$NR^{L1a}$—$C_{1-8}$alkylene-$**^{L1}$, $*^{L1}$—$C_{1-8}$alkylene-$NR^{Lla}$—$**^{L1}$, $*^{L1}$—$NR^{L1a}$C(O)—$**^{L1}$, $*^{L1}$—C(O)$NR^{L1a}$—$**^{L1}$, $*^{L1}$—$NR^{L1a}$C(O)$C_{1-8}$alkylene-$**^{L1}$, $*^{L1}$—C(O)$NR^{L1a}C_{1-8}$alkylene-$**^{L1}$, $*^{L1}$—$C_{1-8}$alkylene$NR^{L1a}$C(O)—$**^{L1}$, $*^{L1}$—$C_{1-8}$alkyleneC(O)$NR^{L1a}$—$**^{L1}$, —$C_{1-8}$alkylene-, —$C_{2-8}$alkenylene-, —$C_{2-8}$alkynylene-, or —[O(C$R^{L1a}R^{L1b}$)$_{u1}$]$_{v1}$—;

each of said —$C_3$-$C_8$cycloalkylene-, $*^{L1}$—O—$C_{1-8}$alkylene-$**^{L1}$, $*^{L1}$—$C_{1-8}$alkylene-O—$**^{L1}$, $*^{L1}$-$SO_2$—$C_{1-8}$alkylene-$**^{L1}$, $*^{L1}$—$C_{1-8}$alkylene-$SO_2$—$**^{L1}$, $*^{L1}$—C(O)—$C_{1-8}$alkylene-$**^{L1}$, $*^{L1}$-$C_{1-8}$alkylene-C(O)—$**^{L1}$, $*^{L1}$-$NR^{L1a}$—$C_{1-8}$alkylene-$**^{L1}$, $*^{L1}$-$C_{1-8}$alkylene-$NR^{L1a}$—$**^{L1}$, $*^{L1}$—$NR^{L1a}$C(O)$C_{1-8}$alkylene-$**^{L1}$, $*^{L1}$—C(O)$NR^{L1a}C_{1-8}$alkylene-$**^{L1}$, $*^{L1}$—$C_{1-8}$alkylene$NR^{L1a}$ C(O)—$**^{L1}$, $*^{L1}$—$C_{1-8}$alkyleneC(O)$NR^{L1a}$—$**^{L1}$, —$C_{1-8}$alkylene-, —$C_{2-8}$alkenylene- or —$C_{2-8}$alkynylene- is optionally substituted with at least one $R^{L1c}$;

u1 and v1 are each independently selected from 1, 2, 3, 4, 5, 6, 7 or 8;

wherein $*^{L1}$ refers to the position attached to the

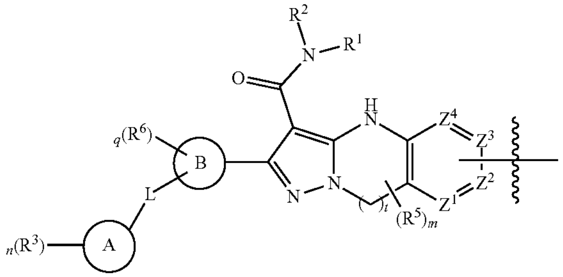

moiety, and $**^{L1}$ refers to the position attached to the

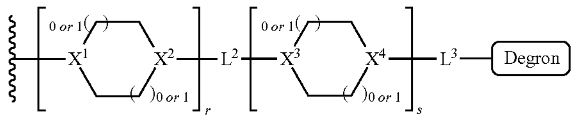

moiety;

$L^2$ is selected from a single bond, —O—, —$SO_2$—, —CO—, —$NR^{L2a}$—, —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, $*^{L2}$—$NR^{L2a}$C(O)—$**^{L2}$, $*^{L2}$—C(O)$NR^{L2a}$—$**^{L2}$, $*^{L2}$—$NR^{L2a}$C(O)$C_{1-8}$alkylene-$**^{L2}$, $*^{L2}$—C(O)$NR^{L2a}C_{1-8}$alkylene-$**^{L2}$, $*^{L2}$—$C_{1-8}$alkylene$NR^{L2a}$C(O)—$**^{L2}$, $*^{L2}$—$C_{1-8}$alkyleneC(O)$NR^{L2a}$—$**^{L2}$, —$C_{1-8}$alkylene-, —$C_{2-8}$alkenylene-, —$C_{2-8}$alkynylene- or —[O(C$R^{L2a}R^{L2b}$)$_{u2}$]$_{v2}$—;

each of said —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, $*^{L2}$—$NR^{L2a}$C(O)$C_{1-8}$alkylene-$**^{L2}$, $*^{L2}$—C(O)$NR^{L2a}C_{1-8}$alkylene-$**^{L2}$, $*^{L2}$—$C_{1-8}$alkylene$NR^{L2a}$C(O)—$**^{L2}$, $*^{L2}$—$C_{1-8}$alkyleneC(O)$NR^{L2a}$—$**^{L2}$, —$C_{1-8}$alkylene-, —$C_{2-8}$alkenylene- or —$C_{2-8}$alkynylene- is optionally substituted with at least one substituent $R^{L2c}$, u2 and v2 are each independently selected from 1, 2, 3, 4, 5, 6, 7 or 8;

wherein $*^{L2}$ refers to the position attached to the

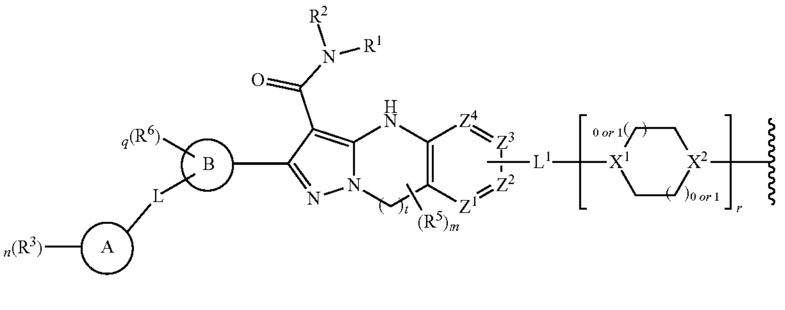

moiety $**^{L2}$ refers to the position attached to the

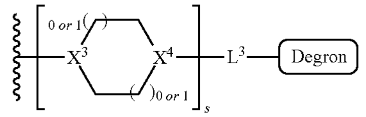

moiety;

$L_3$ is selected from a single bond, —O—, —$SO_2$—, —CO—, —$NR^{L3a}$—, —$C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$-$NR^{L3a}$—$C_{1-8}$alkylene-$**^{L3}$, $*^{L3}$—$C_{1-8}$alkylene-$NR^{L3a}$—$**^{L3}$, $*^{L3}$—$NR^{L3a}$C(O)—$**^{L3}$, $*^{L3}$—C(O)$NR^{L3a}$—$**^{L3}$, $*^{L3}$—$NR^{L3a}$C(O) $C_{1-8}$alkylene-$**^{L3}$, $*^{L3}$—C(O)$NR^{L3a}$ $C_{1-8}$alkylene-$**^{L3}$, $*^{L3}$-$C_{1-8}$alkylene$NR^{L3a}$C(O)—$**^{L3}$, $*^{L3}$-$C_{1-8}$alkyleneC(O)$NR^{L3a}$—$**^{L3}$, —$C_{1-8}$alkylene-, —$C_{2-8}$alkenylene-, —$C_{2-8}$alkynylene- or —[O(C$R^{L3a}R^{L3b}$)$_{u3}$]$_{v3}$—; each of said —$C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$, $*^{L3}$—$NR^{L3a}$ C(O)$C_{1-8}$alkylene-$**^{L3}$, $*^{L3}$—C(O)$NR^{L3a}$ $C_{1-8}$alkylene-$**^{L3}$, $*^{L3}$—$C_{1-8}$alkylene$NR^{L3a}$C(O)—

$**^{L3}$, $*^{L3}$—$C_{1-8}$alkyleneC(O)$NR^{L3a}$—$**^{L3}$, —$C_{1-8}$alkylene-, —$C_{2-8}$alkenylene-, or —$C_{2-8}$alkynylene-, is optionally substituted with at least one substituent $R^{L3c}$, u3 and v3 are each independently selected from 1, 2, 3, 4, 5, 6, 7 or 8;

wherein $*^{L3}$ refers to the position attached to the

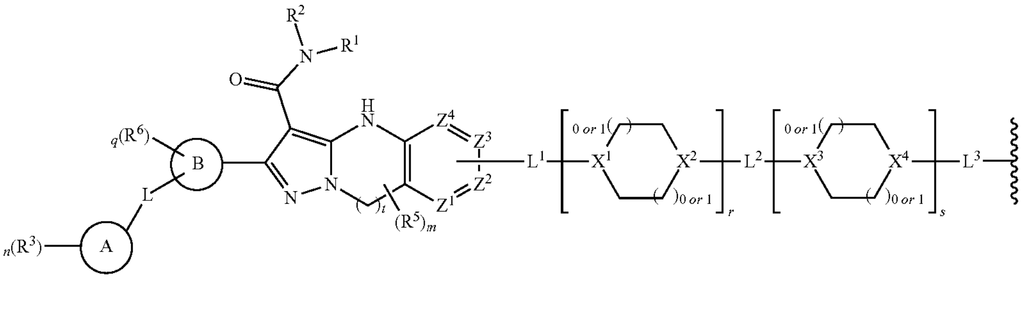

moiety, and $**^{L3}$ refers to the position attached to the

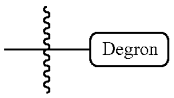

moiety;

$R^{L1a}$, $R^{L1b}$, $R^{L2a}$, $R^{L2b}$, $R^{L3a}$ and $R^{L3b}$ are each independently selected from hydrogen, —$C_{1-8}$alkyl, —$C_{2-8}$alkenyl, —$C_{2-8}$alkynyl, cycloalkyl, heterocyclyl, aryl or heteroaryl, wherein each of said —$C_{1-8}$alkyl, —$C_{2-8}$alkenyl, —$C_{2-8}$alkynyl, cycloalkyl, heterocyclyl, aryl or membered heteroaryl is optionally substituted with at least one substituent $R^{L3d}$, $R^{L3d}$ is halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl.

16. The compound according to claim 1, wherein the

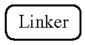

moiety is

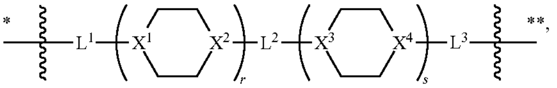

wherein * refers to the position attached to the

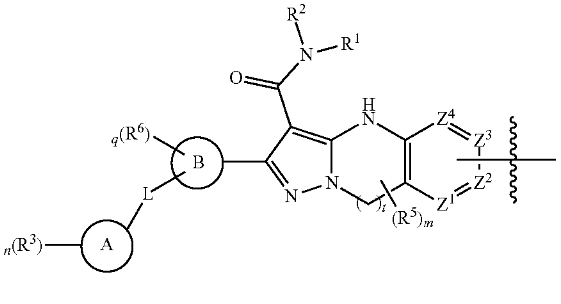

moiety, and ** refers to the position attached to the

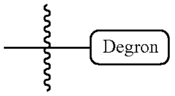

moiety;

$X^1$, $X^2$, $X^3$ and $X^4$ are each independently selected from CH or N;

r and s are each independently 0 or 1;

$L^1$ is a single bond, —O—, —$SO_2$—, —C(O)—, —$NR^{L1a}$—, —$C_3$-$C_8$cycloalkylene-, $*^{L1}$—O—$C_{1-8}$ salkylene-$**^{L1}$, $*^{L1}$—$C_{1-8}$alkylene-O—$**^{L1}$, $*^{L1}$—$SO_2$—$C_{1-8}$alkylene-$**^{L1}$, $*^{L1}$—$C_{1-8}$alkylene-$SO_2$—$**^{L1}$, $*^{L1}$—C(O)—$C_{1-8}$alkylene-$**^{L1}$, $*^{L1}$—$C_{1-8}$alkylene-C(O)—$**^{L1}$, $*^{L1}$-$NR^{L1a}$—$C_{1-8}$alkylene-$**^{L1}$, $*^{L1}$—$C_{1-8}$alkylene-$NR^{L1a}$—$**^{L1}$, $*^{L1}$—$NR^{L1a}$C(O)—$**^{L1}$, $*^{L1}$—C(O)$NR^{L1a}$—$**^{L1}$, $*^{L1}$-$NR^{L1}$C(O)$C_{1-8}$alkylene-$**_{L1}$, $*_{L1}$—C(O)$NR^{L1a}$$C_{1-8}$alkylene-$**^{L1}$, $*^{L1}$—$C_{1-8}$alkylene$NR^{L1a}$C(O)—$**^{L1}$, $*^{L1}$—$C_{1-8}$ alkyleneC(O)$NR^{Lla}$—$**^{L1}$, —$C_{1-8}$alkylene-, —$C_{2-8}$alkenylene-, —$C_{2-8}$alkynylene-, or —[O$(CR^{L1a}R^{L1b})_{u1}]_{v1}$—;

each of said —$C_3$-$C_8$cycloalkylene-, $*^{L1}$—O—$C_{1-8}$alkylene-$**^{L1}$, $*^{L1}$—$C_{1-8}$alkylene-O—$**^{L1}$, $*^{L1}$—$SO_2$—$C_{1-8}$alkylene-$**^{L1}$, $*^{L1}$—$C_{1-8}$alkylene-$SO_2$—$**^{L1}$, $*^{L1}$—C(O)—$C_{1-8}$alkylene-$**^{L1}$, $*^{L1}$-$C_{1-8}$alkylene-C(O)—$**^{L1}$, $*^{L1}$-$NR^{L1a}$—$C_{1-8}$alkylene-$**^{L1}$, $*^{L1}$-$C_{1-8}$alkylene-$NR^{L1a}$_$**^{L1}$, $*^{L1}$-$NR^{L1a}$C(O)$C_{1-8}$alkylene-$**^{L1}$, $*^{L1}$—C(O)$NR^{L1a}$$C_{1-8}$alkylene-$**^{L1}$, $*^{L1}$-$C_{1-8}$alkylene$NR^{L1a}$ C(O)—$**^{L1}$, $*^{L1}$-$C_{1-8}$alkyleneC(O)$NR^{L1a}$—$**^{L1}$, —$C_{1-8}$alkylene-, —$C_{2-8}$alkenylene- or —$C_{2-8}$alkynylene- is optionally substituted with at least one $R^{L1c}$, u1 and v1 are each independently selected from 1, 2, 3, 4, 5, 6, 7 or 8;

wherein $*^{L1}$ refers to the position attached to the

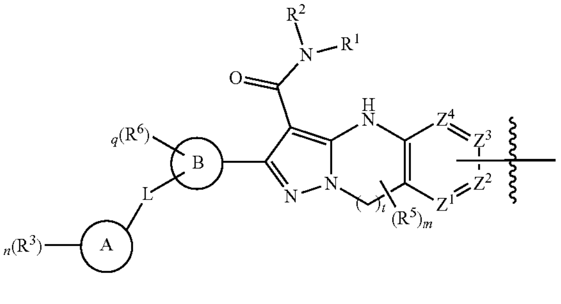

moiety, and $**^{L1}$ refers to the position attached to the

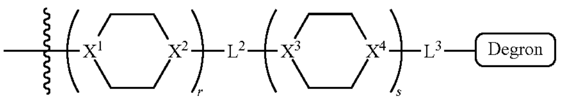

moiety;

$L^2$ is selected from a single bond, —O—, —$SO_2$—, —CO—, —$NR^{L2a}$—, —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, $*^{L2}$—$NR^{L2a}$C(O)—$**^{L2}$, $*^{L2}$—C(O)$NR^{L2a}$—$**^{L2}$, $*^{L2}$—$NR^{L2a}$C(O) $C_{1-8}$alkylene-$**^{L2}$, $*^{L2}$—C(O)$NR^{L2a}$ $C_{1-8}$alkylene-$**^{L2}$, $*^{L2}$—$C_{1-8}$alkylene$NR^{L2a}$C(O)—$**^{L2}$, $*^{L2}$—$C_{1-8}$alkyleneC(O)$NR^{L2a}$—$**^{L2}$, —$C_{1-8}$alkylene-, —$C_{2-8}$alkenylene-, —$C_{2-8}$alkynylene- or —[O($CR^{L2a}R^{L2b}$)[$_{u2}$]$_{v2}$—;

each of said —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, $*^{L2}$—$NR^{L2a}$C(O) $C_{1-8}$alkylene-$**^{L2}$, $*^{L2}$—C(O)$NR^{L2a}$$C_{1-8}$alkylene-$**^{L2}$, $*^{L2}$—$C_{1-8}$alkylene$NR^{L2a}$C(O)—$**^{L2}$, $*^{L2}$—$C_{1-8}$alkyleneC(O)$NR^{L2a}$—$**^{L2}$, —$C_{1-8}$alkylene-, —$C_{2-8}$alkenylene- or —$C_{2-8}$alkynylene- is optionally substituted with at least one substituent $R^{L2c}$, u2 and v2 are each independently selected from 1, 2, 3, 4, 5, 6, 7 or 8;

wherein $*^{L2}$ refers to the position attached to the

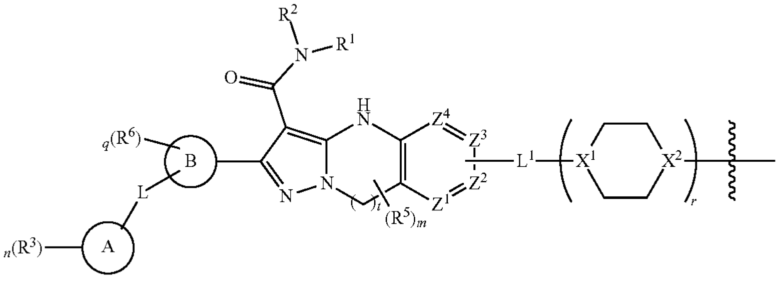

moiety, and $**^{L2}$ refers to the position attached to the

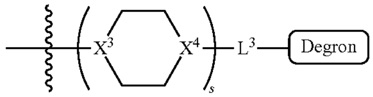

moiety;

$L_3$ is selected from a single bond, —O—, —$SO_2$—, —CO—, —$NR^{L3a}$—, —$C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$, $*^{L3}$—$NR^{L3a}$C(O)—$**^{L3}$, $*^{L3}$—C(O)$NR^{L3a}$—$**^{L3}$, $*^{L3}$—$NR^{L3a}$ C(O)$C_{1-8}$alkylene-$**^{L3}$, $*^{L3}$—C(O)$NR^{L3a}$ $C_{1-8}$alkylene-$**^{L3}$, $*^{L3}$-$C_{1-8}$alkylene$NR^{L3a}$C(O)—$**^{L3}$, $*^{L3}$—$C_{1-8}$alkyleneC(O)$NR^{L3a}$—$**^{L3}$ ', —$C_{1-8}$alkylene-, —$C_{2-8}$alkenylene-, —$C_{2-8}$alkynylene- or —[O($CR^{L3a}R^{L3b}$)$_{u3}$]$_{v3}$—; each of said —$C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$-$SO_2$—$C_{1-8}$alkylene-$**^{L3}$, $*^{L3}$-$C_{1-8}$alkylene-$SO_2$—$**^{L3}$, $*^{L3}$-CO—$C_{1-8}$alkylene-$**^{L3}$, $*^{L3}$—$C_{1-8}$alkylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$, $*^{L3}$, $NR^{L3a}$C(O)$C_{1-8}$alkylene-$**^{L3}$, $*^{L3}$—C(O)N$R^{L3a}$$C_{1-8}$alkylene-$**^{L3}$, $*^{L3}$—$C_{1-8}$alkylene$NR^{L3a}$C(O)—$**^{L3}$, $*^{L3}$—$C_{1-8}$alkyleneC(O)$NR^{L3a}$—$**^{L3}$, —$C_{1-8}$alkylene-, —$C_{2-8}$alkenylene-, or —$C_{2-8}$alkynylene-, is optionally substituted with at least one substituent $R^{L3c}$;

u3 and v3 are each independently selected from 1, 2, 3, 4, 5, 6, 7 or 8;

wherein $*^{L3}$ refers to the position attached to the

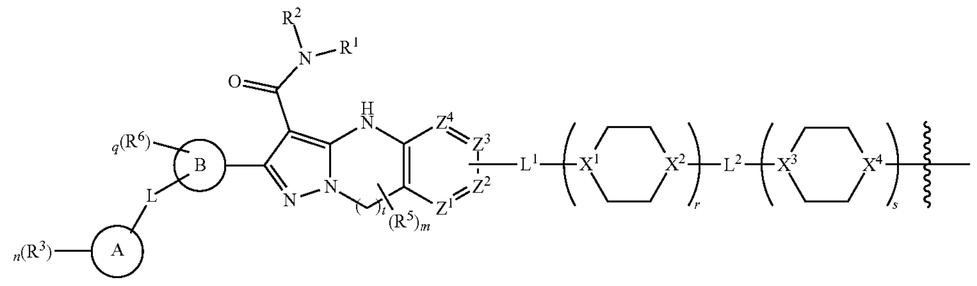

moiety, and $**^{L3}$ refers to the position attached to the

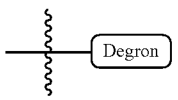

moiety;

$R^{L1a}$, $R^{L1b}$, $R^{L2a}$, $R^{L2b}$, $R^{L3a}$ and $R^{L3b}$ are each independently selected from hydrogen, —$C_{1-8}$alkyl, —$C_{2-8}$alkenyl, —$C_{2-8}$alkynyl, cycloalkyl, heterocyclyl, aryl or heteroaryl, wherein each of said —$C_{1-8}$alkyl, —$C_{2-8}$alkenyl, —$C_{2-8}$alkynyl, cycloalkyl, heterocyclyl, aryl or membered heteroaryl is optionally substituted with at least one substituent $R^{L3d}$; $R^{L3d}$ is halogen, hydroxy, —$C_{1-8}$alkyl, -halo$C_{1-8}$alkyl, —$C_{1-8}$alkoxy, —$C_{2-8}$alkenyl, —$C_{2-8}$alkynyl, cycloalkyl, heterocyclyl, aryl or heteroaryl.

17. The compound according to claim 15, wherein (a) $L^1$ is a single bond, —O—, —$SO_2$—, —C(O)—, —NH—, —N($CH_3$)—, —N($C_2H_5$)—, —N($C_3H_7$)—, $*^{L1}$—O—$CH_2$—$**^{L1}$, $*^{L1}$—O—$CH_4$—$**^{L1}$, $*^{L1}$—O—$C_3H_6$—$**^{L1}$, $*^{L1}$—O—$C_4H_8$—$**^{L1}$, $*^{L1}$—$CH_2$—O—$**^{L1}$, $*^{L1}$—$C_2H_4$—O—$**^{L1}$, $*^{L1}$—$C_3H_6$—O—$**^{L1}$, $*^{L1}$—$C_4H_8$—O—$**^{L1}$, $*^{L1}$—SO—$CH_2$—$**^{L1}$, $*^{L1}$-$SO_2$—$C_2H_4$—$**^{L1}$, $*^{L1}$- $SO_2$—$C_3H_6$—$**^{L1}$, $*^{L1}$-$SO_2$—$C_4H_8$—$**^{L1}$, $*^{L1}$-CH—SO-$_2$$**^{L1}$, $*^{L1}$—$C_2H_4$—$SO_2$—$**^{L1}$, $*^{L1}$—$C_3H_6$—$SO_2$—$**^{L1}$, $*^{L1}$-$C_4H_8$—$SO_2$—$**^{L1}$, $*^{L1}$—C(O)—$CH_2$—$**^{L1}$, $*^{L1}$—C(O)—$C_2H_4$—$**^{L1}$, $*^{L1}$—C(O)—$C_3H_6$—$**^{L1}$, $*^{L1}$—C(O)—$C_4H_8$—$**^{L1}$, $*^{L1}$—$CH_2$—C(O)—$**^{L1}$, $*^{L1}$—$C_2H_4$—C(O)—$**^{L1}$, $*^{L1}$—$C_3H_6$—C(O)—$**^{L1}$, $*^{L1}$—$C_4H_8$—C(O)—$**^{L1}$, $*_{L1}$—NH—$CH_2$—$**^{L1}$, $*^{L1}$-NH—$C_2H_4$—$**^{L1}$, $*^{L1}$-NH—$C_3H_6$—$**^{L1}$, $*^{L1}$-NH—$C_4H_8$—$**^{L1}$, $*^{L1}$—$CH_2$—NH—$**^{L1}$, $*^{L1}$—$C_2H_4$—NH—$**^{L1}$, $*^{L1}$—$C_3H_6$—NH—$**^{L1}$, $*^{L1}$—$C_4H_8$—NH—$**^{L1}$, $*^{L1}$-NHC(O)—$**^{L1}$, $*^{L1}$—C(O)NH—$**^{L1}$, $*^{L1}$—N($CH_3$)C(O)—$**^{L1}$, $*^{L1}$—C(O)N($CH_3$)—$**^{L1}$, $*^{L1}$—N($C_2H_5$) C(O)—$**^{L1}$, $*^{L1}$—C(O)N($C_2H_5$)—$**^{L1}$, $*^{L1}$—N($C_3H_7$)C(O)—$**^{L1}$, $*^{L1}$—C(O)N($C_3H_7$)—$**^{L1}$, $*^{L1}$-NHC(O) $CH_2$—$**^{L1}$, $*^{L1}$-NHC(O)$C_2H_4$—$**^{L1}$, $*^{L1}$—NHC(O)$C_3H_6$—$**^{L1}$, $*^{L1}$-NHC(O) $C_4H_8$—$**^{L1}$, $*^{L1}$—C(O)NH$CH_2$—$**^{L1}$, $*^{L1}$—C(O)NH$C_2H_4$—$**^{L1}$, $*^{L1}$—C(O)NH$C_3H_6$—$**^{L1}$, $*^{L1}$—C(O)NH$C_4H_8$—$**^{L1}$, $*^{L1}$—$CH_2$NHC(O)—$**^{L1}$, $*^{L1}$—$C_2H_4$NHC(O)—$**^{L1}$, $*^{L1}$, $C_3H_6$NHC(O)—$**^{L1}$, $*^{L1}$—$C_4H_8$NHC(O)—$**^{L1}$, $*^{L1}$—$CH_2$C(O)NH—$**^{L1}$, $*^{L1}$—$C_2H_4$C(O)NH—$**^{L1}$, $*^{L1}$—$C_3H_6$C(O)NH—$**^{L1}$, $*^{L1}$-$C_4H_8$C(O)NH—$**^{L1}$, —$CH_2$—, —$C_2H_4$—, —$C_3H_6$—, —$C_4H_8$—, —O($CH_2$)$_2$—, —[O($CH_2$)$_2$]$_2$—, —[O($CH_2$)$_2$]$_3$—, —[O($CH_2$)$_2$]$_4$— O—[O($CH_2$)$_2$]$_5$—;

and/or (b) $L^2$ is a single bond, —O—, —$SO_2$—, —C(O)—, —NH—, —N($CH_3$)—, —N($C_2H_5$)—, —N($C_3H_7$)—, $*^{L2}$-O—$CH_2$—$**^{L2}$, $*^{L2}$—O—$C^2H_4$—$**^{L2}$, $*^{L2}$-O—$C_3H_6$—$**^{L2}$, $*^{L2}$-O—$C_4H_8$—$**^{L2}$, $*^{L2}$—$CH_2$—O—$**^{L2}$, $*^{L2}$—C,$H_4$—O—$**^{L2}$, $*^{L2}$—$C_3H_6$—O—$**^{L2}$, $*^{L2}$—$C_4H_8$—O—$**^{L2}$, $*^{L2}$—$SO_2$—$CH_2$—$**^{L2}$, $*^{L2}$—SO—$C_2H_4$—$**^{L2}$, $*^{L2}$—SO—$C_3H_6$—$**^{L2}$, $*^{L2}$—$SO_2$—$C_4H_8$—$**^{L2}$, $*^{L2}$—$CH_2$—SO-$**^{L2}$, $*^{L2}$—C, $H_4$—SO-$**^{L2}$, $*^{L2}$—$C_3H_6$—$SO_2$—$**^{L2}$, $*^{L2}$—$C_4H_8$—$SO_2$—$**^{L2}$, $*^{L2}$—C(O)—$CH_2$—$**^{L2}$, $*^{L2}$—C(O)—$C_2H_4$—$**^{L2}$, $*^{L2}$—C(O)—$C_3H_6$—$**^{L2}$, $*^{L2}$—C(O)—$C_4H_8$—$**^{L2}$, $*^{L2}$—$CH_2$—C(O)—$**^{L2}$, $*^{L2}$—$C_2H_4$—C(O)—$**^{L2}$, $*^{L2}$—$C_3H_6$—C(O)—$**^{L2}$, $*^{L2}$—$C_4H_8$—C(O)—$**^{L2}$, $*^{L2}$—NH—$CH_2$—$**^{L2}$, $*^{L2}$—NH—$C_2H_4$—$**^{L2}$, $*^{L2}$-NH—$C_3H_6$—$**^{L2}$, $*^{L2}$—NH—$C_4H_8$—$**^{L2}$, $*^{L2}$—$CH_2$NH—$**^{L2}$, $*^{L2}$—$C_2H_4$—NH—$**^{L2}$, $*^{L2}$—$C_3H_6$—NH—$**^{L2}$, $*^{L2}$—$C_4H_8$—NH—$**^{L2}$, $*^{L2}$—NHC(O)—$**^{L2}$, $*^{L2}$—C(O)NH—$**^{L2}$, $*^{L2}$—N($CH_3$)C(O)—$**^{L2}$, $*^{L2}$—N($C_2H_5$)C(O)—$**^{L2}$, $*^{L2}$—C(O)N($C_2H^5$)—$**^{L2}$, $*^{L2}$—N($C_3H_7$)C(O)—$**^{L2}$, $*^{L2}$—C(O)N($C_3H_4$)—$**^{L2}$, $*^{L2}$—NHC(O)$CH_2$—$**^{L2}$, $*^{L2}$—NHC(O)$C_2H_4$—$**^{L2}$, $*^{L2}$—NHC(O)$C_3H_6$—$**^{L2}$, $*^{L2}$—NHC(O)$C_4H_8$—$**^{L2}$, $*^{L2}$—C(O)NH$CH_2$—$**^{L2}$, $*^{L2}$—C(O)NH$C_2H_4$—$**^{L2}$, $*^{L2}$—C(O)NH$C_3H_6$—$**^{L2}$, $*^{L2}$—C(O)NH$C_4H_8$—$**^{L2}$, $*^{L2}$—$CH_3$NHC(O)—$**^{L2}$, $*^{L2}$—$C_2H_4$NHC(O)—$**^{L2}$, $*^{L2}$—$C_3H_6$NHC(O)—$**^{L2}$, $*^{L2}$—$C_4H_8$NHC(O)—$**^{L2}$, $*^{L2}$—$CH_2$C(O)NH—$**^{L2}$, $*^{L2}$—$C_2H_4$C(O)NH—$**^{L2}$, $*^{L2}$—$C_3H_6$C(O)NH—$**^{L2}$, $*^{L2}$—$C_4H_8$C(O)NH—$**^{L2}$, $*^{L2}$—$CH_2$—, —$C_2H_4$—, —$C_3H_6$—, —$C_4H_8$—, —O($CH_2$)$_2$—, —[O($CH_2$)$_2$]$_2$—, —[O($CH_2$)$_2$]$_3$—, —[O($CH_2$)$_2$]$_4$— or —[O($CH_2$)$_2$]$_5$—;

and/or (c) $L^3$ is a single bond, —O—, —$SO_2$—, —C(O)—, —NH—, —N($CH_3$)—, —N($C_2H_5$)—, —N($C_3H_7$)—, $*^{L3}$—O—$CH_2$—$**^{L3}$, $*^{L3}$—O—$C_2H_4$—$**^{L3}$, $*^{L3}$—O—$C_3H_6$—$**^{L3}$, $*^{L3}$—O—$C_4H_8$—$**^{L3}$, $*^{L3}$—$CH_2$—O—$**^{L3}$, $*^{L3}$—$C_2H_4$—O—$**^{L3}$, $*^{L3}$—$C_3H_6$—O—$**^{L3}$, $*^{L3}$—$C_4H_8$—O—$**^{L3}$, $*^{L3}$-$SO_2$—$CH_2$—$**^{L3}$, $*^{L3}$-$SO_2$—$C_2H_4$—$**^{L3}$, $*^{L3}$-$SO_2$—$C_3H_6$—$**^{L3}$, $*^{L3}$—$SO_2$—$C_4H_8$—$**^{L3}$, $*^{L3}$—$CH_2$—$SO_2$—$**^{L3}$, $*^{L3}$—$C_2H_4$—$SO_2$—$**^{L3}$, $*^{L3}$—$C_3H_6$—$SO_2$—$**^{L3}$, $*^{L3}$—$C_4H_8$—$SO_2$—$**^{L3}$, $*^{L3}$—C(O)—$CH_2$—$**^{L3}$, $*^{L3}$—C(O)—$C_2H_4$—$**^{L3}$, $*^{L3}$—C(O)—$C_3H_6$—$**^{L3}$, $*^{L3}$—C(O)—$CH_2$—$**^{L3}$, $*^{L3}$ $CH_2$—C(O)—$**^{L3}$, $*^{L3}$—$C_2H_4$—C(O)—$**^{L3}$, $*^{L3}$—$C_3H_6$—C(O)—$**^{L3}$, $*^{L3}$—$C_4H_8$—C(O)—$**^{L3}$, $*^{L3}$—NH—$CH_2$—$**^{L3}$, $*^{L3}$—

NH—$C_2H_4$—$**^{L3}$, $*^{L3}$—NH—$C_3H_6$—$**^{L3}$, $*^{L3}$—NH—$C_4H_8$—$**^{L3}$, $*^{L3}$—CH—NH—$**^{L3}$, $*^{L3}$—$C_2H_4$—NH—$**^{L3}$, $*^{L3}$—$C_3H_6$—NH—$**^{L3}$, $*^{L3}$—$C_4H_8$—NH—$**^{L3}$, $*^{L3}$—NHC(O)—$**^{L3}$, $*^{L3}$—C(O)NH—$**^{L3}$, $*^{L3}$—N($CH_3$)C(O)—$**^{L3}$, $*^{L3}$—C(O)N($CH_3$)—$**^{L3}$, $*^{L3}$—N($C_2H_5$)C(O)—$**^{L3}$, $*^{L3}$—C(O)N($C_2H_5$)—$**^{L3}$, $*^{L3}$—N($C_3H_7$)C(O)—$**^{L3}$, $*^{L3}$—NHC(O)$CH_2$—$**^{L3}$, $*^{L3}$—NHC(O)$C_2H_4$—$**^{L3}$, $*^{L3}$—C(O)N($C_3H_7$)—$**^{L3}$, $*^{L3}$—NHC(O)$C_3H_6$—$**^{L3}$, $*^{L3}$—NHC(O)$C_4H_8$—$**^{L3}$, $*^{L3}$—C(O)NH$CH_2$—$**^{L3}$, $*^{L3}$ C(O)NH$C_2H_4$—$**^{L3}$, $*^{L3}$—C(O)NH$C_3H_6$—$**^{L3}$, $*^{L3}$—C(O)NH$C_4H_8$—$**^{L3}$, $*^{L3}$—$CH_2$NHC(O)—$**^{L3}$, $*^{L3}$-$C_2H_4$NHC(O)—$**^{L3}$, $*^{L3}$—$C_3H$NHC(O)—$**^{L3}$, $*^{L3}$—$C_4H_8$NHC(O)—$**^{L3}$, $*^{L3}$—$CH_2$C(O)NH—$**^{L3}$, $*^{L3}$-$C_2H_4$C(O)NH—$**^{L3}$, $*^{L3}$—$C_3H_6$C(O)NH—$**^{L3}$, $*^{L3}$-$C_4H_8$C(O)NH—$**^{L3}$, —$CH_2$—, —$C_2H_4$—, —$C_3H_6$—, —$C_4H_8$—, —O$(CH_2)_2$—, —$[O(CH_2)_2]_2$—, —$[O(CH_2)_2]_3$—, —$[O(CH_2)_2]_4$— or —$[O(CH_2)_2]_5$—.

18. The compound according to claim 15, wherein the

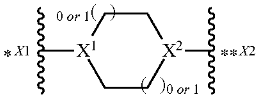

moiety is independently selected from

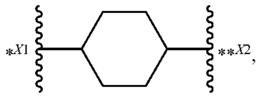, 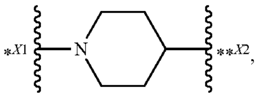,

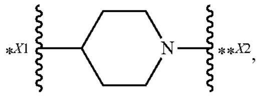, 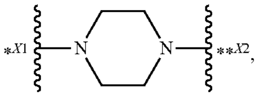,

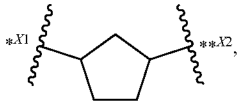, 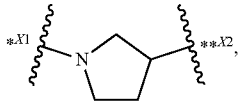,

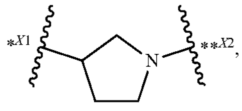, 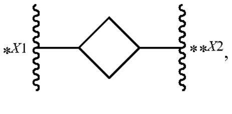,

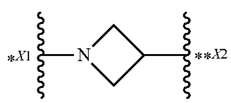 or 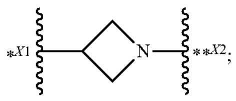;

wherein $*^{X1}$ refers to the position attached to the

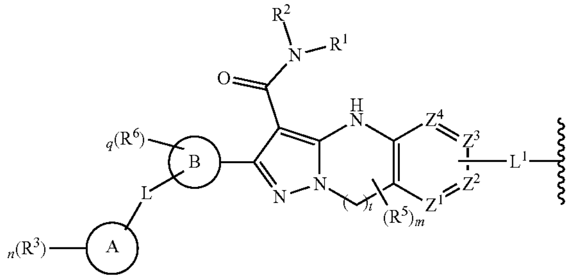

moiety, and $**^{X2}$ refers to the position attached to the

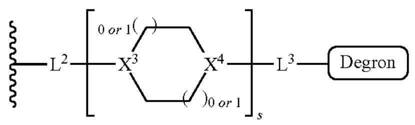

moiety.

19. The compound according to claim 15, wherein the

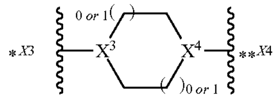

moiety is independently selected from

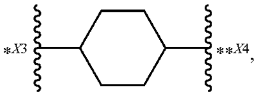, 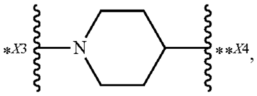,

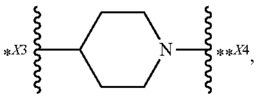, 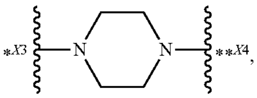,

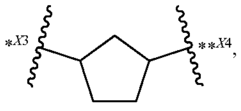, 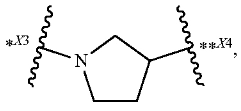,

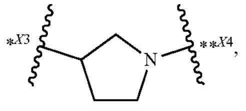, 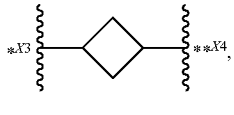,

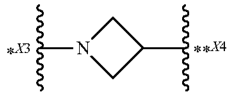 or 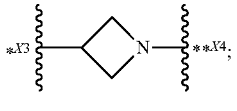;

wherein $*^{X3}$ refers to the position attached to the
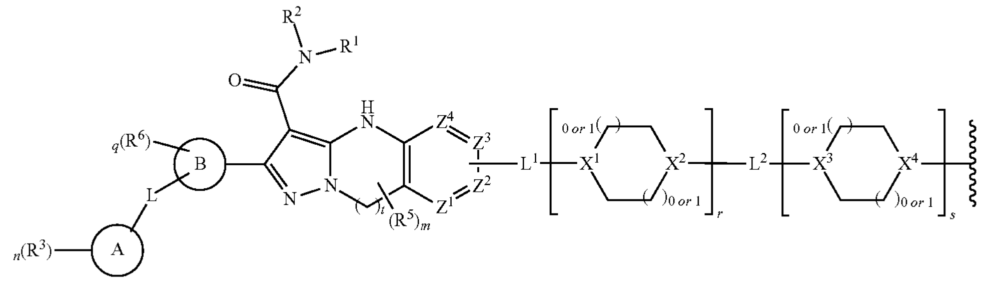
moiety, and $**^{L4}$ refers to the position attached to the
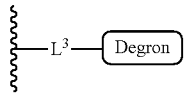
moiety.
20. The compound according to claim 16, wherein the
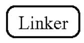
moiety is
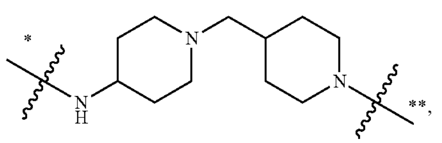
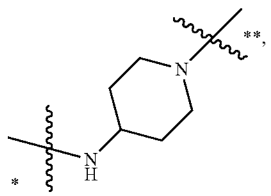
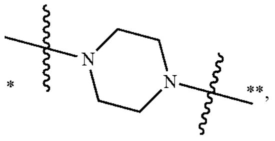
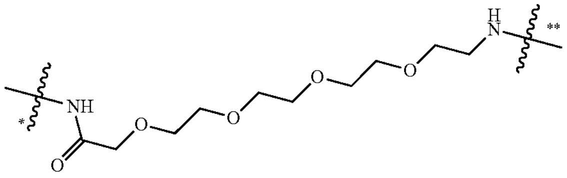
,
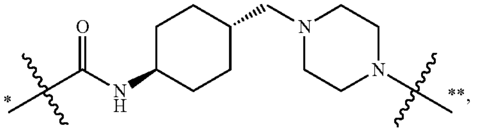
-continued
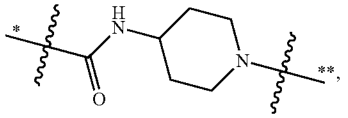
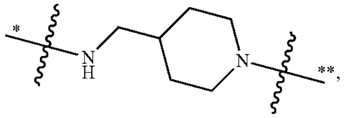
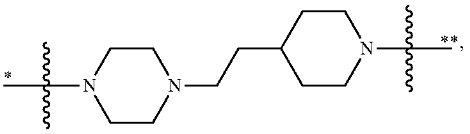
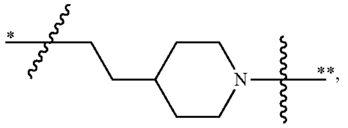
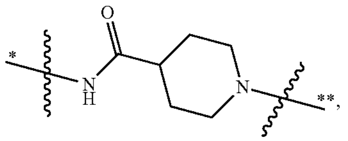
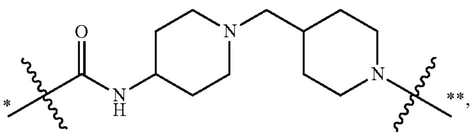
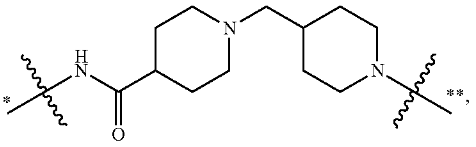
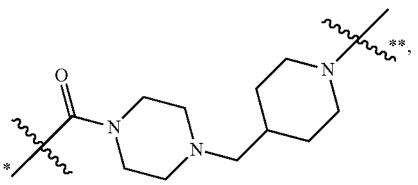
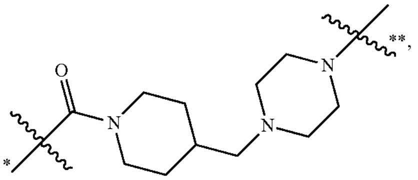

-continued
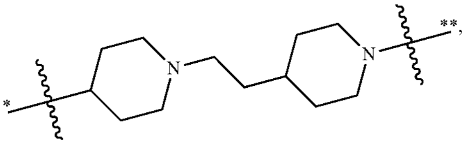
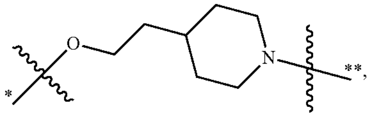
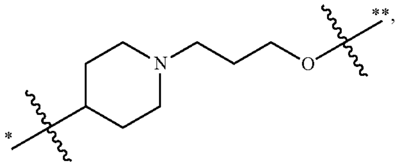
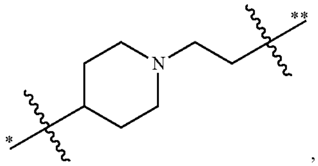
,
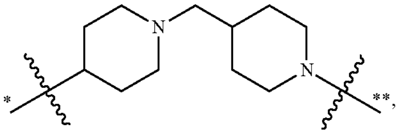
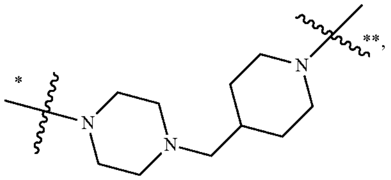
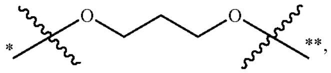
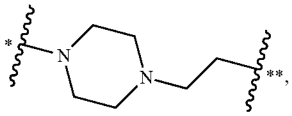
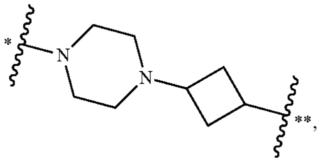
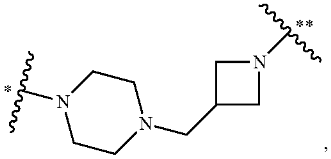
,
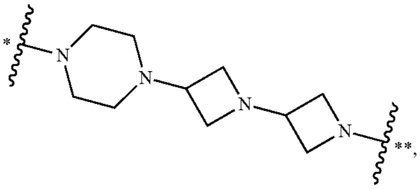
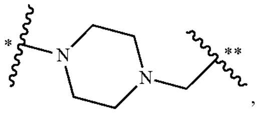
,
-continued
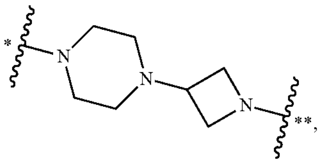
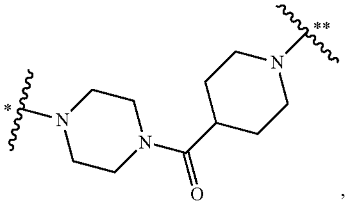
,
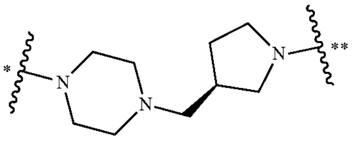
or
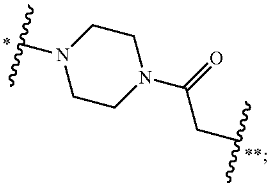
wherein * refers to the position attached to the
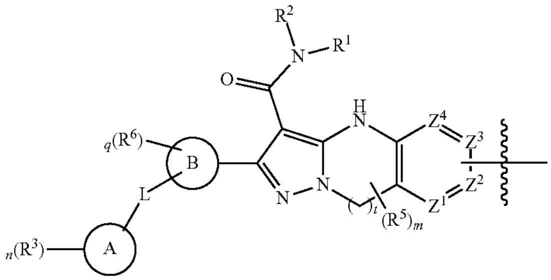
moiety, and ** refers to the position attached to the
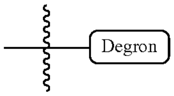
moiety.

21. A compound selected from
1 A4
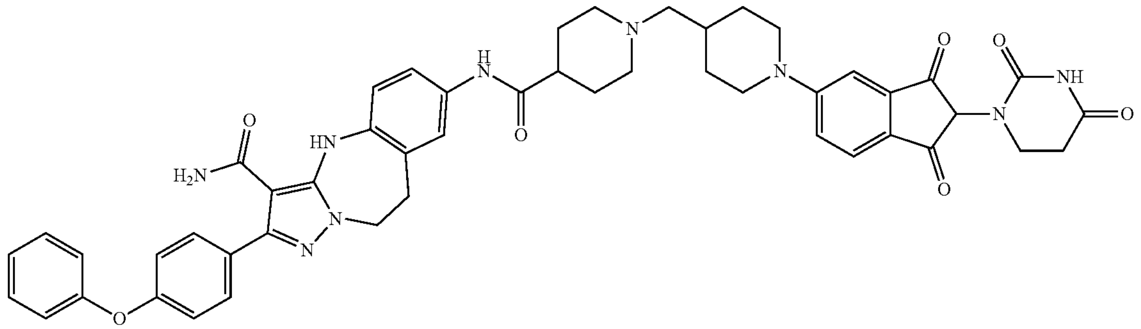
2 A5
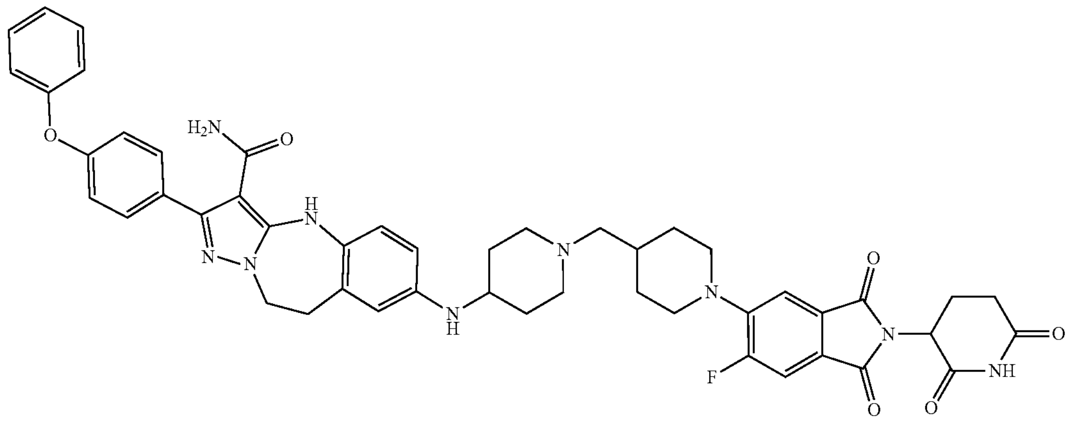
3 A6
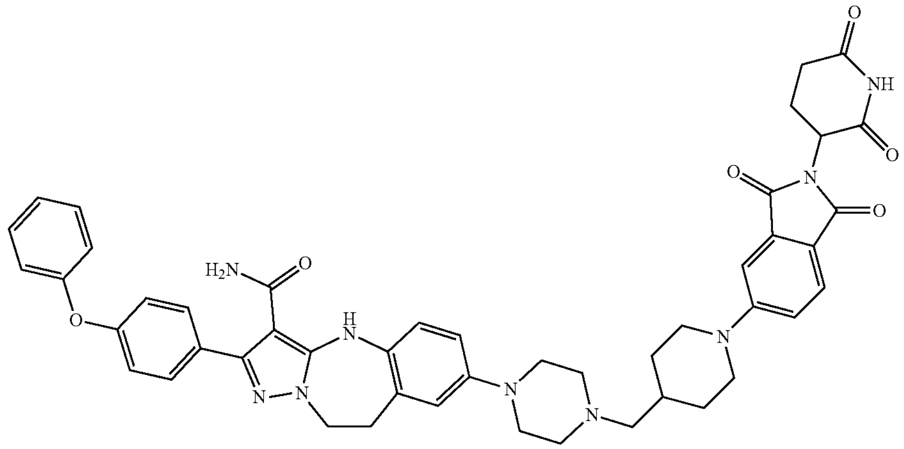
4 A3
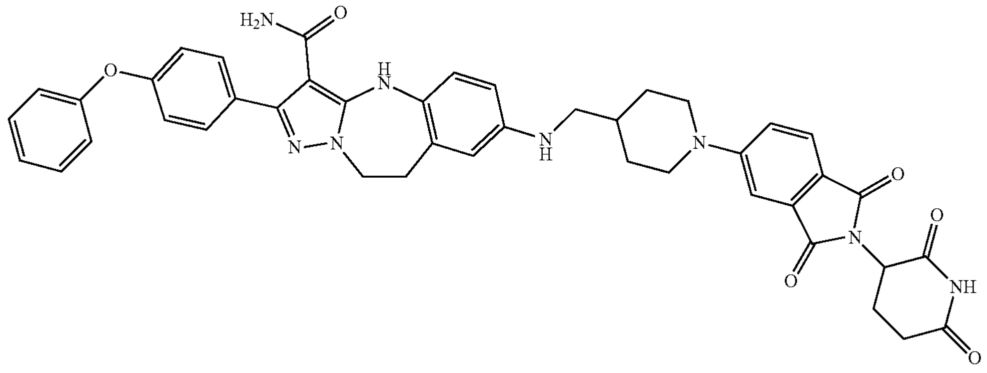

-continued
5 A8
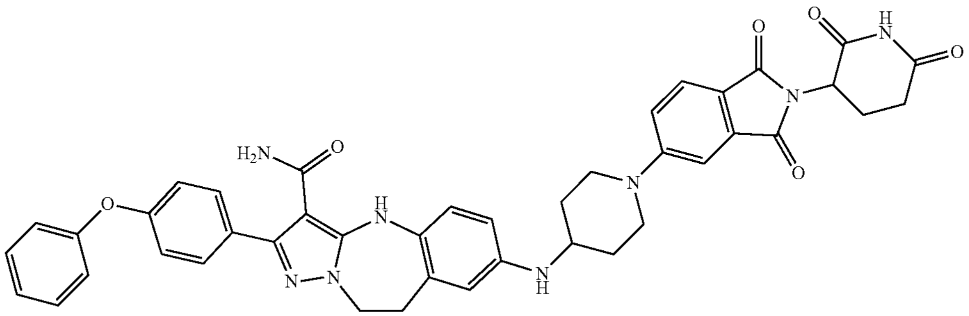
6 A7
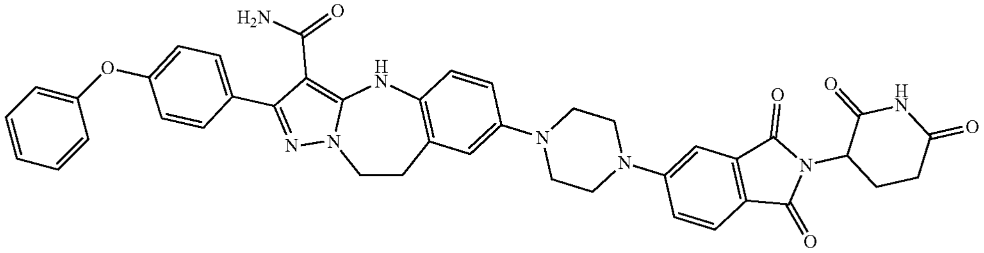
7 A2
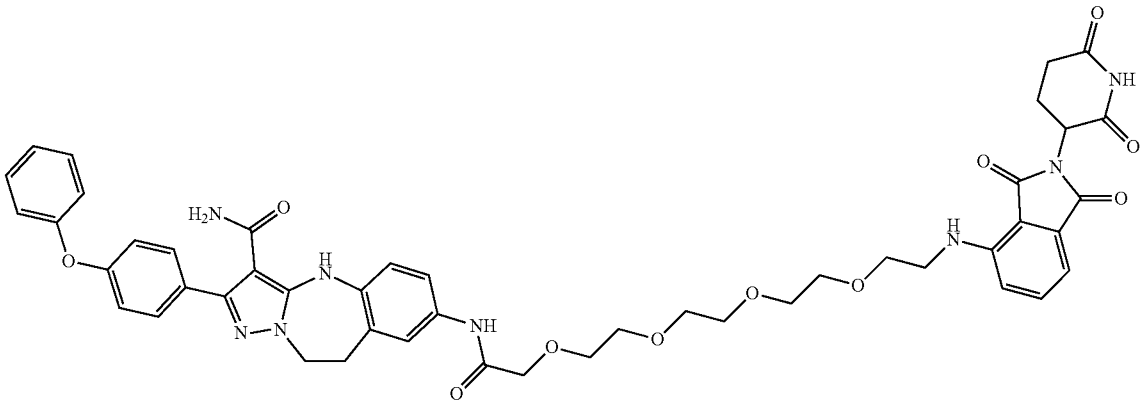
8 A10
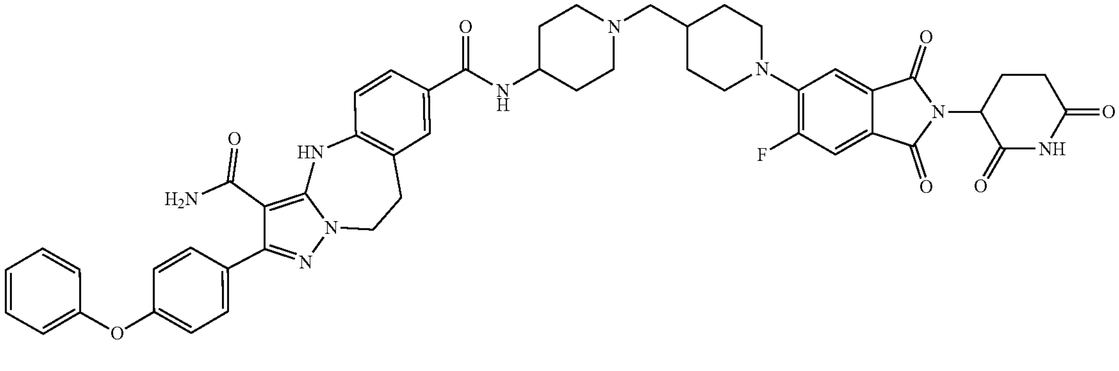

-continued
9 A12
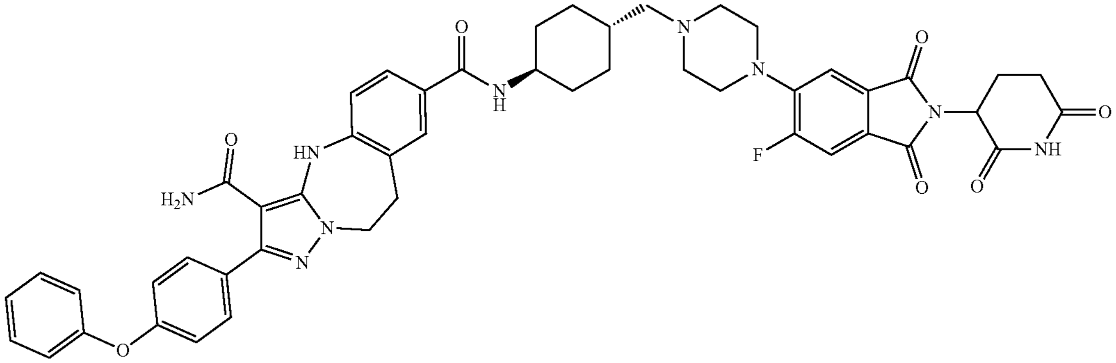
10 A13
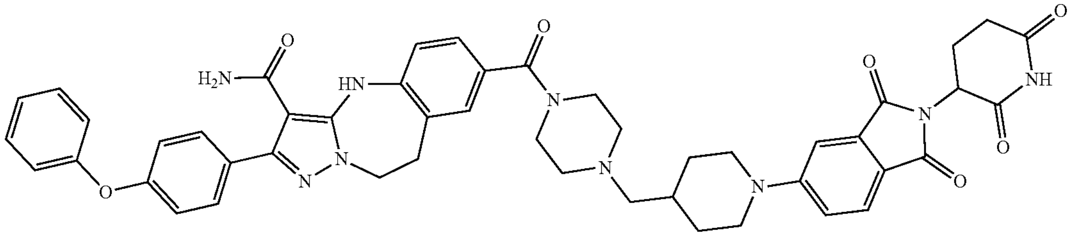
11 A14
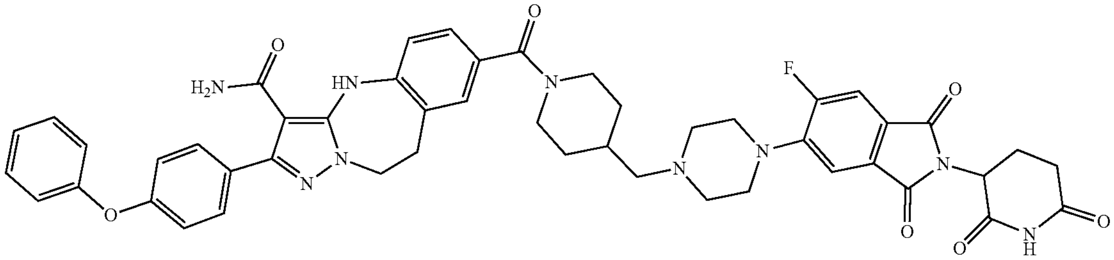
12 A9
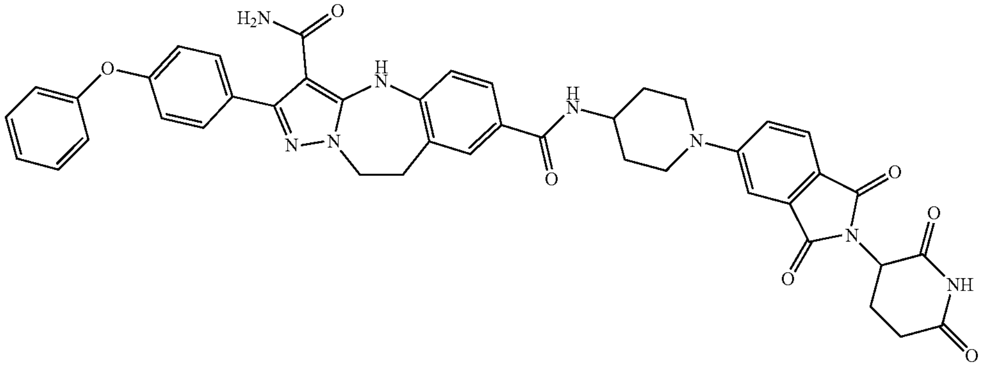
13 A1
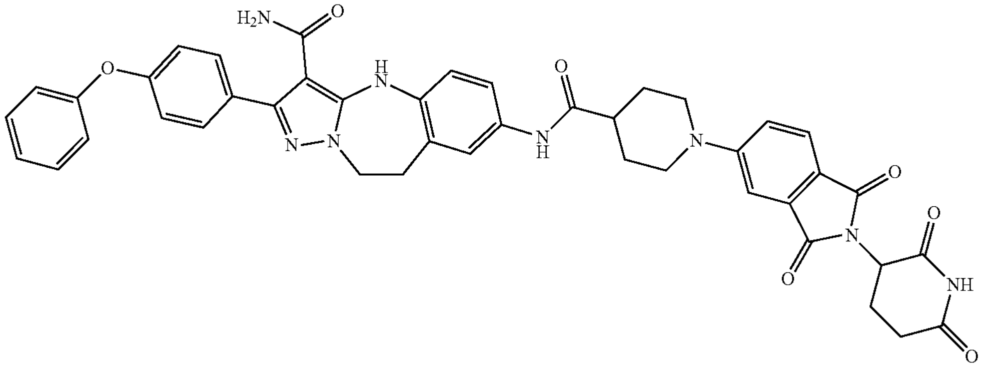

-continued
14 A11
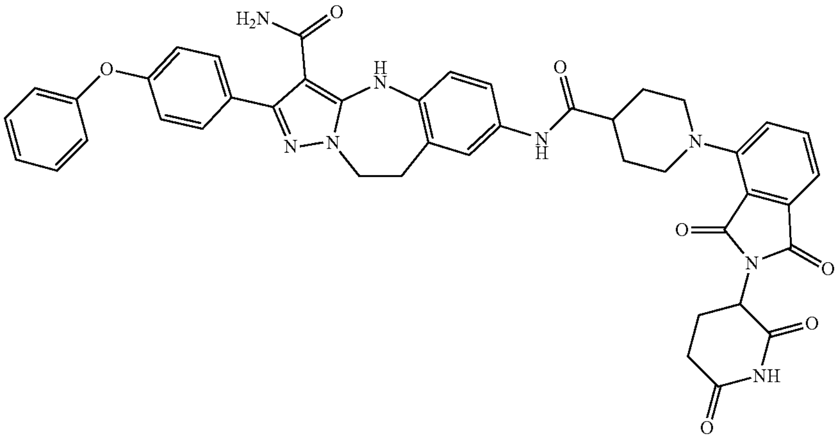
15 A16
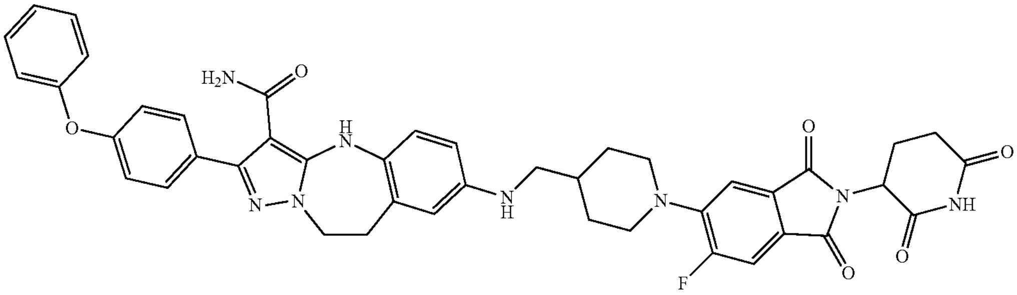
16 A21
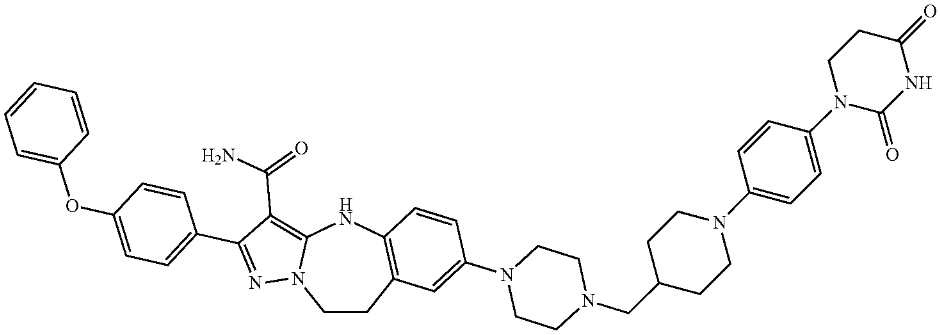
17 A22
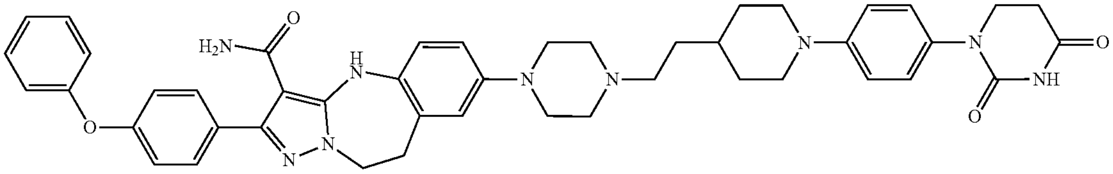
18 A24
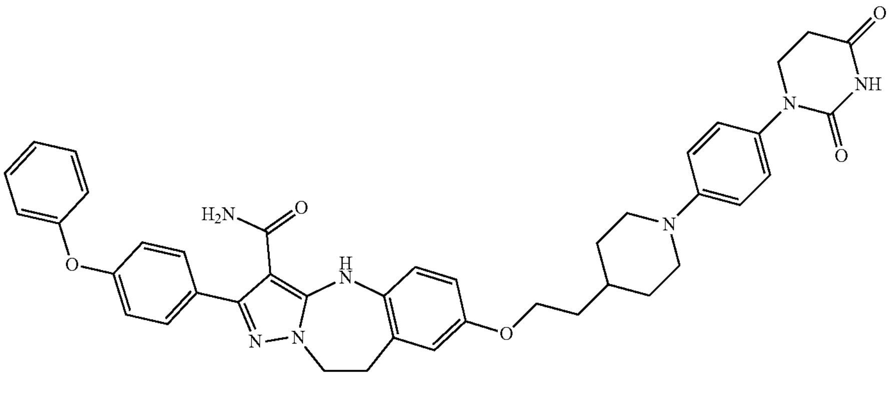

-continued
19 A28
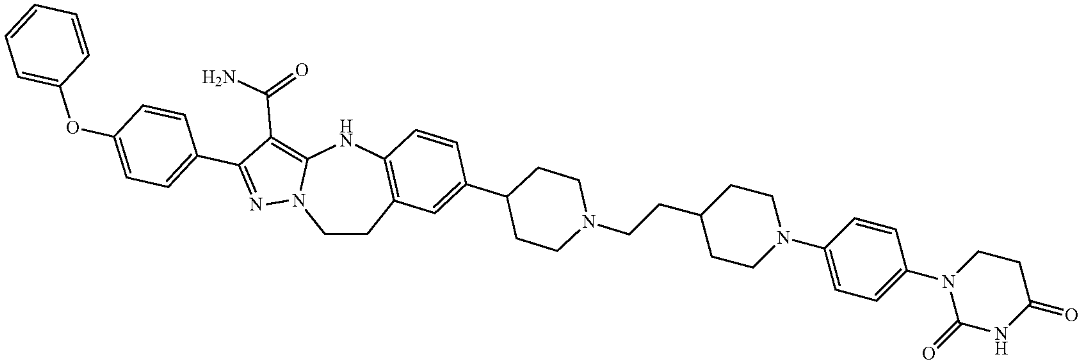
20 A30
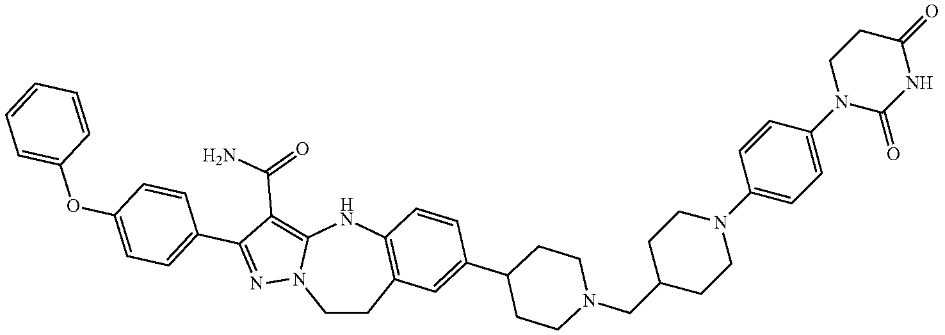
21 A26
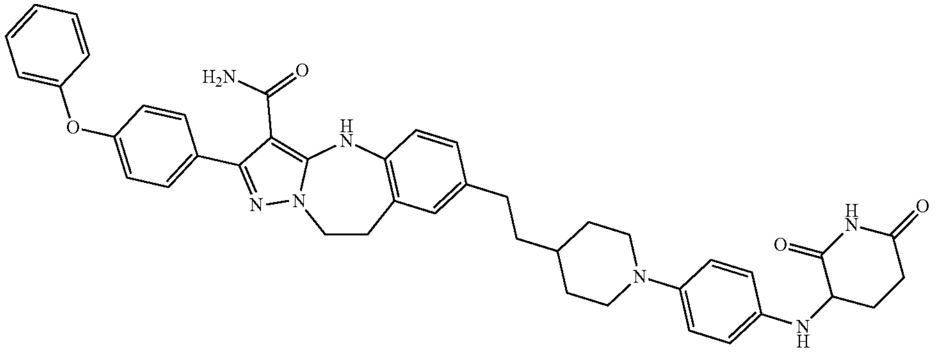
22
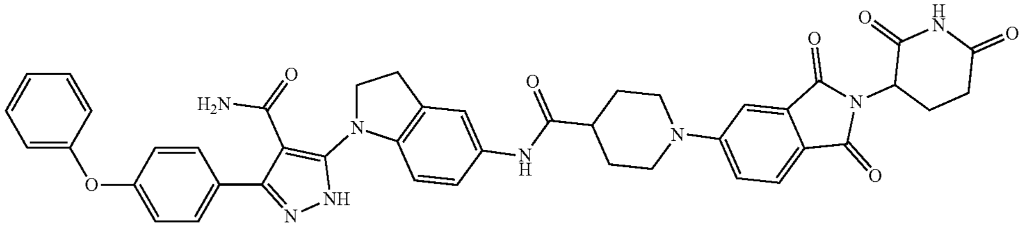

-continued
23 A29
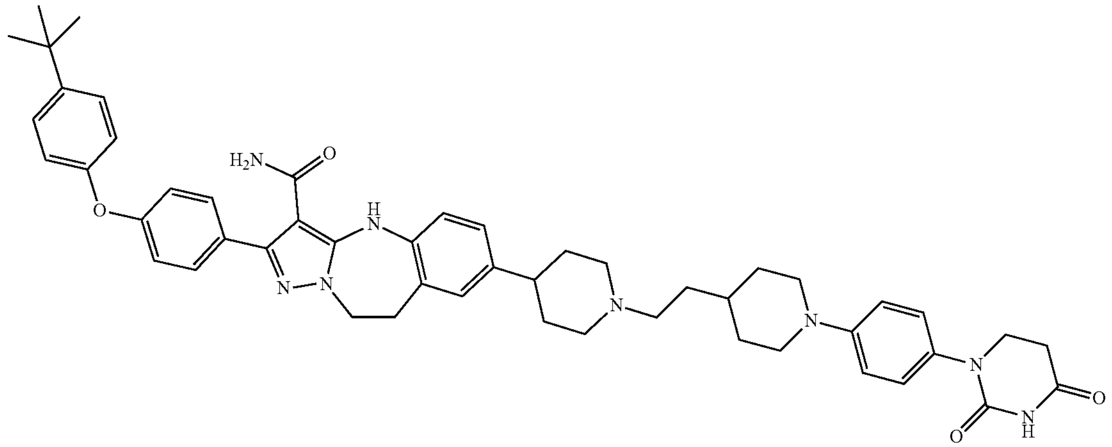
24 A31
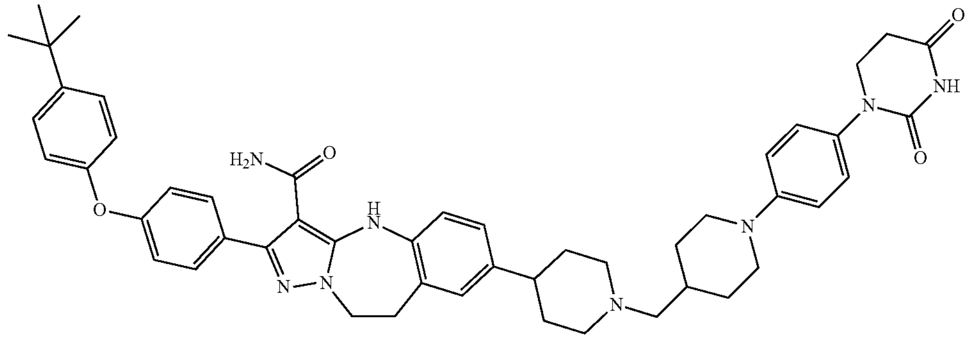
25 A17
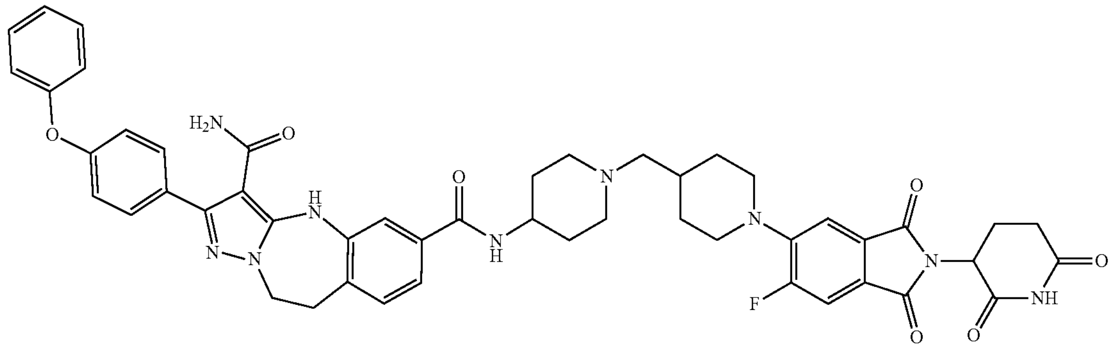
26 A18
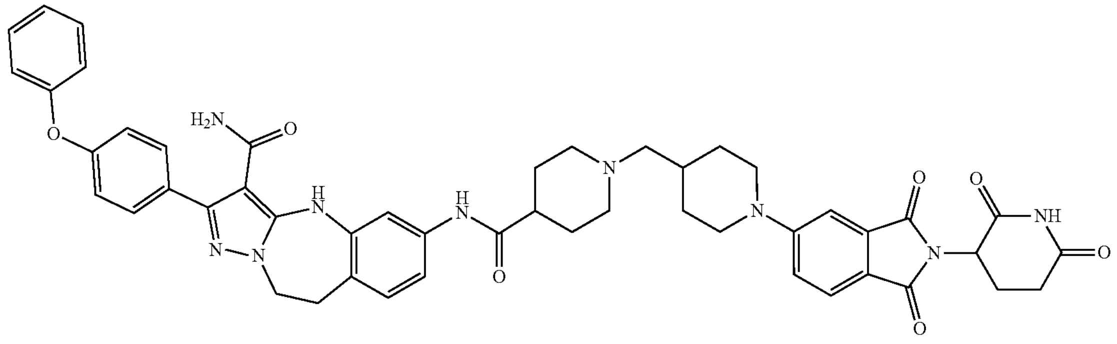

-continued
27 A19
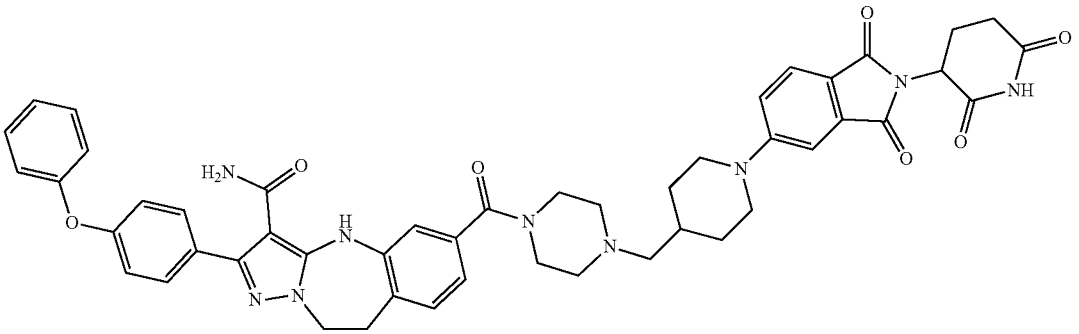
28 A20
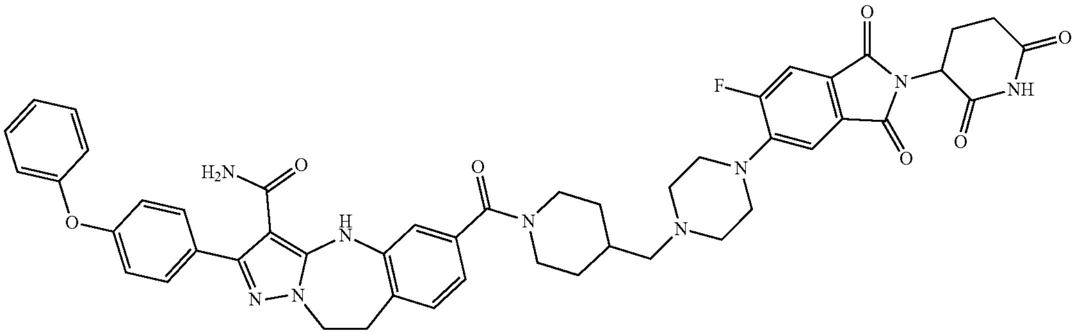
29 A15
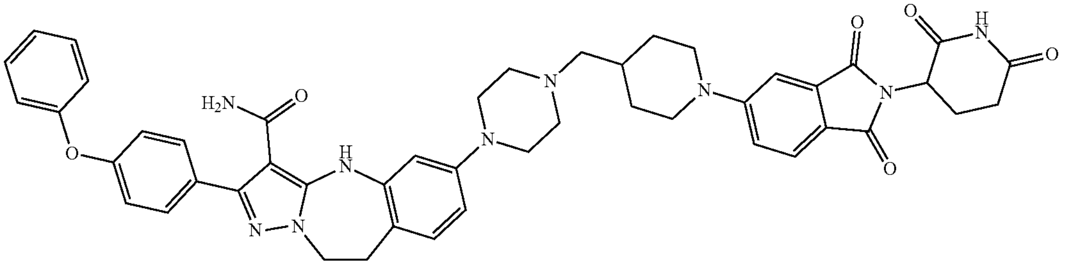
30 A23
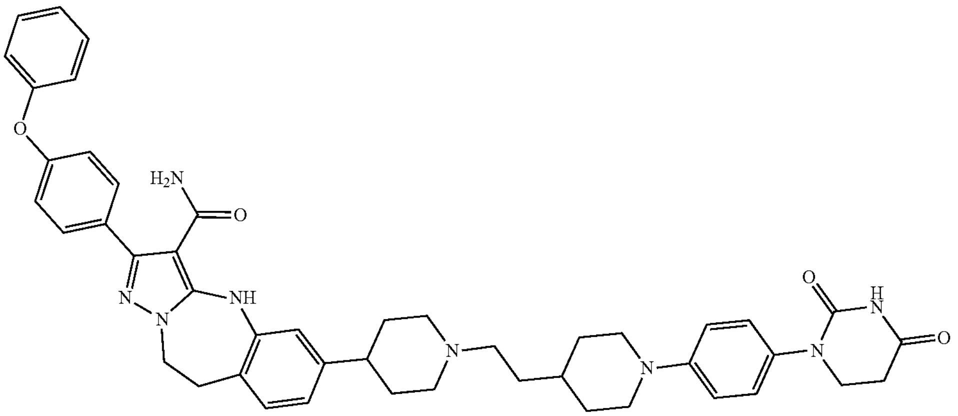

-continued
31 A27
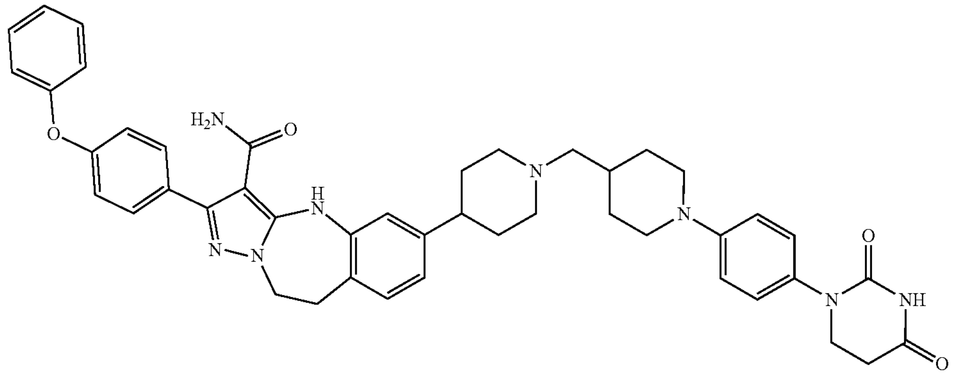
32 A25
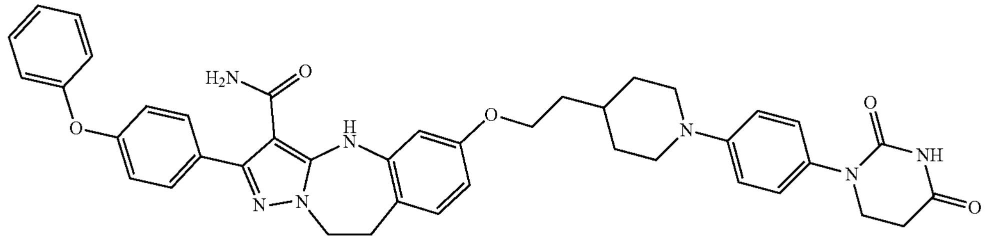
33 A32
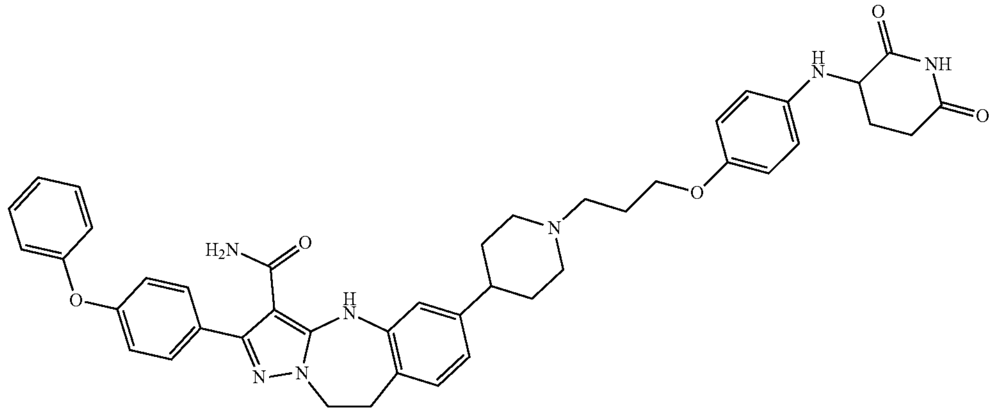
34 A33
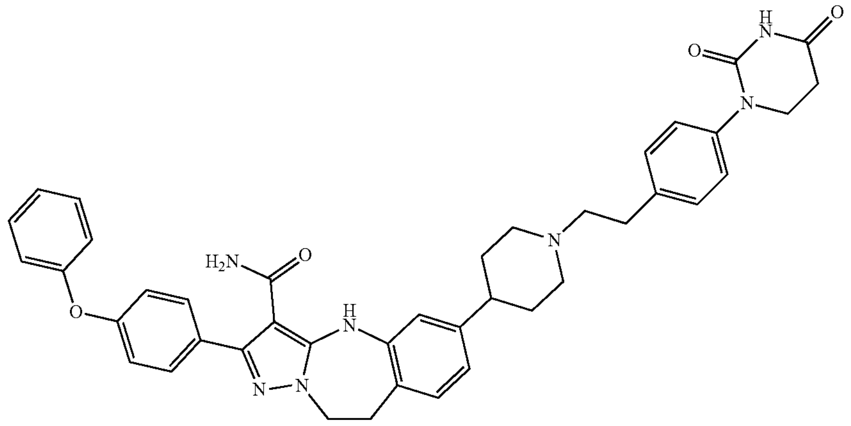

-continued
35 A34
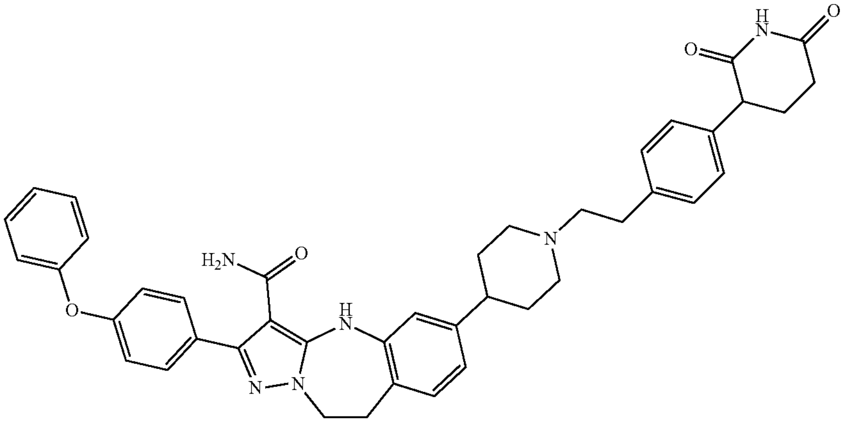
36 A35
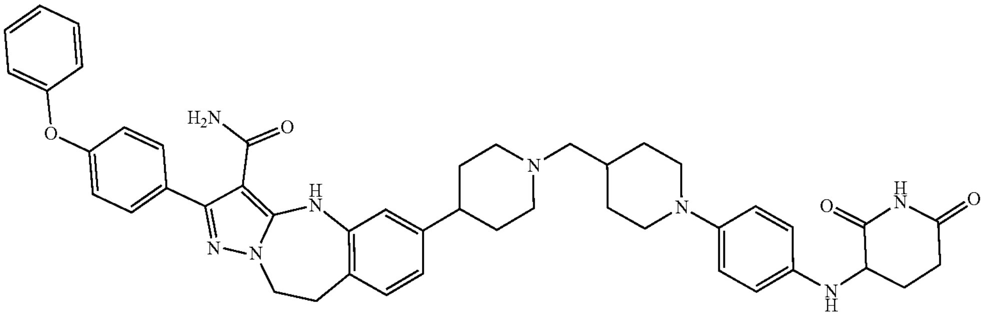
37
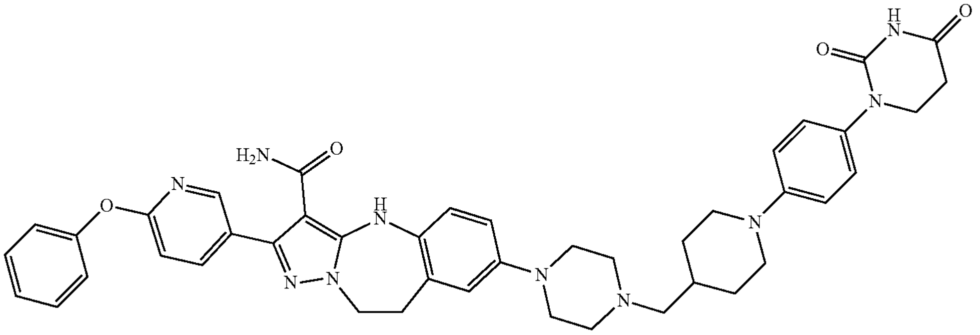
38 A36
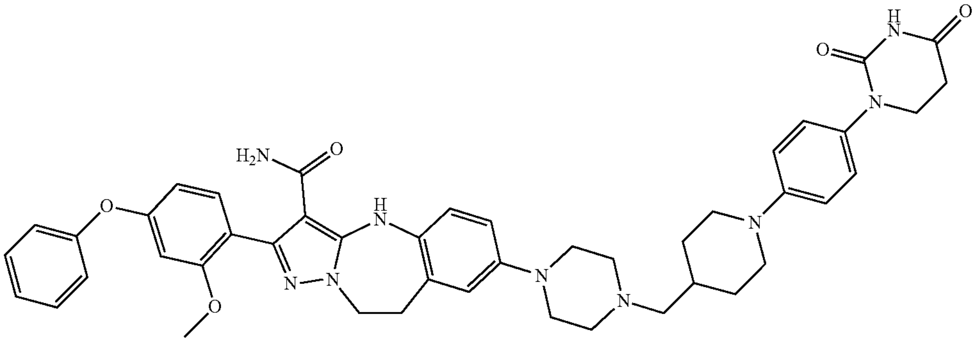

-continued
39 A37
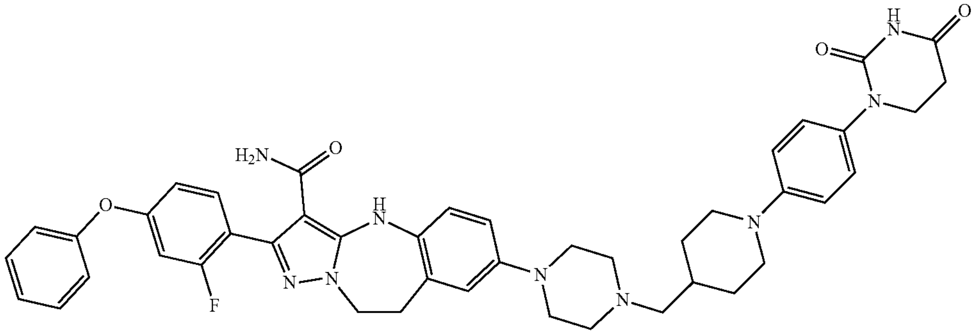
40 A38
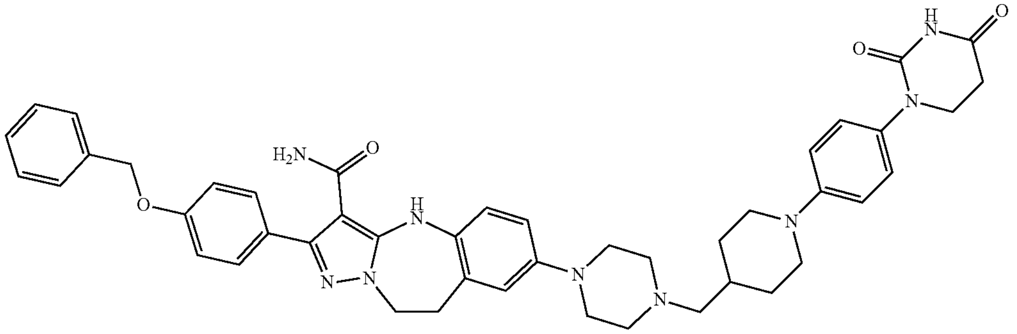
41 B1
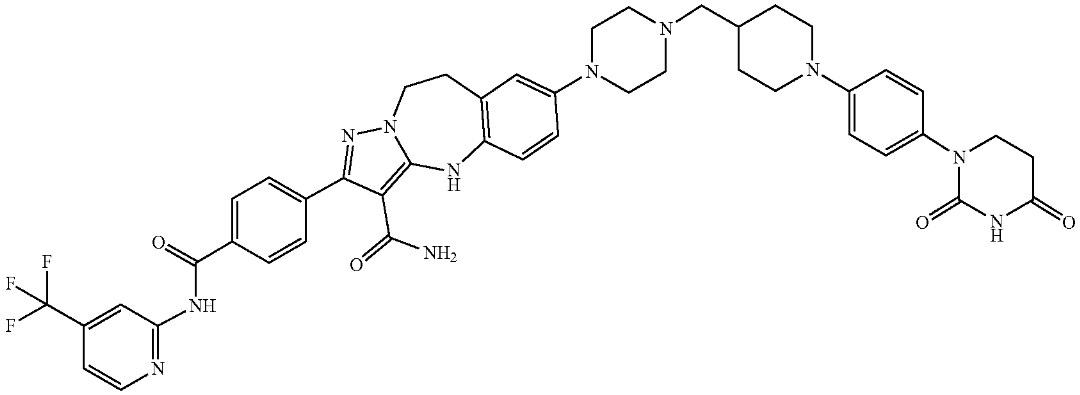
42 B3
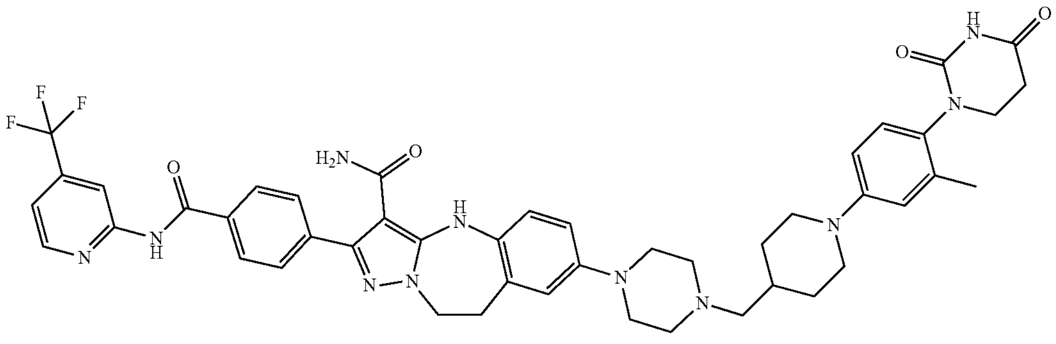

-continued
43 B9
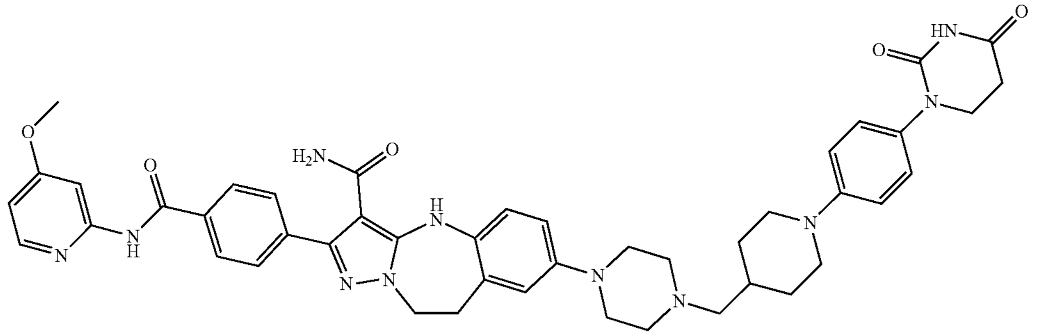
44 B10
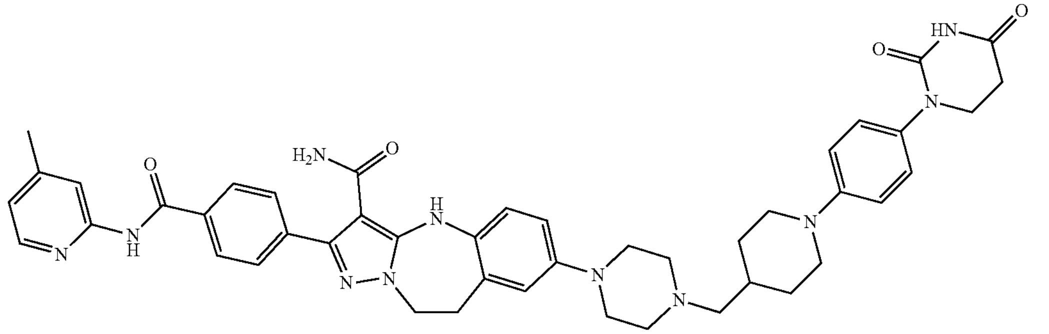
45 B11
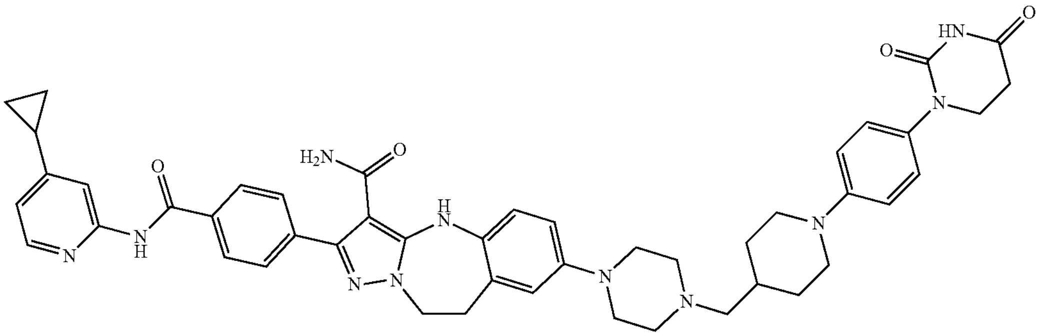
46 B12
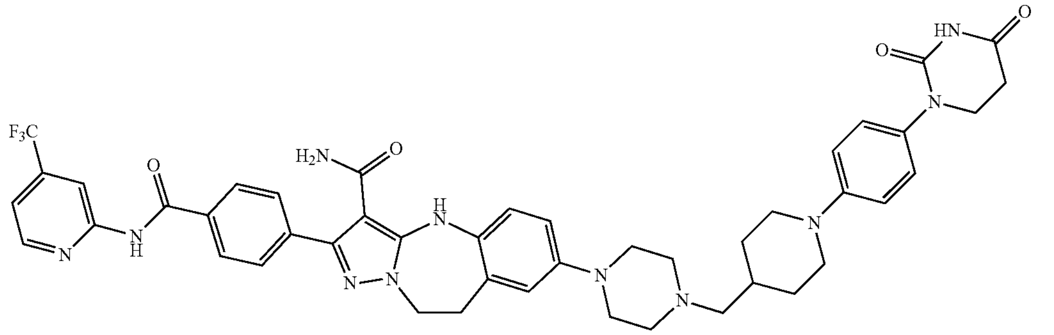

-continued
47 B13
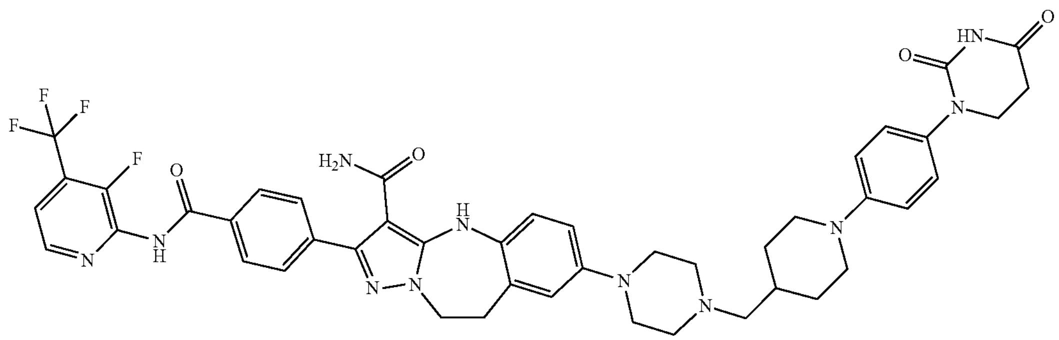
48 B4
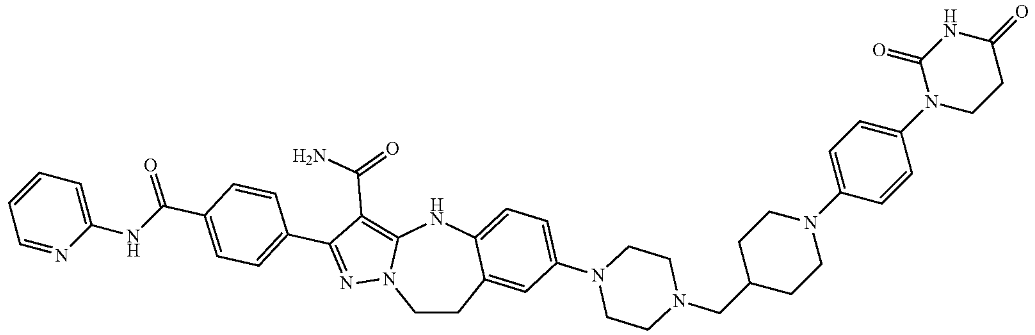
49 B16
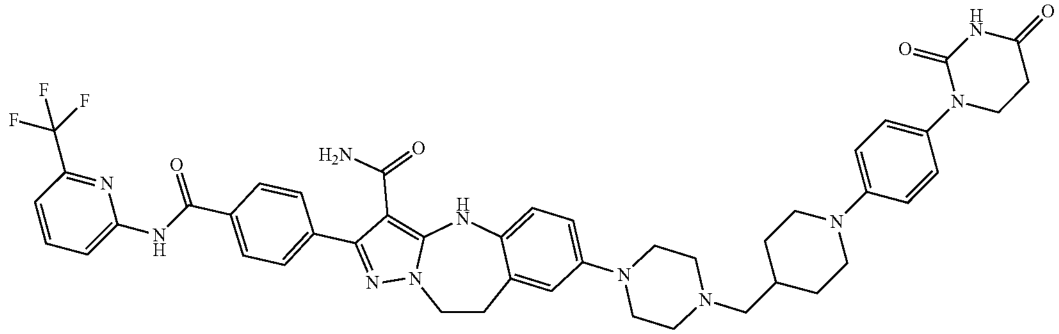
50 B17
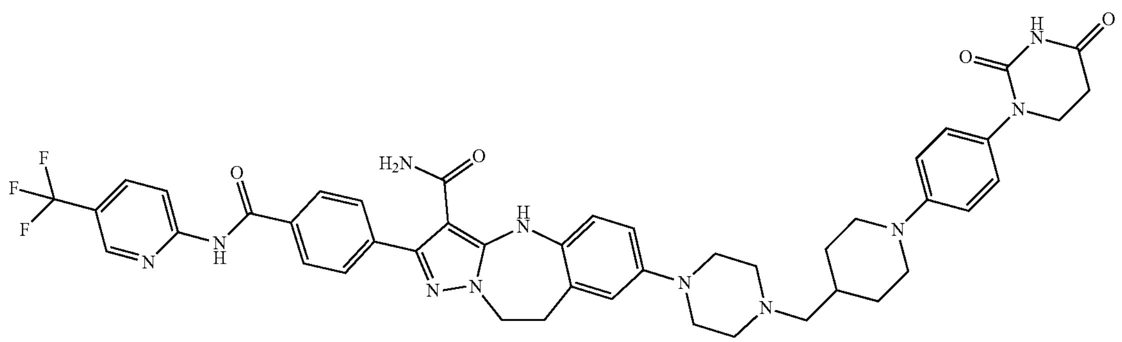

-continued
51 B18
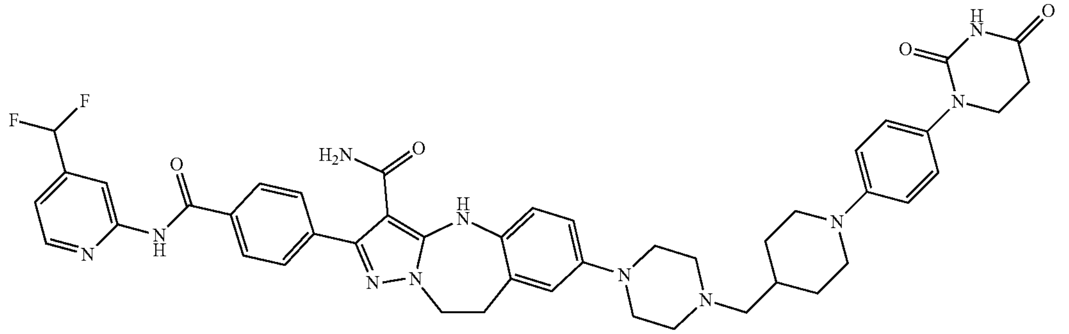
52 B19
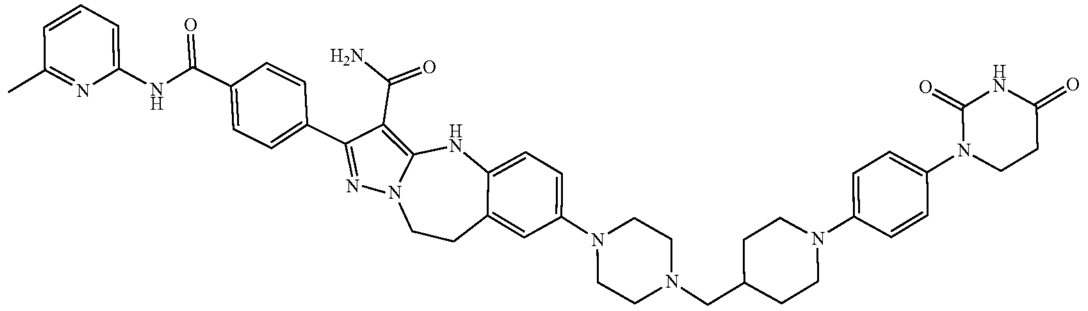
53 B2
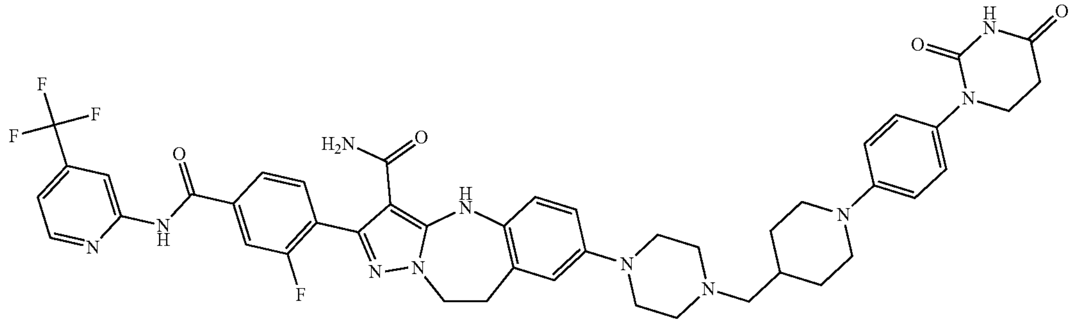
54 B8
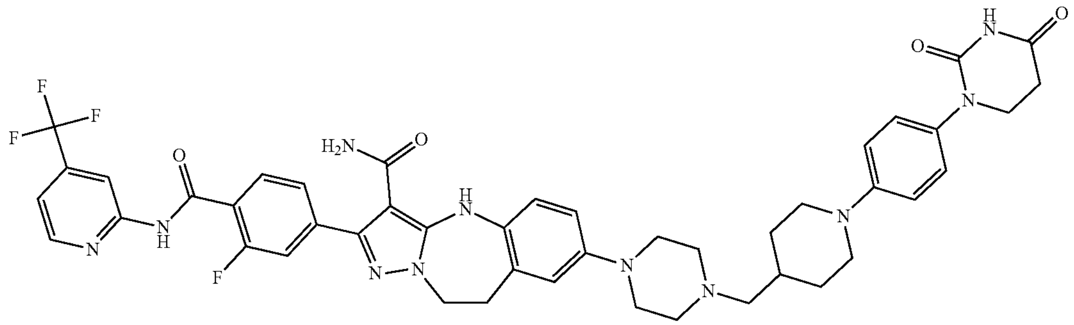

-continued
55 B14
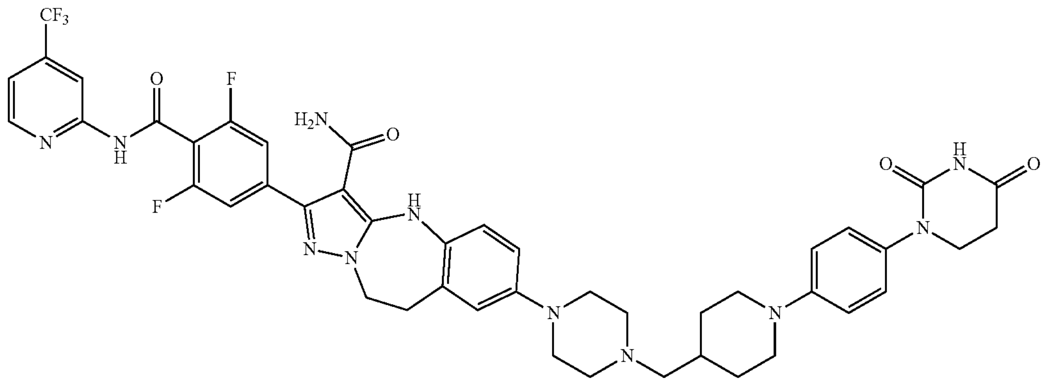
56 B6
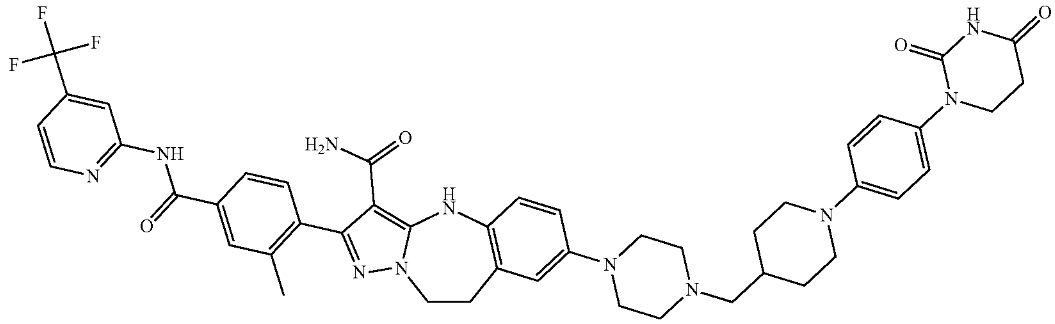
57 B22
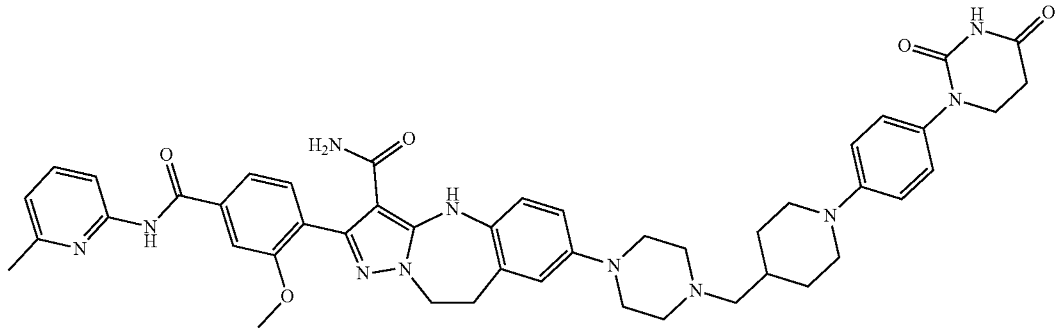
58 B27
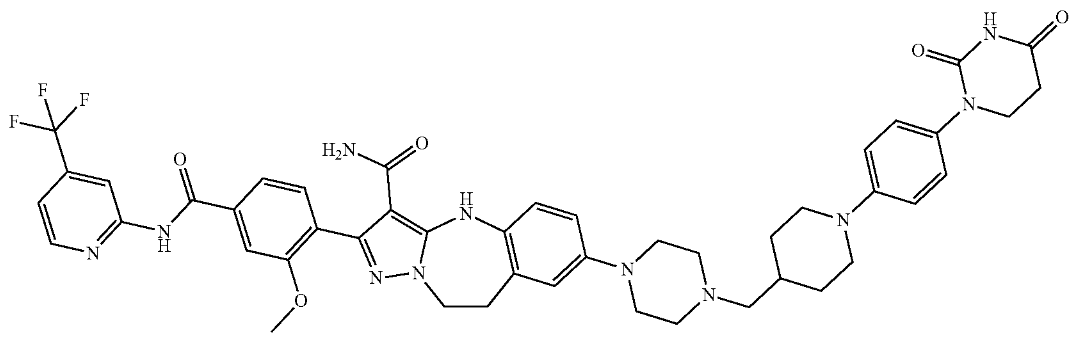

-continued
59 B7
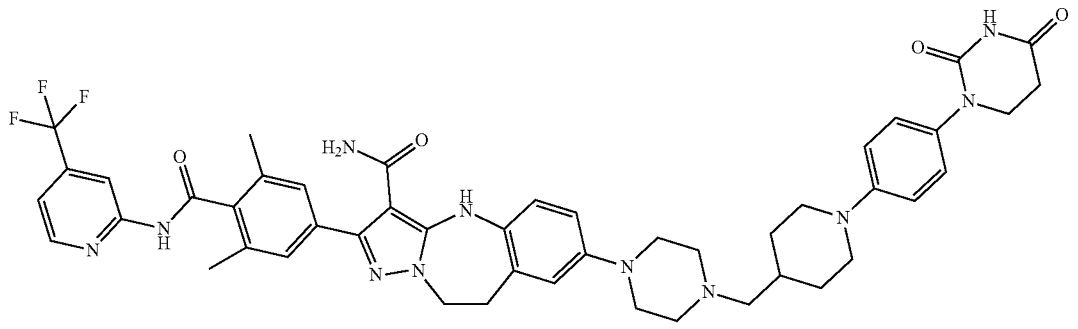
60 B5
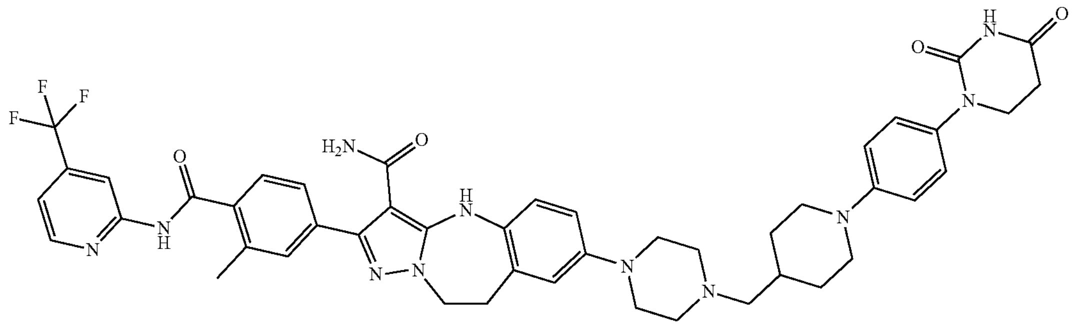
61 B21
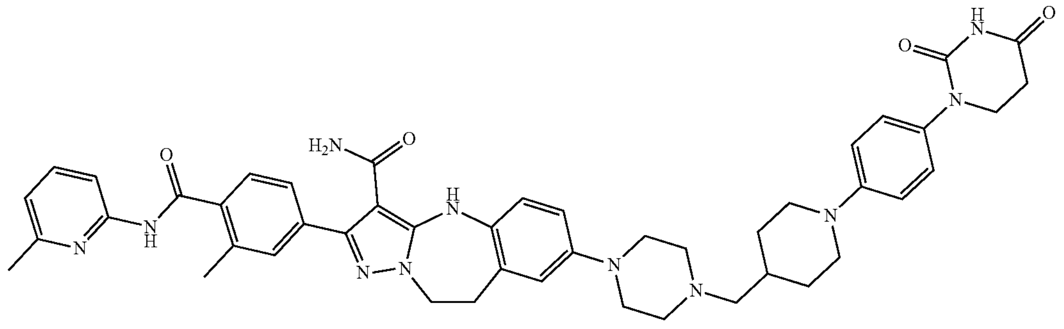
62 B23
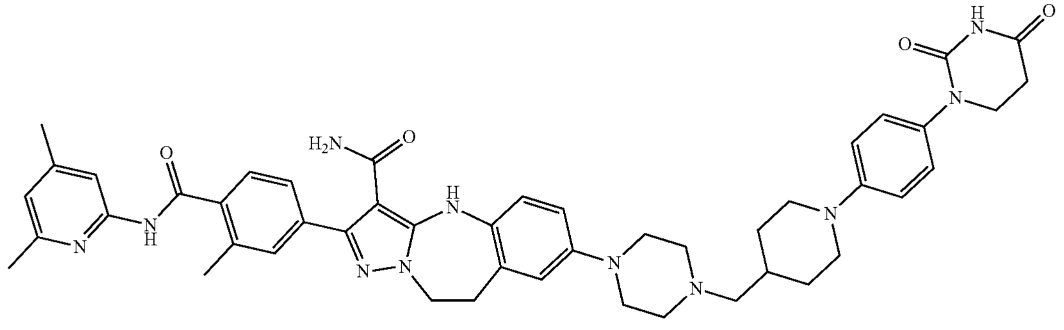
63 B20
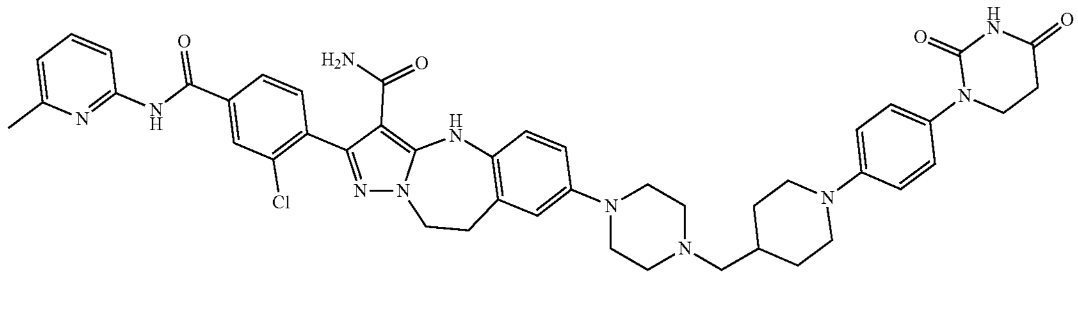

-continued
64 B24
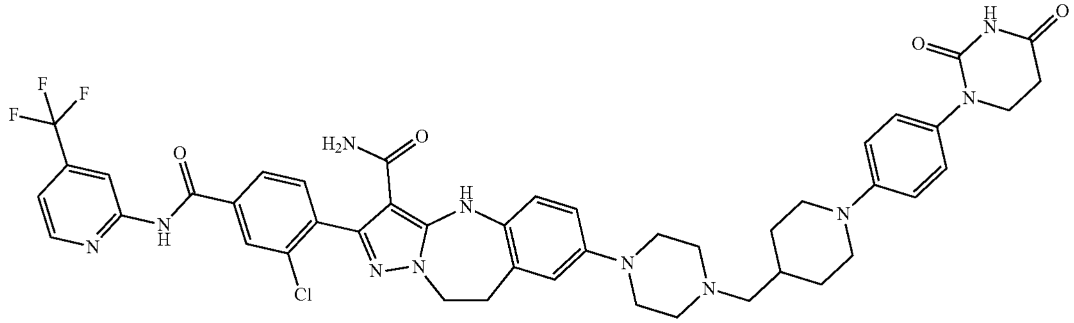
65 B25
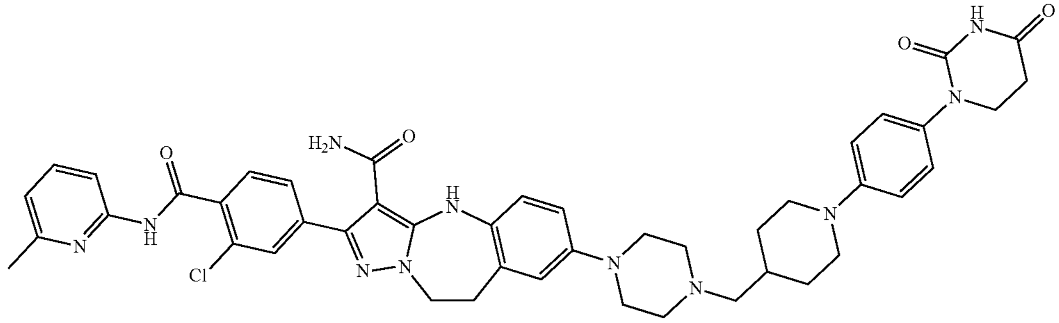
66 B26
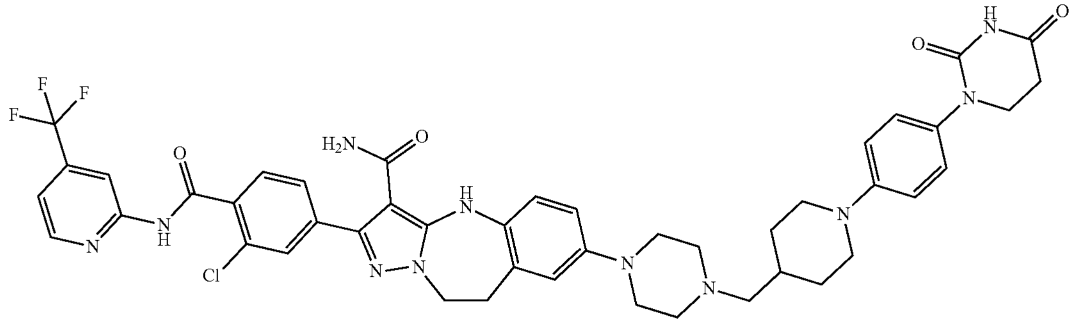
67 B15
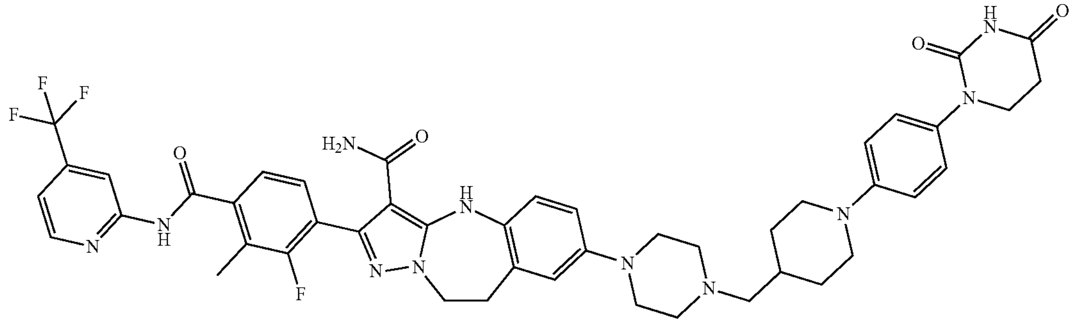
68 B28
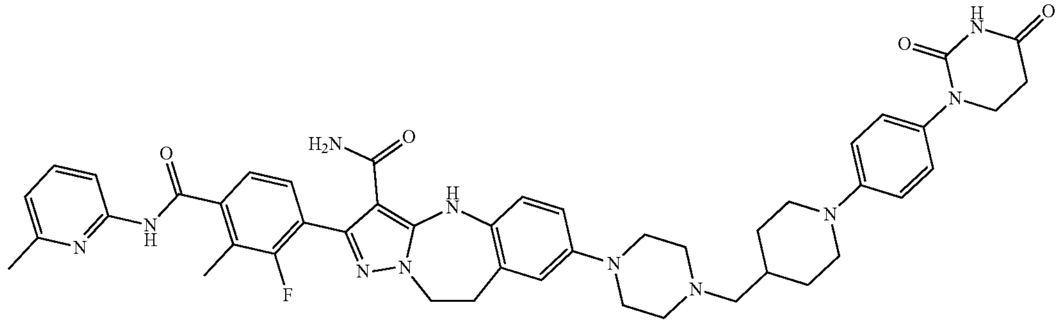

-continued
69 C1
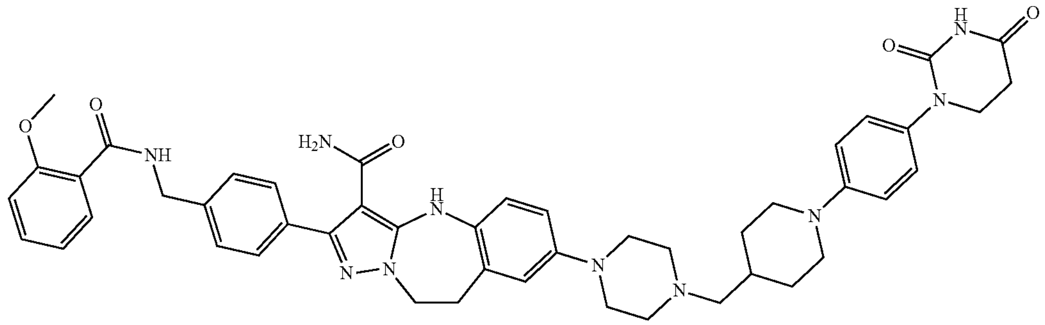
70 C2
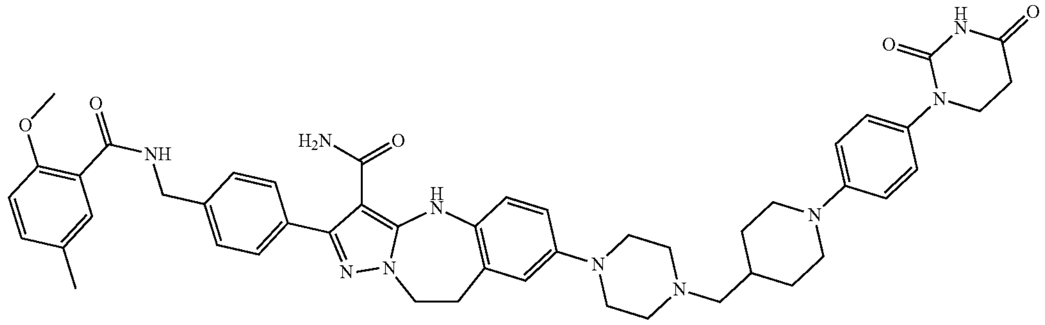
71 C4
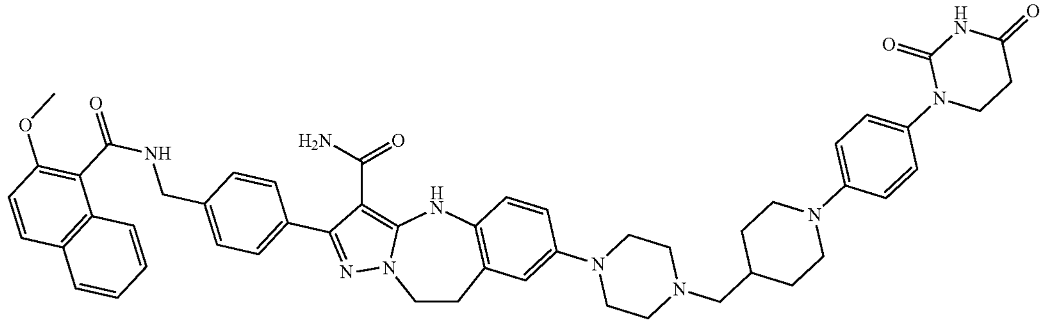
72 C3
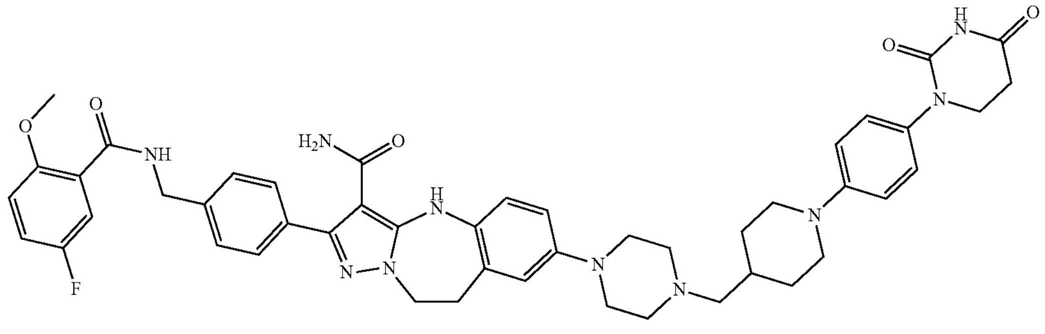

-continued
73 C21
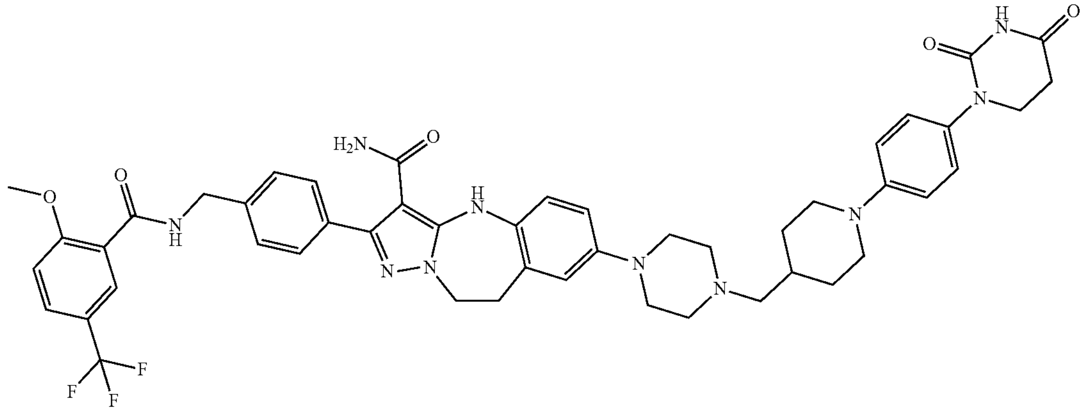
74 C22
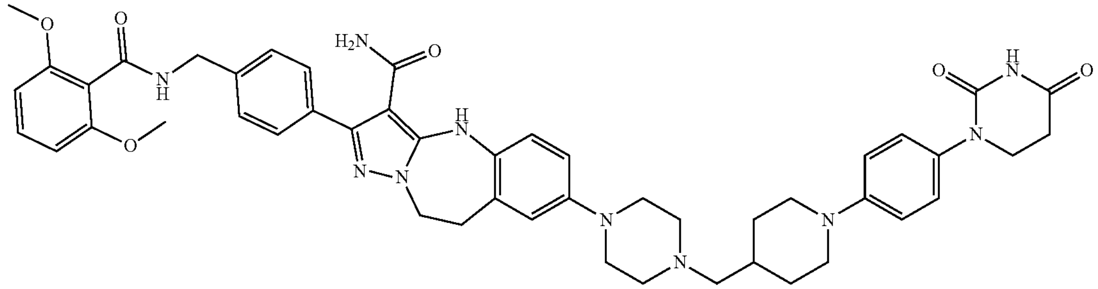
75 C23
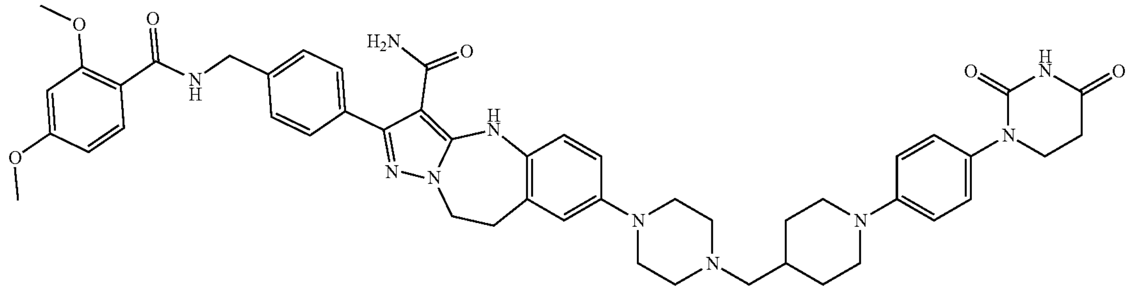
76 C25
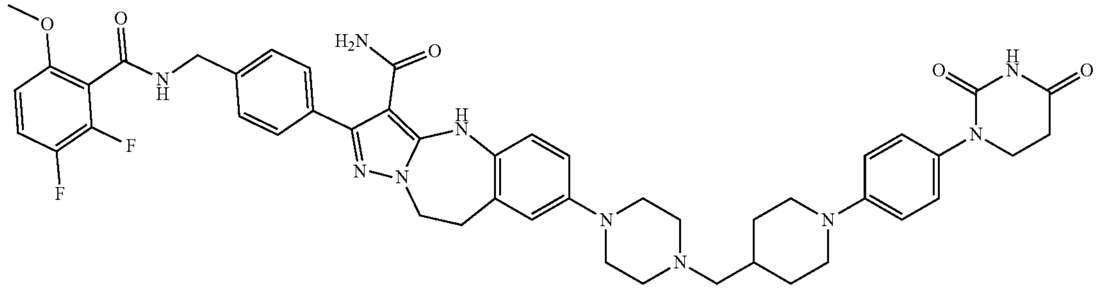
77 C29
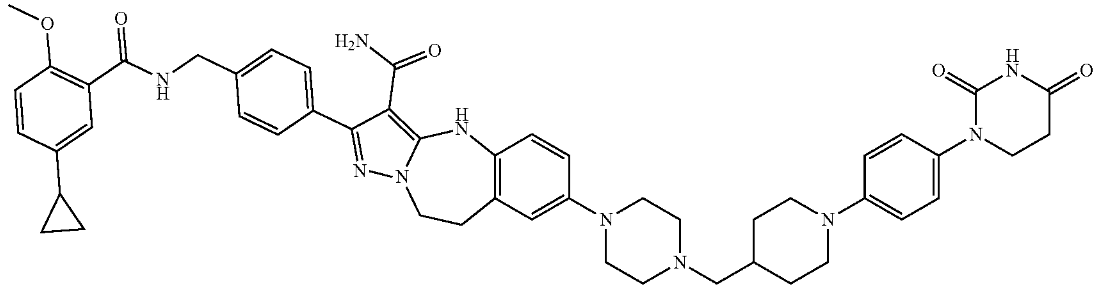

-continued
78 C30
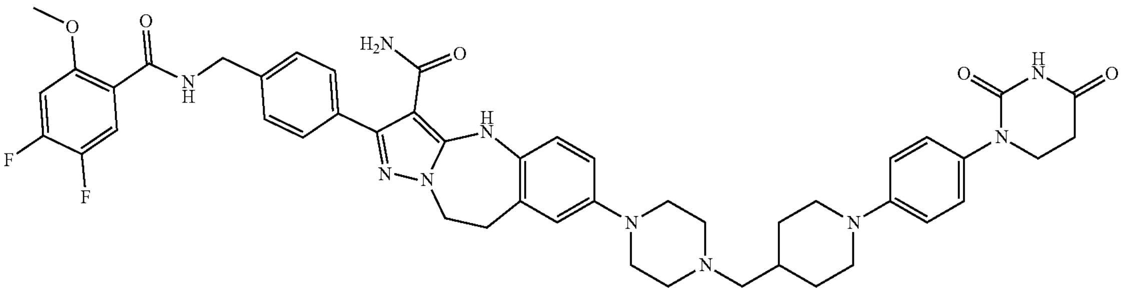
79 C12
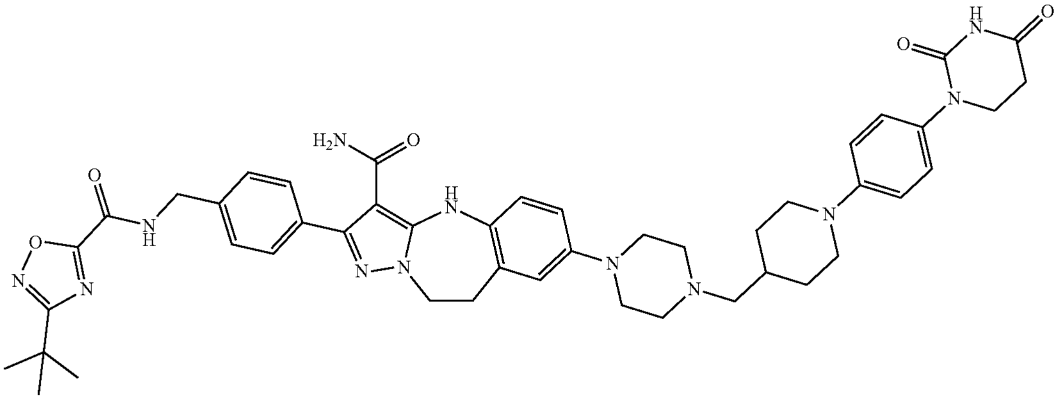
80 C7
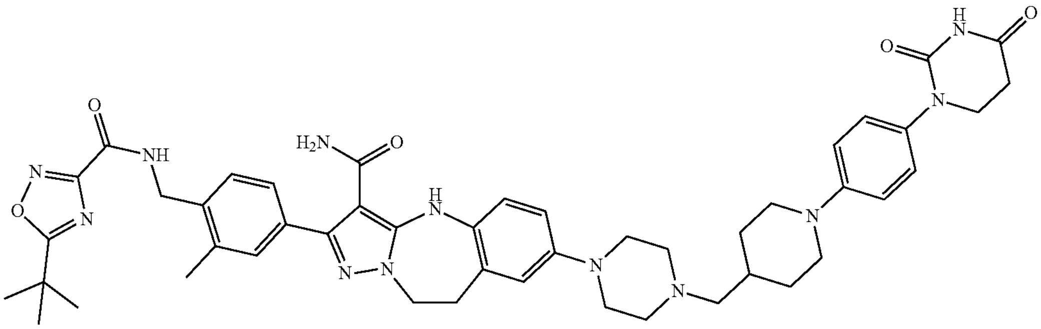
81 C8
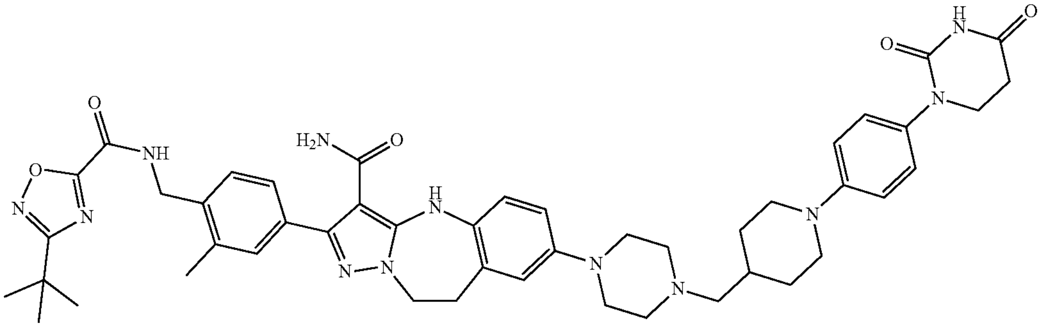

-continued
82 C9
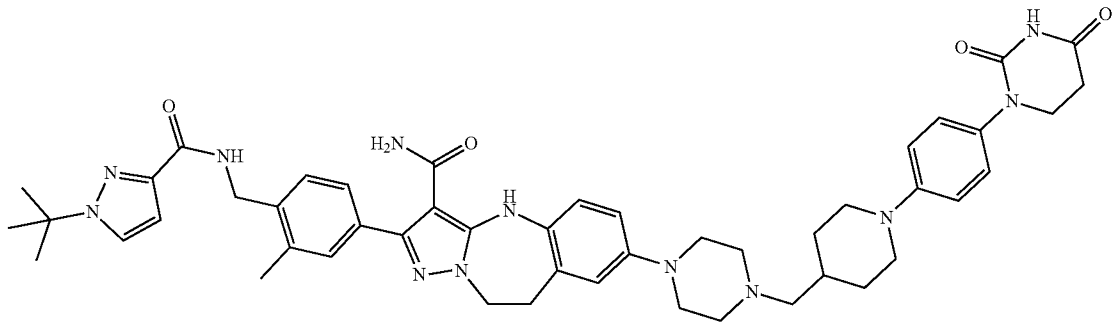
83 C10
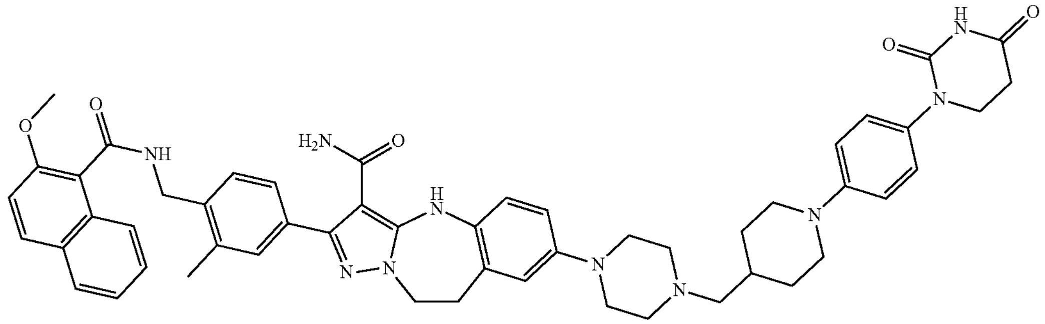
84 C11
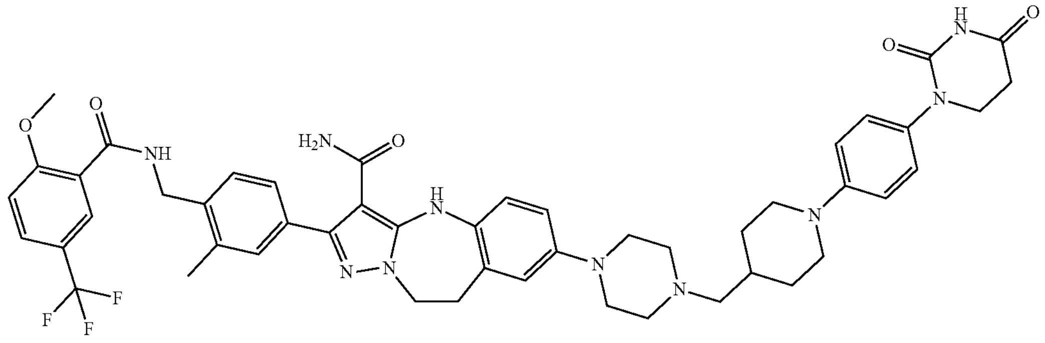
85 C6
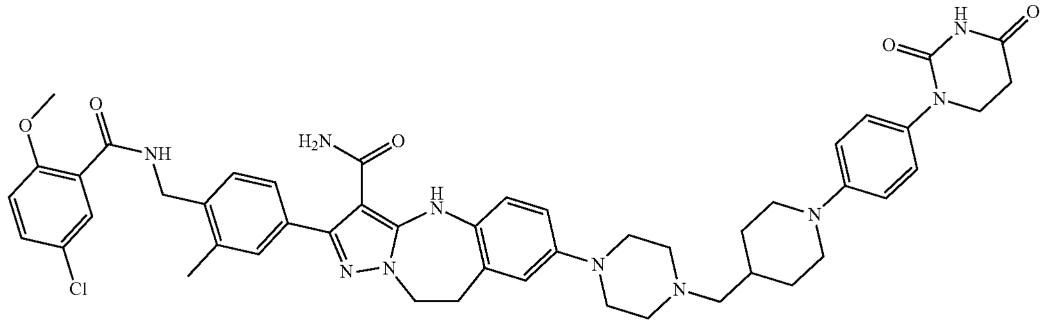

-continued
86 C19
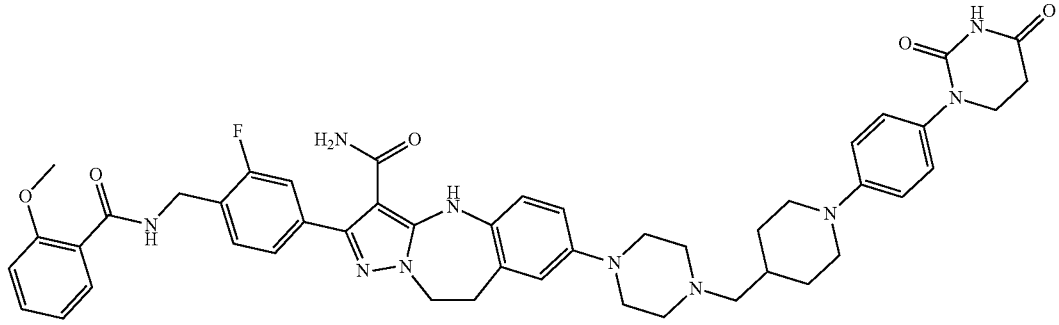
87 C20
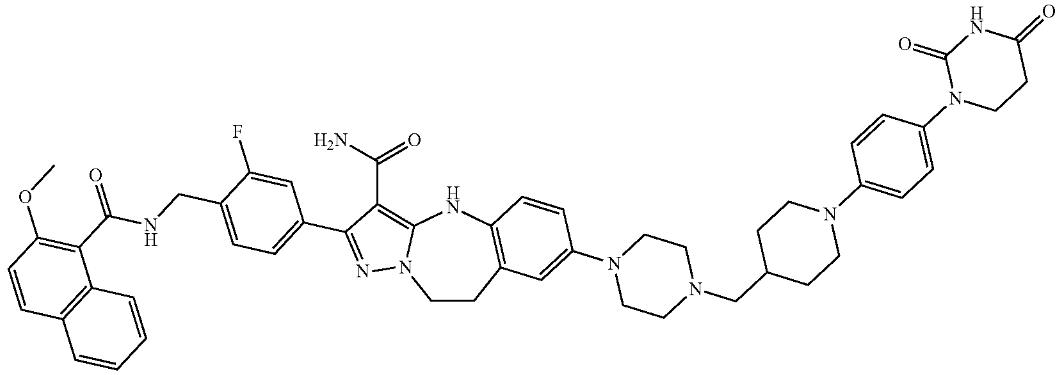
88 C26
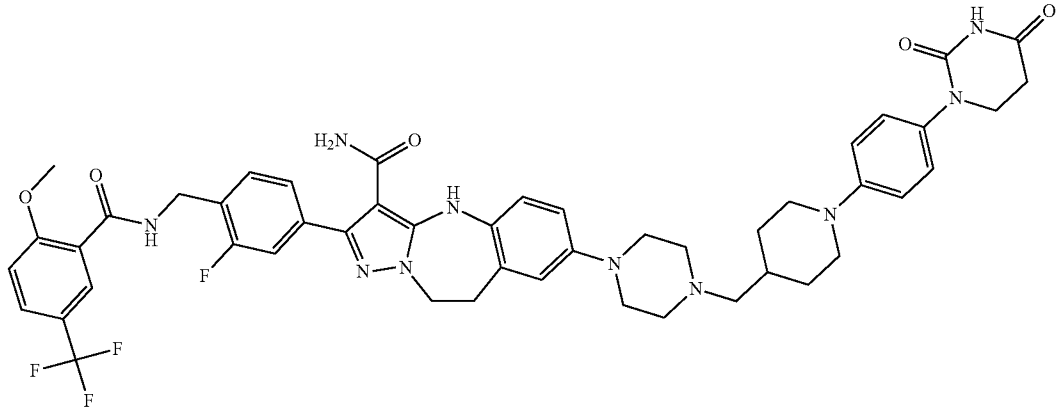
89 C27
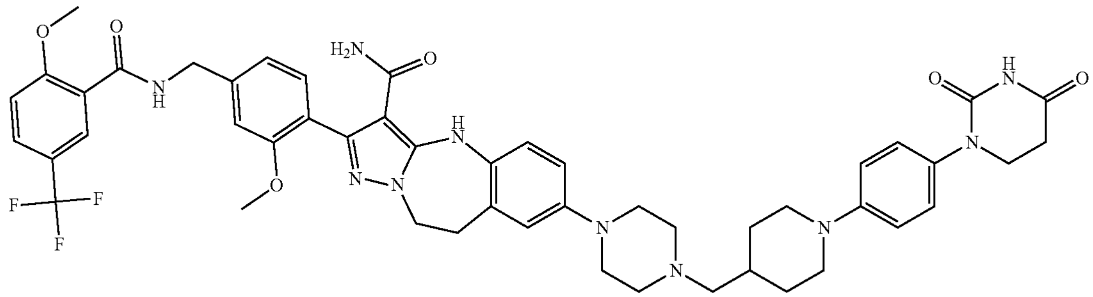

-continued
90 C24
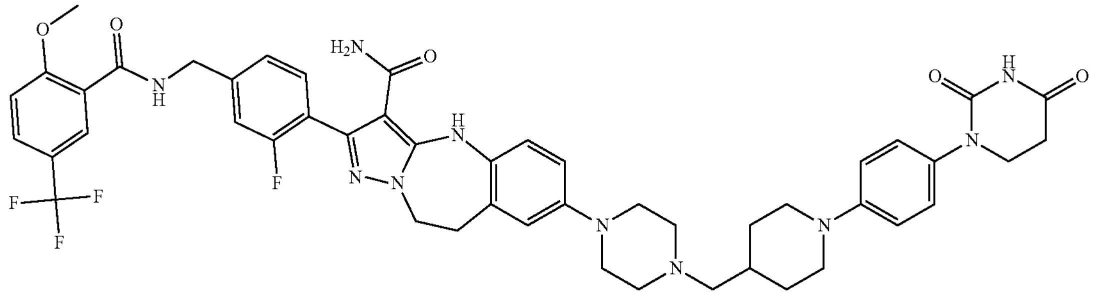
91 C28
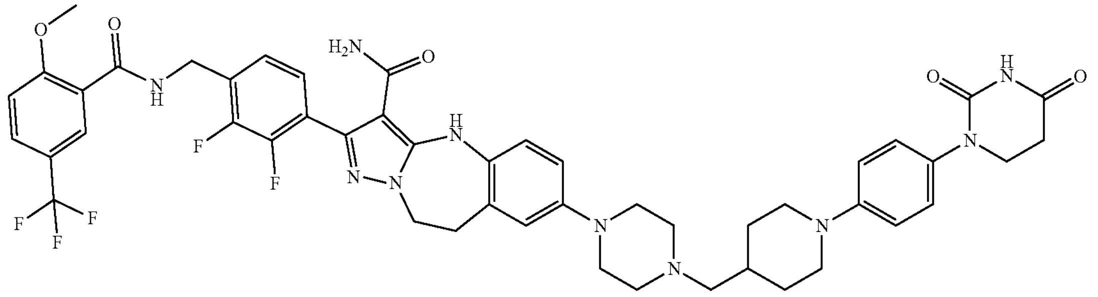
92 C15
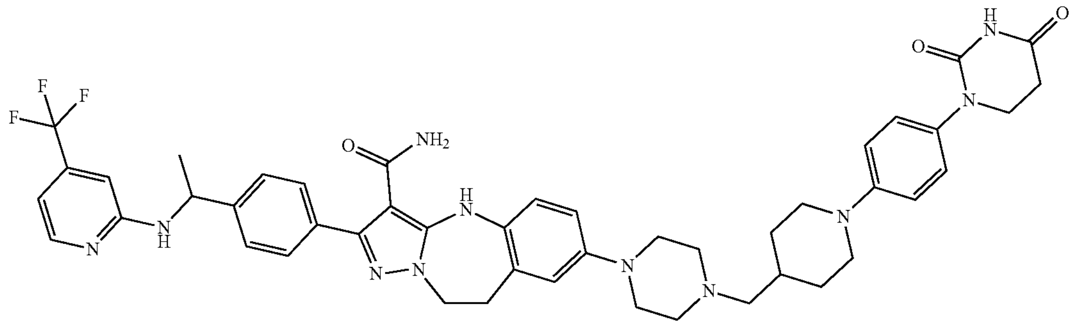
93 C16
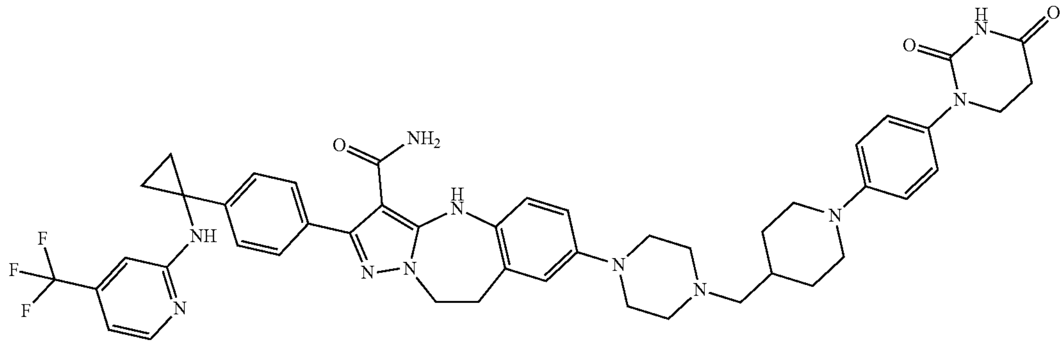
94 C17
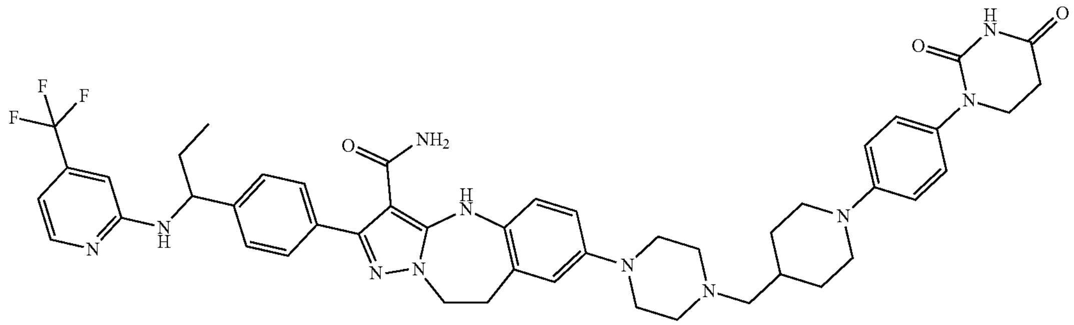

-continued
95 C18
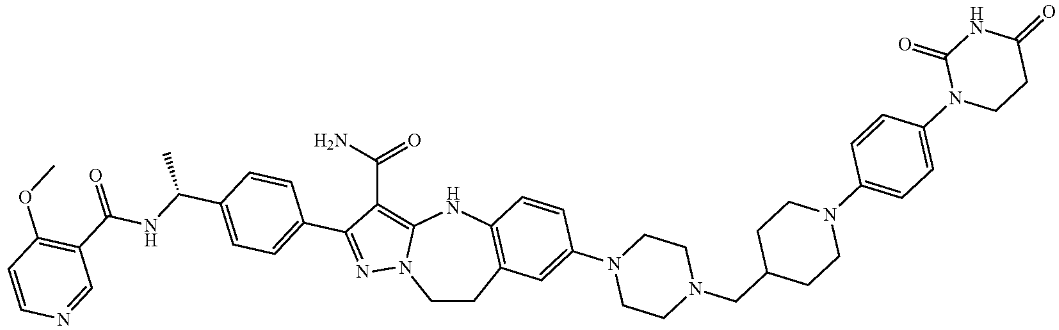
96 C5
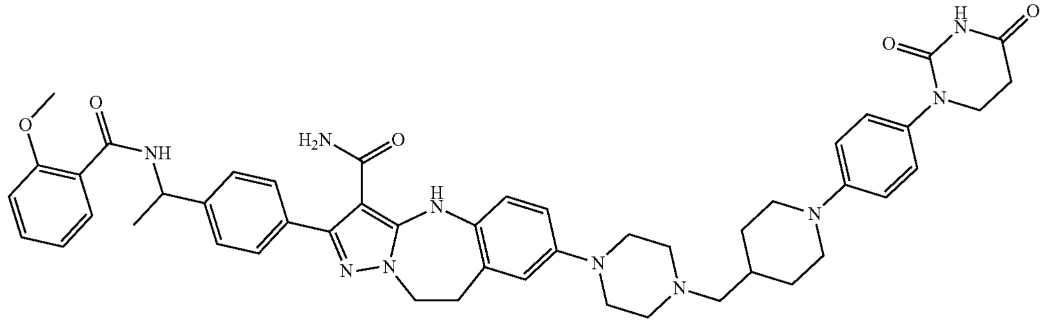
97 C14
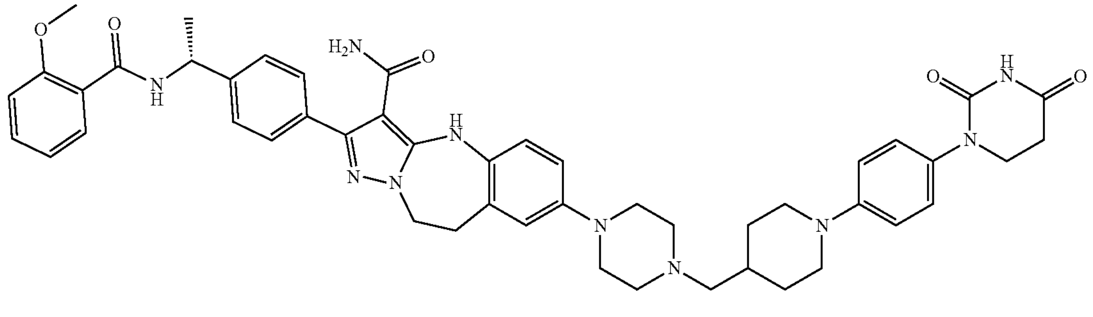
98 C13
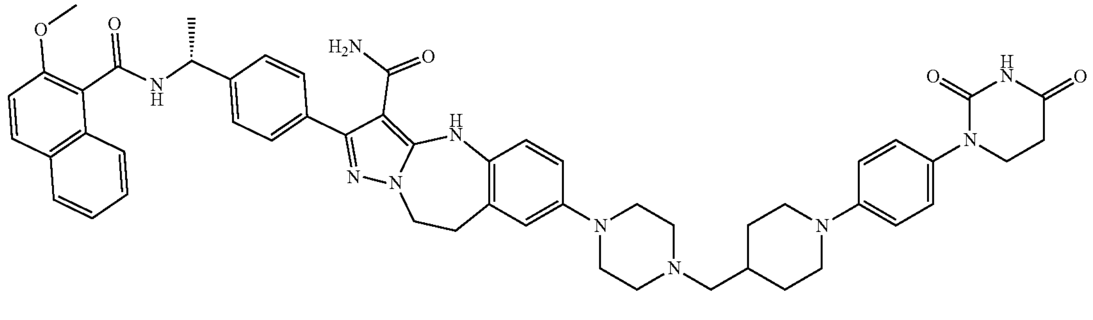

-continued
99
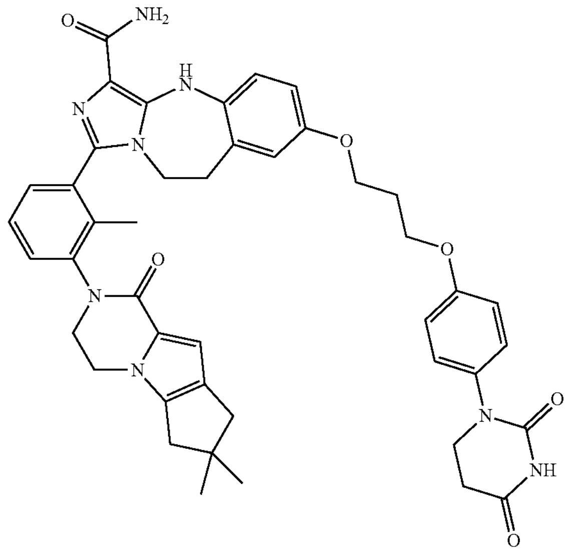
100 B30
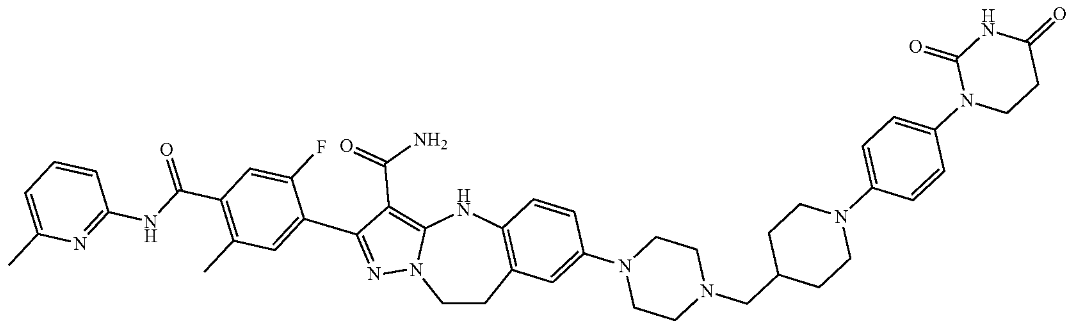
101 B31
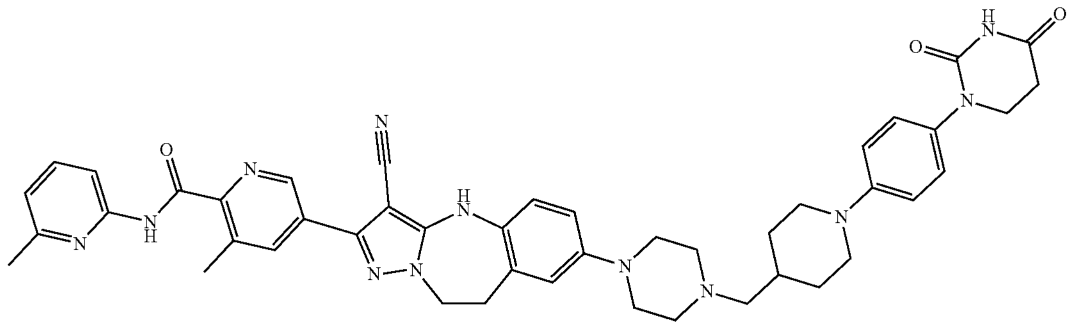
102 B32
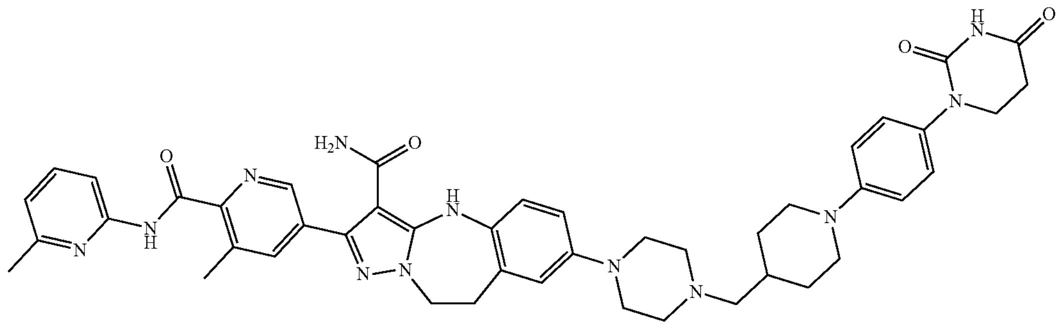

-continued
103 B33
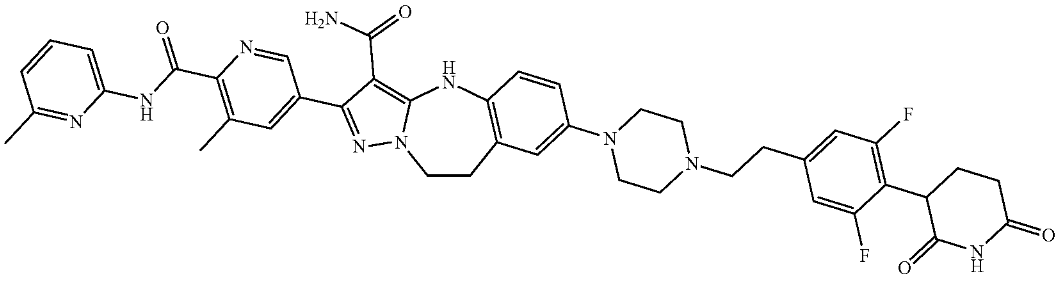
104 B34
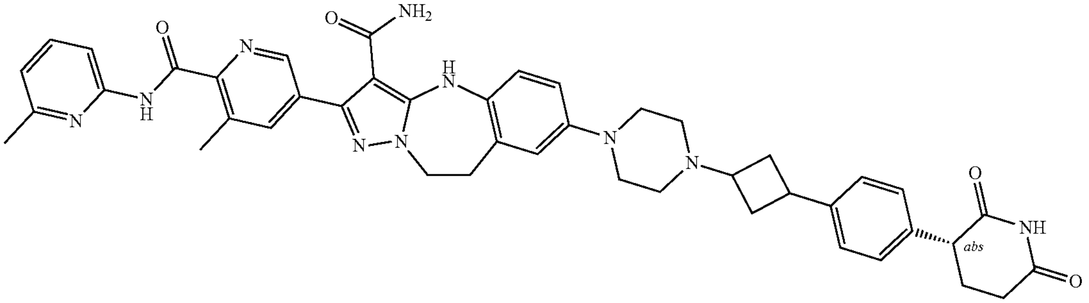
105 B35
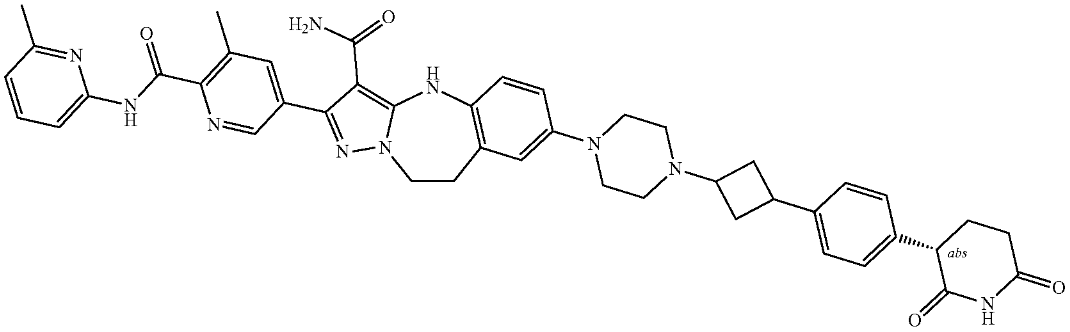
106 B36
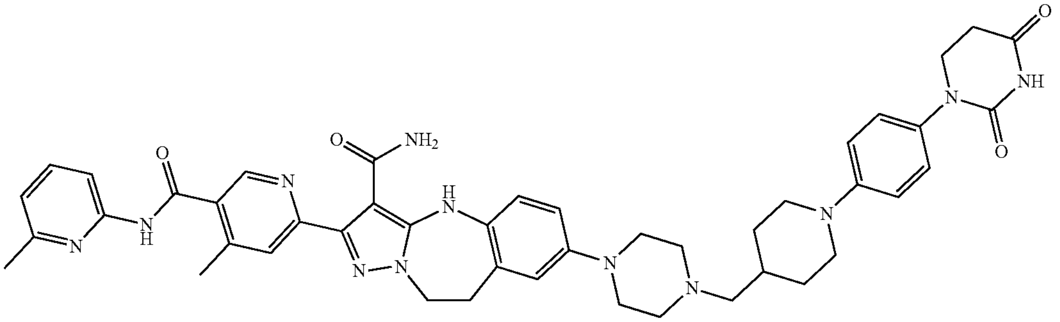
107 B37
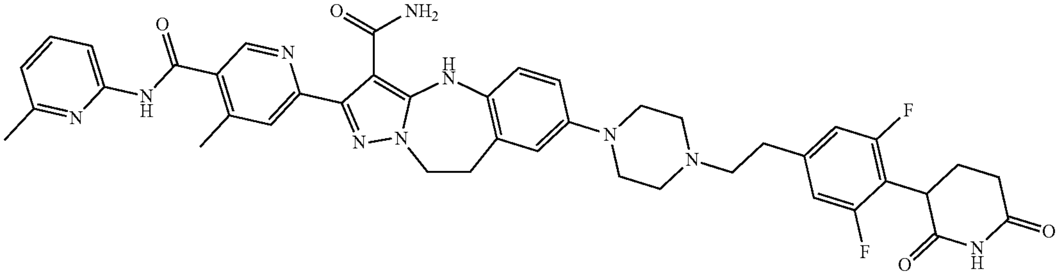

-continued
108 B38
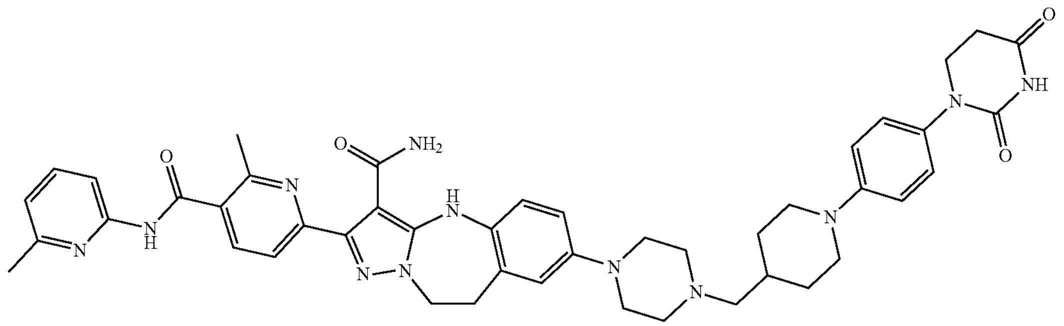
109 B39
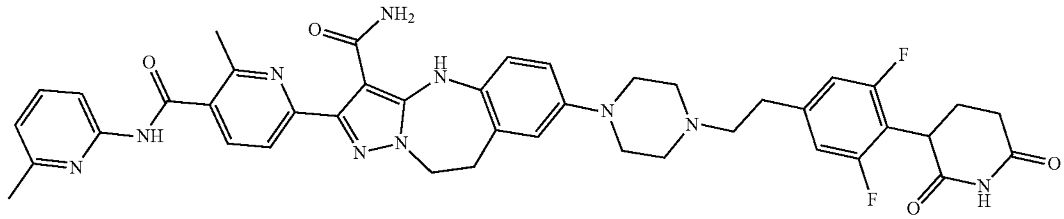
110 B40
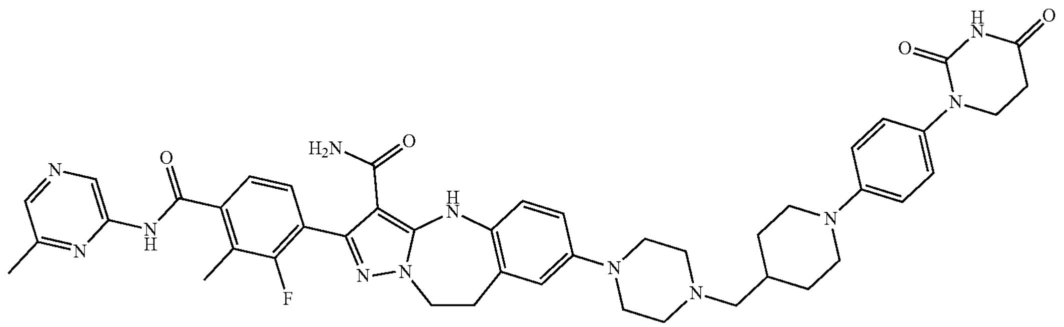
111 B41
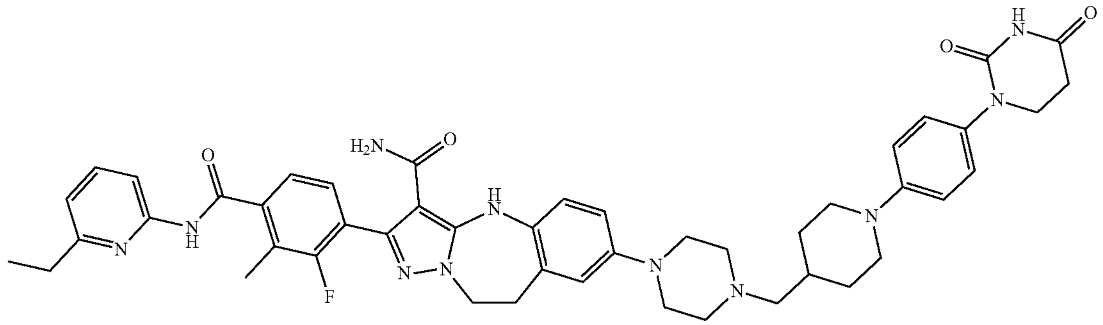
112 B42
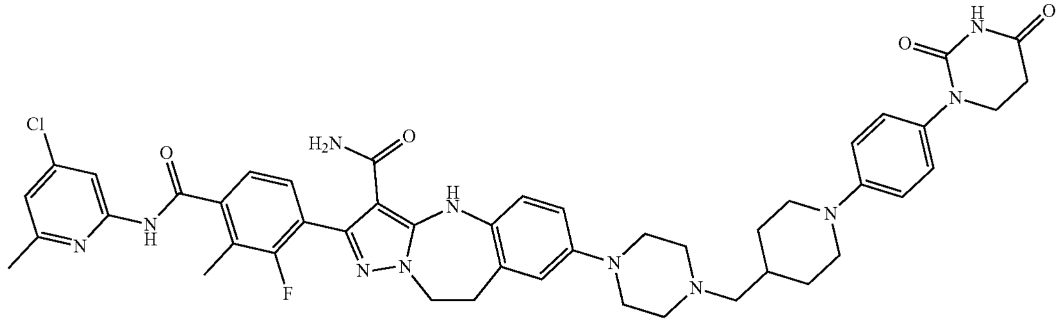

-continued
113 B43
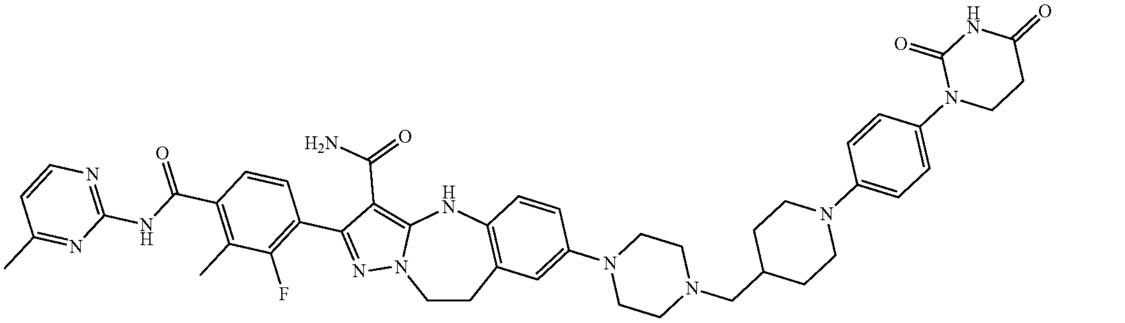
114 B44
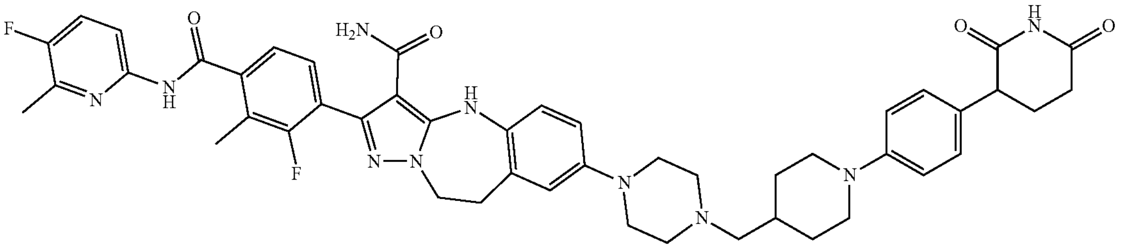
115 B45
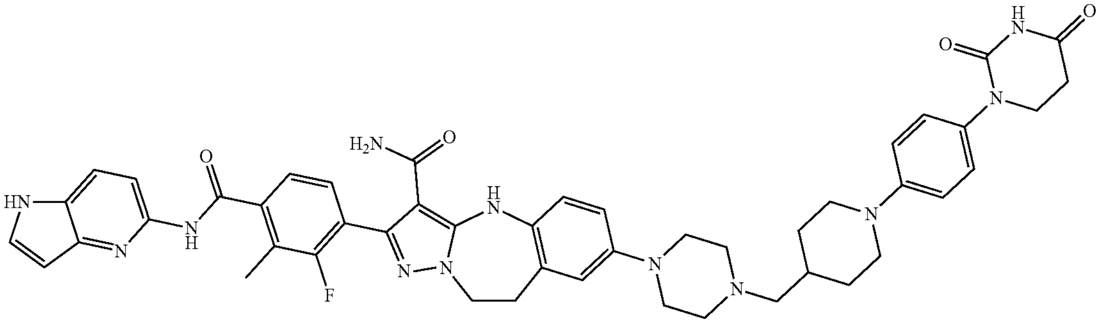
116 B46
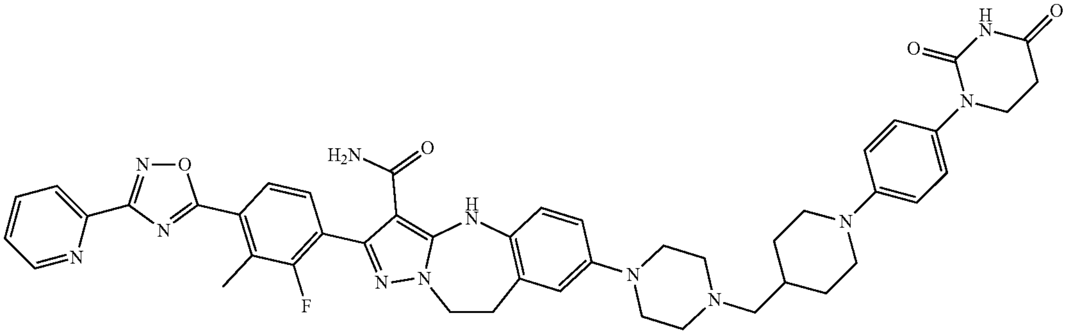

-continued
117 B47
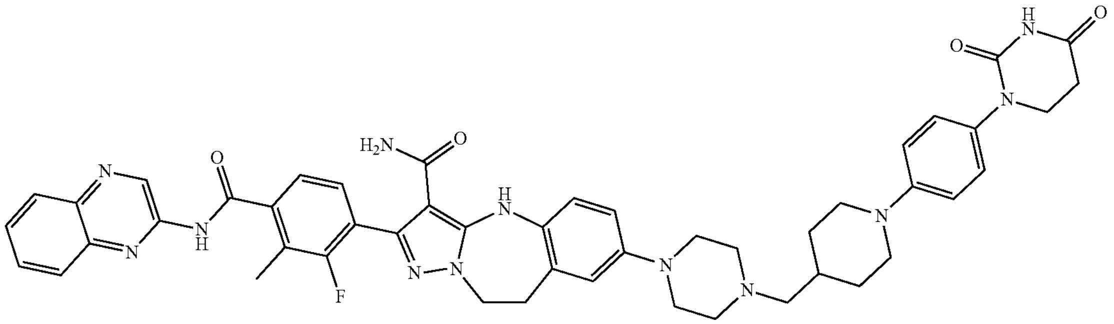
118 B48
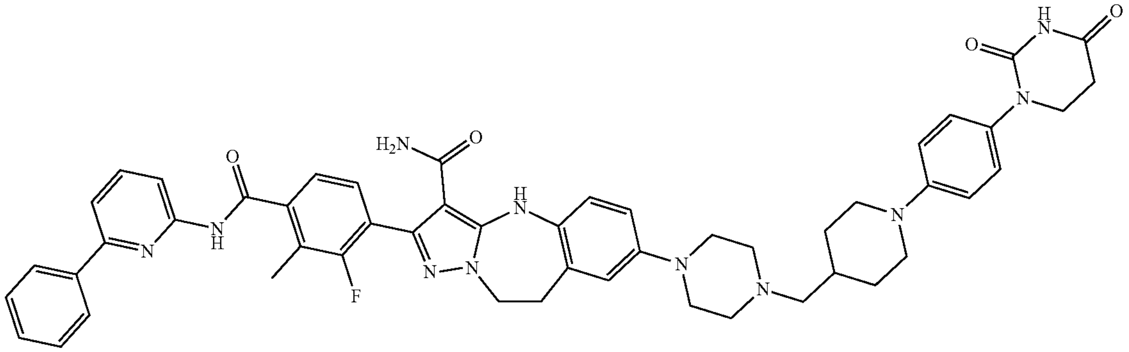
119 B49
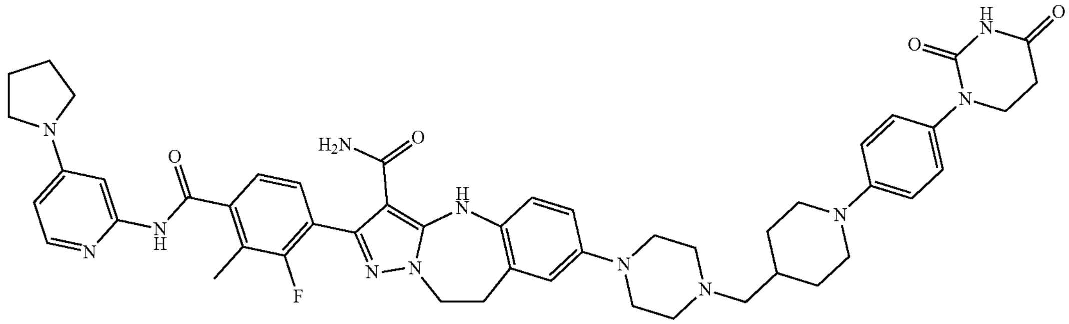
120 B50
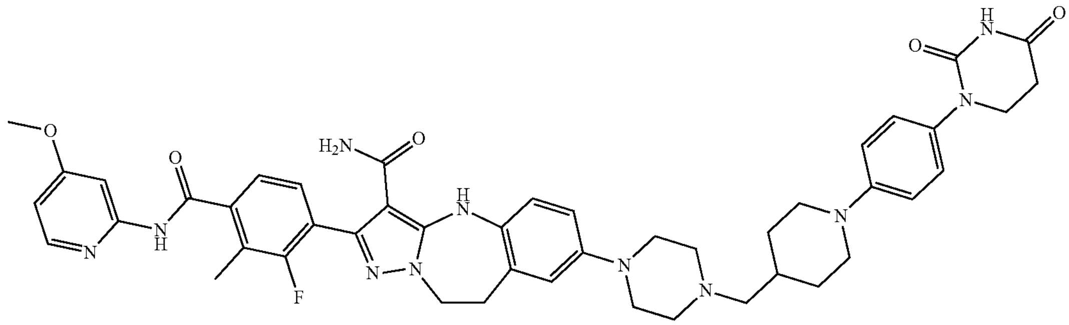

-continued
121 B51
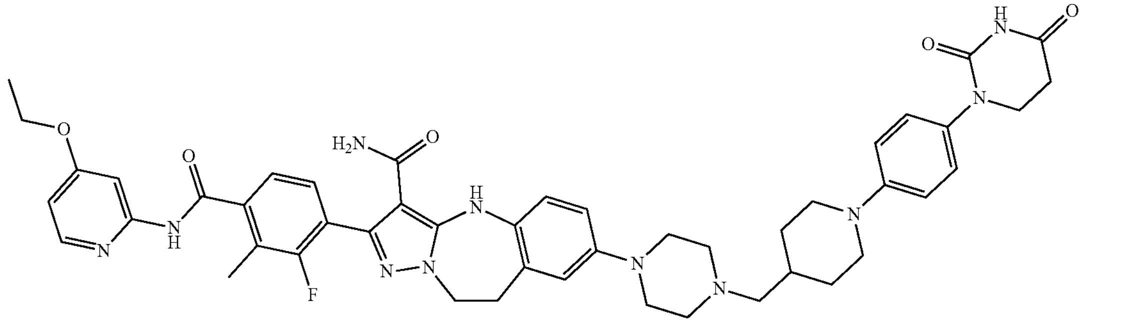
122 B52
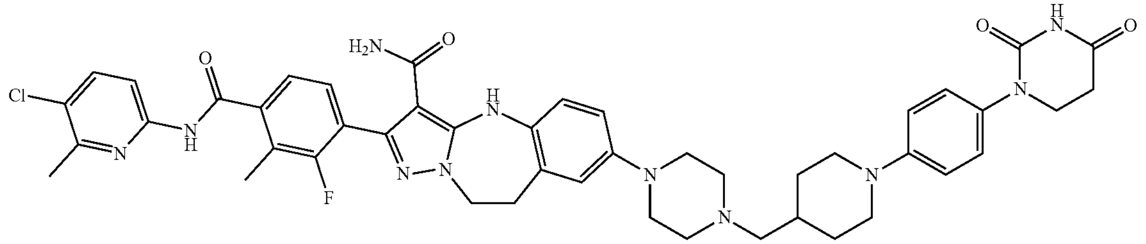
123 B53
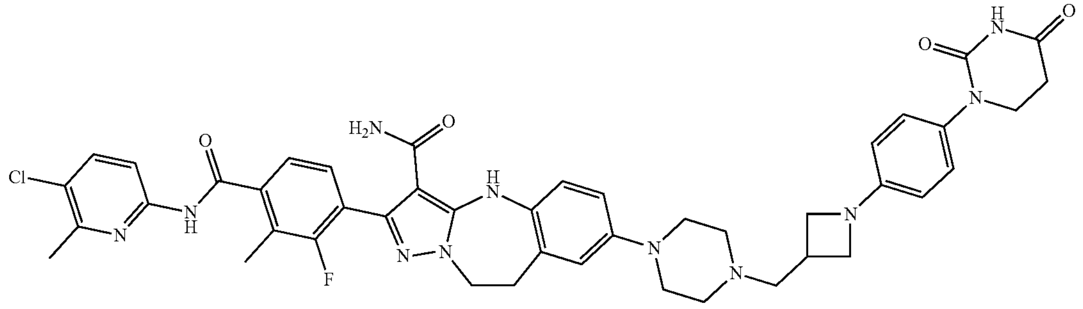
124 B54
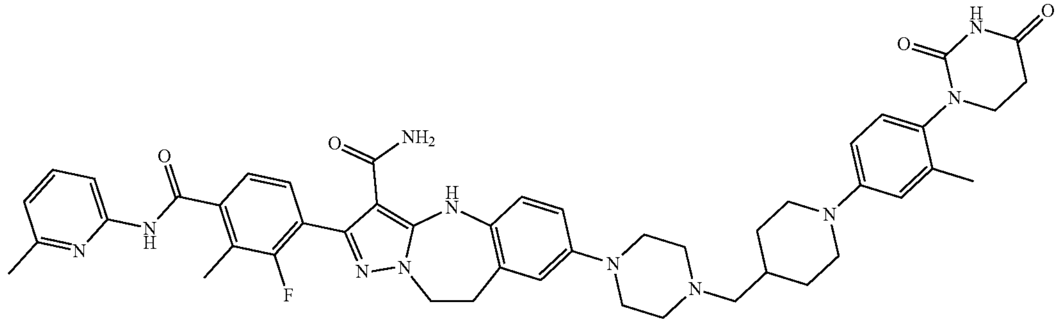
125 B55
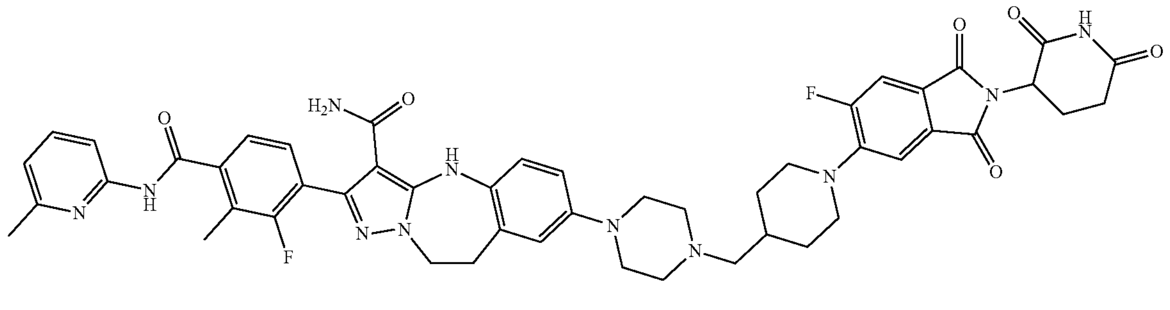

-continued
126 B56
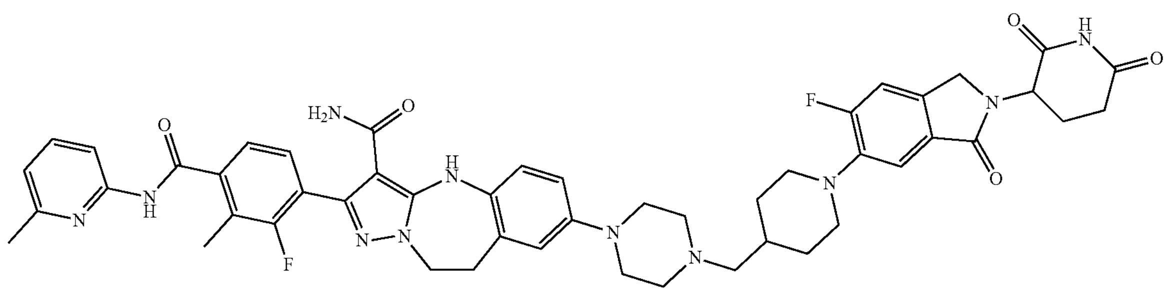
127 B57
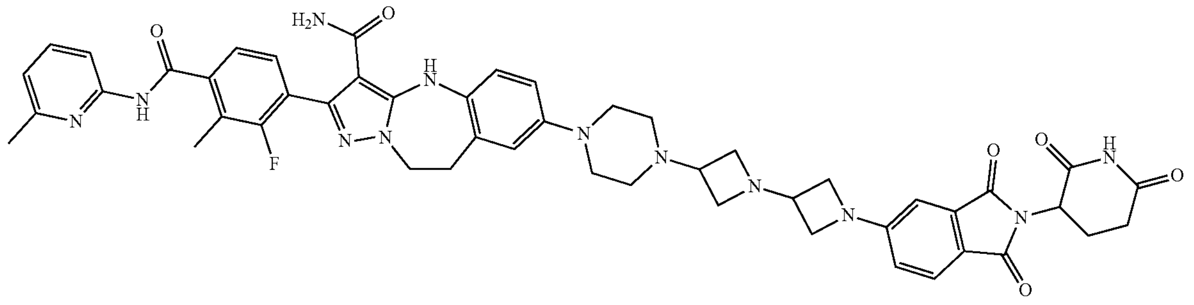
128 B58
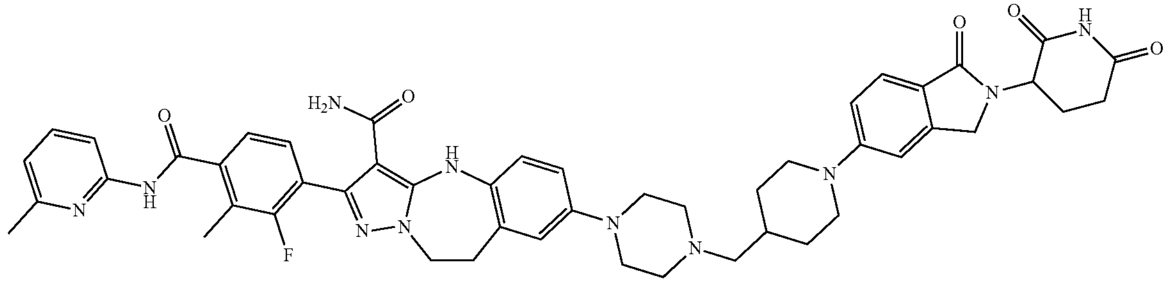
129 B59
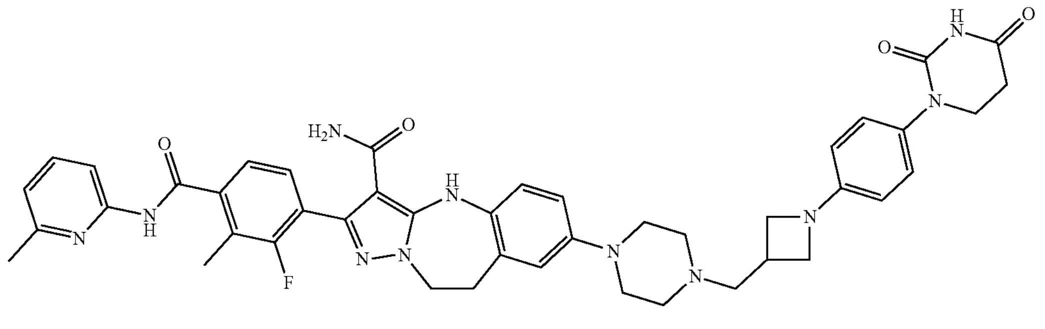
130 B60
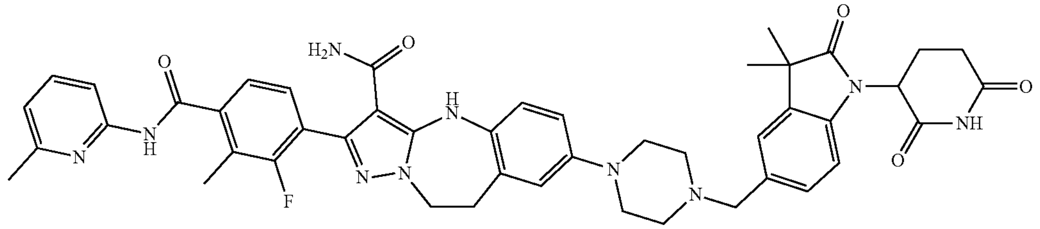

-continued
131 B61
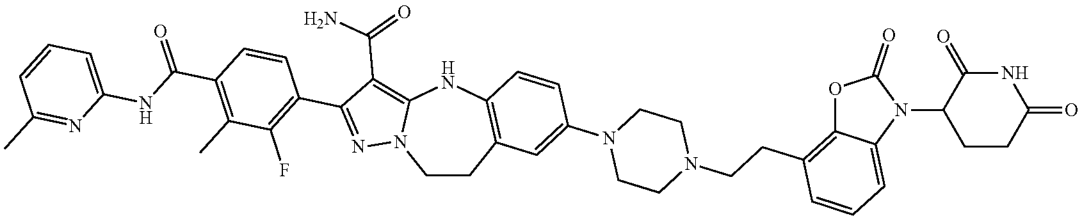
132 B62
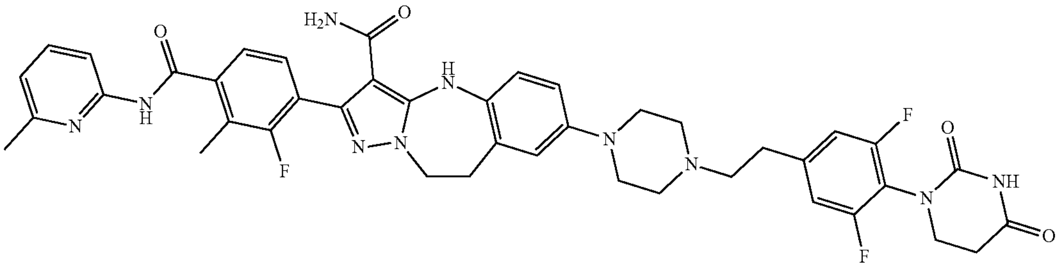
133 B63
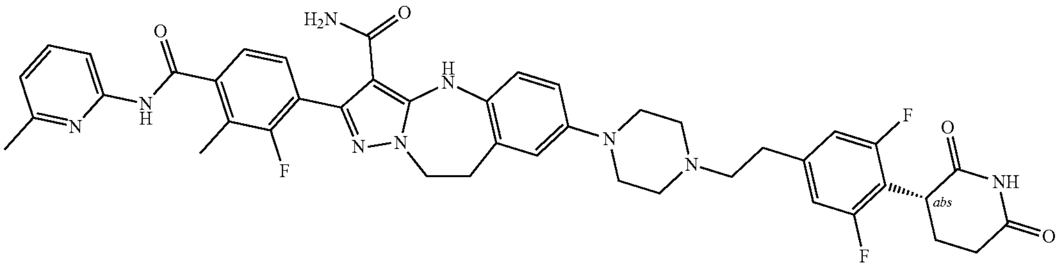
134 B64
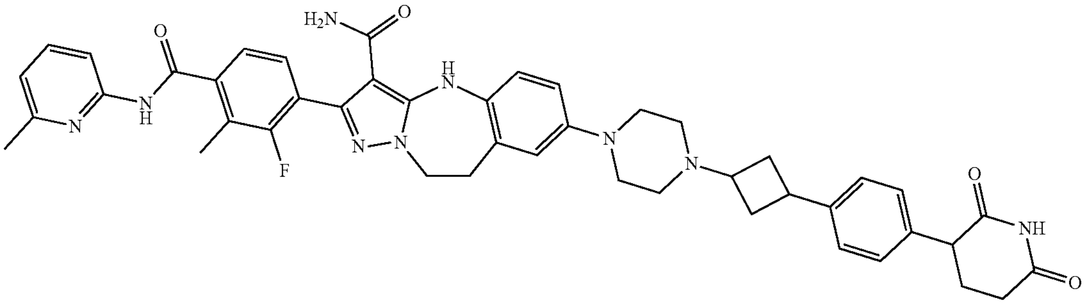
135 B65
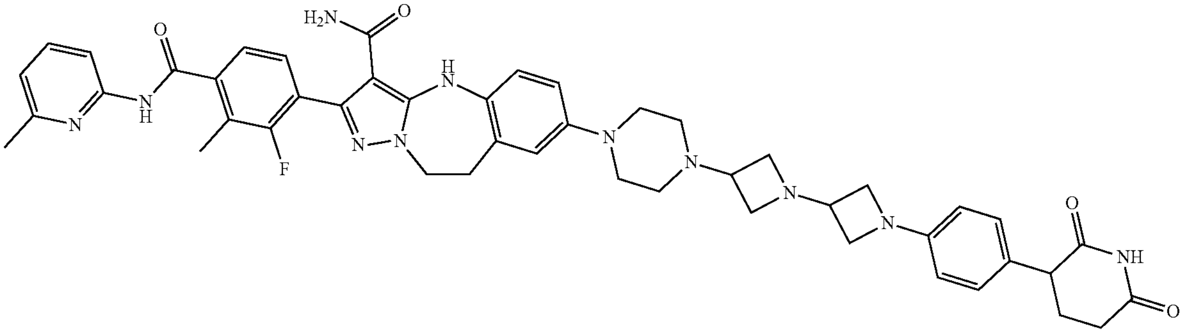

-continued
136 B66
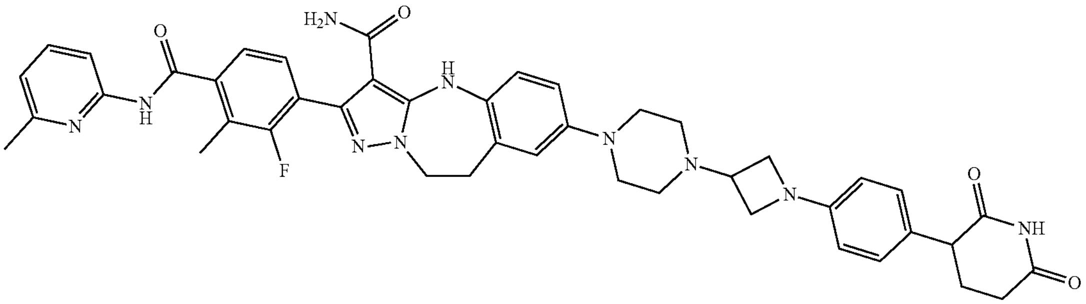
137 B67
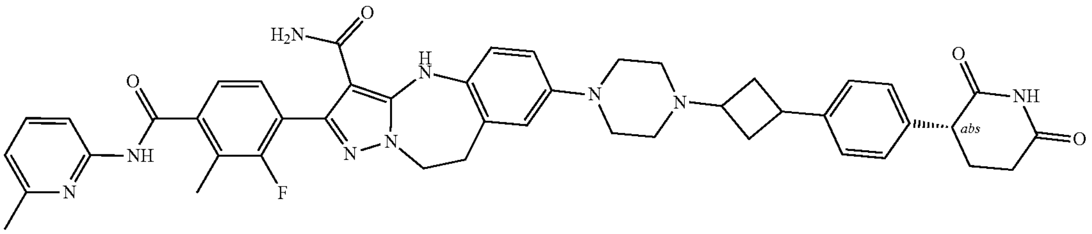
138 B68
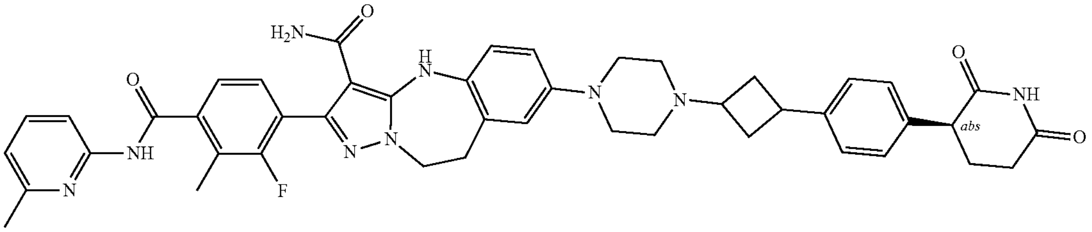
139 B69
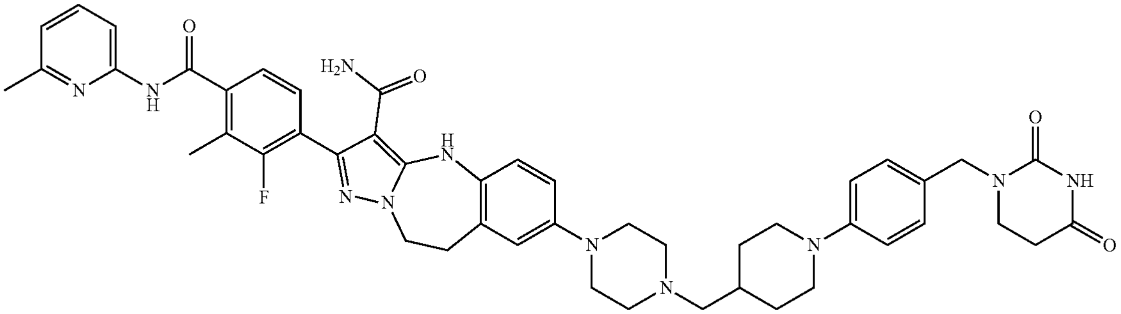
140 B70
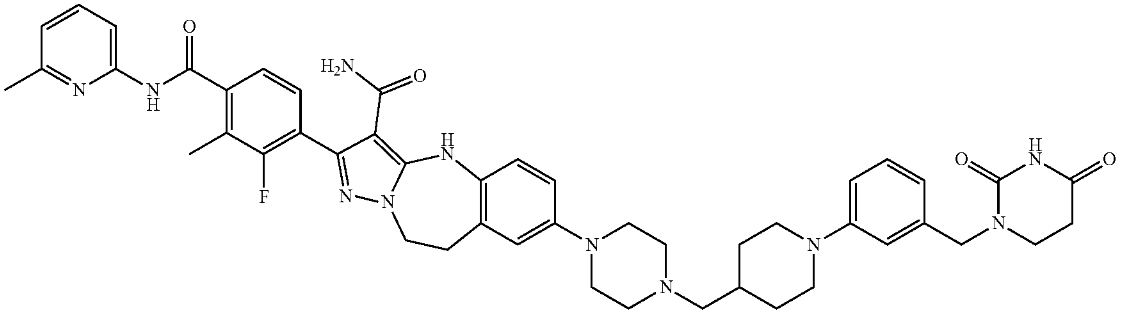

-continued
141 B71
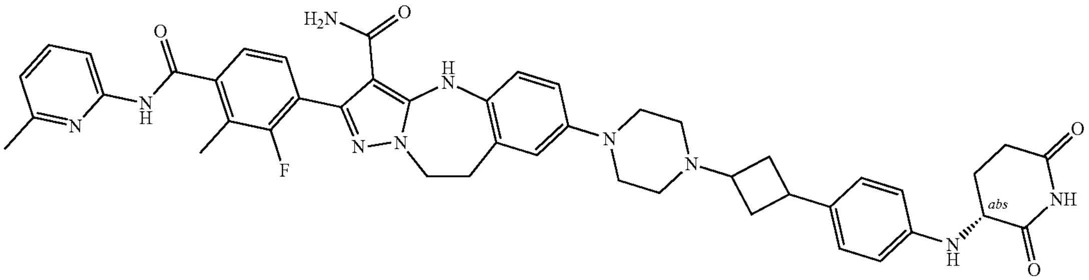
142 B72
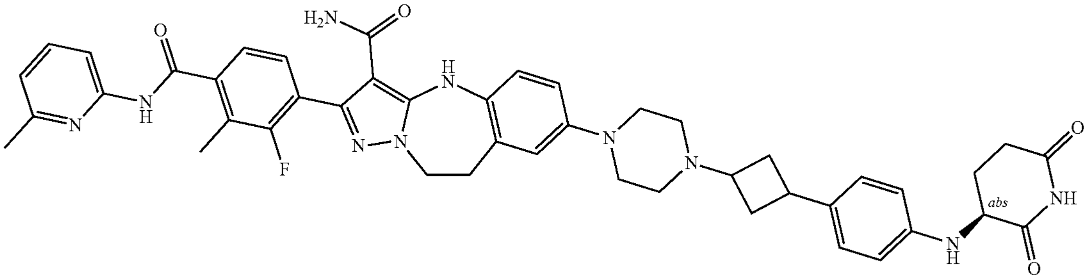
143 B73
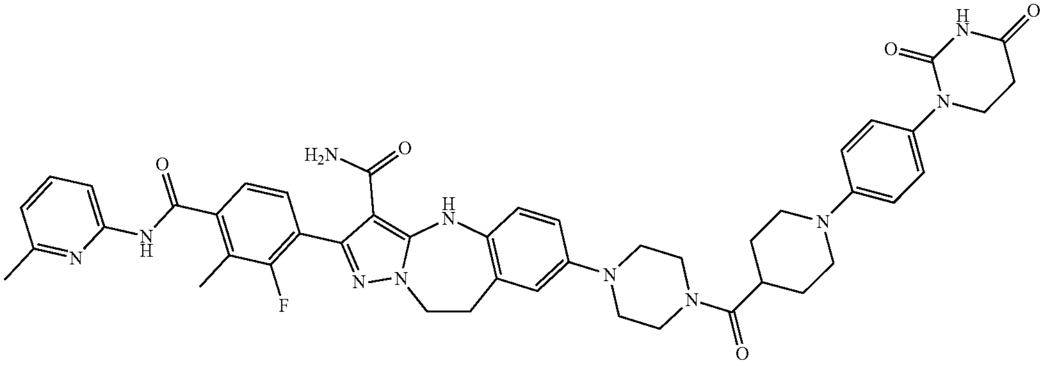
144 B74
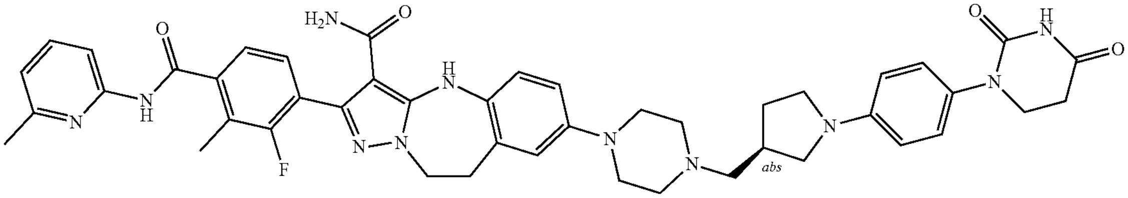
145 B75
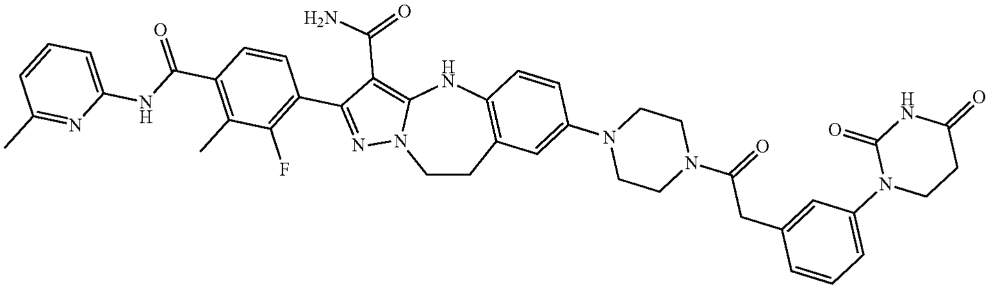

-continued
152 B82
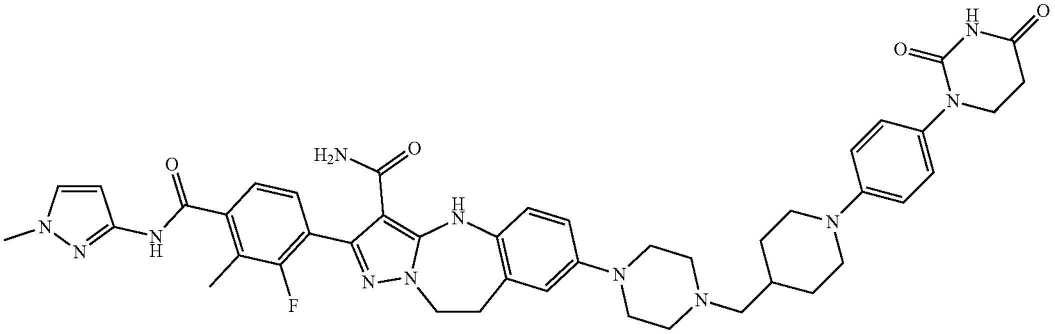
153 B83
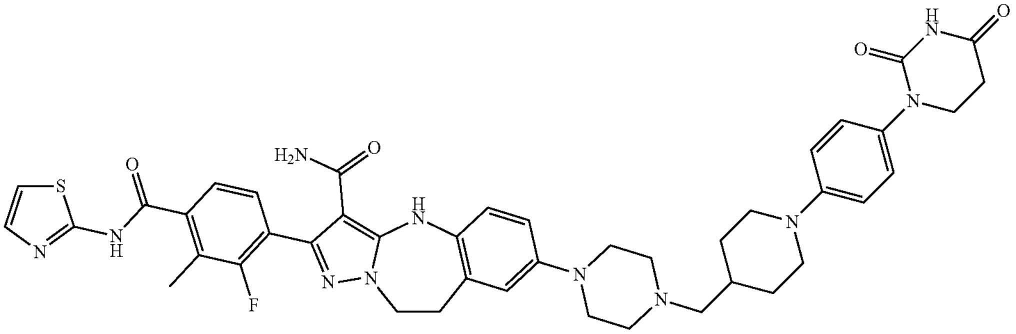
154 B84
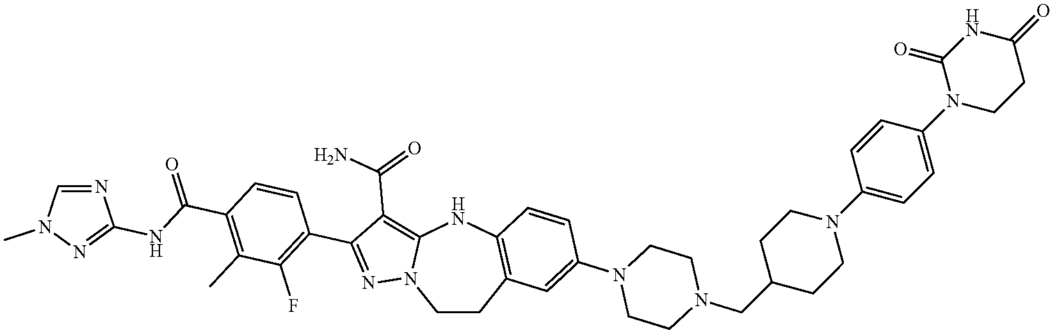
155 B85
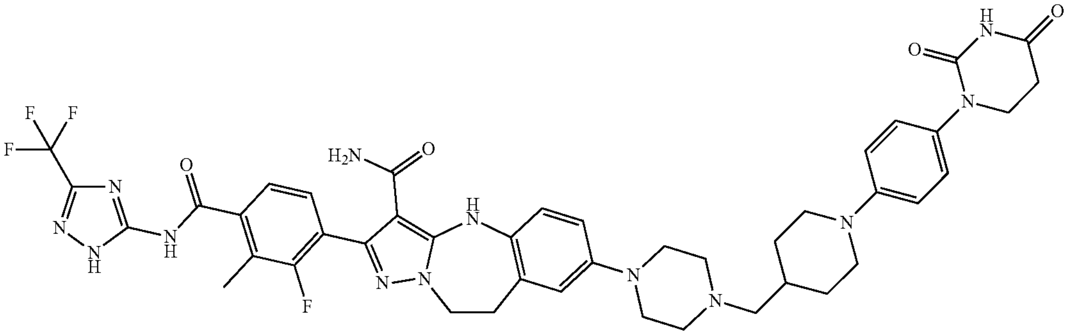

-continued
156 B86
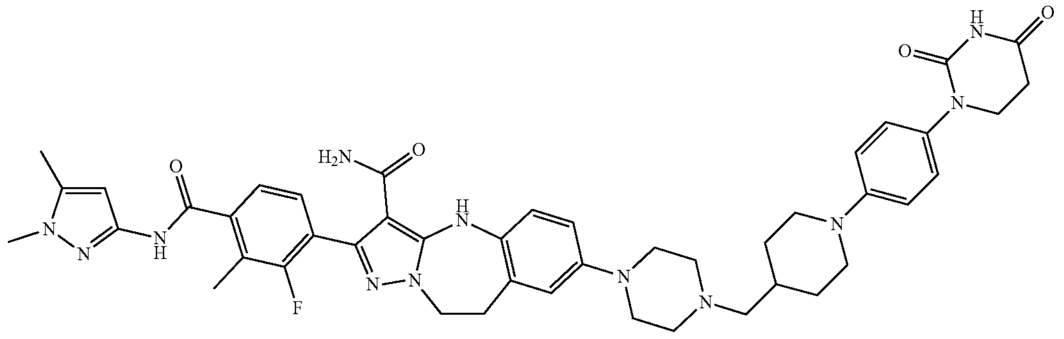
157 B87
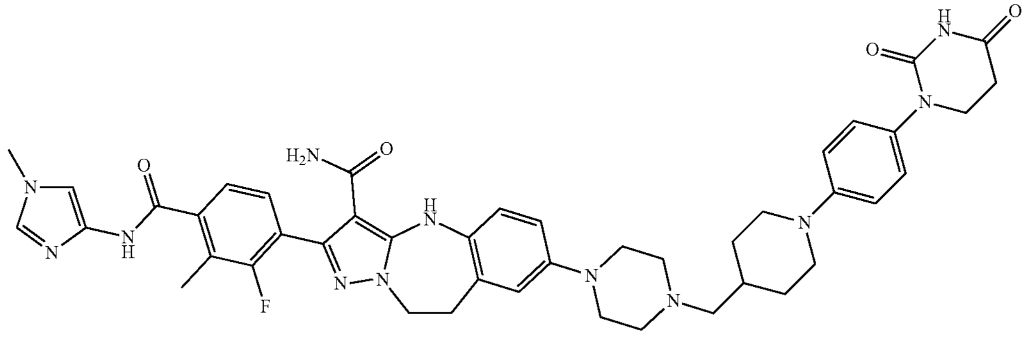
158 B88
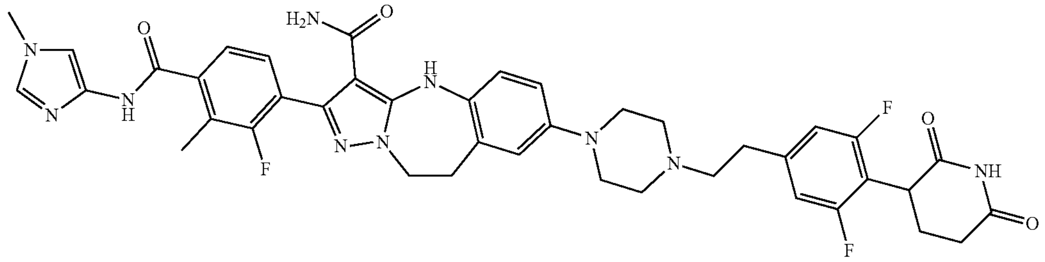
159 B89
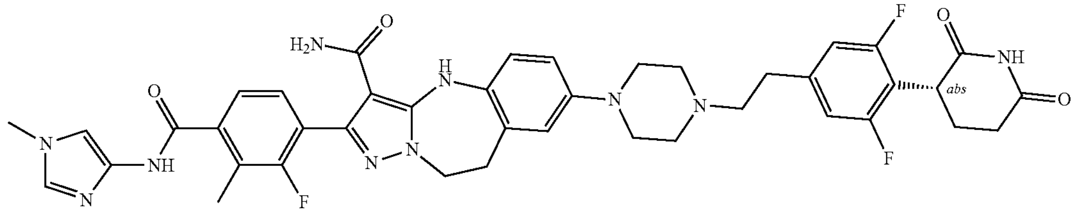
160 B90
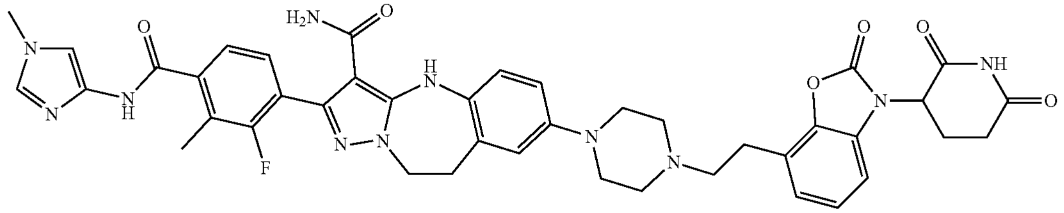

-continued
161 B91
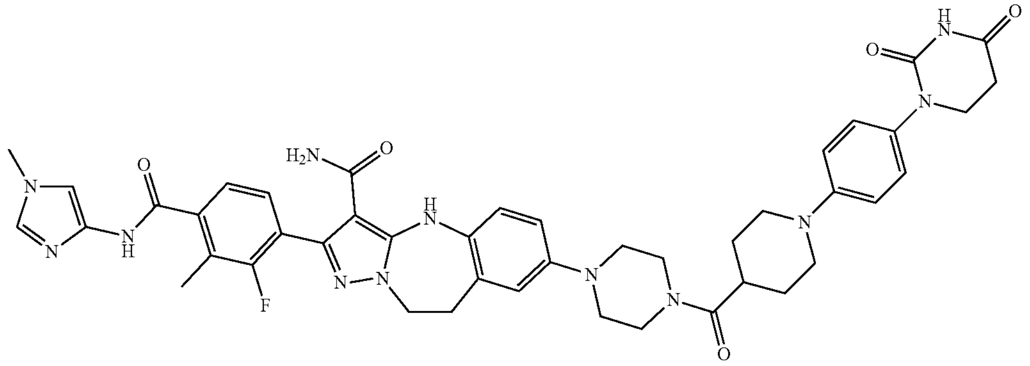
162 B92
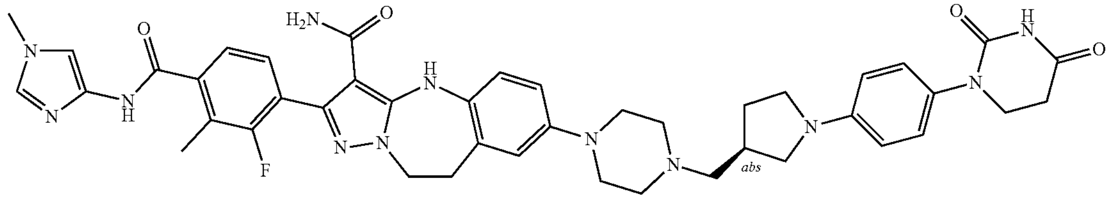
163 B93
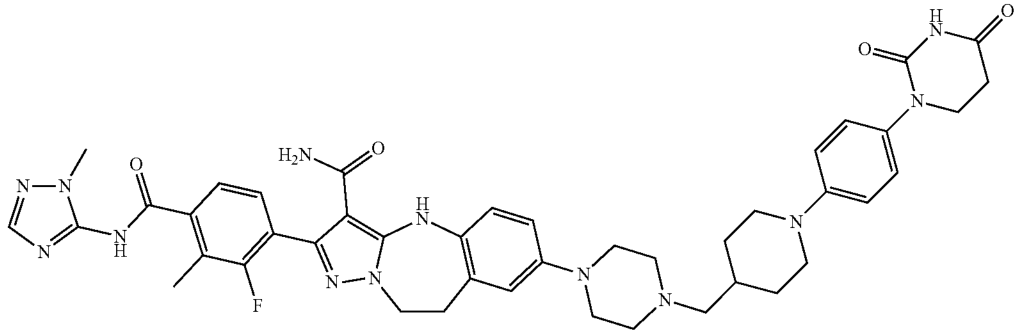
164 B94
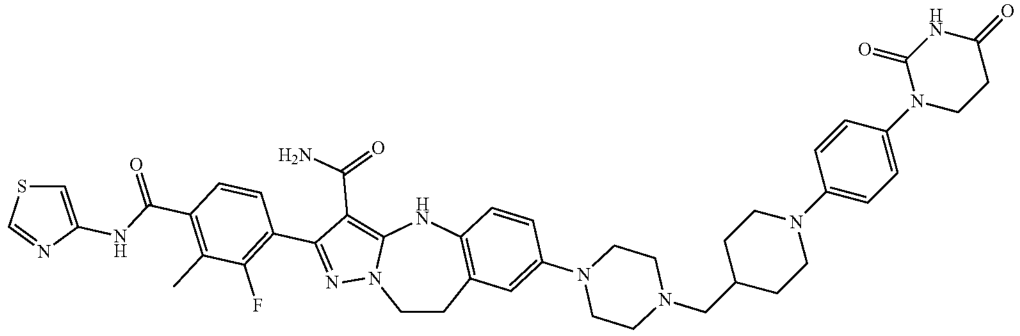
165 B95
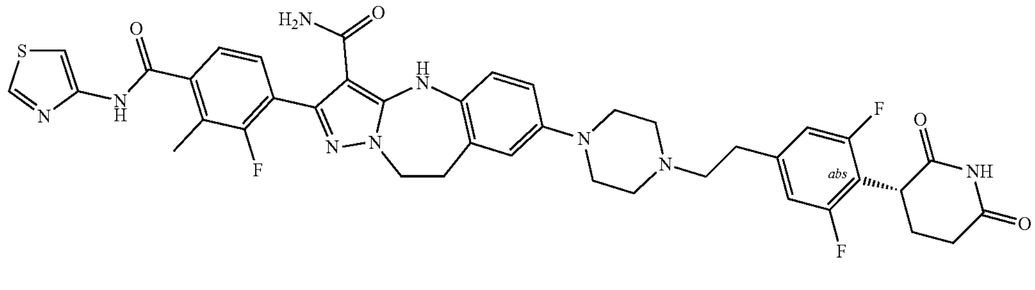

-continued
166 B96
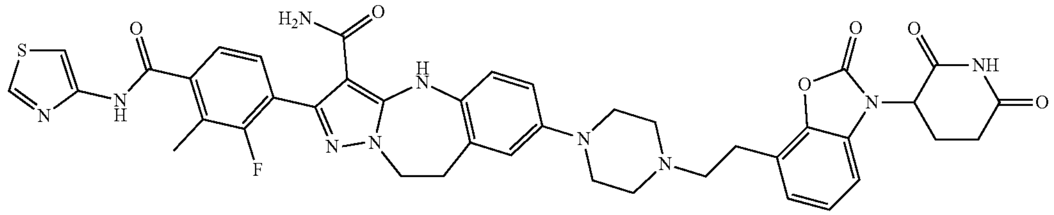
167 B97
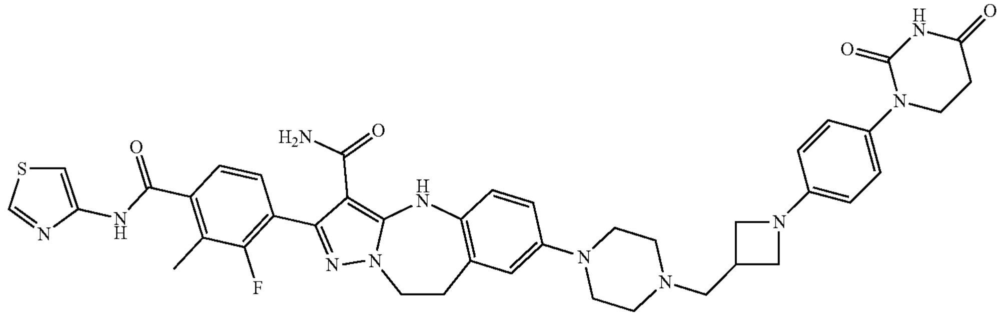
168 B98
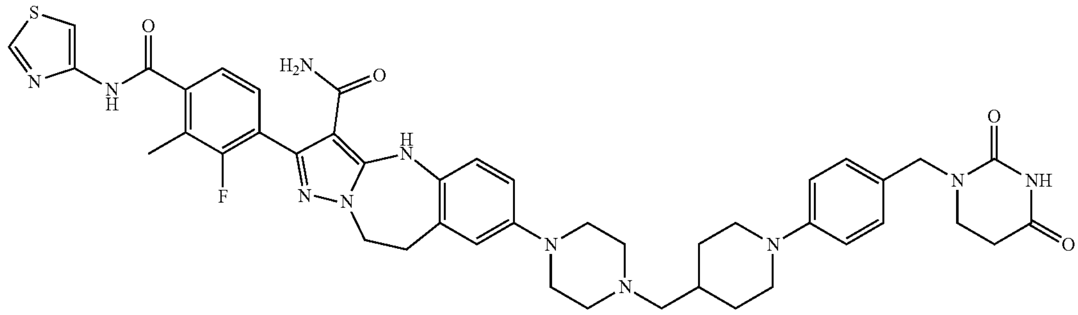
169 B99
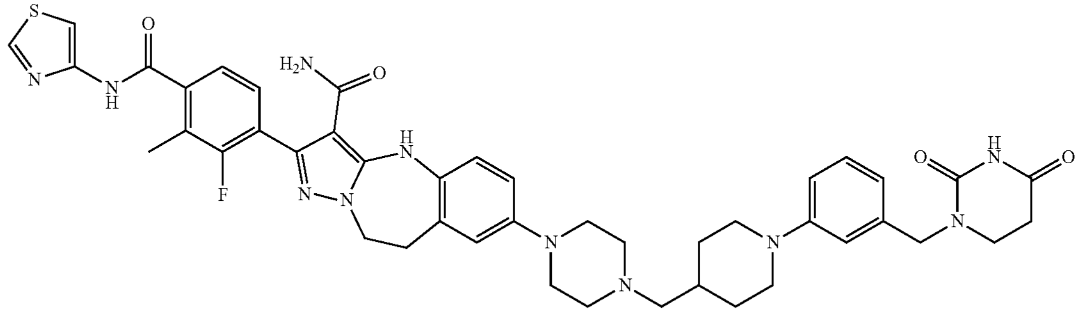
170 B100
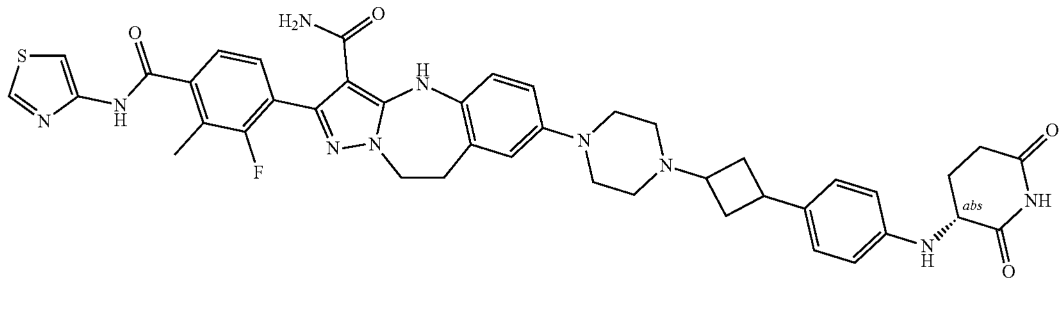

-continued
171 B101
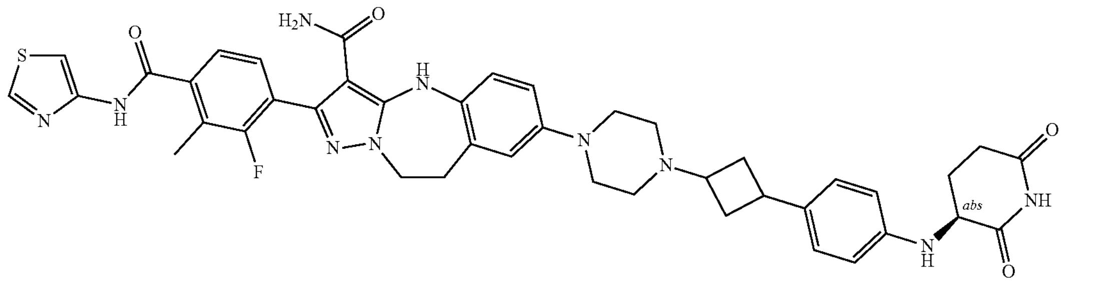
172 B102
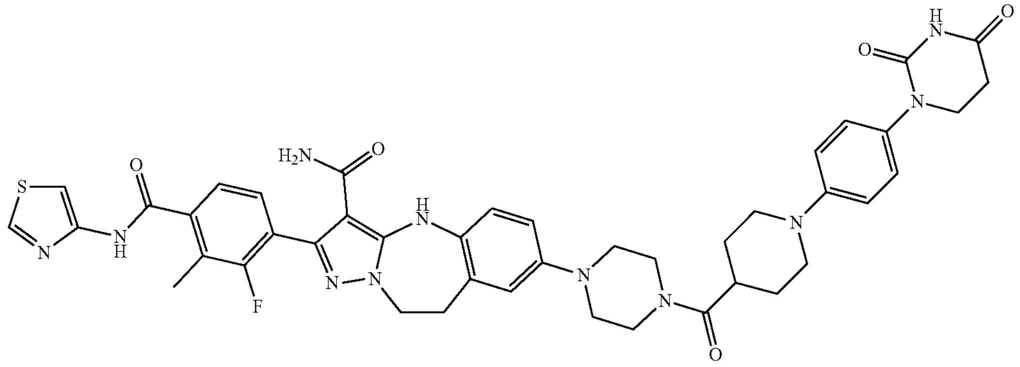
173 B103
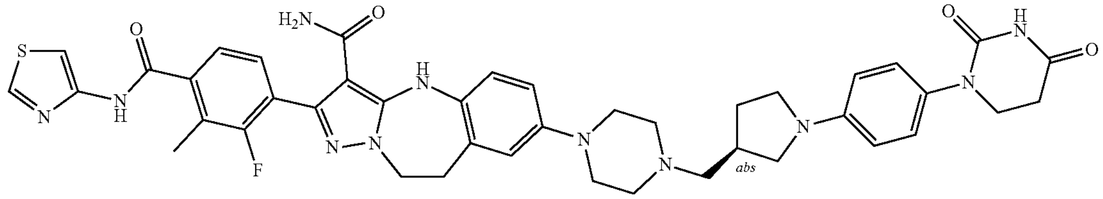
174 C31
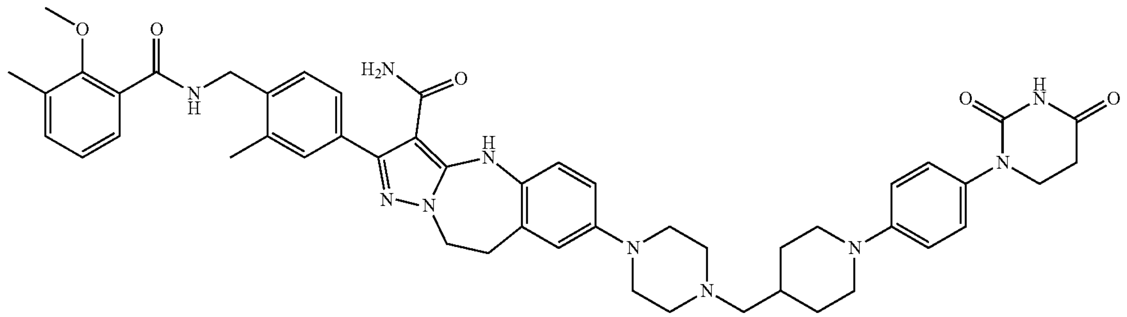
175 C32
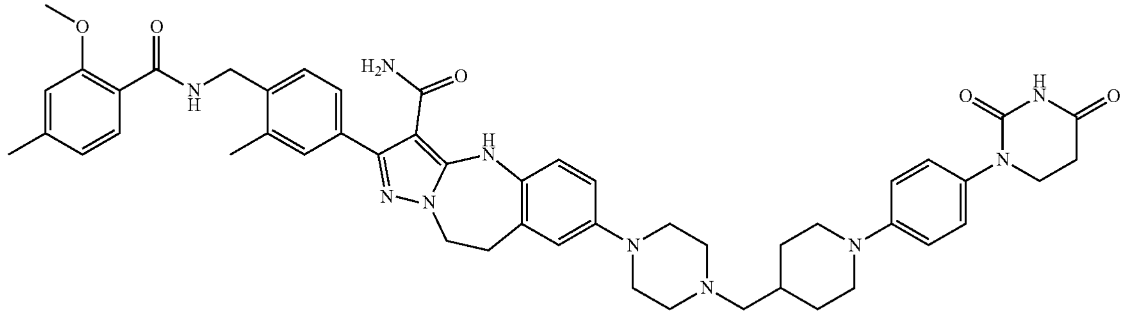

-continued
176 C33
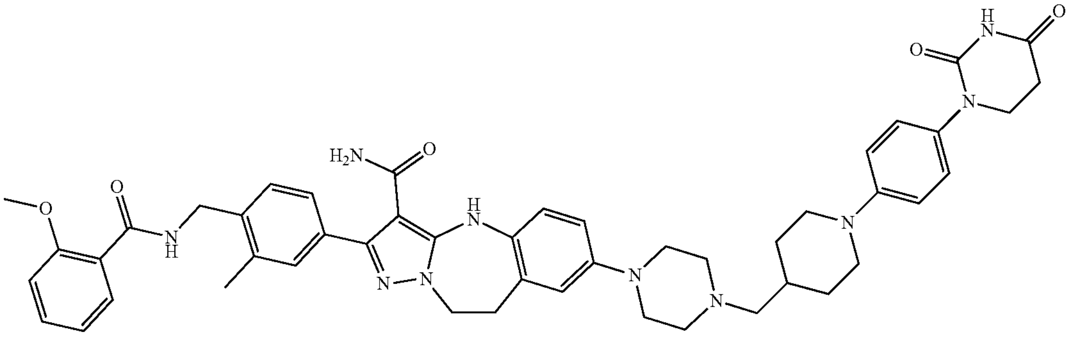
177 C34
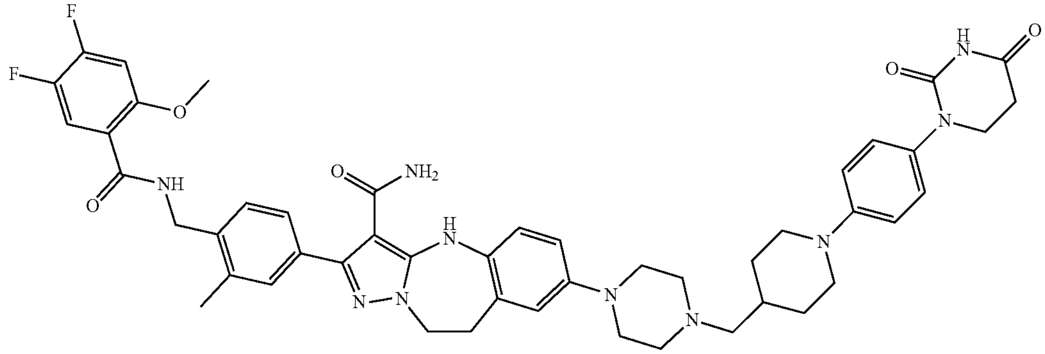
178 C35
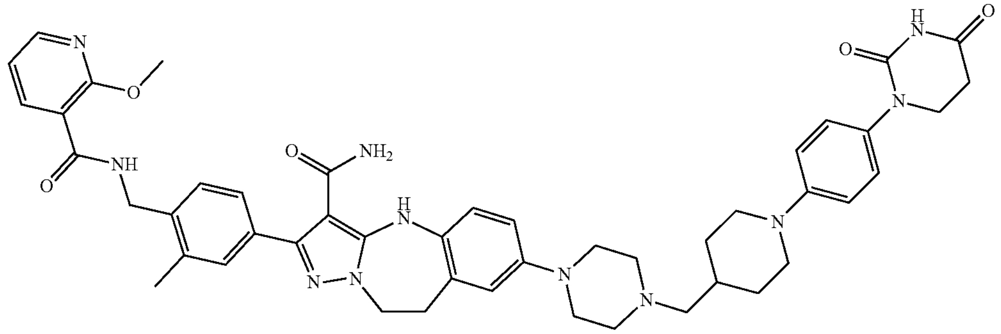
179 C36
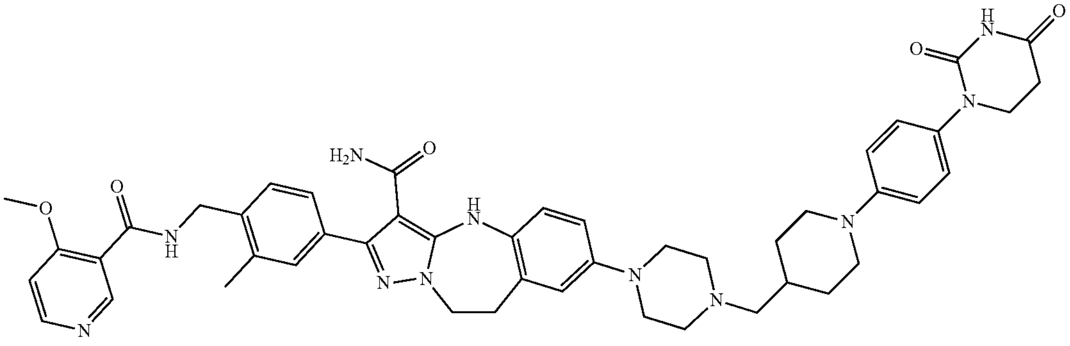

-continued
180 C37
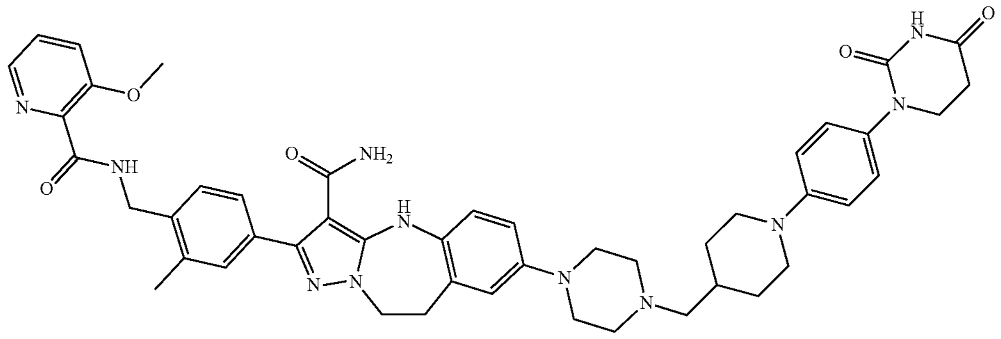
181 C38
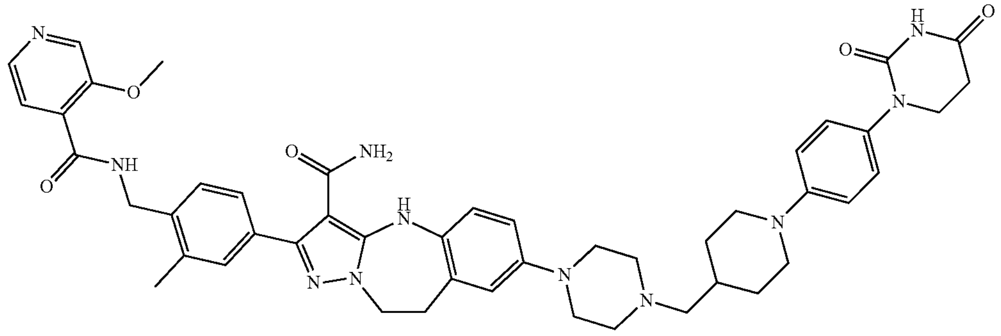
182 C39
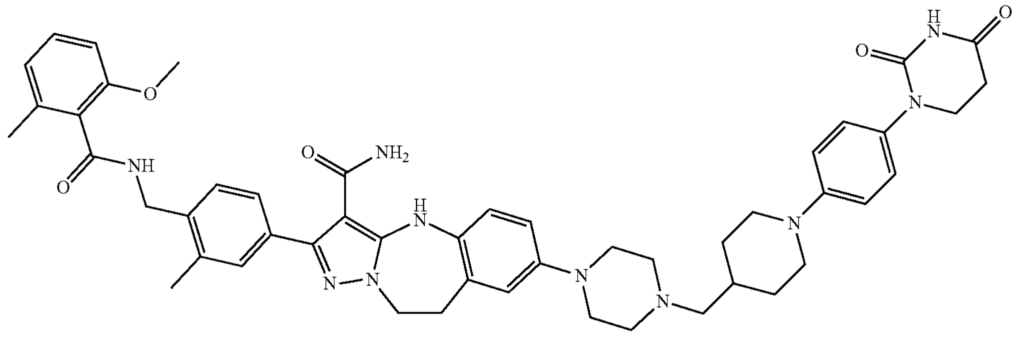
183 C40
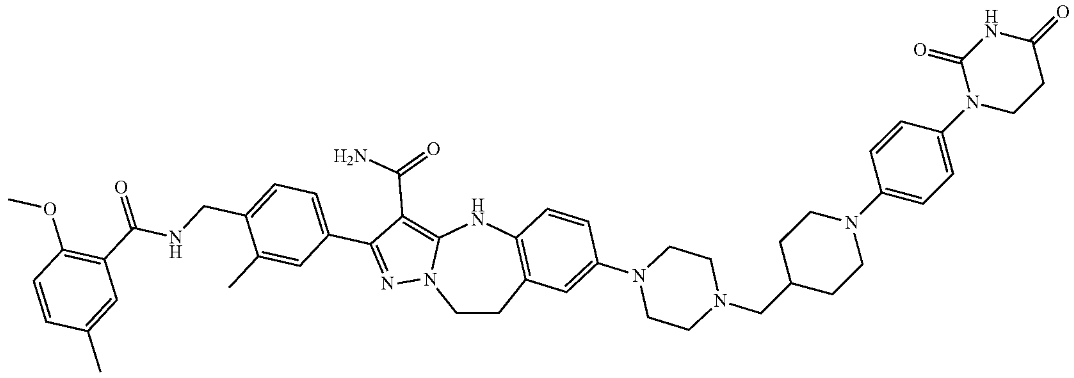

-continued
184 C41
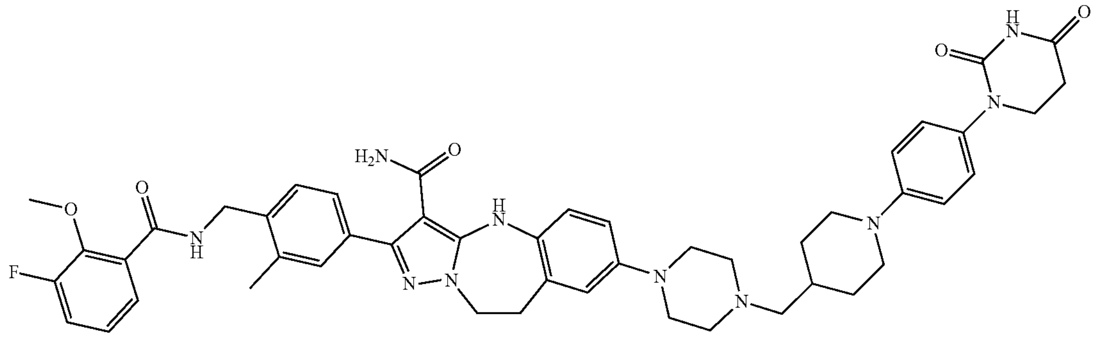
185 C42
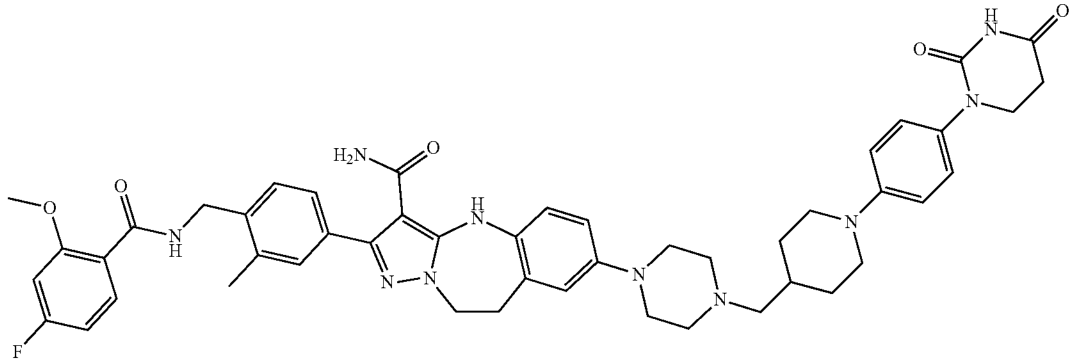
186 C43
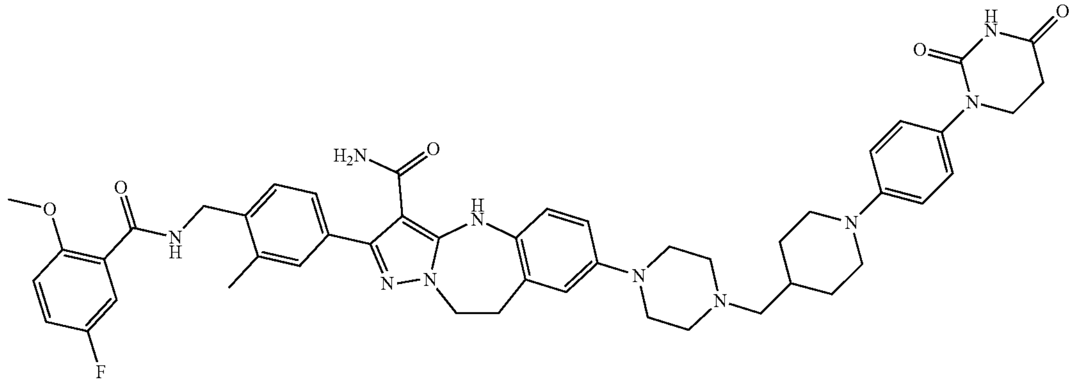
187 C44
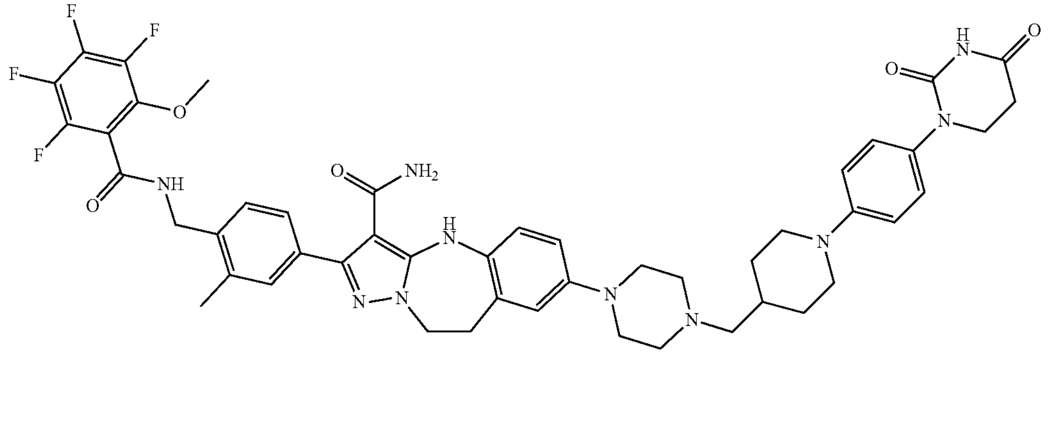

-continued
188 C45
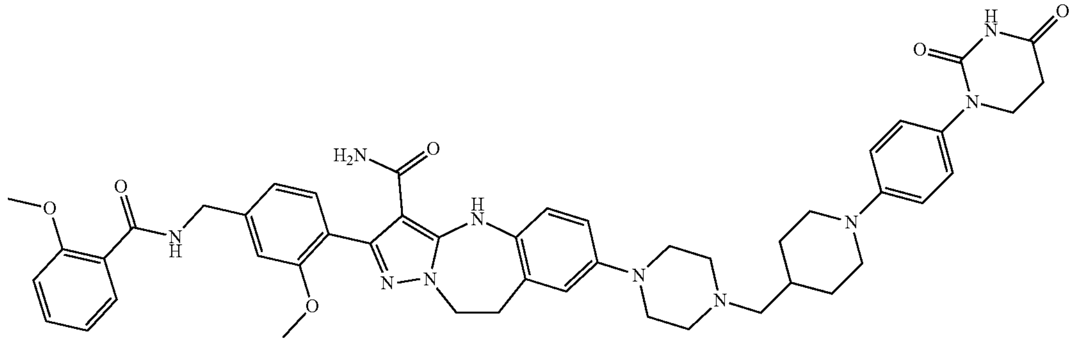
189 C46
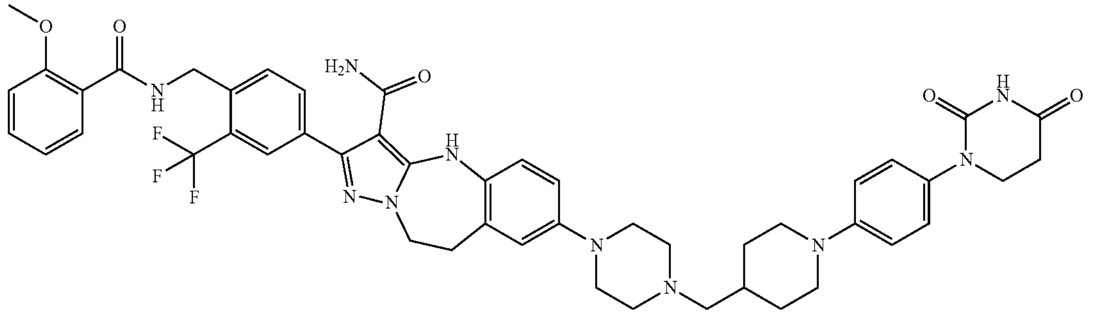
190 C37
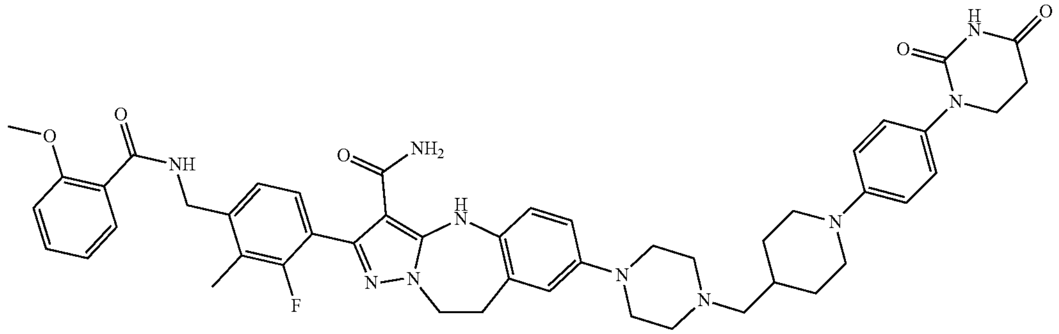
191 C48
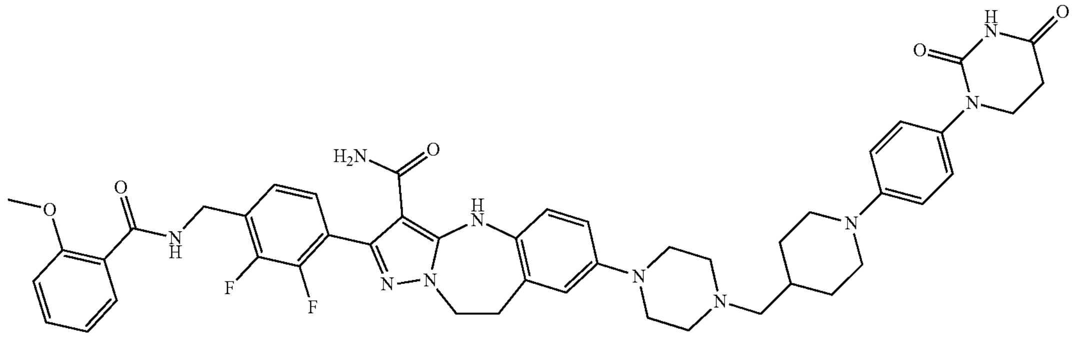

-continued

192 C49

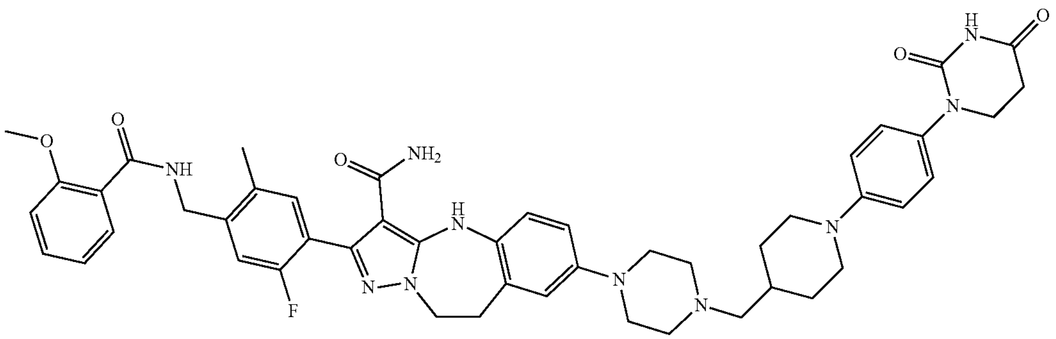

or

193 B29

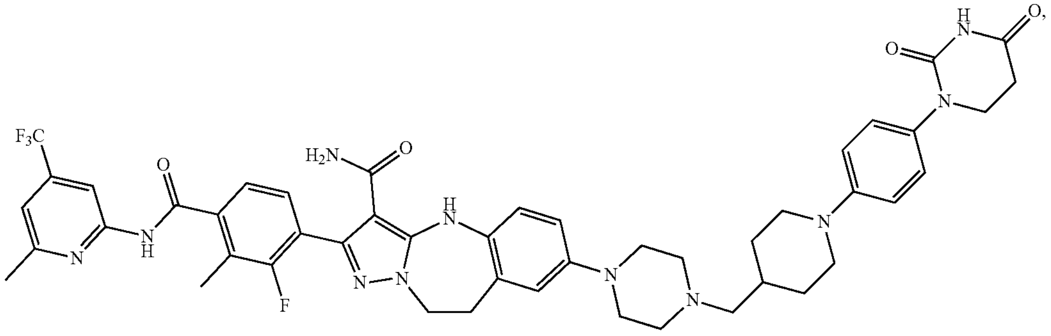

or a pharmaceutically acceptable salt thereof, or a stereoisomer thereof.

22. A prodrug of the compound according to claim 1, wherein the N atom of the compound is substituted with $R^{pro}$, $R^{pro}$ is —$C_{1-8}$alkyl, —$C_{2-8}$alkenyl, —$C_{2-8}$alkynyl, cycloalkyl, heterocyclyl, aryl, or heteroaryl, wherein each of said —$C_{1-8}$alkyl, —$C_{2-8}$alkenyl, —$C_{2-8}$alkynyl, cycloalkyl, heterocyclyl, aryl, or heteroaryl is optionally substituted with $R^{proa}$, $R^{proa}$ is independently selected from hydrogen, halogen, —$C_{1-8}$alkyl, —$C_{2-8}$alkenyl, —$C_{2-8}$alkynyl, cycloalkyl, heterocyclyl, aryl, heteroaryl, —CN, —$NO^2$, —$OR^{prob}$, —$OCOR^{prob}$, —$COR^{prob}$, —$CO_2R^{prob}$, —$CONR^{prob}R^{proc}$, —$NR^{prob}R^{proc}$, —$NIR^{prob}COR^{proc}$, —$NR^{prob}$ $CONR^{proc}R^{prod}$, or —$NR^{prob}CO^2R^{proc}$, wherein $R^{prob}$, $R^{proc}$, $R^{prod}$ are each independently selected from —$C_{1-8}$alkyl, —$C_{2-8}$alkenyl, —$C_{2-8}$alkynyl, cycloalkyl, heterocyclyl, aryl, heteroaryl, cycloalkyl —$C_{1-8}$alkyl-, heterocyclyl-$C_{1-8}$alkyl-, aryl-$C_{1-8}$alkyl-, or heteroaryl-$C_{1-8}$alkyl-.

23. The prodrug of claim 22, wherein $R^{pro}$ is

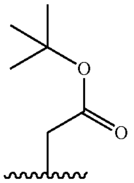

or

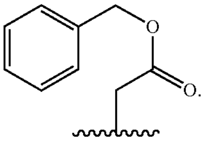

24. A prodrug selected from

146 B76

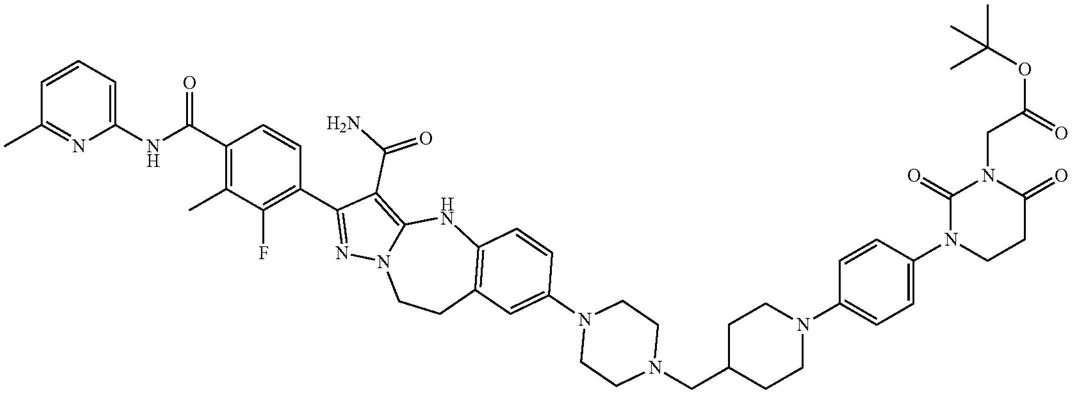

-continued
147 B77
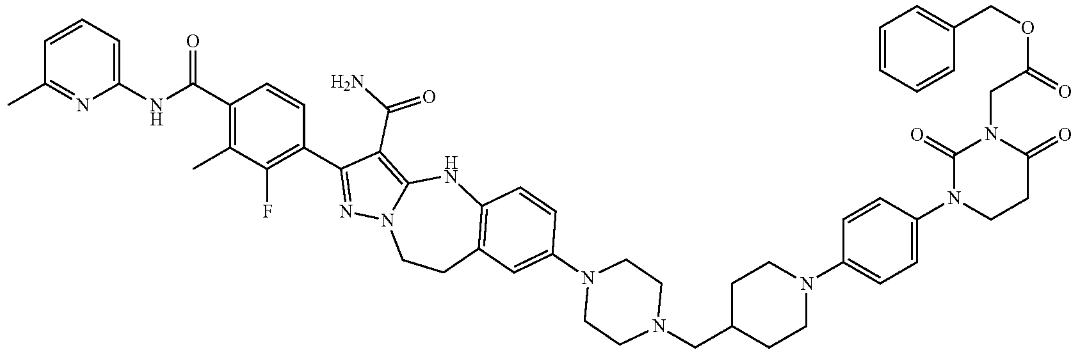
148 B78
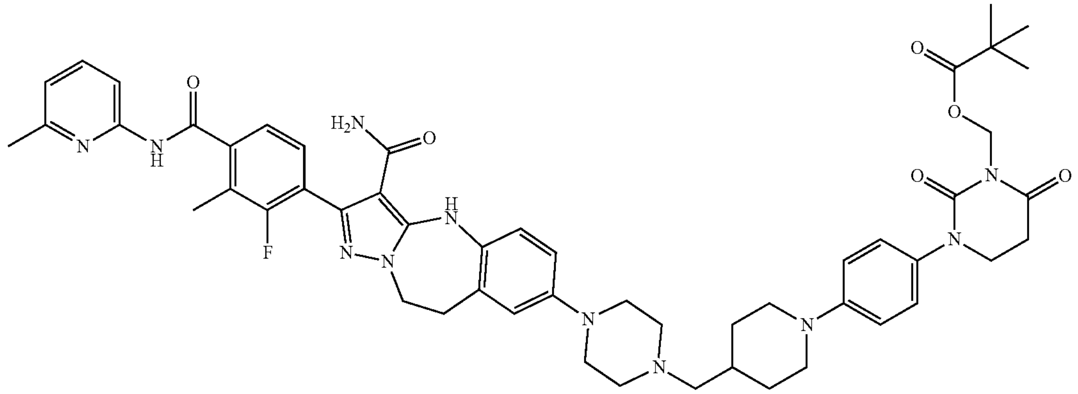
149 B79
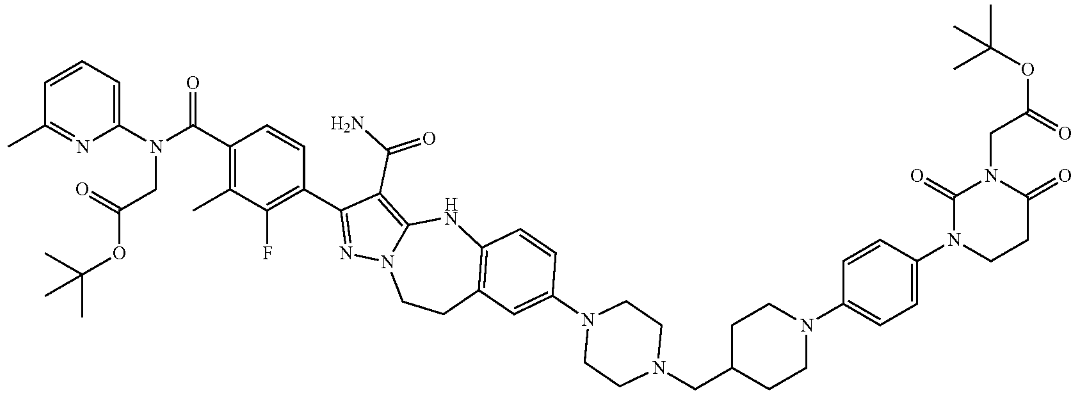
150 B80
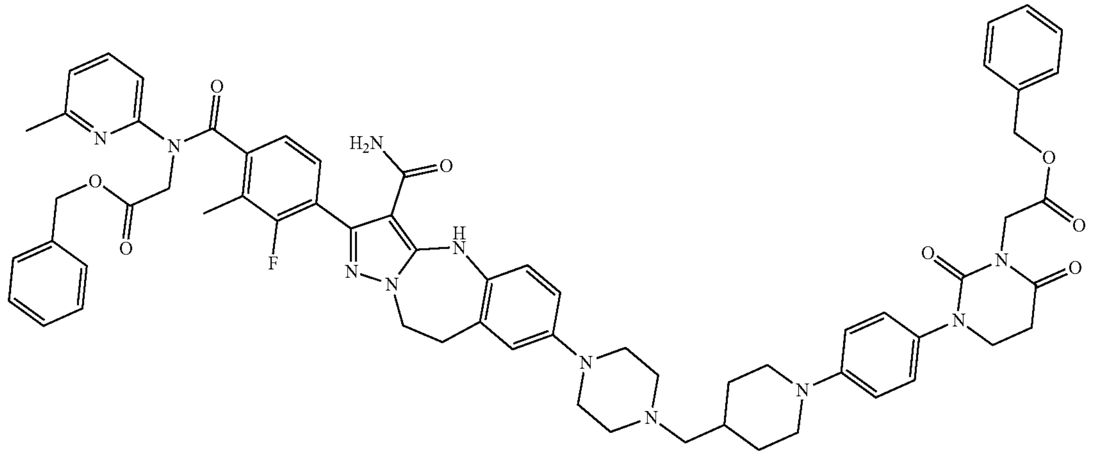

-continued

151 B81

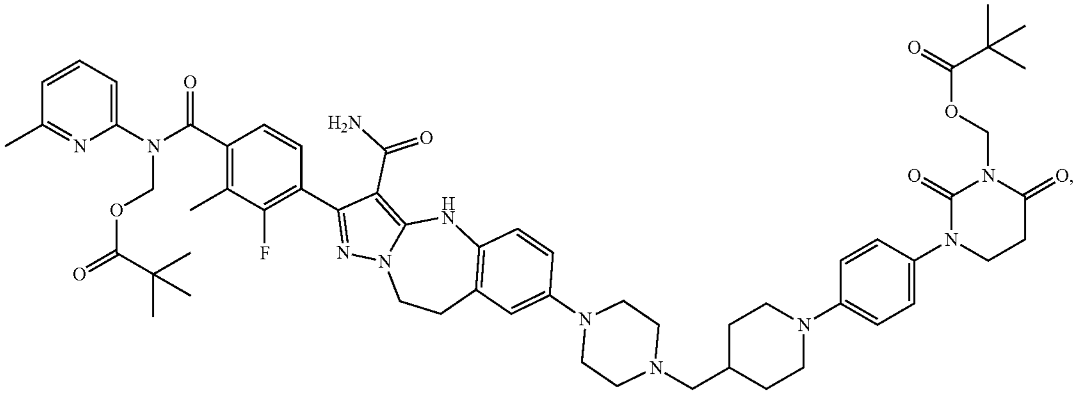

or a pharmaceutically acceptable salt thereof, or a stereoisomer thereof.

25. A pharmaceutical composition comprising the compound according to claim 1, or a pharmaceutically acceptable salt thereof, and at least one pharmaceutically acceptable carrier or excipient.

26. A method of inhibiting BTK activity, which comprises administering to a subject in need thereof an effective amount of the compound according to claim 1, or a pharmaceutically acceptable salt thereof.

27. A method of treating a disease or disorder in a patient in need thereof comprising administering to the patient a therapeutically effective amount of the compound according to claim 1, or a pharmaceutically acceptable salt thereof as an BTK kinase inhibitor, wherein the disease or disorder is associated with inhibition of BTK.

* * * * *